US008591943B2

(12) United States Patent
Deng et al.

(10) Patent No.: US 8,591,943 B2
(45) Date of Patent: Nov. 26, 2013

(54) PYRAZOLO[1,5-A]PYRIMIDINE DERIVATIVES AS MTOR INHIBITORS

(75) Inventors: Yongqi Deng, Newton, MA (US); Binyuan Sun, Chestnut Hill, MA (US); Hongbo Zeng, Westford, MA (US); Matthew Richards, Somerville, MA (US); Gerald W. Shipps, Jr., Stoneham, MA (US); Cliff C. Cheng, Cambridge, MA (US); Yinyan Zhao, Rockville, MD (US); Andrew McRiner, Melrose, MA (US); Zhaoyang Meng, Lansdale, PA (US); Yang Nan, Lansdale, PA (US); Mehul F. Patel, Willow Grove, PA (US); Iwona E. Wrona, Sharon, MA (US); Panduranga Adulla Reddy, Walpole, MA (US); Brian M. Eklov, Kalamazoo, MI (US); Shuyi Tang, Belmont, MA (US); Duan Liu, Arlington, MA (US); Amit K. Mandal, Shrewsbury, MA (US); Lianyun Zhao, Blue Bell, PA (US); M. Arshad Siddiqui, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/263,193

(22) PCT Filed: Apr. 8, 2010

(86) PCT No.: PCT/US2010/030350
§ 371 (c)(1),
(2), (4) Date: Jan. 25, 2012

(87) PCT Pub. No.: WO2010/118207
PCT Pub. Date: Oct. 14, 2010

(65) Prior Publication Data
US 2012/0114739 A1      May 10, 2012

Related U.S. Application Data

(60) Provisional application No. 61/168,093, filed on Apr. 9, 2009.

(51) Int. Cl.
| A61K 9/127 | (2006.01) |
| A61K 39/395 | (2006.01) |
| A61K 31/554 | (2006.01) |
| A61K 31/541 | (2006.01) |
| A61K 31/5377 | (2006.01) |
| A61K 38/50 | (2006.01) |
| A61K 31/553 | (2006.01) |
| A61K 33/24 | (2006.01) |
| A61K 31/704 | (2006.01) |
| A61K 31/551 | (2006.01) |
| A61K 31/538 | (2006.01) |
| A61K 31/519 | (2006.01) |

(52) U.S. Cl.
USPC ....... 424/450; 424/94.6; 424/138.1; 424/623; 424/649; 424/133.1; 514/252.16; 514/233.2; 514/255.5; 514/211.15; 514/252.2; 514/218; 514/210.16; 514/34; 514/228.5; 514/249; 514/259.3; 514/230.5; 514/210.18

(58) Field of Classification Search
None
See application file for complete search history.

(56) References Cited

U.S. PATENT DOCUMENTS

| 2002/0041880 A1 | 4/2002 | DeFeo-Jones et al. |
| 2005/0222171 A1 | 10/2005 | Bold et al. |
| 2007/0082900 A1 | 4/2007 | Guzi et al. |
| 2007/0112005 A1 | 5/2007 | Chen et al. |

FOREIGN PATENT DOCUMENTS

| WO | 9803510 | 1/1998 |
| WO | 03091256 | 11/2003 |
| WO | 2004022560 | 3/2004 |
| WO | 2004022561 | 3/2004 |
| WO | 2004106341 | 12/2004 |
| WO | 2005070431 | 8/2005 |
| WO | 2005077954 | 8/2005 |
| WO | 2006090169 | 8/2006 |
| WO | 2007009773 | 1/2007 |
| WO | 2007044813 | 4/2007 |
| WO | WO-2007-044449 | * 4/2007 |
| WO | WO-2007044449 | * 4/2007 |
| WO | 2007061737 | 5/2007 |
| WO | 2007066099 | 6/2007 |
| WO | 2007087395 | 8/2007 |
| WO | 2008012326 | 1/2008 |

OTHER PUBLICATIONS

Vippagunta et al. "Crystalline Solids," Advanced Drug Delivery Reviews, 2001, 48, pp. 18.*
Ettmayer et al. "Lessons learned from Market and investigational Prodrugs," Journal of Medicinal of Chemistry, 2004, vol. 47, 2394.*

* cited by examiner

Primary Examiner — Ernst Arnold
Assistant Examiner — Jianfeng Song
(74) Attorney, Agent, or Firm — Li Su; David A. Muthard

(57) ABSTRACT

The present invention provides methods for inhibiting mTOR using pyrazolo[1,5-a]pyrimidine compounds and methods of treatment, prevention, inhibition, or amelioration of one or more diseases associated with mTOR using such compounds.

2 Claims, No Drawings

PYRAZOLO[1,5-A]PYRIMIDINE DERIVATIVES AS MTOR INHIBITORS

FIELD OF THE INVENTION

This invention is directed to pyrazolo pyrimidine derivatives as inhibitors of mammalian Target Of Rapamycin (mTOR) kinase, which are also known as FRAP, RAFT, RAPT or SEP and as a result have a role in controlling cell cycle progression and mitogenic signals involved in cell growth and proliferation and as a result are useful in the treatment of cancer.

BACKGROUND OF THE INVENTION

The mammalian target of rapamycin (mTOR) is a central regulator of cell growth and proliferation and plays a gate keeper role in the control of cell cycle progression and mediates mitogenic signals from P13K/AKT through to the downstream targets S6K1 and 4E-BP1 and to Ser 473 on AKT. Recently it has been shown that mTOR exists in two complexes, raptor-mTOR complex (mTORC1), a rapamycin-sensitive complex, signaling to S6K1 and 4E-BP1 and rictor-mTOR complex (mTORC2), a rapamycin-insensitive complex that signals to AKT. Although the precise mechanism by which rapamycin inhibits mTOR function is not well understood, rapamycin partially inhibits mTOR function through mTORC1. It has been found that mTORC2 is involved in the regulation of cell survival and actin cytoskeletal organization in a rapamycin-independent manner, and inhibition of mTOR through inhibition of mTORC1 and mTORC2 is probably important for antitumor activity and better efficacy.

US 2007/0112005 describes the fused bicyclic mTOR inhibitors useful in treatment of cancer.

WO 2007/087395 describes unsaturated mTOR inhibitors useful in treatment of cancer.

WO-2008/012326 describes 2,4-substituted quinozolines as lipid kinase inhibitors useful in treatment of P13K-related diseases, such as proliferative diseases, inflammatory diseases, obstructive airways disorder and transplant related diseases.

WO 2006/090169 describes 2,4-diamineo-pyrido-pyrmidine derivatives and their use as mTOR inhibitors.

WO 2007/066099 describes pyrimidine derivatives useful as mTOR kinase inhibitors for anticancer and various other therapeutic treatments involving mTOR kinase.

WO 2007044813 describes pyridopyrimidinone inhibitors of PI3Ka protein kinase for anticancer or other PI3Ka protein kinase related diseases.

US 2005/0222171, WO 2005/070431, WO 2007/0570431 and WO 2007/009773 describe pyrazolo[1,5 a]pyrimidin-7-yl amine derivatives to treat protein kinase dependent diseases.

US 2002/0041880 describes pyrazolo[1,5 a]pyrimidin-7-yl derivatives to inhibit kinase insert domain-containing receptor to block angiogenesis.

WO 1998/003510 describes pyrazolo[1,5 a]pyrimidin-7-yl derivatives to treat corticotrophin releasing factor dependent diseases.

WO 2003/091256 describes pyrazolo[1,5-a]pyrimidine derivatives to treat NAD(P)H oxidase dependent diseases.

WO 2007/044449, WO 2005/077954, WO 2004/022560 and WO 2004/022561 describe pyrazolopyrimidine derivatives as cyclin-dependent kinase dependent diseases.

WO 2004/106341 describes pyrazolopyrimidine derivatives as fungicides.

There is need in the art for small molecule inhibitors of mTOR kinase that block signaling through mTORC1 and mTORC2 as a potential anticancer treatment or a treatment for other cell proliferative disorders.

SUMMARY OF THE INVENTION

In its many embodiments, the present invention discloses novel compounds having mTOR inhibitory activity, methods of preparing such compounds, pharmaceutical compositions comprising one or more of such compounds, methods of treatment or prevention of one or more diseases associated with mTOR by administering one or more of such compounds or pharmaceutical compositions, the compound being represented by the general Formula I:

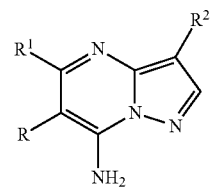

Formula I or a pharmaceutically acceptable salt, solvate, ester, or prodrug thereof,
wherein:
R is independently selected from the group consisting of halo, hydroxyl, amino, —CN, H, —($C_1$-$C_6$)alkyl, alkoxy, —C(═O)alkyl, heteroaryl and aryl, wherein each of said heteroaryl and aryl can be unsubstituted or substituted with one or more alkyl and halo;

$R^1$ is independently selected from the group consisting of heterocycloalkyl, heterocycloalkylalkyl, spiroheterocycloalkyl, heterocyclenyl, —$NR^3R^4$, cycloalkyl, heteroaryl, aryl, alkyl, alkynyl, heterocyclenylalkyl, cycloalkylalkyl, heteroarylalkyl, heteroarylalkynyl, spiroheterocycloalkylalkyl, —N-heteroaryl, -alkyl-NH-heterocyclyl and arylalkyl, wherein each of said heterocycloalkyl, heterocycloalkylalkyl, spiroheterocycloalkyl, heterocyclenyl, cycloalkyl, heteroaryl, aryl, alkyl, alkynyl, heterocyclenylalkyl, cycloalkylalkyl, heteroarylalkyl, heteroarylalkynyl, —N-heteroaryl and arylalkyl can be unsubstituted or substituted with one or more moieties independently selected from the group X;

X is alkoxyl, alkyl, —C(O)alkyl, —C(O)-hydroxyalkyl, —C(O)$_2$alkyl, —C(O)$_2$H, hydroxyalkyl, —S(O)$_2$alkyl, hydroxyl, heterocycloalkyl, —NH-heterocycloalkyl, -trihaloalkyl, -dihaloalkyl, -monohaloalkyl, —N—S(O)$_2$-alkyl, —C(O)-heteroaryl, -alkyl-C(O)$_2$H, -alkyl(CO)N(CH$_3$)—O—CH$_3$, -alkyl(CO)-heteroaryl, -alkyl-C(O)—NH$_2$, —NH$_2$, heteroaryl, -alkyl-CN, —C(O)$_2$-arylalkyl, halo, carboxyesteralkyl, —C(O)—NH$_2$, -alkyl-C(O)$_2$alkyl, heteroarylalkyl, —C(O)-heteroaryl, —C(O)-alkyl-O-alkyl, -alkyl(CO)NS(O)$_2$-cycloalkyl, -alkyl(CO)N—S(O)$_2$—CF$_3$, —N-alkyl, —SO$_2$-cycloalkyl, -alkyl(CO)NS(O)$_2$-alkyl, -alkyl-C(O)—N(alkyl)$_2$, -alkyl-NS(O)$_2$-alkyl, alkyl(CO)NS(O)$_2$-cycloalkyl, —CO—CO$_2$H, —C(O)$_2$-alkyl-aryl, —SO$_2$—CF$_3$ or —C(O)H, wherein each of said heterocycloalkyl, heteroaryl or —C(O)-heteroaryl can be unsubstituted or substituted with one or more alkyl;

$R^2$ is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl;

R³ is cycloalkyl or heteroaryl, wherein each of said cycloalkyl or heteroaryl can be unsubstituted or substituted with one or more moieties independently selected from the group consisting of X; and R⁴ is H.

In another embodiment, the present invention includes a method of inhibiting mammalian Target Of Rapamycin in a patient, wherein the method comprises administering a therapeutically effective amount of at least one compound of the structural Formula I.

In another embodiment, the present invention includes a method of treating, or slowing the progression of, a disease by inhibiting mammalian Target Of Rapamycin in a patient, wherein the method comprises administering a therapeutically effective amount of at least one compound represented by the structural Formula I.

In another embodiment, the present invention includes a method of treating, or slowing the progression of, a disease by inhibiting mammalian Target Of Rapamycin in a patient, wherein the method comprises administering a therapeutically effective amount of at least one compound represented by the structural Formula I, to a patient in need thereof.

In another embodiment, the present invention includes a method of treatment of a disease selected from the group consisting of proliferative inflammatory diseases, allergic diseases, obstructive airways diseases, and disorders commonly occurring in connection with transplantation, diseases that respond to inhibition of mammalian Target Of Rapamycin, wherein the method comprises administering a therapeutically effective amount of compound represented by the structural Formula I, to a patient in need of such treatment.

In another embodiment, the present invention includes a method of treatment of a disease, wherein the method comprises administering a therapeutically effective amount of the compound represented by the structural Formula I.

In another embodiment, the present invention includes a method of treatment of a disease selected from the group consisting of proliferative inflammatory diseases, allergic diseases, obstructive airways diseases, and disorders commonly occurring in connection with transplantation, diseases that respond to inhibition of mammalian Target Of Rapamycin, wherein the method comprises administering a therapeutically effective amount of the compound represented by the structural Formula I, wherein the disease is a proliferative disease, autoimmune disease, viral disease, fungal disease, neurological/neurodegenerative disorder, arthritis, inflammation, neuronal, alopecia or cardiovascular disease.

In another embodiment, the present invention includes a method of treatment of a disease, wherein the method comprises administering a therapeutically effective amount of the compound represented by the structural Formula I, wherein the disease is a proliferative disease.

In another embodiment, the present invention includes a method of treatment of a proliferative disease, wherein the method comprises administering a therapeutically effective amount of the compound represented by the structural Formula I, wherein the proliferative disease is selected from the group consisting of: cancer of the bladder, breast, colon, kidney, liver, lung, small cell lung cancer, non-small cell lung cancer, head and neck, esophagus, gall bladder, ovary, pancreas, stomach, cervix, thyroid, prostate, and skin, squamous cell carcinoma; leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, Burkett's lymphoma; acute and chronic myelogenous leukemia, myelodysplastic syndrome, promyelocytic leukemia; fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, endometrial cancer, gastrointestinal tract cancer and Kaposi's sarcoma.

In another embodiment, the present invention includes a method of treatment of a proliferative disease comprising administering a therapeutically effective amount of the compound represented by the structural Formula I, further comprising treatment with radiation therapy.

In another embodiment, the present invention includes a method of inhibiting a mammalian Target Of Rapamycin, wherein the method comprises administering a therapeutically effective amount of a compound represented by the structural Formula I.

In another embodiment, the present invention relates to the foregoing method of using a compound represented by the structural Formula I:

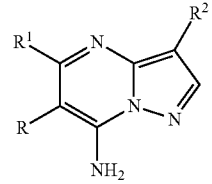

Formula I or a pharmaceutically acceptable salt, solvate, ester, or prodrug thereof,
wherein:

R is independently selected from the group consisting of halo, hydroxyl, amino, —CN, —(C₁-C₆)alkyl, alkoxy, —C(=O)alkyl, heteroaryl and aryl, wherein each of said heteroaryl and aryl can be unsubstituted or substituted with one or more alkyl and halo;

R¹ is heterocycloalkyl, wherein said heterocycloalkyl can be unsubstituted or substituted with one or moieties independently selected from the group X;

X is alkoxyl, alkyl, —C(O)alkyl, —C(O)-hydroxyalkyl, —C(O)₂alkyl, —C(O)₂H, hydroxyalkyl, —S(O)₂alkyl, hydroxyl, heterocycloalkyl, —NH-heterocycloalkyl, -trihaloalkyl, -dihaloalkyl, -monohaloalkyl, —N—S(O)₂-alkyl, —C(O)-heteroaryl, -alkyl-C(O)₂H, -alkyl(CO)N(CH₃)—O—CH₃, -alkyl(CO)-heteroaryl, —C(O)₂-alkyl, -alkyl-C(O)—NH₂, —NH₂, heteroaryl, -alkyl-CN, —C(O)₂-arylalkyl, halo, carboxyesteralkyl, —C(O)—NH₂, -alkyl-C(O)₂alkyl, heteroarylalkyl, —C(O)-heteroaryl, —C(O)-alkyl-O-alkyl, -alkyl(CO)NS(O)₂-cycloalkyl, -alkyl(CO)N—S(O)₂—CF₃, —N-alkyl, —SO₂-cycloalkyl, -alkyl(CO)NS(O)₂-alkyl, -alkyl-C(O)—N(alkyl)₂, -alkyl-NS(O)₂-alkyl, alkyl(CO)NS(O)₂-cycloalkyl, —CO—CO₂H, —C(O)₂-alkyl-aryl, —SO₂—CF₃ or —C(O)H, wherein each of said heterocycloalkyl, heteroaryl or —C(O)-heteroaryl can be unsubstituted or substituted with one or more alkyl;

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl.

In another embodiment, the present invention relates to the foregoing method of using a compound represented by the structural Formula I:

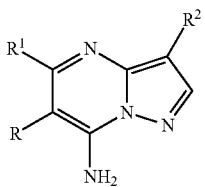

Formula I or a pharmaceutically acceptable salt, solvate, ester, or prodrug thereof,
wherein:

R is independently selected from the group consisting of halo, hydroxyl, amino, —ON, H, —($C_1$-$C_6$)alkyl, alkoxy, —C(=O)alkyl, heteroaryl and aryl, wherein each of said heteroaryl and aryl can be unsubstituted or substituted with one or more alkyl and halo;

$R^1$ is heterocyclenyl, wherein said heterocyclenyl can be unsubstituted or substituted with one or moieties independently selected from the group X;

X is alkoxyl, alkyl, —C(O)alkyl, —C(O)-hydroxyalkyl, —C(O)$_2$alkyl, —C(O)$_2$H, hydroxyalkyl, —S(O)$_2$alkyl, hydroxyl, heterocycloalkyl, —NH-heterocycloalkyl, -trihaloalkyl, -dihaloalkyl, -monohaloalkyl, —N—S(O)$_2$-alkyl, —C(O)-heteroaryl, -alkyl-C(O)$_2$H, -alkyl(CO)N(CH$_3$)—O—CH$_3$, -alkyl(CO)-heteroaryl, —C(O)$_2$-alkyl, -alkyl-C(O)—NH$_2$, —NH$_2$, heteroaryl, -alkyl-CN, —C(O)$_2$-arylalkyl, halo, carboxyesteralkyl, —C(O)—NH$_2$, -alkyl-C(O)$_2$alkyl, heteroarylalkyl, —C(O)-heteroaryl, —C(O)-alkyl-O-alkyl, -alkyl(CO)NS(O)$_2$-cycloalkyl, -alkyl(CO)N—S(O)$_2$—CF$_3$, —N-alkyl, —SO$_2$-cycloalkyl, -alkyl(CO)NS(O)$_2$-alkyl, -alkyl-C(O)—N(alkyl)$_2$, -alkyl-NS(O)$_2$-alkyl, alkyl(CO)NS(O)$_2$-cycloalkyl, —CO—CO$_2$H, —C(O)$_2$-alkyl-aryl, —SO$_2$—CF$_3$ or —C(O)H, wherein each of said heterocycloalkyl, heteroaryl or —C(O)-heteroaryl can be unsubstituted or substituted with one or more alkyl;

$R^2$ is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH$_3$)$_2$CN, trifluoromethyl, difluoromethyl, monofluoromethyl, heterocycloalkyl, and arylalkyl.

In another embodiment, the present invention relates to the foregoing method of using a compound represented by the structural Formula I:

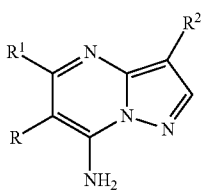

Formula I or a pharmaceutically acceptable salt, solvate, ester, or prodrug thereof,
wherein:

R is independently selected from the group consisting of halo, hydroxyl, amino, —CN, H, —($C_1$-$C_6$)alkyl, alkoxy, —C(=O)alkyl, heteroaryl and aryl, wherein each of said heteroaryl and aryl can be unsubstituted or substituted with one or more alkyl and halo;

$R^1$ is heteroaryl, wherein said heteroaryl can be unsubstituted or substituted with one or moieties independently selected from the group X;

X is alkoxyl, alkyl, —C(O)alkyl, —C(O)-hydroxyalkyl, —C(O)$_2$alkyl, —C(O)$_2$H, hydroxyalkyl, —S(O)$_2$alkyl, hydroxyl, heterocycloalkyl, —NH-heterocycloalkyl, -trihaloalkyl, -dihaloalkyl, -monohaloalkyl, —N—S(O)$_2$-alkyl, —C(O)-heteroaryl, -alkyl-C(O)$_2$H, -alkyl(CO)N(CH$_3$)—O—CH$_3$, -alkyl(CO)-heteroaryl, —C(O)$_2$-alkyl, -alkyl-C(O)—NH$_2$, —NH$_2$, heteroaryl, -alkyl-CN, —C(O)$_2$-arylalkyl, halo, carboxyesteralkyl, —C(O)—NH$_2$, -alkyl(CO)NS(O)$_2$-cycloalkyl, -alkyl(CO)N—S(O)$_2$—CF$_3$, —N-alkyl, —SO$_2$-cycloalkyl, -alkyl(CO)NS(O)$_2$-alkyl, -alkyl-C(O)—N(alkyl)$_2$, -alkyl-NS(O)$_2$-alkyl, alkyl(CO)NS(O)$_2$-cycloalkyl, —CO—CO$_2$H, —C(O)$_2$-alkyl-aryl, —SO$_2$—CF$_3$ or —C(O)H, wherein each of said heterocycloalkyl, heteroaryl or —C(O)-heteroaryl can be unsubstituted or substituted with one or more alkyl;

$R^2$ is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH$_3$)$_2$CN, trifluoromethyl, difluoromethyl, monofluoromethyl, heterocycloalkyl, and arylalkyl.

In another embodiment, the present invention relates to the foregoing method of using a compound represented by the structural Formula I:

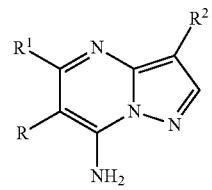

Formula I or a pharmaceutically acceptable salt, solvate, ester, or prodrug thereof,
wherein:

R is independently selected from the group consisting of halo, hydroxyl, amino, —ON, H, —($C_1$-$C_6$)alkyl, alkoxy, —C(=O)alkyl, heteroaryl and aryl, wherein each of said heteroaryl and aryl can be unsubstituted or substituted with one or more alkyl and halo;

$R^1$ is cycloalkyl, wherein said cycloalkyl can be unsubstituted or substituted with one or moieties independently selected from the group X;

X is alkoxyl, alkyl, —C(O)alkyl, —C(O)-hydroxyalkyl, —C(O)$_2$alkyl, —C(O)$_2$H, hydroxyalkyl, —S(O)$_2$alkyl, hydroxyl, heterocycloalkyl, —NH-heterocycloalkyl, trihaloalkyl, -dihaloalkyl, -monohaloalkyl, —N—S(O)$_2$-alkyl, —C(O)-heteroaryl, -alkyl-C(O)$_2$H, -alkyl(CO)N(CH$_3$)—O—CH$_3$, -alkyl(CO)-heteroaryl, —C(O)$_2$-alkyl, -alkyl-C(O)—NH$_2$, —NH$_2$, heteroaryl, -alkyl-CN, —C(O)$_2$-arylalkyl, halo, carboxyesteralkyl, —C(O)—NH$_2$, -alkyl-C(O)$_2$alkyl, heteroarylalkyl, —C(O)-heteroaryl, —C(O)-alkyl-O-alkyl, -alkyl(CO)NS(O)$_2$-cycloalkyl, -alkyl(CO)N—S(O)$_2$—CF$_3$, —N-alkyl, —SO$_2$-cycloalkyl, -alkyl(CO)NS(O)$_2$-alkyl, -alkyl-C(O)—N(alkyl)$_2$, -alkyl-NS(O)$_2$-alkyl, alkyl(CO)NS(O)$_2$-cycloalkyl, —CO—CO$_2$H, —C(O)$_2$-alkyl-aryl, —SO$_2$—CF$_3$ or —C(O)H, wherein each of said heterocycloalkyl, heteroaryl or —C(O)-heteroaryl can be unsubstituted or substituted with one or more alkyl;

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl.

In another embodiment, the present invention relates to the foregoing method of using a compound represented by the structural Formula I:

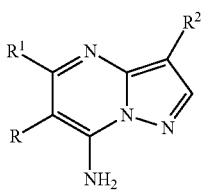

Formula I or a pharmaceutically acceptable salt, solvate, ester, or prodrug thereof,
wherein:

R is independently selected from the group consisting of halo, hydroxyl, amino, —CN, H, —(C₁-C₆)alkyl, alkoxy, —C(=O)alkyl, heteroaryl and aryl, wherein each of said heteroaryl and aryl can be unsubstituted or substituted with one or more alkyl and halo;

R¹ is cycloalkenyl, wherein said cycloalkenyl can be unsubstituted or substituted with one or moieties independently selected from the group X;

X is alkoxyl, alkyl, —C(O)alkyl, —C(O)-hydroxyalkyl, —C(O)₂alkyl, —C(O)₂H, hydroxyalkyl, —S(O)₂alkyl, hydroxyl, heterocycloalkyl, —NH-heterocycloalkyl, -trihaloalkyl, -dihaloalkyl, -monohaloalkyl, —N—S(O)₂-alkyl, —C(O)-heteroaryl, C(O)₂H, -alkyl(CO)N(CH₃)—O—CH₃, -alkyl(CO)-heteroaryl, —C(O)₂-alkyl, -alkyl-C(O)—NH₂, —NH₂, heteroaryl, -alkyl-CN, —C(O)₂-arylalkyl, halo, carboxyesteralkyl, —C(O)—NH₂, -alkyl-C(O)₂alkyl, heteroarylalkyl, —C(O)-heteroaryl, -alkyl(CO)NS(O)₂-cycloalkyl, -alkyl(CO)N—S(O)₂—CF₃, —N-alkyl, —SO₂-cycloalkyl, -alkyl(CO)NS(O)₂-alkyl, -alkyl-C(O)—N(alkyl)₂, -alkyl-NS(O)₂-alkyl, alkyl(CO)NS(O)₂-cycloalkyl, —CO—CO₂H, —C(O)₂-alkyl-aryl, —SO₂—CF₃ or —C(O)H, wherein each of said heterocycloalkyl, heteroaryl or —C(O)-heteroaryl can be unsubstituted or substituted with one or more alkyl;

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl.

In another embodiment, the present invention relates to the foregoing method of using a compound represented by the structural Formula I:

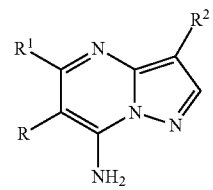

Formula I or a pharmaceutically acceptable salt, solvate, ester, or prodrug thereof,
wherein:

R is independently selected from the group consisting of halo, hydroxyl, amino, —CN, H, —(C₁-C₆)alkyl, alkoxy, —C(=O)alkyl, heteroaryl and aryl, wherein each of said heteroaryl and aryl can be unsubstituted or substituted with one or more alkyl and halo;

R¹ is aryl, wherein said aryl can be unsubstituted or substituted with one or moieties independently selected from the group X;

X is alkoxyl, alkyl, —C(O)alkyl, —C(O)-hydroxyalkyl, —C(O)₂alkyl, —C(O)₂H, hydroxyalkyl, —S(O)₂alkyl, hydroxyl, heterocycloalkyl, —NH-heterocycloalkyl, -trihaloalkyl, -dihaloalkyl, -monohaloalkyl, —N—S(O)₂-alkyl, —C(O)-heteroaryl, -alkyl-C(O)₂H, -alkyl(CO)N(CH₃)—O—CH₃, -alkyl(CO)-heteroaryl, —C(O)₂-alkyl, -alkyl-C(O)—NH₂, —NH₂, heteroaryl, -alkyl-CN, —C(O)₂-arylalkyl, halo, carboxyesteralkyl, —C(O)—NH₂, -alkyl-C(O)₂alkyl, heteroarylalkyl, —C(O)-heteroaryl, —C(O)-alkyl-O-alkyl, -alkyl(CO)NS(O)₂-cycloalkyl, -alkyl(CO)N—S(O)₂—CF₃, —N-alkyl, —SO₂-cycloalkyl, -alkyl(CO)NS(O)₂-alkyl, -alkyl-C(O)—N(alkyl)₂, -alkyl-NS(O)₂-alkyl, alkyl(CO)NS(O)₂-cycloalkyl, —CO—CO₂H, —C(O)₂-alkyl-aryl, —SO₂—CF₃ or —C(O)H, wherein each of said heterocycloalkyl, heteroaryl or —C(O)-heteroaryl can be unsubstituted or substituted with one or more alkyl;

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl.

In another embodiment, the present invention relates to the foregoing method of using a compound represented by the structural Formula I:

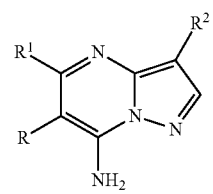

Formula I or a pharmaceutically acceptable salt, solvate, ester, or prodrug thereof,
wherein:

R is independently selected from the group consisting of halo, hydroxyl, amino, —ON, H, —(C₁-C₆)alkyl, alkoxy, —C(=O)alkyl, heteroaryl and aryl, wherein each of said heteroaryl and aryl can be unsubstituted or substituted with one or more alkyl and halo;

R¹ is alkyl, wherein said alkyl can be unsubstituted or substituted with one or moieties independently selected from the group X;

X is alkoxyl, alkyl, —C(O)alkyl, —C(O)-hydroxyalkyl, —C(O)₂alkyl, —C(O)₂H, hydroxyalkyl, —S(O)₂alkyl, hydroxyl, heterocycloalkyl, —NH-heterocycloalkyl, -trihaloalkyl, -dihaloalkyl, -monohaloalkyl, —N—S(O)₂-alkyl, —C(O)-heteroaryl, -alkyl-C(O)₂H, -alkyl(CO)N(CH₃)—O—CH₃, -alkyl(CO)-heteroaryl, —C(O)₂-alkyl, -alkyl-C(O)—NH₂, —NH₂, heteroaryl, -alkyl-CN, —C(O)₂-arylalkyl, halo, carboxyesteralkyl, —C(O)—NH₂, -alkyl-C(O)₂alkyl, heteroarylalkyl, —C(O)-heteroaryl, —C(O)-alkyl-O-alkyl, -alkyl(CO)NS(O)₂-cycloalkyl, -alkyl(CO)N—S(O)₂—CF₃,—N-alkyl,—SO₂-cycloalkyl, -alkyl(CO)NS(O)₂-alkyl, -alkyl-C(O)—N(alkyl)₂, -alkyl-NS(O)₂-alkyl, alkyl(CO)NS(O)₂-cycloalkyl, —CO—CO₂H, —C(O)₂-alkyl-aryl, —SO₂—CF₃ or —C(O)H, wherein each of said heterocycloalkyl, heteroaryl or —C(O)-heteroaryl can be unsubstituted or substituted with one or more alkyl;

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl.

In another embodiment, the present invention relates to the foregoing method of using a compound represented by the structural Formula I:

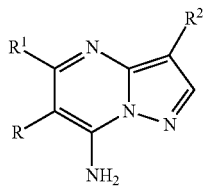

or a pharmaceutically acceptable salt, solvate, ester, or prodrug thereof, wherein:

R is independently selected from the group consisting of halo, hydroxyl, amino, —CN, H, —(C₁-C₆)alkyl, alkoxy, —C(=O)alkyl, heteroaryl and aryl, wherein each of said heteroaryl and aryl can be unsubstituted or substituted with one or more alkyl and halo;

R¹ is alkynyl, wherein said alkynyl can be unsubstituted or substituted with one or moieties independently selected from the group X;

X is alkoxyl, alkyl, —C(O)alkyl, —C(O)-hydroxyalkyl, —C(O)₂alkyl, —C(O)₂H, hydroxyalkyl, —S(O)₂alkyl, hydroxyl, heterocycloalkyl, —NH-heterocycloalkyl, -trihaloalkyl, -dihaloalkyl, -monohaloalkyl, —N—S(O)₂-alkyl, —C(O)-heteroaryl, -alkyl-C(O)₂H, -alkyl(CO)N(CH₃)—O—CH₃, -alkyl(CO)-heteroaryl, —C(O)₂-alkyl, -alkyl-C(O)—NH₂, —NH₂, heteroaryl, -alkyl-CN, —C(O)₂-arylalkyl, halo, carboxyesteralkyl, —C(O)—NH₂, -alkyl-C(O)₂alkyl, heteroarylalkyl, —C(O)-heteroaryl, —C(O)-alkyl-O-alkyl, -alkyl(CO)NS(O)₂-cycloalkyl, -alkyl(CO)N—S(O)₂—CF₃,—N-alkyl,—SO₂-cycloalkyl, -alkyl(CO)NS(O)₂-alkyl, -alkyl-C(O)—N(alkyl)₂, -alkyl-NS(O)₂-alkyl, alkyl(CO)NS(O)₂-cycloalkyl, —CO—CO₂H, —C(O)₂-alkyl-aryl, —SO₂—CF₃ or —C(O)H, wherein each of said heterocycloalkyl, heteroaryl or —C(O)-heteroaryl can be unsubstituted or substituted with one or more alkyl;

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl.

In another embodiment, the present invention relates to the foregoing method of using a compound represented by the structural Formula I:

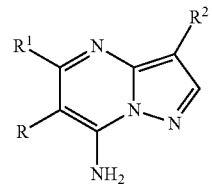

or a pharmaceutically acceptable salt, solvate, ester, or prodrug thereof, wherein:

R is independently selected from the group consisting of halo, hydroxyl, amino, —CN, H, —(C₁-C₆)alkyl, alkoxy, —C(=O)alkyl, heteroaryl and aryl, wherein each of said heteroaryl and aryl can be unsubstituted or substituted with one or more alkyl and halo;

R¹ is spiroheterocycloalkyl, wherein said spiroheterocycloalkyl can be unsubstituted or substituted with one or moieties independently selected from the group X;

X is alkoxyl, alkyl, —C(O)alkyl, —C(O)-hydroxyalkyl, —C(O)₂alkyl, —C(O)₂H, hydroxyalkyl, —S(O)₂alkyl, hydroxyl, heterocycloalkyl, —NH-heterocycloalkyl, -trihaloalkyl, -dihaloalkyl, -monohaloalkyl, —N—S(O)₂-alkyl, —C(O)-heteroaryl, -alkyl-C(O)₂H, -alkyl(CO)N(CH₃)—O—CH₃, -alkyl(CO)-heteroaryl, —C(O)₂-alkyl, -alkyl-C(O)—NH₂, —NH₂, heteroaryl, -alkyl-CN, —C(O)₂-arylalkyl, halo, carboxyesteralkyl, —C(O)—NH₂, -alkyl-C(O)₂alkyl, heteroarylalkyl, —C(O)-heteroaryl, —C(O)-alkyl-O-alkyl, -alkyl(CO)NS(O)₂-cycloalkyl, -alkyl(CO)N—S(O)₂—CF₃,—N-alkyl,—SO₂-cycloalkyl, -alkyl(CO)NS(O)₂-alkyl, -alkyl-C(O)—N(alkyl)₂, -alkyl-NS(O)₂-alkyl, alkyl(CO)NS(O)₂-cycloalkyl, —CO—CO₂H, —C(O)₂-alkyl-aryl, —SO₂—CF₃ or —C(O)H, wherein each of said heterocycloalkyl, heteroaryl or —C(O)-heteroaryl can be unsubstituted or substituted with one or more alkyl;

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl.

In another embodiment, the present invention relates to the foregoing method of using a compound represented by the structural Formula I:

Formula I
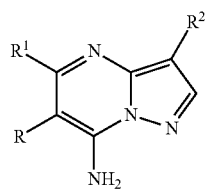
or a pharmaceutically acceptable salt, solvate, ester, or prodrug thereof,
wherein:
R is independently selected from the group consisting of bromo, chloro, —CN, H, methyl, acetyl, pyridyl, phenyl, 1-methyl-pyrazolyl, and thienyl;
$R^1$ is independently selected from the group consisting of:
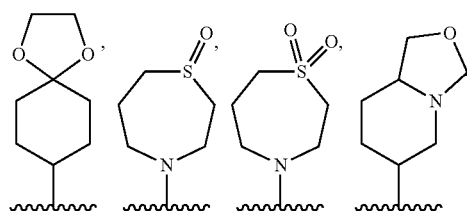
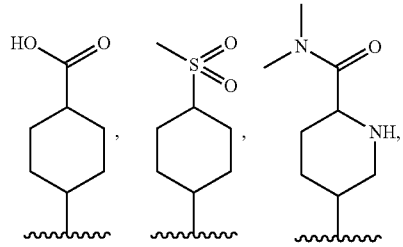
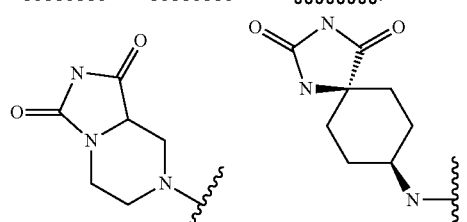
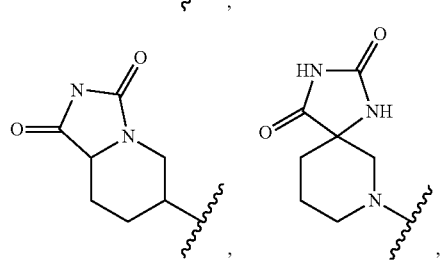
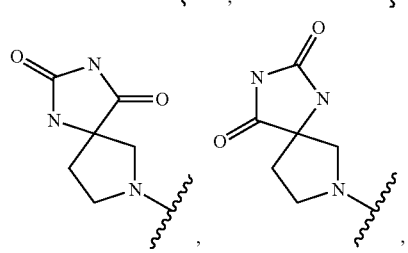
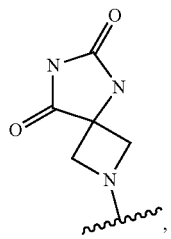 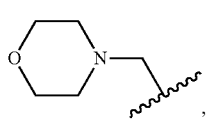
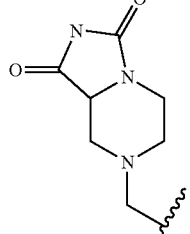

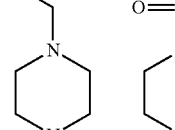

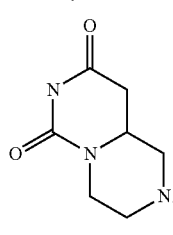
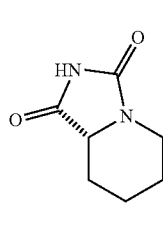
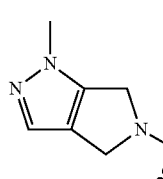
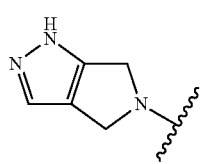

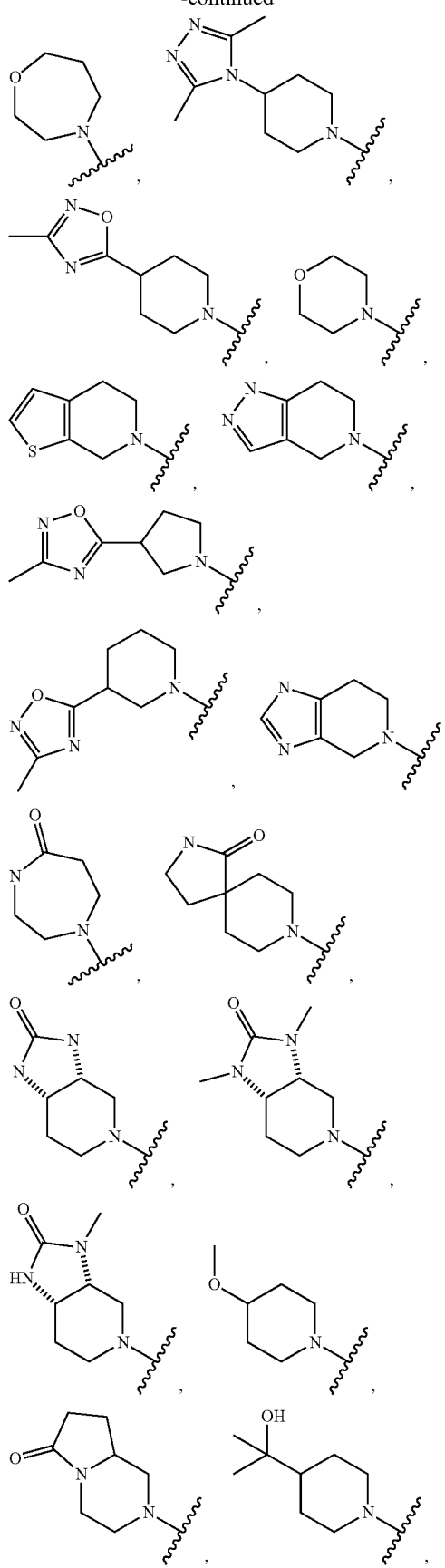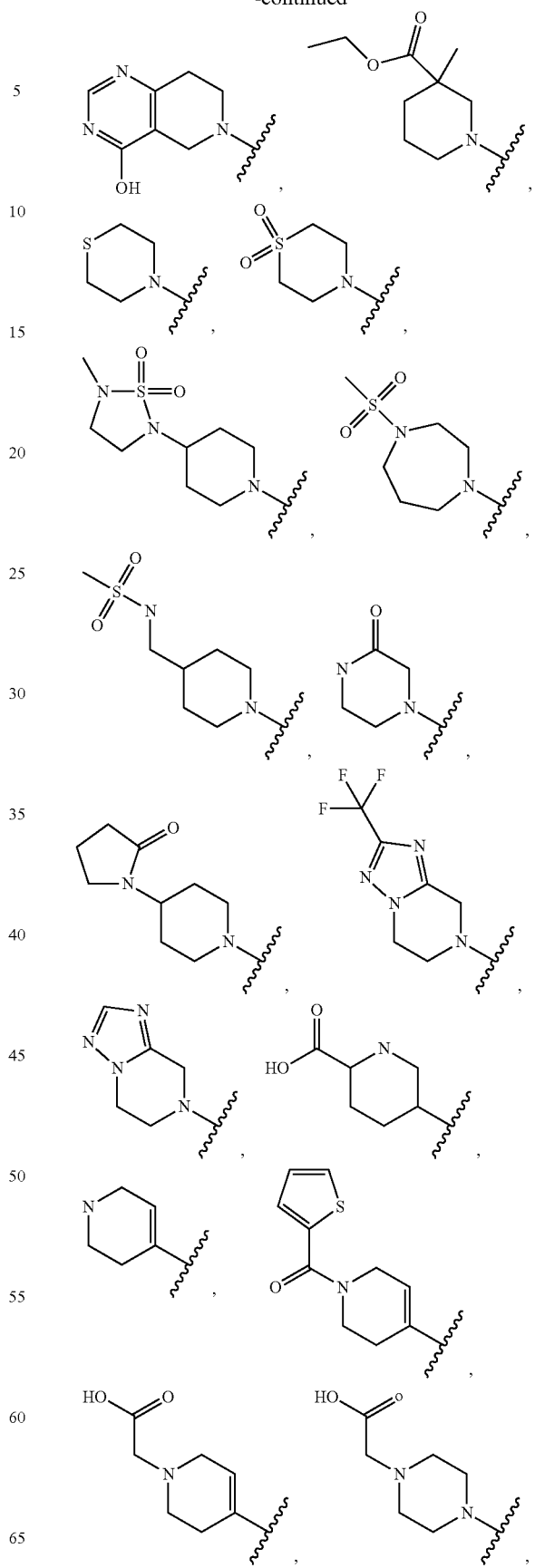

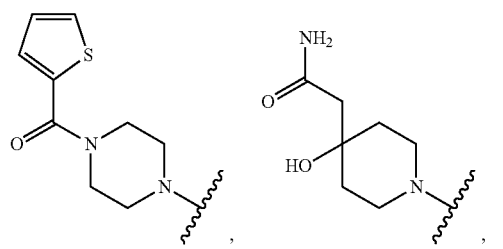,
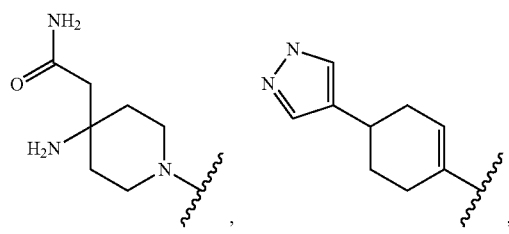,
,
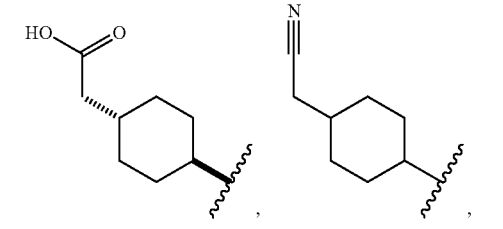,
,
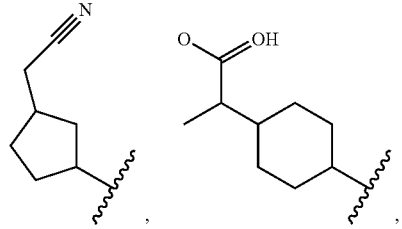,
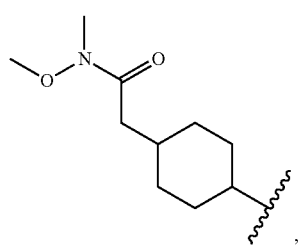,
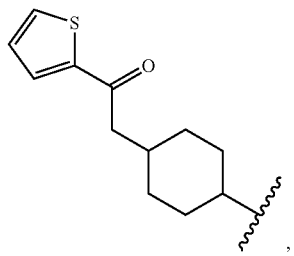,
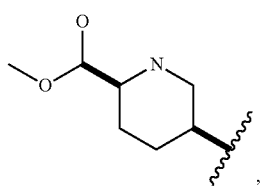,
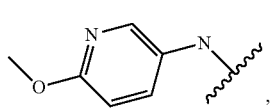 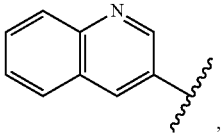,
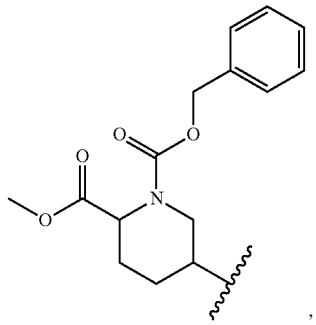,
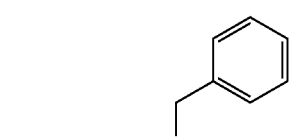,
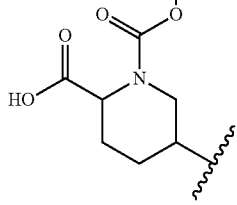,
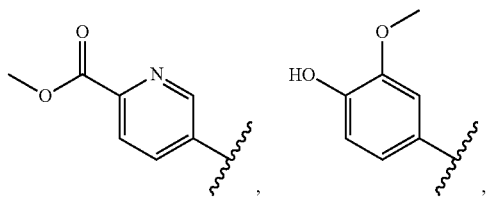,
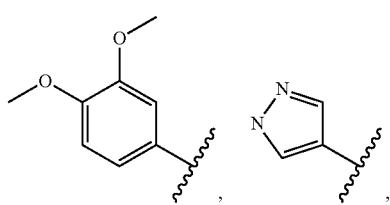,

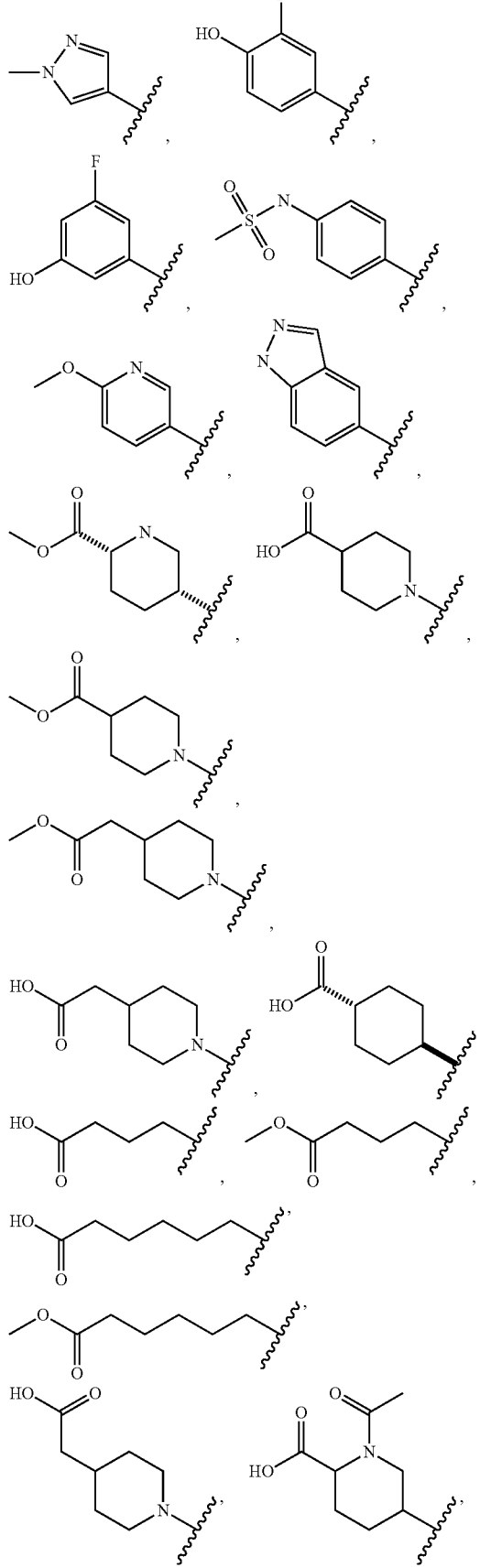
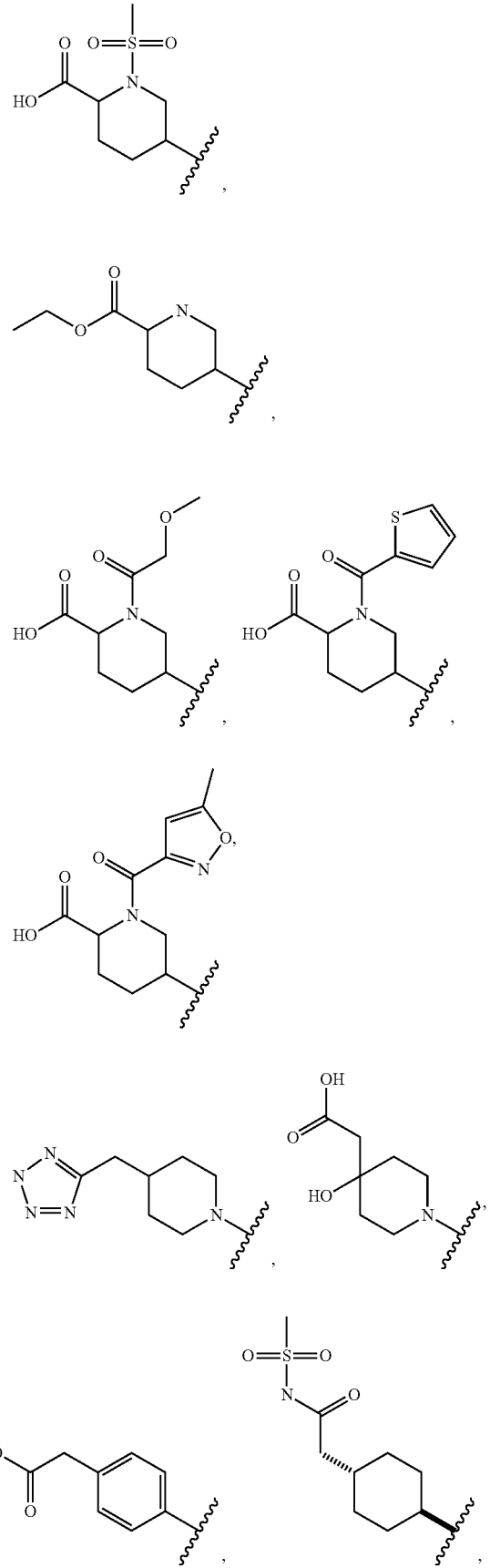

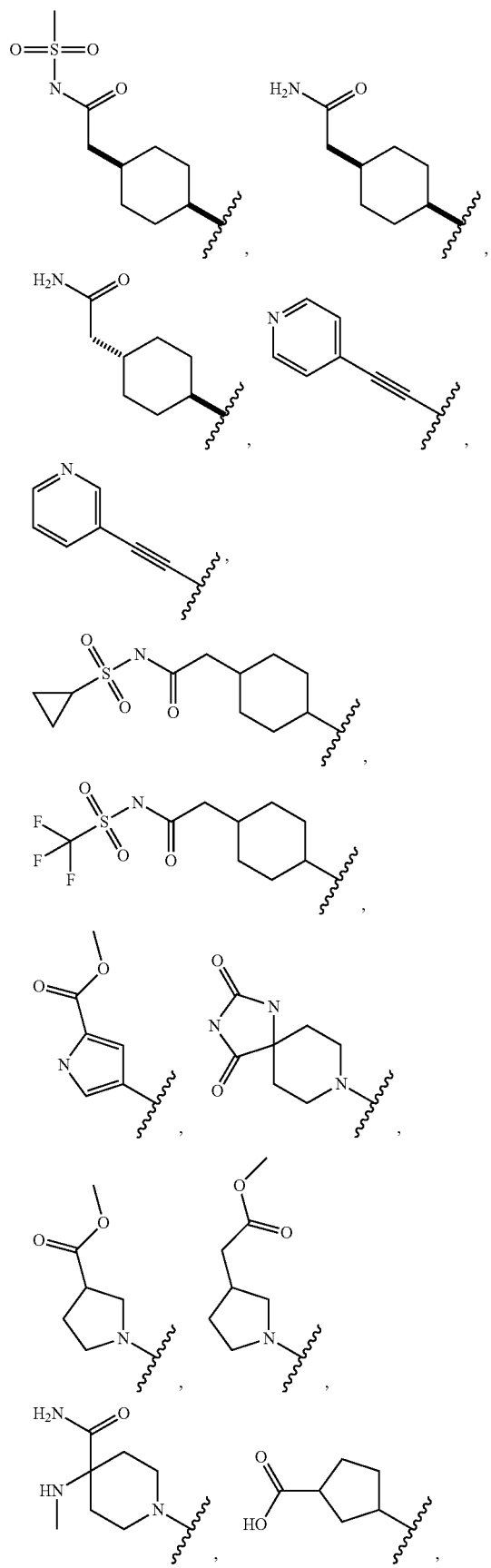
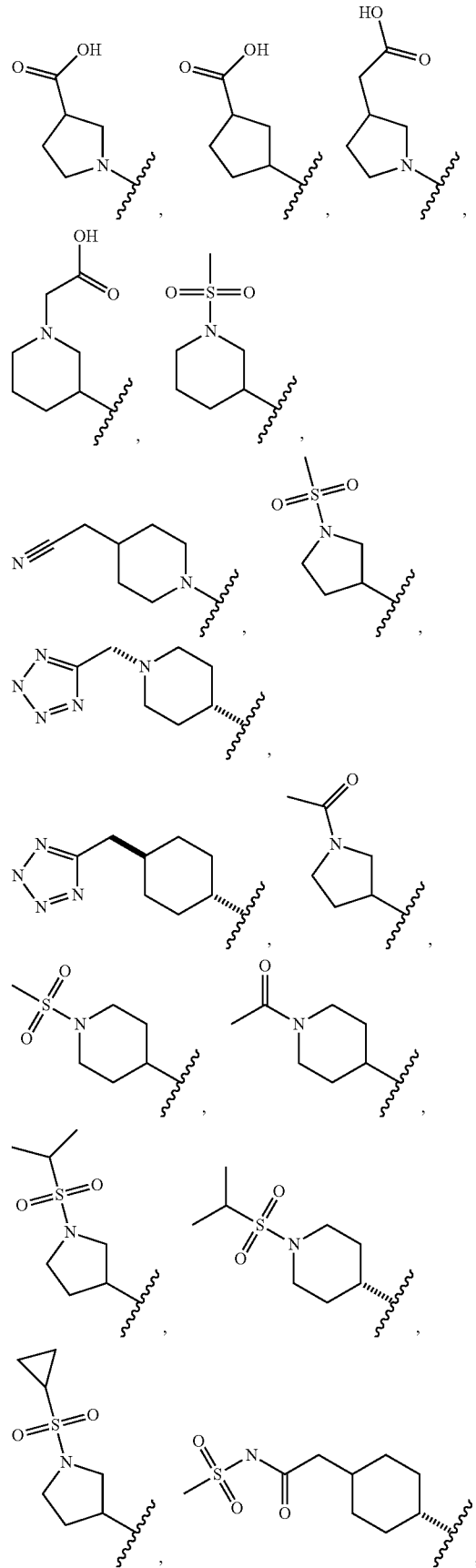

-continued

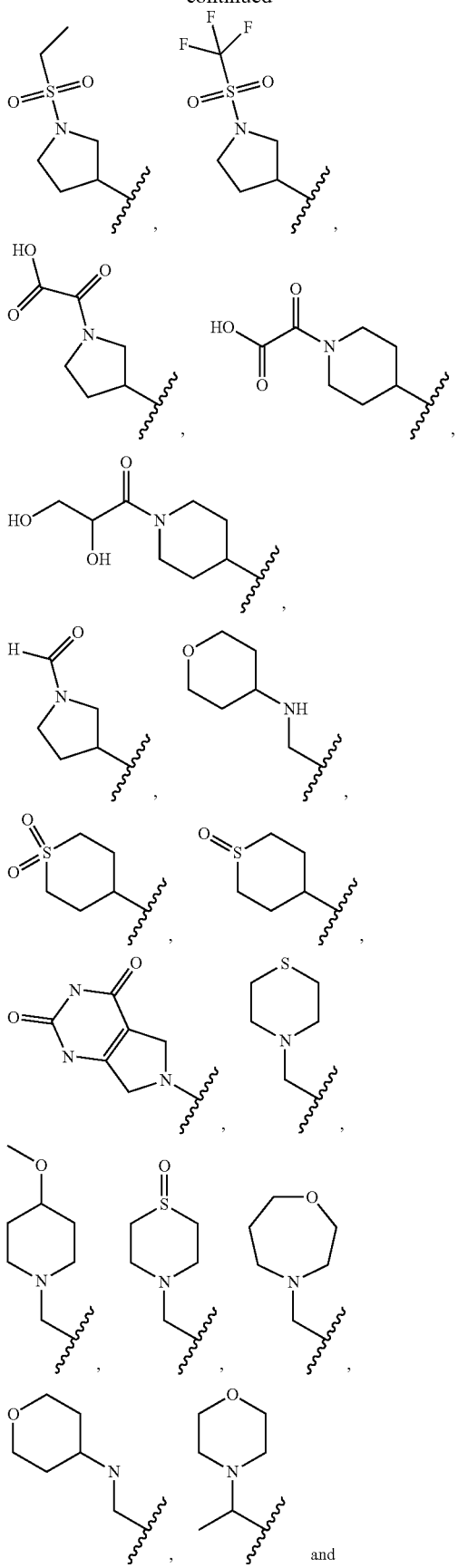

and

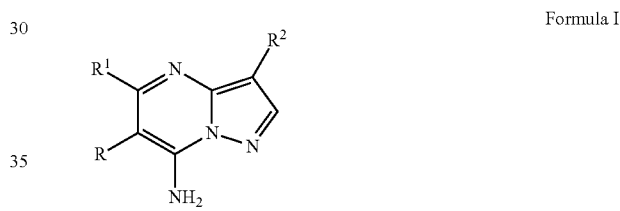

and

R² is quinolinyl, 1-methyl-pyrazolyl, naphtyl, methoxy-naphtyl, cyano-phenyl, methoxy-phenyl, phenoxy-phenyl, biphenyl, chloro-pyridyl, methoxy-pyridyl, bromo-methyl-pyrazolyl, hydroxyl-methoxy-phenyl, di-methoxy-phenyl, 1H-indazolyl, fluoro-hydroxy-phenyl, chloro-quinolyl, morpholino-pyridyl-, 4-(isobutyronitrilo)-phenyl, bromo-quinolyl, 4-trifluoromethyl-phenyl-, benzyl-pyrazolyl, fluoro-pyridyl.

In another embodiment, the present invention relates to the foregoing method of using a compound represented by the structural Formula I:

Formula I

[Structure of Formula I showing pyrazolopyrimidine with R¹, R², R, and NH₂ substituents]

or a pharmaceutically acceptable salt, solvate, ester, or prodrug thereof, wherein:

R is independently selected from the group consisting of bromo, chloro, —CN, H, methyl, acetyl, pyridyl, phenyl, 1-methyl-pyrazolyl, and thienyl;

R¹ is independently selected from the group consisting of:

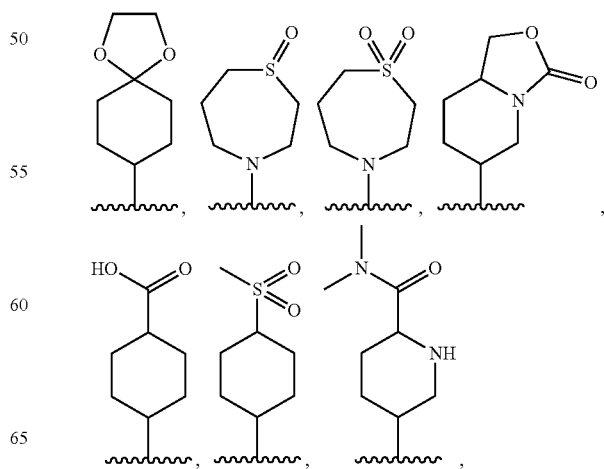

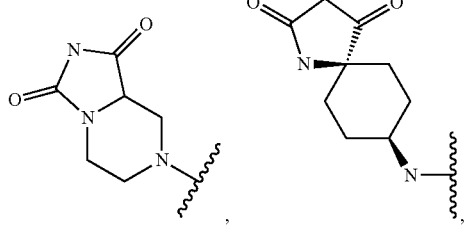
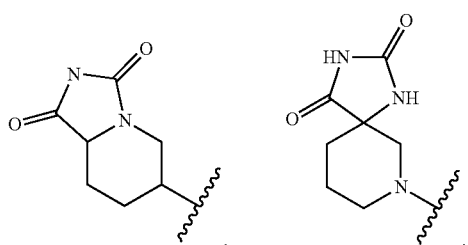
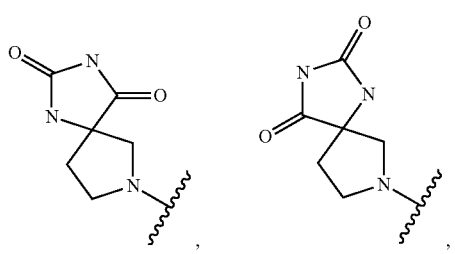
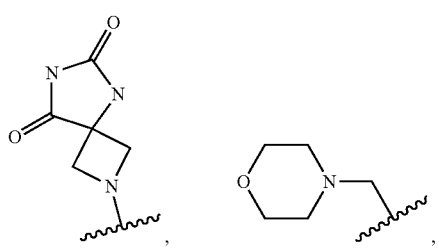
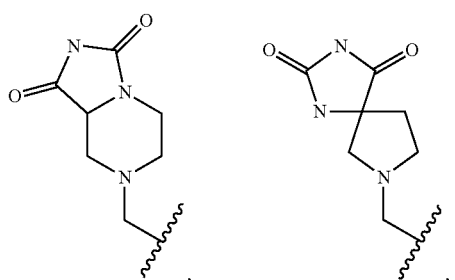
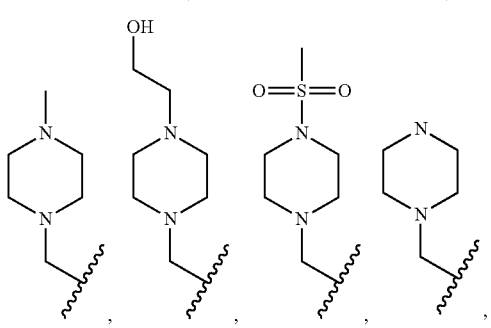
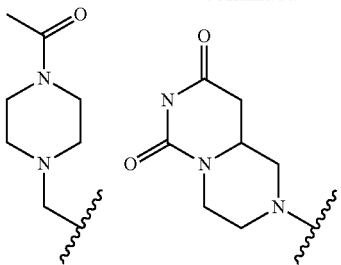
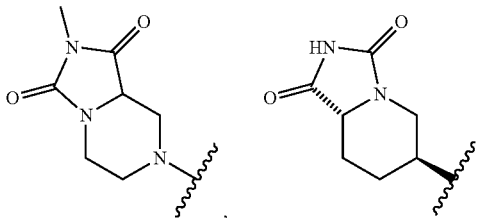
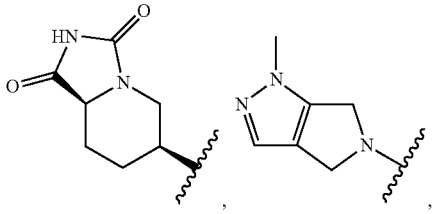
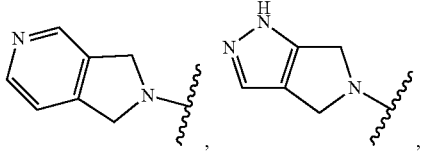
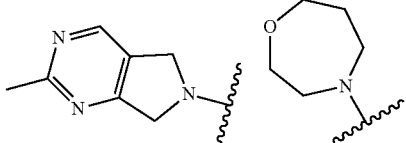
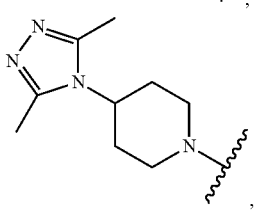
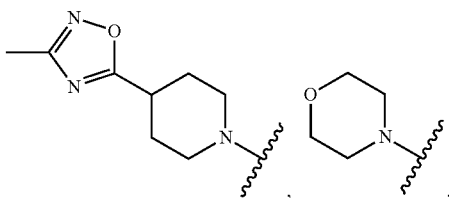
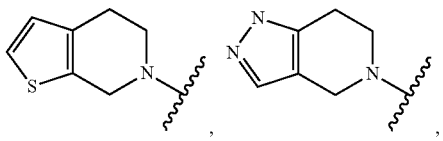
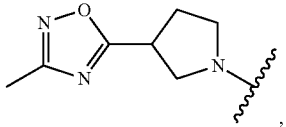

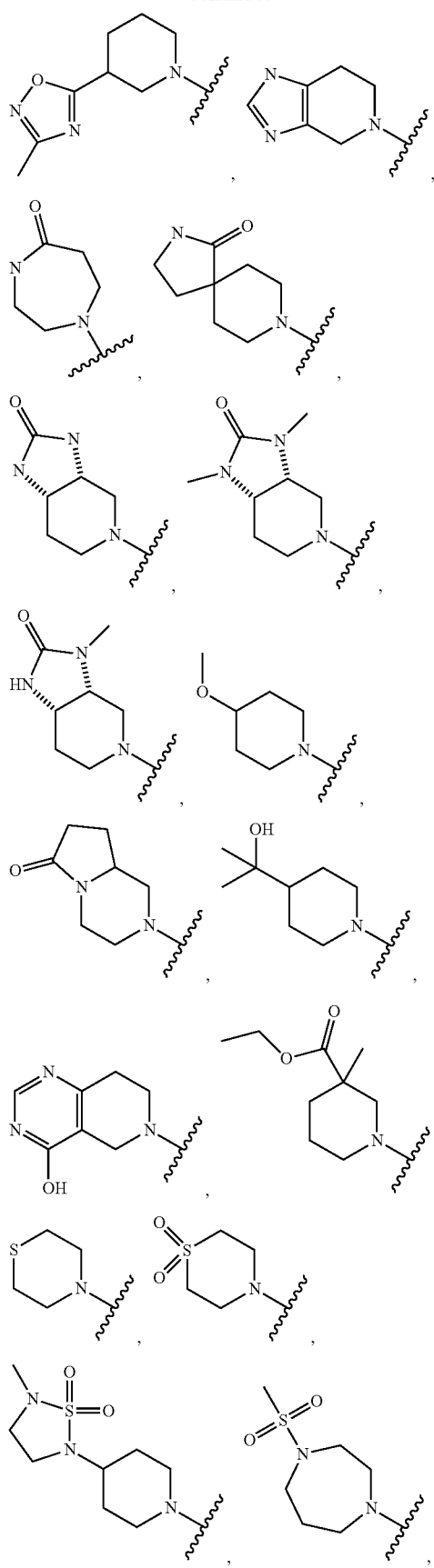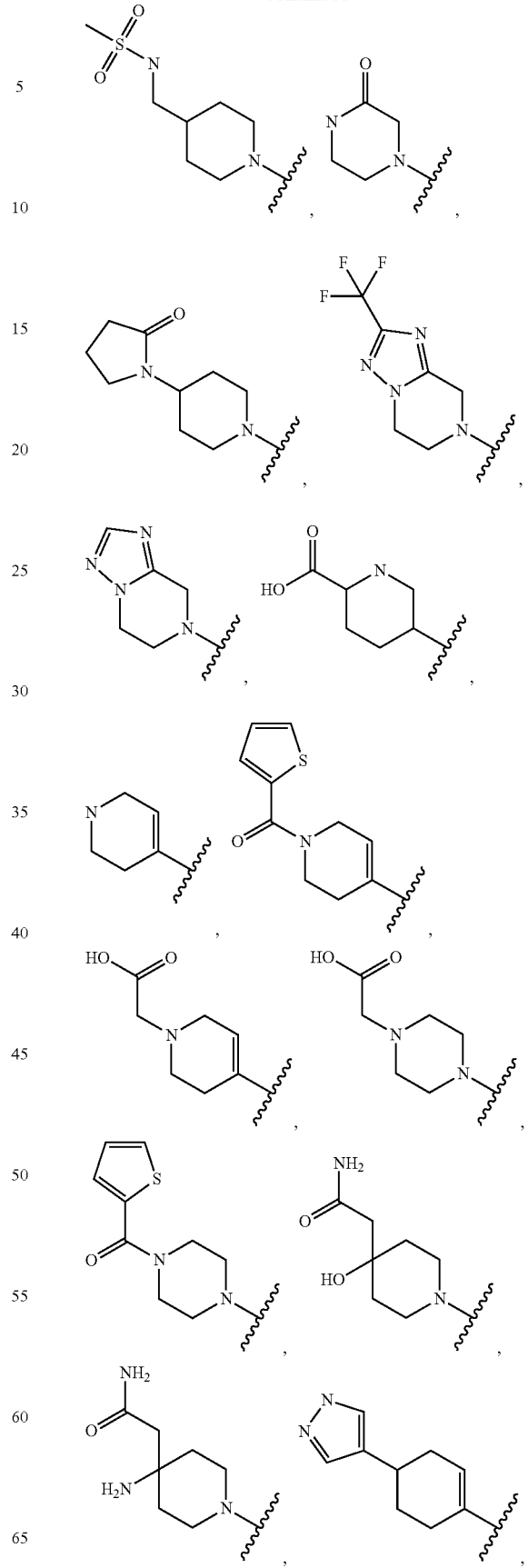

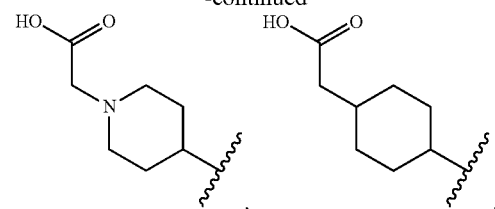
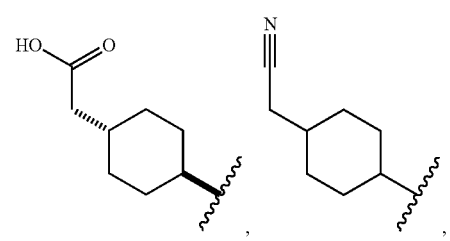
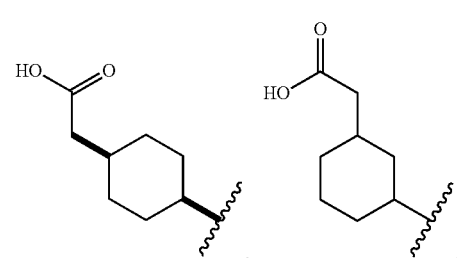
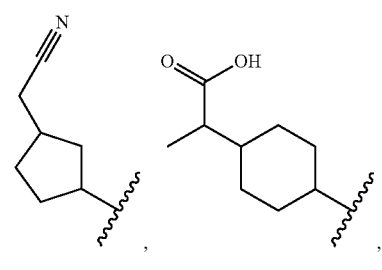
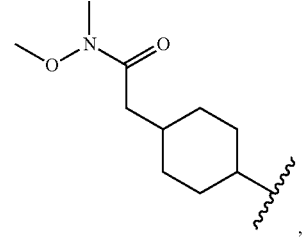
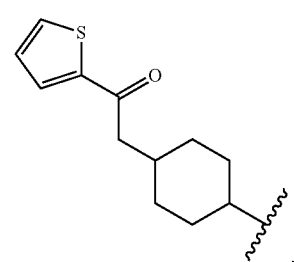
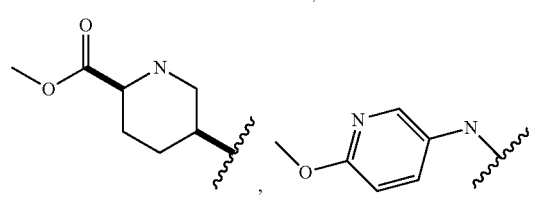
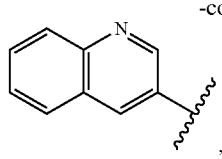
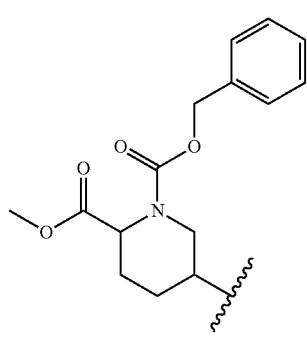
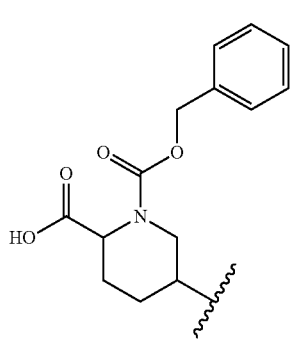
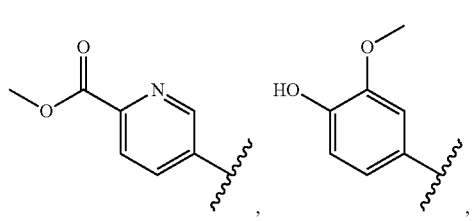
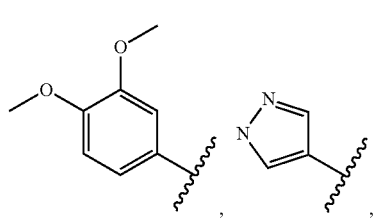
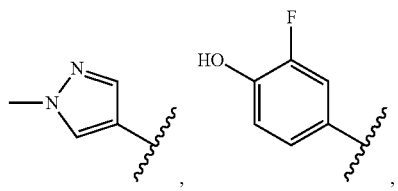
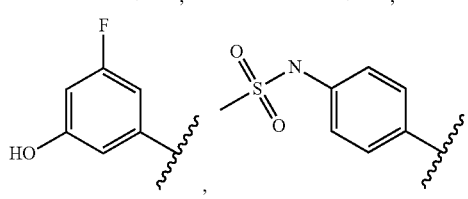

-continued
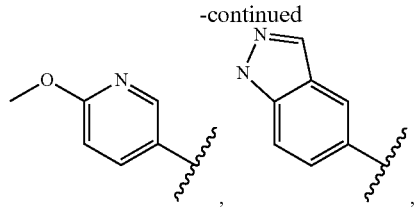
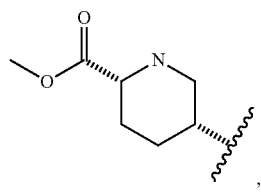
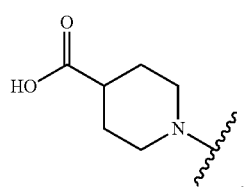
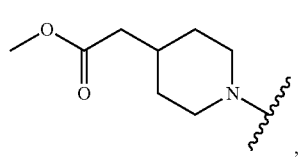
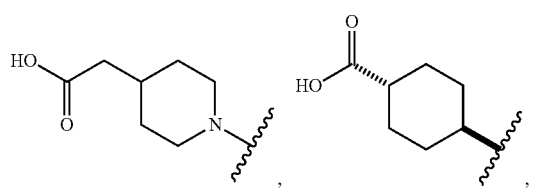
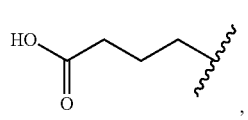
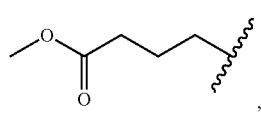
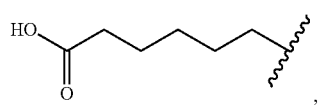
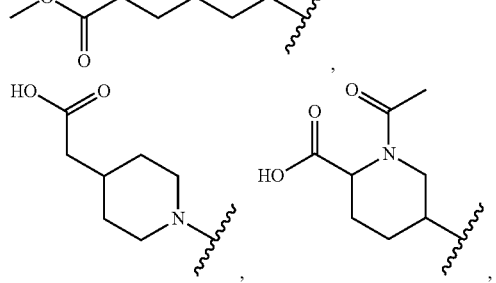
-continued
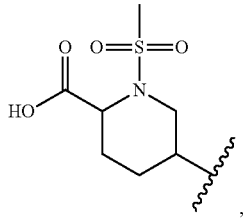
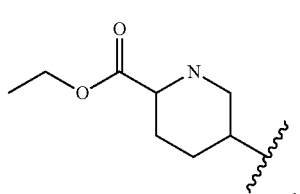
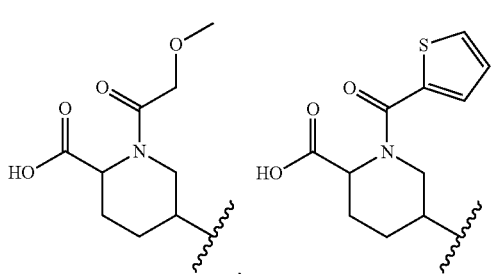
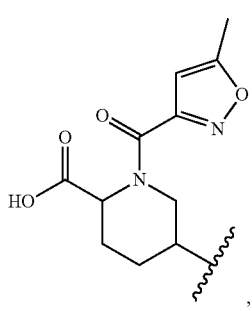
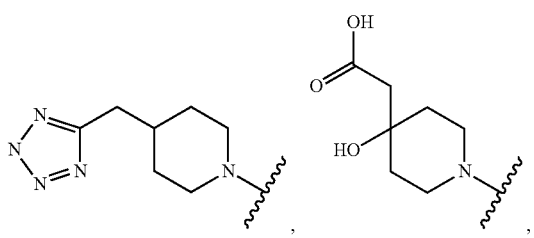
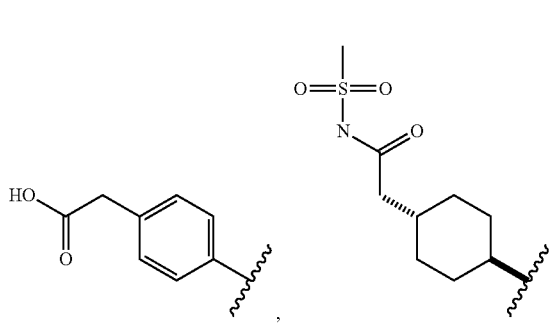

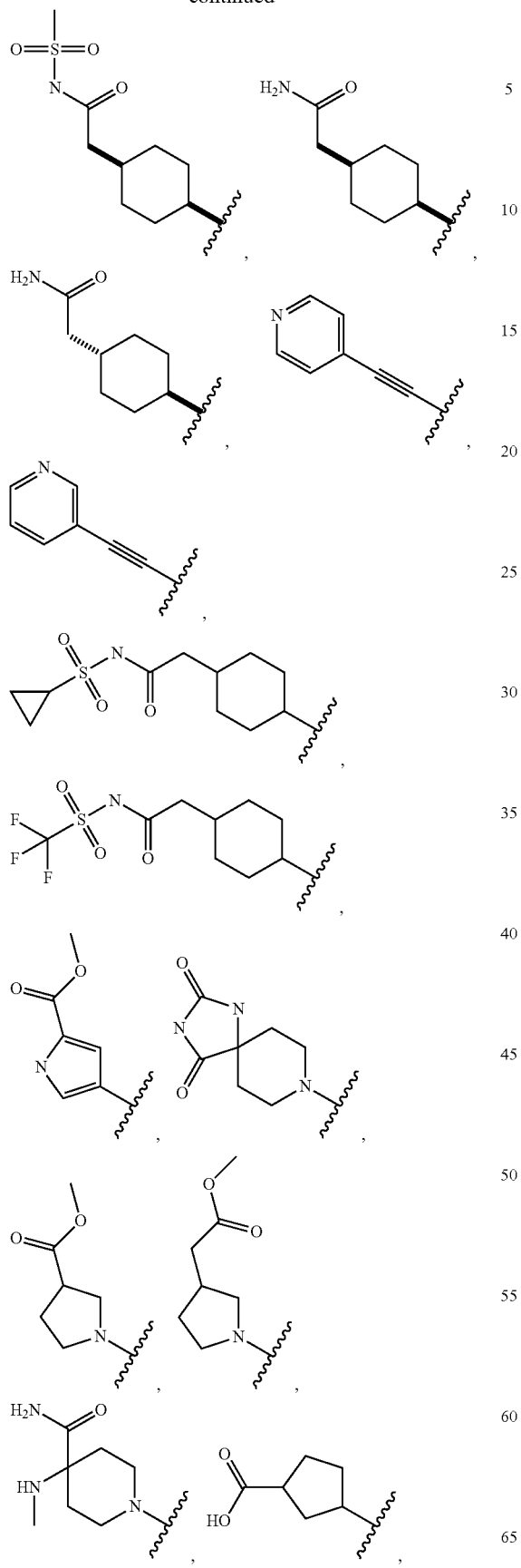
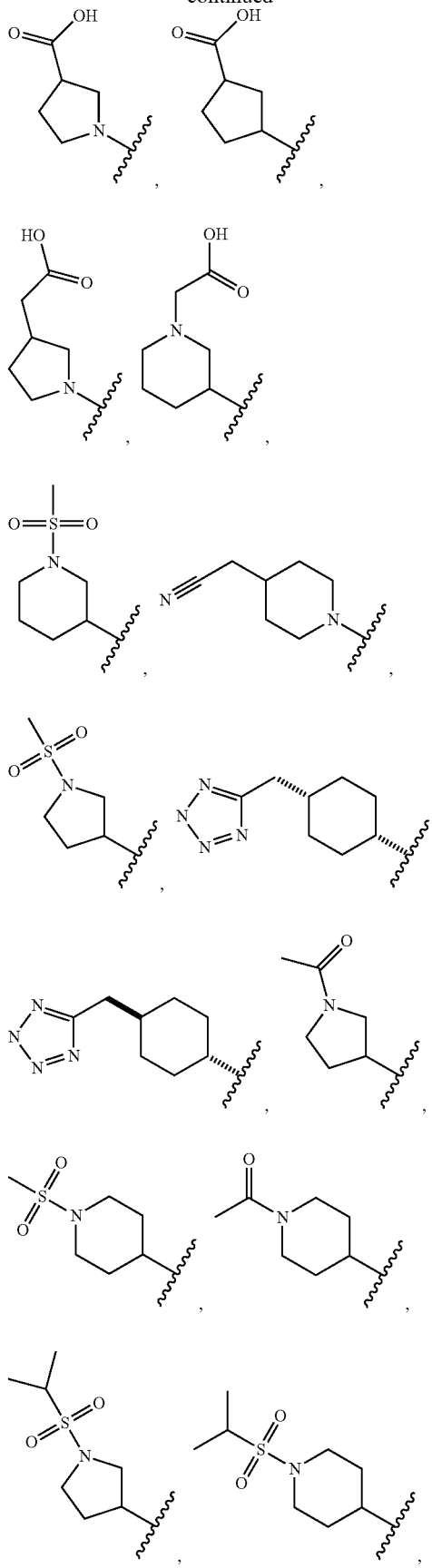

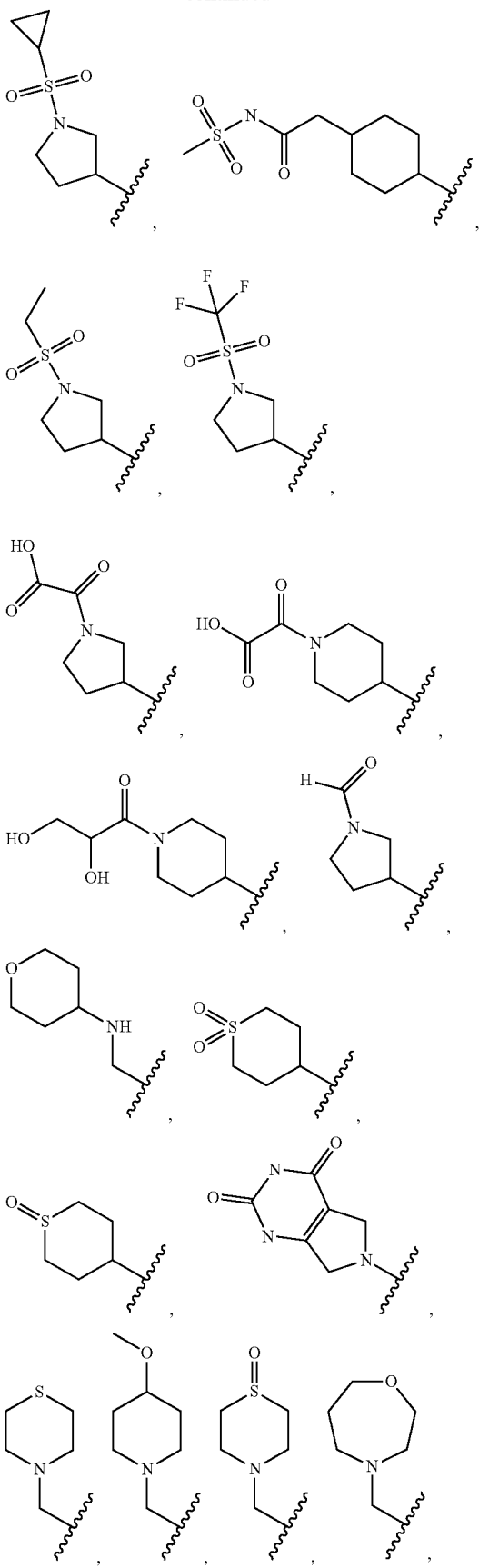

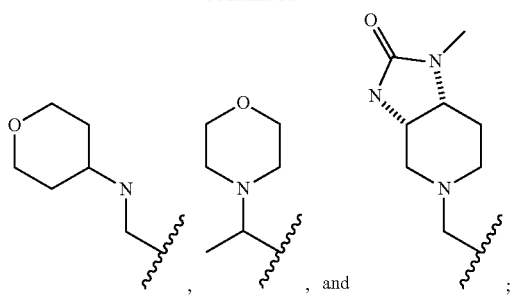

and

R² is indazolyl, wherein said indazolyl can be unsubstituted or substituted with one or more moieties which can be the same or different each moiety being independently selected from the group consisting of halo or alkyl.

In another embodiment, the present invention relates to the foregoing method of using a compound represented by the structural Formula I:

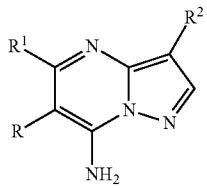

Formula I or a pharmaceutically acceptable salt, solvate, ester, or prodrug thereof, wherein:

R is independently selected from the group consisting of bromo, chloro, —CN, H, methyl, acetyl, pyridyl, phenyl, 1-methyl-pyrazolyl, and thienyl;

R¹ is independently selected from the group consisting of:

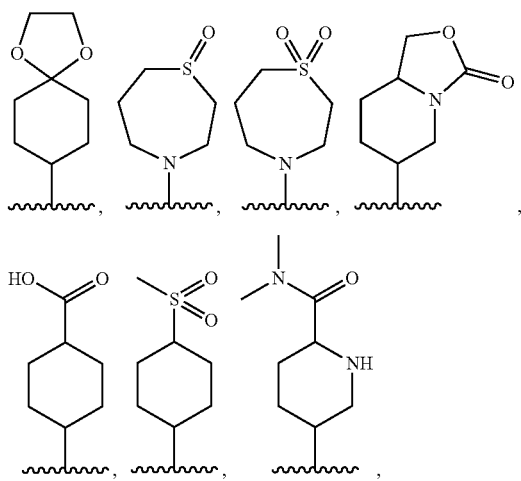

-continued
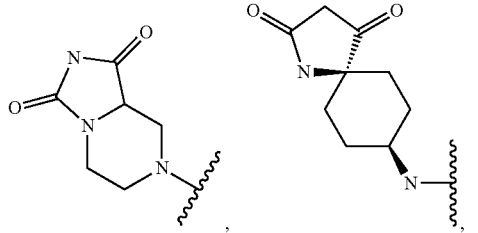
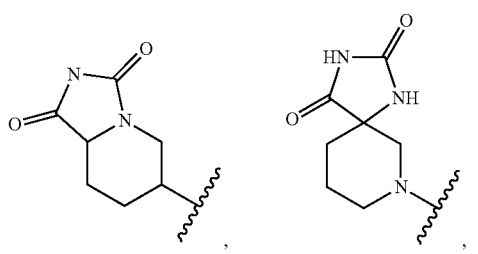
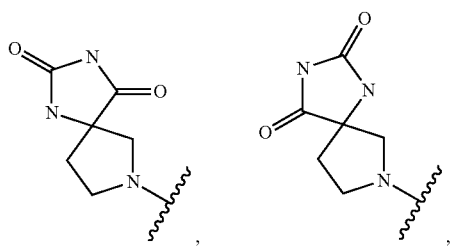
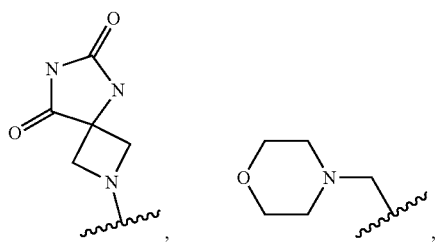
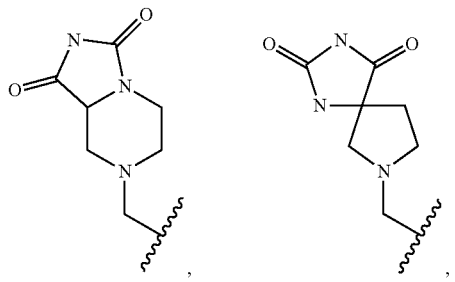
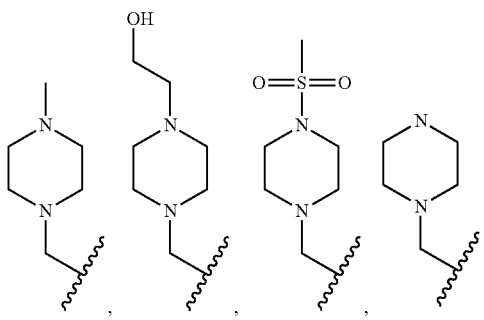
-continued
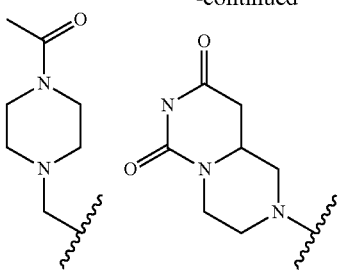
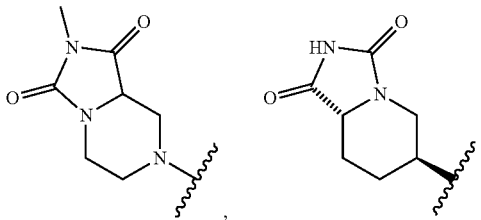
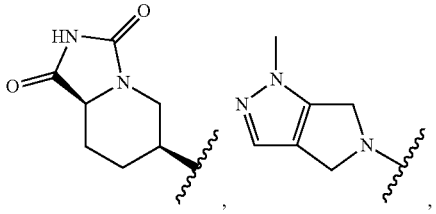
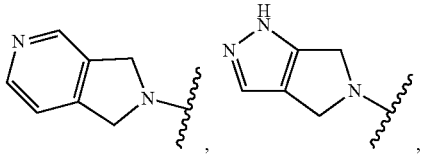
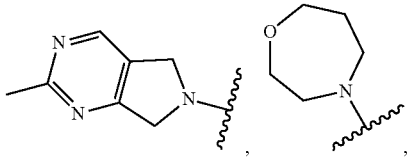
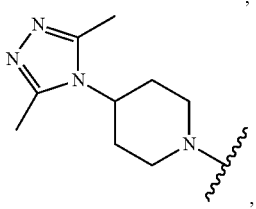
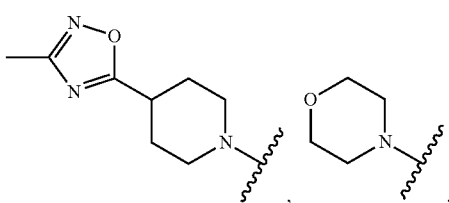
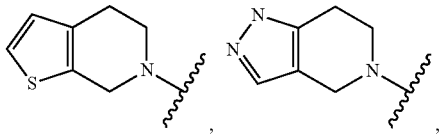
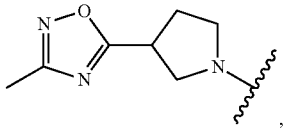

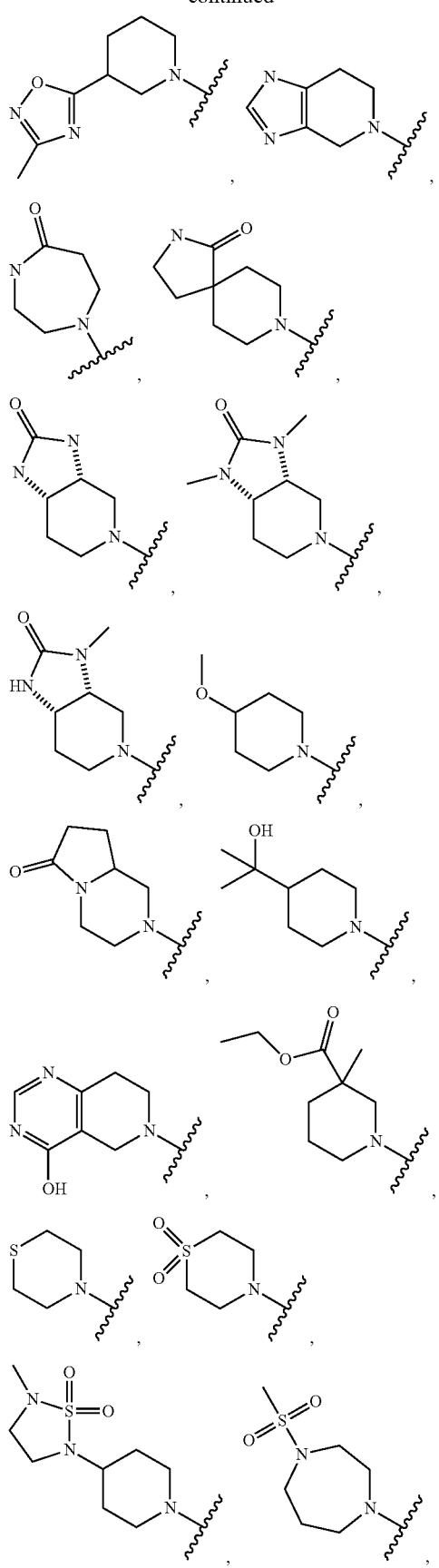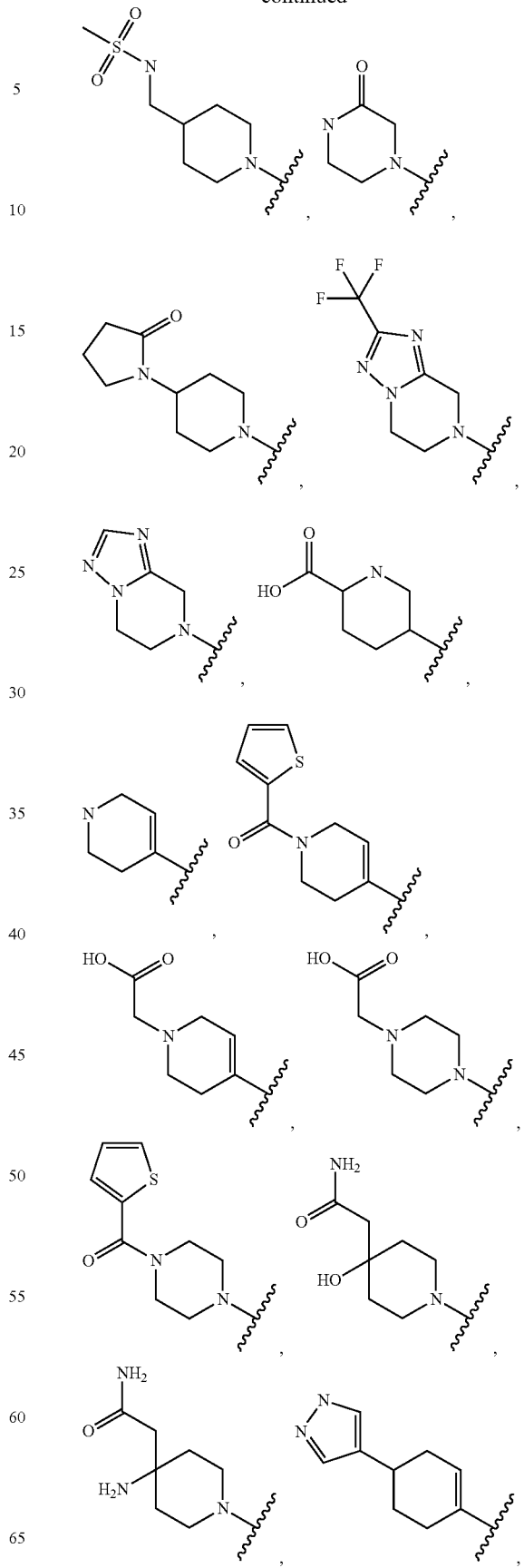

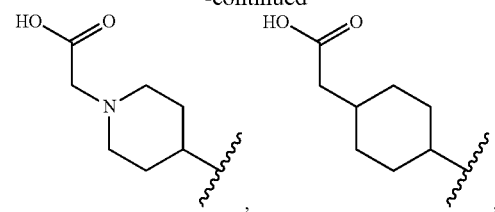
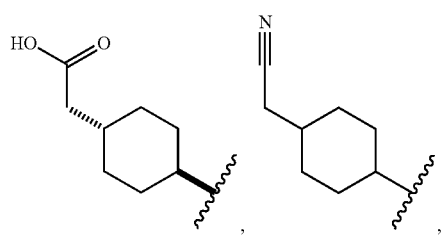
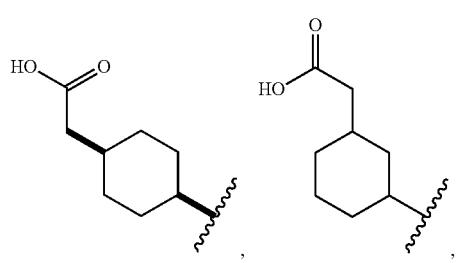
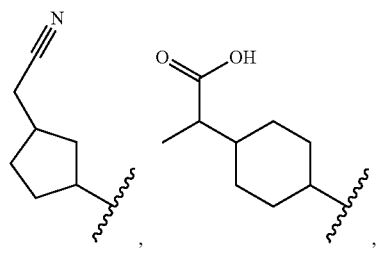
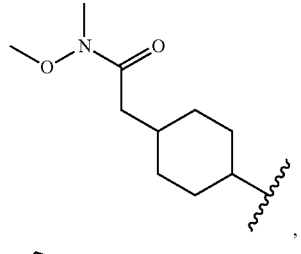
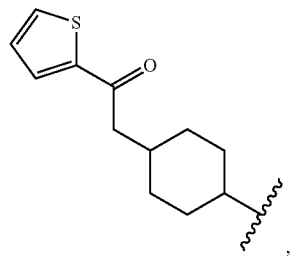
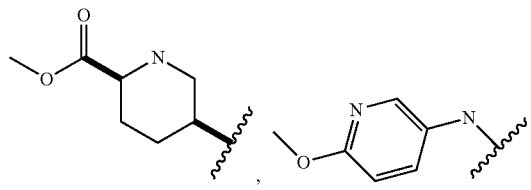
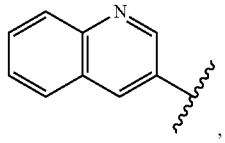
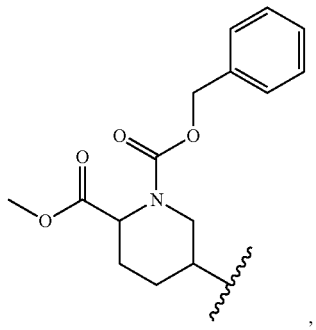
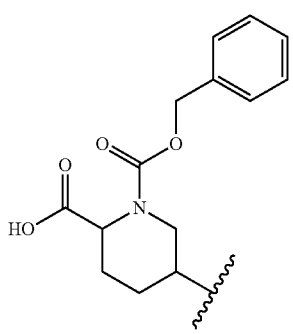
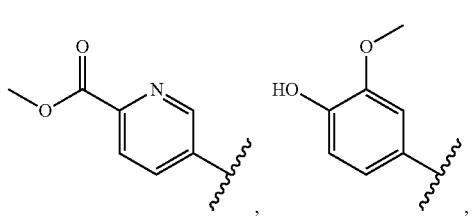
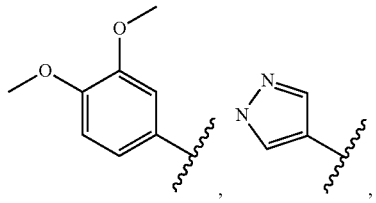
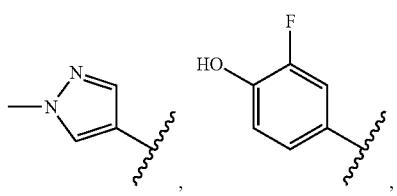
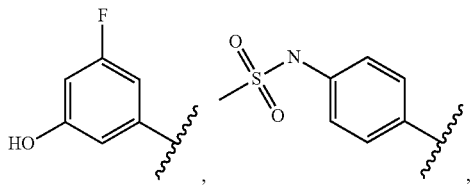

-continued
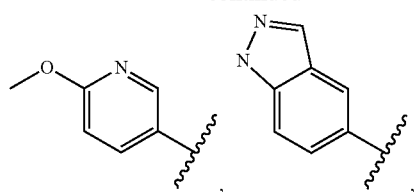
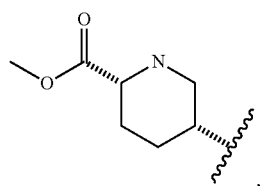
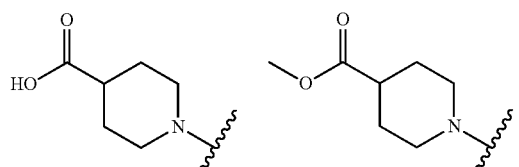
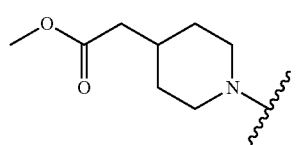
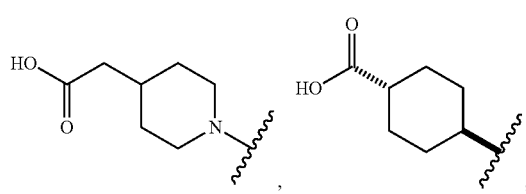
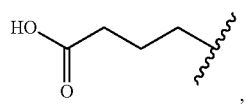
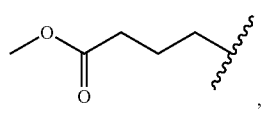
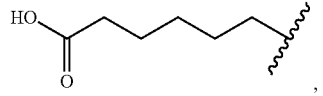
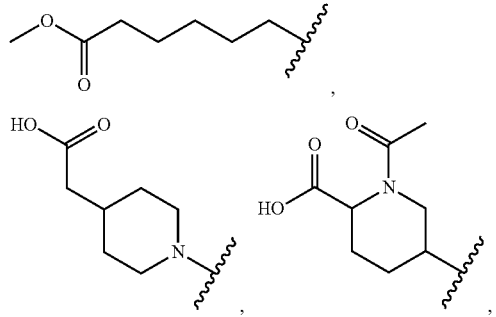
-continued
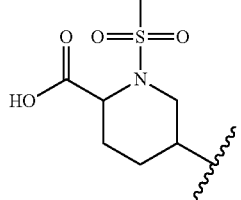
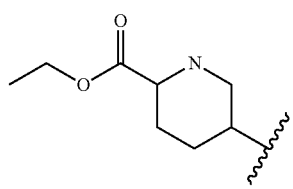
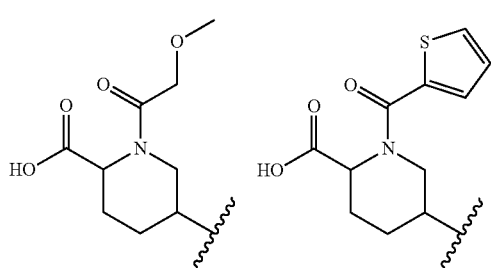
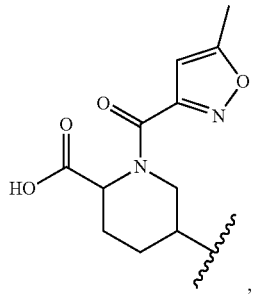
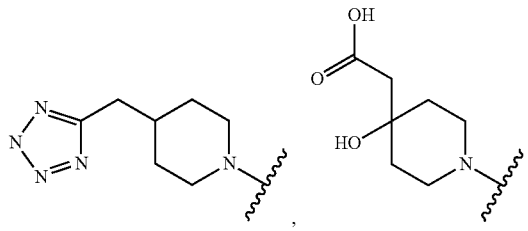
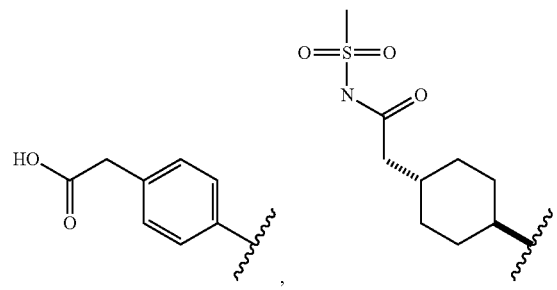

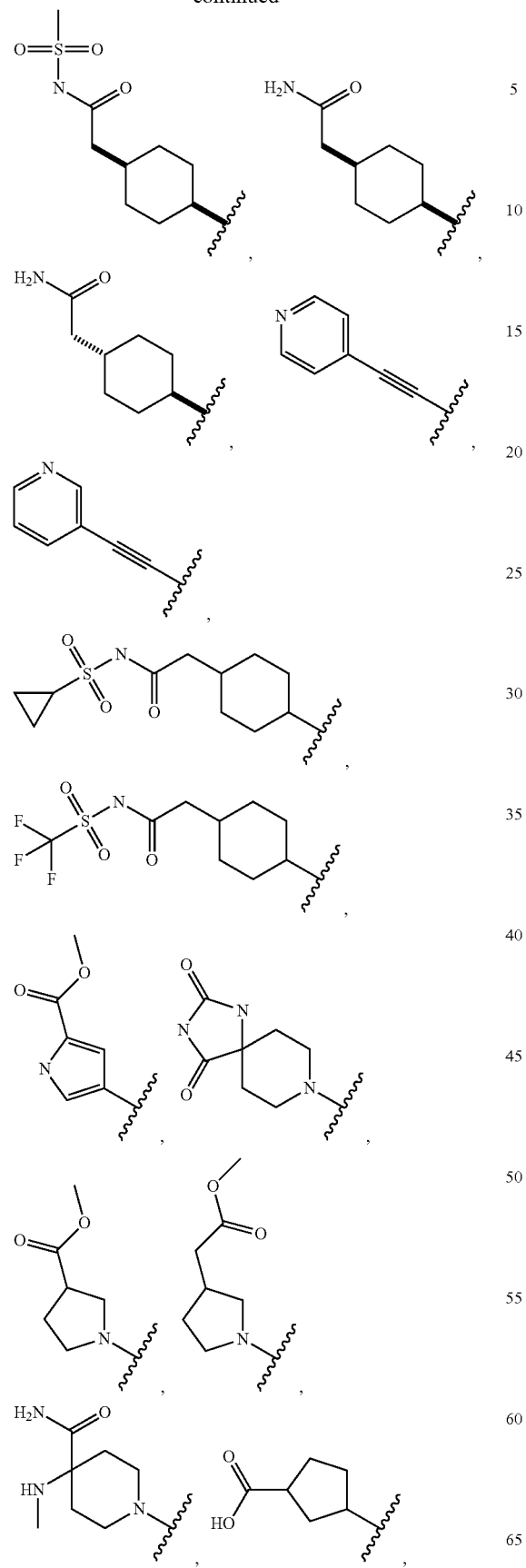
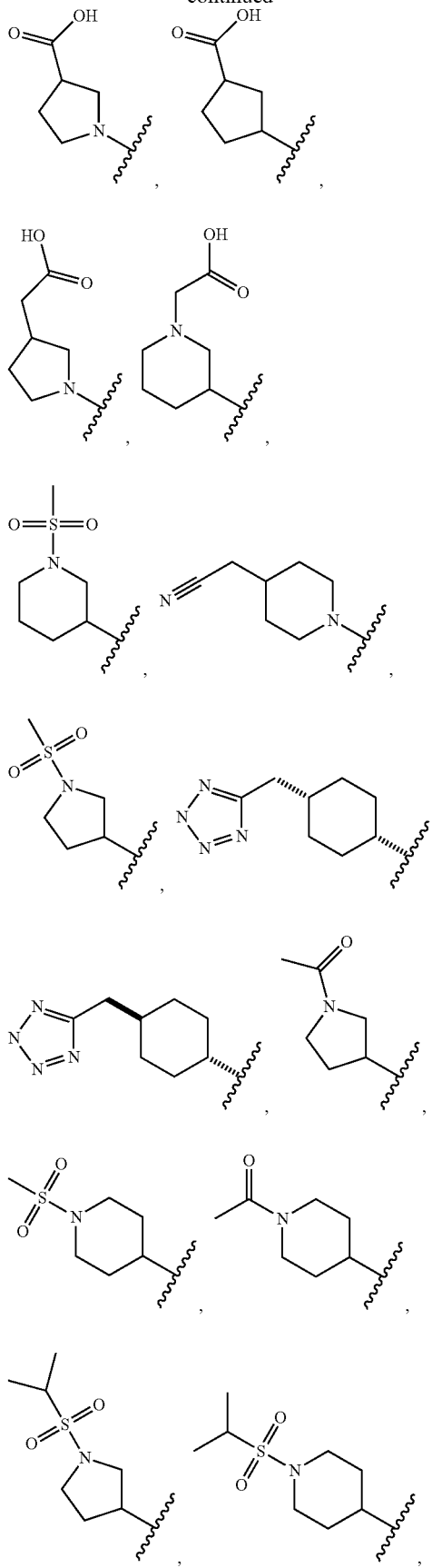

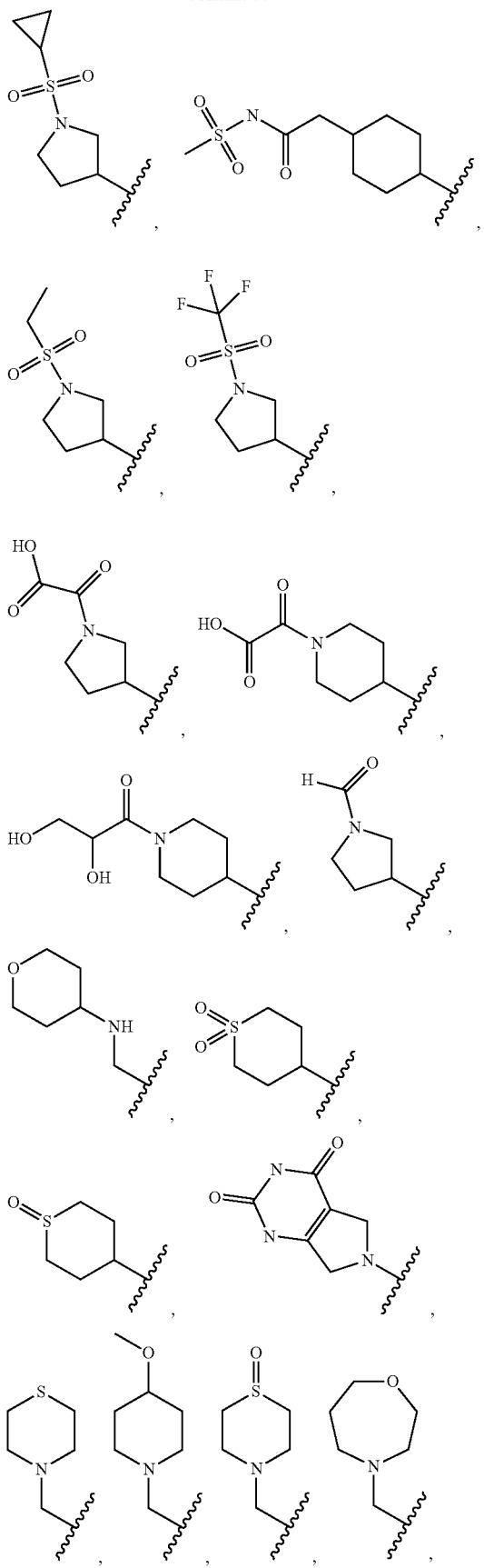

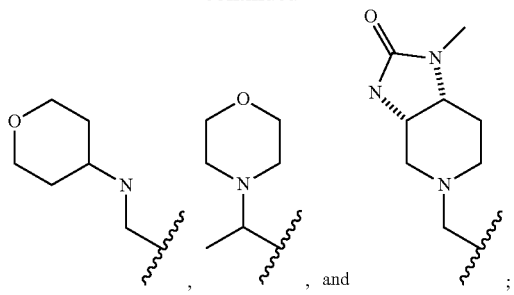

and

R² is phenyl, wherein said phenyl can be unsubstituted or substituted with one or more moieties which can be the same or different each moiety being independently selected from the group consisting of halo, alkyl, alkoxy, —CN, hydroxyl, aryl and heteroaryl.

In another embodiment, the present invention relates to the foregoing method of using a compound represented by the structural Formula I:

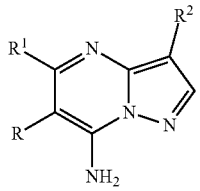

Formula I or a pharmaceutically acceptable salt, solvate, ester, or prodrug thereof, wherein:

R is independently selected from the group consisting of bromo, chloro, —CN, H, methyl, acetyl, pyridyl, phenyl, 1-methyl-pyrazolyl, and thienyl;

R¹ is independently selected from the group consisting of:

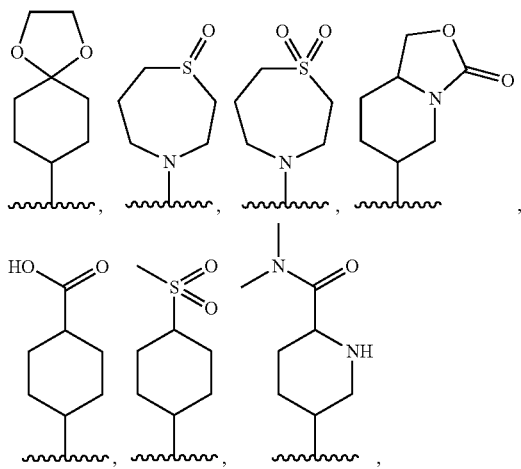

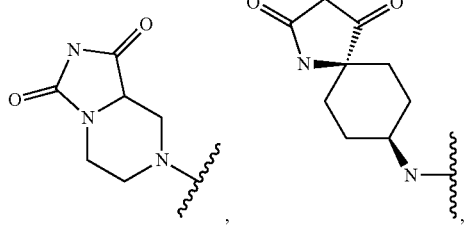
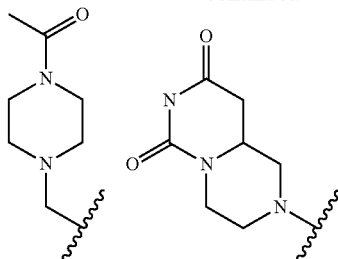
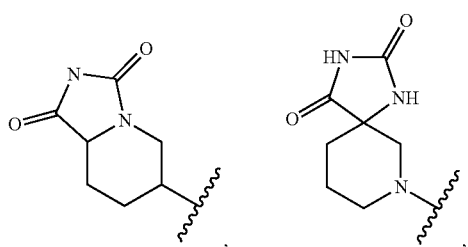
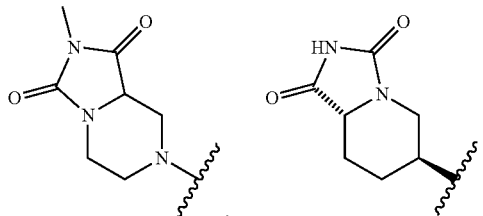
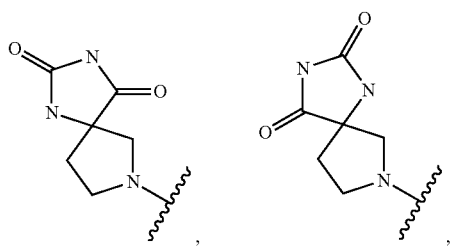
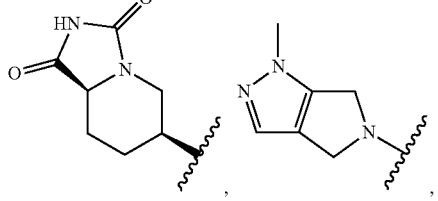
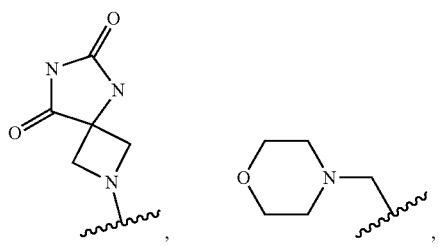
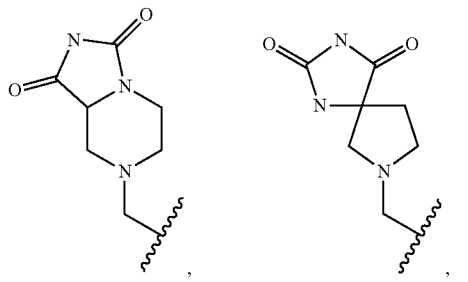
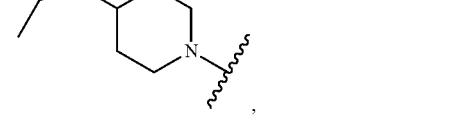
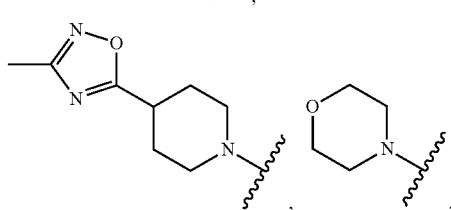
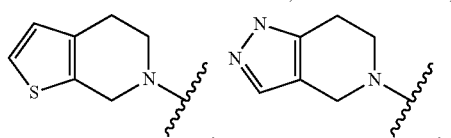
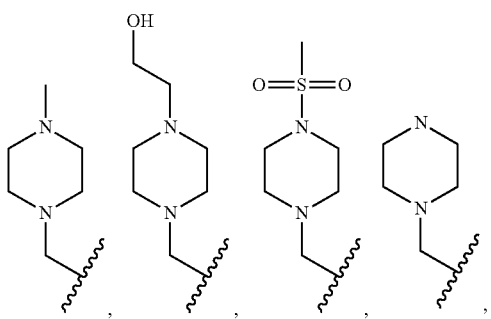
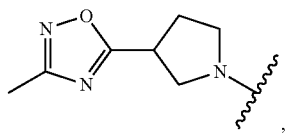

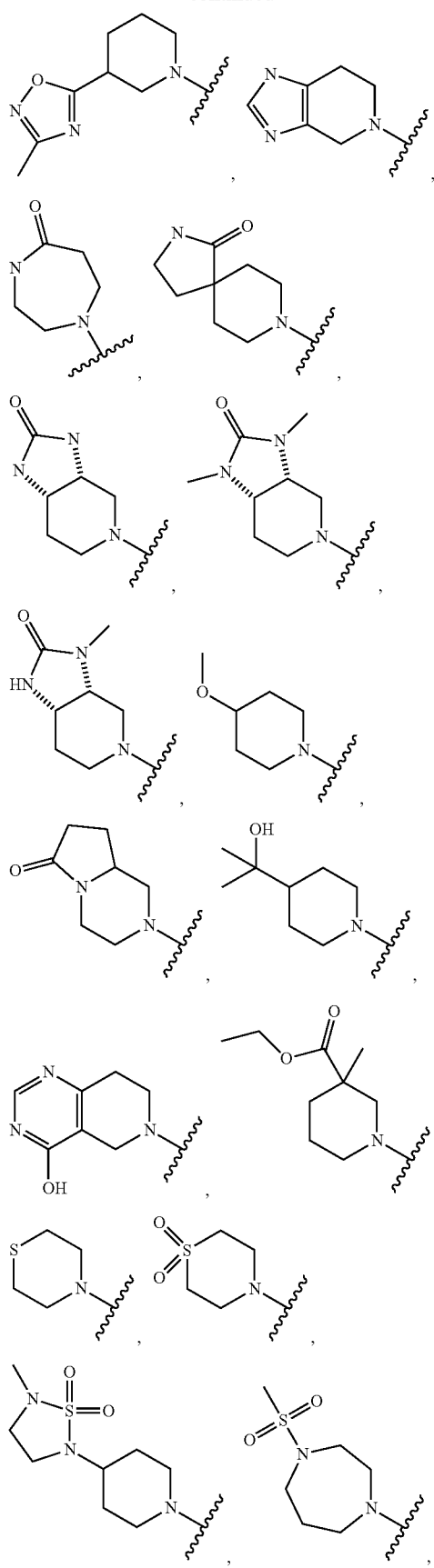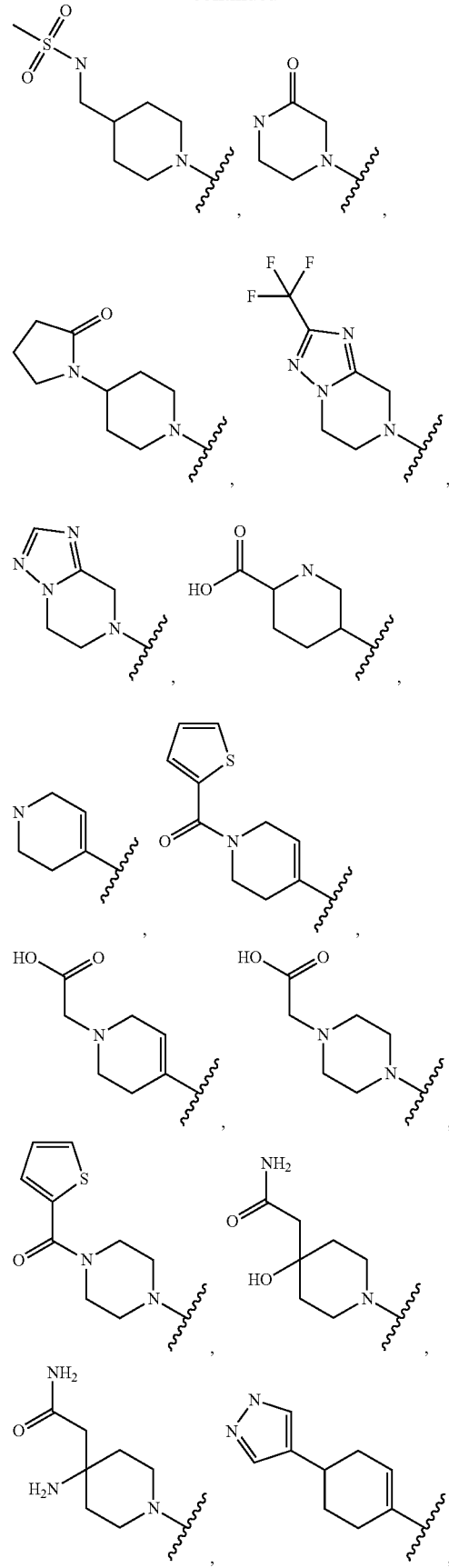

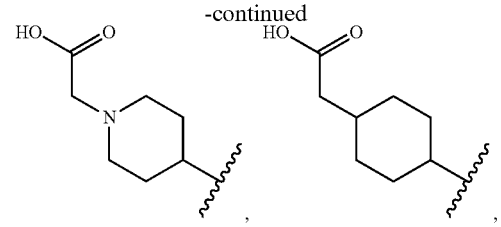,
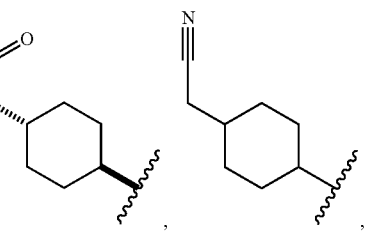,
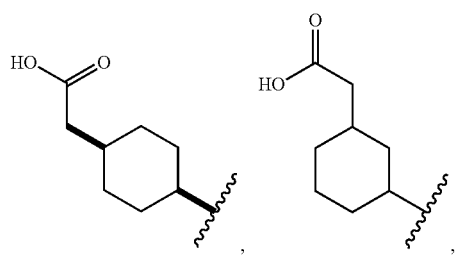,
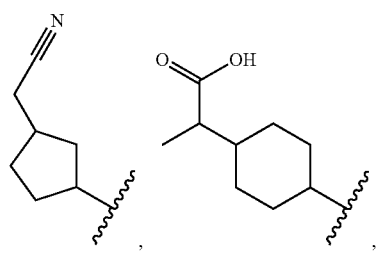,
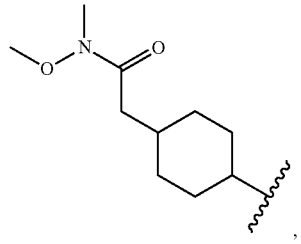,
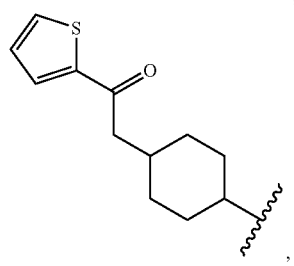,
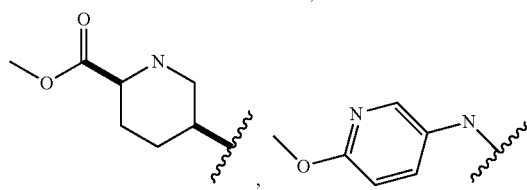,
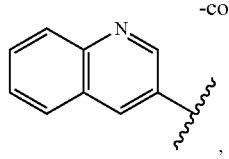,
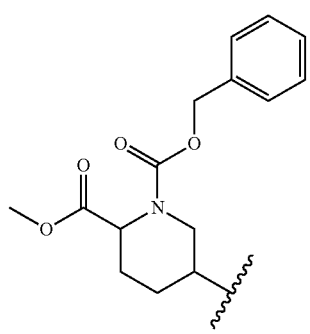,
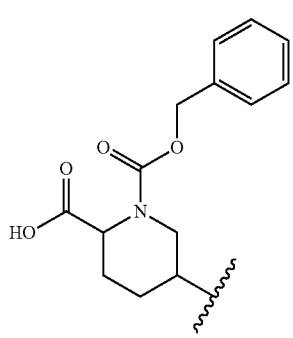,
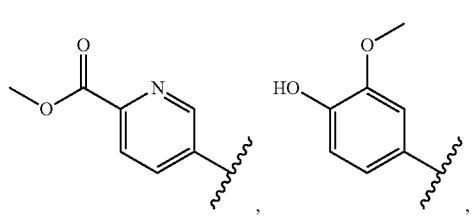,
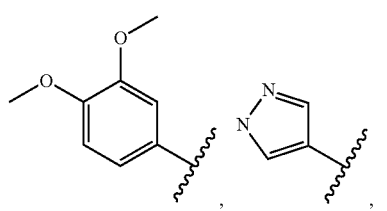,
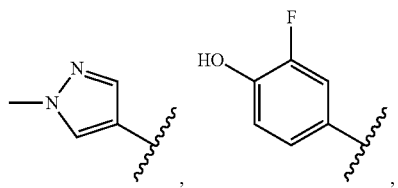,
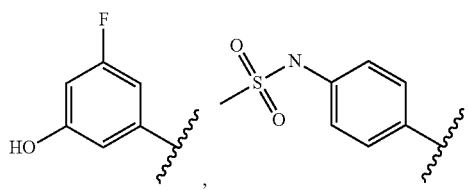, -continued
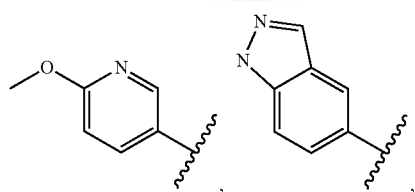
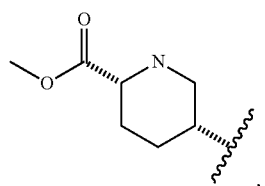
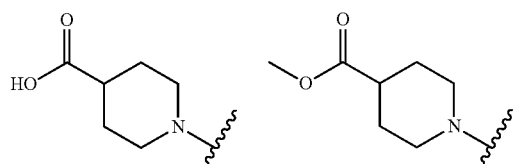
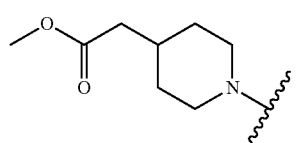
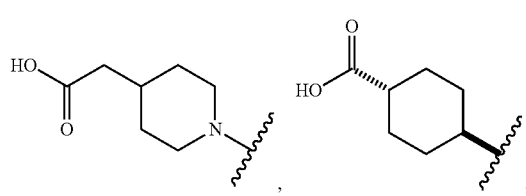
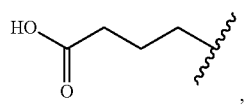
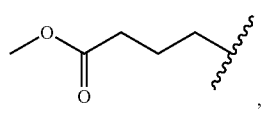
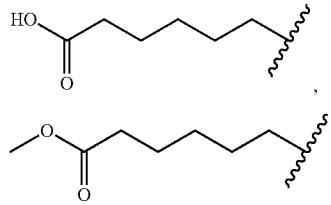
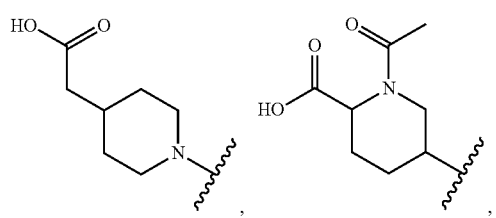
-continued
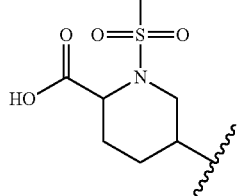
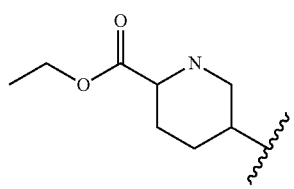
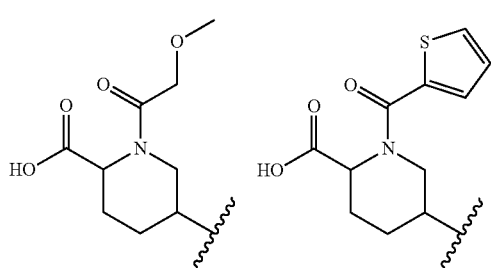
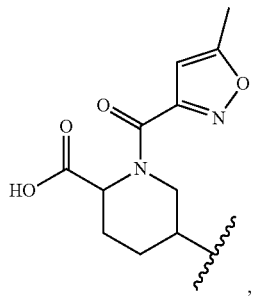
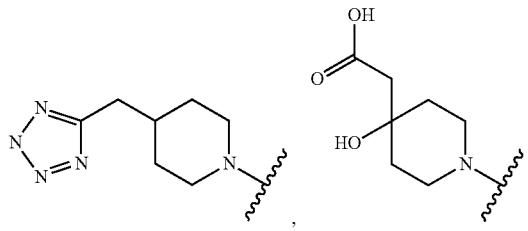
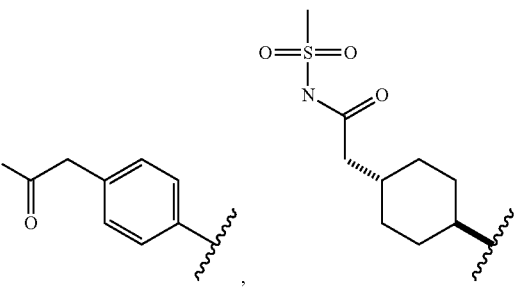

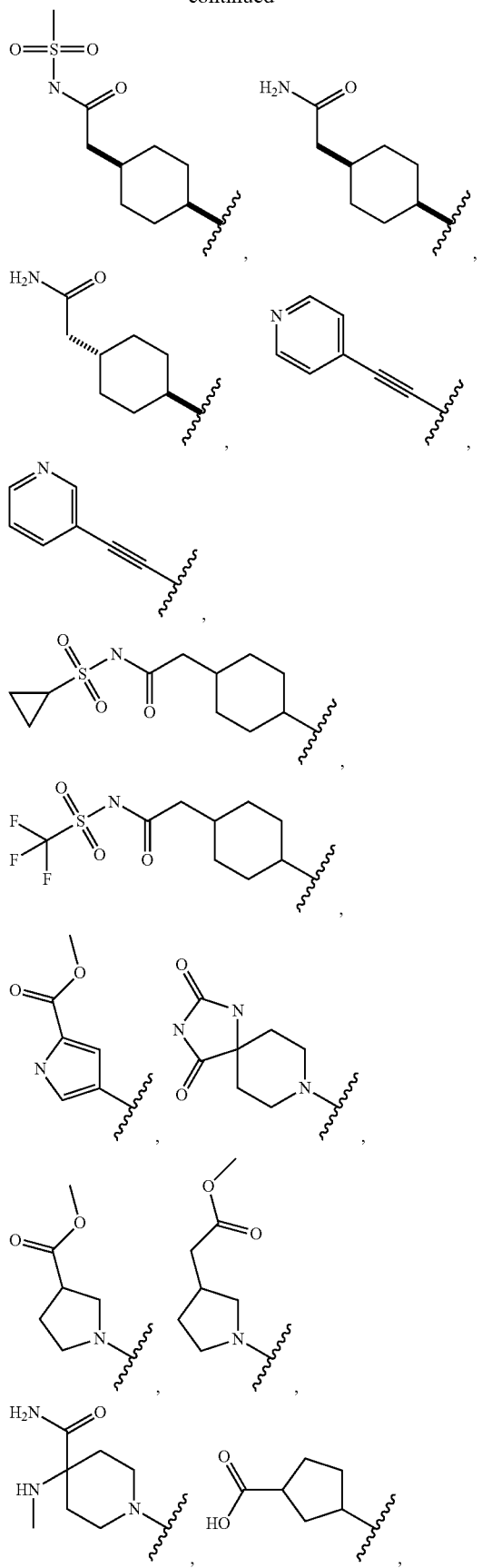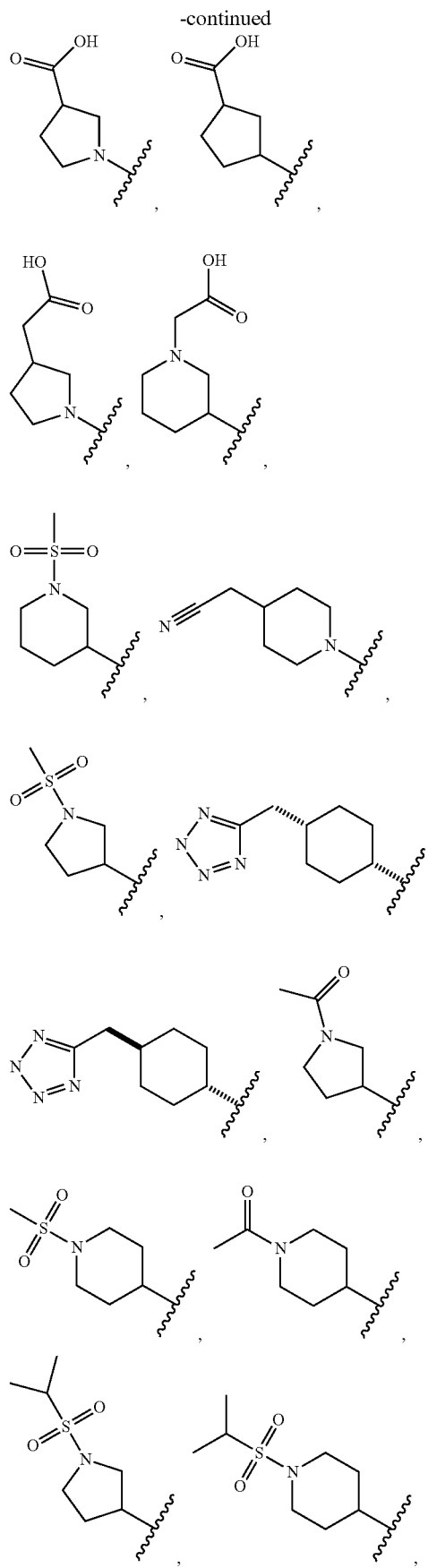

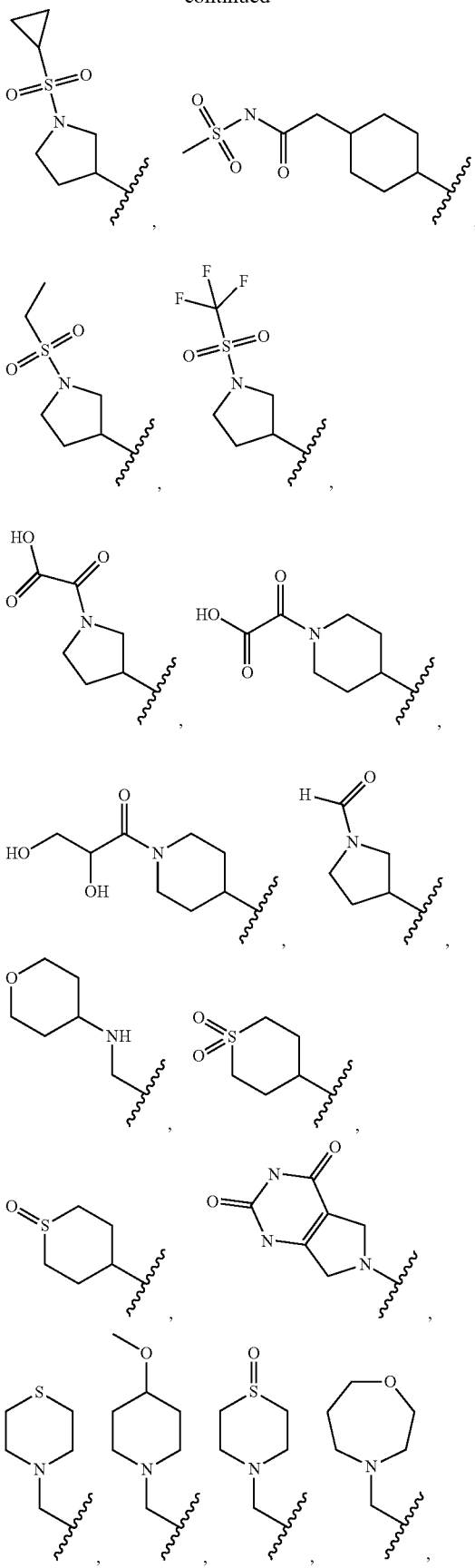

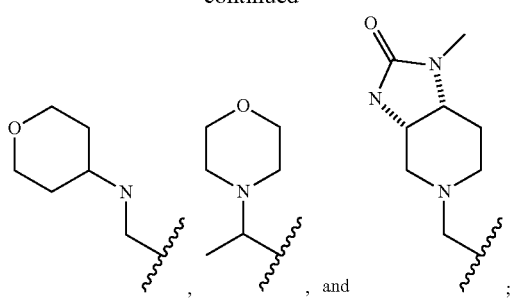

and

R² is naphthyl, wherein said naphthyl can be unsubstituted or substituted with one or more moieties which can be the same or different each moiety being independently selected from the group consisting of halo or alkyl.

In another embodiment, the present invention relates to the foregoing method of using a compound represented by the structural Formula I:

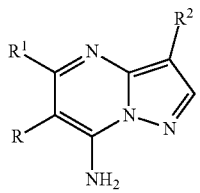

Formula I or a pharmaceutically acceptable salt, solvate, ester, or prodrug thereof, wherein:

R is independently selected from the group consisting of bromo, chloro, —CN, H, methyl, acetyl, pyridyl, phenyl, 1-methyl-pyrazolyl, and thienyl;

R¹ is independently selected from the group consisting of:

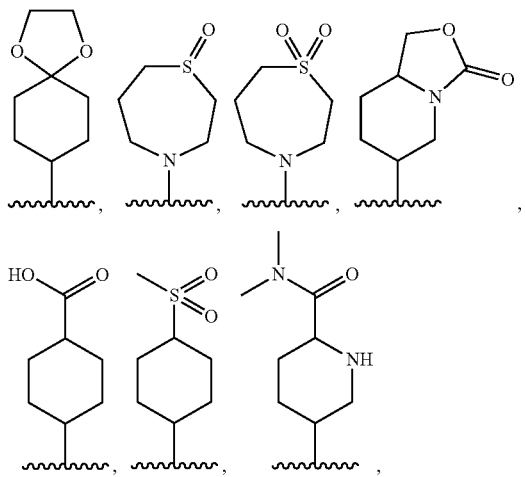

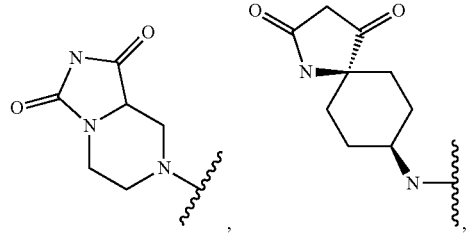
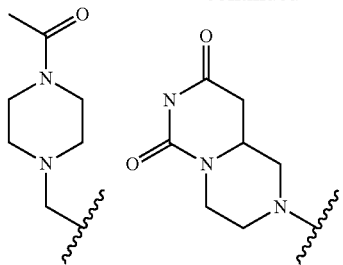
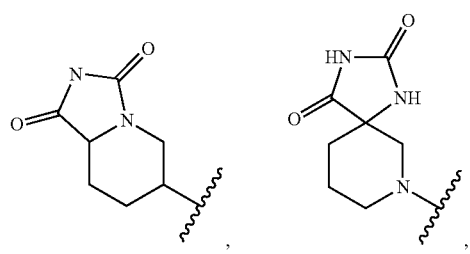
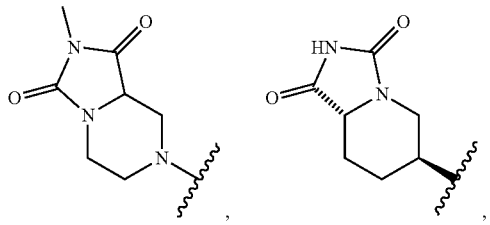
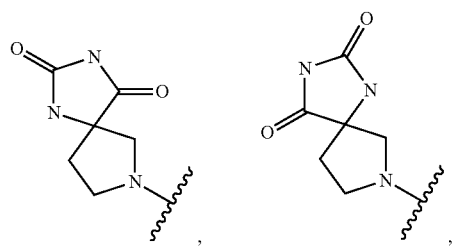
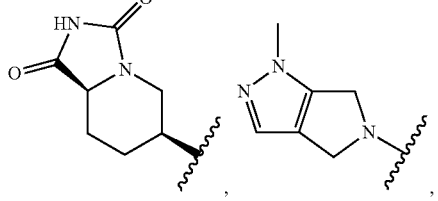
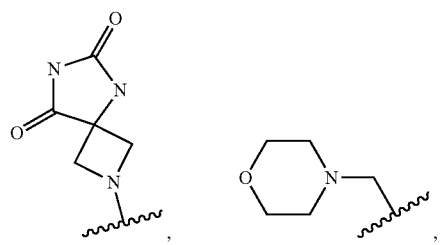
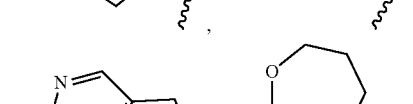
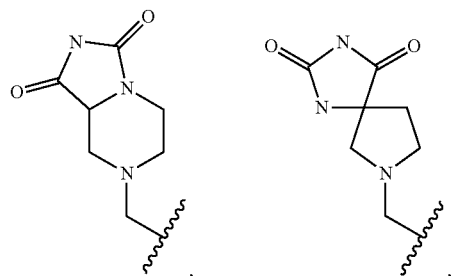
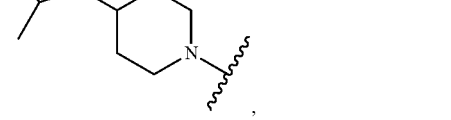
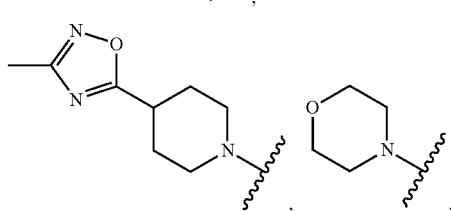
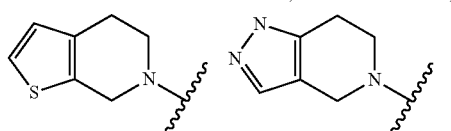
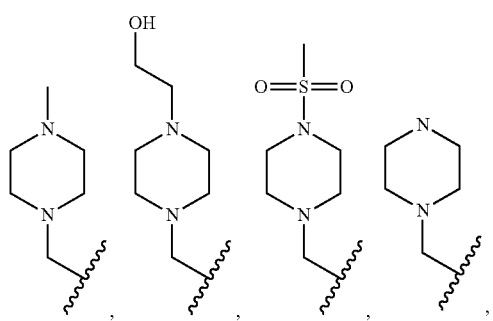
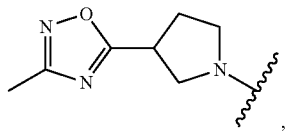

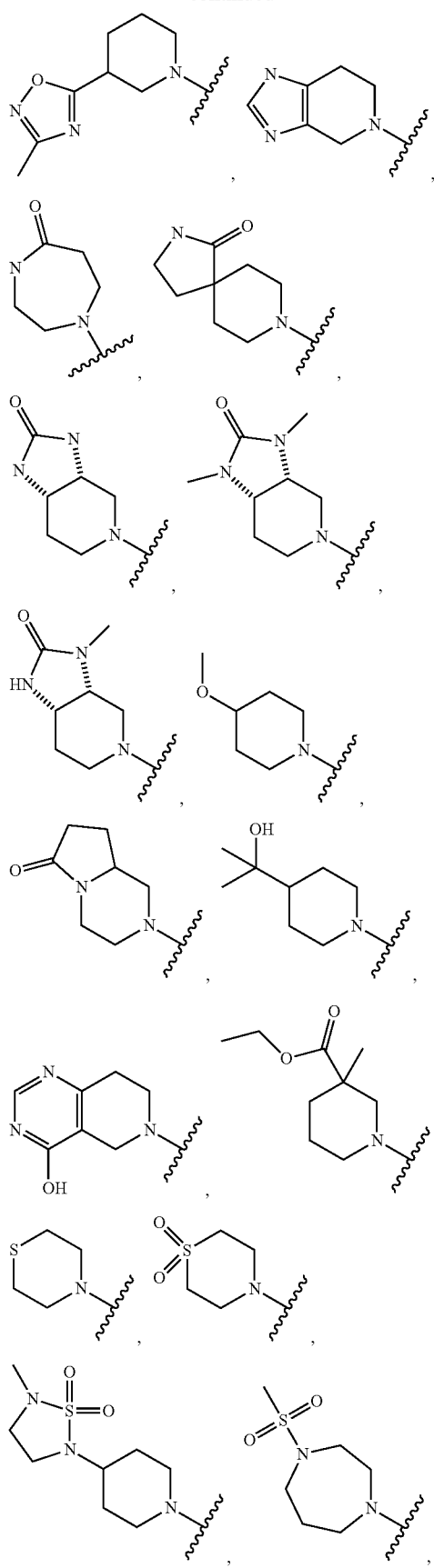
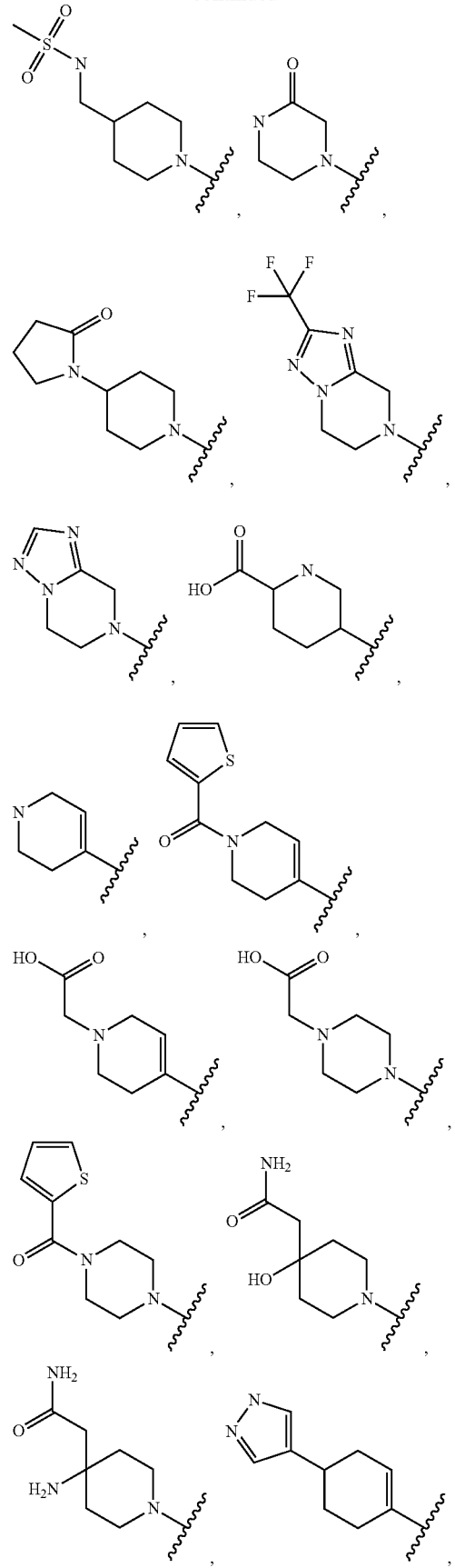

-continued
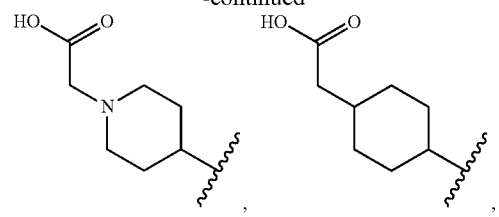
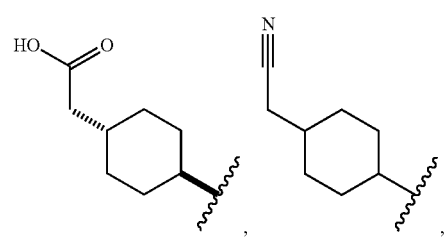
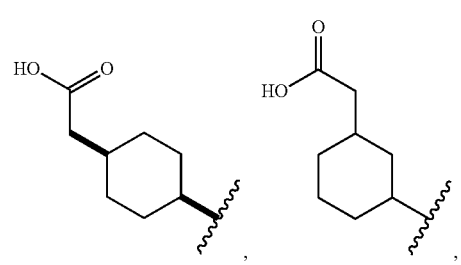
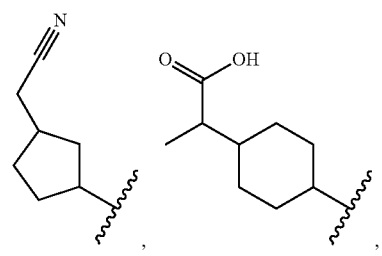
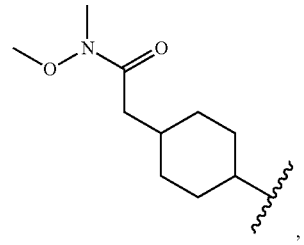
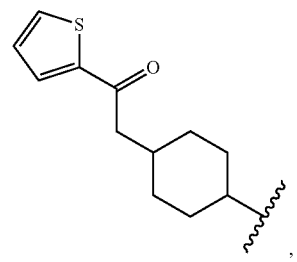
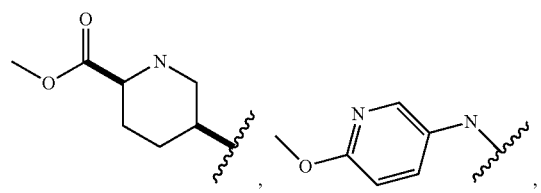
-continued
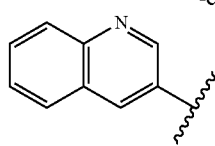
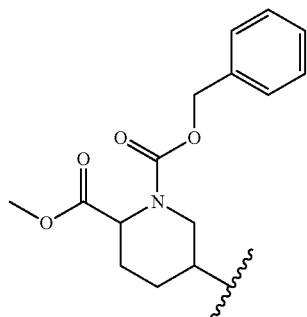
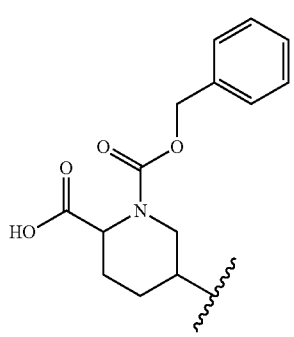
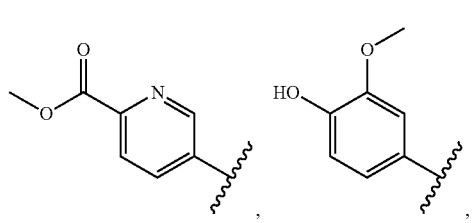
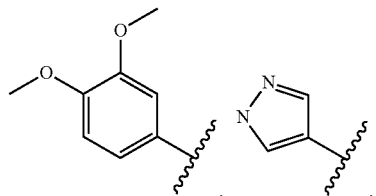
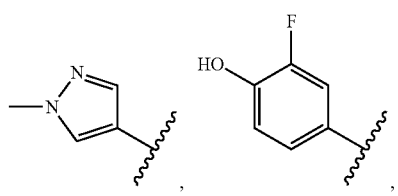
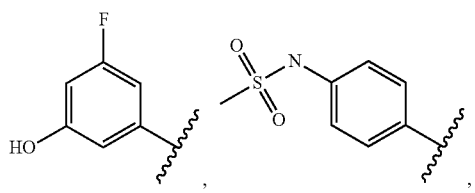

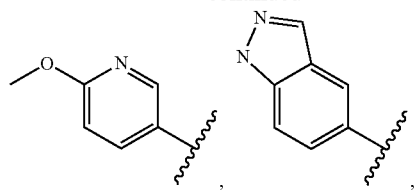
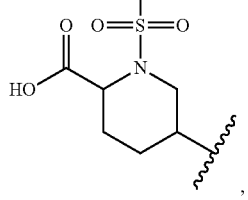
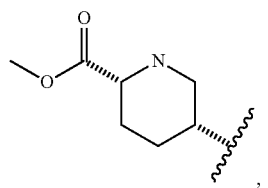
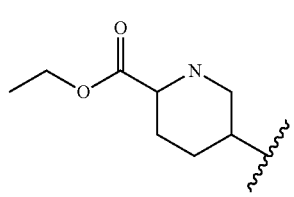
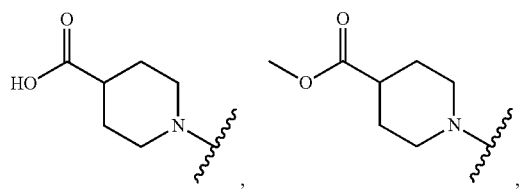
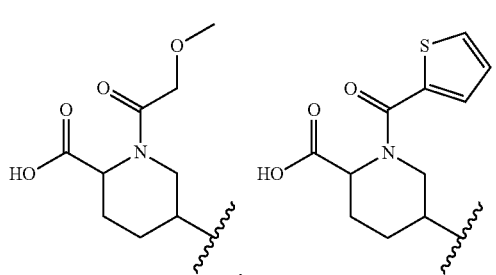
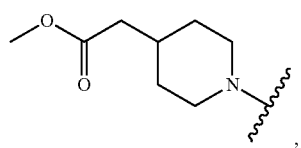
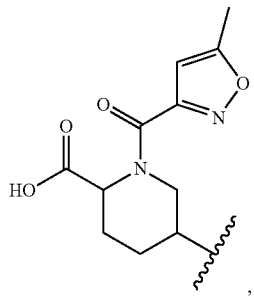
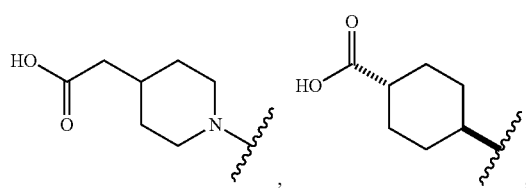
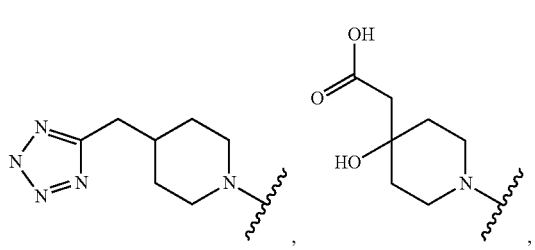
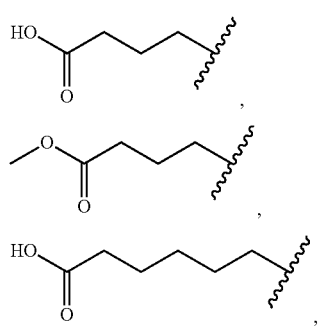
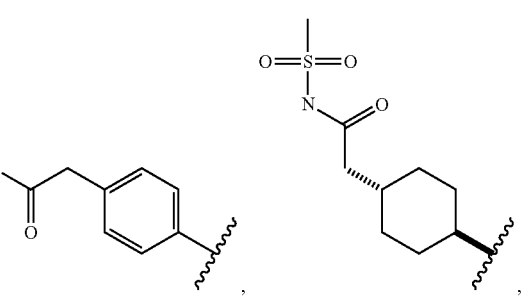
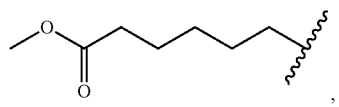
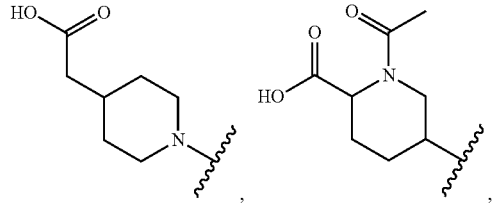

67
-continued
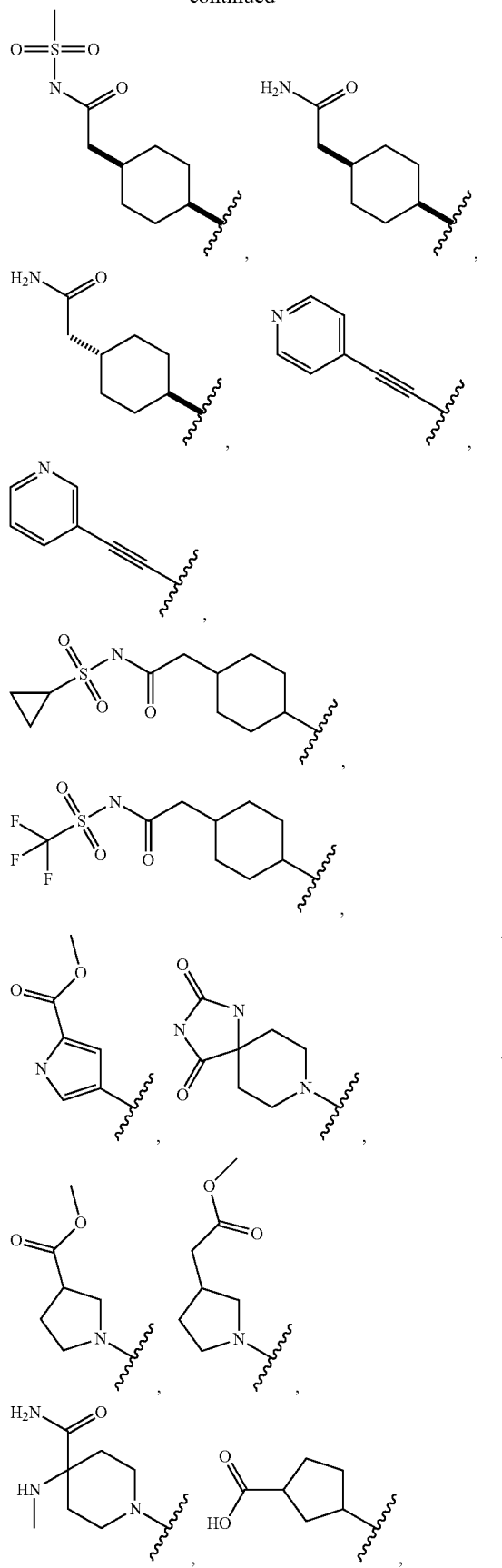
68
-continued
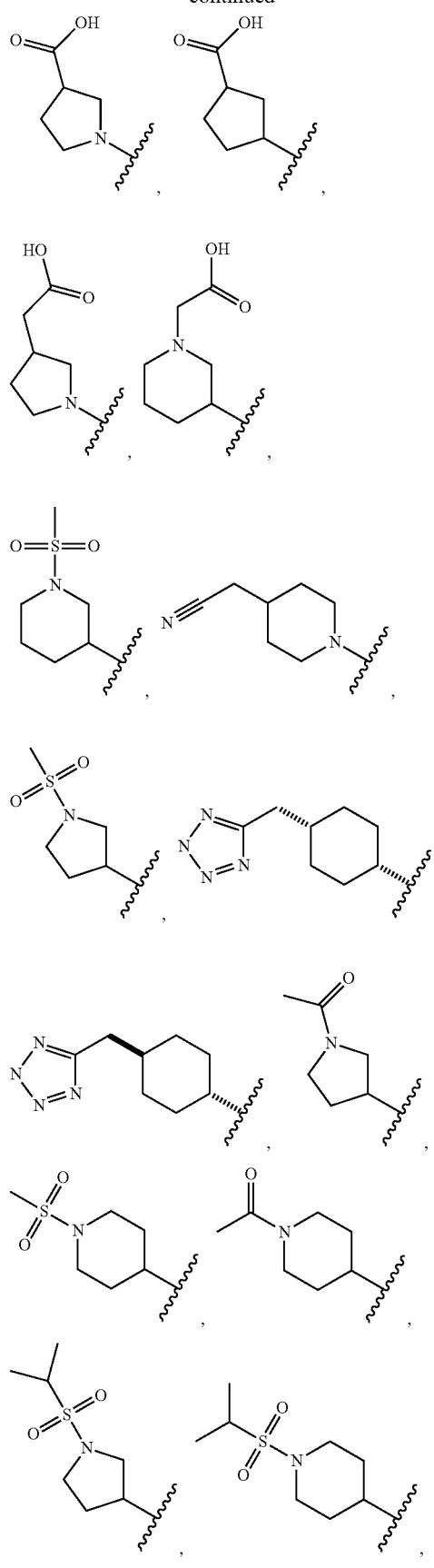

-continued

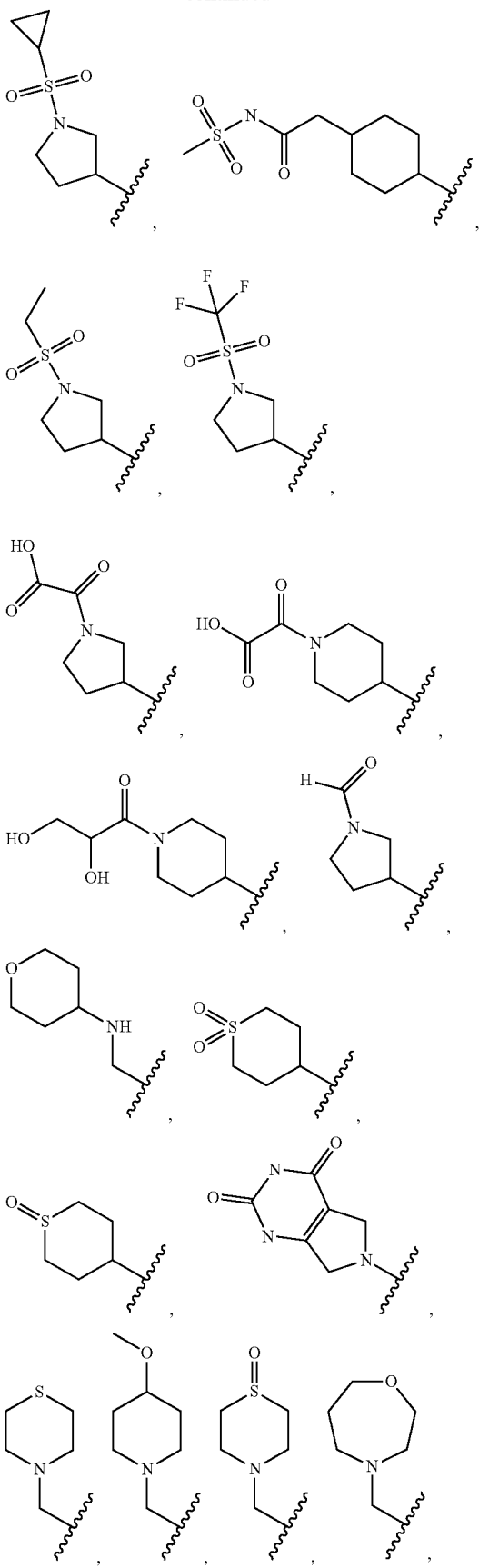

-continued

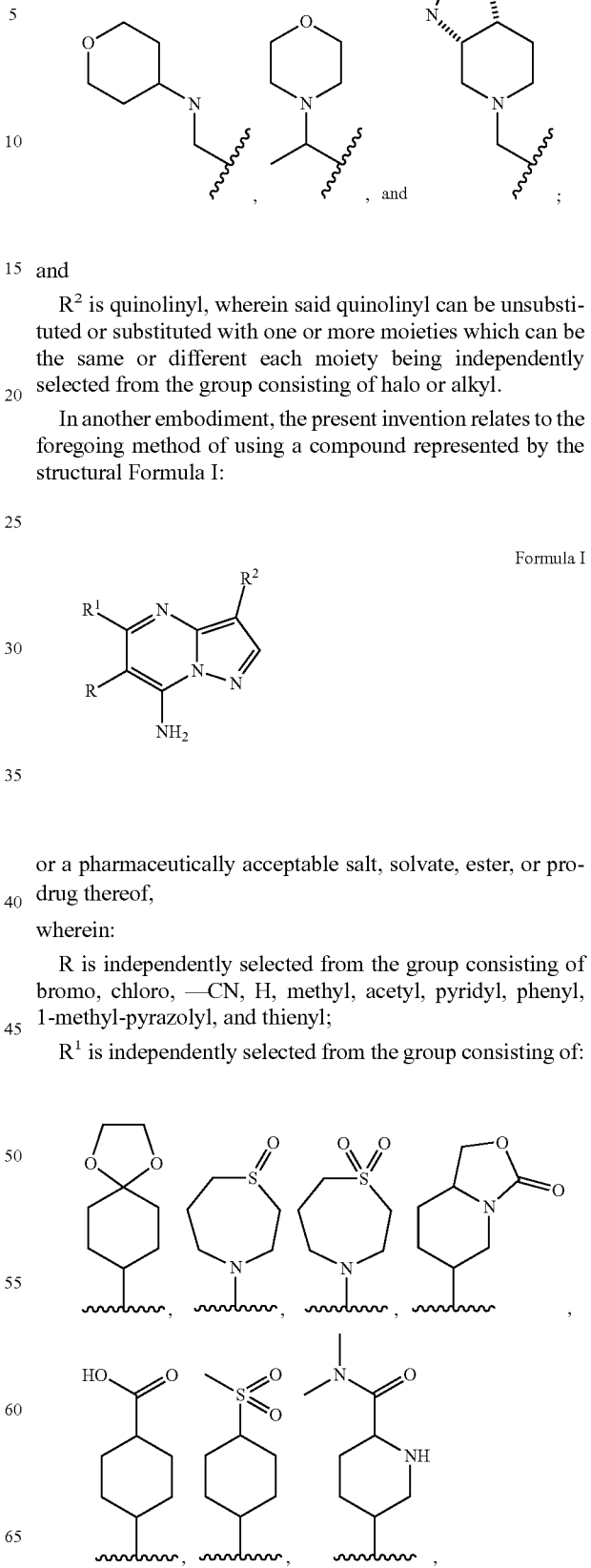

and

R² is quinolinyl, wherein said quinolinyl can be unsubstituted or substituted with one or more moieties which can be the same or different each moiety being independently selected from the group consisting of halo or alkyl.

In another embodiment, the present invention relates to the foregoing method of using a compound represented by the structural Formula I:

Formula I or a pharmaceutically acceptable salt, solvate, ester, or prodrug thereof, wherein:

R is independently selected from the group consisting of bromo, chloro, —CN, H, methyl, acetyl, pyridyl, phenyl, 1-methyl-pyrazolyl, and thienyl;

R¹ is independently selected from the group consisting of:

71
-continued
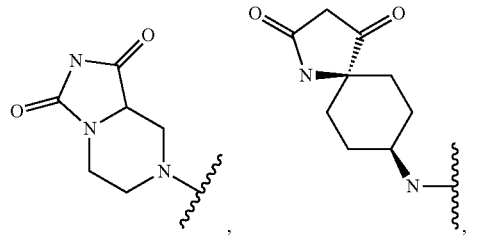
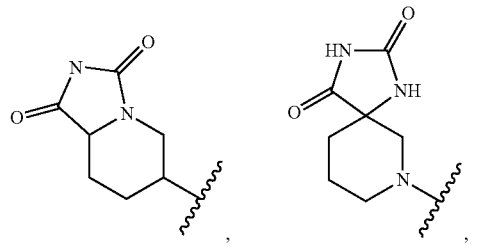
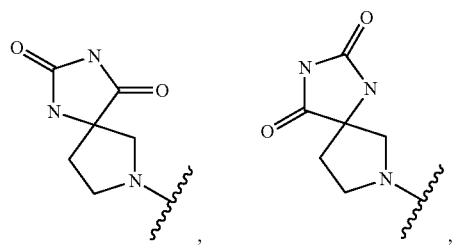
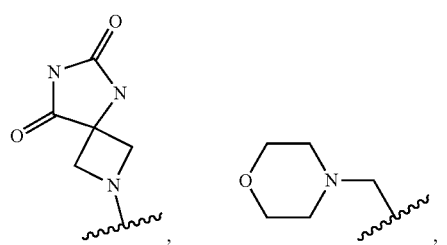
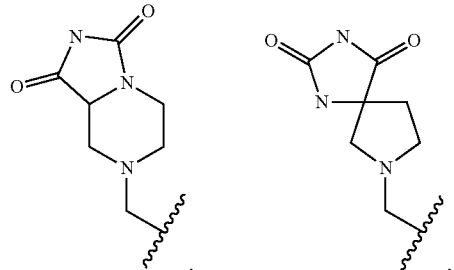
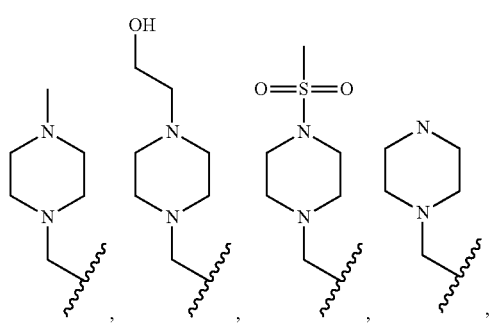
72
-continued
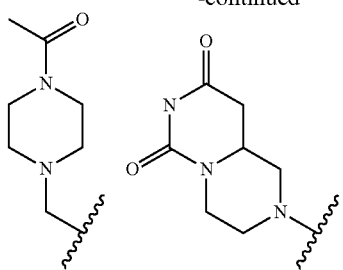
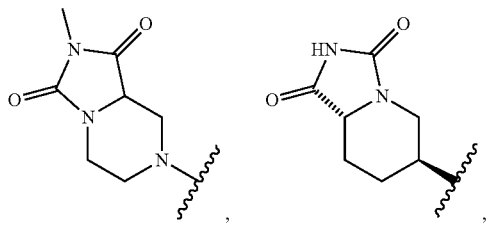
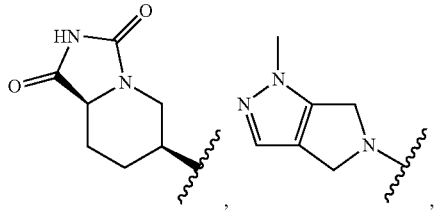
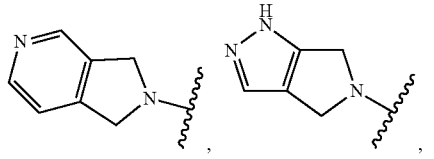
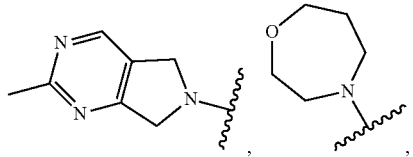
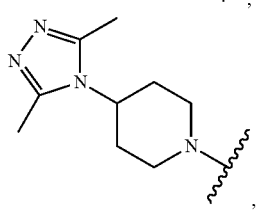
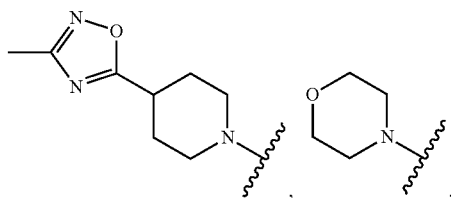
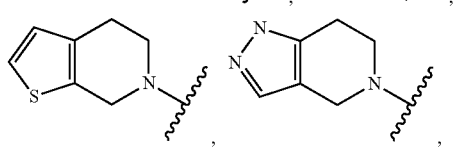
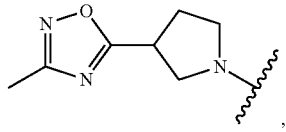

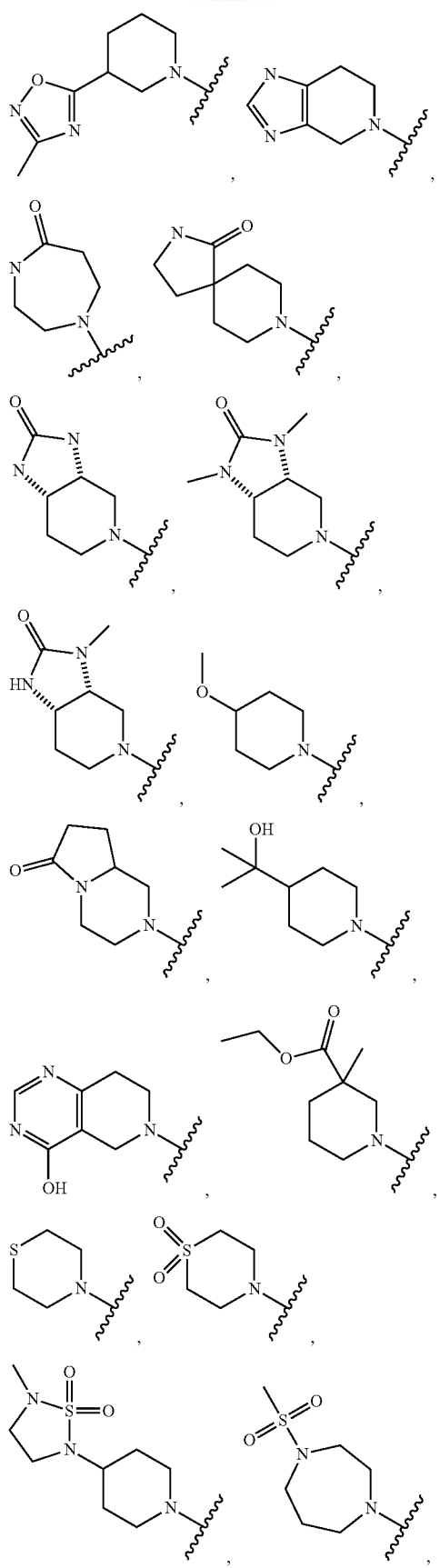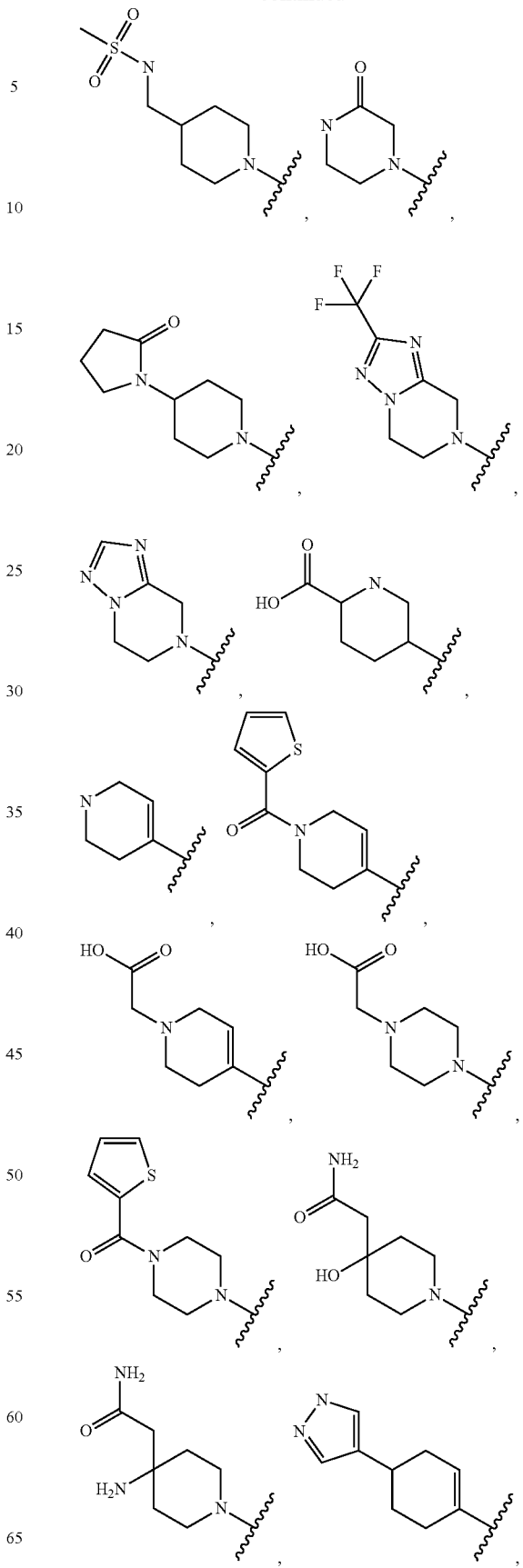

-continued
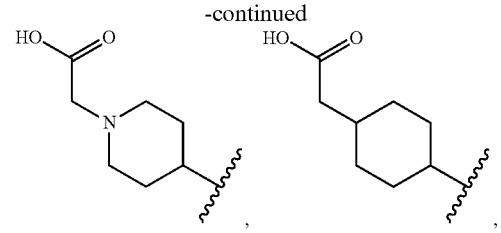
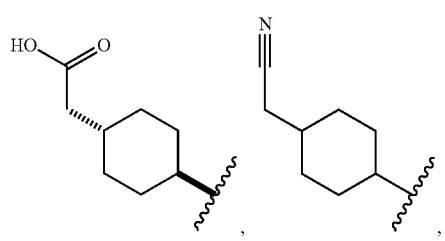
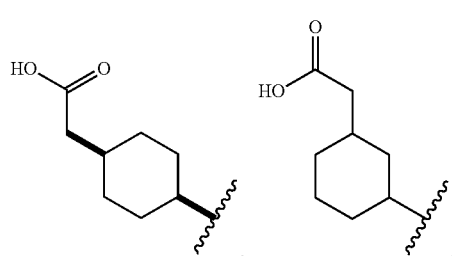
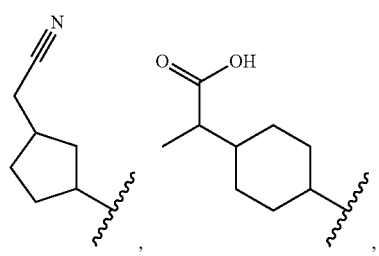
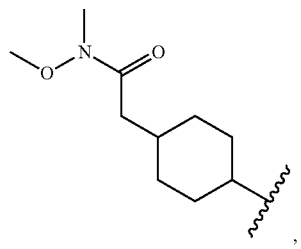
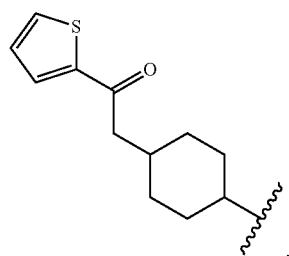
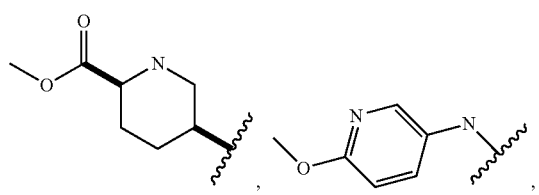
-continued
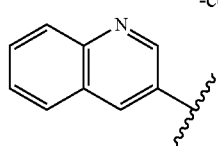
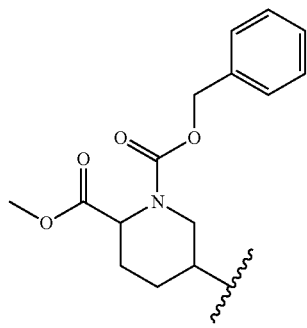
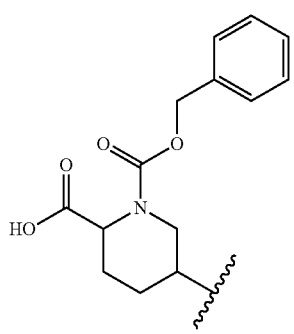
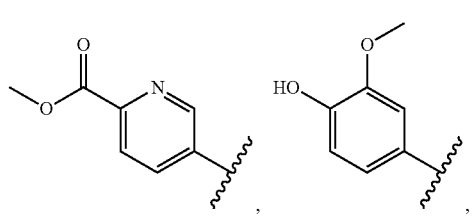
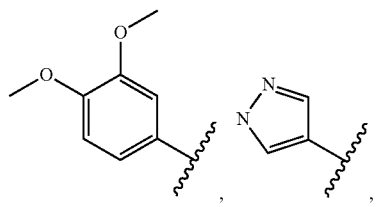
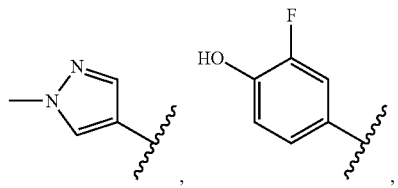
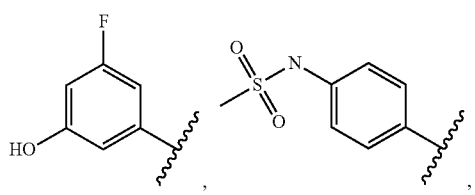

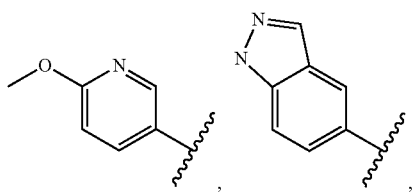
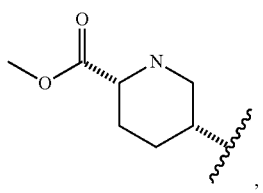
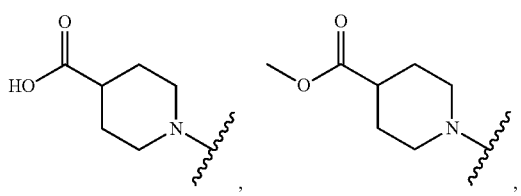
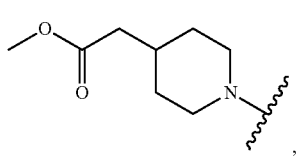
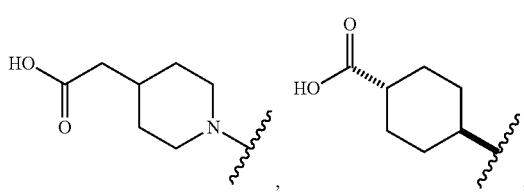
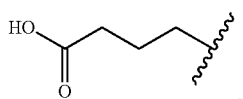
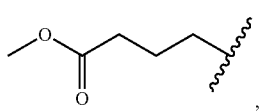
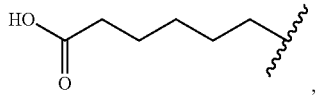
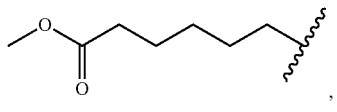
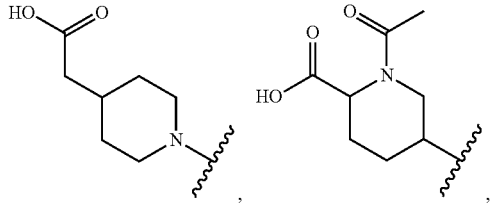
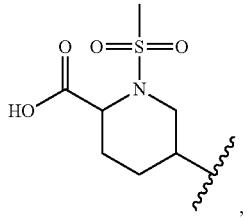
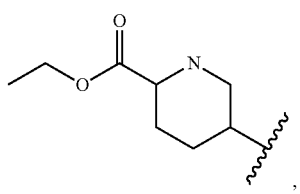
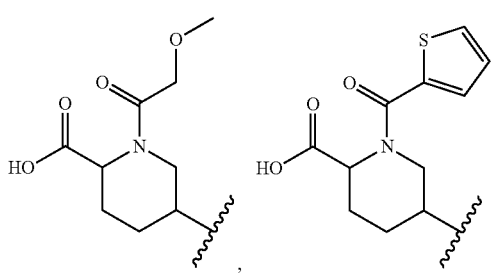
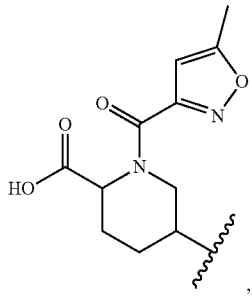
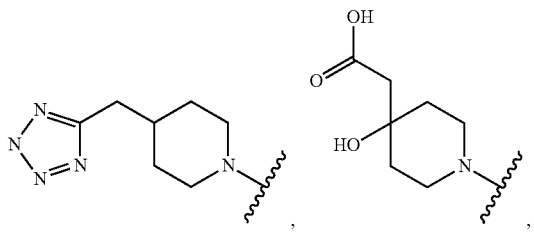
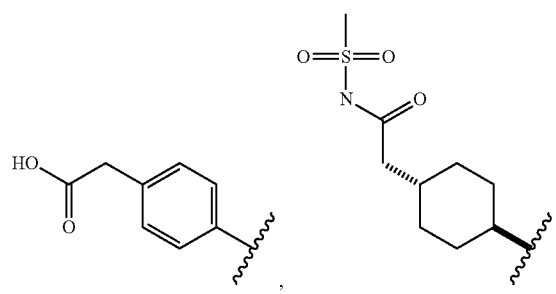

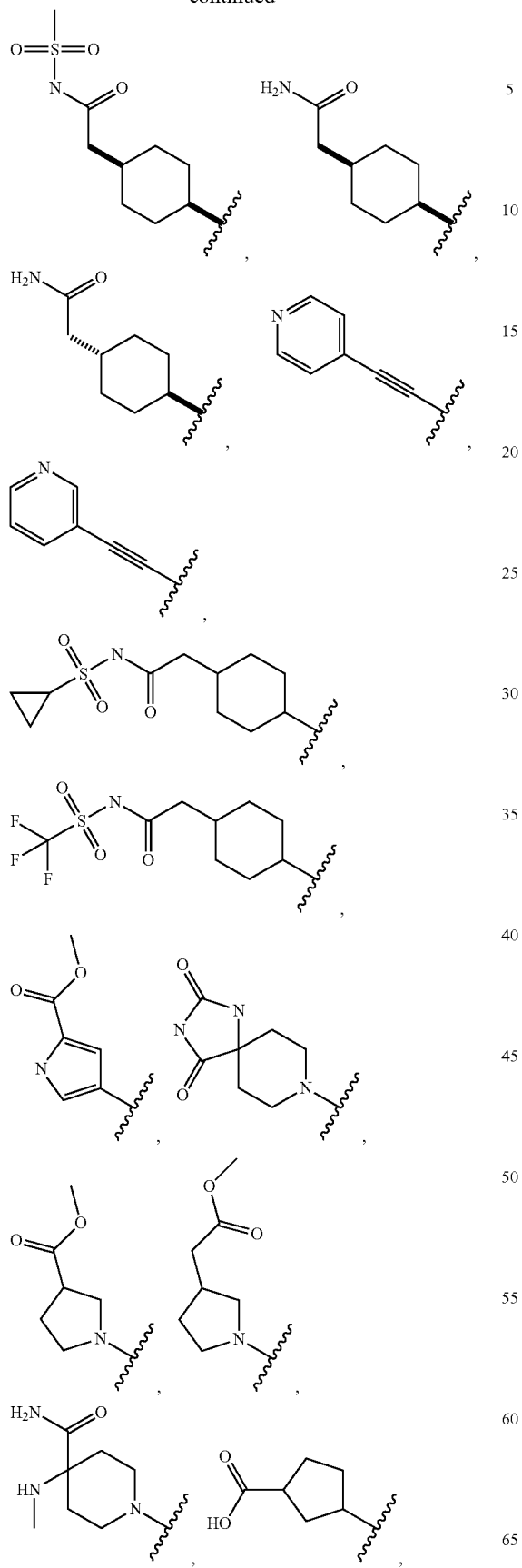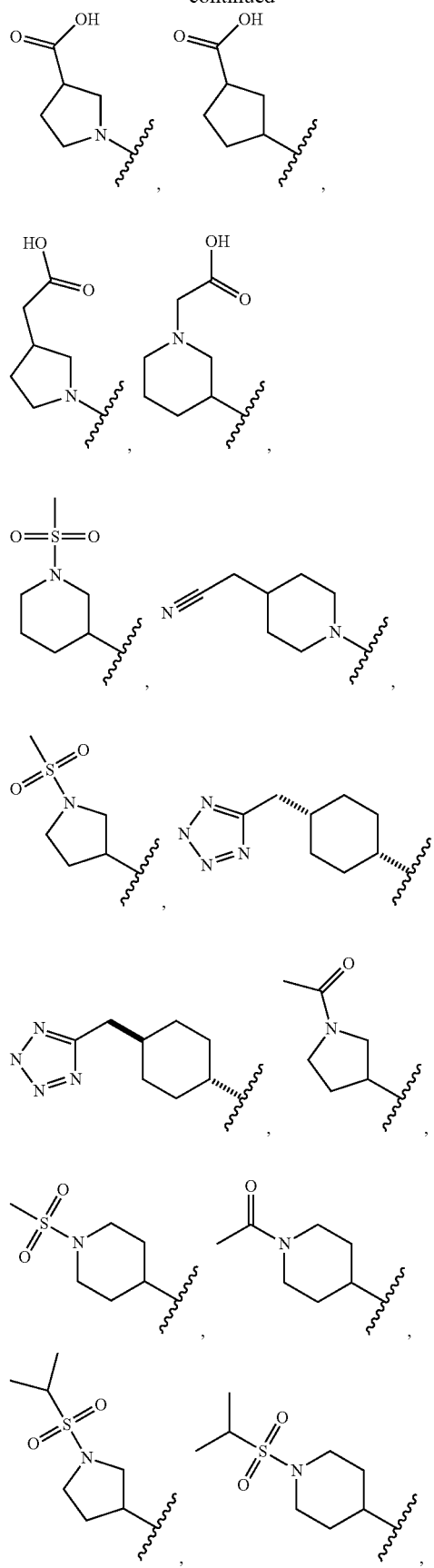

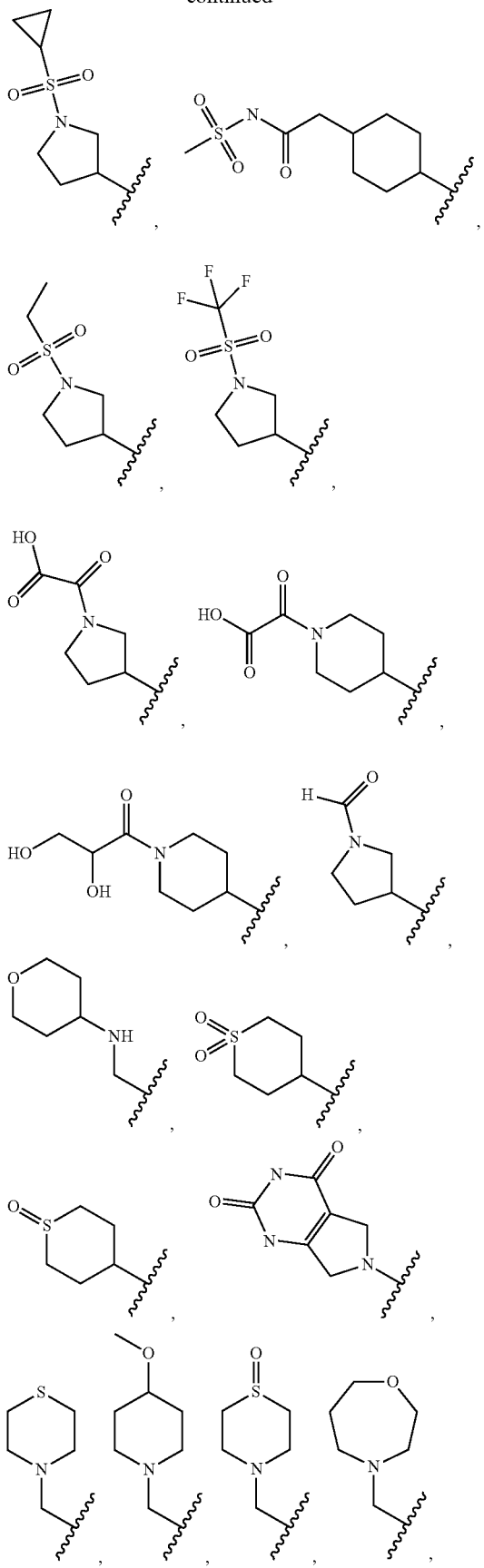

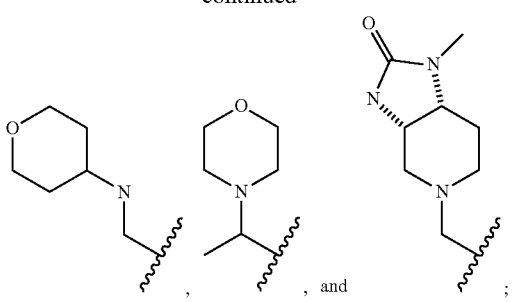

, and

R² is pyrazolyl, wherein said pyrazolyl can be unsubstituted or substituted with one or more moieties which can be the same or different each moiety being independently selected from the group consisting of halo or alkyl.

In another embodiment, the present invention relates to the foregoing method of using a compound represented by the structural Formula I:

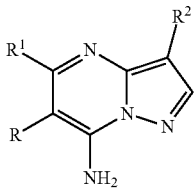

Formula I or a pharmaceutically acceptable salt, solvate, ester, or prodrug thereof, wherein:

R is independently selected from the group consisting of bromo, chloro, —CN, H, methyl, acetyl, pyridyl, phenyl, 1-methyl-pyrazolyl, and thienyl;

R¹ is independently selected from the group consisting of:

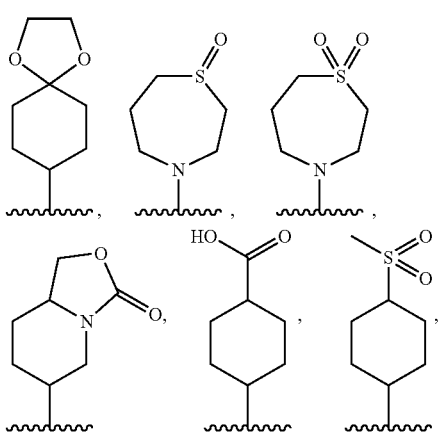

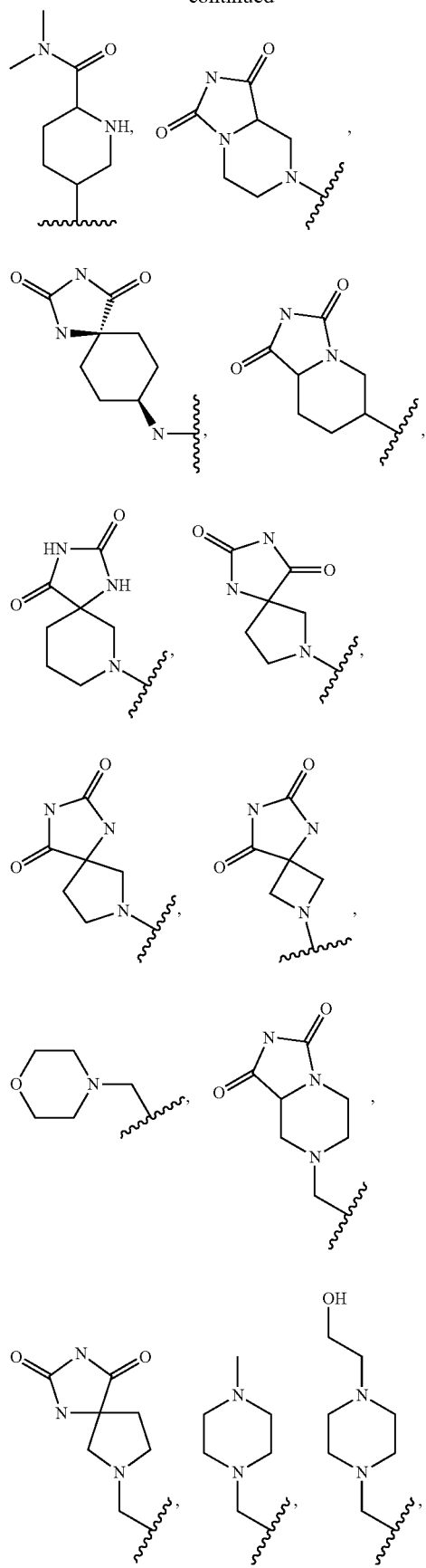
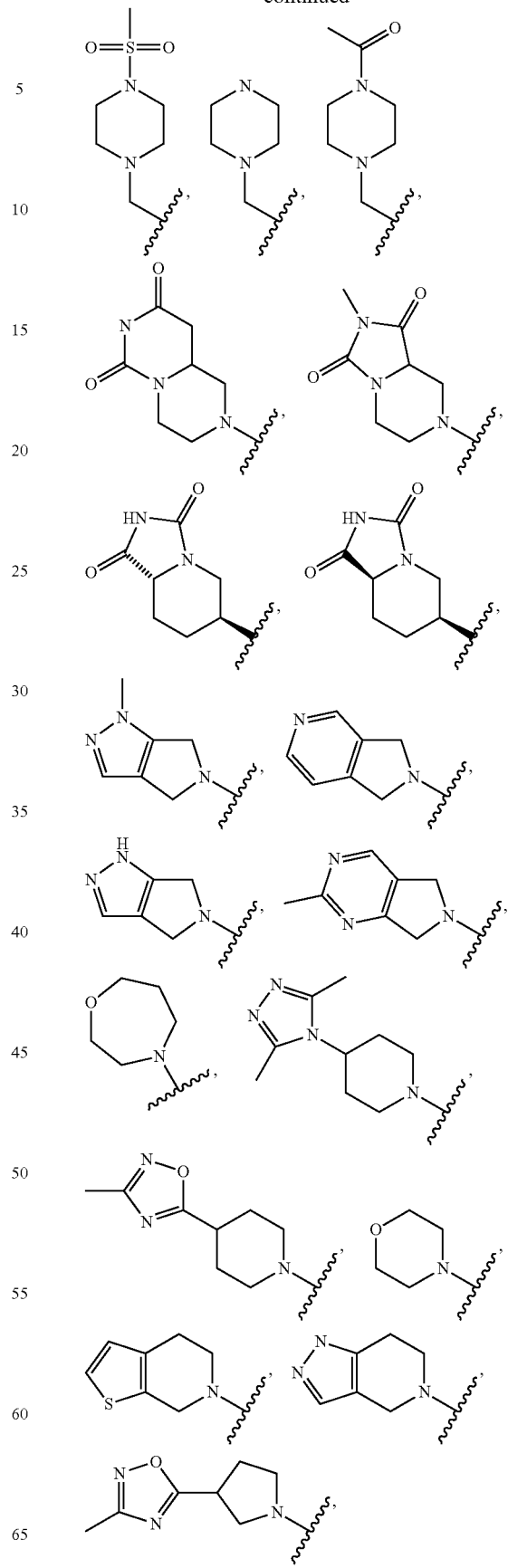

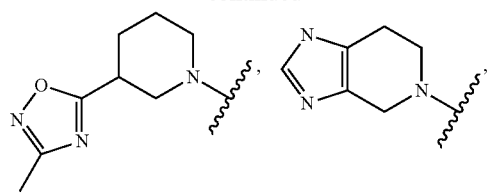
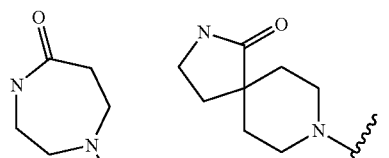
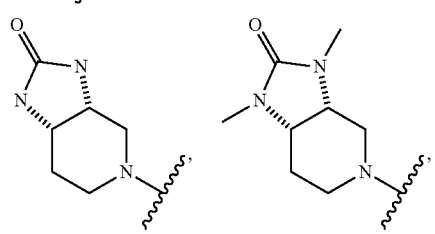
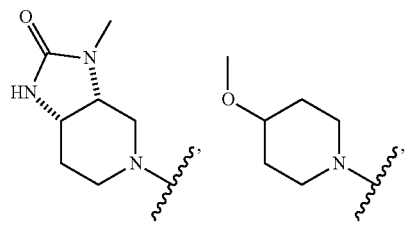
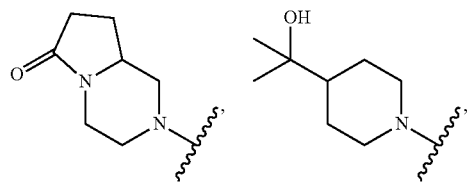
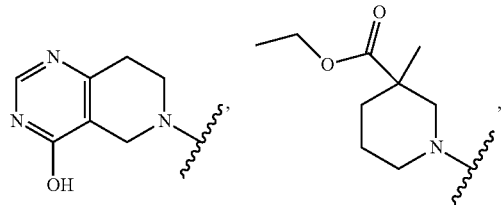
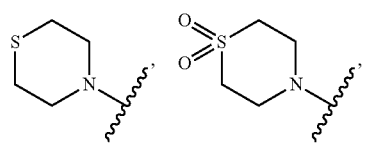
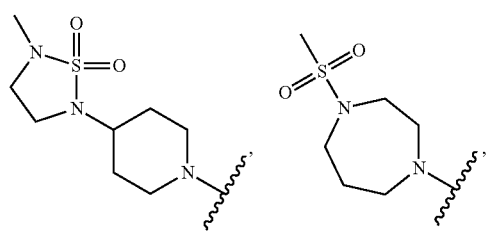
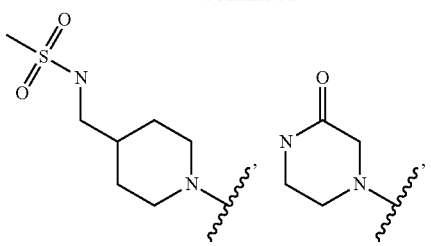
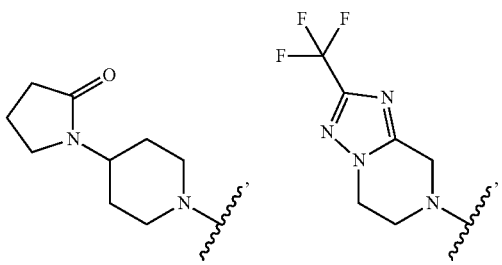
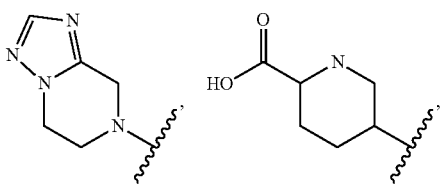
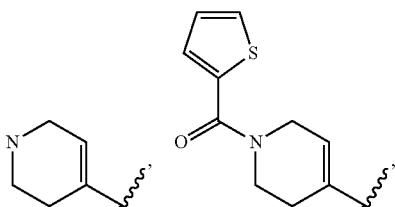
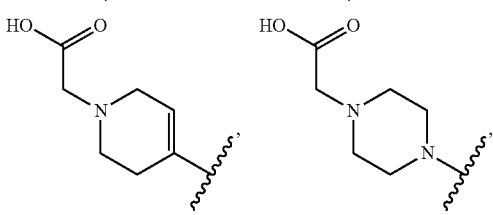
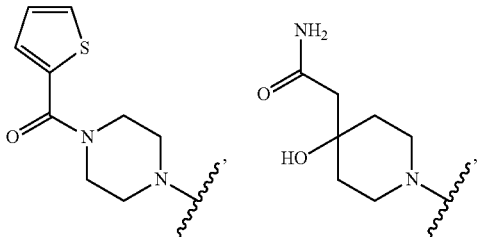
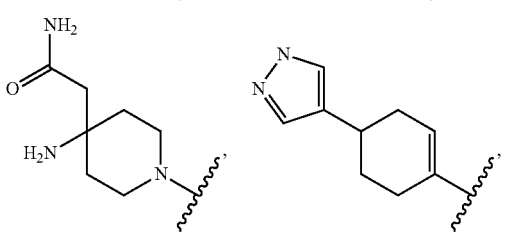

-continued
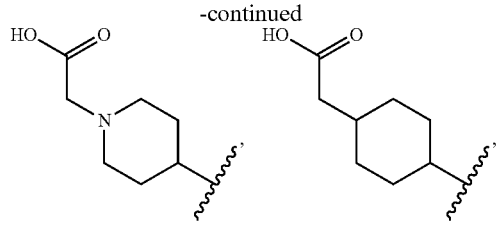
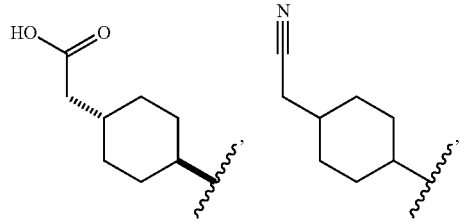
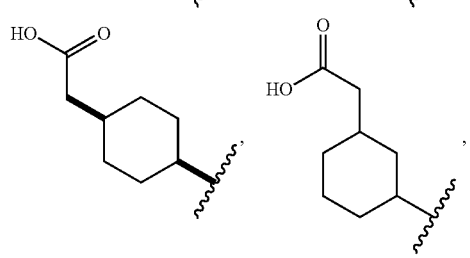
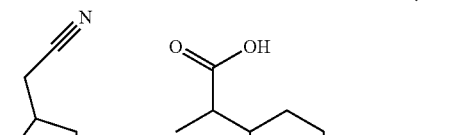
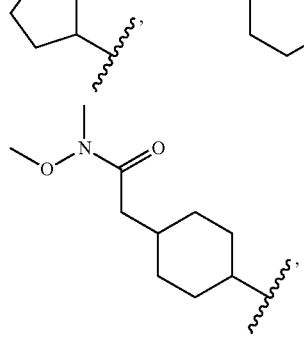
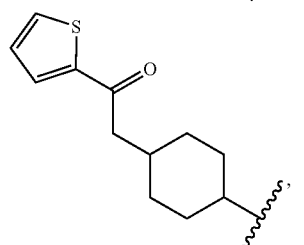
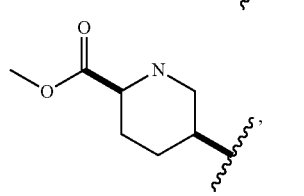
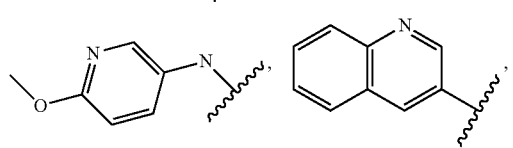
-continued
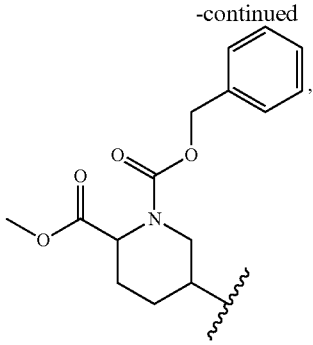
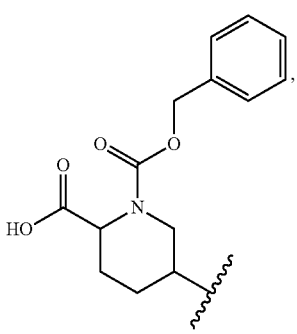
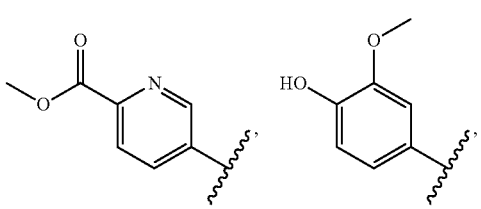
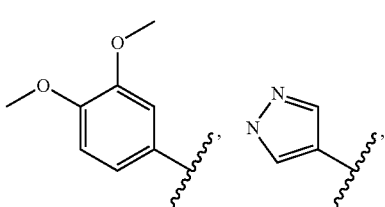
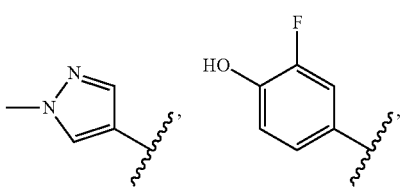
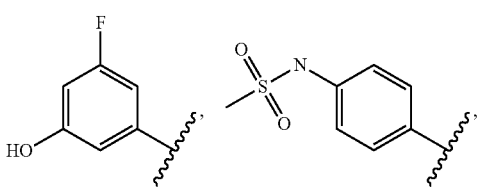
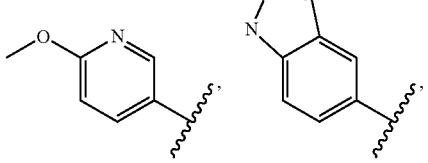

-continued
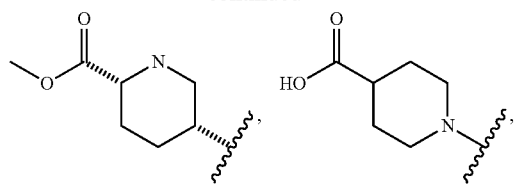
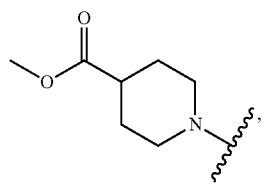
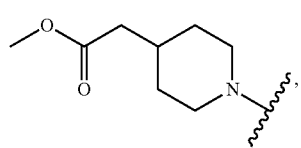
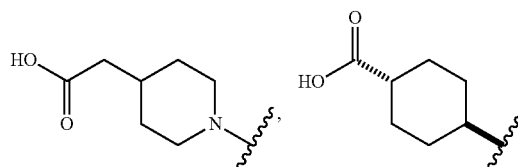
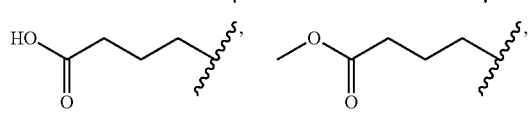
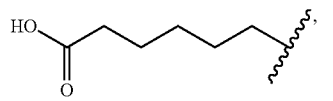
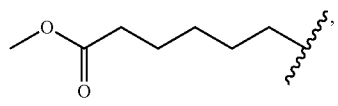
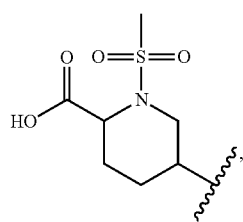
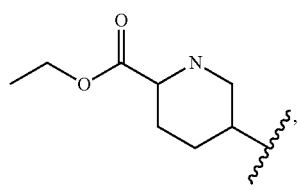
-continued
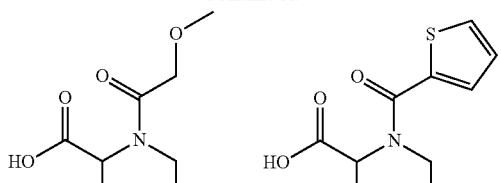
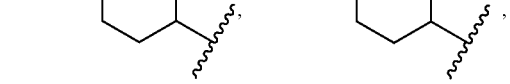
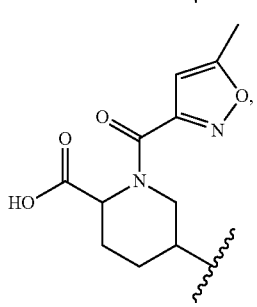
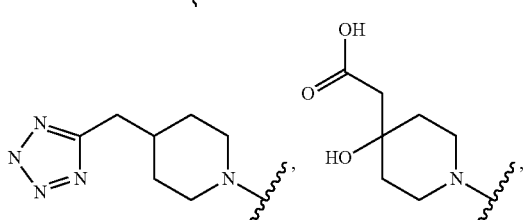
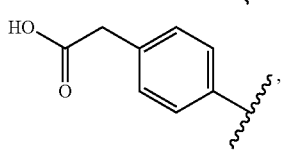
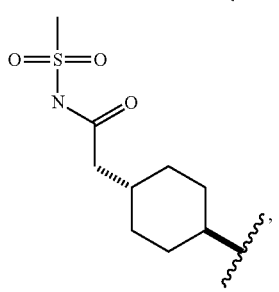
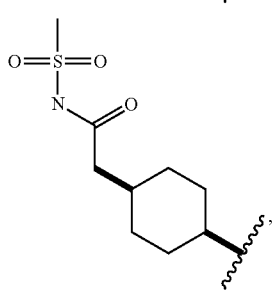
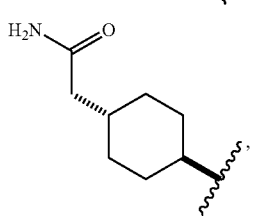
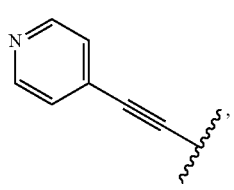

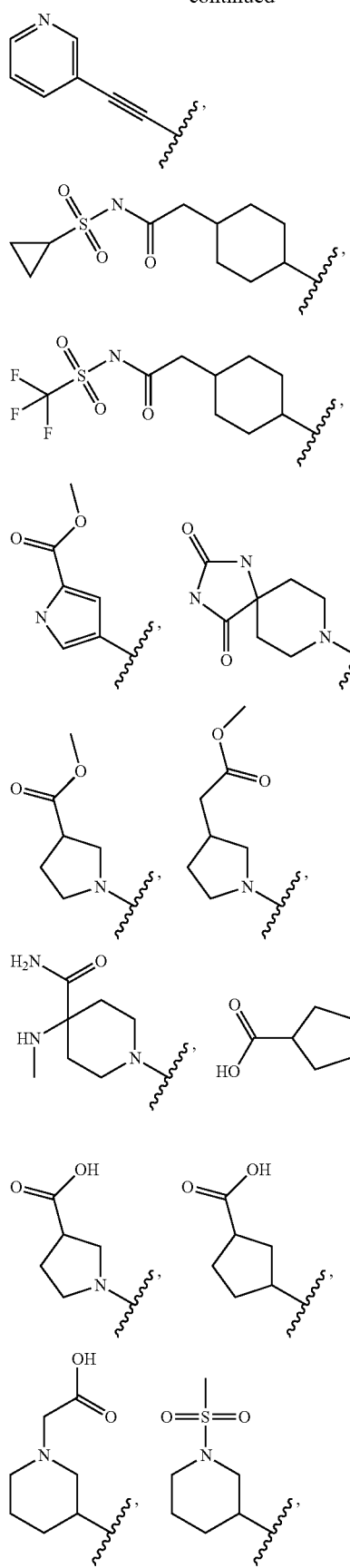
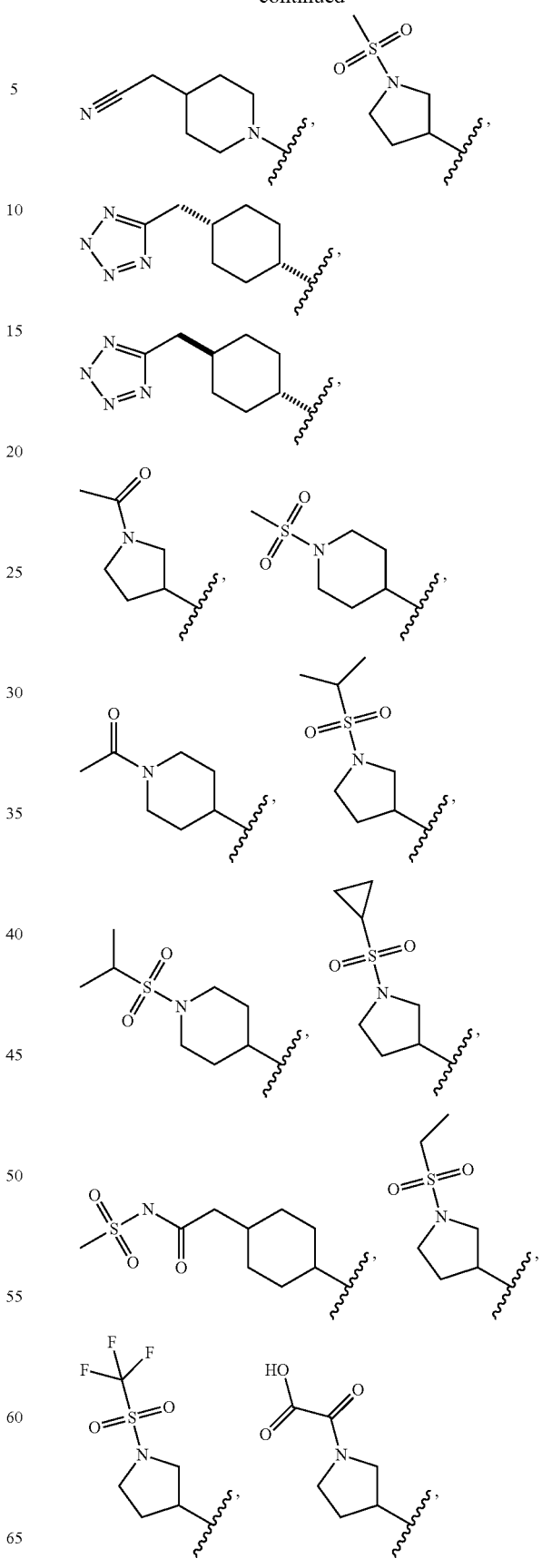

-continued

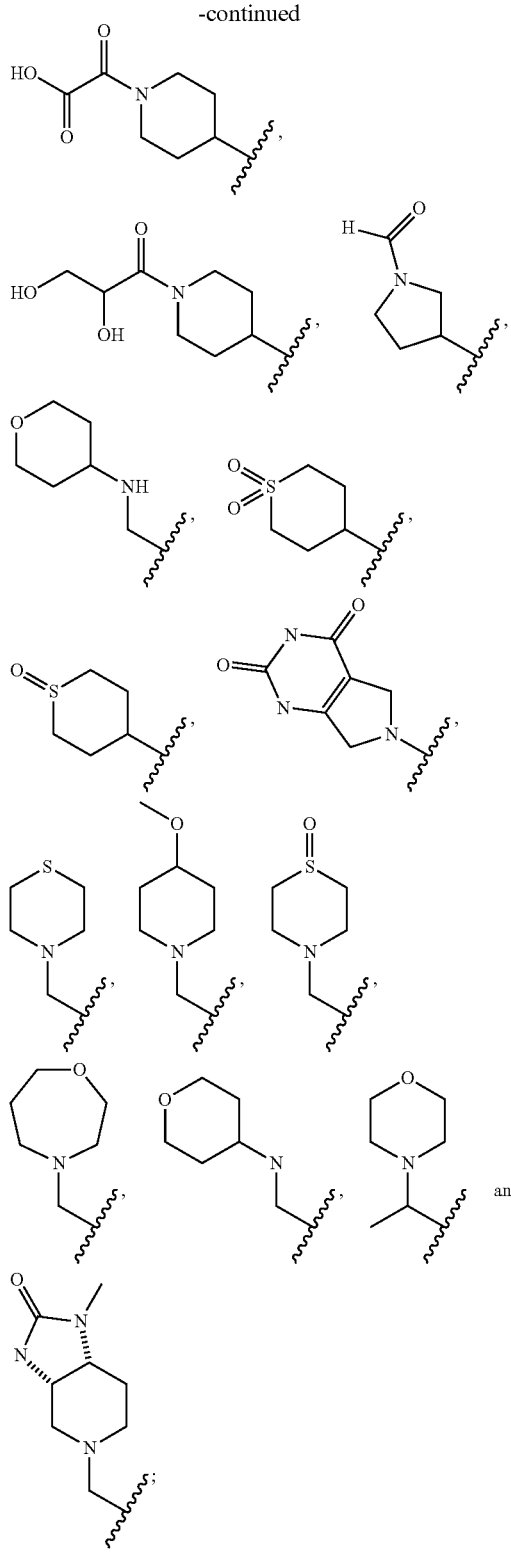

and

R[2] is pyridinyl, wherein said pyridinyl can be unsubstituted or substituted with one or more moieties which can be the same or different each moiety being independently selected from the group consisting of halo, alkyl, heterocyclyl, heteroaryl, aryl and alkoxy.

In another embodiment, the present invention relates to the foregoing method of using a compound represented by the structural Formula I:

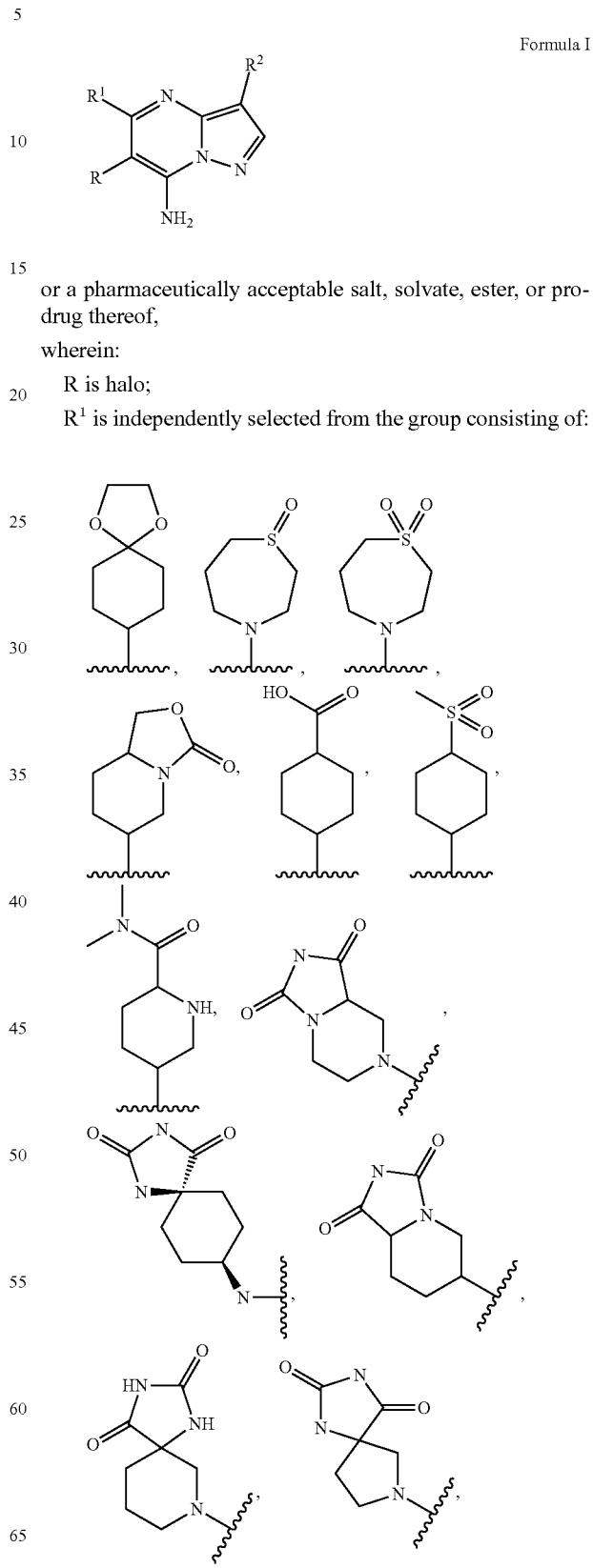

Formula I or a pharmaceutically acceptable salt, solvate, ester, or prodrug thereof, wherein:

R is halo;

R[1] is independently selected from the group consisting of:

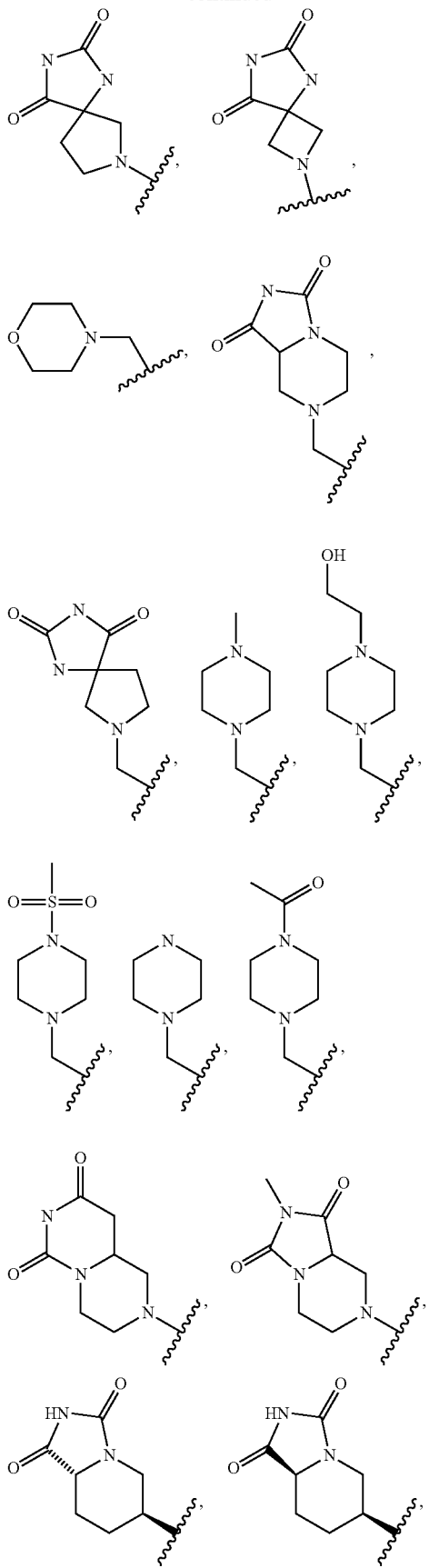
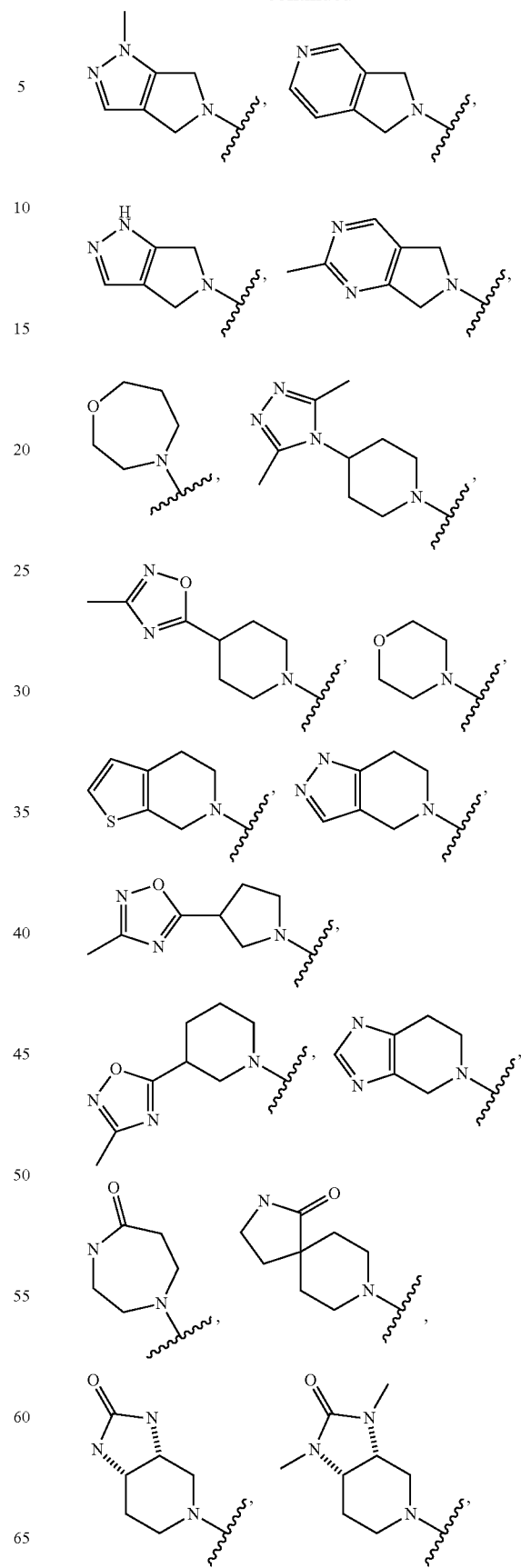

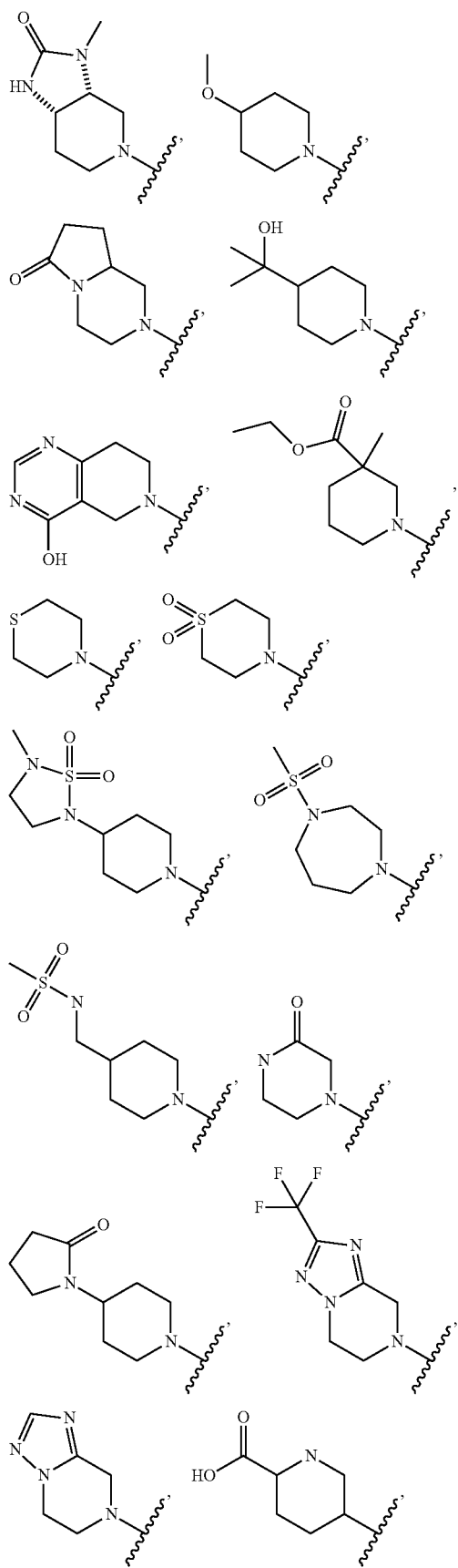
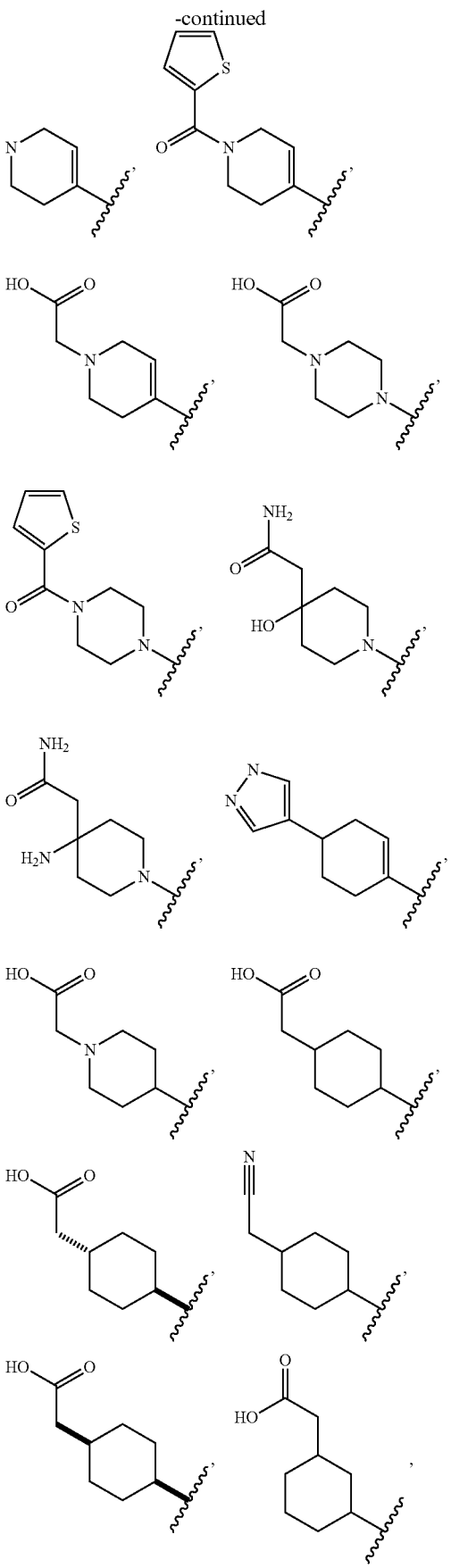

99
-continued
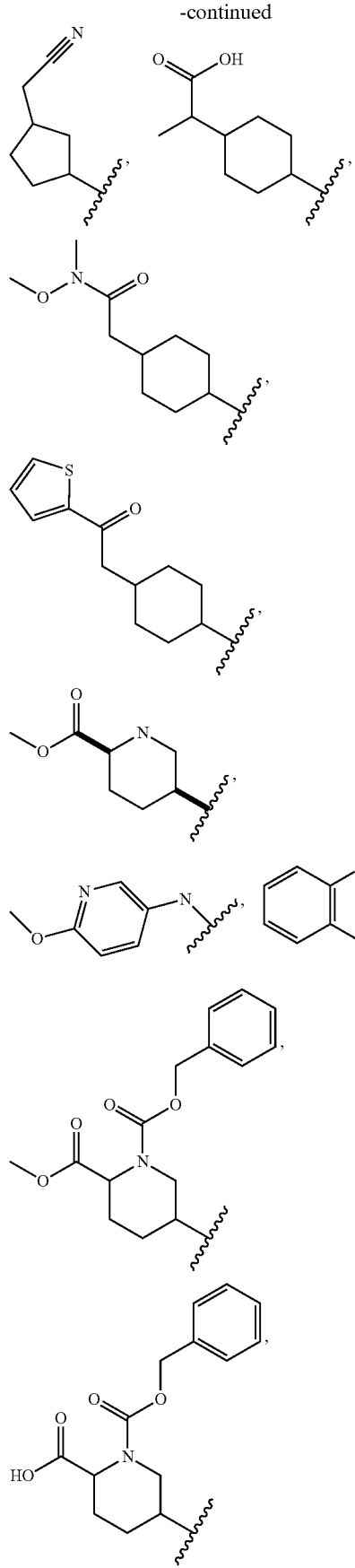
100
-continued
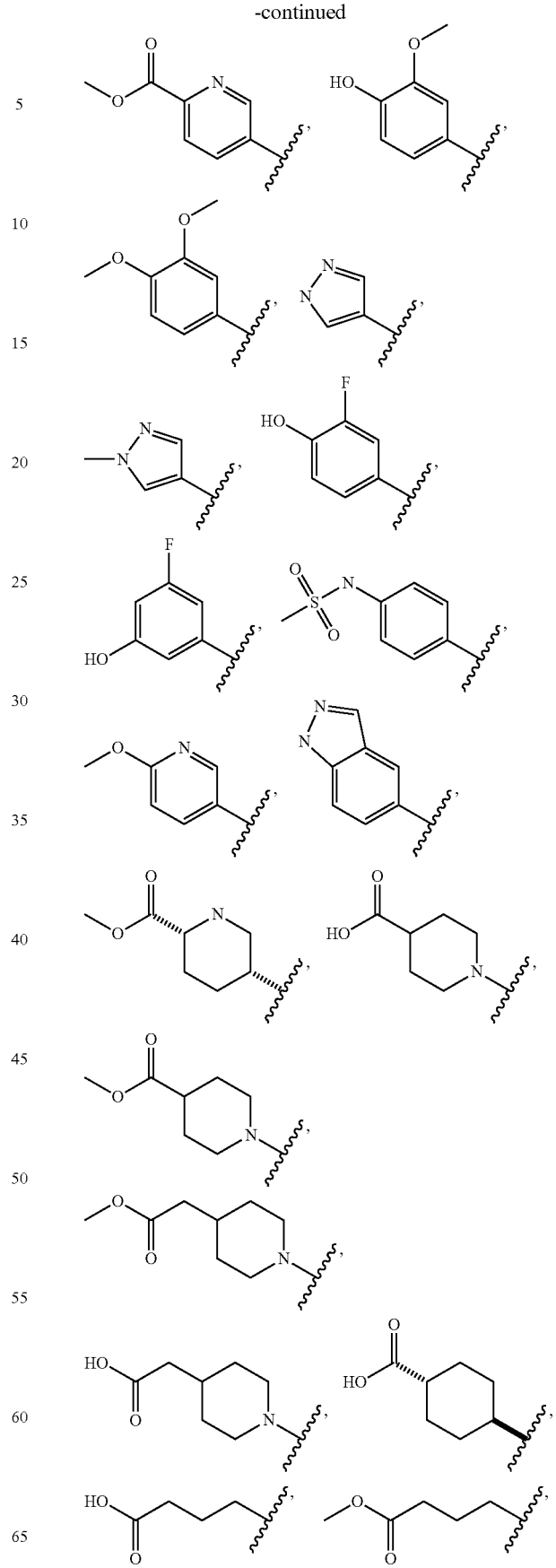

101
-continued
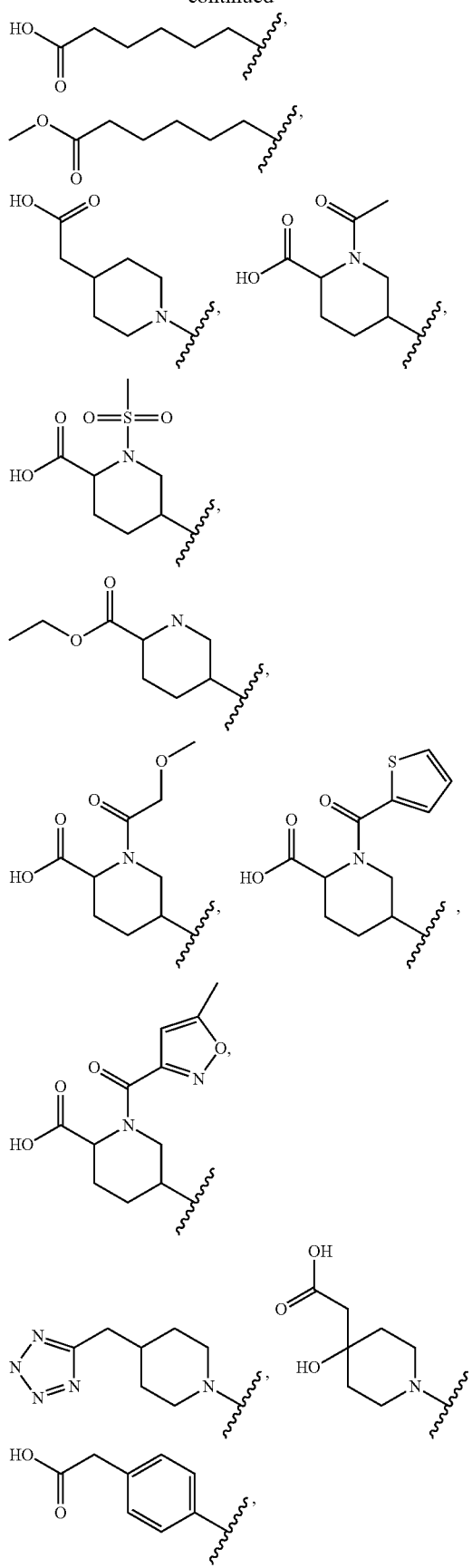
102
-continued
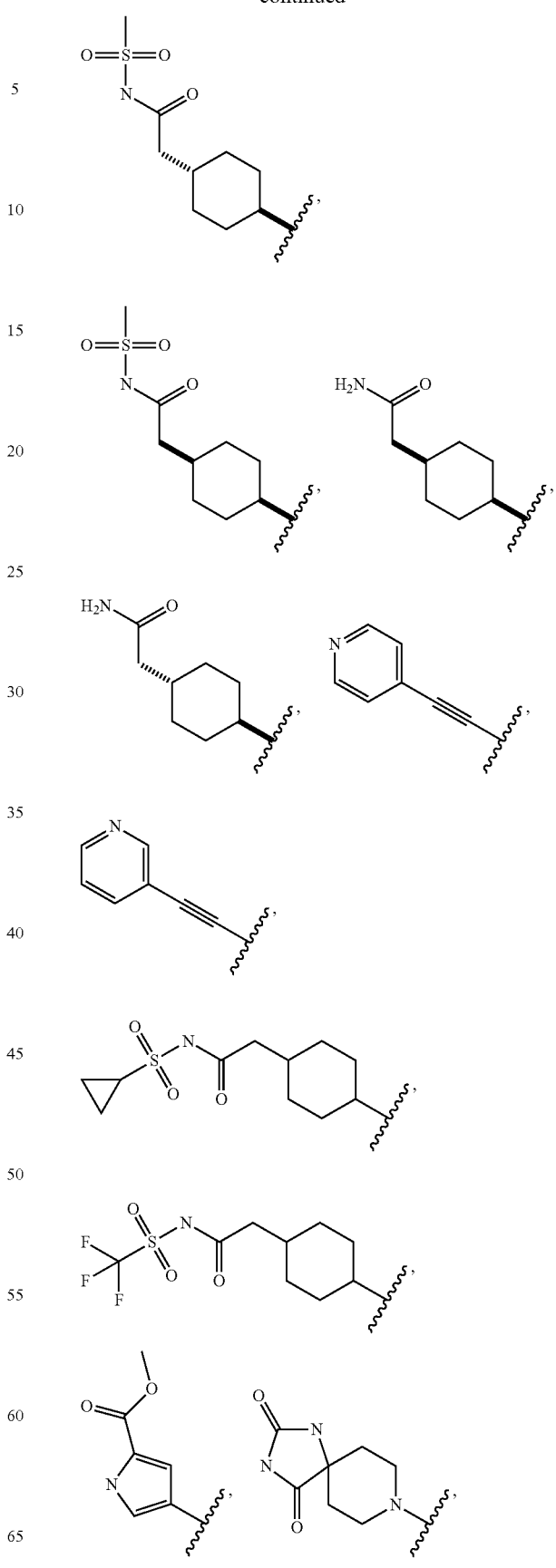

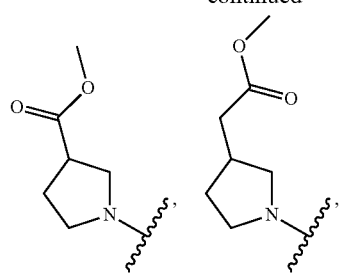
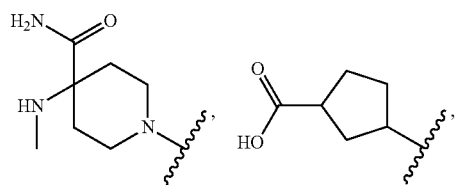
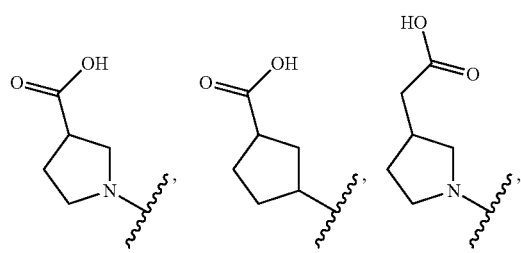
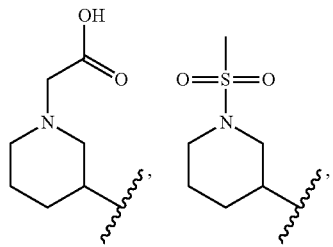
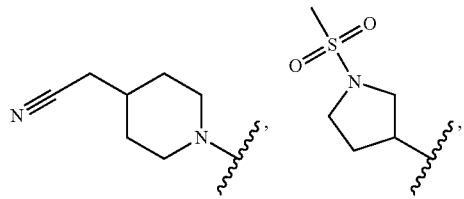
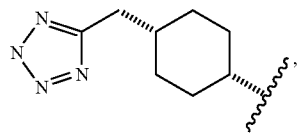
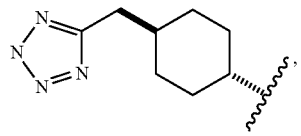
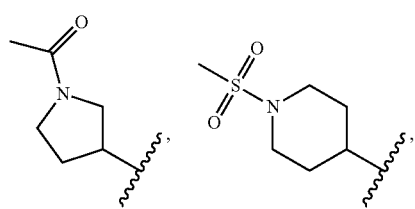
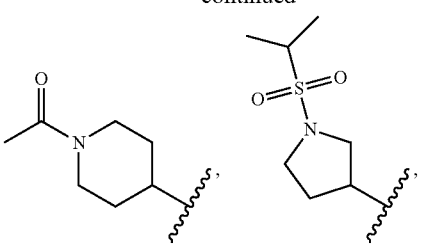
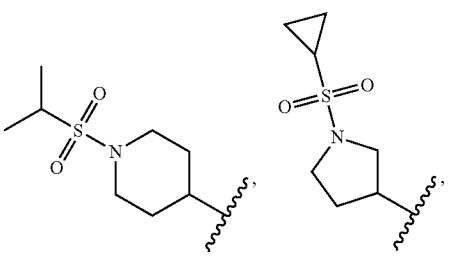
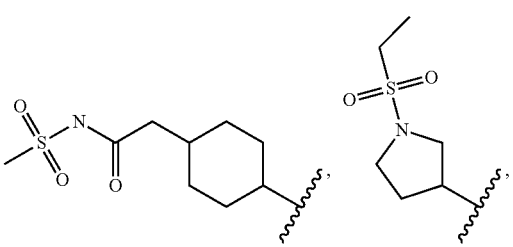
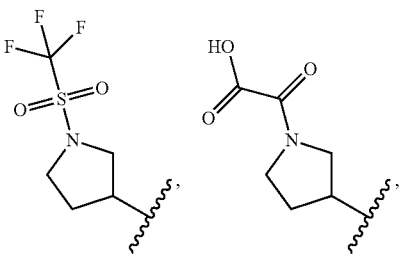
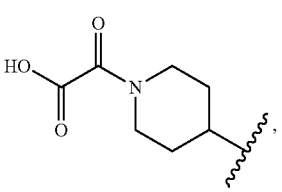
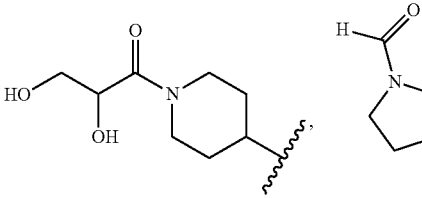
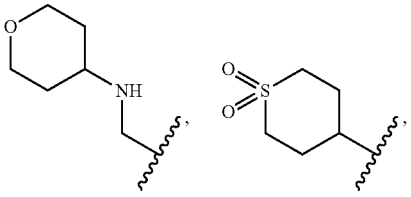

105

-continued

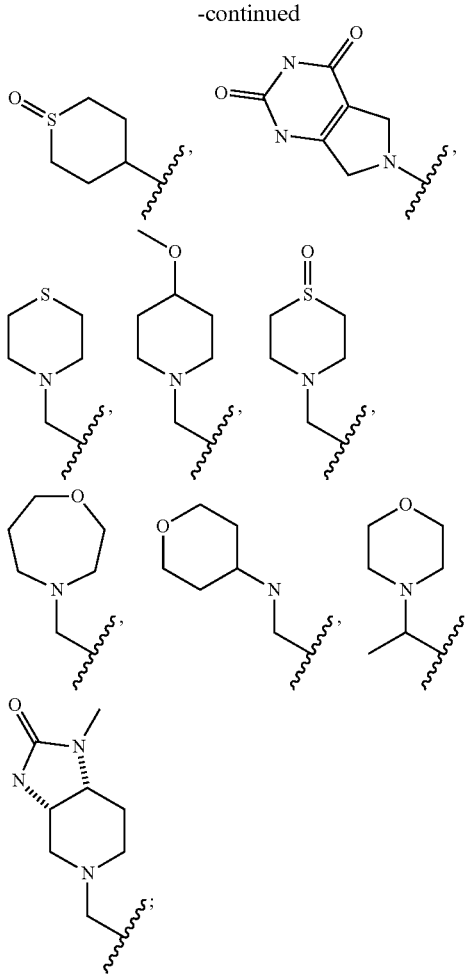

and

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, heteroaryl and arylalkyl.

In another embodiment, the present invention relates to the foregoing method of using a compound represented by the structural Formula I:

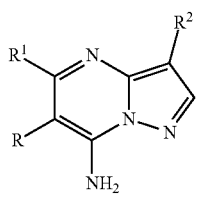

Formula I or a pharmaceutically acceptable salt, solvate, ester, or prodrug thereof,
wherein:
R is thienyl;

106

R¹ is independently selected from the group consisting of:

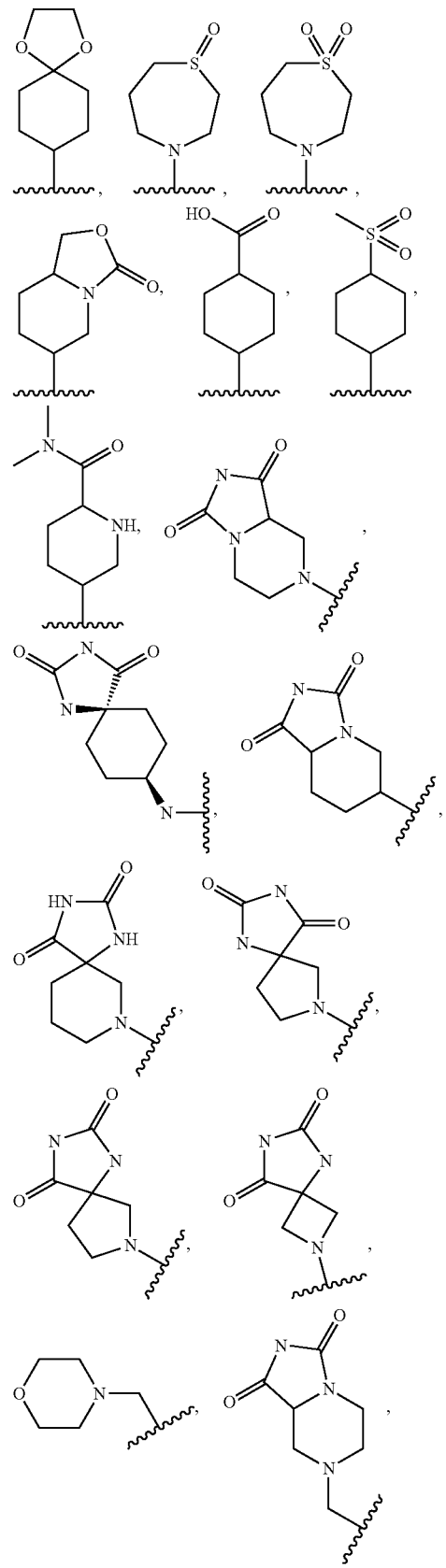

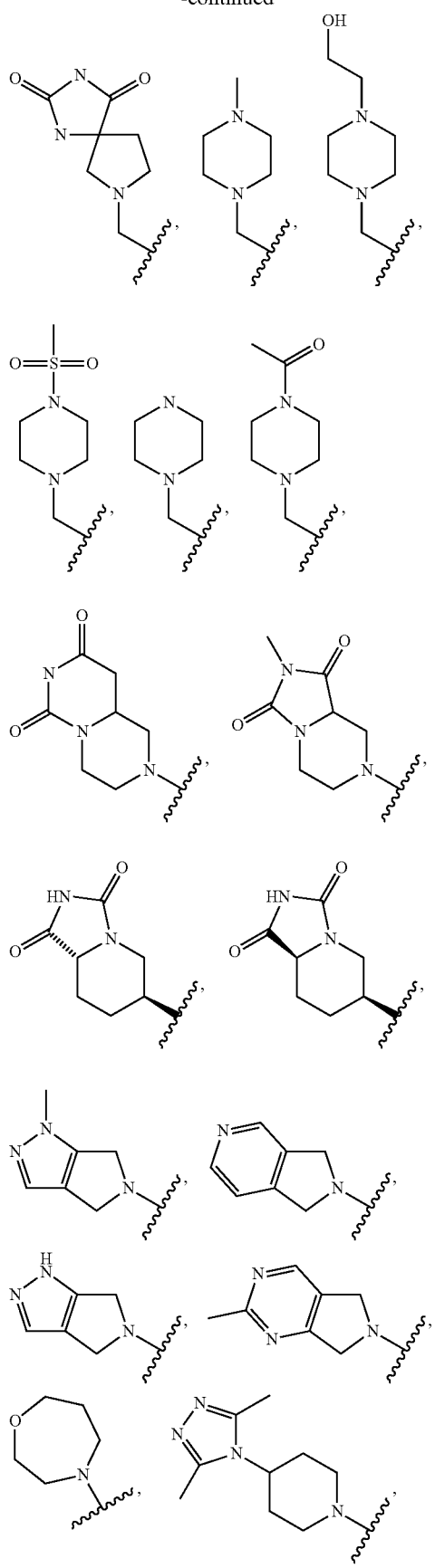
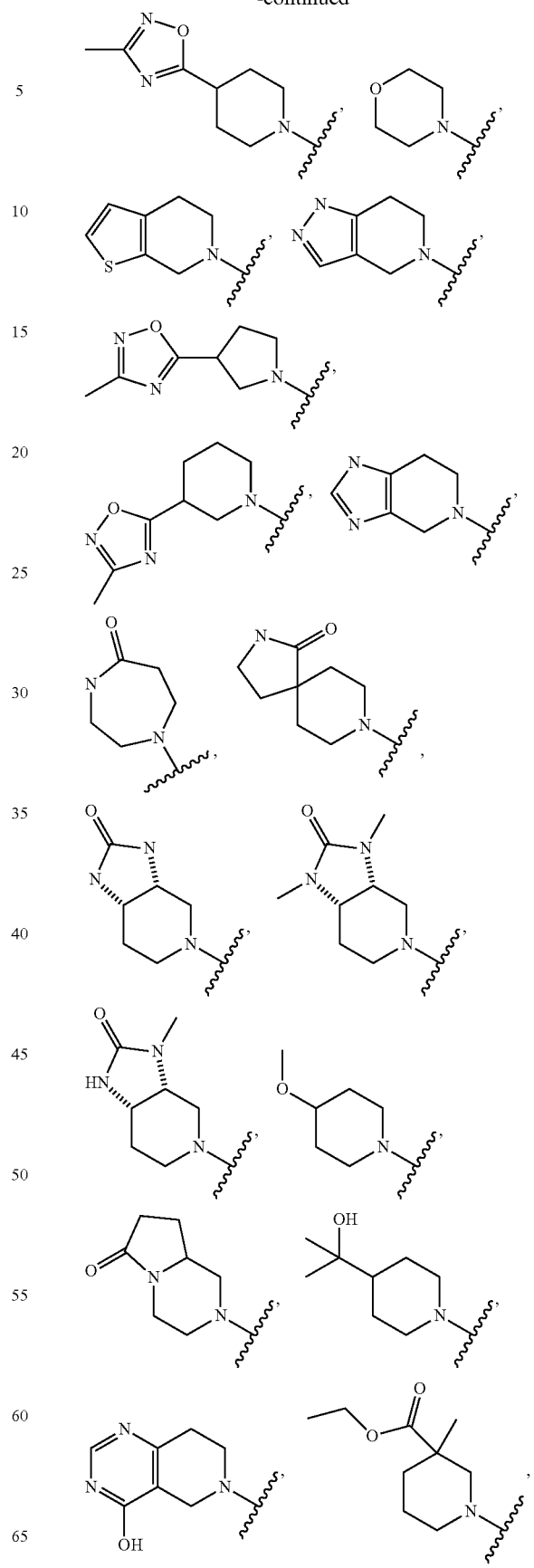

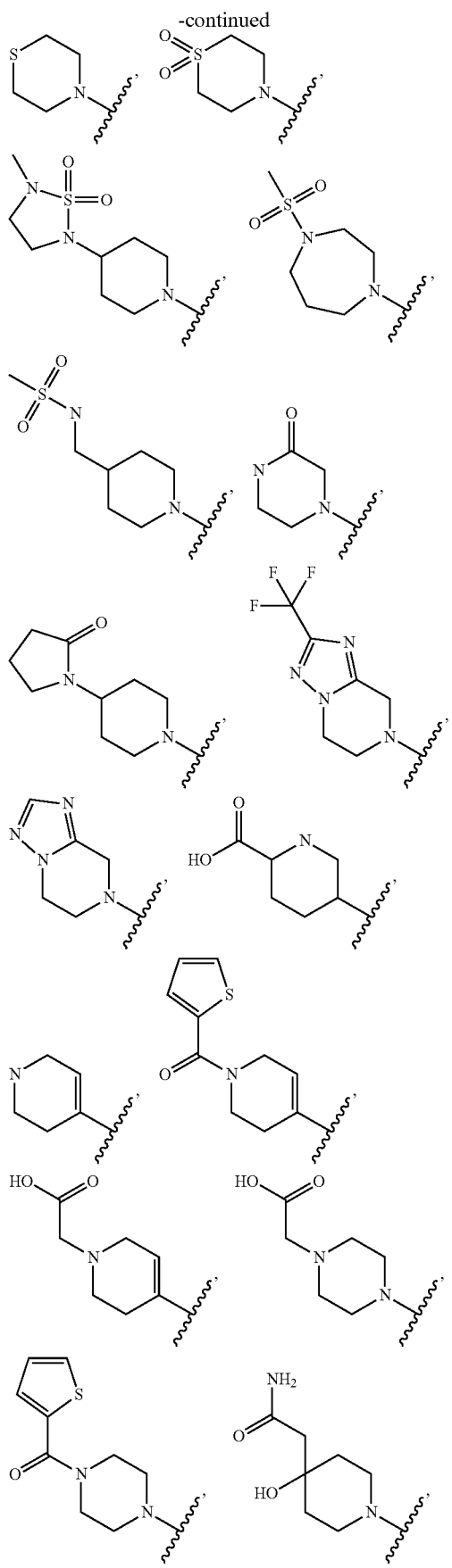
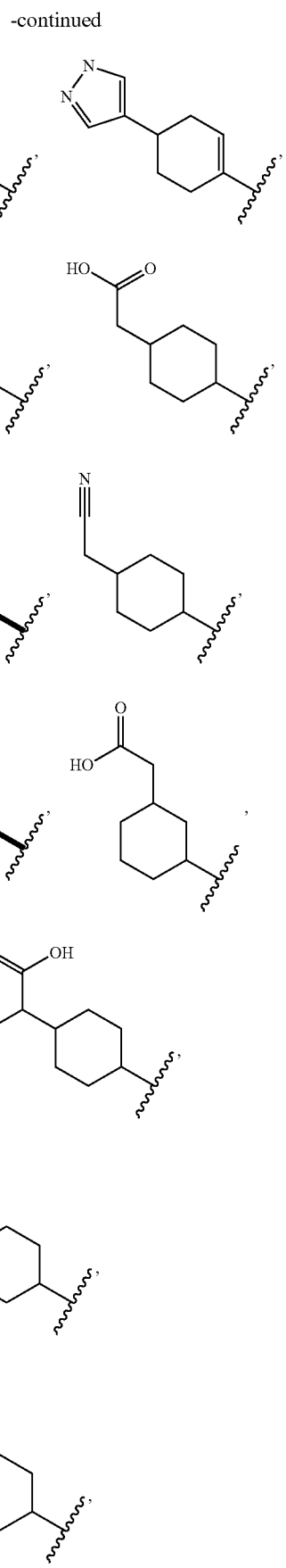

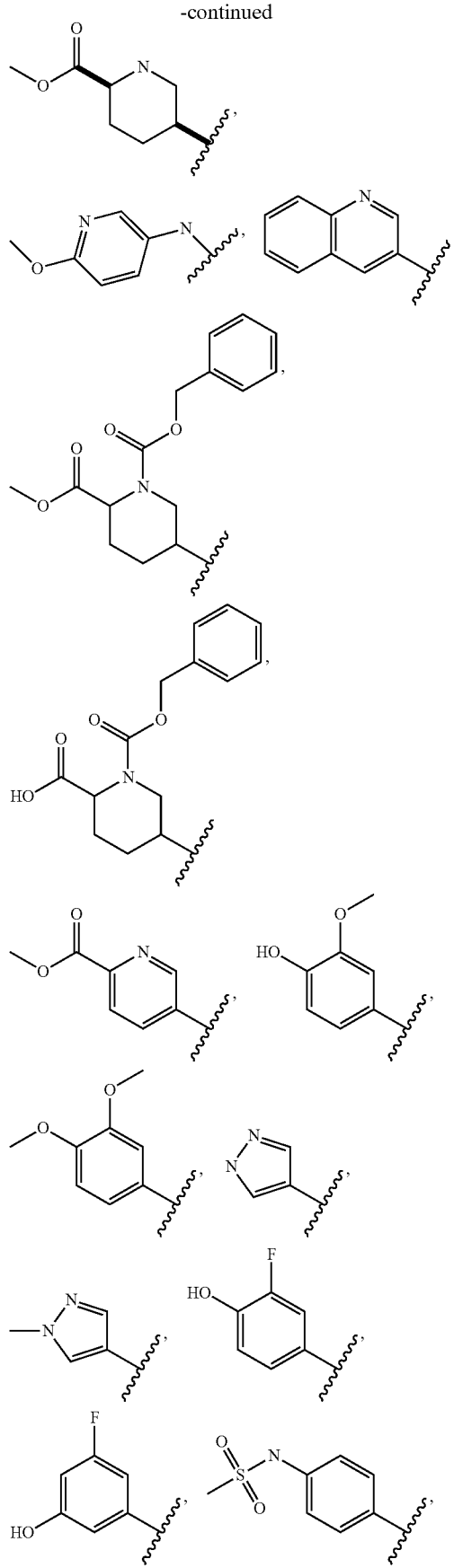
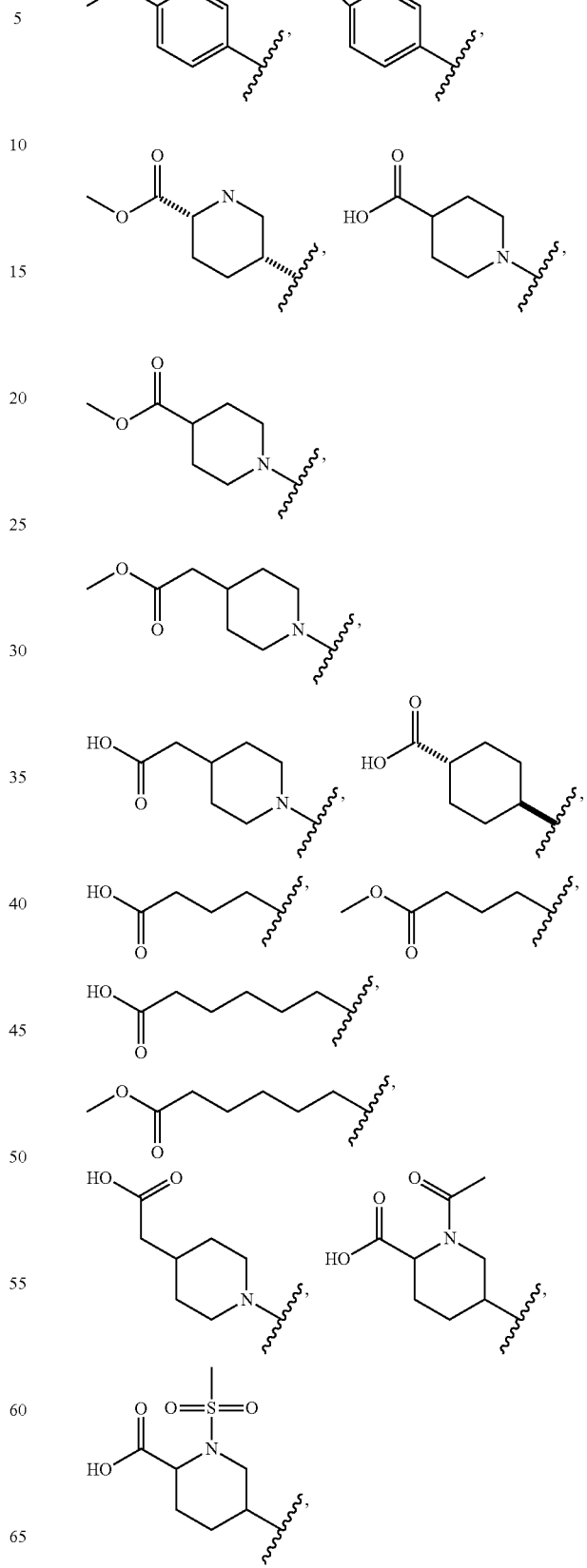

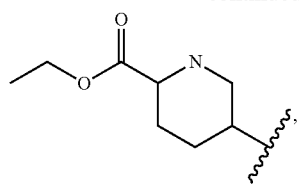
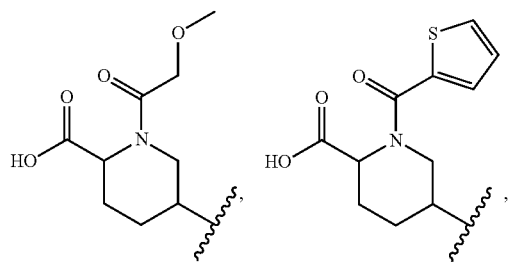
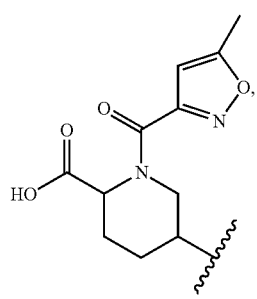
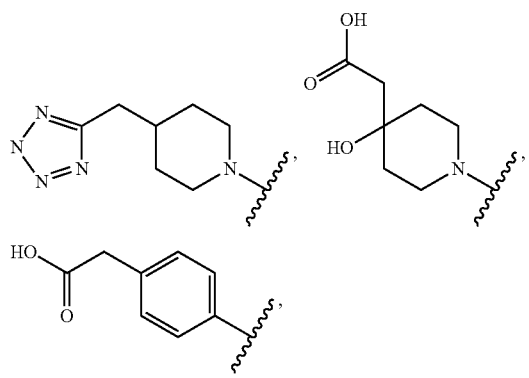
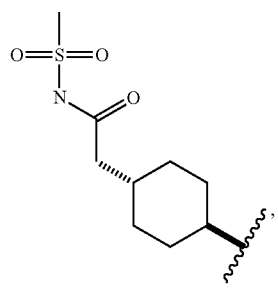
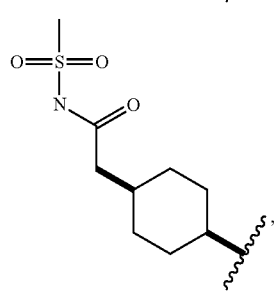
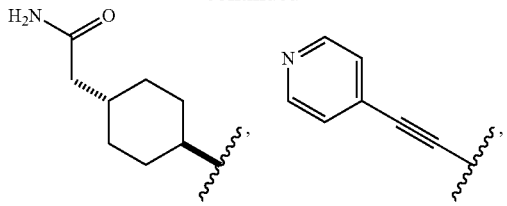
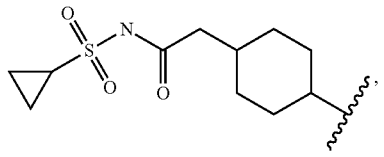
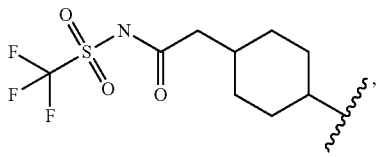
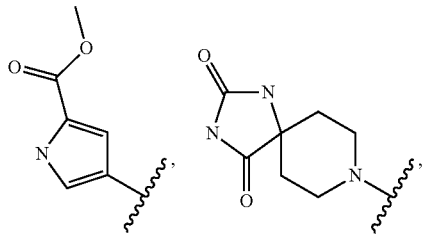
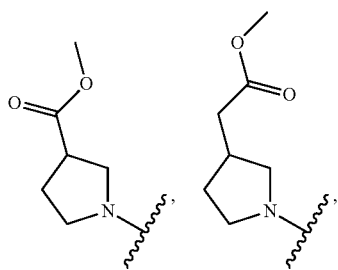
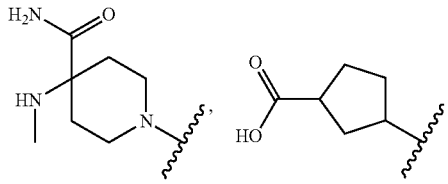
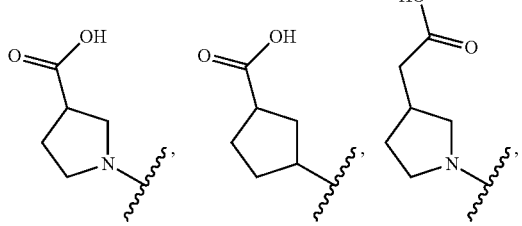

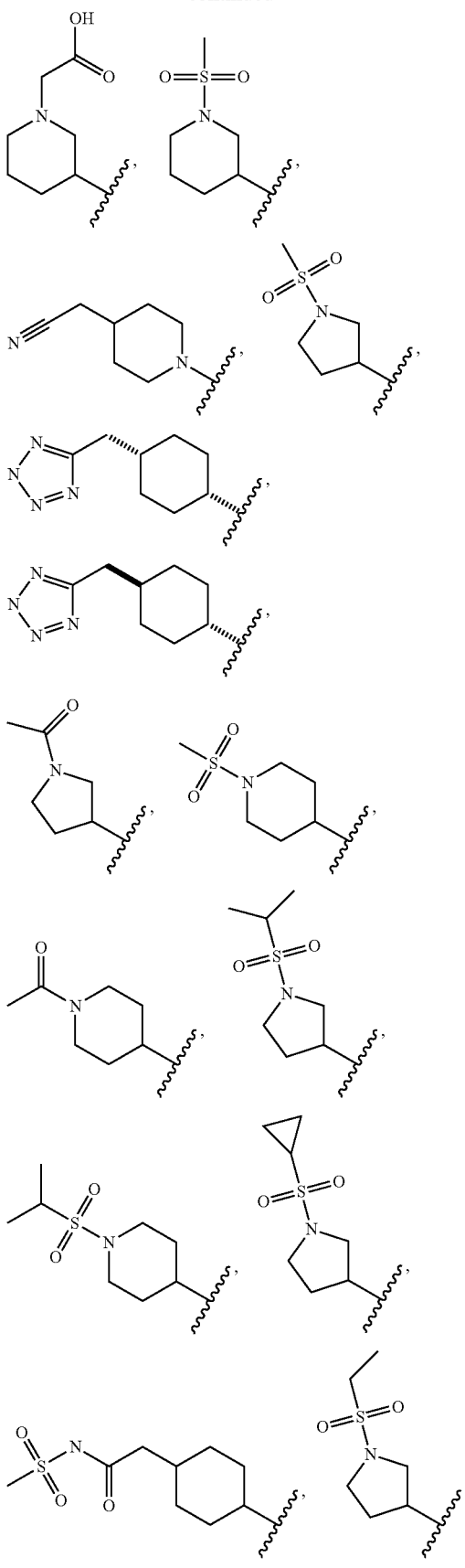
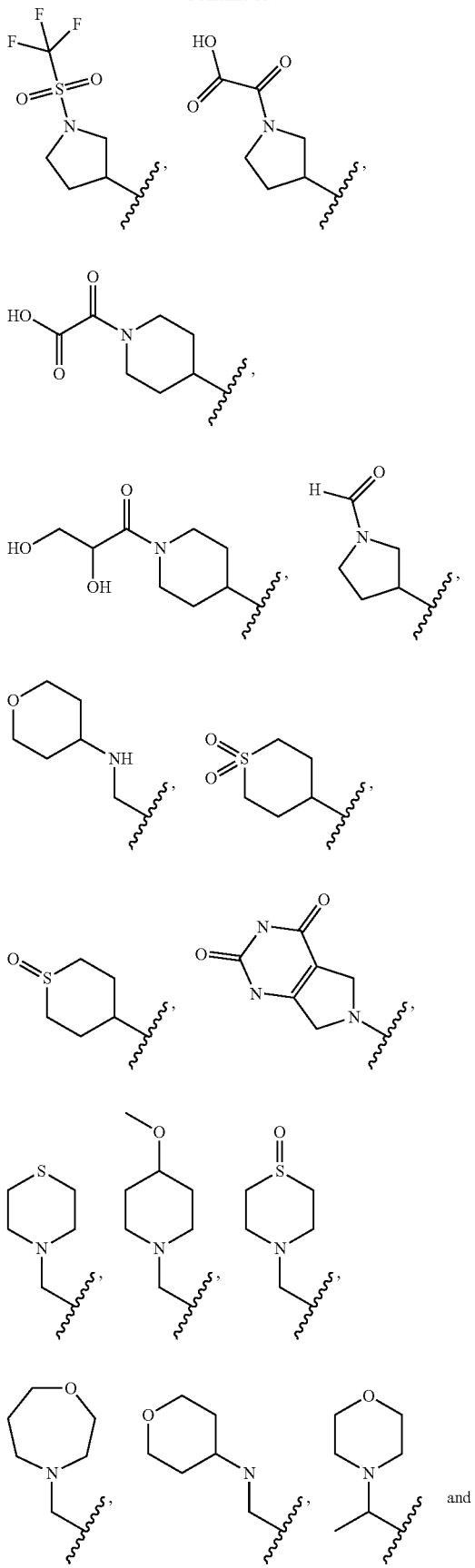

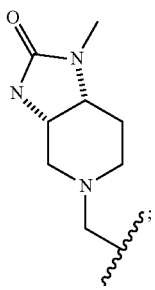

and

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, heteroaryl and arylalkyl.

In another embodiment, the present invention relates to the foregoing method of using a compound represented by the structural Formula I:

Formula I

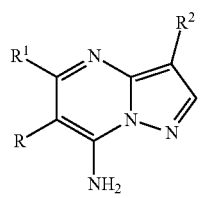

or a pharmaceutically acceptable salt, solvate, ester, or prodrug thereof, wherein:

R is pyrazolyl, wherein said pyrazolyl can be unsubstituted or substituted with alkyl;

R¹ is independently selected from the group consisting of:

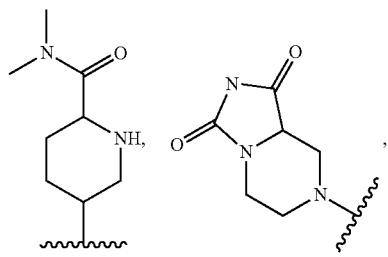

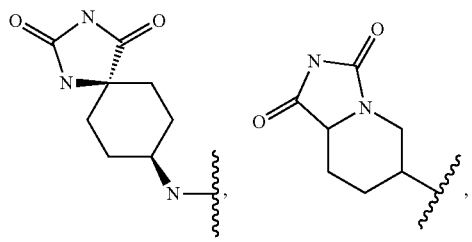

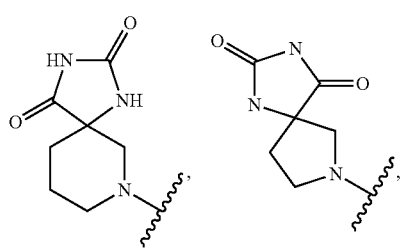

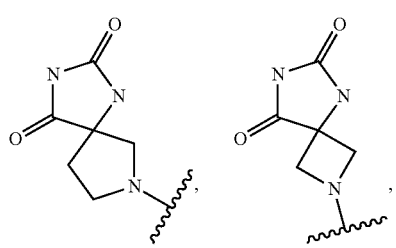

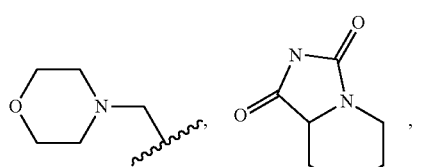

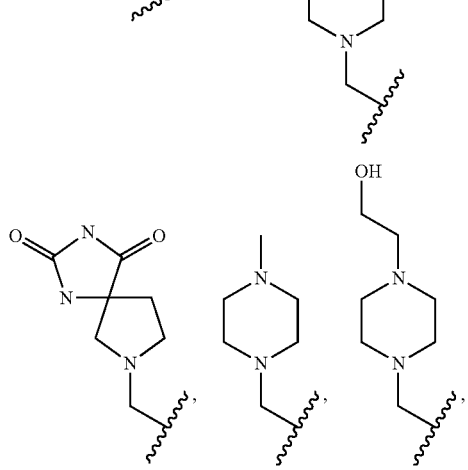

119
-continued
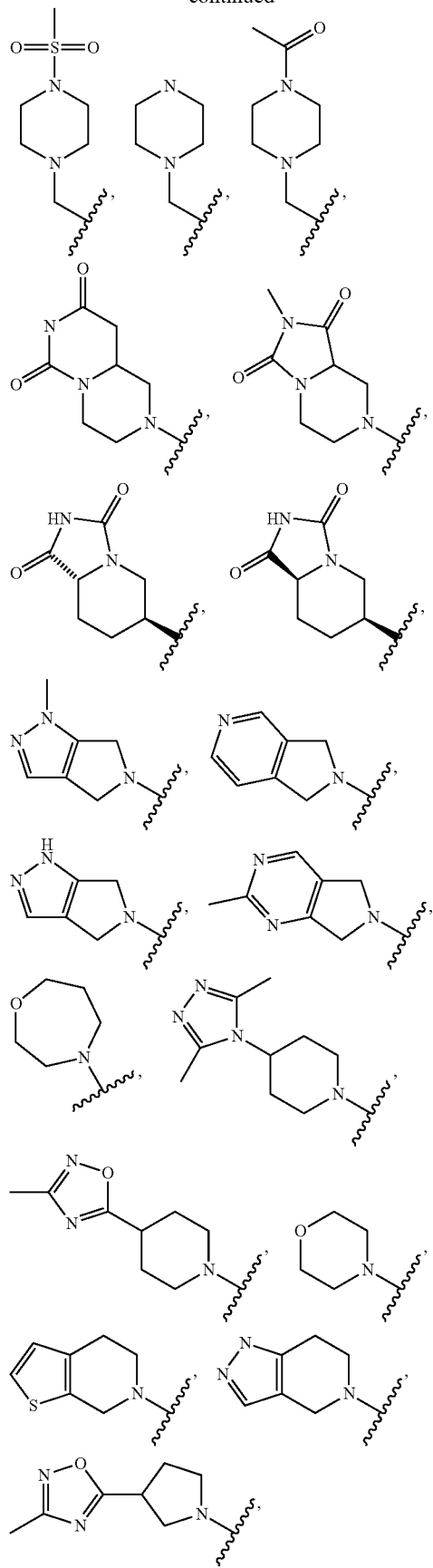
120
-continued
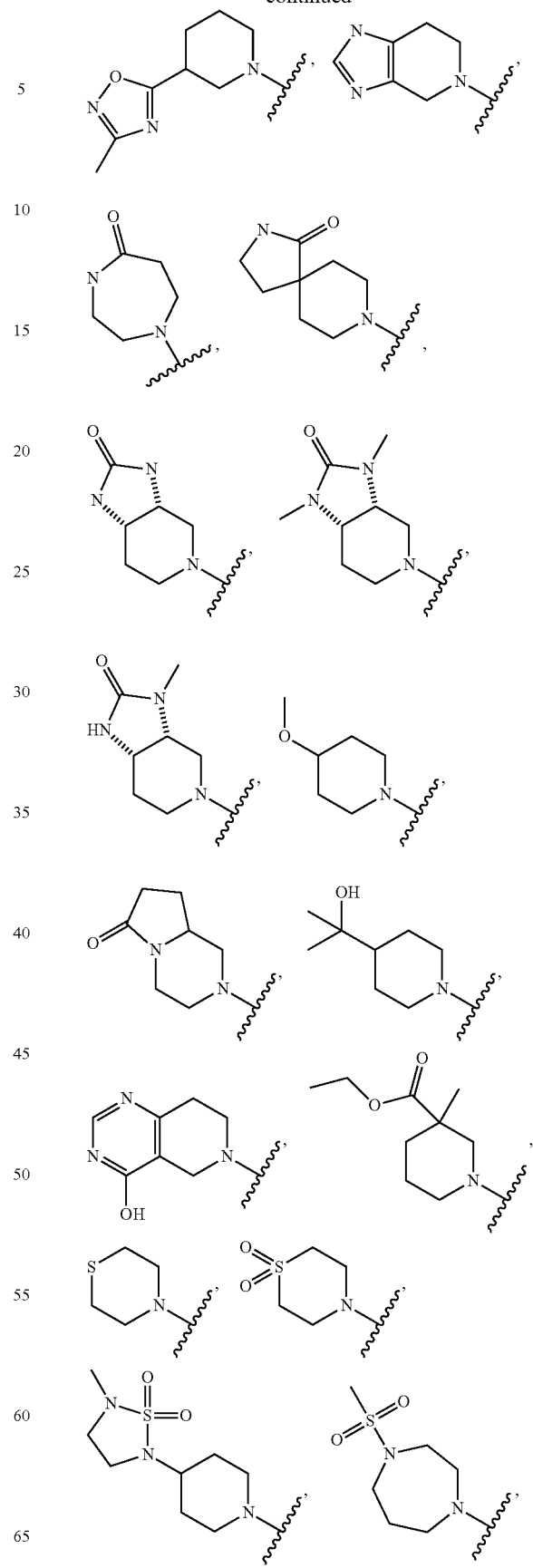

121
-continued
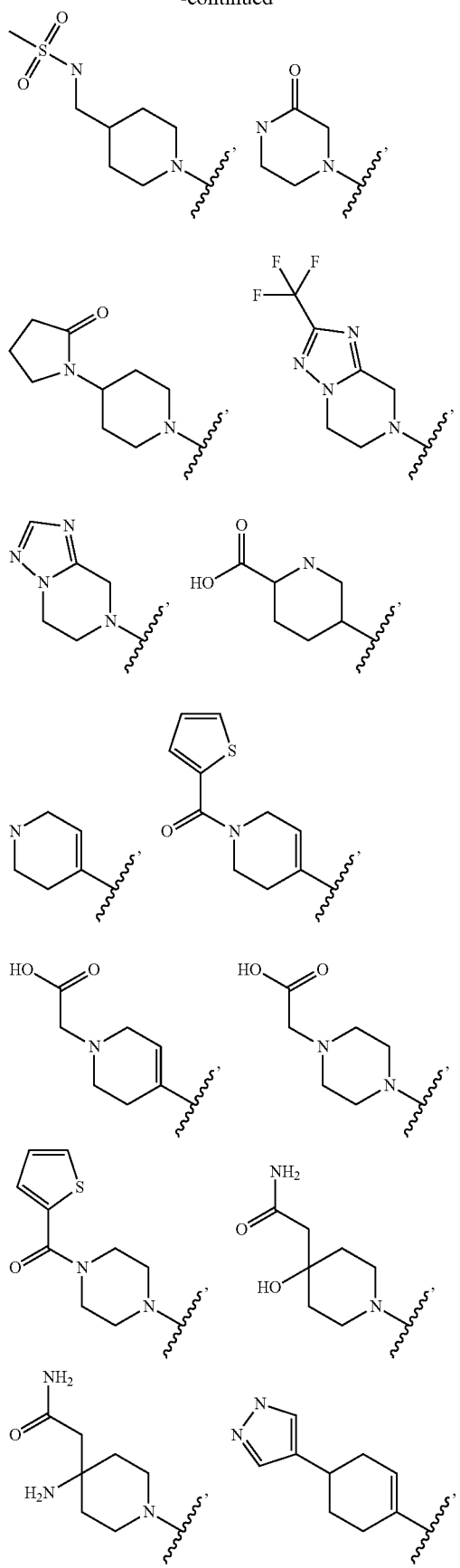
122
-continued
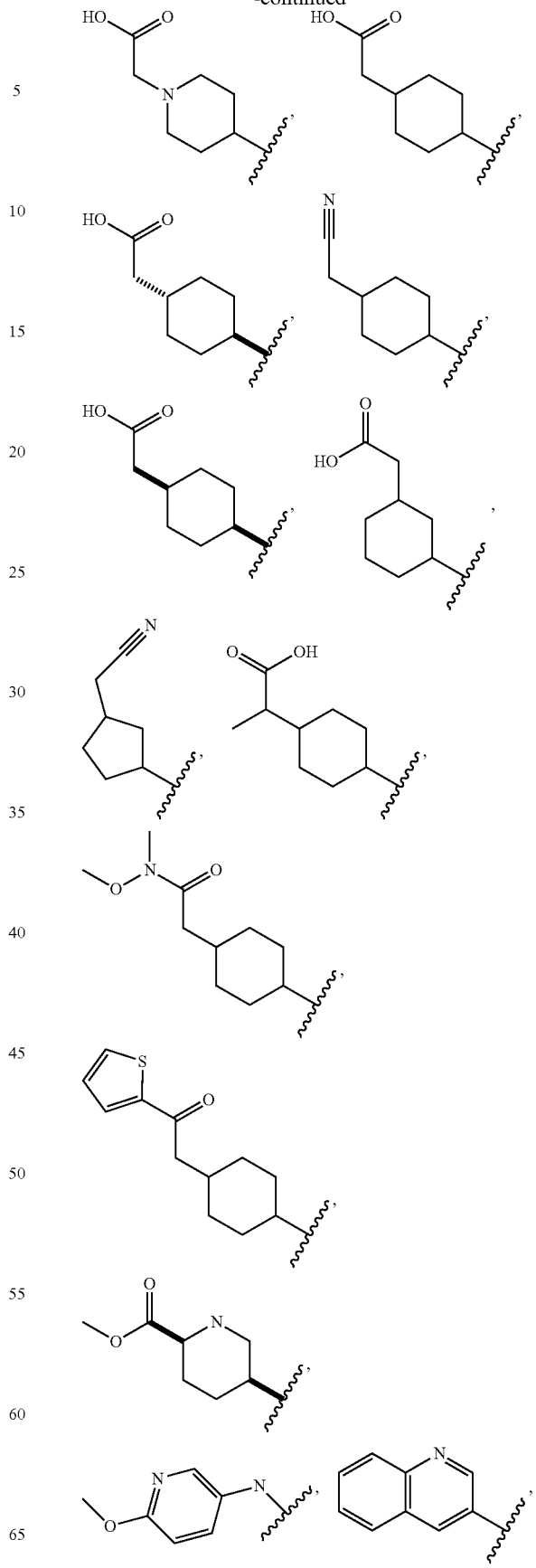

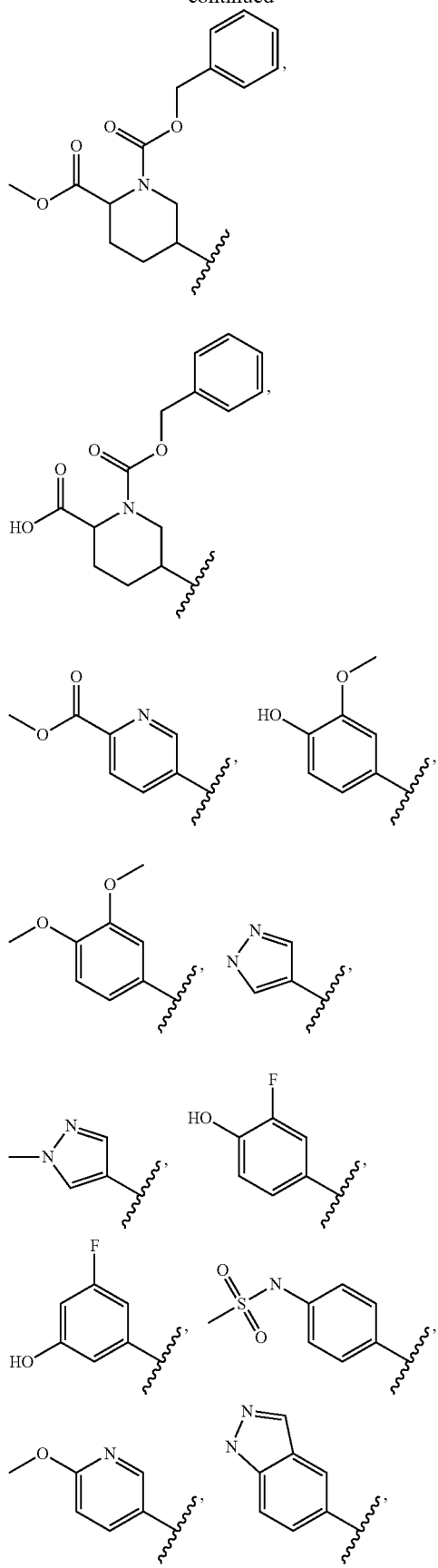
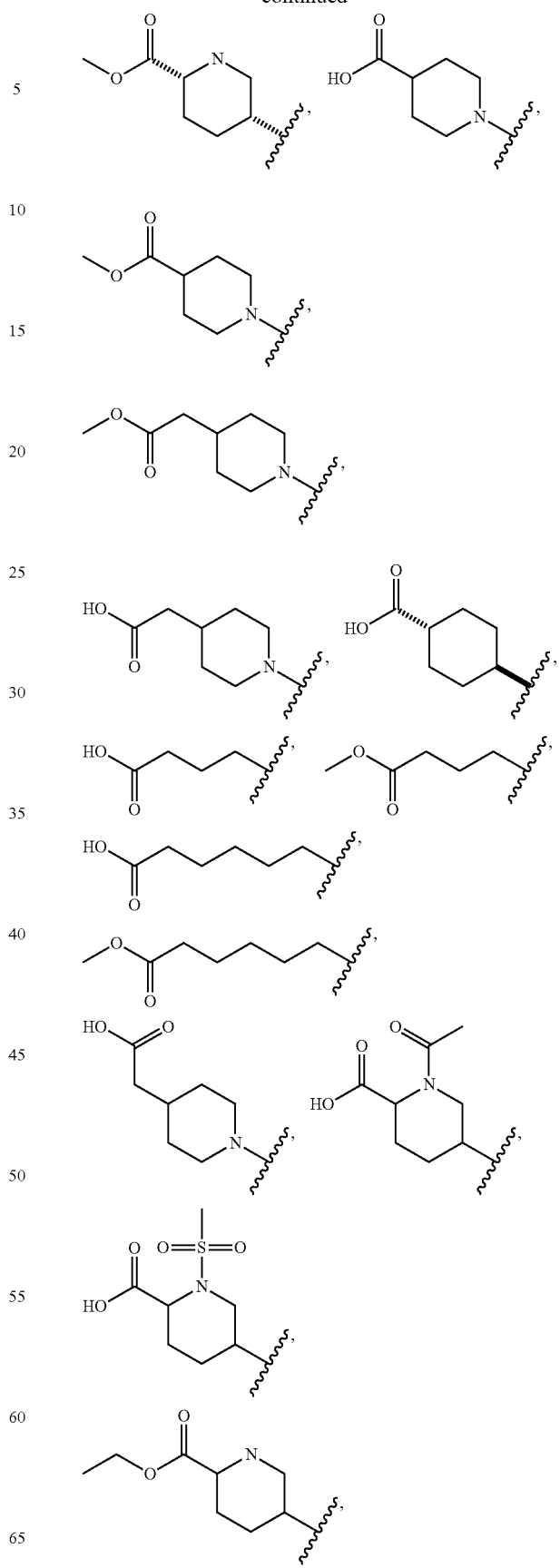

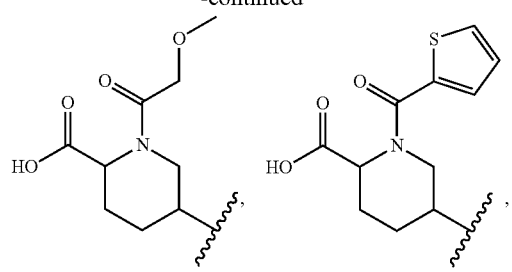
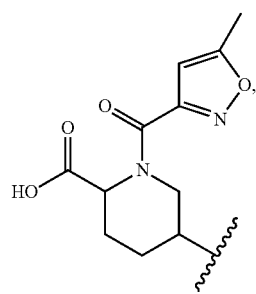
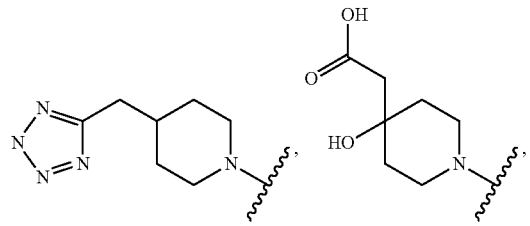
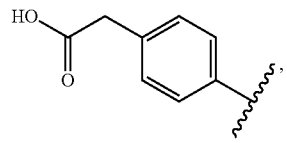
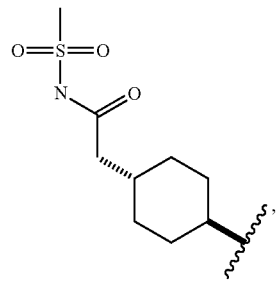
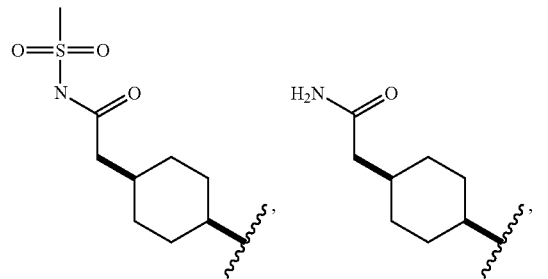
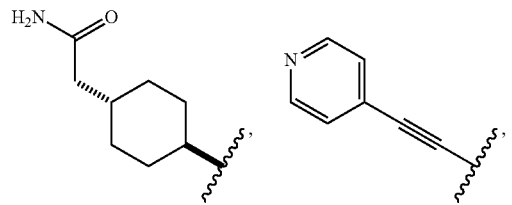
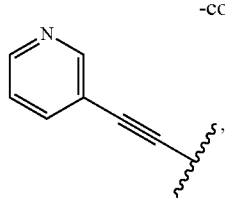
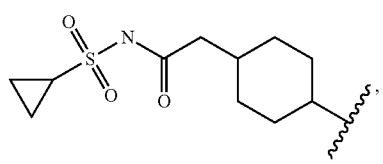
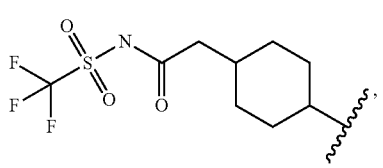
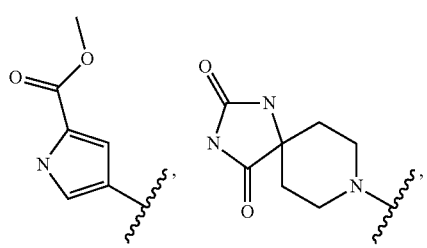
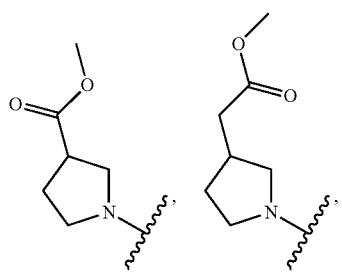
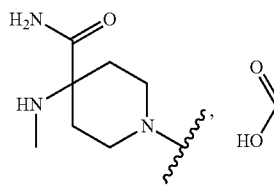
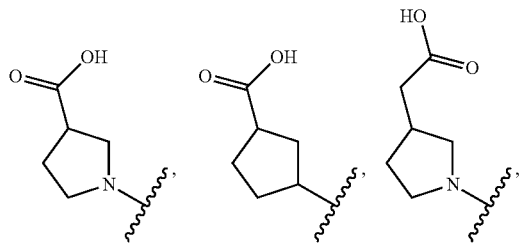
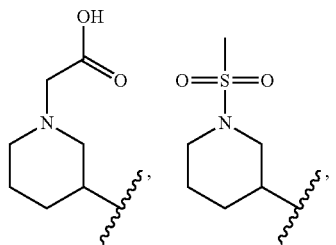

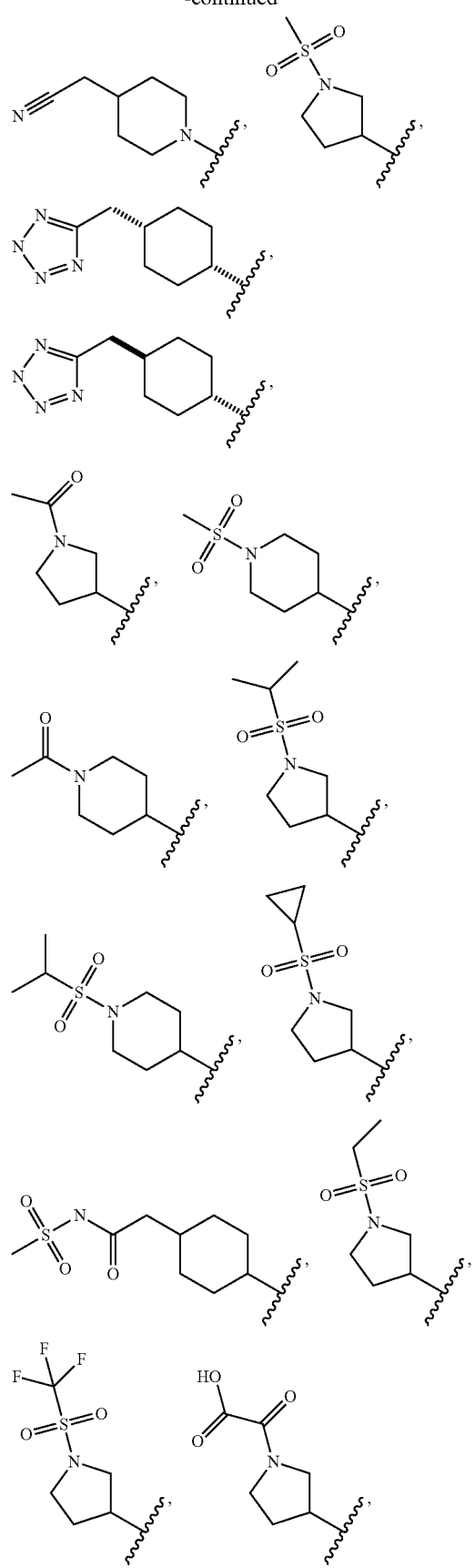
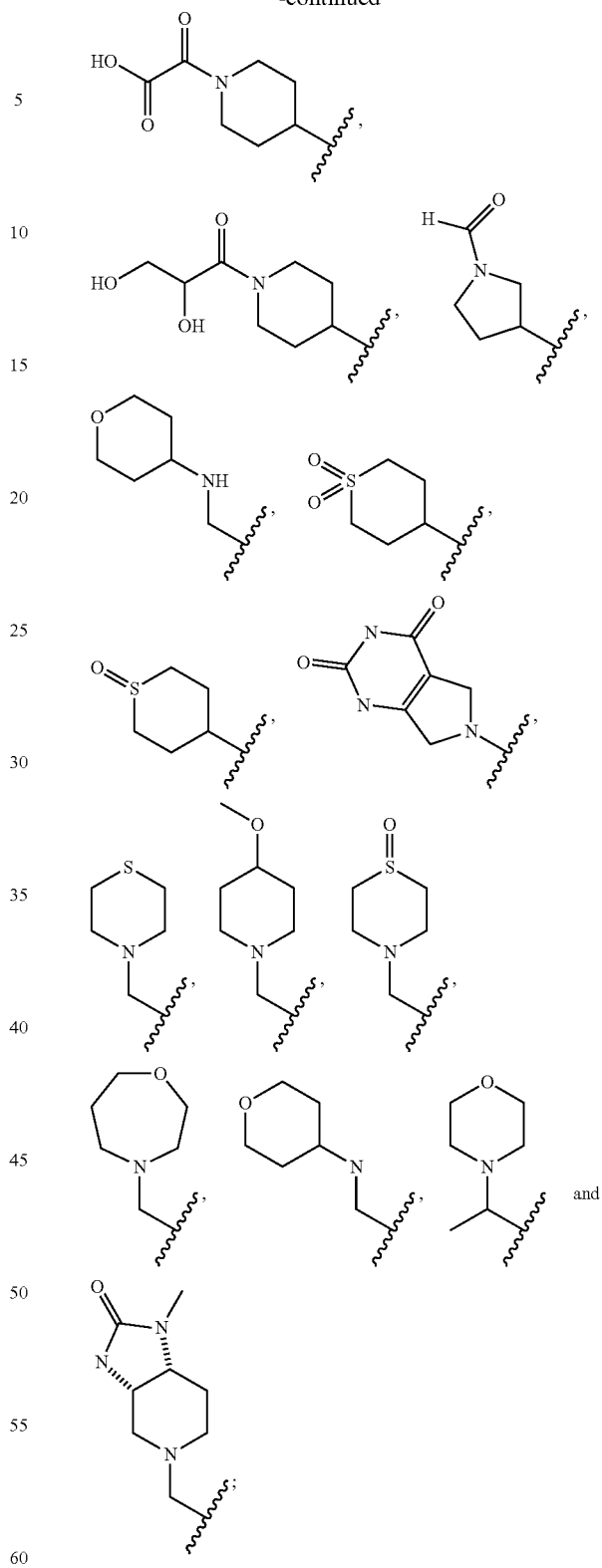
and
R[2] is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, heteroaryl and arylalkyl.

In another embodiment, the present invention relates to the foregoing method of using a compound represented by the structural Formula I:

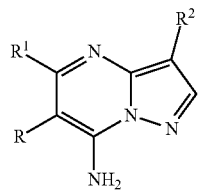

Formula I or a pharmaceutically acceptable salt, solvate, ester, or prodrug thereof, wherein:

R is pyridinyl;

R¹ is independently selected from the group consisting of:

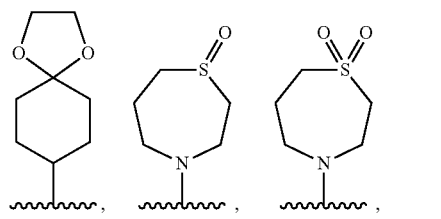

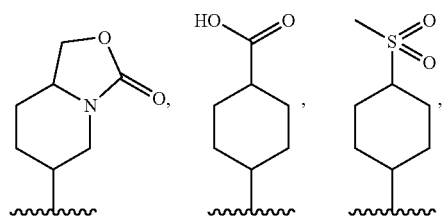

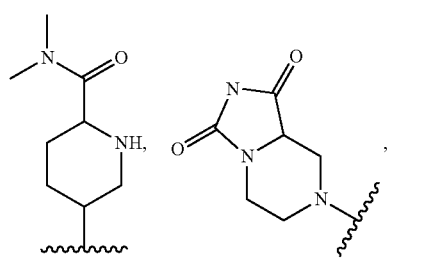

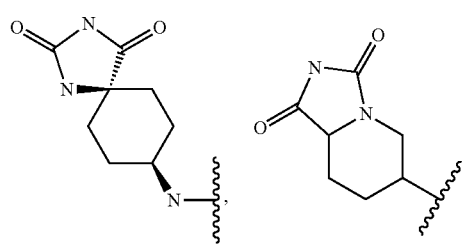

-continued

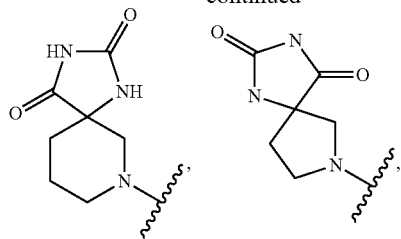

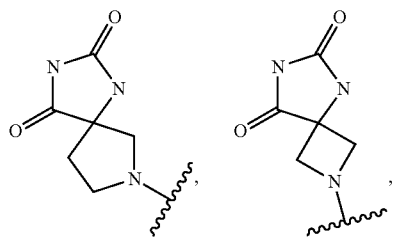

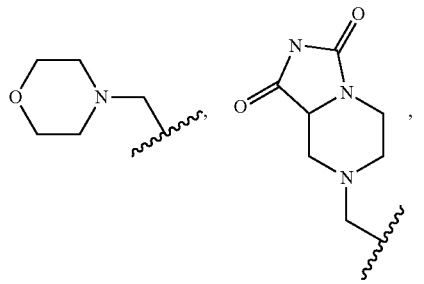

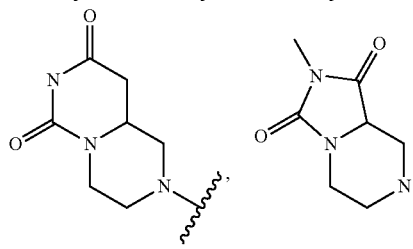

131
-continued
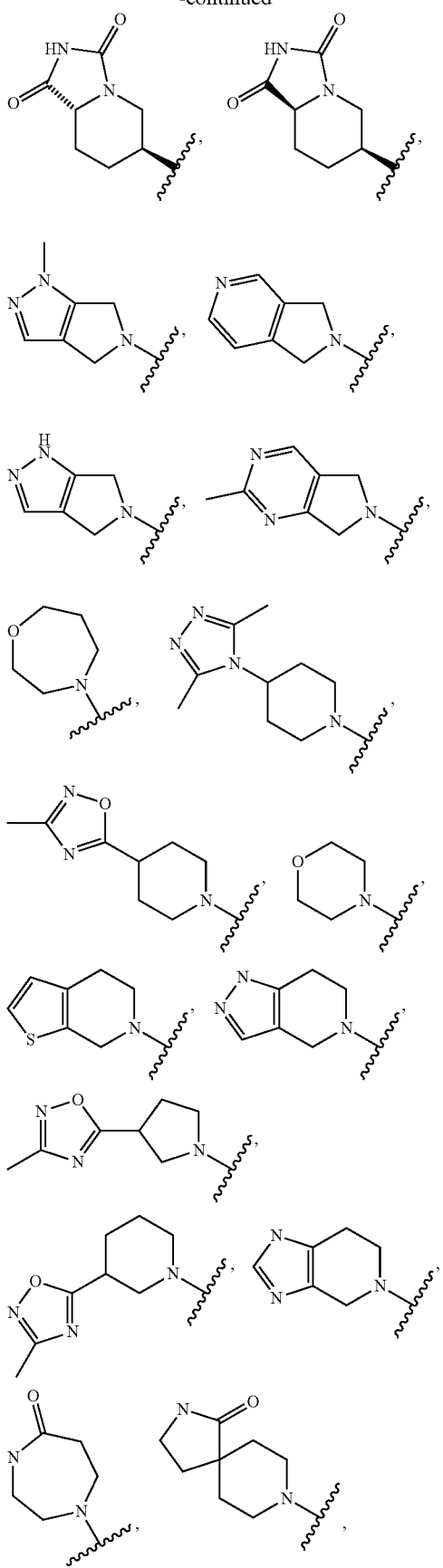
132
-continued
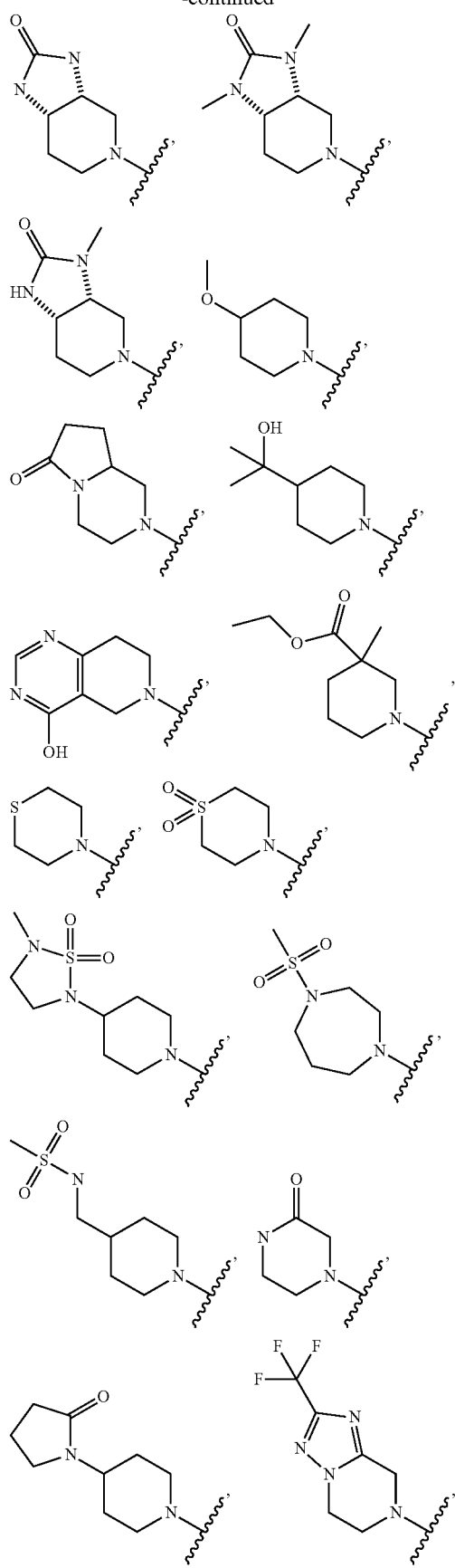

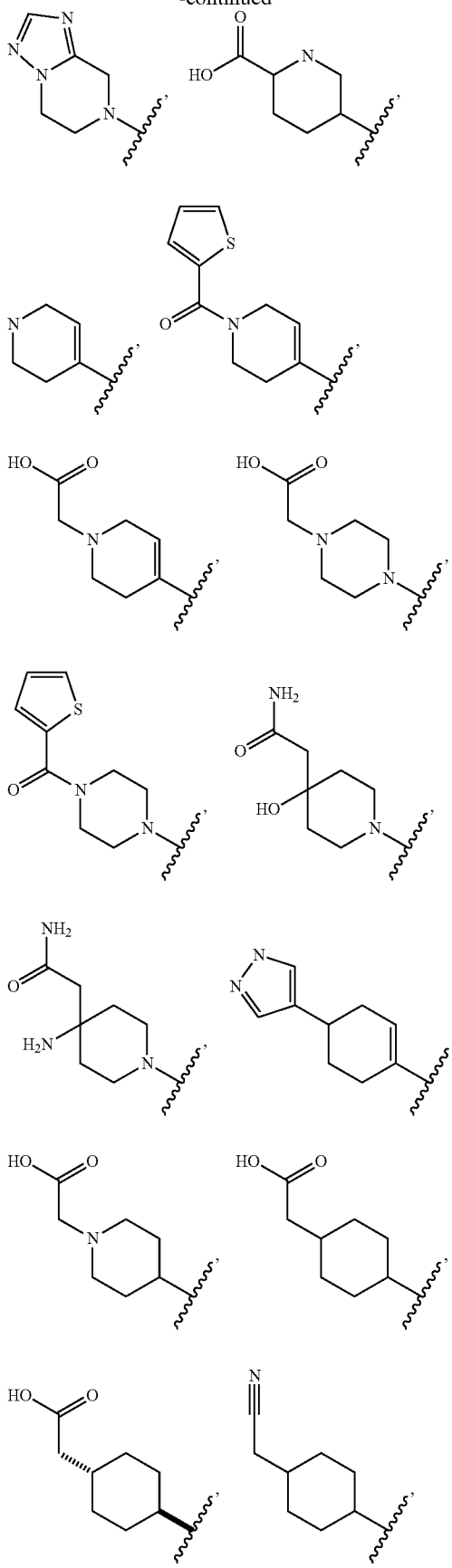
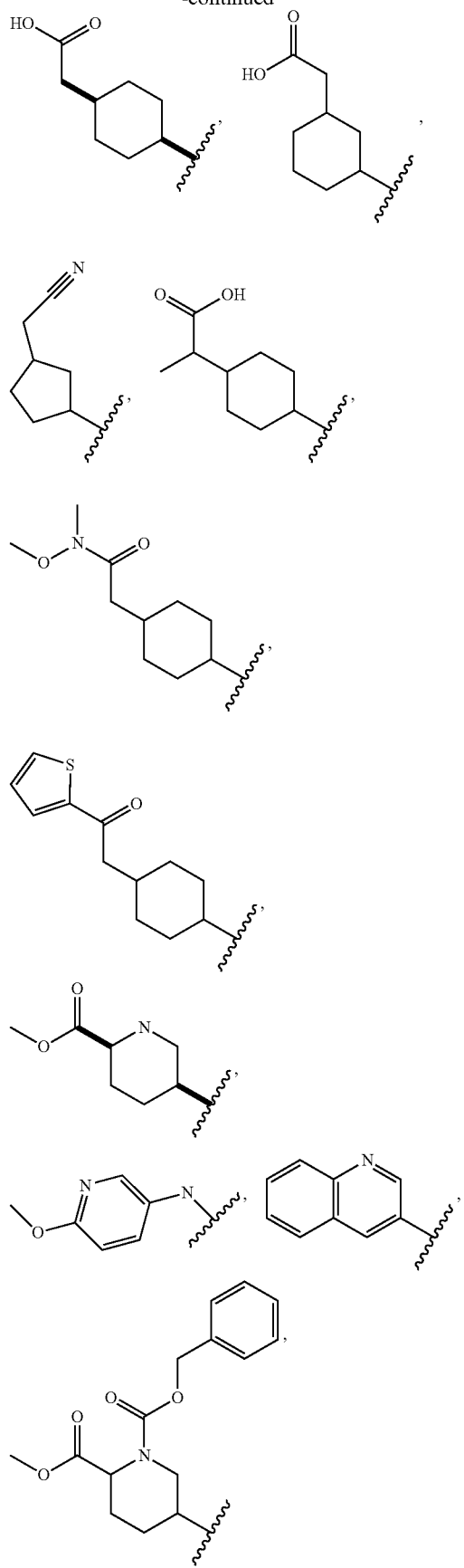

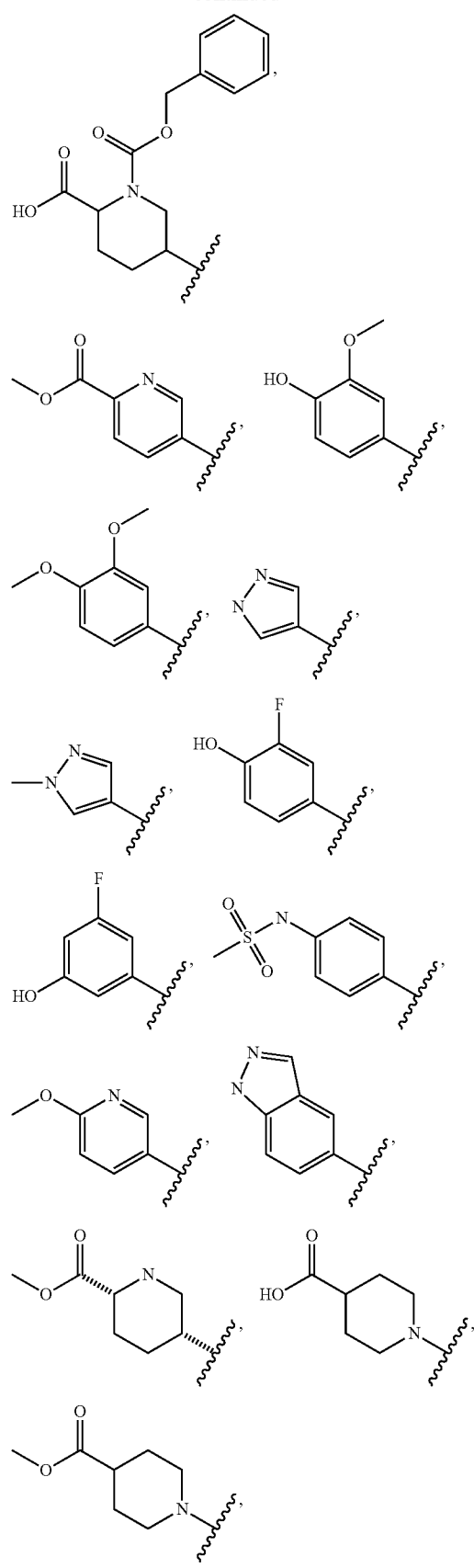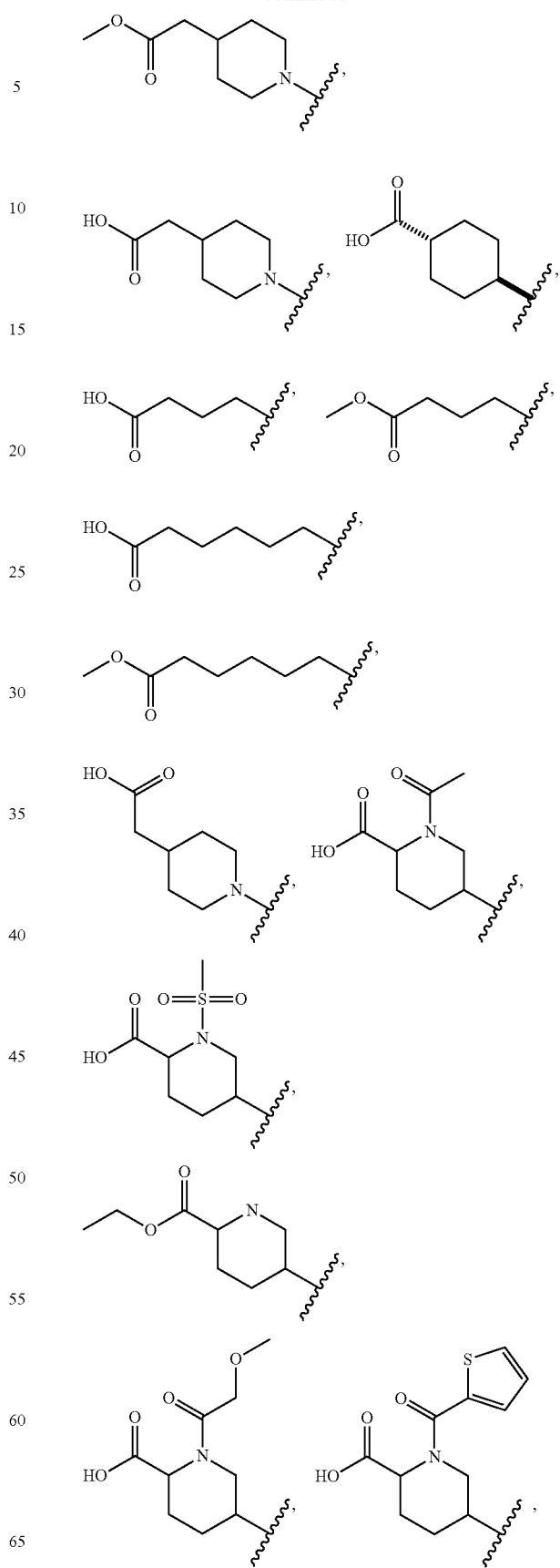

137 138
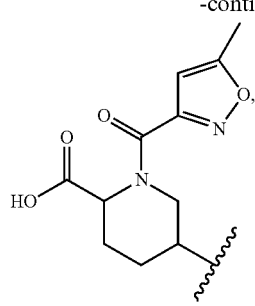 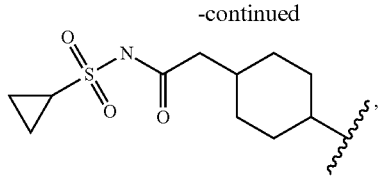
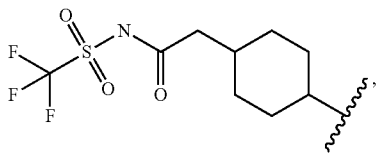
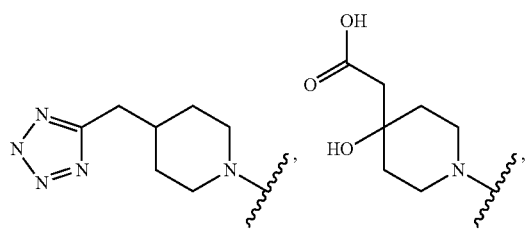 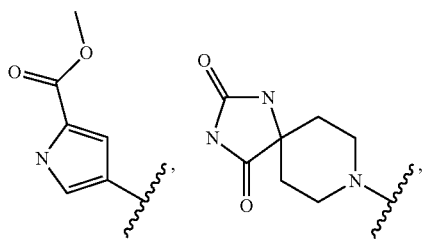
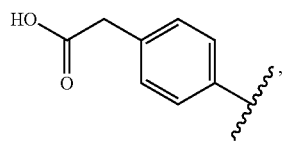 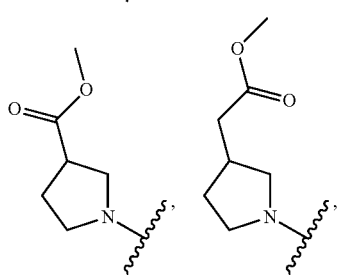
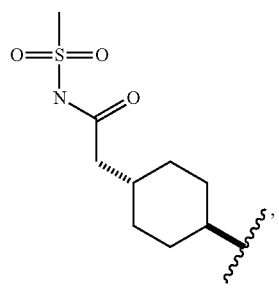 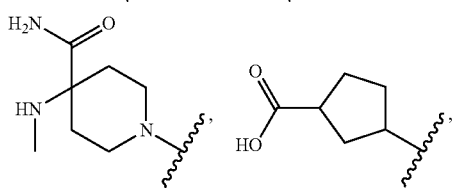
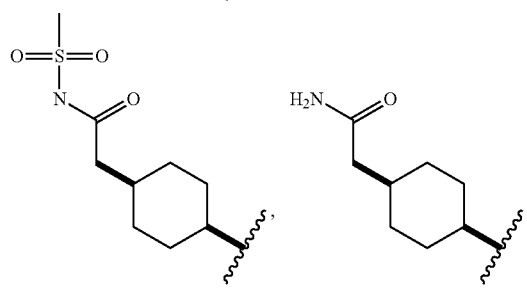 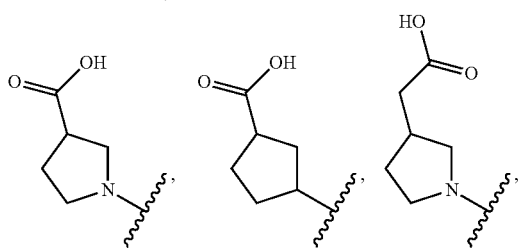
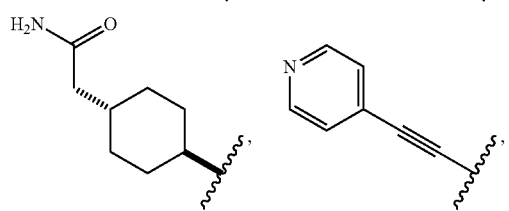 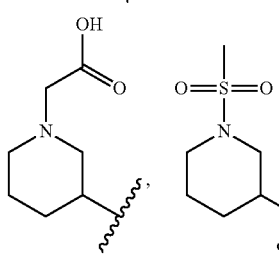
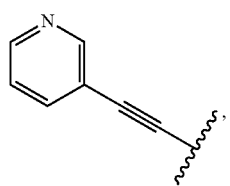 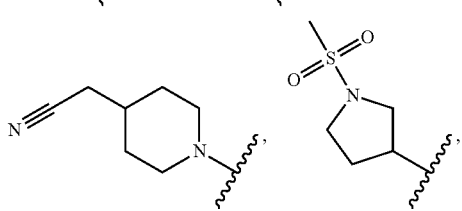

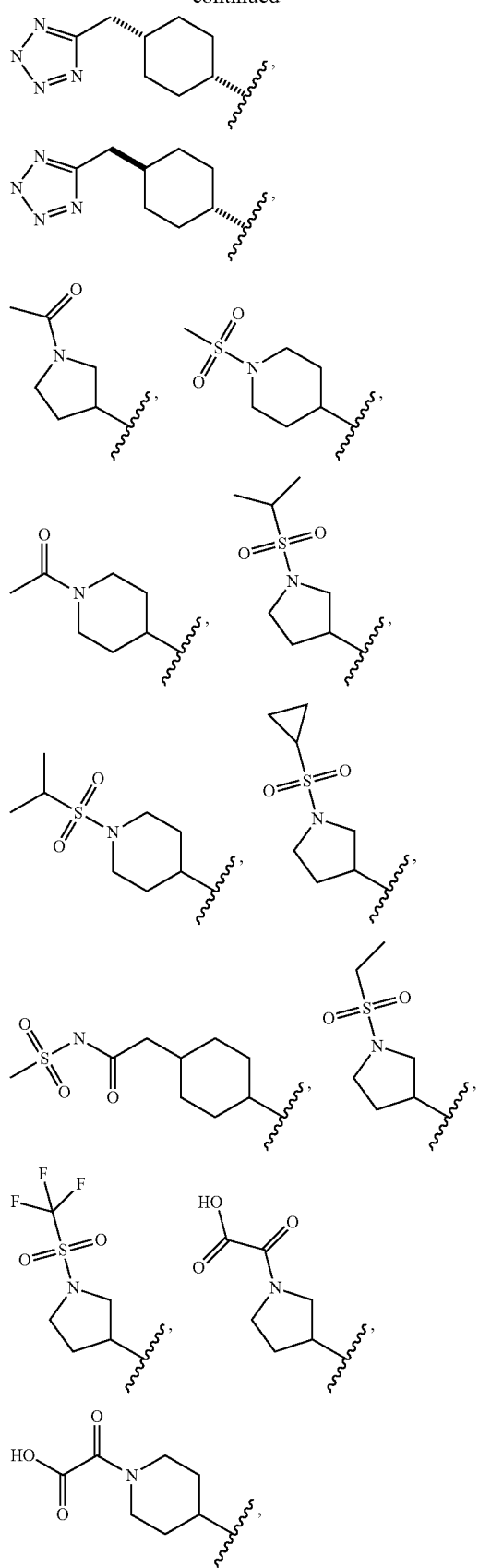
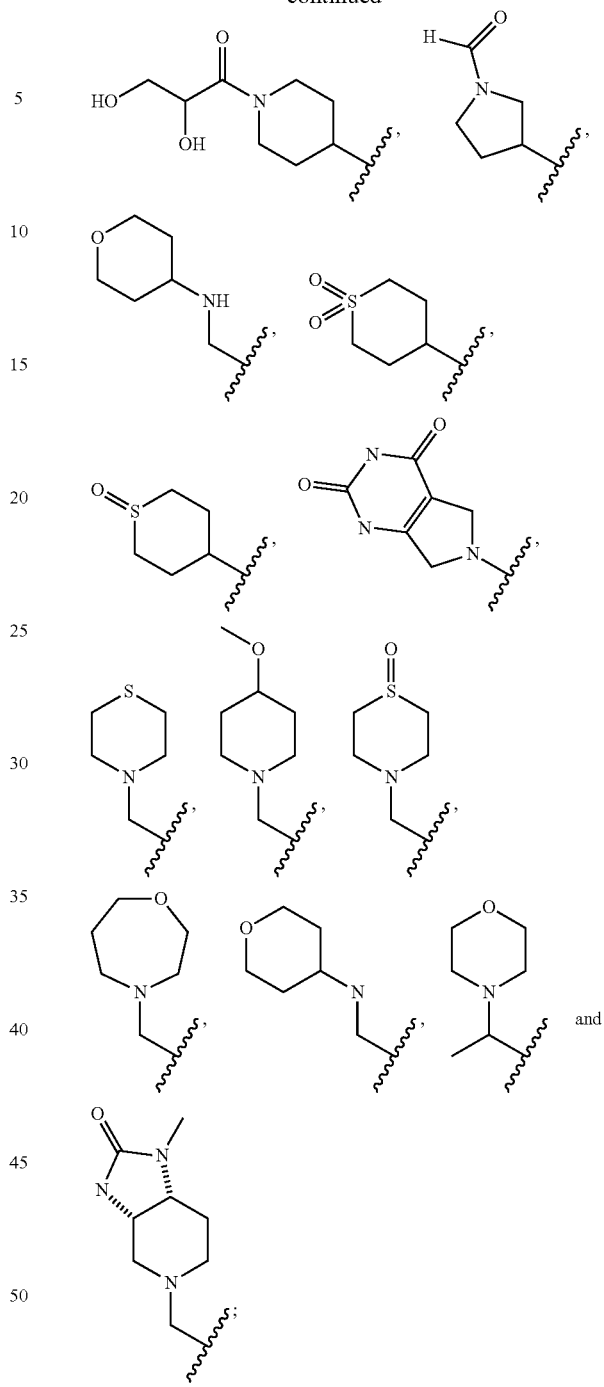

and

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, heteroaryl and arylalkyl.

In another embodiment, the present invention relates to the foregoing method of using a compound represented by the structural Formula I:

Formula I
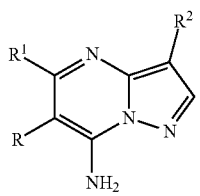
or a pharmaceutically acceptable salt, solvate, ester, or prodrug thereof,
wherein:
R is methyl;
R¹ is independently selected from the group consisting of:
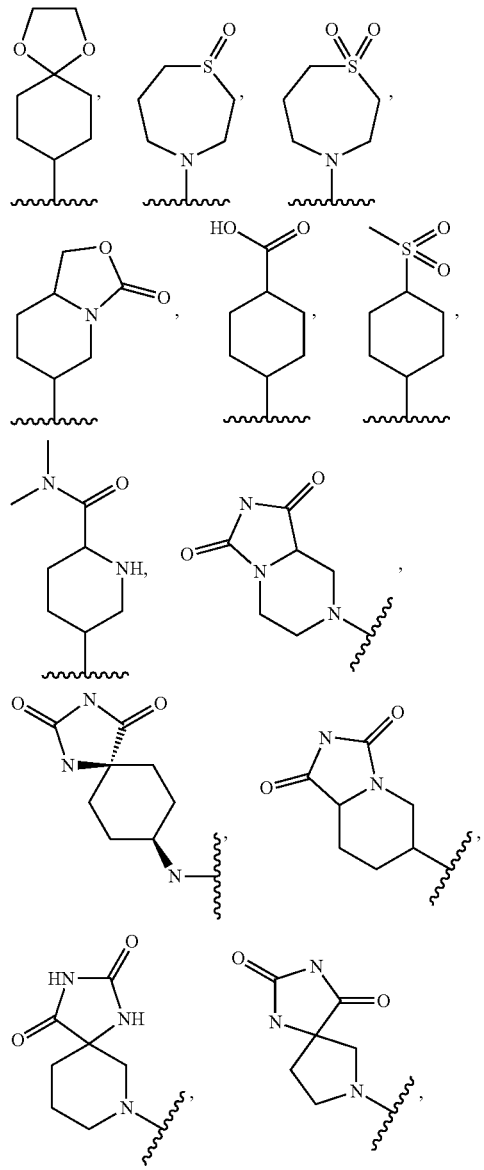
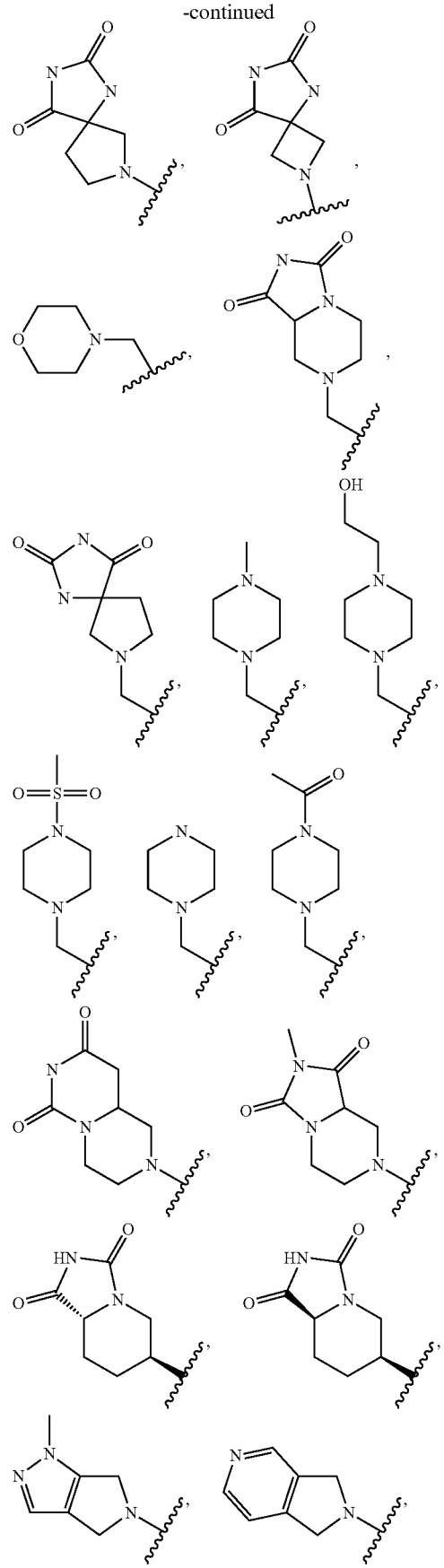

143 144
-continued -continued

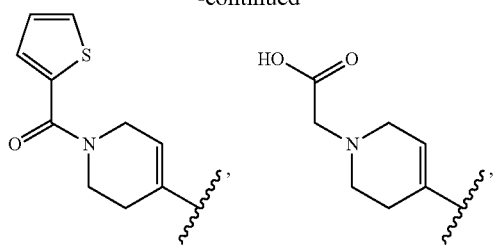
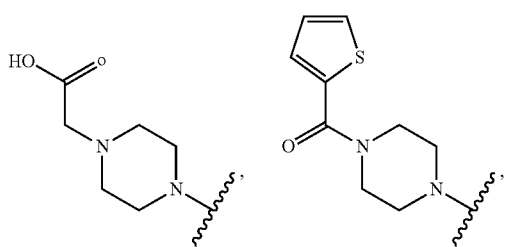
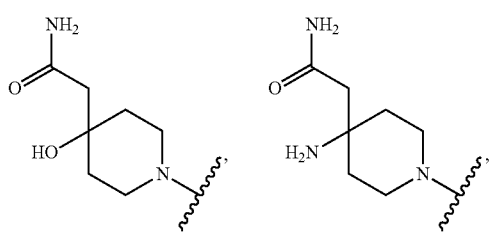
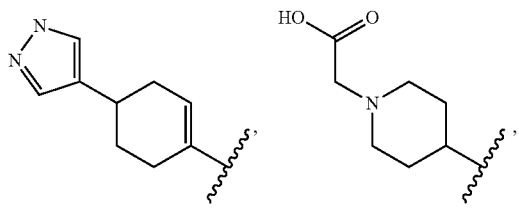
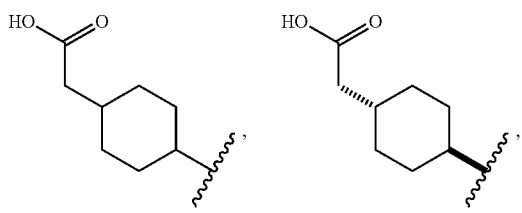
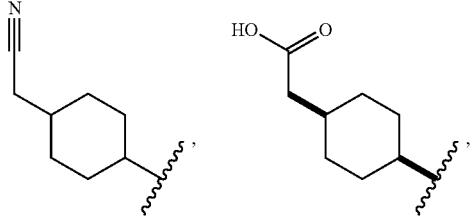
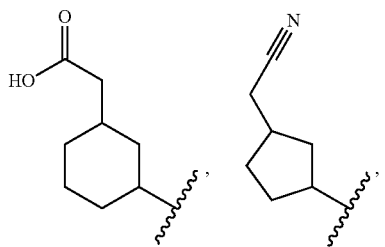
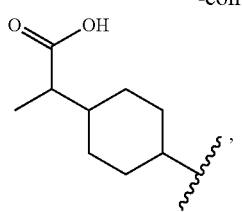
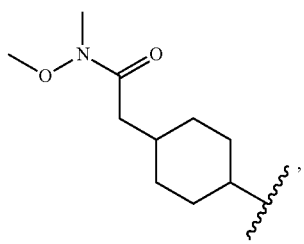
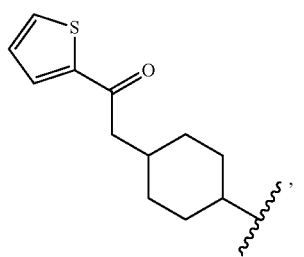
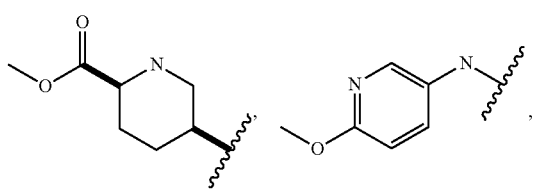
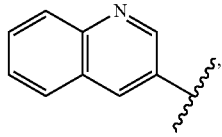
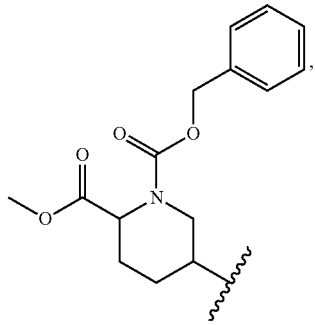
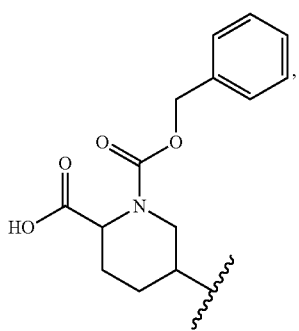

147
-continued
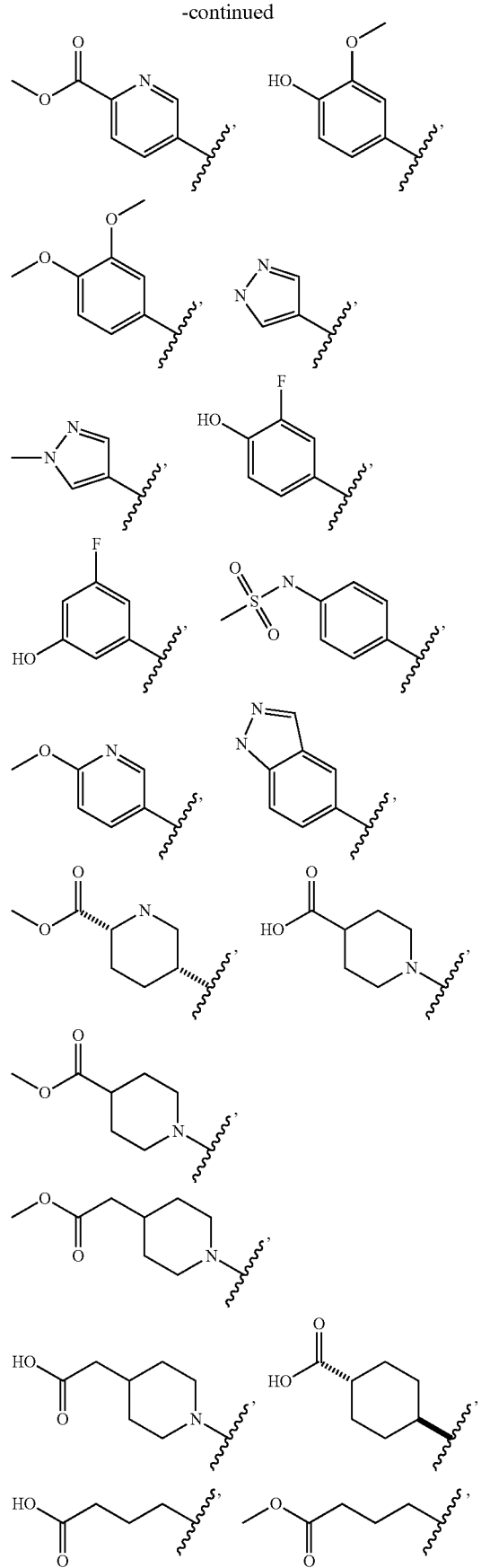
148
-continued
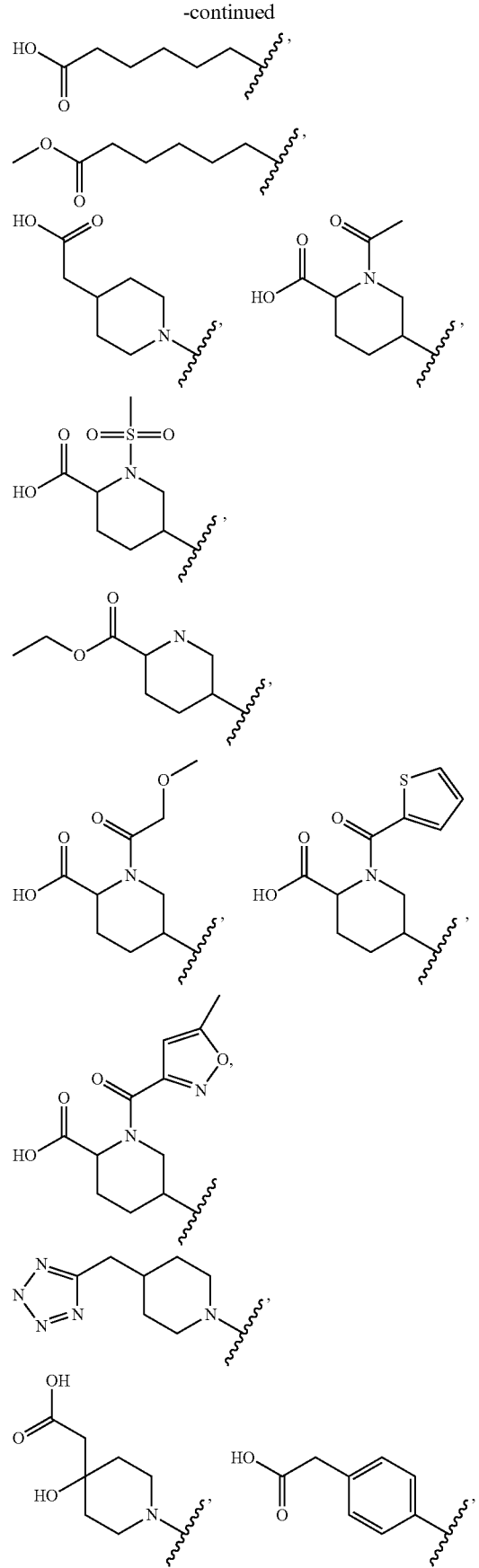

149
-continued
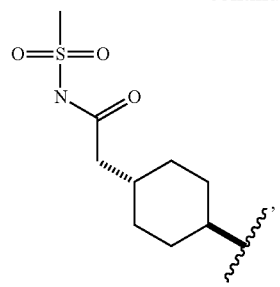
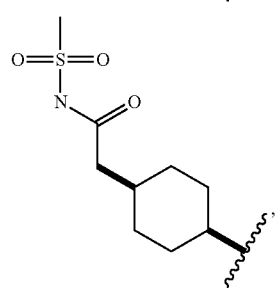
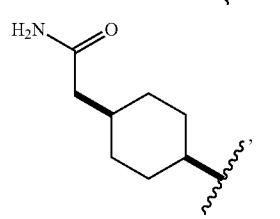
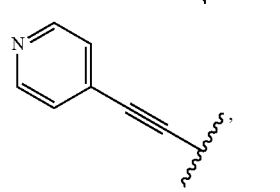
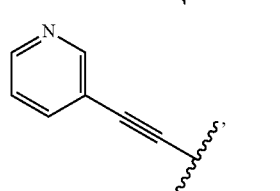
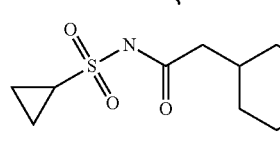
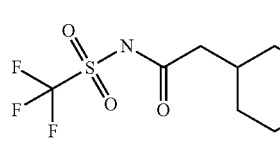
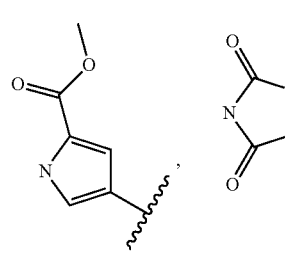
150
-continued
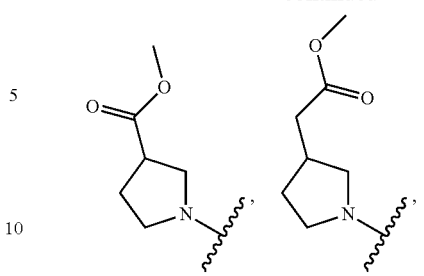
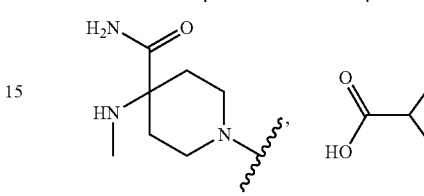
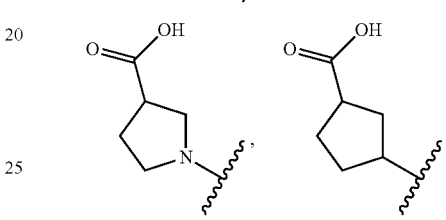
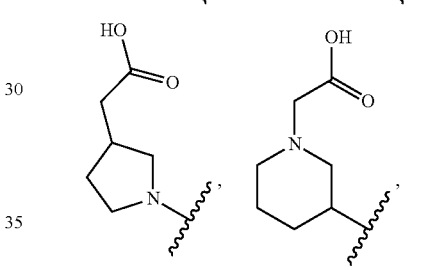
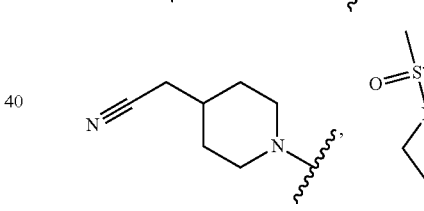
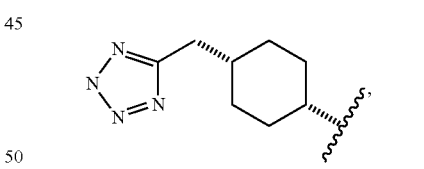
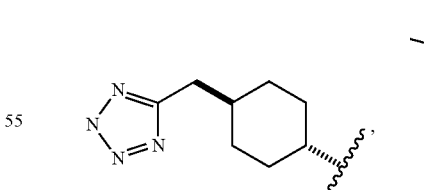
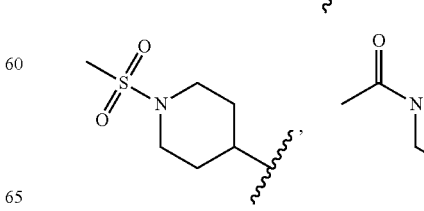

-continued

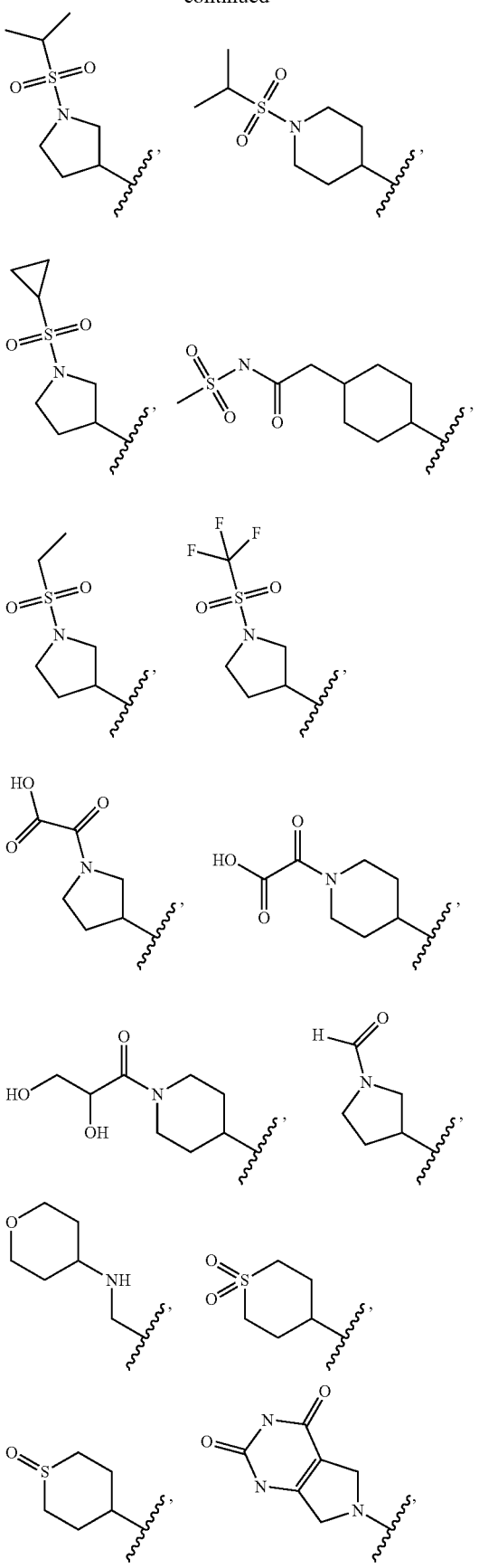

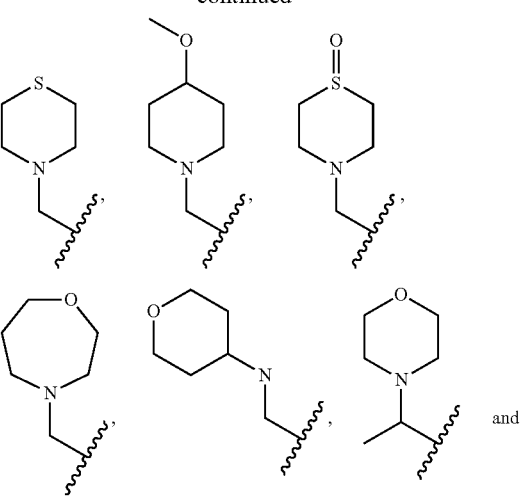

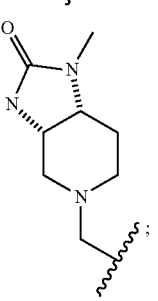

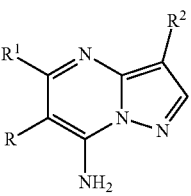

and

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, heteroaryl and arylalkyl.

In another embodiment, the present invention relating to the foregoing method of using a compound represented by the structural Formula I:

Formula I or a pharmaceutically acceptable salt, solvate, ester, or prodrug thereof, wherein:

R is phenyl, wherein said phenyl can be unsubstituted or substituted with one or more moieties which can be the same or different each moiety being independently selected from the group consisting of halo or alkyl;

$R^1$ is independently selected from the group consisting of:
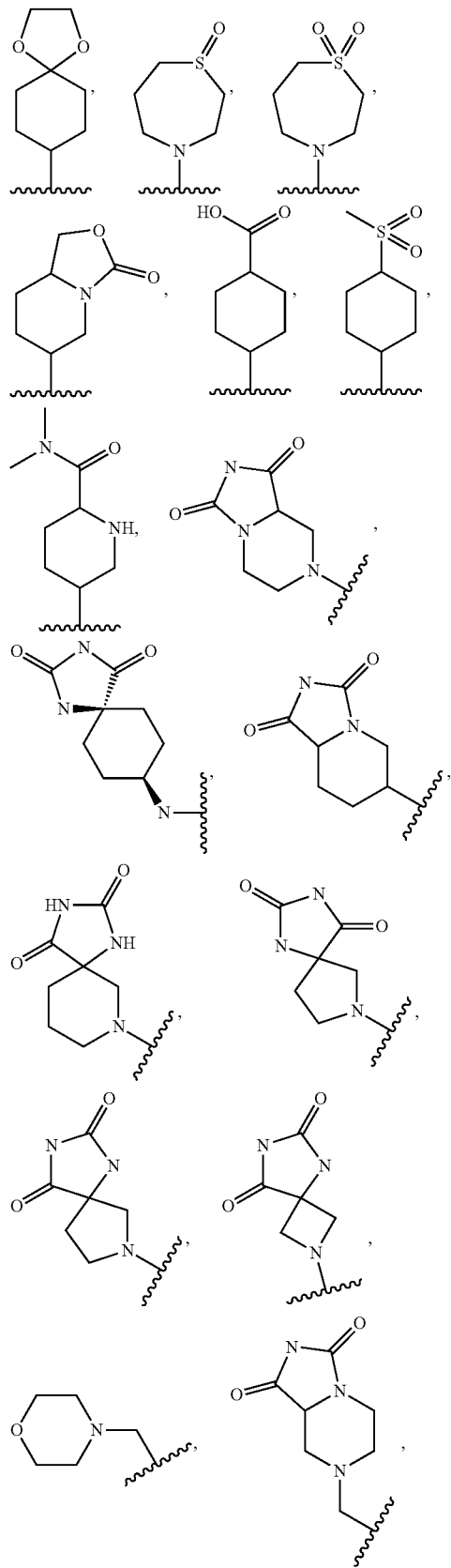
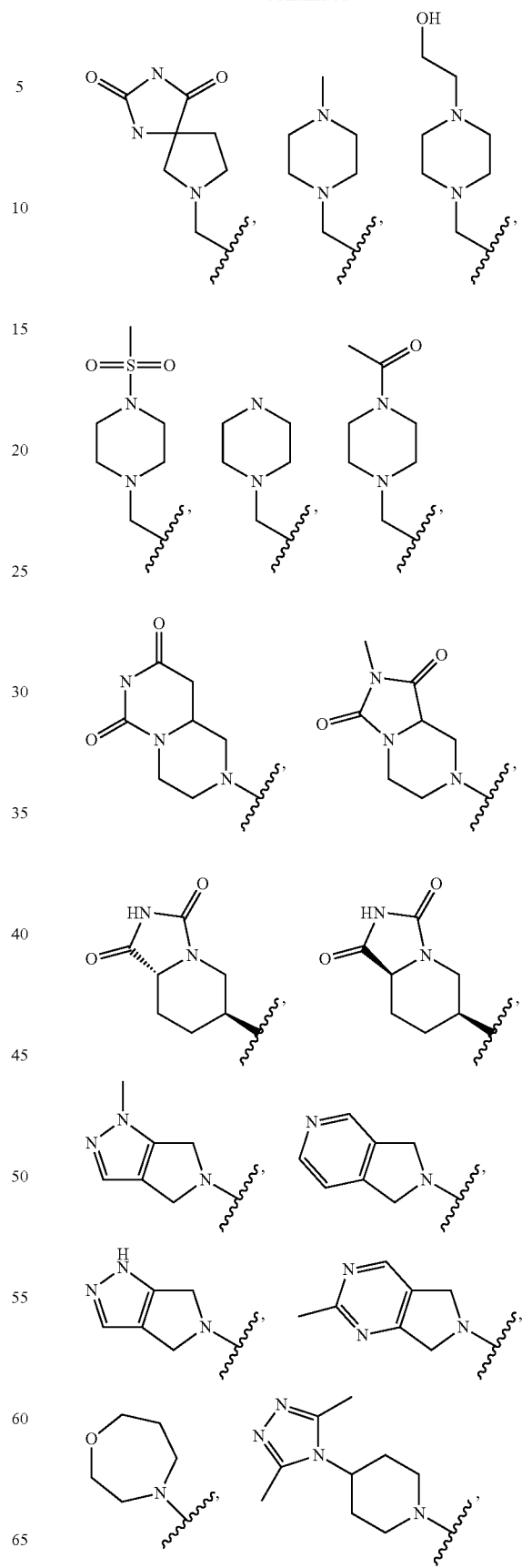

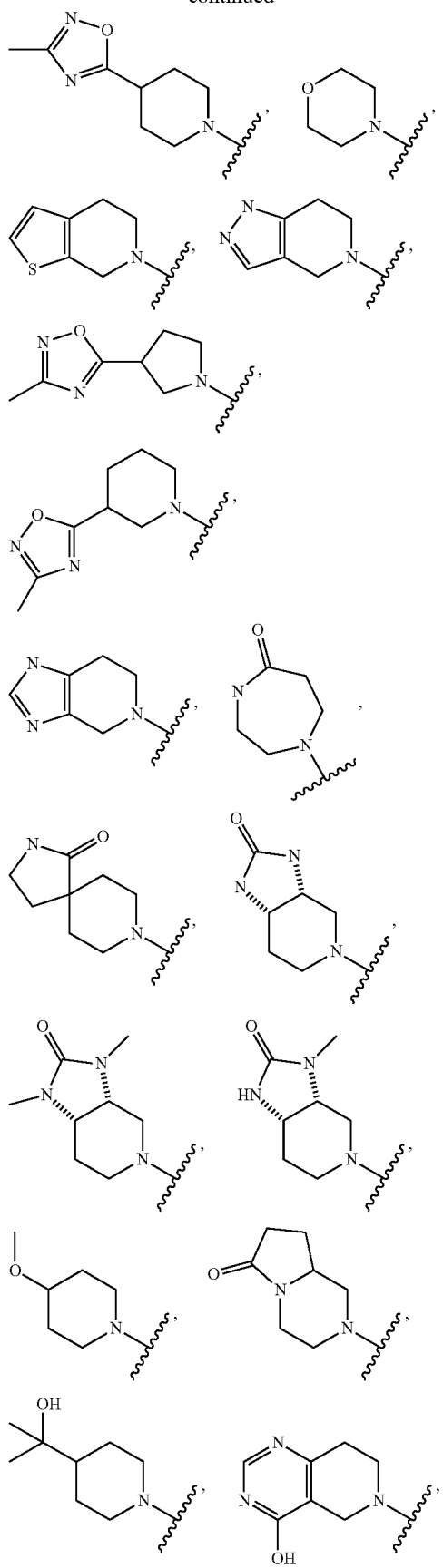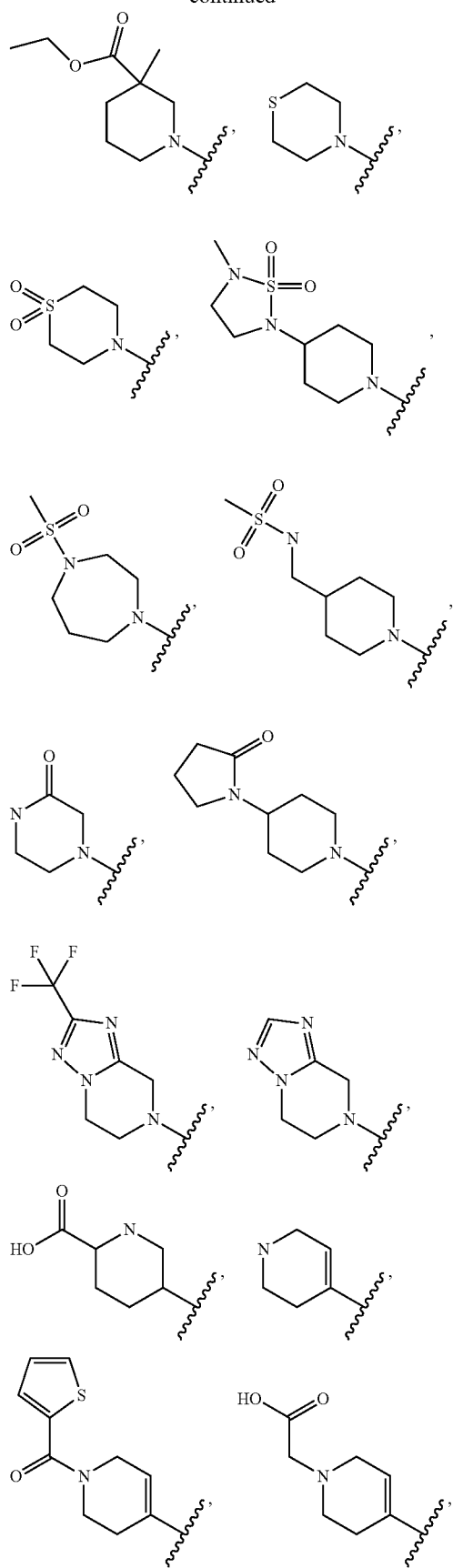

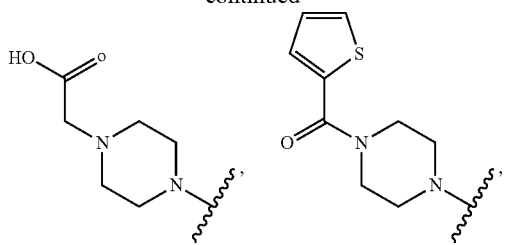
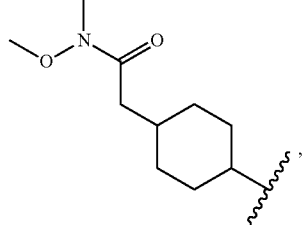
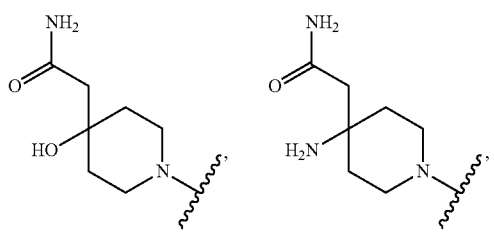
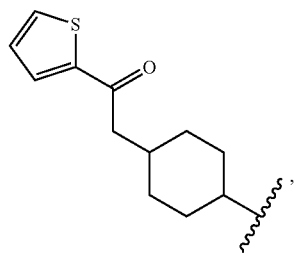
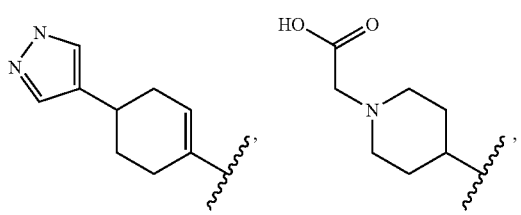
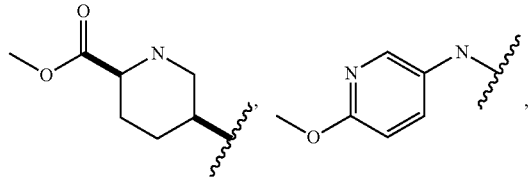
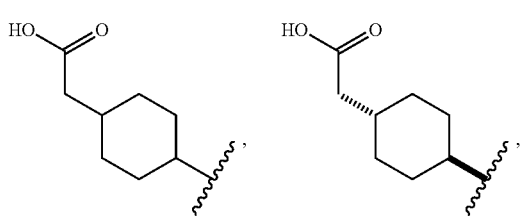
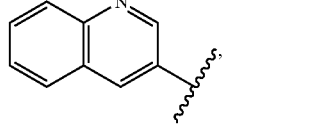
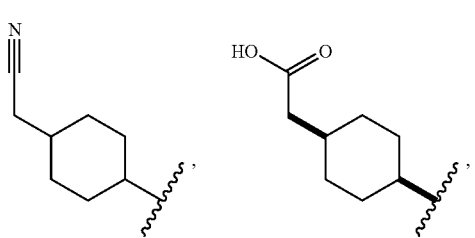
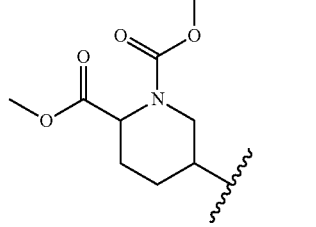
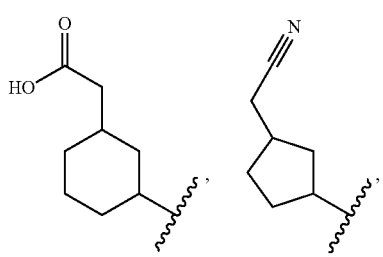
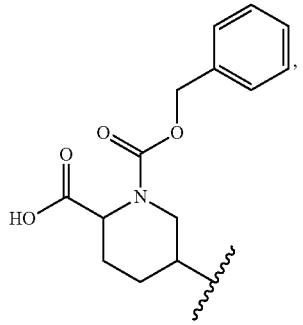
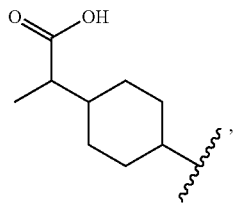
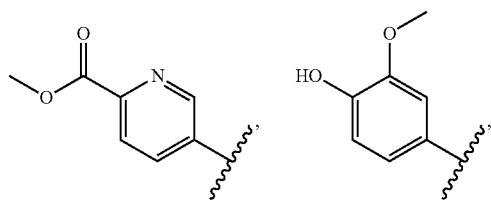

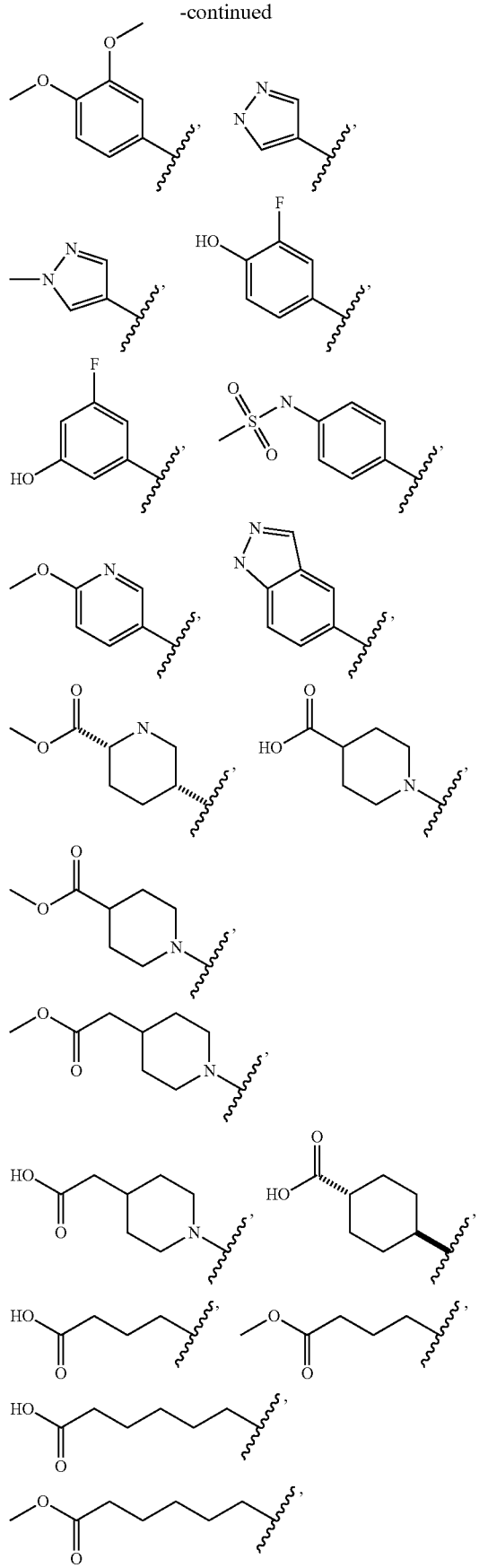
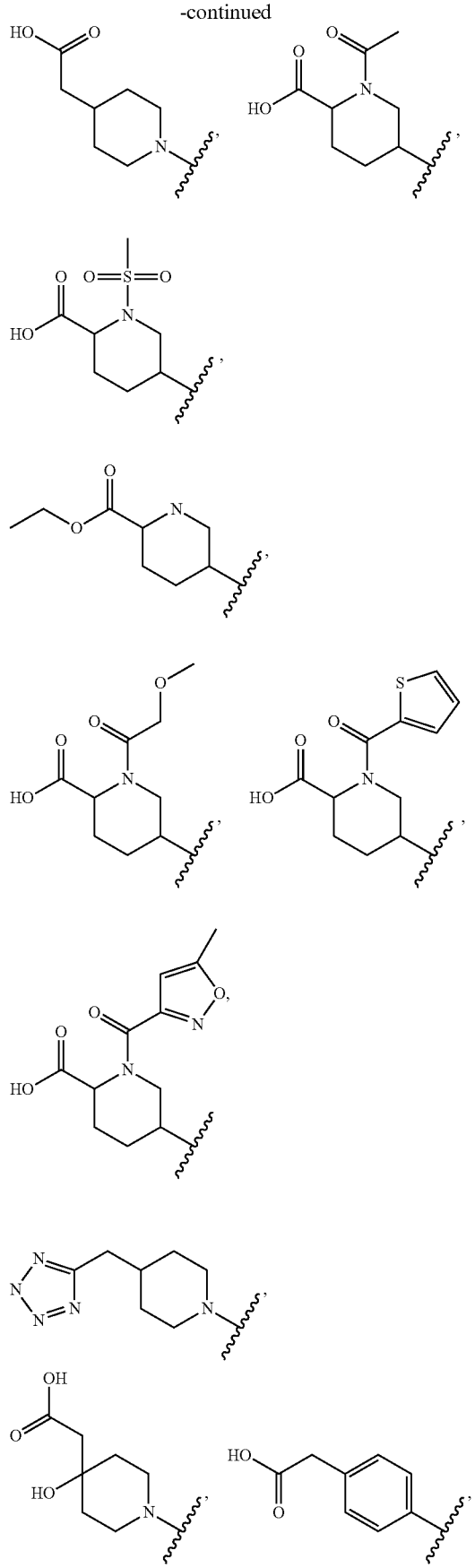

161
-continued
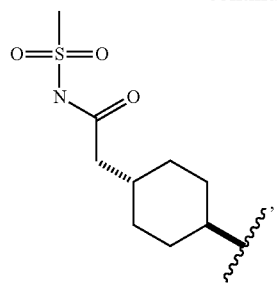
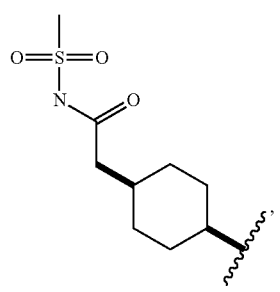
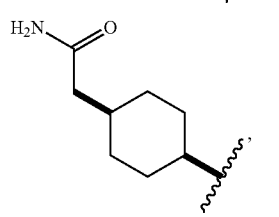
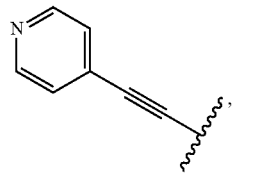
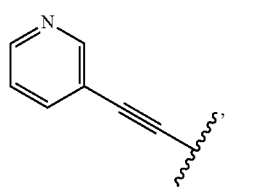
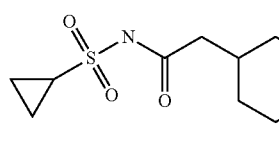
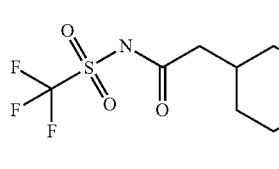
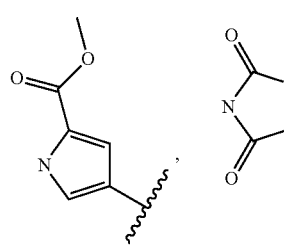
162
-continued
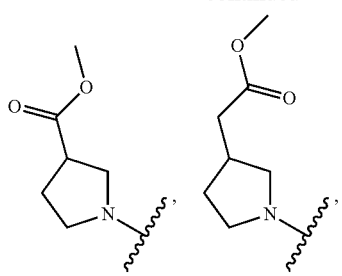
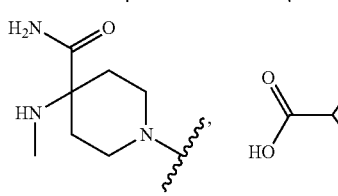
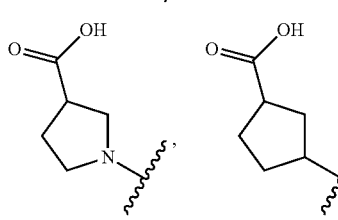
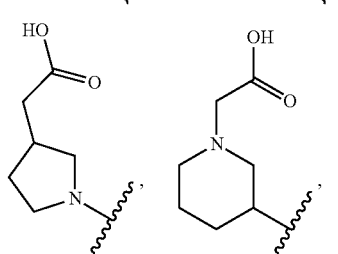
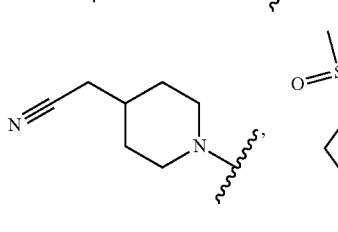
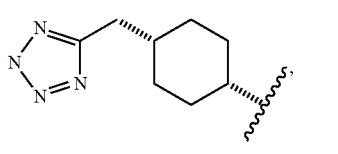
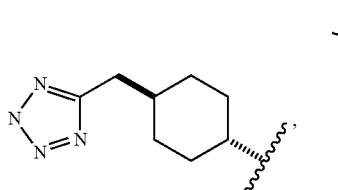
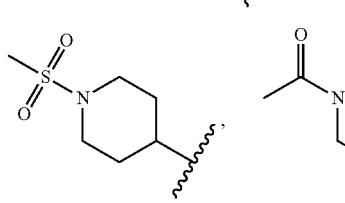

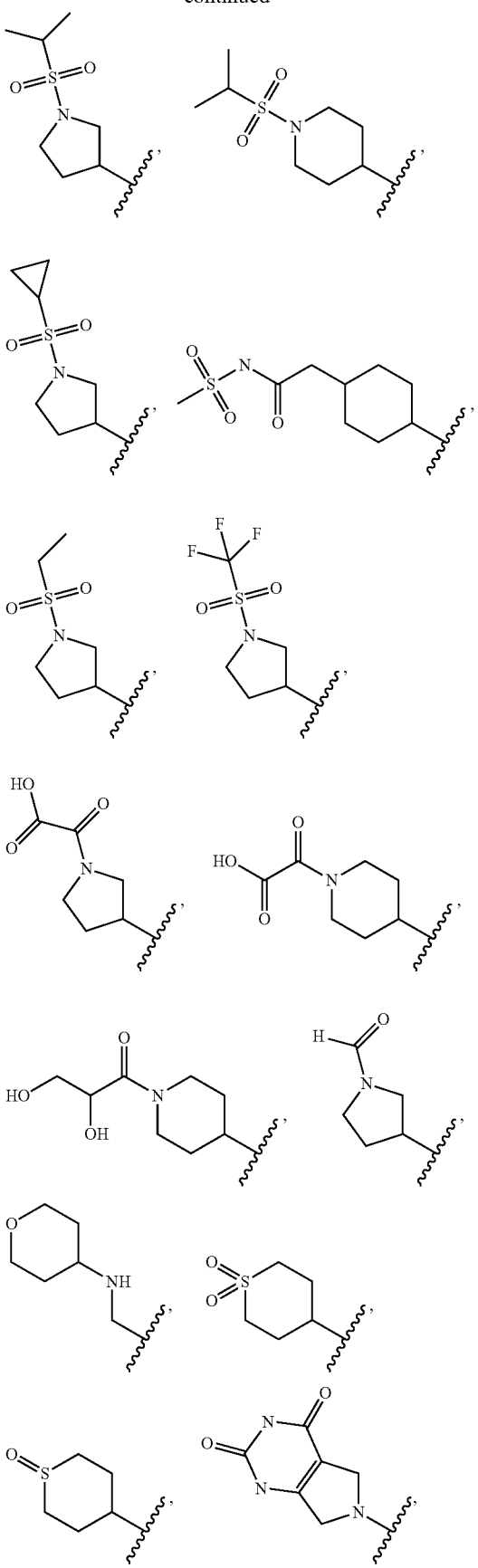
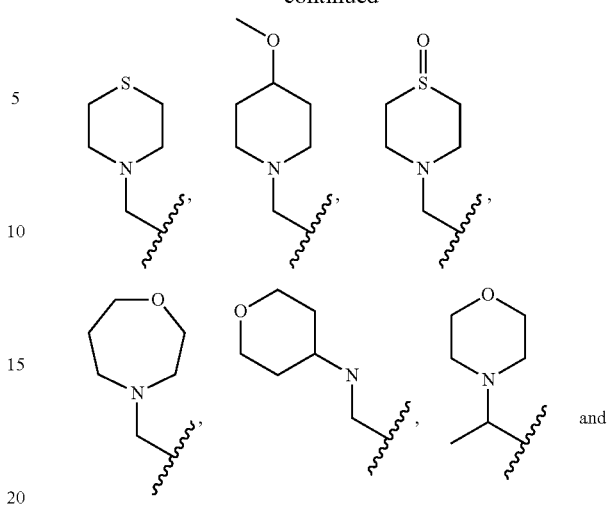
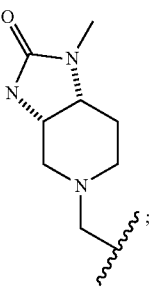
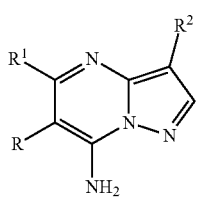

and

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, heteroaryl and arylalkyl.

In another embodiment, the present invention relates to the foregoing method of using a compound represented by the structural Formula I:

Formula I or a pharmaceutically acceptable salt, solvate, ester, or prodrug thereof, wherein:

R is acetyl;

$R^1$ is independently selected from the group consisting of:
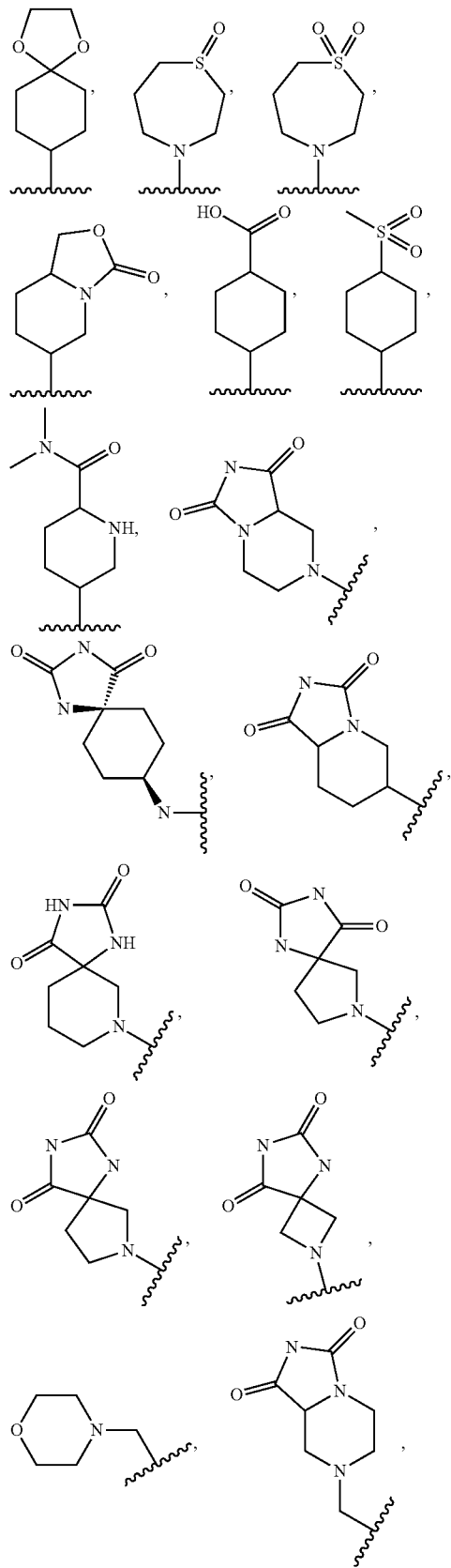
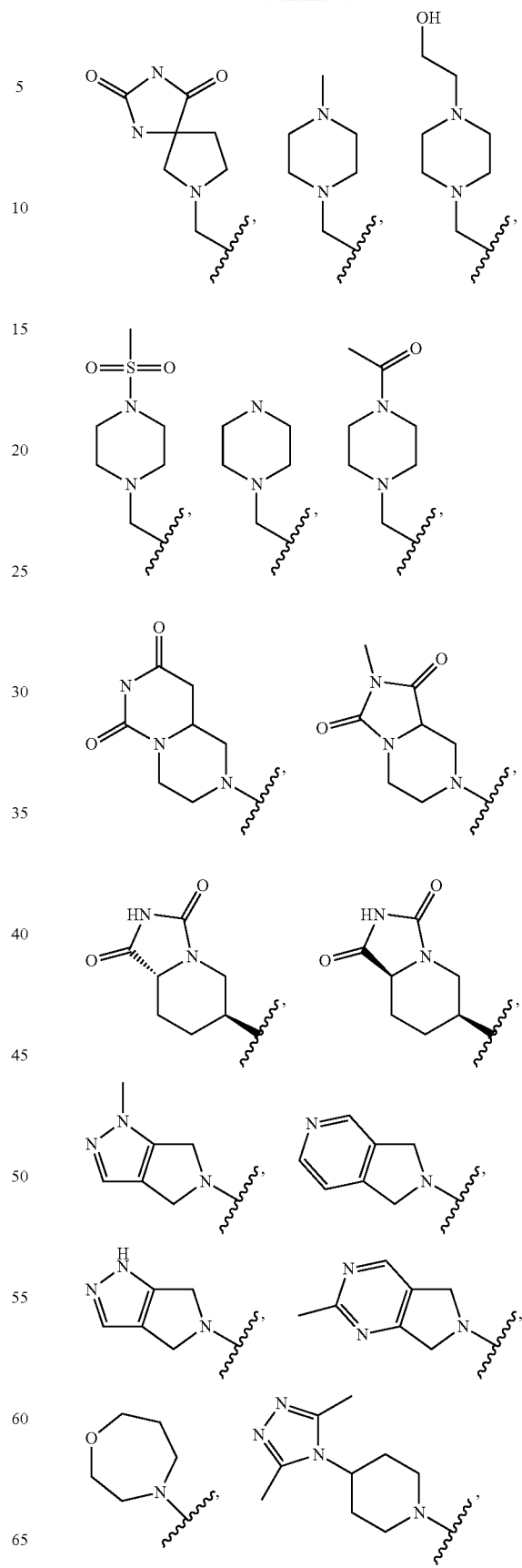

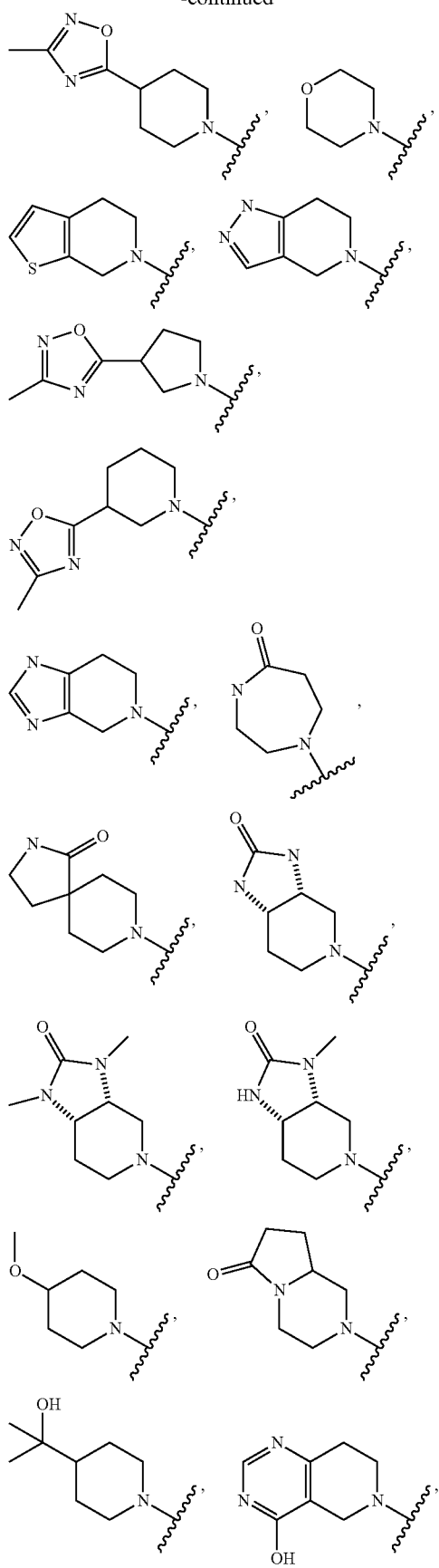
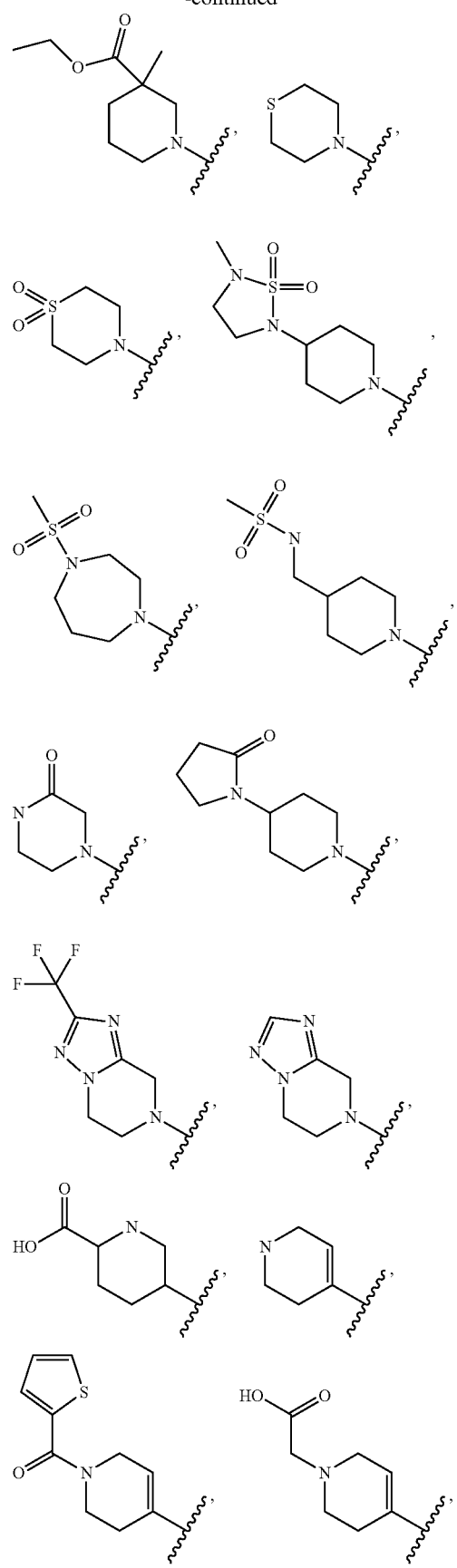

-continued
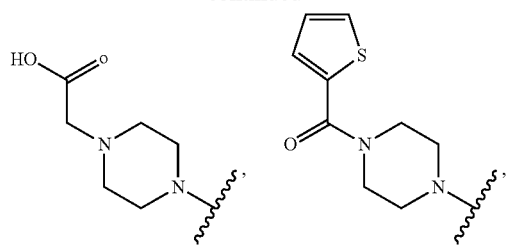
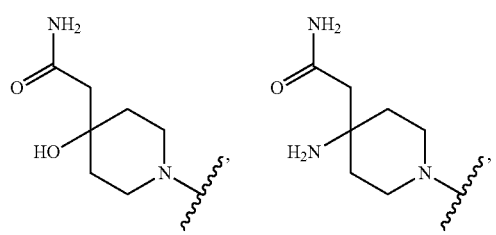
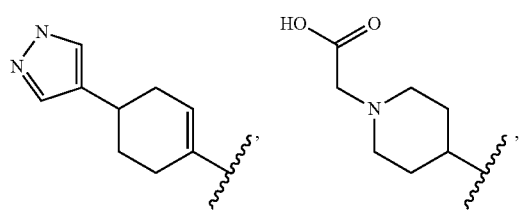
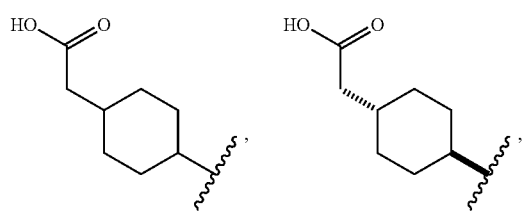
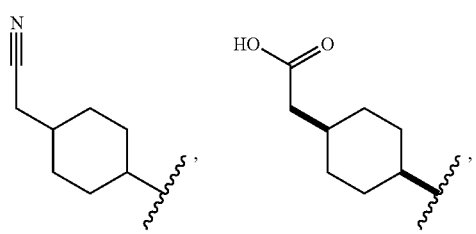
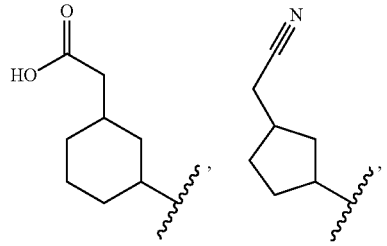
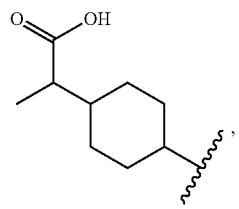
-continued
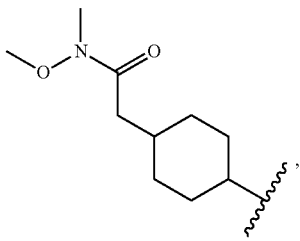
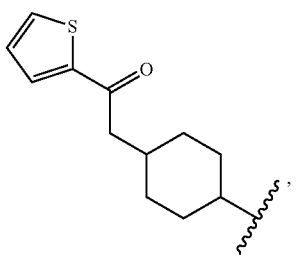
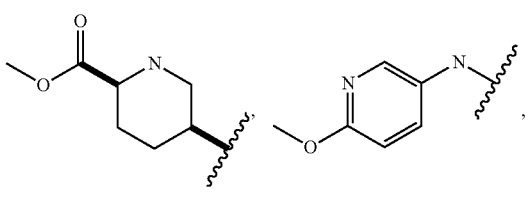
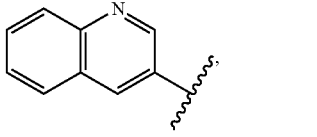
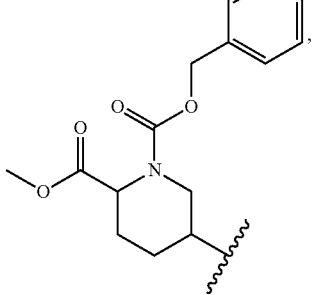
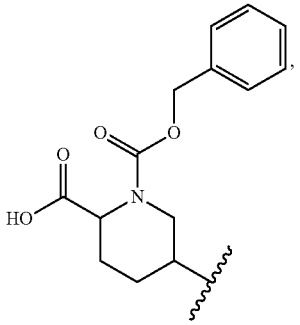
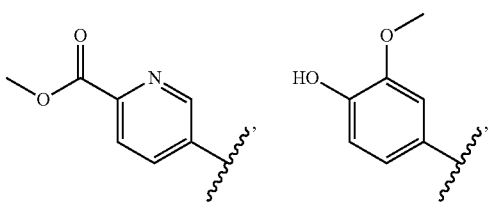

171
-continued
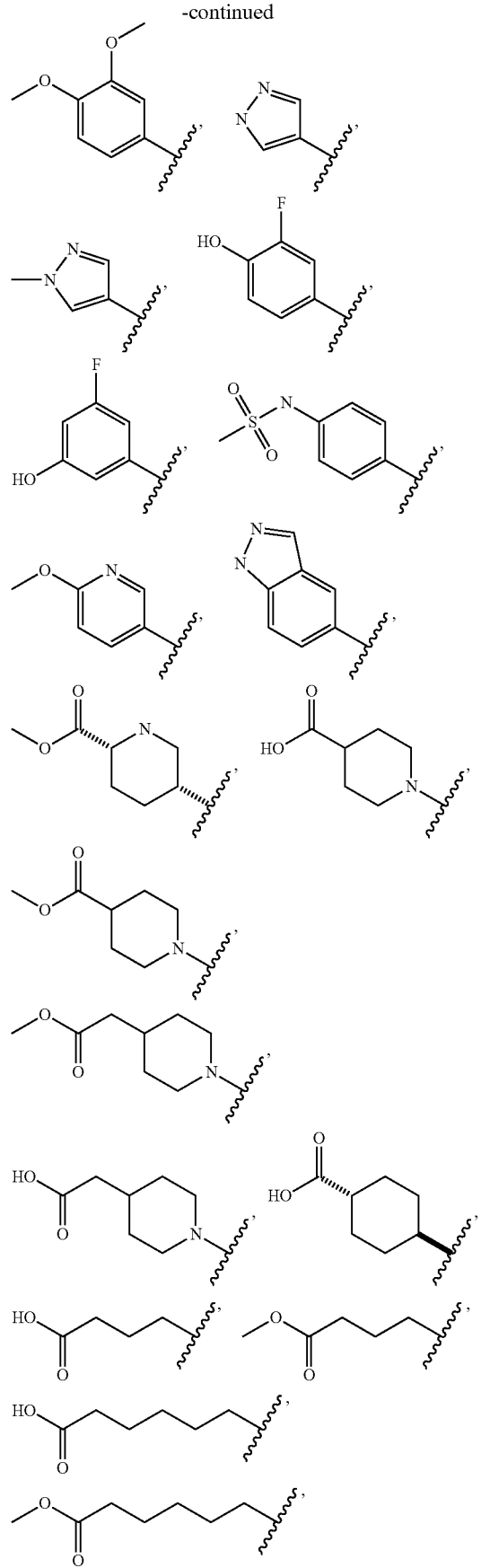
172
-continued
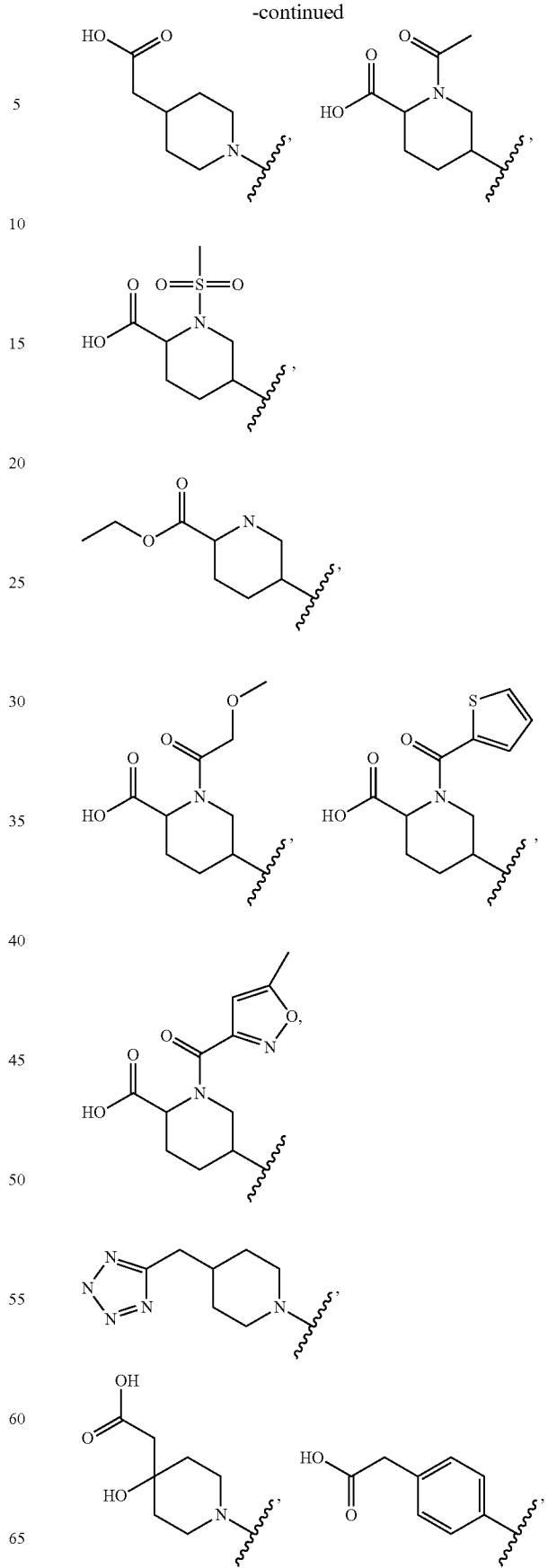

173
-continued
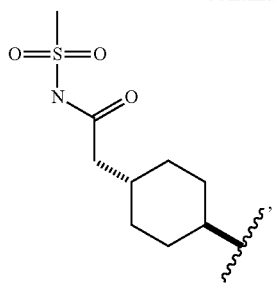
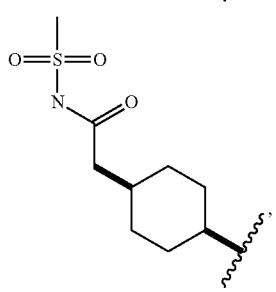
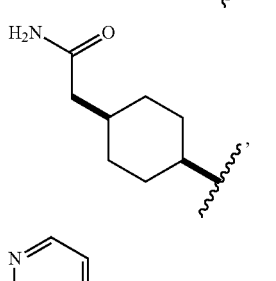
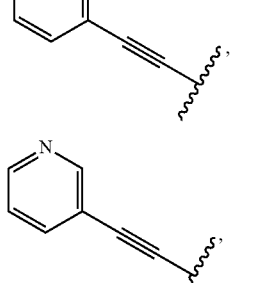
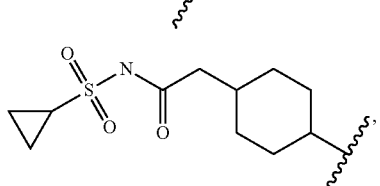
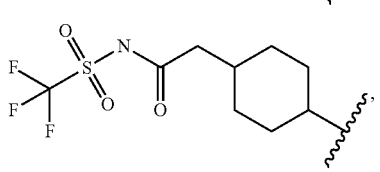
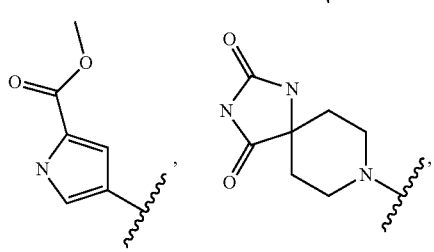
174
-continued
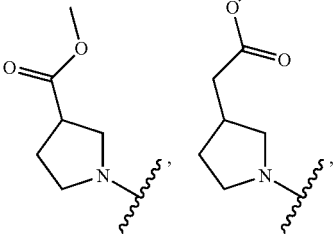
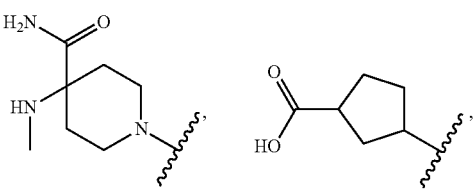
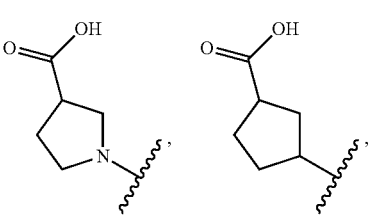
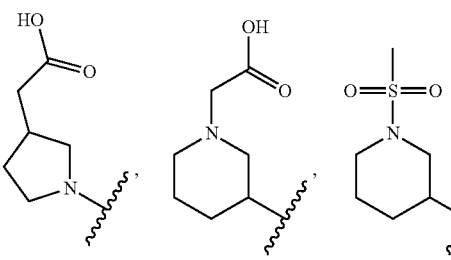
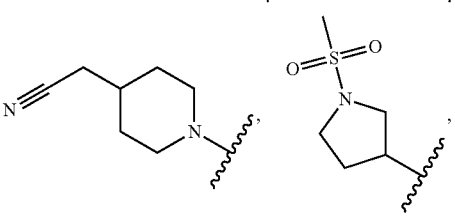
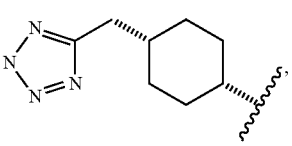
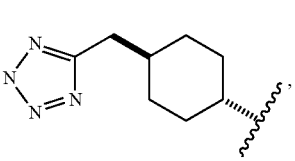
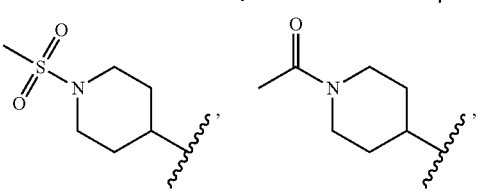

175
-continued

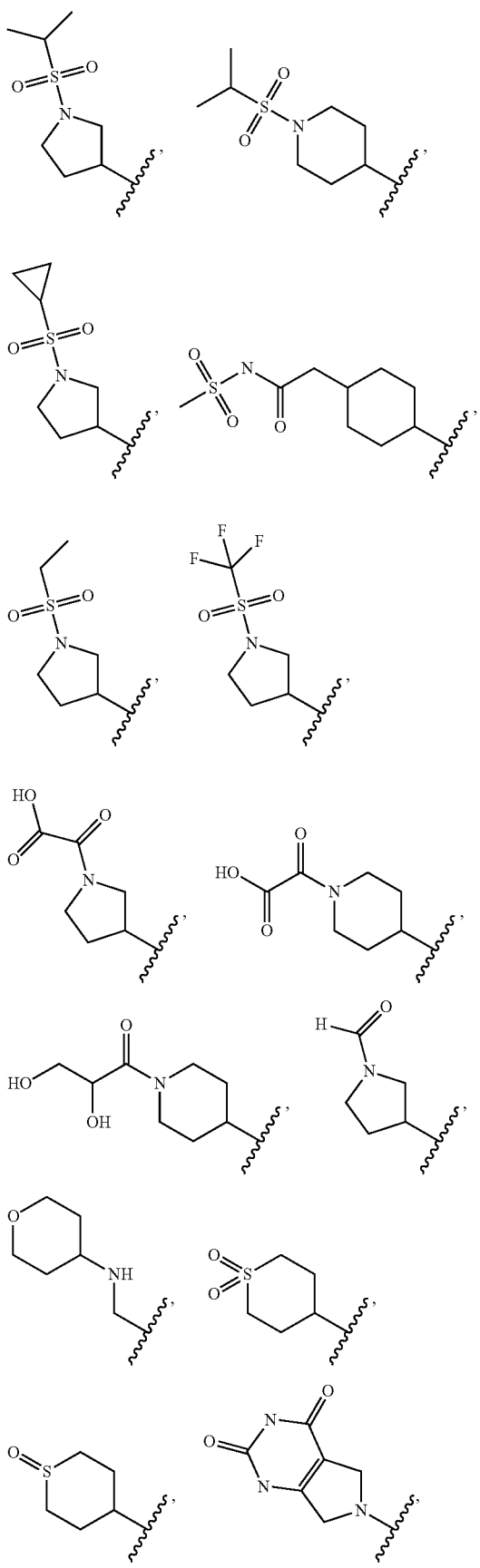

176
-continued

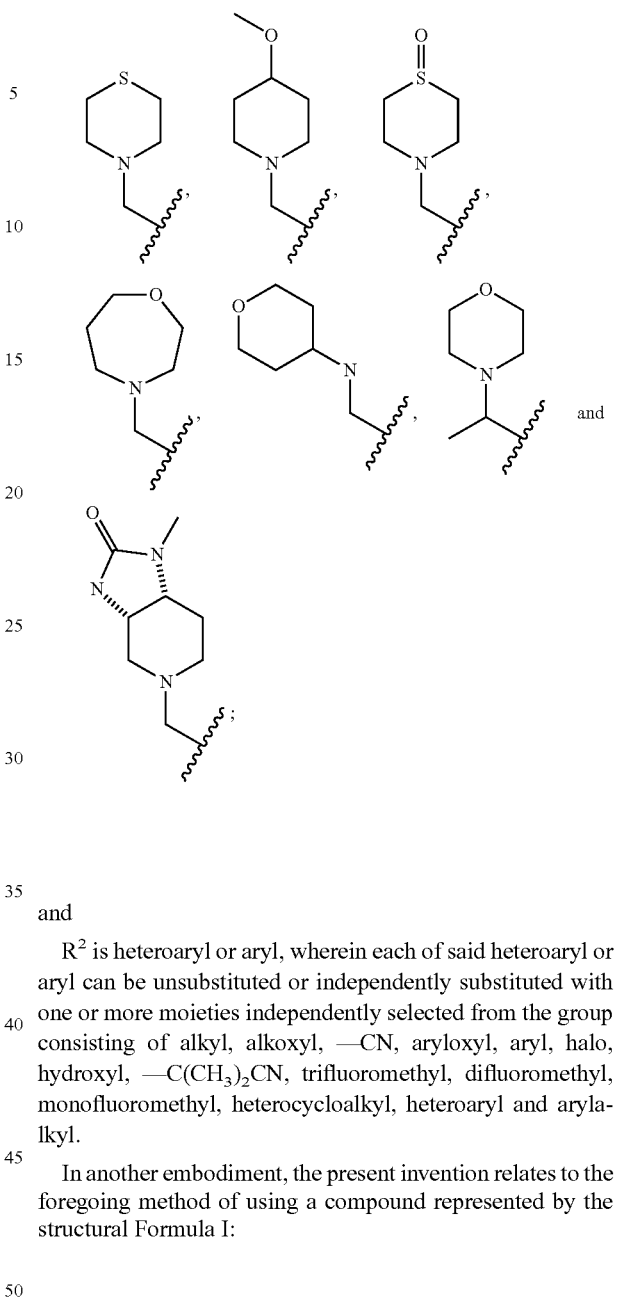

and

R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, heteroaryl and arylalkyl.

In another embodiment, the present invention relates to the foregoing method of using a compound represented by the structural Formula I:

Formula I

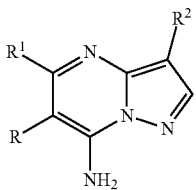

or a pharmaceutically acceptable salt, solvate, ester, or prodrug thereof, wherein:

R is —CN;

$R^1$ is independently selected from the group consisting of:
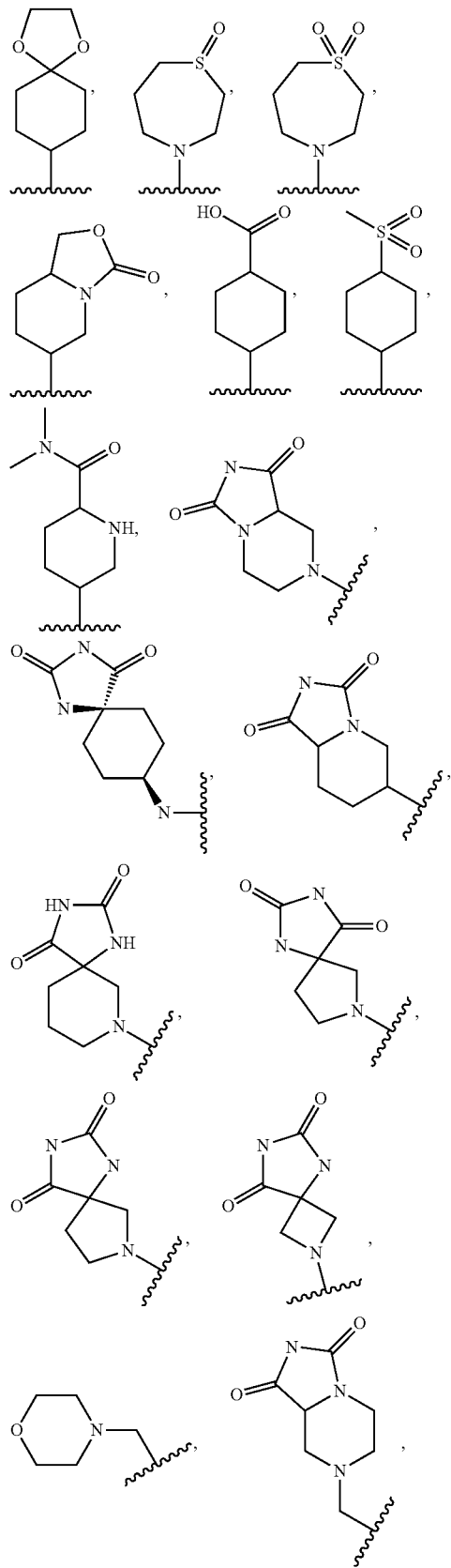
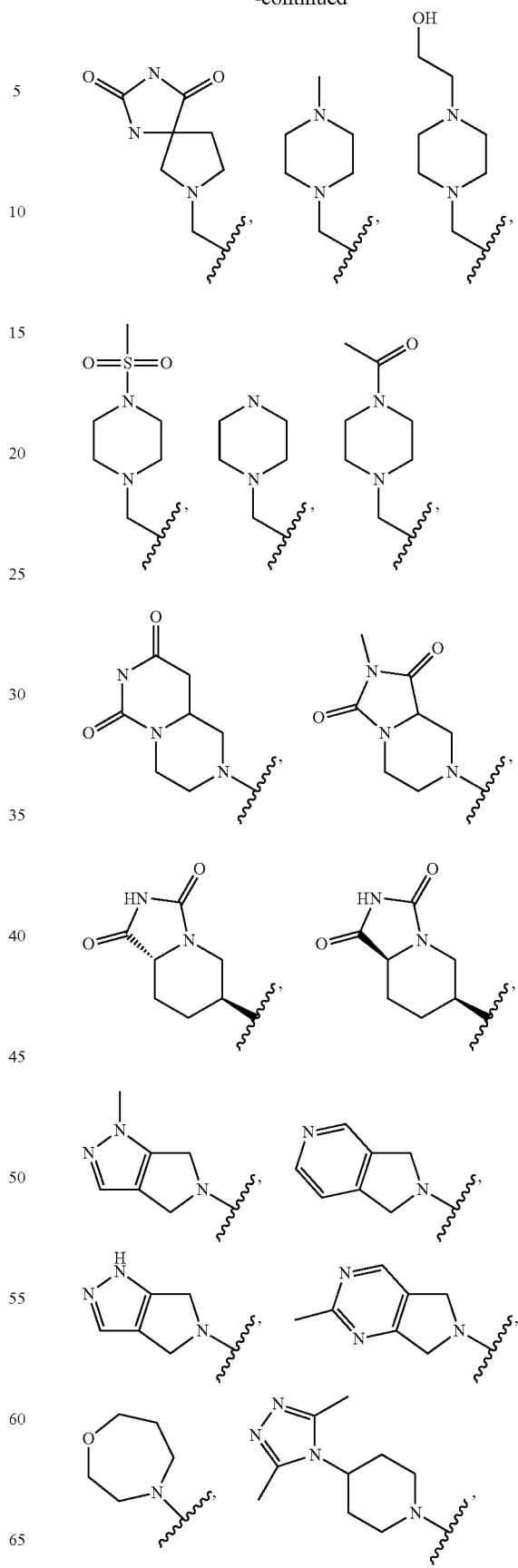

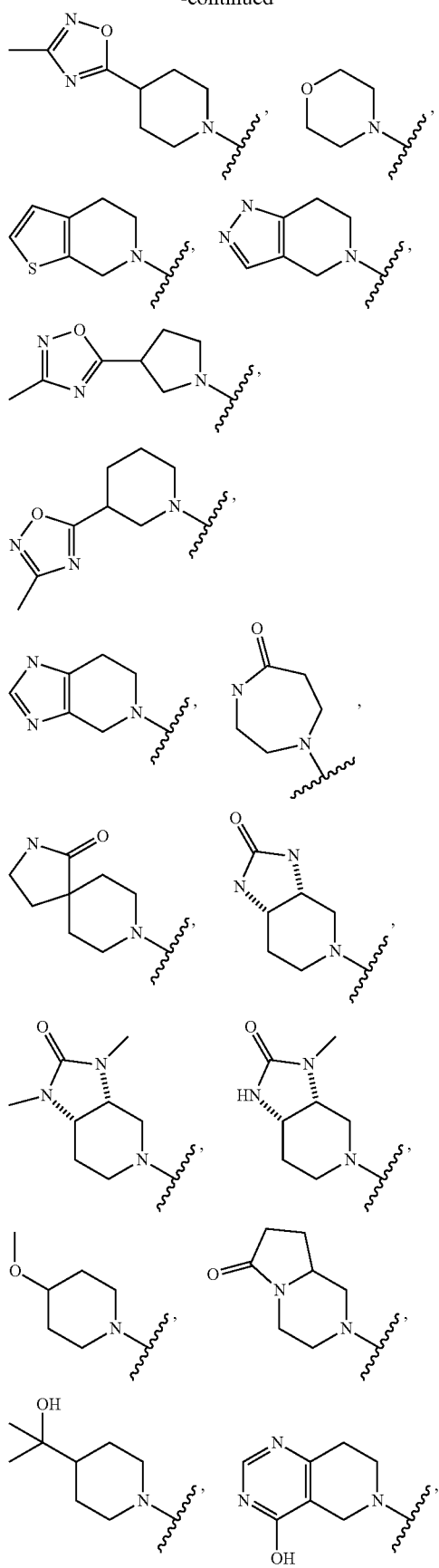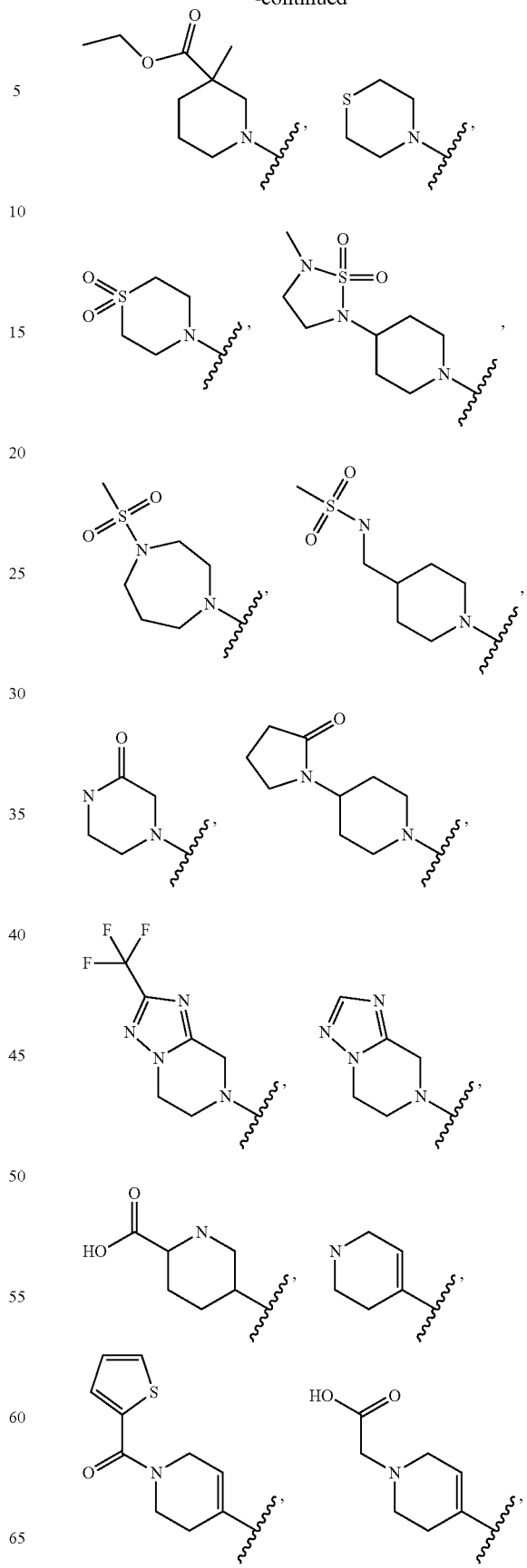

-continued
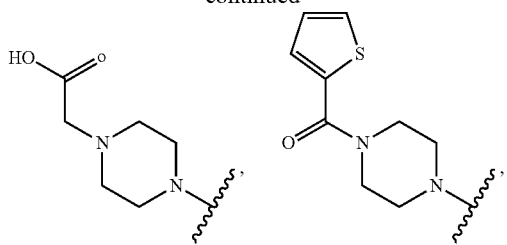
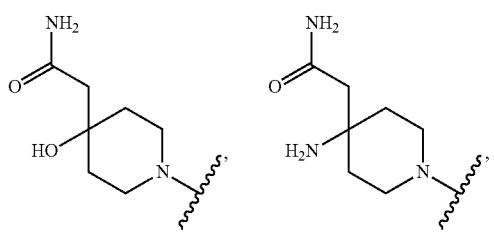
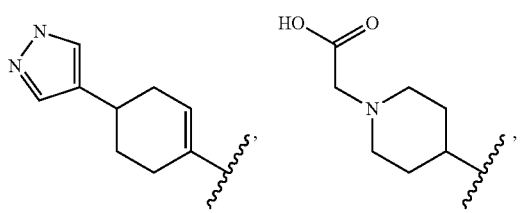
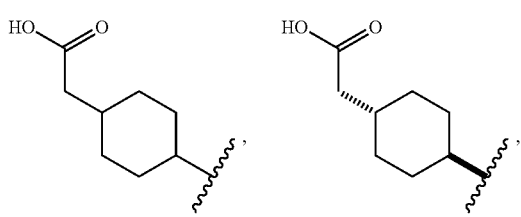
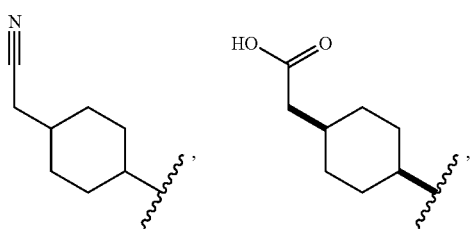
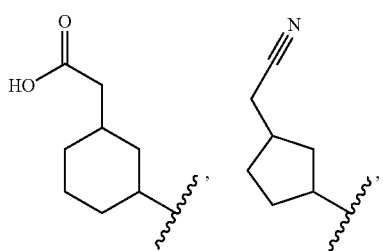
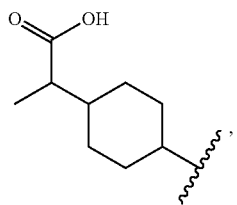
-continued
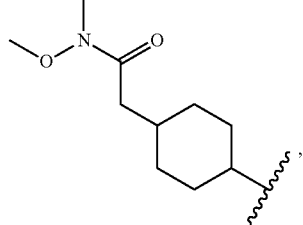
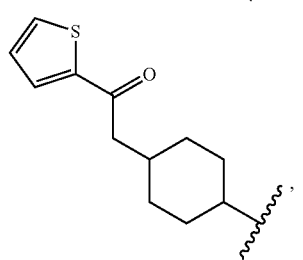
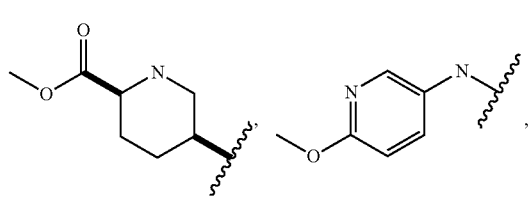
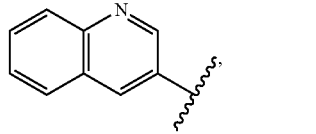
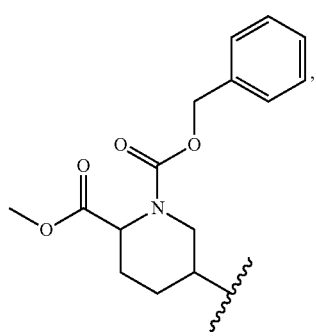
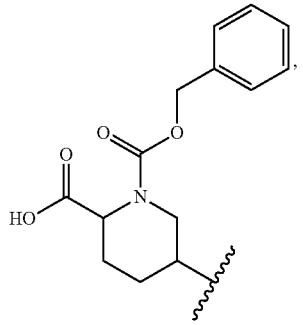
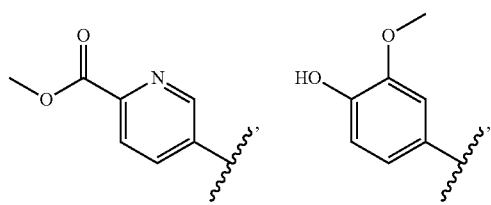

183
-continued
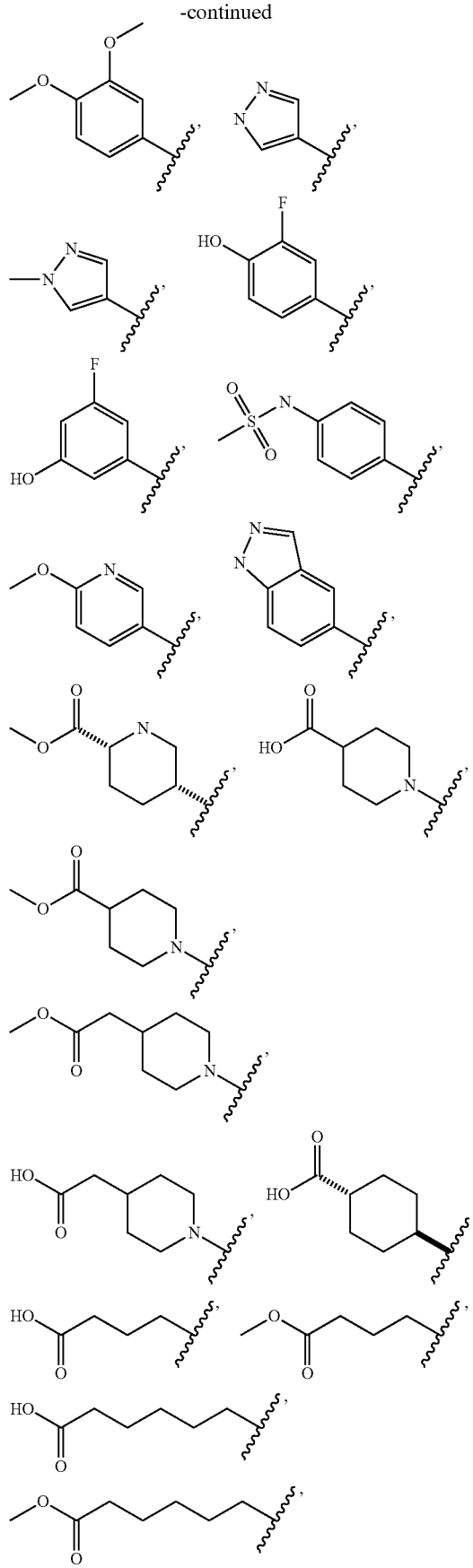
184
-continued
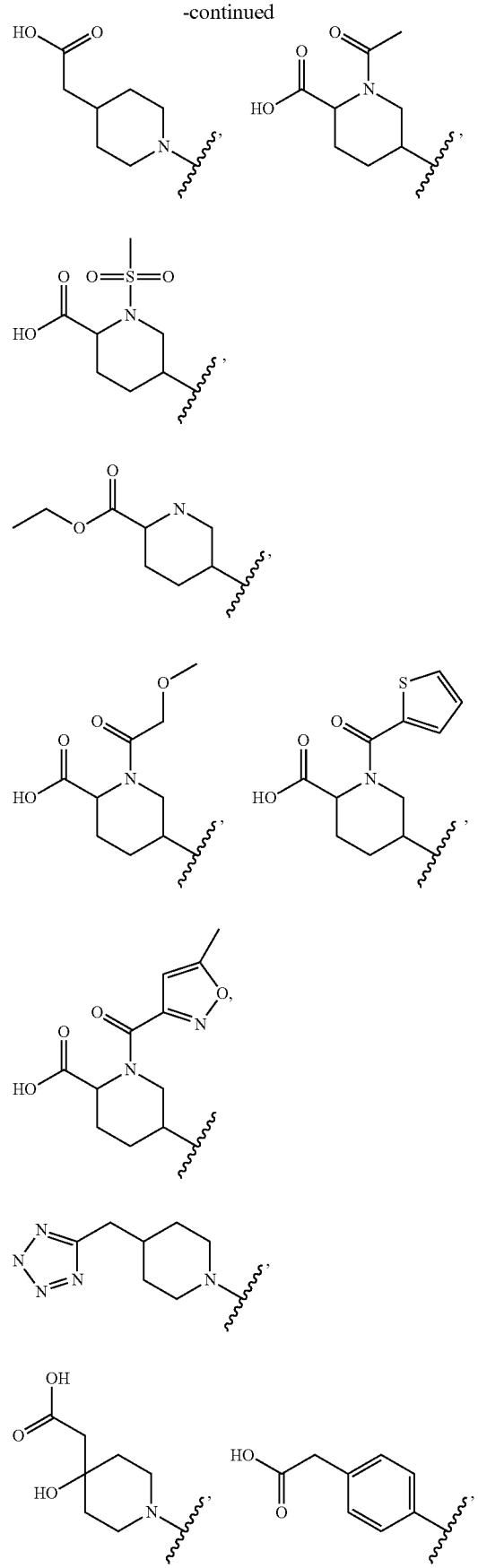

185
-continued
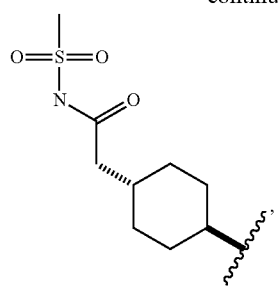
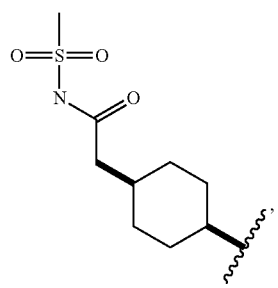
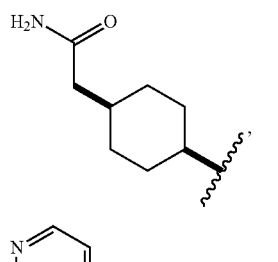
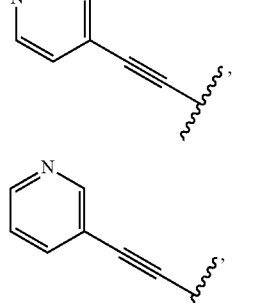
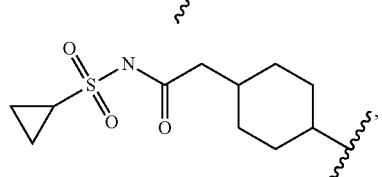
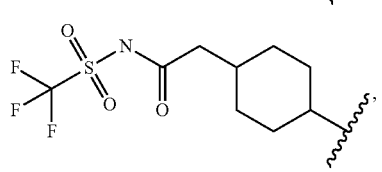
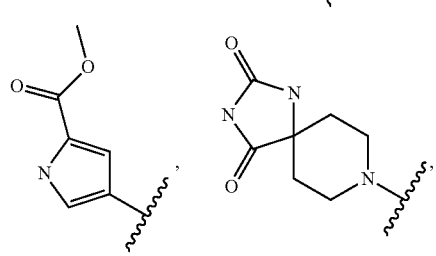
186
-continued
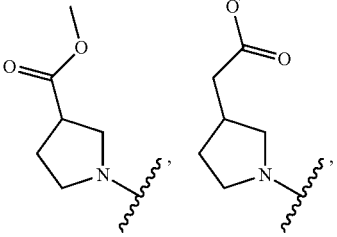
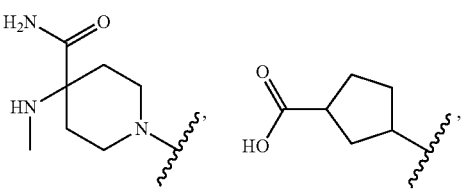
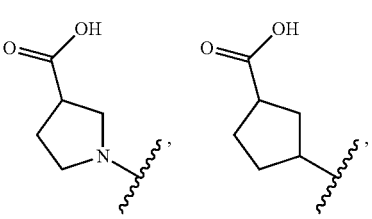
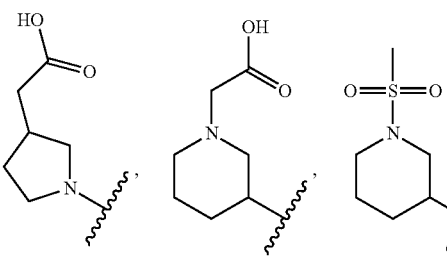
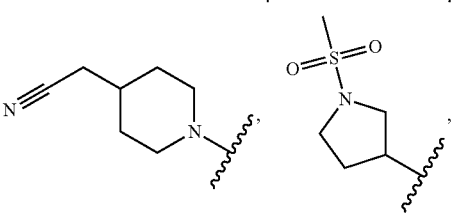
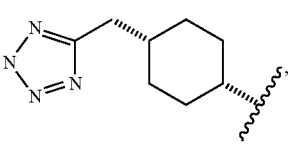
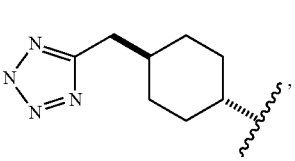
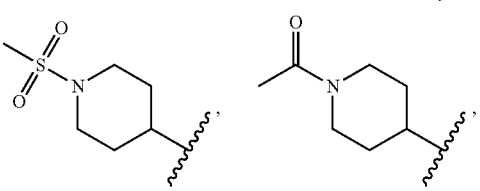

187
-continued

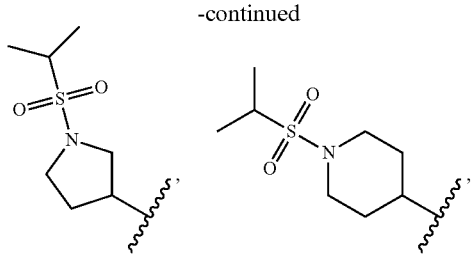
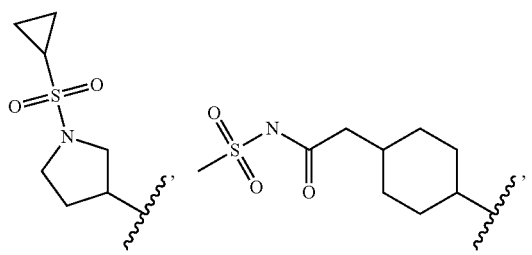
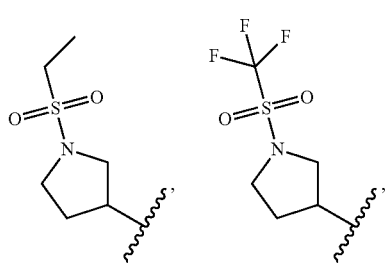
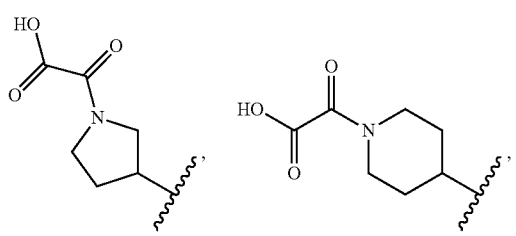
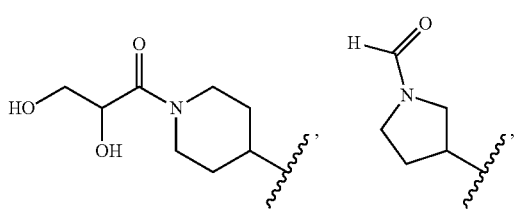
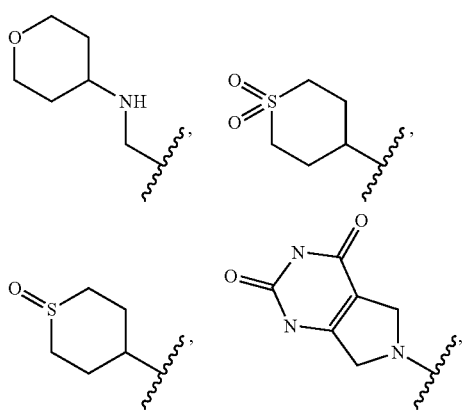

188
-continued

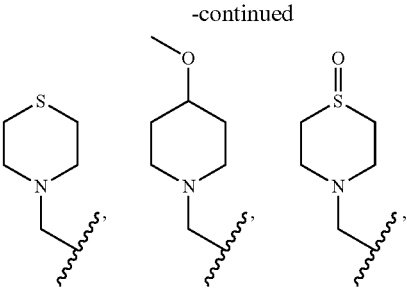
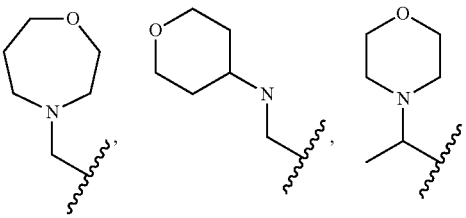
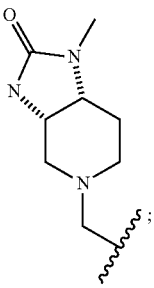

and and $R^2$ is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH$_3$)$_2$CN, trifluoromethyl, difluoromethyl, monofluoromethyl, heterocycloalkyl, heteroaryl and arylalkyl.

Non-limiting examples of the compounds of the present invention include:

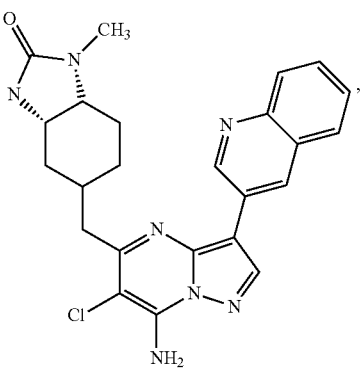

189
-continued
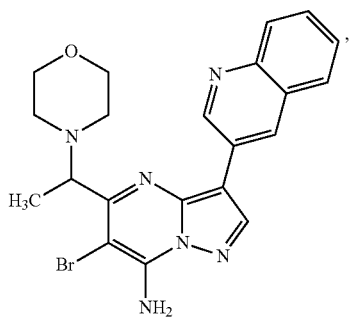
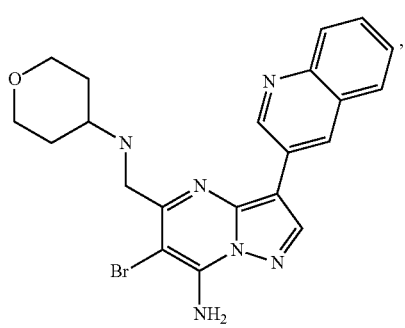
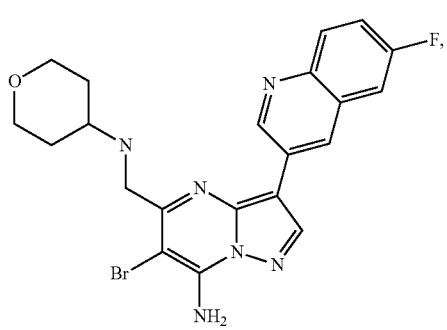
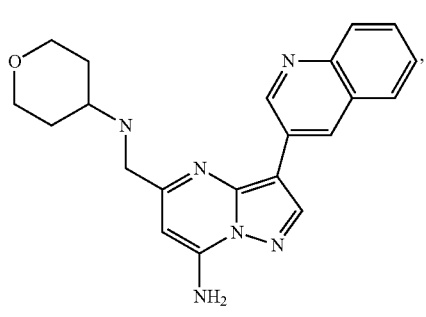
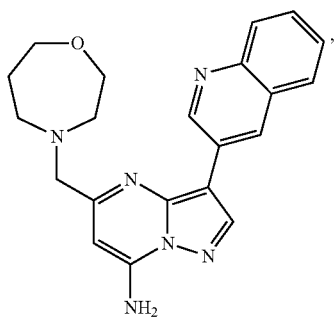
190
-continued
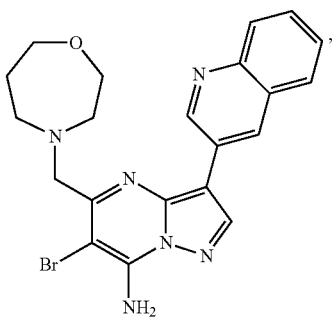
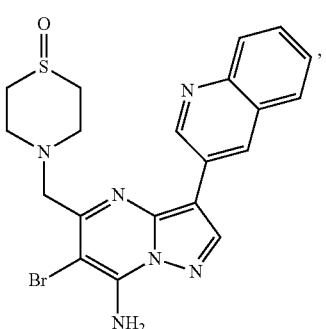
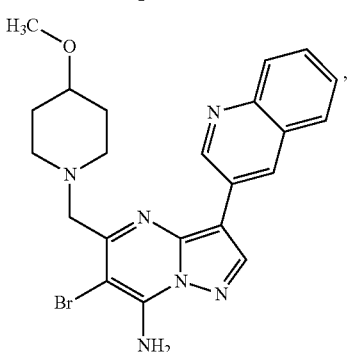
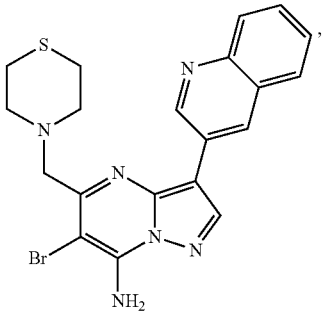
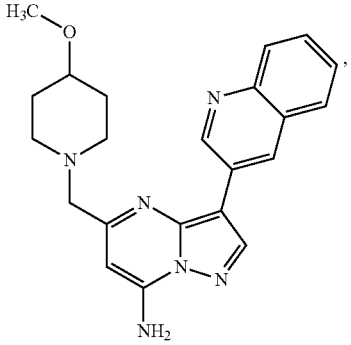

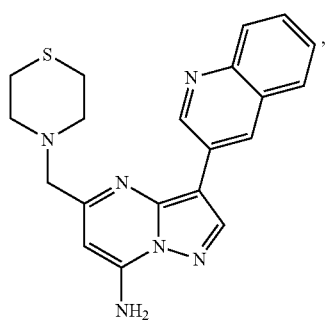
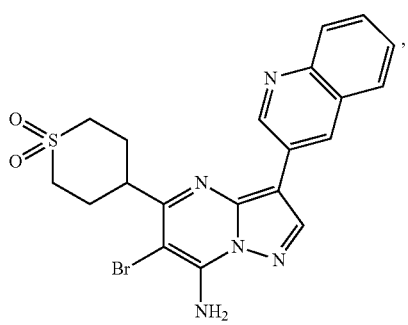
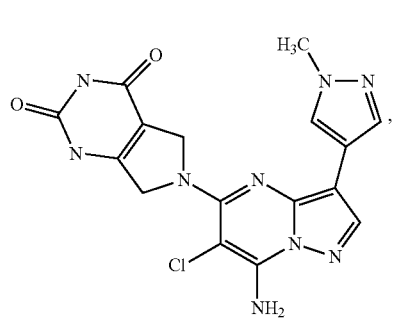
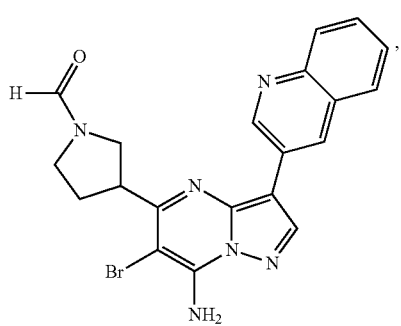
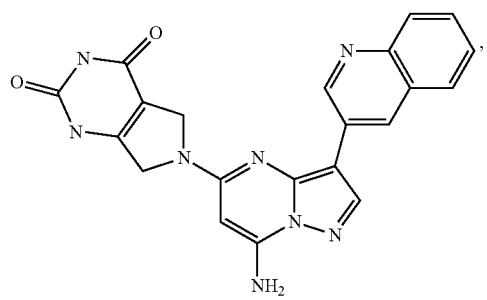
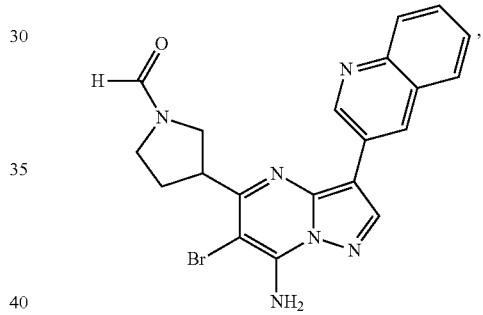
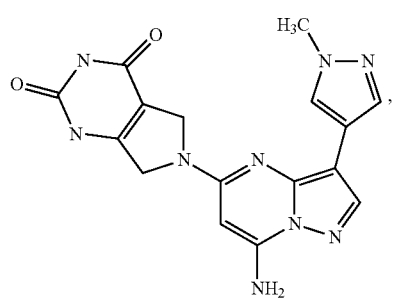
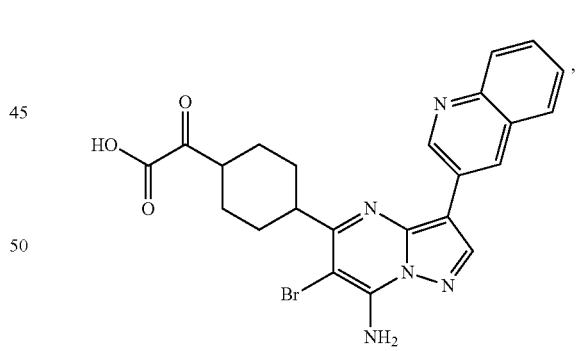
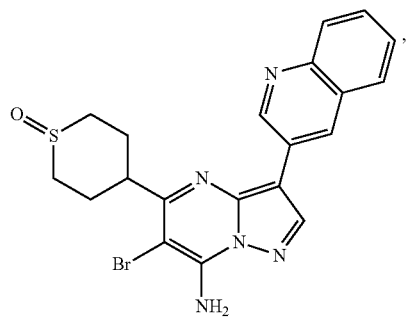
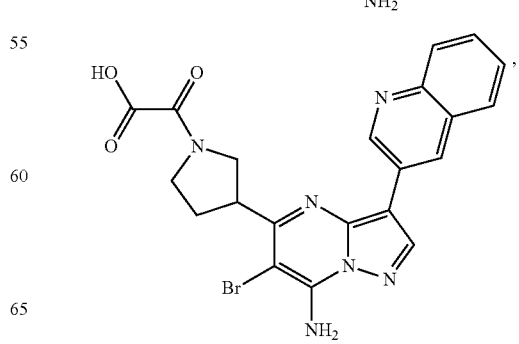

193
-continued
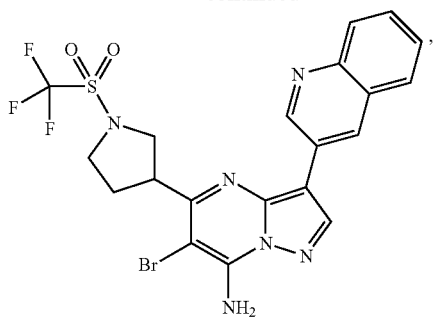
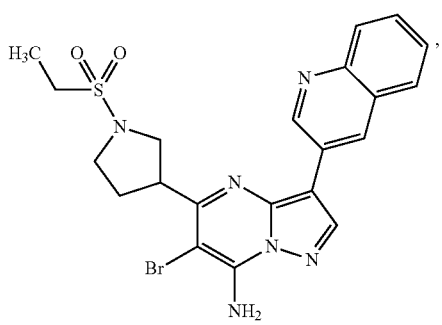
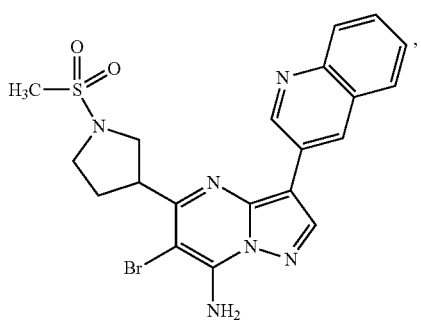
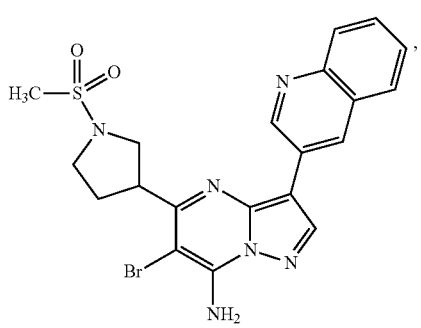
194
-continued
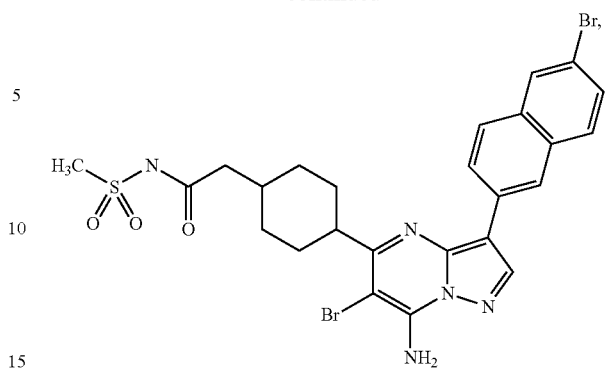
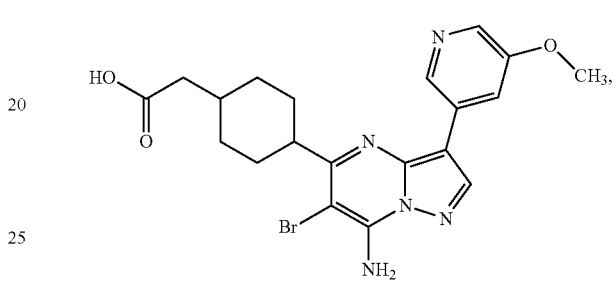
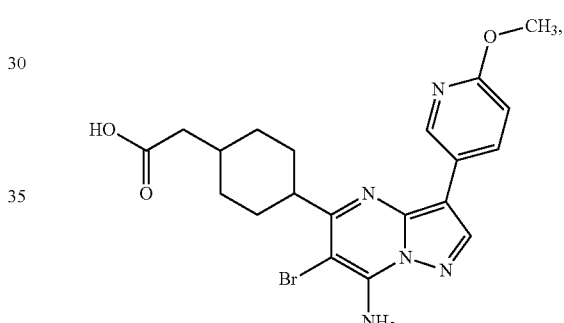
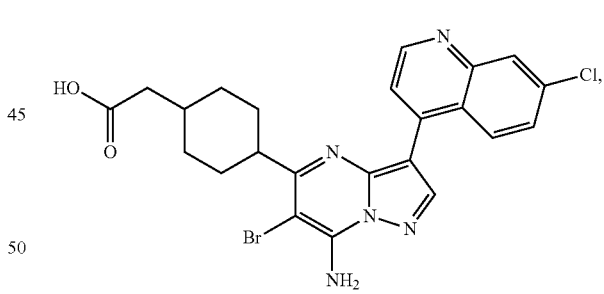
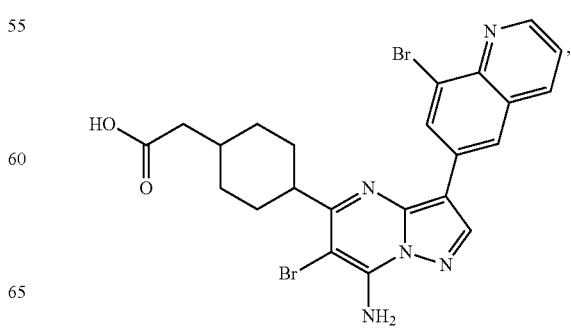

195
-continued
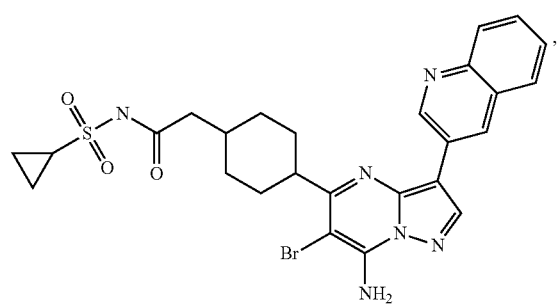
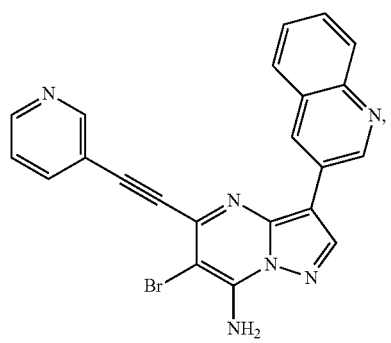
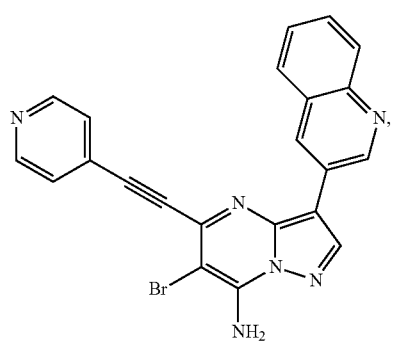
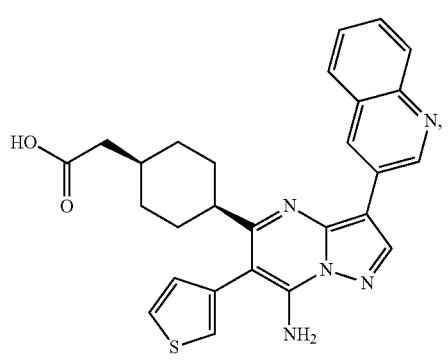
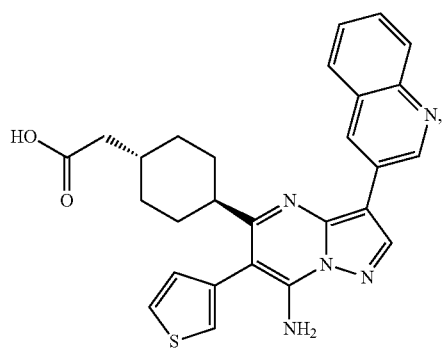
196
-continued
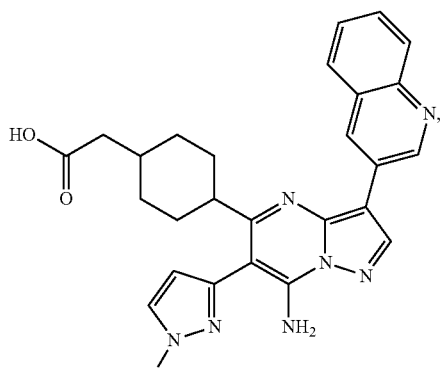
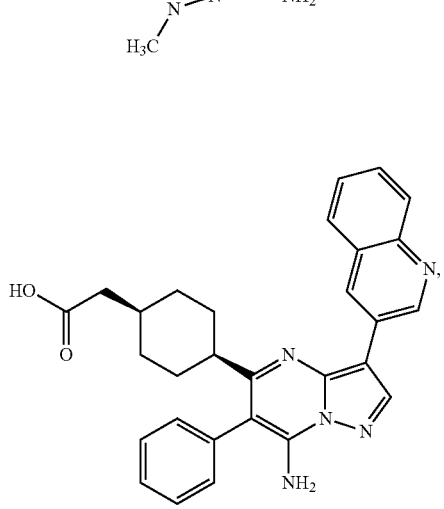
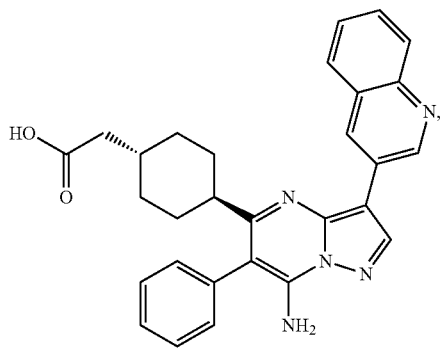
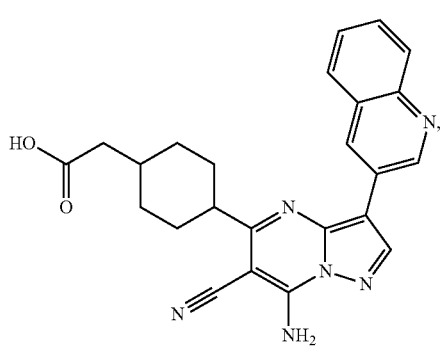

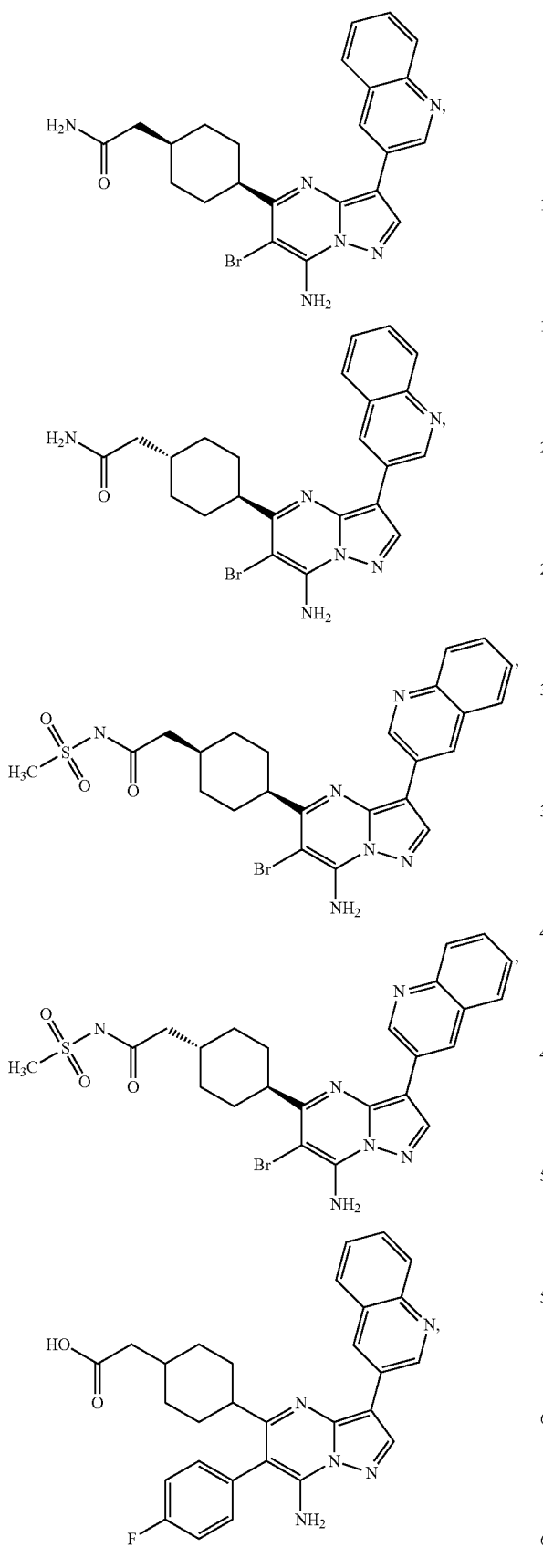
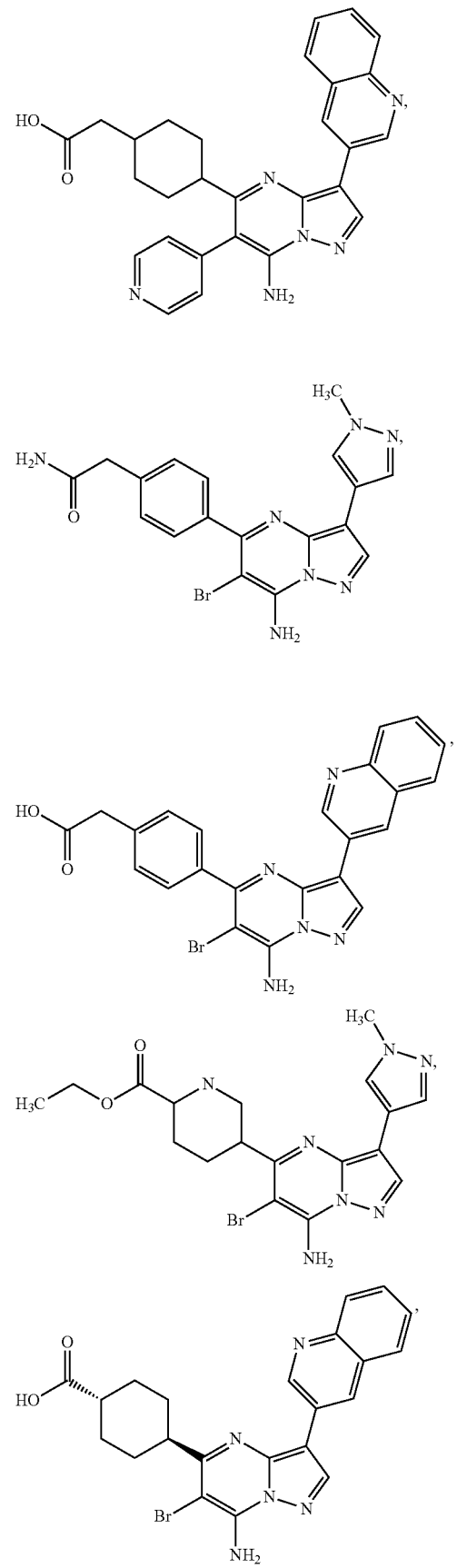

199
-continued
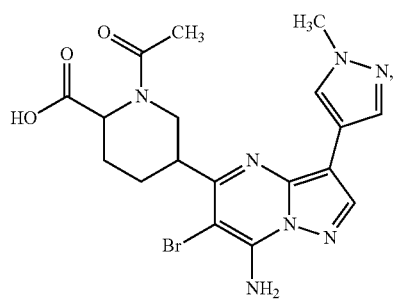
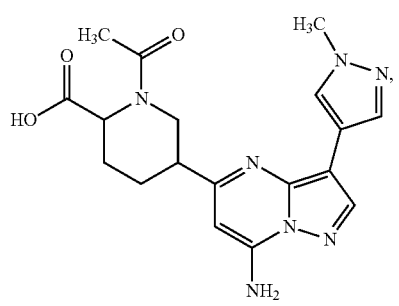
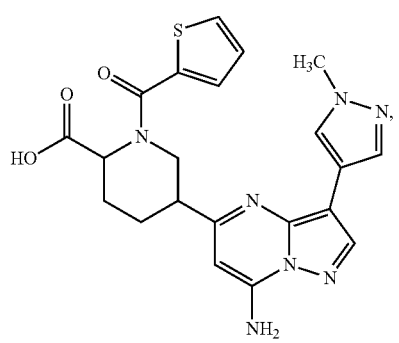
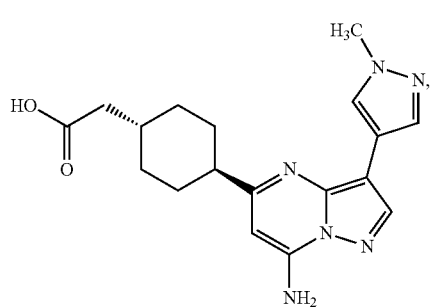
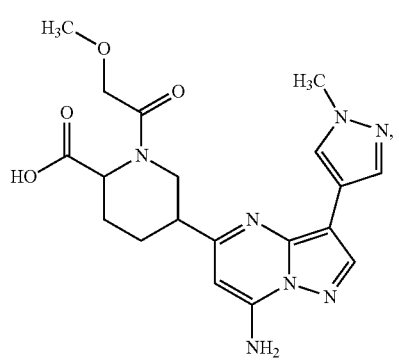
200
-continued
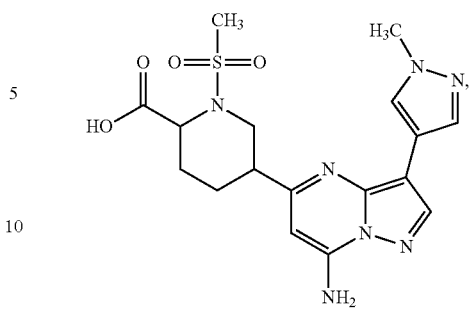
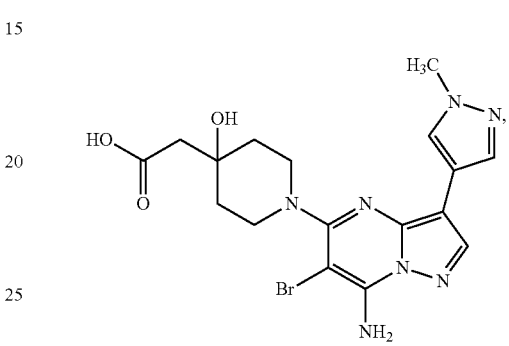
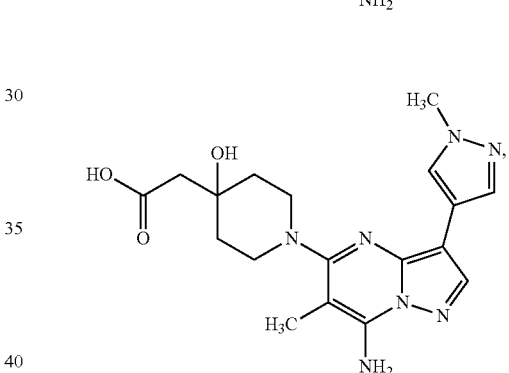
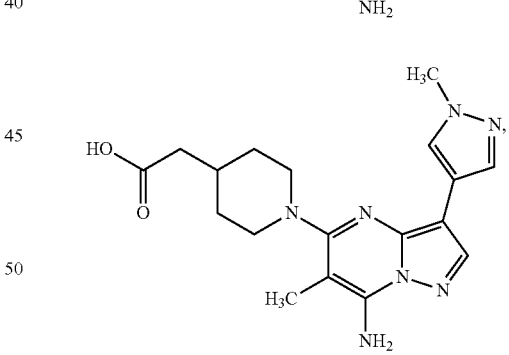

201
-continued
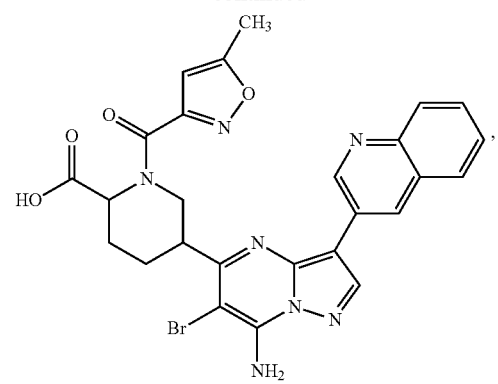
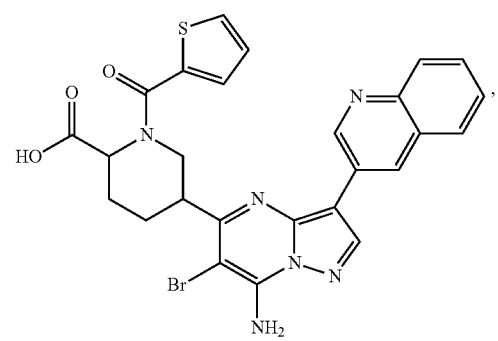
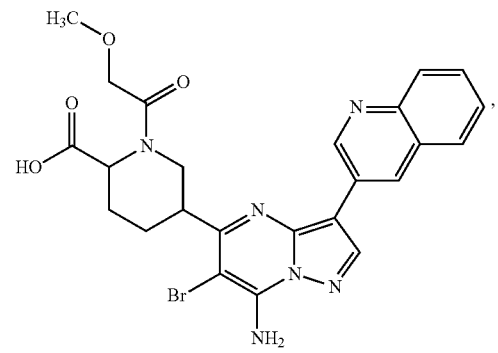
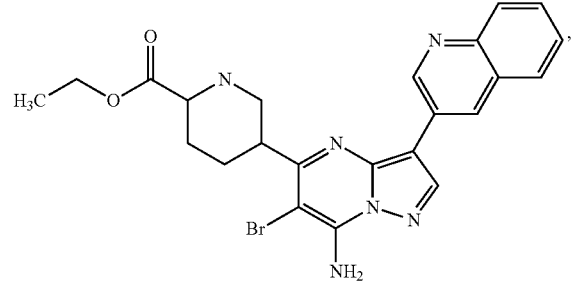
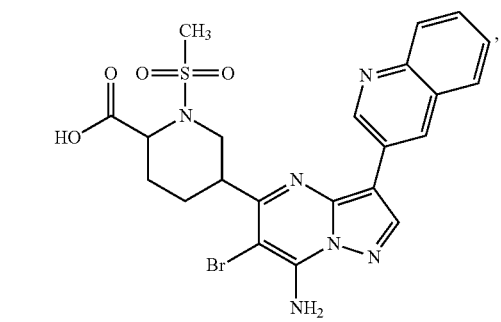
202
-continued
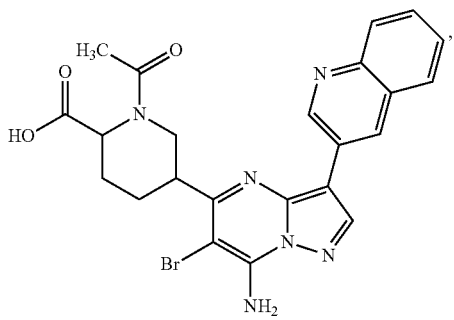
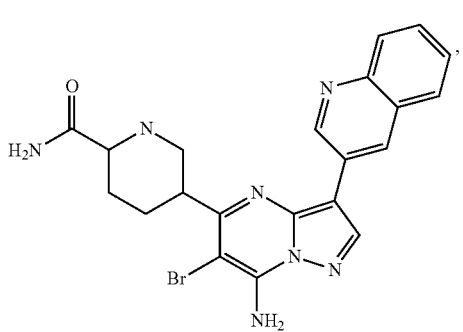
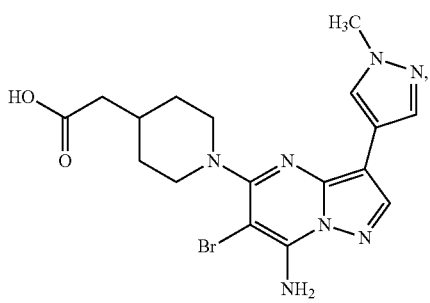
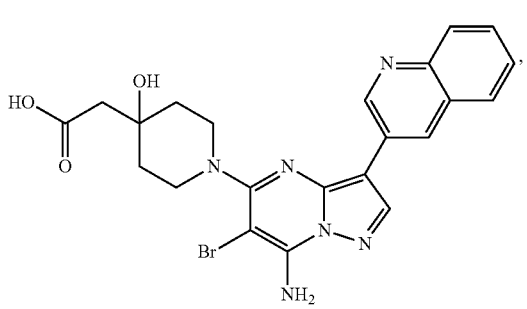
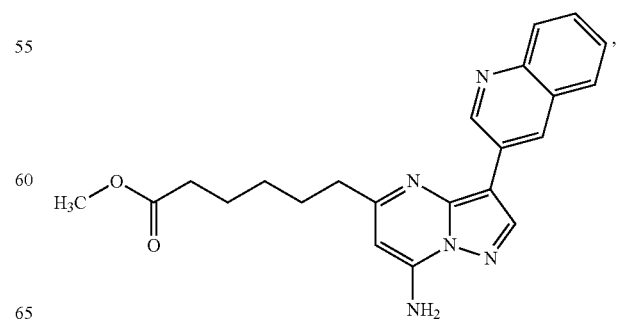

203
-continued
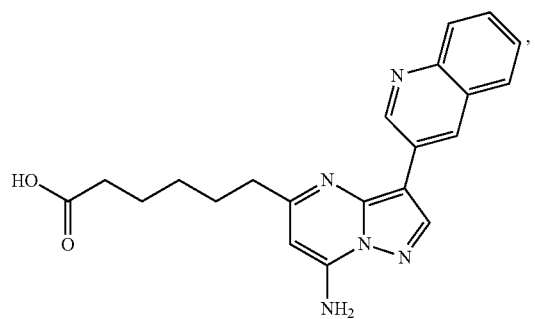
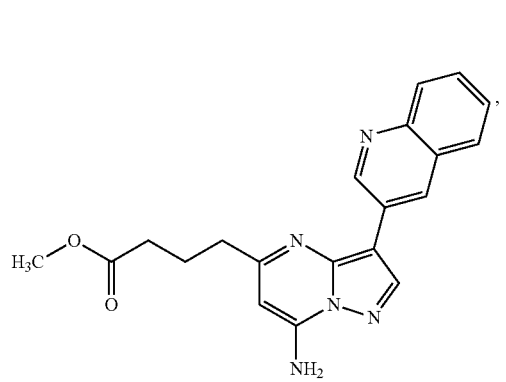
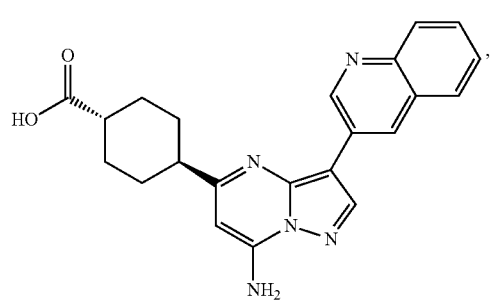
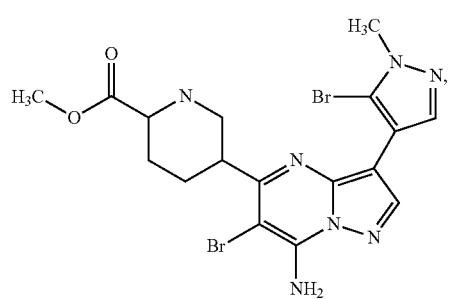
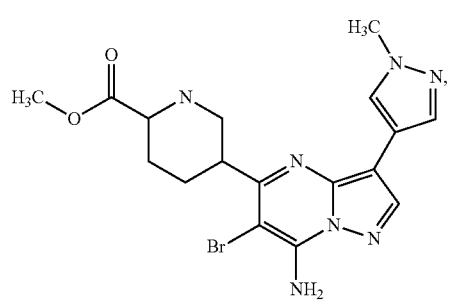
204
-continued
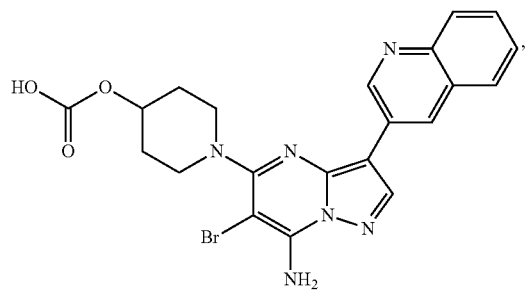
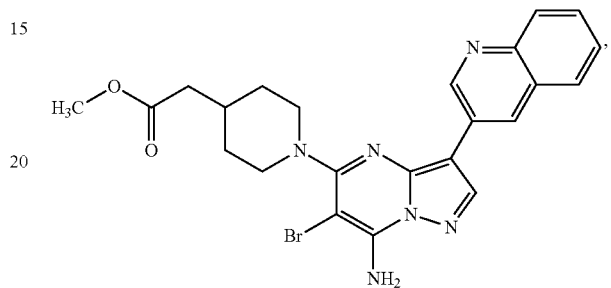
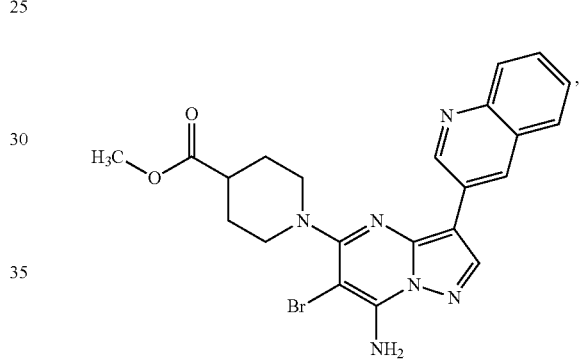
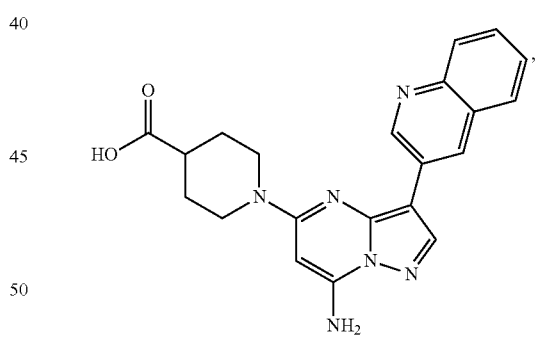
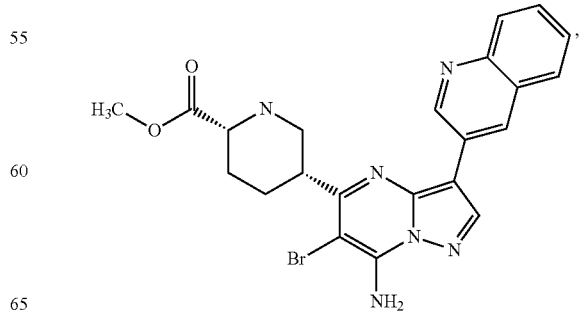

205
-continued
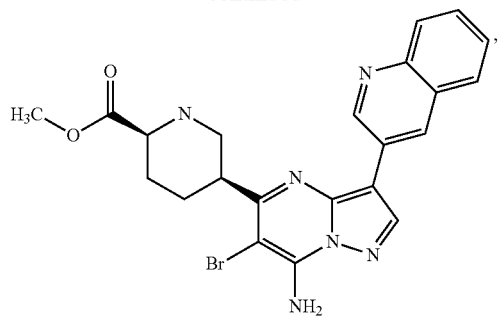
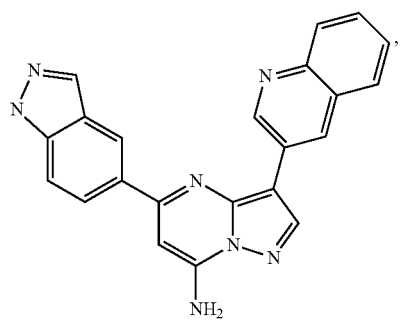
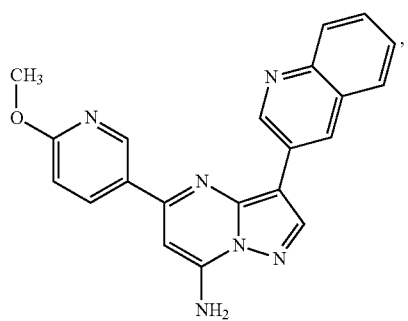
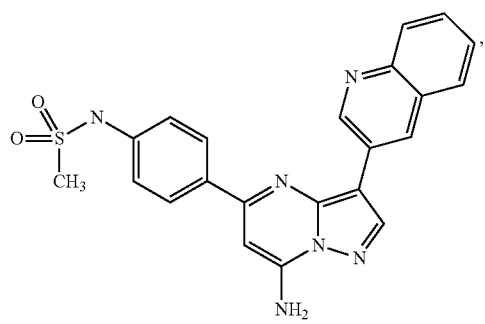
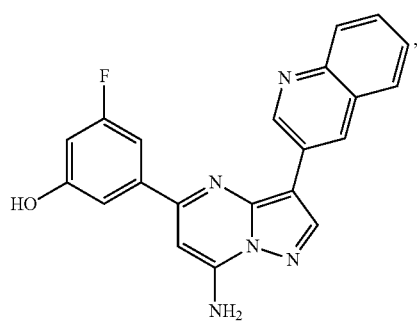
206
-continued
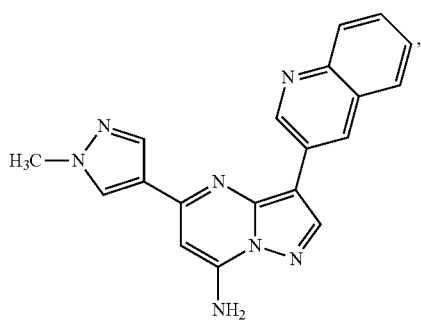
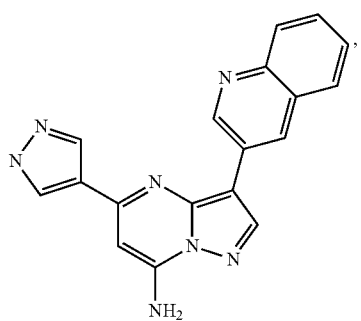
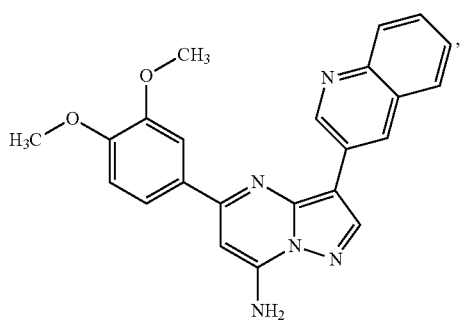
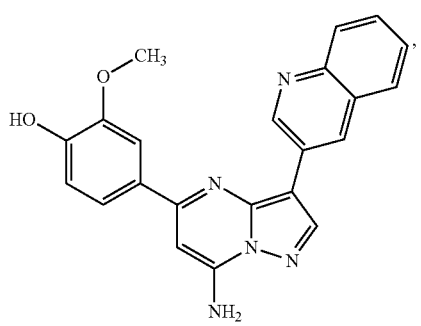

207
-continued
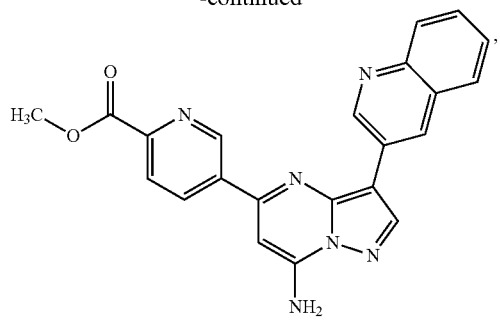
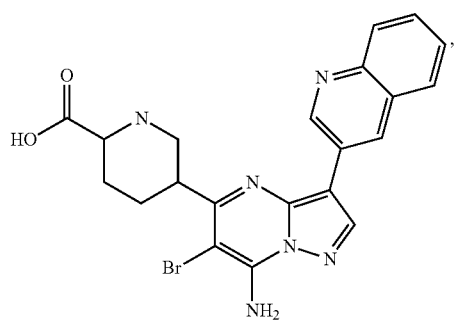
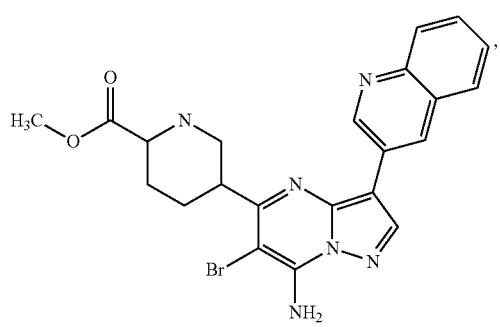
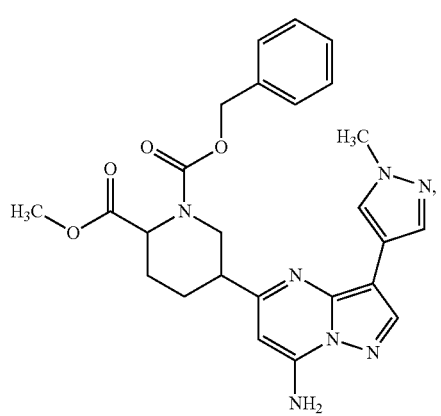
208
-continued
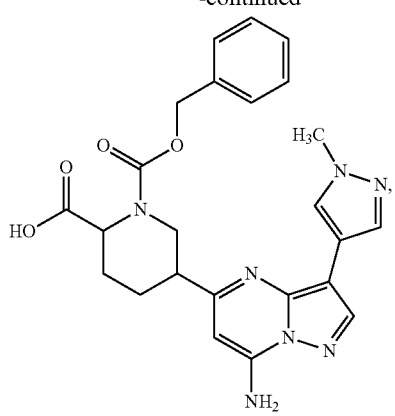
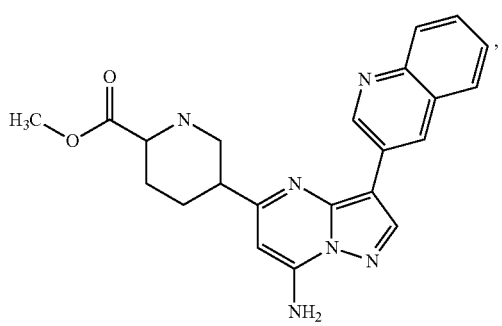
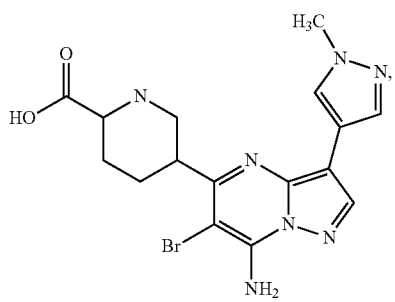
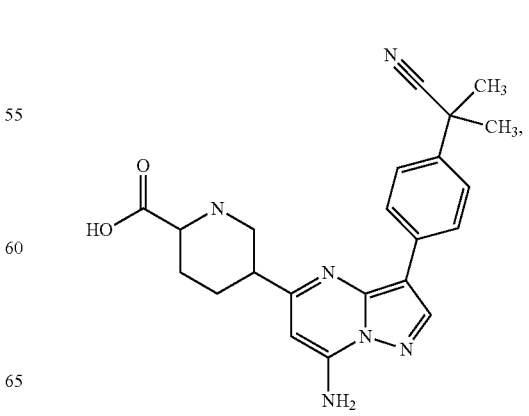

209
-continued
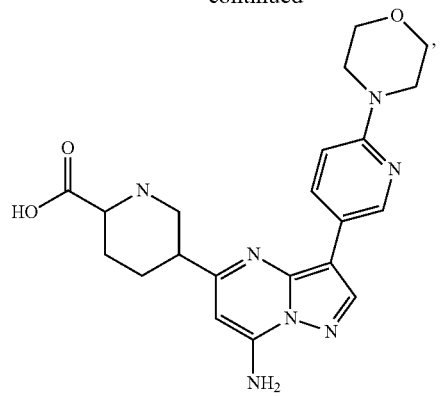
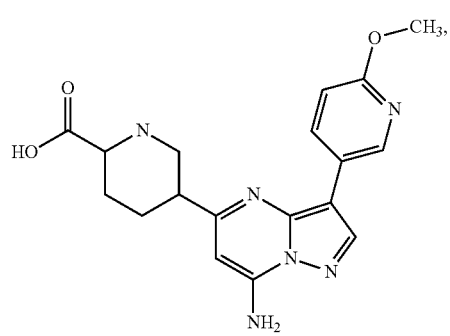
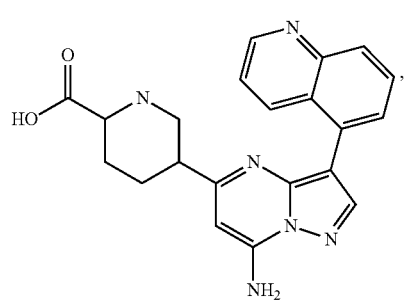
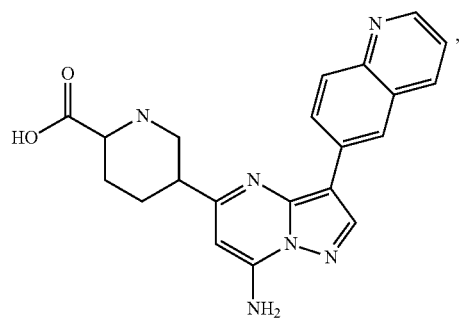
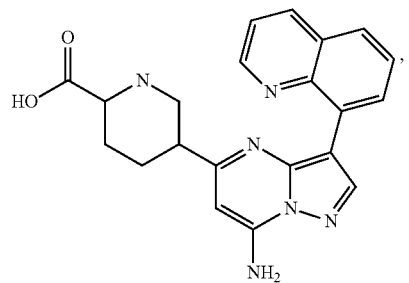
210
-continued
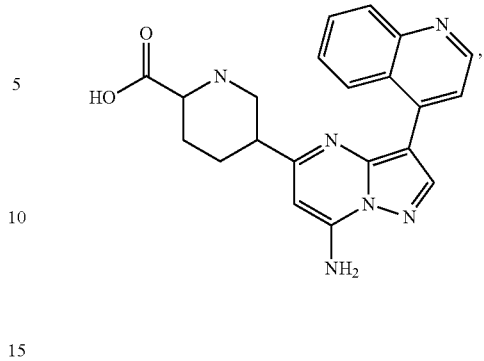
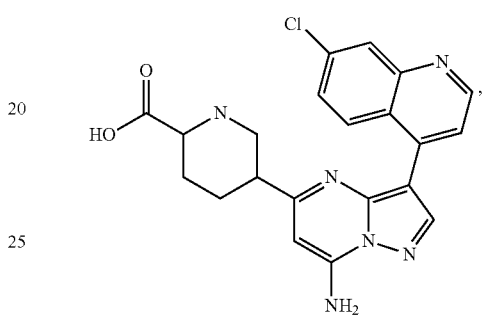
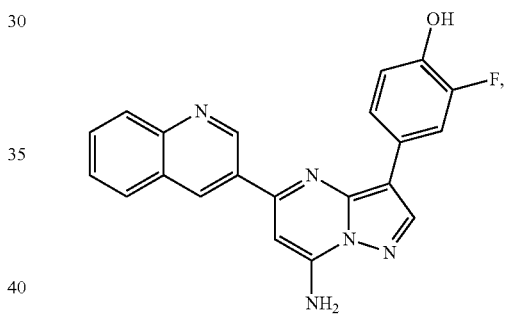
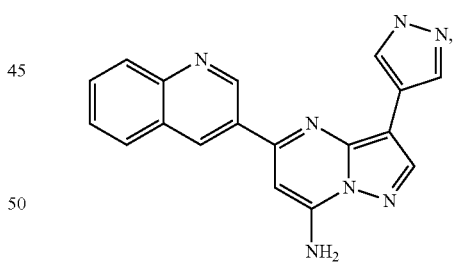
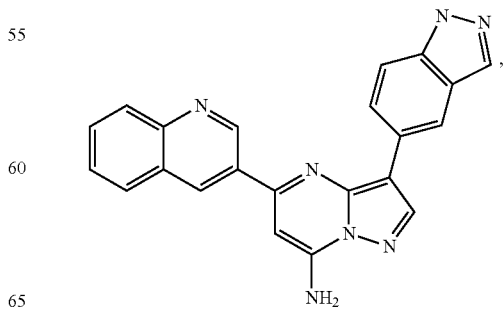

211
-continued
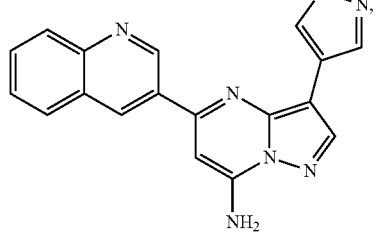
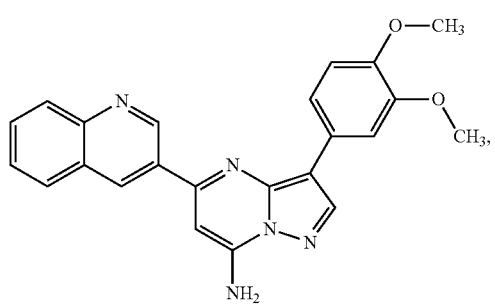
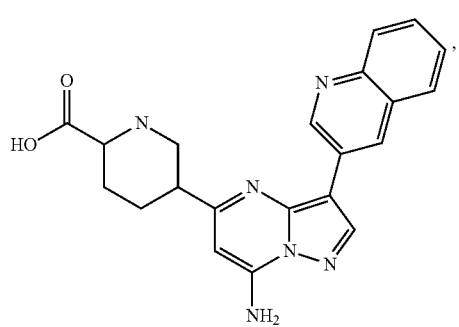
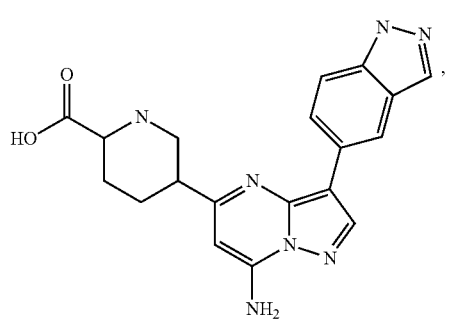
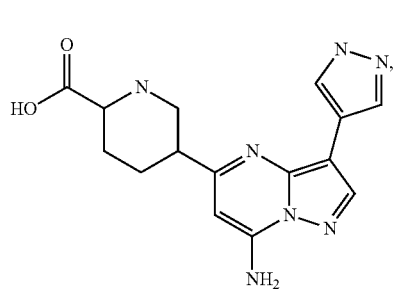
212
-continued
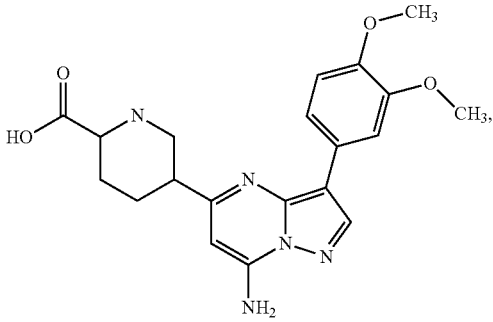
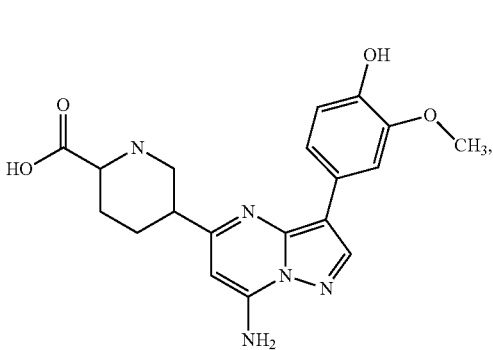
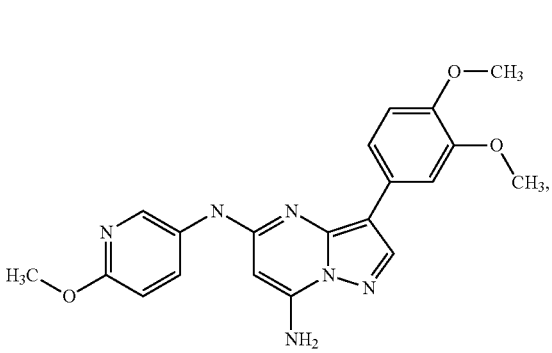
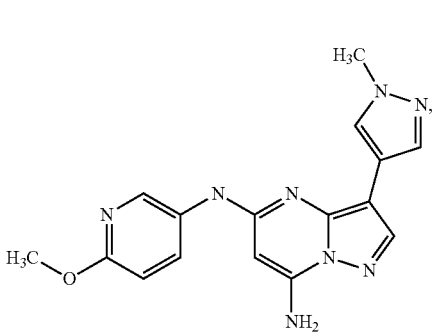
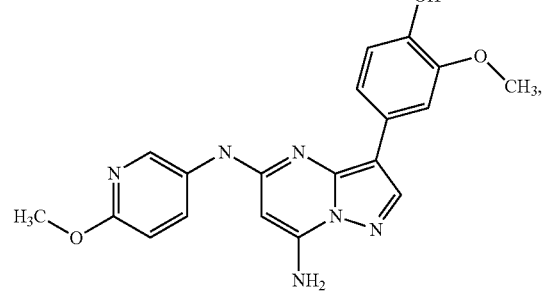

213
-continued
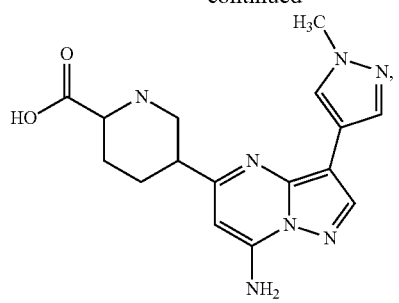
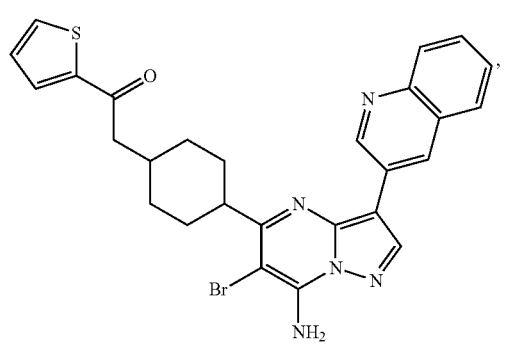
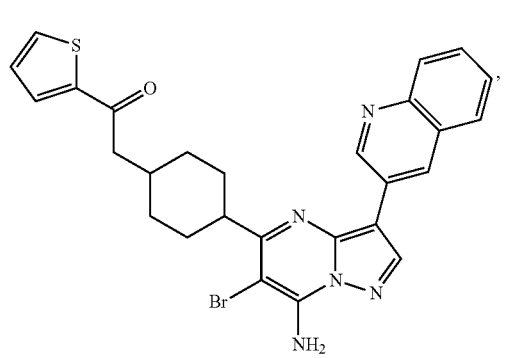
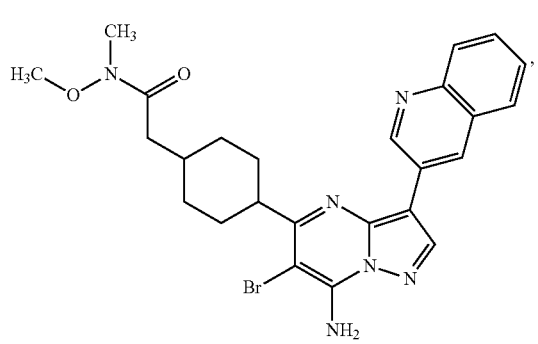
214
-continued
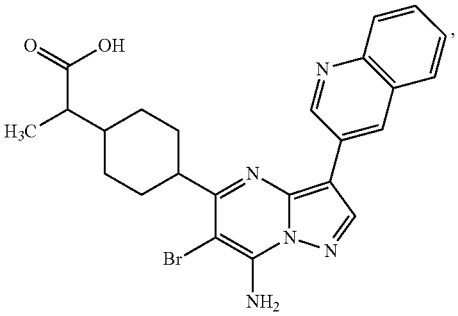
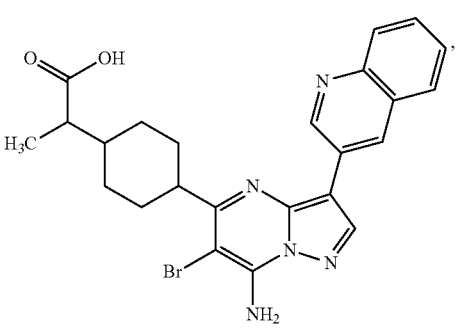
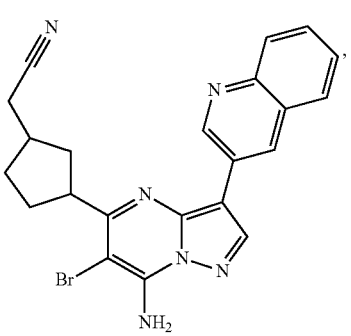
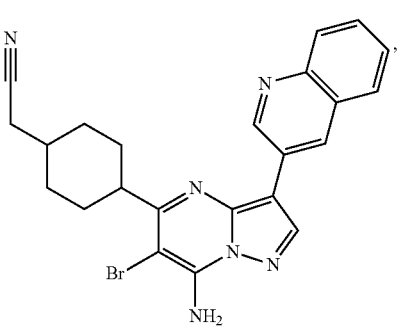
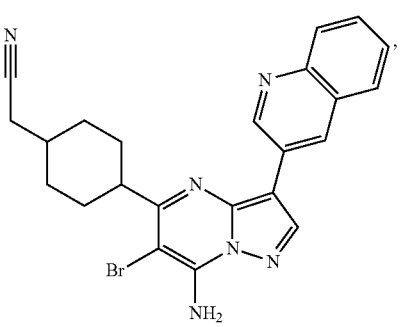

215
-continued
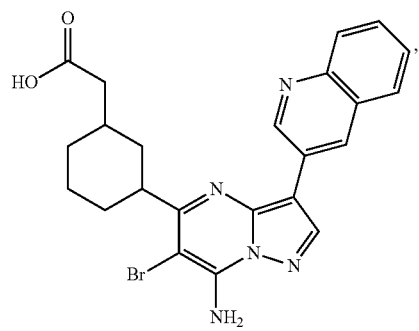
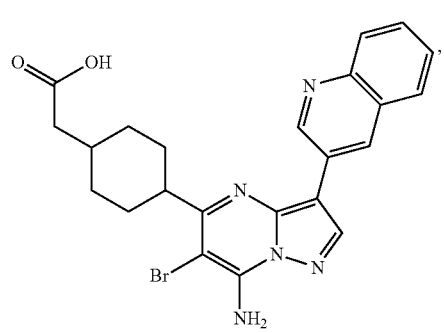
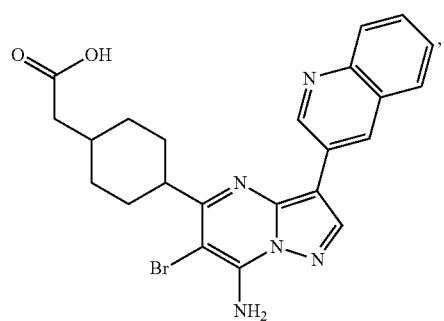
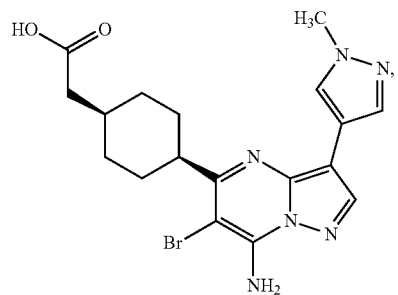
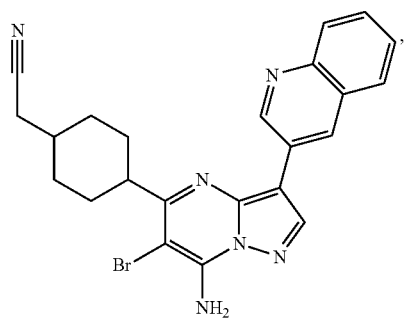
216
-continued
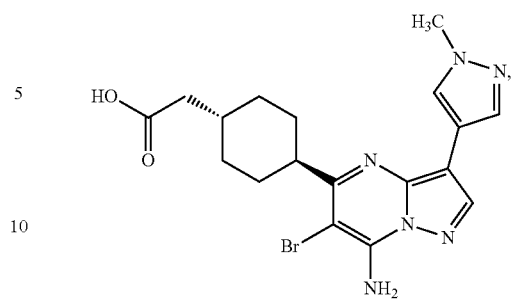
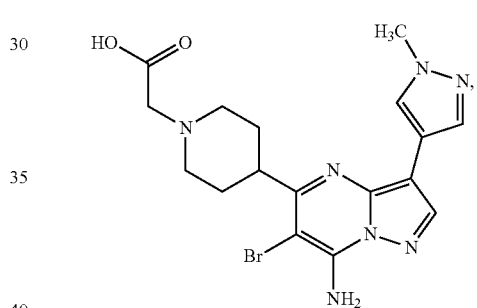
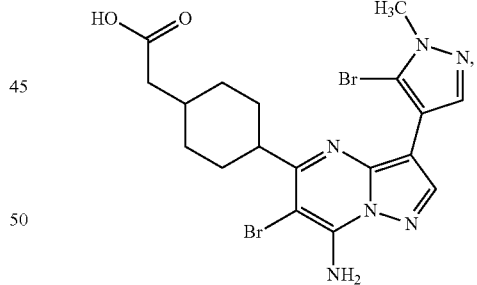
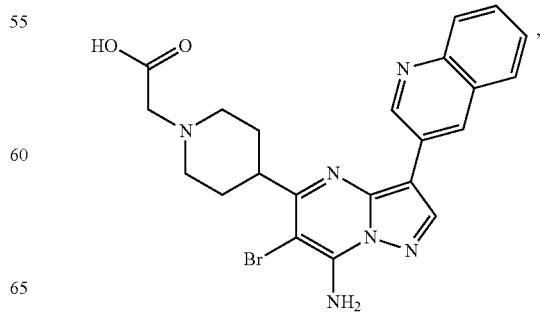

217
-continued
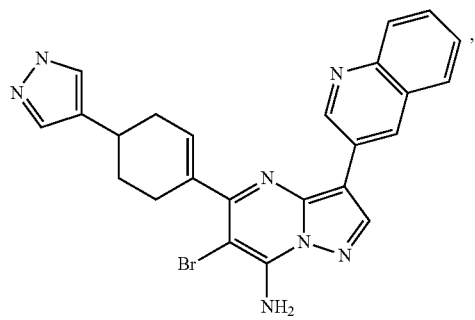
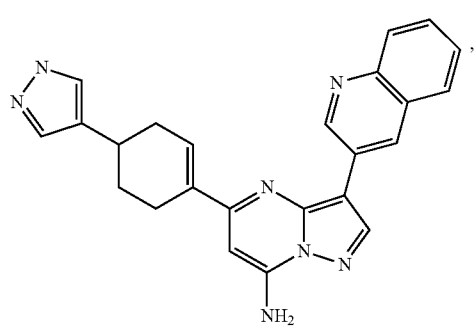
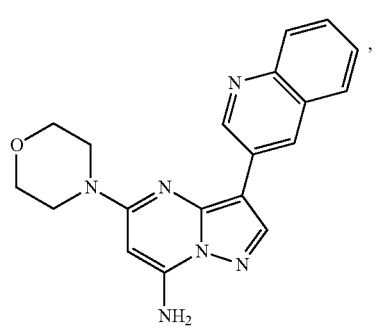
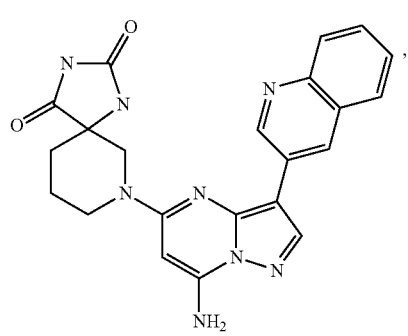
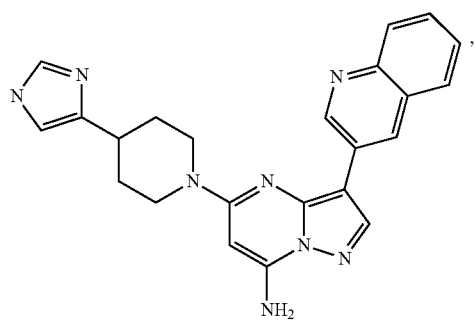
218
-continued
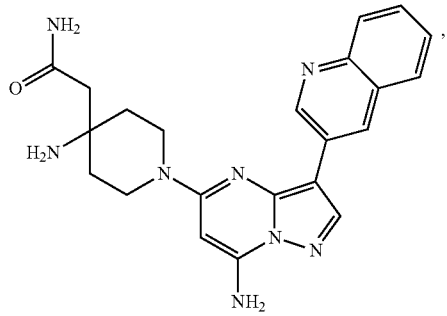
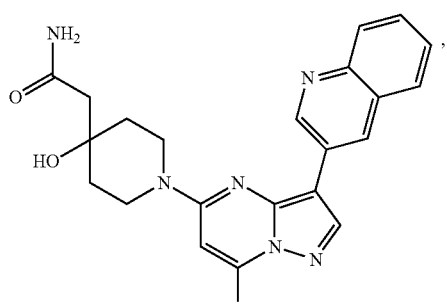
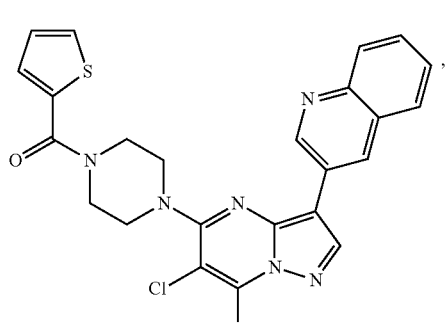
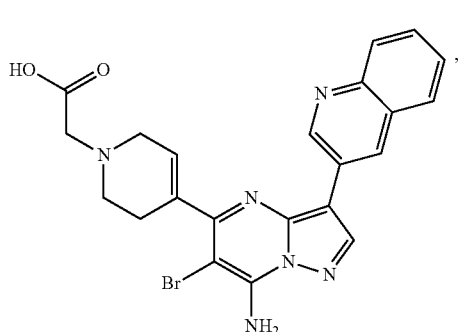
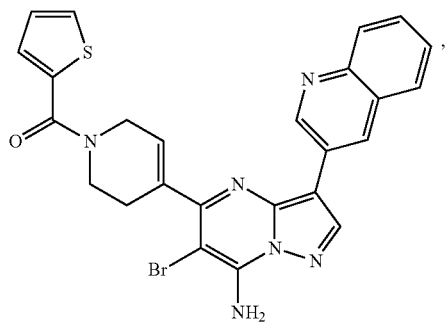

219
-continued
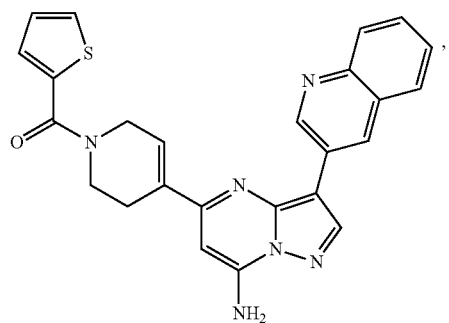
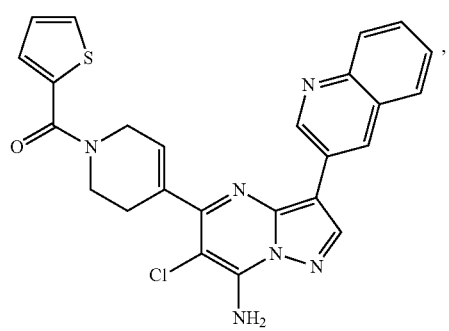
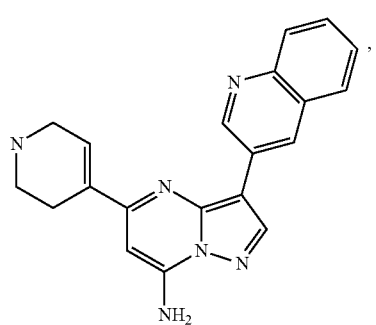
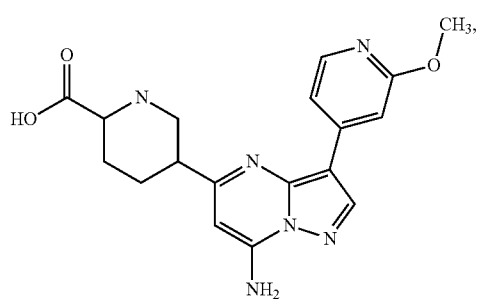
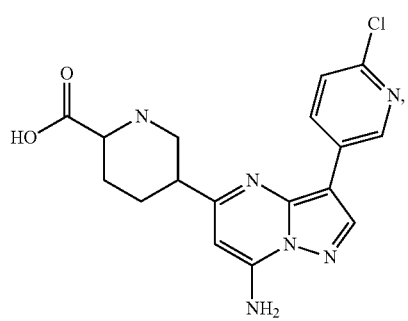
220
-continued
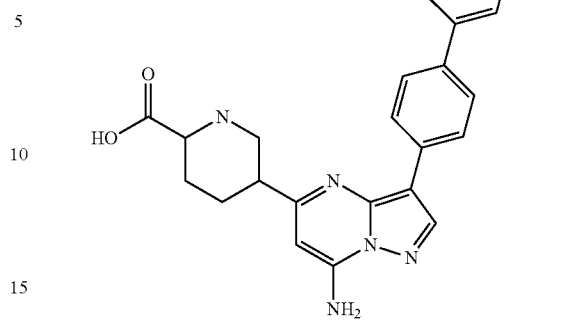
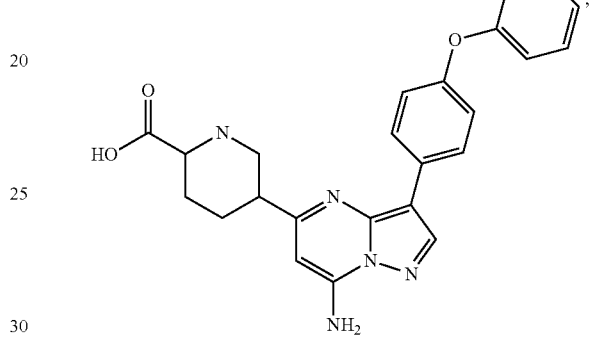
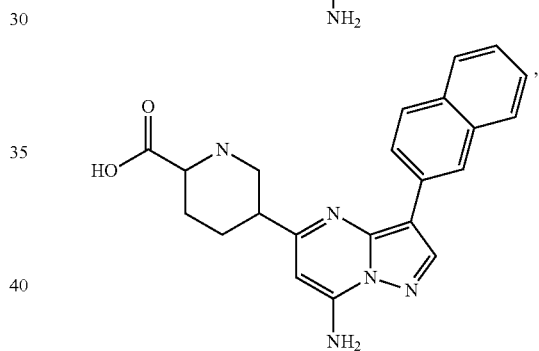
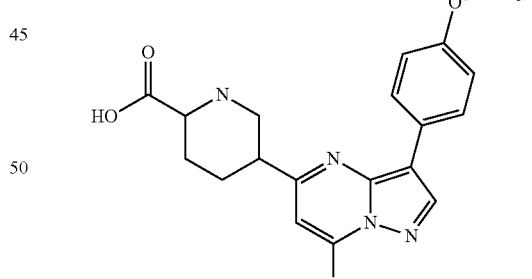
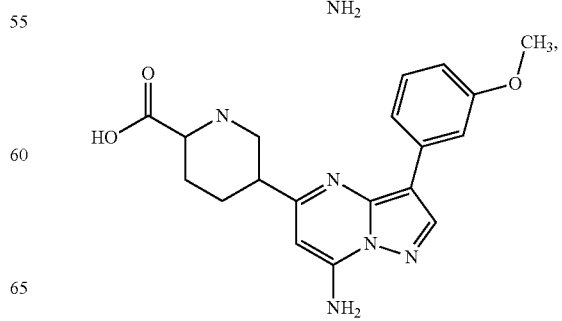

221
-continued

222
-continued

| 223 | 224 |
|---|---|
| -continued | -continued |
| 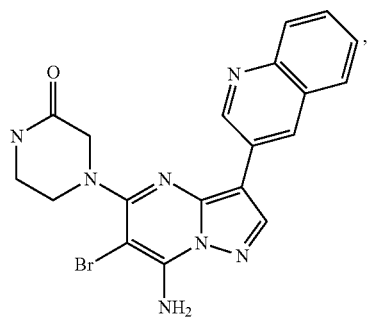 | 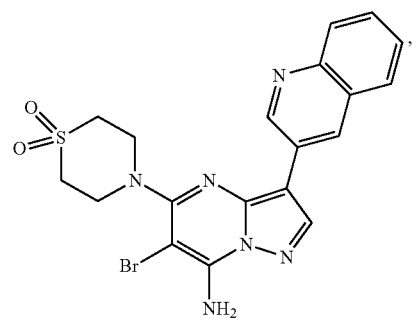 |
| 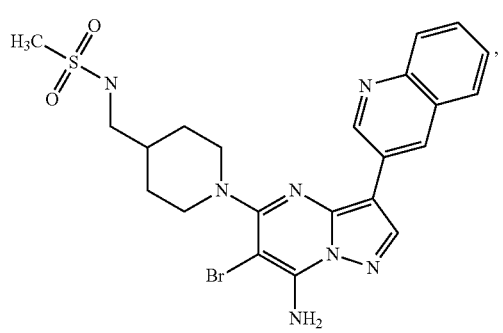 | 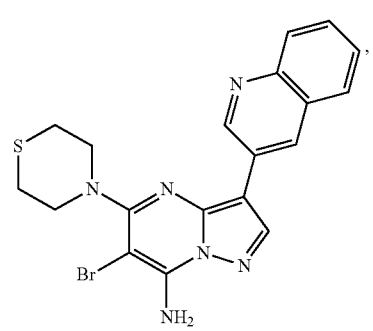 |
| 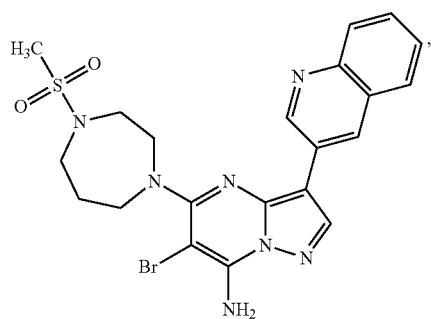 | 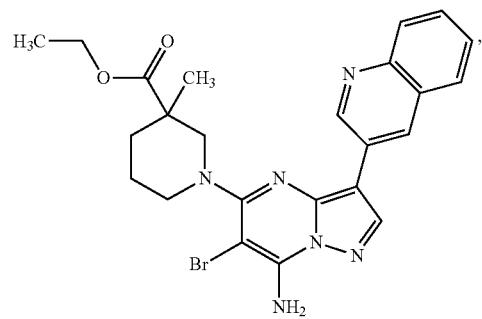 |
| 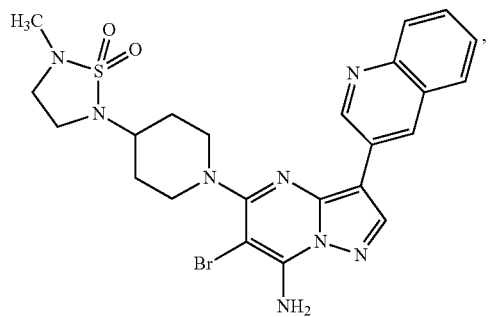 | 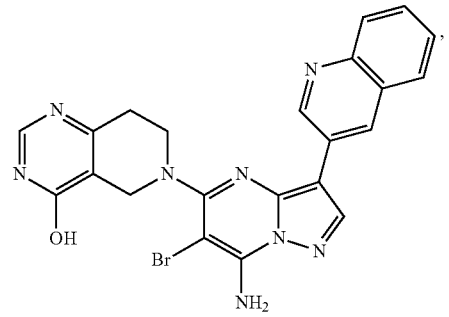 |
| 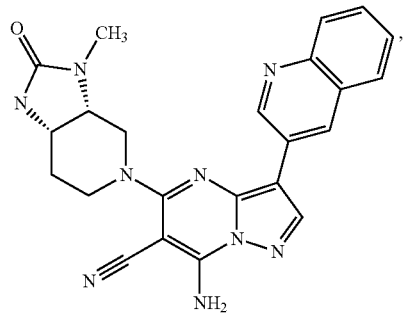 | 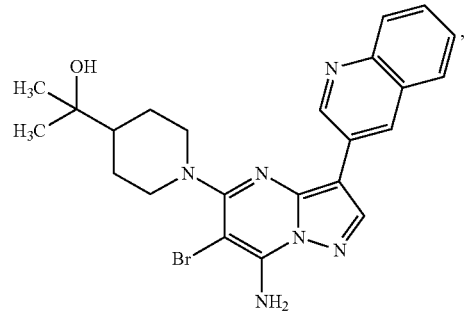 |

225
-continued
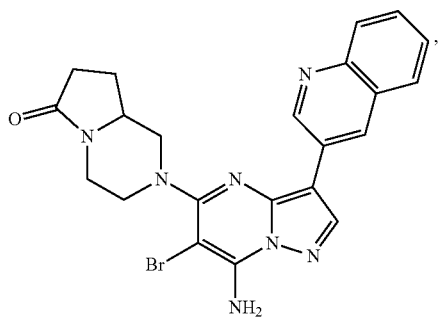
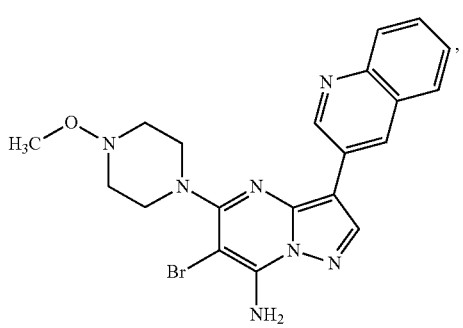
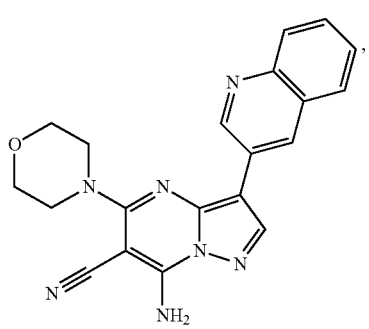
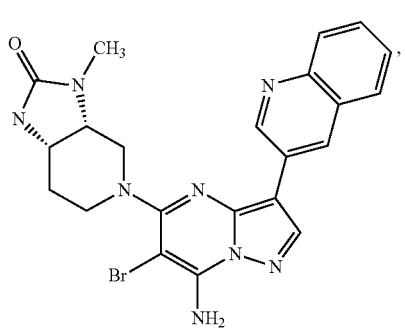
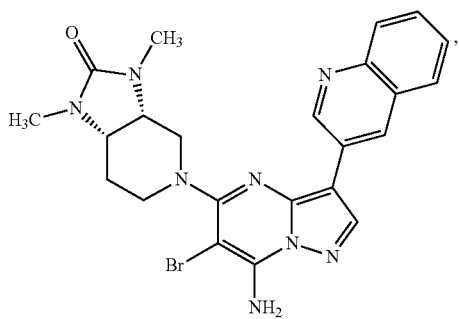
226
-continued
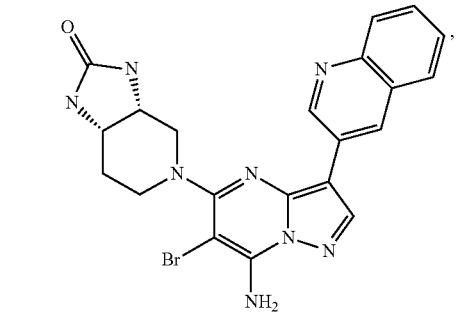
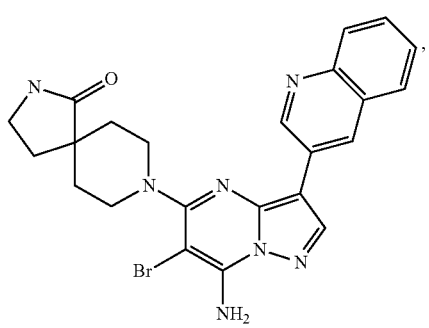
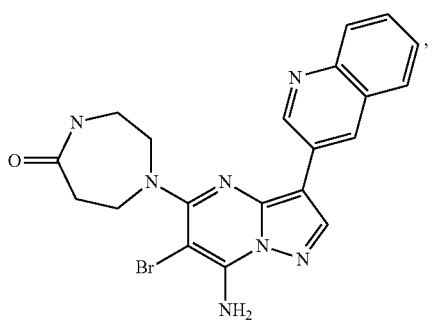
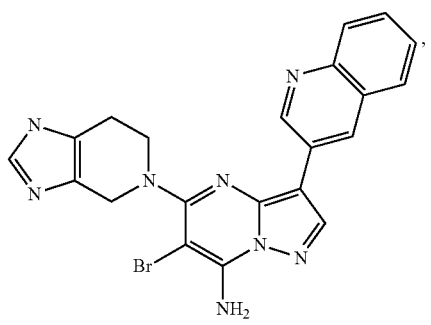
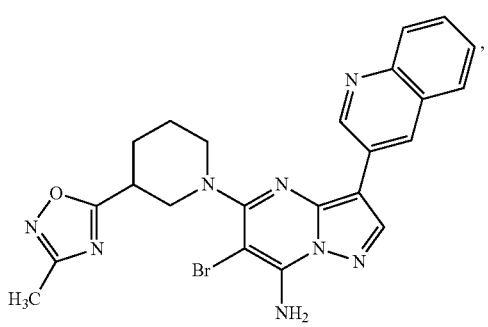

227
-continued
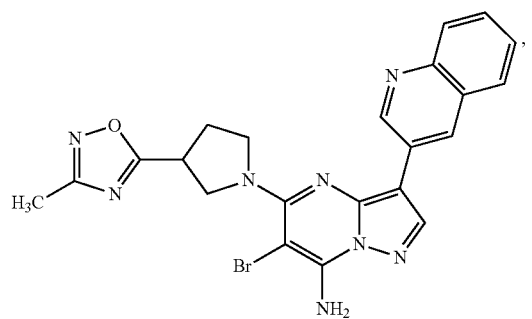
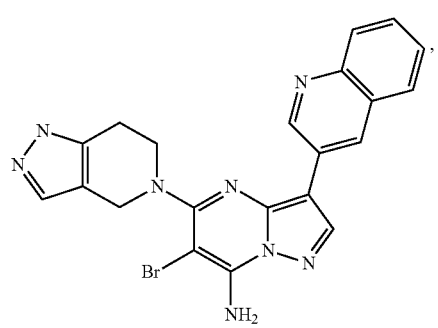
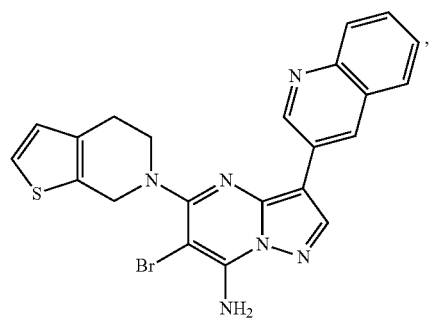
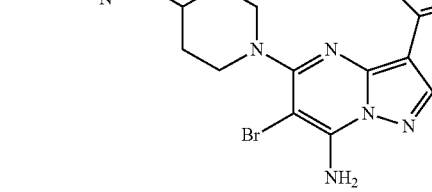
228
-continued
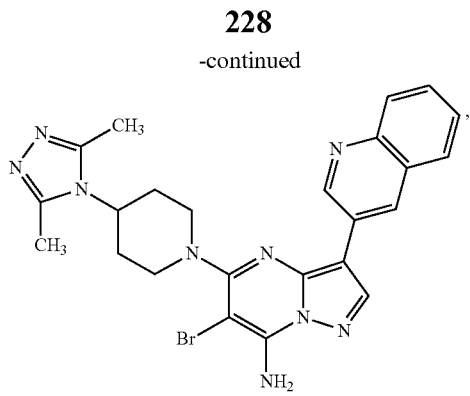
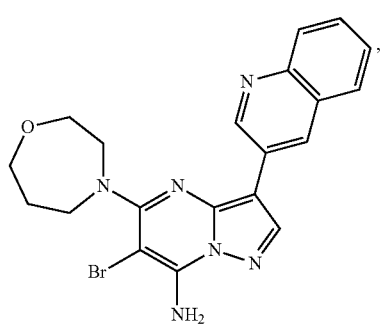
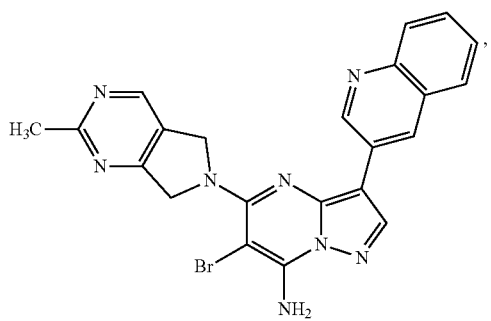
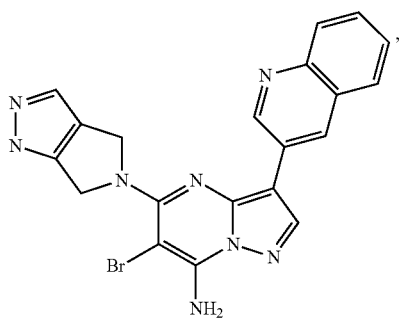
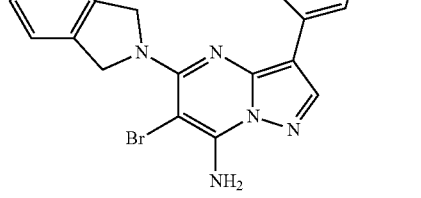

229
-continued
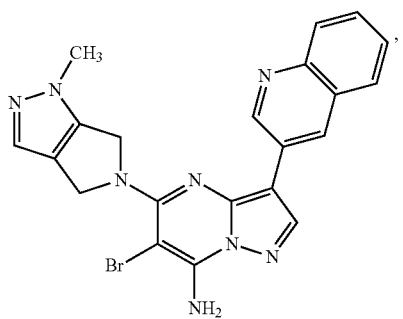
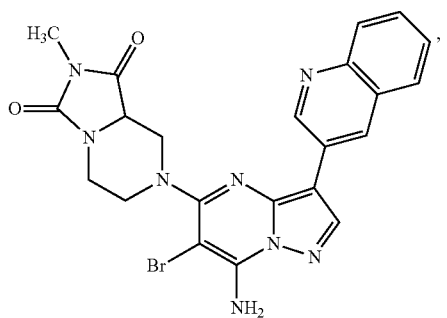
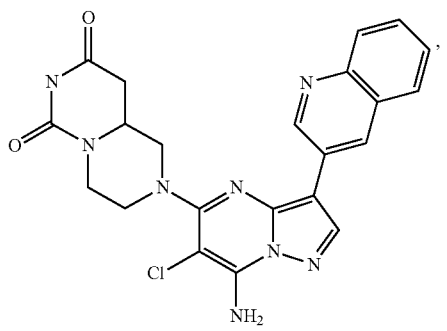
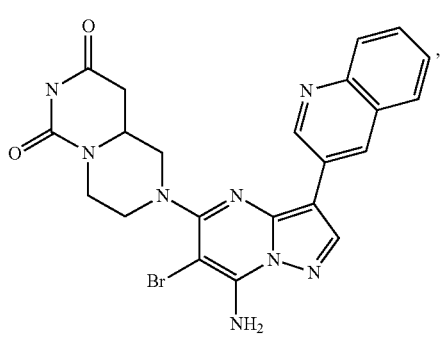
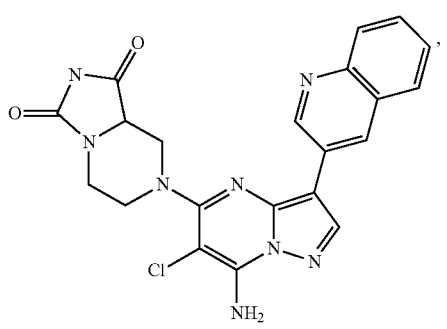
230
-continued
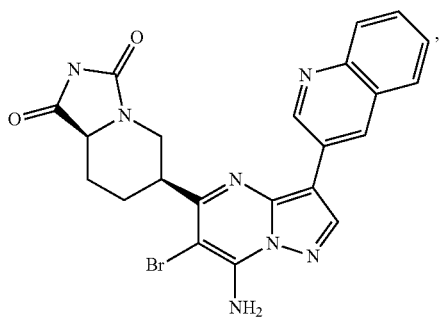
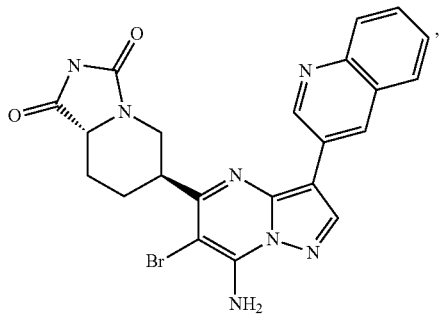
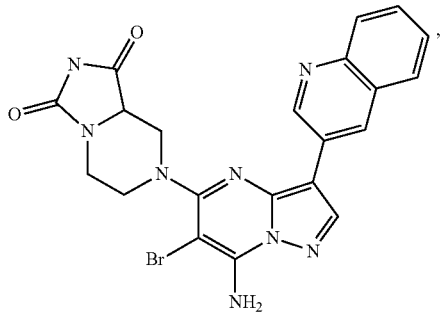
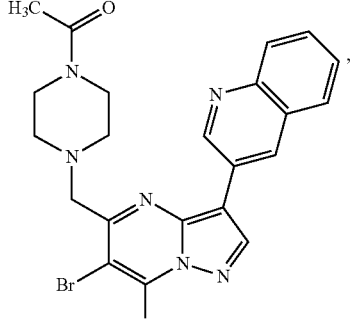
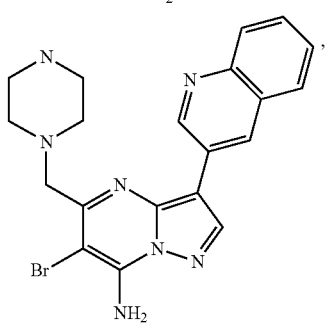

231
-continued
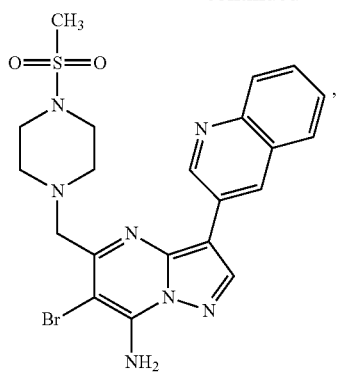
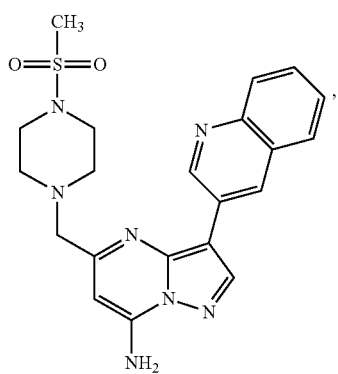
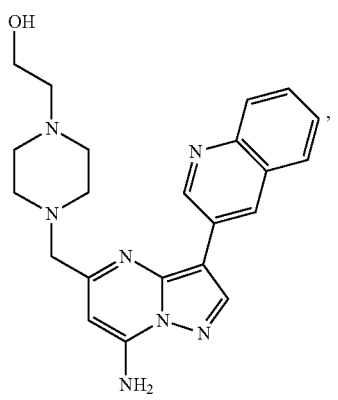
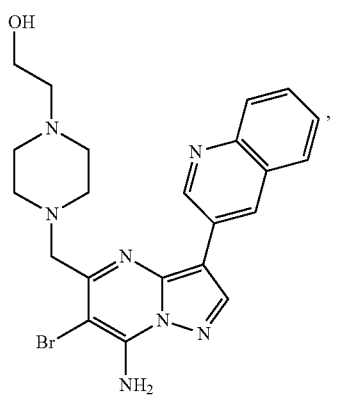
232
-continued
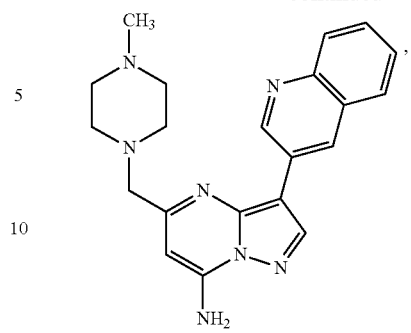
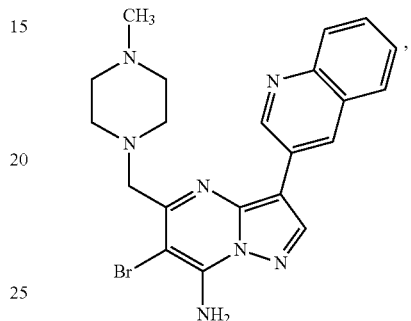
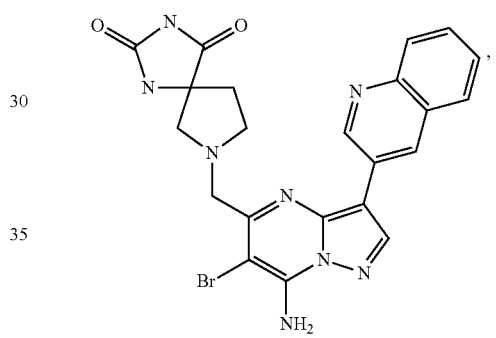
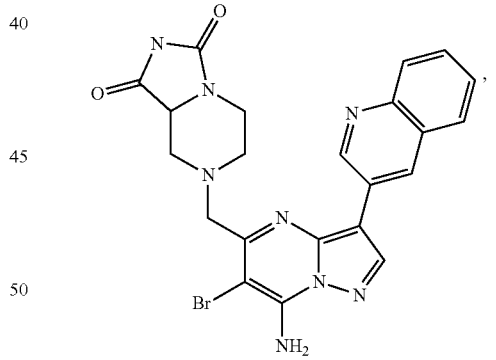
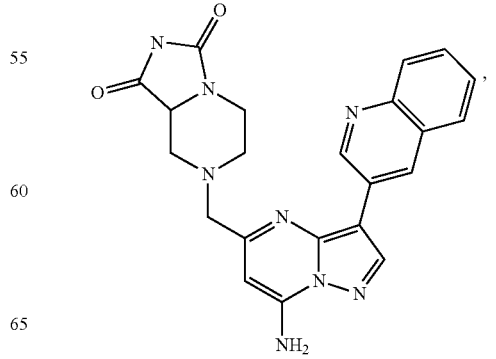

233
-continued
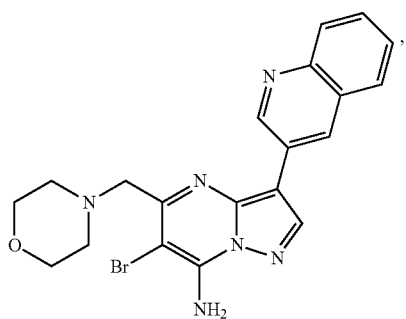
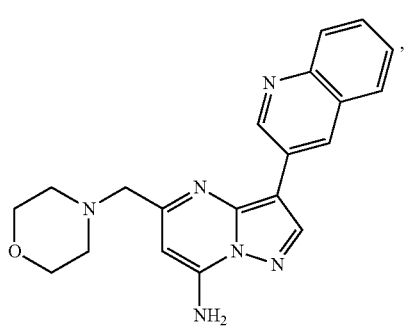
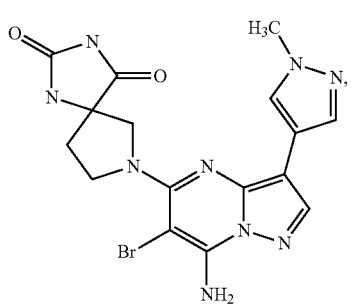
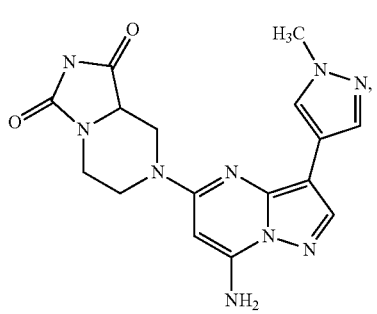
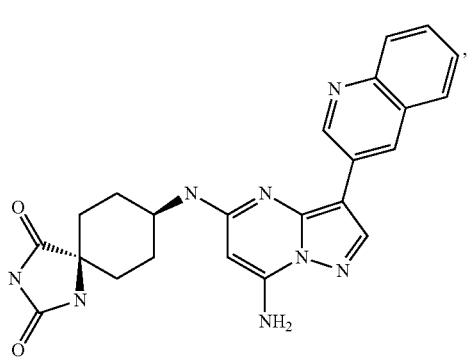
234
-continued
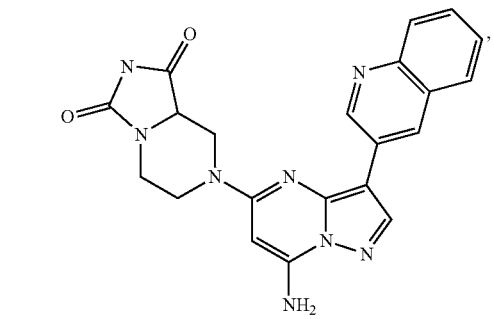
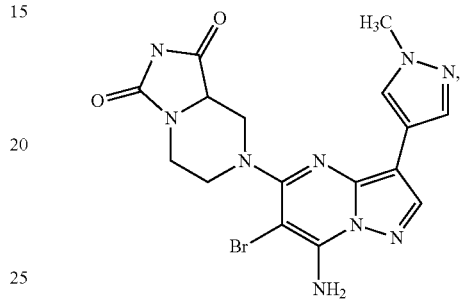
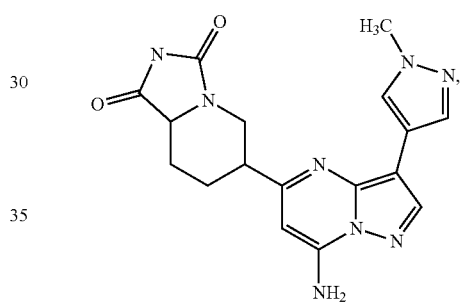
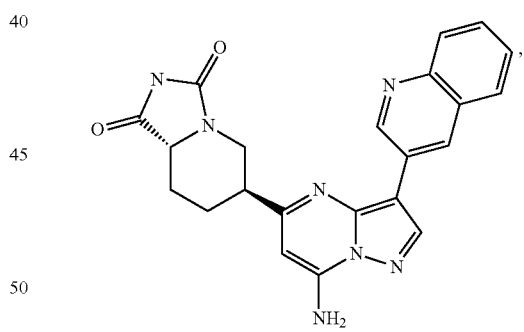
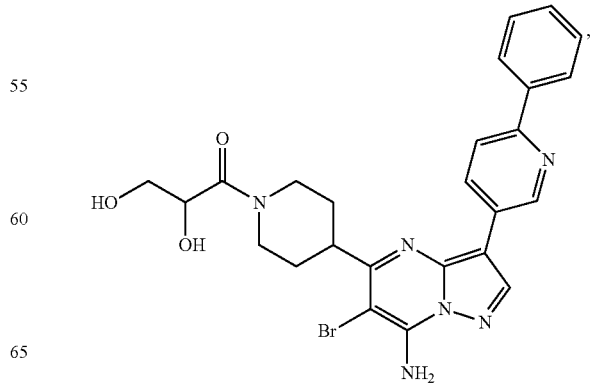

235
-continued
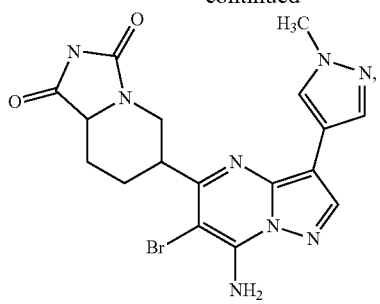
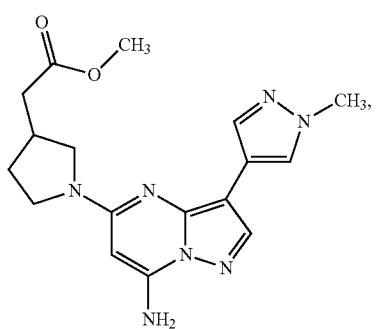
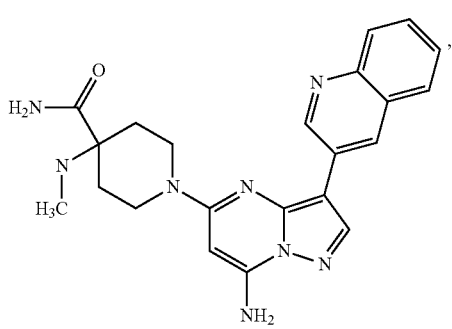
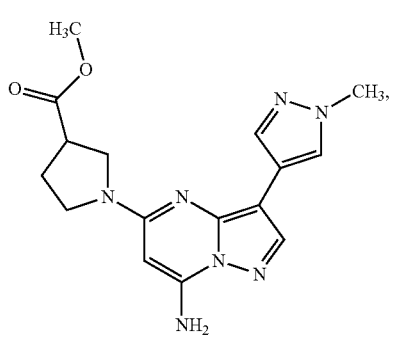
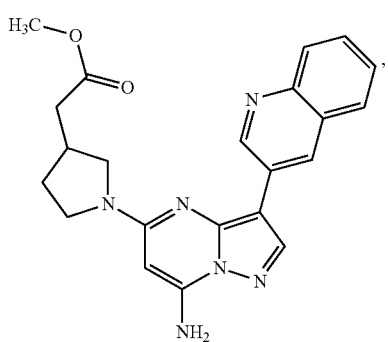
236
-continued
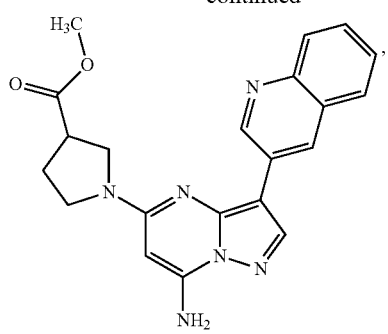
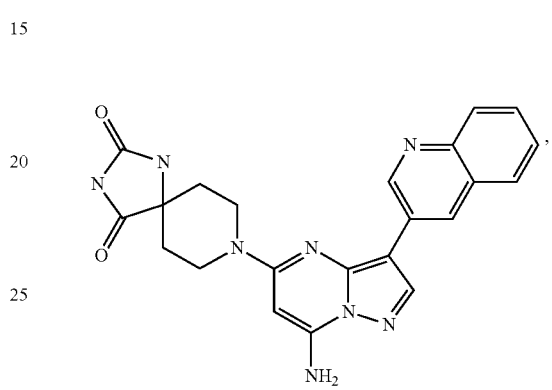
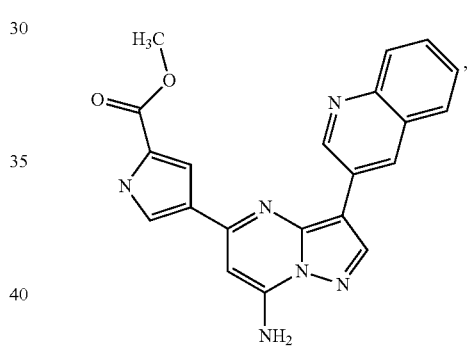
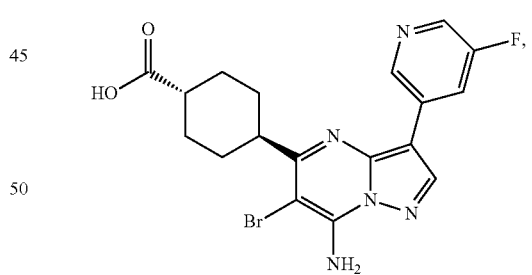
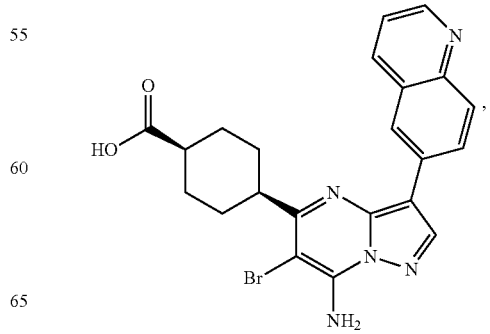

237
-continued
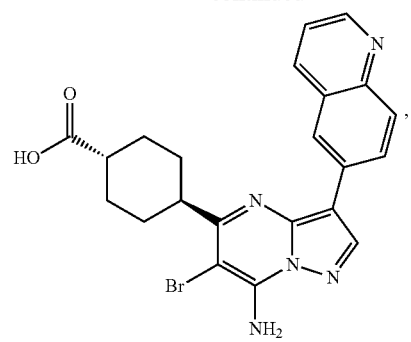
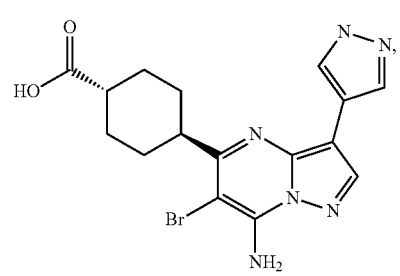
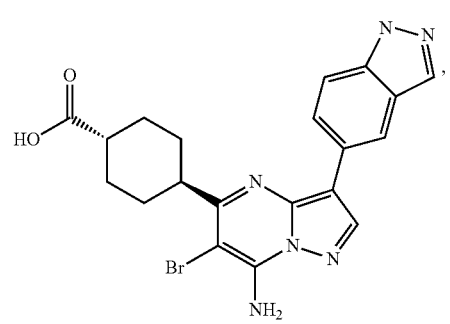
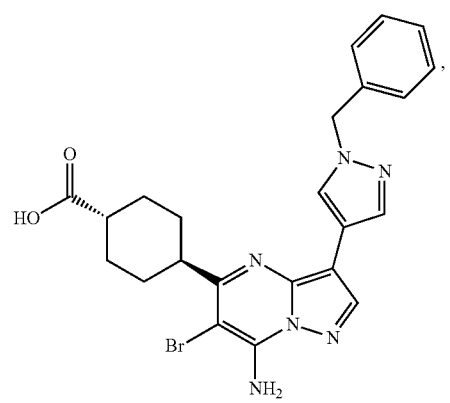
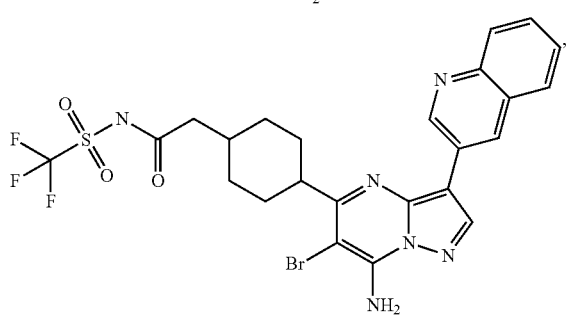
238
-continued
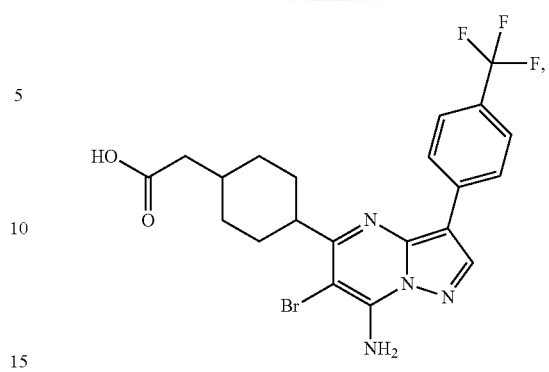
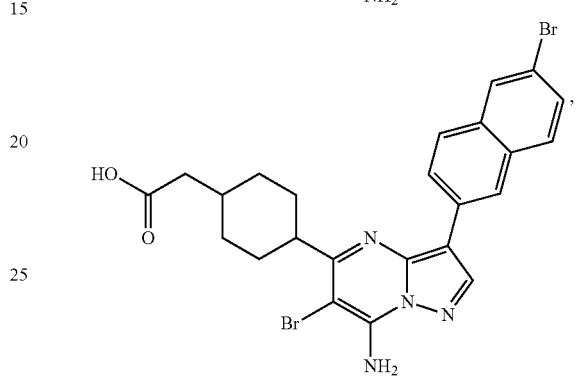
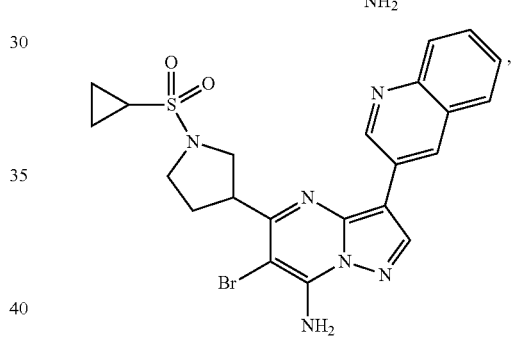
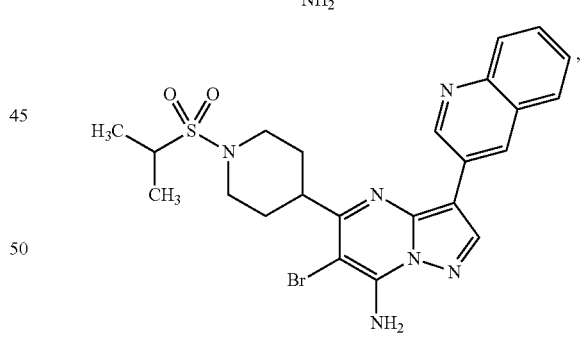
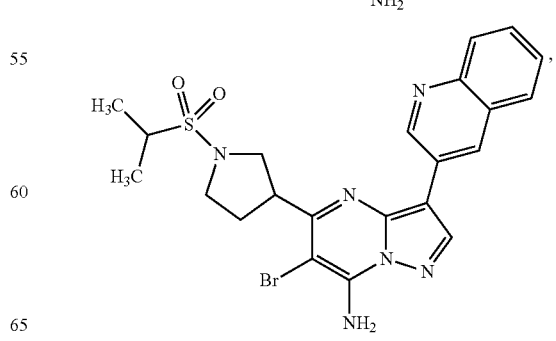

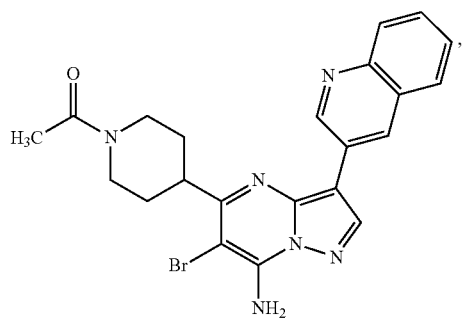
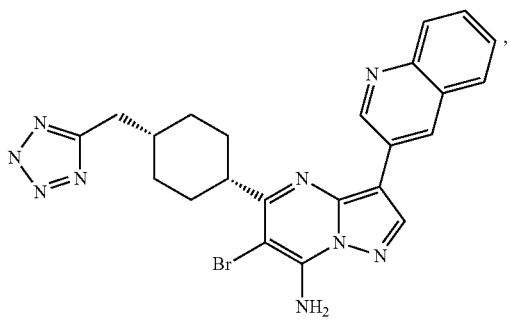

241
-continued
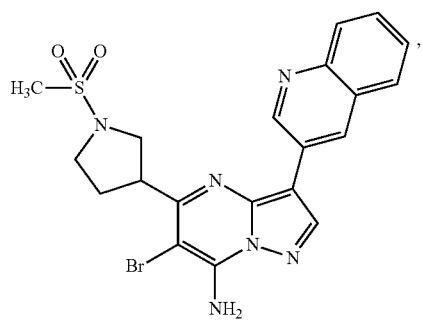
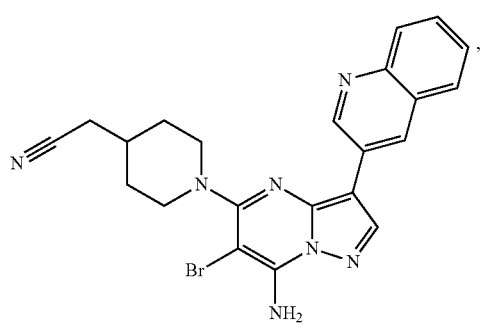
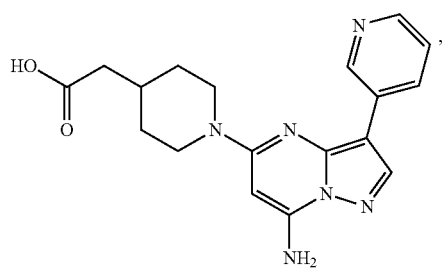
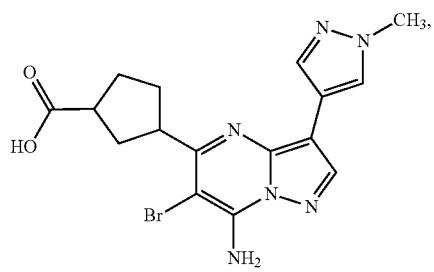
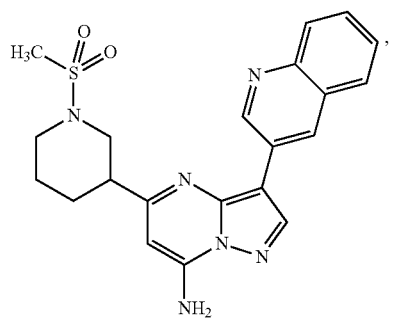
242
-continued
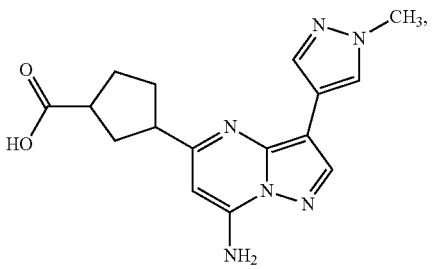
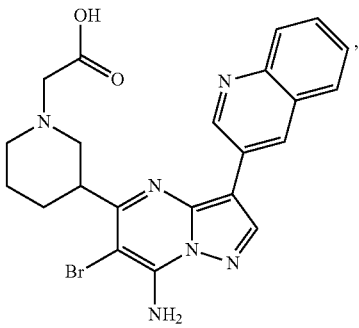
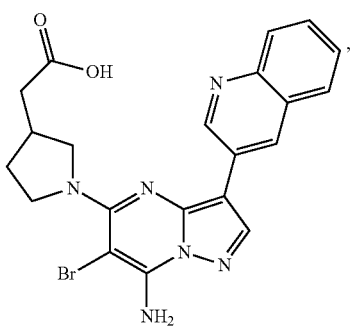
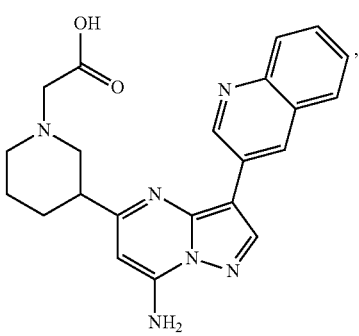
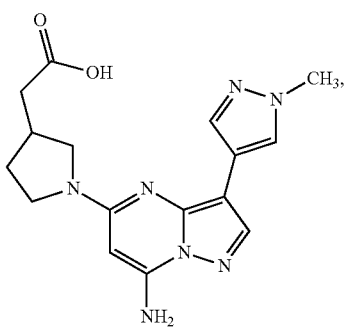

243
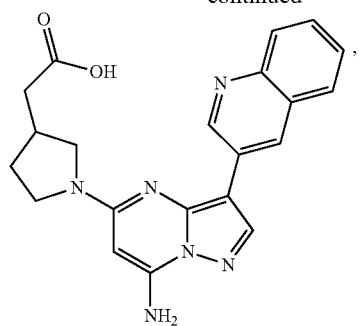
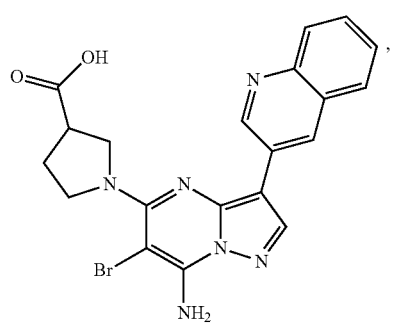
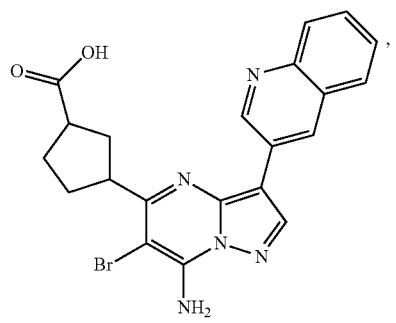
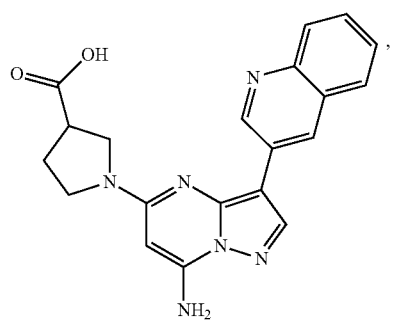
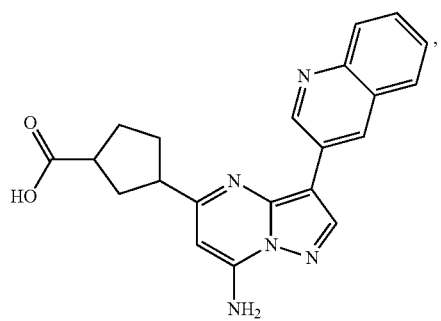
244
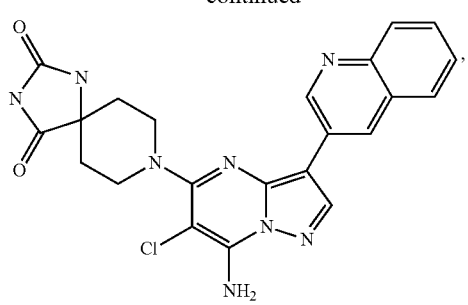
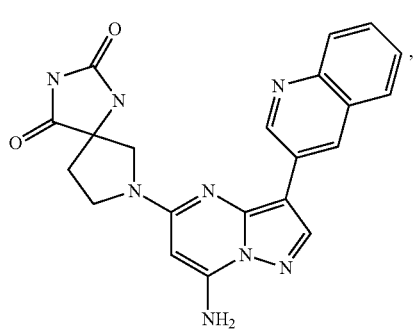
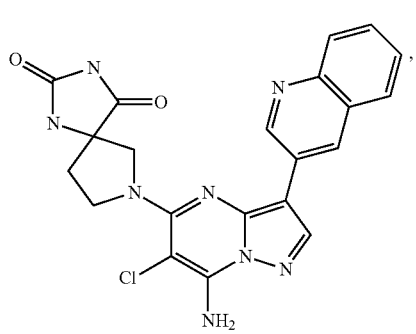
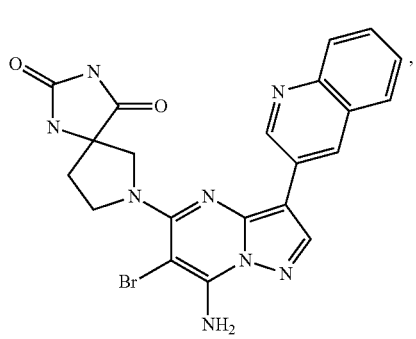
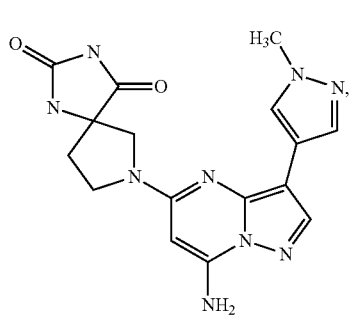

245
-continued
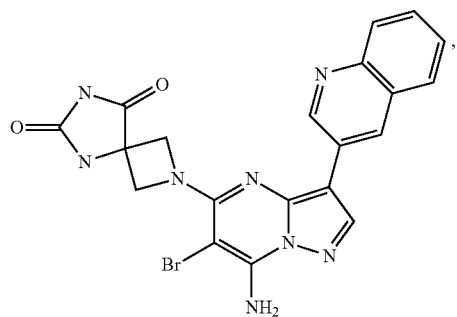
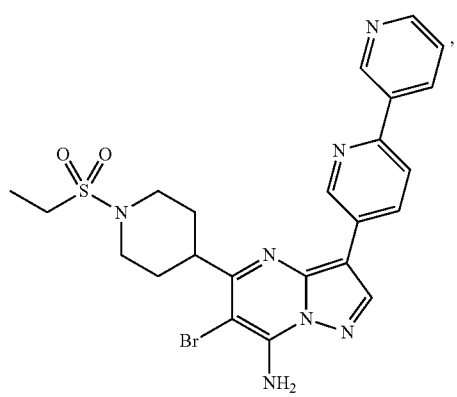
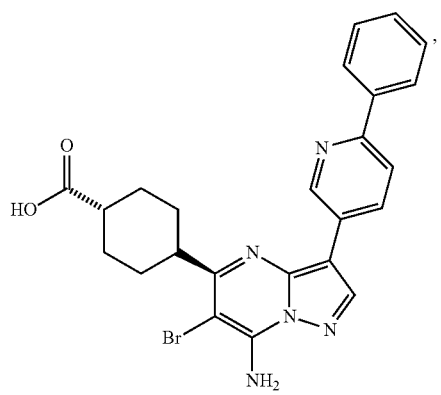
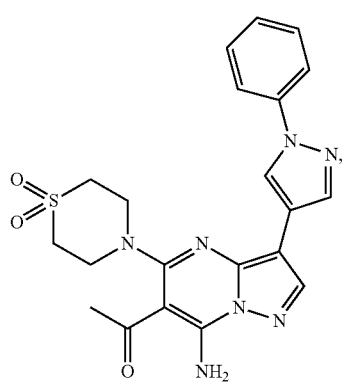
246
-continued
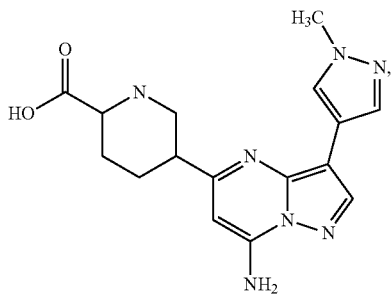
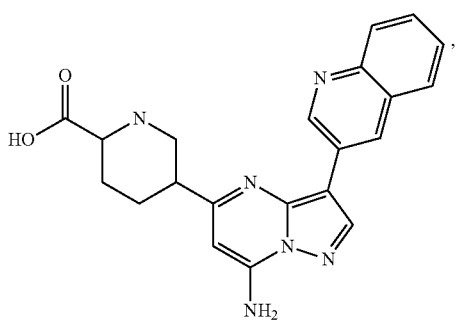
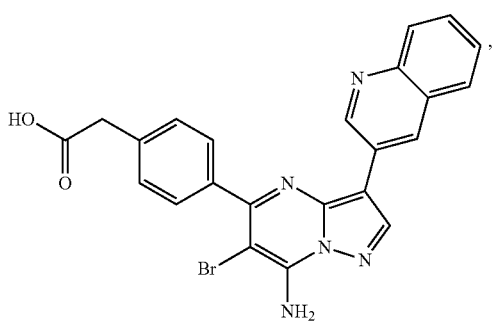
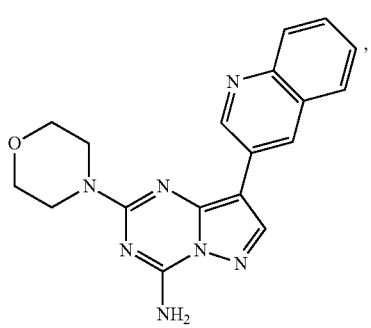
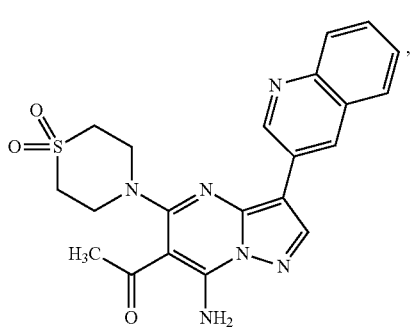

247
-continued
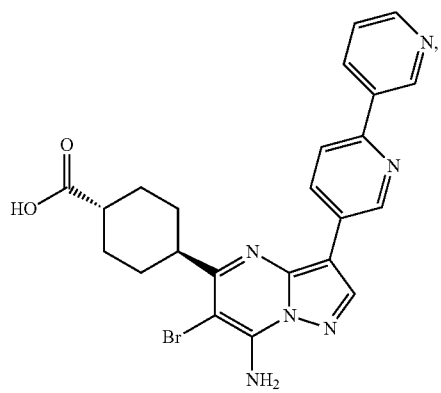
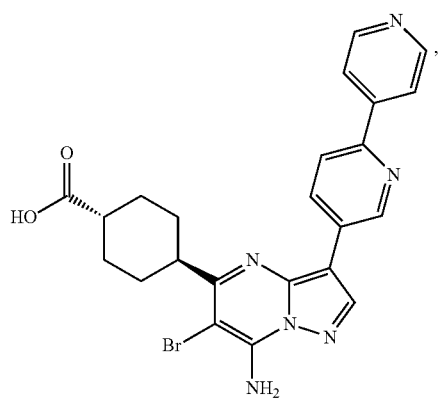
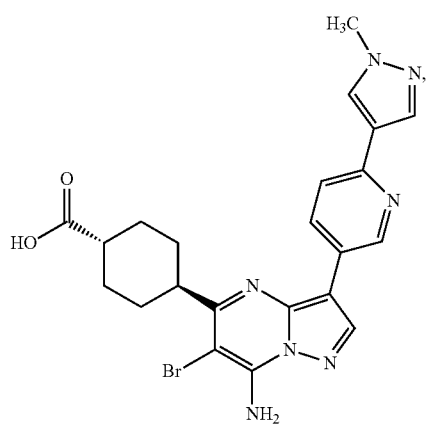
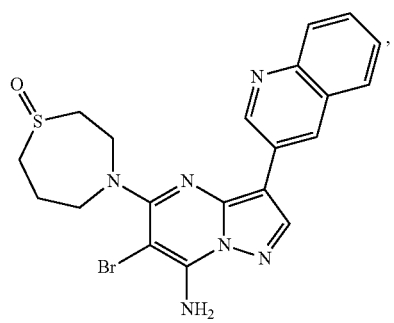
248
-continued
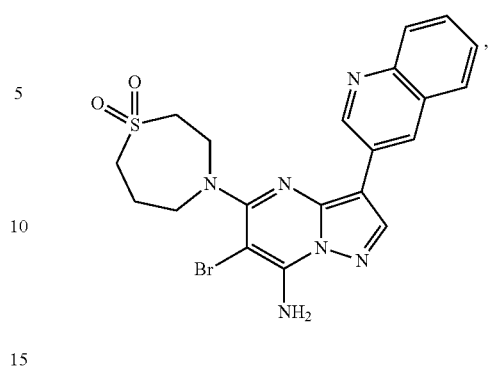
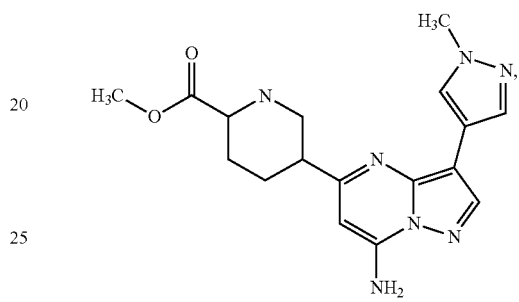
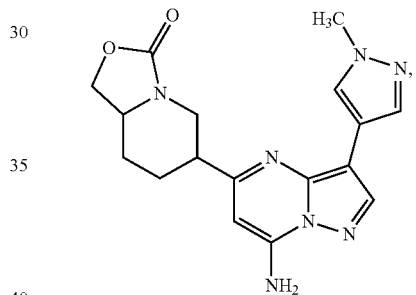
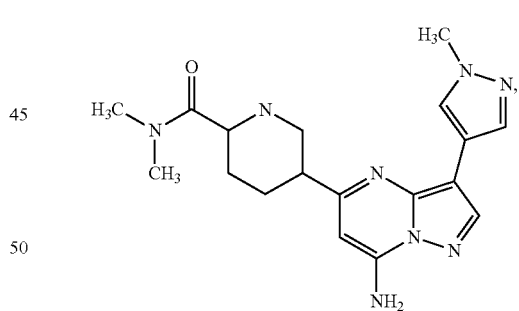
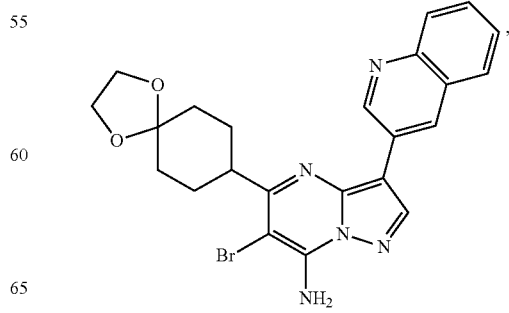

-continued
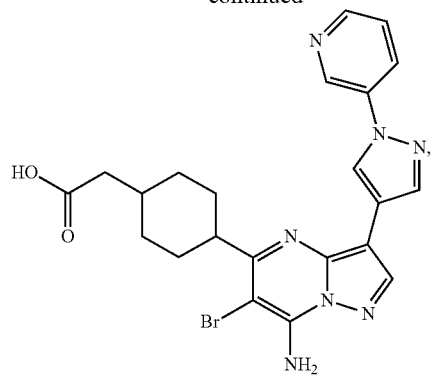
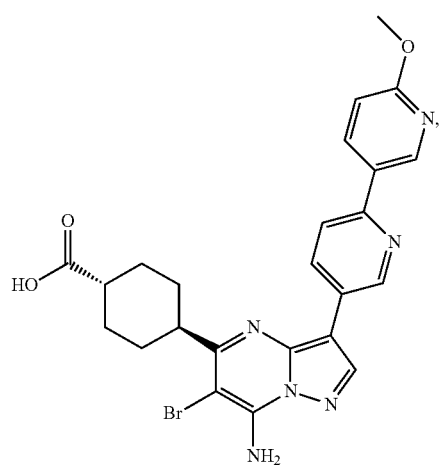
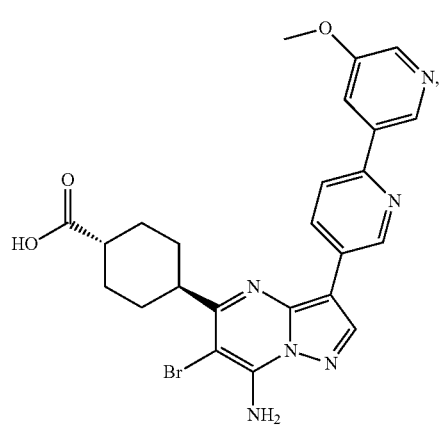
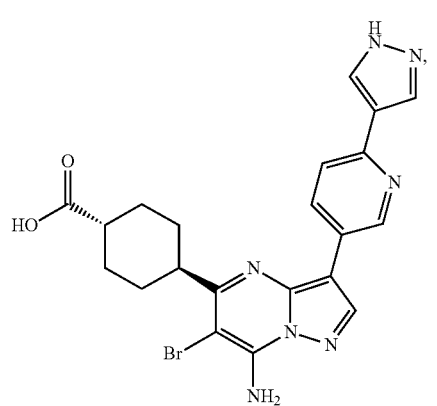
-continued
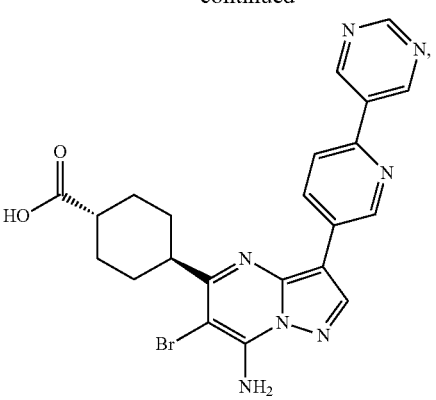
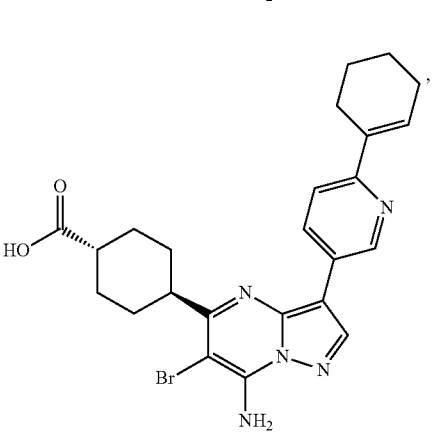
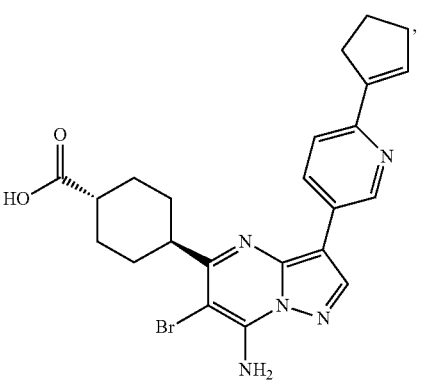
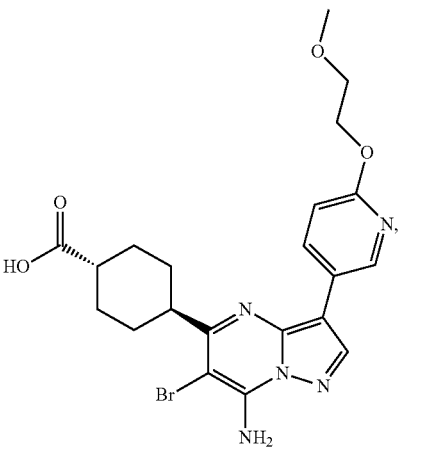

251
-continued
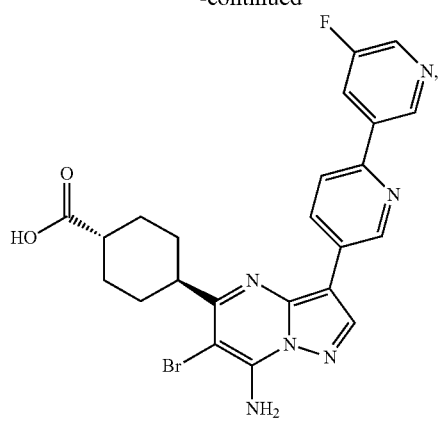
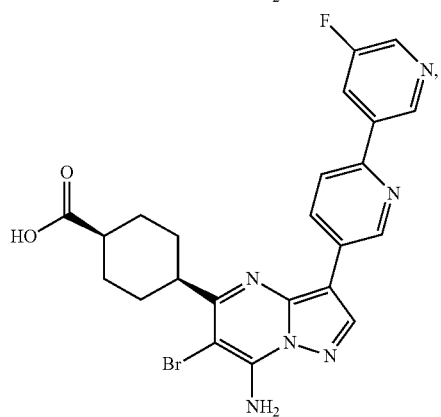
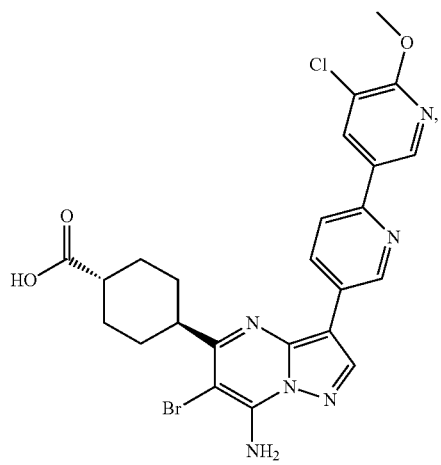
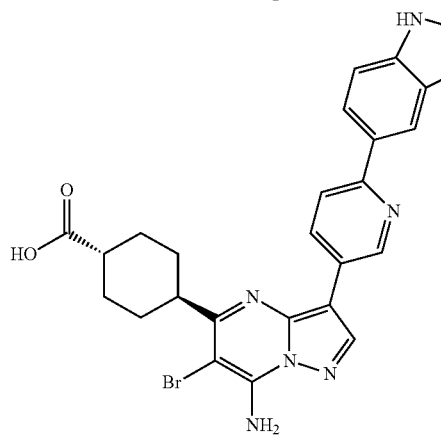
252
-continued
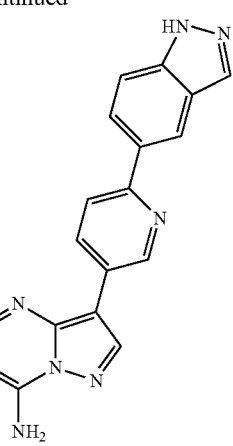
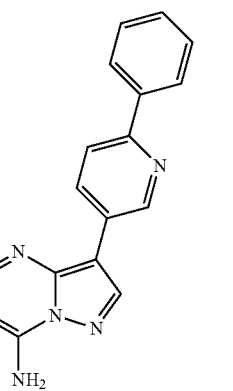
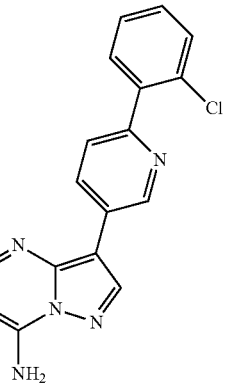
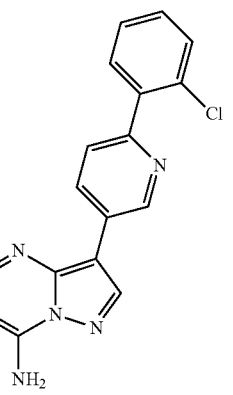

253
-continued
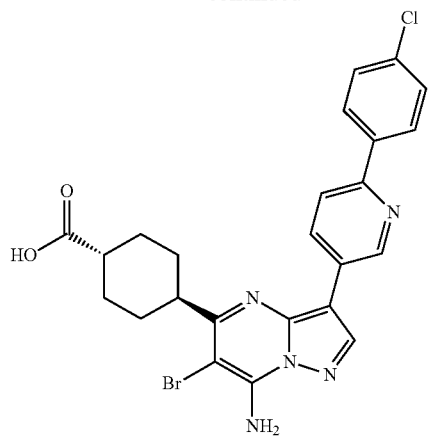
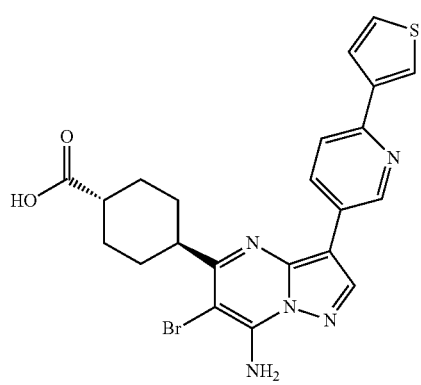
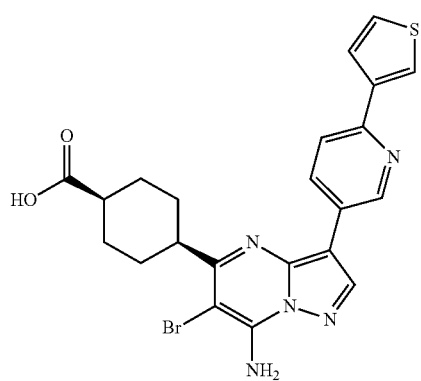
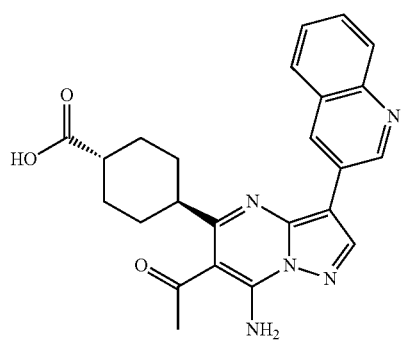
254
-continued
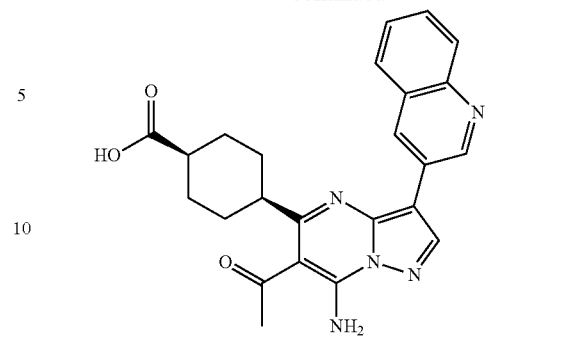
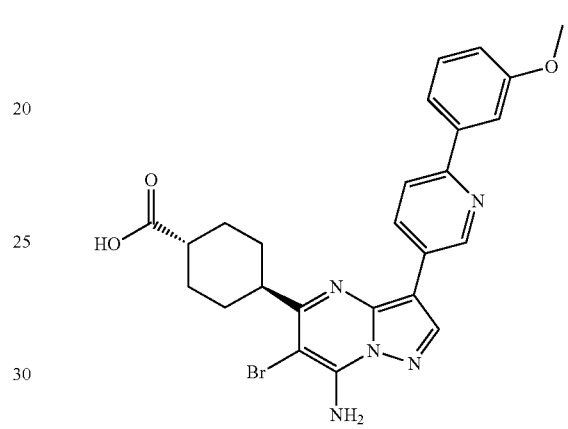
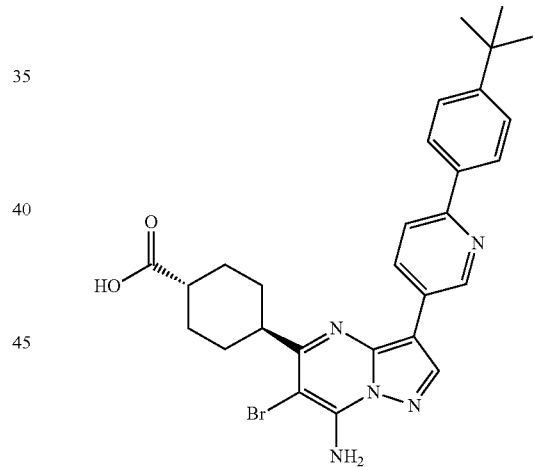
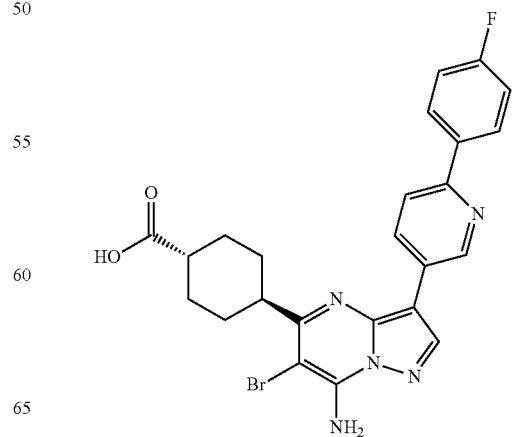

255
-continued
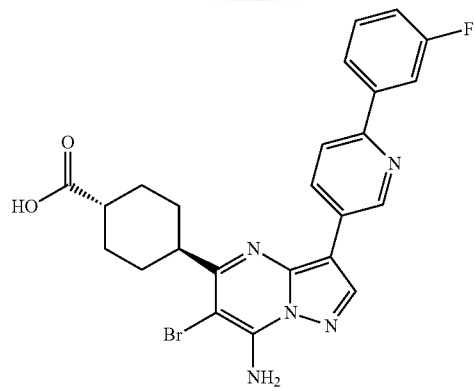
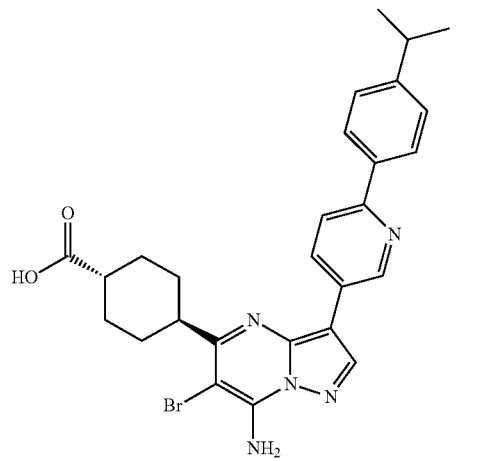
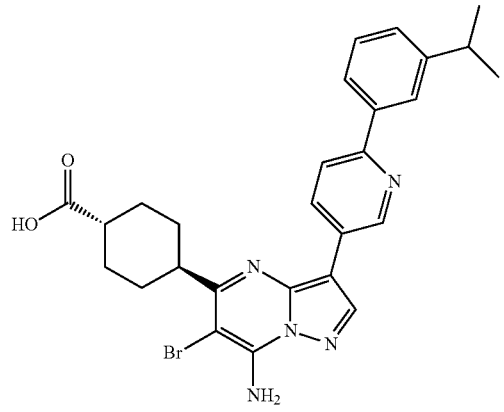
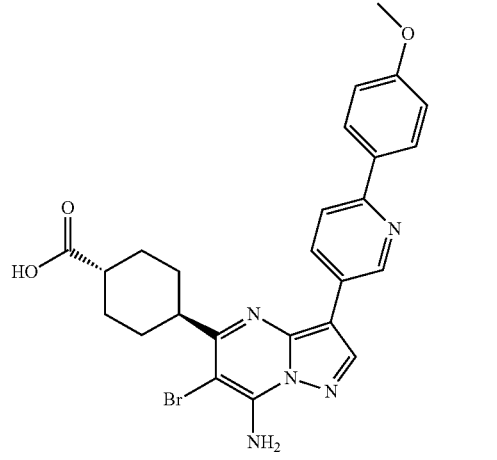
256
-continued
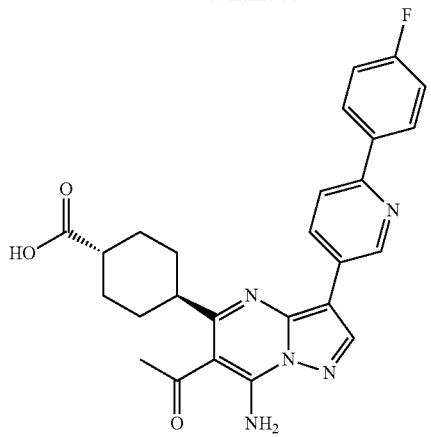
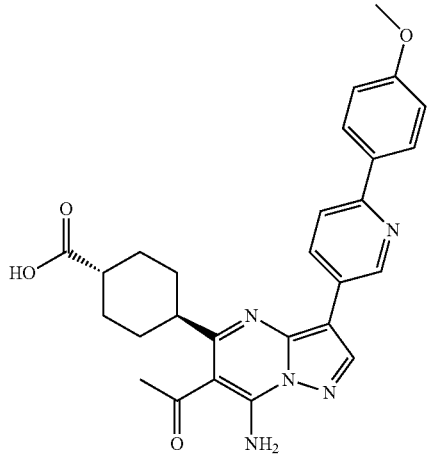
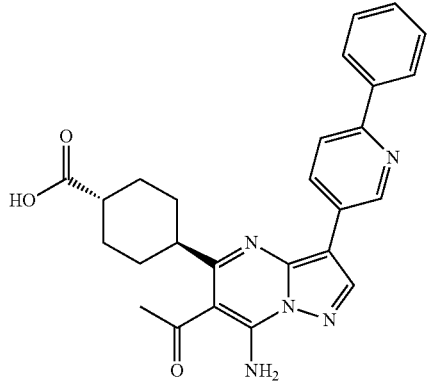
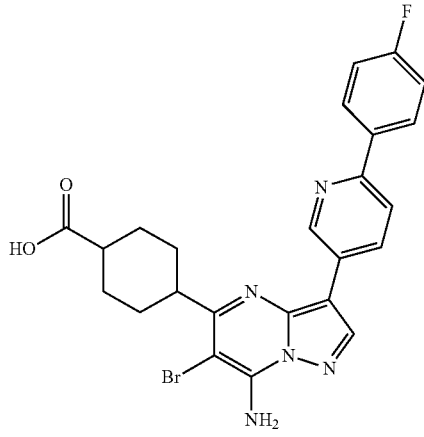

257
-continued
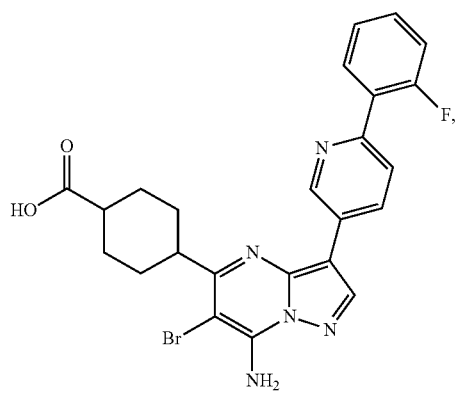
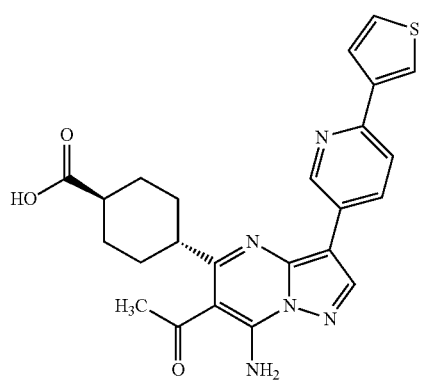
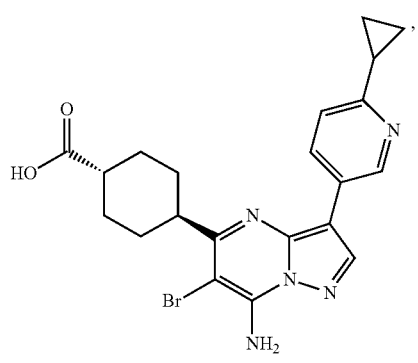
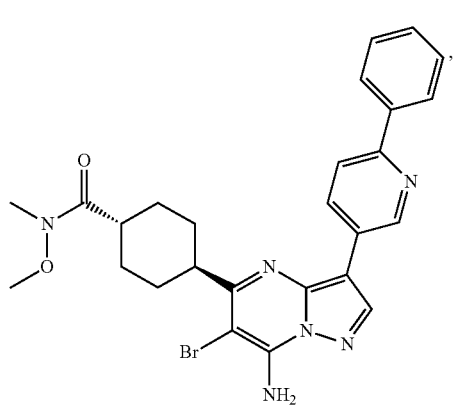
258
-continued
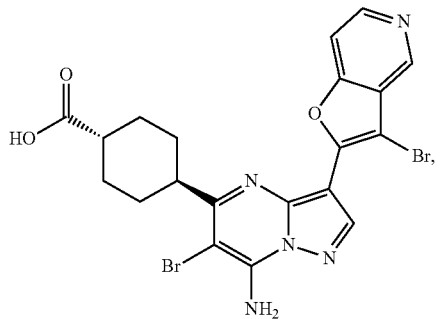
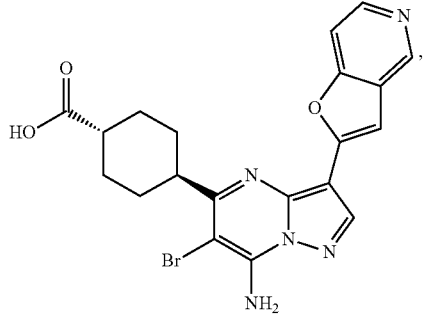
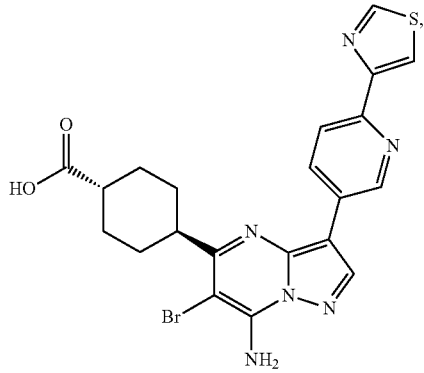
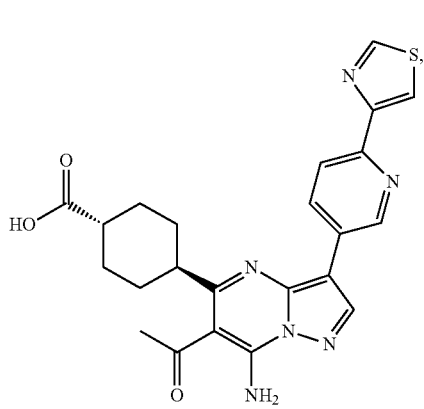

259
-continued
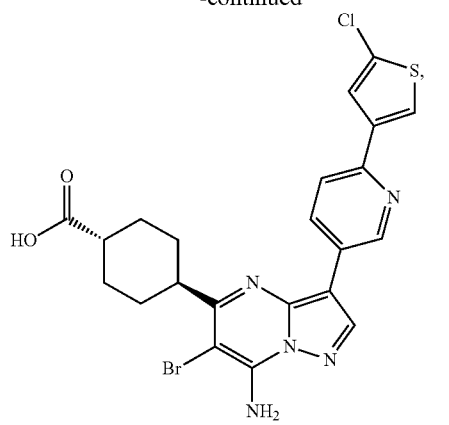
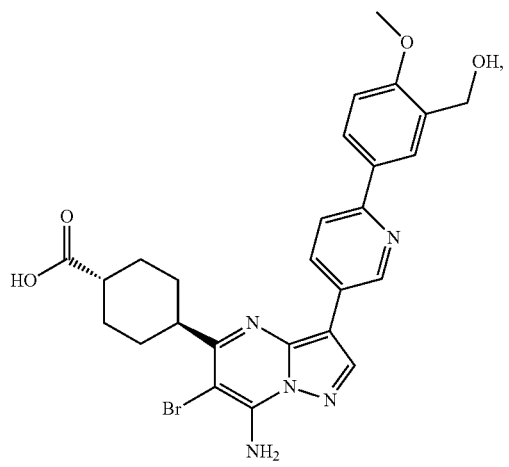
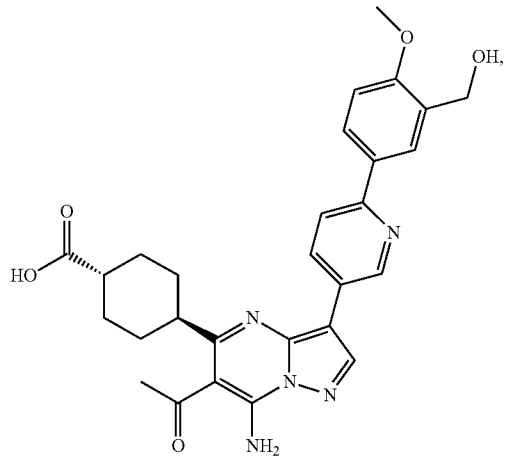
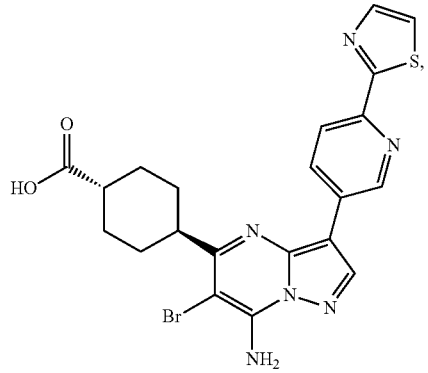
260
-continued
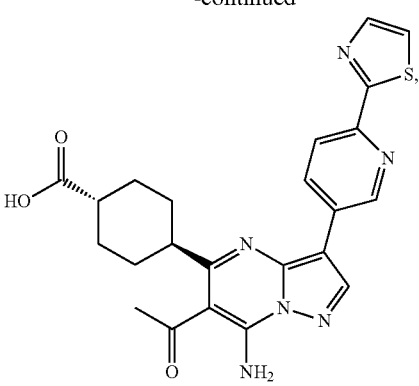
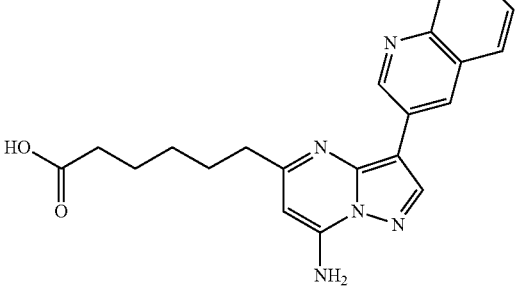
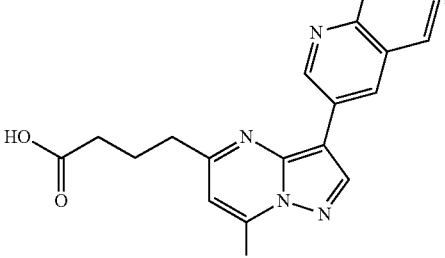
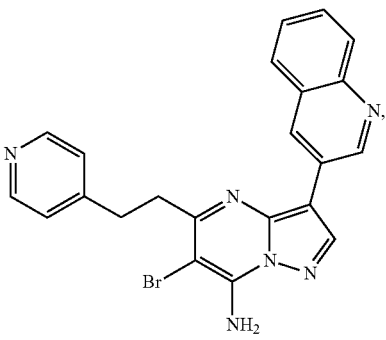
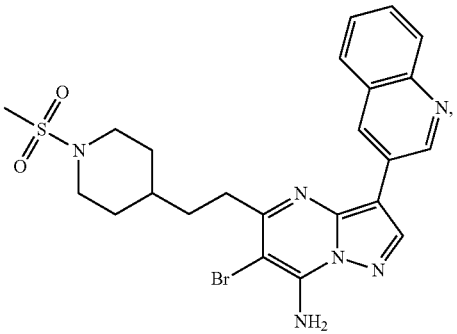

261
-continued
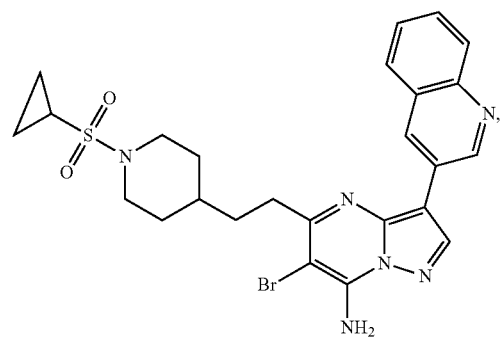
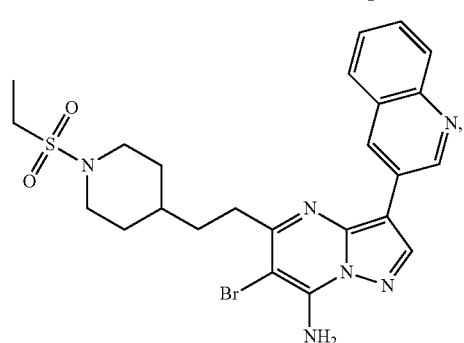
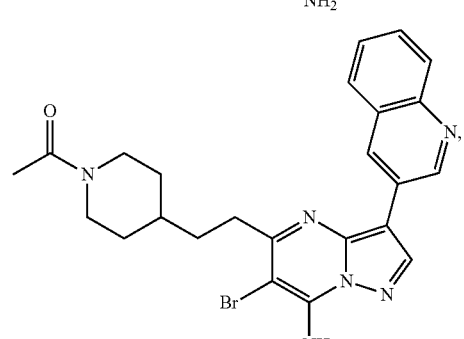
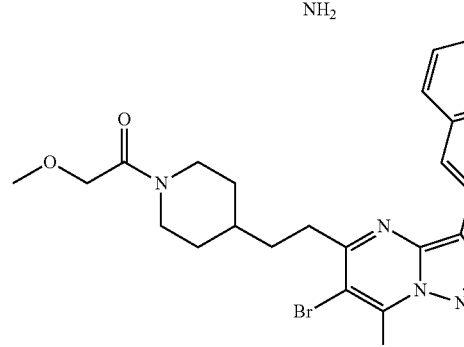
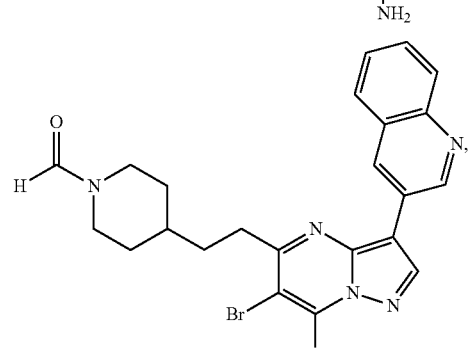
262
-continued
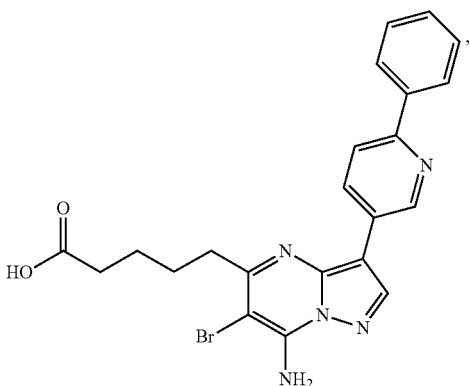
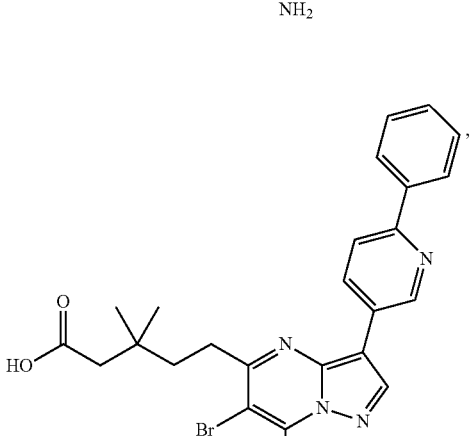
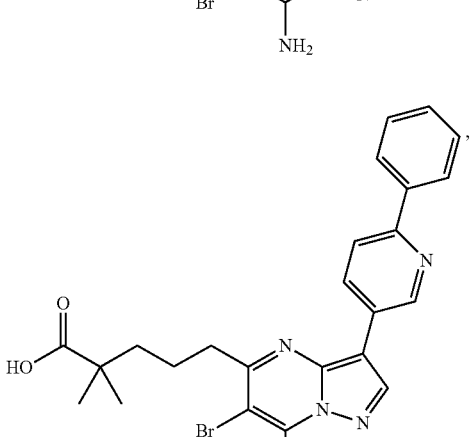
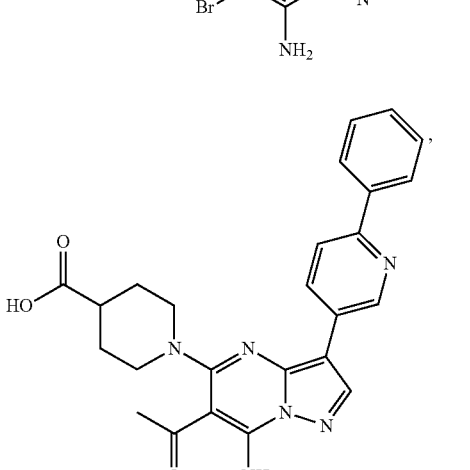

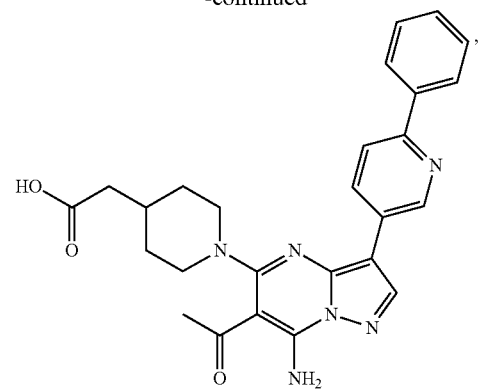
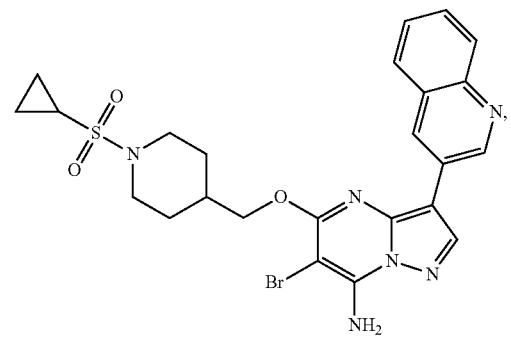
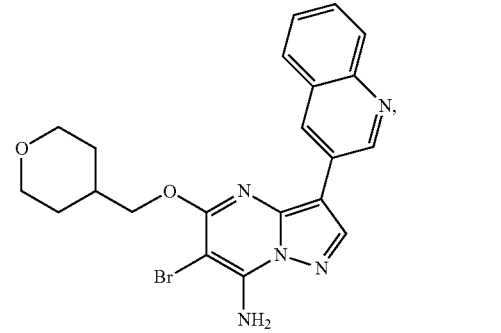
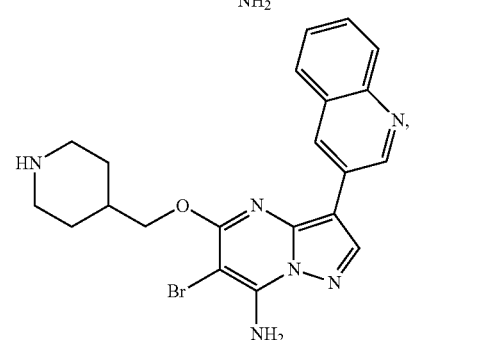

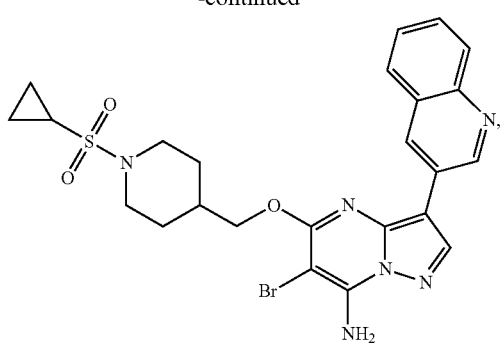
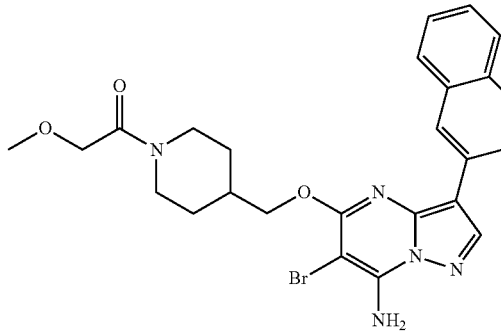
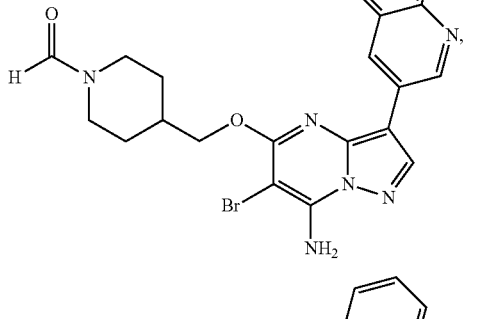
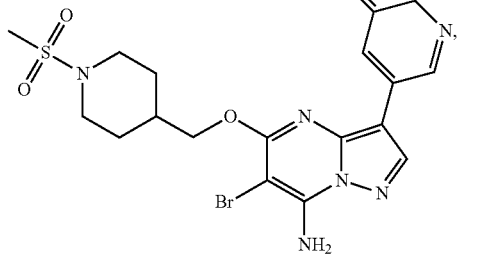
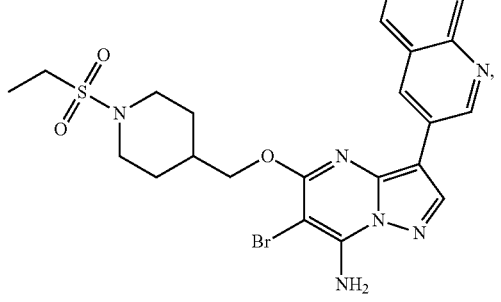

265
-continued
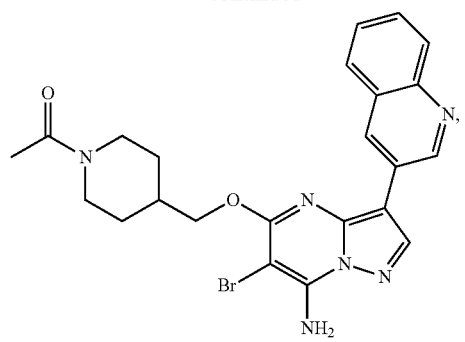
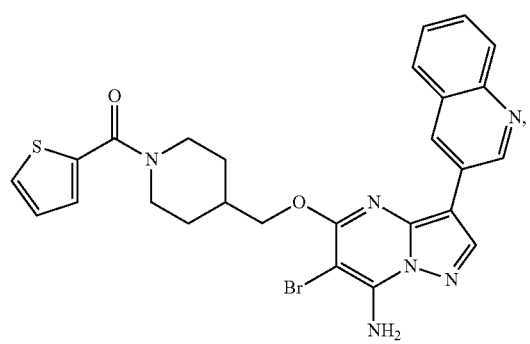
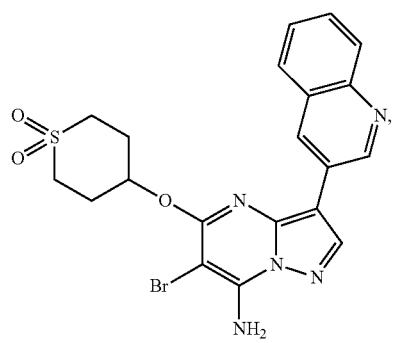
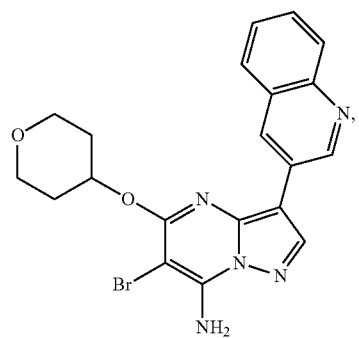
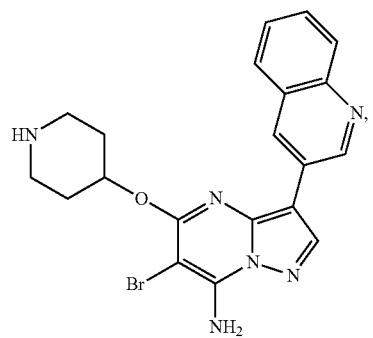
266
-continued
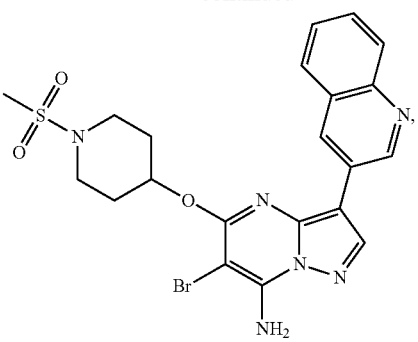
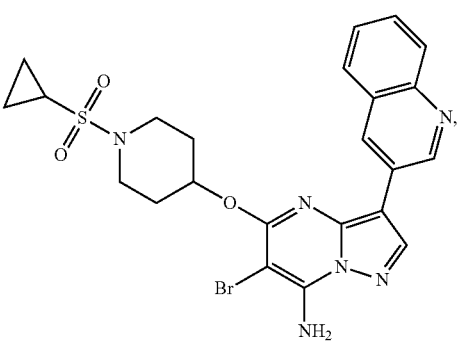

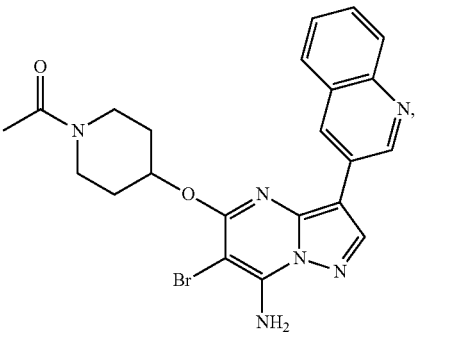
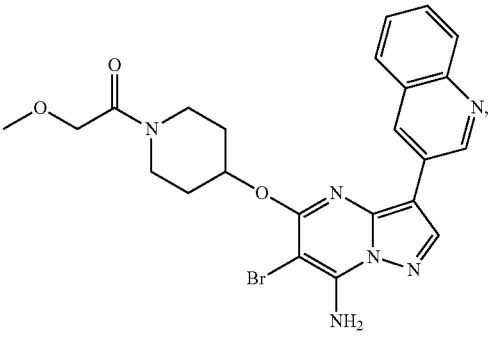

-continued
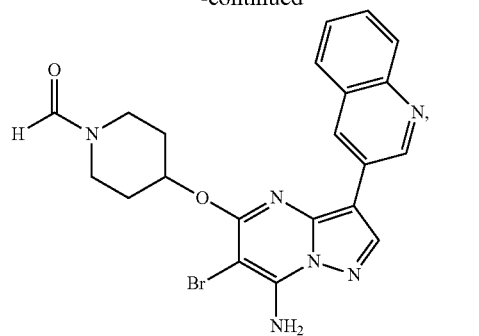
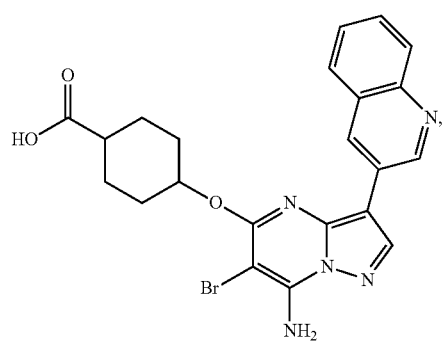
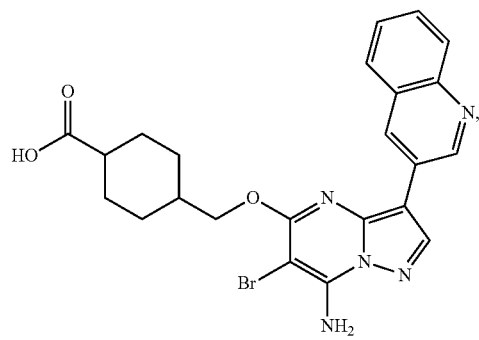
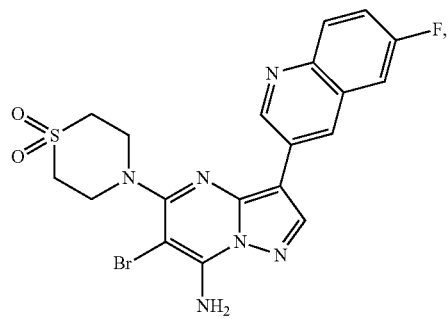
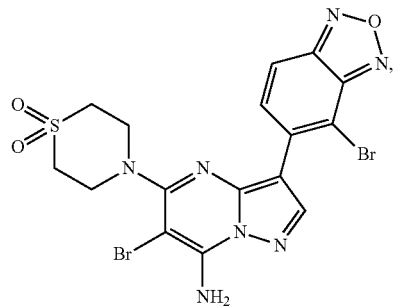
-continued
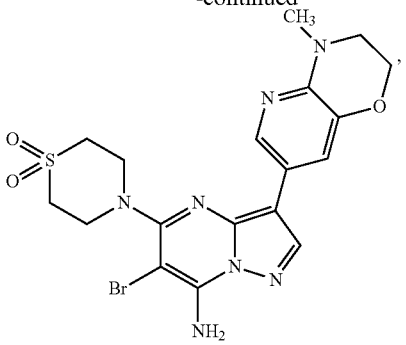
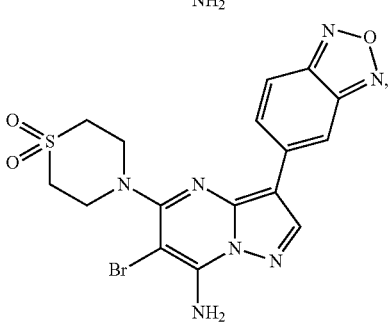
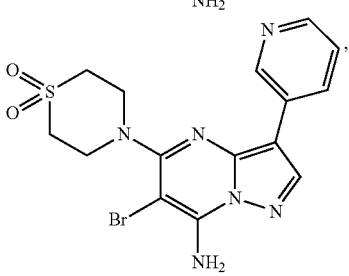
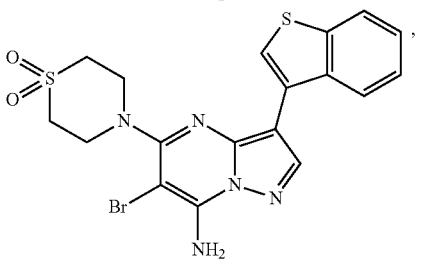
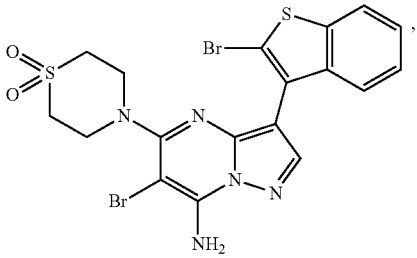
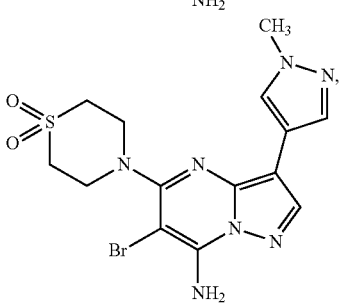

-continued
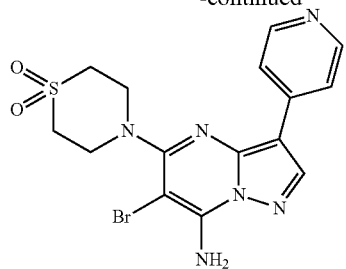
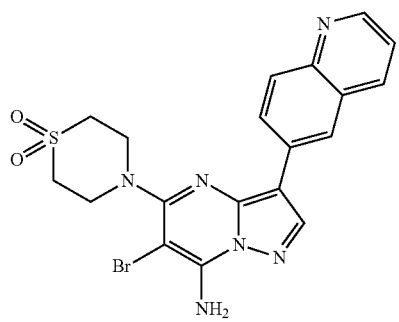
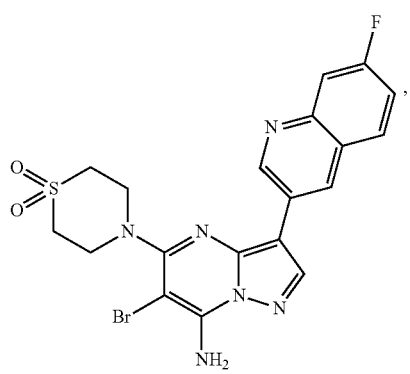
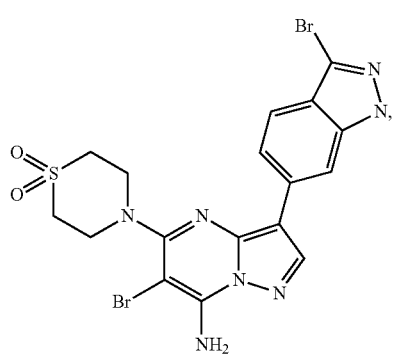
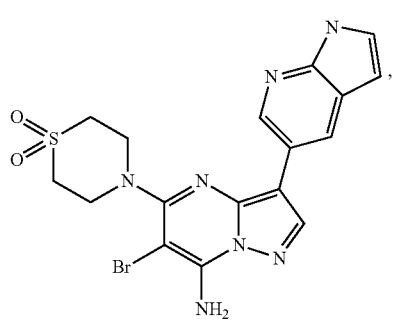
-continued
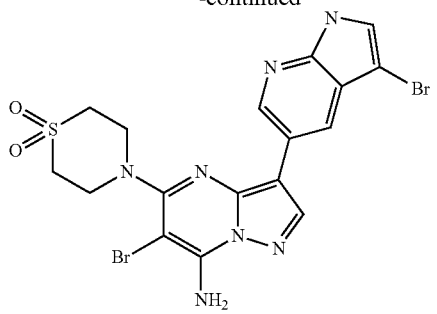
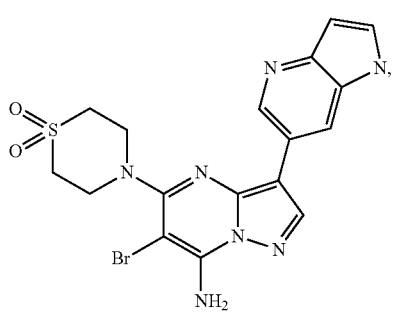
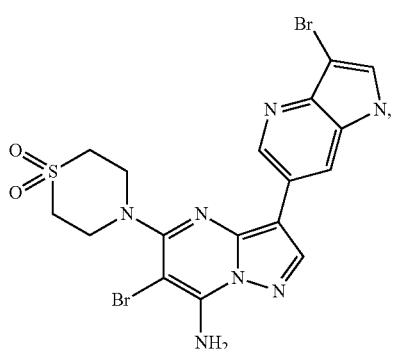
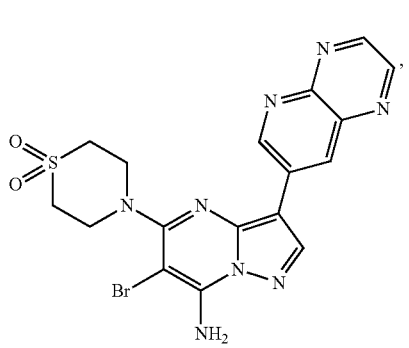
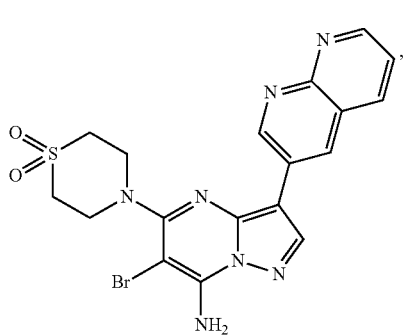

271
-continued
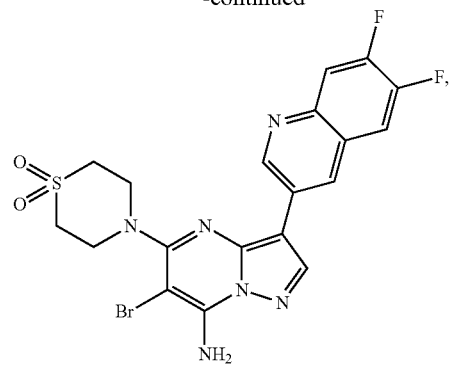
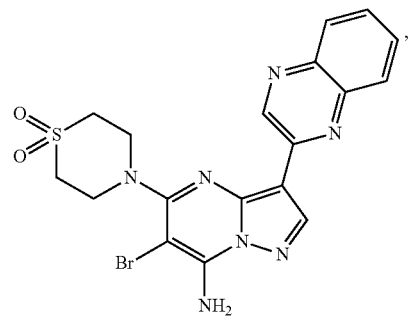
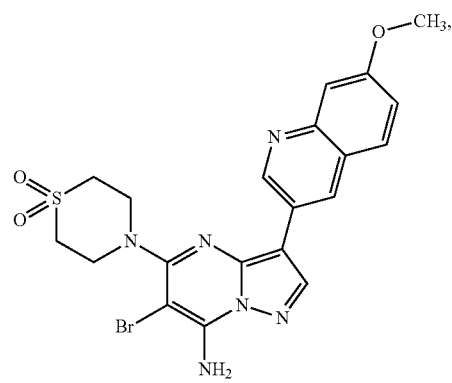
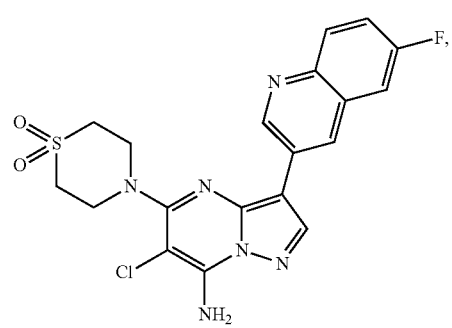
272
-continued
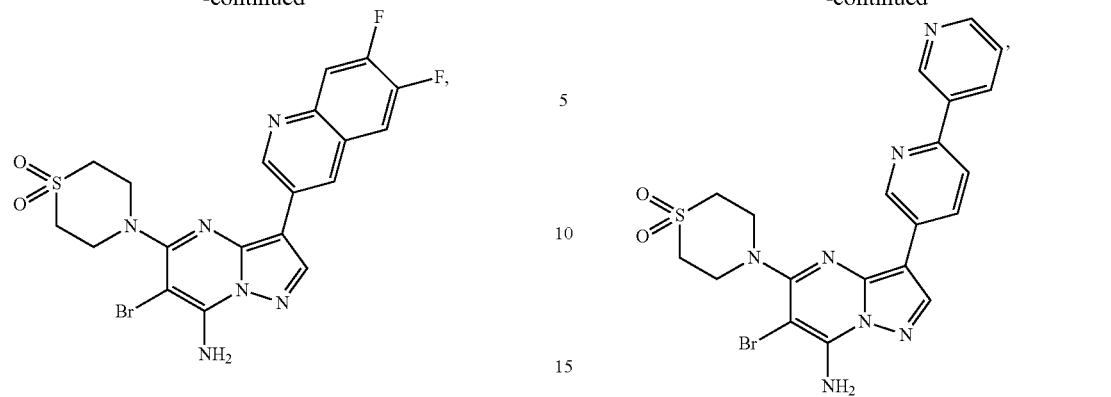

273
-continued
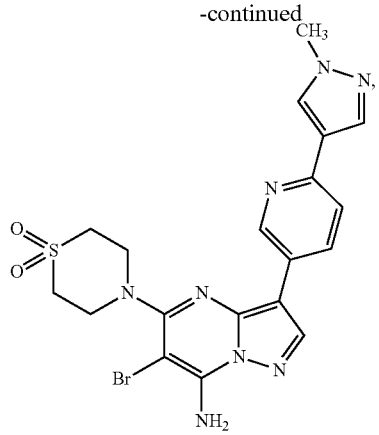
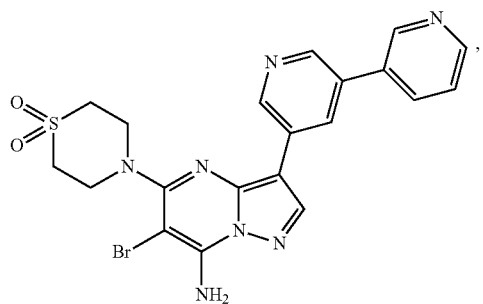
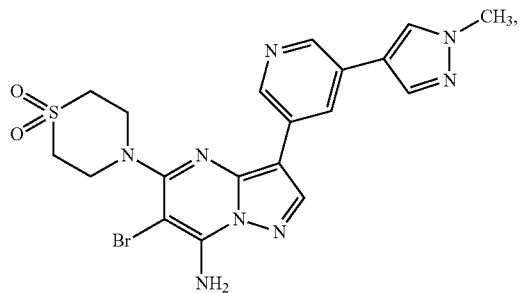
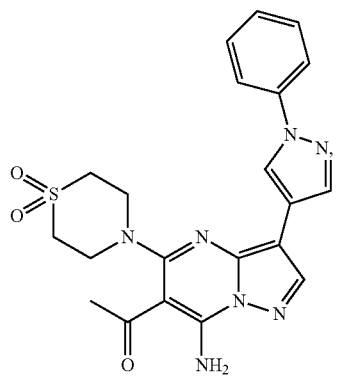
274
-continued
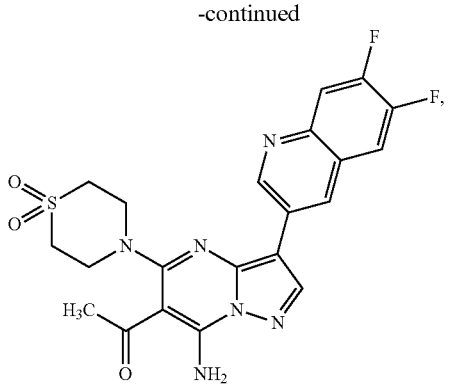
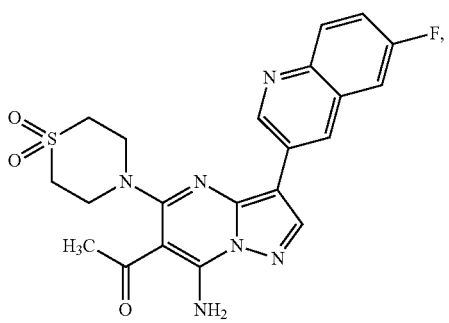
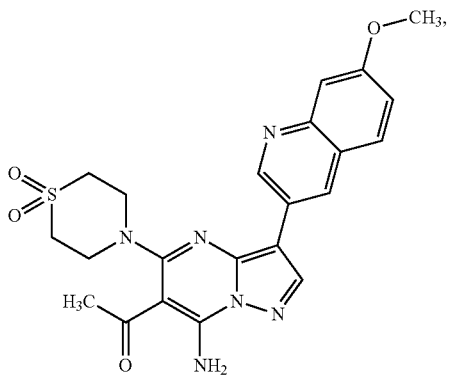
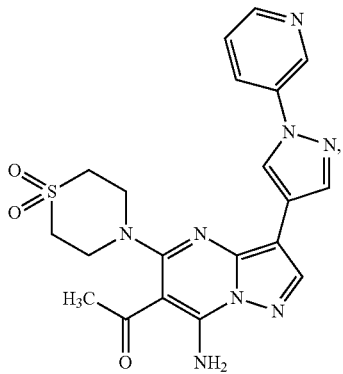

275
-continued
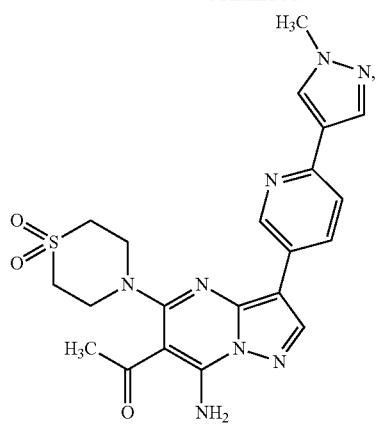
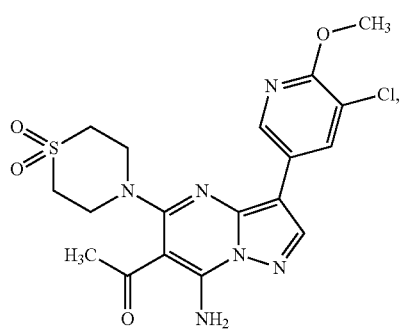
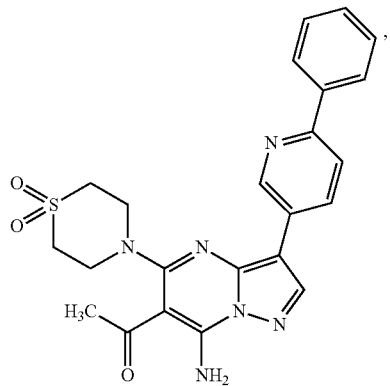
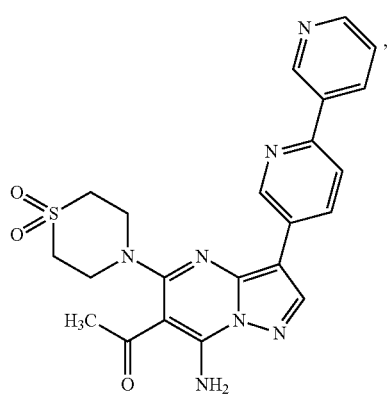
276
-continued
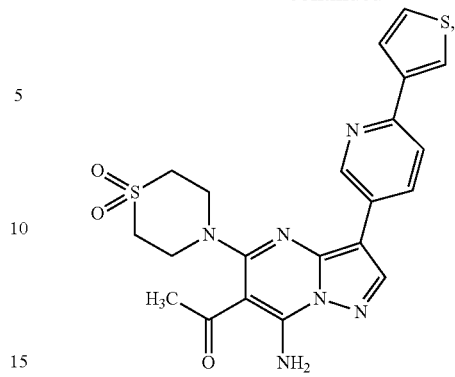
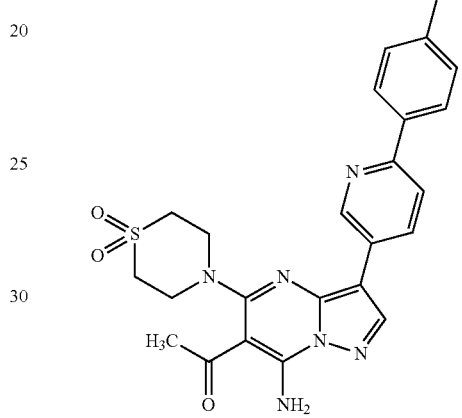
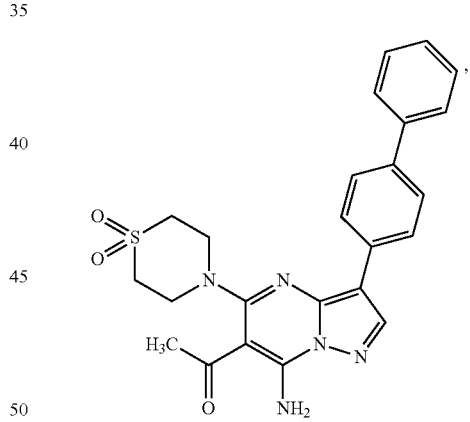
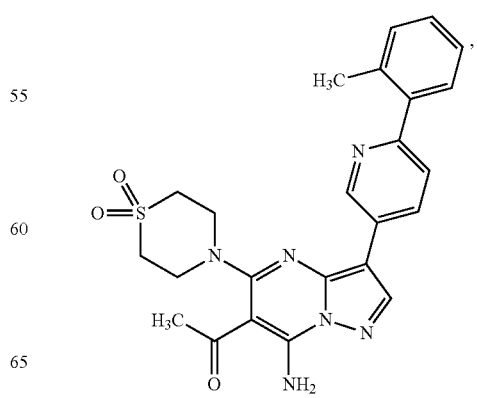

277
-continued
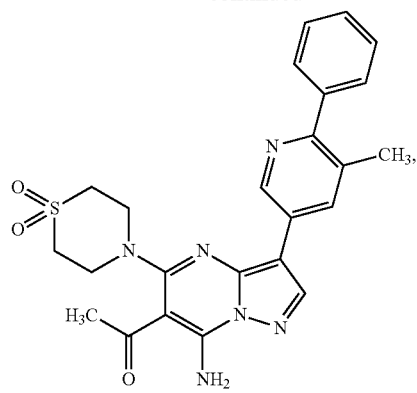
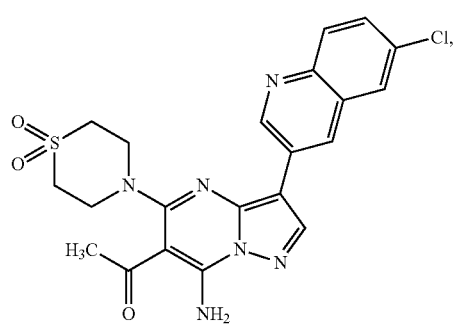
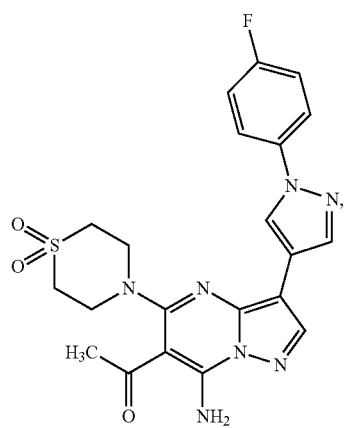
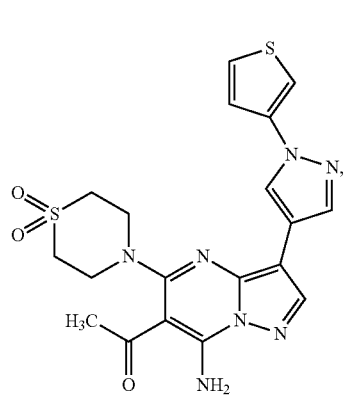
278
-continued
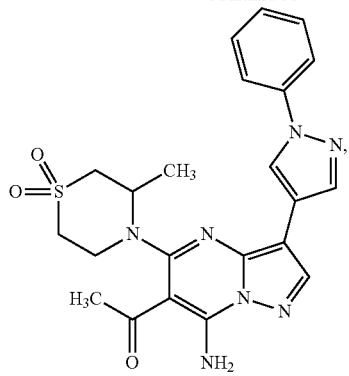
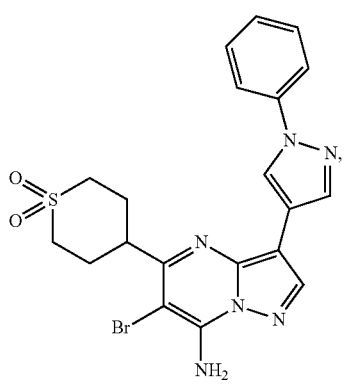
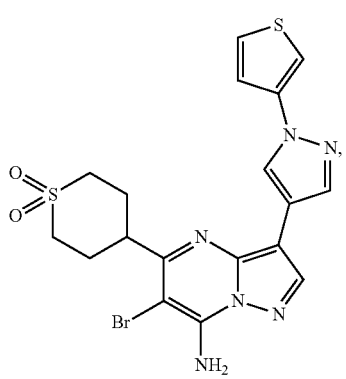
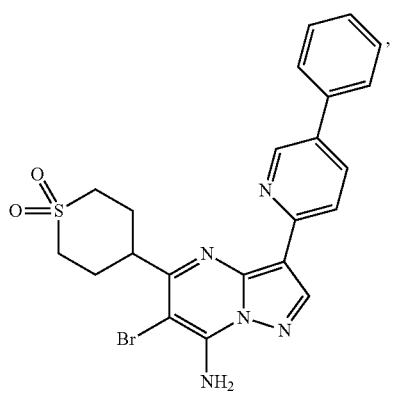

279
-continued
280
-continued
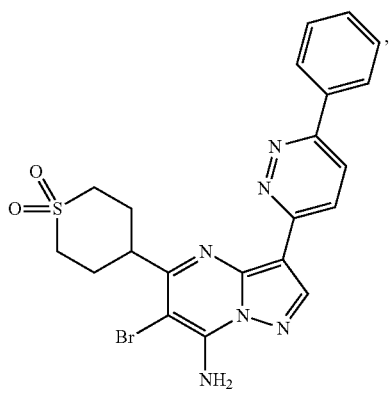
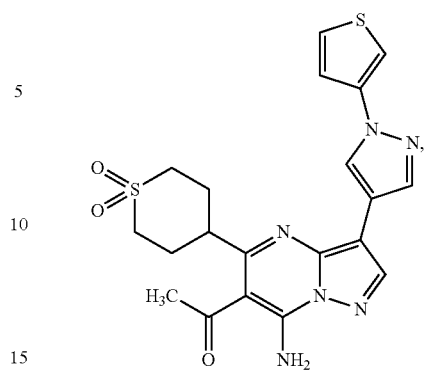
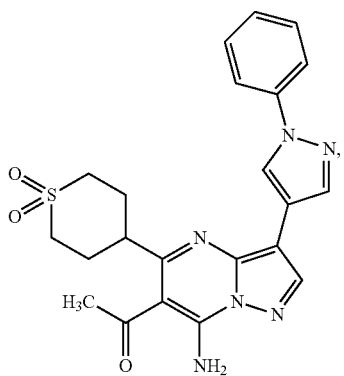
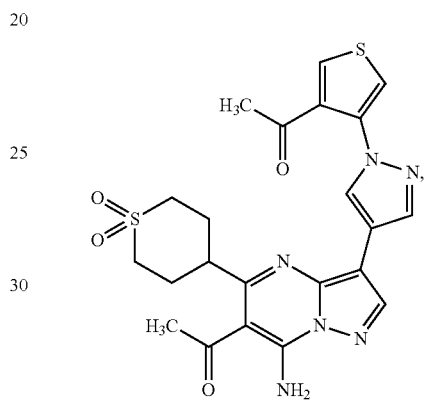
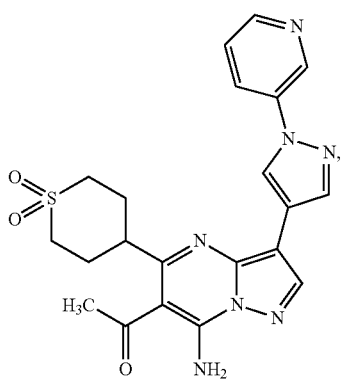
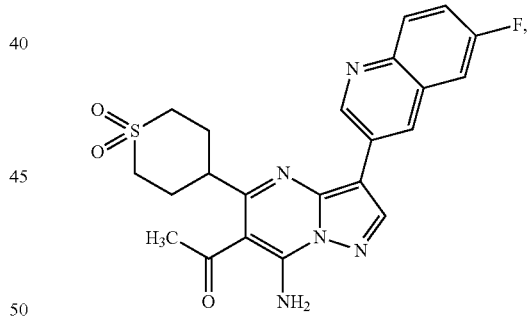
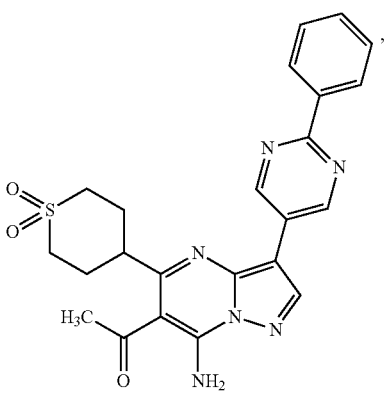

-continued
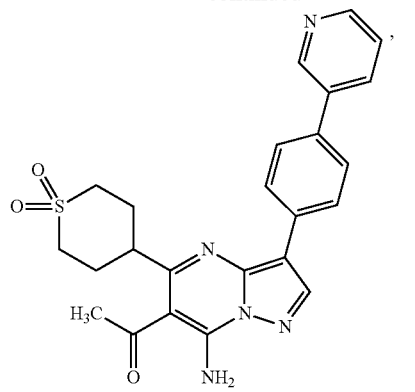
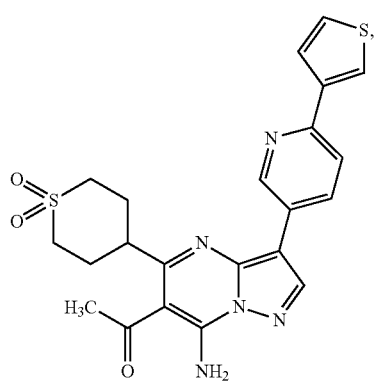
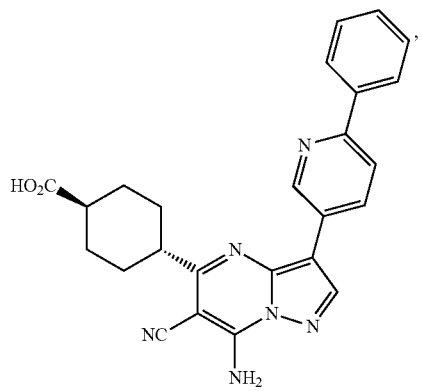
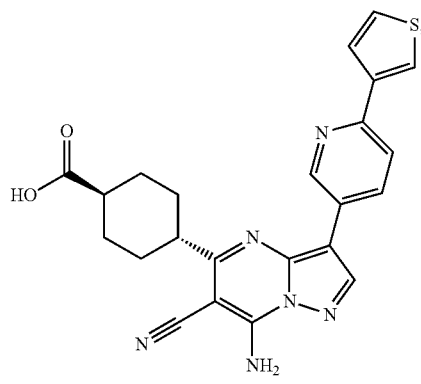
-continued
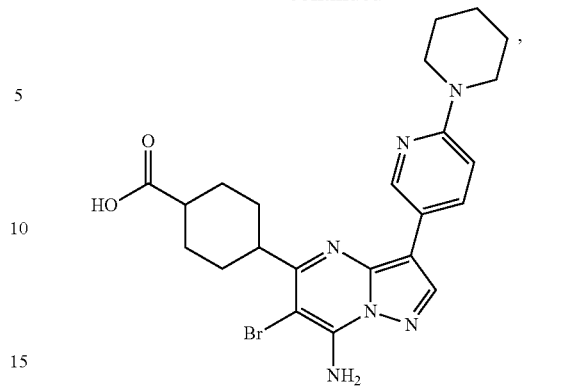
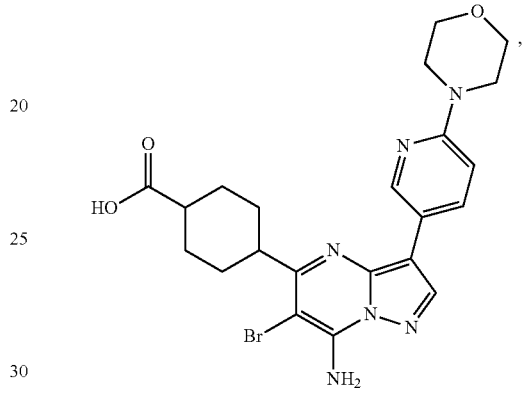
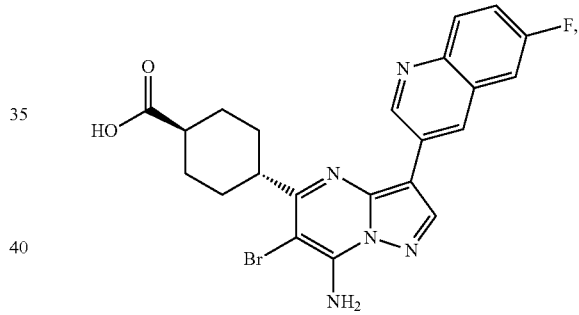
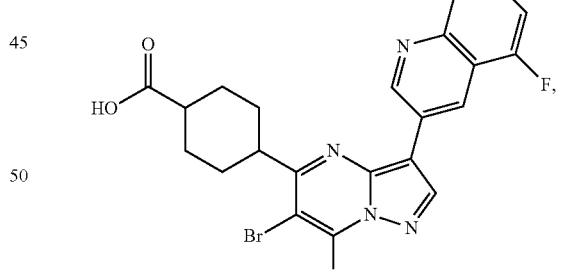
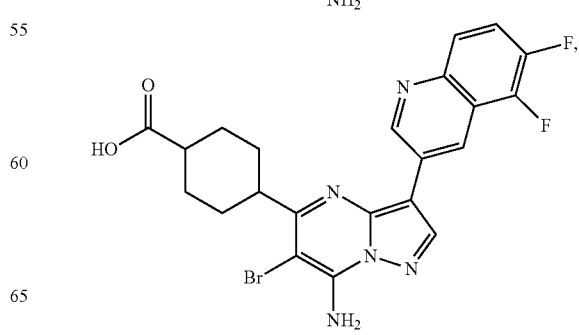

-continued
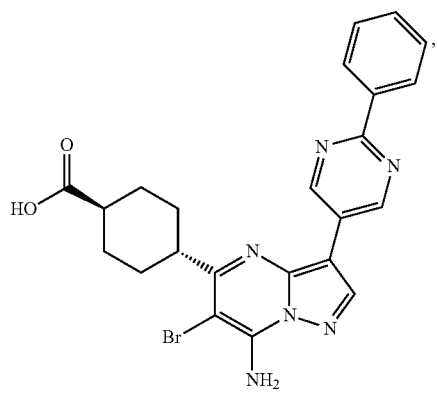
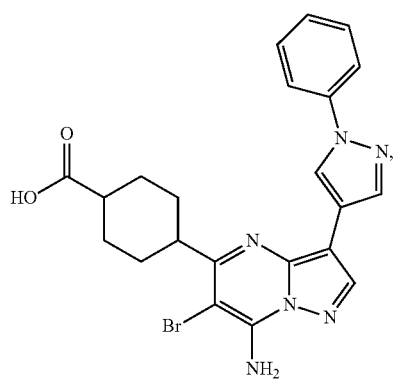
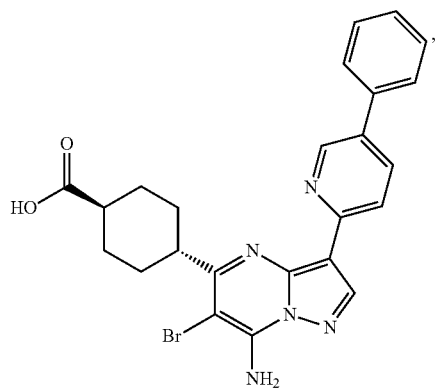
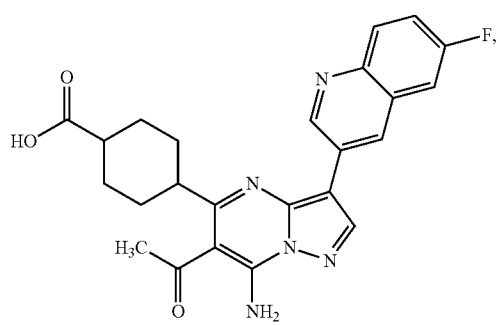
-continued
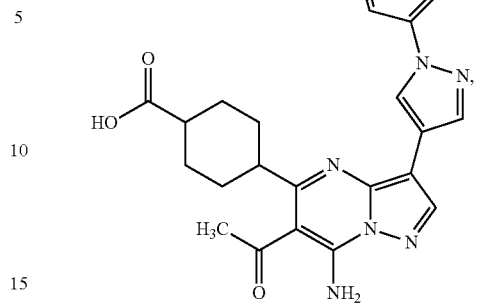
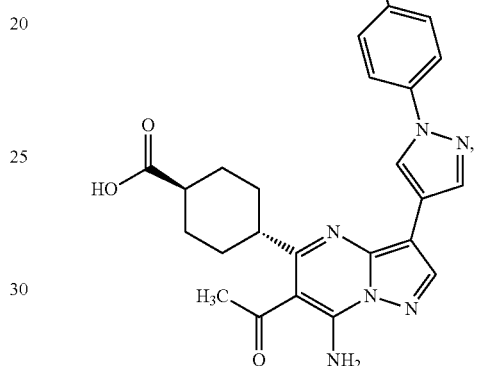
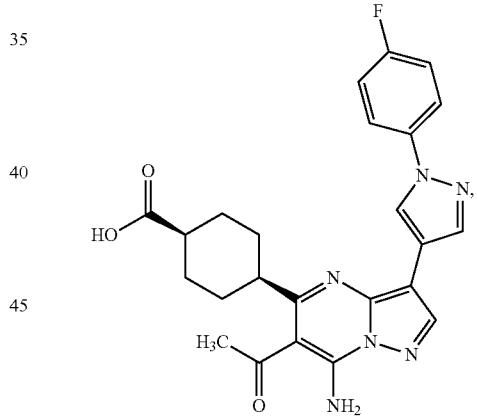
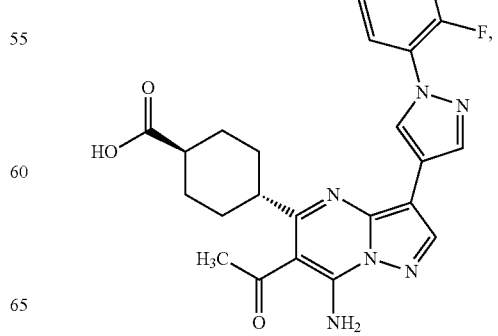

285
-continued
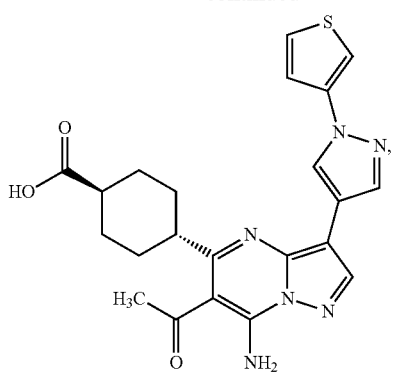
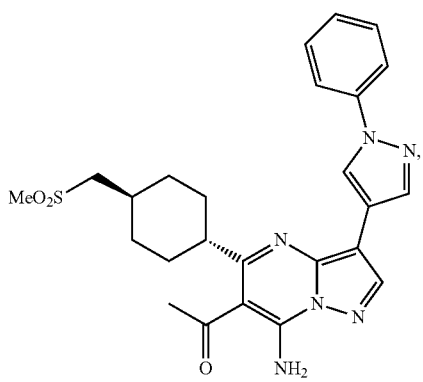
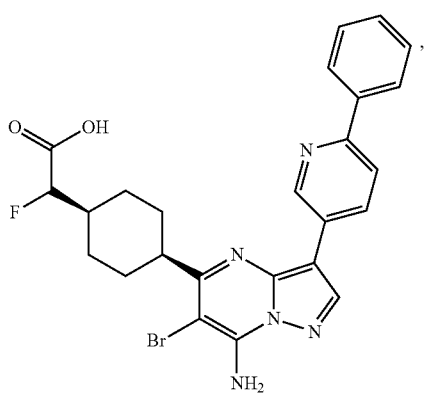
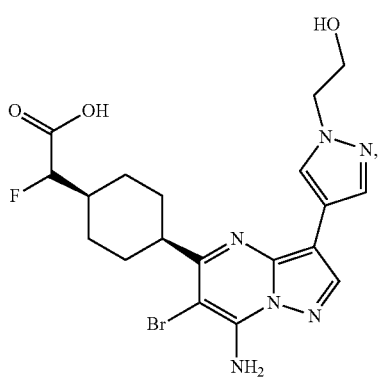
286
-continued
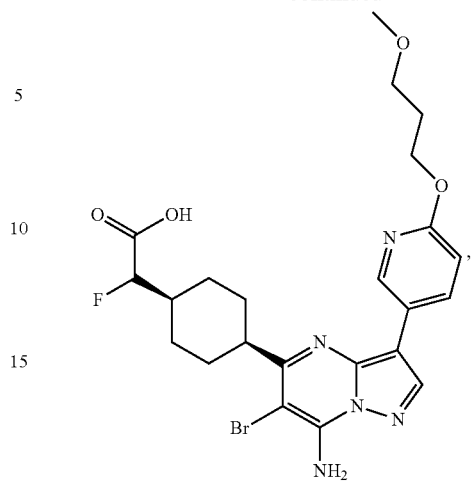
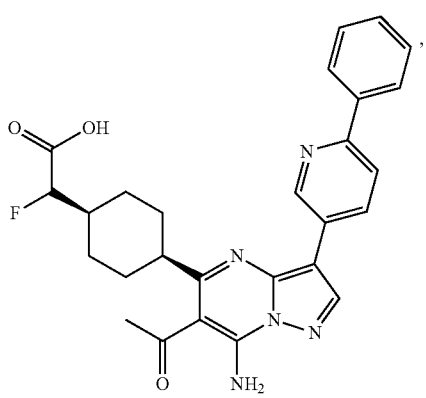
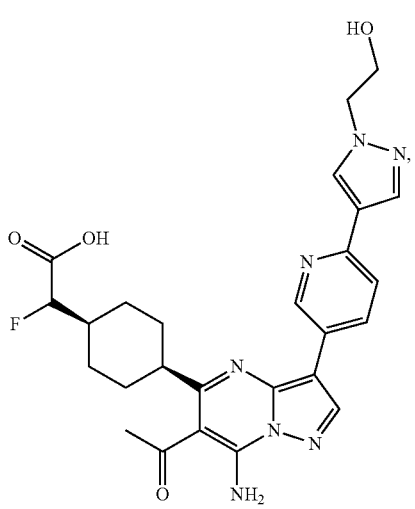

287
-continued
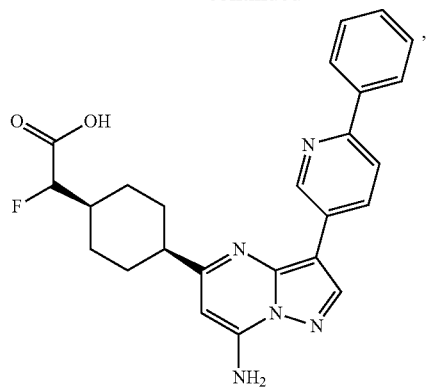
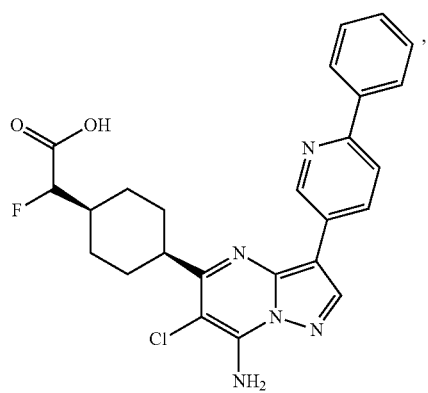
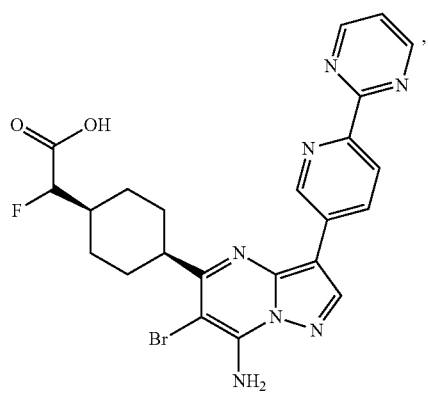
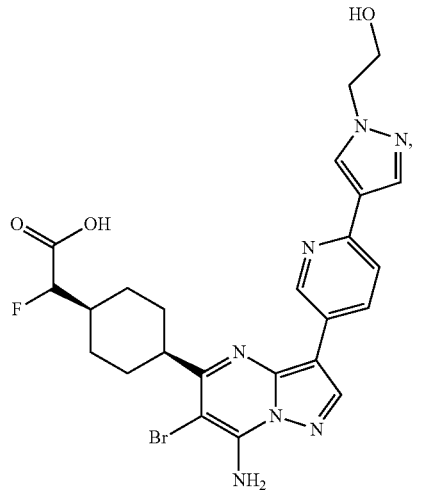
288
-continued
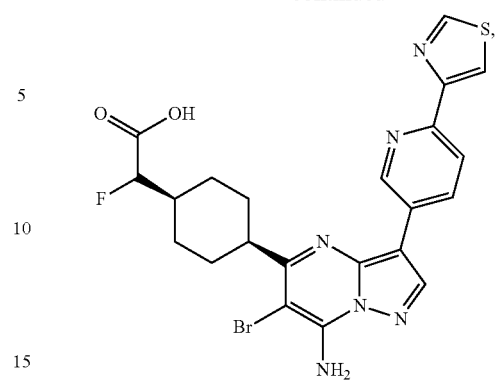
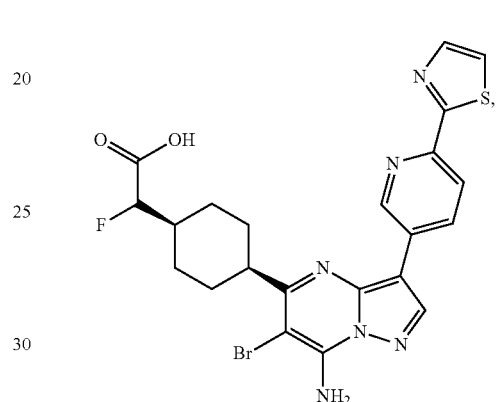
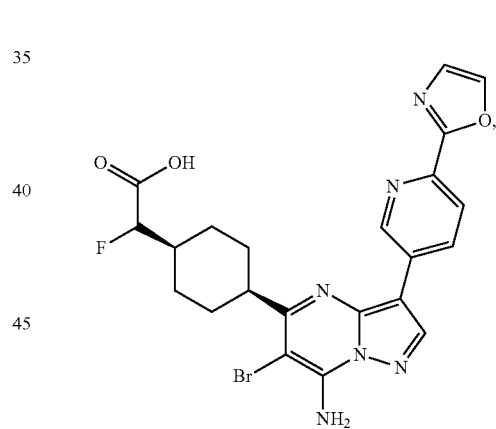
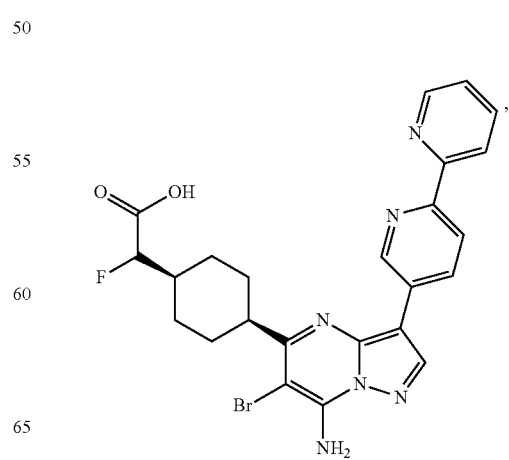

289
-continued
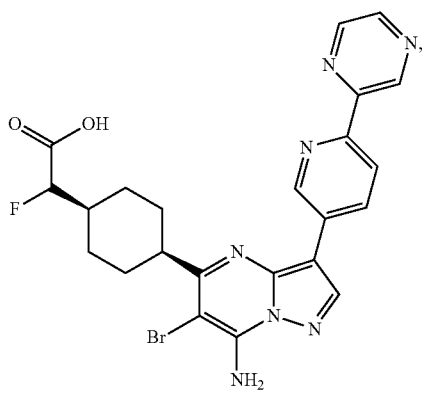
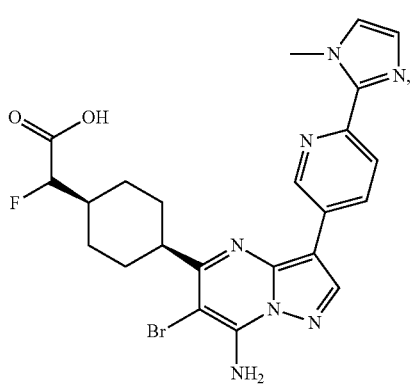
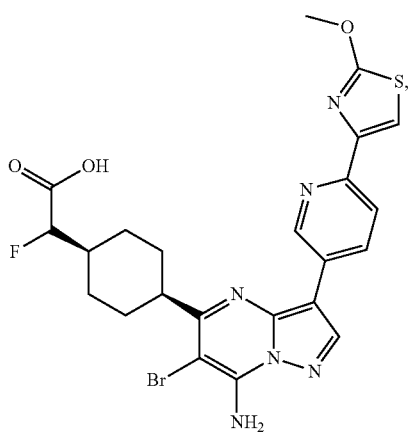
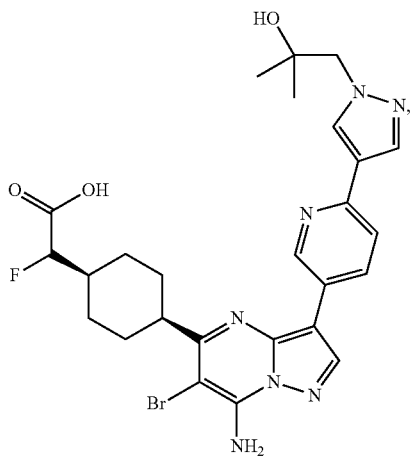
290
-continued
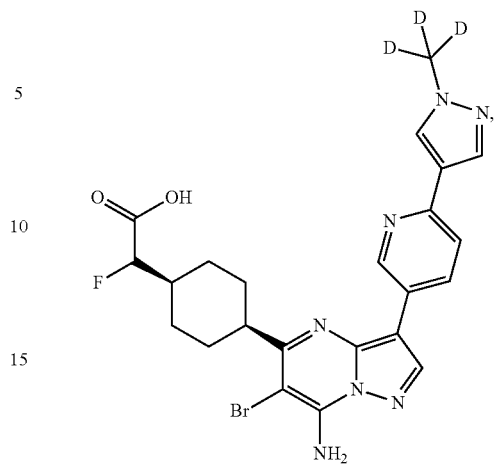
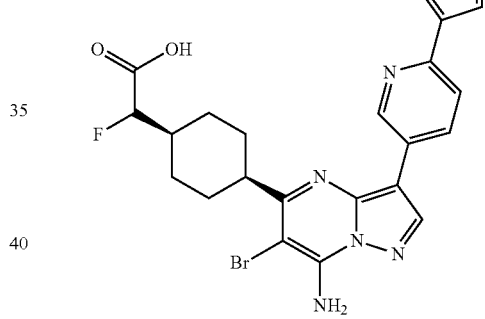
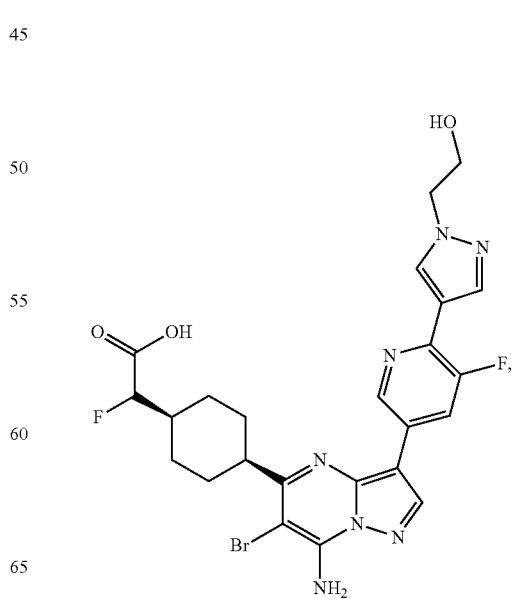

291
-continued
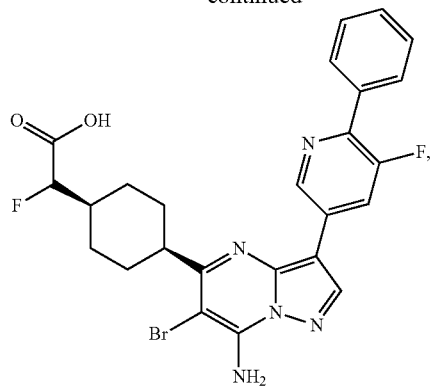
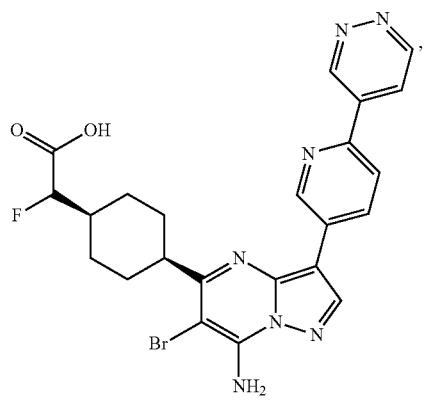
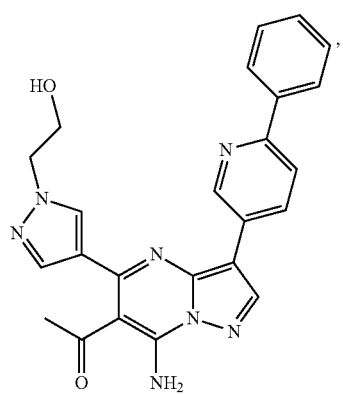
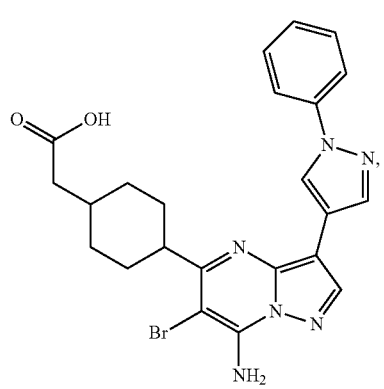
292
-continued
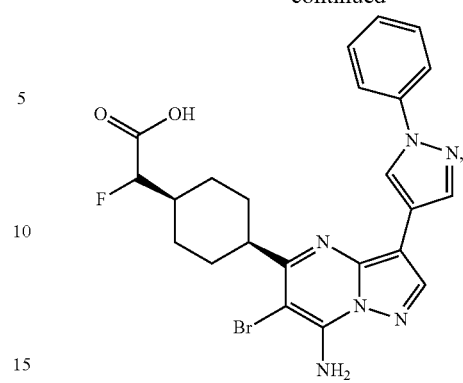
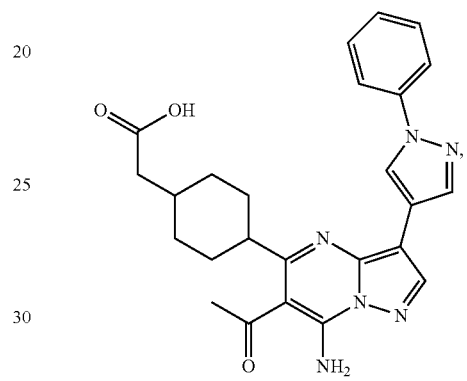
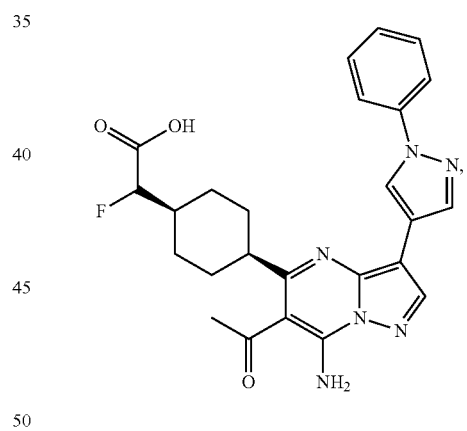
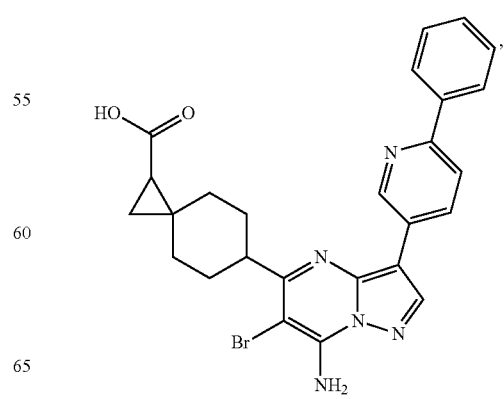

293
-continued
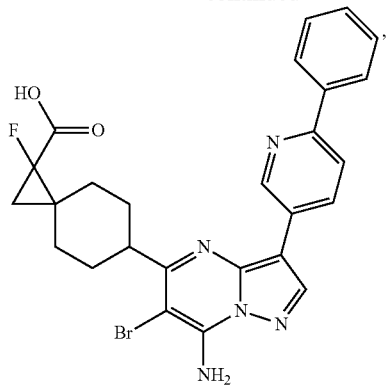
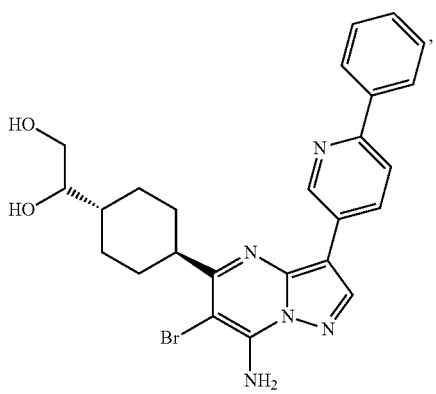
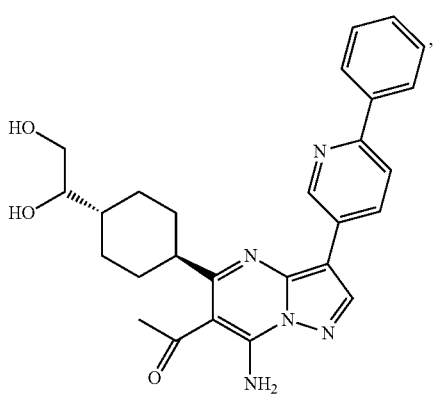
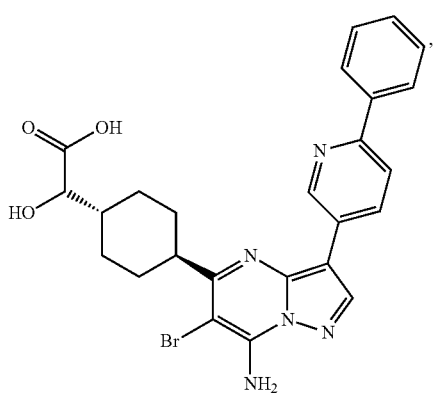
294
-continued
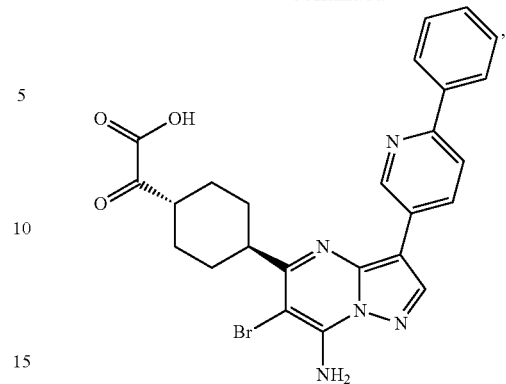
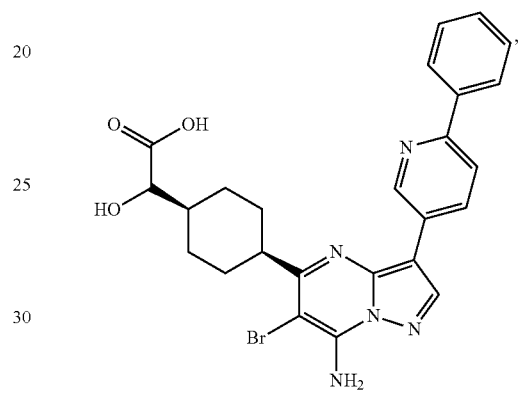
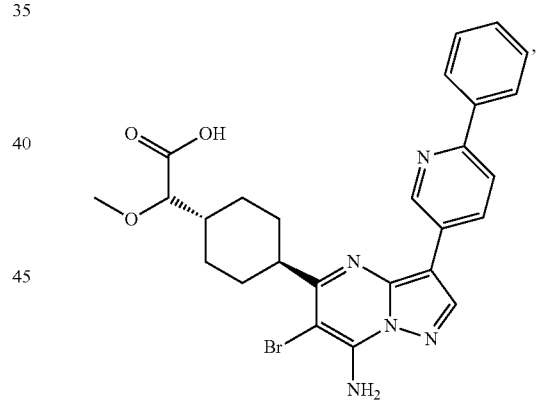
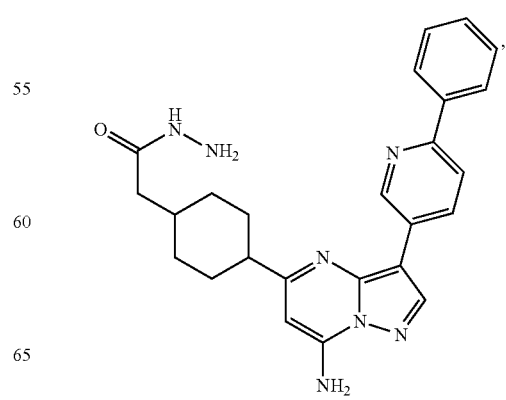

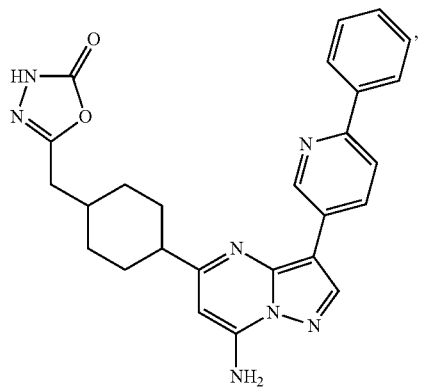
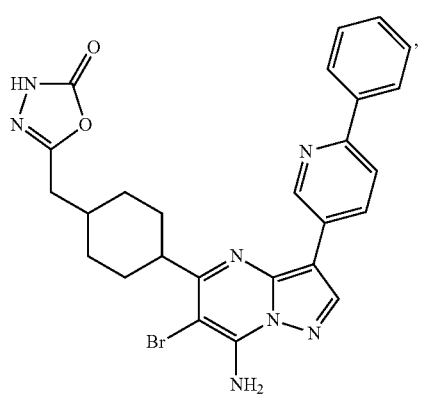
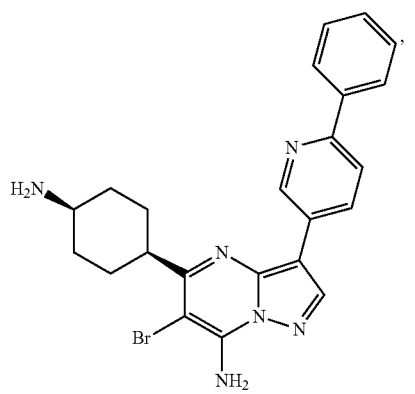
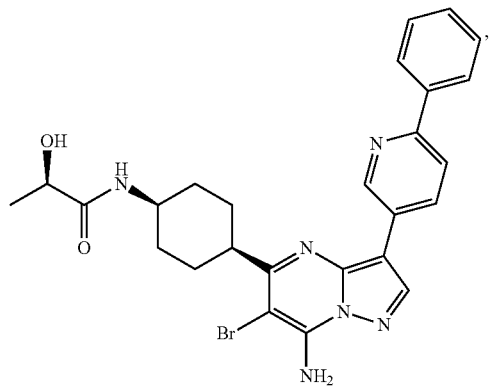
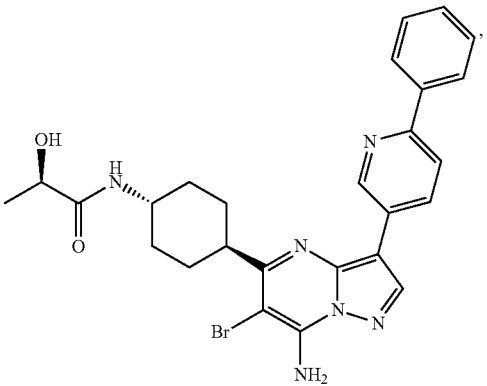
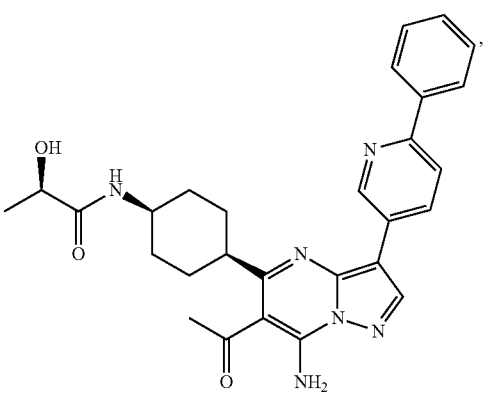
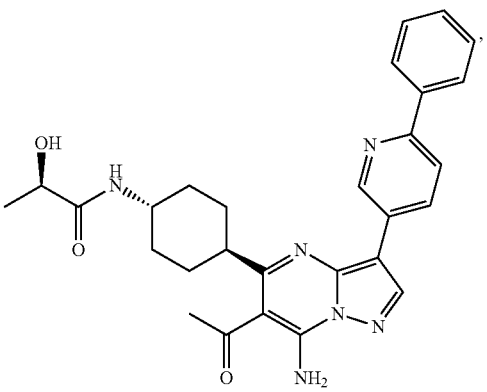
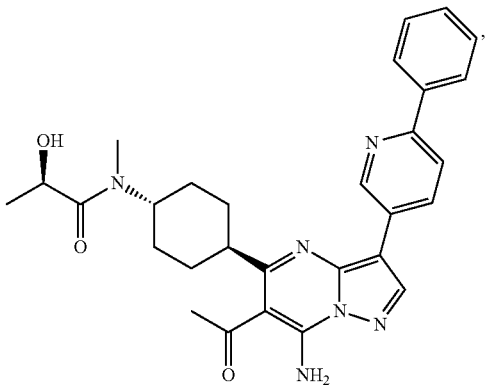

297
-continued
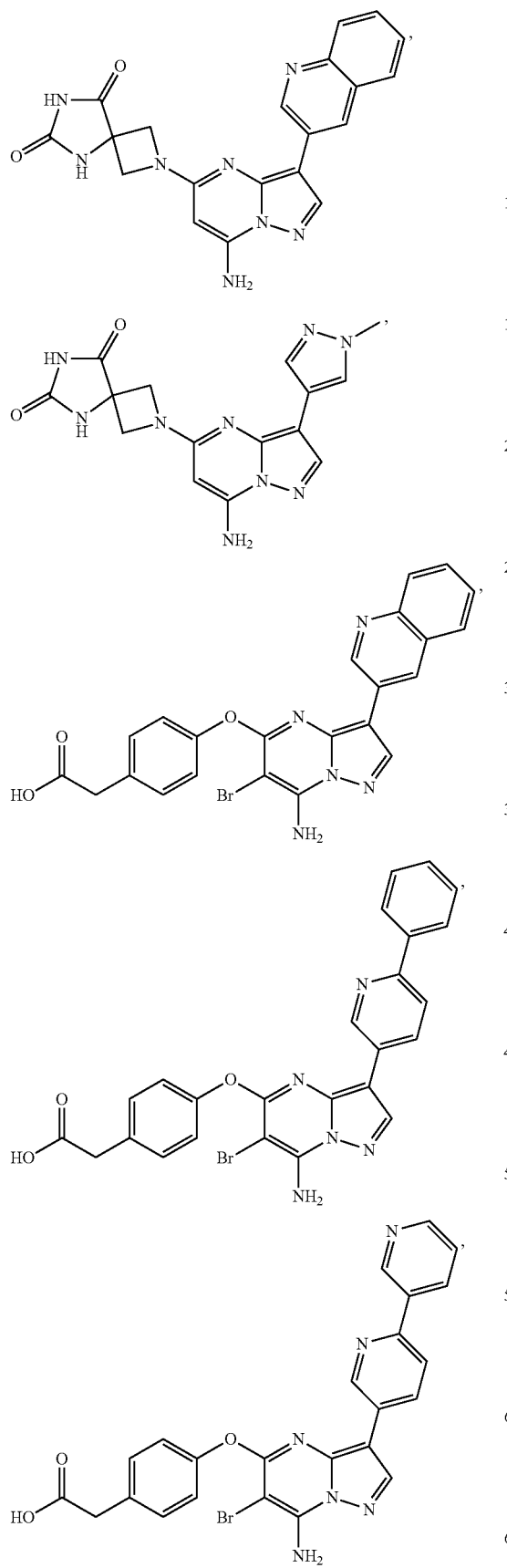
298
-continued
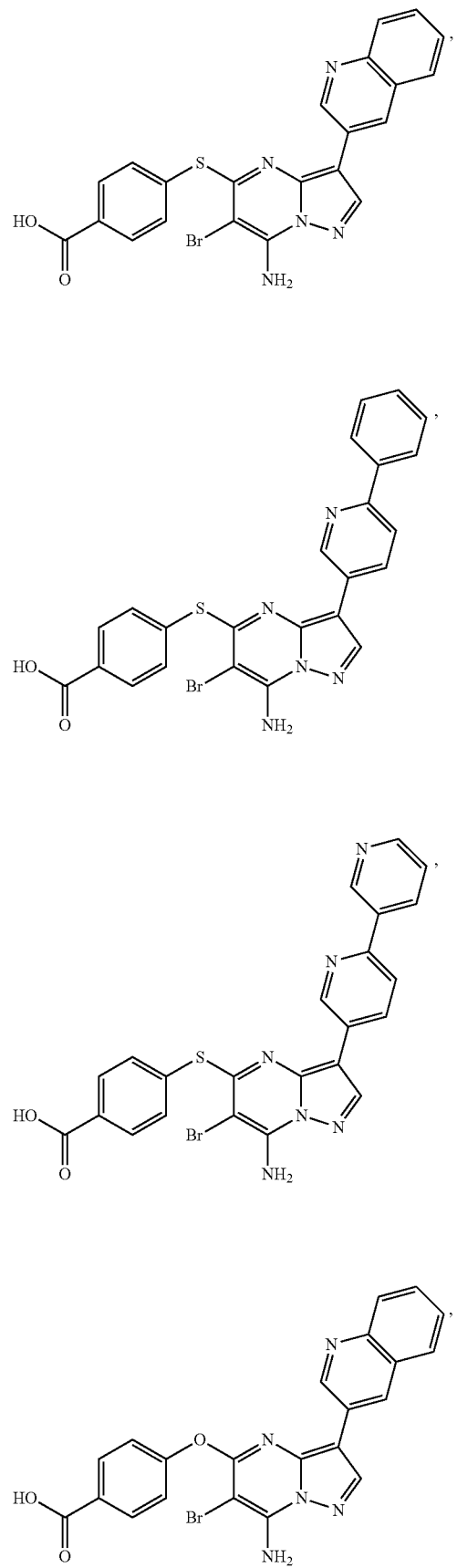

299
-continued
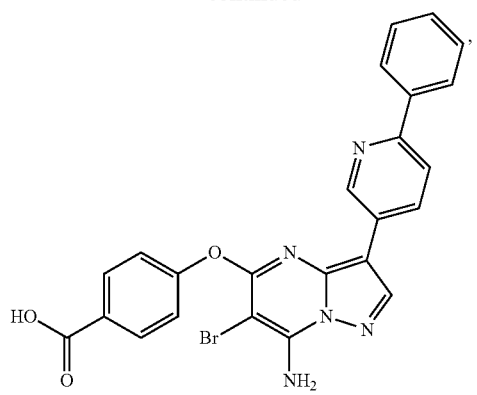
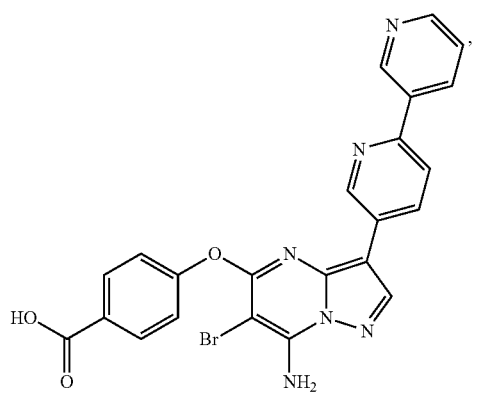
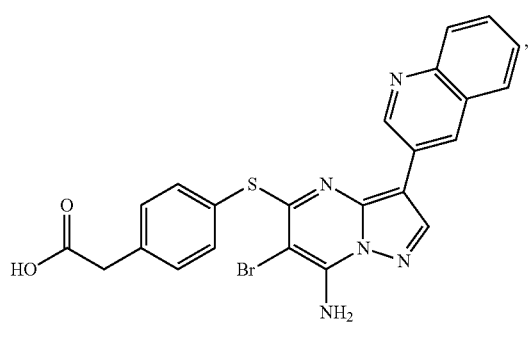
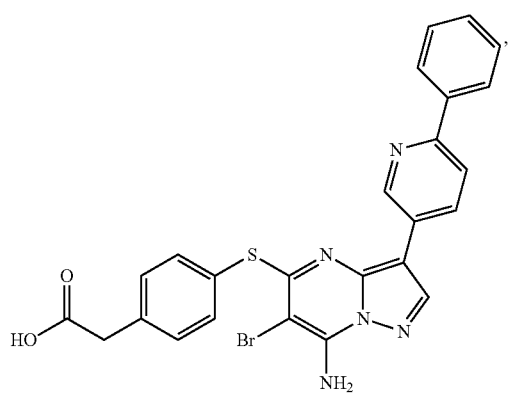
300
-continued
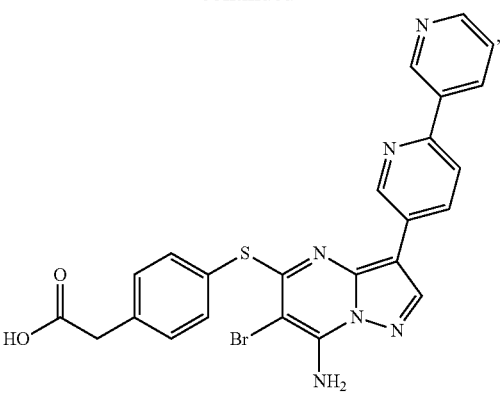
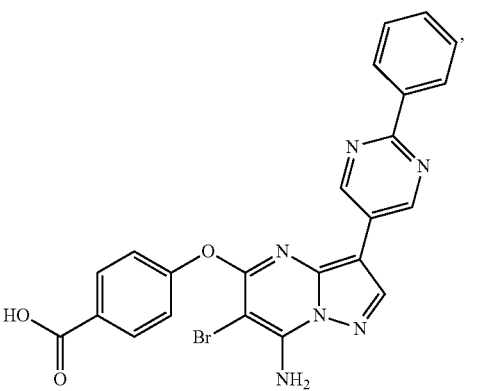
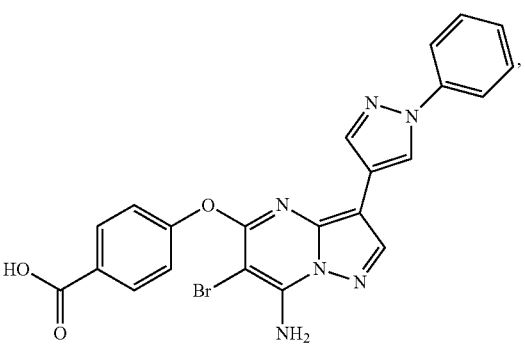
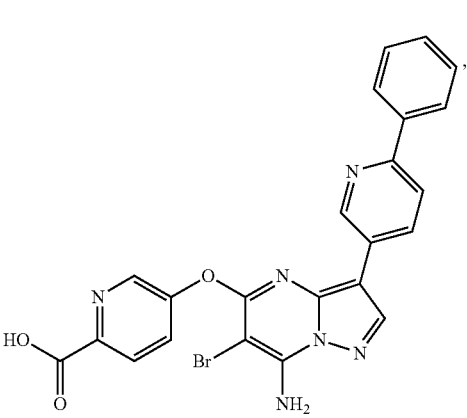

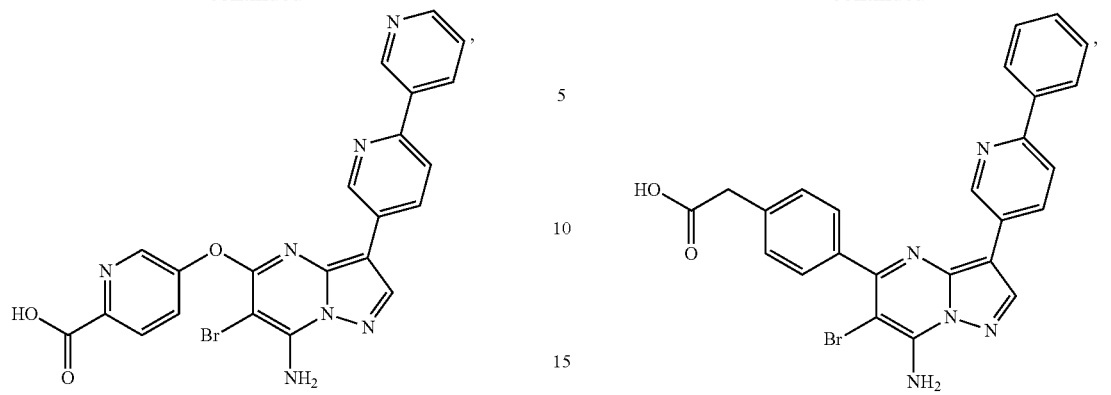
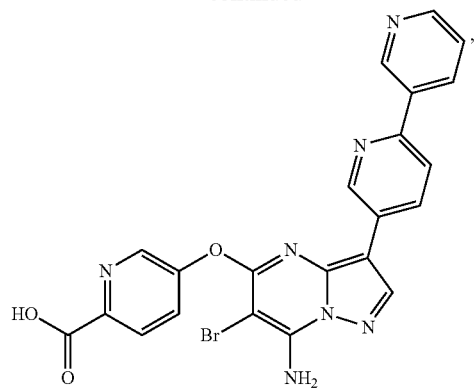
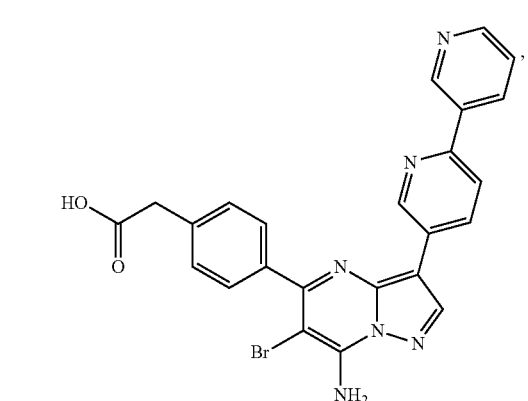
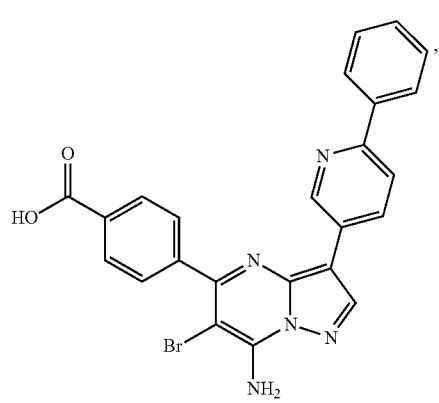
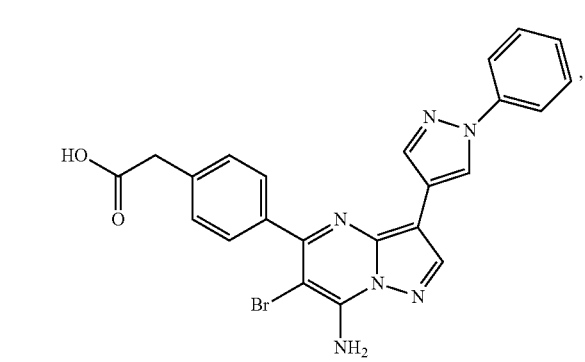
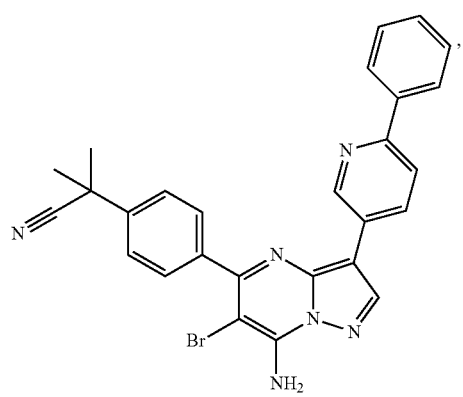
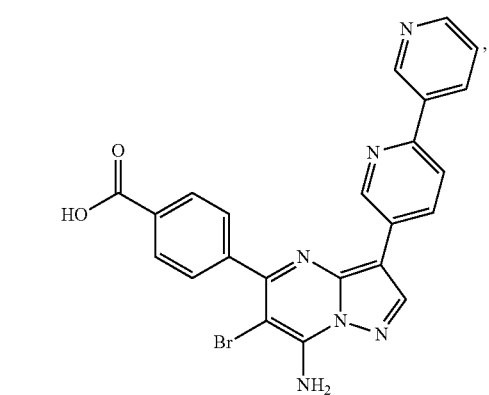
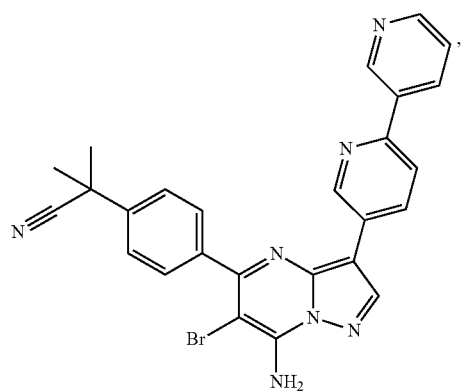

303
-continued
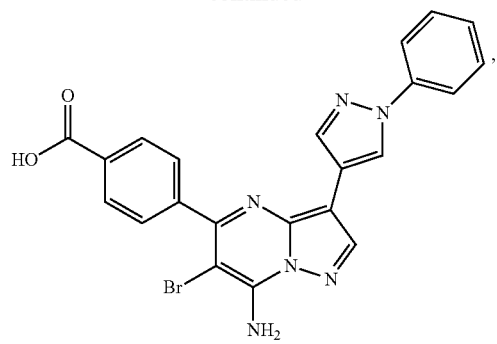
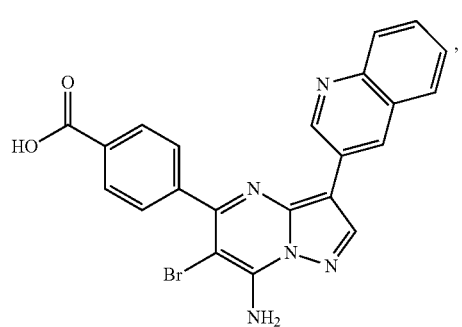
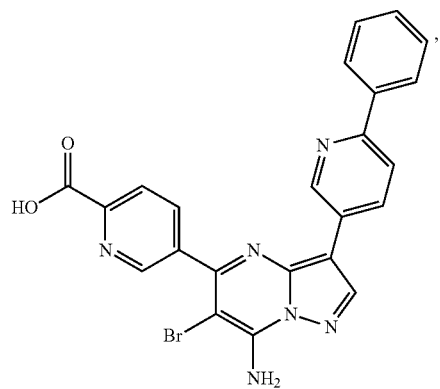
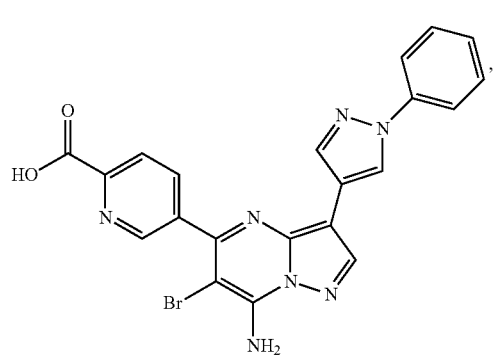
304
-continued
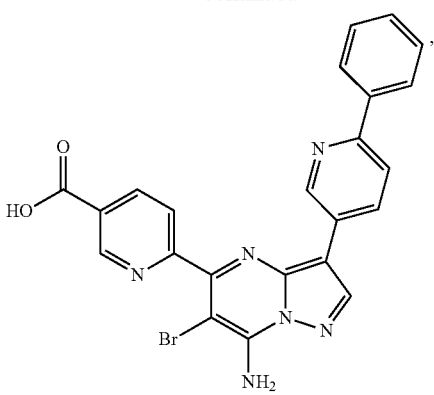
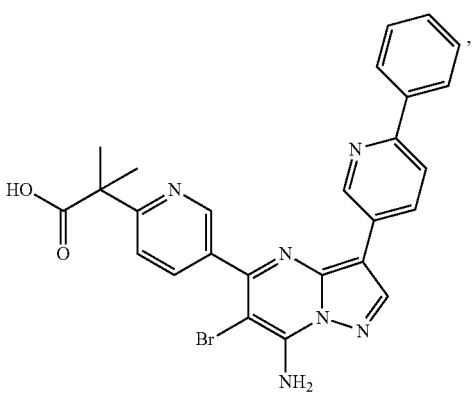
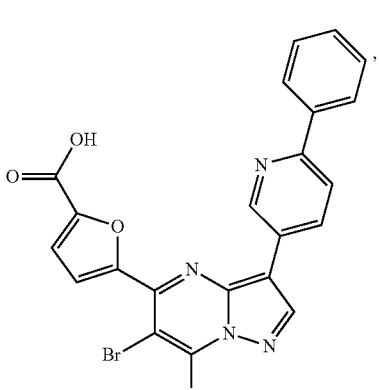
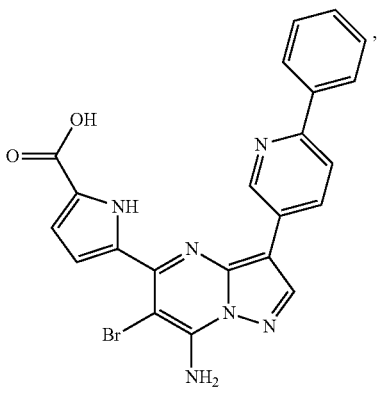

305
-continued
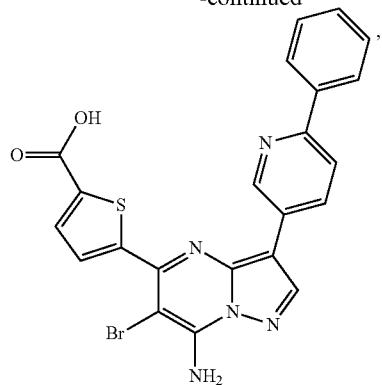,
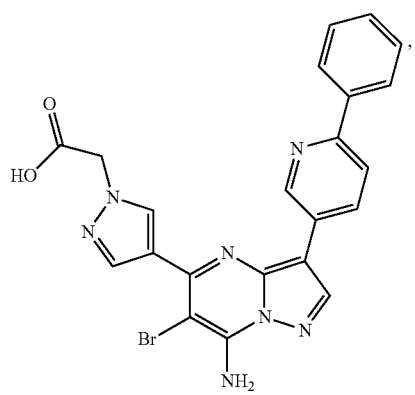,
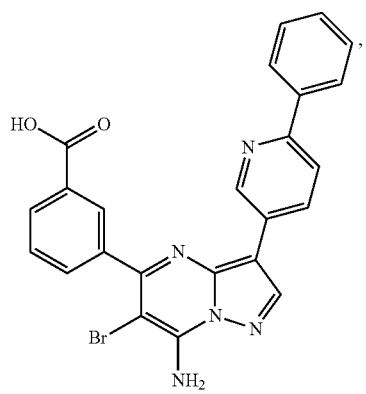,
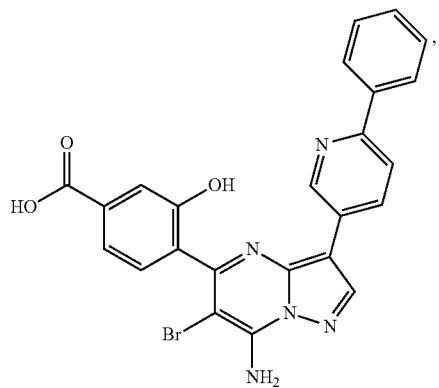,
306
-continued
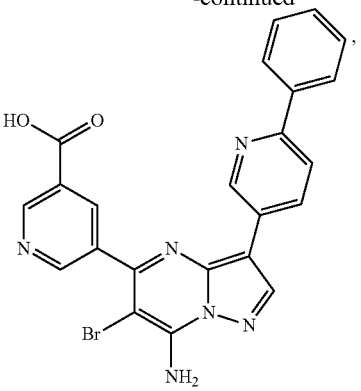,
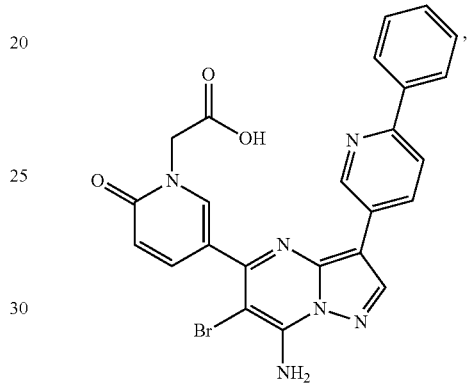,
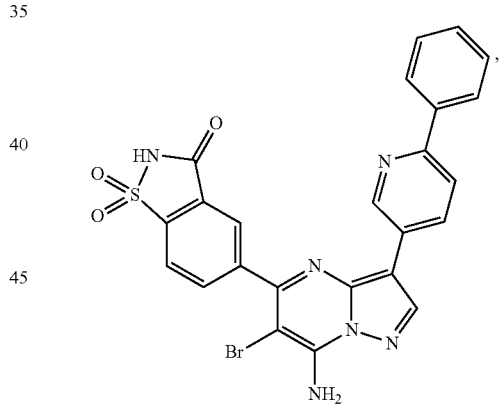,
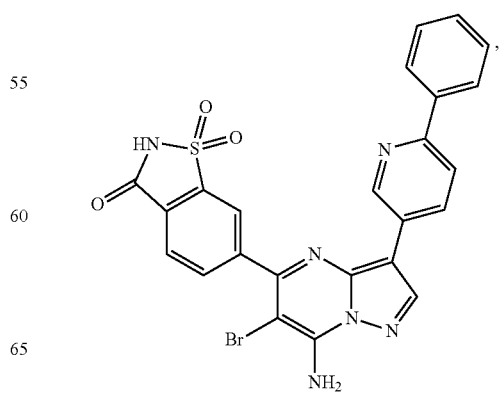,

307
-continued
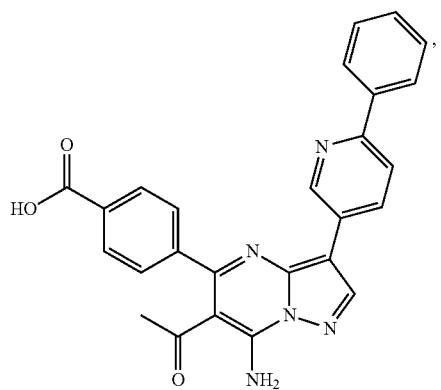
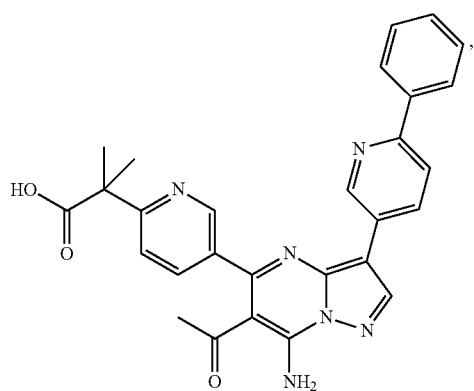
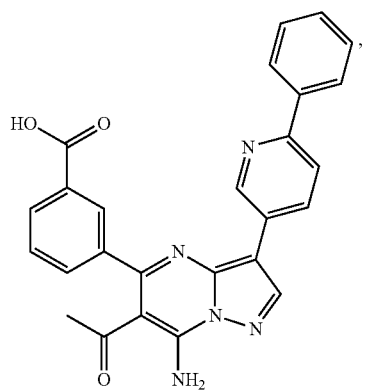
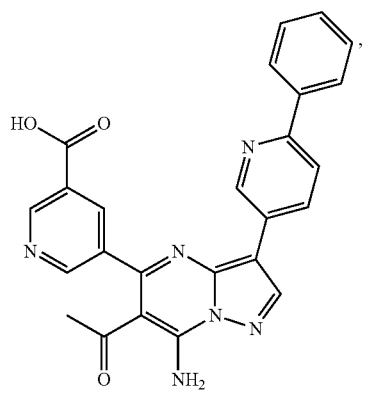
308
-continued
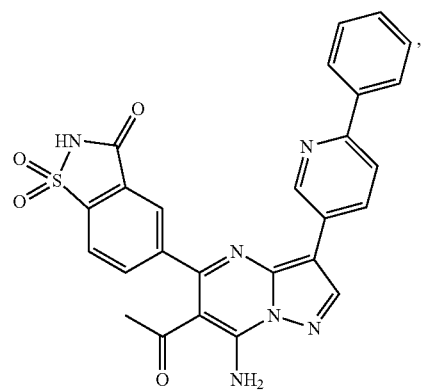
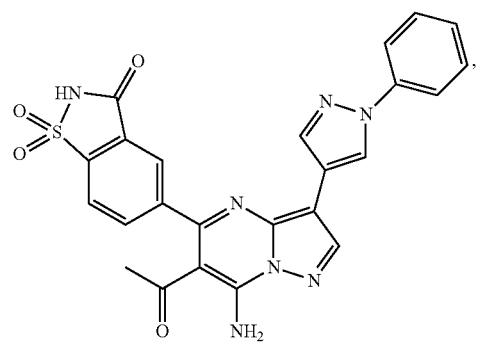
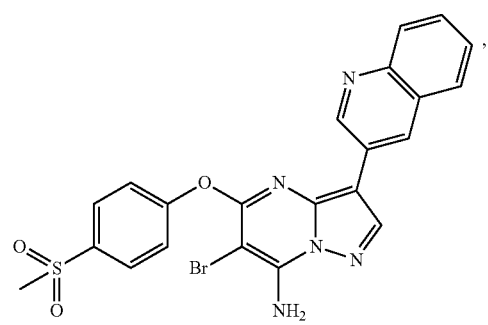
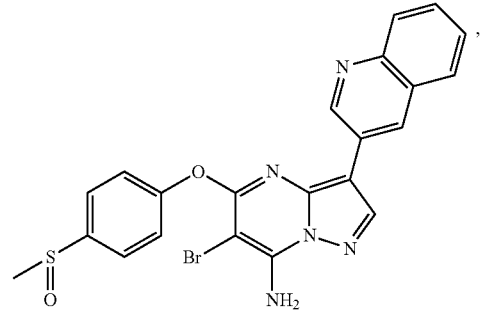

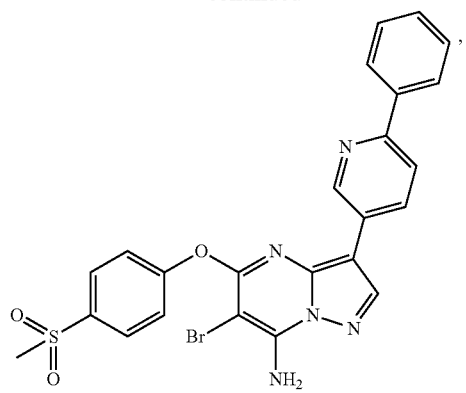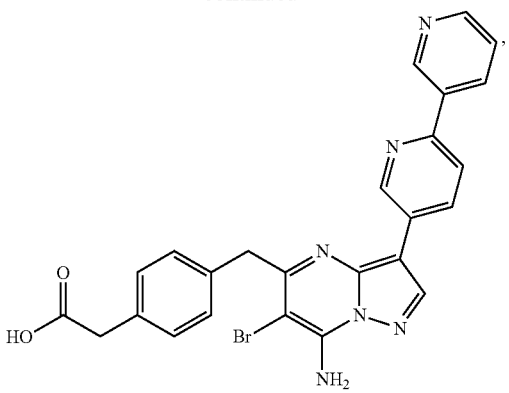

311
-continued
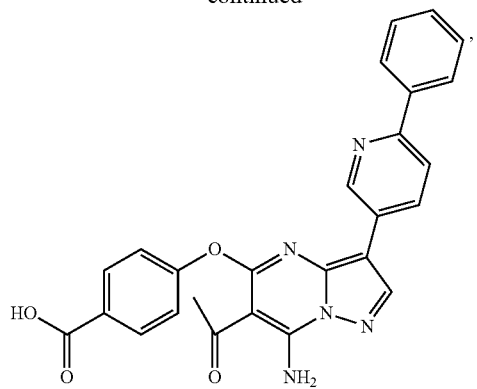
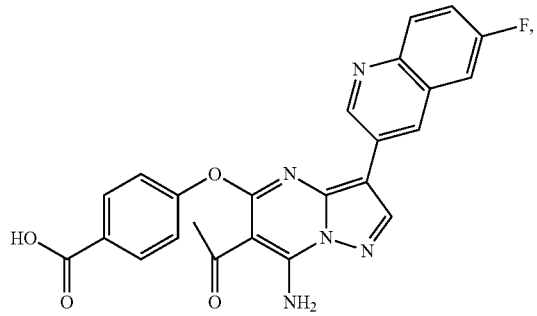
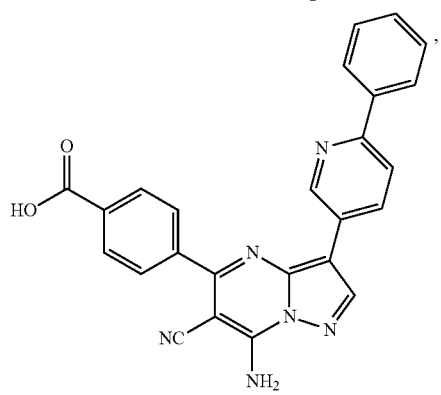
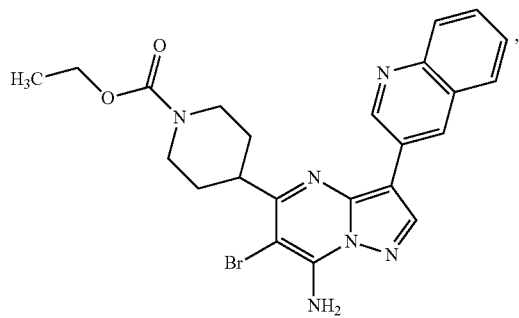
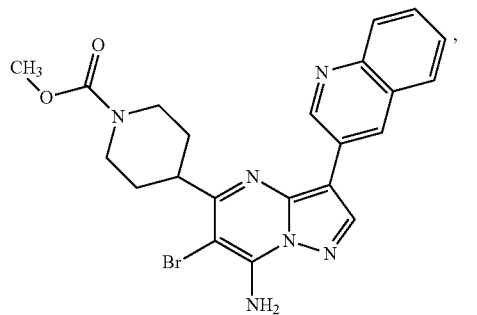
312
-continued
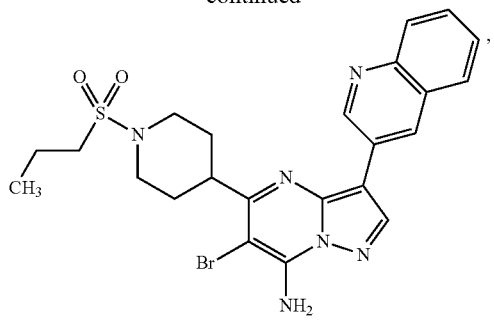
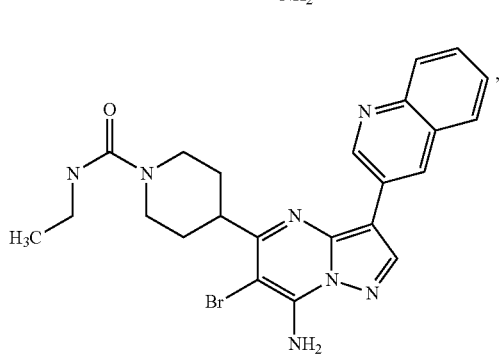
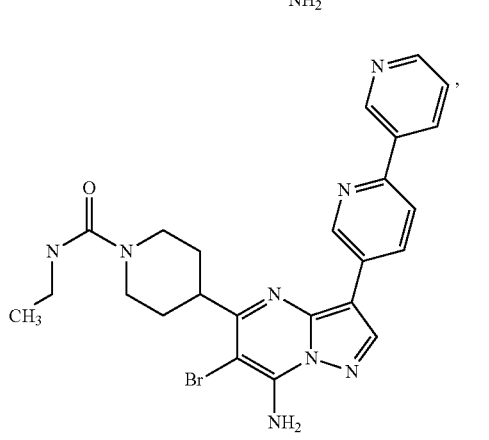
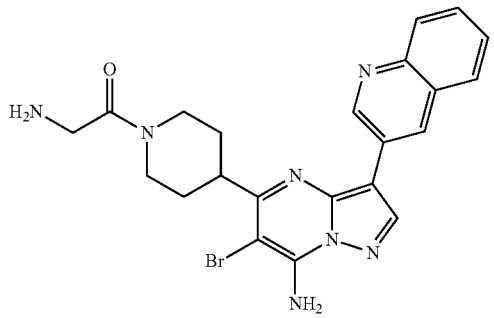
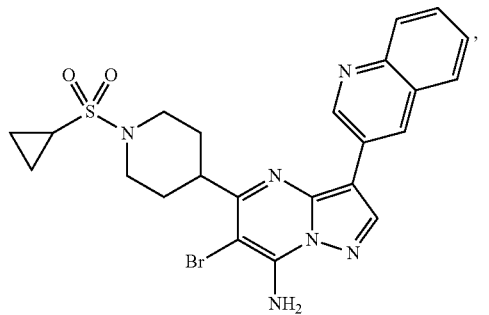

313
-continued
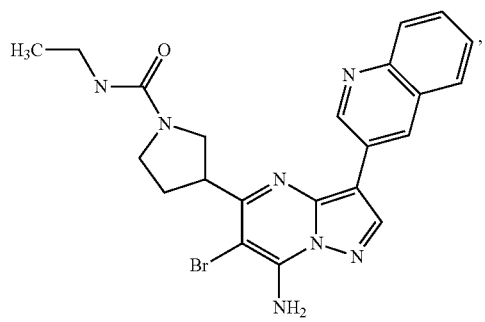
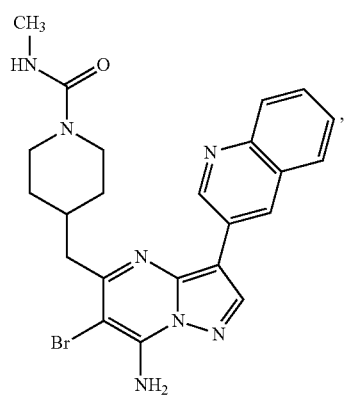
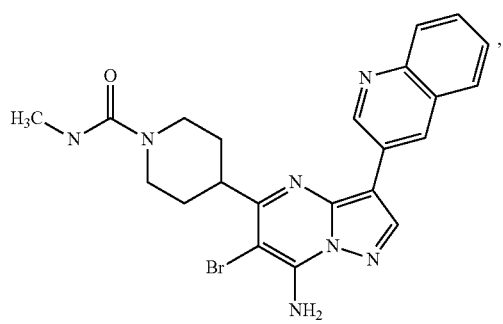
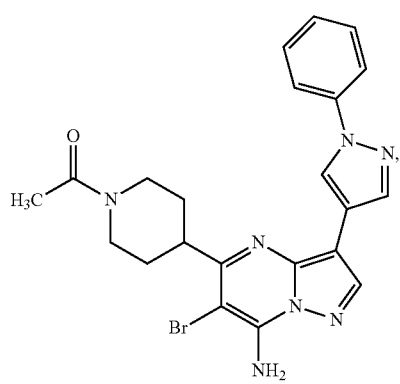
314
-continued
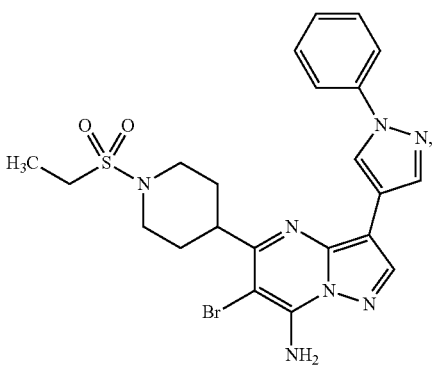
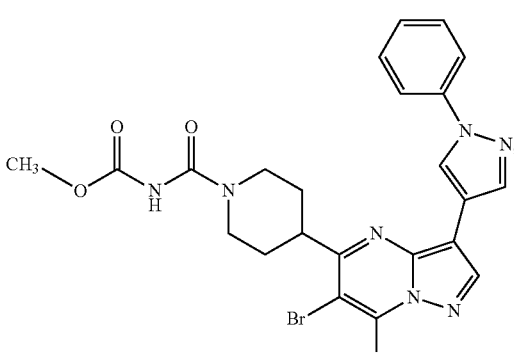
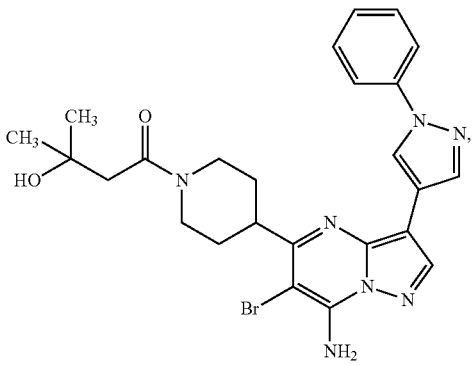
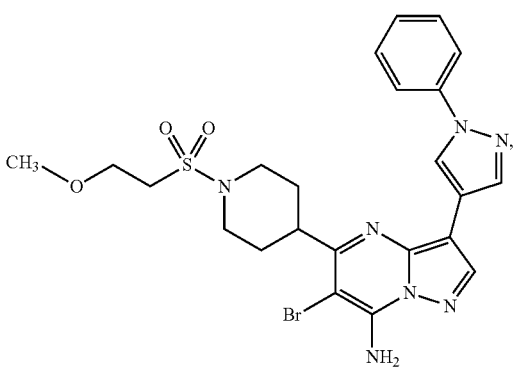

315
-continued
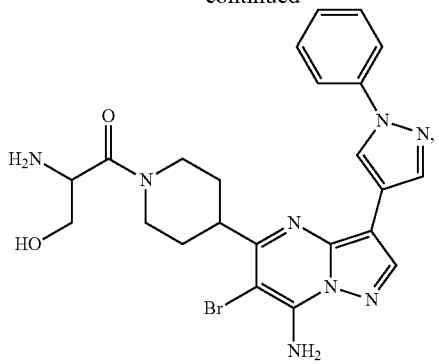
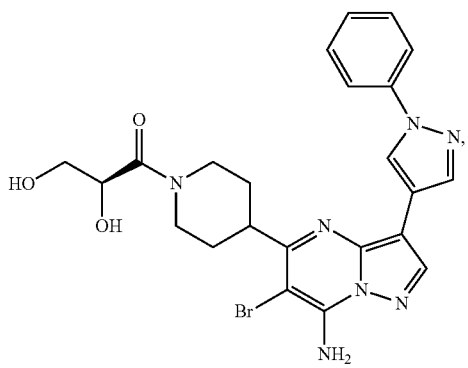
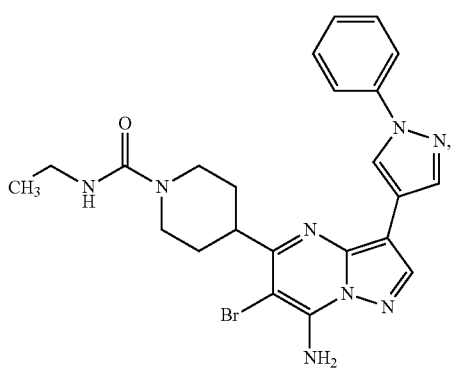
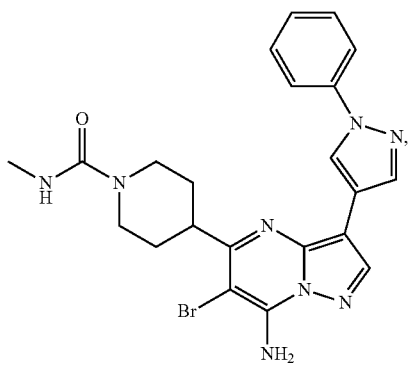
316
-continued
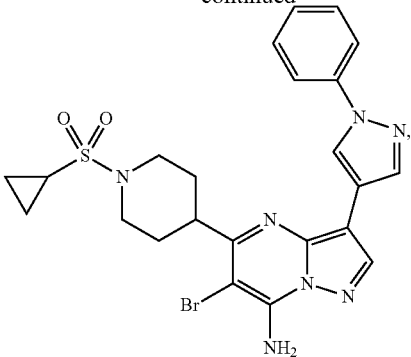
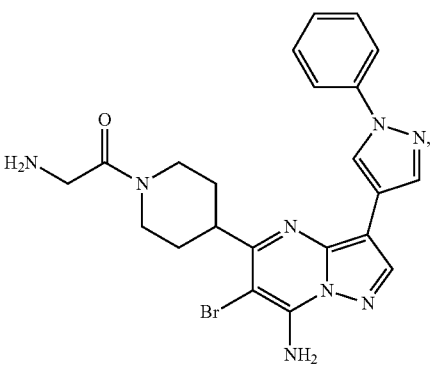
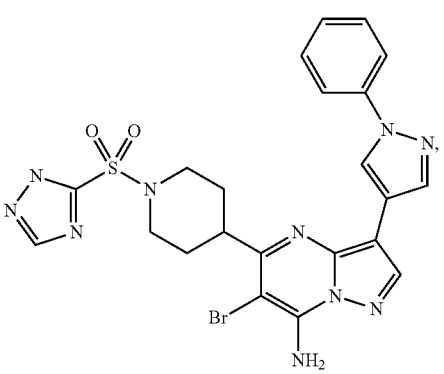
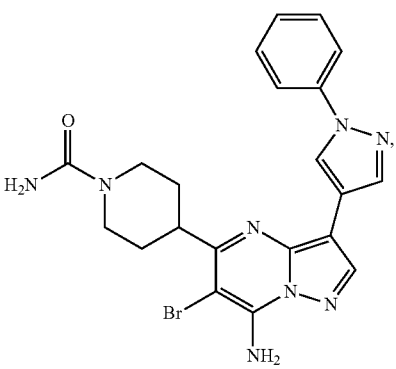

317
-continued
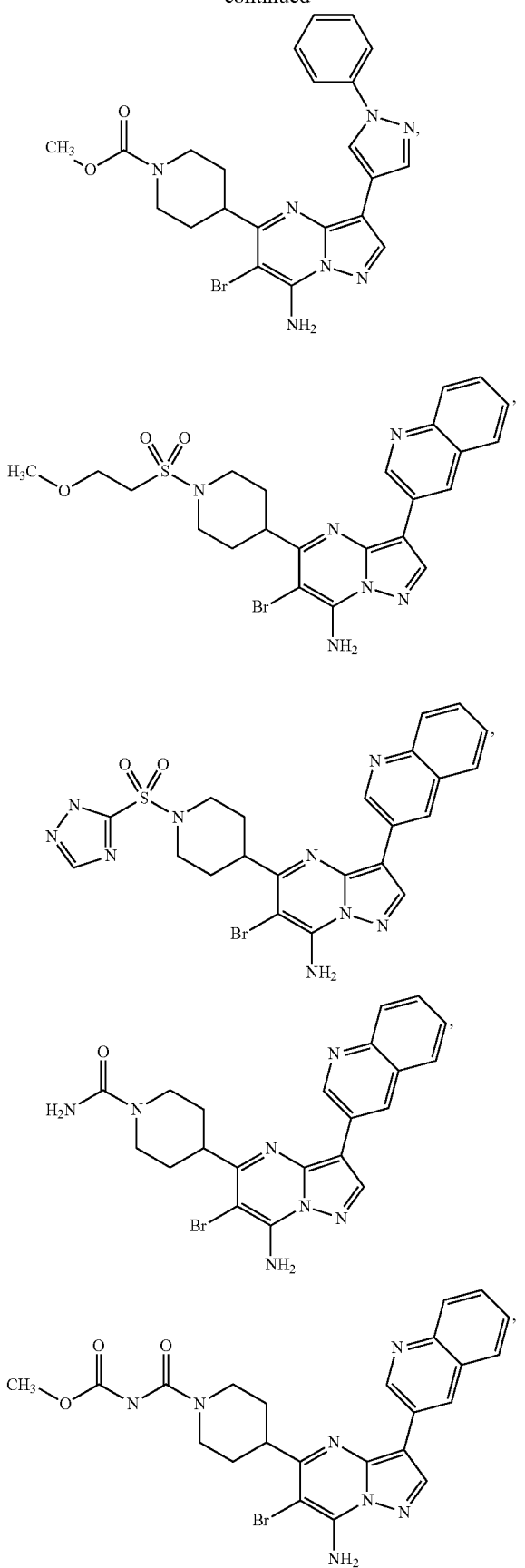
318
-continued
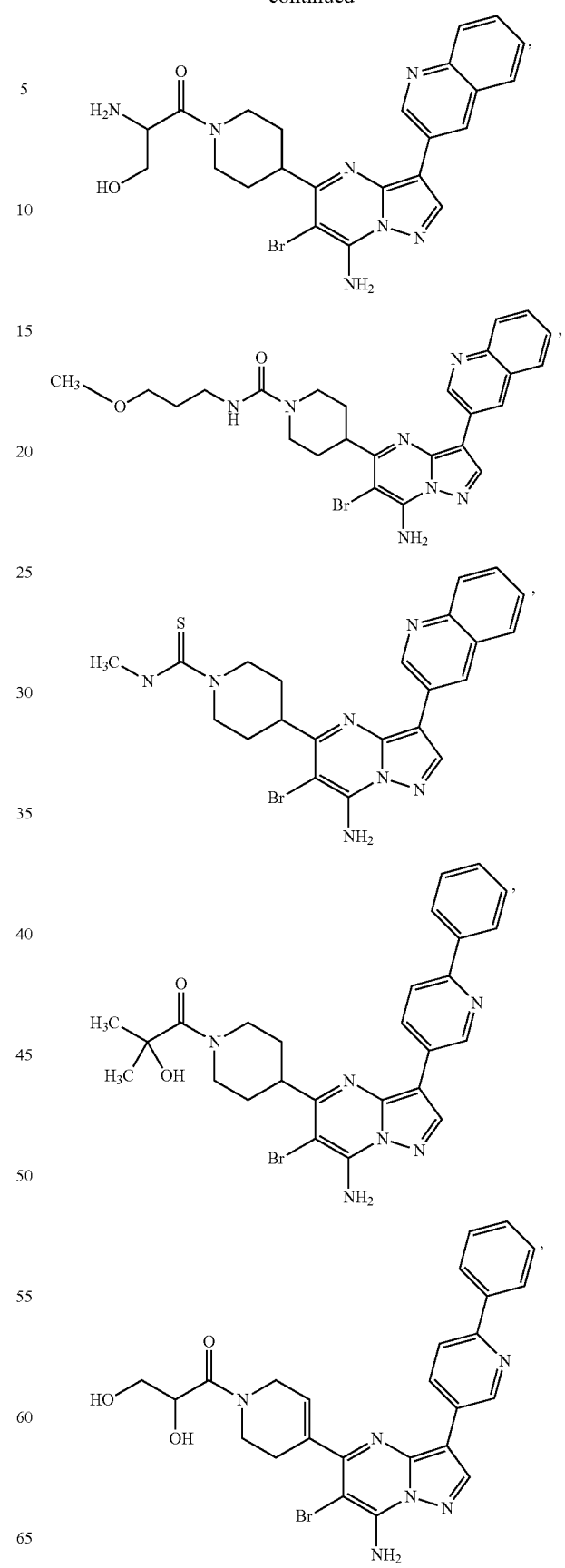

319
-continued
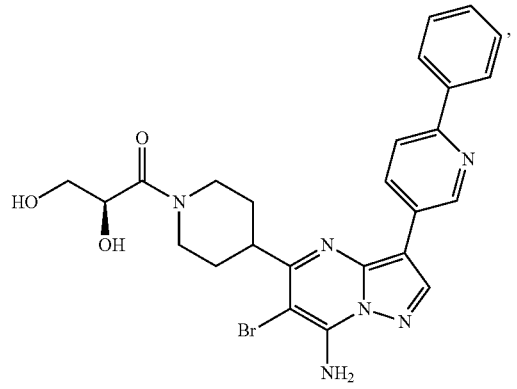
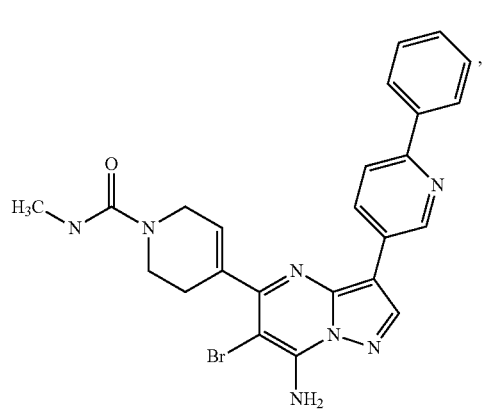
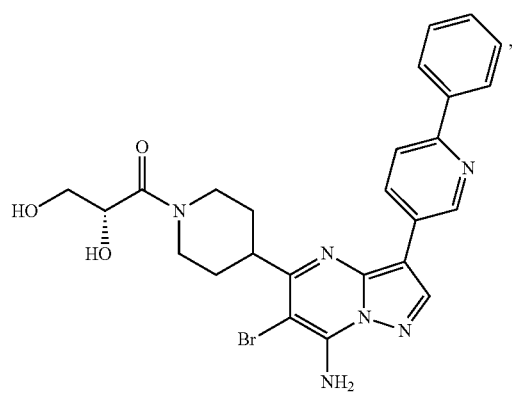
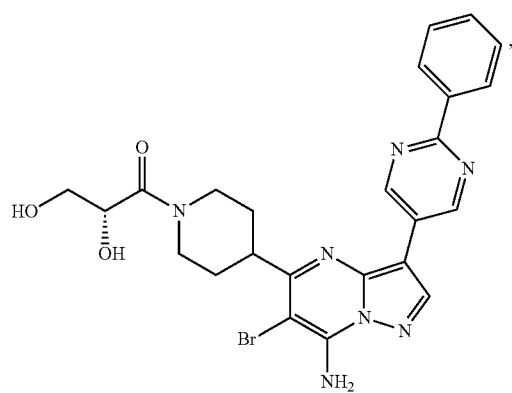
320
-continued
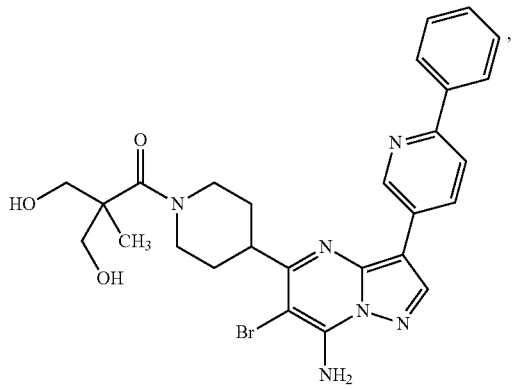
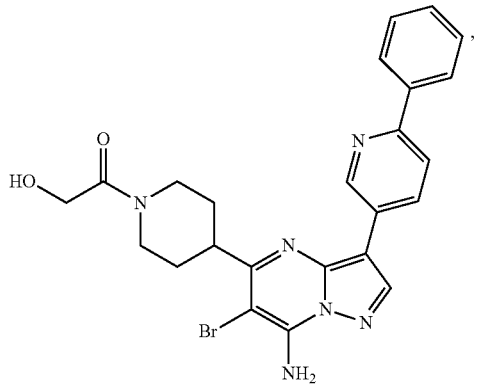
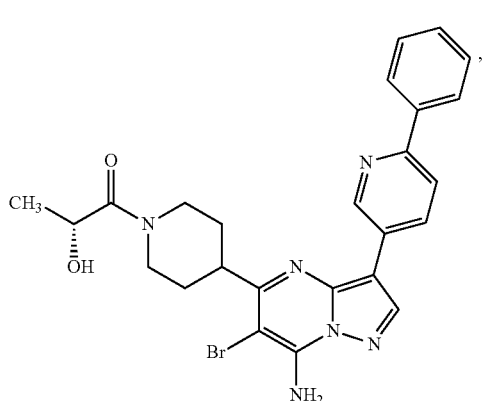
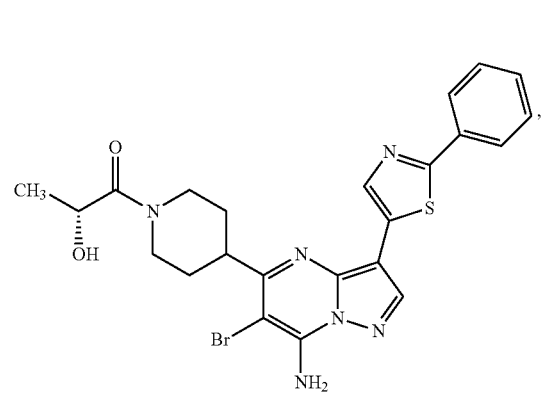

321
-continued
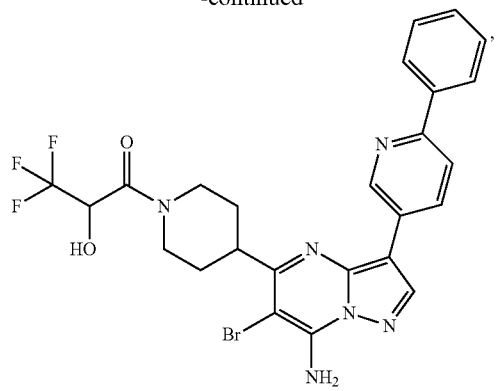
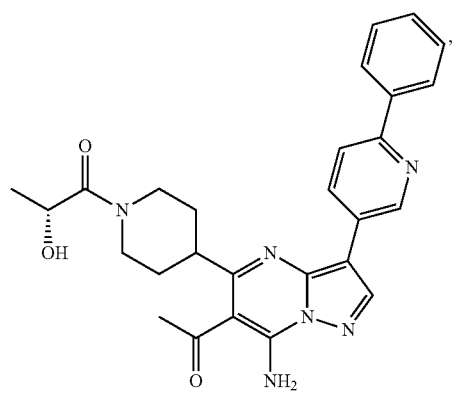
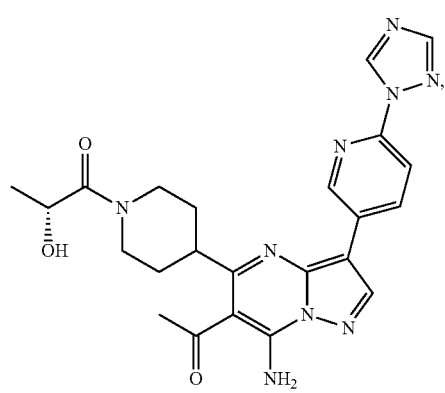
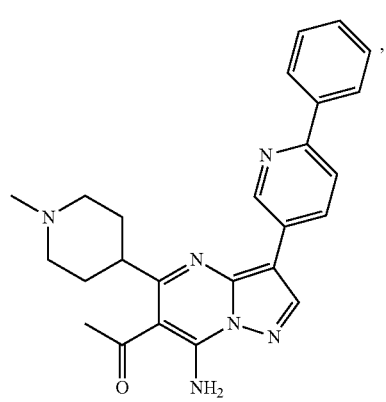
322
-continued
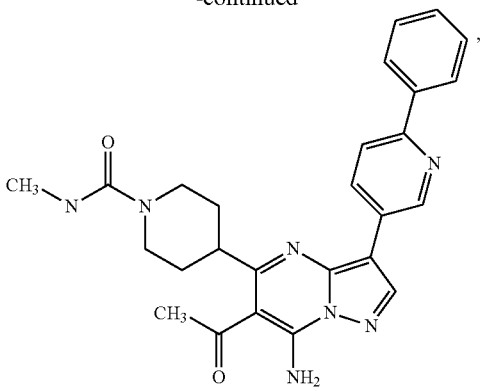
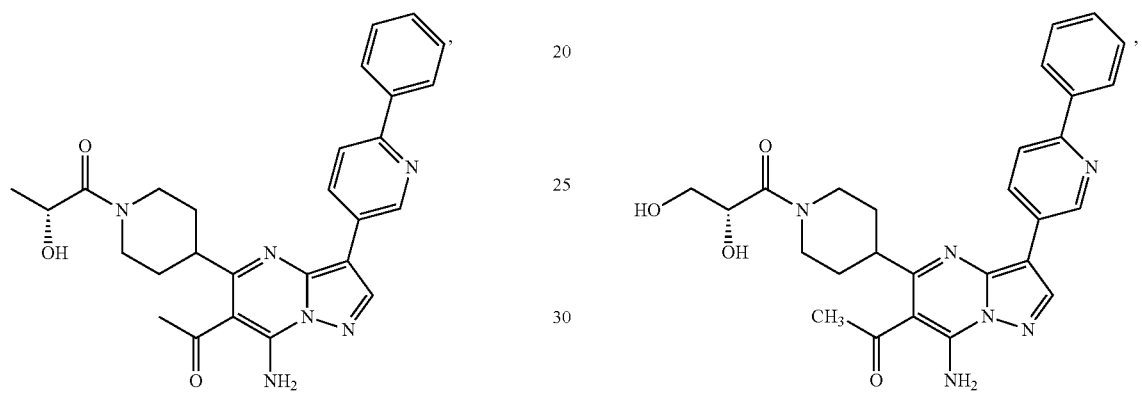
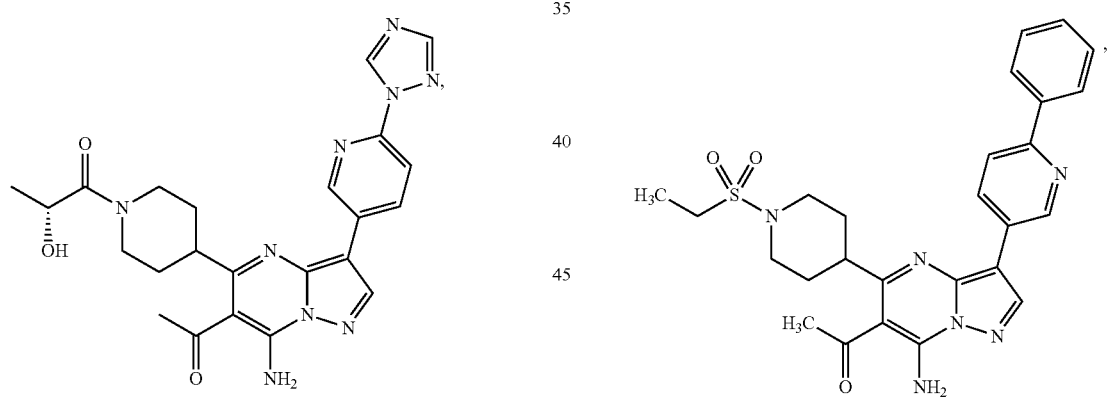
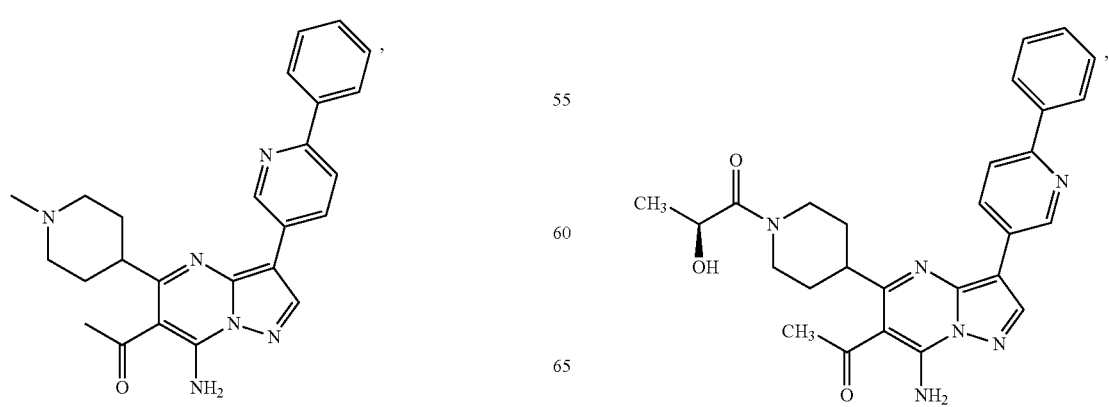

323
-continued
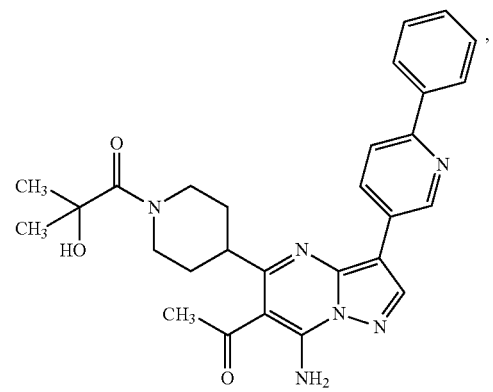
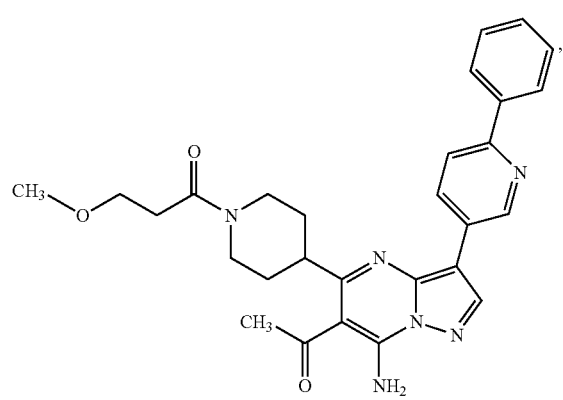
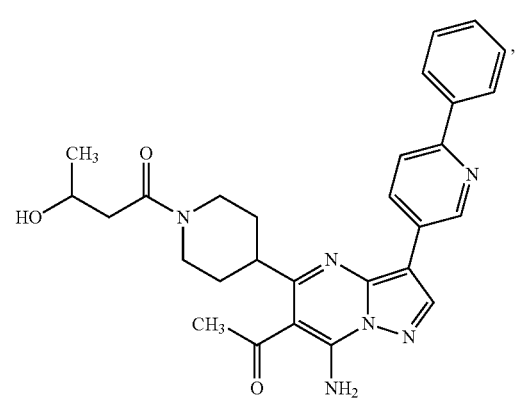
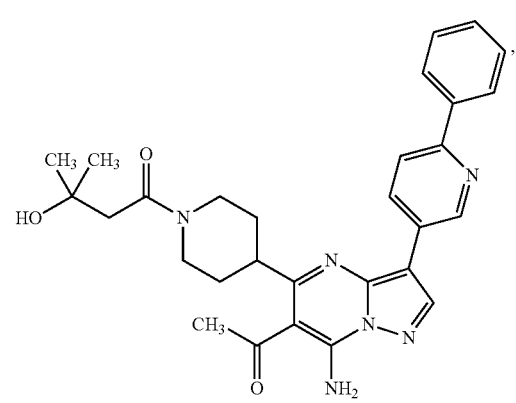
324
-continued
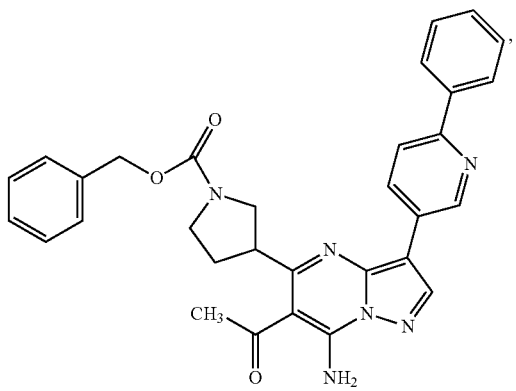
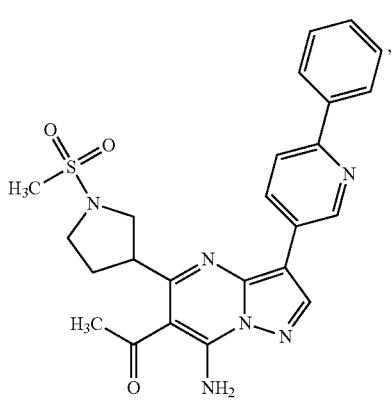
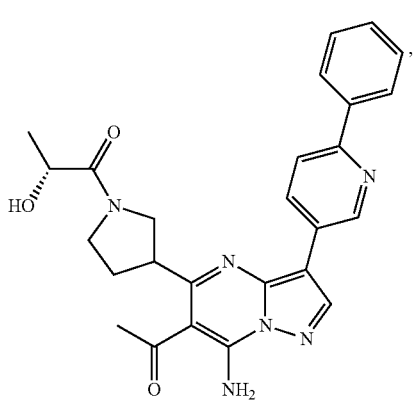
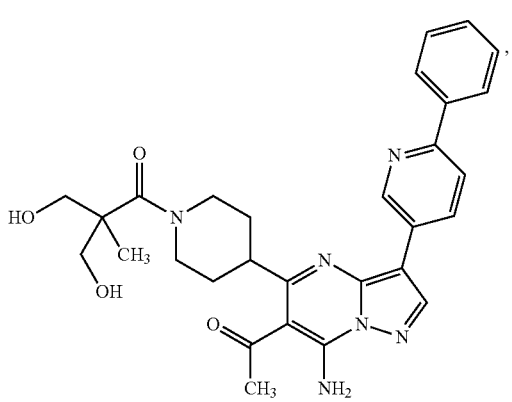

325
-continued
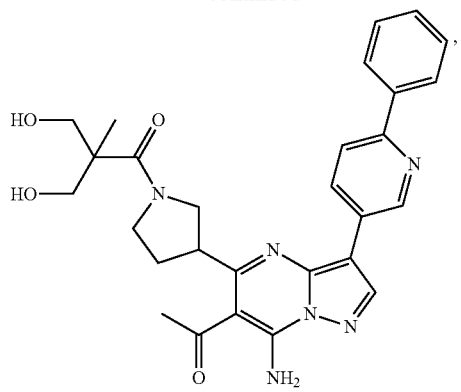
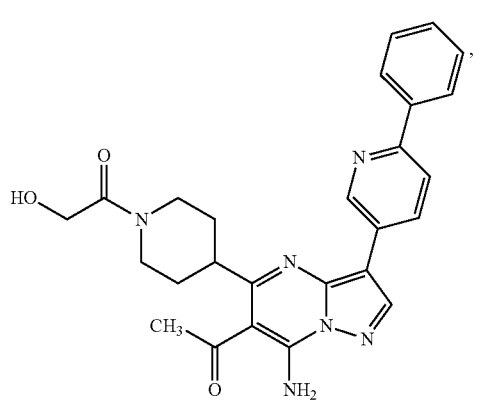
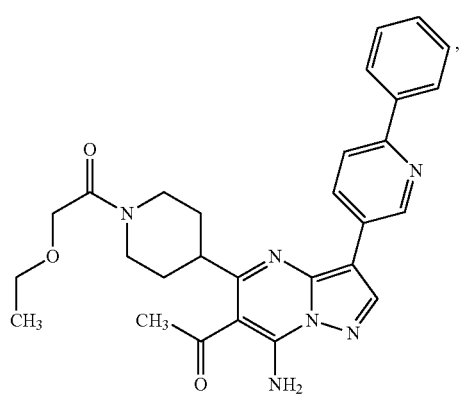
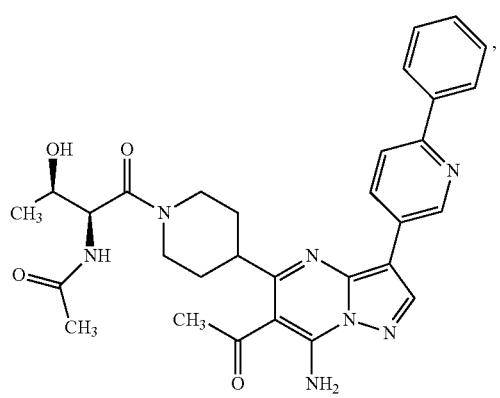
326
-continued
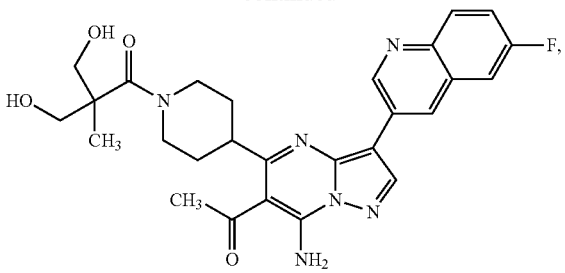
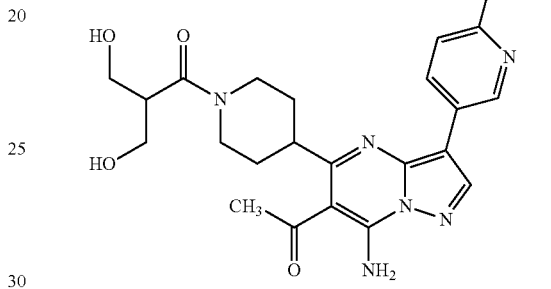
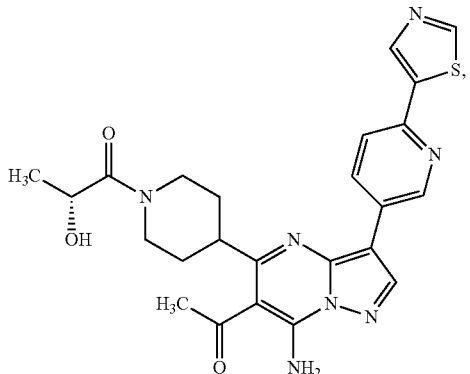
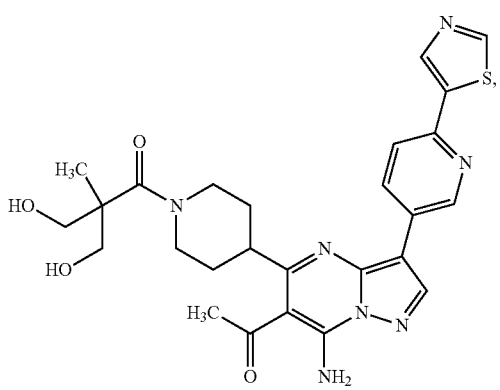

327
-continued
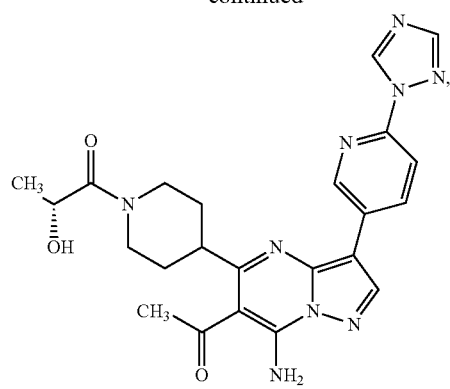
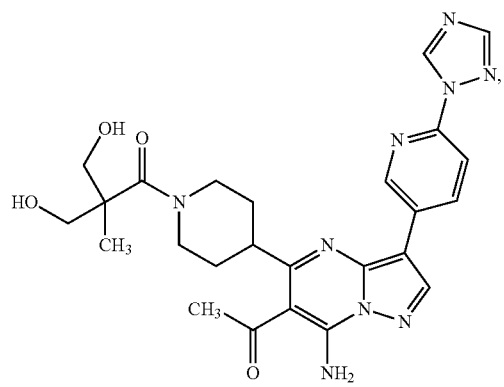
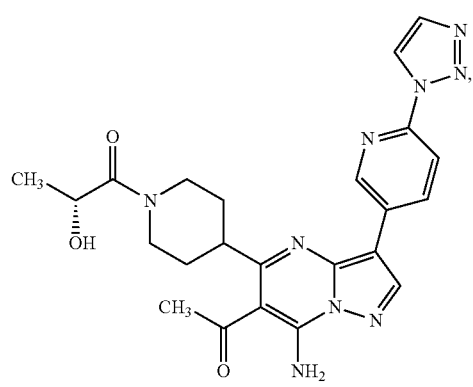
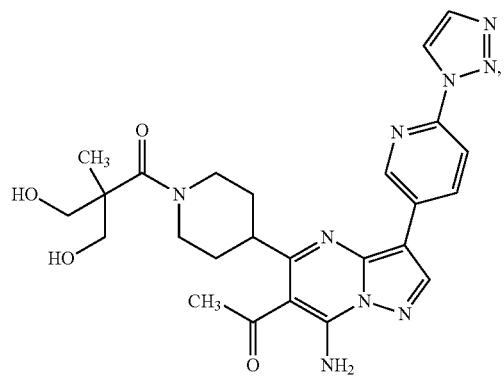
328
-continued
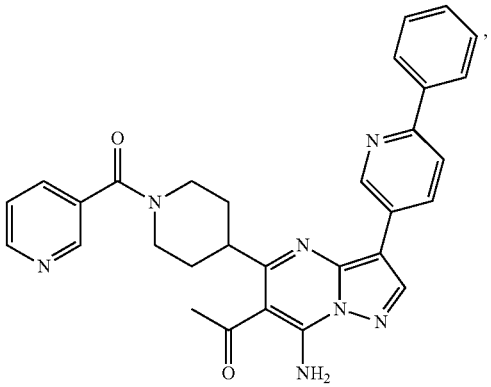

329
-continued
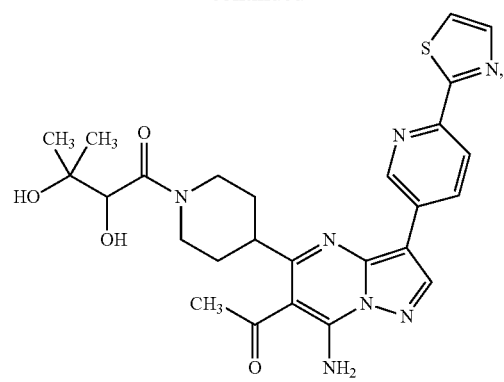
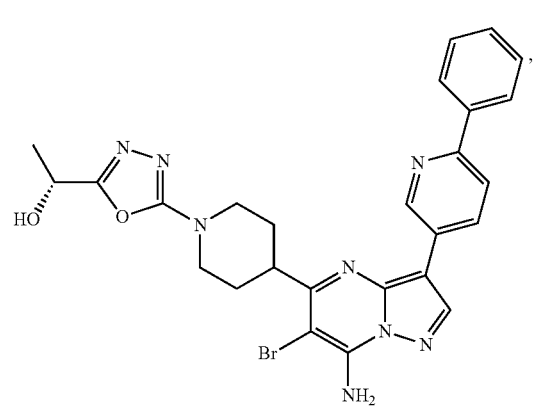
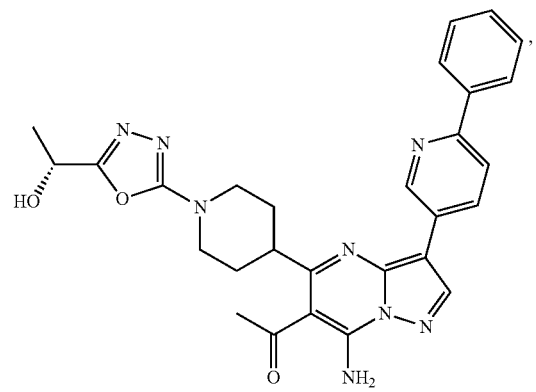
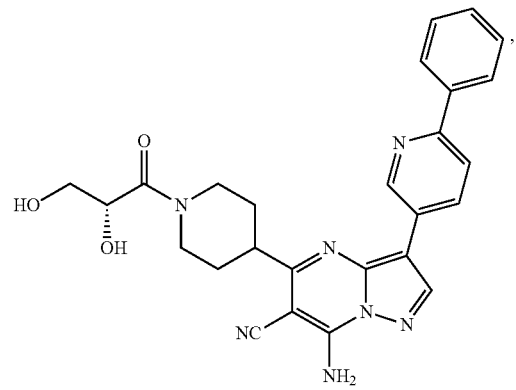
330
-continued
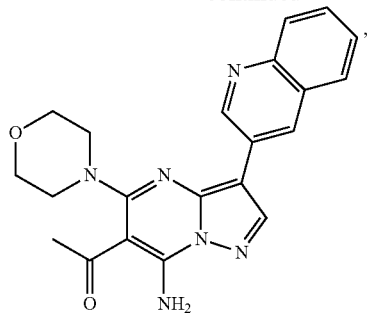
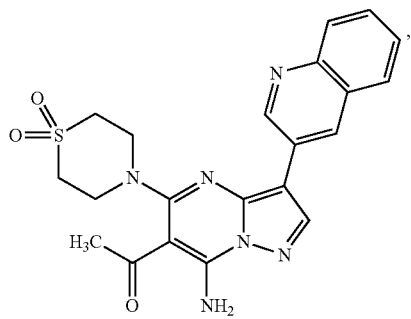
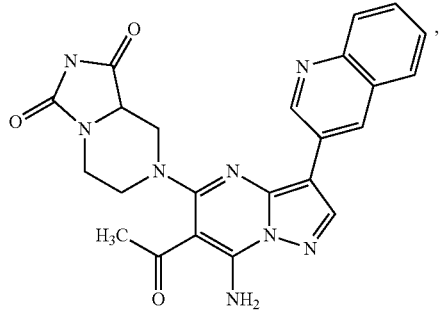
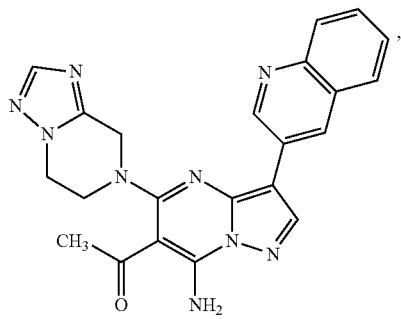

331
-continued
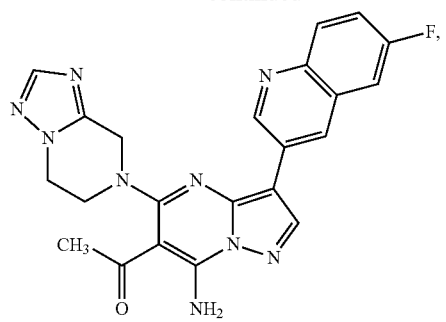
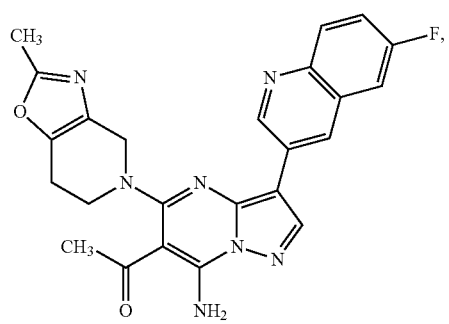
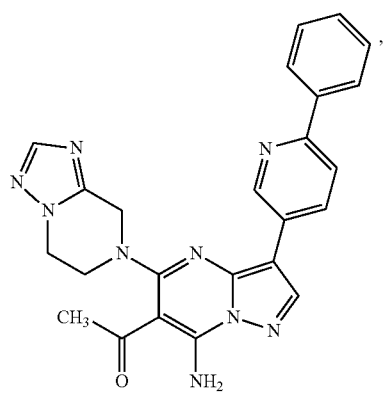
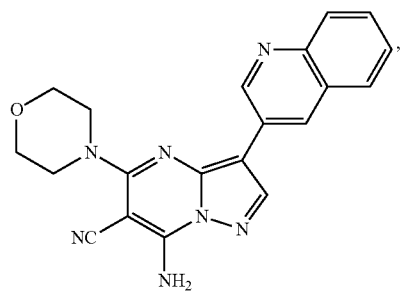
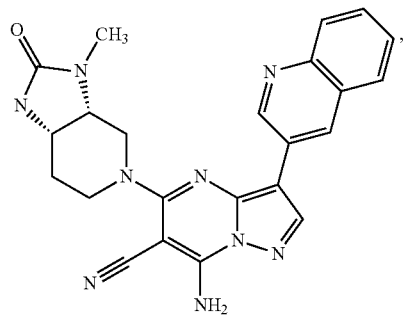
332
-continued
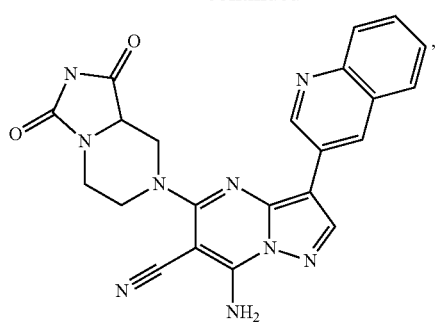
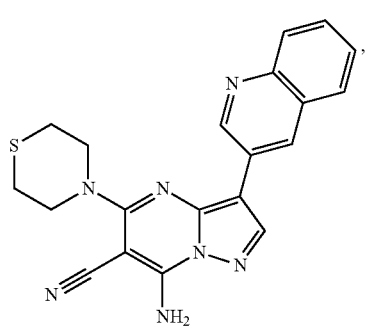
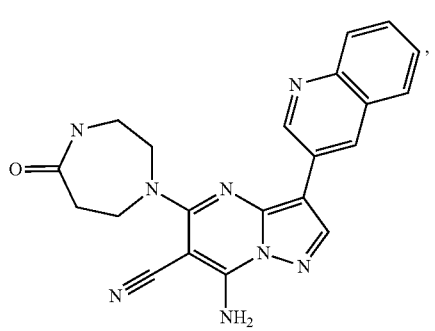
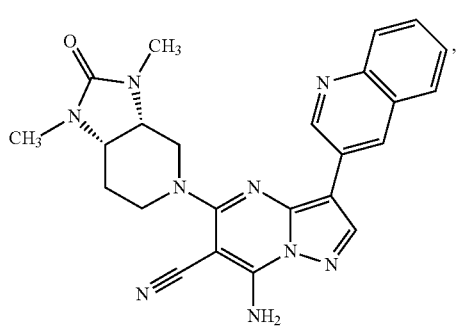
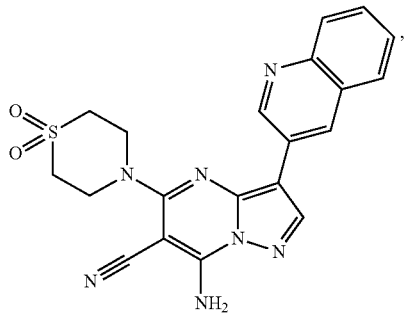

333
-continued
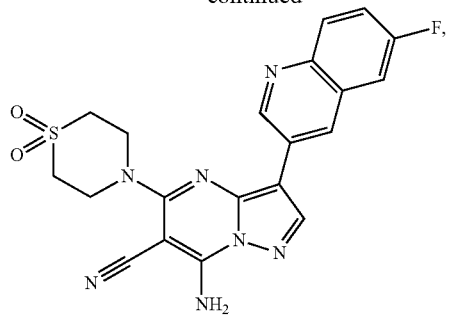
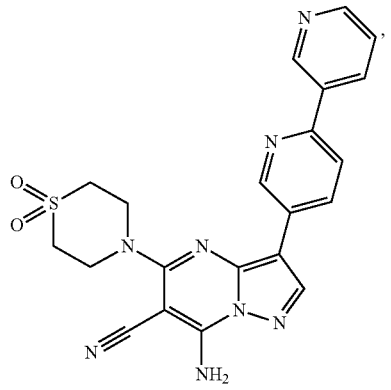
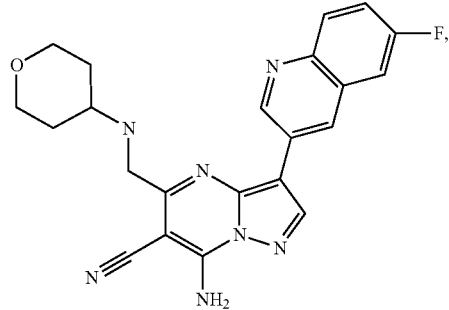
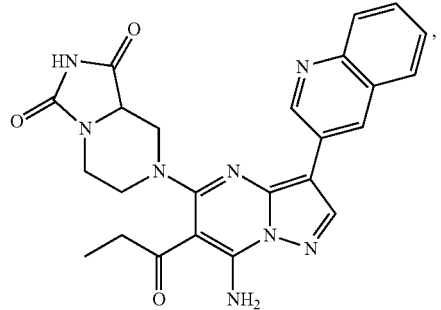
334
-continued
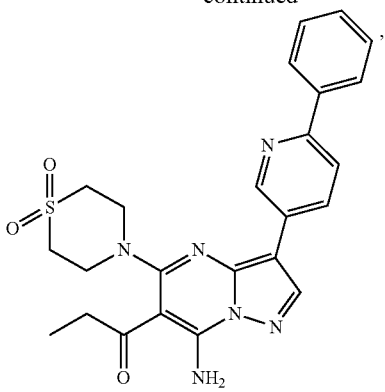
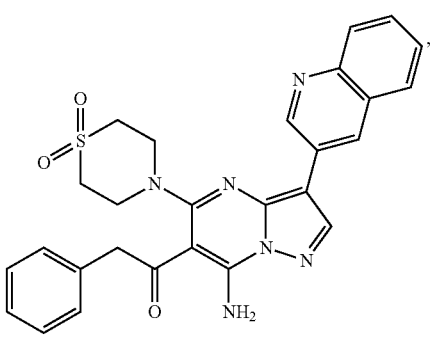
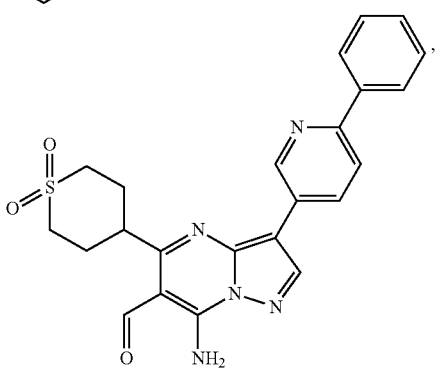
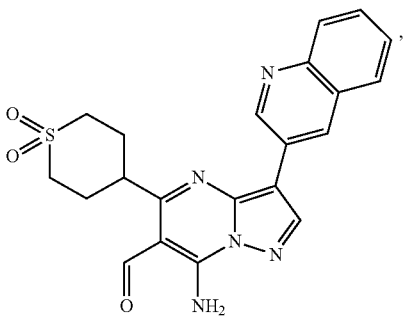
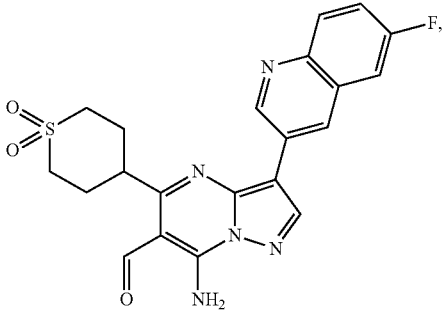

335
-continued
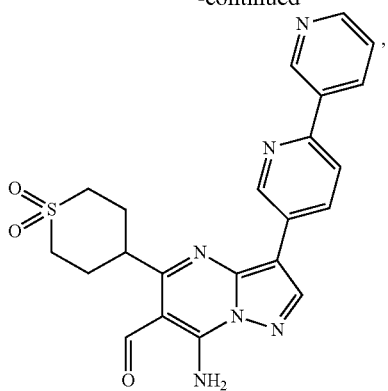
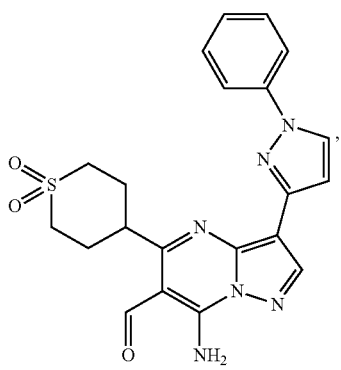
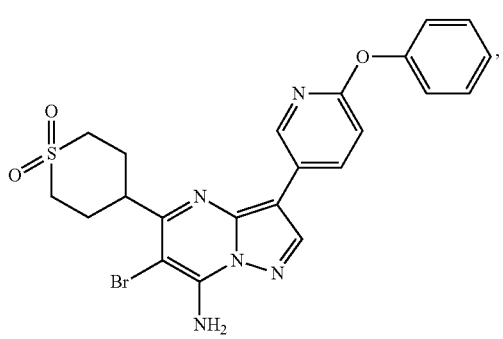
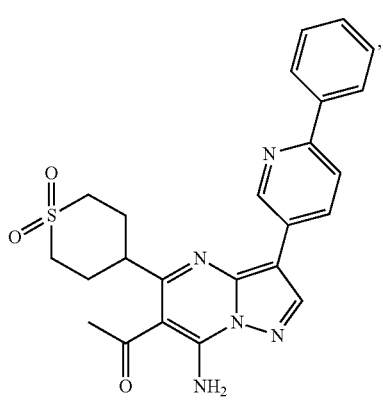
336
-continued
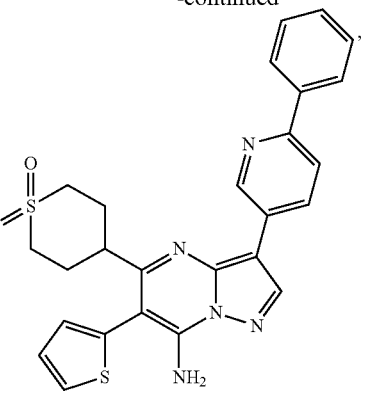
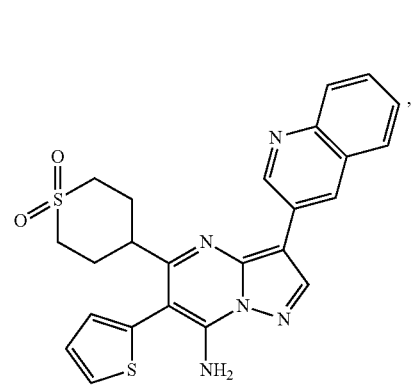
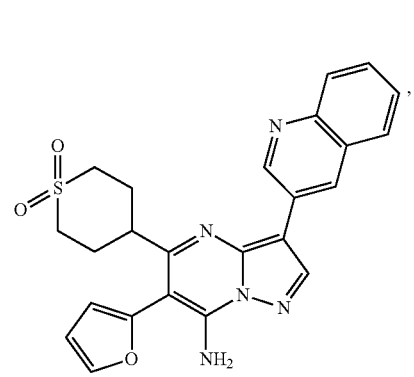
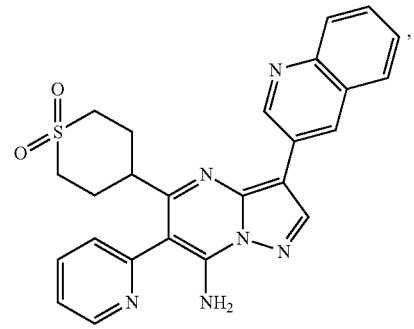

337
-continued
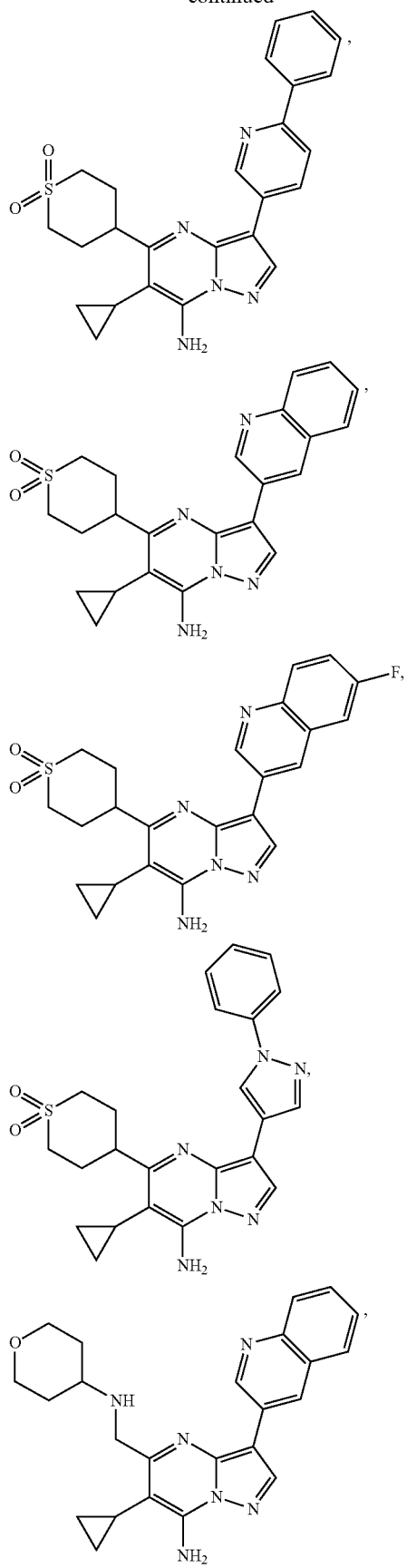
338
-continued
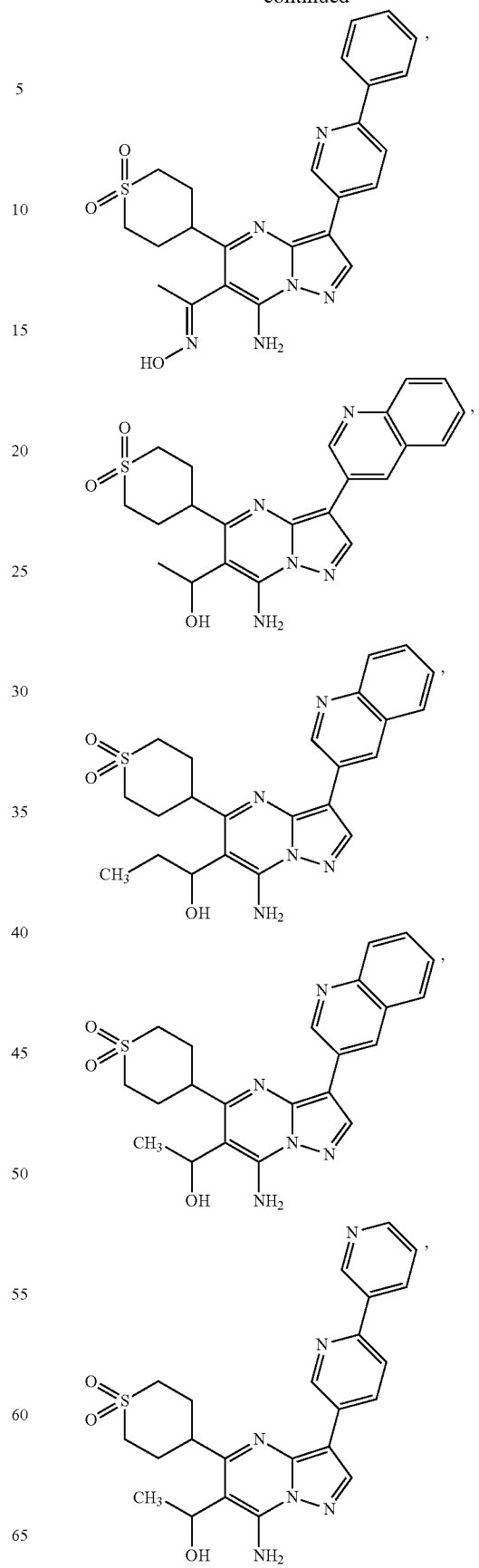

339
-continued
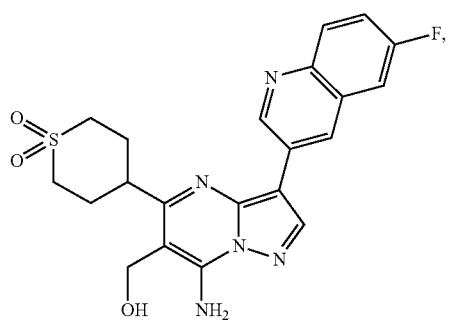
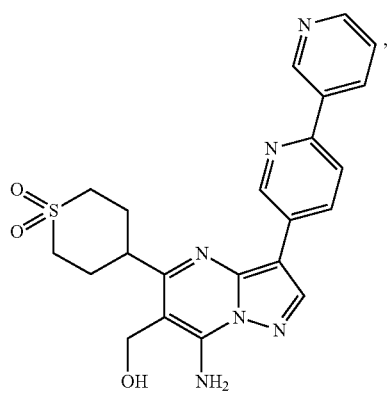
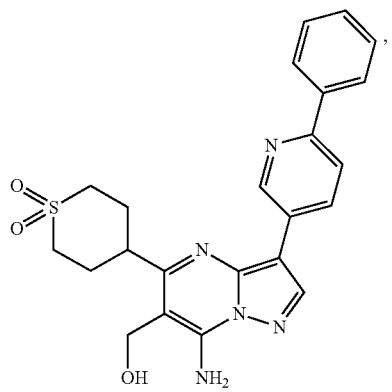
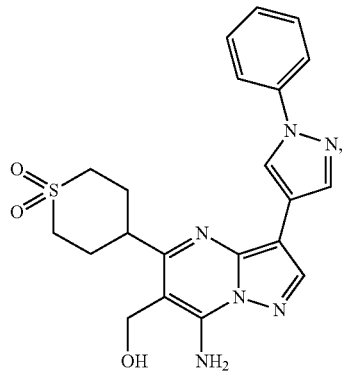
340
-continued
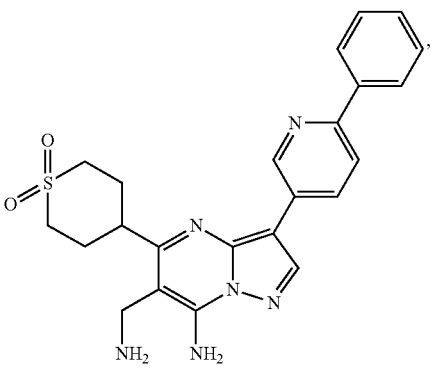
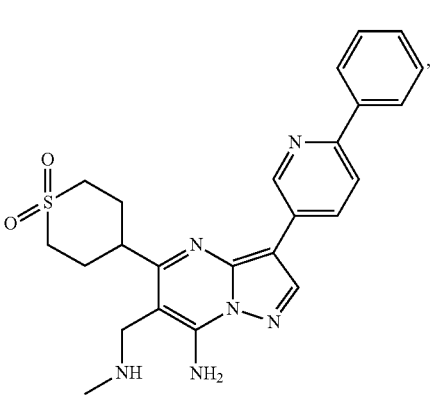
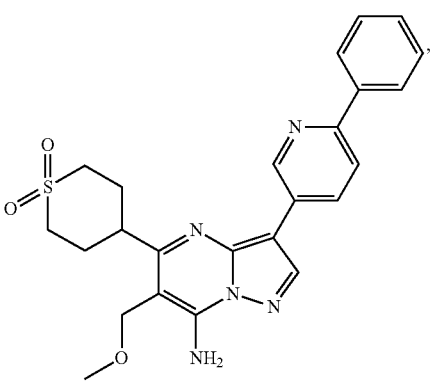
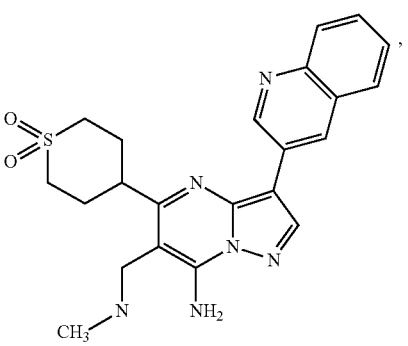

-continued
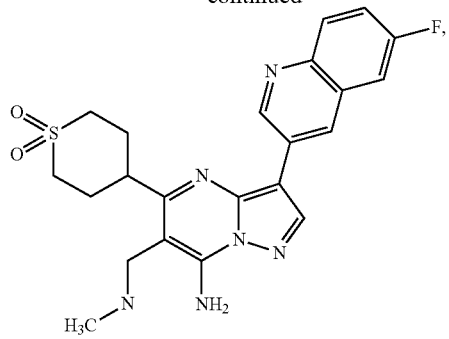
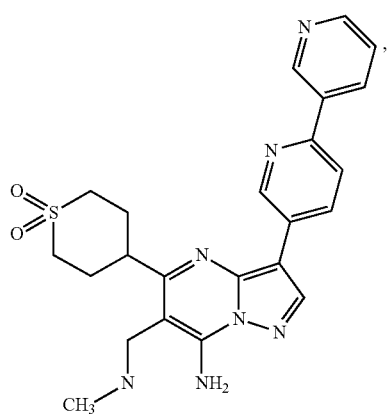
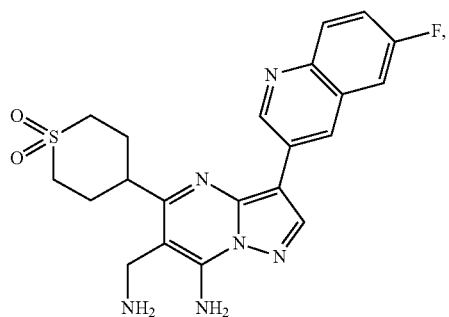
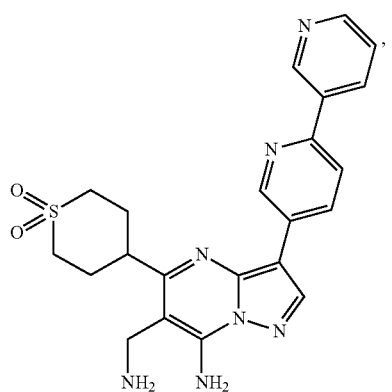
-continued
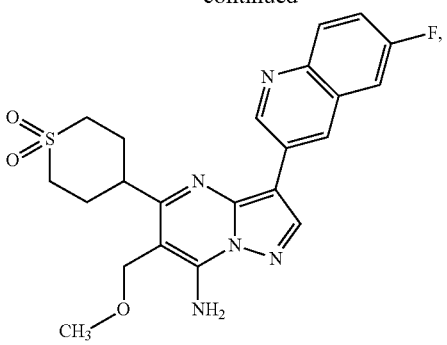
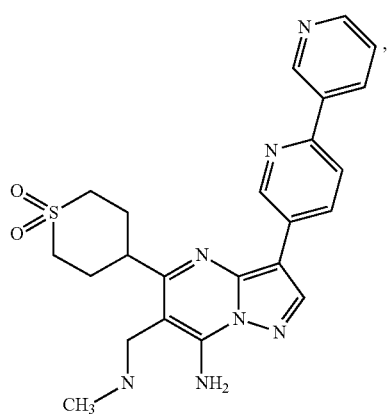
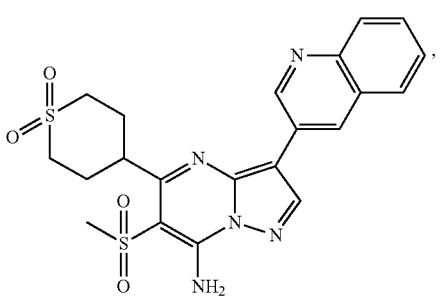
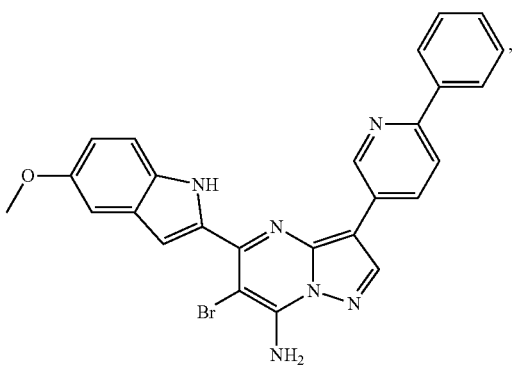

343
-continued
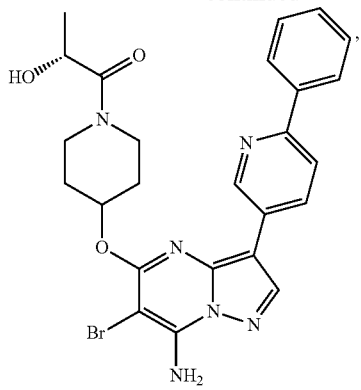
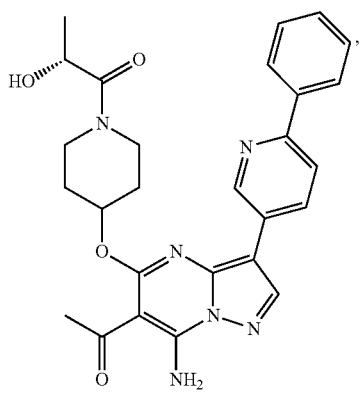
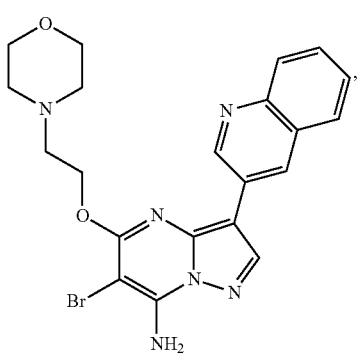
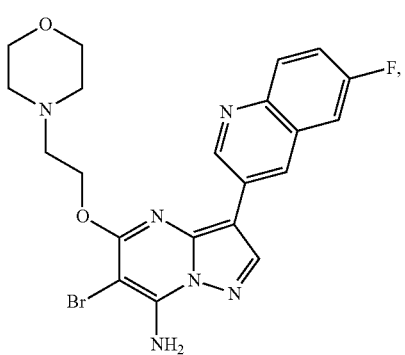
344
-continued
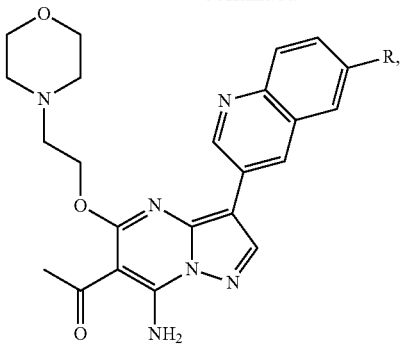
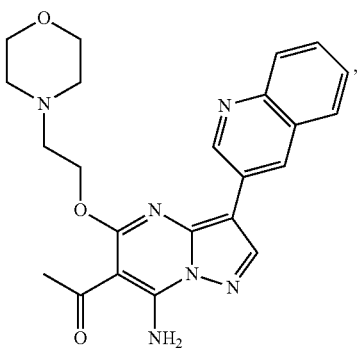
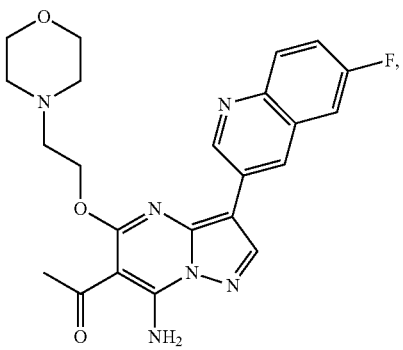
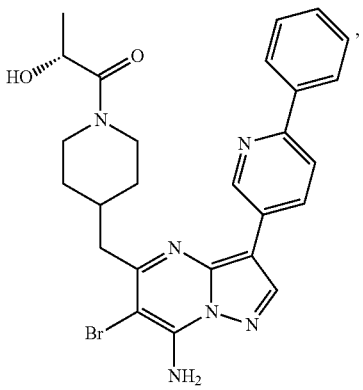

345
-continued
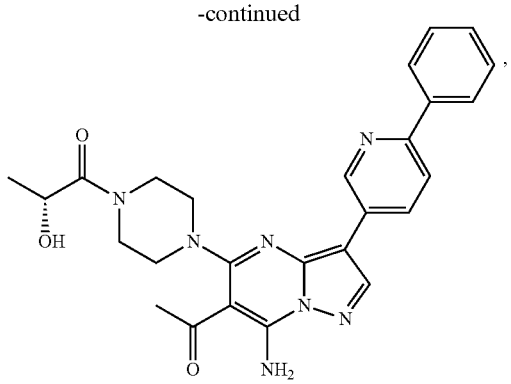
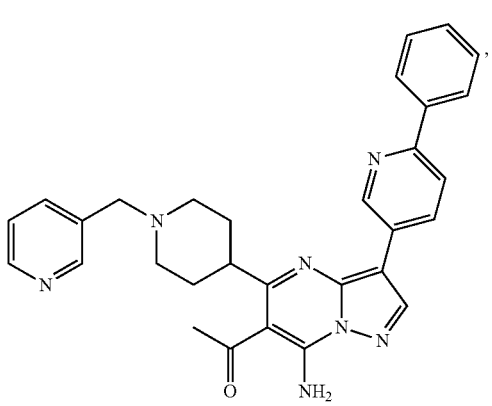
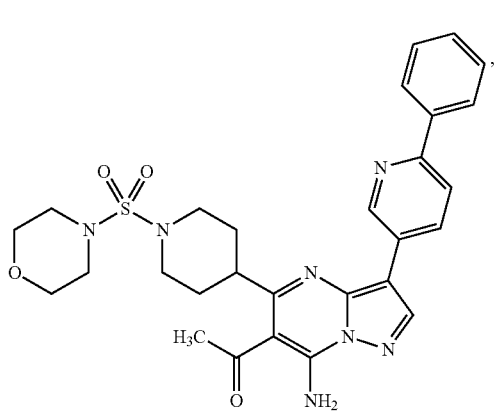
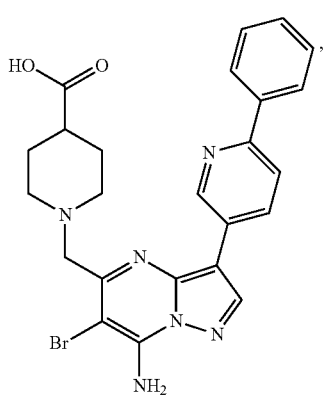
346
-continued
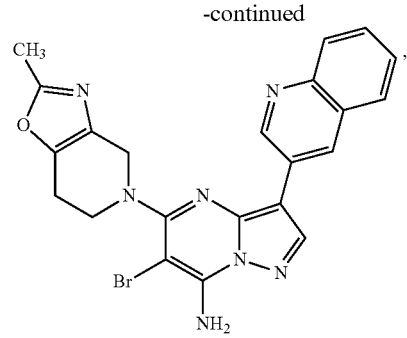
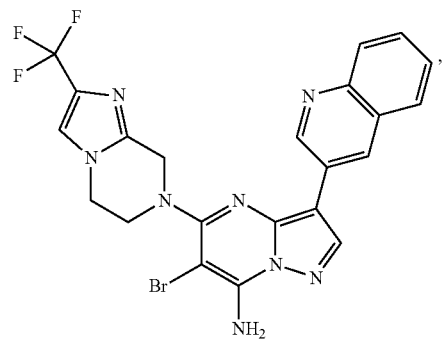
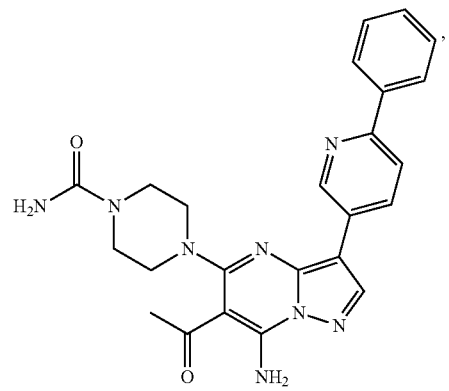
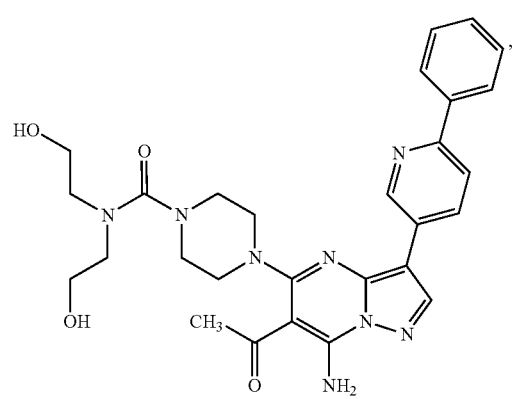

347
-continued
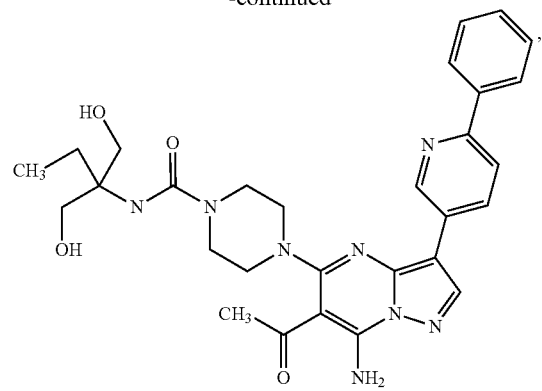
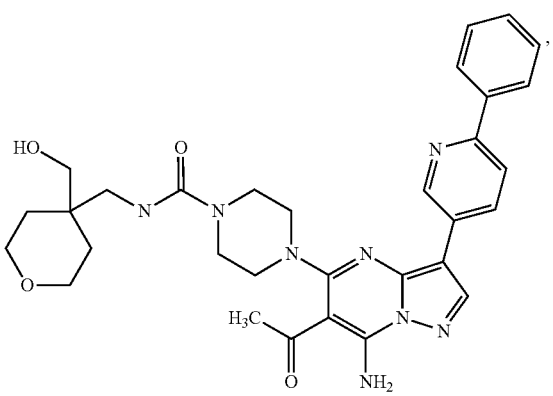
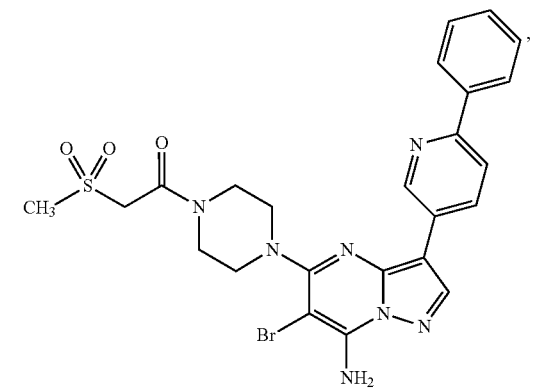
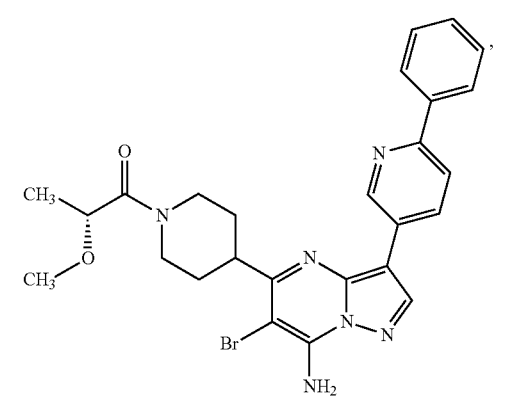
348
-continued
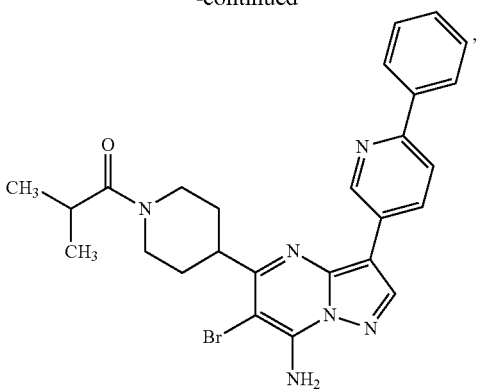

349
-continued
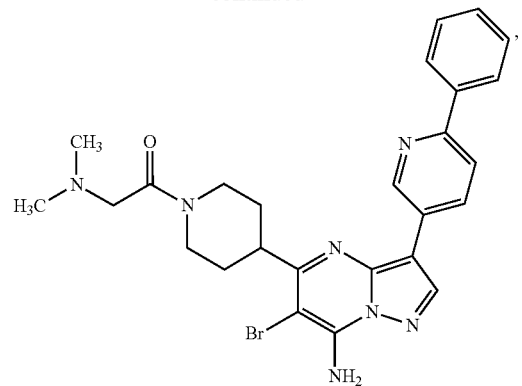
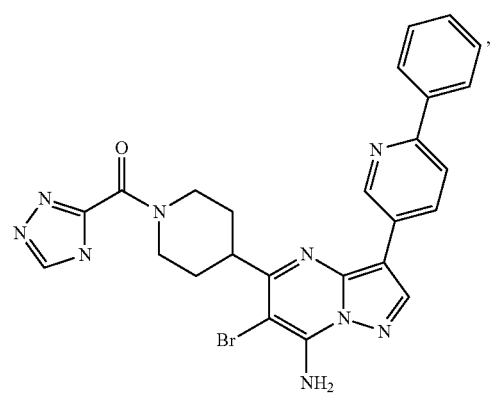
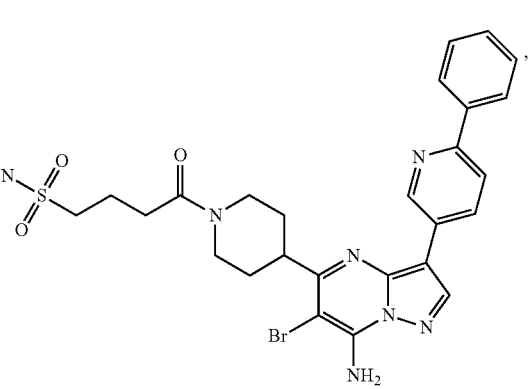
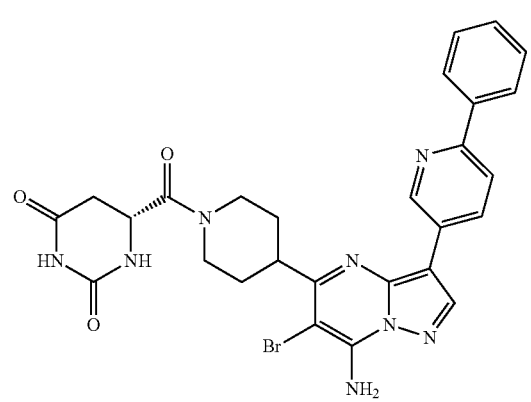
350
-continued
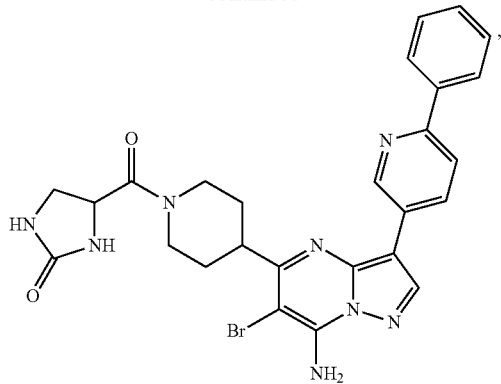
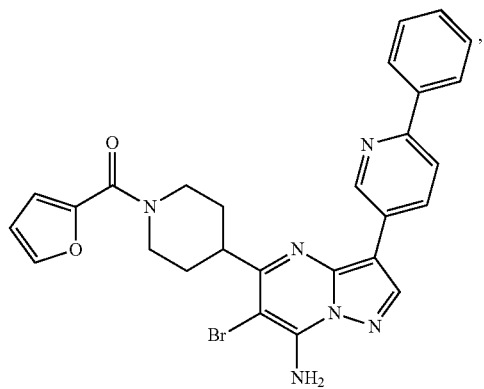
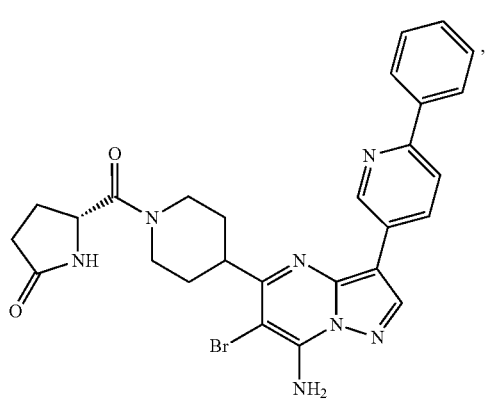
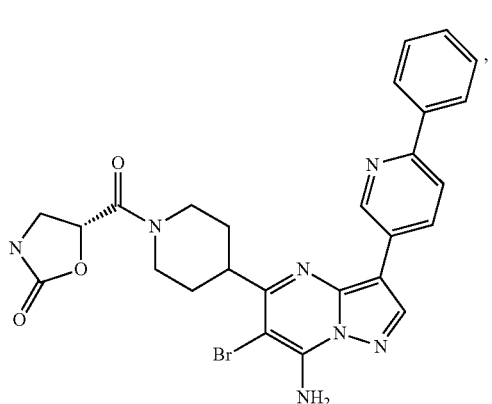

351
-continued
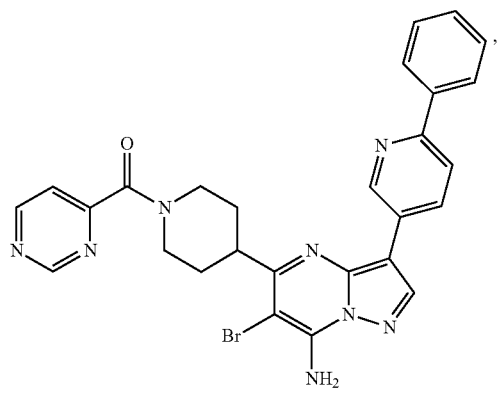
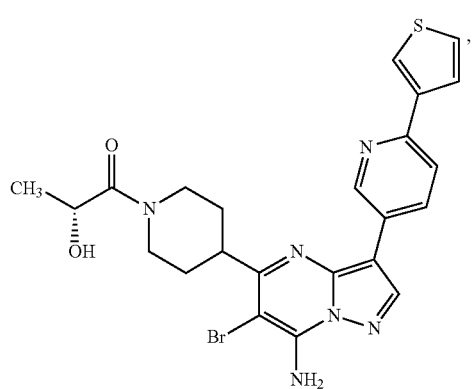
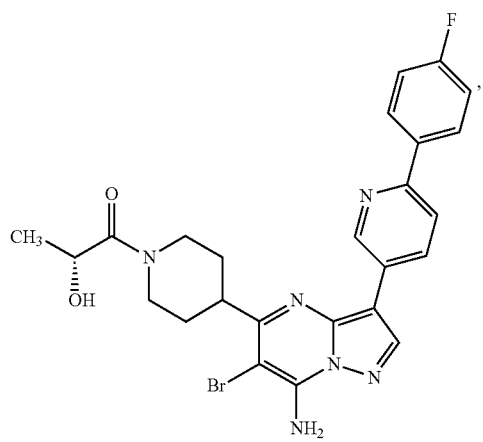
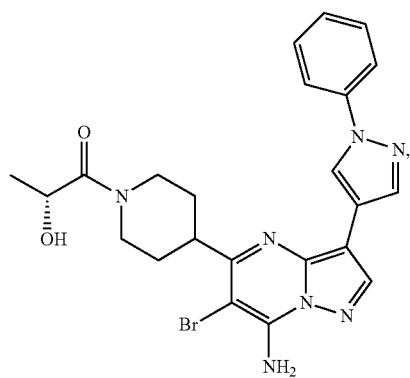
352
-continued
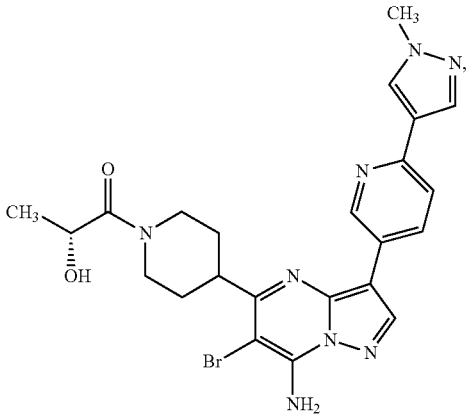
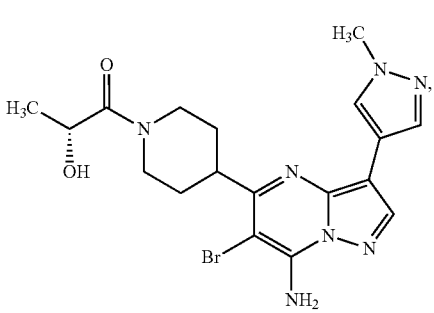
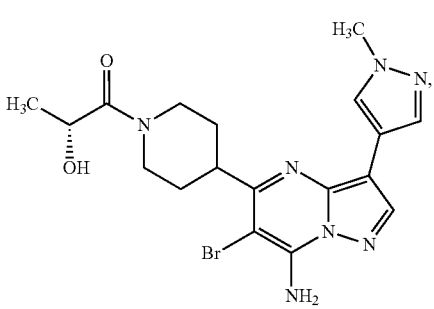
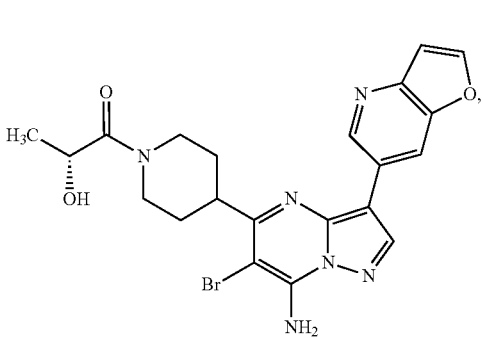
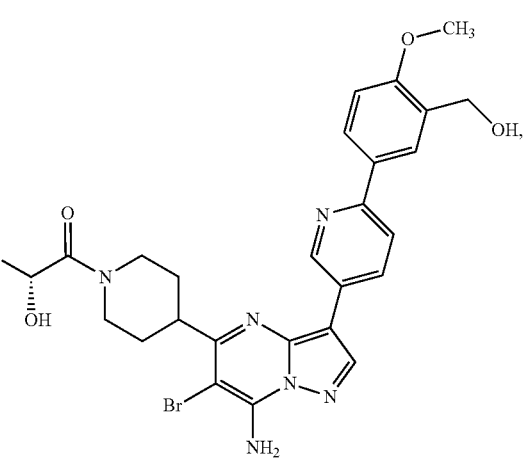

353
-continued
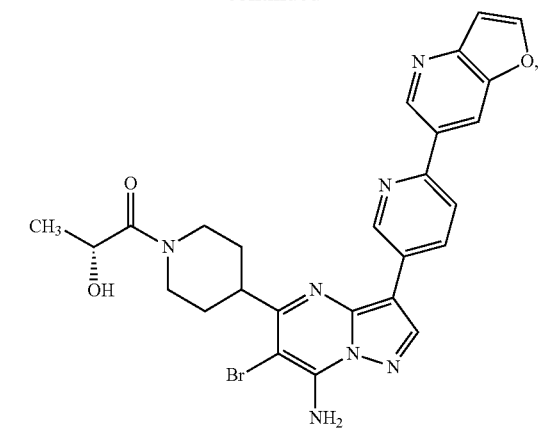 [SMILES: C[C@@H](O)C(=O)N1CCC(c2nc3c(-c4ccc(-c5cnc6c(c5)OCO6)nc4)cnn3c(N)c2Br)CC1]
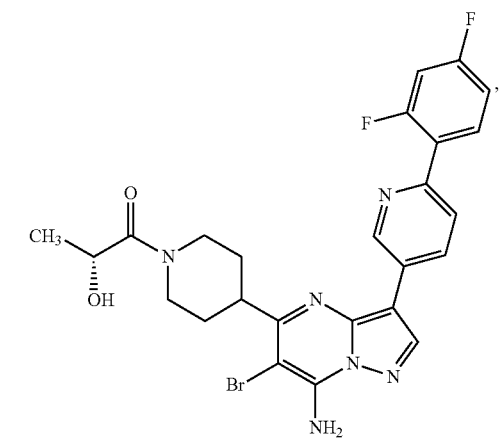

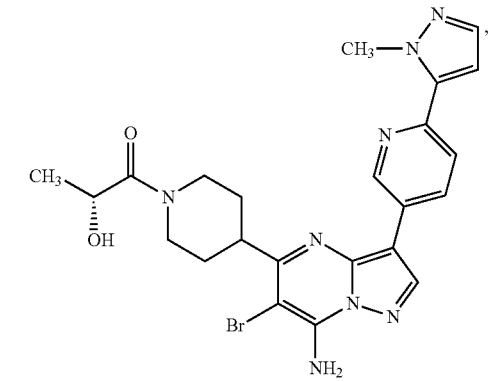
354
-continued
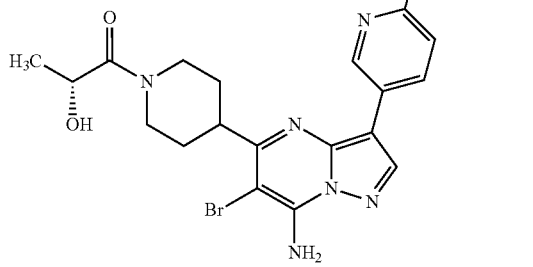
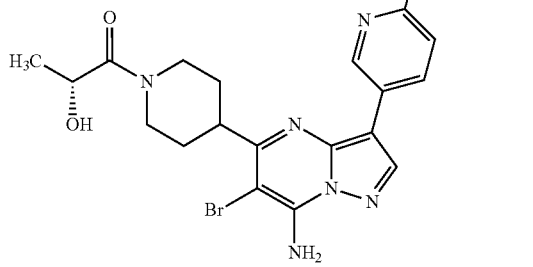
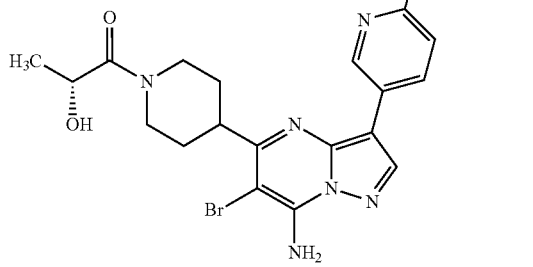
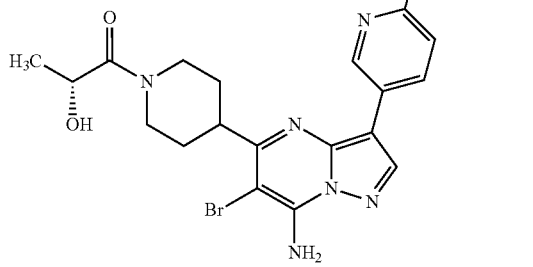

355
-continued
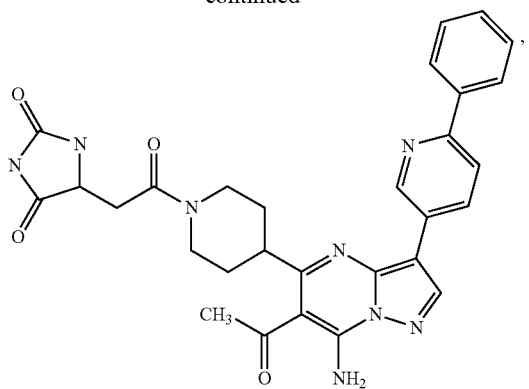
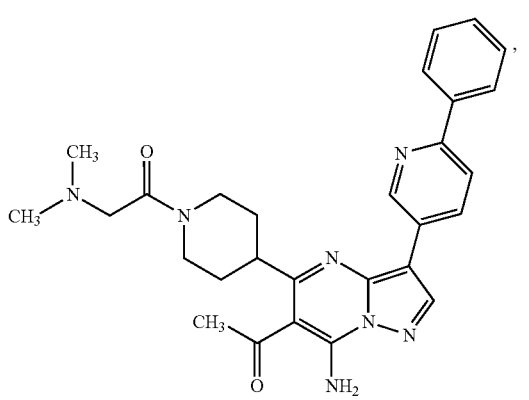
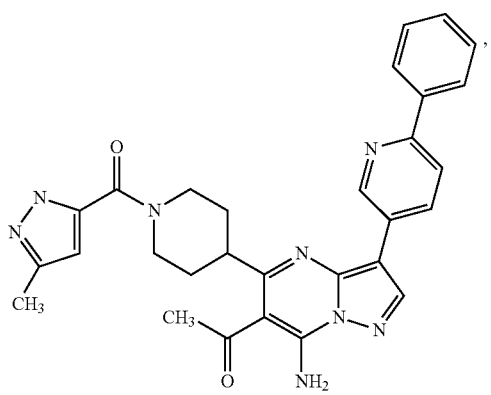
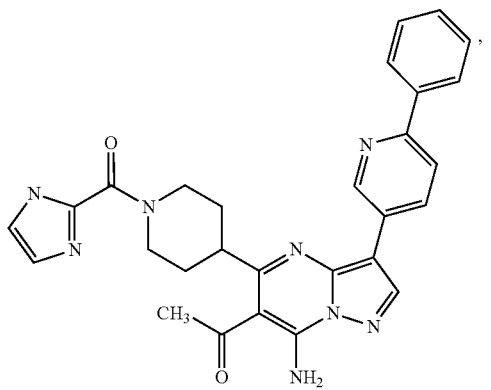
356
-continued
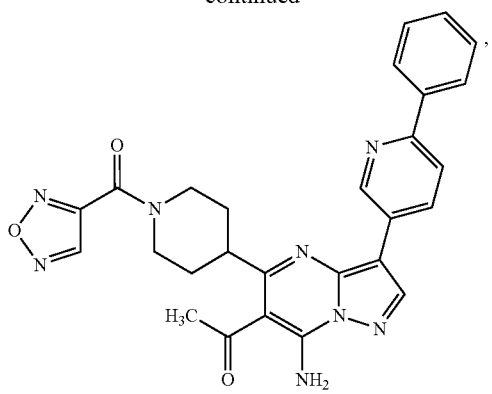
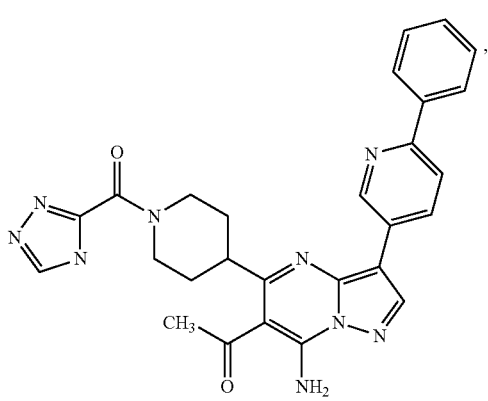
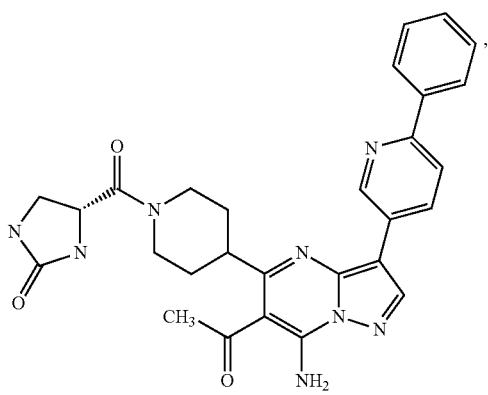
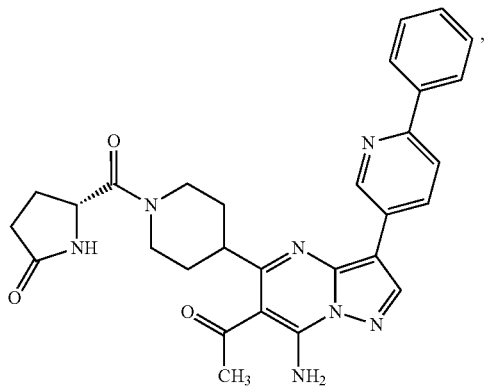

357
-continued
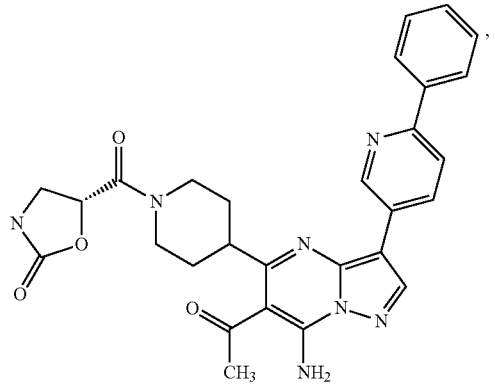
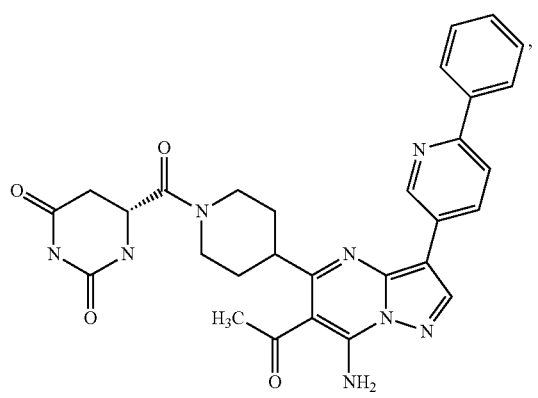
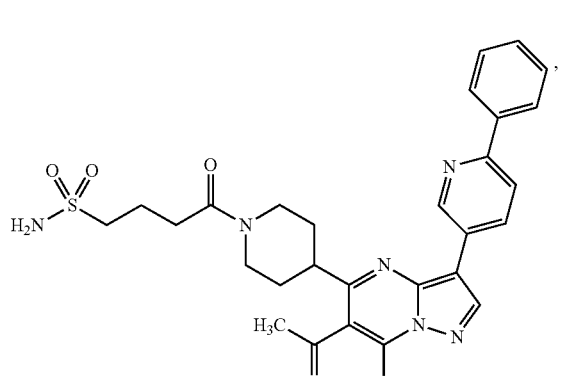
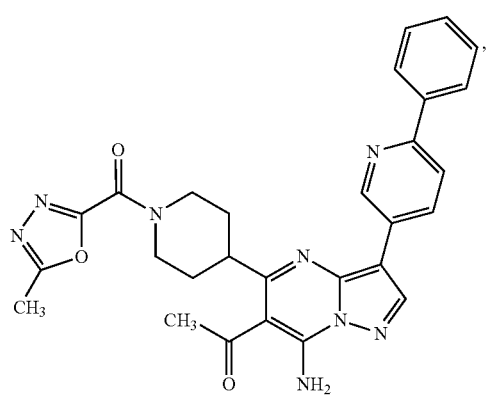
358
-continued
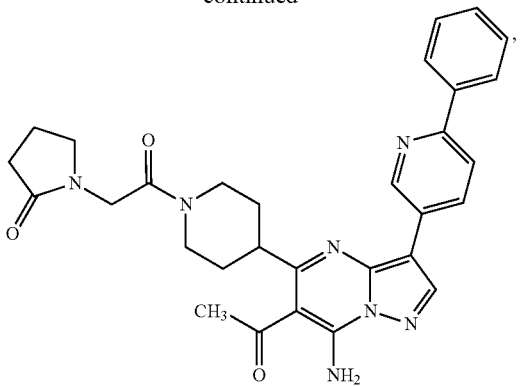
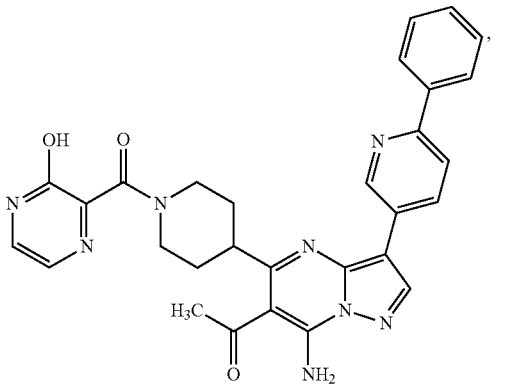
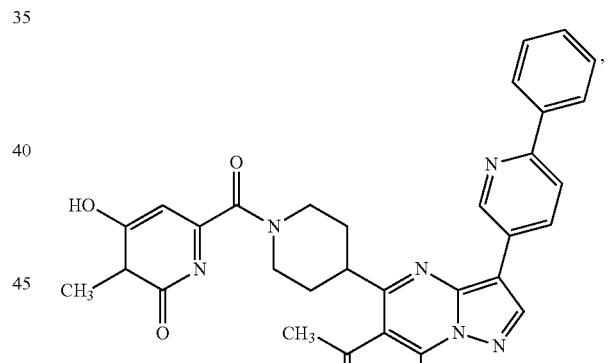
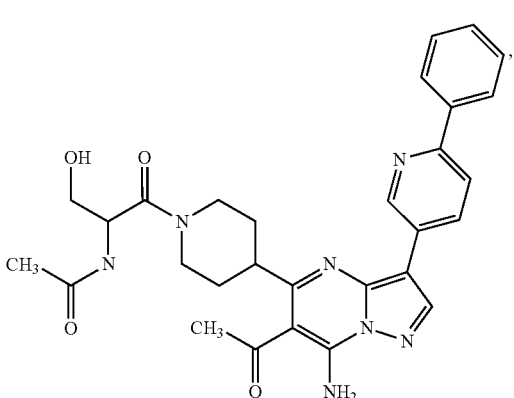

359
-continued
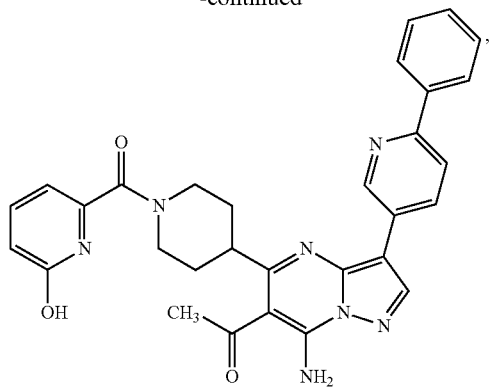
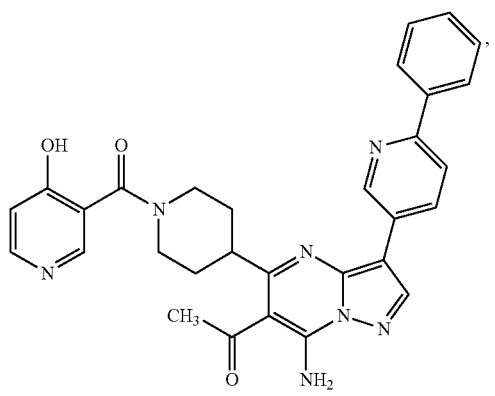
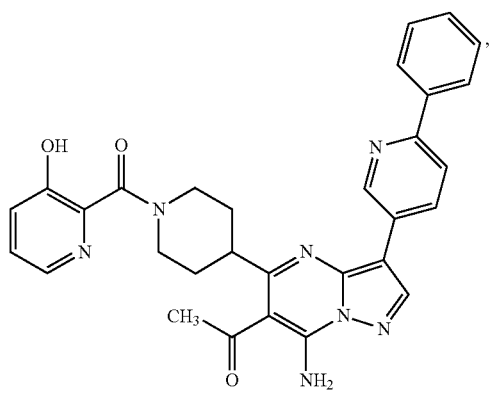
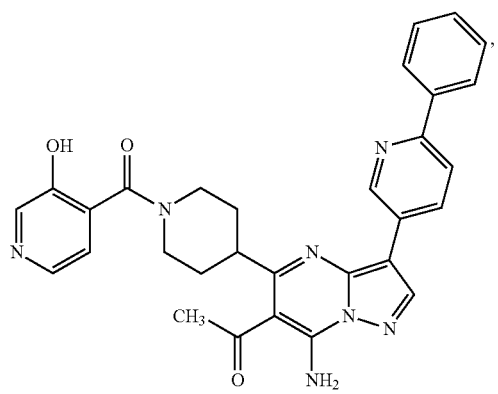
360
-continued
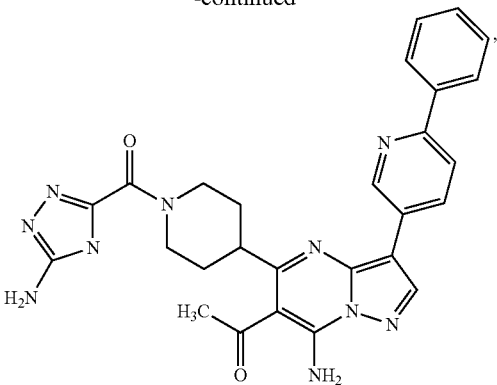
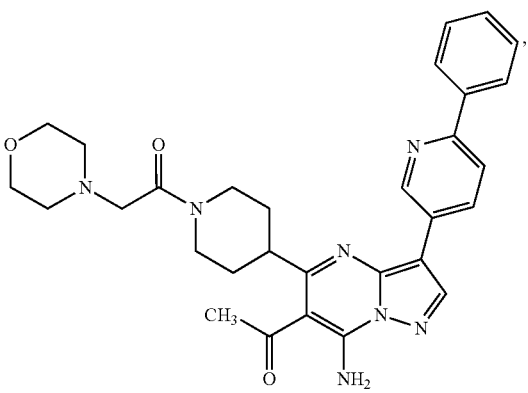
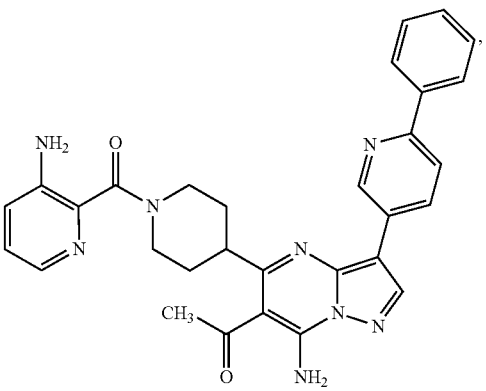
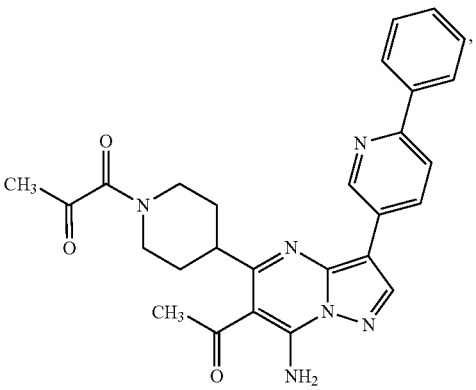

361
-continued
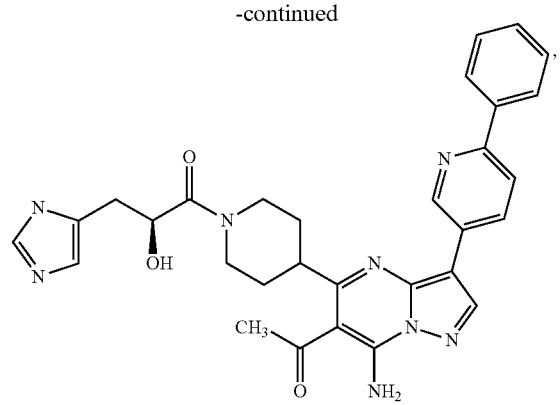
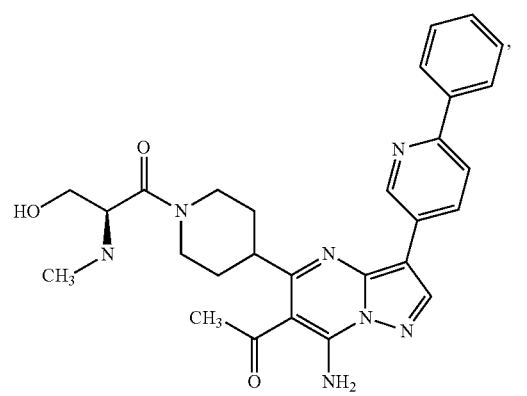
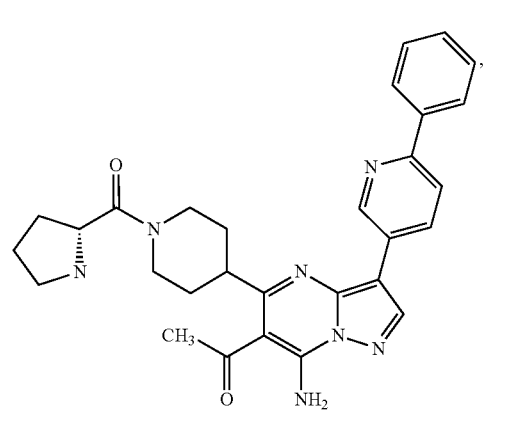
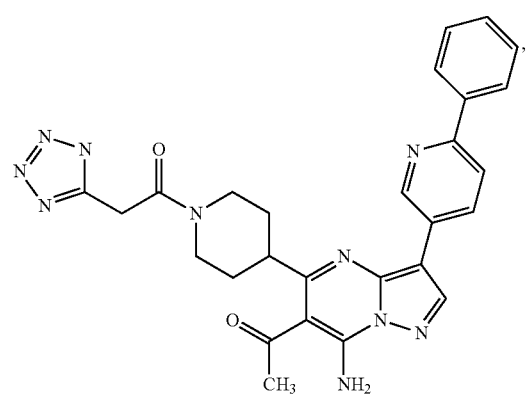
362
-continued
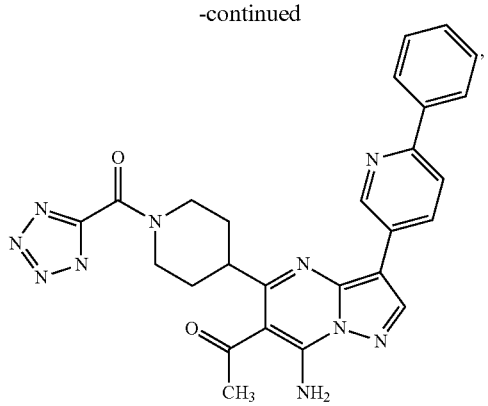
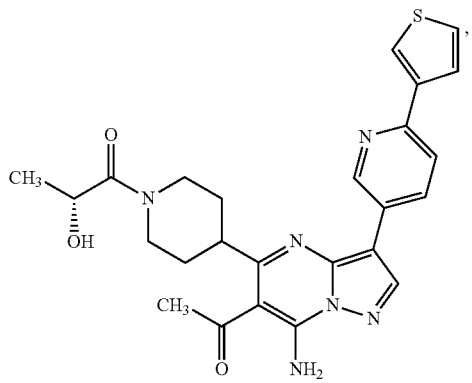
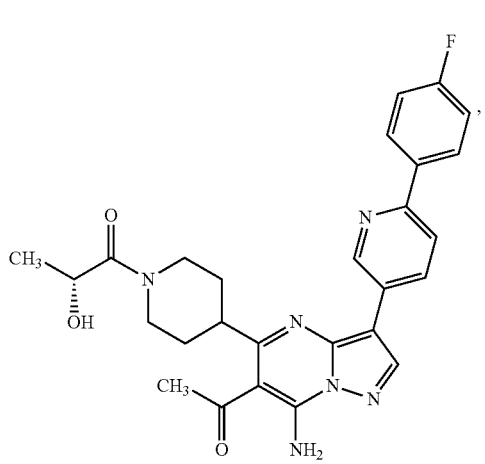
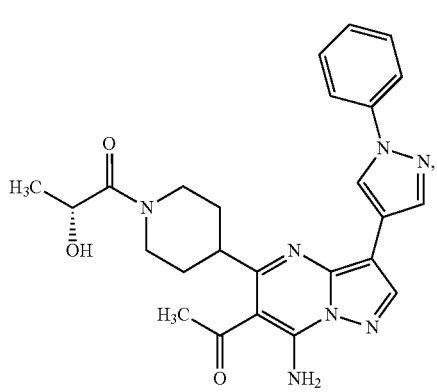

-continued
363
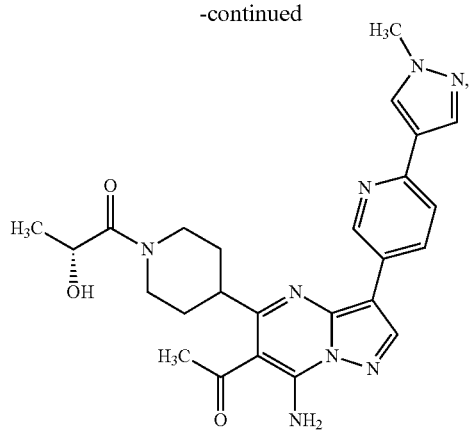
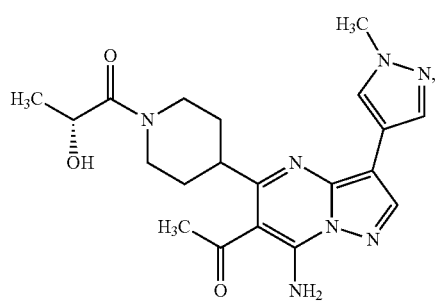
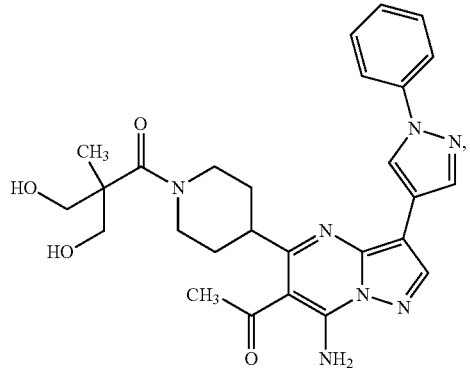
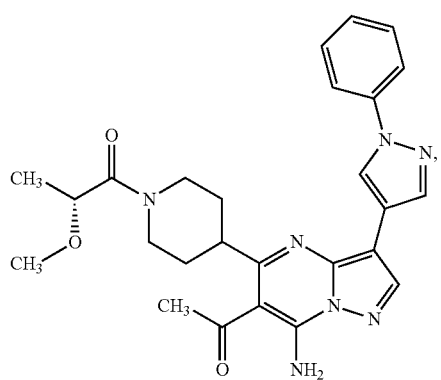
364
-continued
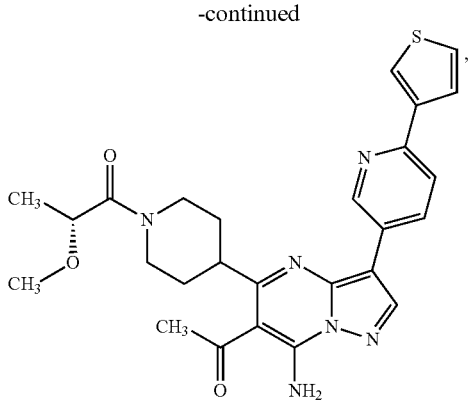
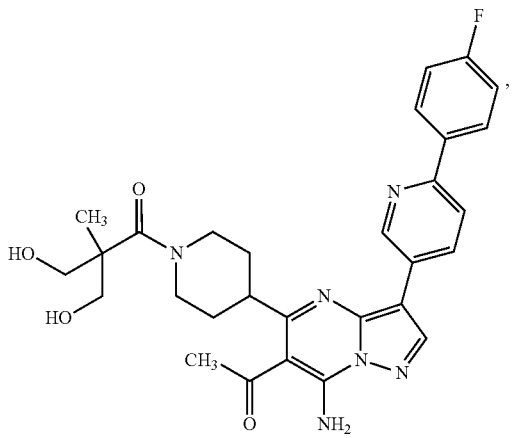
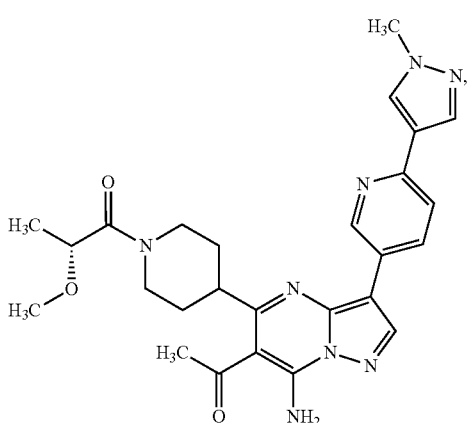
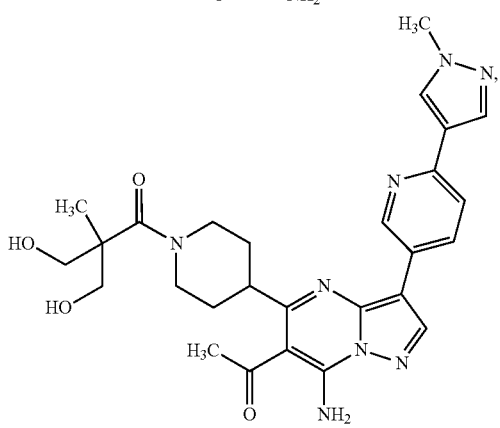

365
-continued
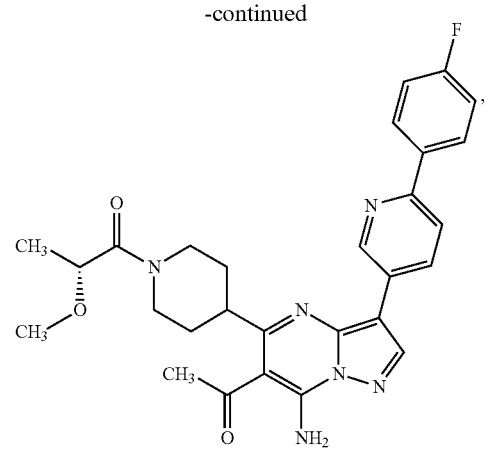
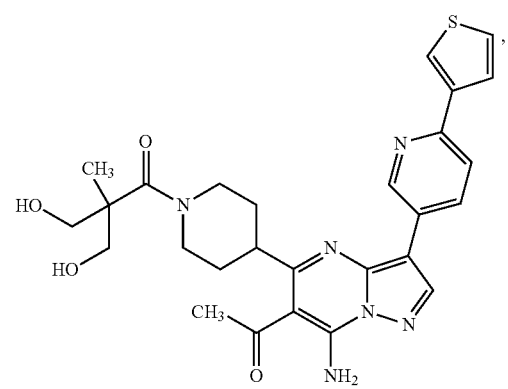
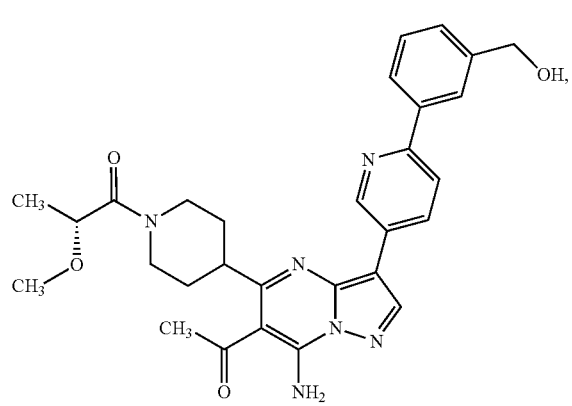
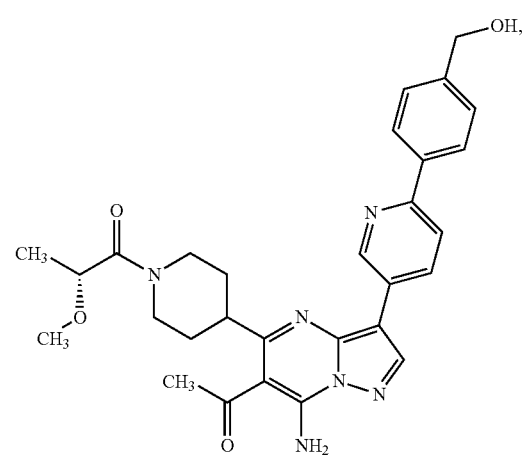
366
-continued
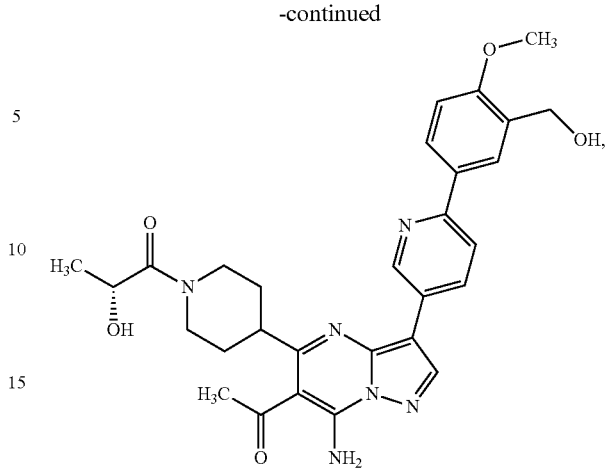
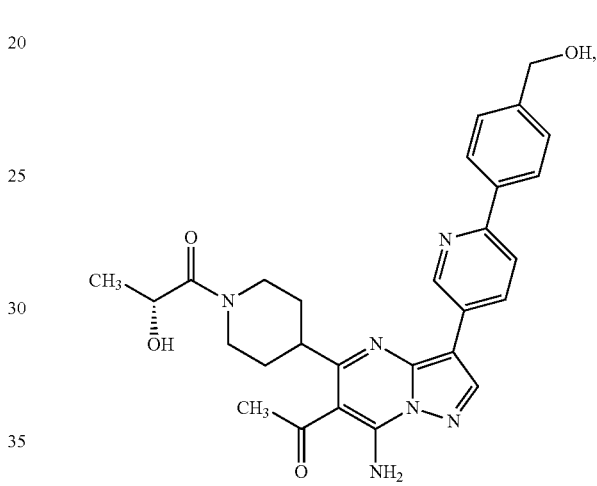
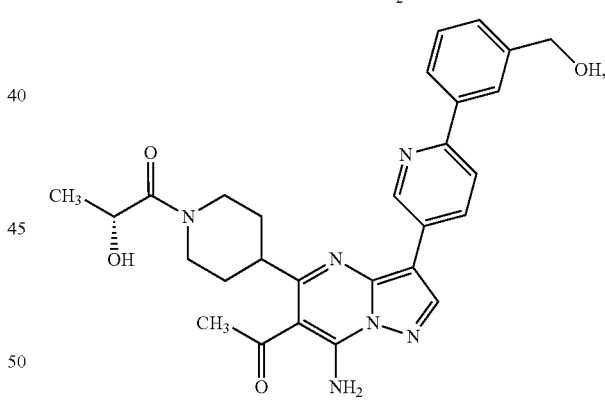
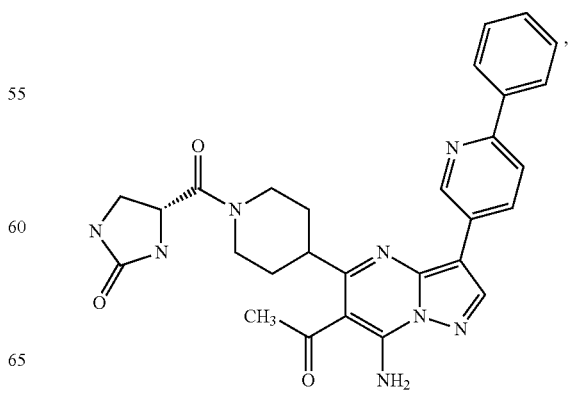

367
-continued
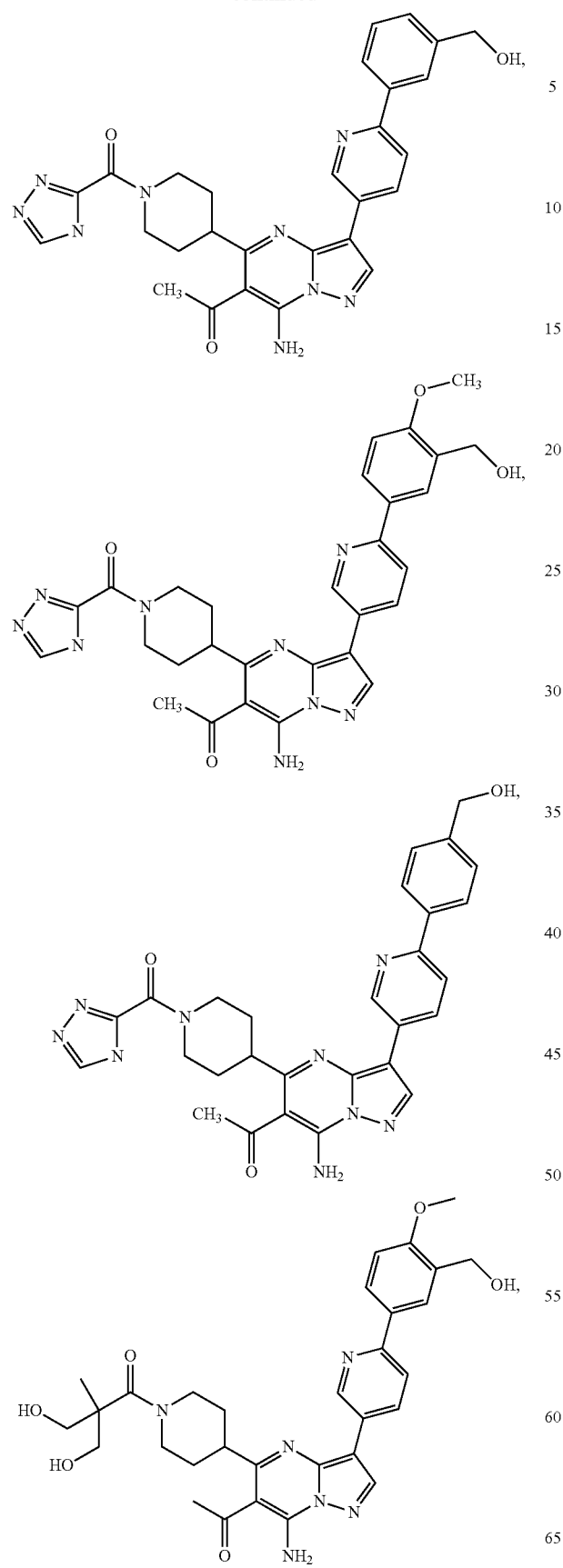
368
-continued
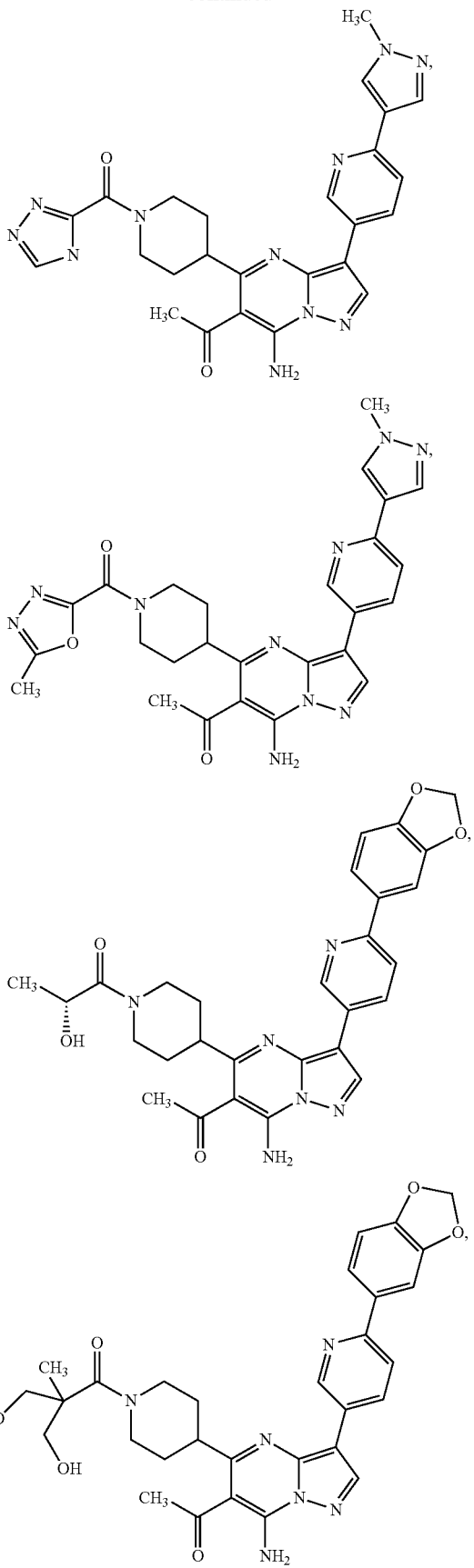

369
-continued
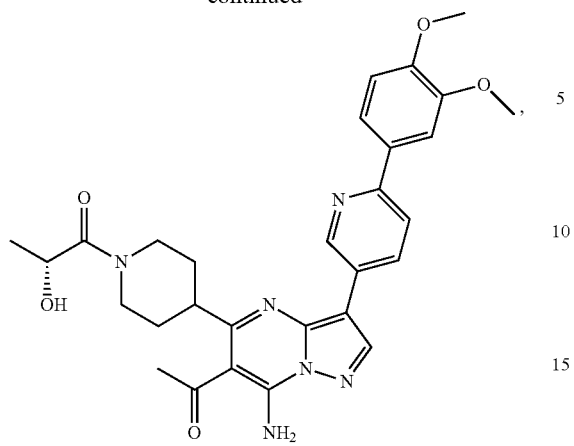
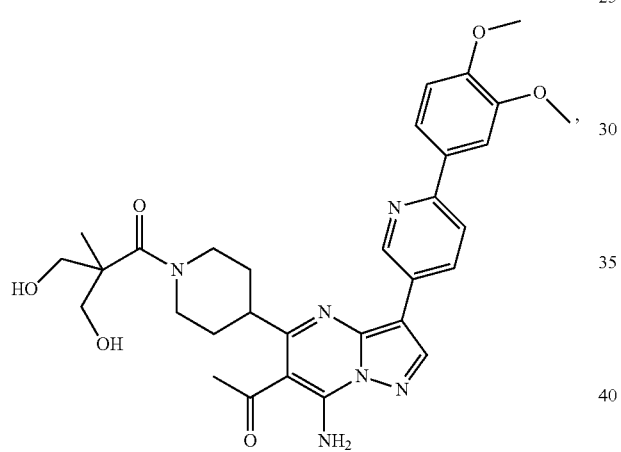
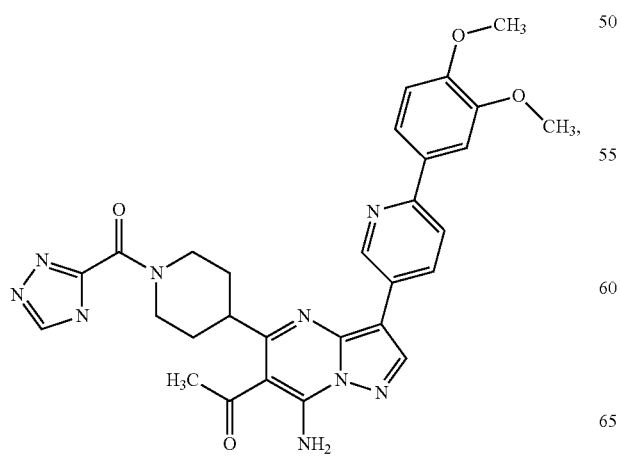
370
-continued
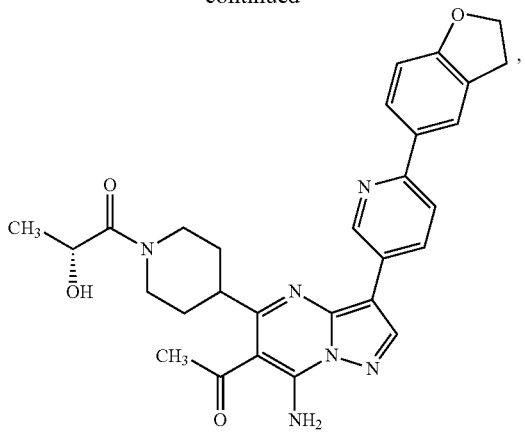
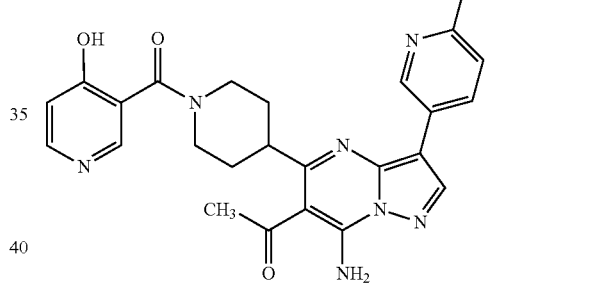
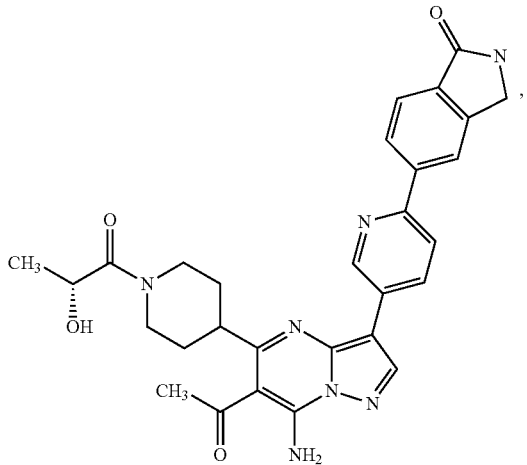

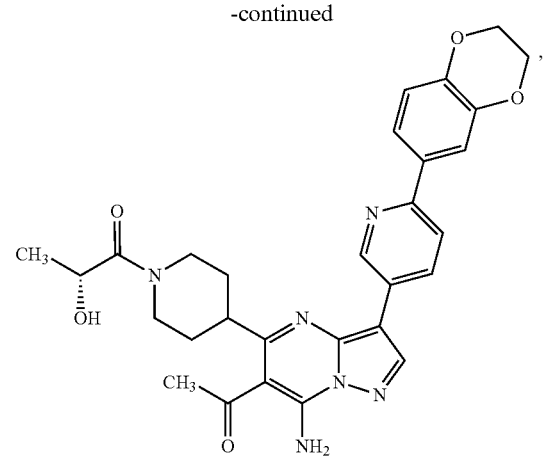
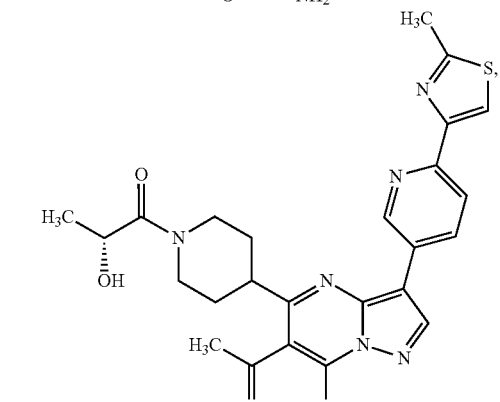
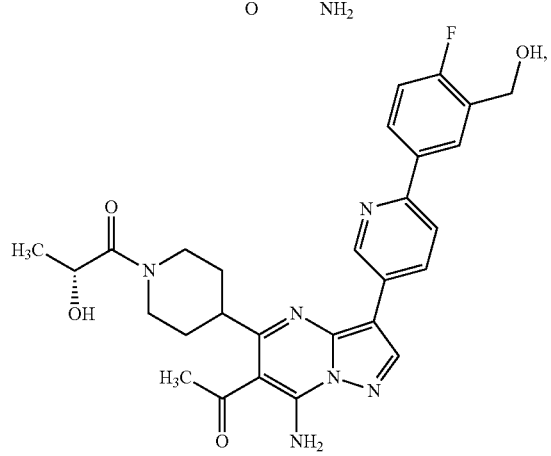
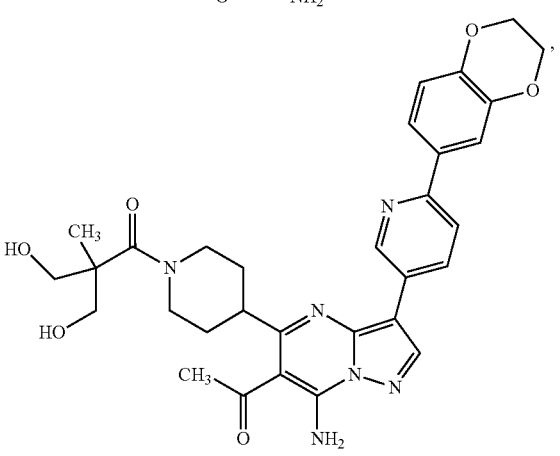

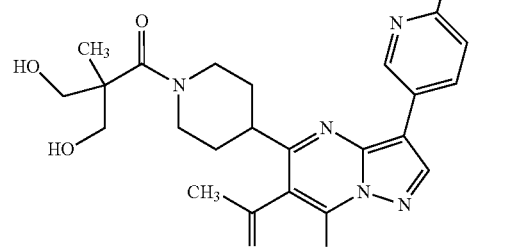

373
-continued
374
-continued
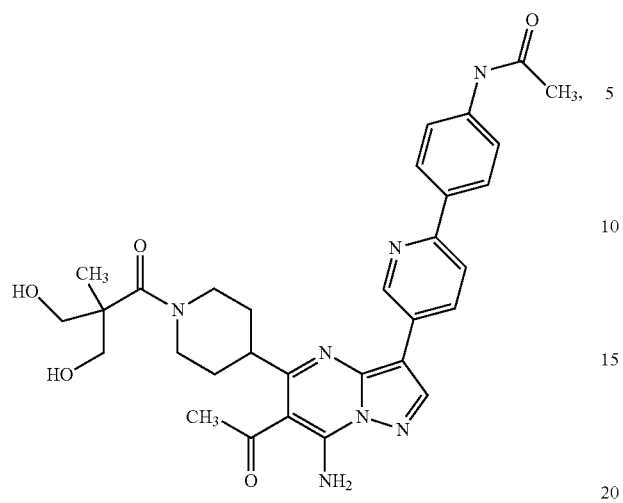
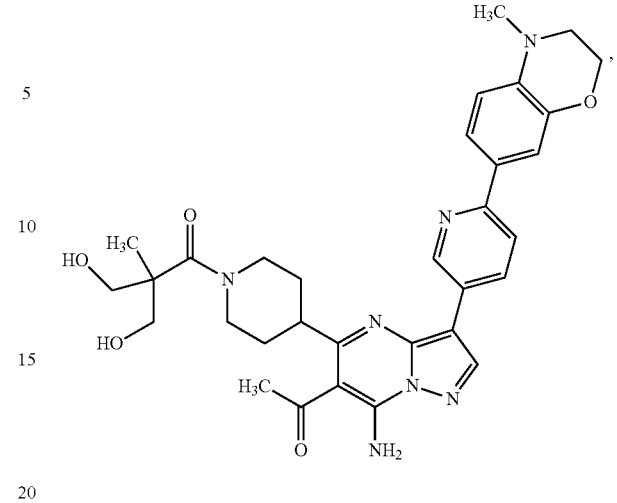
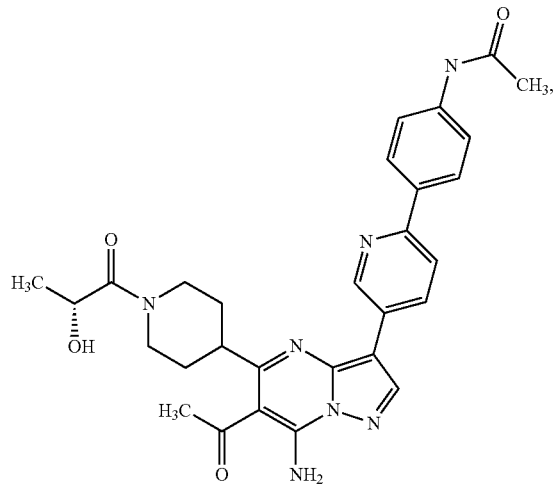
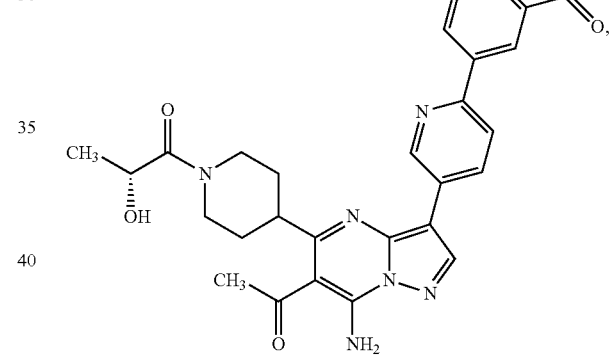
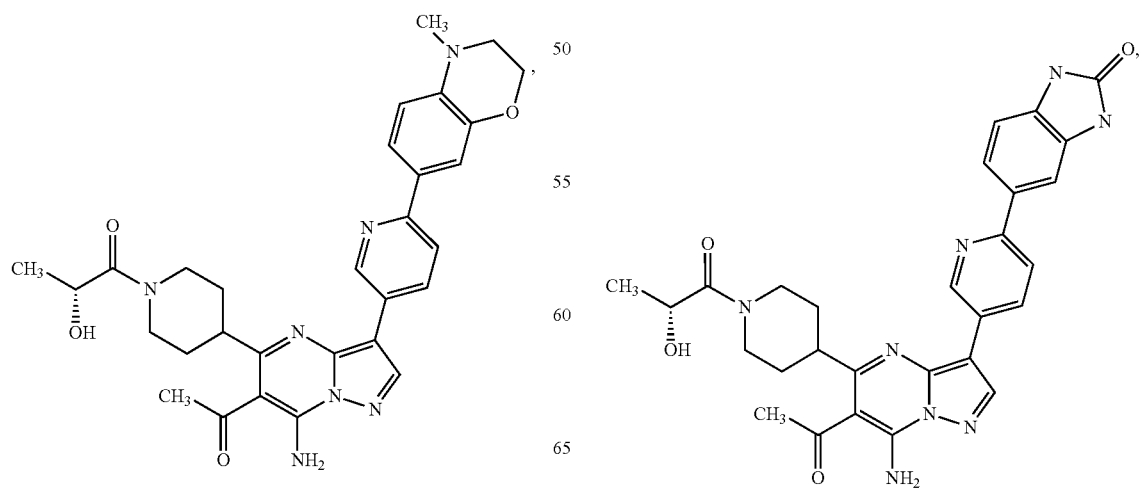

375
-continued
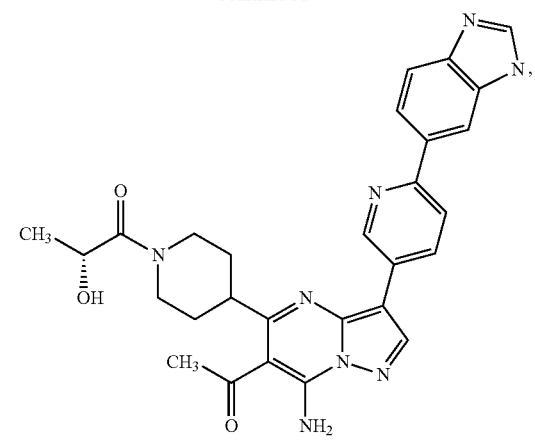

376
-continued
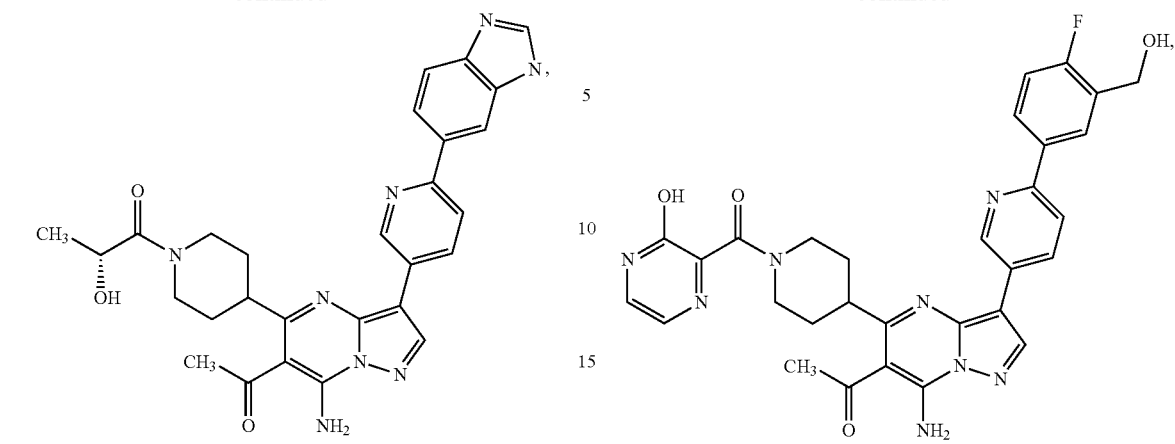
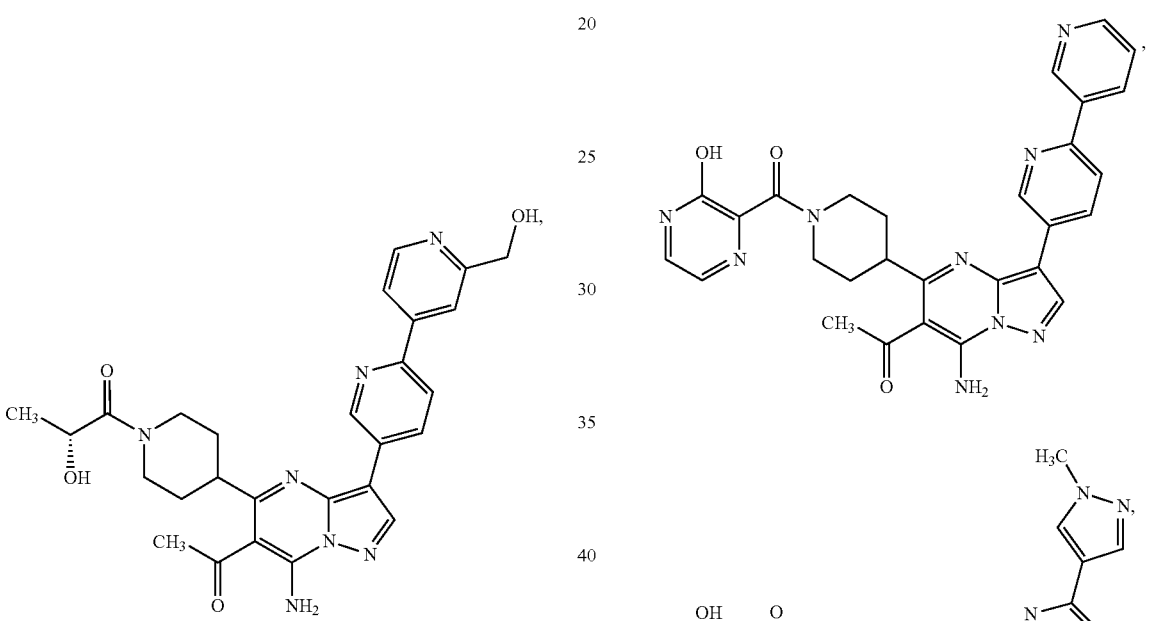
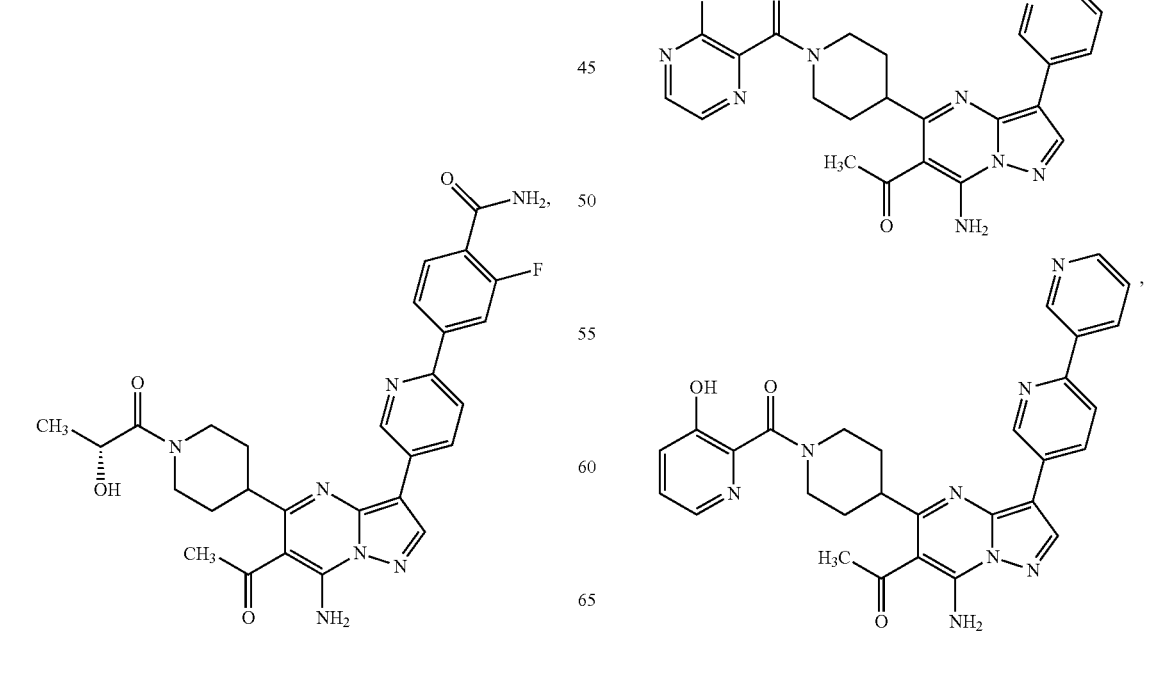

377
-continued
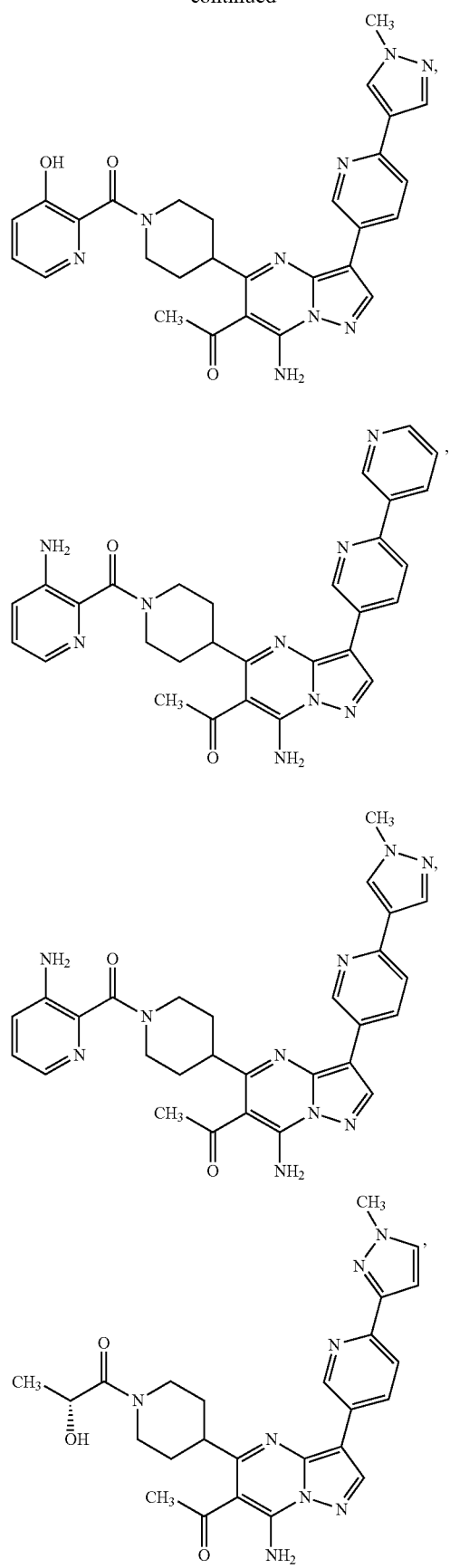
378
-continued
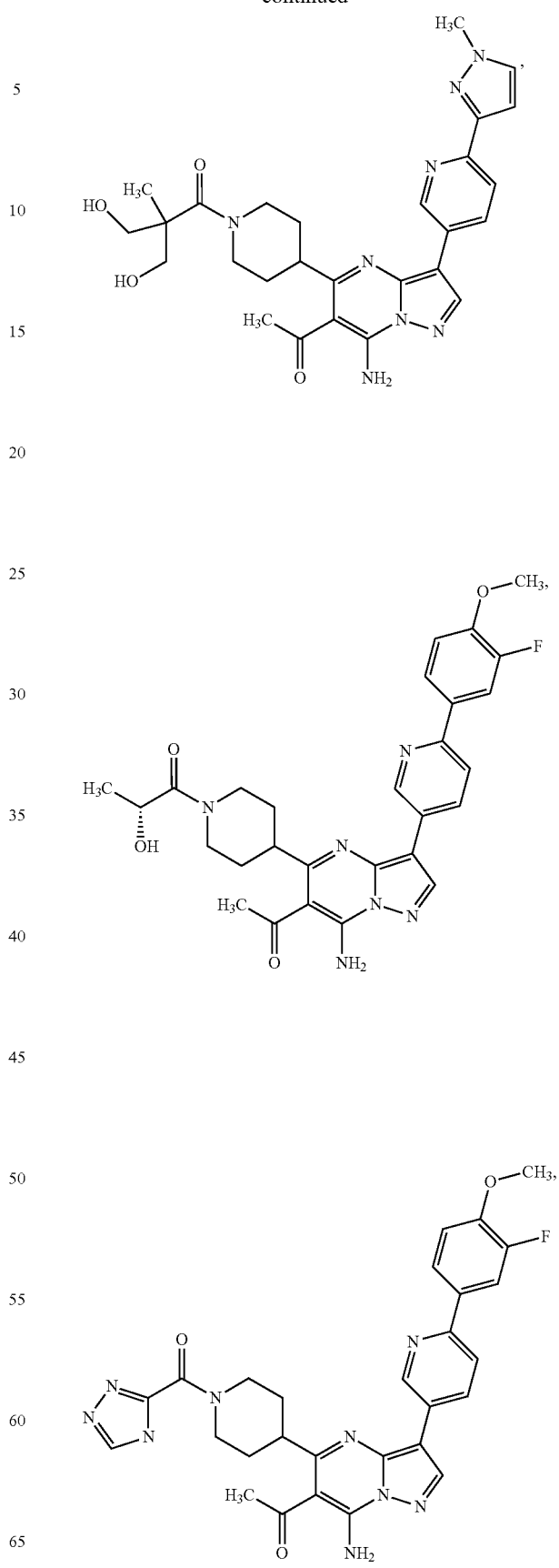

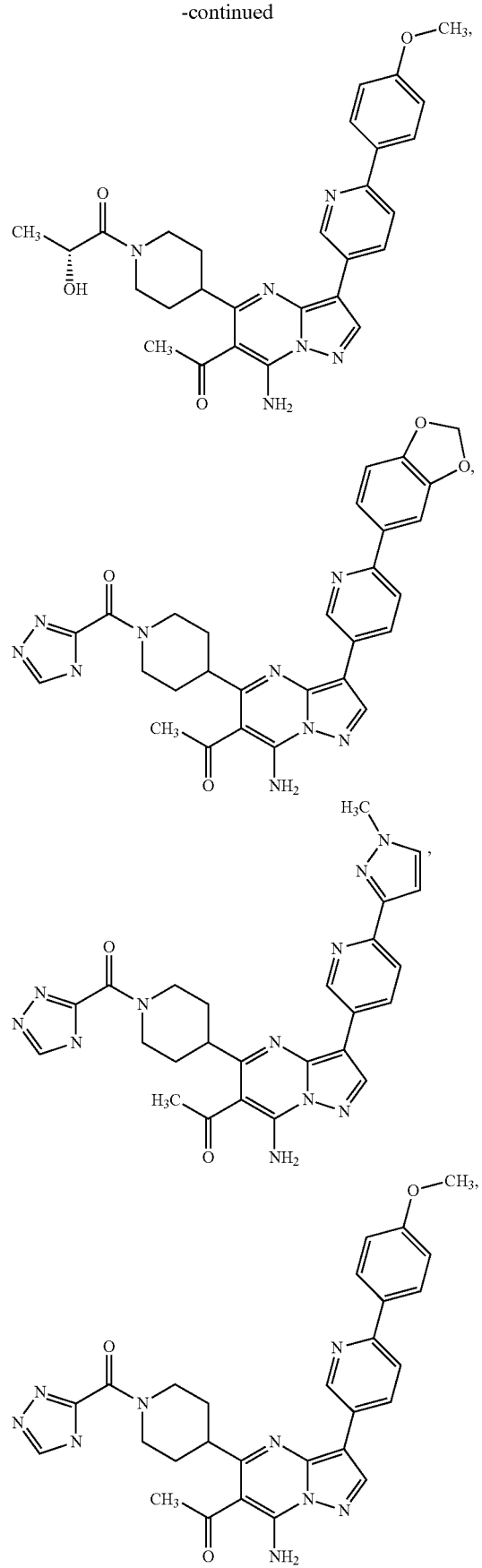
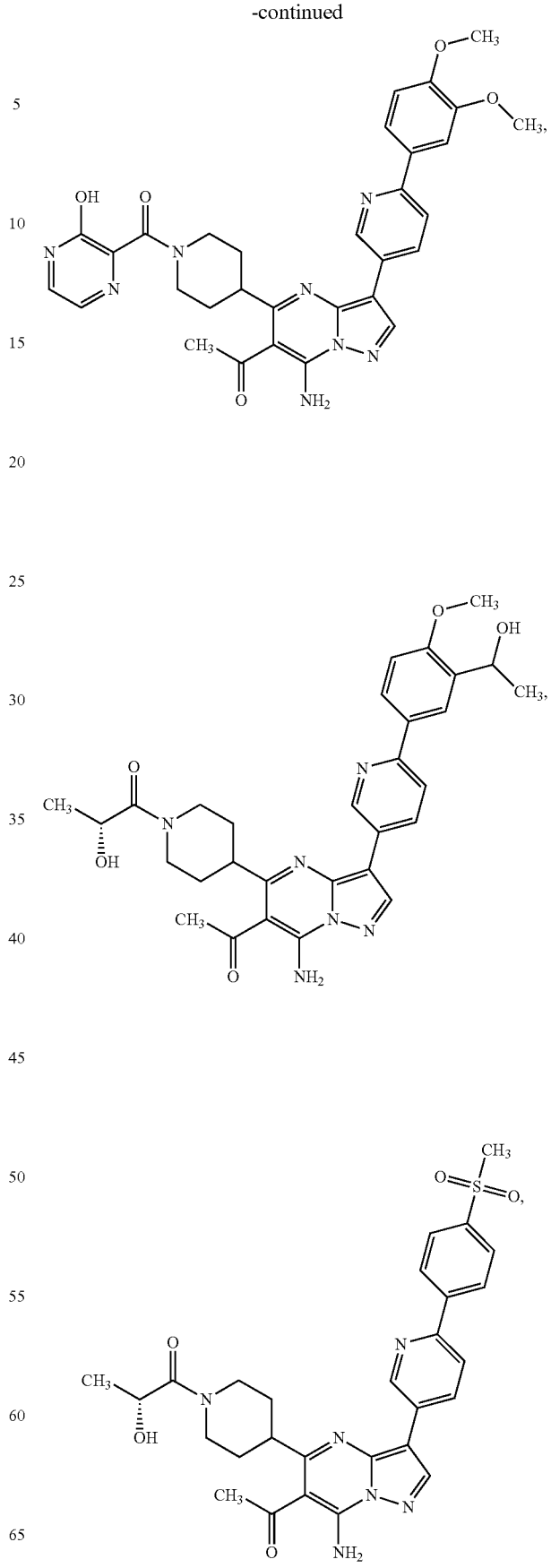

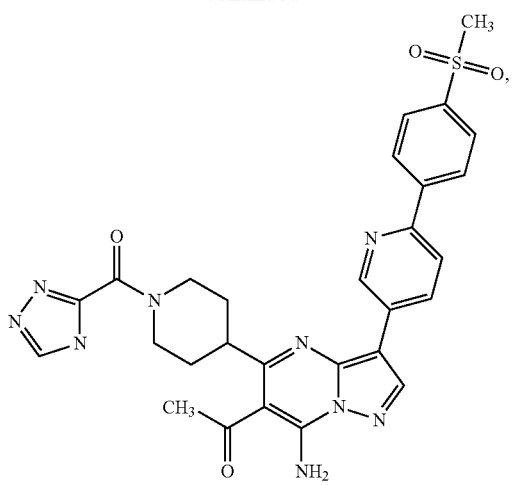
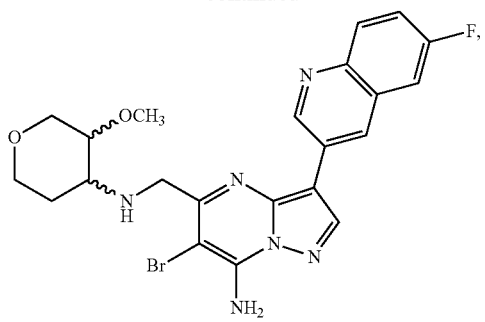

383
-continued
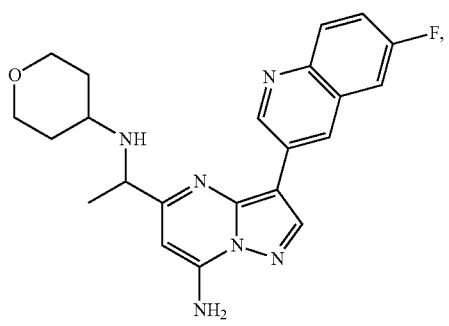
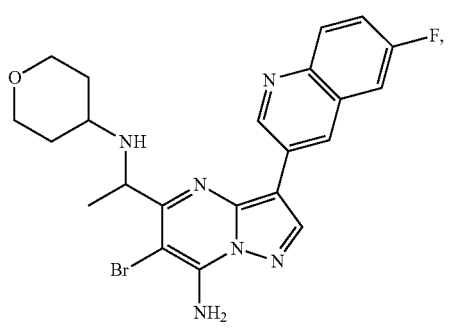
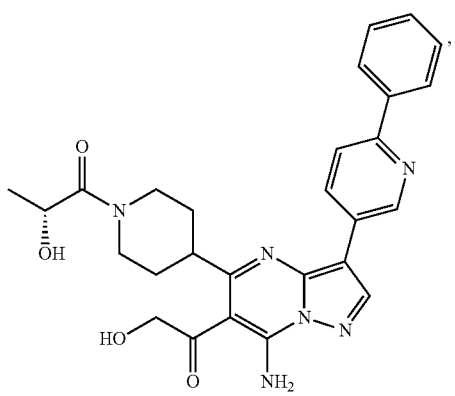
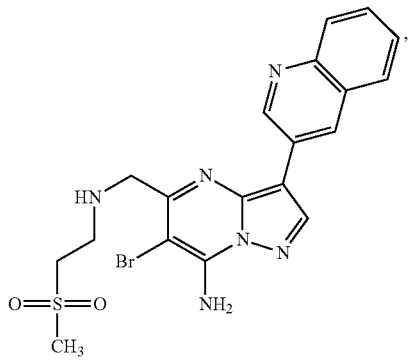
384
-continued
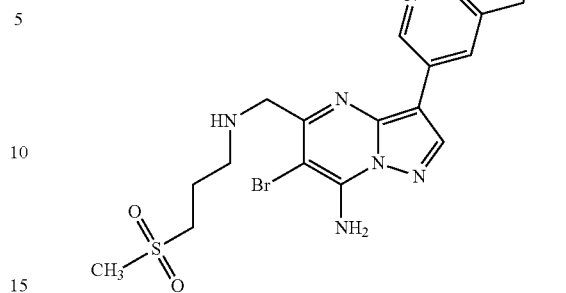
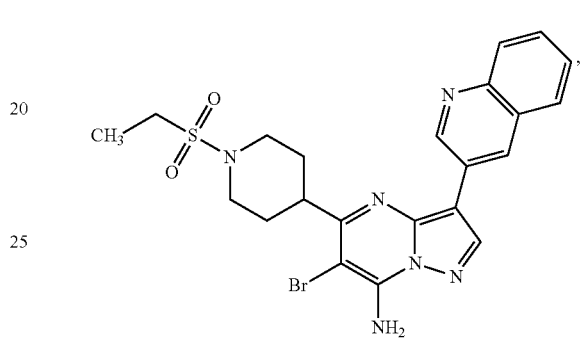
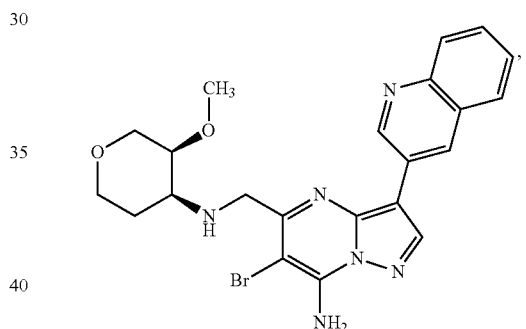
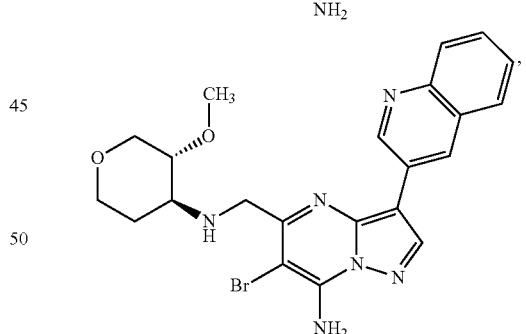
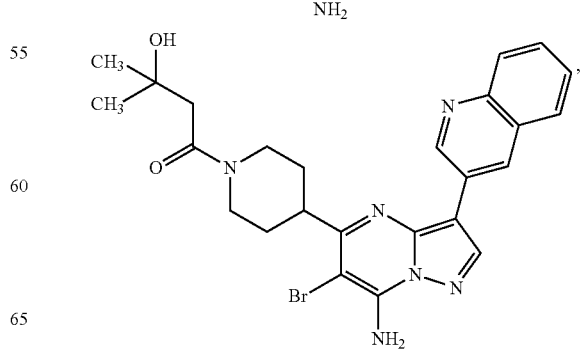

385
-continued
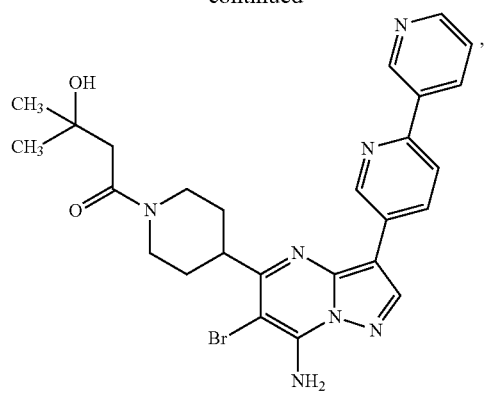
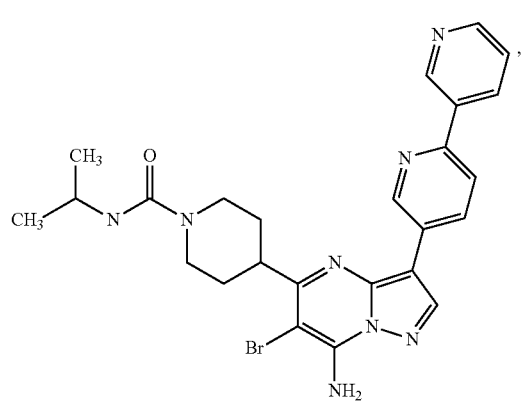
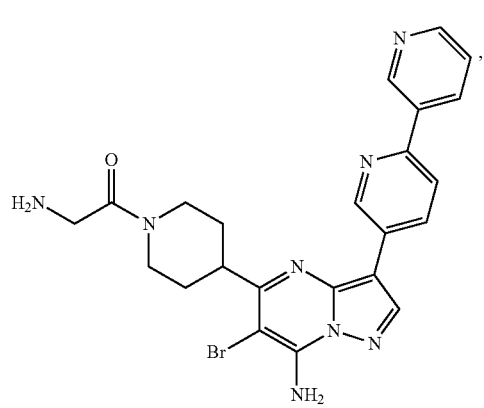
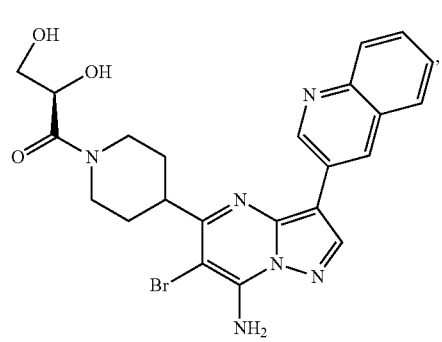
386
-continued
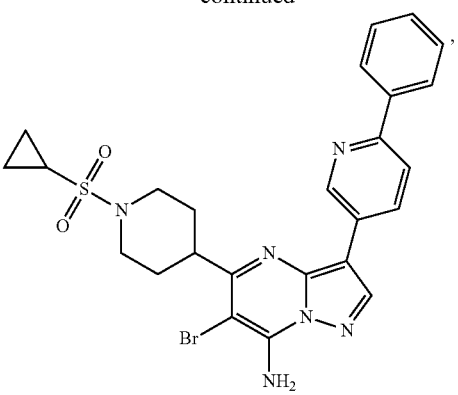
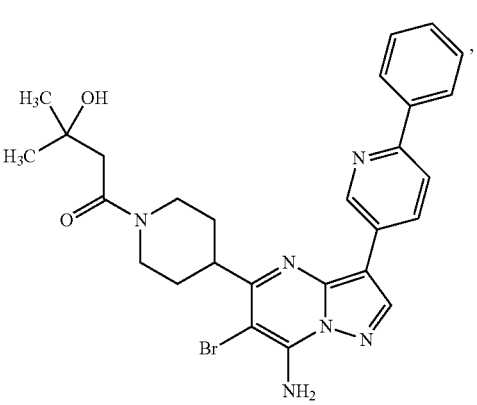
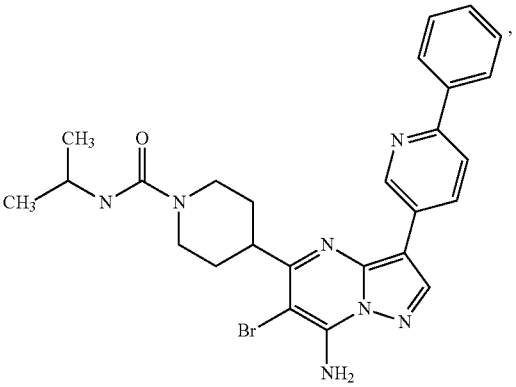
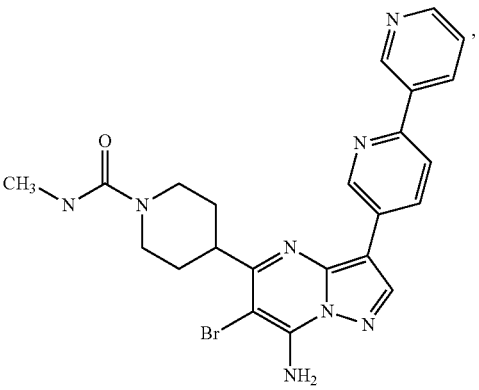

387
-continued
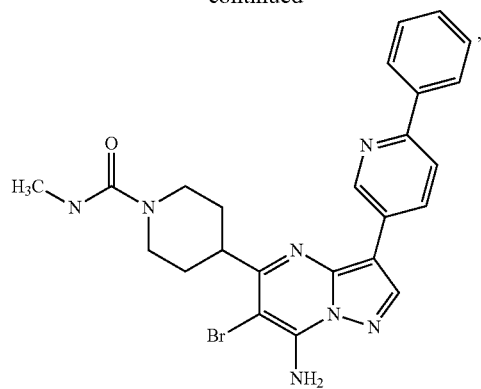
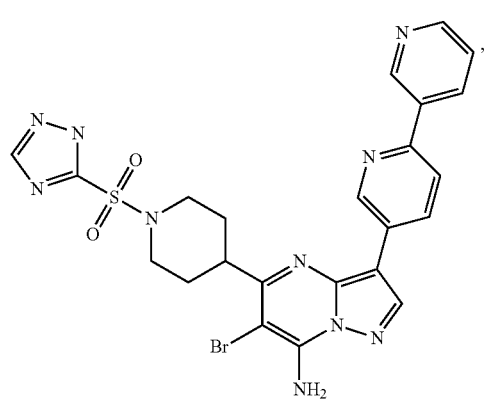
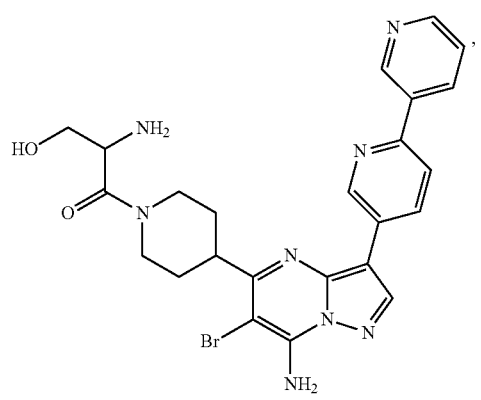
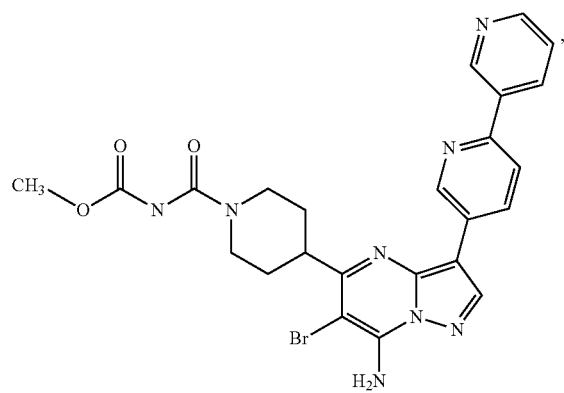
388
-continued
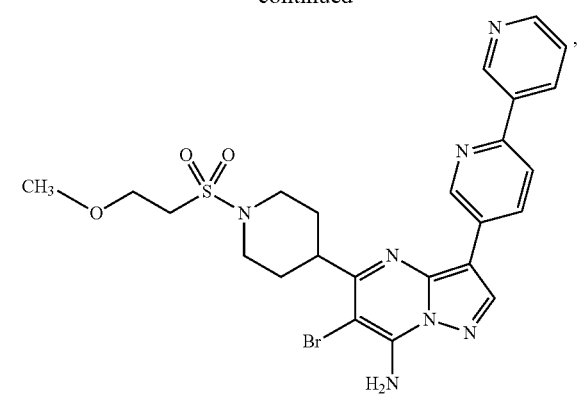
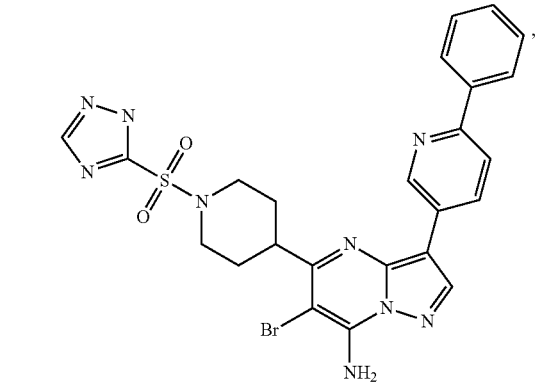
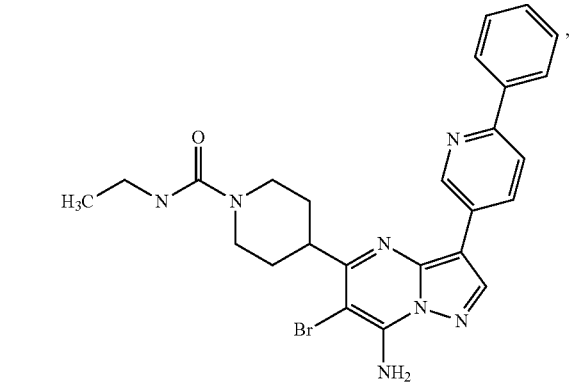
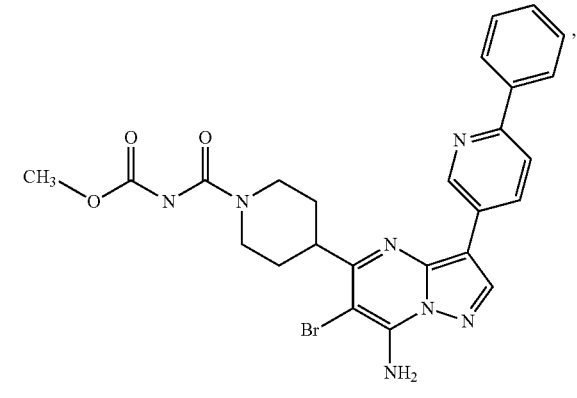

389
-continued
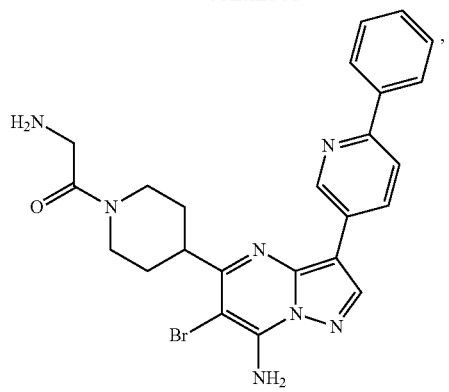
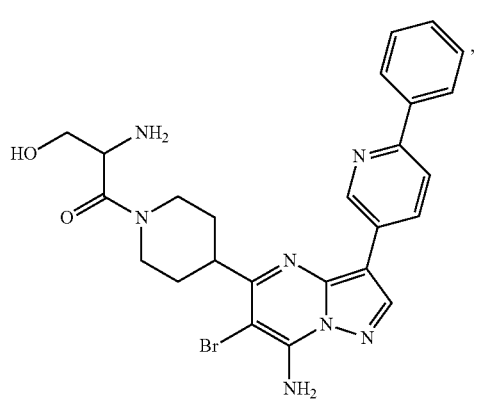
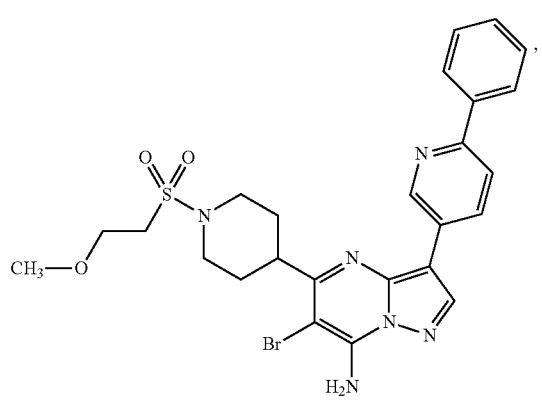
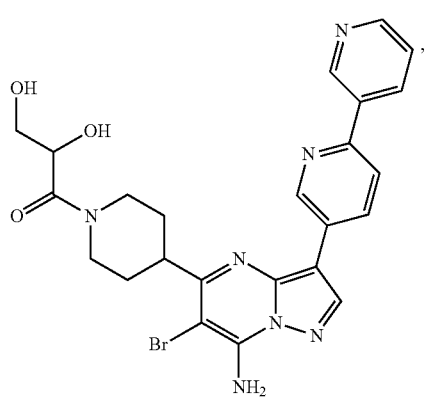
390
-continued
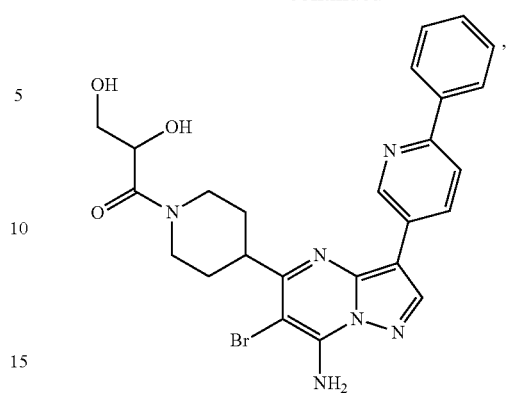
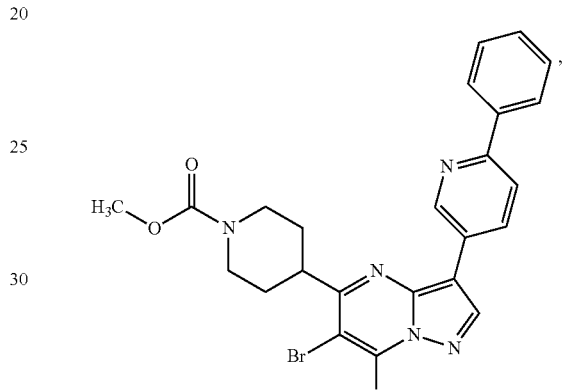
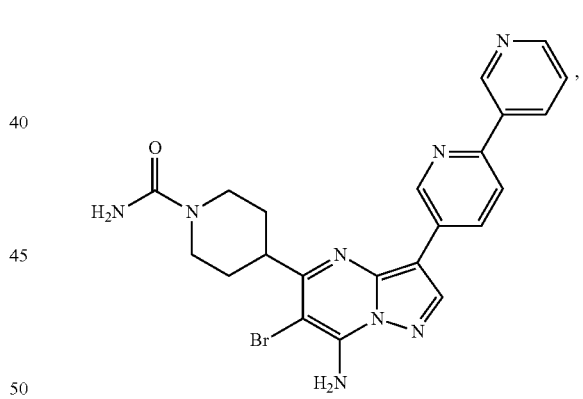
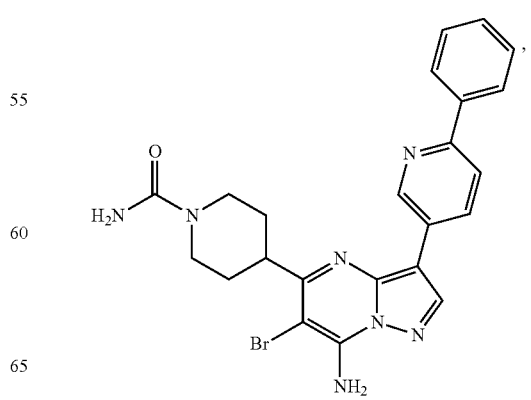

391
-continued
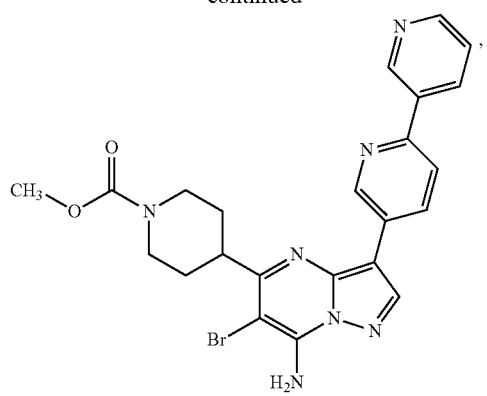
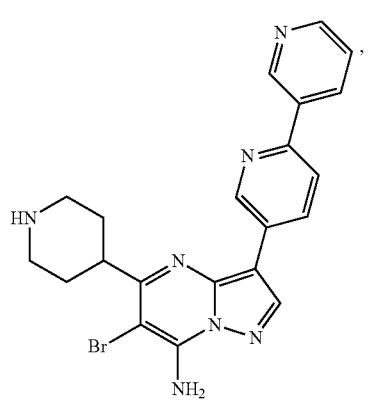
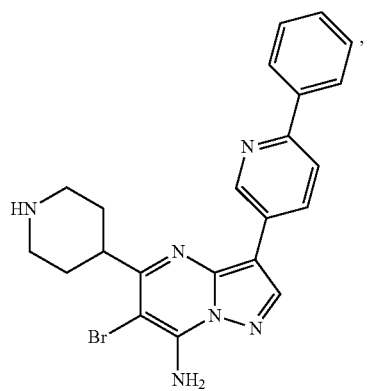
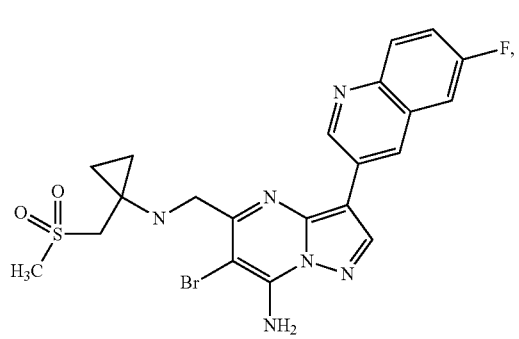
392
-continued
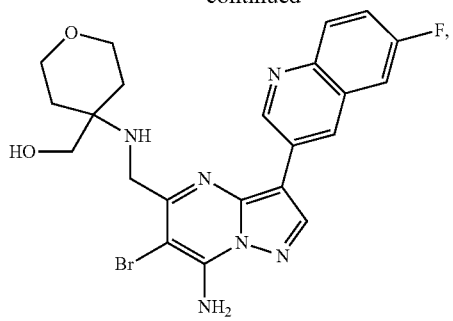
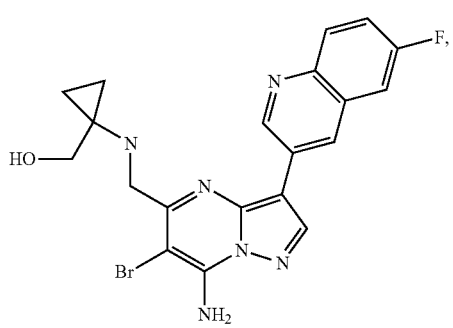
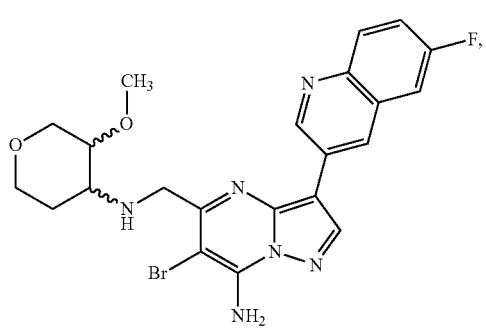
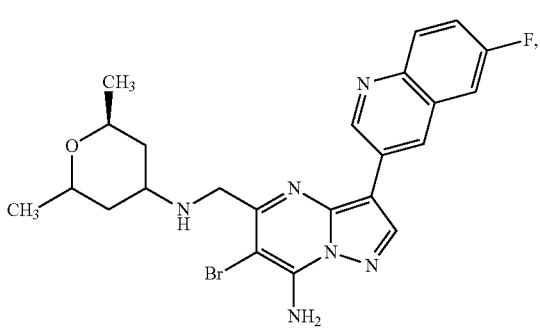
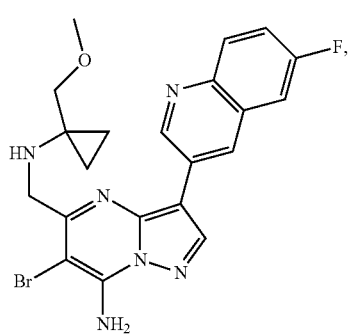

393
-continued
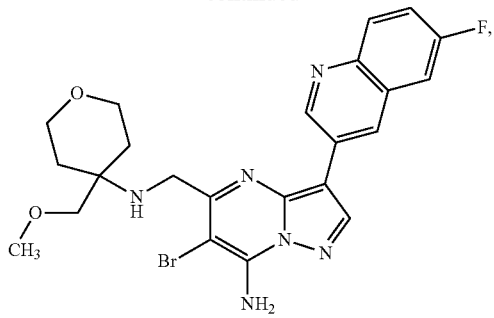
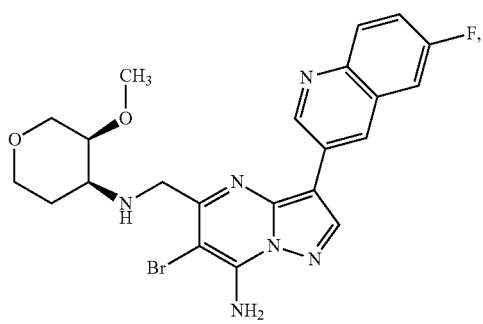
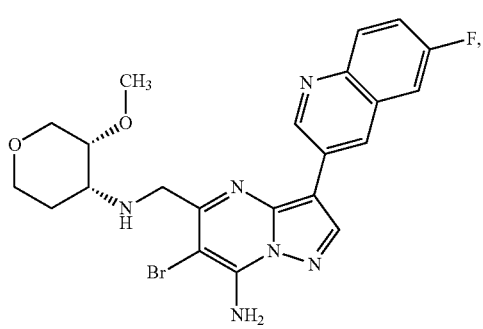
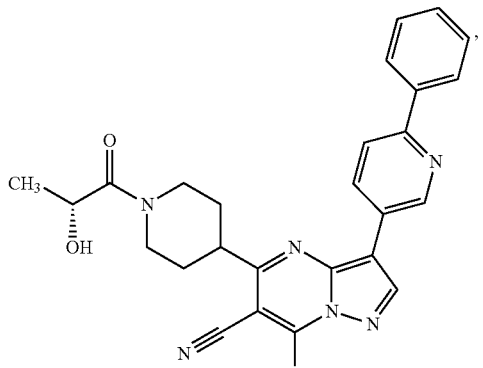
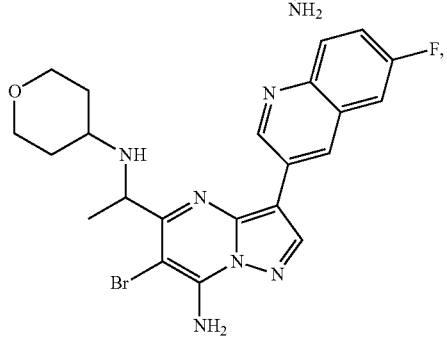
394
-continued
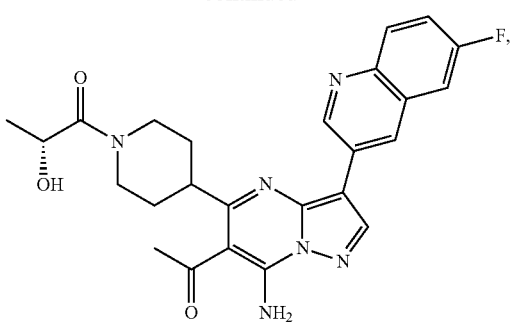
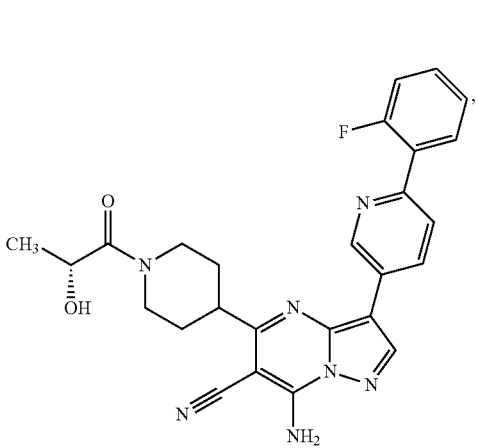
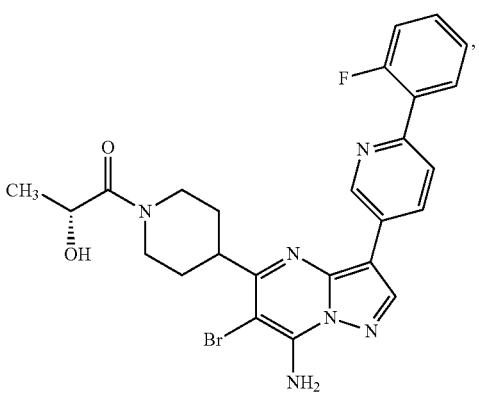
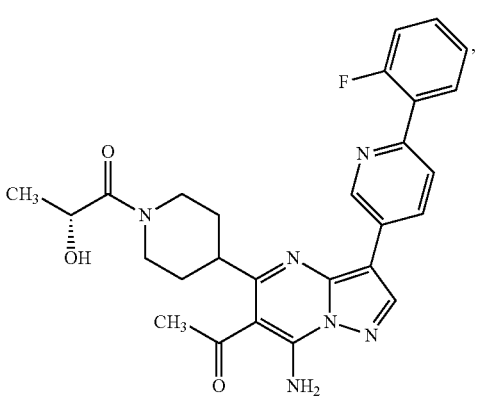

395
-continued
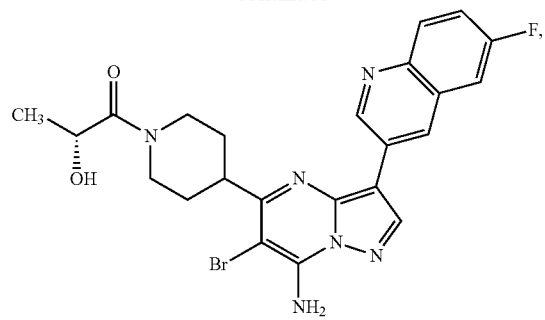
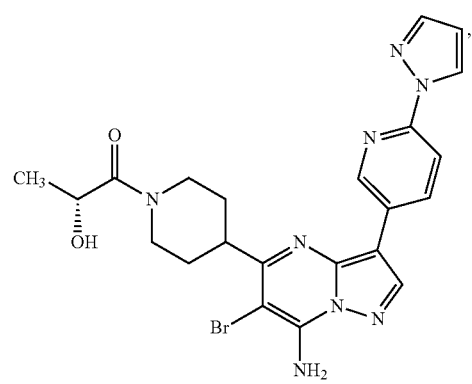
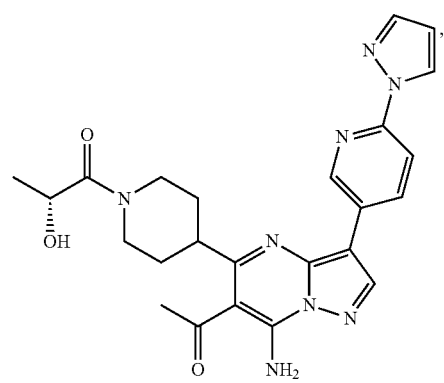
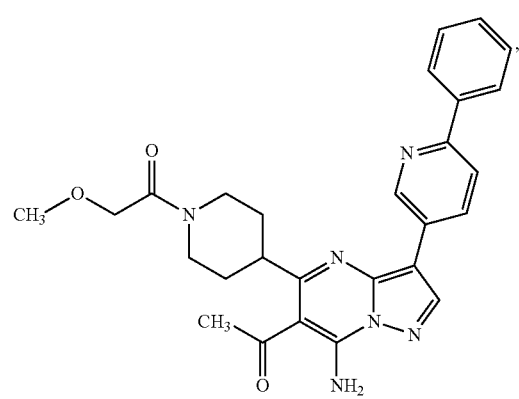
396
-continued
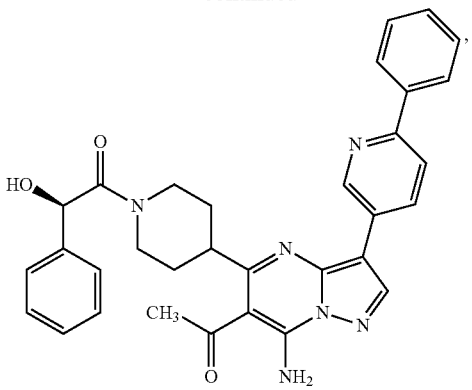
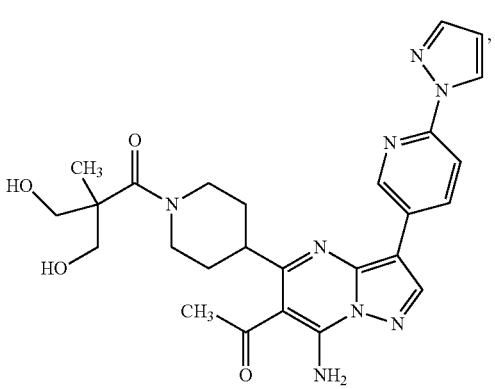
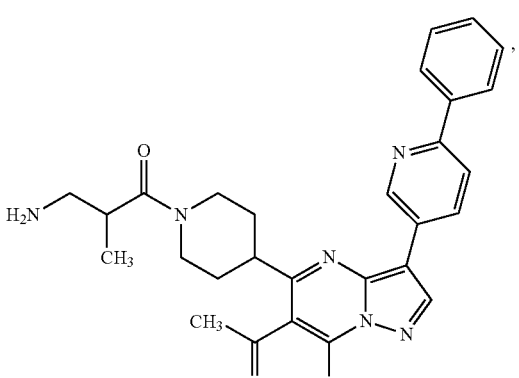
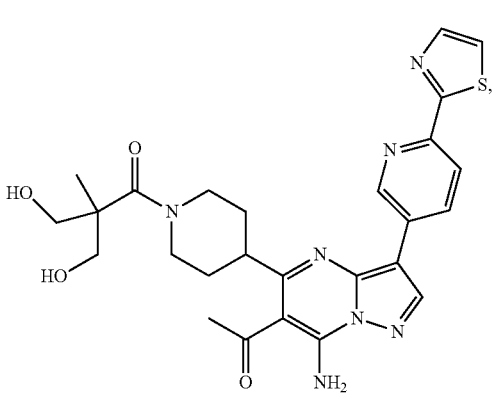

397
-continued
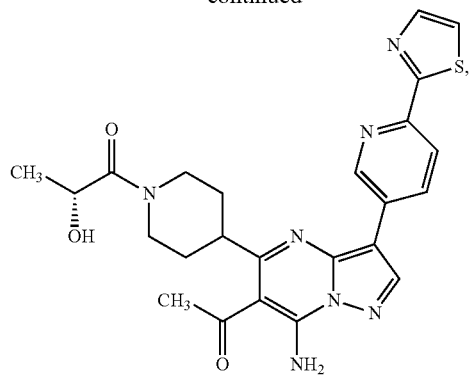
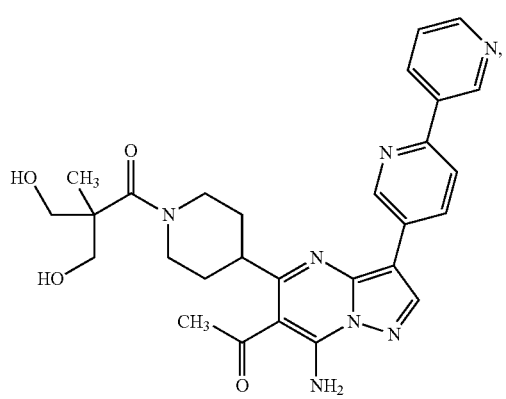
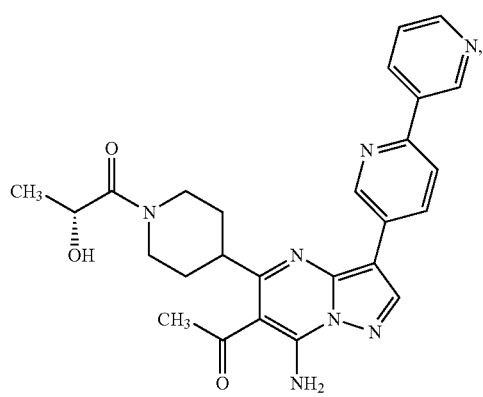
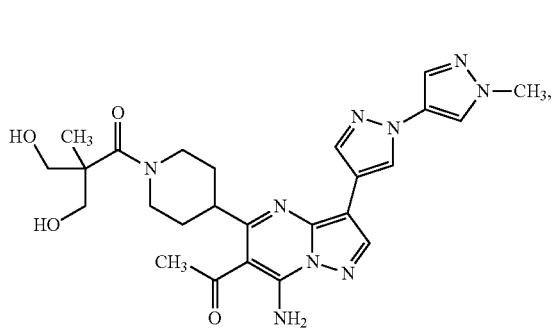
398
-continued
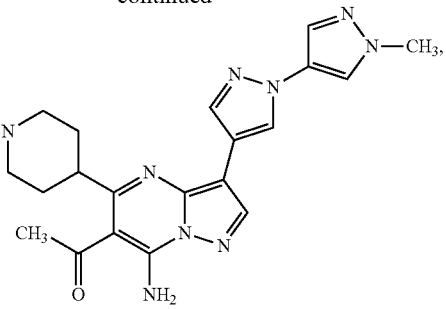
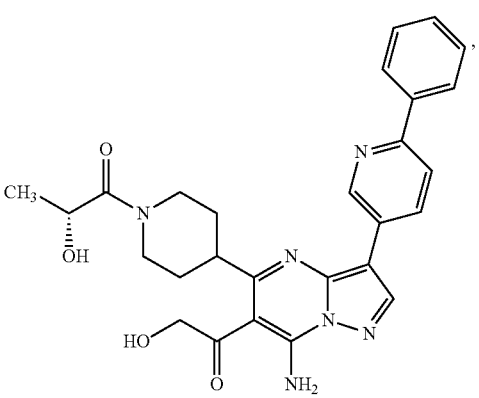
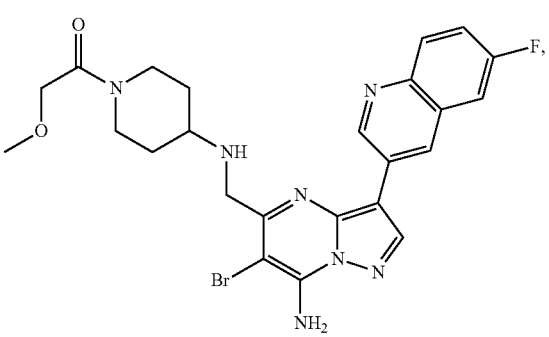
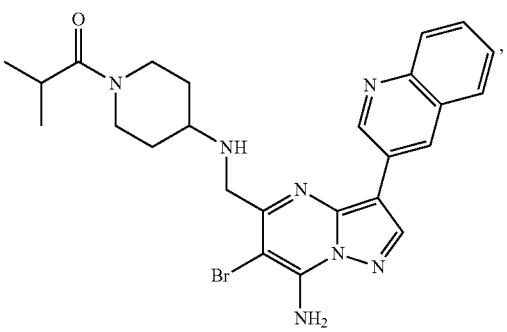

399
-continued
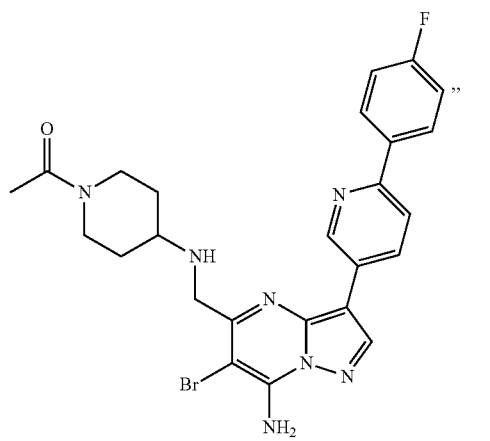
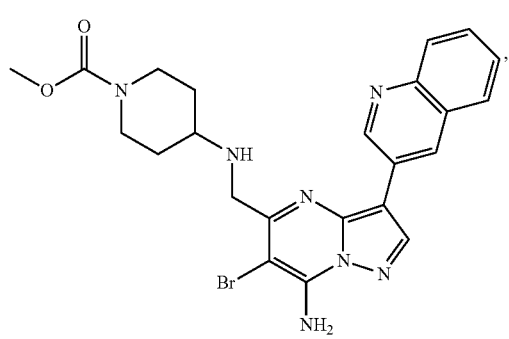
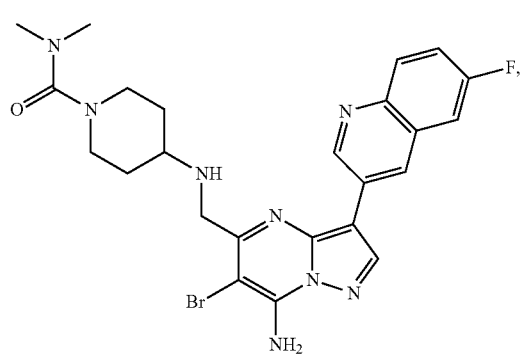
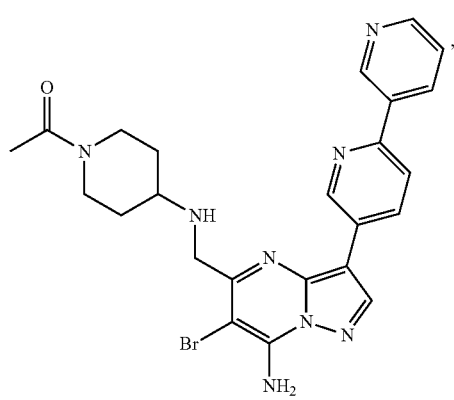
400
-continued
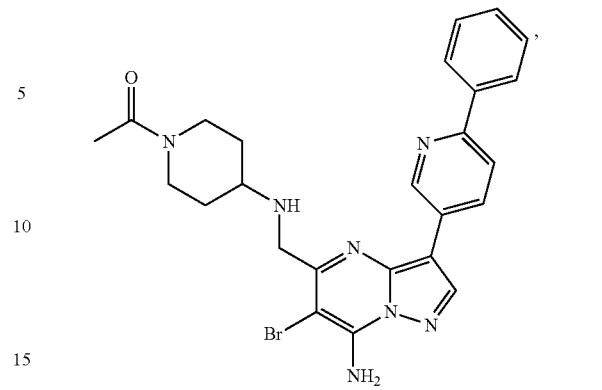
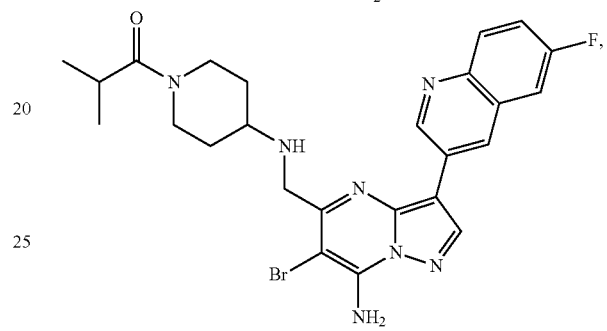
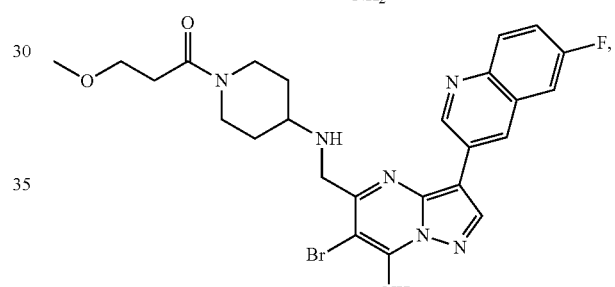
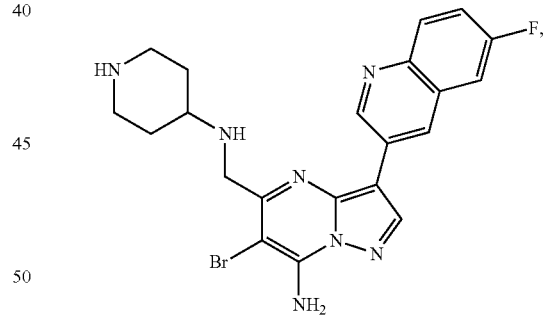
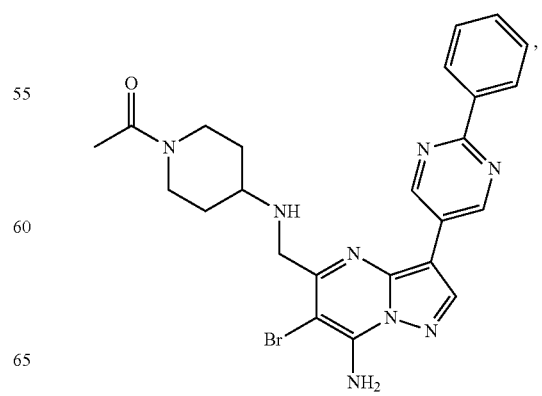

401
-continued
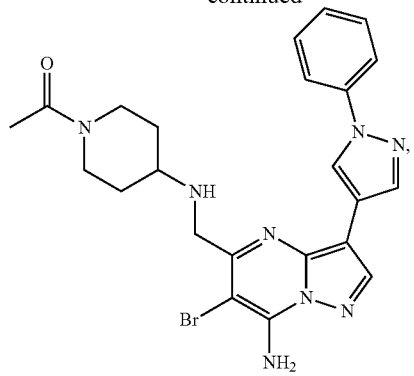
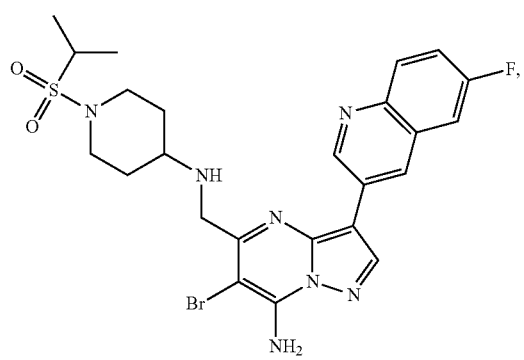
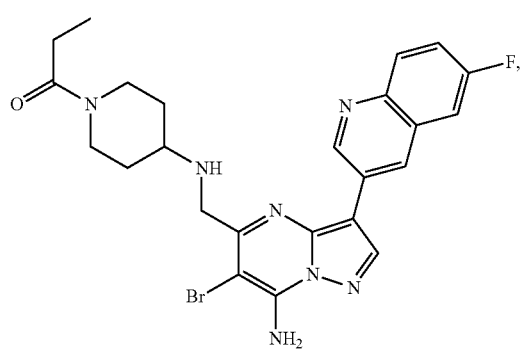
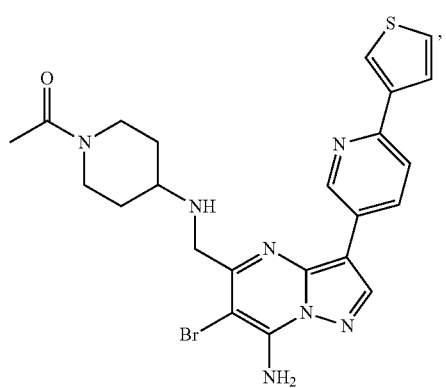
402
-continued
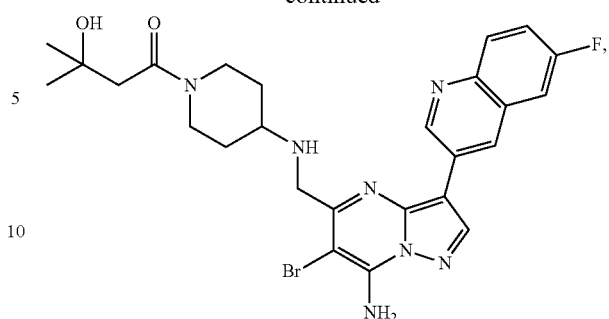
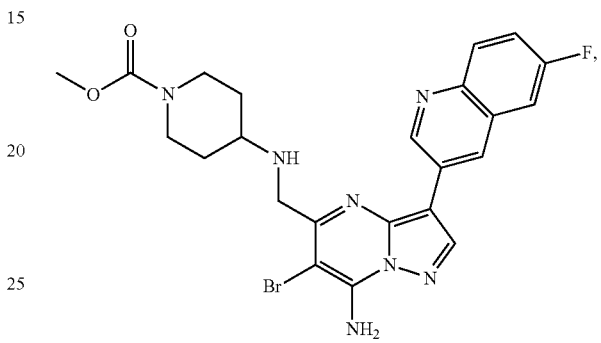
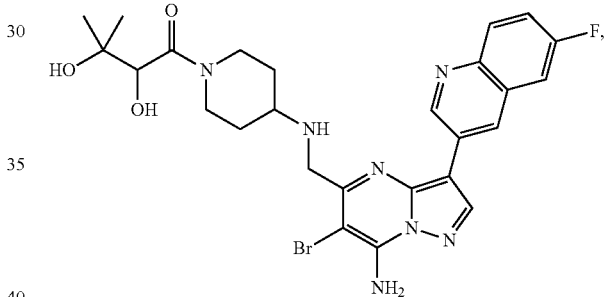
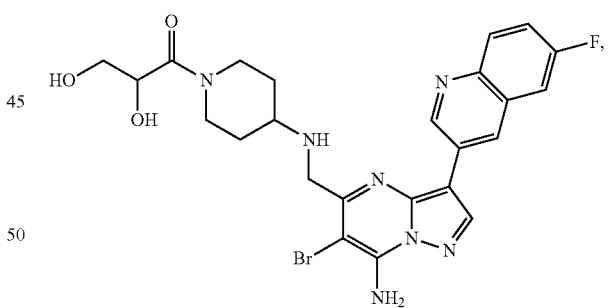

403
-continued
404
-continued
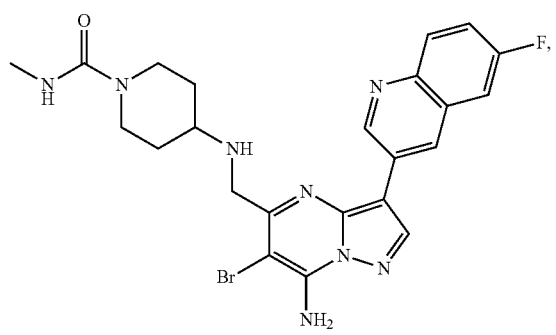
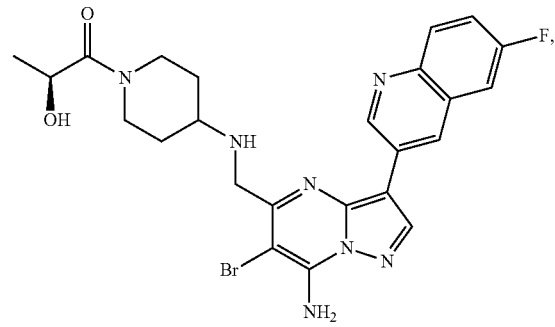

405
-continued
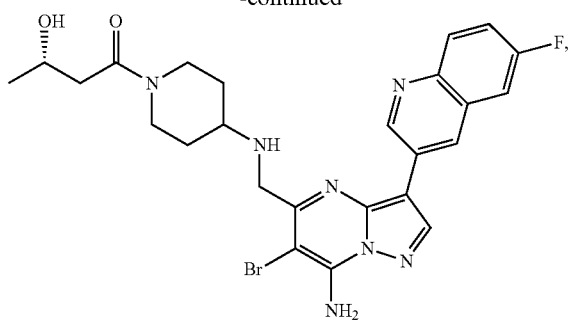
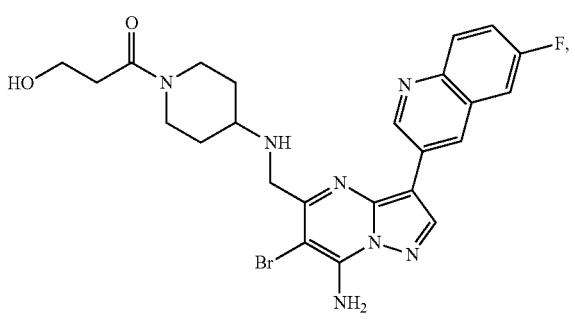
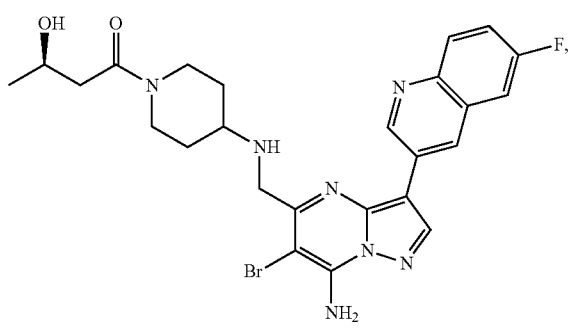
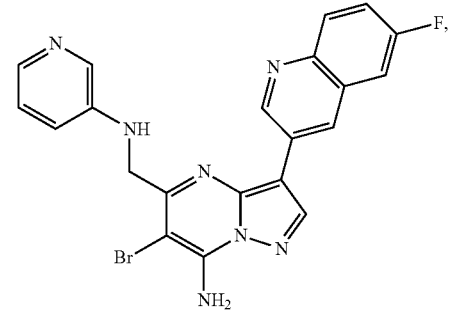
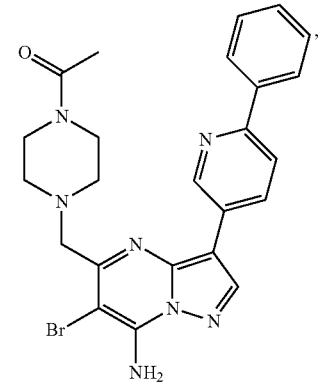
406
-continued
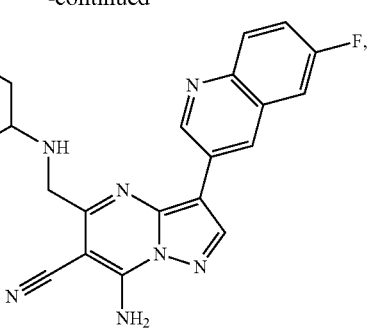
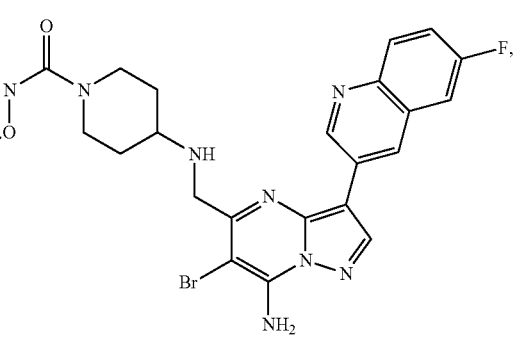
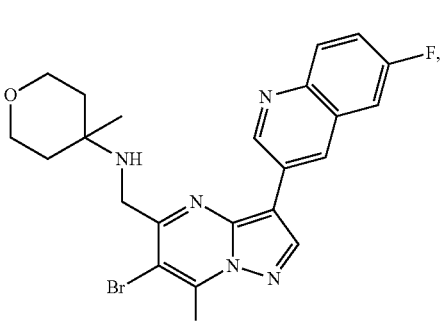
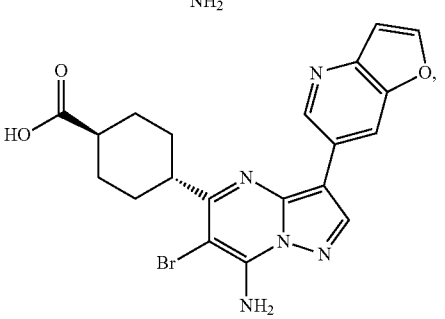
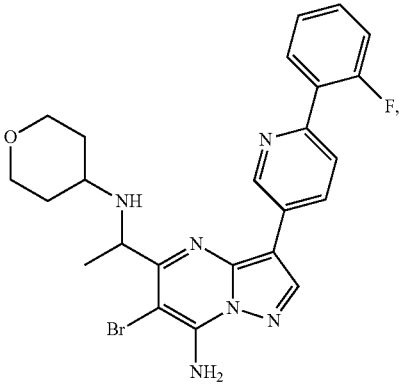

407
-continued
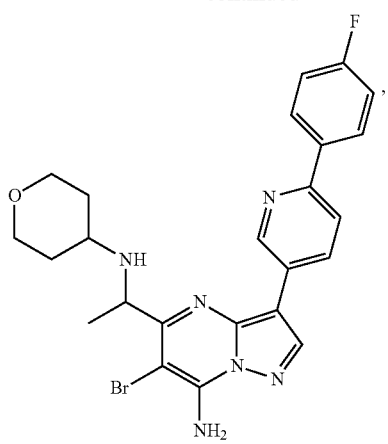
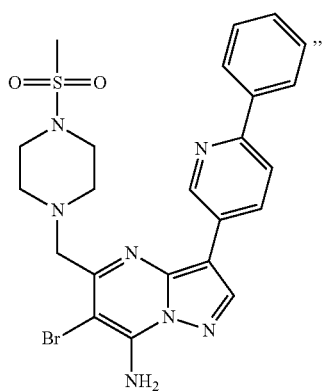
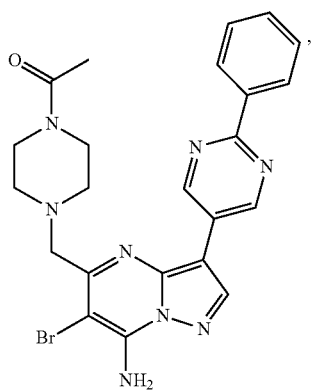
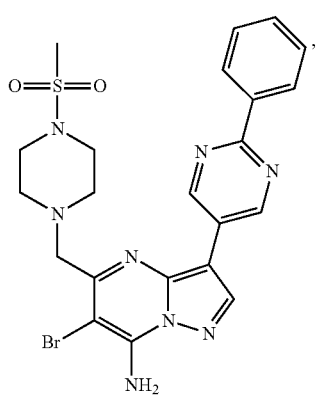
408
-continued

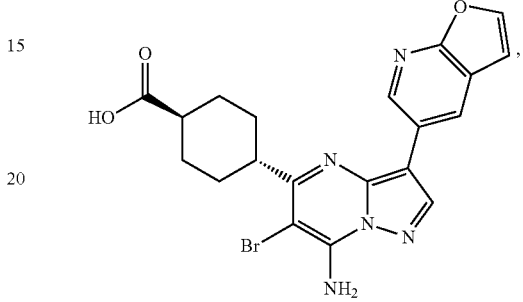
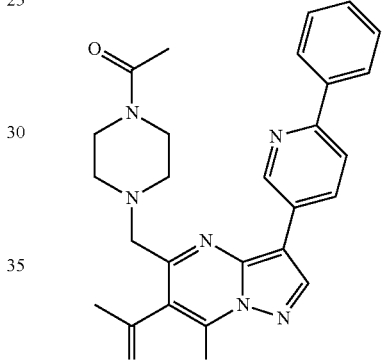
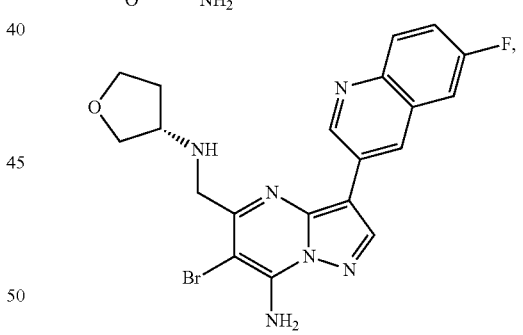
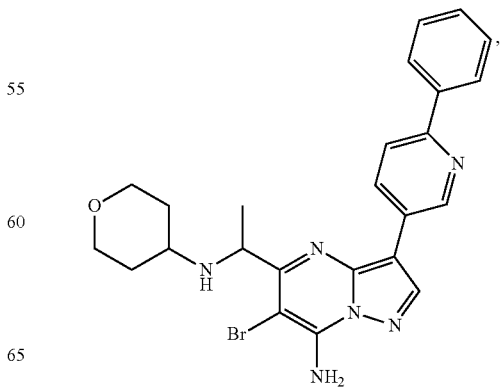

409
-continued
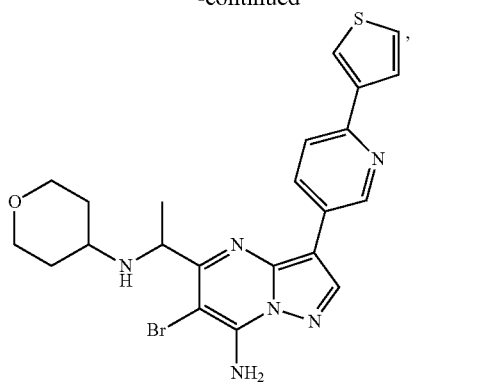
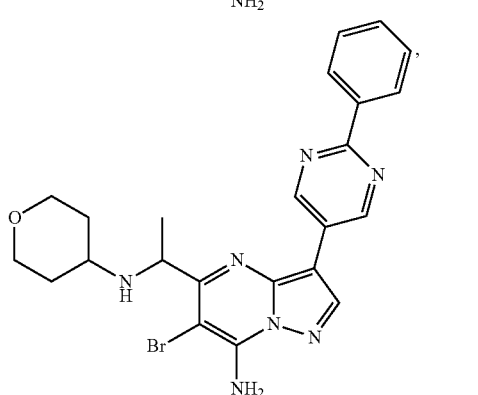
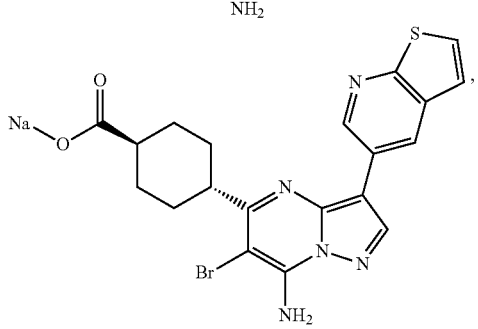
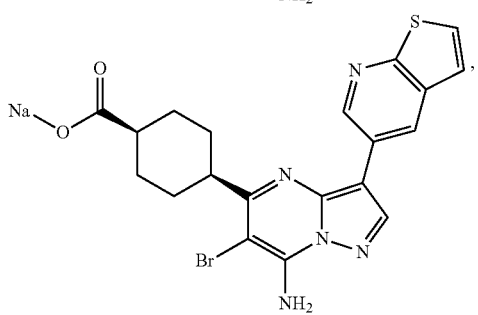
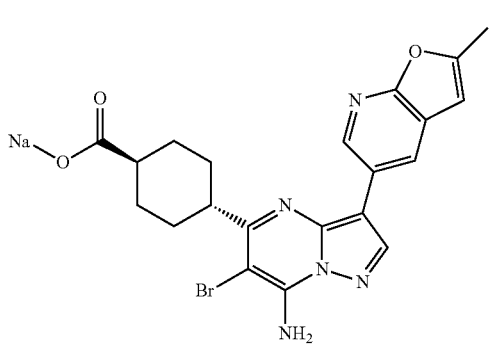
410
-continued
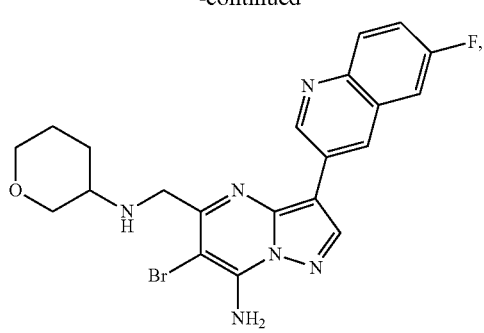
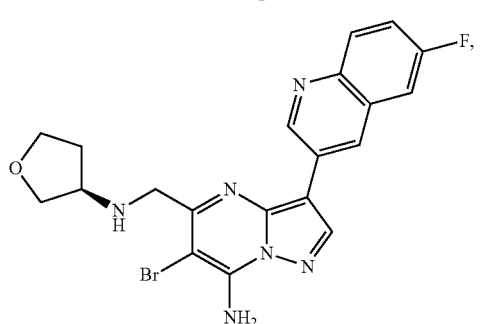
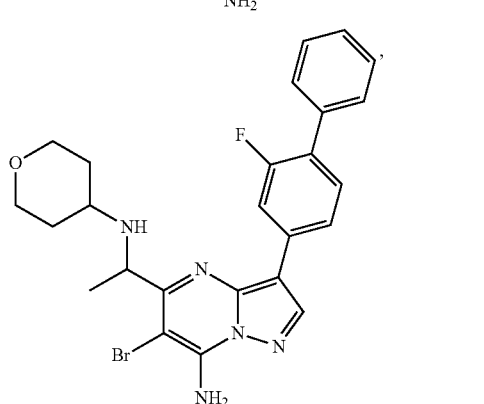
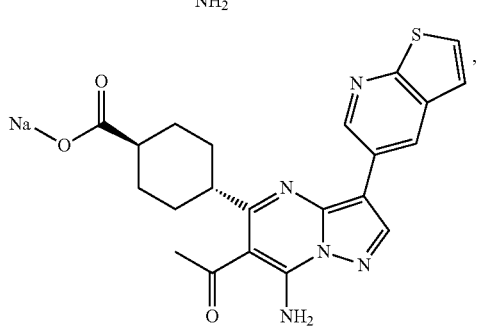
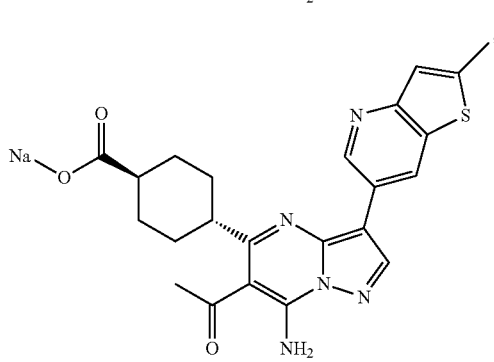

| 411 -continued | 412 -continued |
|---|---|
| 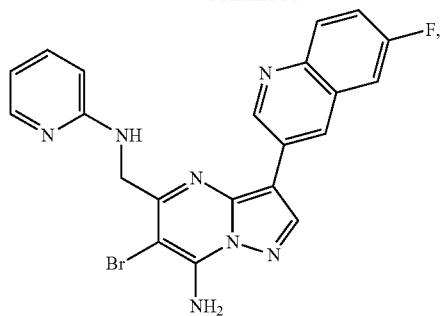 | 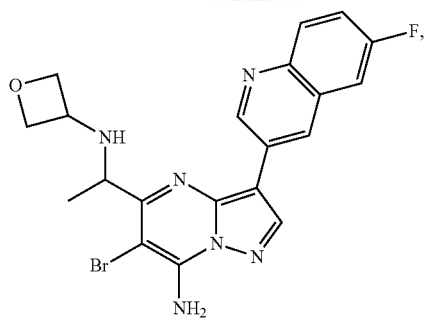 |
| 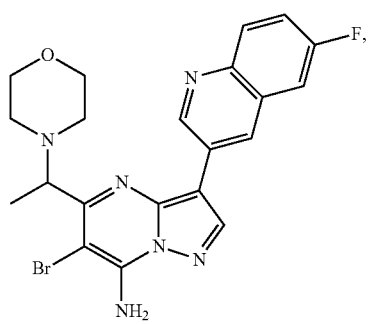 | 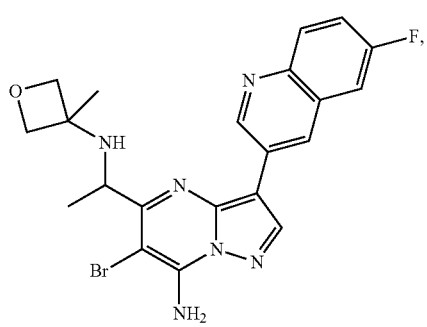 |
| 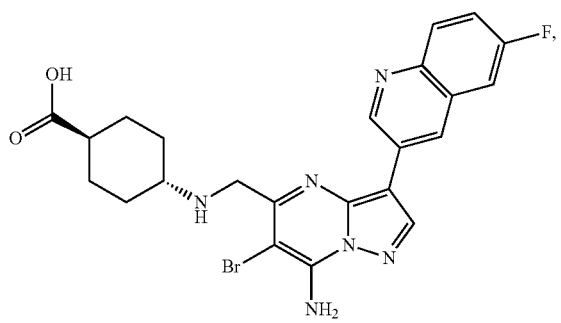 | 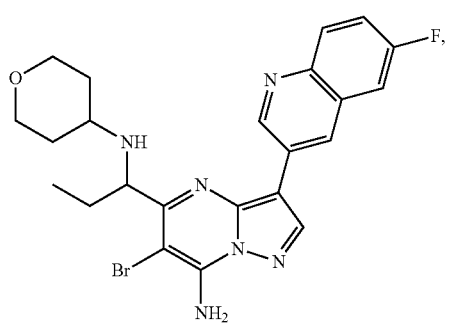 |
| 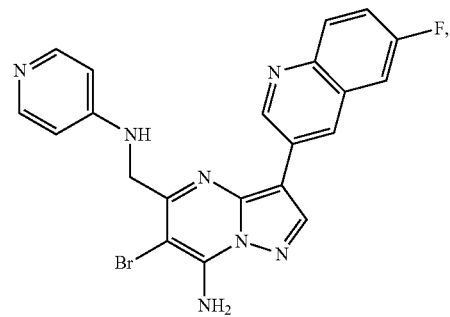 | 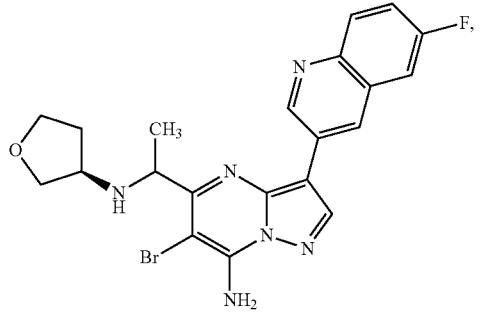 |
| 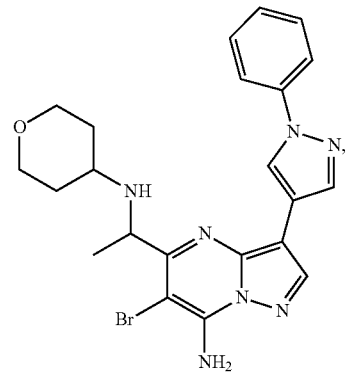 | 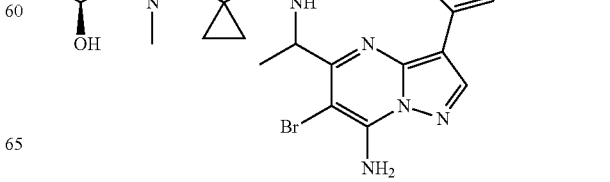 |

413
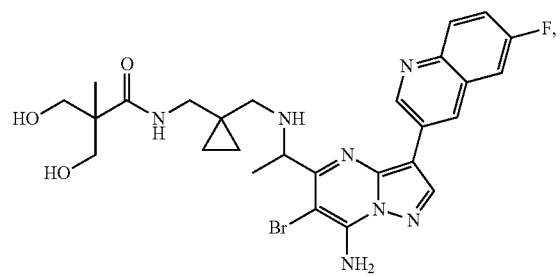
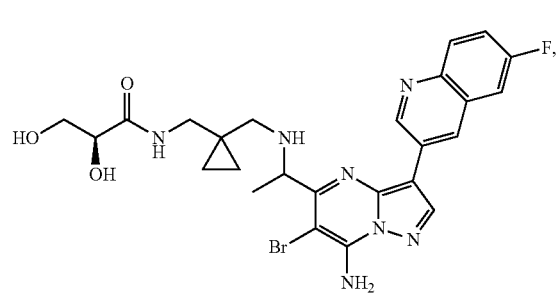
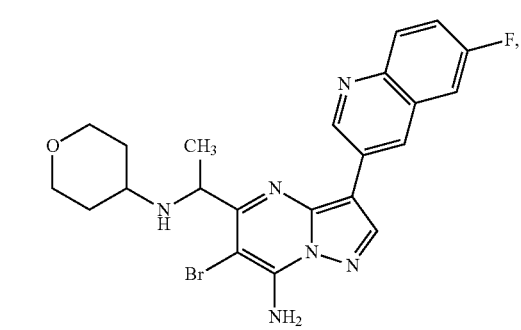
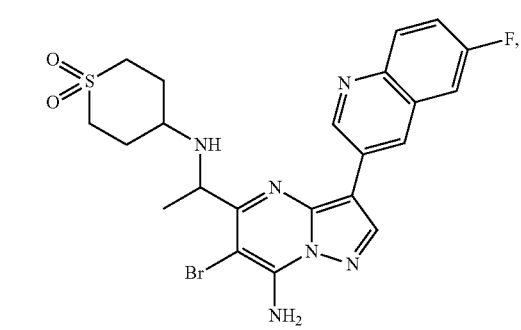
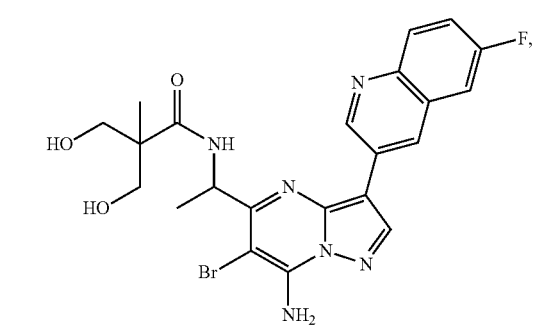
414
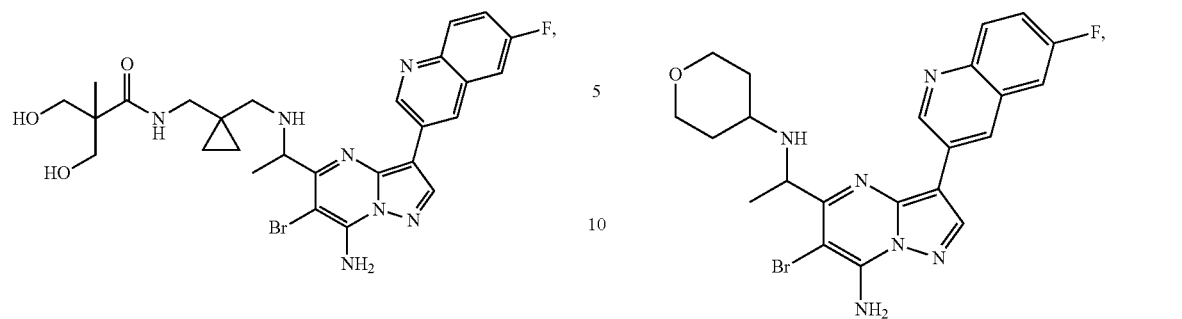
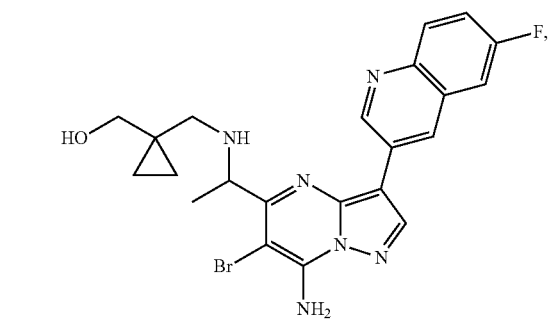
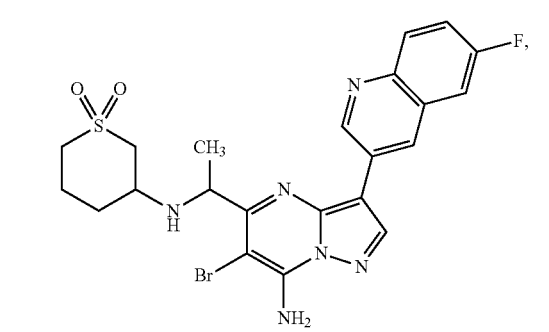
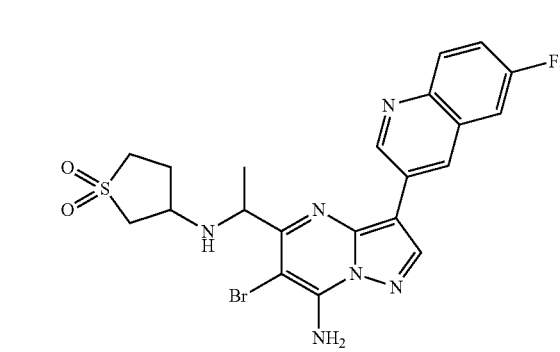
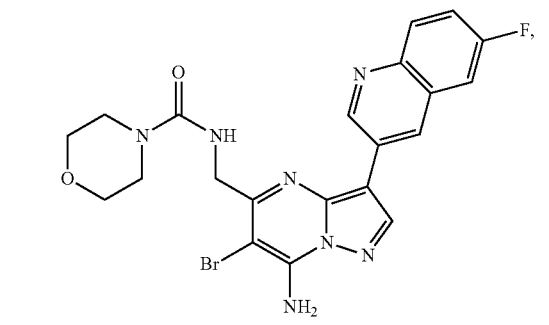

415
-continued
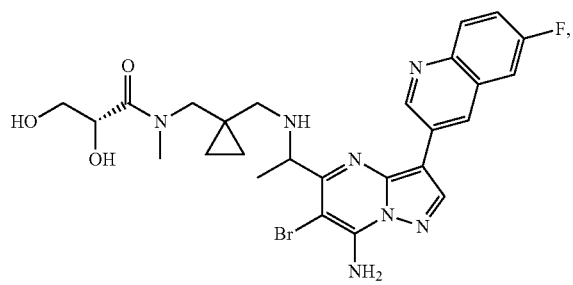
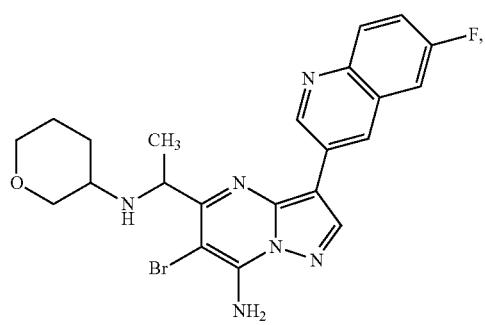
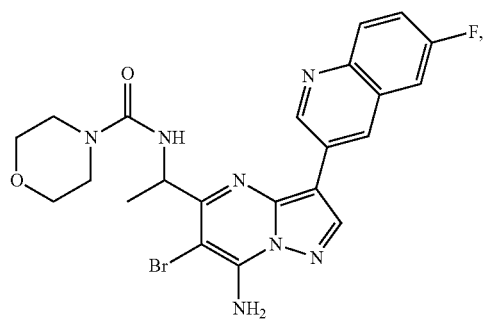
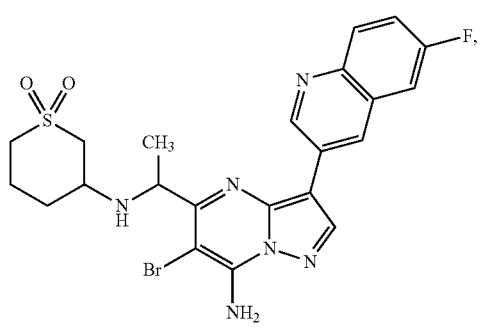
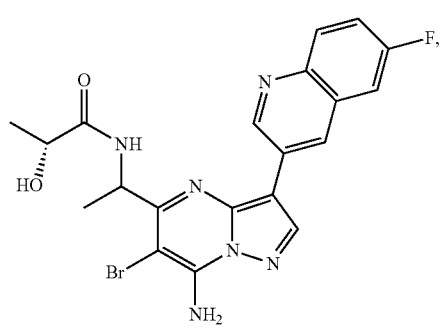
416
-continued
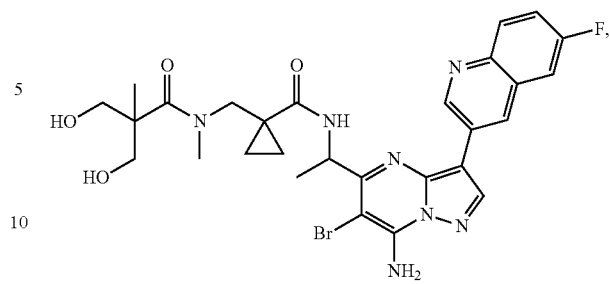
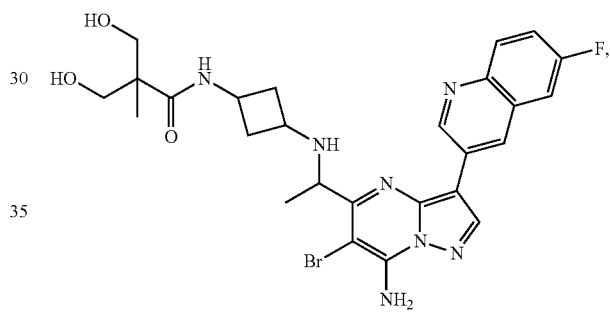
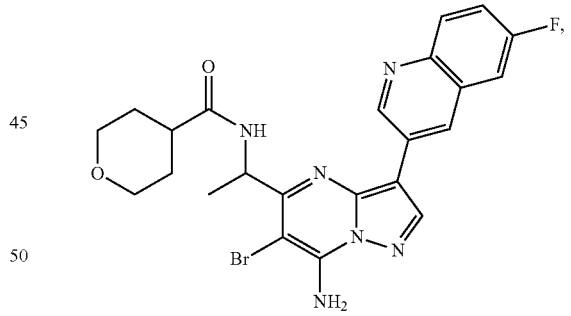
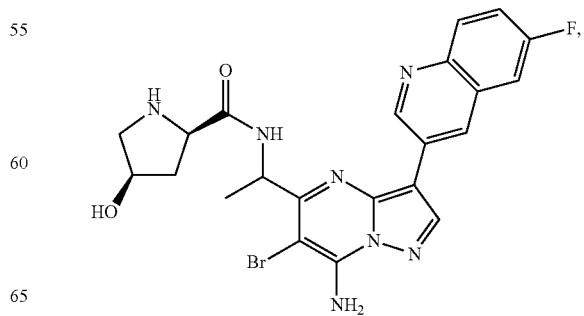

417
-continued
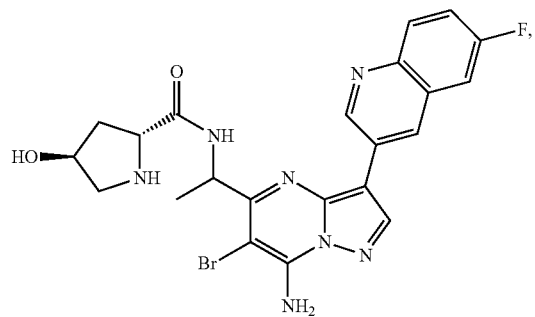
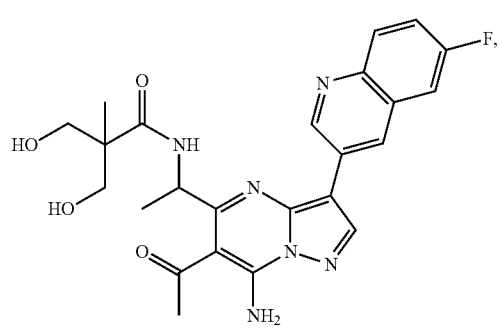
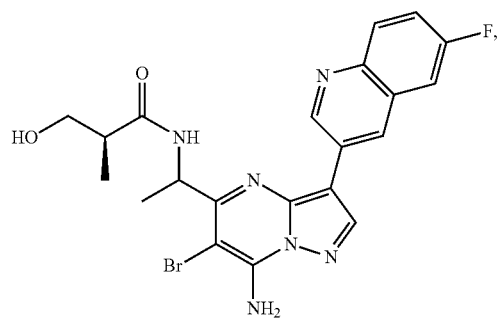
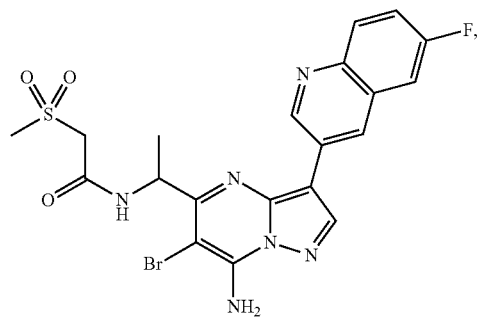
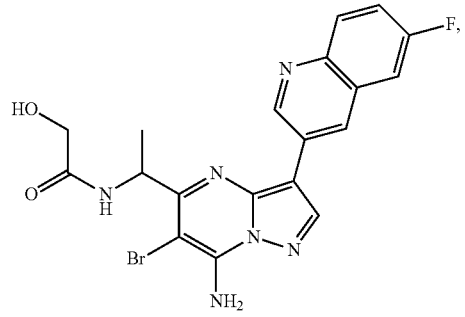
418
-continued
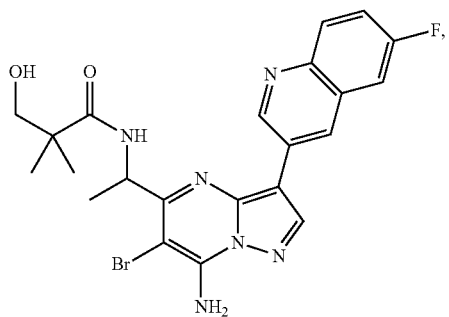
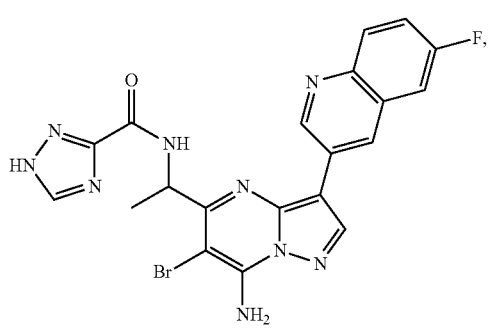
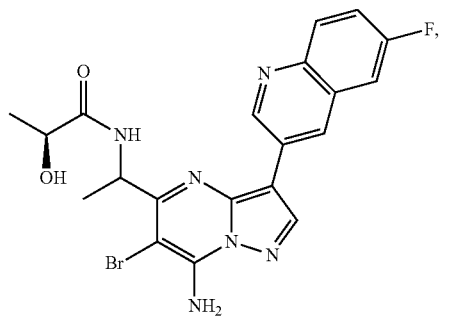
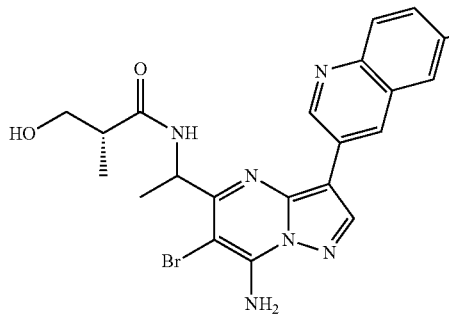
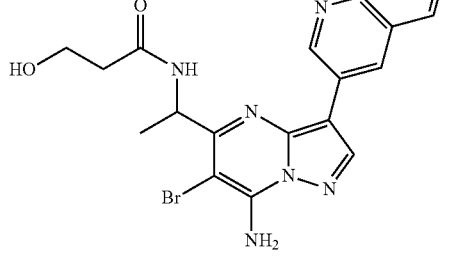

-continued
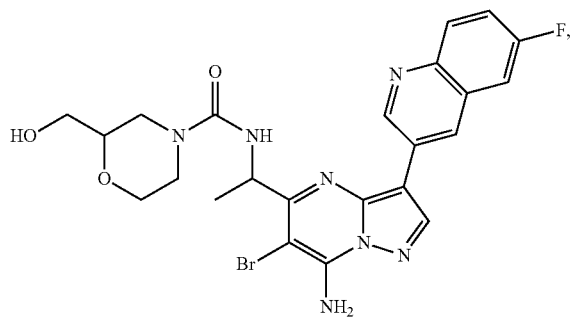
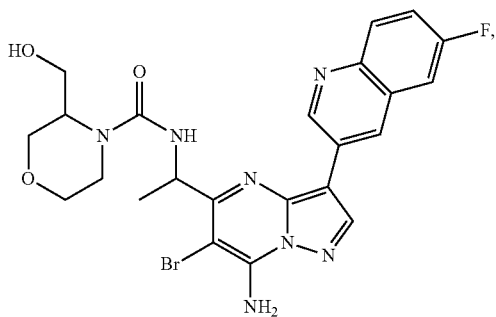
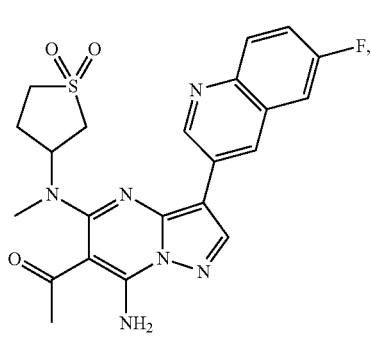
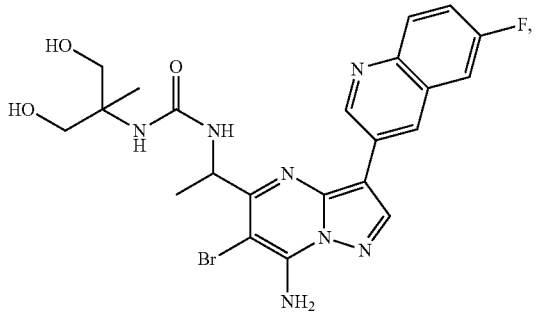
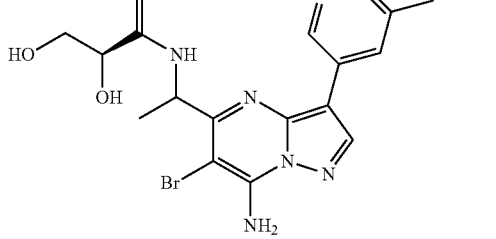
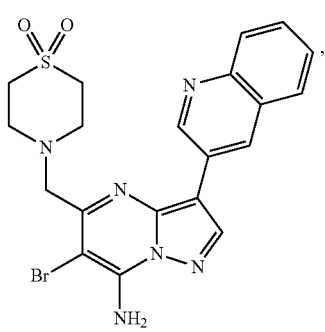

421
-continued
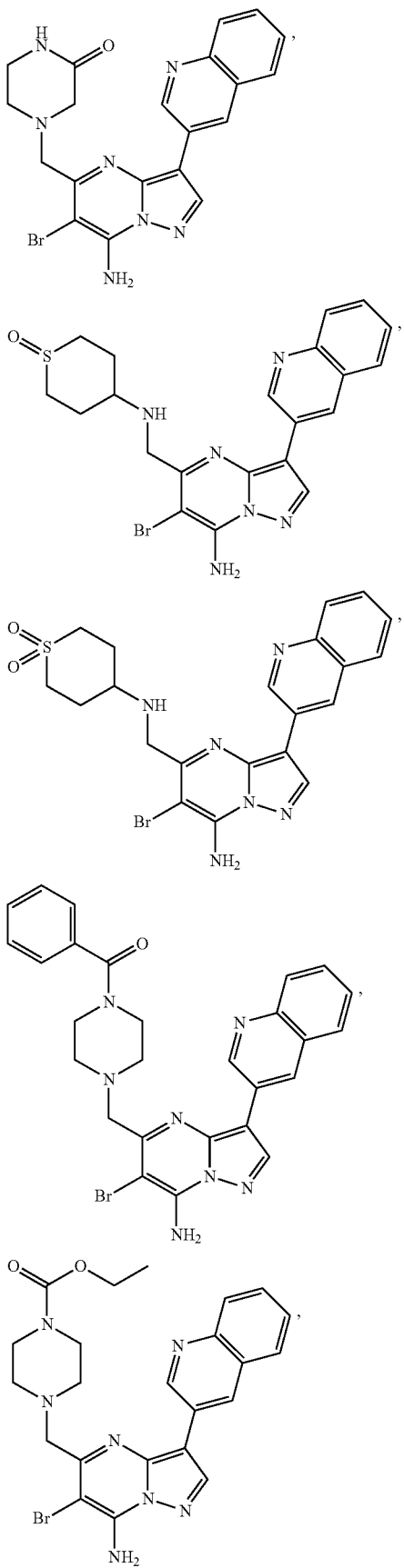
422
-continued
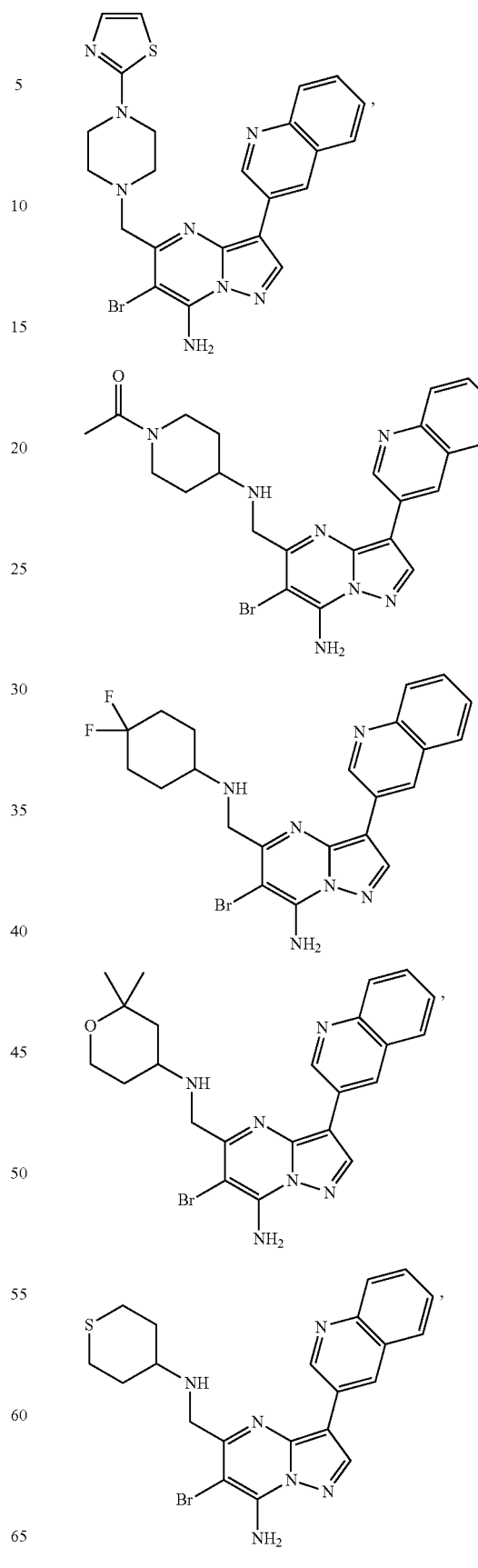

423
-continued
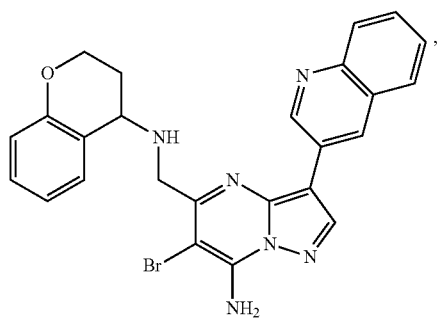
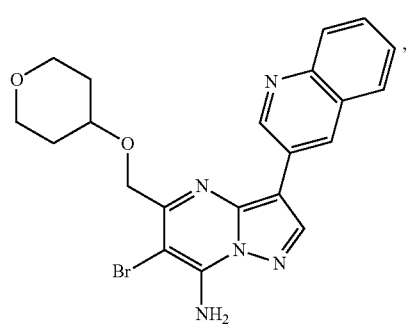
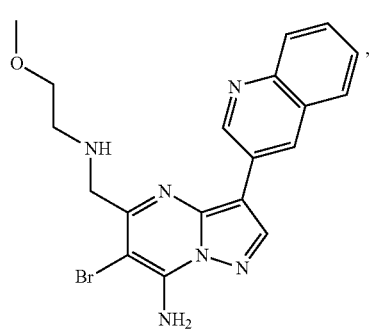
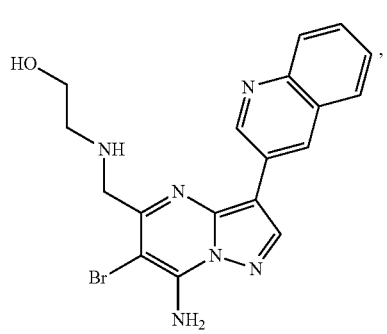
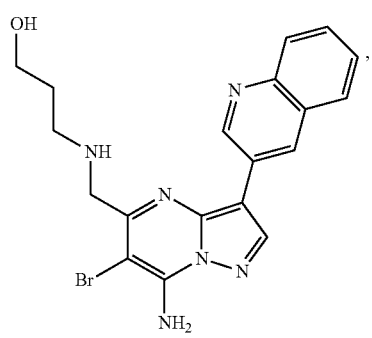
424
-continued
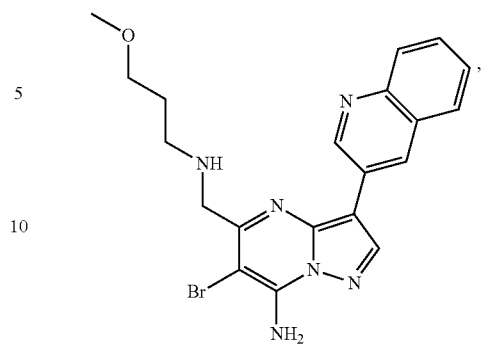
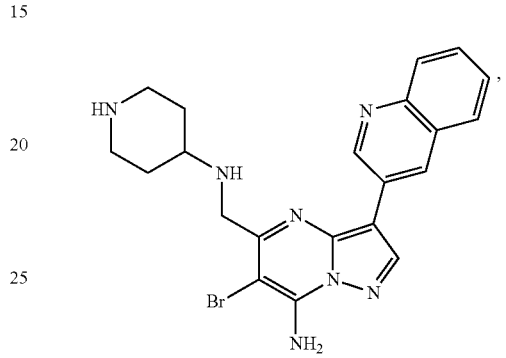
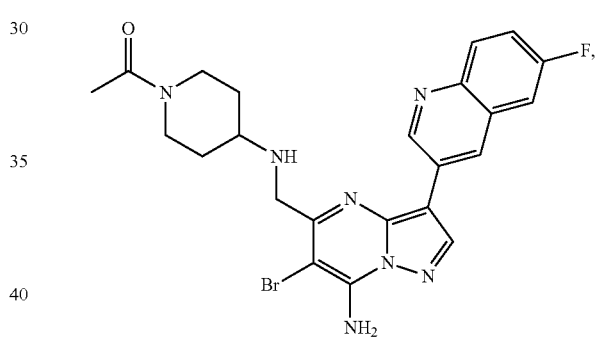
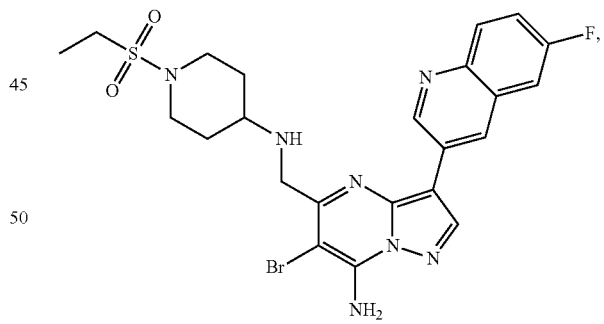
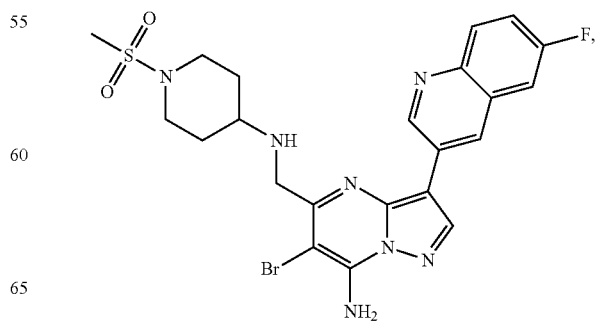

425
-continued
426
-continued
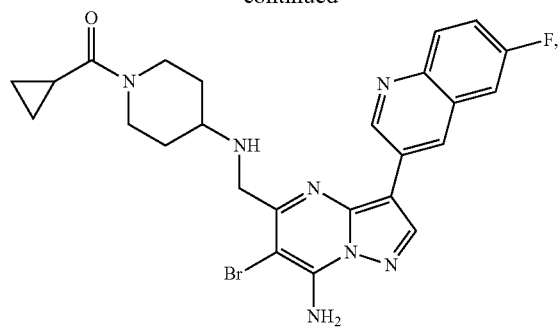
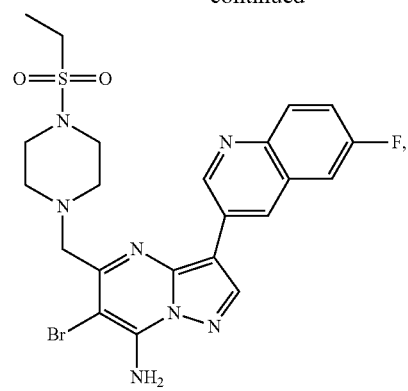
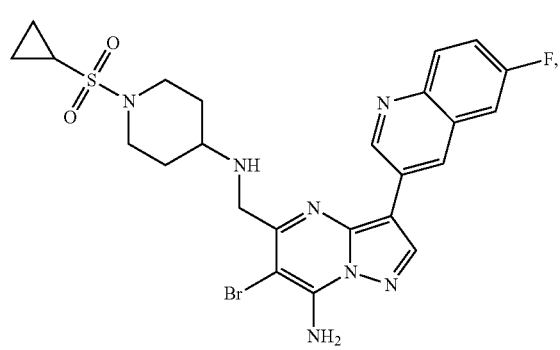
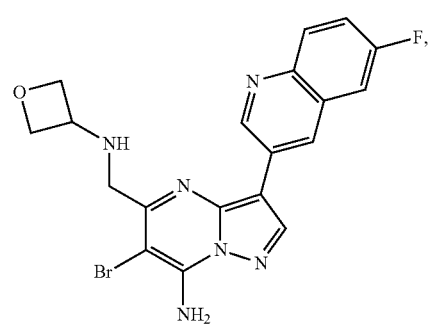
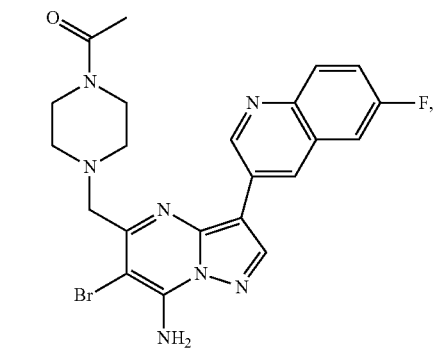
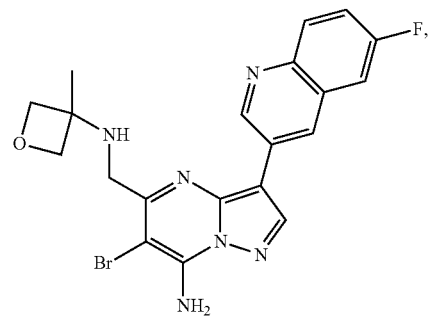
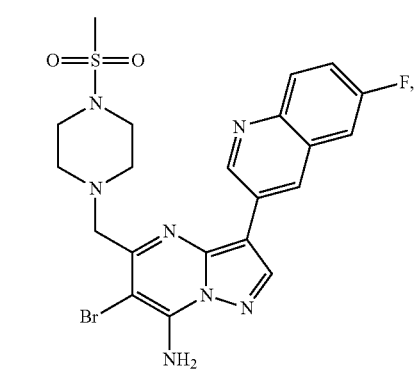
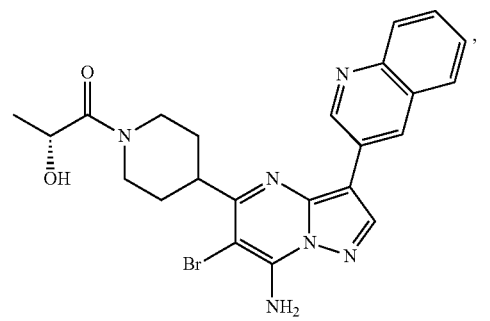
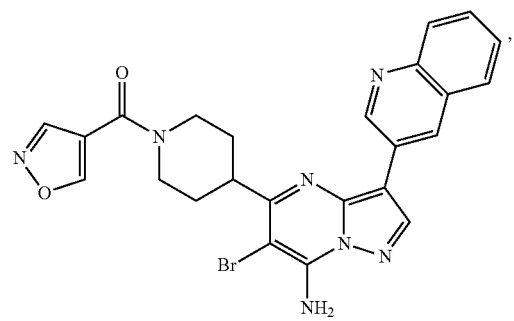

427
-continued
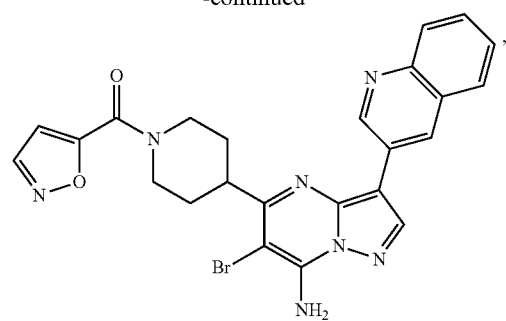
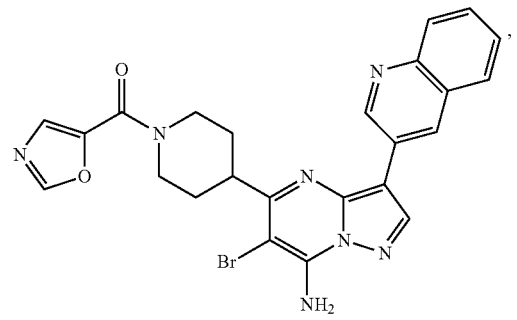
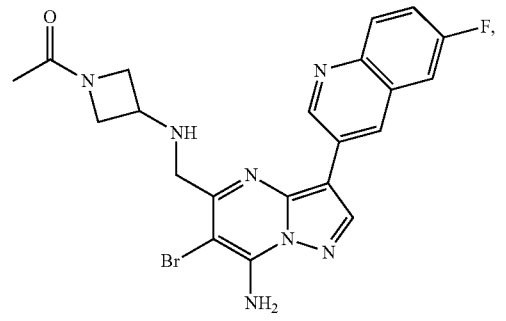
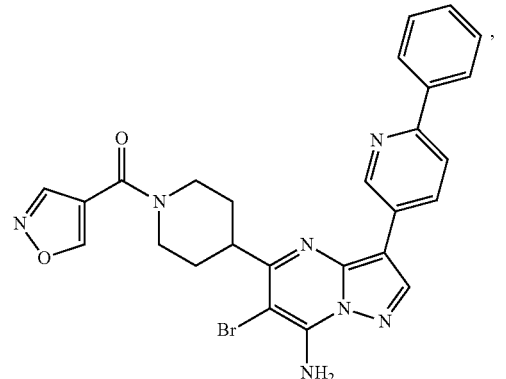
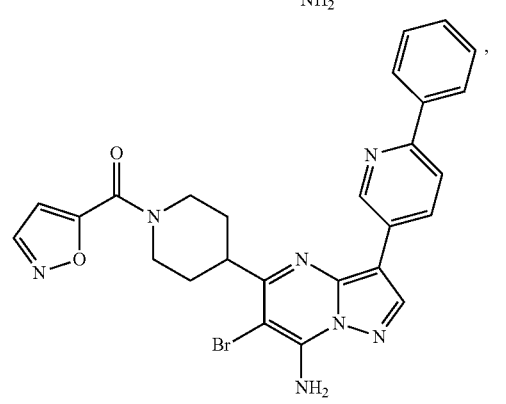
428
-continued
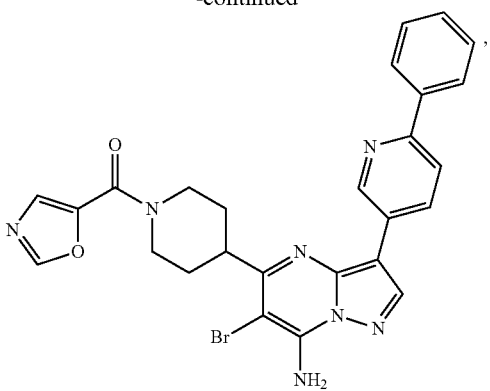
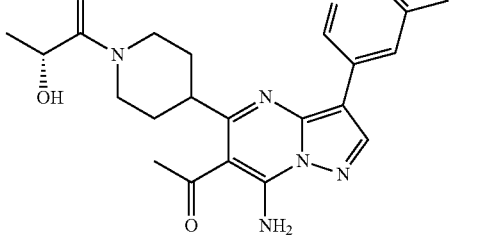
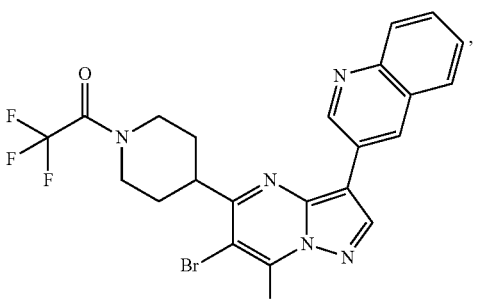
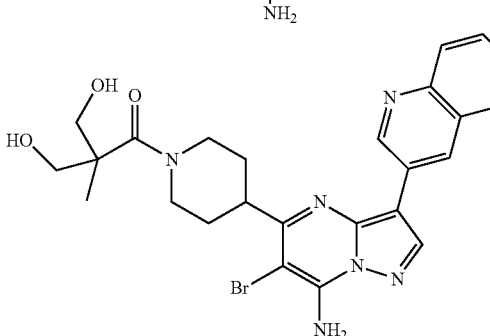
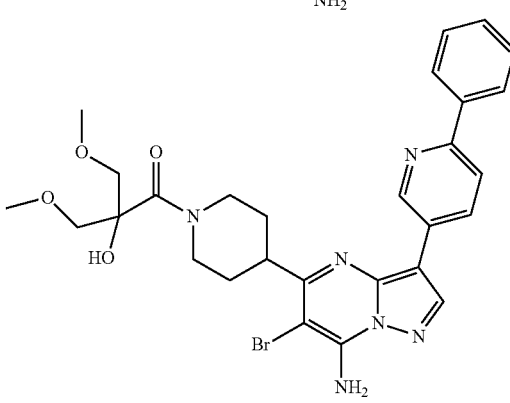

429
-continued
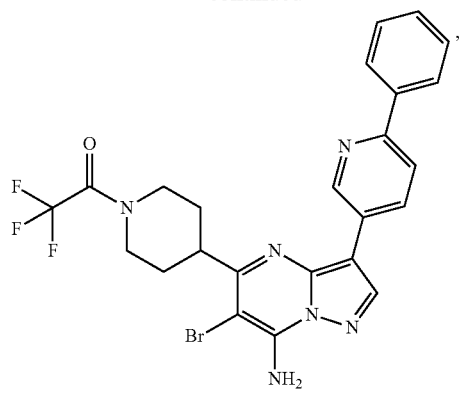
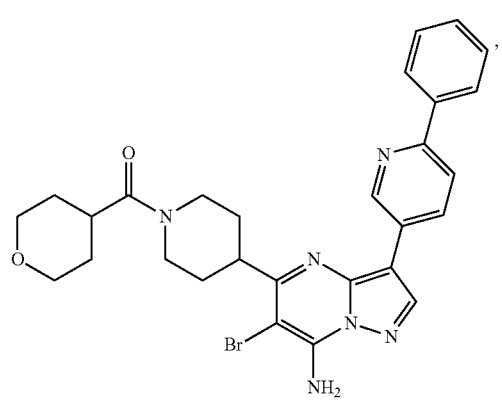
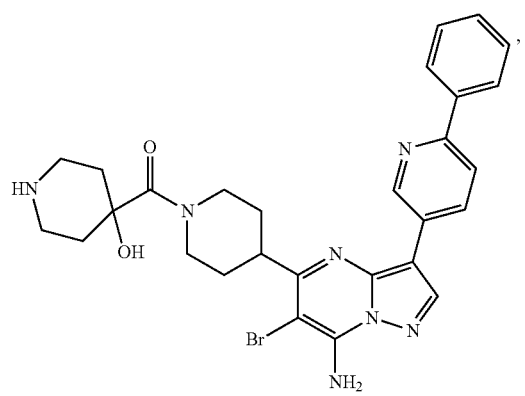
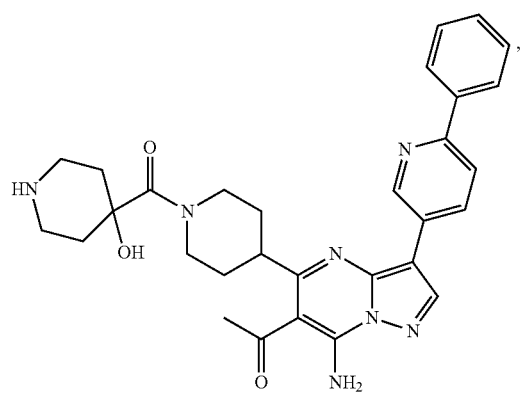
430
-continued
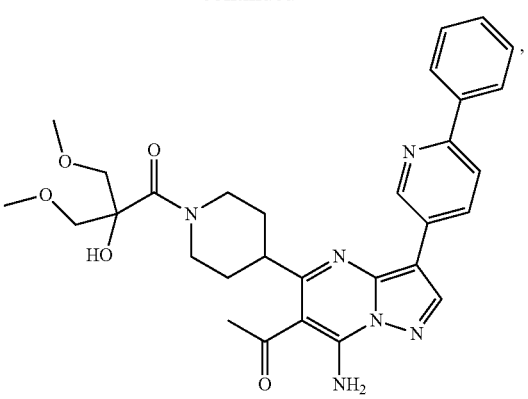
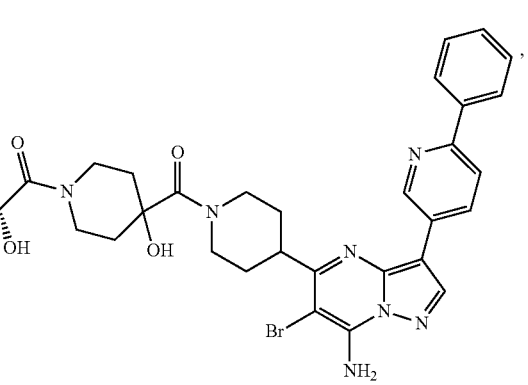
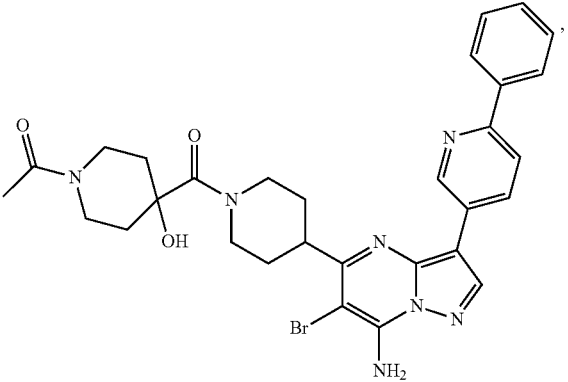
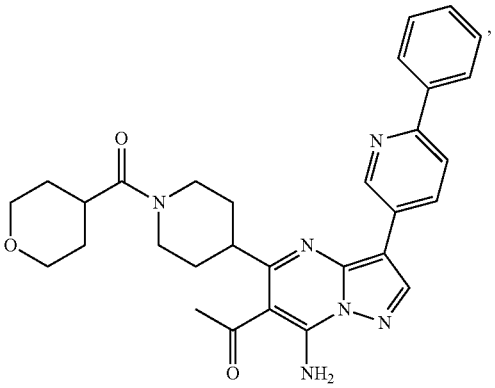

431
-continued
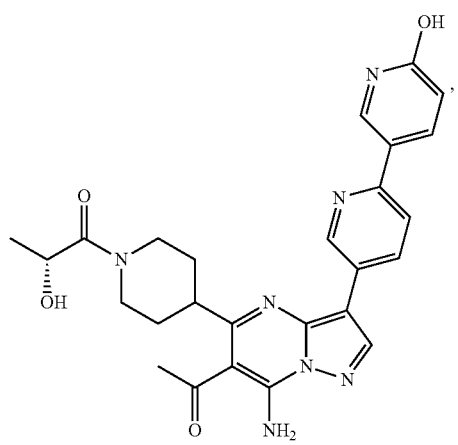
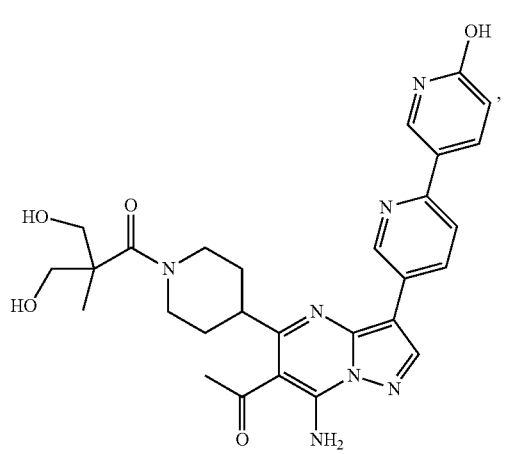
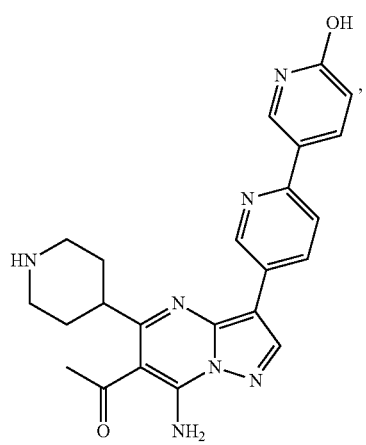
432
-continued
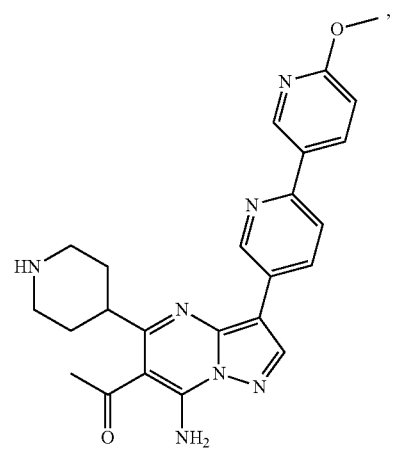
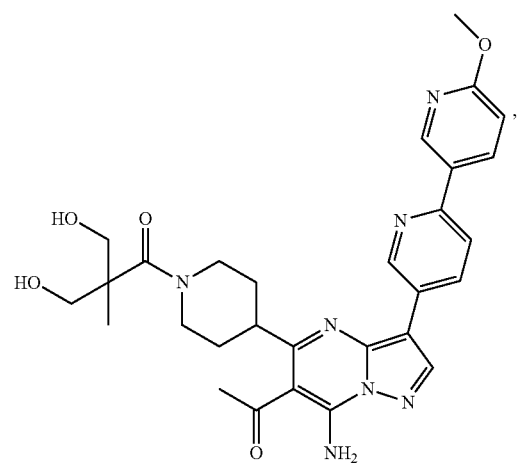
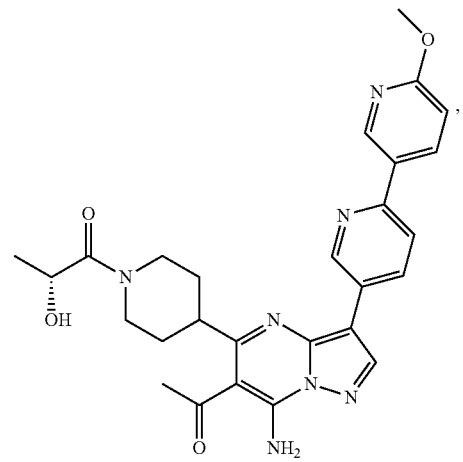

433
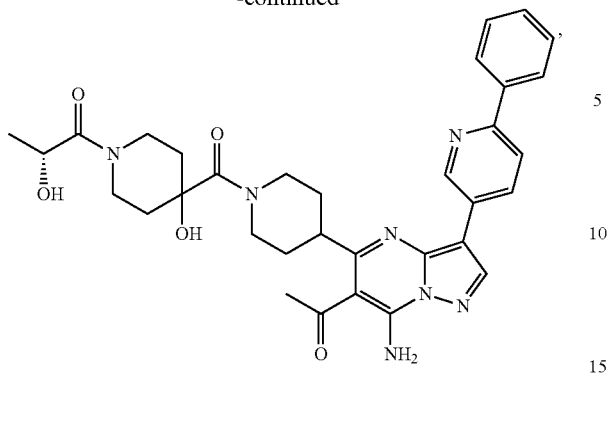
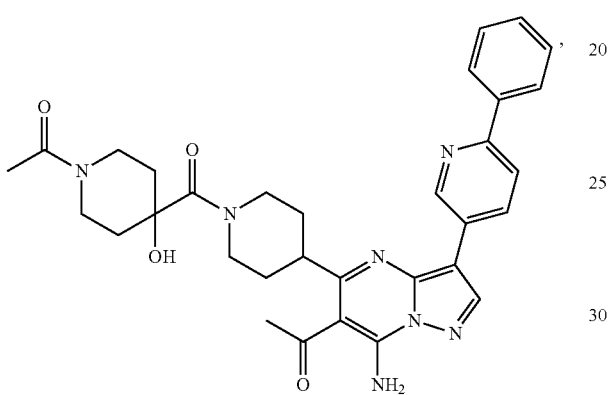
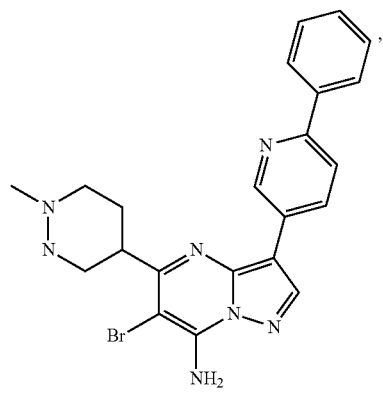
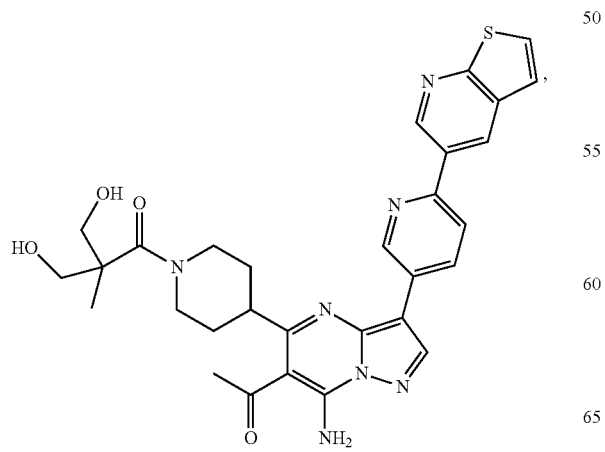
434
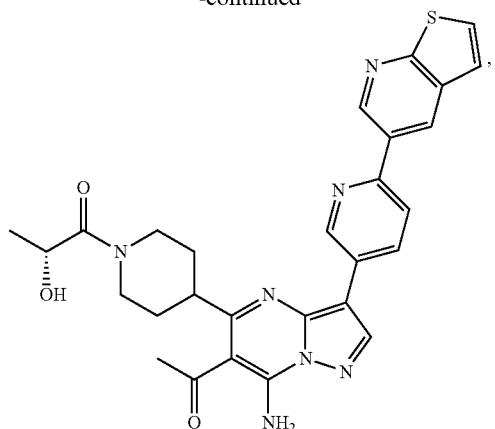
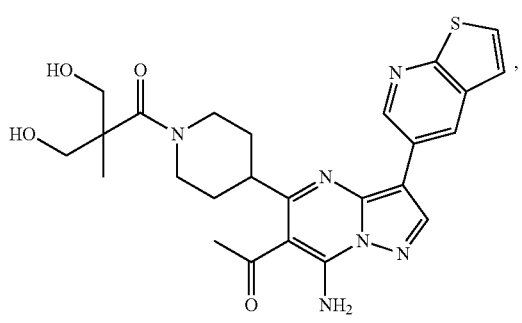
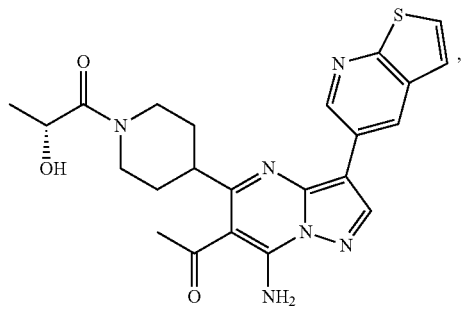
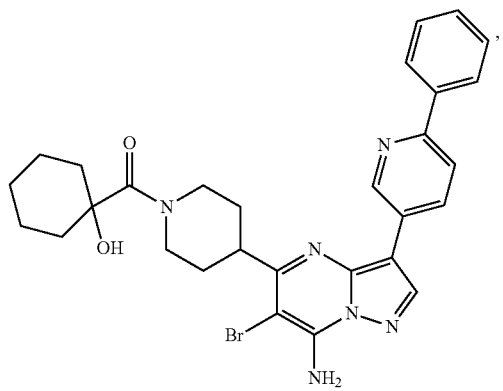

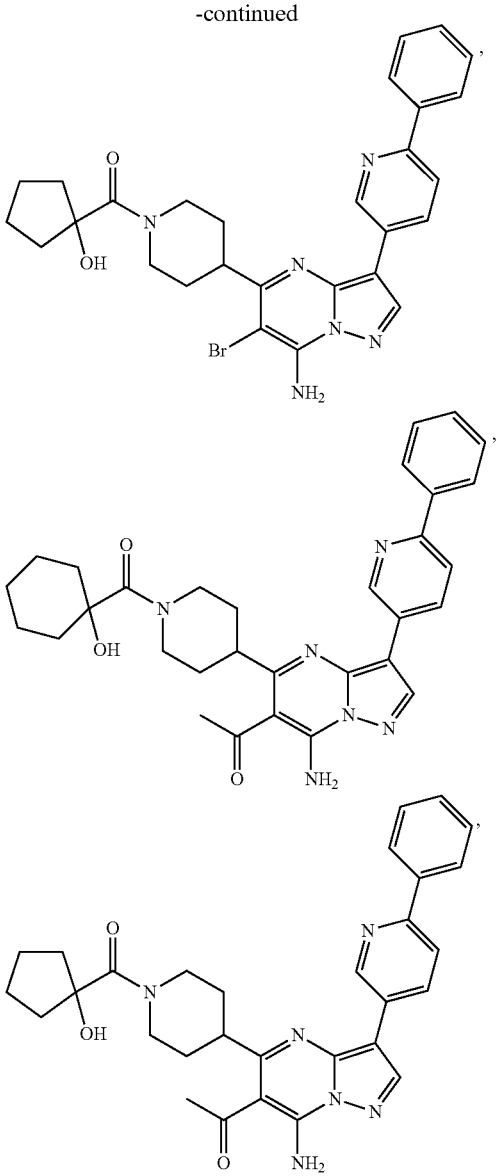

and
or pharmaceutically acceptable salt, ester, solvate or prodrug thereof.

In another embodiment, the present invention relates to a compound represented by the structural Formula I or a pharmaceutically acceptable salt, ester, solvate or prodrug thereof, in purified form.

In another embodiment, the present invention relates to a compound represented by the structural Formula I or a pharmaceutically acceptable salt, ester, solvate or prodrug thereof, in isolated form.

In another embodiment, the present invention includes a composition comprising a therapeutically effective amount of at least one compound from the group of compounds listed above or a pharmaceutically acceptable salt, solvate, ester, or prodrug thereof, in combination with at least one pharmaceutically acceptable carrier.

In another embodiment, the present invention includes a method of treating, or slowing the progression of, a disease by inhibiting mammalian Target Of Rapamycin in a patient, said method comprising administering a therapeutically effective amount of at least one compound from the group of compounds listed above, or a pharmaceutically acceptable salt, solvate, ester or prodrug of the compound, to a patient in need thereof.

In another embodiment, the present invention includes a composition comprising a therapeutically effective amount of at least one compound from the group of compounds listed above or a pharmaceutically acceptable salt, solvate, ester or prodrug thereof, and an anti-cancer agent.

In another embodiment, the present invention includes a composition comprising a therapeutically effective amount of at least one compound from the group of compounds listed above or a pharmaceutically acceptable salt, solvate, ester or prodrug thereof, and an anti-neoplastic, anti-tumor, anti-angiogenic, or chemotherapeutic agent.

In another embodiment, the present invention includes a method of treatment of a disease selected from the group consisting of proliferative inflammatory diseases, allergic diseases, obstructive airways diseases, and disorders commonly occurring in connection with transplantation, diseases that respond to inhibition of mTOR, comprising administering a therapeutically effective amount of at least one compound from the group of compounds listed above or a pharmaceutically acceptable salt, solvate, ester or prodrug thereof to a patient in need of such treatment.

In another embodiment, the present invention includes a method of treatment of a proliferative disease, autoimmune disease, viral disease, fungal disease, neurological/neurodegenerative disorder, arthritis, inflammation, neuronal, alopecia or cardiovascular disease comprising administering a therapeutically effective amount of at least one compound from the group of compounds listed above or a pharmaceutically acceptable salt, solvate, ester or prodrug thereof to a patient in need of such treatment.

In another embodiment, the present invention includes a method of treatment of a proliferative disease.

In another embodiment, the present invention includes a method of treatment of a proliferative disease, wherein the proliferative disease is selected from the group consisting of: cancer of the bladder, breast, colon, kidney, liver, lung, head and neck, esophagus, gall bladder, ovary, pancreas, stomach, cervix, thyroid, prostate, and skin; small cell lung cancer, non-small cell lung cancer, squamous cell carcinoma; leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, Burkett's lymphoma; acute and chronic myelogenous leukemia, myelodysplastic syndrome, promyelocytic leukemia; fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, endometrial cancer, gastrointestinal tract cancer and Kaposi's sarcoma.

In another embodiment, the present invention includes a method of treatment of hamartoma syndromes, transplant rejection, bowel disorders, inflammatory bowel disease, multiple sclerosis, immunosuppression, immune tolerance, autoimmune diseases, inflammation, bone loss, rheumatoid arthritis, restinosis, cardiac allograft vasculopathy, psoriasis, ocular conditions such as dry eye, hepatic fibrosis, hepatic necrosis, beta-thalassaemia, comprising administering a therapeutically effective amount of at least one compound from the group of compounds listed above or a pharmaceutically acceptable salt, solvate, ester or prodrug thereof to a patient in need of such treatment.

In another embodiment, the present invention includes a method of treatment of cancer of the bladder, breast, colon, kidney, liver, lung, small cell lung cancer, non-small cell lung cancer, head and neck, esophagus, gall bladder, ovary, pancreas, stomach, cervix, thyroid, prostate, and skin, squamous cell carcinoma; leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, Burkett's lymphoma; acute and chronic myelogenous leukemia, myelodysplastic syndrome, promyelocytic leukemia; fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, endometrial cancer, gastrointestinal tract cancer and Kaposi's sarcoma comprising administering a therapeutically effective amount of at least one compound from the group of compounds listed above or a pharmaceutically acceptable salt, solvate, ester or prodrug thereof, further comprising treatment with radiation therapy to a patient in need of such treatment.

In another embodiment, the present invention includes a method of treating a disease by inhibiting a mTOR, comprising administering to a patient in need of such treatment an amount of a first compound from the group of compounds listed above or a pharmaceutically acceptable salt, solvate, ester or prodrug thereof; and an amount of at least one second compound, said second compound being an anti-cancer agent;

wherein said anti-cancer agent is selected from the group consisting of Adriamycin, Altretamine, Amidox, Aminoglutethimide, Amsacrine, Anastrazole, Antibodies to EGFR, 3-AP, Aphidicolon, Ara-C, Arsenic trioxide, L-Asparaginase, Bevacizumab, Bleomycin, BMS 214662, Bortezomib, Busulfan, Campath, Camptostar, Capecitabine, Carboplatin, Carmustine, Centrosome associated protein E ("CENP-E") inhibitors, Cetuximab, Cladribine, Chlorambucil, Chlormethine, Chlorotrianisene, Cisplatin, Clofarabine, cyclophosphamide, Cytarabine, a Cytostatic agent, Cytoxan, Dacarbazine, Dactinomycin, Daunorubicin, Dasatinib, Deforolimus (described in PCT publication No. 2003/064383), Deoxycoformycin, Didox, Diethylstilbestrol, Docetaxel, Doxorubicin, Dromostanolone, Droloxafine, Epirubicin, Epothilones, ERK inhibitors, Erlotinib. Etoposide, 17α-Ethinylestradiol, Estramustine, Exemestane, Floxuridine, Fludarabine, Fludarabine phosphate, 5-Fluorouracil, Fluoxymesterone, Flutamide, Fulvestrant, Gefitinib, Gemcitabine, Gemtuzumab ozogamcicin, Goserelin, GSK-923295, Hexamethylmelamine, Hydroxyprogesterone, Hydroxyurea, Ibritumomab Tiuxetan, Idarubicin, Ifosfamide, Imatinib mesylate, Intron, Ihnotecan, ispinesib, KSP inhibitors, L778,123, Lapatinib, Leucovirin, Leuprolide, Lerozole, Letrazole, Levamisole, Liposomal Doxorubicin, Liposomal, Lomustine, Lonafarnib, Medroxyprogesteroneacetate, Megestrolacetate, Melphalan, 6-Mercaptopurine, Methoxtrexate, Methylprednisolone, Methyltestosterone, Mithramycin, Mitomycin-C, Mitotane, Mitoxantrone, Navelbene, Nilotinib, Oxaliplatin, Paclitaxel, Panitubimab, Pentostatin, Pipobroman, Porfimer, Prednisolone, Prednisone propionate, Procarbazine, Reloxafine, Rituximab, Satriplatin, SB-743921, Sml1, Sorafinib, Streptozocin, Sunitinib, Tamoxifen, Taxotere, Taxol, Temozolomide, Teniposide, Testolactone, Testosterone, Tezacitabine, 6-Thioguanine, Thiotepa, Tipifarnib, Topotecan, Toremifene, Tositumomab, Trastuzumab, Triamcinolone, Triapine, Triethylenemelamine, Triethylenethiophosphoramine, Trimidox, Uracil mustard, Vinblastine, Vincristine, Vindesine, and Vinorelbine;

wherein the amounts of the first compound and said second compound result in a therapeutic effect.

In another embodiment, the present invention includes a method of treating, or slowing the progression of, a disease by inhibiting mammalian Target Of Rapamycin in a patient, said method comprising administering a therapeutically effective amount of at least one compound of Formula I, or a pharmaceutically acceptable salt, solvate, ester or prodrug of the compound, to a patient in need thereof.

In another embodiment, the present invention includes a method of treatment of a disease selected from the group consisting of proliferative inflammatory diseases, allergic diseases, obstructive airways diseases, diseases related to transplant rejection and diseases that respond to inhibition of mTOR, comprising administering a therapeutically effective amount of a compound of Formula I or a pharmaceutically acceptable salt, solvate, ester or prodrug thereof to a patient in need of such treatment.

In another embodiment, the present invention includes a method of treatment of a disease selected from the group consisting of proliferative inflammatory diseases, allergic diseases, obstructive airways diseases, diseases related to transplant rejection and diseases that respond to inhibition of mTOR, comprising administering a therapeutically effective amount of at least one compound of Formula I or a pharmaceutically acceptable salt, solvate, ester or prodrug thereof.

In another embodiment, the present invention includes a compound from the group of compounds listed above or a pharmaceutically acceptable salt, solvate, ester or prodrug thereof exhibiting mTOR inhibition which is at least five-fold the inhibition of CDK2 or CHK-1 by said compound.

In another embodiment, the present invention includes a compound from the group of compounds listed above or a pharmaceutically acceptable salt, solvate, ester or prodrug thereof exhibiting mTOR inhibition which is at least ten-fold the inhibition of CDK2 or CHK-1 by said compound.

In another embodiment, the present invention includes a compound from the group of compounds listed above or a pharmaceutically acceptable salt, solvate, ester or prodrug thereof exhibiting mTOR inhibition which is at least fifty-fold the inhibition of CDK2 or CHK-1 by said compound.

The compounds of this invention can be used to inhibit the following kinases: ABL1, ABL2, AFK, ALK, AMPK, ATM, ATR, Aurora A, Aurora B, Axl, BCKDK, BLK, BMPR1B, BMX, Brk, BRSK1, BTK, CaM-KIalpha, CaM-KIIalpha, CaM-KIV, CaM-KKalpha, CaM-KKbeta, CCDPK, CCRK, CDK1, CDK11, CDK2, CDK4, CDK5, CDK6, CDK7, CDK9, Chak1, CHK1, CHK2, CK1 alpha, CK1 delta, CDk1 epsilon, CDK2 beta, CLK1, CSF1R, Csk, DAPK1, DAPK2, DAPK3, DCAMKL1, DNA-PK, DYRK1A, DYRK1B, DYRK2, DYRK3, eEF2K, Eg3, EGFR, EIF2AK2, EphA2, EphA3, EphA4, EphA8, EphB1, EphB2, EphB3, EphB5, ErbB2, FAK, Fer, Fes, FGFR1, FGFR3, FGFR4, Fgr, FLT1, FLT3, FLT4, Fyn, GRK-1, GRK-2, GRk-3, GRK-4, GRK-5, GRK-6, GSK-3alpha, GSK-3beta, HCK, HIPK2, HIPK3, HRI, ICK, IGF1R, IKK-alpha, IKK-beta, IKK-epsilon, ILK, InsR, IPL1, IRAK1, IRAK4, ITK, JAK1, JAK2, JAK3, JNK1, JNK2, JNK3, KDR, KIS, Kit, KSR1, Lck, LIMK1, LIMK2, LKB1, LOK, Lyn, MAP2K1, MAP2K2, MAP2K3, MAP2K4, MAP2K6, MAP2K7, MAP3K1, MAP3K11, MAP3K14, MAP3K5, MAP3K7, MAP3K8, MAP4K1, MAP4K2, MAP4K4, MAPK1, MAPK10, MAPK11, MAPK12, MAPK13, MAPK14, MAPK3, MAPK4, MAPK6, MAPK7, MAPK8, MAPK9, MAPKAPK2, Mer, Met, MHCK, MLCK, Mnk1, Mnk2, MOS, MRCKa, MST1, MST3, NDR1, NDR2, NEK1, NEK2, NEK6, NEK9, NLK, NuaK1, p37, p38, p70S6K, p70S6 Kb, PAK1, PAK2, PAK2, PAK3, PAK5, PAK6, PASK, P-CIP2, PCTAIRE1, PDGFR alpha, PDGFR beta, PDHK1, PDHK2, PDHK3, PDHK4, PDK-1, PDK-2, PHK, PIK3CA, PIK3CB, PIK3CD, PIK3CG, Pim-1, PKA alpha, PKB beta, PKC alpha, PKC beta, PKC delta, PKC epsilon, PKC eta, PKC gamma, PKC iota, PKC theta, PKC zeta, PKD1, PKD2, PKD3, PKG1/cGK-I, PKG1/cGK-II, PKN1, PLK1, PLK2, PLK3, PRP4, PYK2, RAF1, Ret, ROCK1, ROCK2, Ron, RPL10, RSK-1, RSK-2, RSK-3, RSK-5, SDK1, SIK, Sky, Src, STLK3, Syk, TBK1, Tec, TESK1, TESK2, TGFbR1, TGFbR2, Tie1, Tie2, Titin kinase, TNK2, TRKA, TRB, tropomyosin kinase, TSSK3, TXK, Tyk2, VRK1, Wee1, Wnk1, Yes, and ZAP70.

As used above, and throughout this disclosure, the following terms, unless otherwise indicated, shall be understood to have the following meanings, including any possible substitutions of the stated groups or moieties:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more, lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Bridged cyclic ring" is a hydrocarbon ring such as cycloalkyl, cyclenyl, or aryl or heteroatom containing ring such as, heterocyclyl, heterocyclenyl, or heteroaryl as described herein, that contains a bridge, which is a valence bond or an atom or an unbranched chain of atoms connecting two different parts of the ring. The two tertiary carbon atoms connected through the bridge are termed "bridgeheads".

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-Limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, amide, —CHO, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogen on two adjacent carbon atoms (one H on each carbon) on a ring system. Examples of such moiety are methylene dioxy, ethylenedioxy, —C(CH$_3$)$_2$— and the like which form moieties such as, for example:

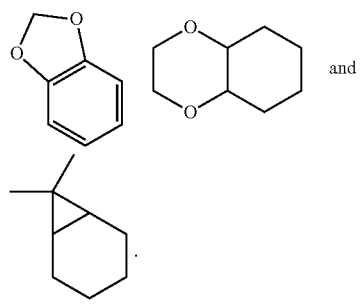

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogen on the same carbon atom on a ring system. Example of such moiety is pyrrolidone:

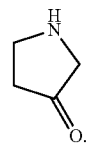

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogen on the same carbon atom on a ring system. Example of such moiety is pyrrolidinone:

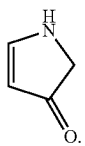

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

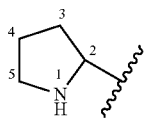

there is no —OH attached directly to carbons marked 2 and 5.

It should also be noted that tautomeric forms such as, for example, the moieties:

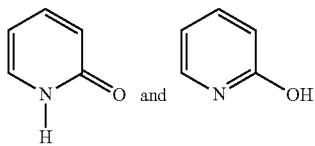 [SMILES: O=c1cccc[nH]1 ; "and" ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Spiro ring systems" have two or more rings linked by one common atom. Preferred spiro ring systems include spiroheteroaryl, spiroheterocyclenyl, spiroheterocyclyl, spirocycloalkyl, spirocyclenyl, and spiroaryl. The spiro ring systems can be optionally substituted by one or more ring system substituents, wherein "ring system substituent" is as defined above. Non-limiting examples of suitable spiro ring systems include

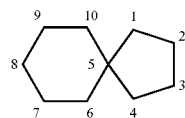

spiro[4.5]decane,

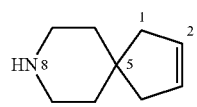

8-azaspiro[4.5]dec-2-ene, and

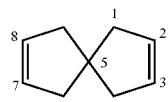

spiro[4.4]nona-2,7-diene.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogen on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in The present invention, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of the present invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$) alkyl, and the like.

Similarly, if a compound of the present invention contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of the present invention incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al., *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the present invention can form salts which are also within the scope of this invention. Reference to a compound of the present invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the present invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the The present invention may be formed, for example, by reacting a compound of the present invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of the present invention, and salts, solvates, esters and prodrugs thereof, may exist in their tautomeric form (for example, as an amide or imino ether). All such tautomeric forms are contemplated herein as part of the present invention.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the present invention may be atropisomers (e.g., substituted biaryls) and are considered as part of this invention. Enantiomers can also be separated by use of chiral HPLC column.

It is also possible that the compounds of the present invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the present invention incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of the present invention, and of the salts, solvates, esters and prodrugs of the compounds of the present invention, are intended to be included in the present invention.

The compounds according to the invention have pharmacological properties; in particular, the compounds of the present invention can be inhibitors, regulators or modulators of mTOR protein kinases.

The compounds of the present invention can be inhibitors of protein kinases such as, for example, the inhibitors of the mTOR. Preferred compounds can exhibit $IC_{50}$ values of less than about 5 μm, preferably about 0.001 to about 1.0 μm, and more preferably about 0.001 to about 0.1 μm. The assay methods are described in the Examples set forth below.

The compounds of the present invention can be useful in the therapy of proliferative diseases such as cancer, autoimmune diseases, viral diseases, fungal diseases, neurological/neurodegenerative disorders, arthritis, inflammation, antiproliferative (e.g., ocular retinopathy), neuronal, alopecia and cardiovascular disease. Many of these diseases and disorders are listed in U.S. Pat. No. 6,413,974, incorporated by reference herein.

More specifically, the compounds of the present invention can be useful in the treatment of a variety of cancers, including (but not limited to) the following: tumor of the bladder, breast (including BRCA-mutated breast cancer, colorectal, colon, kidney, liver, lung, small cell lung cancer, non-small cell lung cancer, head and neck, esophagus, bladder, gall bladder, ovary, pancreas, stomach, cervix, thyroid, prostate, and skin, including squamous cell carcinoma;

leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma;

chronic lymphocytic leukemia ("CLL"), acute and chronic myelogenous leukemia, myelodysplastic syndrome and promyelocytic leukemia;

fibrosarcoma, rhabdomyosarcoma;

head and neck, mantle cell lymphoma, myeloma;

astrocytoma, neuroblastoma, glioma, glioblastoma, malignant glial tumors, astrocytoma, hepatocellular carcinoma, gastrointestinal stromal tumors ("GIST") and schwannomas;

melanoma, multiple myeloma, seminoma, teratocarcinoma, osteosarcoma, xenoderma pigmentosum, keratoctanthoma, thyroid follicular cancer, endometrial cancer, gastrointestinal tract cancer and Kaposi's sarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of the present invention may induce or inhibit apoptosis. The apoptotic response is aberrant in a variety of human diseases. Compounds of the present invention, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of the present invention, as inhibitors of kinases, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of the present invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of the present invention may also be useful in inhibiting tumor angiogenesis and metastasis.

Another aspect of this invention is a method of treating a mammal (e.g., human) having a disease or condition associated with mTOR kinases by administering a therapeutically effective amount of at least one compound of the present invention, or a pharmaceutically acceptable salt, solvate, ester or prodrug of said compound to the mammal.

A preferred dosage is about 0.001 to 1000 mg/kg of body weight/day of the compound of the present invention. An especially preferred dosage is about 0.01 to 25 mg/kg of body weight/day of a compound of the present invention, or a pharmaceutically acceptable salt, solvate, ester or prodrug of said compound. The compounds of this invention may also be useful in combination (administered together or sequentially) with one or more of anti-cancer treatments such as radiation therapy, and/or one or more anti-cancer agents different from the compound of the present invention. The compounds of the present invention can be present in the same dosage unit as the anti-cancer agent or in separate dosage units.

Another aspect of the present invention is a method of treating one or more diseases associated with a mTOR protein kinase, comprising administering to a mammal in need of such treatment: an amount of a first compound, which is a compound of the present invention, or a pharmaceutically acceptable salt, solvate, ester or prodrug thereof; and an amount of at least one second compound, the second compound being an anti-cancer agent different from the compound of the present invention, wherein the amounts of the first compound and the second compound result in a therapeutic effect.

Non-limiting examples of suitable anti-cancer agent is selected from the group consisting of a Cytostatic agent, Cisplatin, Deforolimus (described in PCT publication No. 2003/064383), Doxorubicin, liposomal doxorubicin (e.g., Caelyx®, Myocet®, Doxil®), Taxotere, Taxol, Etoposide, Irinotecan, Camptostar, Topotecan, Paclitaxel, Docetaxel, Epothilones, Tamoxifen, 5-Fluorouracil, Methoxtrexate, Temozolomide, cyclophosphamide, SCH 66336, R115777®, L778,123®, BMS 214662®, Iressa®, Tarceva®, Antibodies to EGFR, antibodies to IGFR (including, for example, those published in US 2005/0136063 published Jun. 23, 2005), ESK inhibitors, KSP inhibitors (such as, for example, those published in WO 2006/098962 and WO 2006/098961; ispinesib, SB-743921 from Cytokinetics), Centrosome associated protein E ("CENP-E") inhibitors (e.g., GSK-923295), Gleevec®, Intron, Ara-C, Adriamycin, Cytoxan, Gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Oxaliplatin, Leucovirin, ELOXATIN™, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, bortezomib ("Velcade"), Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225®, Satriplatin, mylotarg, Avastin, Rituxan, Panitubimab, Sutent, Sorafinib, Sprycel (dastinib), Nilotinib, Tykerb (Lapatinib) and Campath.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of the present invention may also be administered sequentially with known anticancer or cytotoxic agents when a combination formulation is inappropriate. The invention is not limited in the sequence of administration; compounds of the present invention may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of the present invention, or a pharmaceutically acceptable salt, solvate, ester or prodrug thereof, and an amount of one or more anti-cancer treatments and anti-cancer agents listed above wherein the amounts of the compounds/treatments result in desired therapeutic effect.

Another aspect of the present invention is a method of inhibiting one or more mTOR protein kinases in a patient in need thereof, comprising administering to the patient a therapeutically effective amount of at least one compound of the present invention or a pharmaceutically acceptable salt, solvate, ester or prodrug thereof.

Another aspect of the present invention is a method of treating, or slowing the progression of, a disease associated with one or more mTOR protein kinases in a patient in need thereof, comprising administering a therapeutically effective amount of at least one compound of the present invention or a pharmaceutically acceptable salt, solvate, ester or prodrug thereof.

Yet another aspect of the present invention is a method of treating one or more diseases associated with mTOR protein kinases, comprising administering to a mammal in need of such treatment an amount of a first compound, which is a compound of the present invention, or a pharmaceutically acceptable salt, solvate, ester or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with one or more mTOR protein kinases in a patient in need thereof, comprising administering a therapeutically effective amount of a pharmaceutical composition comprising in combination at least one pharmaceutically acceptable carrier and at least one compound according to The present invention, or a pharmaceutically acceptable salt, solvate, ester or prodrug thereof.

In the above methods, the mTOR protein kinases to be inhibited can exist in two complexes, mTORC1 and mTORC2.

ERK inhibitors (i.e., ERK1 inhibitors and/or ERK2 inhibitors) include but are not limited to the following compounds:

a) Formula II

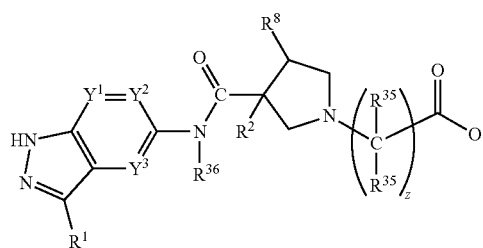

II or the pharmaceutically acceptable salts, esters and solvates thereof, wherein:

$Y^1$, $Y^2$, and $Y^3$ are each independently selected from the group consisting of: —CH═, —N═ and —$CR^9$═;

z is 1 to 3;

Q is a substituent selected from the group consisting of:

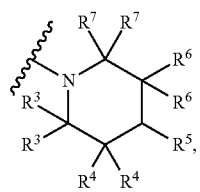

(2.1)

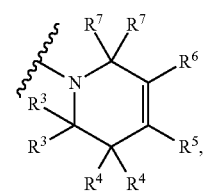

(2.2)

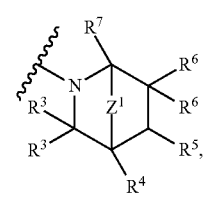

(2.3)

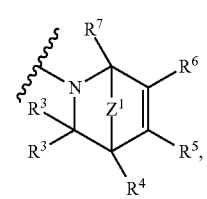

(2.4)

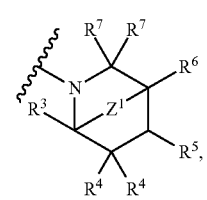

(2.5)

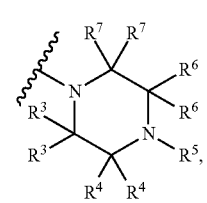

(2.6)

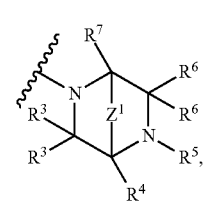

(2.7)

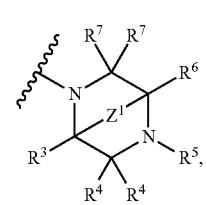

(2.8)

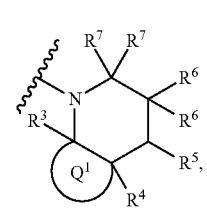

(2.9)

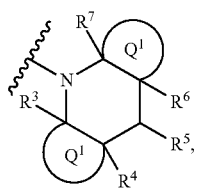 (2.10)

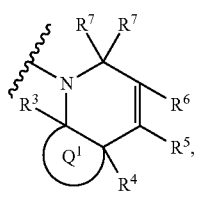 (2.11)

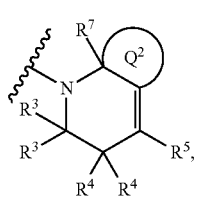 (2.12)

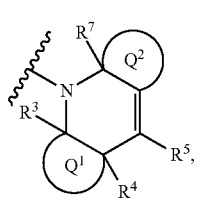 (2.13)

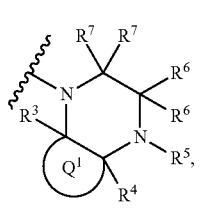 (2.14)

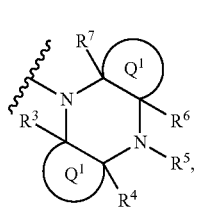 (2.15)

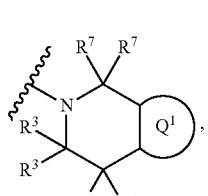 (2.16)

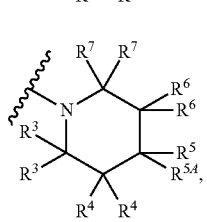 (2.17)

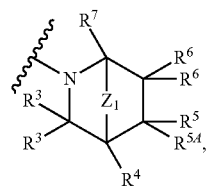 (2.18)

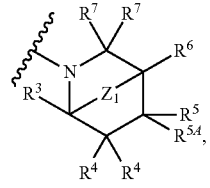 (2.19)

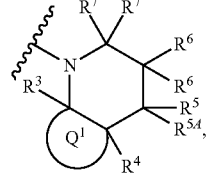 (2.20)

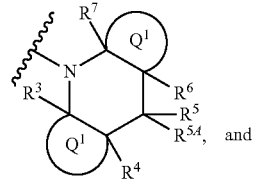 (2.21)

and

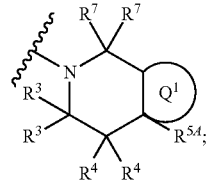 (2.22)

Each $Q^1$ represents a ring independently selected from the group consisting of: cycloalkyl, substituted cycloalkyl, heterocycloalkyl, substituted heterocycloalkyl, aryl, substituted aryl, heteroaryl, and substituted heteroaryl, wherein said substituted rings are substituted with 1 to 3 substituents independently selected from the group consisting of: halo and the $R^{10}$ moieties; provided that when $Q^1$ is aryl, heteroaryl, substituted aryl or substituted heteroaryl then the carbon atoms at the ring junction are not substituted;

$Q^2$ represents a ring selected from the group consisting of: cycloalkyl, substituted cycloalkyl, heterocycloalkyl, and substituted heterocycloalkyl, wherein said substituted rings are substituted with 1 to 3 substituents independently selected from the group consisting of: the $R^{10}$ moieties;

$Z^1$ represents —$(C(R^{24})_2)_w$— wherein each $R^{24}$ is independently selected from the group consisting of: H, alkyl and F, and wherein w is 1, 2 or 3;

$Z^2$ is selected from the group consisting of: —$N(R^{44})$—, —O— and —$C(R^{46})_2$—;

m is 1 to 6;
n is 1 to 6;
p is 0 to 6;
t is 0, 1, or 2;
$R^1$ is selected from the group consisting of:
(1) —CN,
(2) —NO$_2$, (3) —OR$^{10}$,
(4) —SR$^{10}$,
(5) —N(R$^{10}$)$_2$,
(6) R$^{10}$,
(7) —C(O)R$^{10}$,
(8) —(C(R$^{30}$)$_2$)$_n$—NR$^{32}$—C(O)—R$^{10}$,
(9) —(C(R$^{30}$)$_2$)$_n$—NR$^{32}$—S(O)$_t$—R$^{10}$,
(10) —(C(R$^{30}$)$_2$)$_n$—NR$^{32}$—C(O)—N(R$^{32}$)—R$^{10}$,

(11)
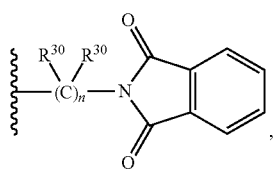

(12) —CF$_3$,
(13) —C(O)OR$^{10}$,
(14) —(C(R$^{30}$)$_2$)$_n$R$^{13}$ (e.g., —(CH$_2$)$_n$R$^{13}$),
(15) alkenyl,
(16) —NR$^{32}$—C(O)—R$^{14}$,

(17)
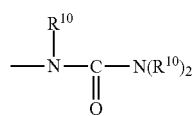

wherein each R$^{10}$ is independently selected,

(18)
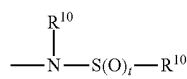

wherein each R$^{10}$ is independently selected,

(19)
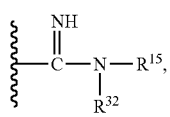

(20) —C(O)—NR$^{32}$—(C(R$^{30}$)$_2$)$_p$—OR$^{10}$,
(21) —C(O)N(R$^{10}$)$_2$ wherein each R$^{10}$ is independently selected,
(22) —C(O)—NR$^{32}$—C(R$^{13}$)$_3$,
(23) —C(O)—NR$^{32}$—(C(R$^{30}$)$_2$)$_n$—C(O)—N(R$^{10}$)$_2$,
(24) heterocycloalkenyl,

(25)
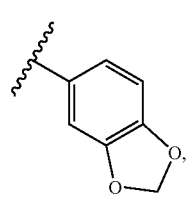

and
(26) arylalkenyl-;

R$^2$ is selected from the group consisting of:
(1) H,
(2) —CN,
(3) halo,
(4) alkyl,
(5) substituted alkyl wherein said substituted alkyl is substituted with 1 to 3 substitutents selected from the group consisting of: (a) —OH, (b) —O-alkyl (e.g., —O—(C$_1$-C$_3$alkyl), (c) —O-alkyl substituted with 1 to 3 F atoms, and (d) —N(R$^{40}$)$_2$ wherein each R$^{40}$ is independently selected from the group consisting of: (i) H, (ii) C$_1$-C$_3$ alkyl, (iii) —CF$_3$, and (e) halo,
(6) alkynyl,
(7) alkenyl,
(8) —(CH$_2$)$_m$R$^{11}$,
(9) —N(R$^{26}$)$_2$,
(10) —OR$^{23}$,
(11) —N(R$^{26}$)C(O)R$^{42}$,
(12) cycloalkyl,
(13) cycloalkylalkyl,

(14)
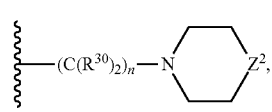

(15) —O-(substituted alkyl) wherein said substituted alkyl is substituted with 1 to 3 F atoms,
(16) —S(O)$_t$-alkyl,
(17) —C(O)-alkyl,

(18)
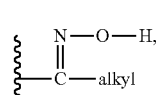

(19)
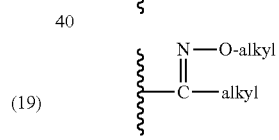

wherein each alkyl is independently selected,

(20)
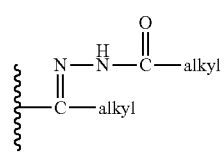

which each alkyl is independently selected,

(21)
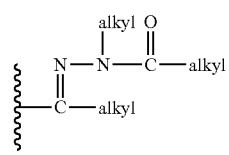

wherein each alkyl is independently selected,

(22) —N($R^{48}$)—C(O)—$R^{48}$ wherein each $R^{48}$ is independently selected from the group consisting of: H and alkyl, and

(23) —C(O)-alkyl, such as, for example, —C(O)—($C_1$-$C_6$ alkyl), such as, for example, —C(O)$CH_3$;

each $R^3$, $R^4$, $R^5$, $R^6$ and $R^7$ is independently selected from the group consisting of:
(1) H,
(2) alkenyl,
(3) substituted alkenyl,
(4) alkyl,
(5) substituted alkyl,
(6) cycloalkyl,
(7) substituted cycloalkyl,
(8) cycloalkylalkyl-,
(9) substituted cycloalkylalkyl-,
(10) heterocycloalkyl,
(11) substituted heterocycloalkyl,
(12) heterocycloalkylalkyl-,
(13) substituted heterocycloalkylalkyl-,
(14) —C(O)$R^{10}$,
(15) arylheteroaryl-,
(16) substituted arylheteroaryl-,
(17) heteroarylaryl-,
(18) substituted heteroarylaryl-,
(19) aryl,
(20) substituted aryl,
(21) heteroaryl,
(22) substituted heteroaryl,
(23) heteroarylheteroaryl-,
(24) substituted heteroarylheteroaryl-,
(25) arylaminoheteroaryl-,
(26) substituted arylaminoheteroaryl-,
(27) arylalkynyl-,
(28) substituted arylalkynyl-,
(29) heteroarylalkynyl-,
(30) substituted heteroarylalkynyl-, and
(31) benzoheteroaryl, wherein said $R^3$, $R^4$, $R^5$, $R^6$ and $R^7$ substituted groups (7), (9), (11), (13), (16), (18), (20), (22), (24), (26), (28) and (30) are substituted with 1 to 3 substituents independently selected from the group consisting of: —$NH_2$, —$NHR^{20}$, —N($R^{20}$)$_2$ wherein each $R^{20}$ is independently selected, alkyl, alkenyl, halo, —C(O)—NH—$R^{28}$, —C(O)$OR^{28}$, —C(O)$R^{28}$, and —$OR^{20}$, and wherein said $R^3$, $R^4$, $R^5$, $R^6$ and $R^7$ substituted groups (3) and (5) are substituted with 1 to 3 substituents independently selected from the group consisting of: —$NH_2$, halo (e.g., F, Cl and Br, and in another example F), —C(O)—NH—$R^{28}$ (e.g., —C(O)—NH—$CH_3$), —C(O)$OR^{28}$ (e.g., —C(O)O$C_2H_5$), and —C(O)$R^{28}$ (e.g., —C(O)$CH_3$);

$R^{54}$ is selected from the group consisting of: halo, —OH, alkyl, and —O-alkyl;

$R^8$ is selected from the group consisting of: H, —OH, —N($R^{10}$)$_2$, —$NR^{10}$C(O)$R^{12}$, and alkyl;

each $R^9$ is independently selected from the group consisting of: halogen, —CN, —$NO_2$, —$OR^{10}$, —$SR^{10}$, —N($R^{10}$)$_2$, and $R^{10}$;

each $R^{10}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkyl heteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl-, substituted alkylaryl-, heterocycloalkenyl, and substituted heterocycloalkenyl, and wherein:

said $R^{10}$ substituted alkyl is substituted with 1 to 3 substituents independently selected from the group consisting of: —$NH_2$, —$NHR^{20}$, —$NO_2$, —CN, —$OR^{26}$, halo, —C(O)—NH—$R^{26}$, —C(O)$OR^{26}$, and —C(O)$R^{26}$, and said $R^{10}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —$NH_2$, (2) —$NO_2$, (3) —CN, (4) —OH, (5) —$OR^{20}$, (6) —$OCF_3$, (7) alkyl substituted with 1 to 3 independently selected halo atoms, (8) —C(O)$R^{38}$, (9) alkyl, (10) alkenyl, (11) halo, (12) —C(O)—NH—$R^{26}$, (13) —C(O)$OR^{38}$, (14) —C(O)—$NR^{32}$—(C($R^{30}$)$_2$)$_n$—N($R^{38}$)$_2$, (15) —S(O)$_r$$R^{38}$, (16) —C(O)—$NR^{32}$—$R^{38}$, (17) —$NR^{32}$—C(O)—$R^{38}$,

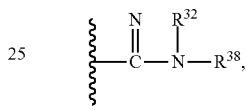

(18)

(19) —$NHR^{20}$, (20) cycloalkyl, (21) —O-alkyl-O—$R^{20}$, (22) hydroxyalkyl, (23) —N($R^{20}$)$_2$ wherein each $R^{20}$ is independently selected, (24) -alkyl-$OR^{20}$, (25) —O-alkyl-OH, (26) —NH(hydroxyalkyl), and (27) oxazolidinone;

$R^{11}$ is selected from the group consisting of: F, —OH, —CN, —$OR^{10}$, —$NHNR^1R^{10}$, —$SR^{10}$ and heteroaryl;

$R^{12}$ is selected from the group consisting of: alkyl, aryl, heteroaryl, cycloalkyl, cycloalkylalkyl, heterocycloalkyl and heterocycloalkylalkyl;

$R^{14}$ is selected from the group consisting of: alkyl, aryl, heteroaryl, cycloalkyl, cycloalkylalkyl-, heterocycloalkyl, alkylheterocycloalkyl, heterocycloalkylalkyl-, alkylheteroaryl- and alkylaryl-;

$R^{15}$ is selected from the group consisting of: H, —OH, alkyl, aryl, heteroaryl, cycloalkyl, cycloalkylalkyl-, heterocycloalkyl and heterocycloalkylalkyl-, alkylheteroaryl- and alkylaryl-;

$R^{20}$ represents alkyl;

$R^{23}$ is selected from the group consisting of: H, alkyl, aryl, cycloalkyl, and cycloalkylalkyl-;

each $R^{26}$ is independently selected from the group consisting of: H and alkyl;

$R^{28}$ is alkyl;

each $R^{30}$ is independently selected from the group consisting of: H, alkyl, and F;

each $R^{32}$ is independently selected from the group consisting of: H and alkyl, and wherein each $R^{32}$ is generally H;

each $R^{35}$ is independently selected from the group consisting of: H and $C_1$ to $C_6$ alkyl;

$R^{36}$ is selected from the group consisting of: H, alkyl, and —O-alkyl;

each $R^{38}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said $R^{38}$ substituted alkyl is substituted with 1 to 3 substituents independently selected from the group consisting of: —$NH_2$, —$NO_2$, —CN, —$OR^{26}$, halo, —C(O)—NH—$R^{28}$, —C(O)$OR^{28}$, and —C(O)$R^{28}$, and said $R^{38}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —$NH_2$, (2) —$NO_2$, (3) —CN, (4) —OH, (5) —$OR^{20}$, (6) —$OCF_3$, (7) —$CF_3$, (8) —C(O)$R^{26}$, (9) alkyl, (10) alkenyl, (11) halo, (12) —C(O)—NH—$R^{26}$, (13) —C(O)$OR^{26}$, (14) —C(O)—$NR^{32}$—$(C(R^{30})_2)_n$—$N(R^{26})_2$, (15) —S(O)$_rR^{26}$, (16) —C(O)N($R^{32}$)($R^{26}$), (17) —$NR^{32}$C(O)$R^{26}$, (18)

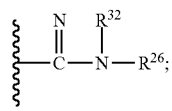

and

(19) —$NHR^{20}$;

$R^{42}$ is selected from the group consisting of: alkyl, aryl, heteroaryl, and cycloalkyl;

$R^{44}$ is selected from the group consisting of: H, alkyl, cycloalkyl, and cycloalkylalkyl;

Each $R^{46}$ is independently selected from the group consisting of: H, alkyl, cycloalkyl, and cycloalkylalkyl; and provided that:

(1) $Q^1$ is a substituted ring wherein at least one substitutent is halo; and/or (2) $R^2$ is substituted alkyl wherein said substituent is —$OCH_3$, or $R^2$ is selected from the group consisting of: —$CH_2OH$ and —$CH_2OCH_3$; and/or (3) at least one of $R^3$, $R^4$, $R^5$, $R^6$, and $R^7$ is:

(i) selected from the group consisting of: oxadiazolylphenyl-, pyridazinylphenyl-, pyrimidinylpyrazinyl-, substituted oxadiazolylphenyl-, substituted pyridazinylphenyl-, substituted pyrimidinylpyrazinyl-, and benzoheteroaryl; or (ii) selected from the group consisting of:
   (a) substituted cycloalkyl,
   (b) substituted cycloalkylalkyl-,
   (c) substituted heterocycloalkyl,
   (d) substituted heterocycloalkylalkyl-,
   (e) substituted arylheteroaryl-,
   (f) substituted heteroarylaryl-,
   (g) substituted aryl,
   (h) substituted heteroaryl,
   (i) substituted heteroarylheteroaryl-,
   (j) substituted arylaminoheteroaryl-,
   (k) substituted arylalkynyl-, and
   (l) substituted heteroarylalkynyl-, and wherein at least one substitutent on at least one at least one of said (ii)(a) to (ii)(l) $R^3$, $R^4$, $R^5$, $R^6$, or $R^7$ group is selected from the group consisting of: —$NHR^{20}$, —$N(R^{20})_2$ (wherein each $R^{20}$ is independently selected), and —$OR^{20}$; and/or (4) $R^{54}$ is alkyl; and/or (5) $R^{10}$ is a substituted aryl, and at least one substituent is selected from the group consisting of:

(a) —S(O)$_rR^{38}$ wherein $R^{38}$ is isopropyl,
(b) —O-alkyl-O—$R^{20}$,
(c) hydroxyalkyl,
(d) —N($R^{20}$)$_2$,
(e) -alkyl-$OR^{20}$,
(f) —O-alkyl-OH,
(g) —NH(hydroxyalkyl), and
(h) oxazolidinone; and/or (6) $R^{20}$ is isopropyl;

Formula II is described in PCT publication No. 2007/070398, herein incorporated by reference;

b) Formula III

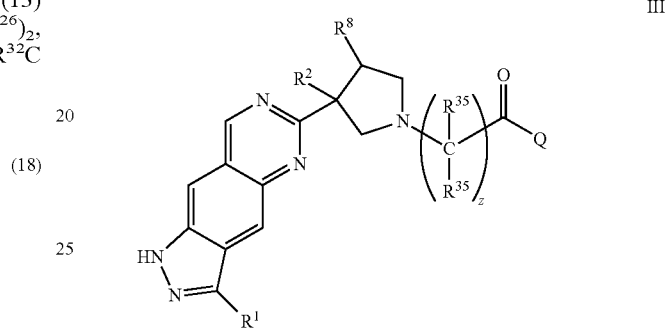

III or the pharmaceutically acceptable salts, esters or solvates thereof, wherein:

z is 1 to 3;

Q is a substituent selected from the group consisting of:

(2.1)

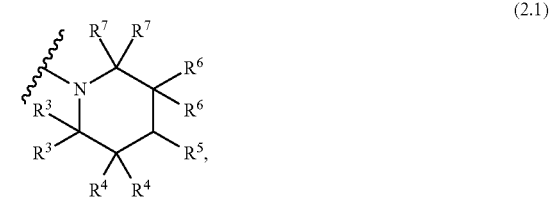

(2.2)

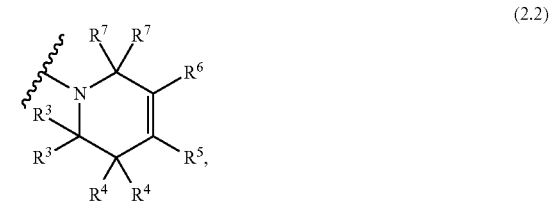

(2.3)

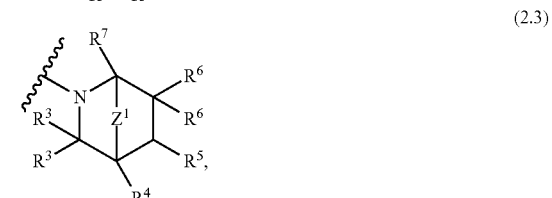

(2.4)

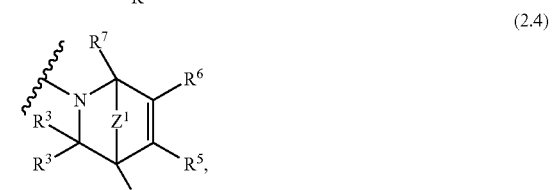

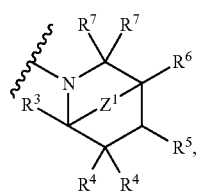 (2.5)
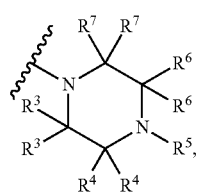 (2.6)
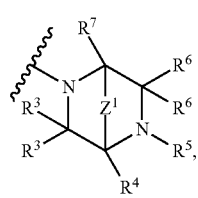 (2.7)
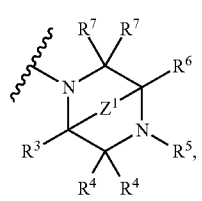 (2.8)
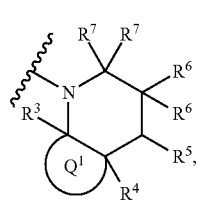 (2.9)
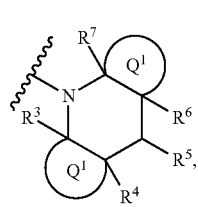 (2.10)
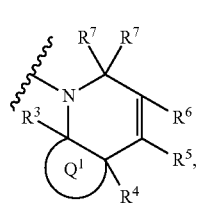 (2.11)
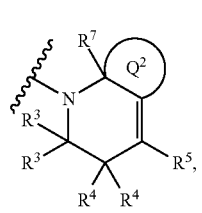 (2.12)
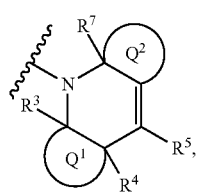 (2.13)
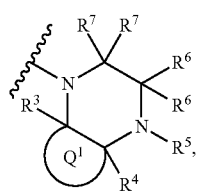 (2.14)
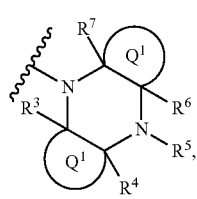 (2.15)
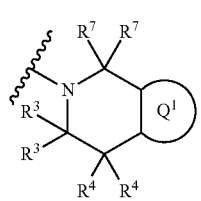 (2.16)
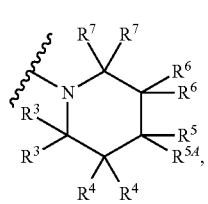 (2.17)
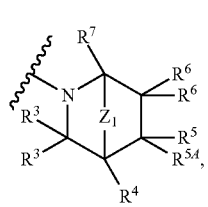 (2.18)
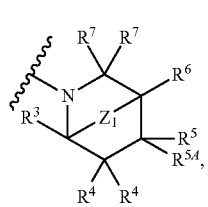 (2.19)
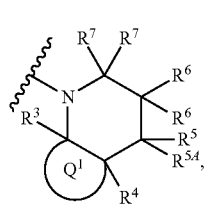 (2.20)

-continued

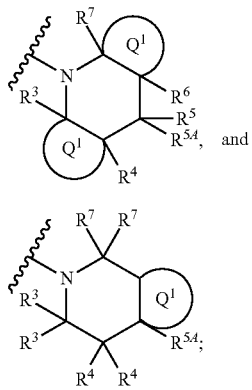

(2.21)

(2.22)

Each $Q^1$ represents a ring independently selected from the group consisting of: cycloalkyl, substituted cycloalkyl, heterocycloalkyl, substituted heterocycloalkyl, aryl, substituted aryl, heteroaryl, and substituted heteroaryl, wherein said substituted rings are substituted with 1 to 3 substituents independently selected from the group consisting of: halo and the $R^{10}$ moieties; provided that when $Q^1$ is aryl, heteroaryl, substituted aryl or substituted heteroaryl then the carbon atoms at the ring junction are not substituted;

$Q^2$ represents a ring selected from the group consisting of: cycloalkyl, substituted cycloalkyl, heterocycloalkyl, and substituted heterocycloalkyl, wherein said substituted rings are substituted with 1 to 3 substituents independently selected from the group consisting of: the $R^{10}$ moieties;

$Z^1$ represents $-(C(R^{24})_2)_w-$ wherein each $R^{24}$ is independently selected from the group consisting of: H, alkyl and F, and wherein w is 1, 2 or 3;

$Z^2$ is selected from the group consisting of: $-N(R^{44})-$, $-O-$ and $-C(R^{46})_2-$;

m is 1 to 6;
n is 1 to 6;
p is 0 to 6;
t is 0, 1, or 2;

$R^1$ is selected from the group consisting of:
(1) —CN,
(2) —NO$_2$,
(3) —OR$^{10}$,
(4) —SR$^{10}$,
(5) —N(R$^{10}$)$_2$,
(6) R$^{10}$,
(7) —C(O)R$^{10}$,
(8) —(C(R$^{30}$)$_2$)$_n$—NR$^{32}$—C(O)—R$^{10}$, wherein in one example n is 1, each R$^{30}$ is H, R$^{32}$ is H, and R$^{10}$ is selected from the group consisting of: cycloalkyl and alkyl,
(9) —(C(R$^{30}$)$_2$)$_n$—NR$^{32}$—S(O)$_t$—R$^{10}$,
(10) —(C(R$^{30}$)$_2$)$_n$—NR$^{32}$—C(O)—N(R$^{32}$)—R$^{10}$, (11)

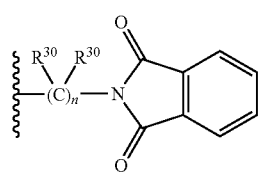

(12) —CF$_3$,
(13) —C(O)OR$^{10}$,

(14) —(C(R$^{30}$)$_2$)$_n$R$^{13}$,
(15) alkenyl (e.g., —CH=CHCH$_3$),
(16) —NR$^{32}$—C(O)—R$^{14}$,

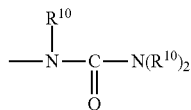

(17)

wherein each $R^{13}$ is independently selected,

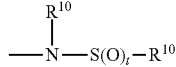

(18)

wherein each $R^{13}$ is independently selected,

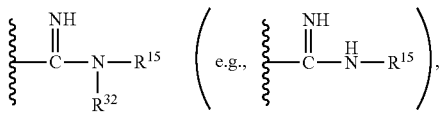

(19)

(20) —C(O)—NR$^{32}$—(C(R$^{30}$)$_2$)$_p$—OR$^{13}$,
(21) —C(O)N(R$^{10}$)$_2$ wherein each $R^{10}$ is independently selected,
(22) —C(O)—NR$^{32}$—C(R$^{18}$)$_3$,
(23) —C(O)—NR$^{32}$—(C(R$^{30}$)$_2$)$_n$—C(O)—N(R$^{10}$)$_2$,
(24) heterocycloalkenyl, such as, for example:

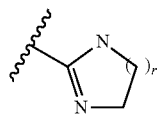

wherein r is 1 to 3,

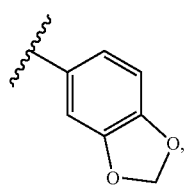

(25)

(26) arylalkenyl-, and
(27) halo;

$R^2$ is selected from the group consisting of:
(1) H,
(2) —CN,
(3) halo,
(4) alkyl,
(5) substituted alkyl wherein said substituted alkyl is substituted with 1 to 3 substitutents selected from the group consisting of: (a) —OH, (b) —O-alkyl, (c) —O-alkyl substituted with 1 to 3 F atoms, and (d) —N(R$^{40}$)$_2$ wherein each $R^{40}$ is independently selected from the group consisting of: (i) H, (ii) $C_1$-$C_3$ alkyl, (iii) —$CF_3$, and (e) halo,
(6) alkynyl,
(7) alkenyl,
(8) —$(CH_2)_m R^{11}$,
(9) —$N(R^{26})_2$,
(10) —$OR^{23}$,
(11) —$N(R^{26})C(O)R^{42}$,
(12) cycloalkyl,
(13) cycloalkylalkyl,

(14) 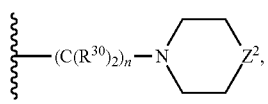

(15) —O-(substituted alkyl) wherein said substituted alkyl is substituted with 1 to 3 F atoms,
(16) —$S(O)_t$-alkyl,
(17) —C(O)-alkyl,

(18) 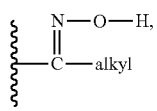

(19) 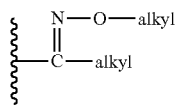

wherein each alkyl is independently selected,

(20) 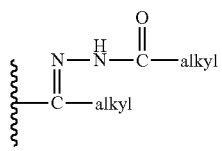

wherein each alkyl is independently selected,

(21) 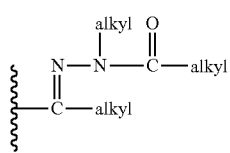

wherein each alkyl is independently selected,
(22) —$N(R^{48})$—C(O)—$R^{48}$ wherein each $R^{48}$ is independently selected from the group consisting of: H and alkyl, and
(23) —C(O)-alkyl;
each $R^3$, $R^4$, $R^6$, $R^6$ and $R^7$ is independently selected from the group consisting of:
(1) H,
(2) alkenyl,
(3) substituted alkenyl,
(4) alkyl,
(5) substituted alkyl,
(6) cycloalkyl,
(7) substituted cycloalkyl,
(8) cycloalkylalkyl-,
(9) substituted cycloalkylalkyl-,
(10) heterocycloalkyl,
(11) substituted heterocycloalkyl,
(12) heterocycloalkylalkyl-,
(13) substituted heterocycloalkylalkyl-,
(14) —$C(O)R^{10}$,
(15) arylheteroaryl-,
(16) substituted arylheteroaryl-,
(17) heteroarylaryl-,
(18) substituted heteroarylaryl-,
(19) aryl,
(20) substituted aryl,
(21) heteroaryl,
(22) substituted heteroaryl,
(23) heteroarylheteroaryl-,
(24) substituted heteroarylheteroaryl-,
(25) arylaminoheteroaryl-,
(26) substituted arylaminoheteroaryl-,
(27) arylalkynyl-,
(28) substituted arylalkynyl-,
(29) heteroarylalkynyl-,
(30) substituted heteroarylalkynyl-,
(31) benzoheteroaryl;
wherein said $R^3$, $R^4$, $R^5$, $R^6$ and $R^7$ substituted groups (7), (9), (11), (13), (16), (18), (20), (22), (24), (26), (28) and (30) are substituted with 1 to 3 substituents independently selected from the group consisting of: —$NH_2$, —$NHR^{20}$, —$N(R^{20})_2$ wherein each $R^{20}$ is independently selected, alkyl, alkenyl, halo, —C(O)—NH—$R^{28}$, —$C(O)OR^{28}$, —$C(O)R^{28}$, and —$OR^{20}$,
wherein said $R^3$, $R^4$, $R^5$, $R^6$ and $R^7$ substituted groups (3) and (5) are substituted with 1 to 3 substituents independently selected from the group consisting of: —$NH_2$, halo, —C(O)—NH—$R^{28}$, —$C(O)OR^{28}$, and —$C(O)R^{28}$;
$R^{5A}$ is selected from the group consisting of: halo, —OH, alkyl, —O-alkyl;
$R^8$ is selected from the group consisting of: H, —OH, —$N(R^{10})_2$, —$NR^{10}C(O)R^{12}$;
each $R^9$ is independently selected from the group consisting of: halogen, —CN, —$NO_2$, —$OR^{10}$, —$SR^{10}$, —$N(R^{10})_2$, and $R^{10}$;
each $R^{10}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl-, substituted alkylaryl-, heterocycloalkenyl

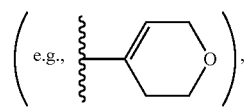

and substituted heterocycloalkenyl, and wherein:
said $R^{10}$ substituted alkyl is substituted with 1 to 3 substituents independently selected from the group consisting of:

—NH$_2$, —NHR$^{20}$, —NO$_2$, —CN, —OR$^{26}$, halo, —C(O)—NH—R$^{26}$, —C(O)OR$^{26}$, and —C(O)R$^{26}$, and said R$^{10}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —OR$^{20}$, (6) —OCF$_3$, (7) alkyl substituted with 1 to 3 independently selected halo atoms, (8) —C(O)R$^{38}$, (9) alkyl, (10) alkenyl, (11) halo, (12) —C(O)—NH—R$^{26}$, (13) —C(O)OR$^{38}$, (14) —C(O)—NR$^{32}$—(C(R$^{30}$)$_2$)$_n$—N(R$^{38}$)$_2$, (15) —S(O)$_r$R$^{38}$, (16) —C(O)—NR$^{32}$—R$^{38}$, (17) —NR$^{32}$—C(O)—R$^{38}$,

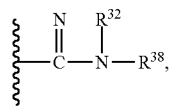

(18)

(19) —NHR$^{20}$, (20) cycloalkyl, (21) —O-alkyl-O—R$^{20}$, (22) hydroxyalkyl, (23) —N(R$^{20}$)$_2$ wherein each R$^{20}$ is independently selected, (24) -alkyl-OR$^{20}$, (25) —O-alkyl-OH, (26) —NH(hydroxyalkyl), and (27) oxazolidinone;

R$^{11}$ is selected from the group consisting of: F, —OH, —CN, —OR$^{10}$, —NHNR$^1$R$^{10}$, —SR$^{10}$ and heteroaryl;

R$^{12}$ is selected from the group consisting of: alkyl, aryl, heteroaryl, cycloalkyl, cycloalkylalkyl, heterocycloalkyl and heterocycloalkylalkyl;

R$^{14}$ is selected from the group consisting of: alkyl, aryl, heteroaryl, cycloalkyl, cycloalkylalkyl-, heterocycloalkyl, alkylheterocycloalkyl, heterocycloalkylalkyl-, alkylheteroaryl- and alkylaryl-;

R$^{15}$ is selected from the group consisting of: H, —OH, alkyl, aryl, heteroaryl, cycloalkyl, cycloalkylalkyl-, heterocycloalkyl and heterocycloalkylalkyl-, alkylheteroaryl- and alkylaryl-;

R$^{20}$ represents alkyl;

R$^{23}$ is selected from the group consisting of: H, alkyl, aryl, cycloalkyl, and cycloalkylalkyl-;

each R$^{26}$ is independently selected from the group consisting of: H and alkyl;

R$^{28}$ is alkyl;

each R$^{30}$ is independently selected from the group consisting of: H, alkyl, and F;

each R$^{32}$ is independently selected from the group consisting of: H and alkyl;

each R$^{35}$ is independently selected from the group consisting of: H and C$_1$ to C$_6$ alkyl;

each R$^{38}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said R$^{38}$ substituted alkyl is substituted with 1 to 3 substituents independently selected from the group consisting of: —NH$_2$, —NO$_2$, —CN, —OR$^{26}$, halo, —C(O)—NH—R$^{28}$, —C(O)OR$^{28}$, and said R$^{38}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —OR$^{20}$, (6) —OCF$_3$, (7) —CF$_3$, (8) —C(O)R$^{26}$, (9) alkyl, (10) alkenyl, (11) halo, (12) —C(O)—NH—R$^{26}$, (13) —C(O)OR$^{26}$, (14) —C(O)—NR$^{32}$—(C(R$^{30}$)$_2$)$_a$—N(R$^{26}$)$_2$, (15) —S(O)$_r$R$^{26}$, (16) —C(O)N(R$^{32}$)(R$^{26}$), (17) —NR$^{32}$C(O)R$^{26}$,

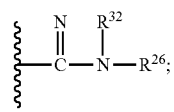

(18)

and (19) —NHR$^{20}$;

R$^{42}$ is selected from the group consisting of: alkyl, aryl (e.g., phenyl), heteroaryl, and cycloalkyl;

R$^{44}$ is selected from the group consisting of: H, alkyl, cycloalkyl, and cycloalkylalkyl; and Each R$^{46}$ is independently selected from the group consisting of: H, alkyl, cycloalkyl, and cycloalkylalkyl;

Formula III is described in PCT publication No. 2008/156739, herein incorporated by reference; or c) Formula IV:

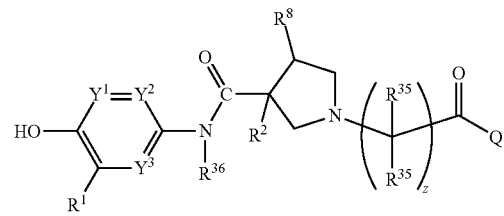

IV or the pharmaceutically acceptable salts thereof, wherein:

Y$^1$, Y$^2$, and Y$^3$ are each independently selected from the group consisting of: —CH=, —N= and —CR$^9$=;

z is 1 to 3;

Q is a substituent selected from the group consisting of:

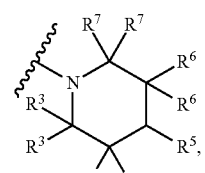

(2.1)

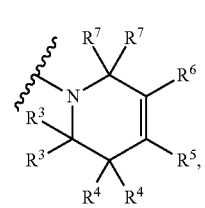

(2.2)

(2.3) 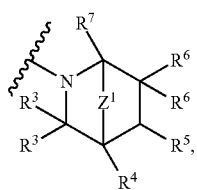

(2.4) 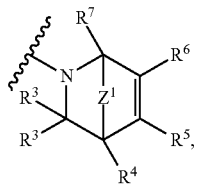

(2.5) 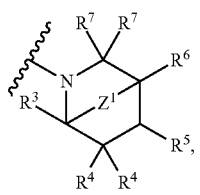

(2.6) 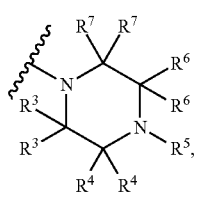

(2.7) 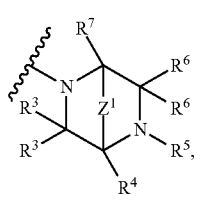

(2.8) 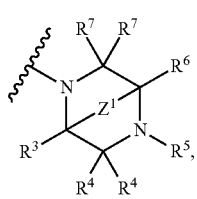

(2.9) 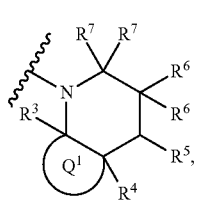

(2.10) 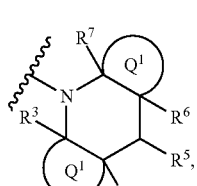

(2.11) 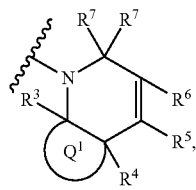

(2.12) 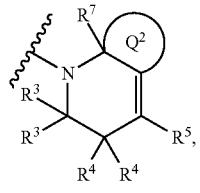

(2.13) 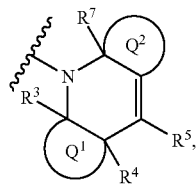

(2.14) 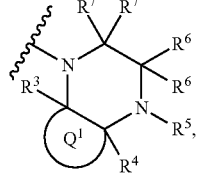

(2.15) 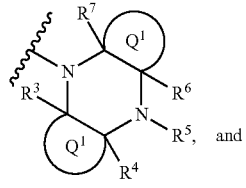

and (2.16) 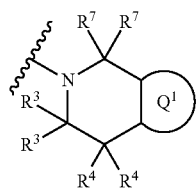

;

Each $Q^1$ represents a ring independently selected from the group consisting of: cycloalkyl, substituted cycloalkyl, heterocycloalkyl, substituted heterocycloalkyl, aryl, substituted aryl, heteroaryl, and substituted heteroaryl, wherein said substituted rings are substituted with 1 to 3 substituents independently selected from the group consisting of: the $R^{10}$ moieties; provided that when $Q^1$ is aryl, heteroaryl, substituted aryl or substituted heteroaryl then the carbon atoms at the ring junction are not substituted;

$Q^2$ represents a ring selected from the group consisting of: cycloalkyl, substituted cycloalkyl, heterocycloalkyl, and substituted heterocycloalkyl, wherein said substituted rings are substituted with 1 to 3 substituents independently selected from the group consisting of: the $R^{10}$ moieties;

$Z^1$ represents $—(C(R^{24})_2)_w—$ wherein each $R^{24}$ is independently selected from the group consisting of: H, alkyl and F, and wherein w is 1, 2 or 3, and generally w is 1 or 2, and usually w is 1, and wherein in one example each $R^{24}$ is H, and in another example w is 1, and in another example each $R^{24}$ is H and w is 1, preferably w is 1 and each $R^{24}$ is H;

$Z^2$ is selected from the group consisting of: —N($R^{44}$)—, —O— and —C($R^{46}$)$_2$—;

m is 1 to 6;
n is 1 to 6;
p is 0 to 6;
t is 0, 1, or 2;
$R^1$ is selected from the group consisting of:
(1) —CN,
(2) —NO$_2$,
(3) —OR$^{10}$,
(4) —SR$^{10}$,
(5) —N($R^{10}$)$_2$,
(6) $R^{10}$,
(7) halo,
(8) —CF$_3$;
(9) alkenyl;
(10) —C(O)N($R^{10}$)$_2$ wherein each $R^{10}$ is independently selected, and preferably each $R^{10}$ is independently selected from the group consisting of: (a) H, (b) alkyl, (c) heteroaryl, (d) aryl, and (e) cycloalkyl, wherein for example, each $R^{10}$ is selected from the group consisting of: H, methyl, butyl, i-propyl, pyridyl, phenyl and cyclopropyl, wherein, for example, said —C(O)N($R^{10}$)$_2$ moiety is selected from the group consisting of: —C(O)NH$_2$, —C(O)NH(CH$_3$), —C(O)NH(CH)(CH$_3$)$_2$, —C(O)NH(C$_4$H$_9$), —C(O)NH(C$_6$H$_5$), —C(O)NH(C$_3$H$_5$), and —C(O)NH(C$_5$H$_4$N);
(11) arylalkenyl-;

$R^2$ is selected from the group consisting of:
(1) H,
(2) —CN,
(3) halo,
(4) alkyl,
(5) substituted alkyl wherein said substituted alkyl is substituted with 1 to 3 substituents selected from the group consisting of: (a) —OH, (b) —O-alkyl (e.g., —O—(C$_1$-C$_3$alkyl), (c) —O-alkyl (e.g., —O—(C$_1$-C$_3$alkyl)) substituted with 1 to 3 F atoms, and (d) —N($R^{40}$)$_2$ wherein each $R^{40}$ is independently selected from the group consisting of: (i) H, (ii) C$_1$-C$_3$ alkyl and (iii) —CF$_3$,
(6) alkynyl,
(7) alkenyl,
(8) —(CH$_2$)$_m$R$^{11}$,
(9) —N($R^{26}$)$_2$,
(10) —OR$^{23}$,
(11) —N($R^{26}$)C(O)R$^{42}$,
(12) cycloalkyl,
(13) cycloalkylalkyl, and

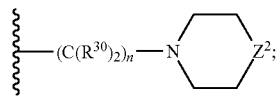
(14)

each $R^3$, $R^4$, $R^5$, $R^6$ and $R^7$ is independently selected from the group consisting of:
(1) H,
(2) alkenyl,
(3) substituted alkenyl,
(4) alkyl,
(5) substituted alkyl,
(6) cycloalkyl,
(7) substituted cycloalkyl,
(8) cycloalkylalkyl-,
(9) substituted cycloalkylalkyl-,
(10) heterocycloalkyl,
(11) substituted heterocycloalkyl,
(12) heterocycloalkylalkyl-,
(13) substituted heterocycloalkylalkyl-,
(14) —C(O)R$^{10}$ wherein in one example $R^{10}$ is selected from the group consisting of: alkyl,
(15) arylheteroaryl-,
(16) substituted arylheteroaryl-,
(17) heteroarylaryl-, such as, for example, pyrimidinyiphenyl-, pyrazinylphenyl-, pyridinyiphenyl-, furanylphenyl-, thienylphenyl-, and thiazolylphenyl-,
(18) substituted heteroarylaryl-, such as, for example, substituted pyrimidinyiphenyl-, substituted pyrazinylphenyl-, substituted pyridinyiphenyl-, substituted furanylphenyl-, substituted thienylphenyl-, substituted thiazolylphenyl-, and substituted pyrimidinyiphenyl,
(19) aryl,
(20) substituted aryl,
(21) heteroaryl,
(22) substituted heteroaryl,
(23) heteroarylheteroaryl-,
(24) substituted heteroarylheteroaryl-,
(25) arylaminoheteroaryl-,
(26) substituted arylaminoheteroaryl-,
(27) arylalkynyl-,
(28) substituted arylalkynyl-,
(29) heteroarylalkynyl-,
(30) substituted heteroarylalkynyl-,
(31) —C(O)NHR$^{28}$,
(32) cycloalkylheteroarylaryl-,
(33) substituted arylaryl-,
(34) arylalkenylaryl-,
(35) arylaryl-,
(36) substituted arylalkyl-,
(37) arylalkyl-,
(38) —SO$_2$aryl,
(39) benzoheteroaryl-C(O)-(substituted heterocycloalkyl)-,
(40) substituted heterocycloalkyl,
(41) heterocycloalkyl-C(O)-alkyl-, and
(42) benzo[1,3]dioxolyl, wherein said $R^3$, $R^4$, $R^5$, $R^6$ and $R^7$ substituted groups (7), (9), (11), (13), (16), (18), (20), (22), (24), (26), (28), (30), (33), (36), (39) and (40) are substituted with 1 to 3 substituents independently selected from the group consisting of: —CH$_2$OH, CN, —OH, —NH$_2$, alkyl, alkenyl, halo, —C(O)—NH—R$^{28}$, —C(O)NH$_2$, —C(O)OR$^{28}$, —C(O)R$^{28}$, —C(alkyl)=NOH, —C(alkyl)=NO(alkyl), alkoxy, hydroxyl substituted alkyl, dialkylamine wherein each alkyl group is independently selected, —CF$_3$, —SO$_2$alkyl, and —NHC(O)H, wherein said $R^3$, $R^4$, $R^5$, $R^6$ and $R^7$ substituted groups (3) and (5) are substituted with 1 to 3 substituents independently selected from the group consisting of: —NH$_2$, halo, —C(O)—NH—R$^{28}$, —C(O)OR$^{28}$, and —C(O)R$^{28}$;

$R^8$ is selected from the group consisting of: H, —OH, alkyl, aryl, —N($R^{10}$)$_2$ and —N$R^{10}$C(O)$R^{12}$;

each $R^9$ is independently selected from the group consisting of: halogen, —CN, —NO$_2$, —O$R^{10}$, —S$R^{10}$, —N($R^{10}$)$_2$, and $R^{10}$;

each $R^{10}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said $R^{10}$ substituted alkyl is substituted with 1 to 3 substituents independently selected from the group consisting of: —NH$_2$, —NH$R^{20}$, —NO$_2$, —CN, —O$R^{26}$, halo, —C(O)—NH—$R^{26}$, —C(O)O$R^{26}$, and —C(O)$R^{26}$, and said $R^{10}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —O$R^{20}$, (6) —OCF$_3$, (7) —CF$_3$, (8) —C(O)$R^{36}$, (9) alkyl, (10) alkenyl, (11) halo, (12) —C(O)—NH—$R^{26}$, (13) —C(O)O$R^{38}$, (14) —C(O)—N$R^{32}$—(C($R^{30}$)$_2$)$_n$—N($R^{38}$)$_2$, (15) —S(O)$_r$$R^{38}$, (16) —C(O)—N$R^{32}$—$R^{38}$, (17) —N$R^{32}$—C(O)—$R^{38}$,

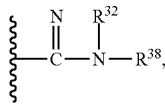

(18)

and

(19) —NH$R^{20}$;

$R^{11}$ is selected from the group consisting of: F, —OH, —CN, —O$R^{10}$, —NHN$R^1$$R^{10}$, —S$R^{10}$ and heteroaryl;

$R^{12}$ is selected from the group consisting of: alkyl, aryl, heteroaryl, cycloalkyl, cycloalkylalkyl, heterocycloalkyl and heterocycloalkylalkyl;

$R^{14}$ is selected from the group consisting of: alkyl, aryl, heteroaryl, cycloalkyl, cycloalkylalkyl-, heterocycloalkyl, alkylheterocycloalkyl, heterocycloalkylalkyl-, alkylheteroaryl- and alkylaryl-;

$R^{15}$ is selected from the group consisting of: H, —OH, alkyl, aryl, heteroaryl, cycloalkyl, cycloalkylalkyl-, heterocycloalkyl and heterocycloalkylalkyl-, alkylheteroaryl- and alkylaryl-;

$R^{20}$ represents alkyl;

$R^{23}$ is selected from the group consisting of: H, alkyl, aryl, cycloalkyl, and cycloalkylalkyl-;

each $R^{26}$ is independently selected from the group consisting of: H and alkyl;

$R^{28}$ is alkyl;

each $R^{30}$ is independently selected from the group consisting of: H, alkyl, and F;

each $R^{32}$ is independently selected from the group consisting of: H and alkyl;

each $R^{35}$ is independently selected from the group consisting of: H and C$_1$ to C$_6$ alkyl;

$R^{36}$ is selected from the group consisting of: H and alkyl;

each $R^{38}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said $R^{38}$ substituted alkyl is substituted with 1 to 3 substituents independently selected from the group consisting of: —NH$_2$, —NO$_2$, —CN, —O$R^{26}$, halo, —C(O)—NH—$R^{28}$, —C(O)O$R^{28}$, and —C(O)$R^{28}$, and said $R^{38}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —O$R^{20}$, (6) —OCF$_3$, (7) —CF$_3$, (8) —C(O)$R^{26}$, (9) alkyl, (10) alkenyl, (11) halo, (12) —C(O)—NH—$R^{26}$, (13) —C(O)O$R^{26}$, (14) —C(O)—N$R^{32}$—(C($R^{30}$)$_2$)$_n$—N($R^{26}$)$_2$, (15) —S(O)$_r$$R^{26}$, (16) —C(O)N($R^{32}$)($R^{26}$), (17) —N$R^{32}$C(O)$R^{26}$,

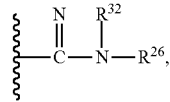

(18)

and

(19) —NH$R^{26}$;

$R^{42}$ is selected from the group consisting of: alkyl, aryl, heteroaryl, and cycloalkyl;

$R^{44}$ is selected from the group consisting of: H, alkyl, cycloalkyl, and cycloalkylalkyl; and Each $R^{46}$ is independently selected from the group consisting of: H, alkyl, cycloalkyl, and cycloalkylalkyl;

Formula IV is described in U.S. publication No. 2007/0232610, herein incorporated by reference.

Non-limiting examples of ERK inhibitors are selected from the group consisting of:

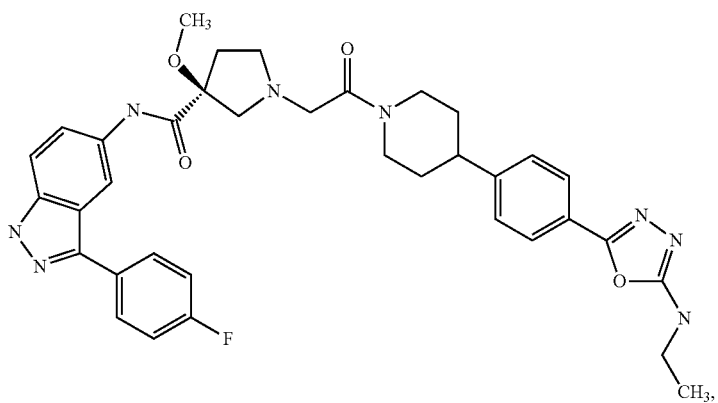
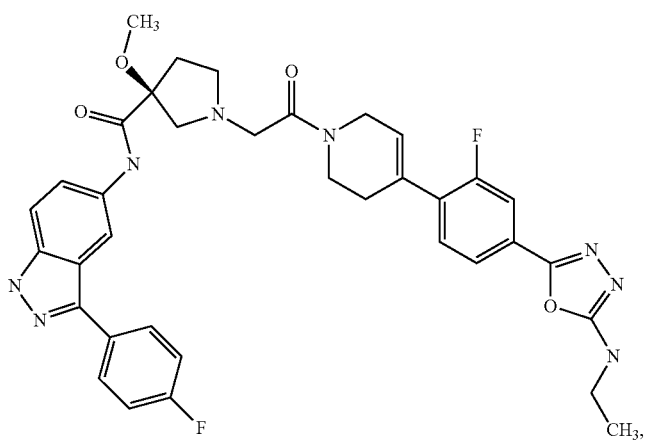
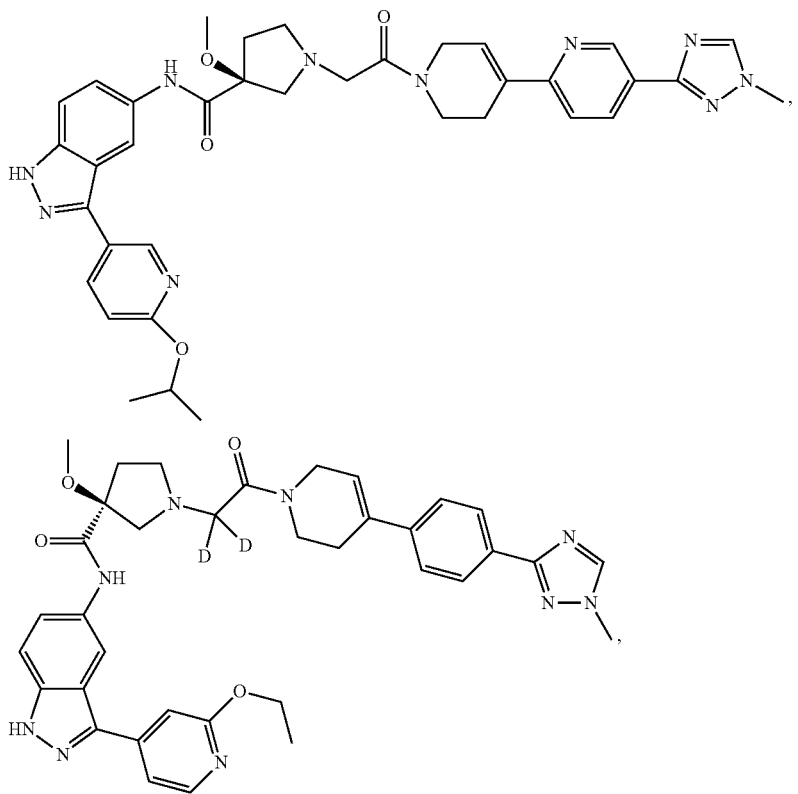

-continued
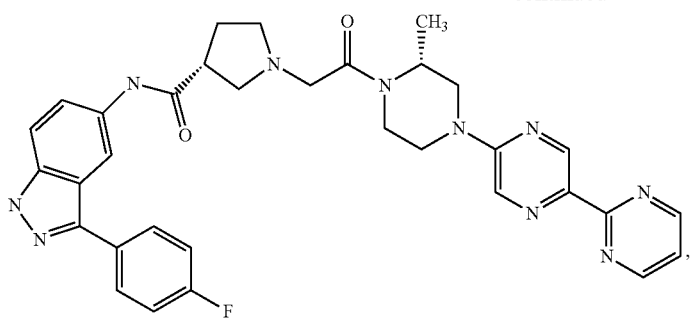
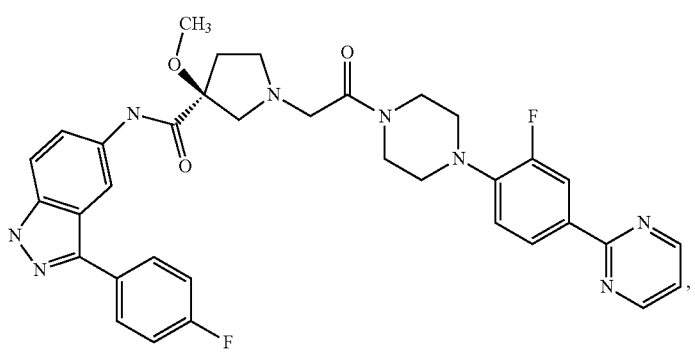
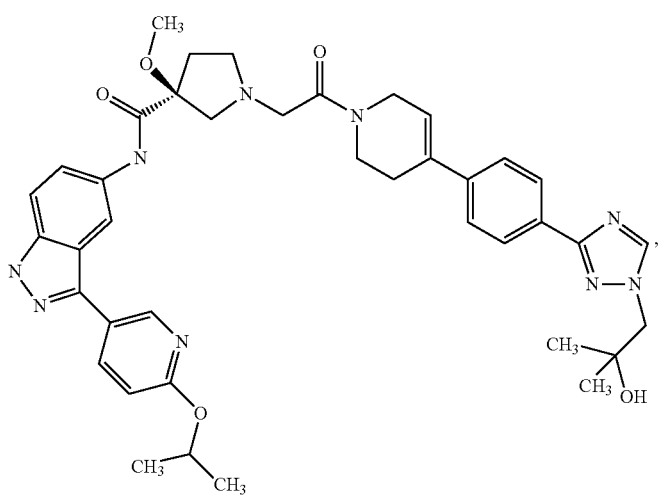
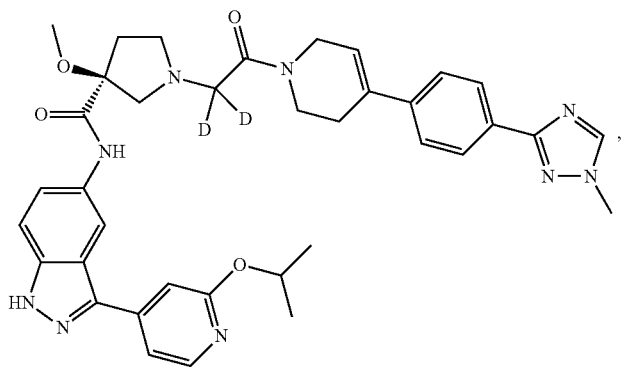

481 482
-continued
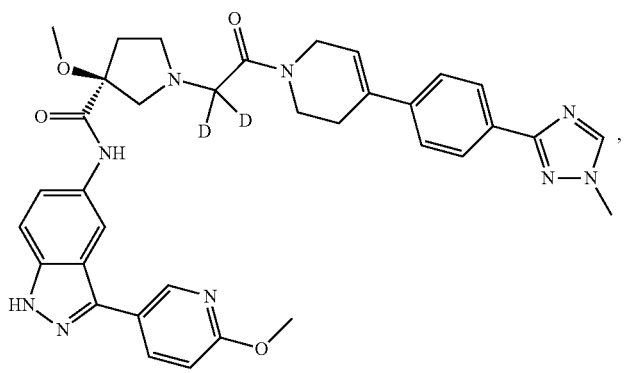
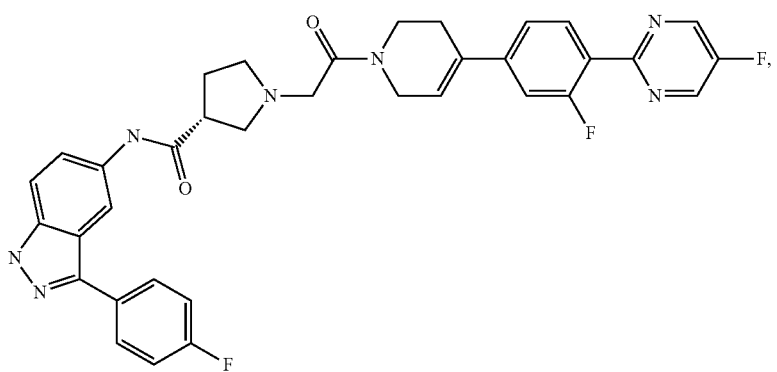
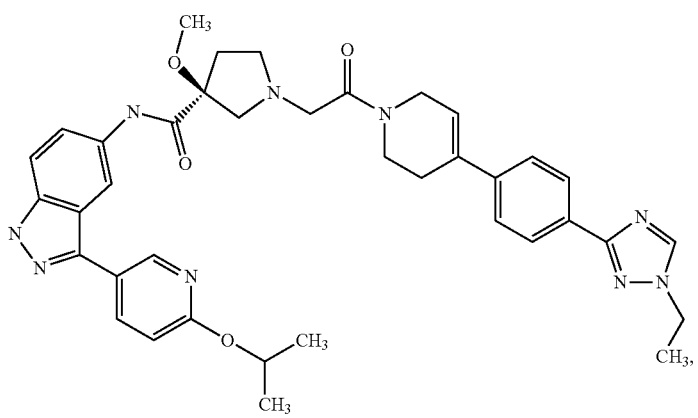
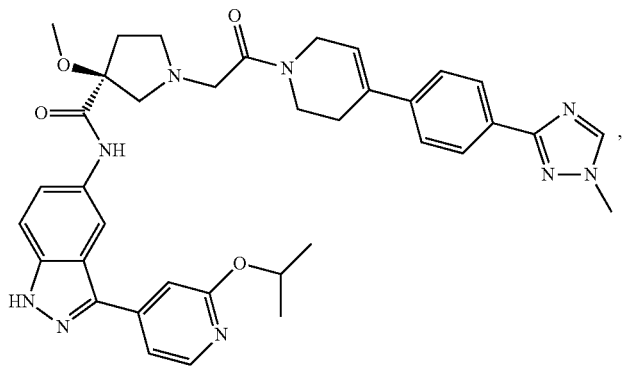

-continued
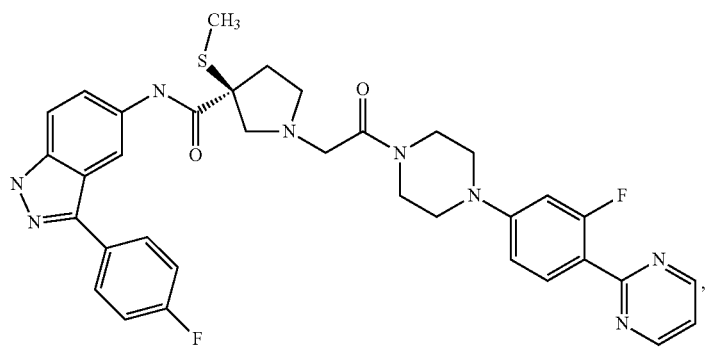
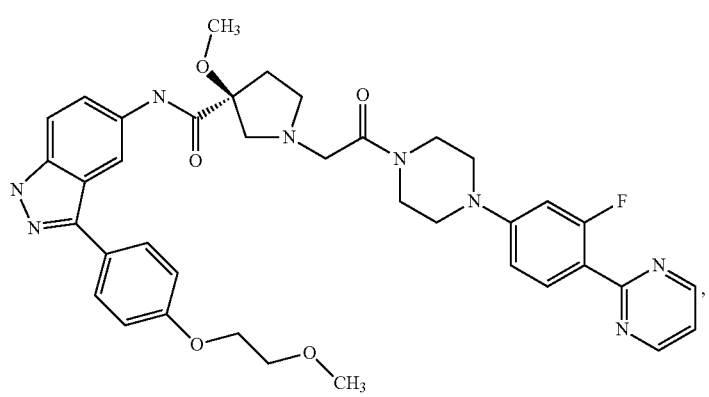
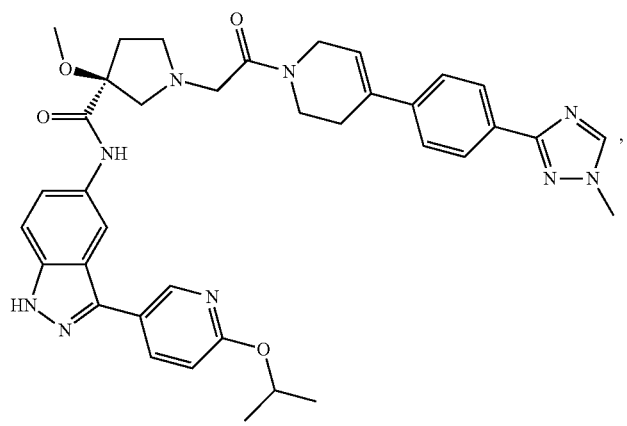
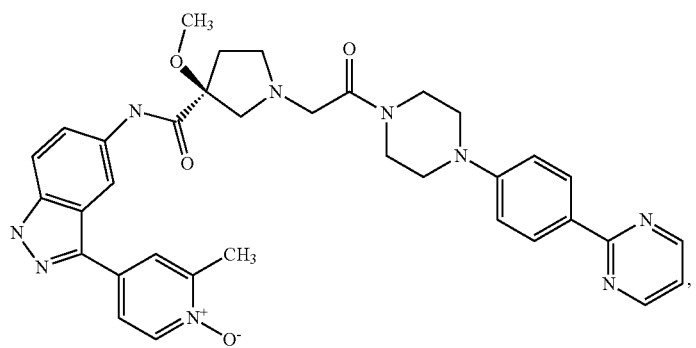

-continued
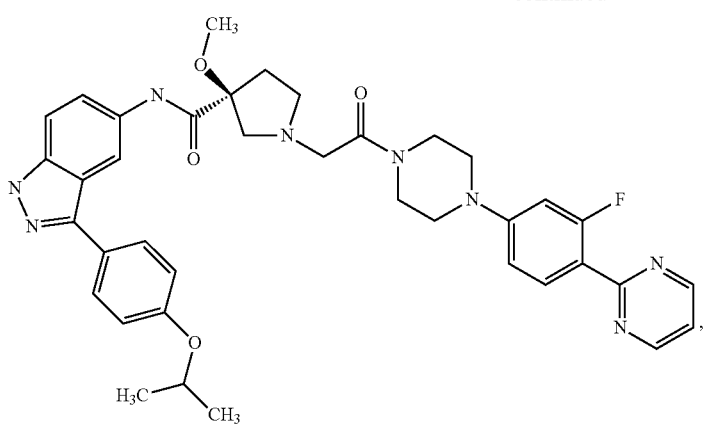
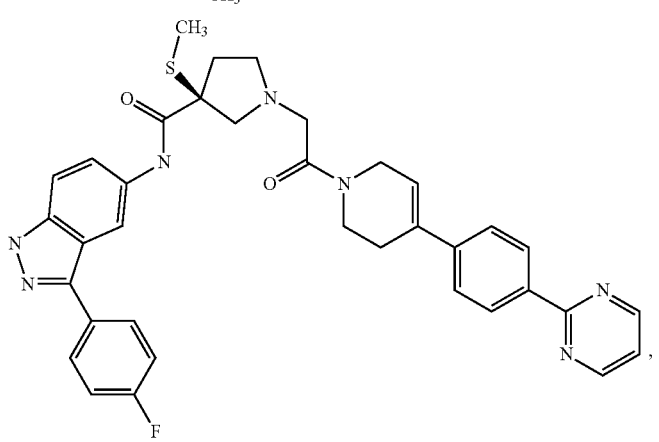
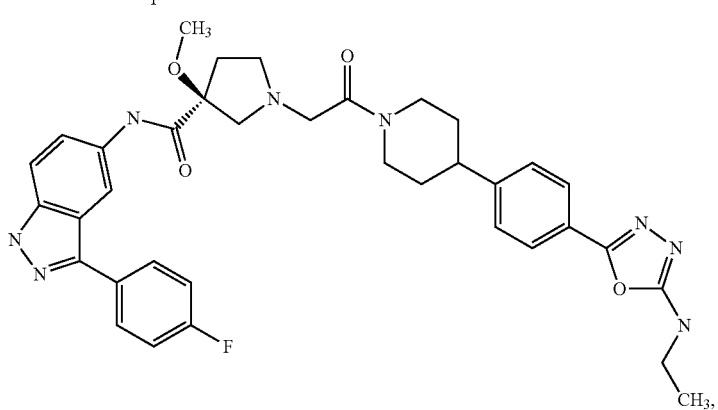
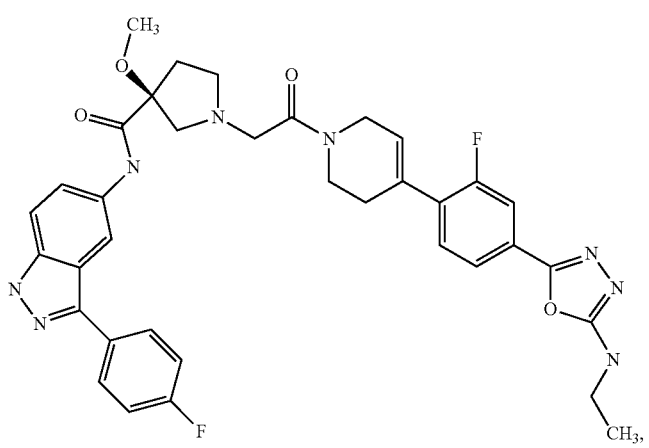

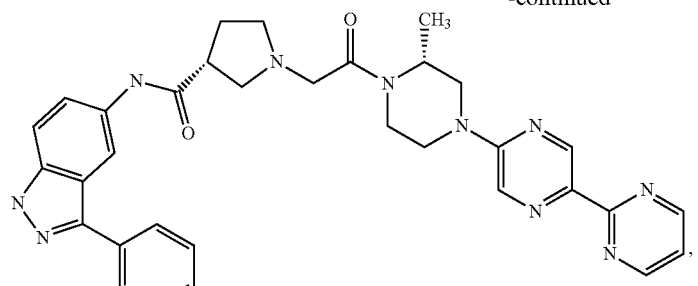
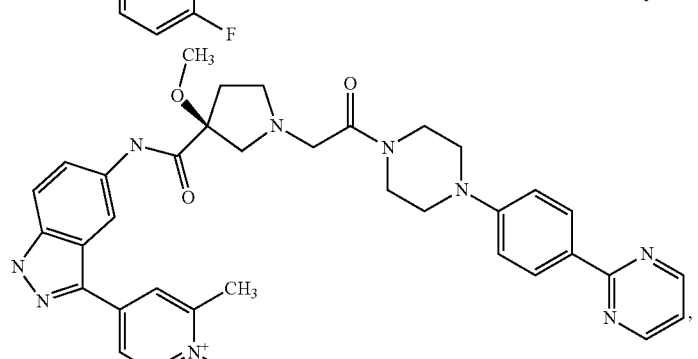
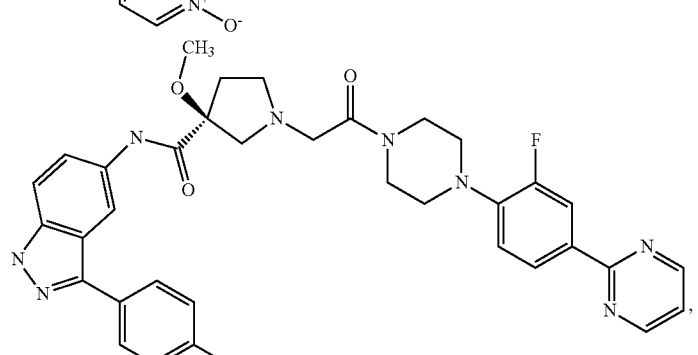
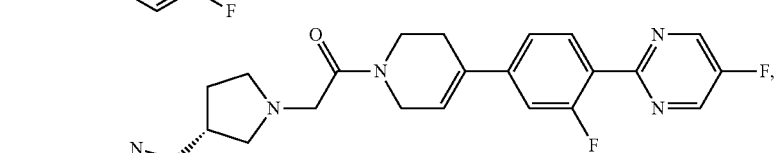
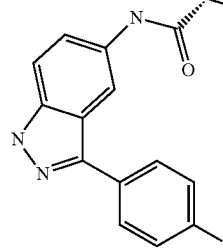
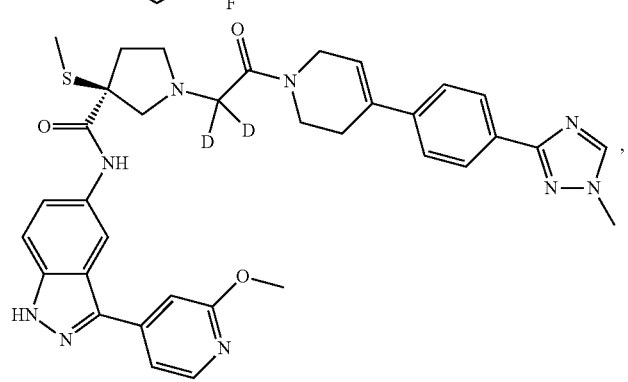

-continued
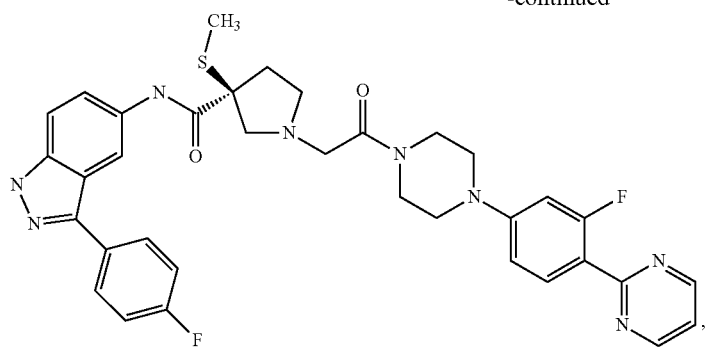
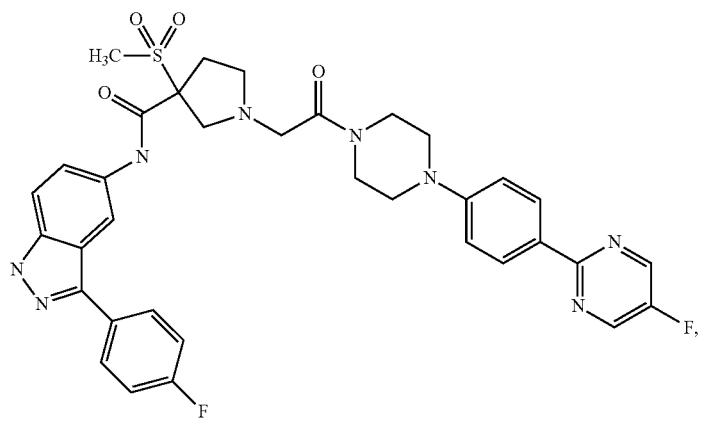
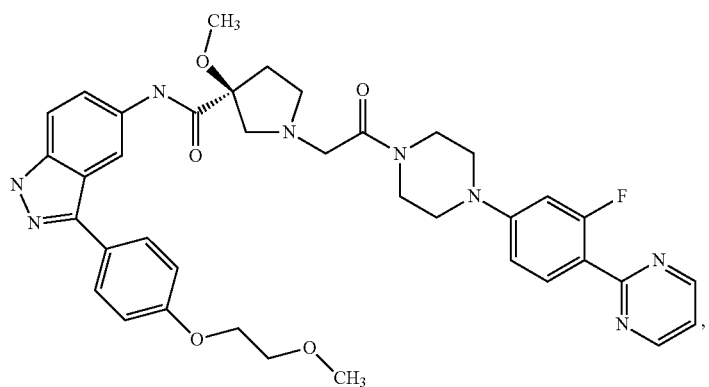
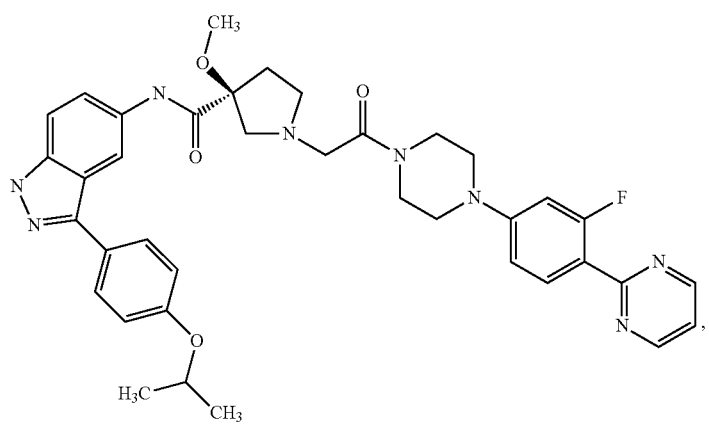

-continued
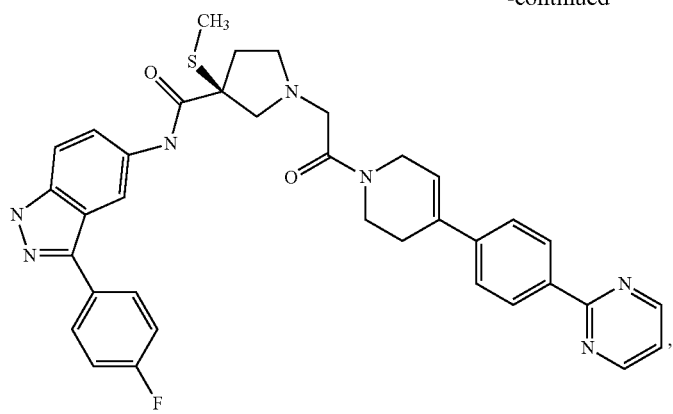
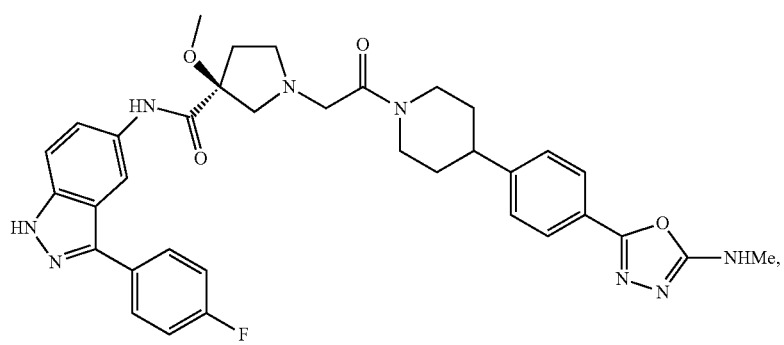
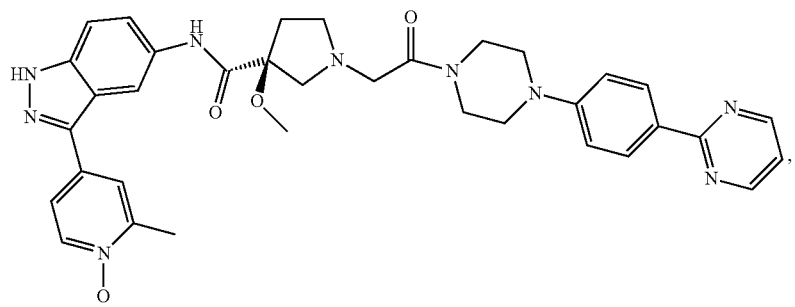
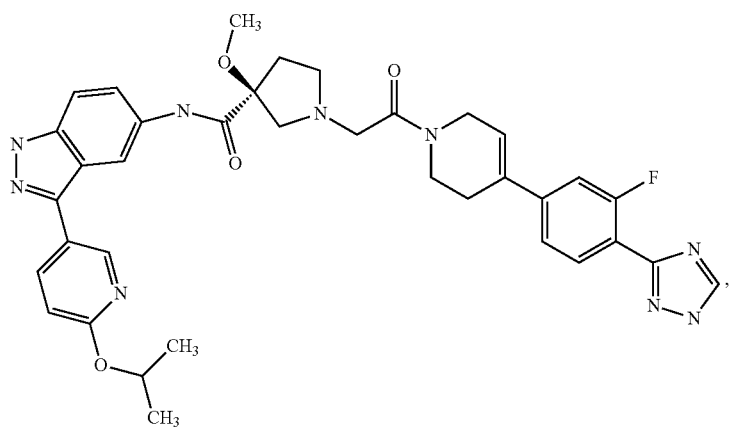

-continued
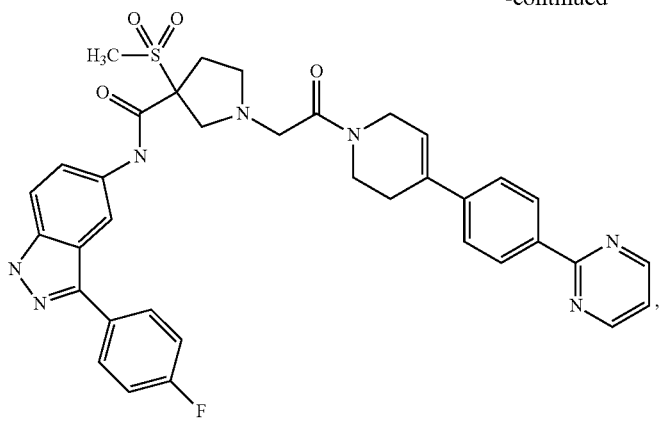
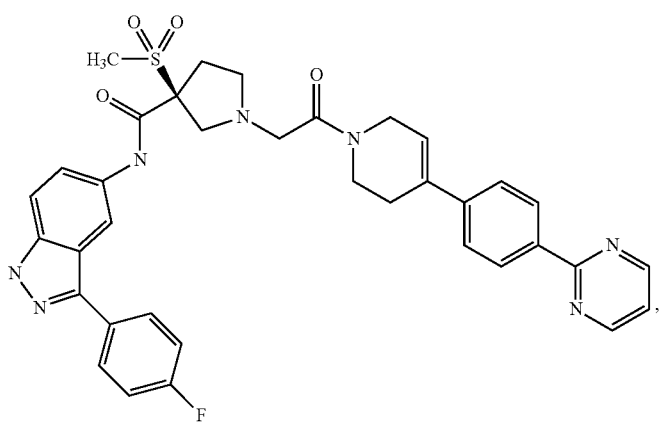
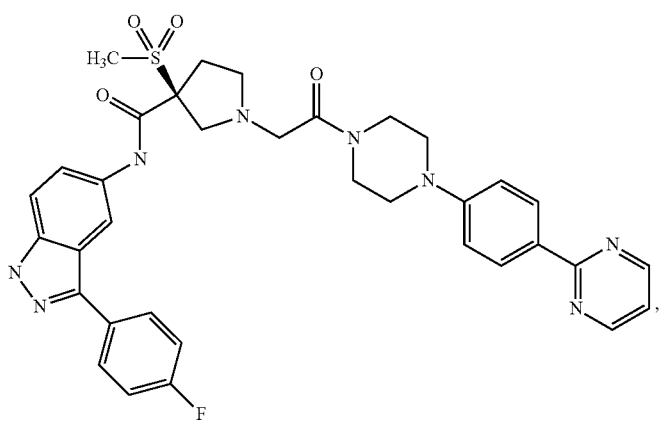
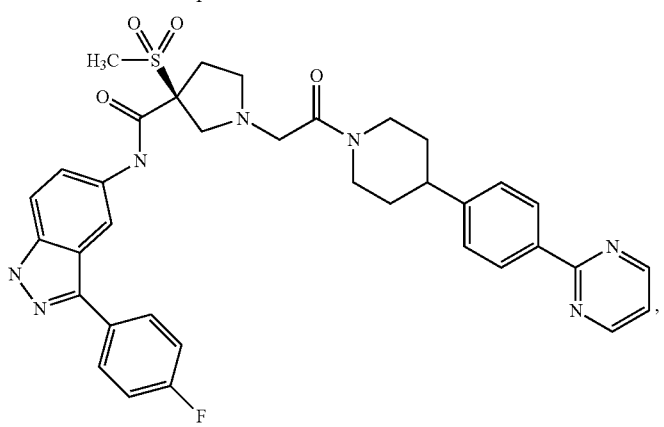

-continued
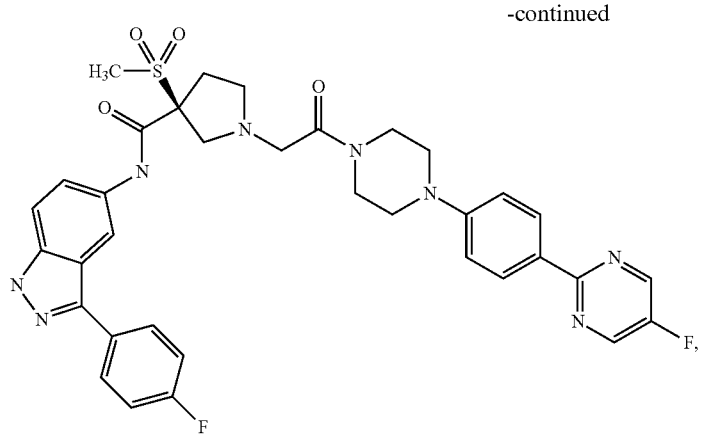
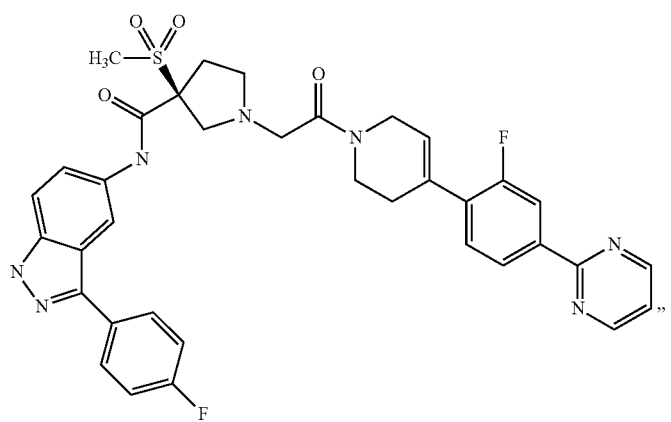
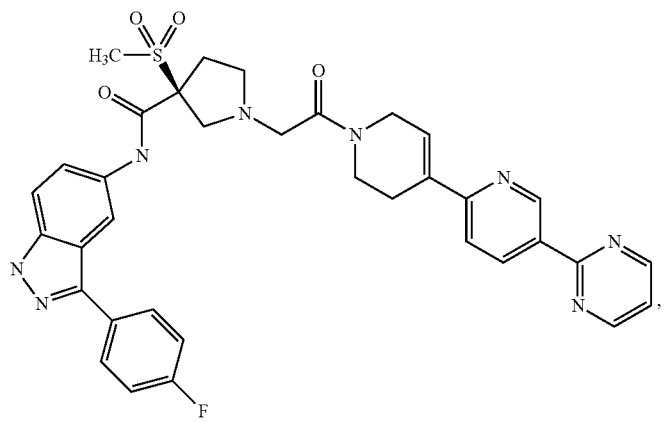
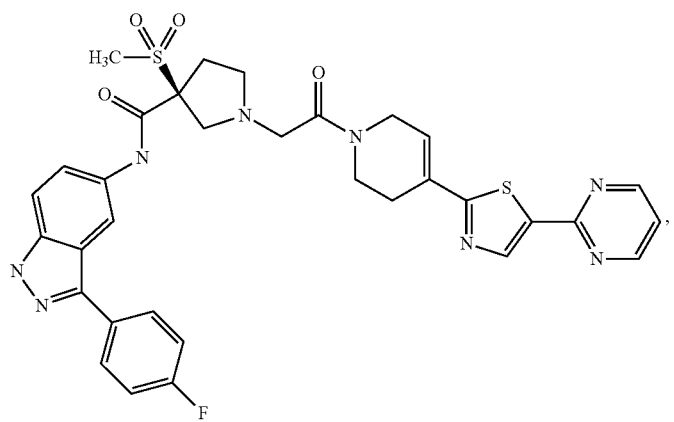

-continued
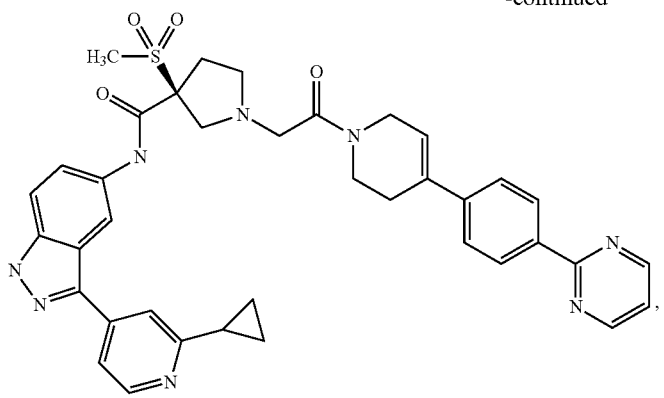
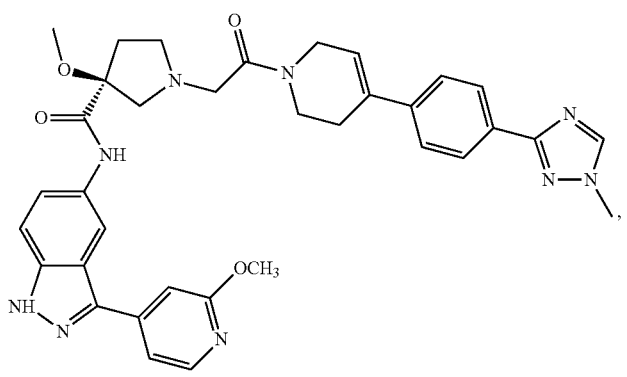
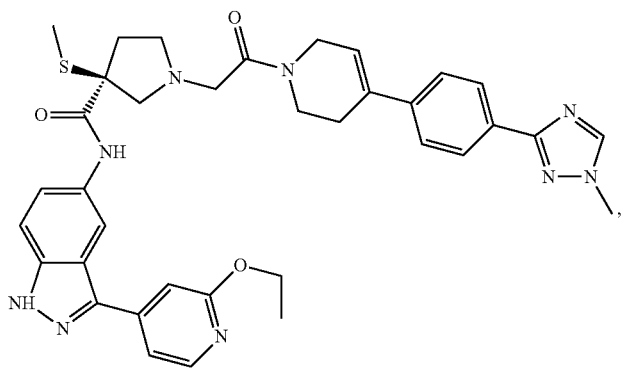
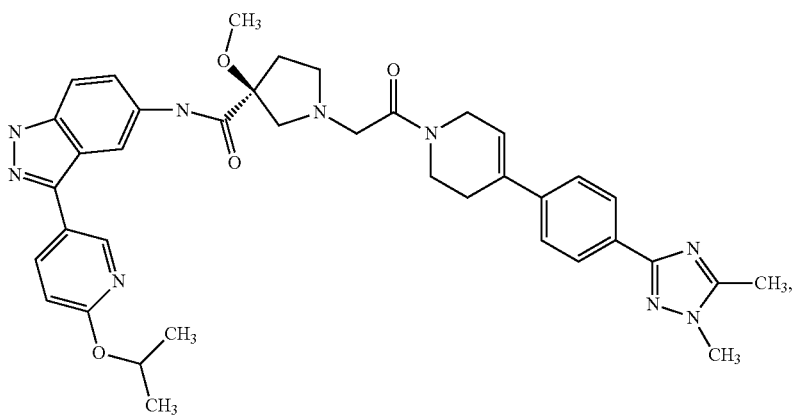

-continued
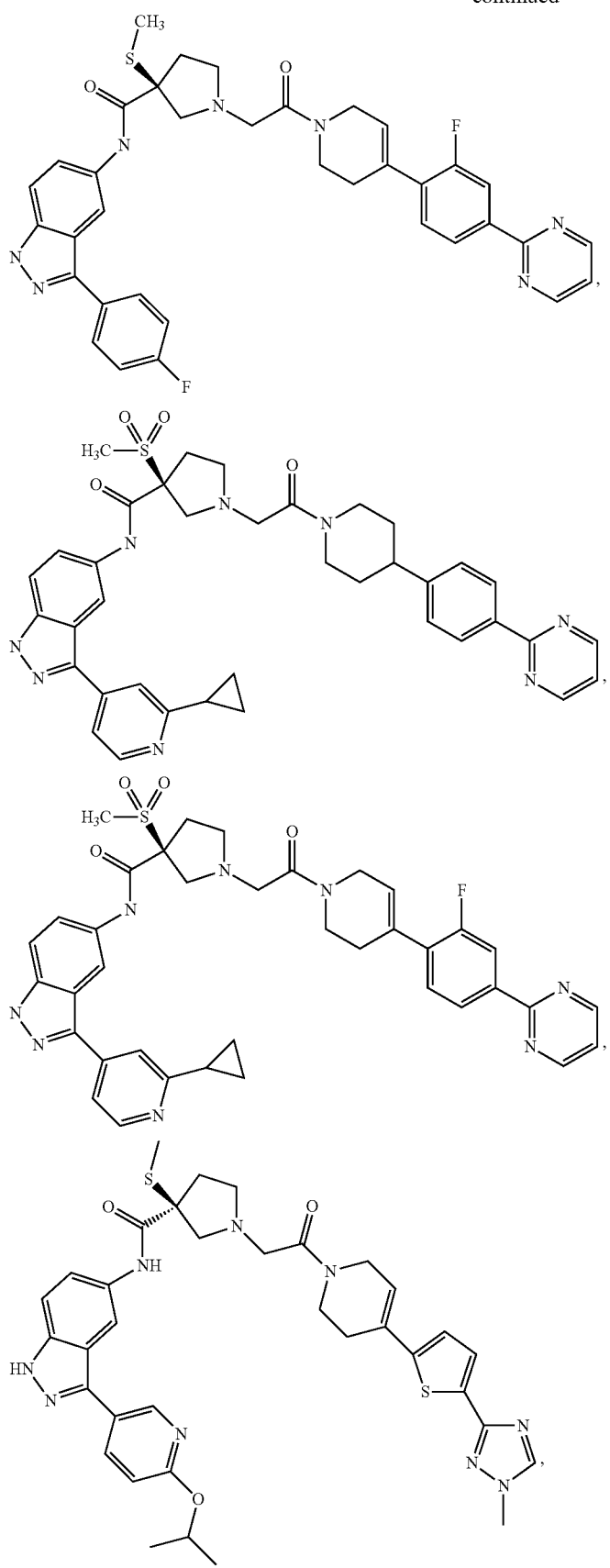

-continued
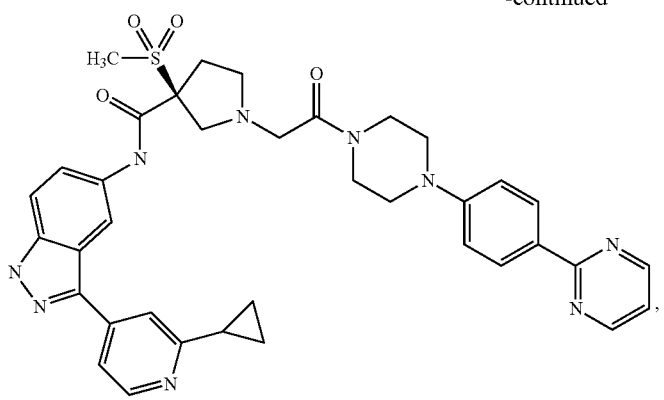
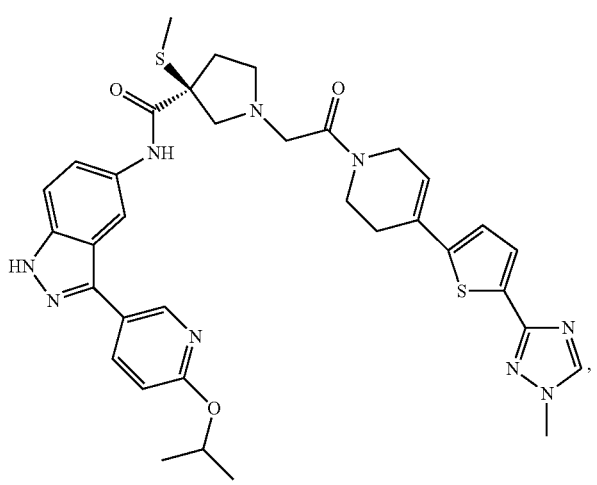
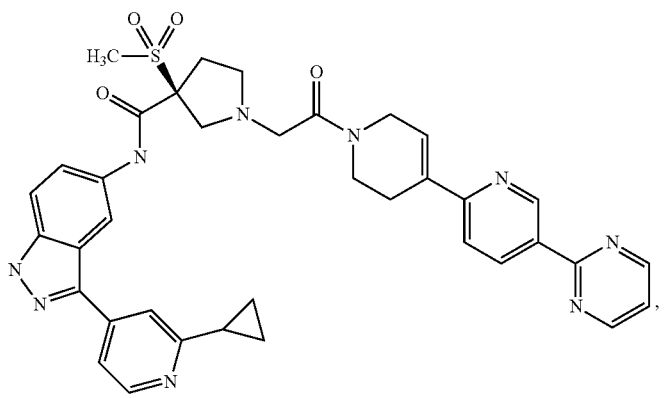
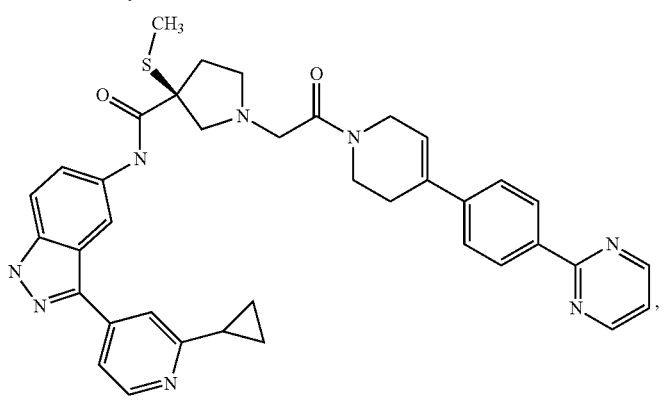

-continued
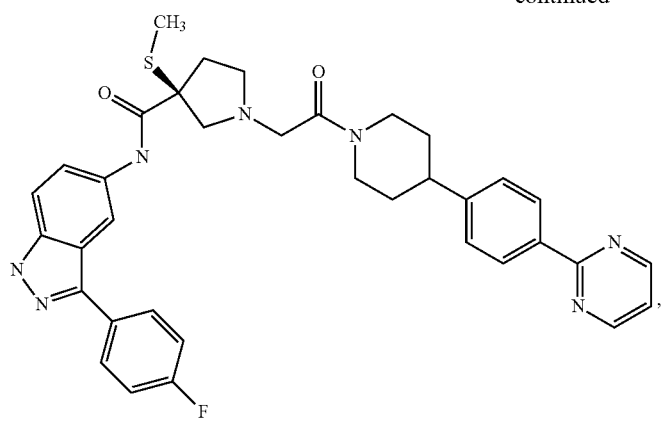
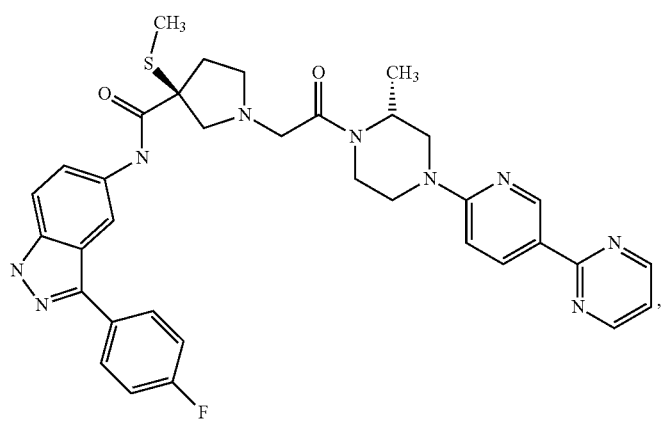
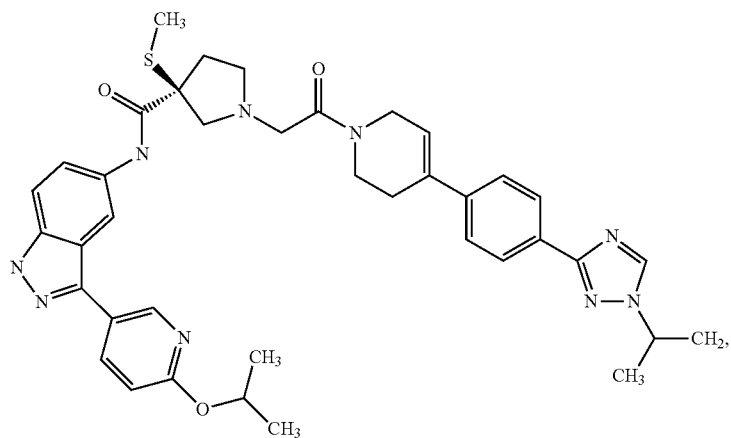
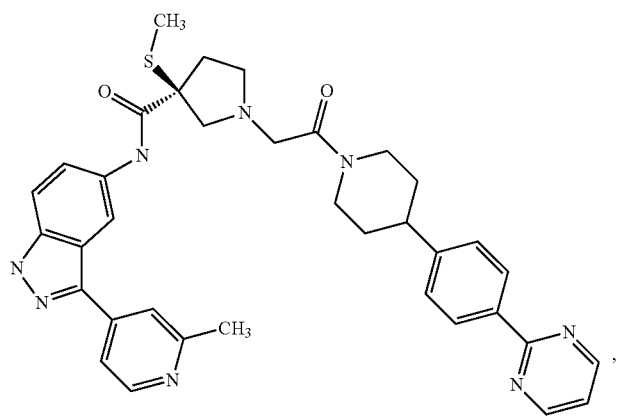

-continued
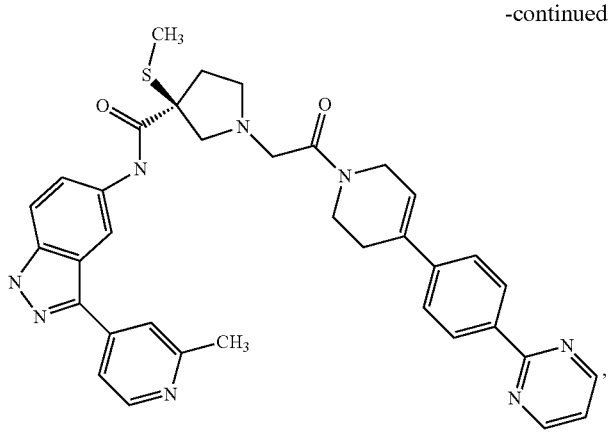
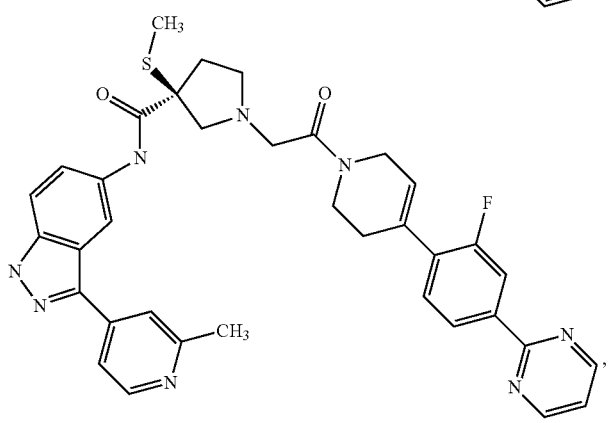
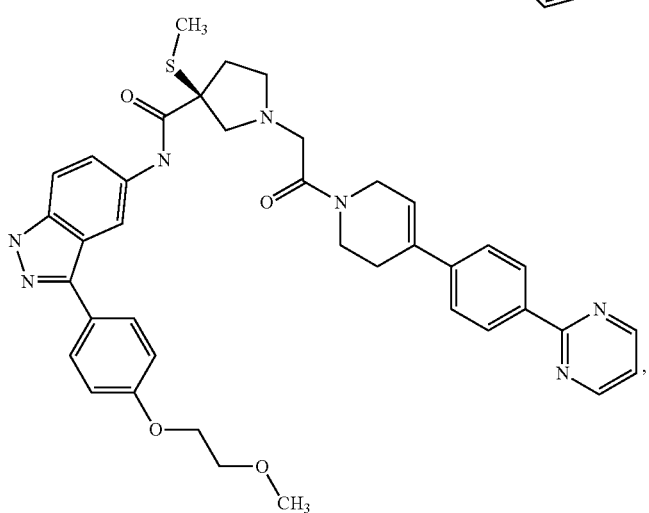
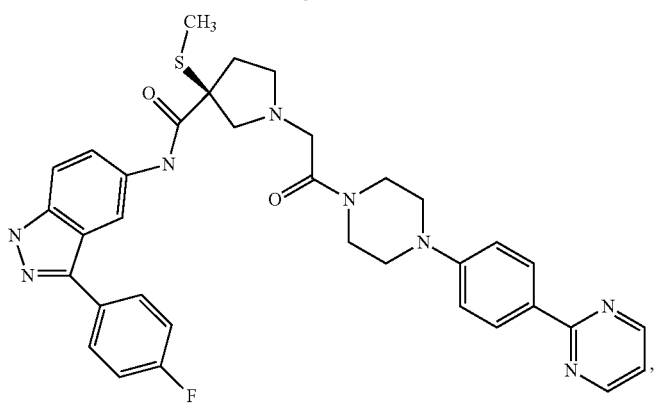

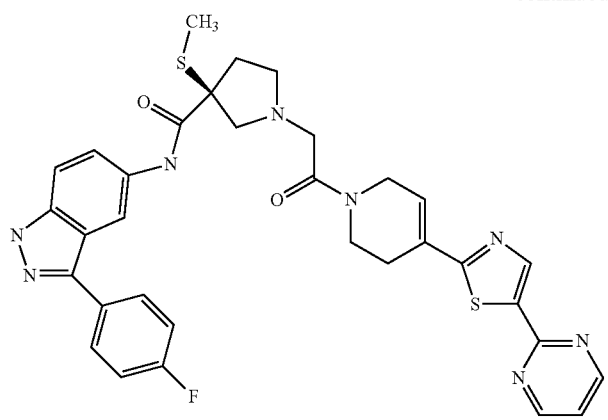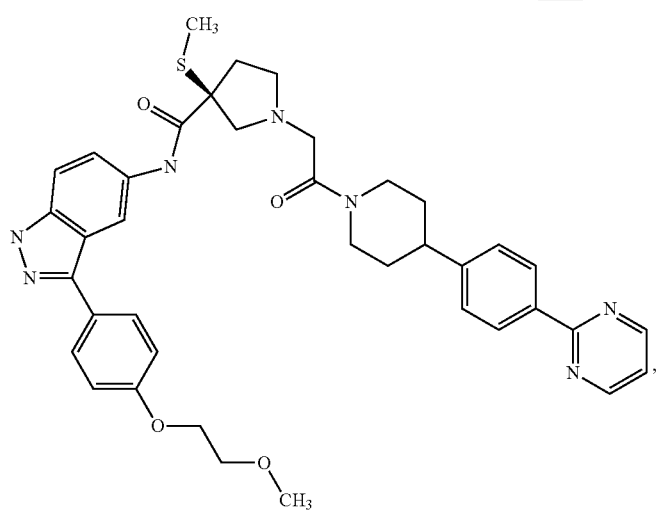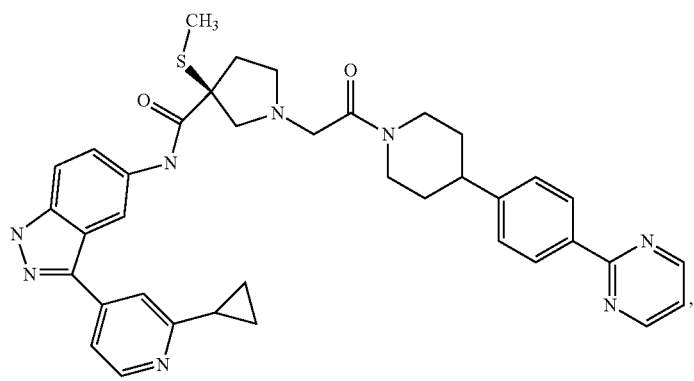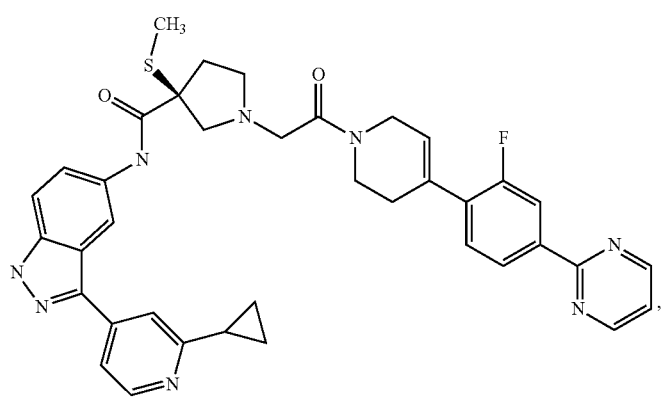

-continued
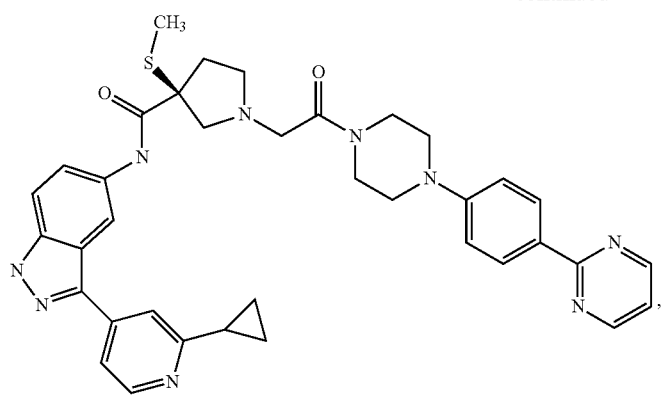
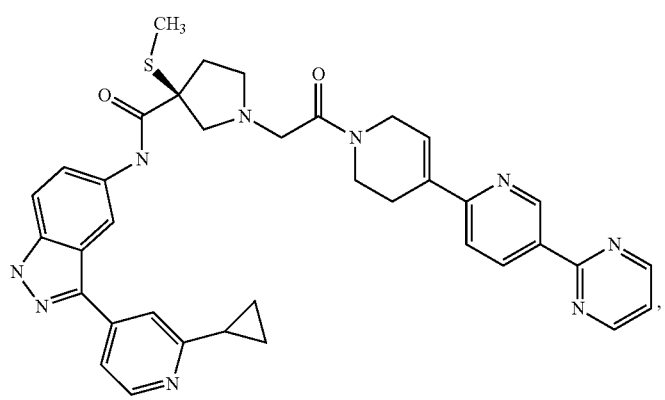
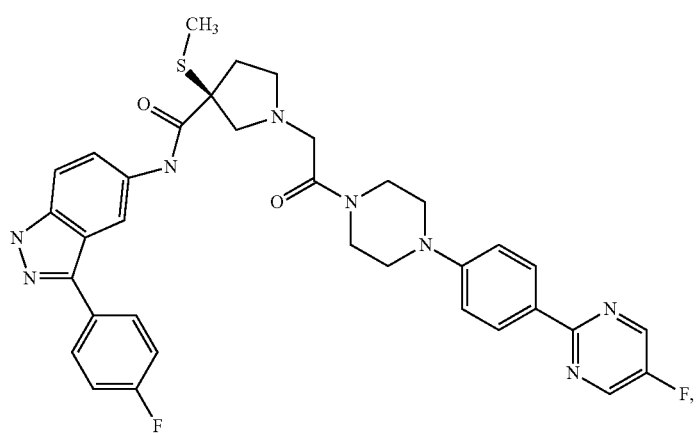
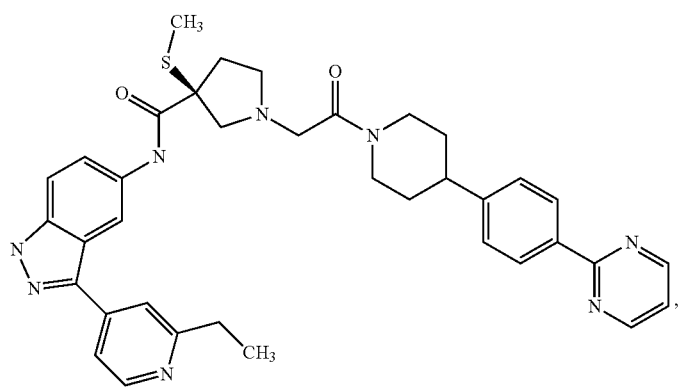

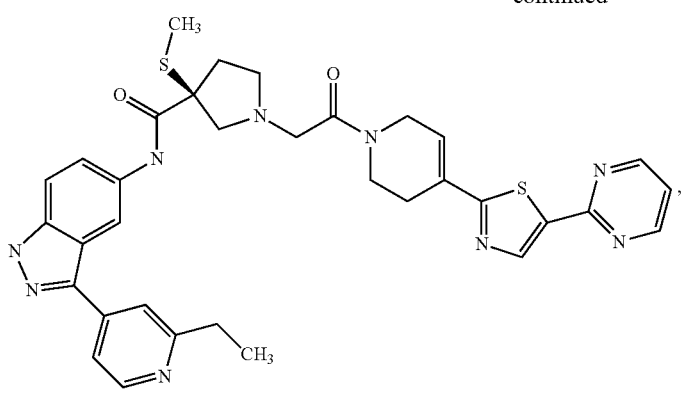
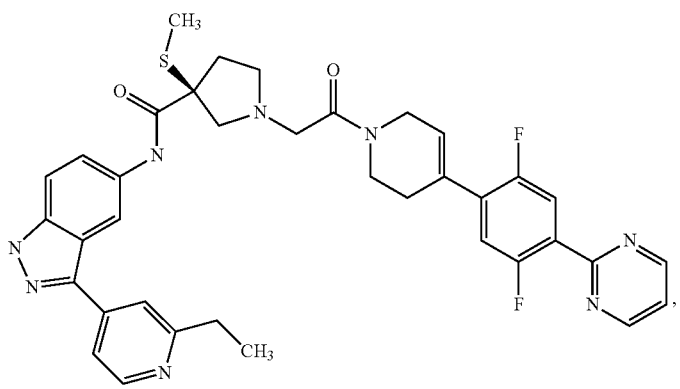
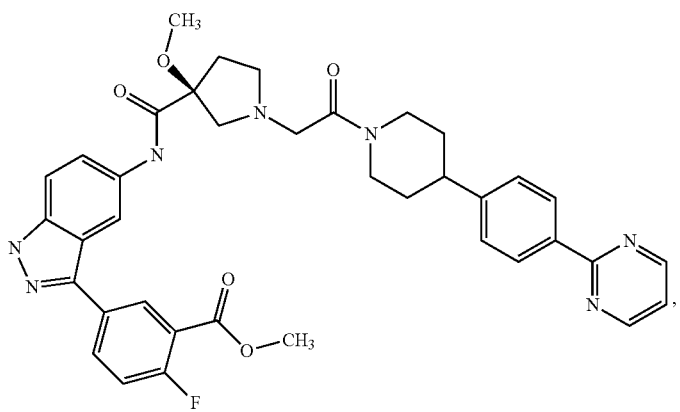
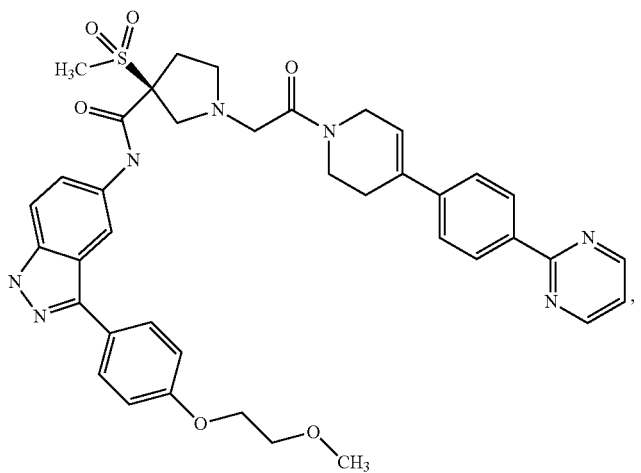

-continued
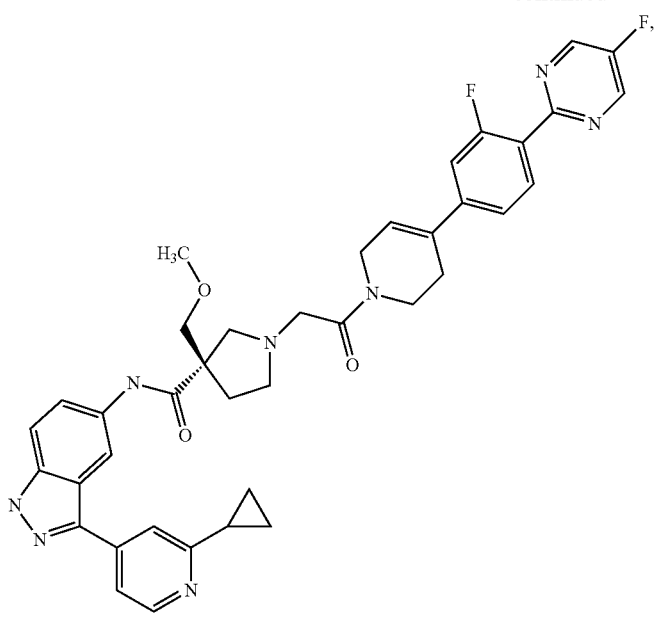
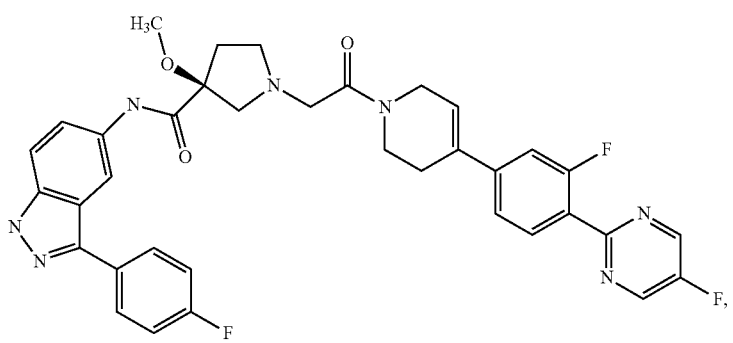
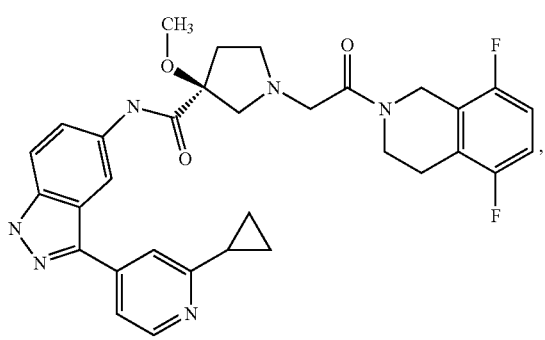
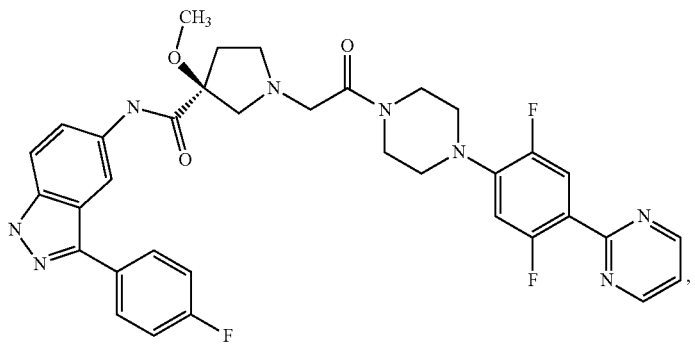

-continued
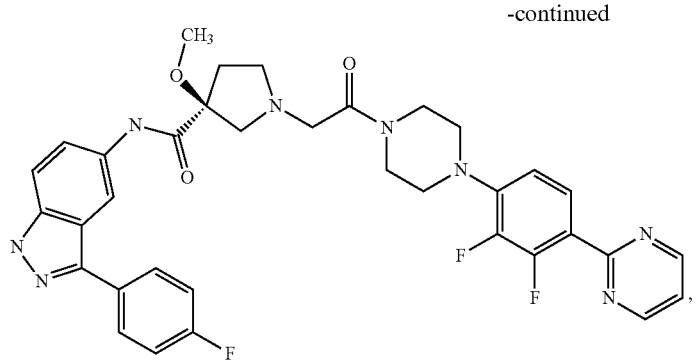
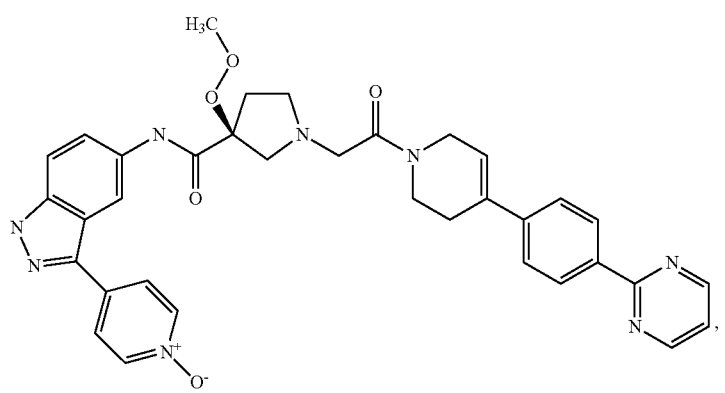
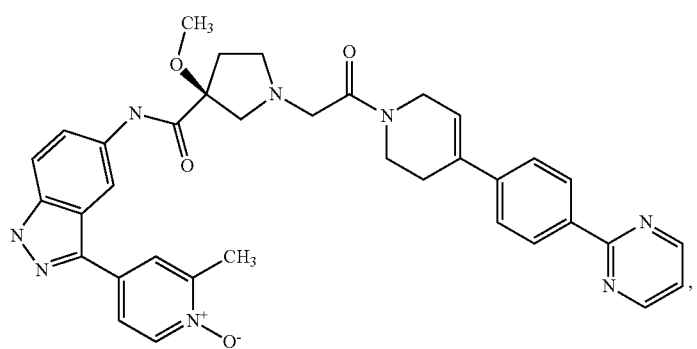
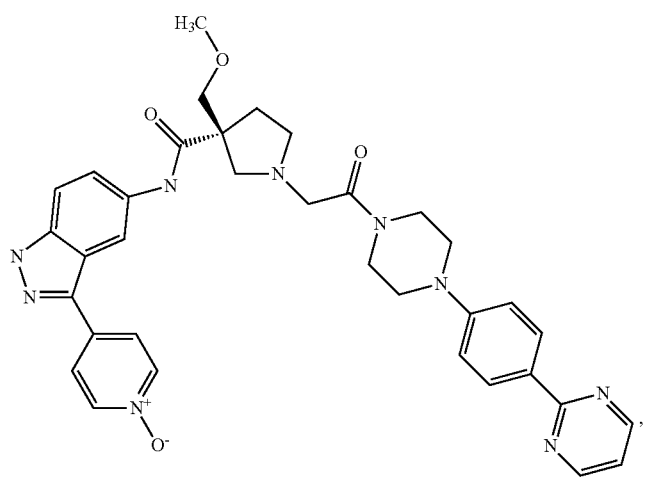

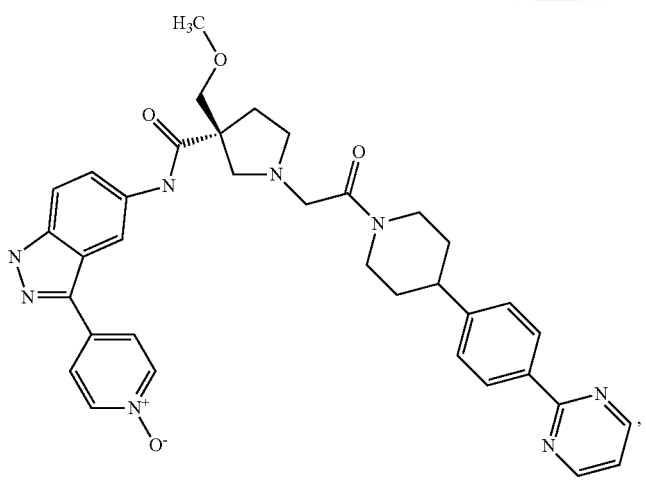
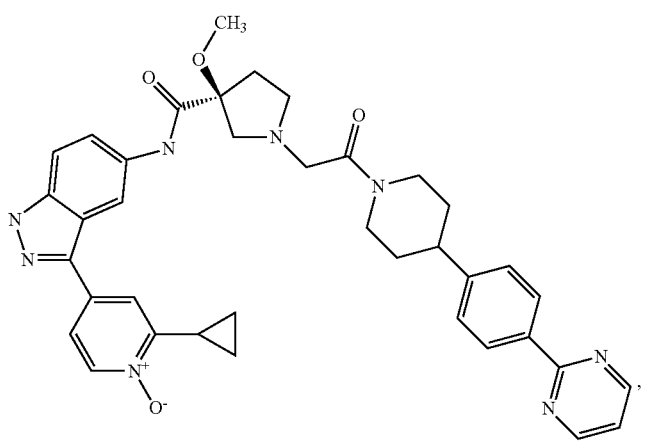
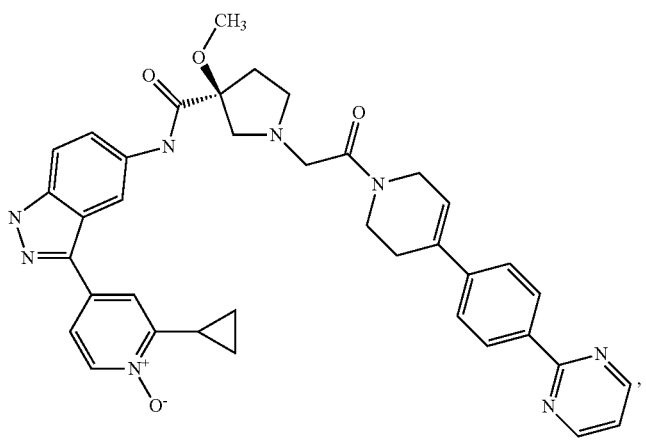
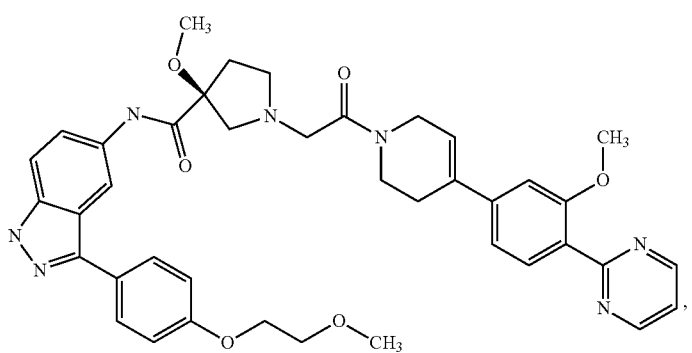

-continued
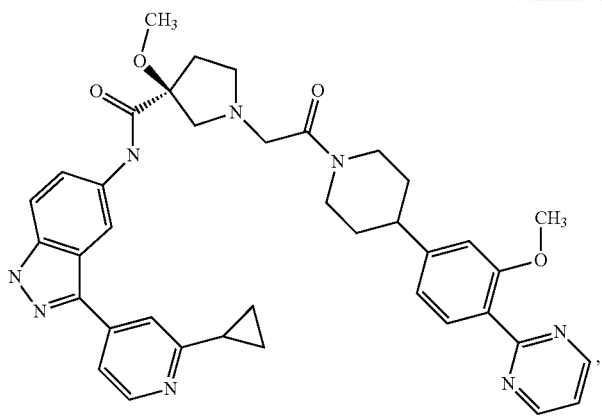
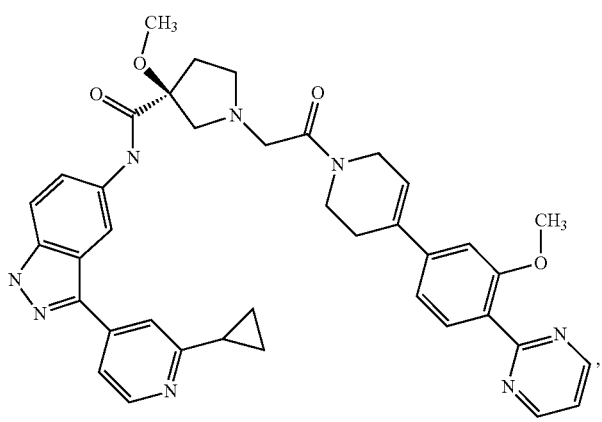
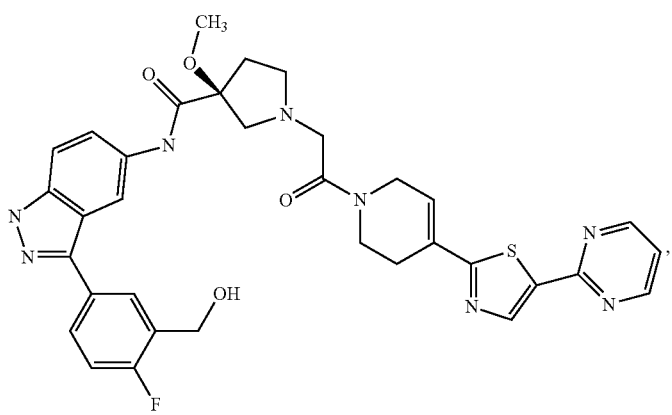
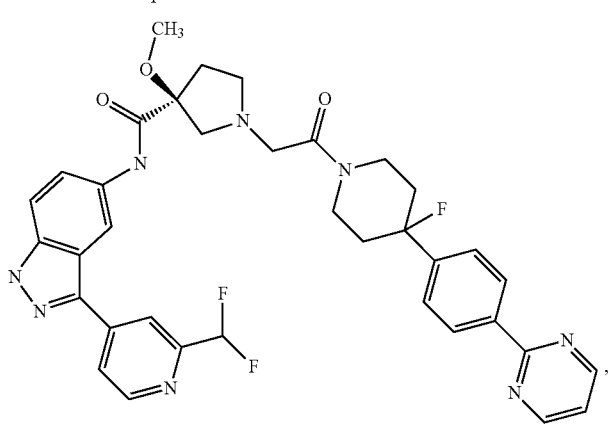

-continued
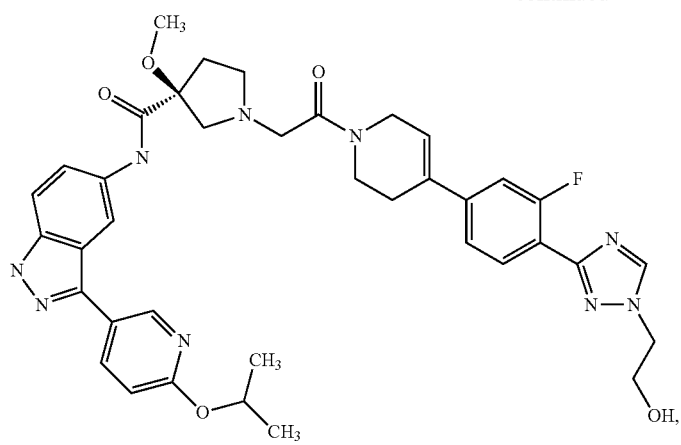
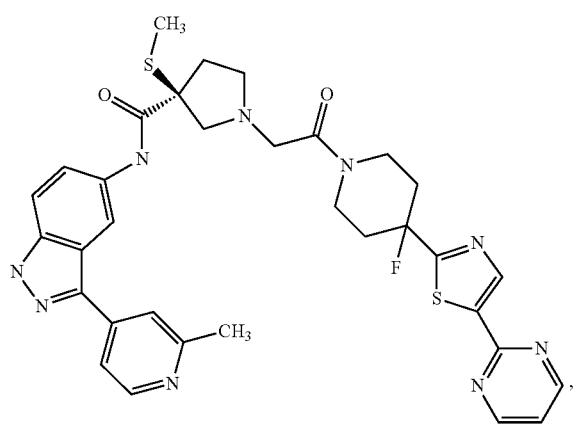
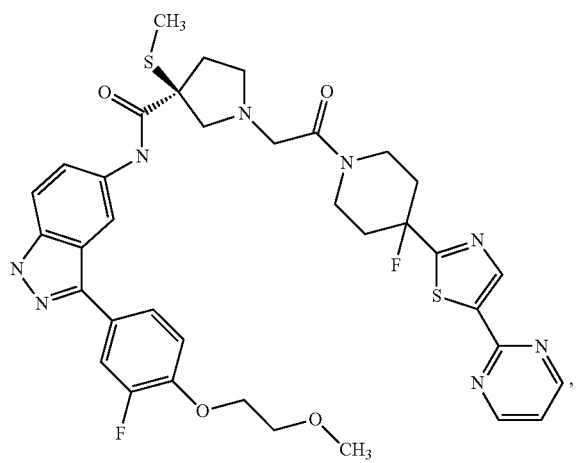

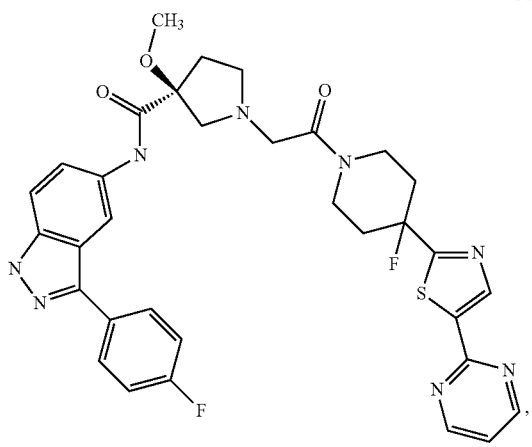,
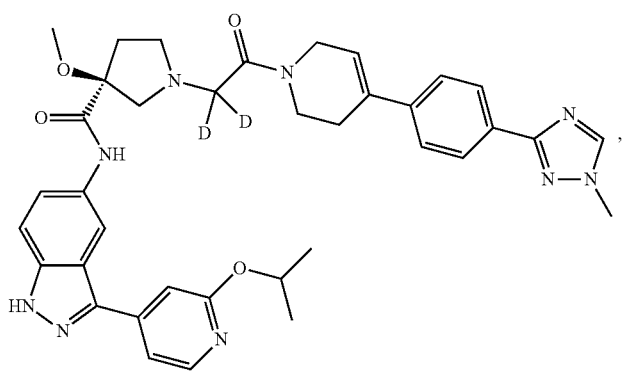,
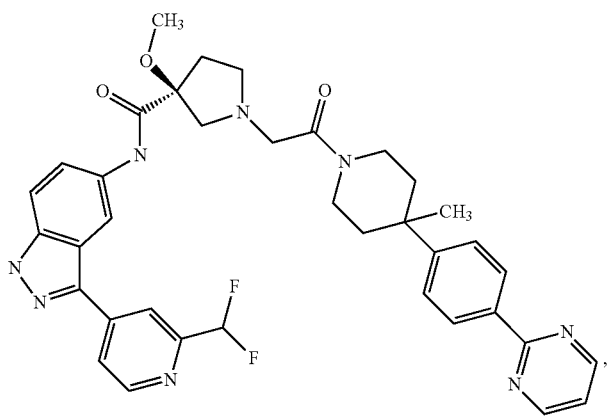,
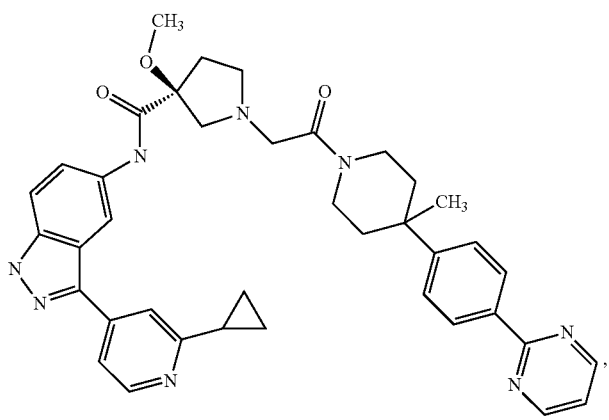,

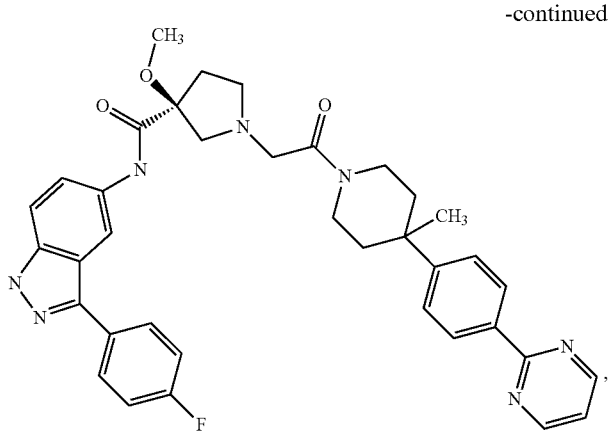
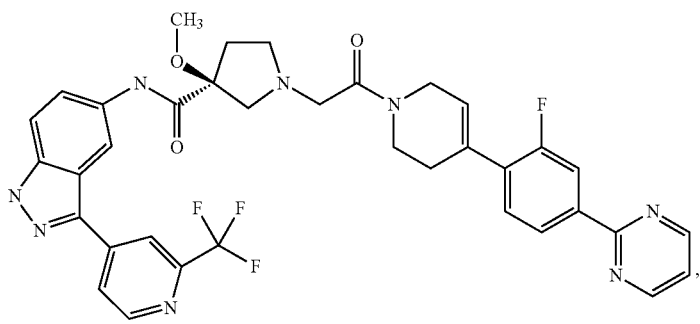
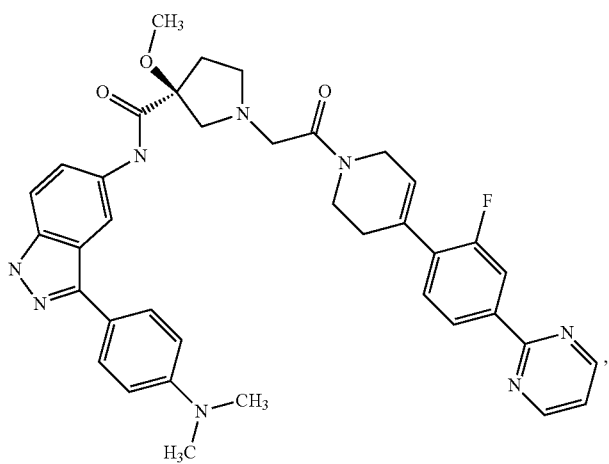
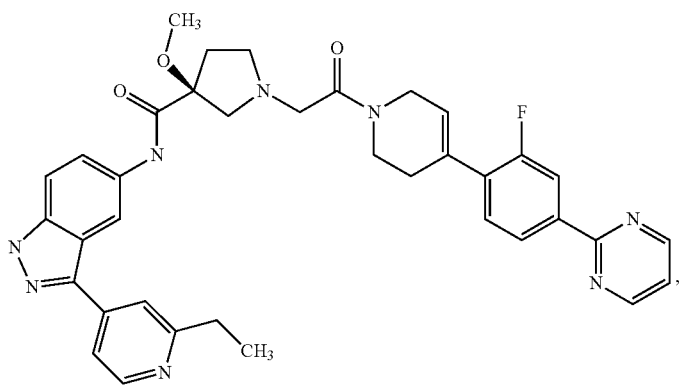

-continued
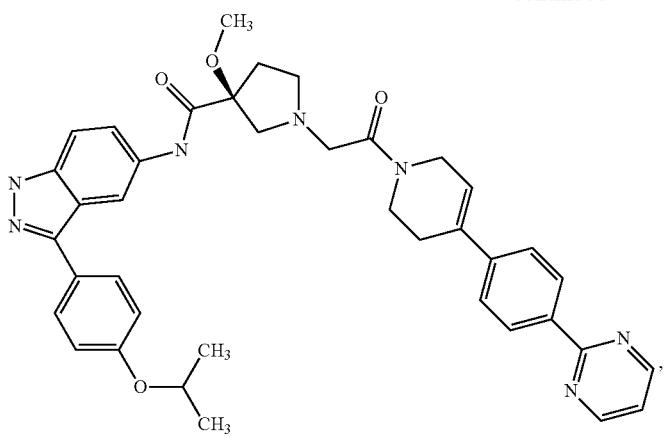
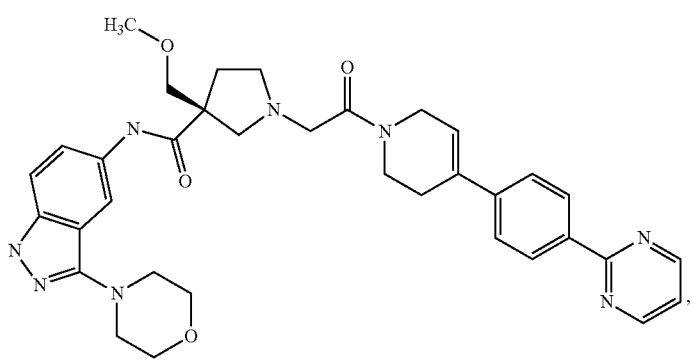
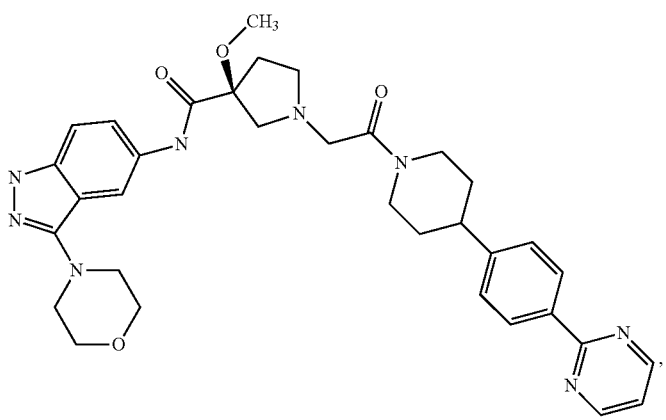
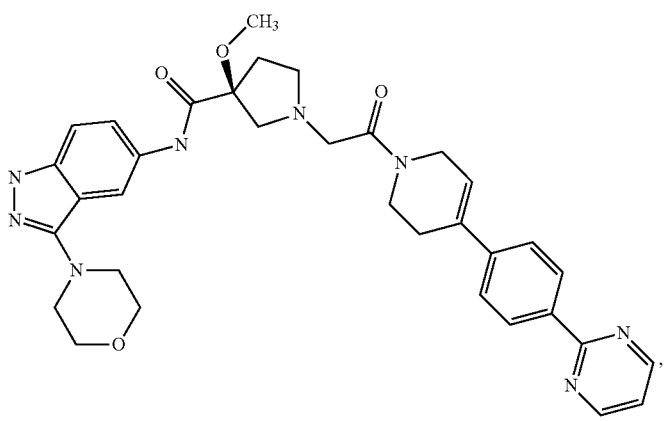

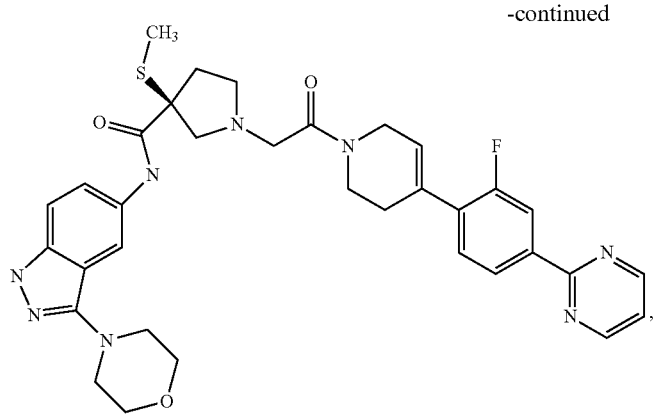
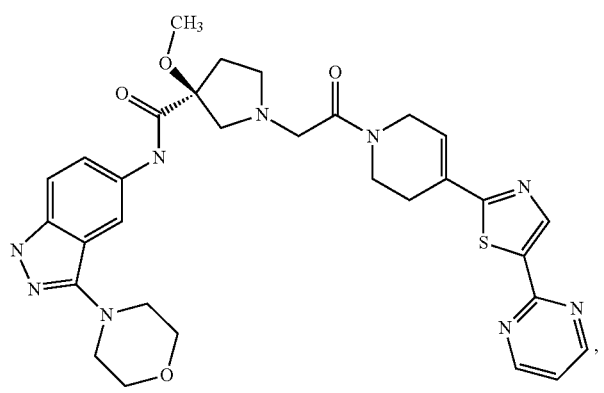
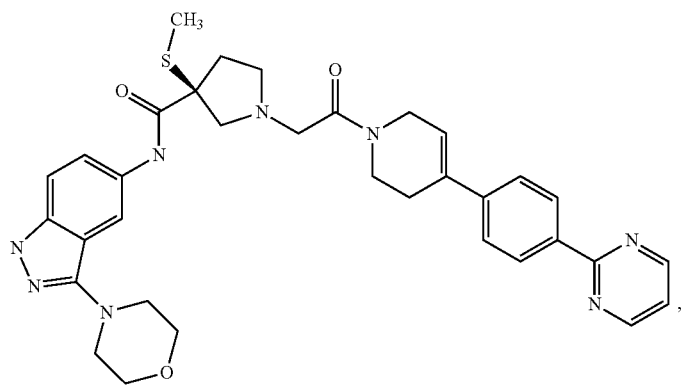

-continued
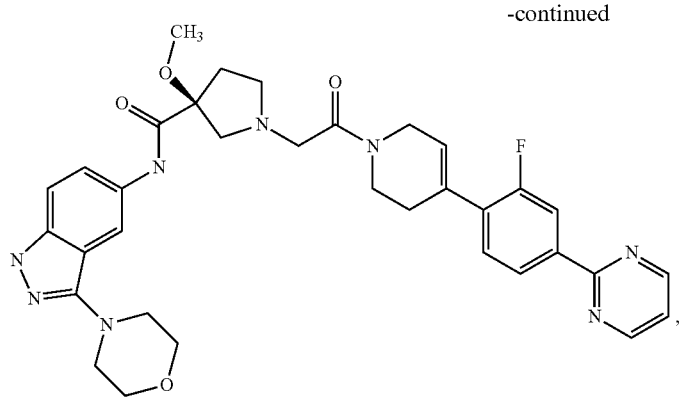
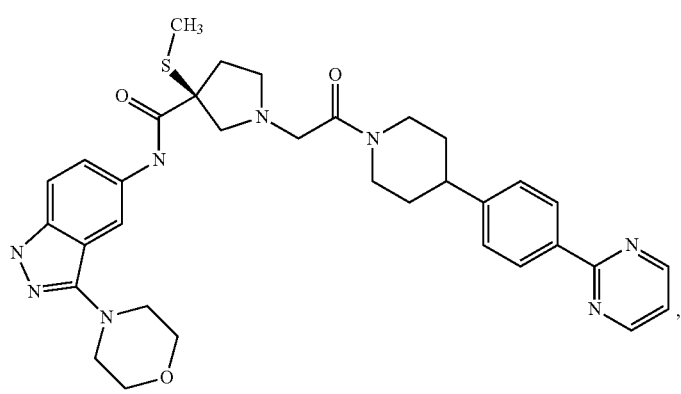
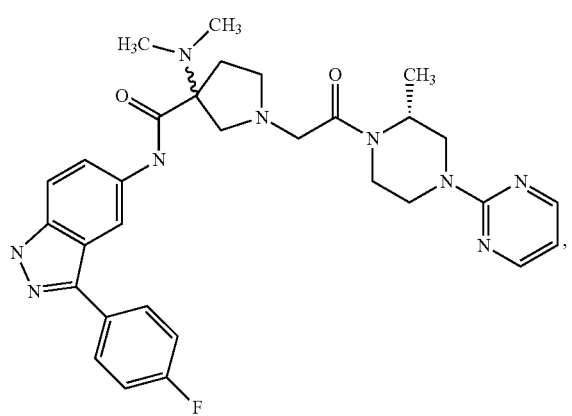
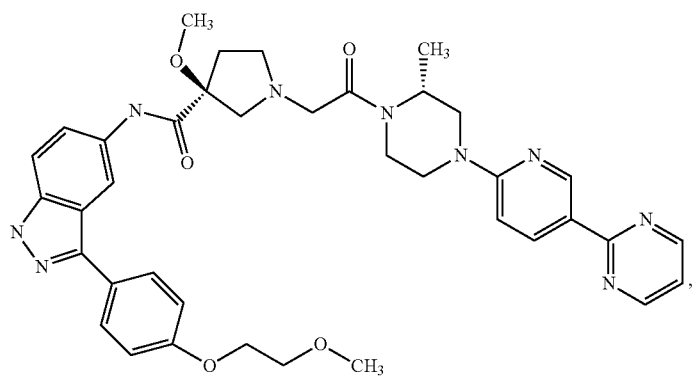

-continued
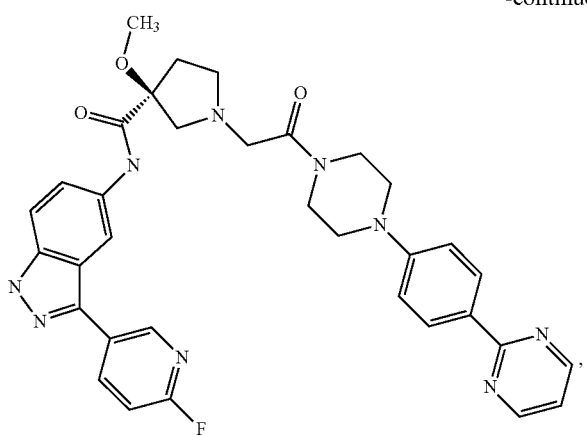
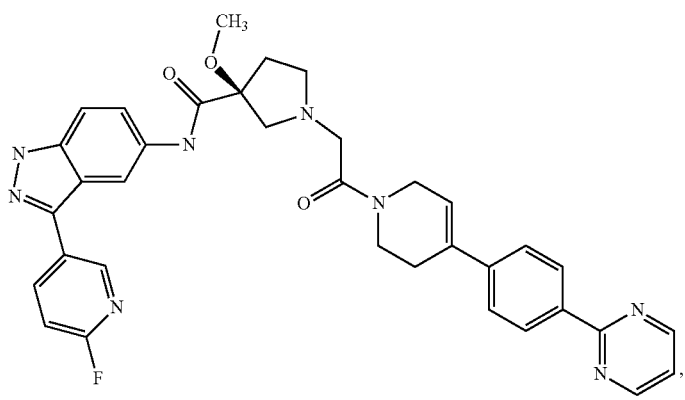
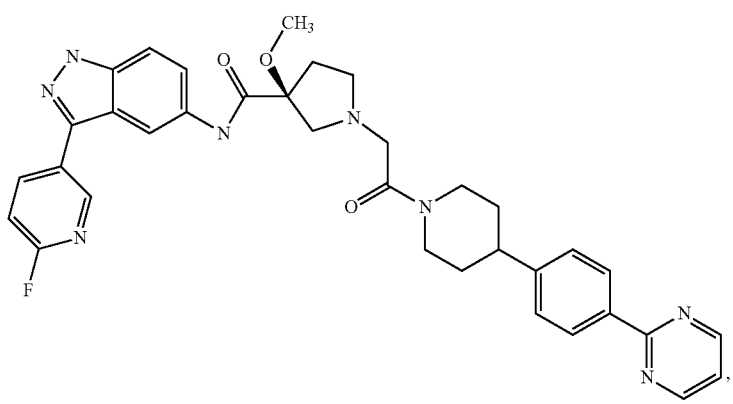
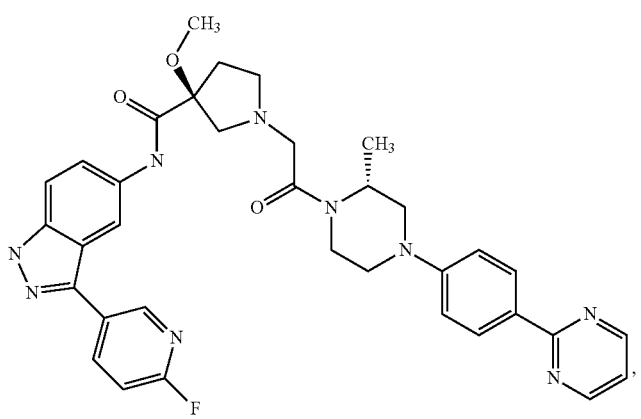

-continued
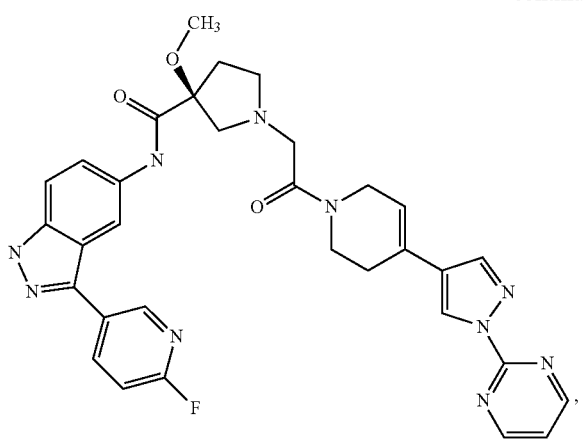
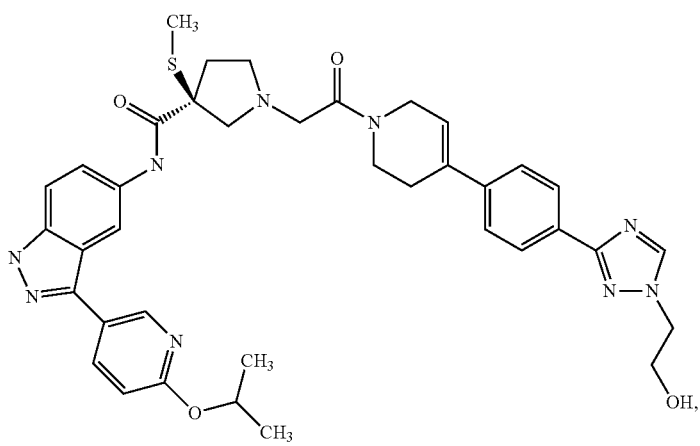
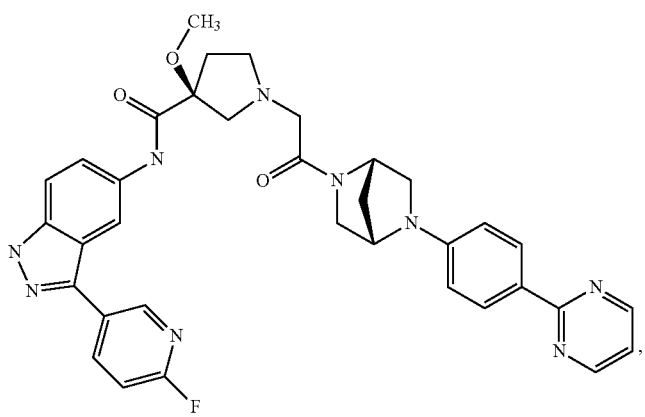
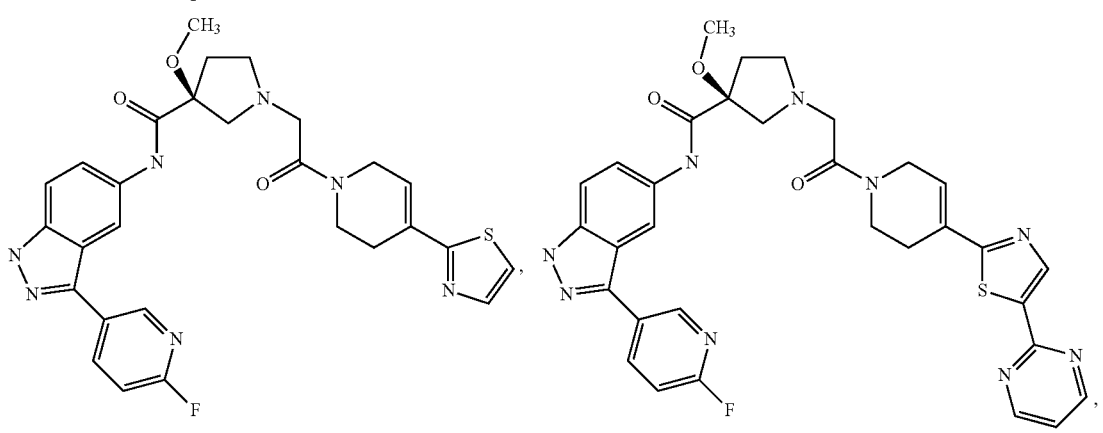

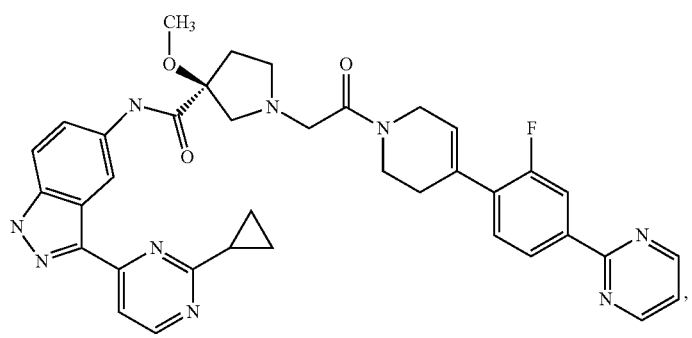
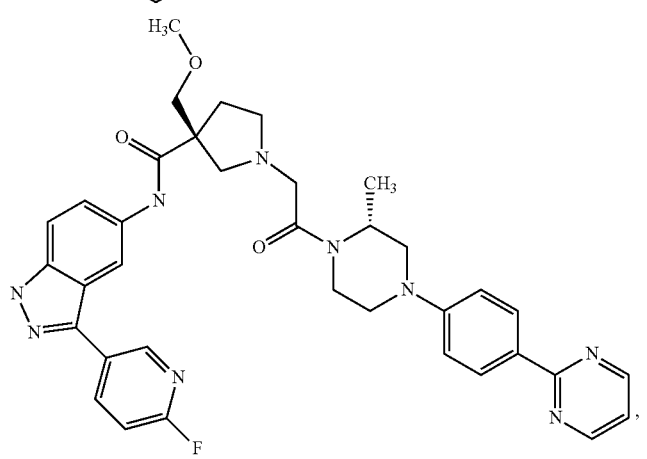
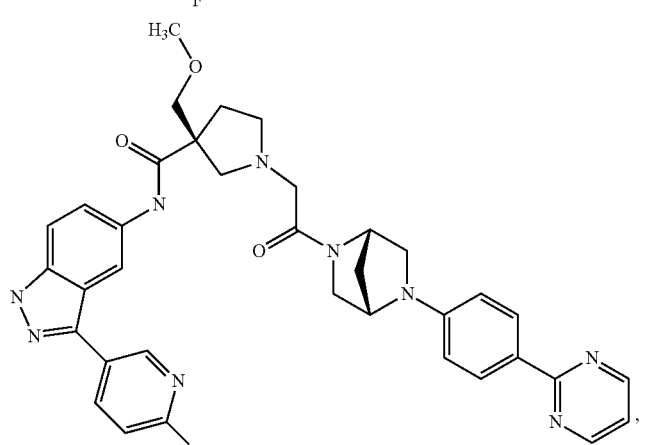
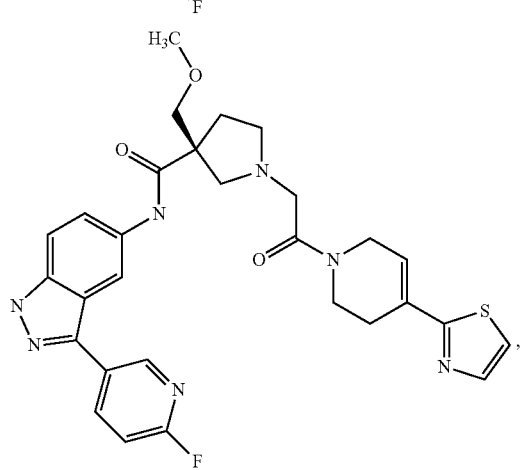

-continued
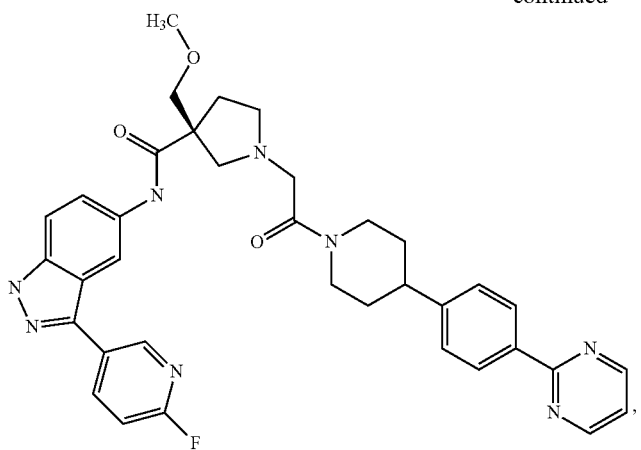
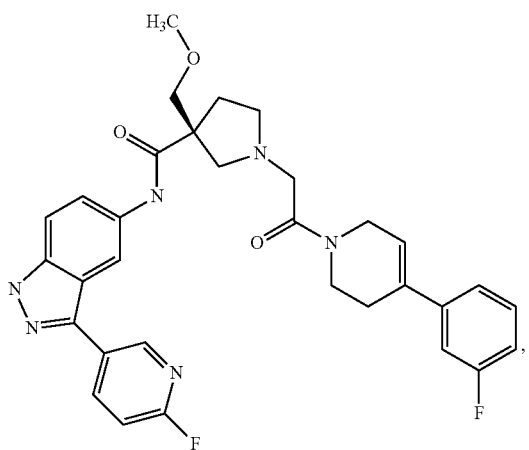
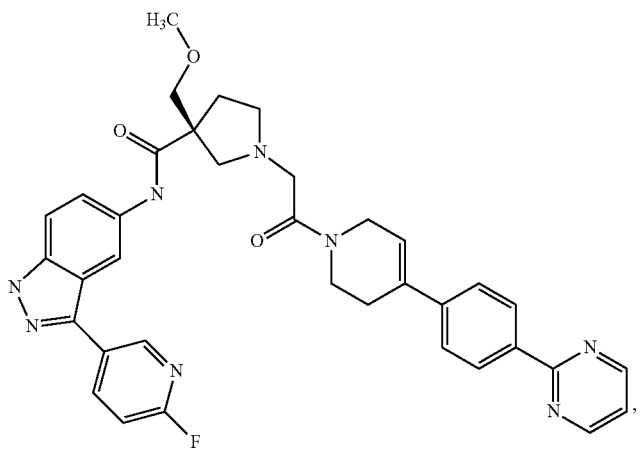

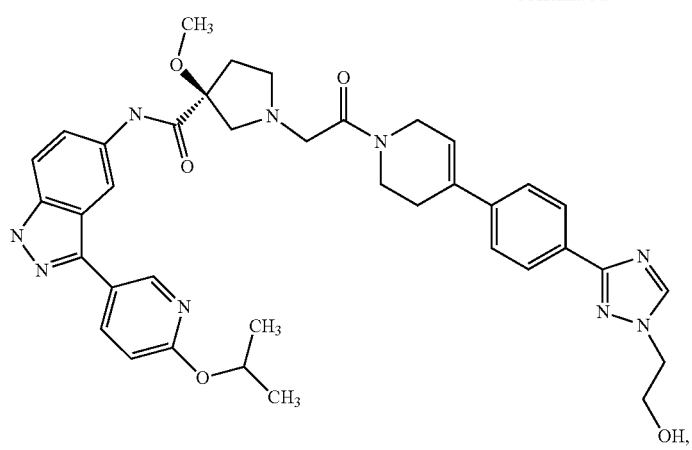
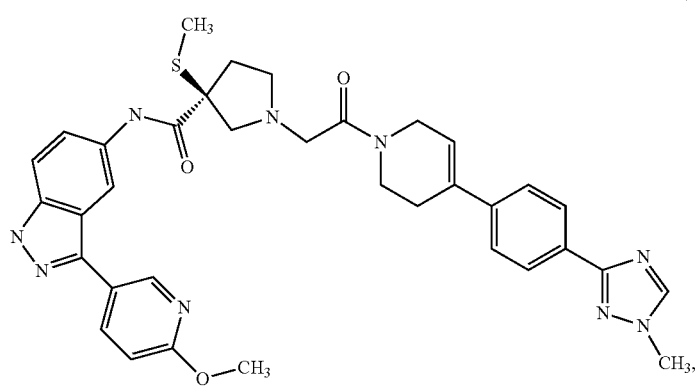
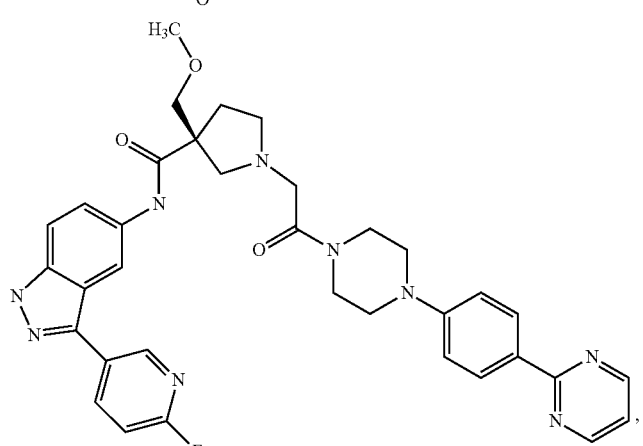
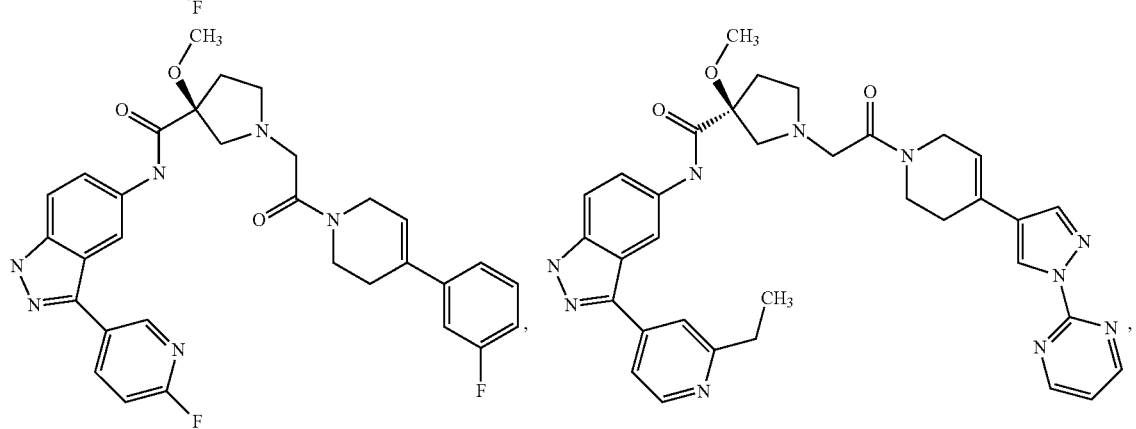

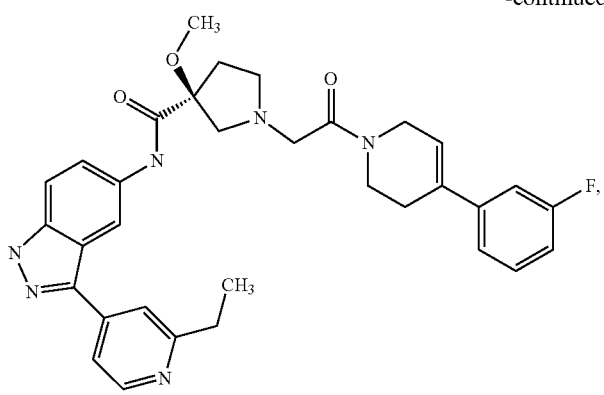
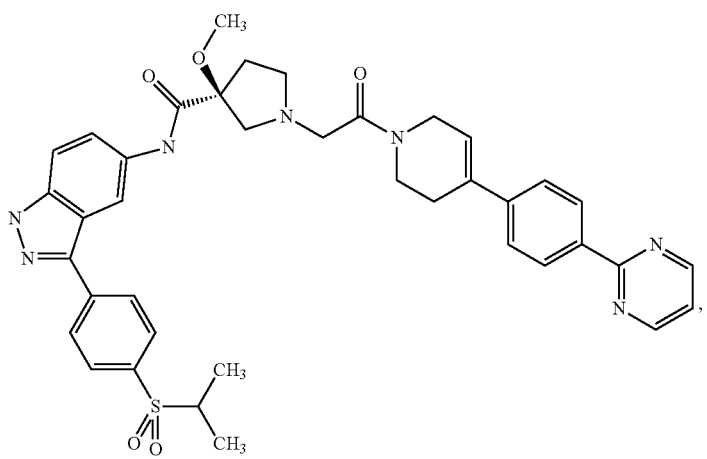
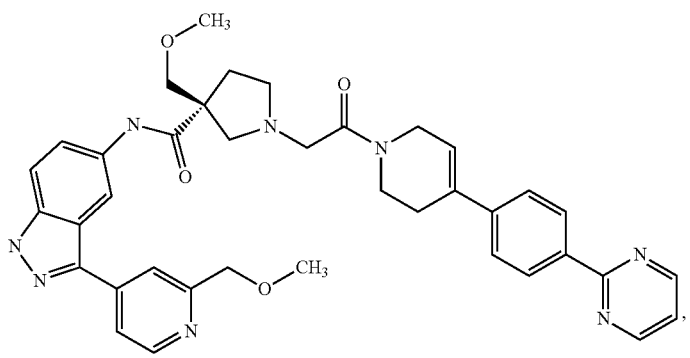
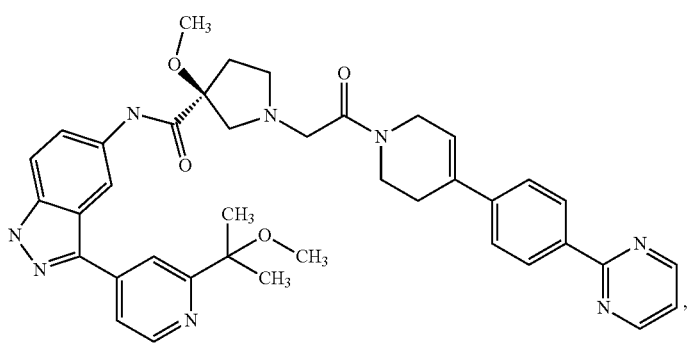

-continued
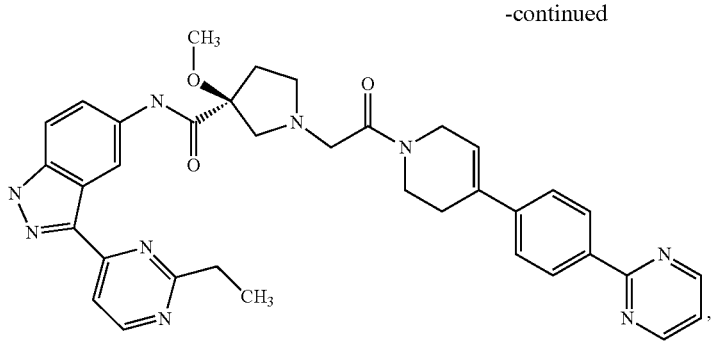
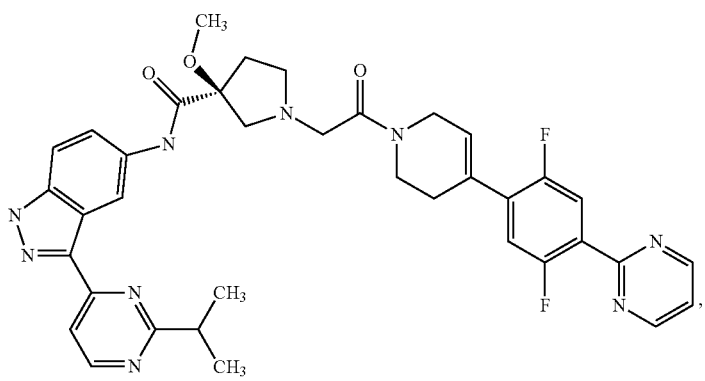
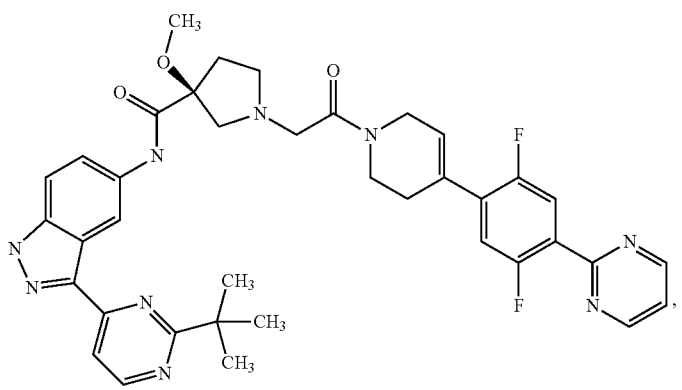
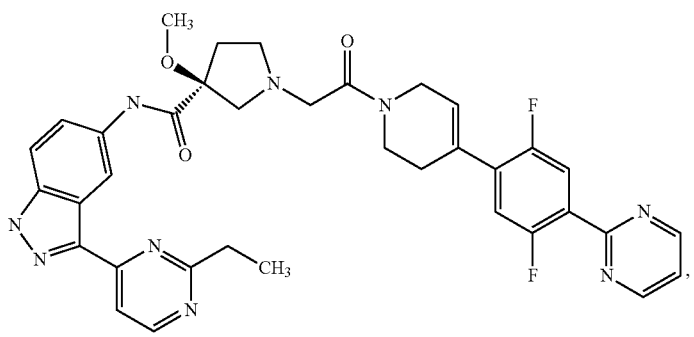

-continued
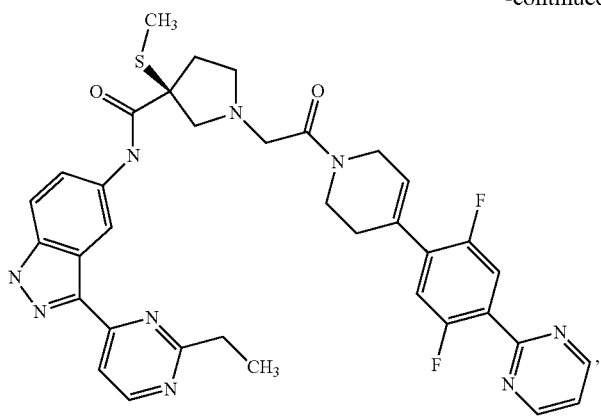
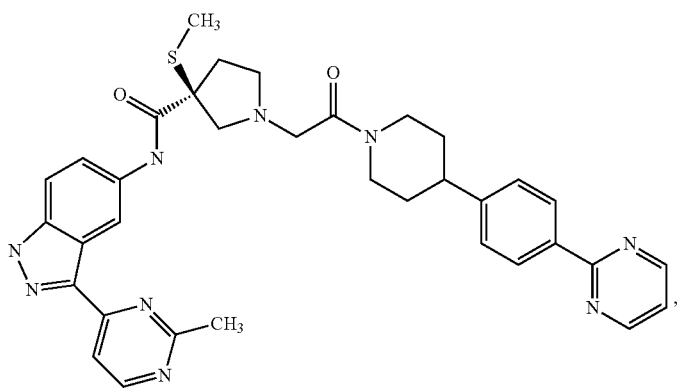
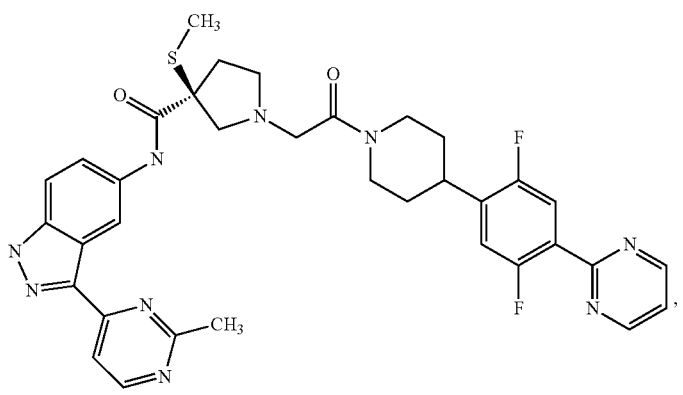
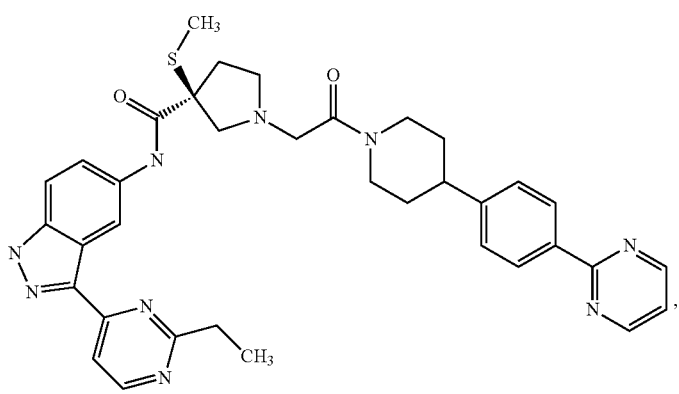

-continued
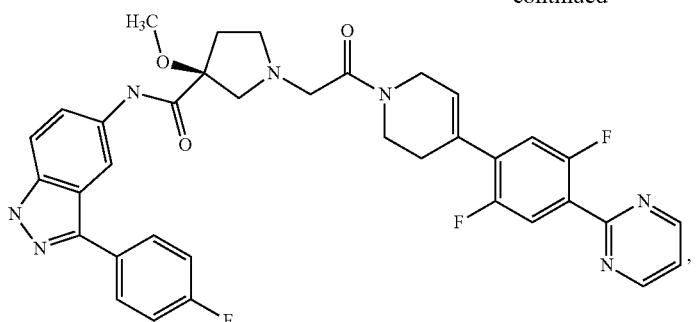
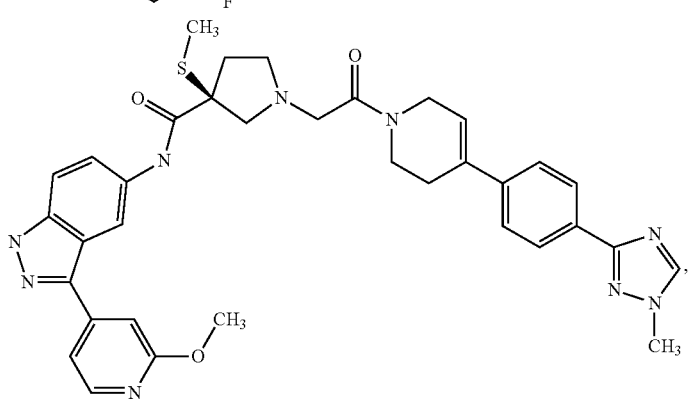
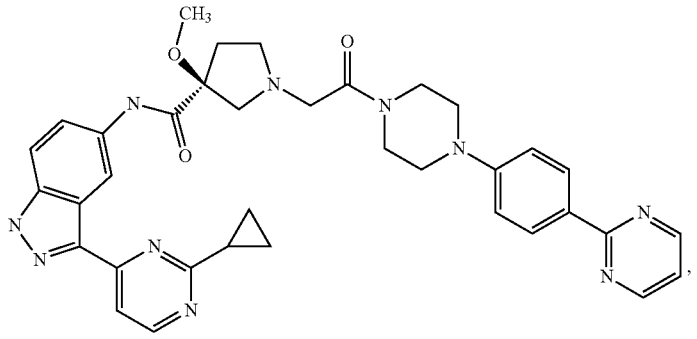
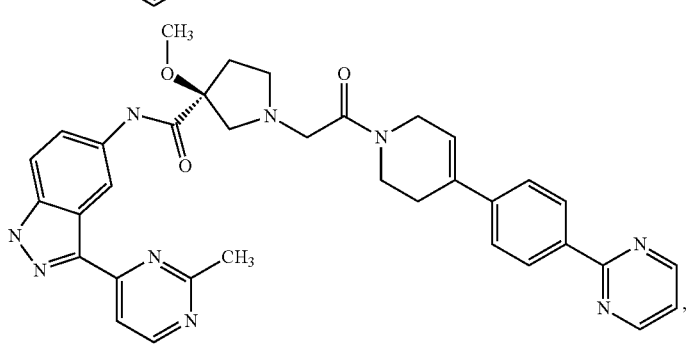
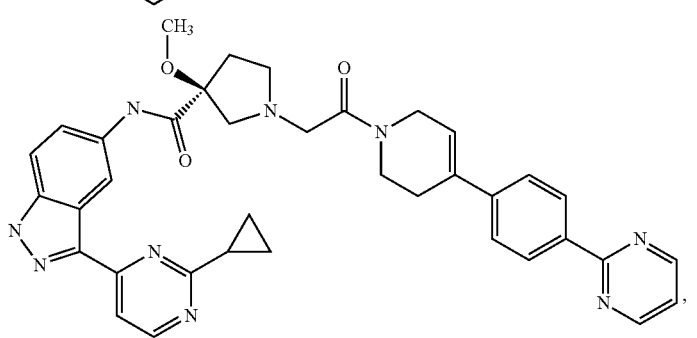

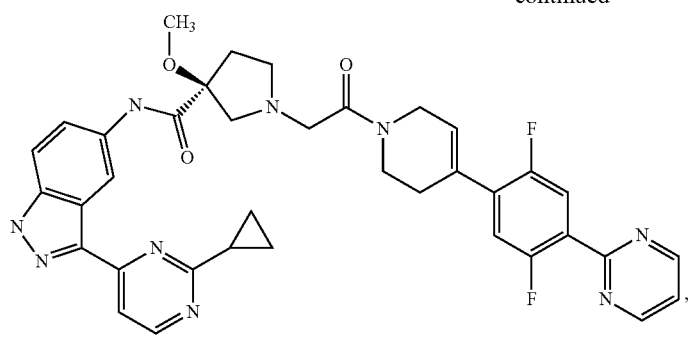
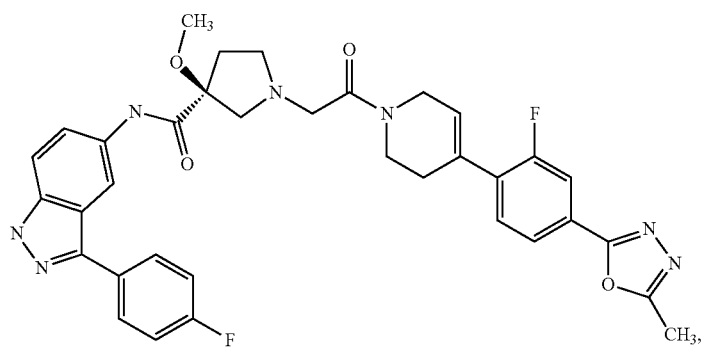
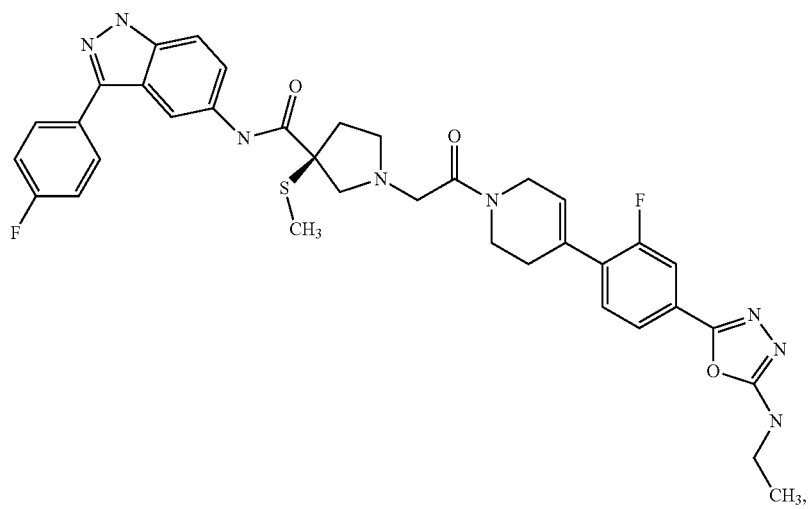
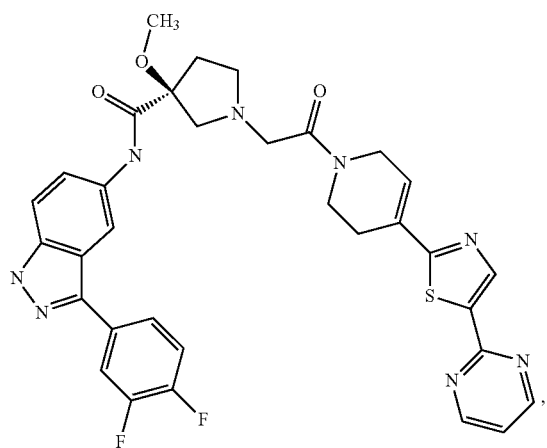

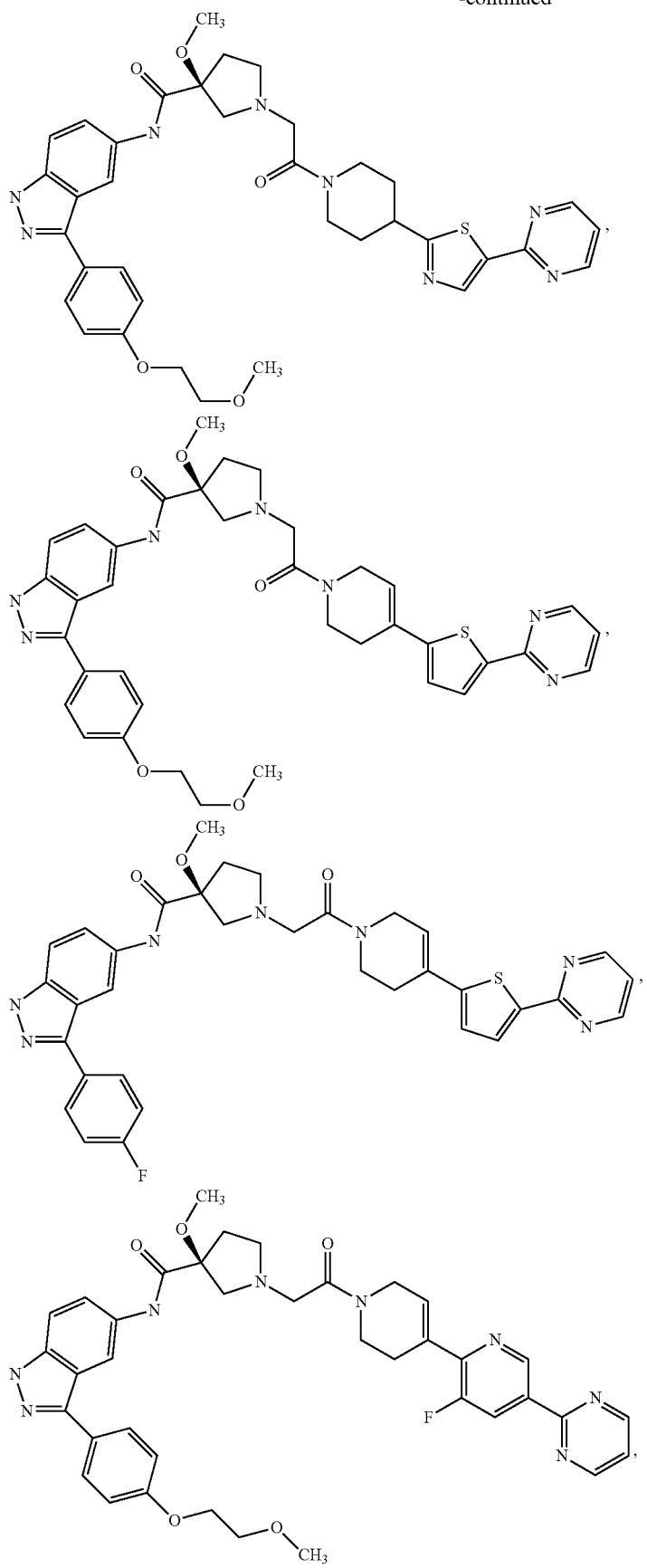

-continued
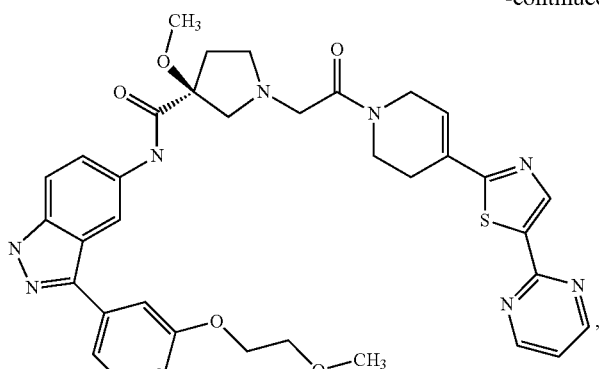
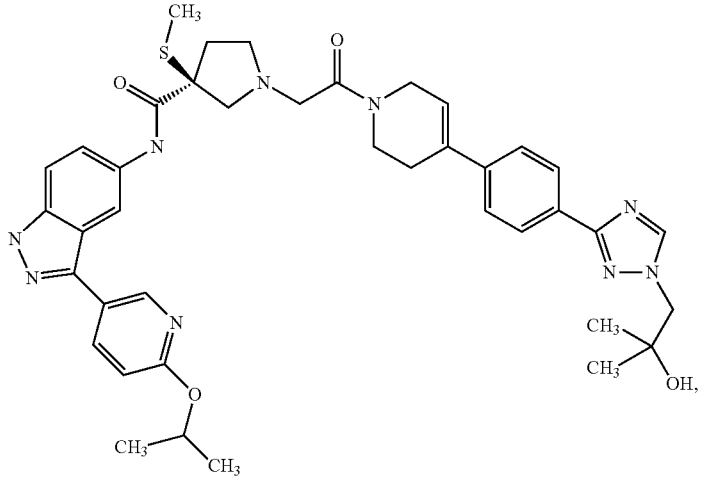
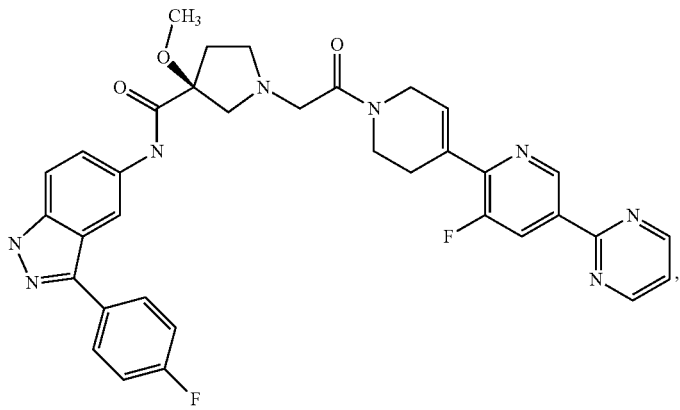
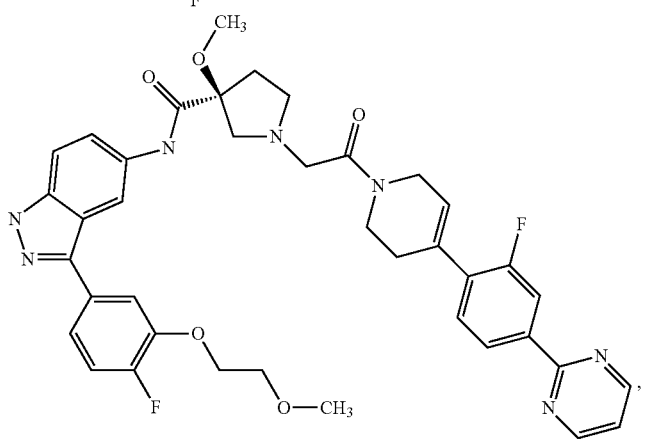

-continued
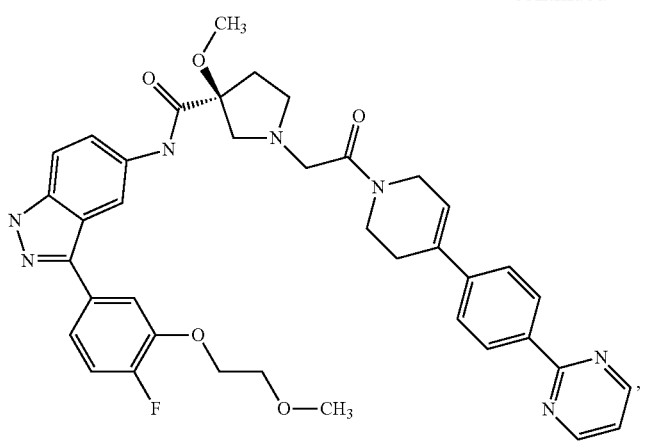
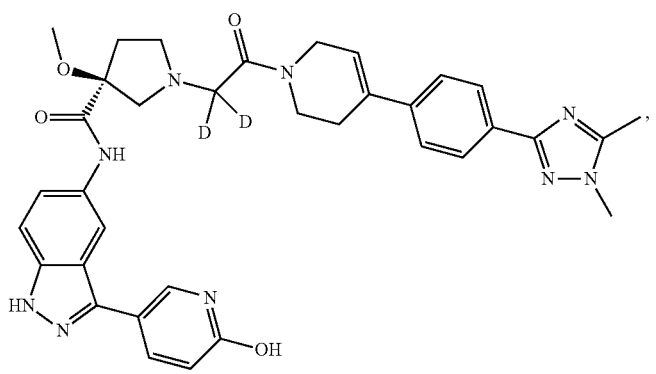
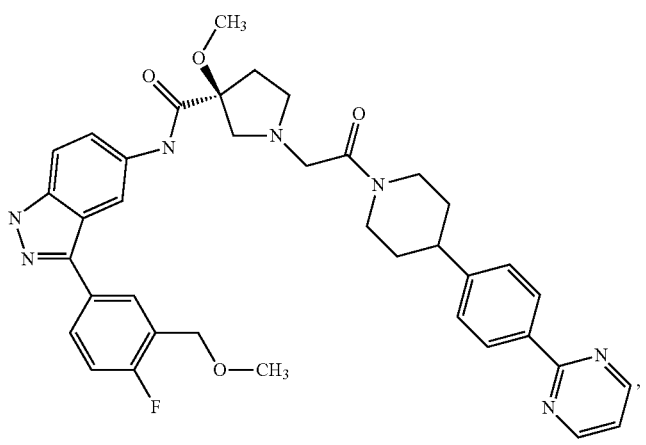

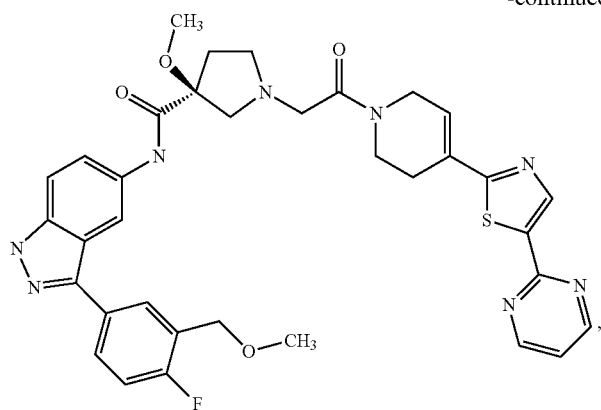
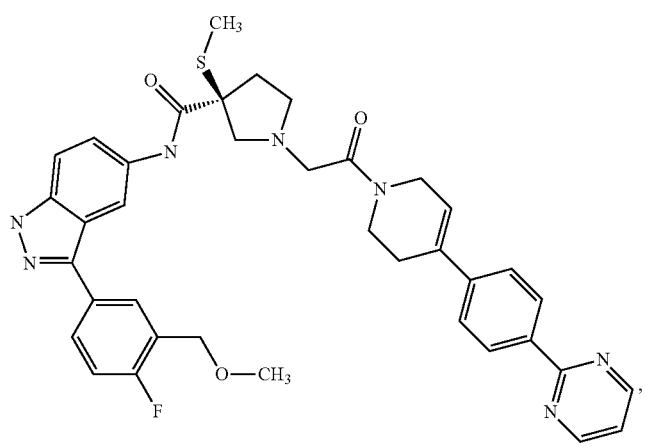
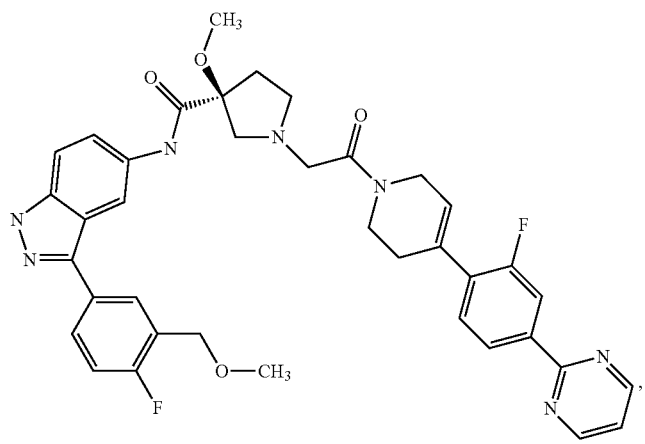

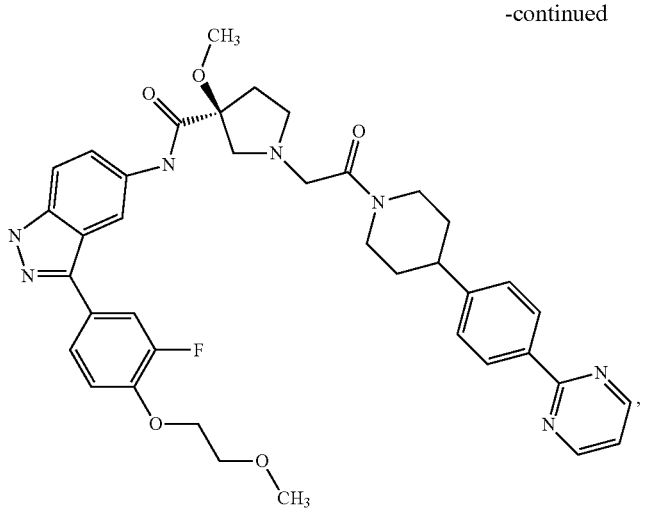
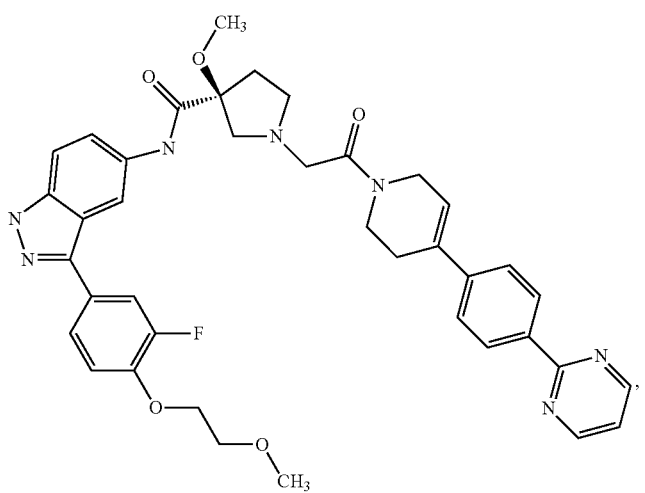
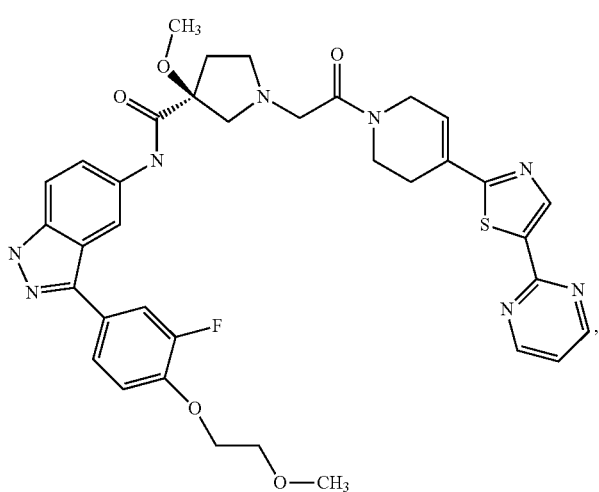

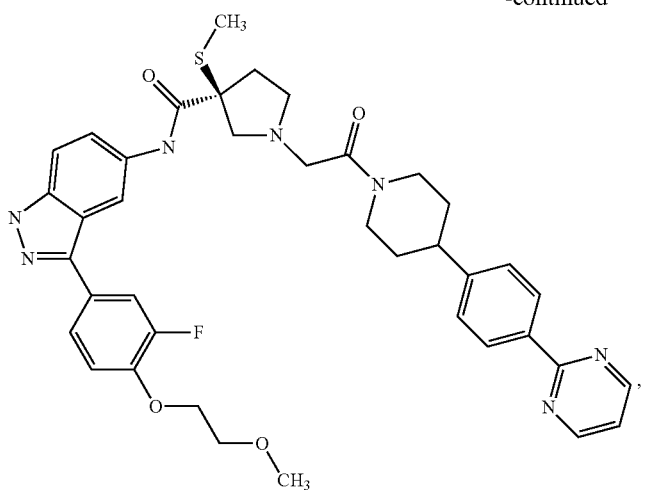
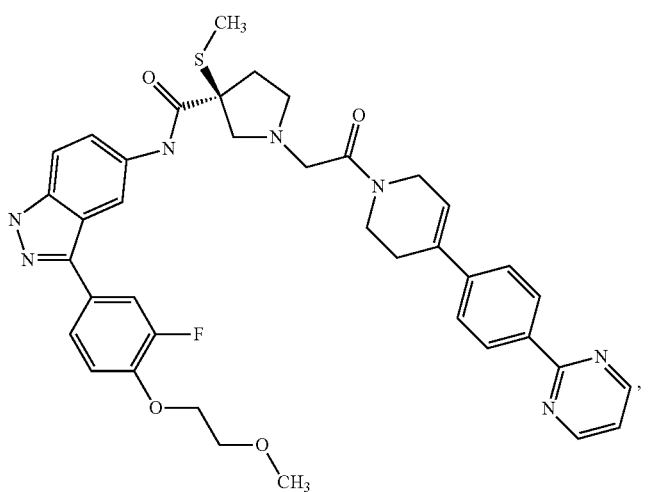
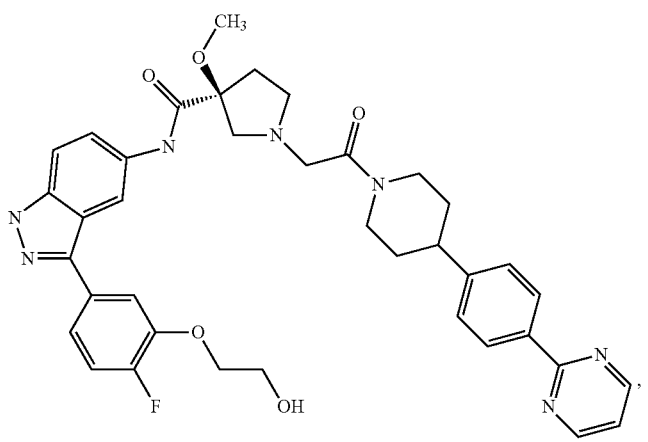

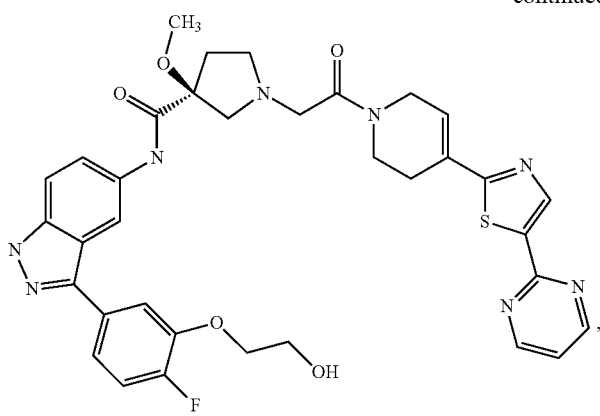
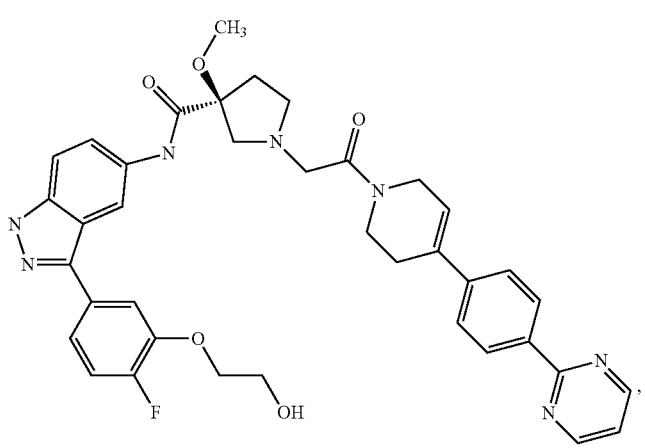
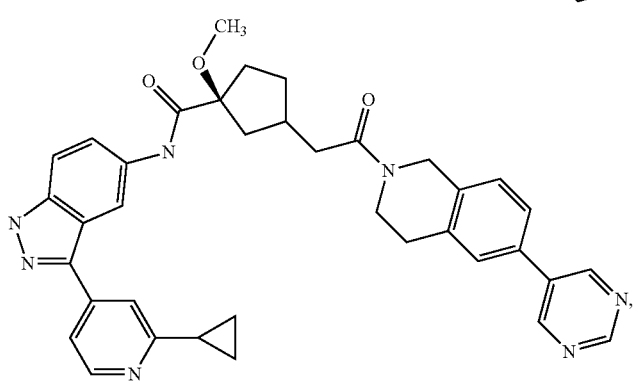
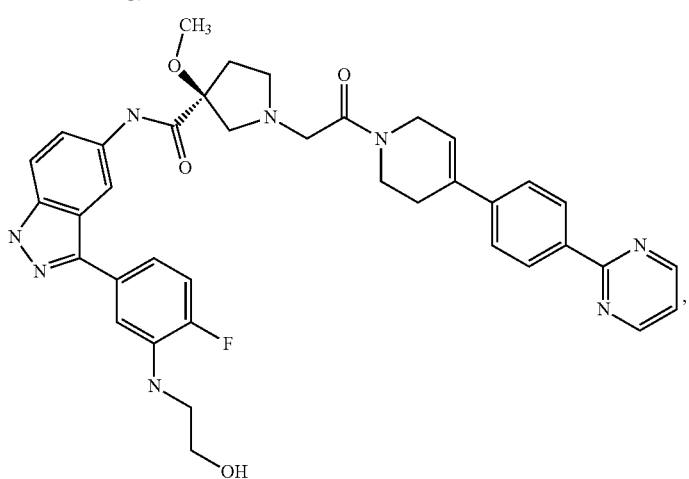

-continued
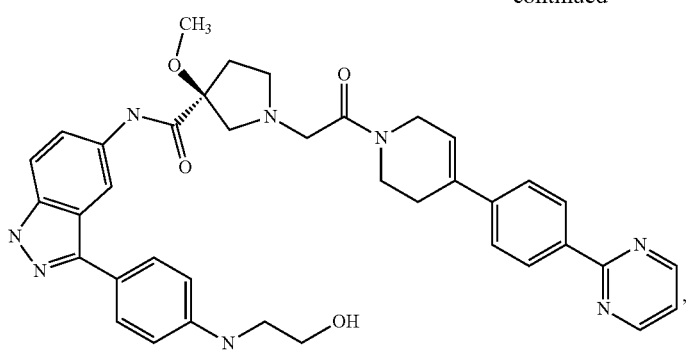
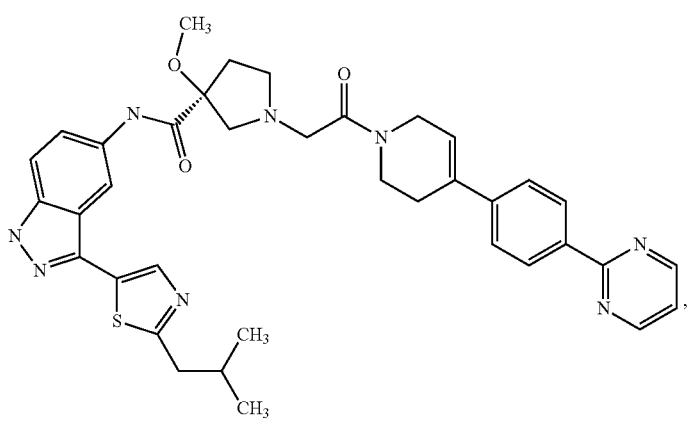
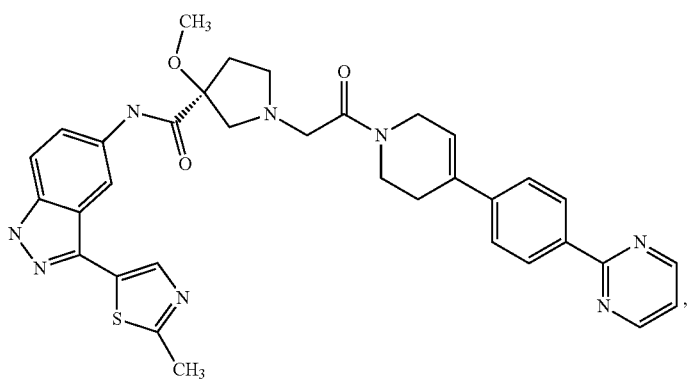
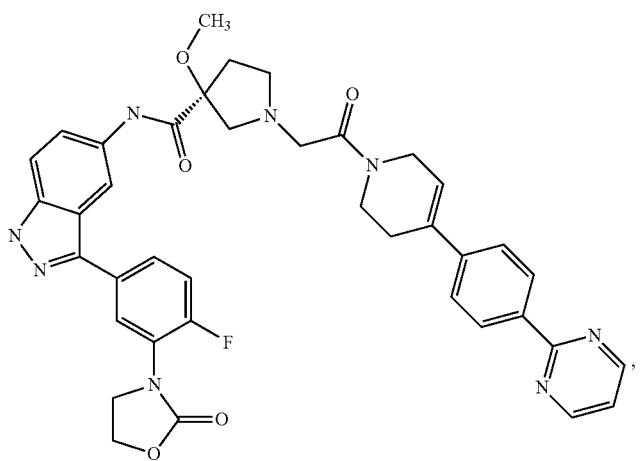

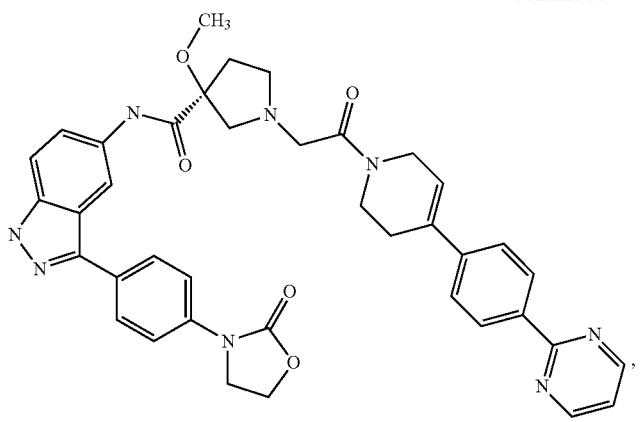
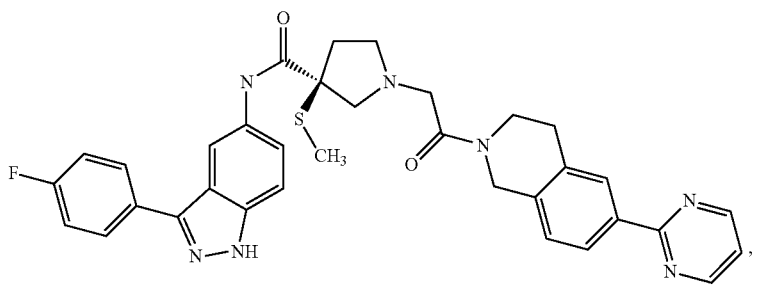
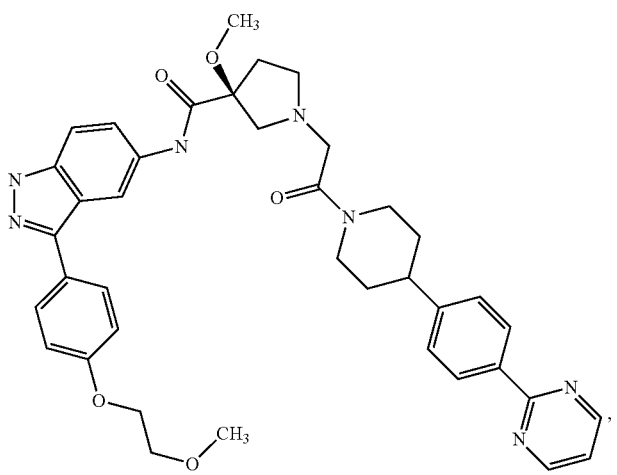
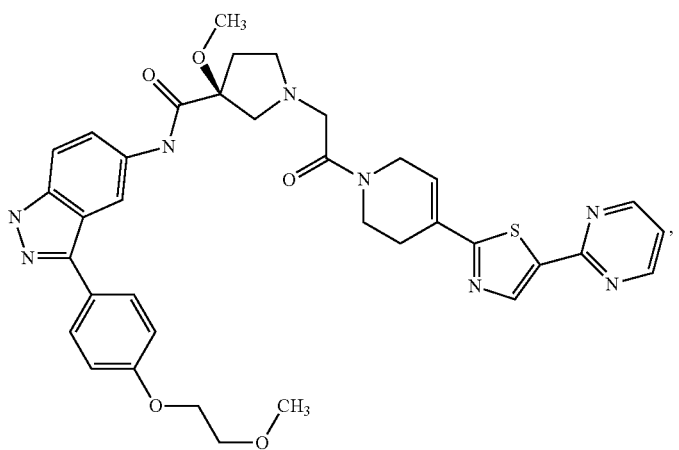

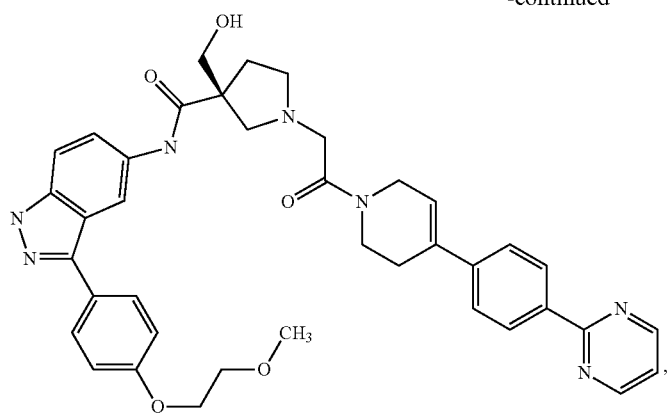
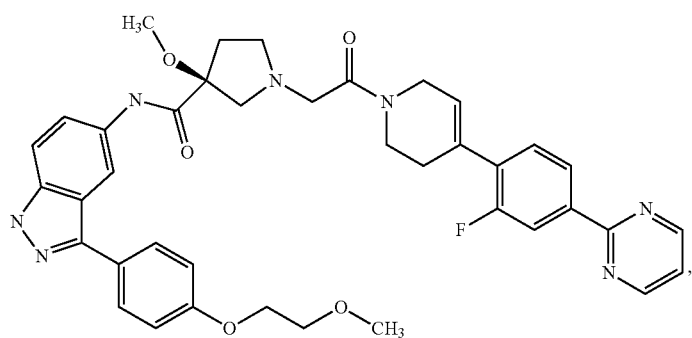
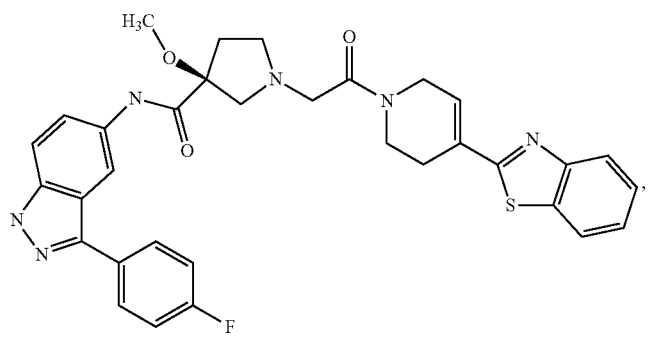
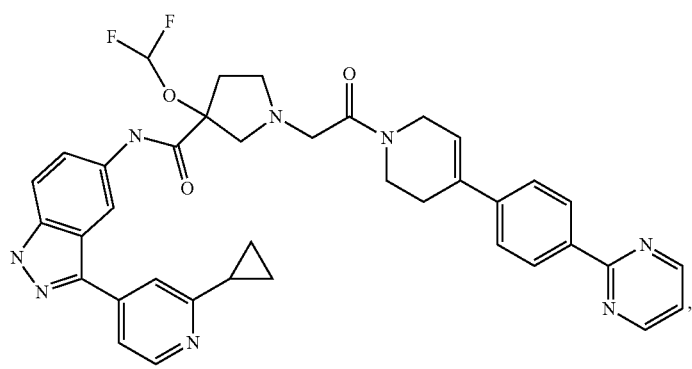

-continued
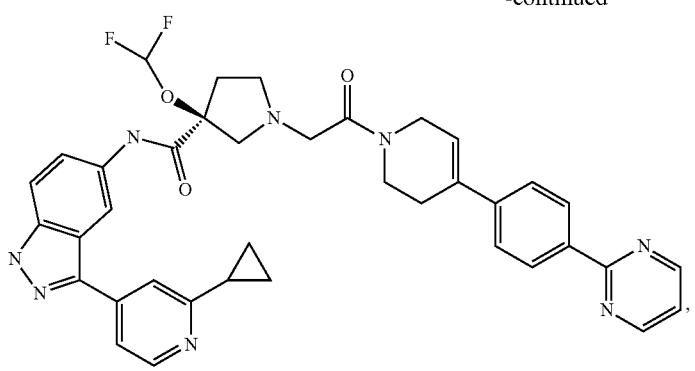
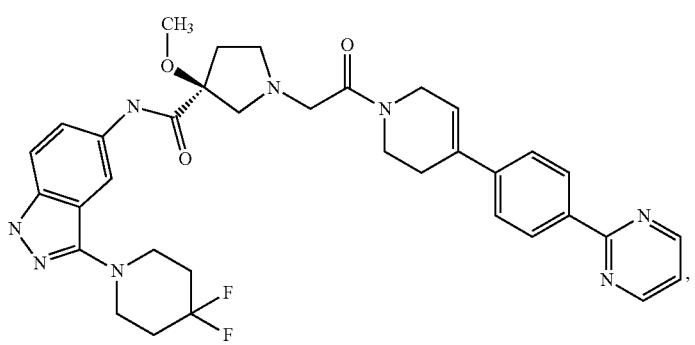
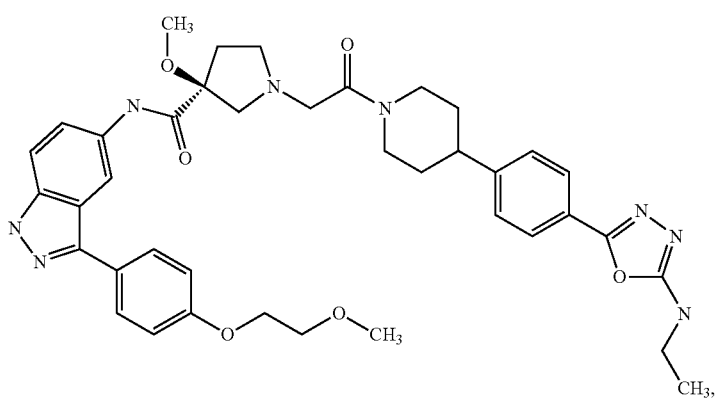
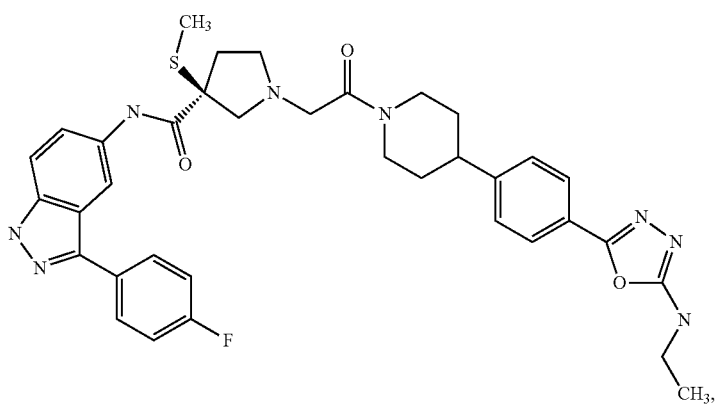

-continued
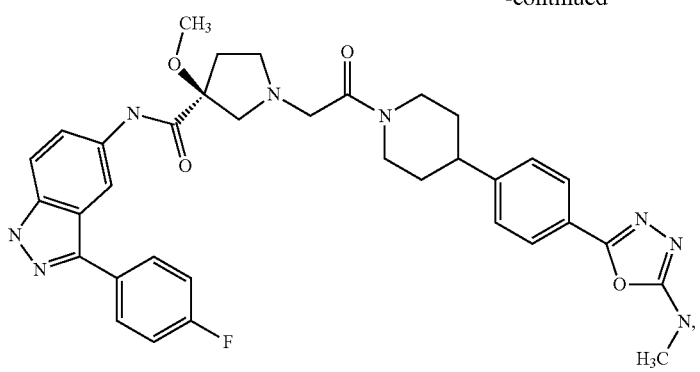
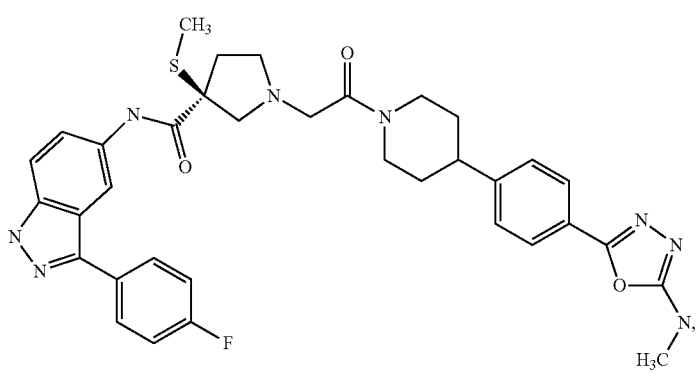
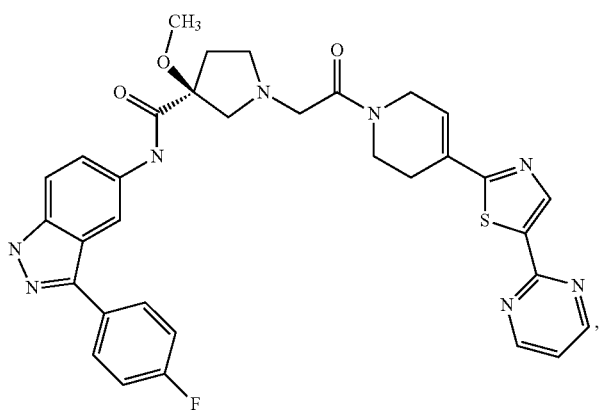
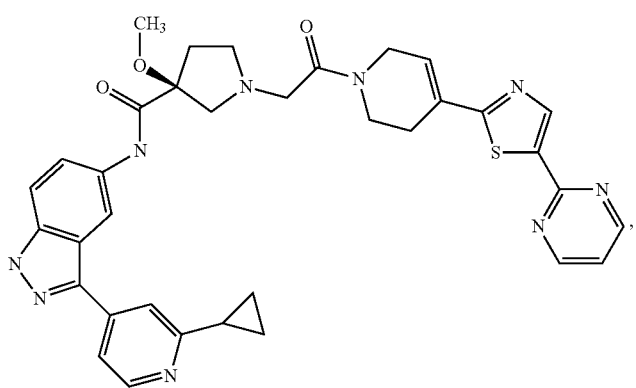

-continued
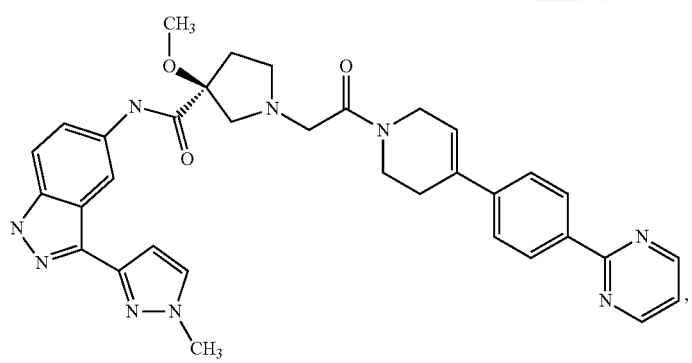
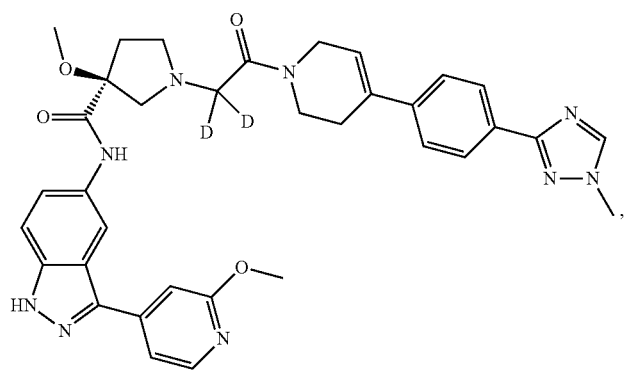
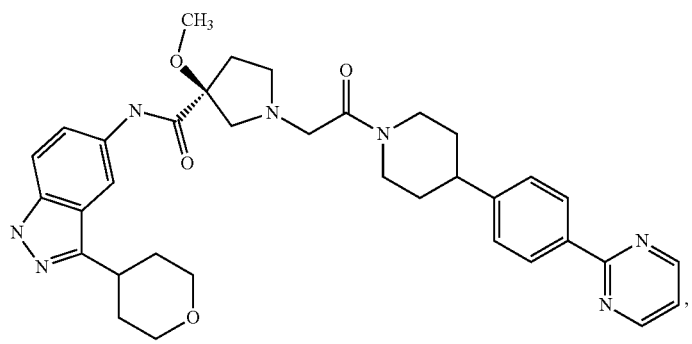
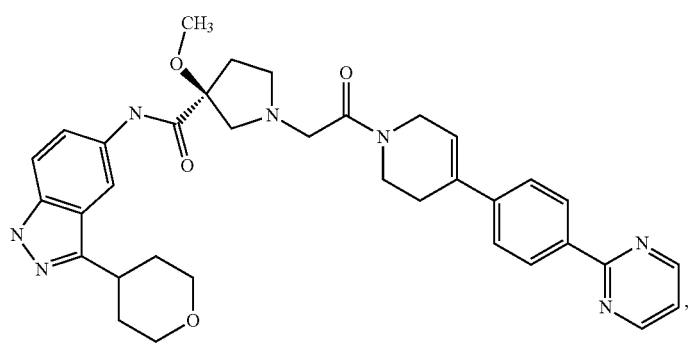

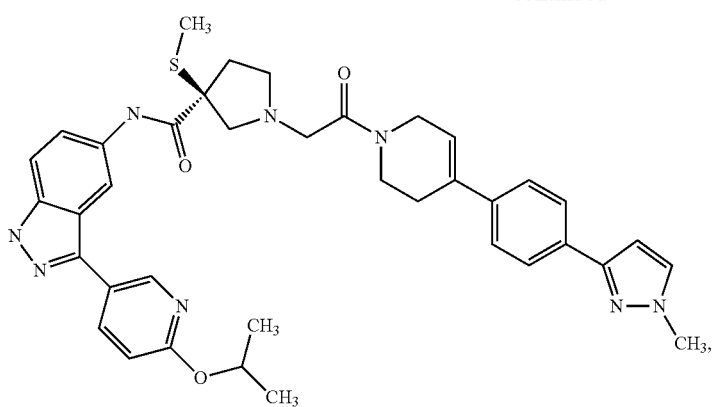
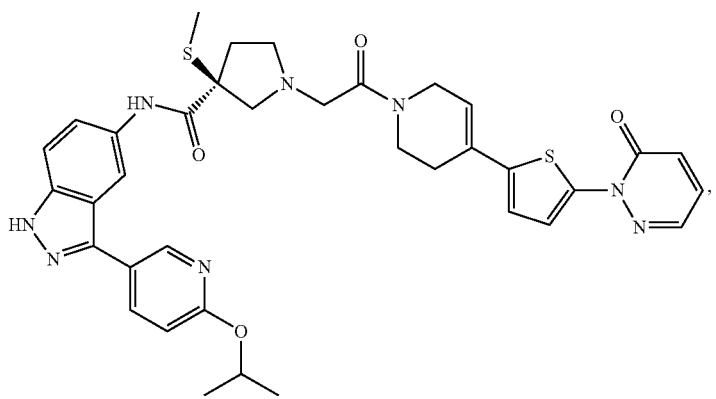
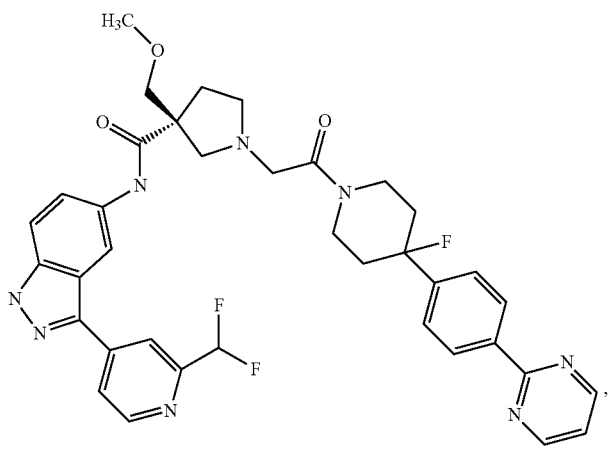
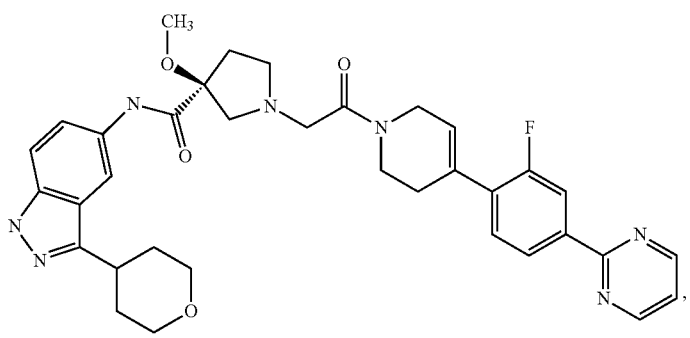

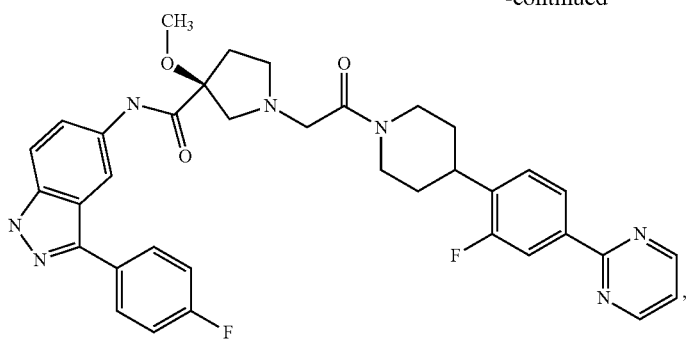
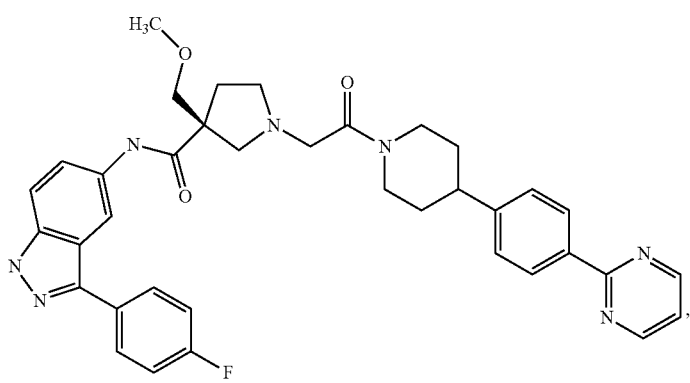
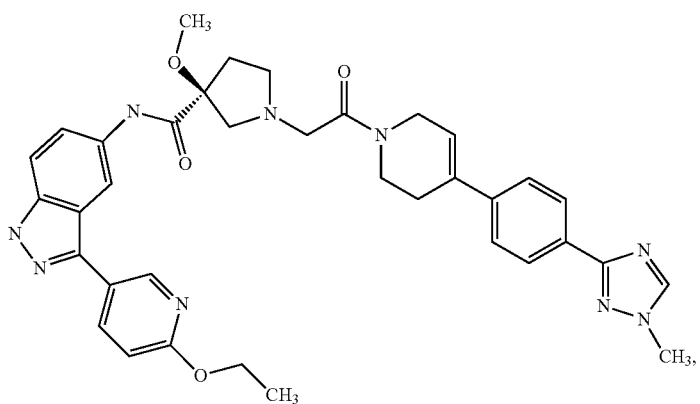
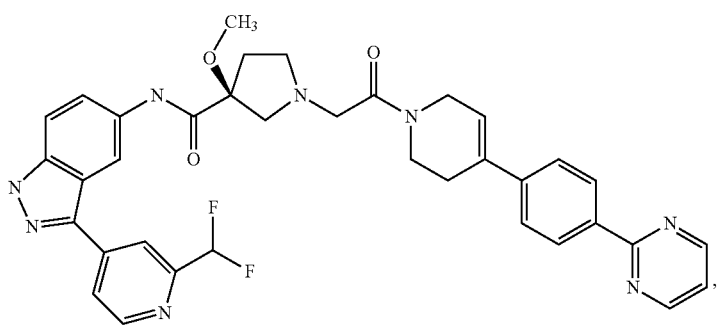

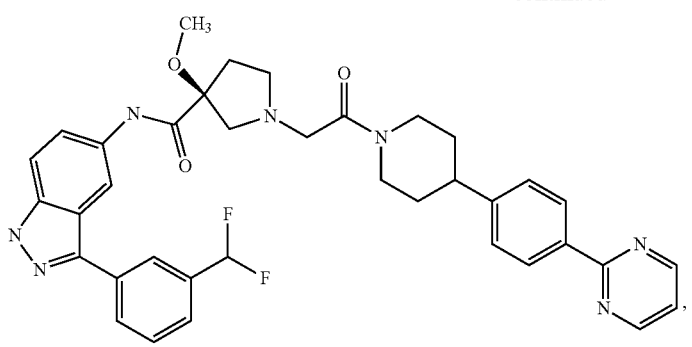
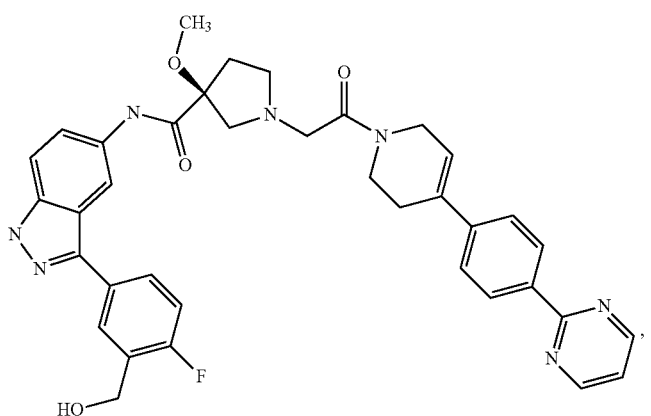
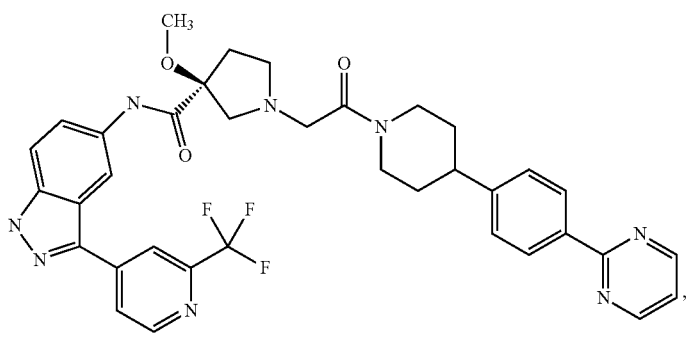
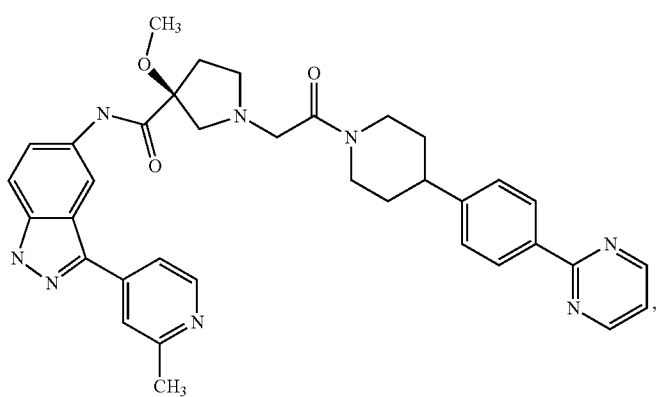

-continued
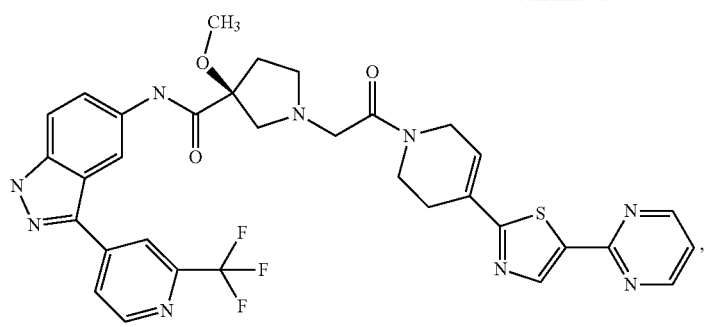
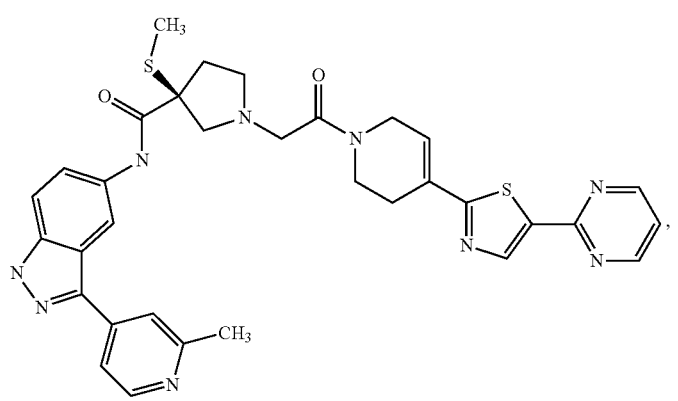
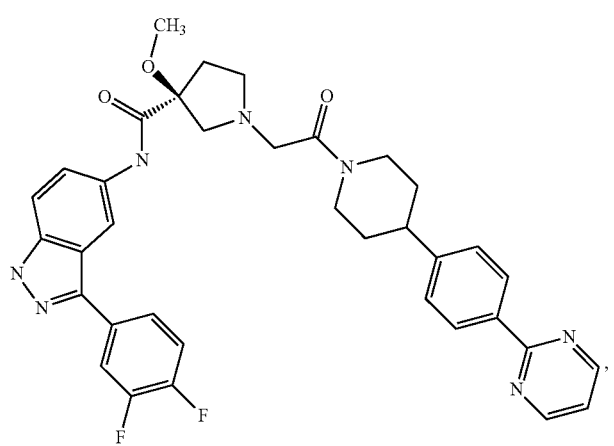
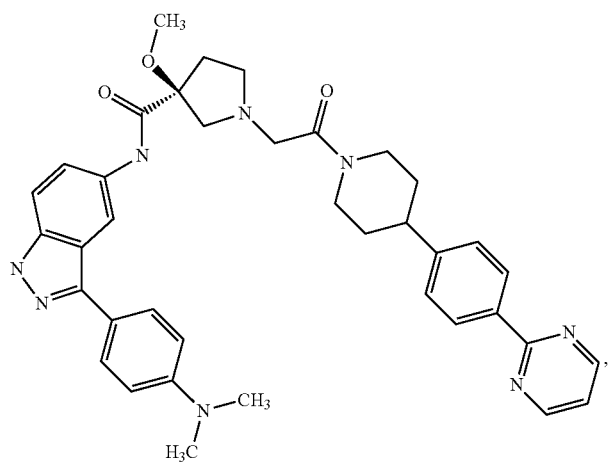

-continued
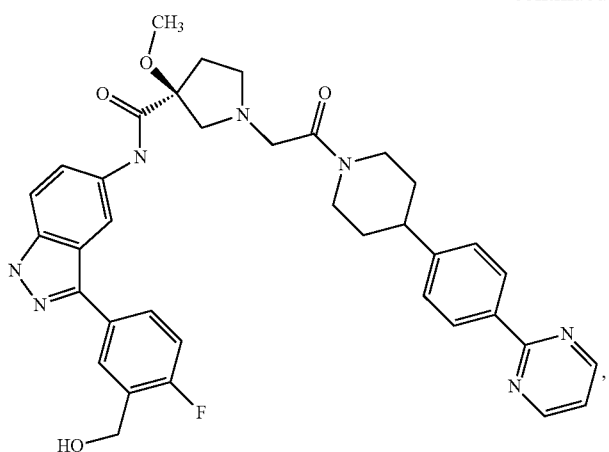
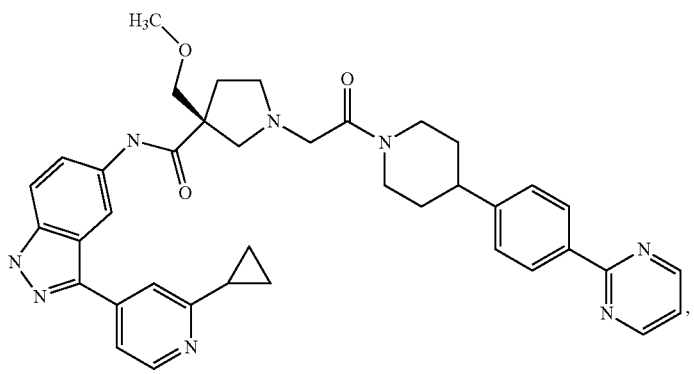
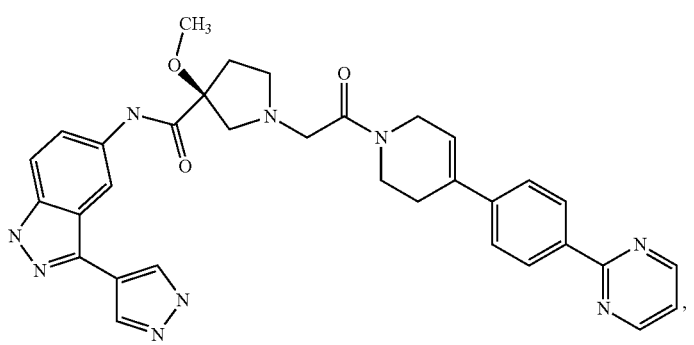
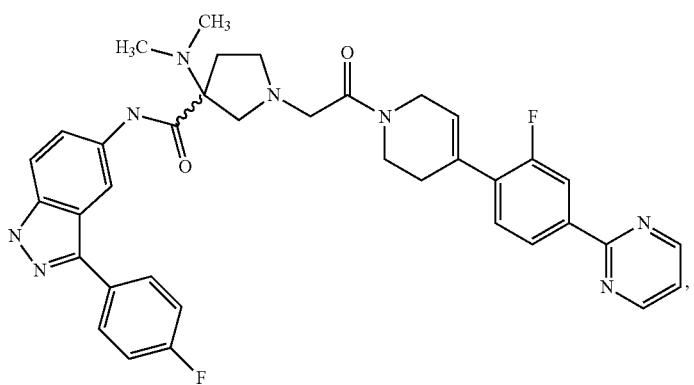

-continued
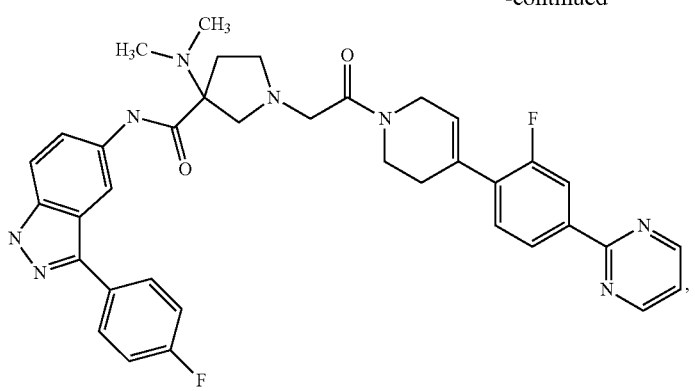
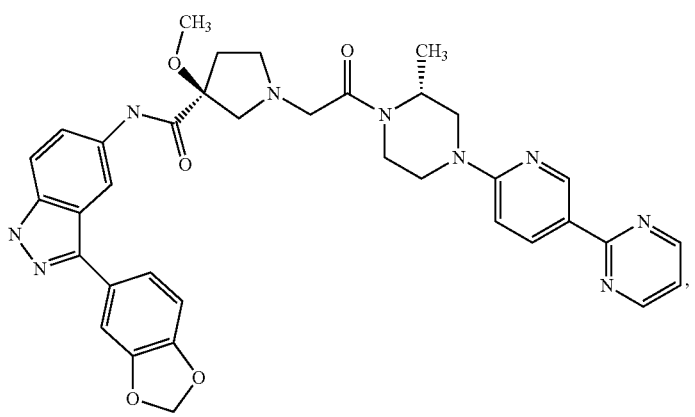
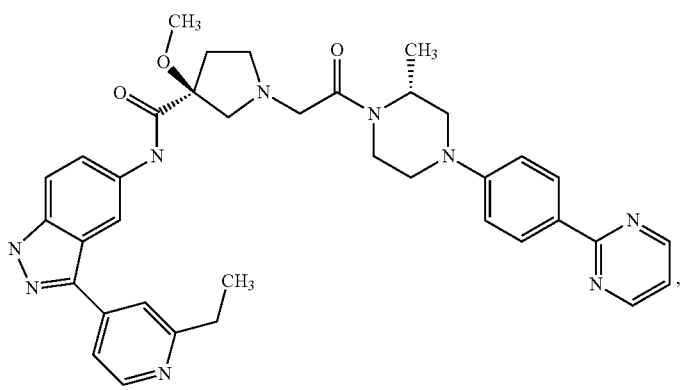
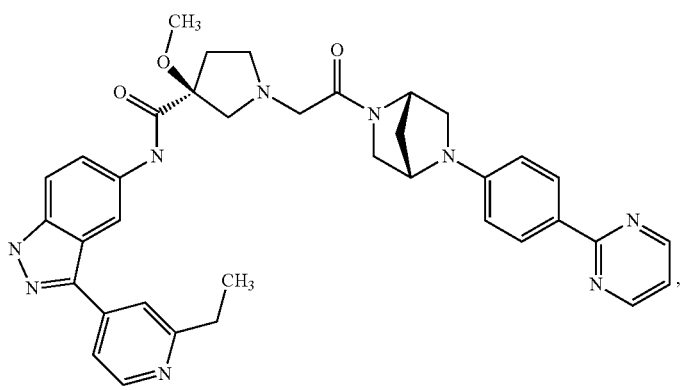

-continued
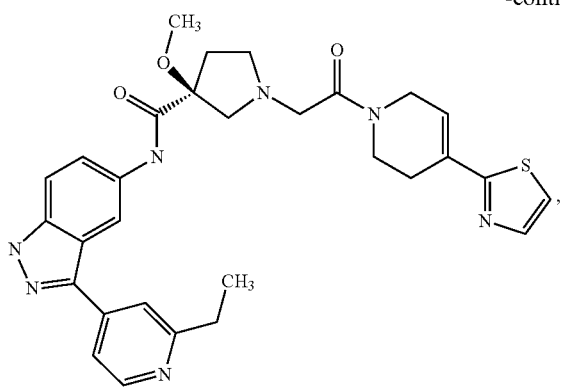
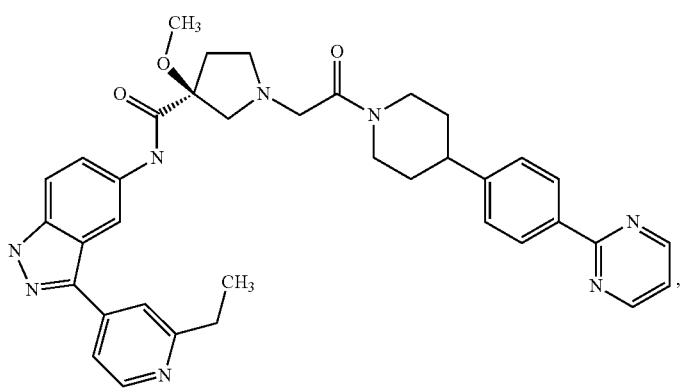
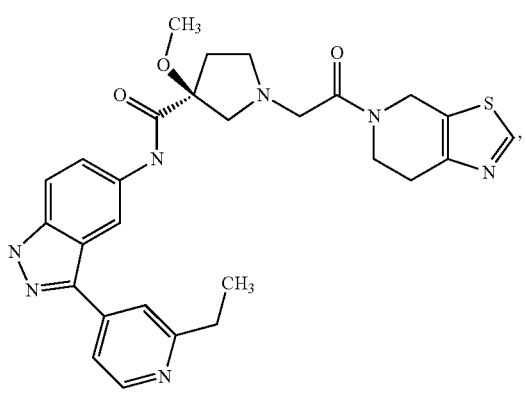
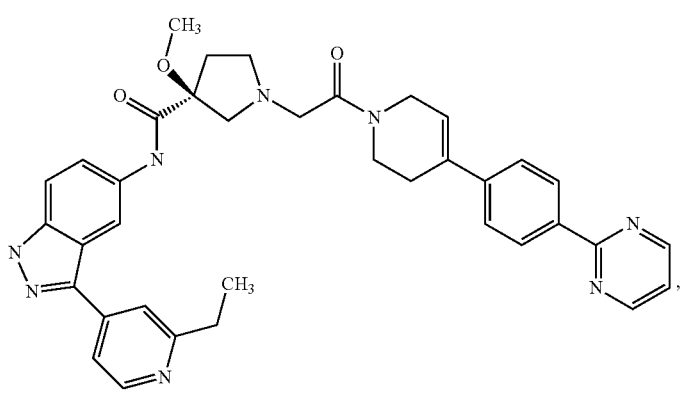

-continued
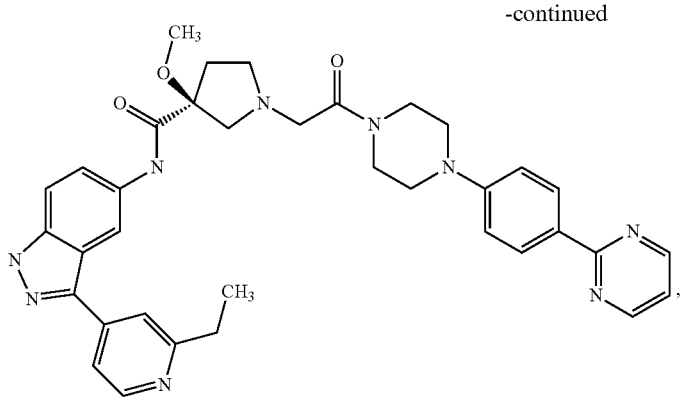
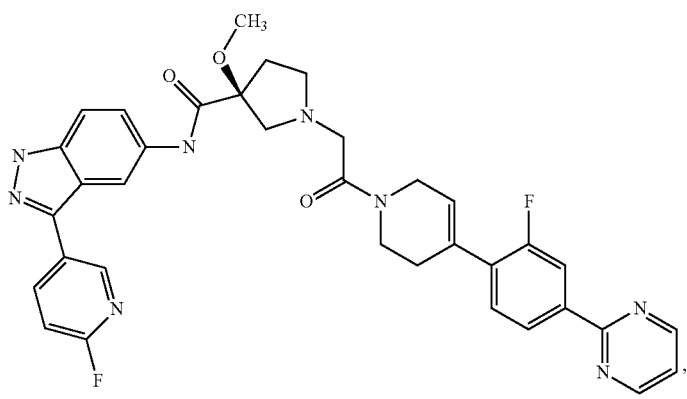
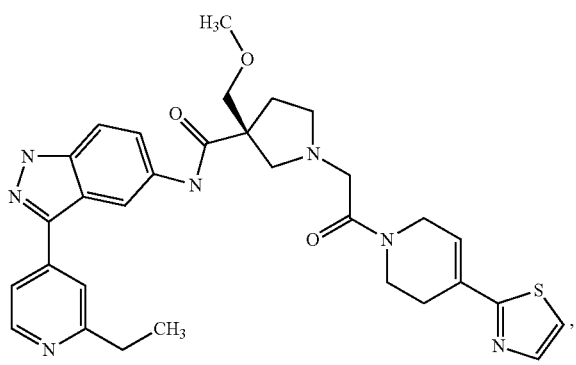
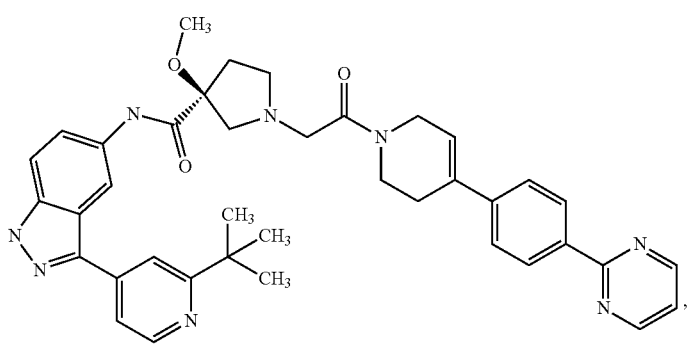

-continued
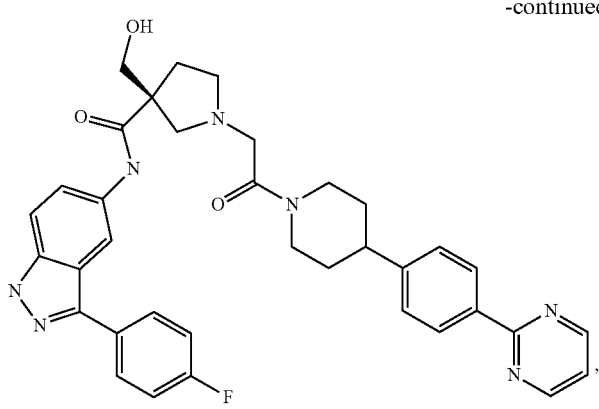
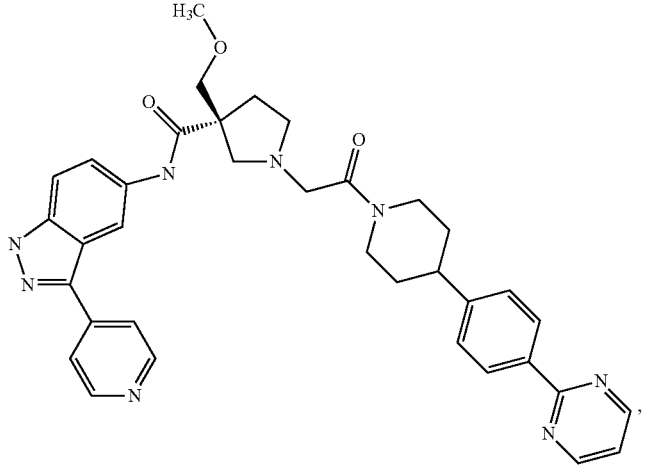
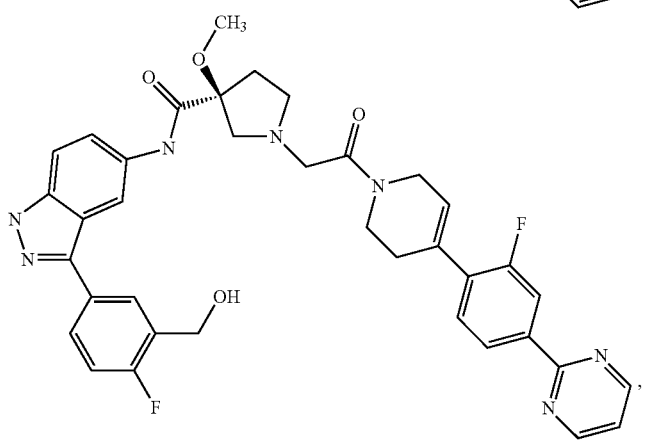
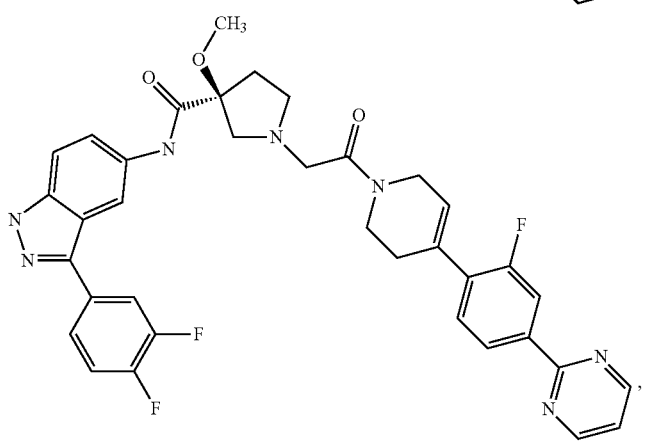

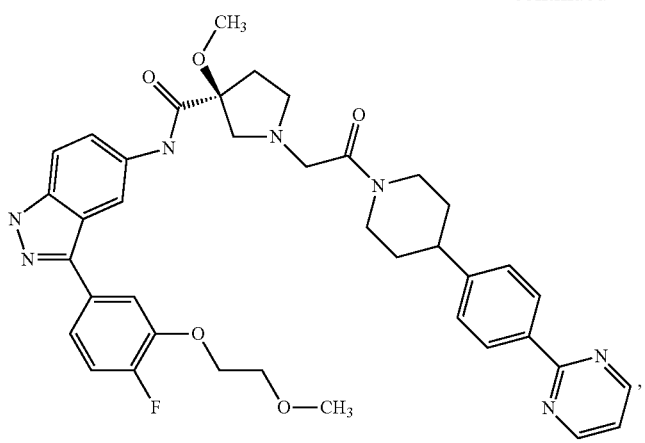
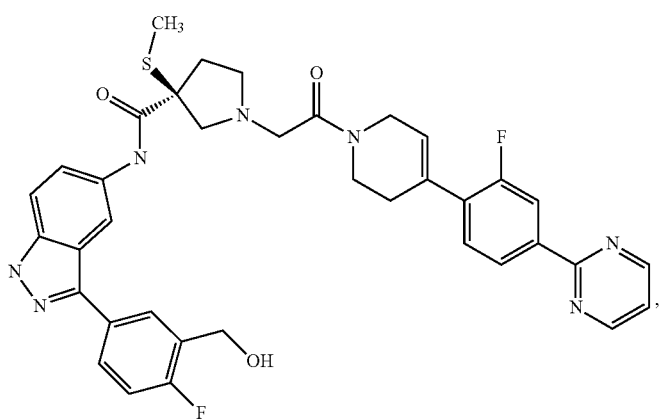
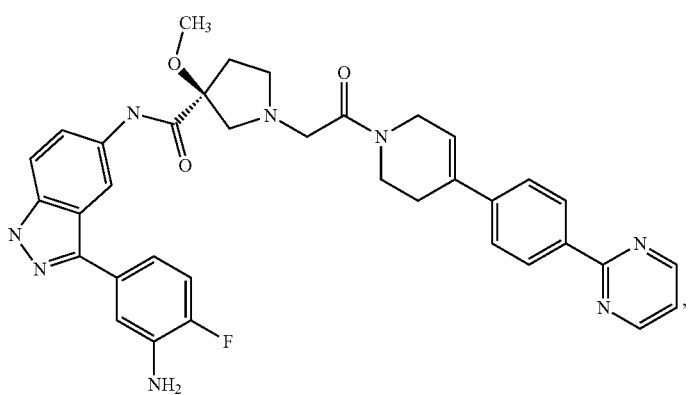
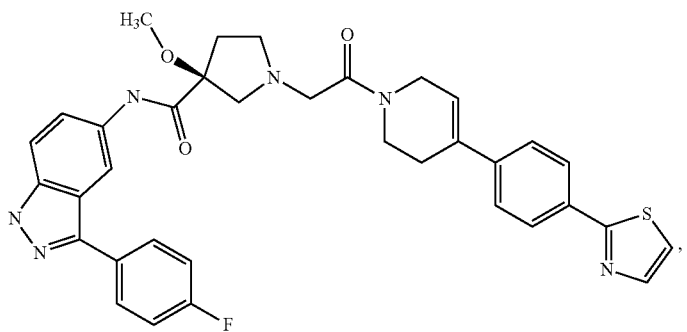

-continued
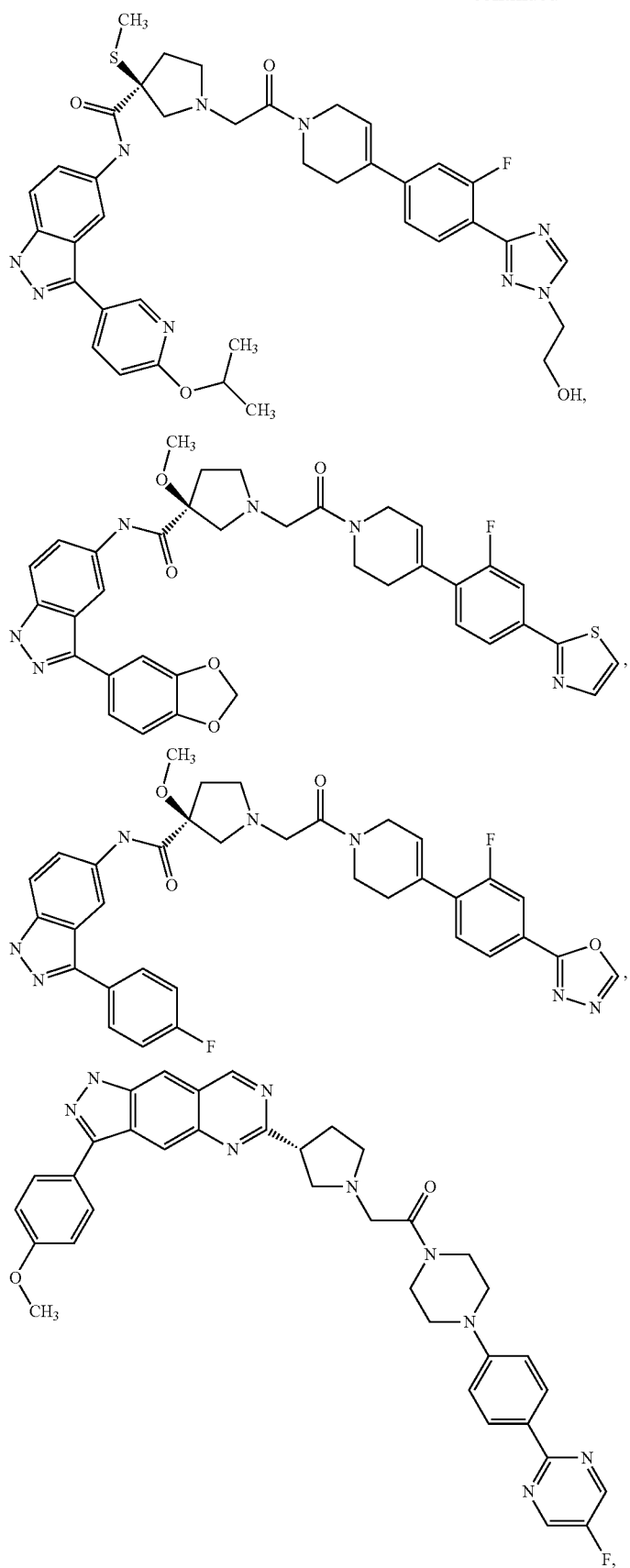

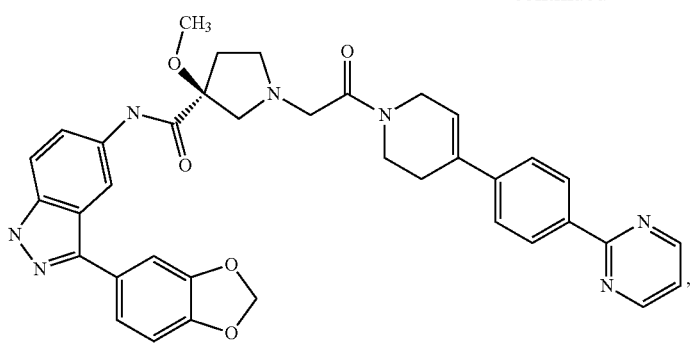
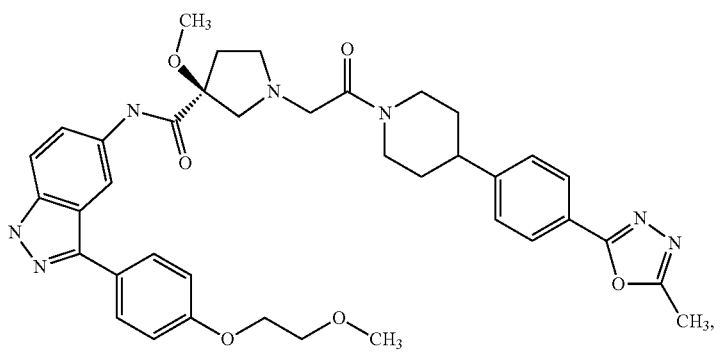
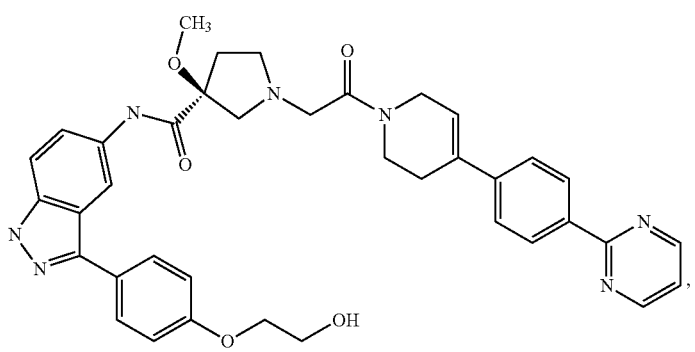
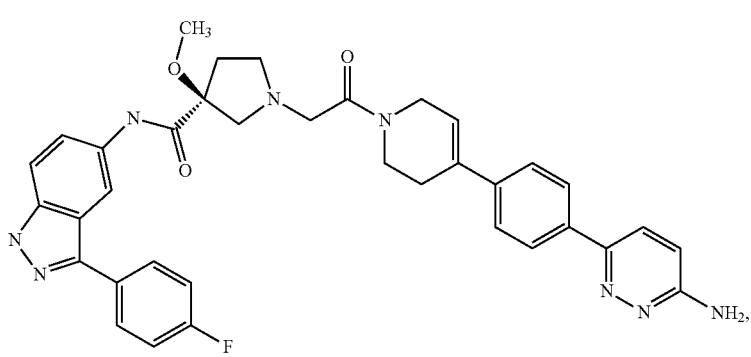
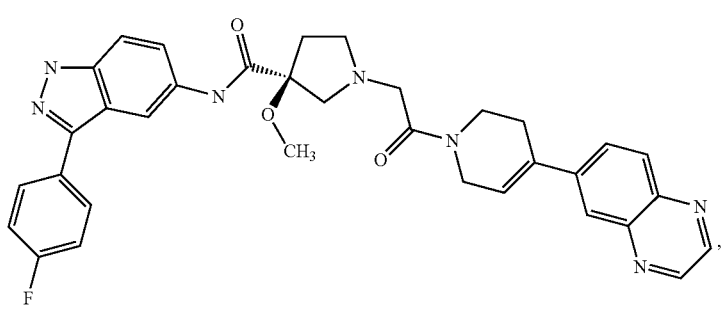

603
604
-continued
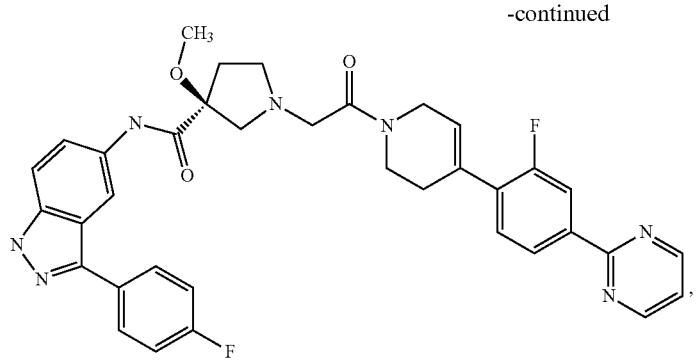
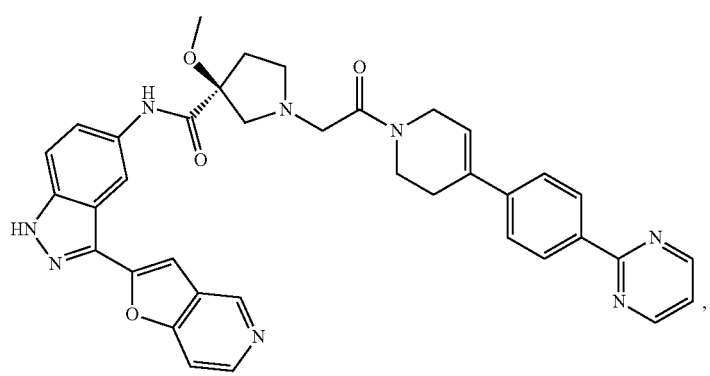
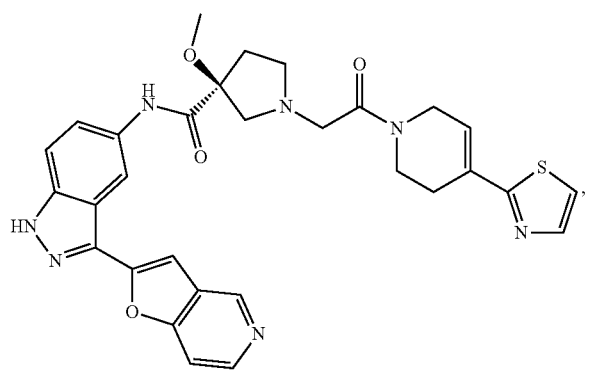
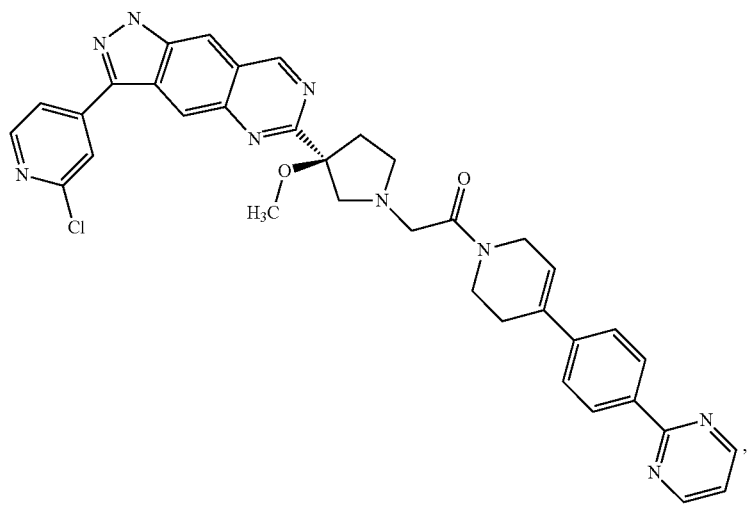

605
606
-continued
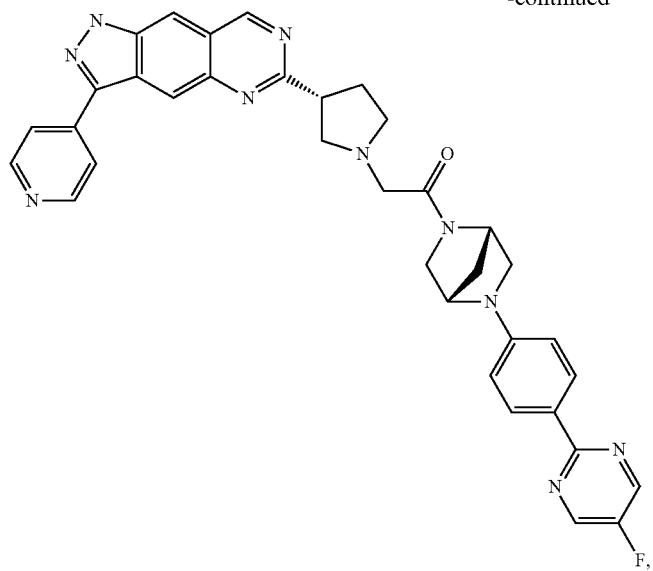
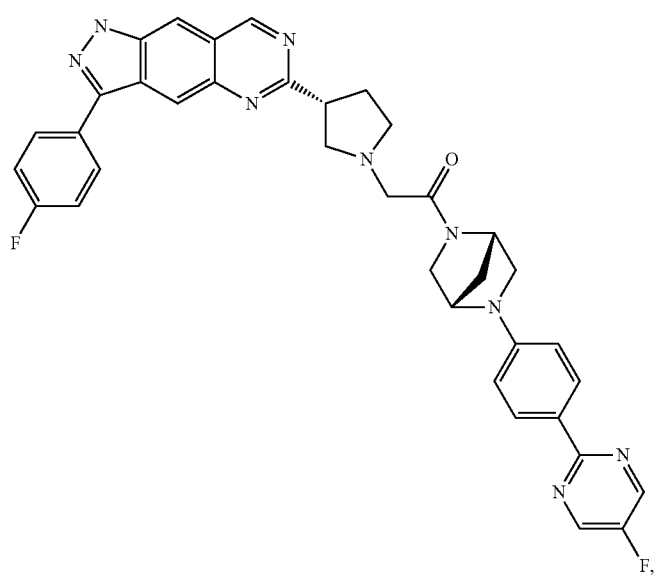
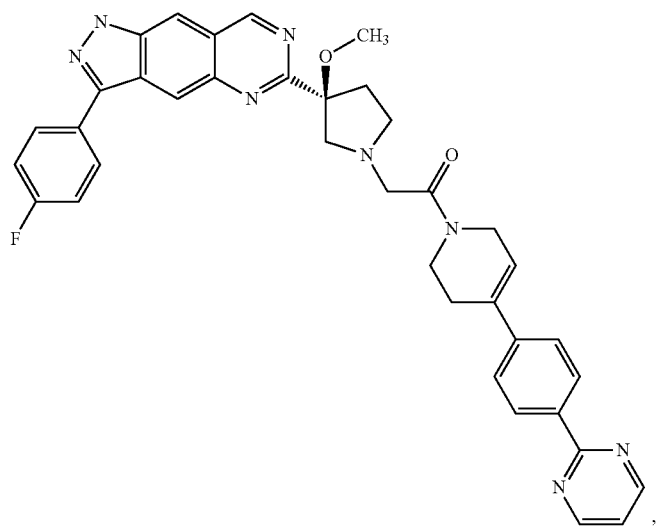

607
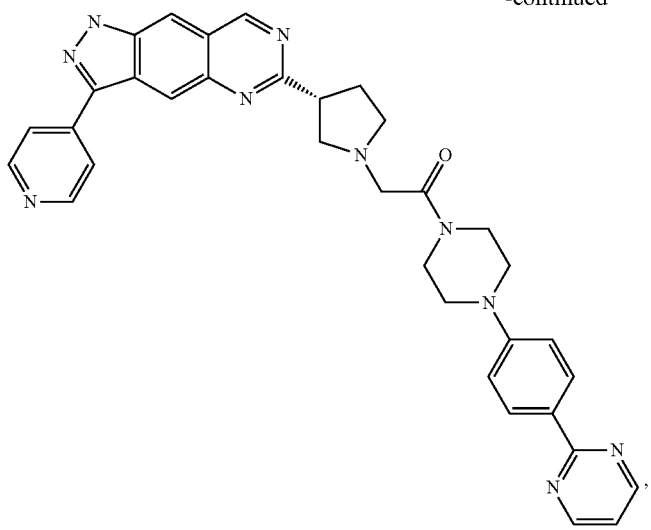
-continued
608
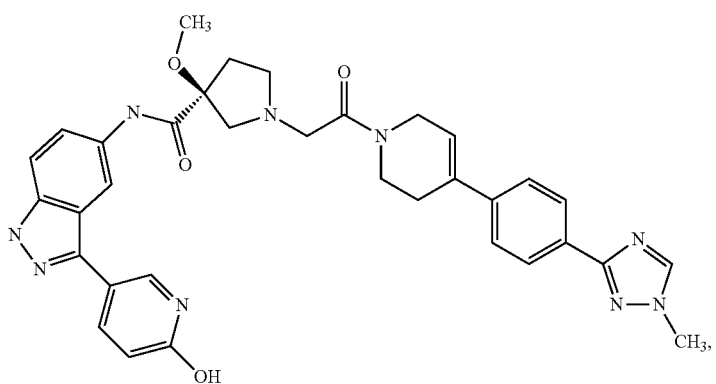
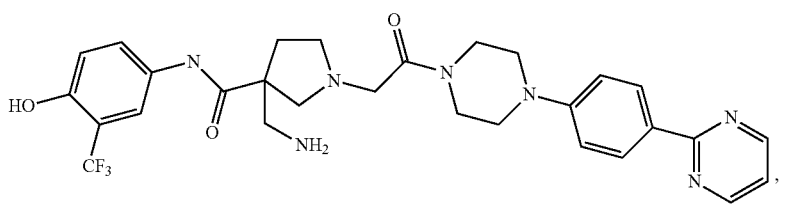
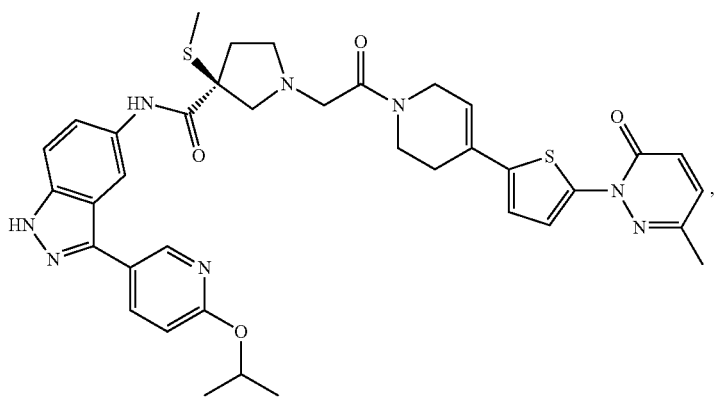

609
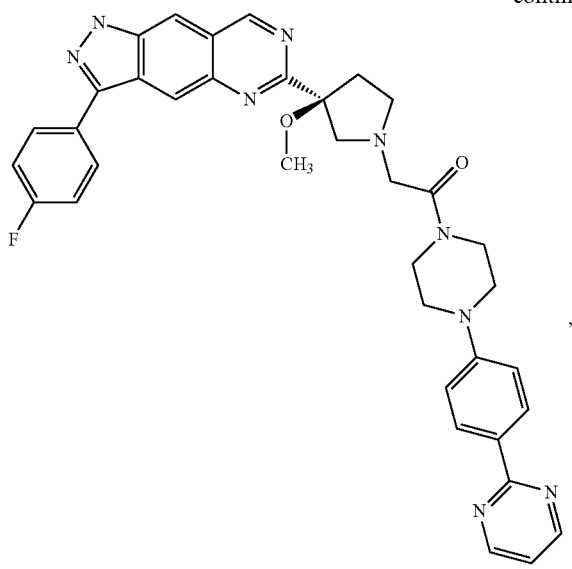
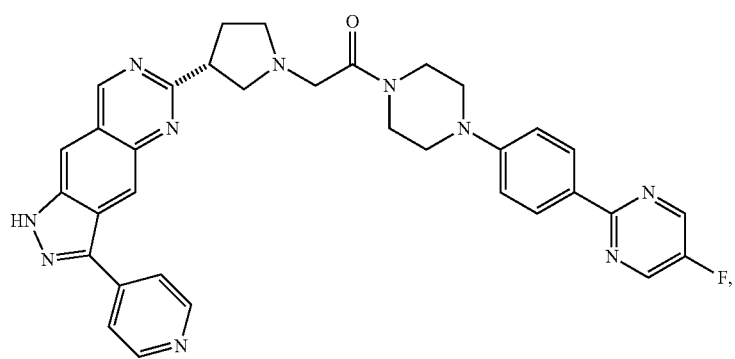
610
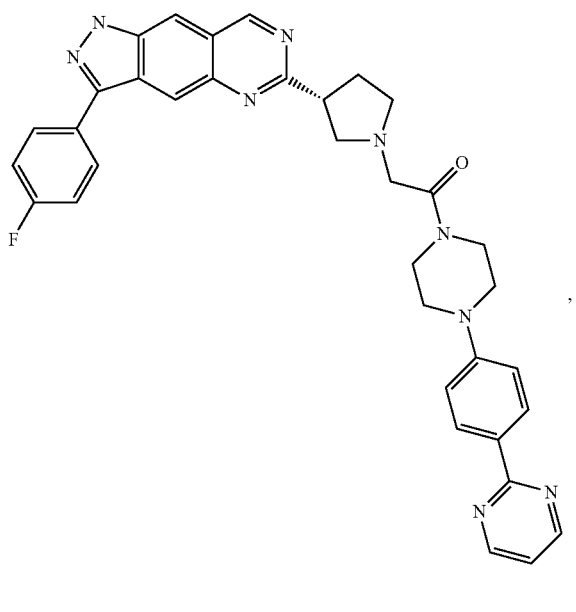
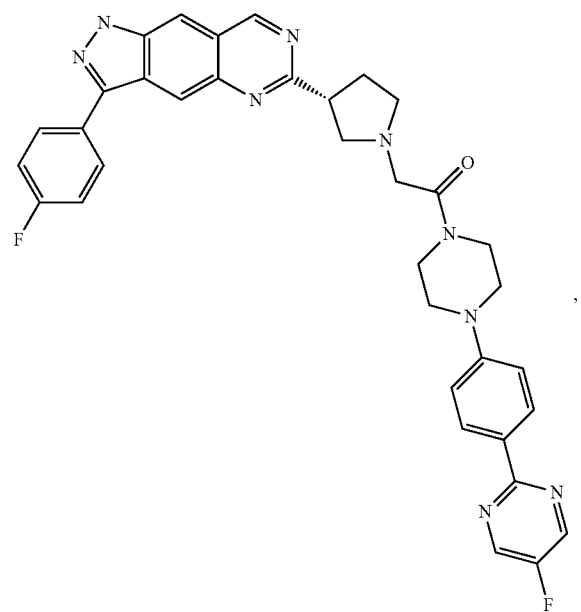

-continued
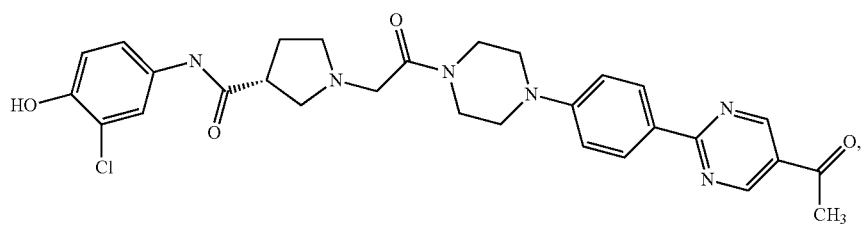
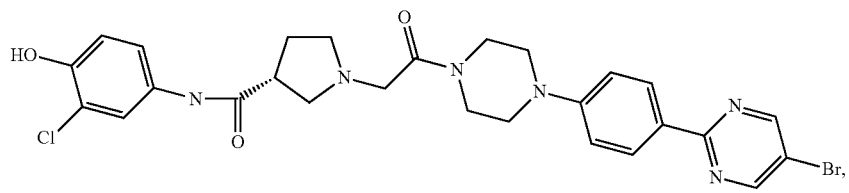
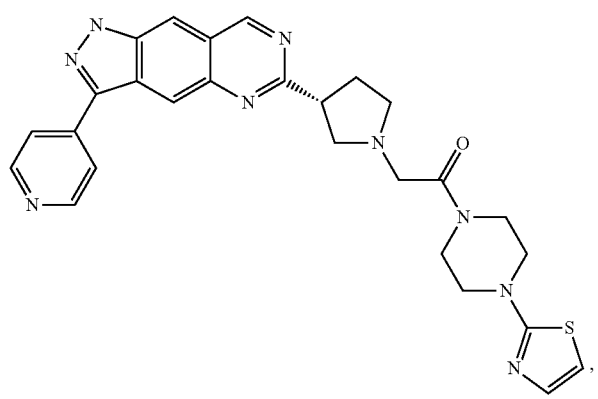
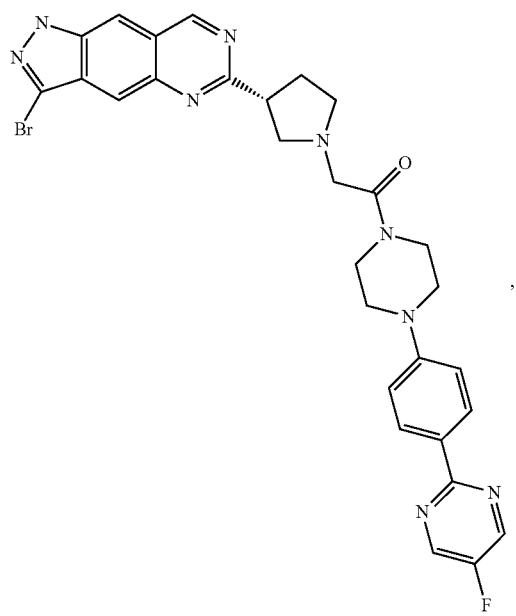
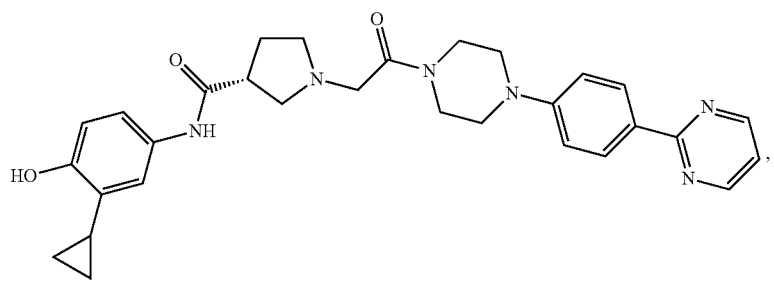

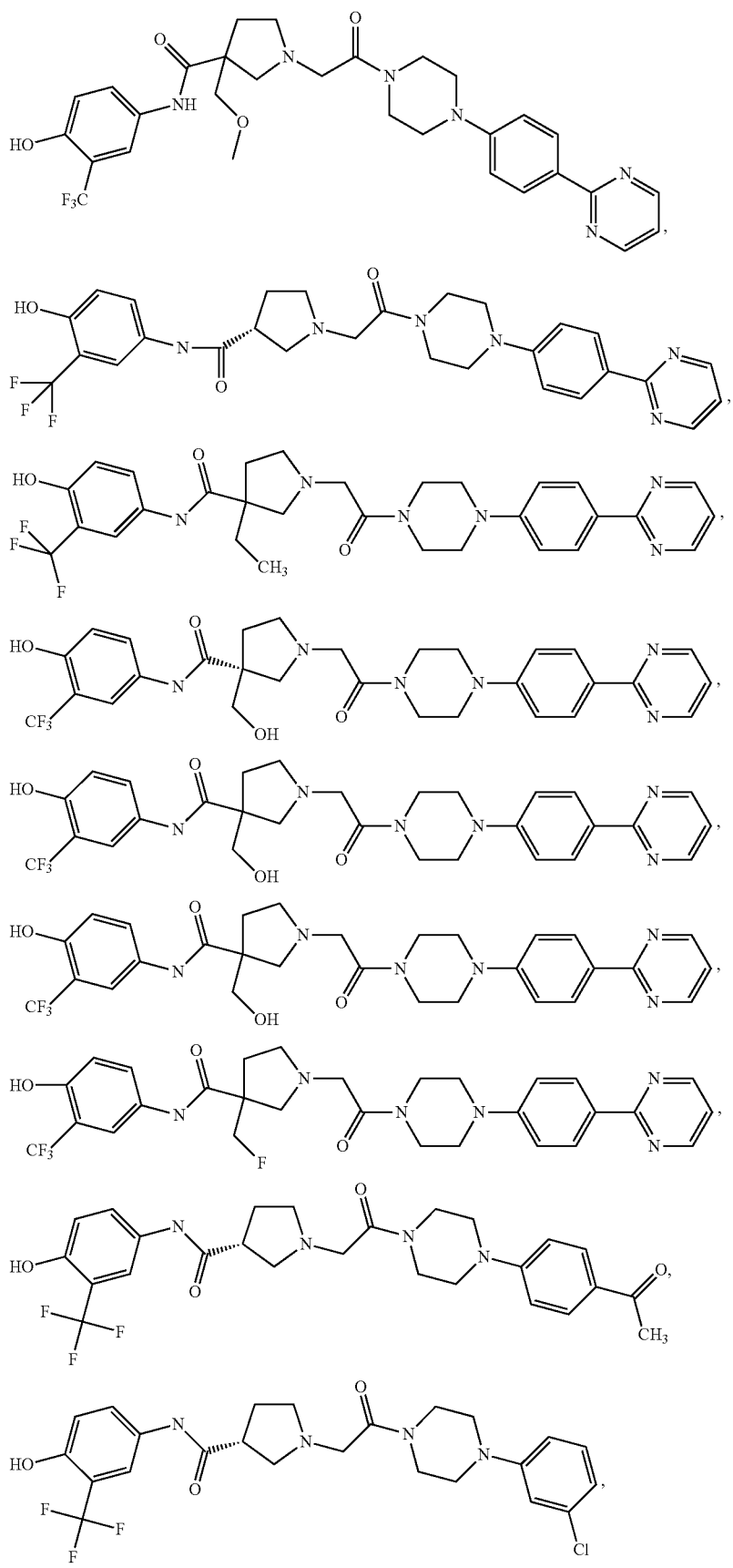

-continued
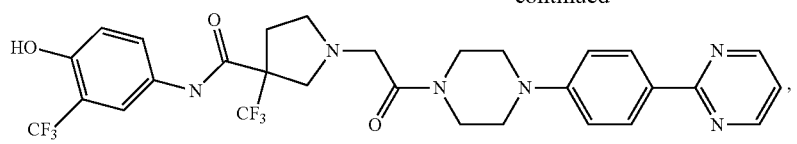
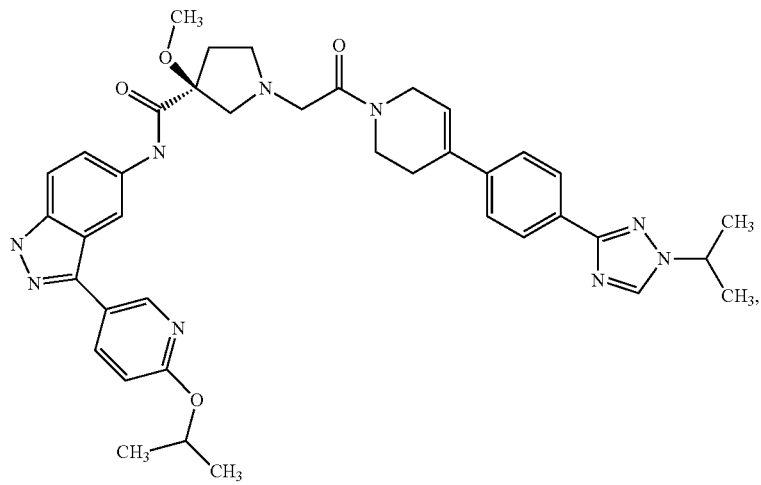
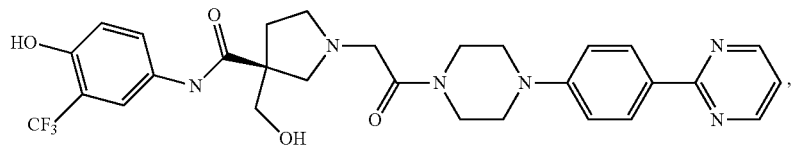
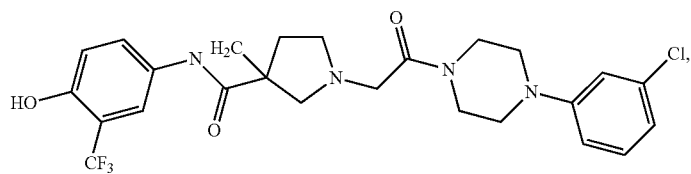
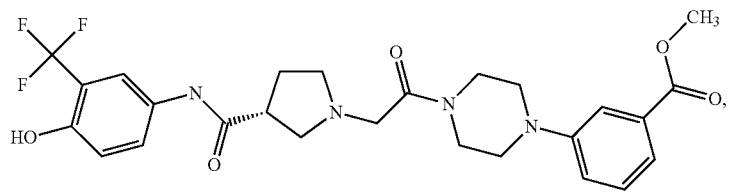
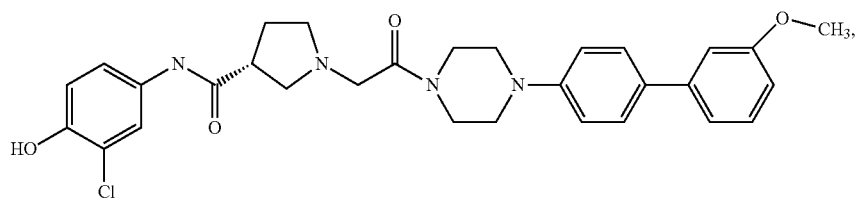
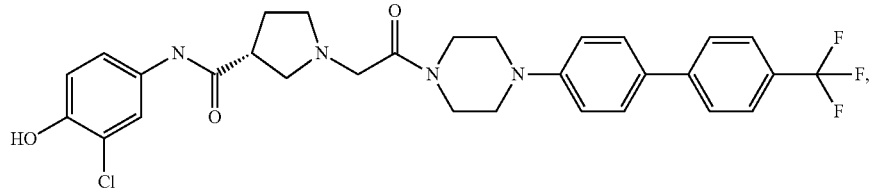

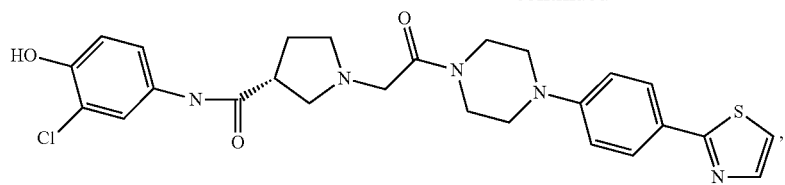
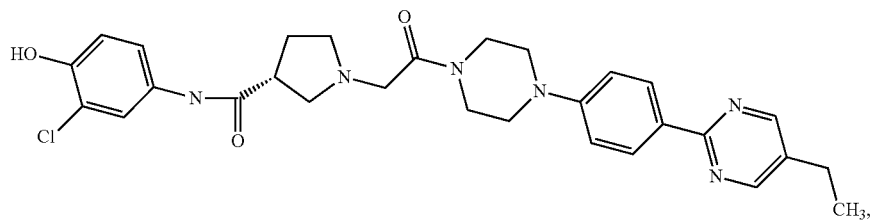
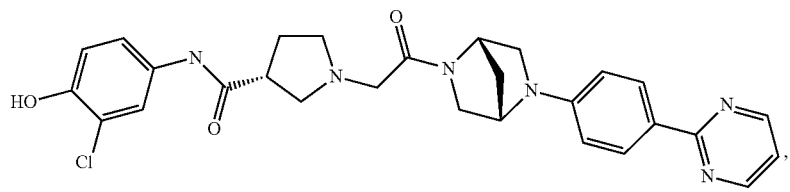
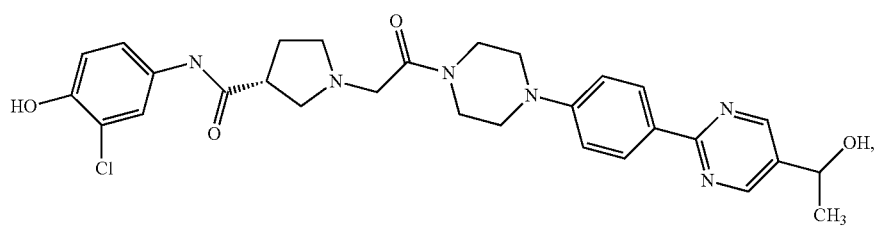
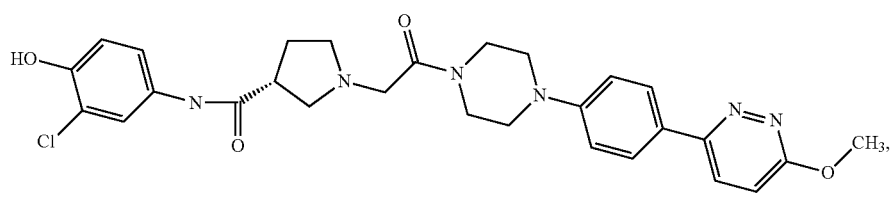
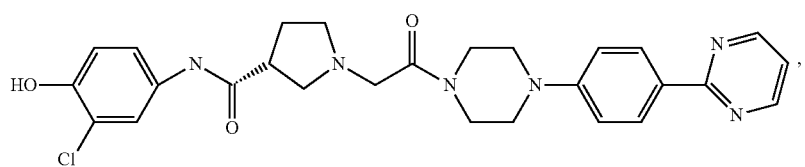
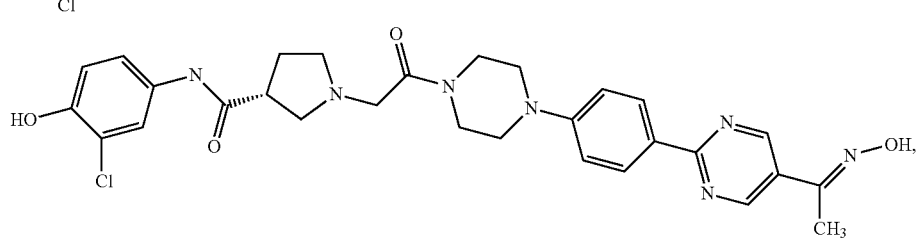
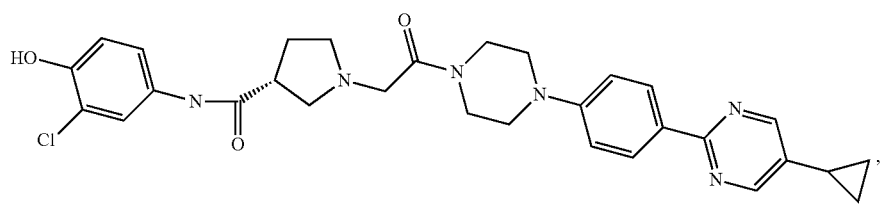

-continued
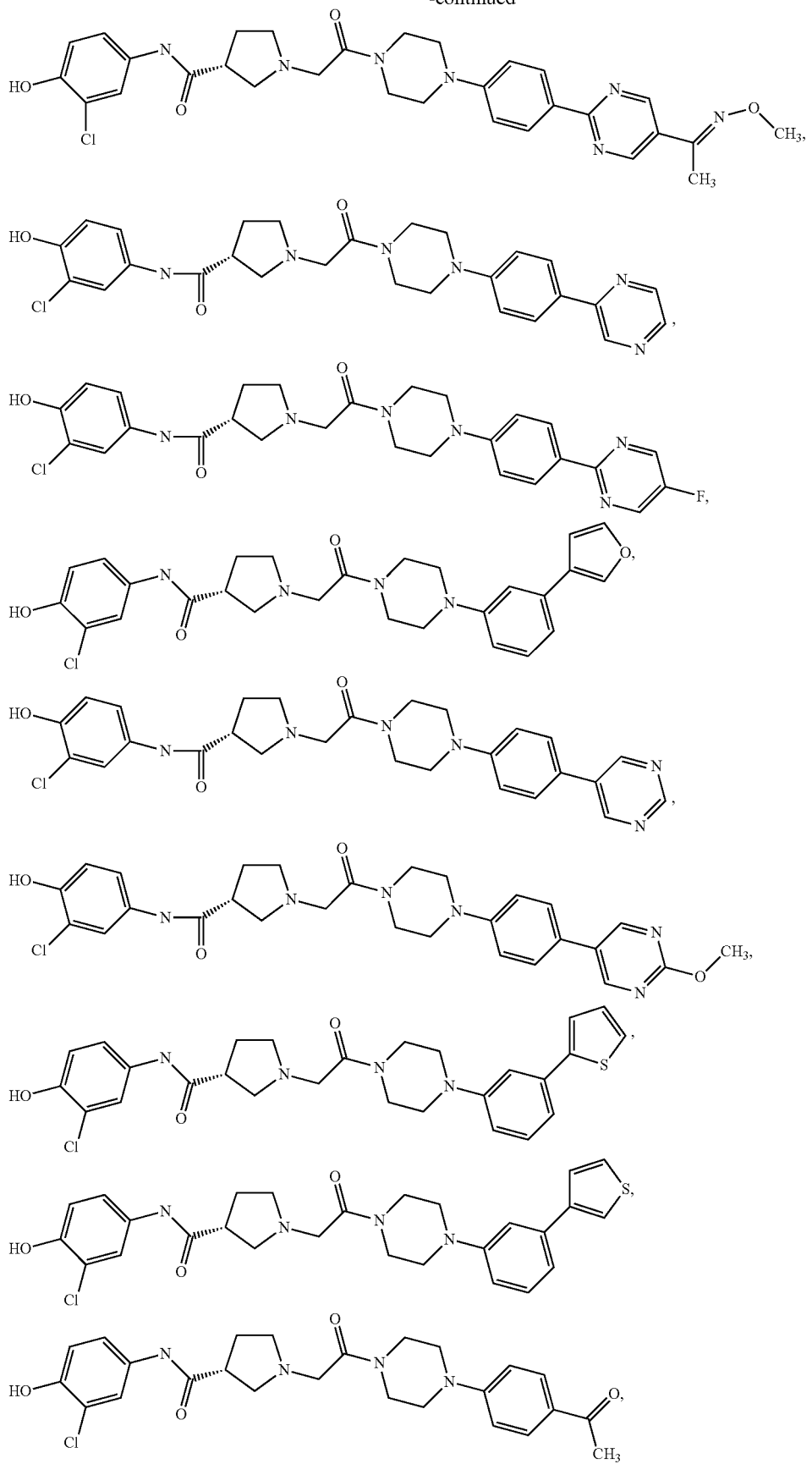

-continued
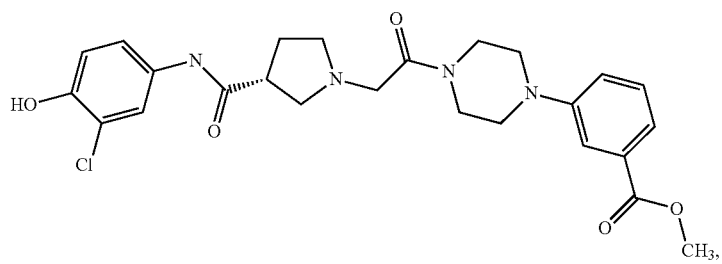
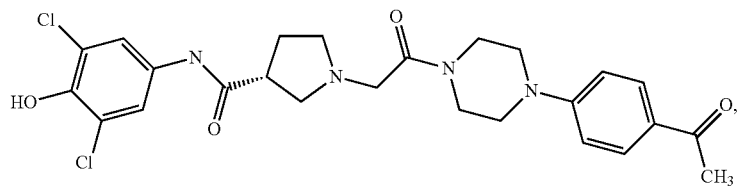
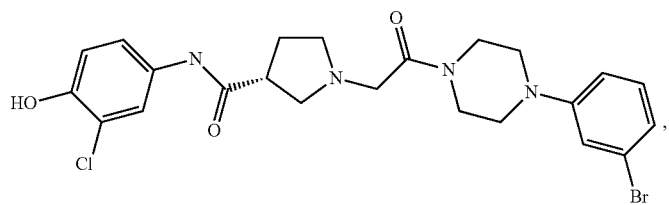
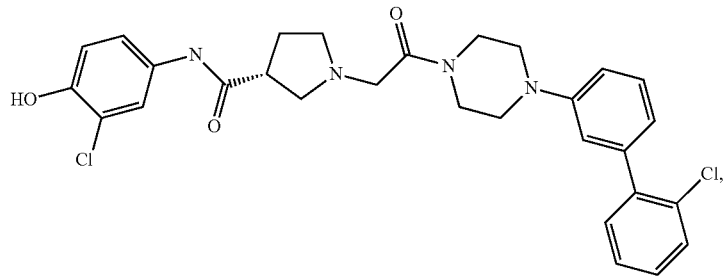
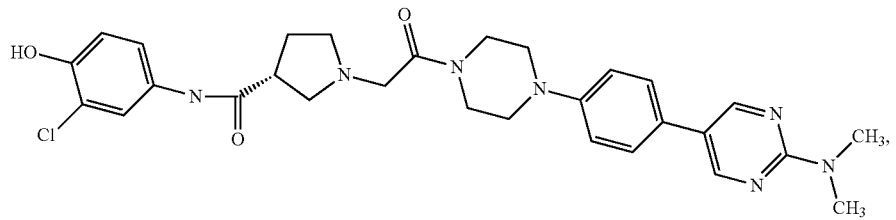
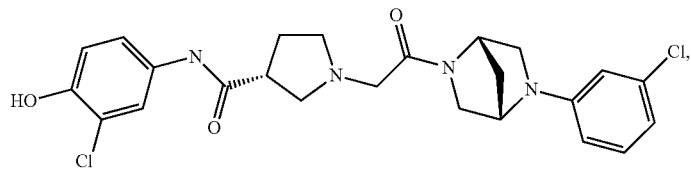
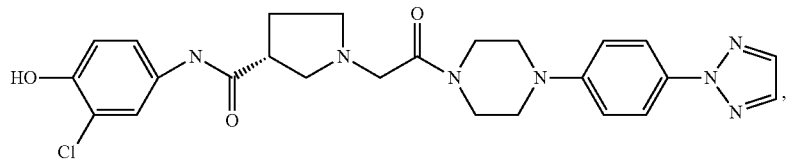
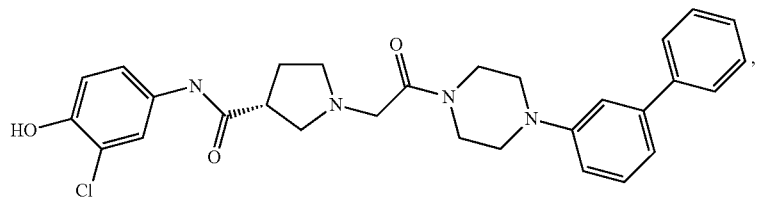

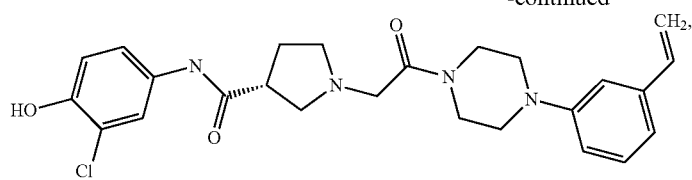
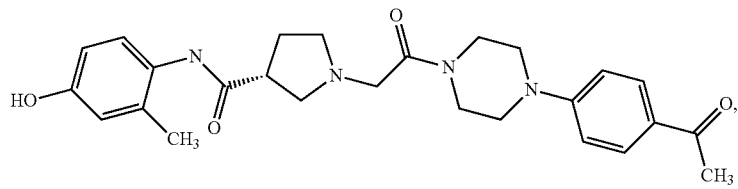
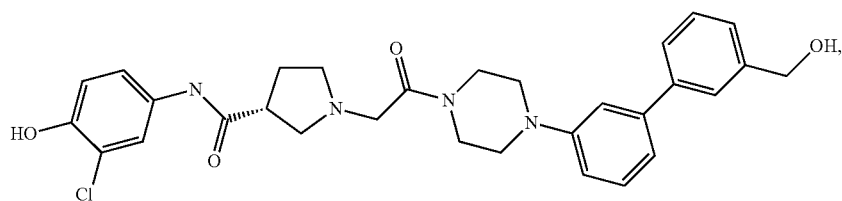
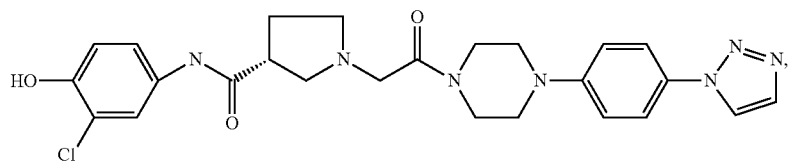
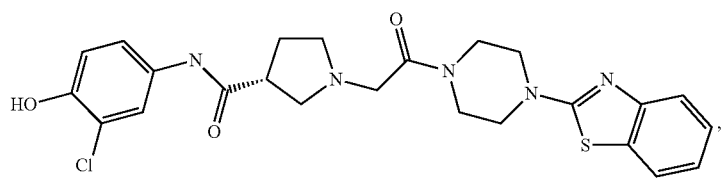
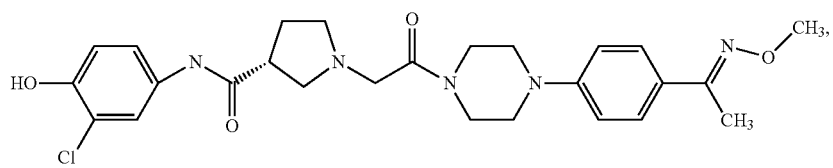
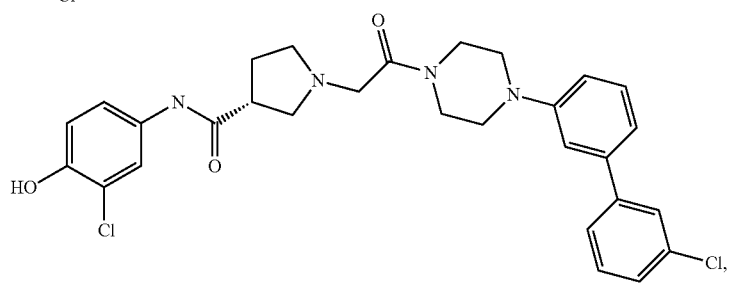
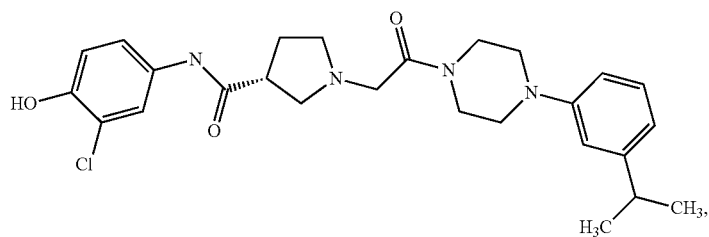

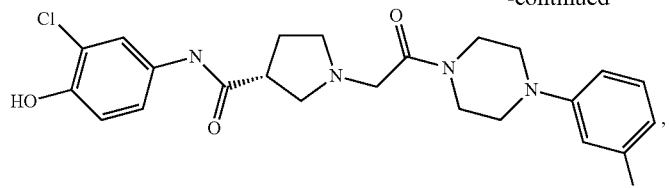
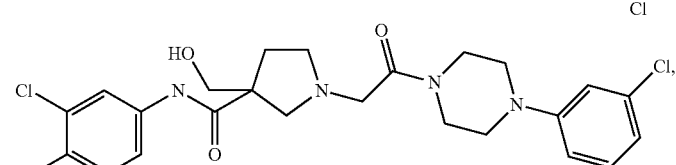
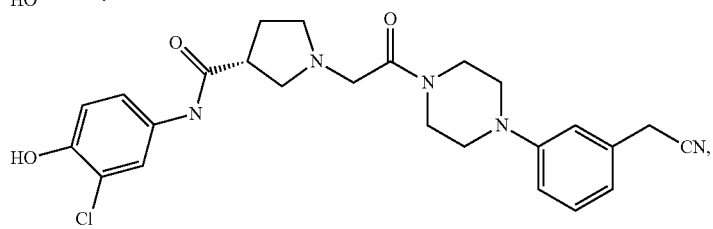
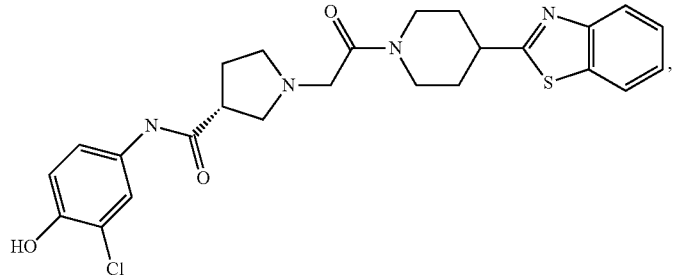
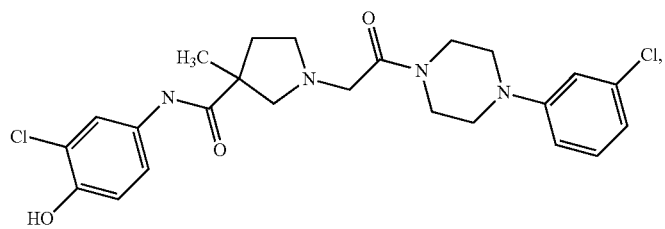
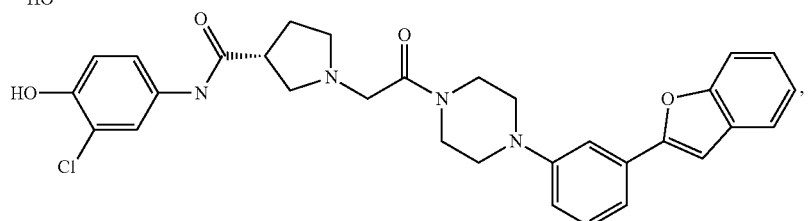
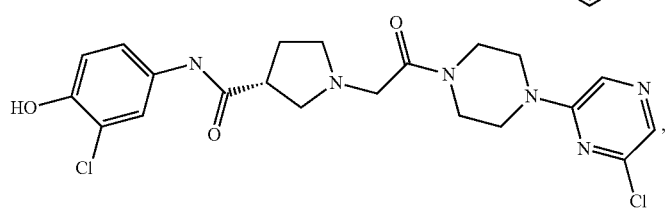
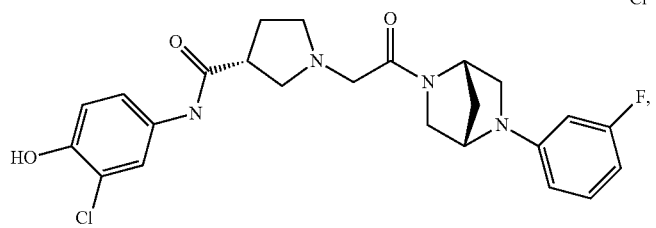

-continued
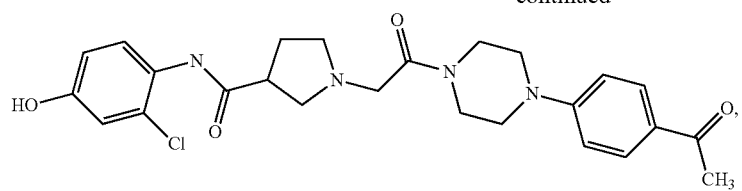
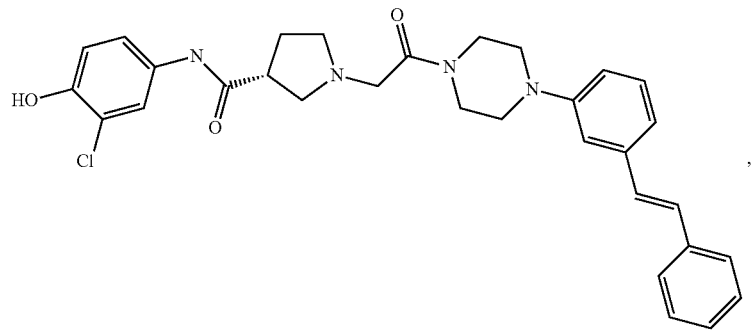
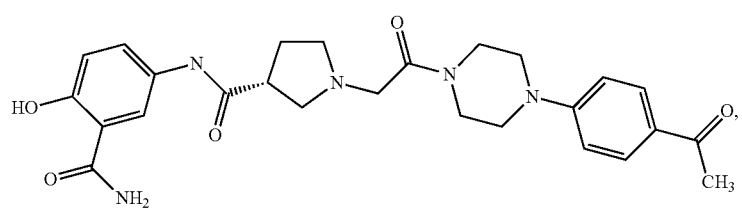
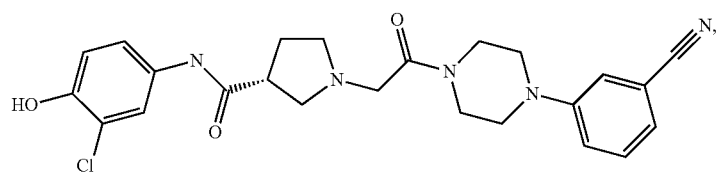
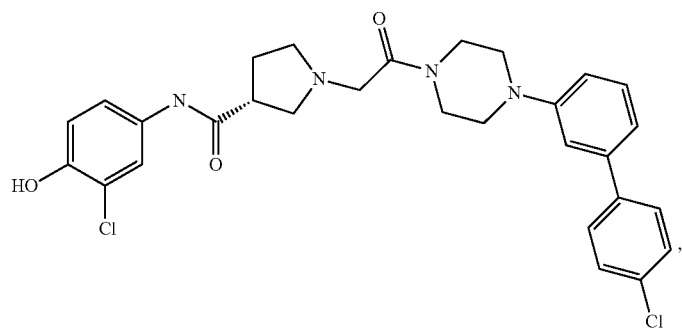
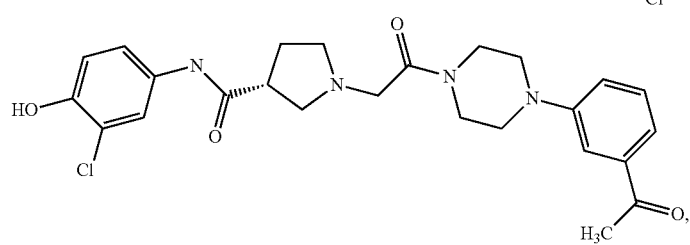
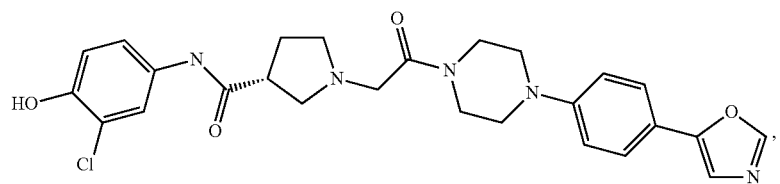

-continued
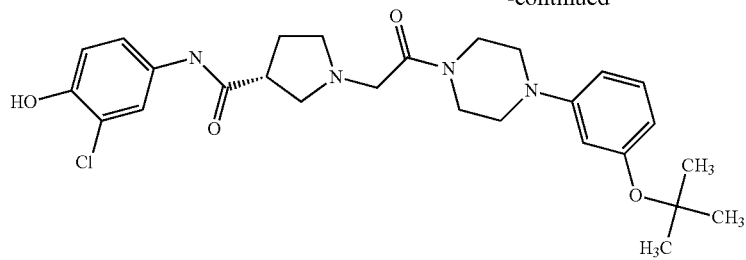
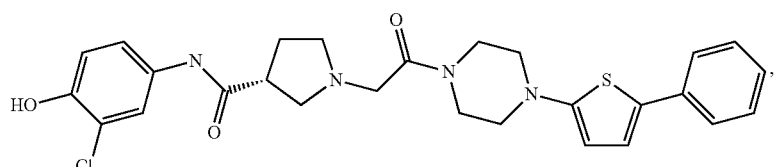
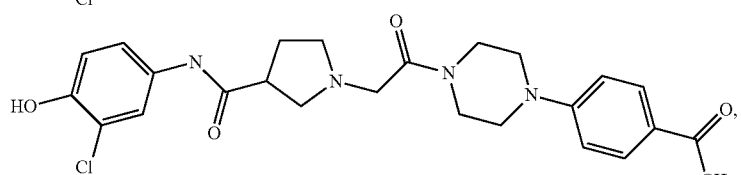
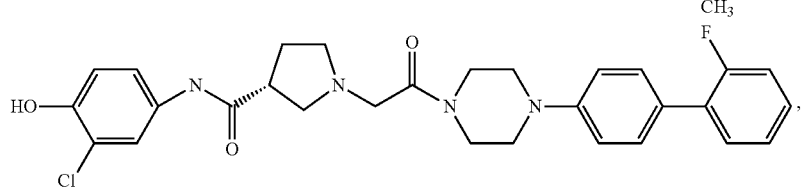
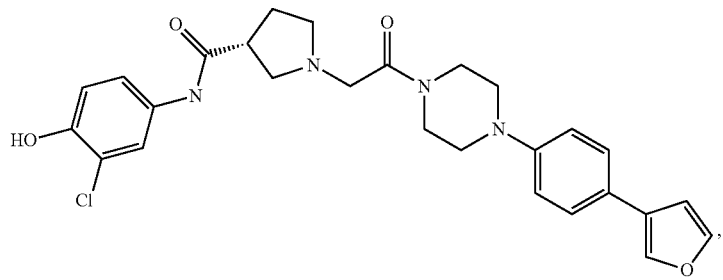
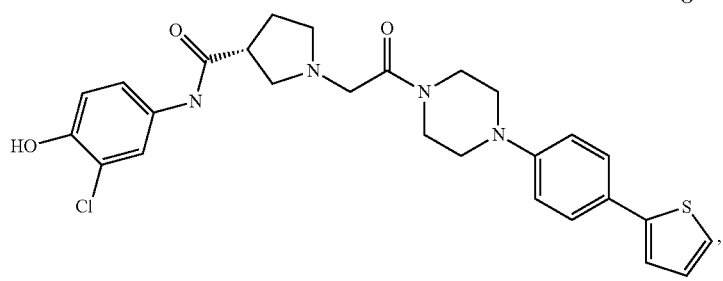
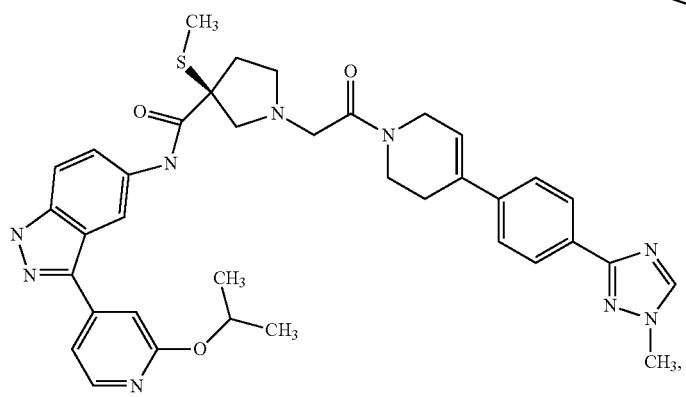

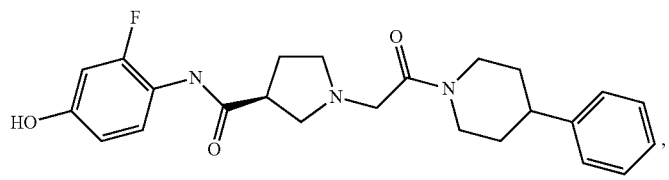
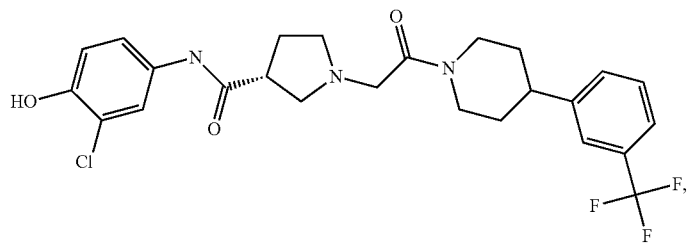
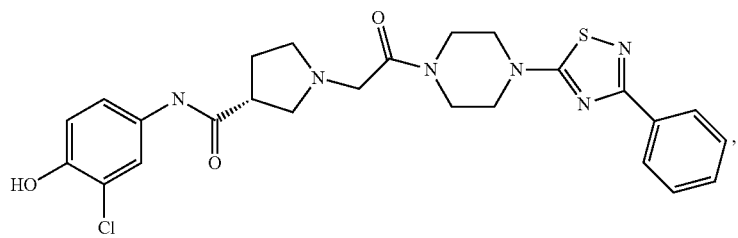
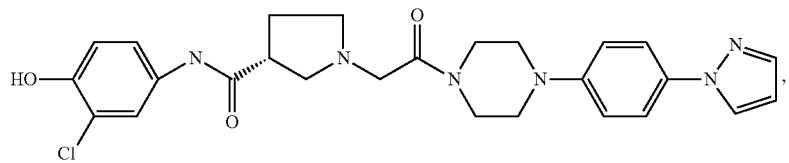
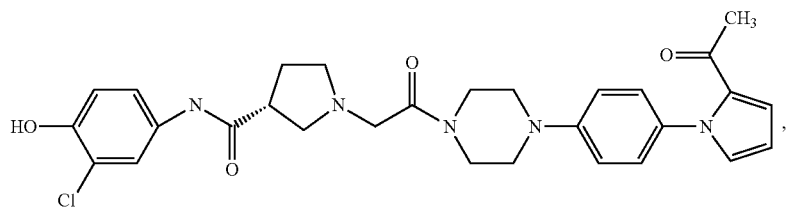
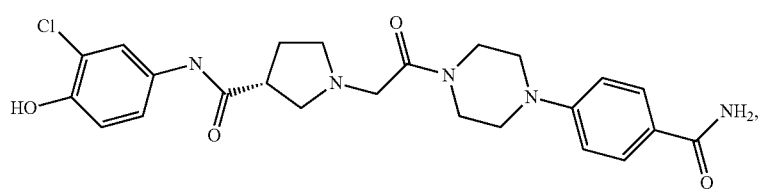
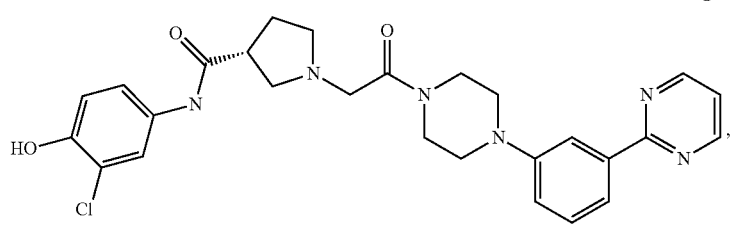
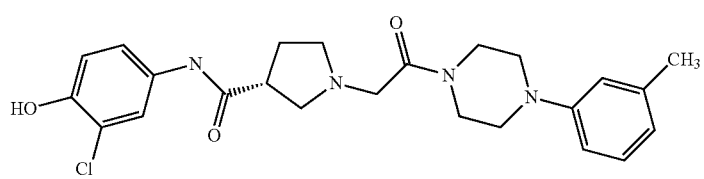

-continued
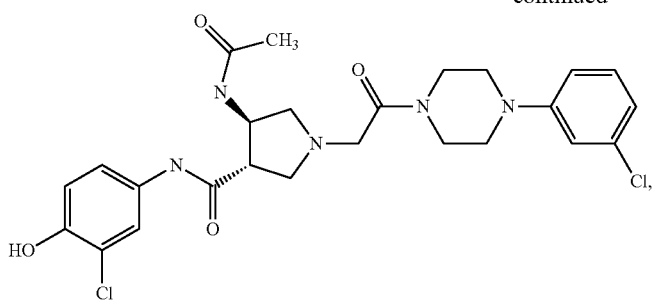
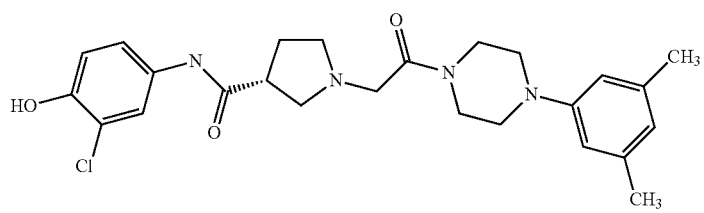
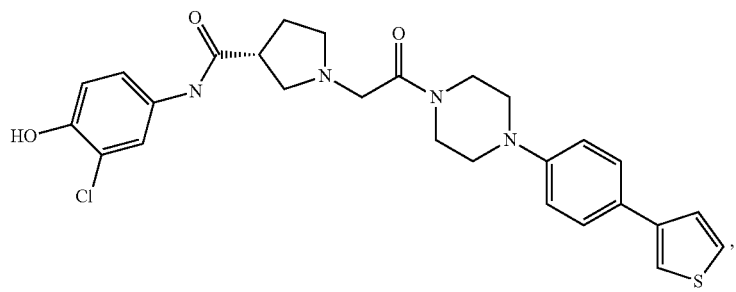
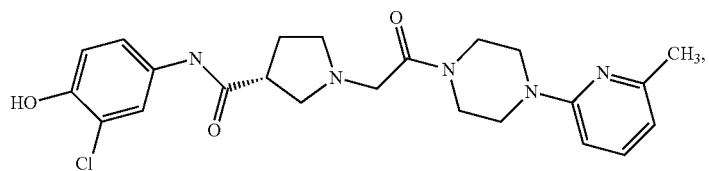
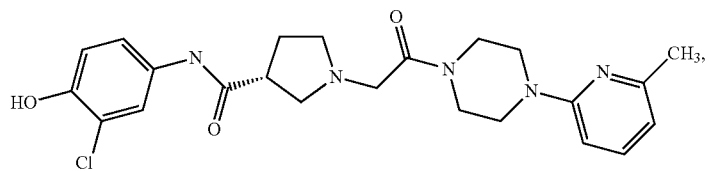
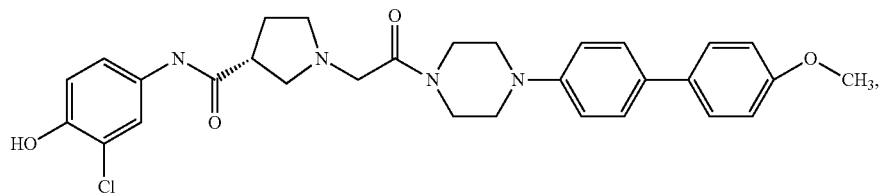
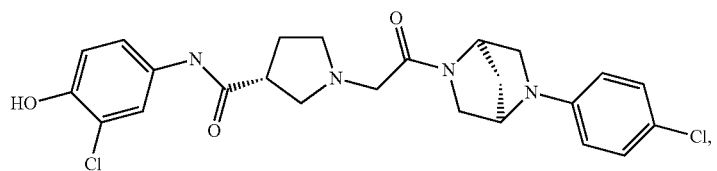

-continued
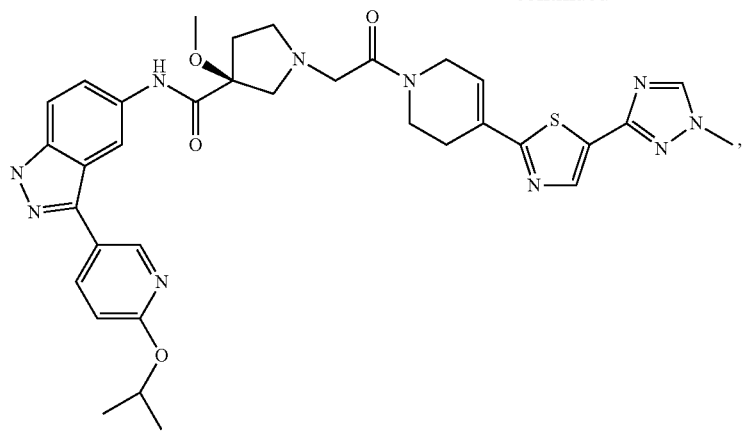
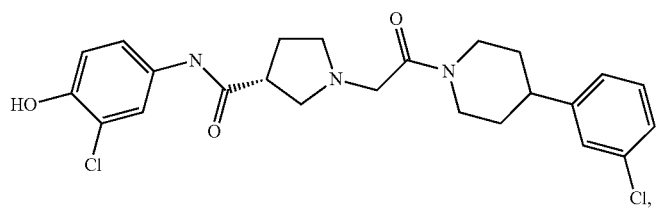
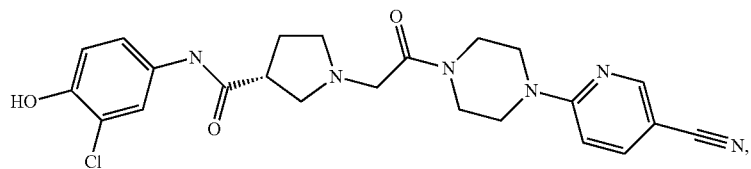
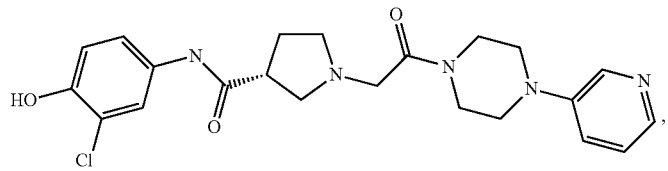
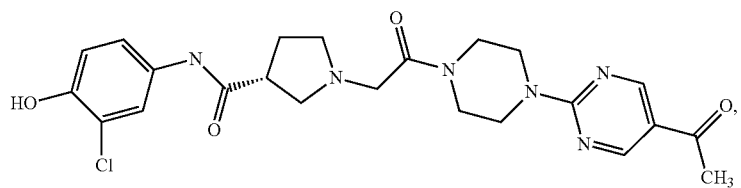
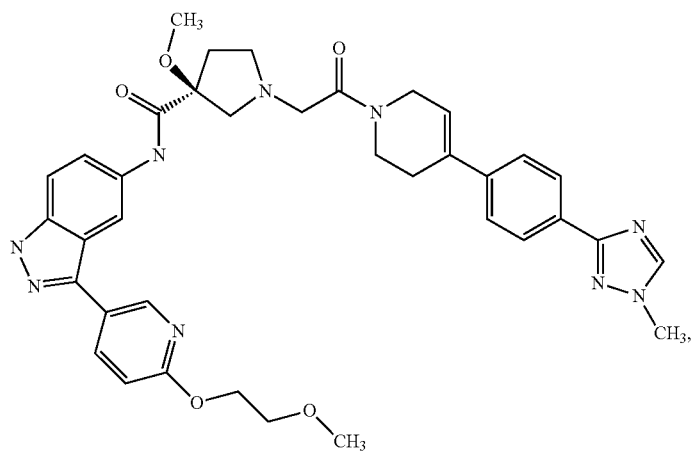

-continued
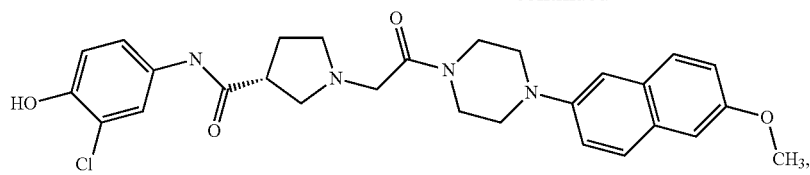
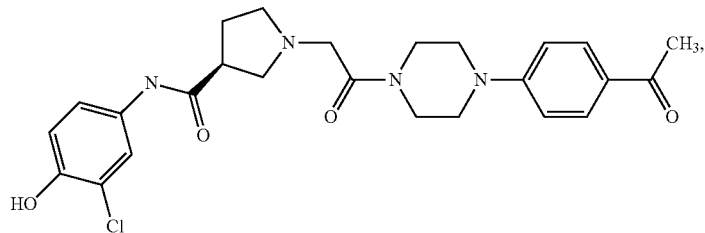
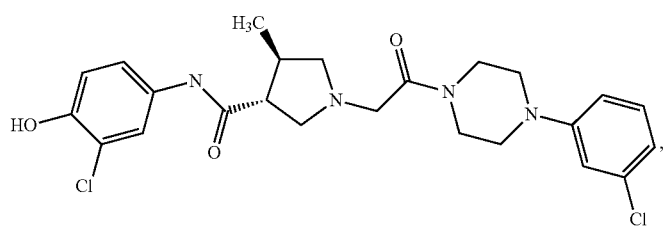
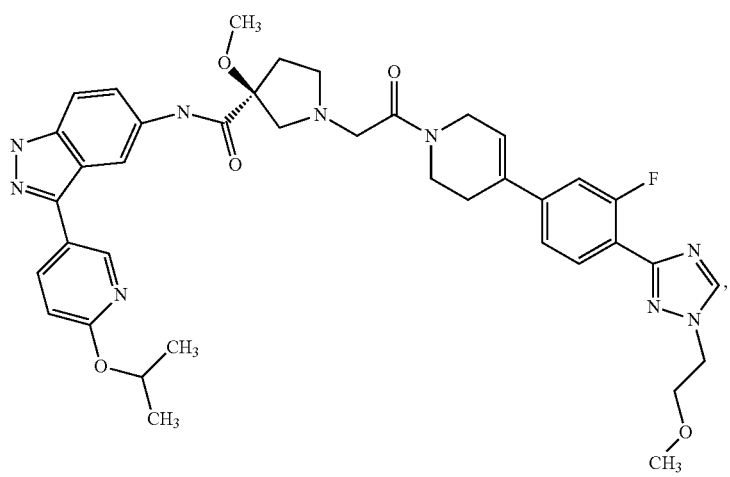
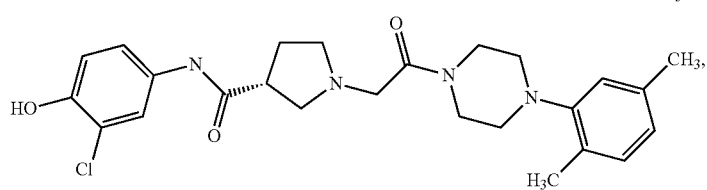
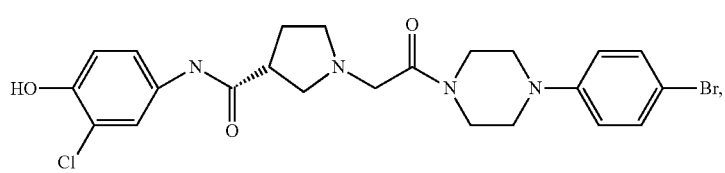
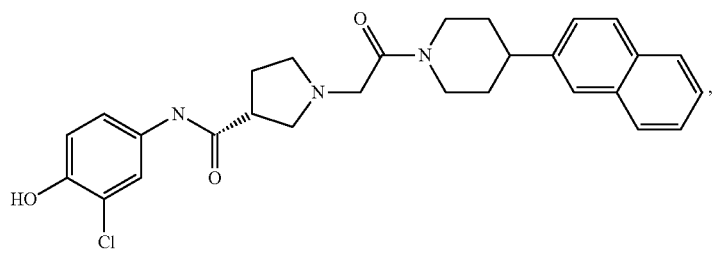

-continued
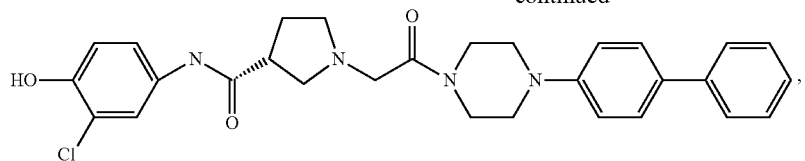
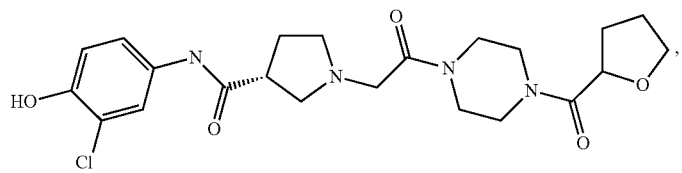
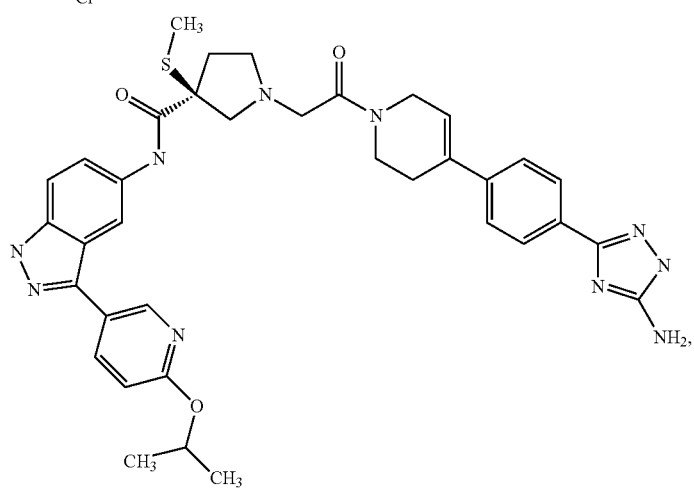
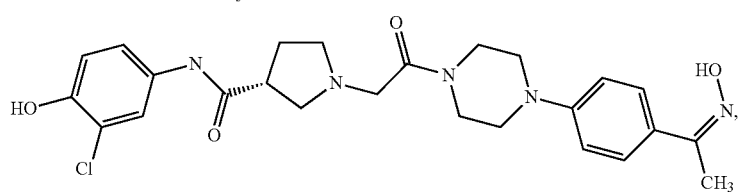
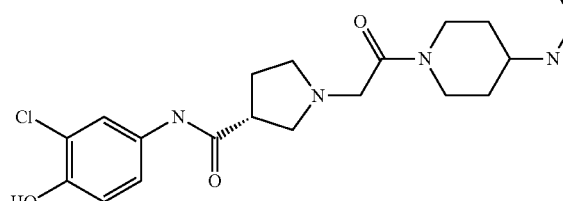
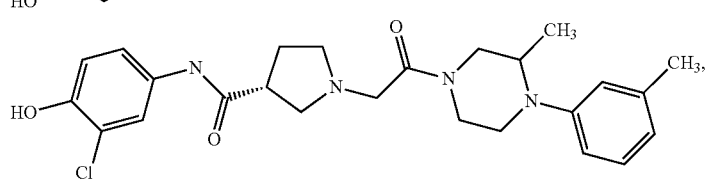
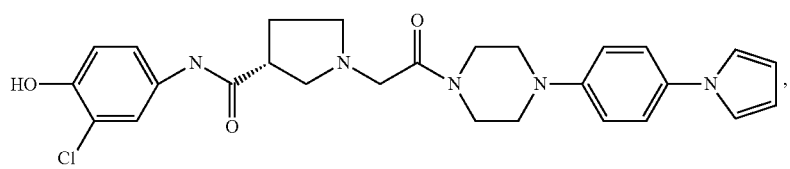

-continued
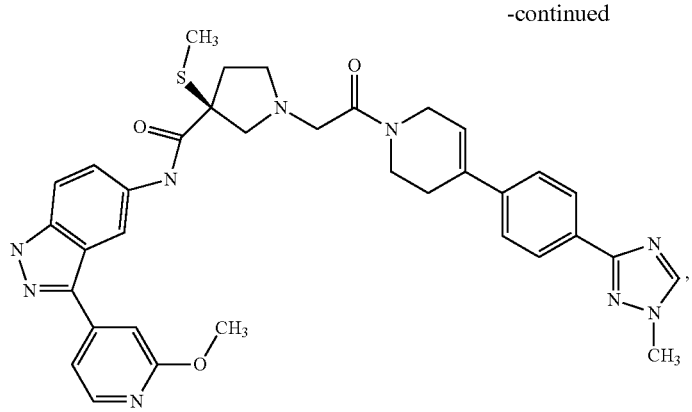
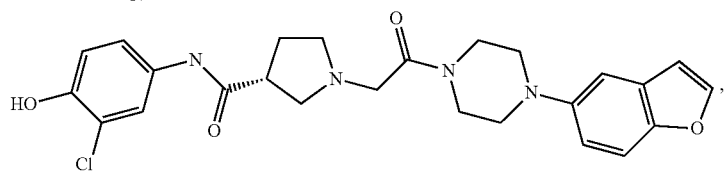
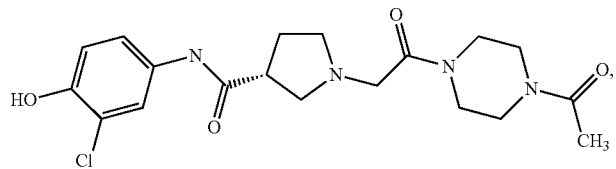
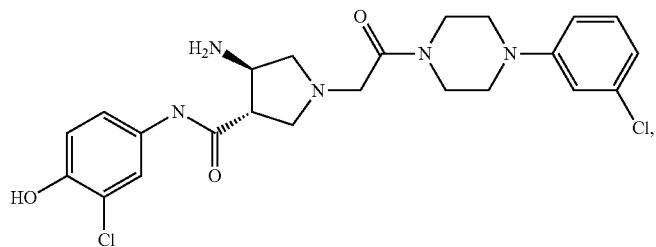
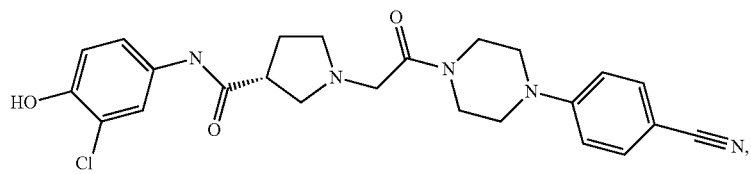
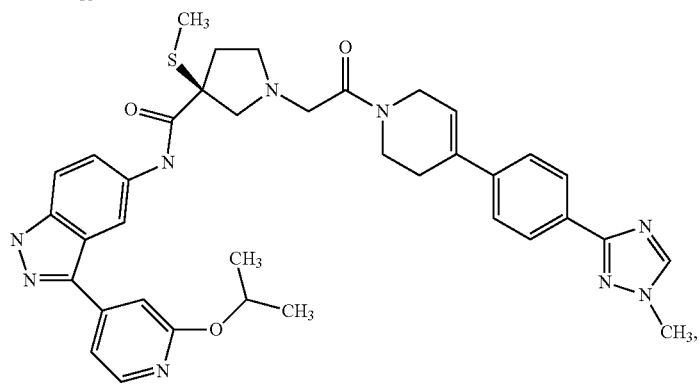
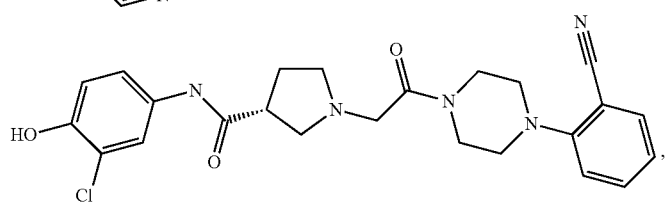

-continued
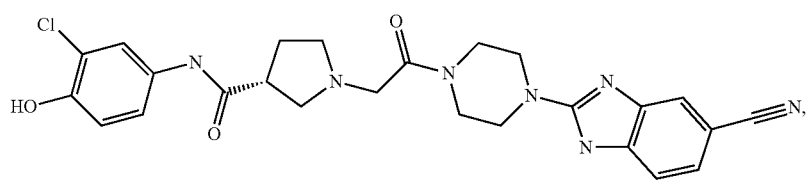
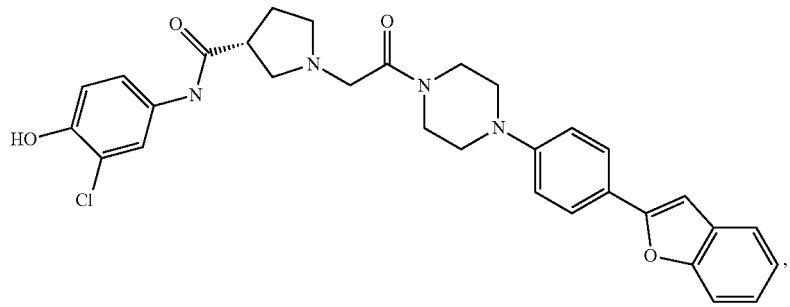
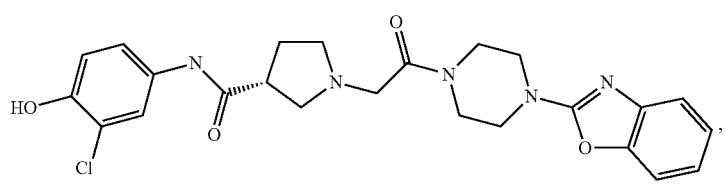
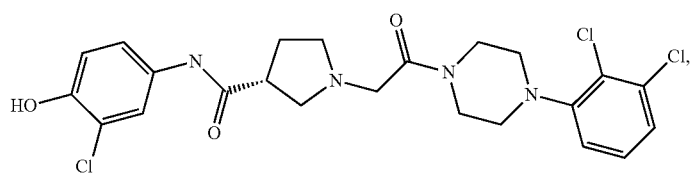
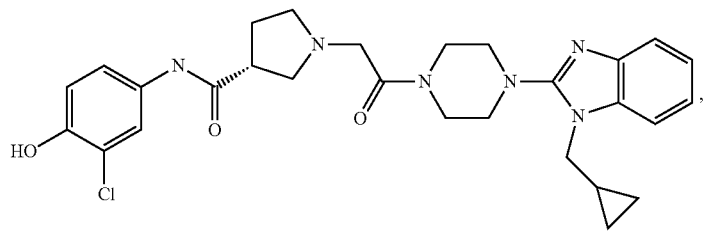
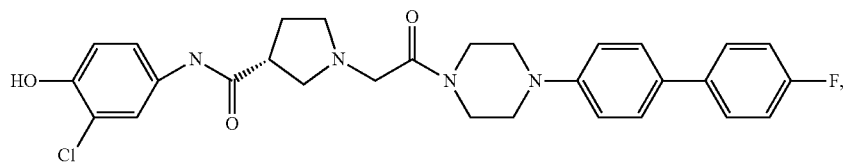
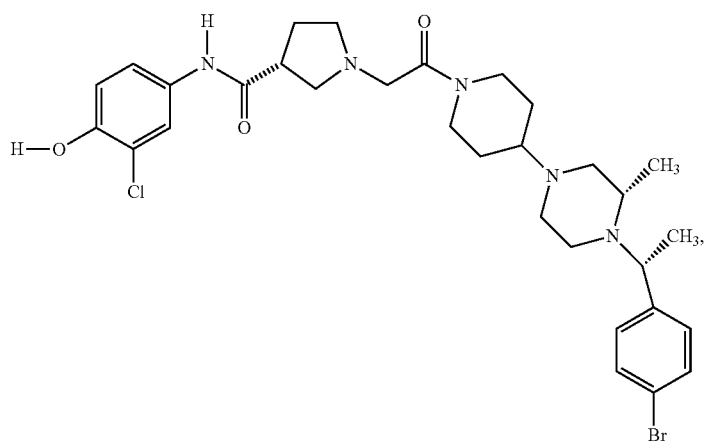

-continued
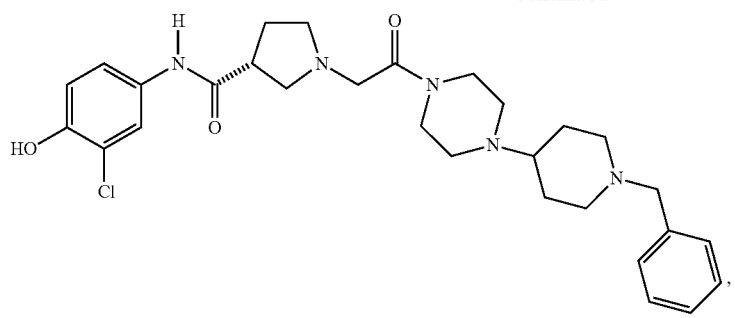
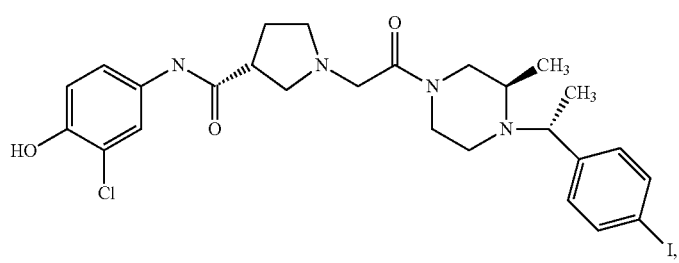
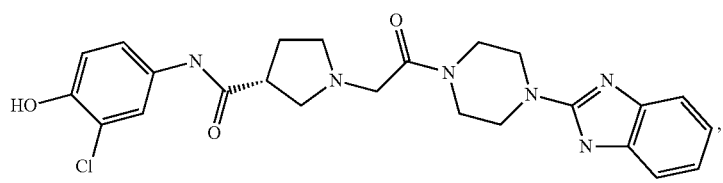
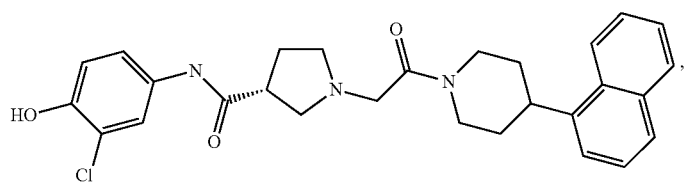
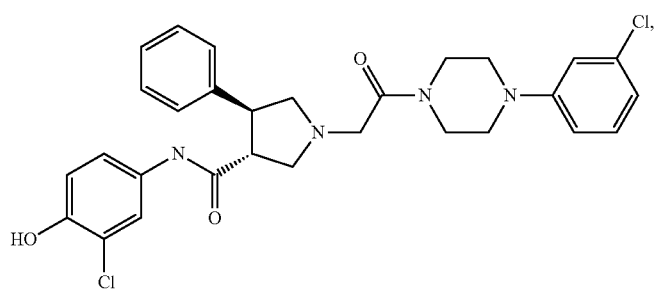
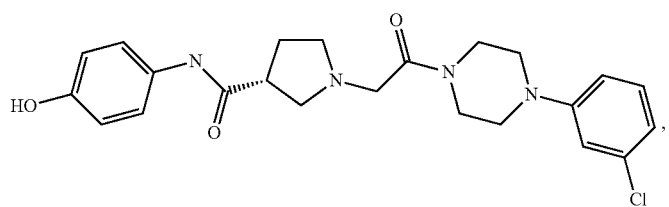

-continued
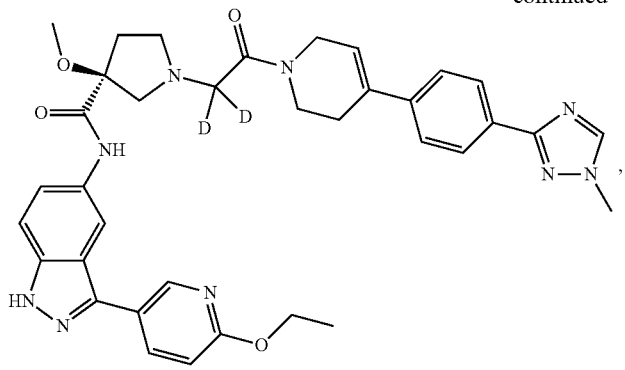
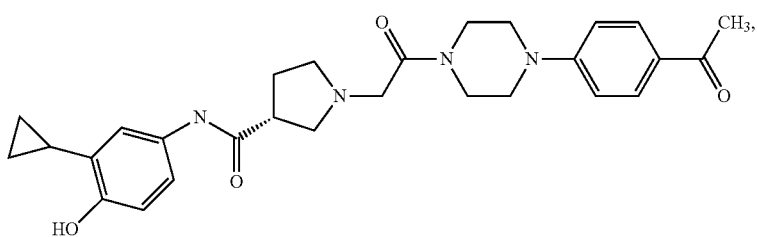
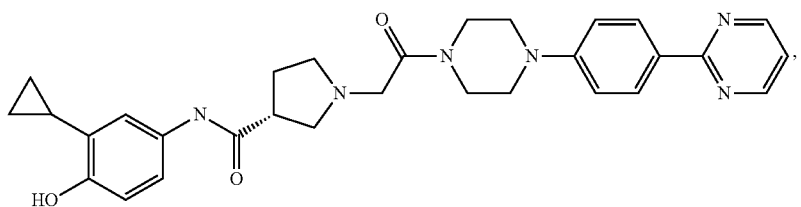
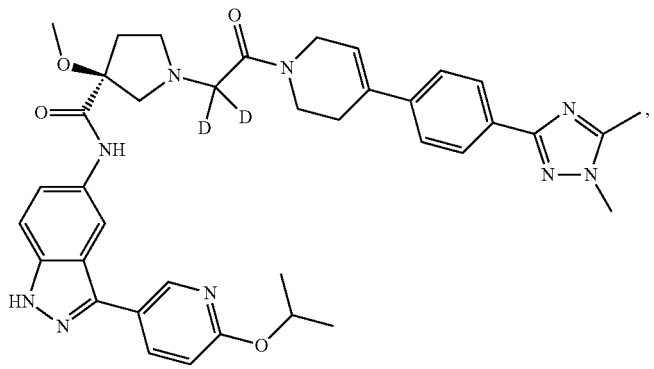
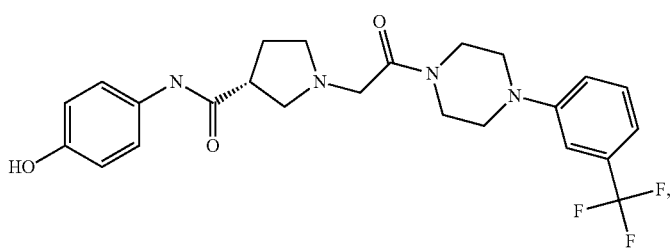
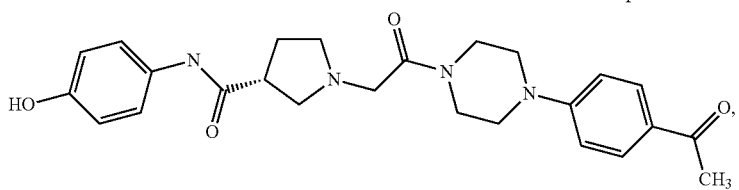

-continued
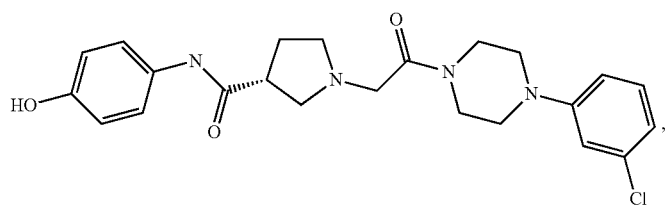
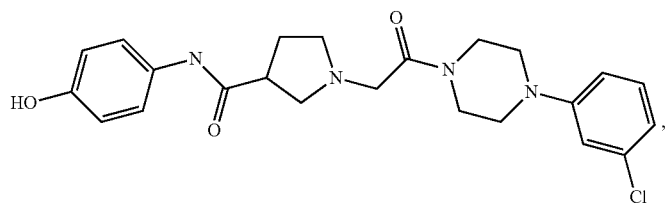
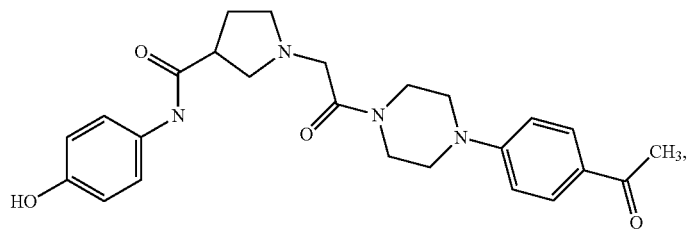
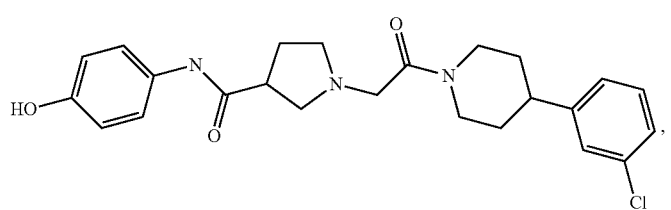
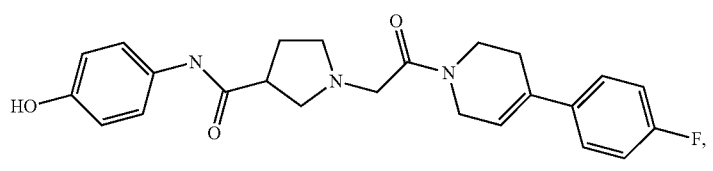
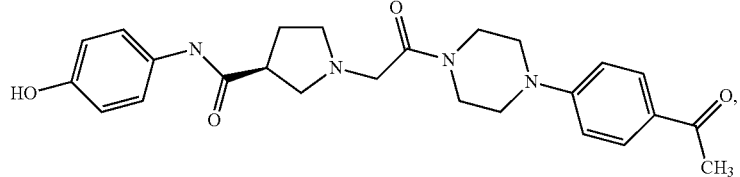
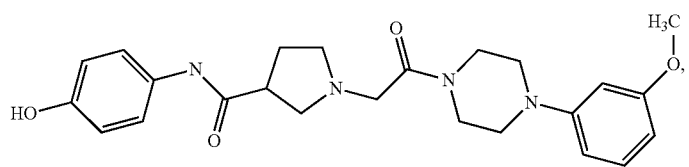
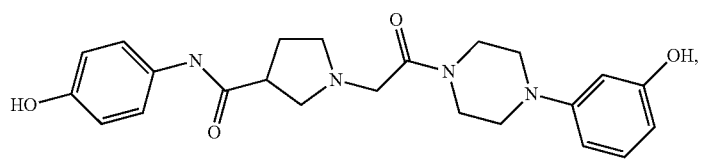

-continued
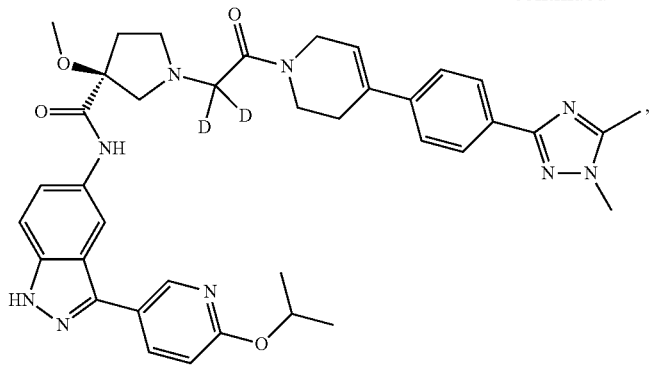
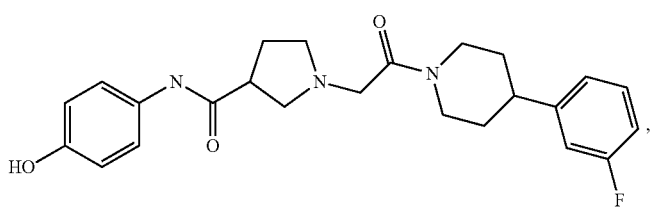
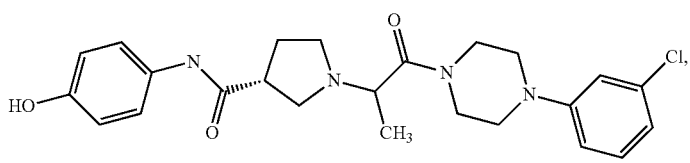
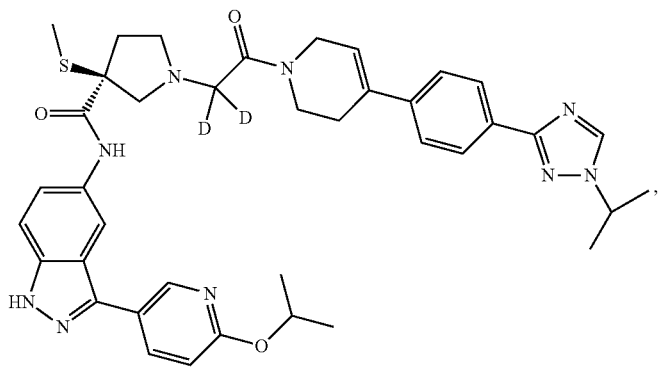
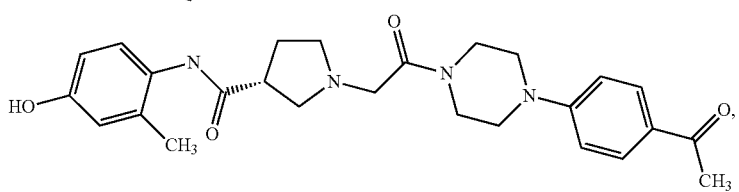
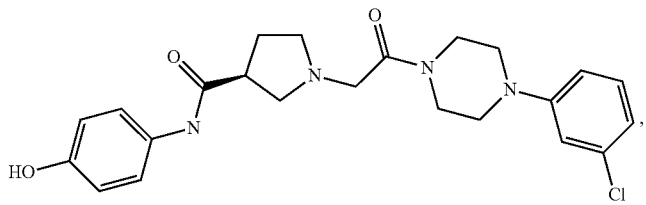
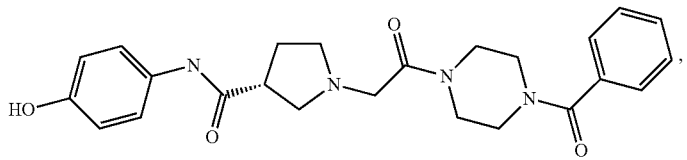

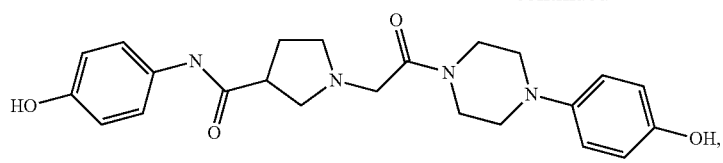
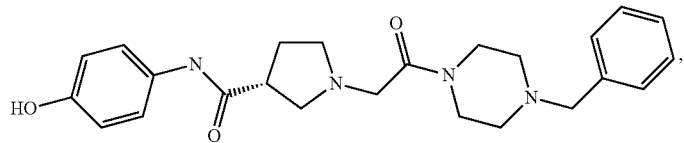
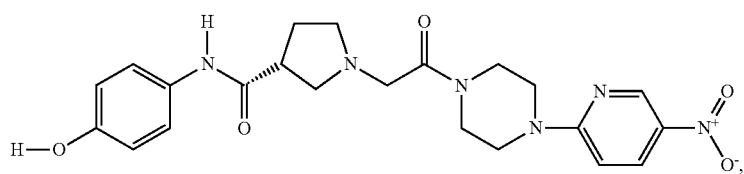
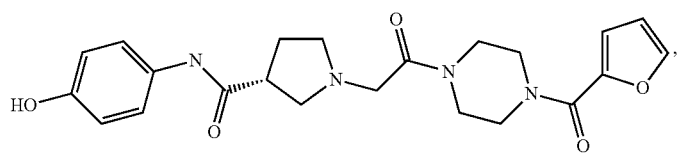
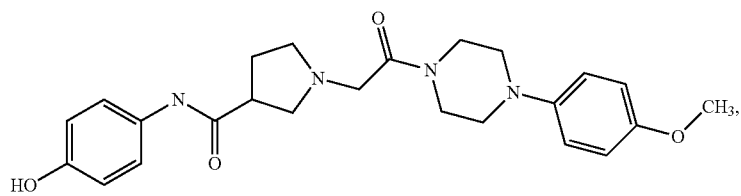
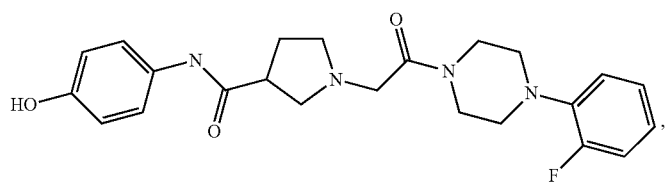
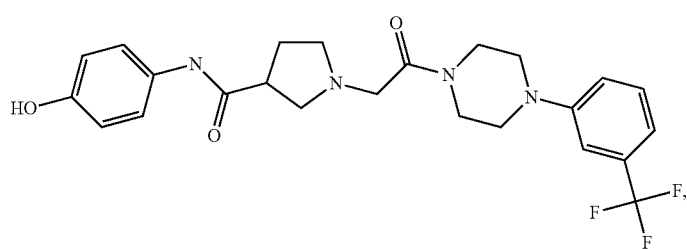
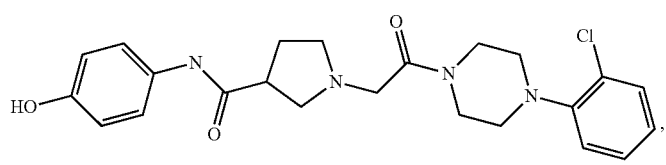
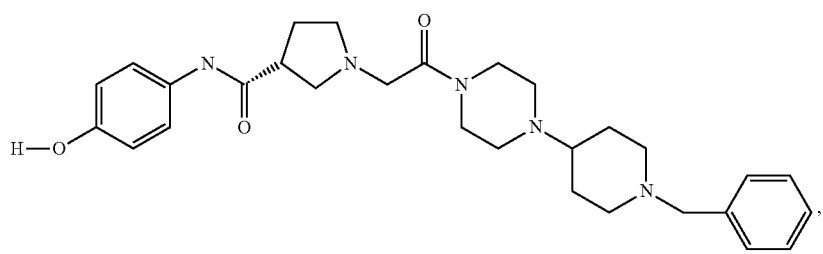

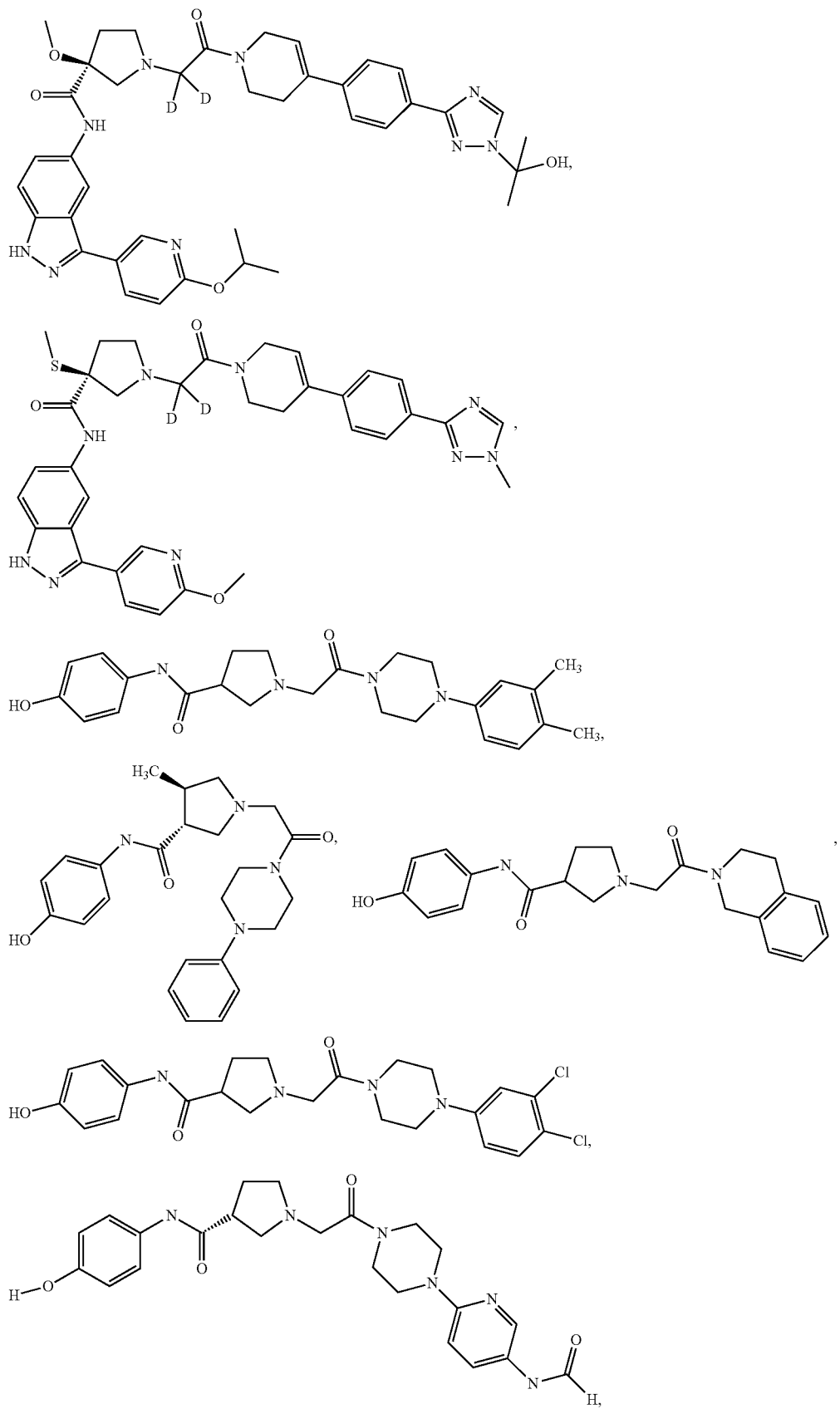

-continued
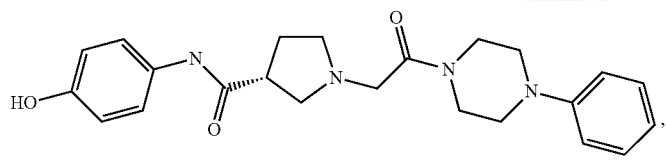
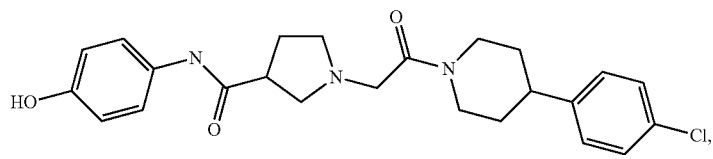
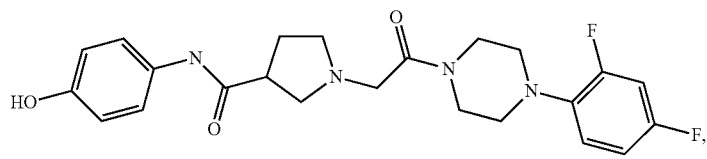
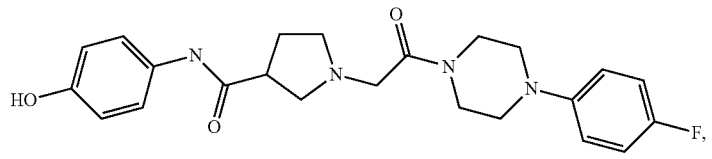
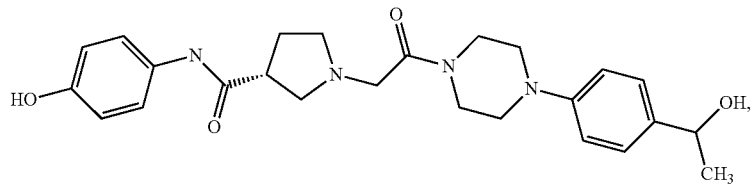
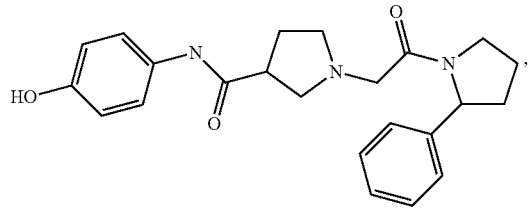
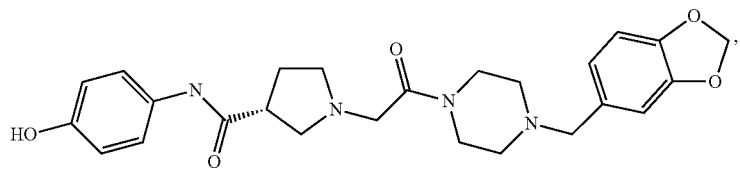
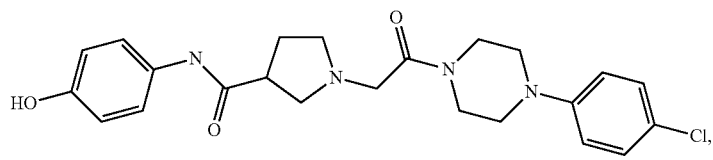
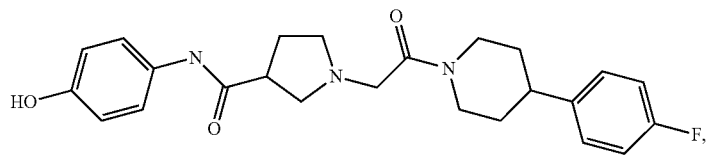
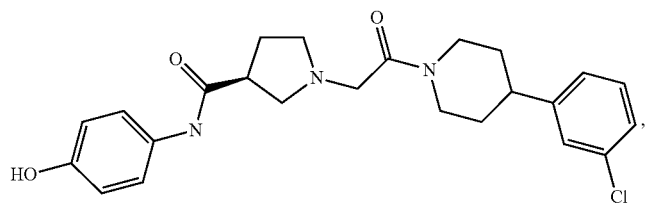

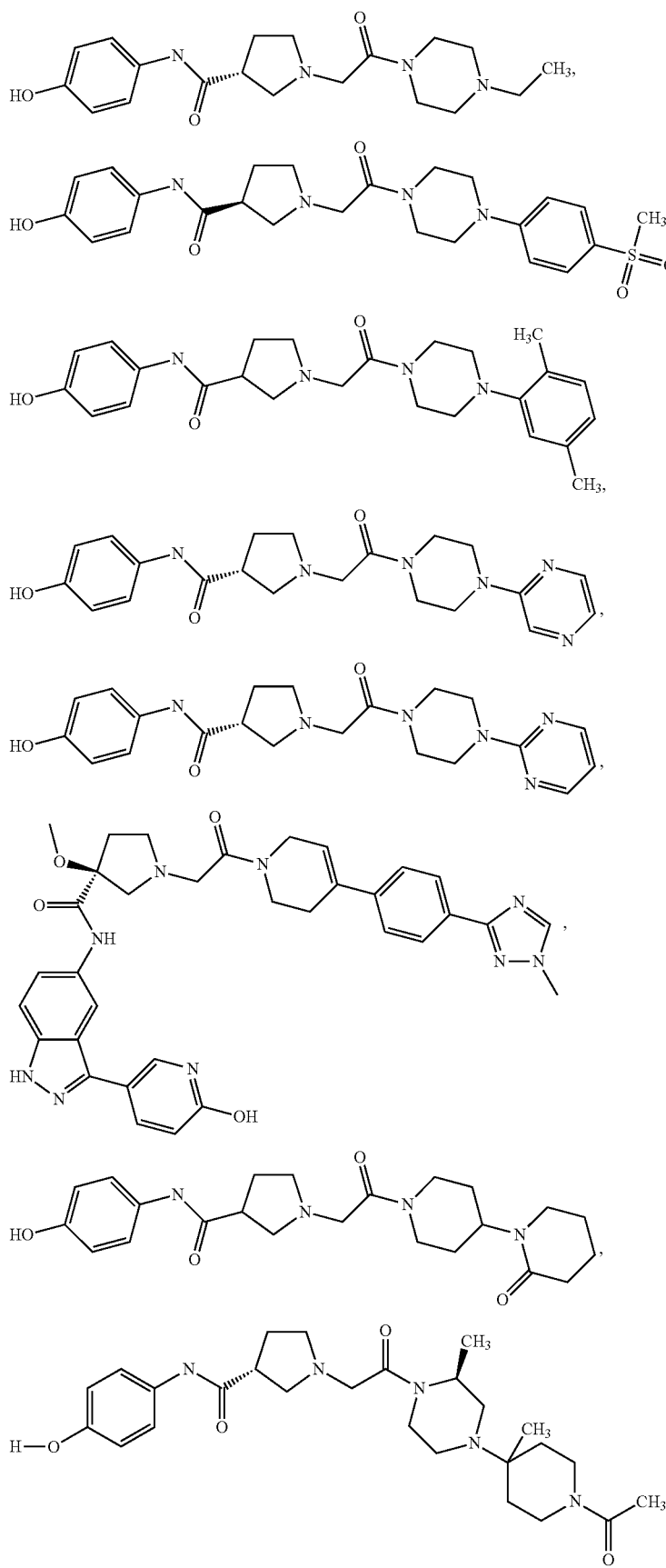

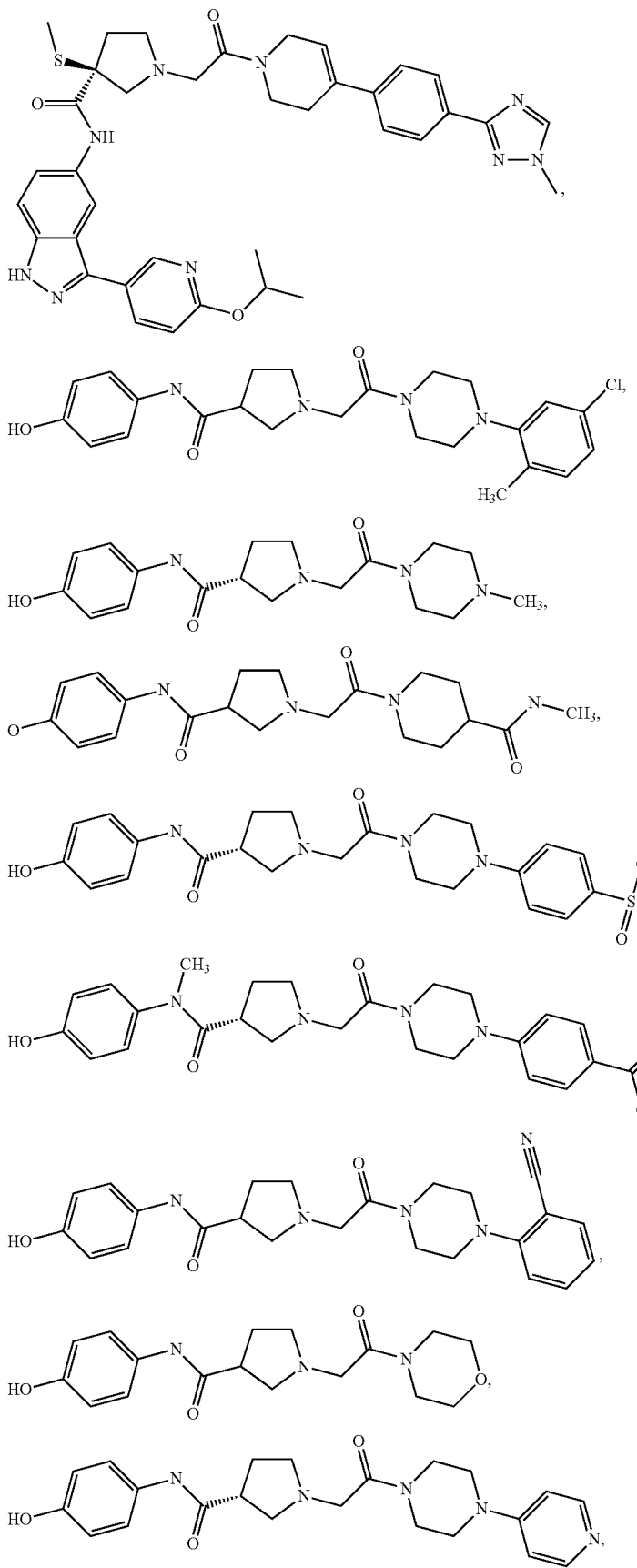

-continued
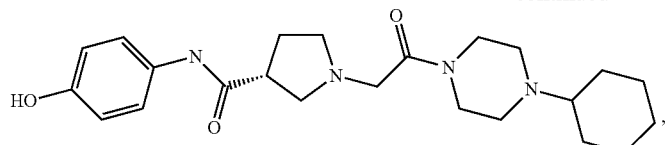
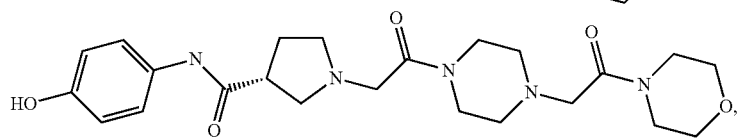
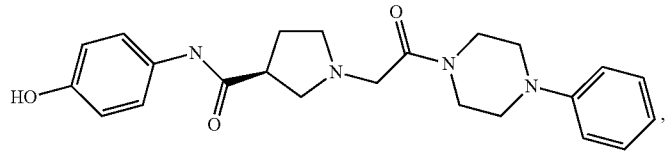
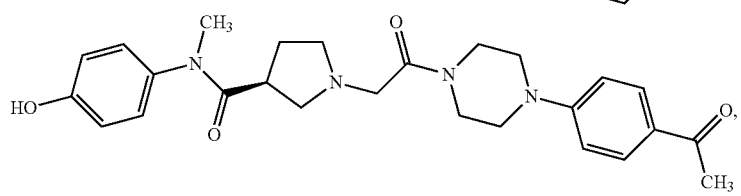
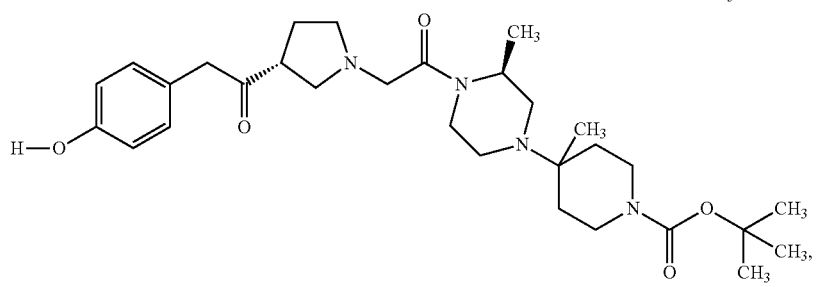
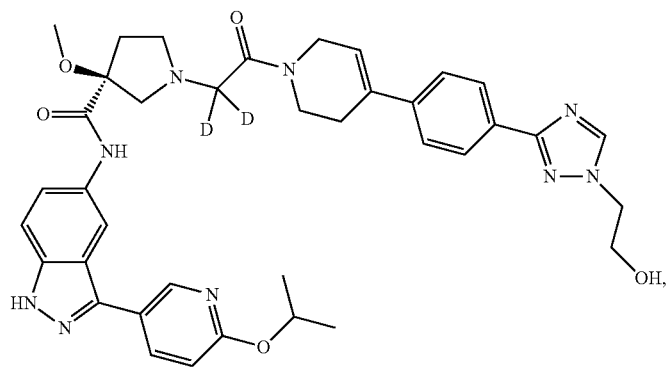
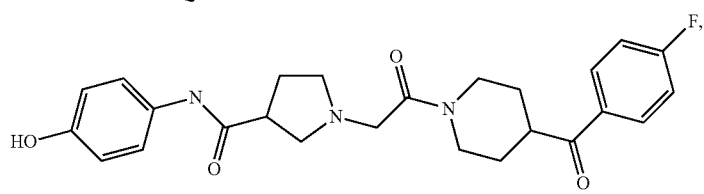
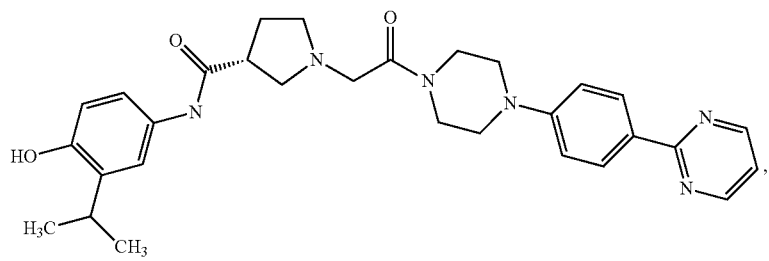

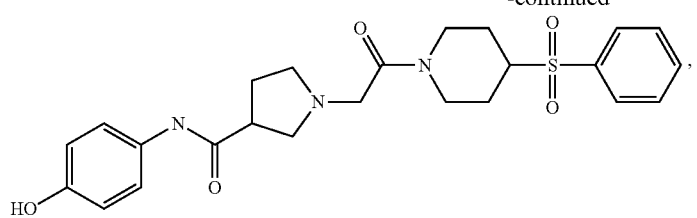
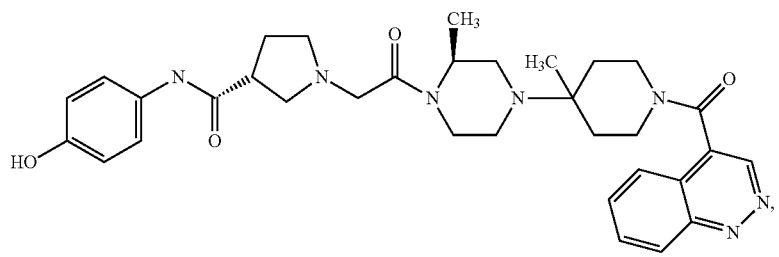
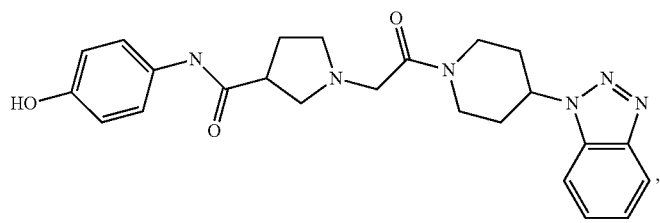
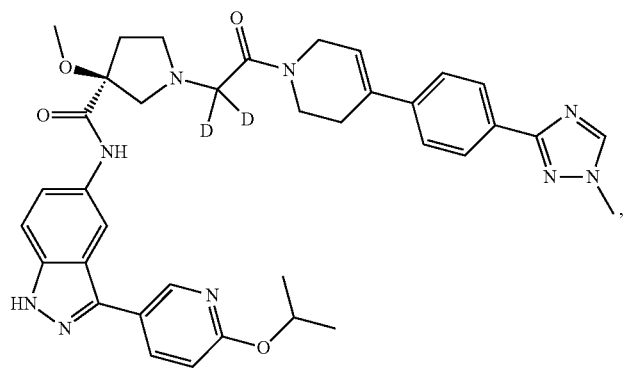
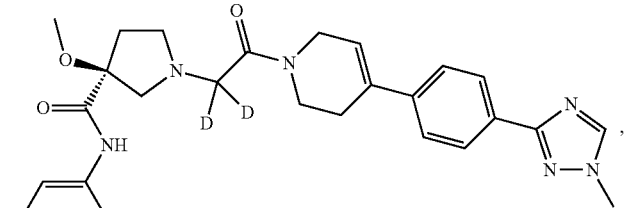
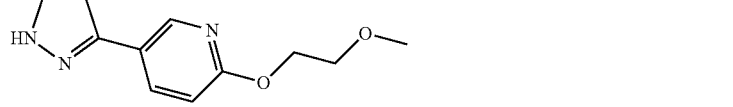
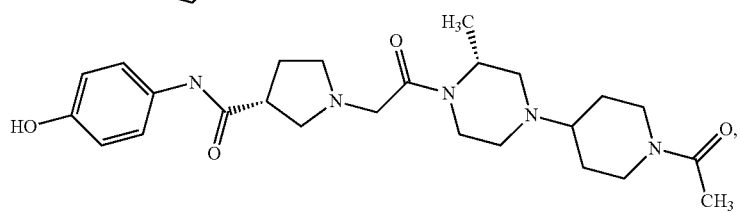

-continued
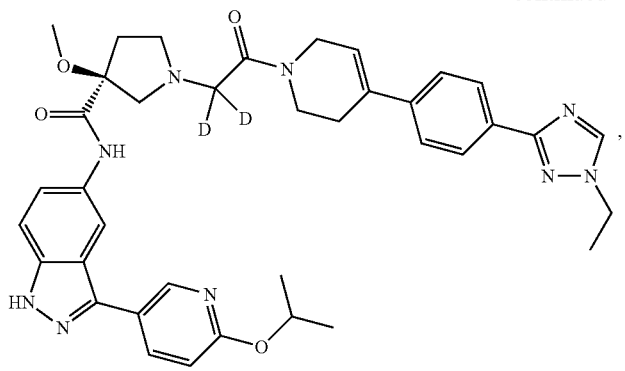
,
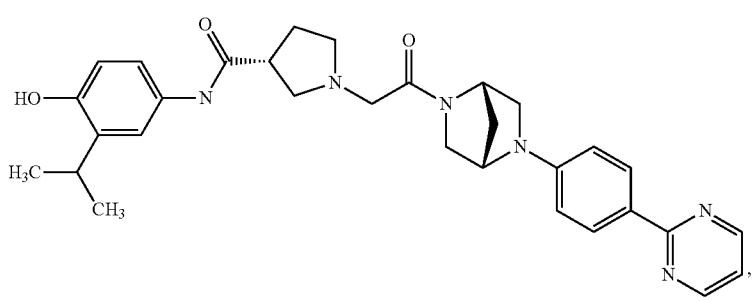
,
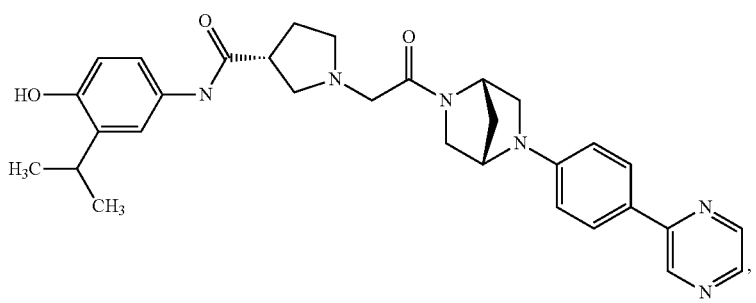
,
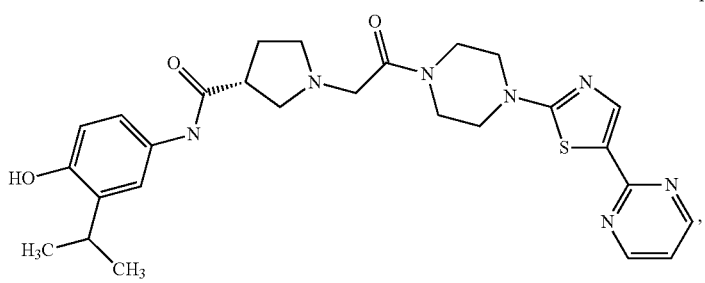
,
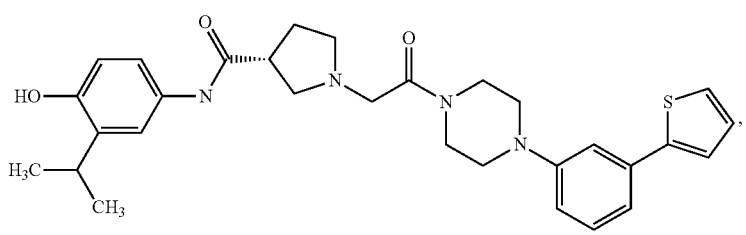
,
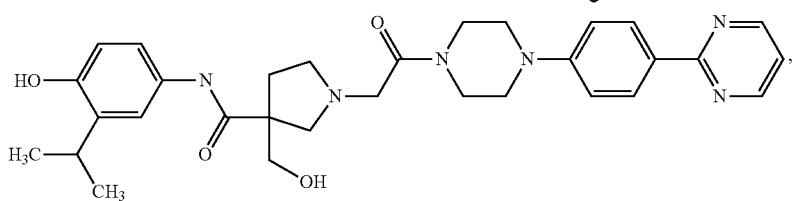
,

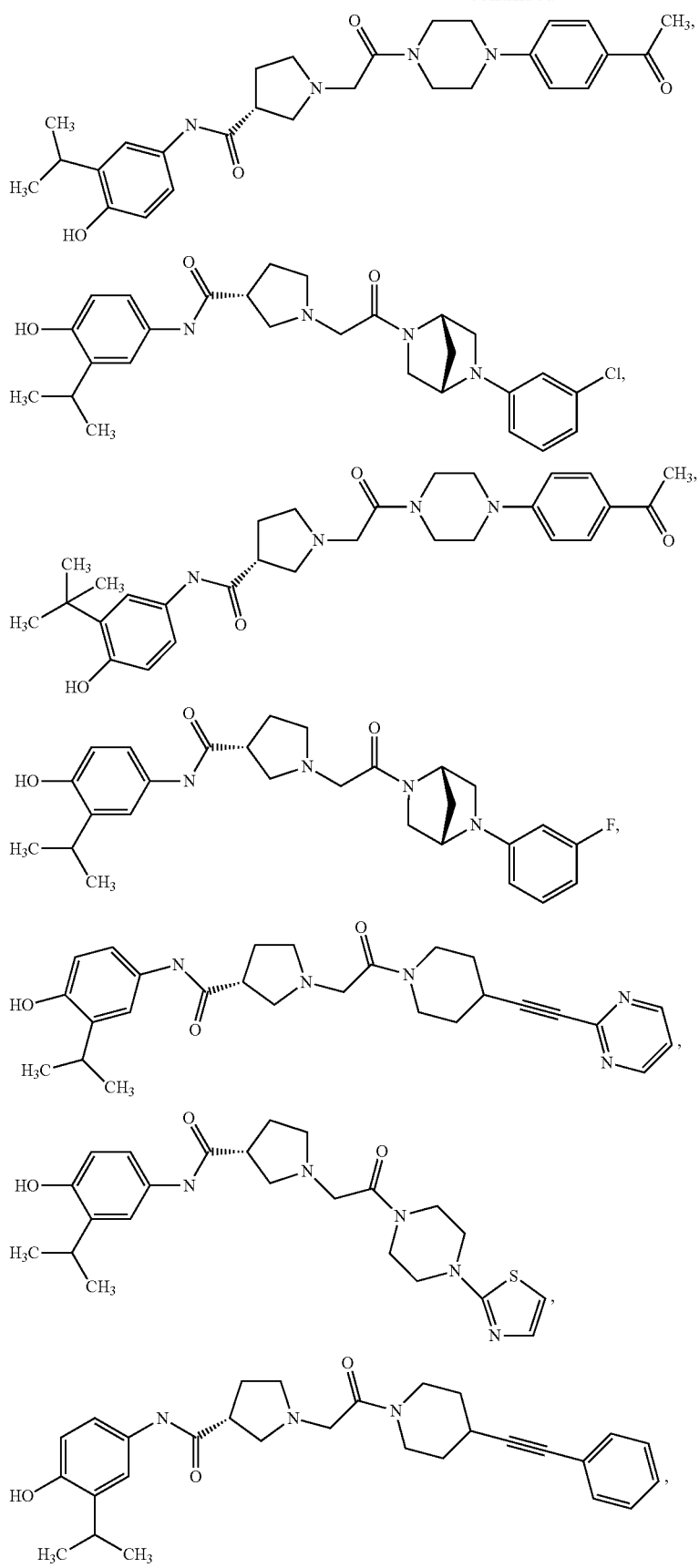

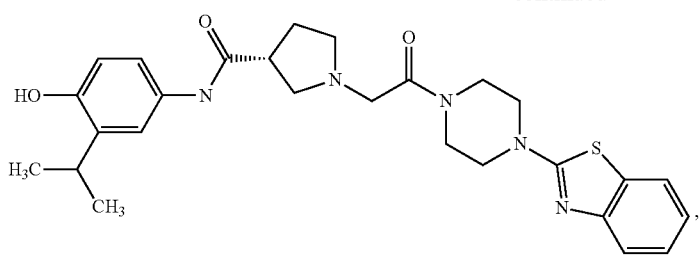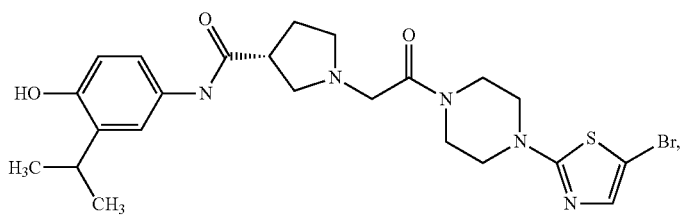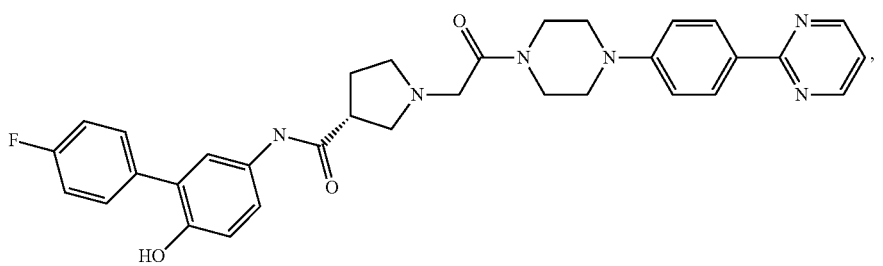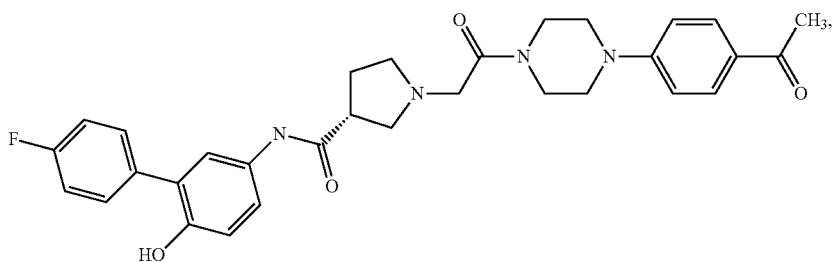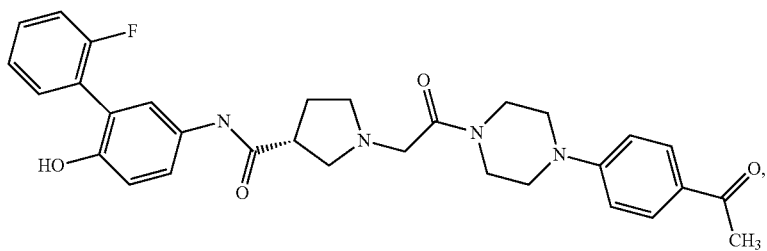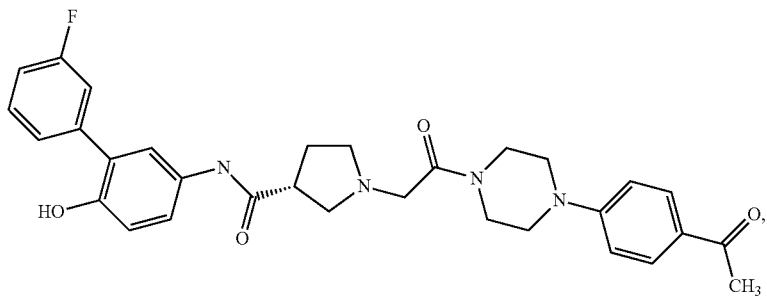

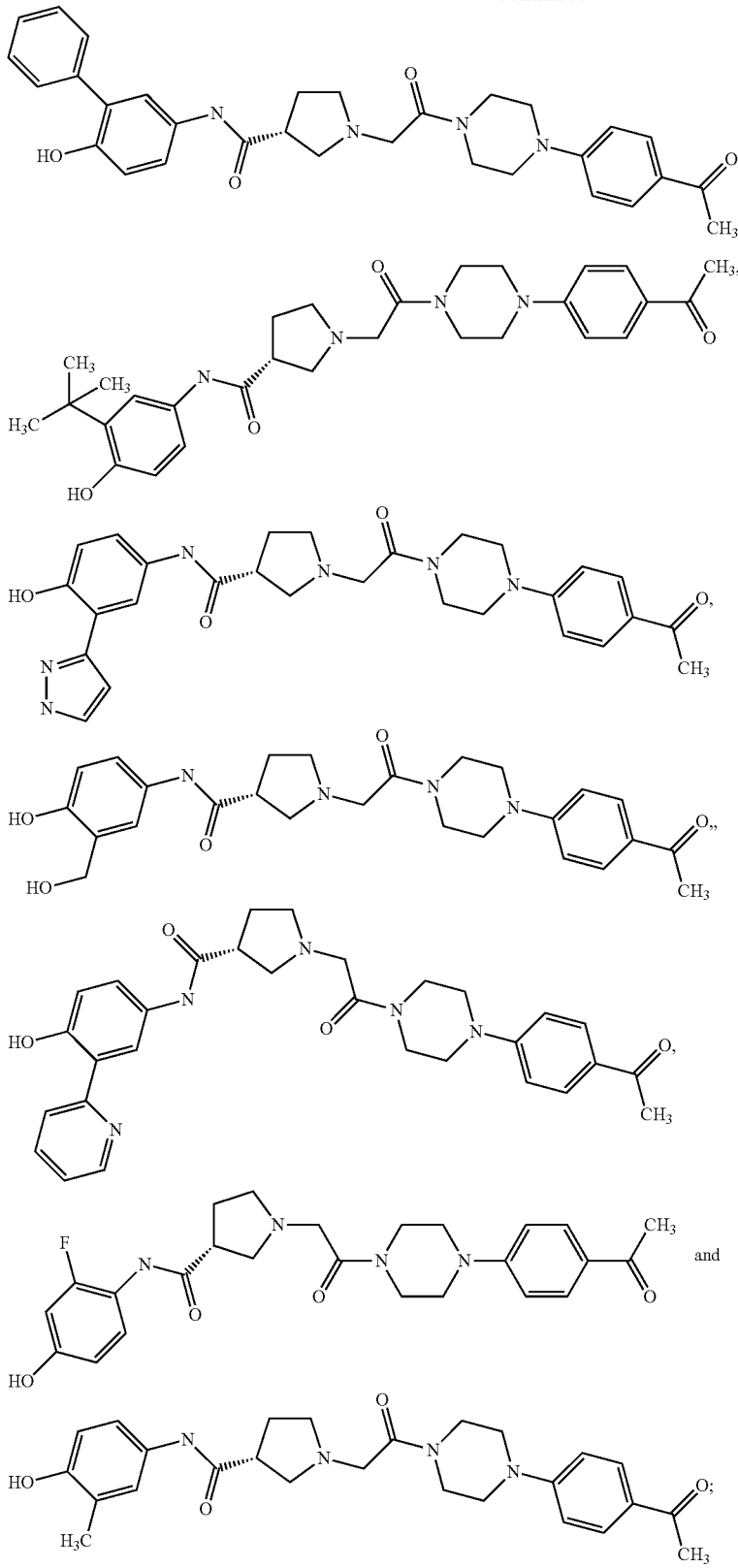
or a pharmaceutically acceptable isomer, salt, solvate or co-crystal form thereof. These compounds are described in PCT publication No. WO 2007/070398, U.S. application No. U.S. 61/030,407, PCT publication No. WO 2008/156739 and U.S. publication No. 2007/0232610, herein incorporated by reference.

The pharmacological properties of the compounds of this invention may be confirmed by a number of pharmacological assays. The exemplified pharmacological assays which are described herein below have been carried out with compounds according to the invention and their salts, solvates, esters or prodrugs.

This invention is also directed to pharmaceutical compositions which comprise at least one compound of the present invention, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Also contemplated are delivery methods that are combinations of the above-noted delivery methods, Such methods are typically decided by those skilled in the art.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of the present invention, or a pharmaceutically acceptable salt, solvate, ester or prodrug of said compound and a pharmaceutically acceptable carrier, vehicle or diluent.

Yet another aspect of this invention is a kit comprising an amount of at least one compound of the present invention, or a pharmaceutically acceptable salt, solvate, ester or prodrug of said compound and an amount of at least one anticancer therapy and/or anti-cancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents, reagents and reaction conditions may be referred to by their abbreviations:
Aq: aqueous
g: grams
psi: pounds per square inch
pH: percent Hydrogen
° C.: degrees Celsius
h: hours
THF: Tetrahydrofuran
HMDS:
Et$_2$O: diethyloxide
SEM: 2-(trimethylsilyl)ethoxymethyl
LC-MS: Liquid chromatography mass spectrometry
DCM: dichloromethane
N: Normal
ml: milliliter
NBS: N-Bromosuccinimide
rt: room temperature
MeOH: methanol
DIEA: diisopropylethylamine
EtOAc: ethyl acetate
EtOH: ethanol
DMF: dimethylformamide
WT %: weight percent
m/z: mass per charge
LiOH: lithium hydroxide
DMSO: dimethylsulfoxide
HPLC: high performance liquid chromatography
Ret: retention
RP: reverse phase
CH$_3$CN: acetonitrile
MeCN: acetonitrile
pTSA: para-toluene sulfonic acid
RT: retention time NaOH: sodium hydroxide
CDI: N,N'-carbonyldiimidazole
mg: milligram
PMA: phosphomolybdic acid
CO₂: carbon dioxide
LiHMDS: lithium hexamethyldisilazane
HMDS: hexamethyldisilazane
Pd/C: palladium on carbon
H₂: hydrogen gas
NIS: N-iodosuccinimide
PDCl₂(dppf): [1,1'-bis(diphenylphosphino)ferrocene]dichloropalladium(II)
μmol: micromole
TFA: trifluoroacetic acid
NMP: N-methyl-2-pyrrolidone
min: minute
NaIO₄: sodium periodate
DME: dimethylethane
OsO₄: osmium tetroxide
Na₂S₂O₃: sodium thiosulfate
AcOH: acetic acid
NaBH₃CN: sodium cyanoborohydride
H₂O: water
BBN: 9-borabicyclo[3.3.1]nonane
CH₂Cl₂: dichloromethane
BOC: tertiary-butyloxycarbonyl
POCl₃: phosphorous oxychloride
NaHCO₃: sodium bicarbonate
NH₄Cl: ammonium chloride
Na₂SO₄: sodium sulphate
HCl: hydrogen chloride
M: Molar
mmol: millimolar
NH₃: ammonia
DIEA: diisopropylethylamine
Bu₃SnCN: tributyltin cyanide
Pd[P(t-Bu)₃]₂: bis(tributyl)Phosphine) palladium
Pd(PPh₃)₄: tetrakis(triphenylphosphine) palladium
K₂CO₃: potassium carbonate
EDC: 1-ethyl-3-(3-dimethylaminopropyl)-carbodiimide
UV: ultraviolet
K₃PO₄: potassium phosphate
LDA: lithium diisopropylamide
Tf: trifluoromethanesulfonyl
NaH: sodium hydride Scheme 1

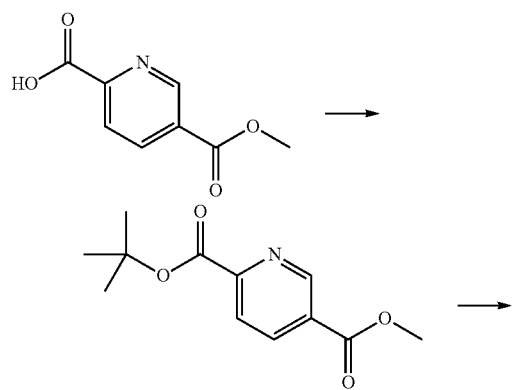

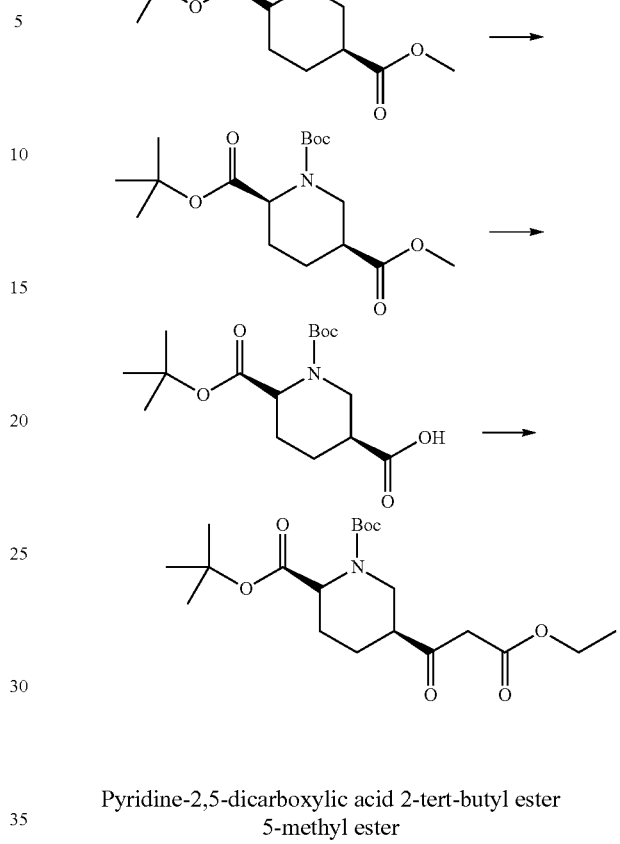

Pyridine-2,5-dicarboxylic acid 2-tert-butyl ester 5-methyl ester

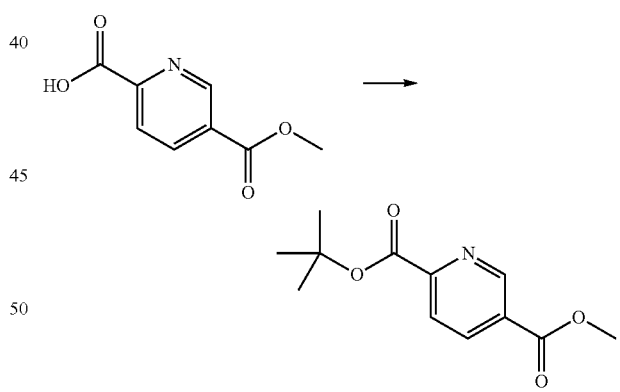

5-(Methoxycarbonyl)pyridine-2-carboxylic acid (7.72 g, 42.65 mmol) was suspended in tert-butanol (70 mL) and pyridine (25 mL) and cooled in an ice-water bath. 4-Toluenesulfonyl chloride (19.4 g, 102 mmol) was added in one portion and the mixture was stirred 30 minutes in the ice-water bath. The reaction mixture was warmed to room temperature and stirred for 16 h. The reaction mixture was then slowly poured into a stirring mixture of saturated aqueous sodium bicarbonate (300 mL) and ethyl ether (150 mL). The resulting two-phase mixture was then extracted with ethyl ether (3×150 mL). The extracts were combined, washed with brine, dried with anhydrous sodium sulfate, filtered and concentrated under reduced pressure. The crude product (5.8 g, 51% yield) was used in the next step without further purification.

Piperidine-2,5-dicarboxylic acid 2-tert-butyl ester 5-methyl ester

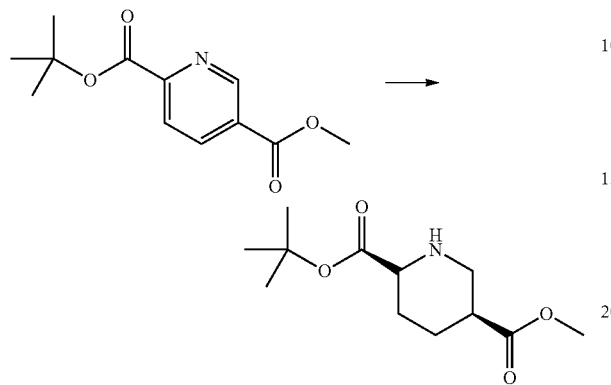

Pyridine-2,5-dicarboxylic acid 2-tert-butyl ester 5-methyl ester (5.8 g, 24.45 mmol) was dissolved in glacial acetic acid (30 mL) and hydrogenated at 50-60 psi for 3 days with 10% palladium on carbon catalyst (0.6 g). The reaction mixture was filtered through a pad of Celite which was then washed with methanol. The filtrates were combined and concentrated under reduced pressure. The residue was dissolved in water (100 mL) and solid sodium carbonate (15 g) was added to bring the pH to 8. The solution was extracted with dichloromethane (2×100 mL). The combined organic layers were washed with brine, dried over anhydrous sodium sulfate, filtered and concentrated under reduced pressure to give the title compound (5.2 g, 87%).

Piperidine-1,2,5-tricarboxylic acid 1,2-di-tert-butyl ester 5-methyl ester

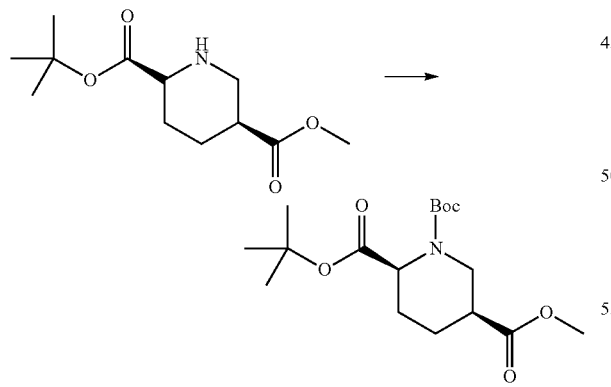

Piperidine-2,5-dicarboxylic acid 2-tert-butyl ester 5-methyl ester (9.0 g, 37.0 mmol) and triethylamine (15.5 ml, 111 mmol) were combined in dichloromethane (70 mL) and cooled to 0° C. Di-tert-butyldicarbonate (12.2 g, 55.5 mmol) was added and reaction mixture was warmed to room temperature and stirred for 16 h. The reaction mixture was diluted with water (100 mL) and extracted with dichloromethane (2×100 mL). The combined extracts were washed with brine, dried over anhydrous sodium sulfate, filtered and concentrated under reduced pressure. The residue was purified by Biotage chromatography column (hexanes/EtOAc, 9:1 to 8:2). A colorless oil was obtained (12.6 g, 99%).

1,6-bis(tert-butoxycarbonyl)piperidine-3-carboxylic acid

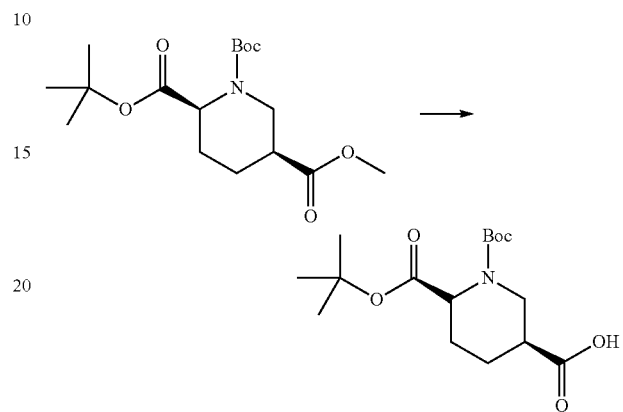

Piperidine-1,2,5-tricarboxylic acid 1,2-di-tert-butyl ester 5-methyl ester (36.7 mmol, 12.6 g) was dissolved in 180 mL of 2:1 THF:H$_2$O. To this solution was added 2N sodium hydroxide solution (52 mL) and the reaction mixture was stirred for 16 h at room temperature. The reaction mixture is acidified to pH=3 with 1N HCl$_{(aq)}$ and extracted with dichloromethane (3×100 mL). The combined organics are then dried over Na$_2$SO$_4$ and the solvent removed in vacuo to yield the title compound (12.0 g, 100% yield).

Di-tert-butyl 5-(3-ethoxy-3-oxopropanoyl)piperidine-1,2-dicarboxylate

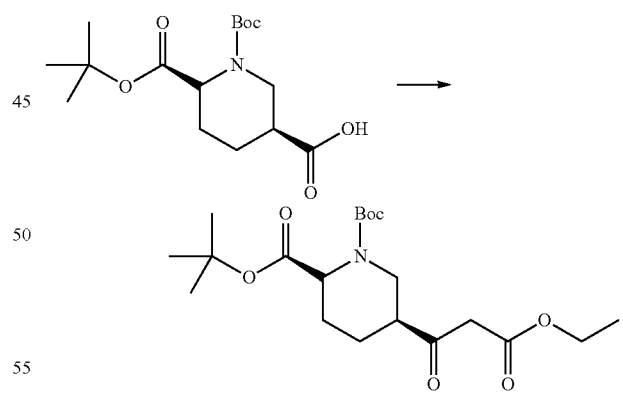

1,6-bis(tert-butoxycarbonyl)piperidine-3-carboxylic acid (41.4 mmol, 13.6 g) and N,N'-carbonyldiimidazole (CDI) (51.75 mmol, 8.4 g) in anhydrous THF (140 mL) were stirred 16 h at room temperature under argon. In a separate, sealed and argon-flushed flask, lithium HMDS (1.0 M in THF, 86.9 mmol) is added to 80 mL anhydrous THF stirring at −78° C. To this solution is added dropwise anhydrous ethyl acetate (89 mmol, 8.69 mL). This solution is allowed to stir at −78° C. for 1 hour prior to the dropwise addition of the original CDI/acid solution that had been stirred overnight. The reaction mixture is allowed to stir and warm to room temperature overnight. The reaction is then quenched with saturated NH₄Cl$_{(aq)}$ (250 mL) and extracted with Et₂O (100×2). The combined organics are then washed with water, saturated brine, and dried over Na₂SO₄. The solvent is removed in vacuo and the residue (12.6 g) was used in the next step without further purification.

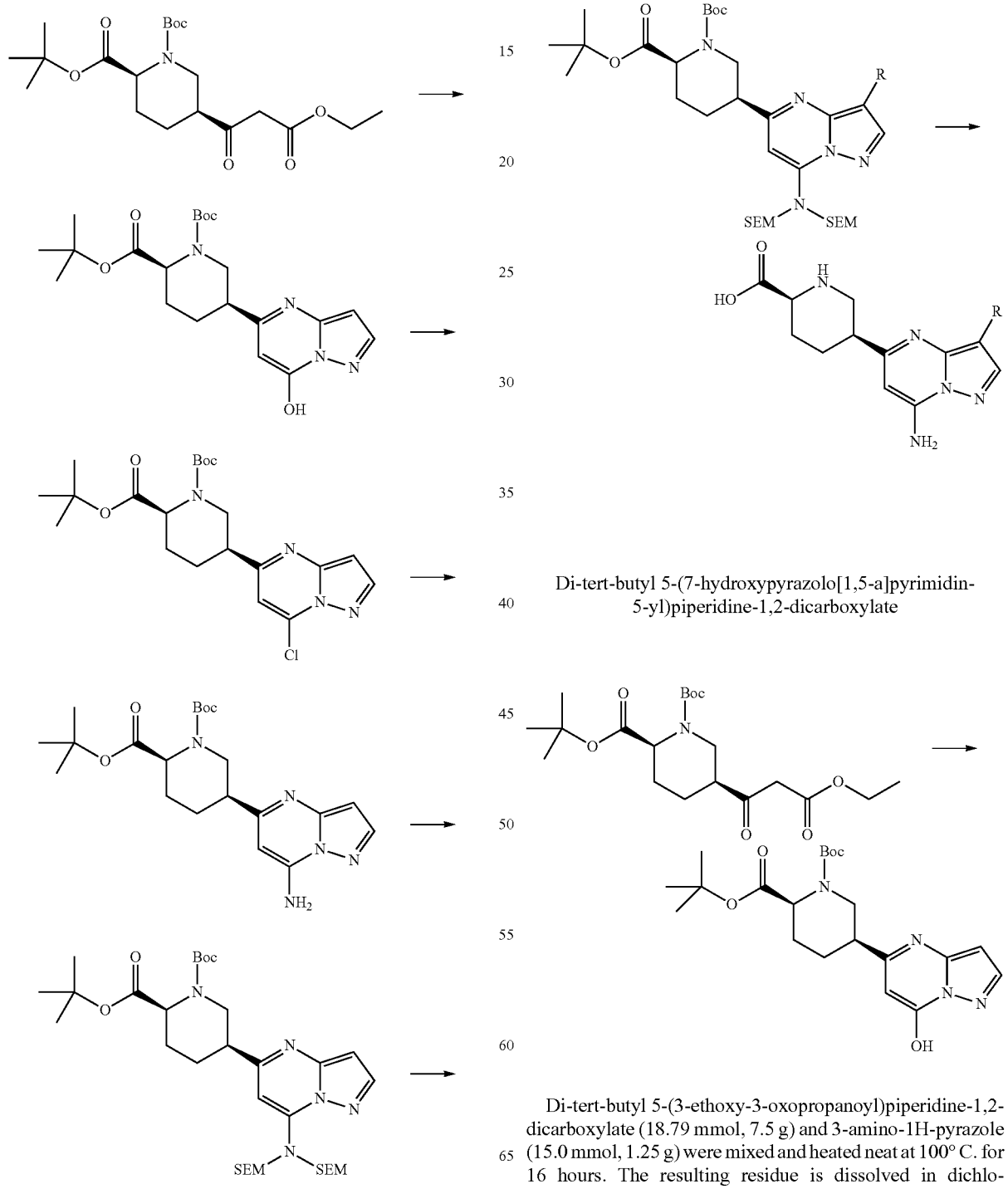

Di-tert-butyl 5-(7-hydroxypyrazolo[1,5-a]pyrimidin-5-yl)piperidine-1,2-dicarboxylate Di-tert-butyl 5-(3-ethoxy-3-oxopropanoyl)piperidine-1,2-dicarboxylate (18.79 mmol, 7.5 g) and 3-amino-1H-pyrazole (15.0 mmol, 1.25 g) were mixed and heated neat at 100° C. for 16 hours. The resulting residue is dissolved in dichloromethane (100 mL) and concentrated in vacuo to remove Di-tert-butyl 5-(7-chloropyrazolo[1,5-a]pyrimidin-5-yl)piperidine-1,2-dicarboxylate

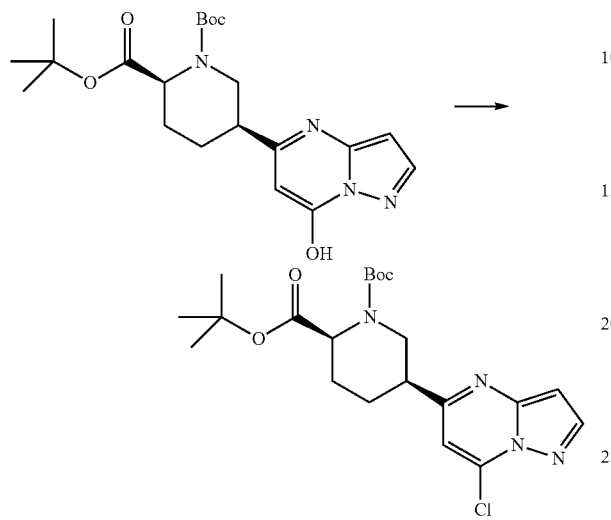

Di-tert-butyl 5-(7-hydroxypyrazolo[1,5-a]pyrimidin-5-yl)piperidine-1,2-dicarboxylate (16.7 mmol, 7.0 g), N,N'-diisopropylethylamine (51.9 mmol, 9.0 ml) and POCl₃ (80 mL) were mixed and stirred at room temperature for 18 hours. The solution is concentrated in vacuo and cooled to 0° C. in an ice bath. The reaction is then quenched with sat. NaHCO₃(aq) and extracted with DCM (100 mL×3). The combined organics are dried with Na₂SO₄ and the solvent removed in vacuo. LC-MS: 437 [M+H]. The resulting oil was used in the next step without further purification.

Di-tert-butyl 5-(7-aminopyrazolo[1,5-a]pyrimidin-5-yl)piperidine-1,2-dicarboxylate

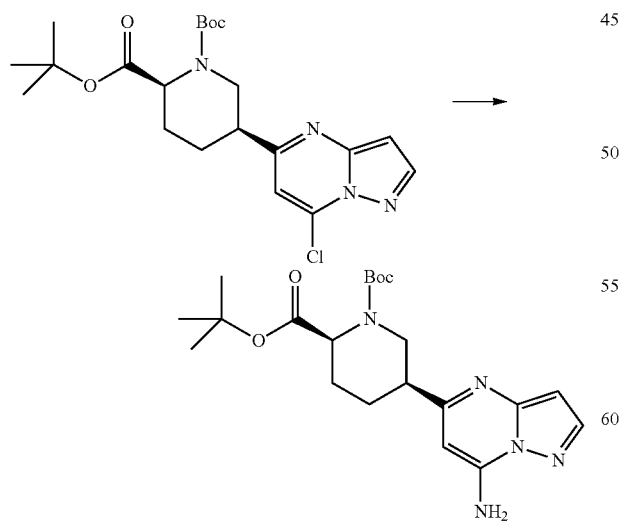

Di-tert-butyl 5-(7-chloropyrazolo[1,5-a]pyrimidin-5-yl)piperidine-1,2-dicarboxylate was dissolved in 30 mL ~7N ammonia in methanol in a sealed vessel. The reaction mixture was heated at 80° C. for 16 hours. After 16 hours, the reaction mixture is cooled to room temperature and concentrated in vacuo to yield a brown solid. LC-MS: 418 [M+H]. The title compound was used in the next step without further purification.

Di-tert-butyl 5-(7-(bis((2-(trimethylsilyl)ethoxy)methyl)amino)pyrazolo[1,5-a]pyrimidin-5-yl)piperidine-1,2-dicarboxylate

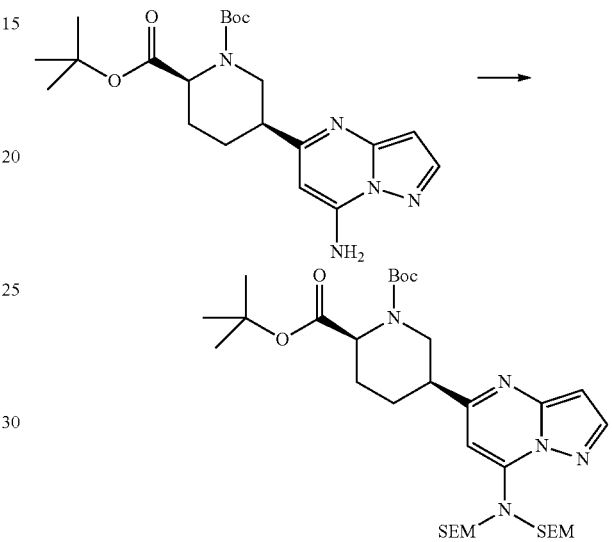

Di-tert-butyl 5-(7-aminopyrazolo[1,5-a]pyrimidin-5-yl)piperidine-1,2-dicarboxylate (5.5 g, 13.18 mmol) was dissolved in 1,2-dichloroethane (60 mL). To this solution was added N,N'-diisopropylethylamine (92.28 mmol, 16.1 mL). The resulting solution was stirred at room temperature while 2-(trimethylsilyl)ethoxymethyl chloride (SEM-Cl, 8.14 mL, 46.14 mmol) was added dropwise. After the addition is completed, the reaction mixture was stirred at 90° C. for 2 h. The solvent is removed in vacuo and the residue is purified on silica gel column (0% to 60% ethyl acetate in hexanes gradient) to yield the title compound (3.8 g, 34% yield over three steps) as pale yellow oil. LC-MS: 678 [M+H].

Di-tert-butyl 5-(7-(bis((2-(trimethylsilyl)ethoxy)methyl)amino)-3-iodopyrazolo[1,5-a]pyrimidin-5-yl)piperidine-1,2-dicarboxylate

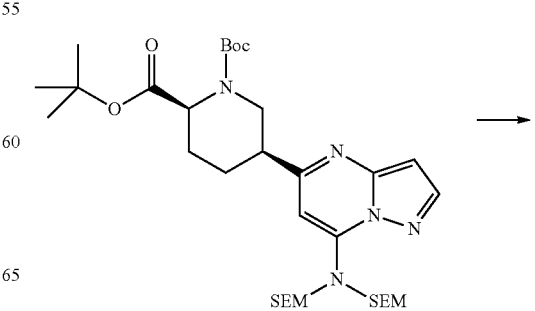

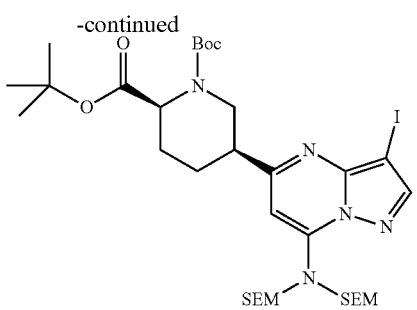

N-Iodosuccinimide (1.26 g, 5.61 mmol, dissolved in 25 ml acetonitrile) was added into a solution of di-tert-butyl 5-(7-(bis((2-(trimethylsilyl)ethoxy)methyl)amino)pyrazolo[1,5-a]pyrimidin-5-yl)piperidine-1,2-dicarboxylate (3.8 g, 5.61 mmol) in acetonitrile (26 mL). The reaction mixture was stirred at room temperature for 16 hours. The reaction mixture was concentrated in vacuo and purified via silica gel chromatography (0% to 30% ethyl acetate in hexanes gradient) to yield the title compound (3.16 g, 70% yield) at clear oil. LC-MS: 804 [M+H].

Di-tert-butyl 5-(7-(bis((2-(trimethyl)silyl)ethoxy) methyl)amino)-3-(quinolin-3-yl)pyrazolo[1,5-a]pyrimidin-5-yl)piperidine-1,2-dicarboxylate

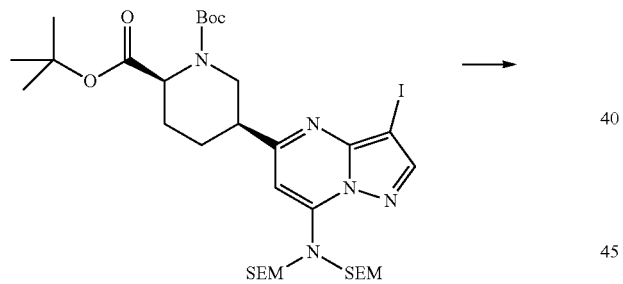

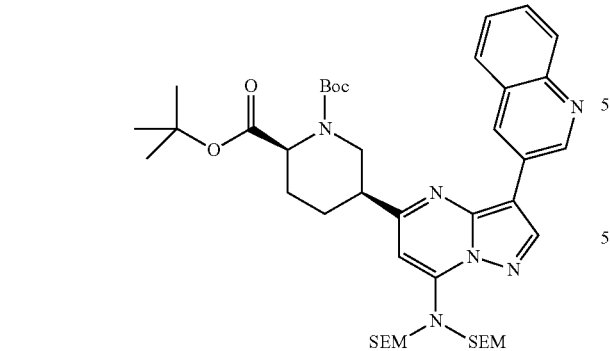

3-Quinoline boronic acid (1.25 mmol, 216 mg), K₃PO₄ (1.87 mmol, 400 mg), and PdCl₂(dppf).CH₂Cl₂ (0.062 mmol, 51 mg) was added to a solution of di-tert-butyl 5-(7-(bis((2-(trimethylsilyl)ethoxy)methyl)amino)-3-iodopyrazolo[1,5-a]pyrimidin-5-yl)piperidine-1,2-dicarboxylate (0.62 mmol, 500 mg) in dioxane (5 mL). To this suspension was added distilled H₂O (0.5 mL). The reaction mixture was stirred at 100° C. under an argon atmosphere for 18 hours. The reaction mixture was concentrated in vacuo and then purified via silica gel chromatography (0% to 60% ethyl acetate in hexanes gradient) to yield the title compound (450 mg, 90% yield) as yellow oil. LC-MS: 805 [M+H].

5-(7-amino-3-(quinolin-3-yl)pyrazolo[1,5-a]pyrimidin-5-yl)piperidine-2-carboxylic acid

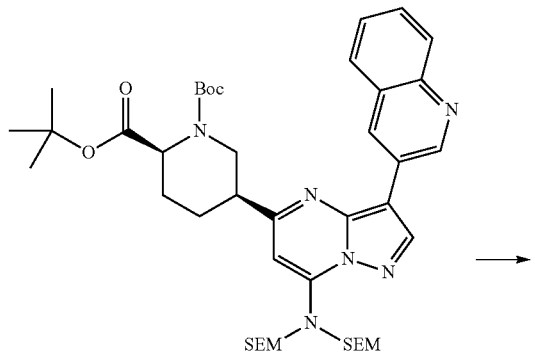

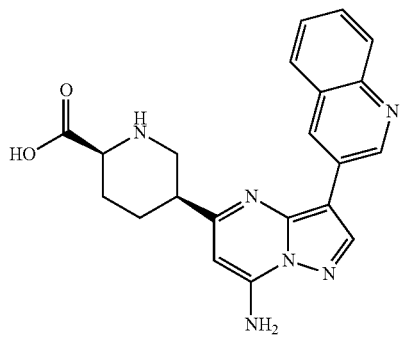

Di-tert-butyl 5-(7-(bis((2-(trimethylsilyl)ethoxy)methyl) amino)-3-(quinolin-3-yl)pyrazolo[1,5-a]pyrimidin-5-yl)piperidine-1,2-dicarboxylate (45 mg, 0.056 mmol) was dissolved in ethanol (1 ml) and treated with 3N hydrochloride solution (1.4 ml) at 65° C. for 4 h. The reaction solution was concentrated and purified by prep-LC to afford the title compound (9.6 mg): LC/MS RT=2.01 min. Mass calculated for, M+H 389.17, observed 389.17.

By essentially the same procedure given in Scheme 2, the compounds listed in Table 1 can be prepared.

TABLE 1

| Compound ID | Structures | M + H (calc.) | M + H (observed) | Retention time, (min) |
|---|---|---|---|---|
| 1.1 | 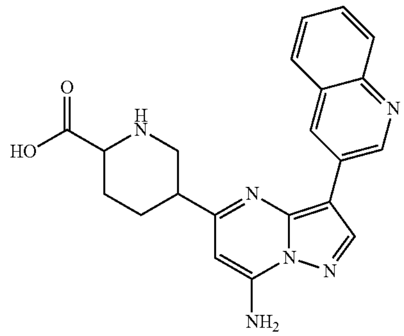 [SMILES: Nc1cc(C2CCC(C(=O)O)NC2)nc2c(-c3cnc4ccccc4c3)cnn12] | 389.17 | 389.17 | 2.01 |
| 1.2 | 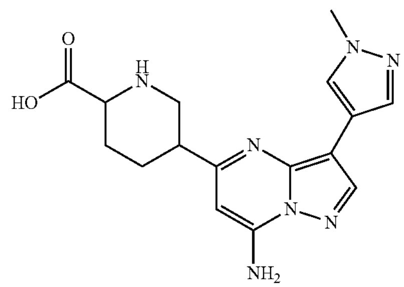 [SMILES: Cn1cc(-c2cnn3c(N)cc(C4CCC(C(=O)O)NC4)nc23)cn1] | 342.16 | 342.16 | 1.62 |
| 1.3 | 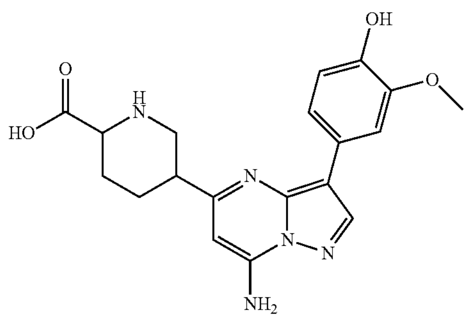 [SMILES: COc1cc(-c2cnn3c(N)cc(C4CCC(C(=O)O)NC4)nc23)ccc1O] | 384.16 | 384.16 | 2.22 |
| 1.4 | 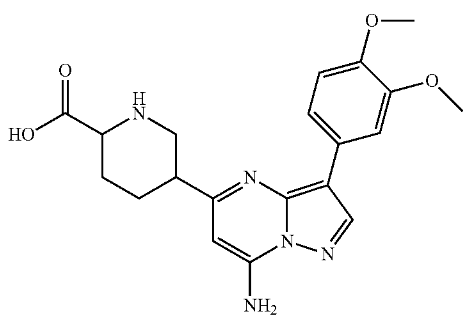 [SMILES: COc1ccc(-c2cnn3c(N)cc(C4CCC(C(=O)O)NC4)nc23)cc1OC] | 398.18 | 398.18 | 2.59 |
| 1.5 | 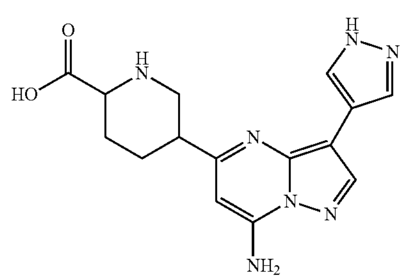 [SMILES: Nc1cc(C2CCC(C(=O)O)NC2)nc2c(-c3cn[nH]c3)cnn12] | 328.15 | 328.15 | 1.57 |

TABLE 1-continued

| Compound ID | Structures | M + H (calc.) | M + H (observed) | Retention time, (min) |
| --- | --- | --- | --- | --- |
| 1.6 | 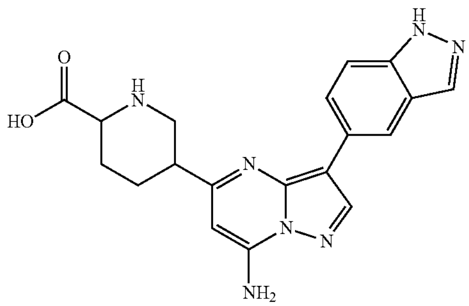 [SMILES: Nc1cc(C2CCC(C(=O)O)NC2)nc2c(-c3ccc4[nH]ncc4c3)cnn12] | 378.16 | 378.16 | 2.18 |
| 1.7 | 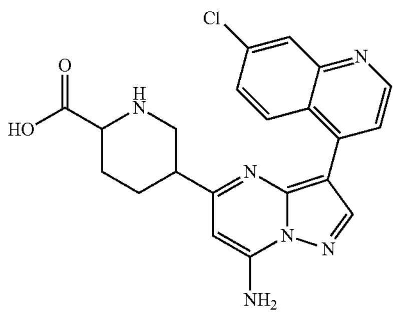 [SMILES: Nc1cc(C2CCC(C(=O)O)NC2)nc2c(-c3ccnc4cc(Cl)ccc34)cnn12] | 423.13 | 423.13 | 2.15 |
| 1.8 | 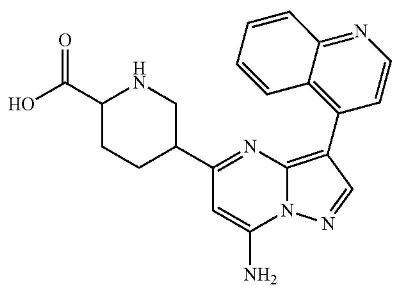 [SMILES: Nc1cc(C2CCC(C(=O)O)NC2)nc2c(-c3ccnc4ccccc34)cnn12] | 389.17 | 389.17 | 1.82 |
| 1.9 | 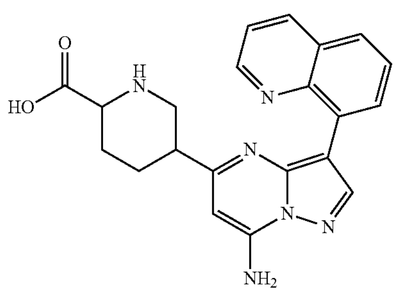 [SMILES: Nc1cc(C2CCC(C(=O)O)NC2)nc2c(-c3cccc4cccnc34)cnn12] | 389.17 | 389.17 | 1.88 |
| 1.10 | 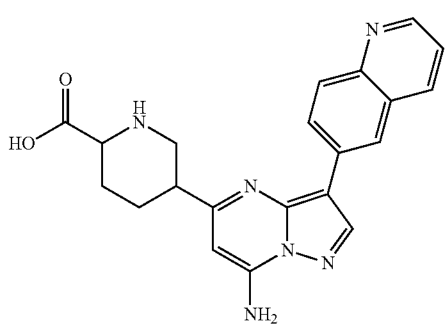 [SMILES: Nc1cc(C2CCC(C(=O)O)NC2)nc2c(-c3ccc4ncccc4c3)cnn12] | 389.17 | 389.17 | 1.87 |

TABLE 1-continued

| Compound ID | Structures | M + H (calc.) | M + H (observed) | Retention time, (min) |
| --- | --- | --- | --- | --- |
| 1.11 | 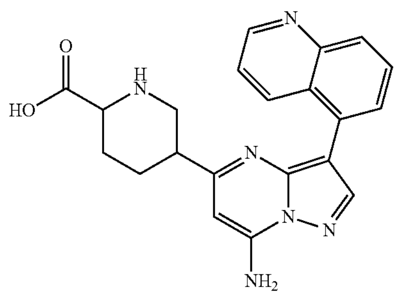 [SMILES: Nc1cc(C2CCC(C(=O)O)NC2)nc2c(-c3cccc4ncccc34)cnn12] | 389.17 | 389.17 | 1.69 |
| 1.12 | 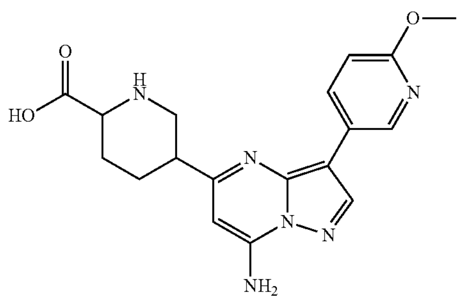 [SMILES: COc1ccc(-c2cnn3c(N)cc(C4CCC(C(=O)O)NC4)nc23)cn1] | 369.16 | 369.16 | 2.08 |
| 1.13 | 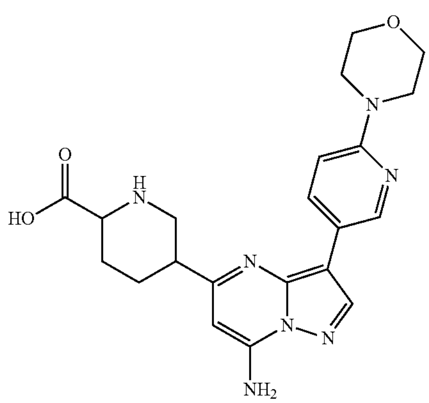 [SMILES: Nc1cc(C2CCC(C(=O)O)NC2)nc2c(-c3ccc(N4CCOCC4)nc3)cnn12] | 424.20 | 424.20 | 1.76 |
| 1.14 | 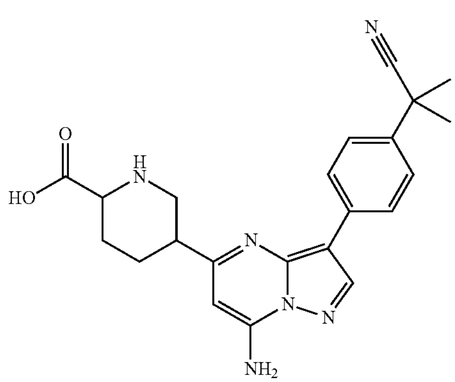 [SMILES: CC(C)(C#N)c1ccc(-c2cnn3c(N)cc(C4CCC(C(=O)O)NC4)nc23)cc1] | 405.20 | 405.20 | 3.12 |

TABLE 1-continued

| Compound ID | Structures | M + H (calc.) | M + H (observed) | Retention time, (min) |
|---|---|---|---|---|
| 1.15 | 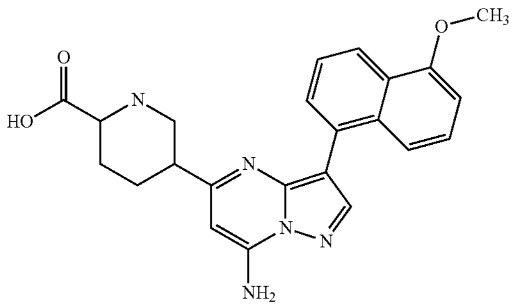 [SMILES: COc1cccc2c(-c3cnn4c(N)cc(C5CCC(C(=O)O)NC5)nc34)cccc12] | 417.18 | 418.2 | 3.41 |
| 1.16 | 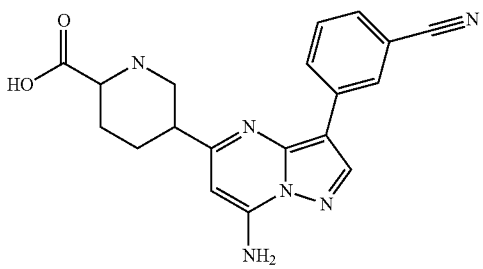 [SMILES: N#Cc1cccc(-c2cnn3c(N)cc(C4CCC(C(=O)O)NC4)nc23)c1] | 362.14 | 363.1 | 2.73 |
| 1.17 | 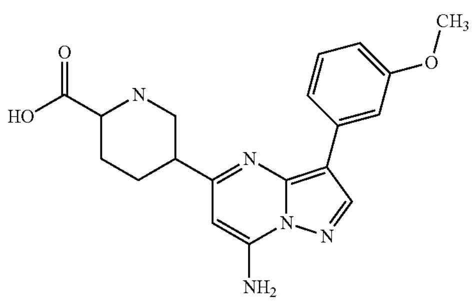 [SMILES: COc1cccc(-c2cnn3c(N)cc(C4CCC(C(=O)O)NC4)nc23)c1] | 368.16 | 368.2 | 2.72 |
| 1.18 | 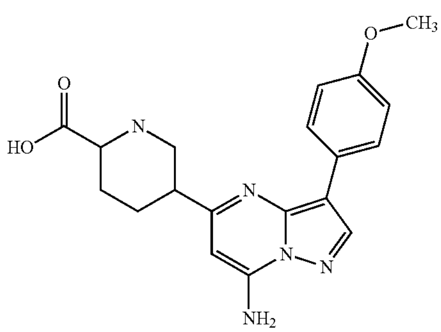 [SMILES: COc1ccc(-c2cnn3c(N)cc(C4CCC(C(=O)O)NC4)nc23)cc1] | 36.16 | 368.2 | 2.72 |
| 1.19 | 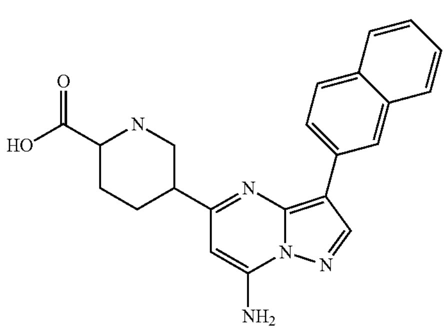 | 388.17 | 388.2 | 3.37 |

TABLE 1-continued

| Compound ID | Structures | M + H (calc.) | M + H (observed) | Retention time, (min) |
|---|---|---|---|---|
| 1.20 | 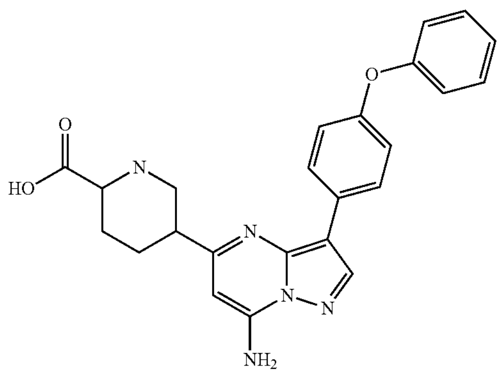 [SMILES: Nc1cc(C2CCC(C(=O)O)NC2)nc2c(-c3ccc(Oc4ccccc4)cc3)cnn12] | 430.18 | 430.2 | 3.76 |
| 1.21 | 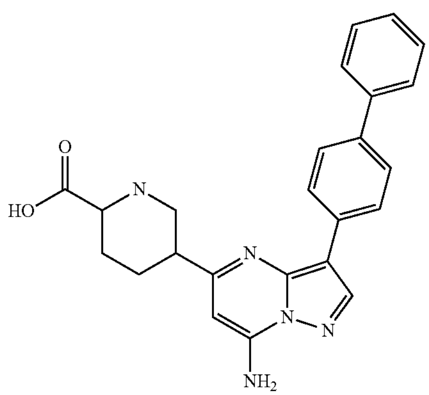 [SMILES: Nc1cc(C2CCC(C(=O)O)NC2)nc2c(-c3ccc(-c4ccccc4)cc3)cnn12] | 414.18 | 414.1 | 3.93 |
| 1.22 | 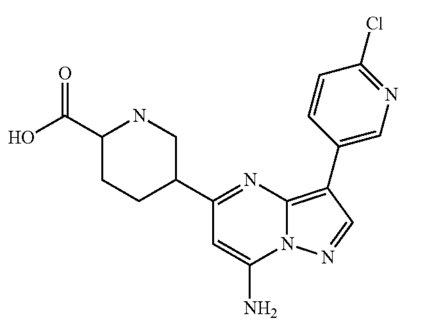 [SMILES: Nc1cc(C2CCC(C(=O)O)NC2)nc2c(-c3ccc(Cl)nc3)cnn12] | 373.11 | 373.2 | 2.78 |
| 1.23 | 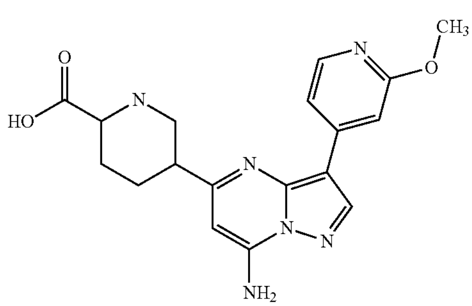 [SMILES: COc1cc(-c2cnn3c(N)cc(C4CCC(C(=O)O)NC4)nc23)ccn1] | 369.16 | 369.3 | 2.29 |

Scheme 3

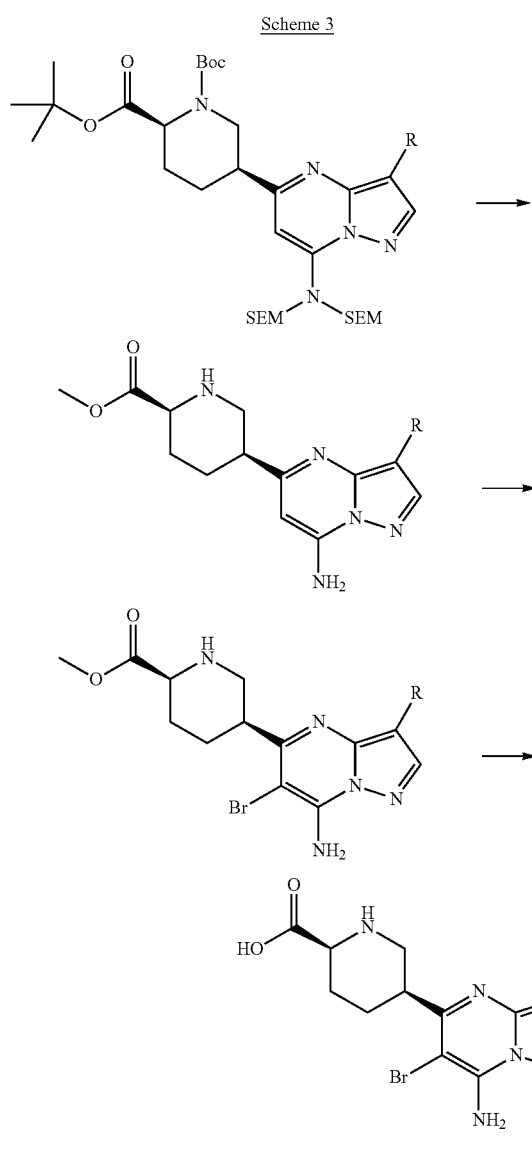

Methyl 5-(7-amino-3-(quinolin-3-yl)pyrazolo[1,5-a]pyrimidin-5-yl)piperidine-2-carboxylate

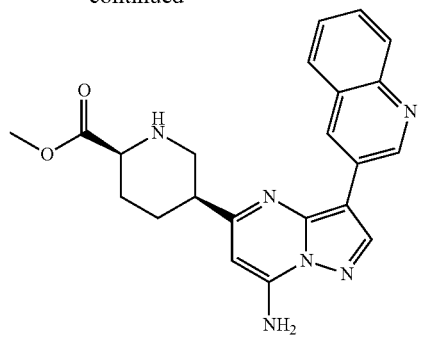

-continued

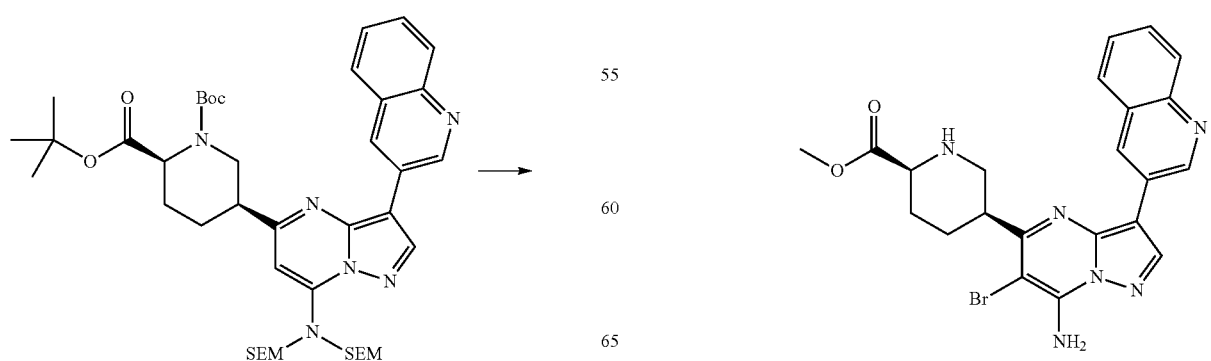

Di-tert-butyl 5-(7-(bis((2-(trimethylsilyl)ethoxy)methyl)amino)-3-(quinolin-3-yl)pyrazolo[1,5-a]pyrimidin-5-yl)piperidine-1,2-dicarboxylate (370 mg, 0.46 mmol) in methanol (12.6 mL) was treated with 4N hydrogen chloride in dioxane (5.4 ml). The reaction mixture was heated at 80° C. for 16 h, cooled to room temperature and concentrated in vacuo. The residue was purified by prep-LC to afford the title compound: LC/MS RT=2.31 min. Mass calculated for, M+H 403.18, observed 403.18.

Methyl 5-(7-amino-6-bromo-3-(quinolin-3-yl)pyrazolo[1,5-a]pyrimidin-5-yl)piperidine-2-carboxylate N-bromosuccinimide (44 mg, 0.249 mmol) was added into a solution of methyl 5-(7-amino-3-(quinolin-3-yl)pyrazolo[1,5-a]pyrimidin-5-yl)piperidine-2-carboxylate (100 mg, 0.249 mmol) in acetonitrile (1.5 mL) and methanol (0.5 ml). The resulting solution is stirred at room temperature for 1 hour. The reaction was concentrated in vacuo and purified by prep-LC to afford the title compound (22.32 mg): LC/MS RT=2.56 min. Mass calculated for, M+H 481.09, observed 481.09.

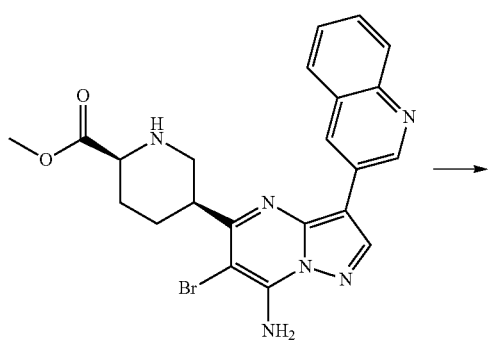

→

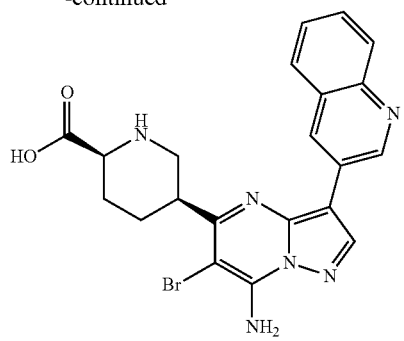

5-(7-amino-6-bromo-3-(quinolin-3-yl)pyrazolo[1,5-a]pyrimidin-5-yl)piperidine-2-carboxylic acid Methyl 5-(7-amino-6-bromo-3-(quinolin-3-yl)pyrazolo[1,5-a]pyrimidin-5-yl)piperidine-2-carboxylate (11 mg, 0.023 mmol) in 2:1 THF:H$_2$O (1.5 mL) was treated with 2N NaOH$_{(aq)}$ (0.25 mL). The resulting solution was stirred at room temperature for 18 hours. This solution is reduced in vacuo and purified by prep-LC to afford the title compound (8.9 mg): LC/MS RT=2.16 min. Mass calculated for, M+H 467.08, observed 467.08.

By essentially the same procedure given in Scheme 3, the compounds listed in Table 2 can be prepared.

TABLE 2

| Compound ID | Structures | M + H (calc.) | M + H (observed) | Retention Time, (min) |
|---|---|---|---|---|
| 2.1 | 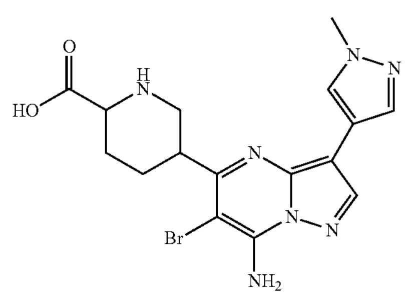 [SMILES: Cn1cc(-c2cnn3c(N)c(Br)c(C4CCC(C(=O)O)NC4)nc23)cn1] | 420.07 | 420.07 | 2.21 |
| 2.2 | 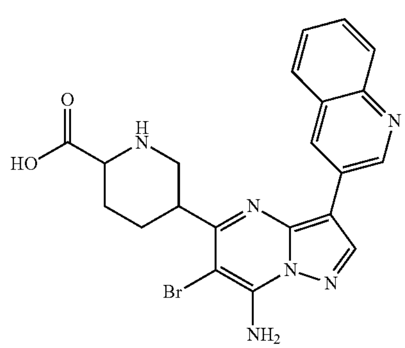 [SMILES: Nc1c(Br)c(C2CCC(C(=O)O)NC2)nc2c(-c3cnc4ccccc4c3)cnn12] | 467.08 | 467.08 | 2.16 |

TABLE 2-continued

| Compound ID | Structures | M + H (calc.) | M + H (observed) | Retention Time, (min) |
| --- | --- | --- | --- | --- |
| 2.3 | 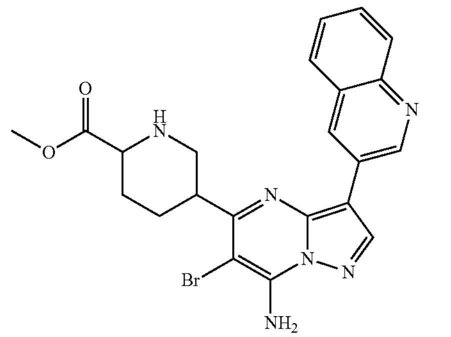 [SMILES: COC(=O)C1CCC(c2nc3c(-c4cnc5ccccc5c4)cnn3c(N)c2Br)CN1] | 481.09 | 481.09 | 2.56 |
| 2.4 | 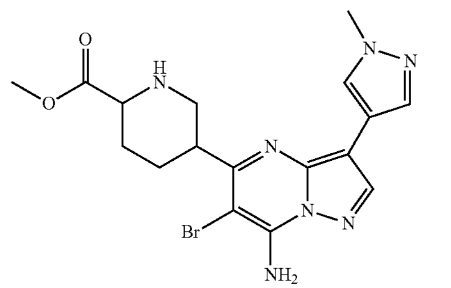 [SMILES: COC(=O)C1CCC(c2nc3c(-c4cnn(C)c4)cnn3c(N)c2Br)CN1] | 434.09 | 434.09 | 2.62 |
| 2.5 | 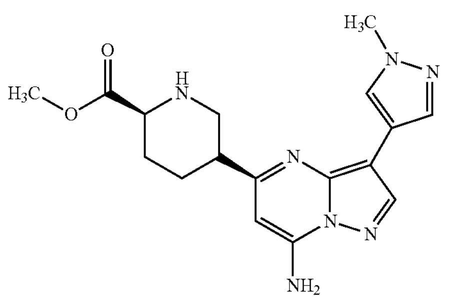 | 356.18 | 356.18 | 2.59 |
| 2.6 | 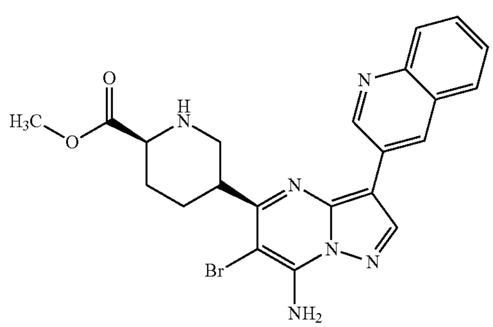 | 481.09 | 481.09 | 3.05 |
| 2.7 | 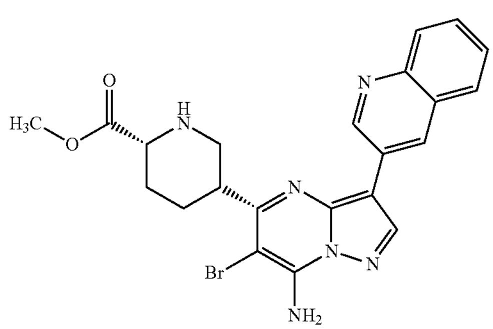 | 481.09 | 491.09 | 2.85 |

TABLE 2-continued

| Compound ID | Structures | M + H (calc.) | M + H (observed) | Retention Time, (min) |
|---|---|---|---|---|
| 2.8 | 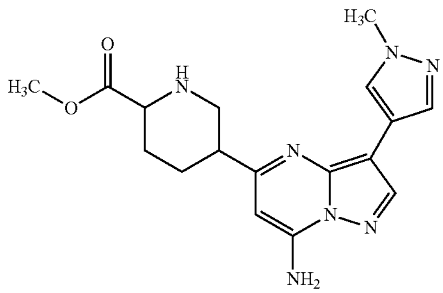 [SMILES: COC(=O)C1CCC(c2cc(N)n3ncc(-c4cnn(C)c4)c3n2)CN1] | | | |
| 2.9 | 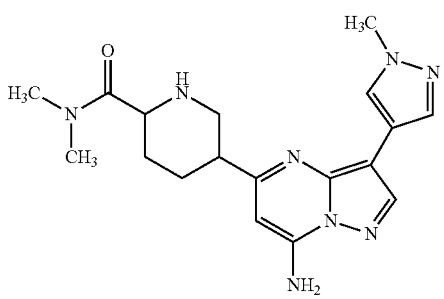 [SMILES: CN(C)C(=O)C1CCC(c2cc(N)n3ncc(-c4cnn(C)c4)c3n2)CN1] | 369 | 369 | 2.14 |

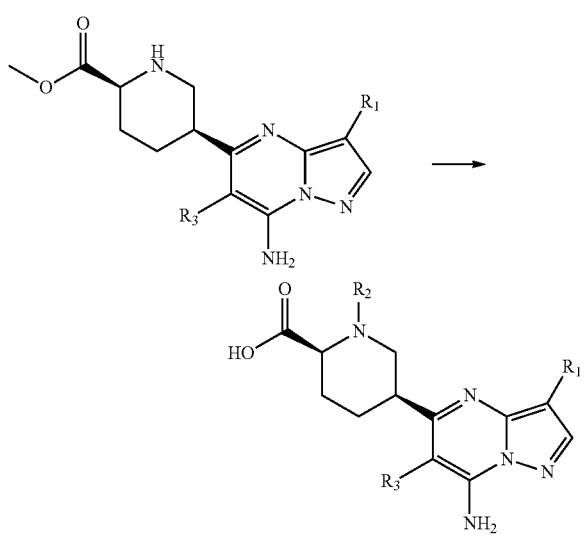

Scheme 4

5-(7-Amino-6-bromo-3-quinolin-3-yl-pyrazolo[1,5-a]pyrimidin-5-yl)-1-(2-methoxy-acetyl)-piperidine-2-carboxylic acid A mixture of 5-(7-amino-6-bromo-3-quinolin-3-yl-pyrazolo[1,5-a]pyrimidin-5-yl)-piperidine-2-carboxylic acid methyl ester (20 mg, 0.042 mmol), methoxy-acetyl chloride (13 mg, 0.071 mmol) and triethylamine (0.024 ml, 0.167 mmol) in THF:DMF (0.5 ml:0.5 ml) was stirred at room temperature for 16 h. The crude mixture was treated with 2.0 N sodium hydroxide solution (0.14 ml) at room temperature for 16 h. The reaction mixture was acidified with 1.0 N aqueous hydrogen chloride solution (0.5 ml), concentrated and purified by prep-LC to afford the title compound (7.94 mg): LC/MS RT=3.06 min. Mass calculated for, M+H 539.10, observed 539.10.

By essentially the same procedure given in Scheme 4, the compounds listed in Table 3 can be prepared.

TABLE 3

| Compound ID | Structures | M + H (calc.) | M + H (observed) | Retention Time, (min) |
|---|---|---|---|---|
| 3.1 | 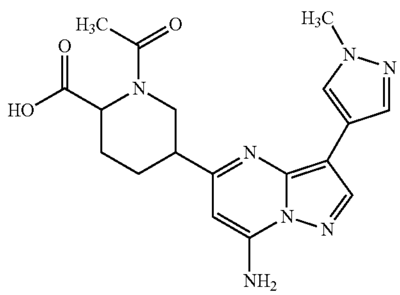 [SMILES: CC(=O)N1CC(c2cc(N)n3ncc(-c4cnn(C)c4)c3n2)CCC1C(=O)O] | 384.17 | 384.1 | 2.61 |
| 3.2 | 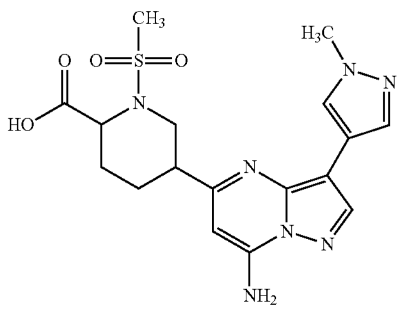 [SMILES: Cn1cc(-c2cnn3c(N)cc(C4CCC(C(=O)O)N(S(C)(=O)=O)C4)nc23)cn1] | 498.05 | 498.1 | 2.51 |
| 3.3 | 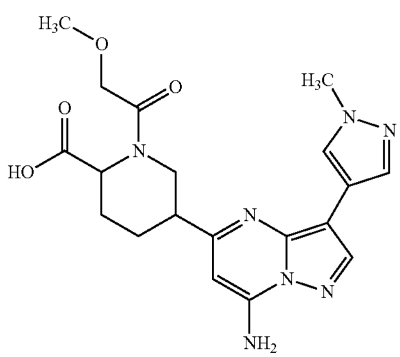 [SMILES: COCC(=O)N1CC(c2cc(N)n3ncc(-c4cnn(C)c4)c3n2)CCC1C(=O)O] | 492.09 | 492.1 | 2.63 |
| 3.4 | 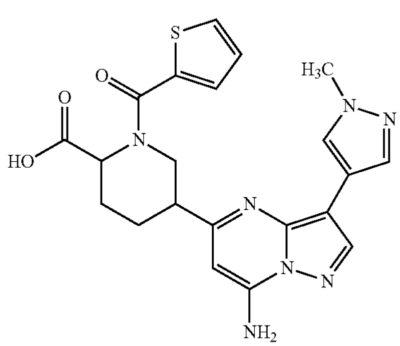 [SMILES: Cn1cc(-c2cnn3c(N)cc(C4CCC(C(=O)O)N(C(=O)c5cccs5)C4)nc23)cn1] | 452.14 | 452.14 | 2.73 |

TABLE 3-continued
| Compound ID | Structures | M + H (calc.) | M + H (observed) | Retention Time, (min) |
|---|---|---|---|---|
| 3.5 | 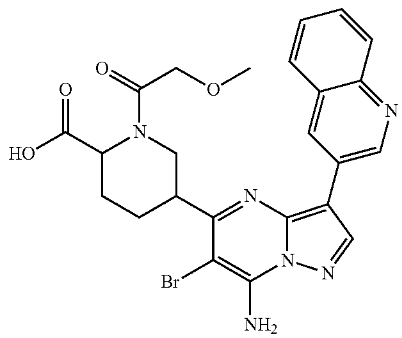 [SMILES: COCC(=O)N1CC(c2nc3c(-c4cnc5ccccc5c4)cnn3c(N)c2Br)CCC1C(=O)O] | 539.10 | 539.10 | 3.06 |
| 3.6 | 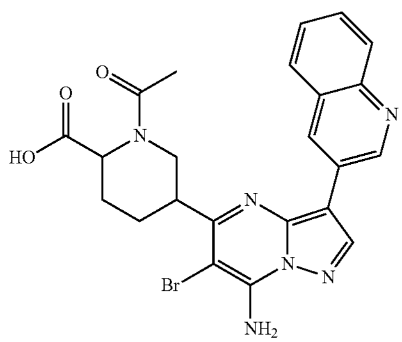 [SMILES: CC(=O)N1CC(c2nc3c(-c4cnc5ccccc5c4)cnn3c(N)c2Br)CCC1C(=O)O] | 509.09 | 509.09 | 3.02 |
| 3.7 | 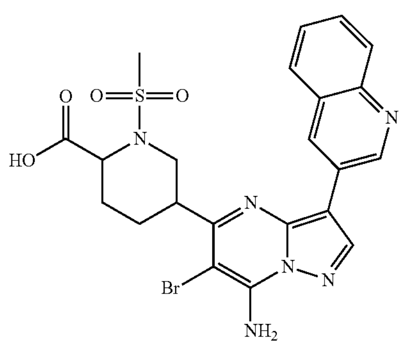 [SMILES: CS(=O)(=O)N1CC(c2nc3c(-c4cnc5ccccc5c4)cnn3c(N)c2Br)CCC1C(=O)O] | 545.05 | 545.05 | 3.21 |
| 3.8 | 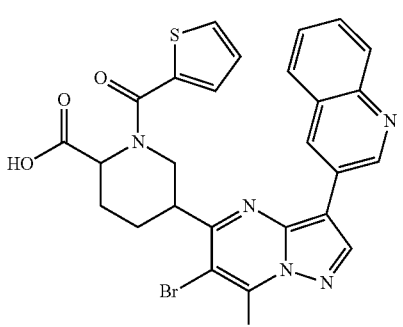 | 577.06 | 577.06 | 3.63 |

TABLE 3-continued

| Compound ID | Structures | M + H (calc.) | M + H (observed) | Retention Time, (min) |
|---|---|---|---|---|
| 3.9 | 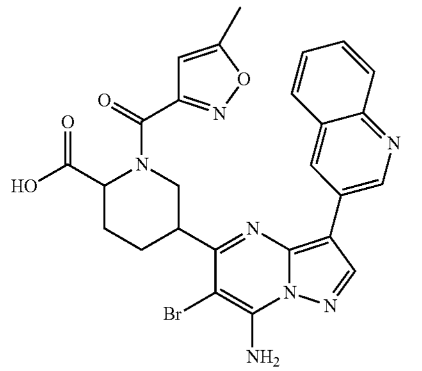 [SMILES: Cc1cc(C(=O)N2CC(c3nc4c(-c5cnc6ccccc6c5)cnn4c(N)c3Br)CCC2C(=O)O)no1] | 576.09 | 576.09 | 3.50 |
| 3.10 | 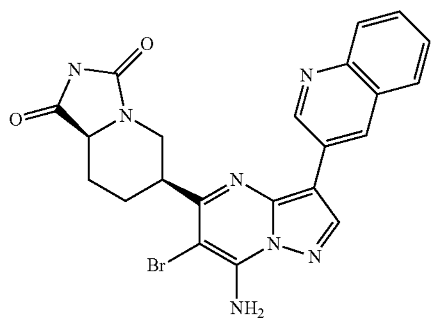 [SMILES: Nc1c(Br)c([C@H]2CC[C@H]3C(=O)NC(=O)N3C2)nc2c(-c3cnc4ccccc4c3)cnn12] | 492.3 | 492.10 | 2.89 |
| 3.11 | 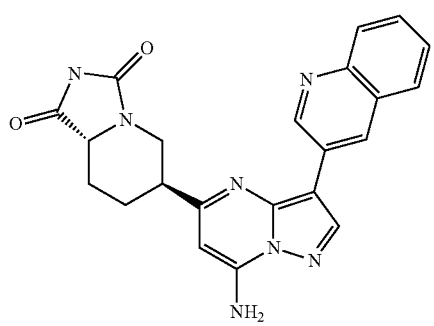 [SMILES: Nc1cc([C@H]2CC[C@@H]3C(=O)NC(=O)N3C2)nc2c(-c3cnc4ccccc4c3)cnn12] | 413.4 | 414.20 | 2.60 |
| 3.12 | 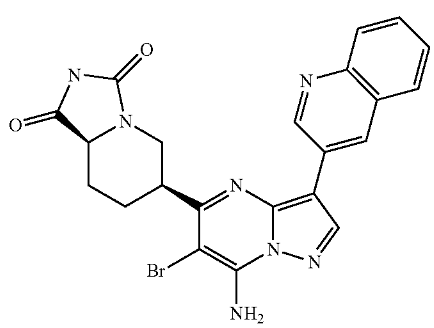 [SMILES: Nc1c(Br)c([C@H]2CC[C@H]3C(=O)NC(=O)N3C2)nc2c(-c3cnc4ccccc4c3)cnn12] | 492.3 | 492.10 | 2.89 |

TABLE 3-continued
| Compound ID | Structures | M + H (calc.) | M + H (observed) | Retention Time, (min) |
|---|---|---|---|---|
| 3.13 | 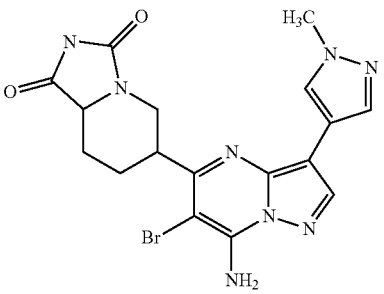 [SMILES: Cn1cc(-c2cnn3c(N)c(Br)c(C4CCC5C(=O)NC(=O)N5C4)nc23)cn1] | 445.3 | 445.10 | 3.00 |
| 3.14 | 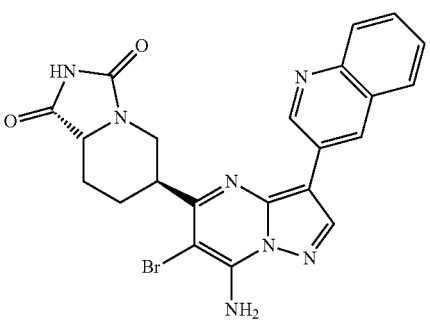 | 492.0 | 492.0 | 2.9 |
Scheme 5
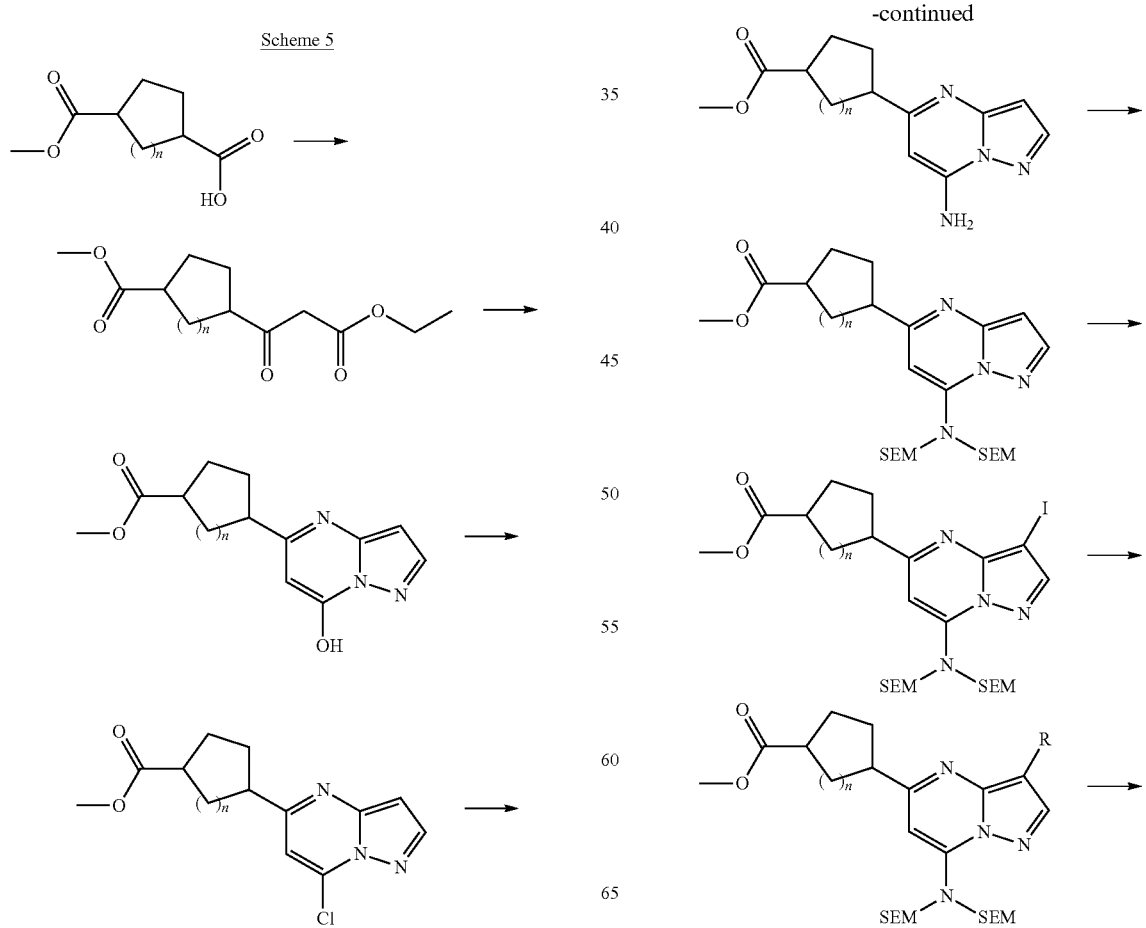

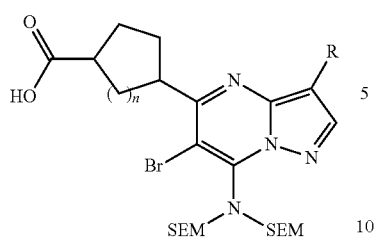

4-(2-Ethoxycarbonyl-acetyl)-cyclohexanecarboxylic acid methyl ester

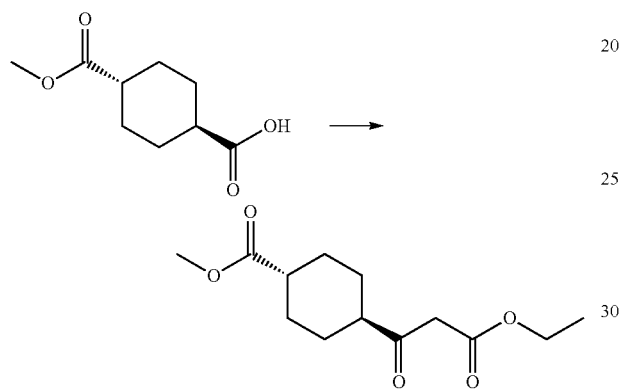

Cyclohexane-1,4-dicarboxylic acid monomethyl ester (26.9 mmol, 5.0 g) and N,N'-carbonyldiimidazole (33.6 mmol, 5.44 g) in anhydrous THF (80 mL) were stirred 16 h at room temperature under argon. In a separate, sealed and argon-flushed flask, lithium HMDS (1.0 M in THF, 56.5 ml) is added to 40 mL anhydrous THF stirring at −78° C. To this solution is added dropwise anhydrous ethyl acetate (57.8 mmol, 5.65 mL). This solution is allowed to stir at −78° C. for 1 hour prior to dropwise addition of original CDI/acid solution that had been stirring overnight. The reaction mixture was allowed to stir and warm to room temperature overnight. The reaction is then quenched with saturated $NH_4Cl_{(aq)}$ (200 mL) and extracted with $Et_2O$ (100×2). The combined organics are then washed with water, saturated brine, and dried over $Na_2SO_4$. The solvent was removed in vacuo and the crude residue (8.5 g) was used in the next step without further purification.

4-(7-Hydroxy-pyrazolo[1,5-a]pyrimidin-5-yl)-cyclohexanecarboxylic acid methyl ester

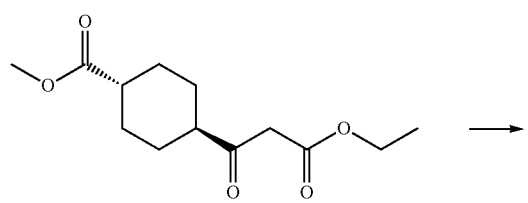

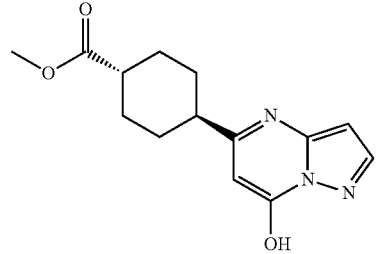

4-(2-Ethoxycarbonyl-acetyl)-cyclohexanecarboxylic acid methyl ester (8.5 g) and 3-amino-1H-pyrazole (26.5 mmol, 2.2 g) were mixed and heated neat at 100° C. for 16 hours. The resulting residue is dissolved in dichloromethane (100 mL) and concentrated in vacuo to remove water formed during cyclization. This solid is taken forward without further purification. LC-MS: 403 [M+H].

4-(7-Chloro-pyrazolo[1,5-a]pyrimidin-5-yl)-cyclohexanecarboxylic acid methyl ester

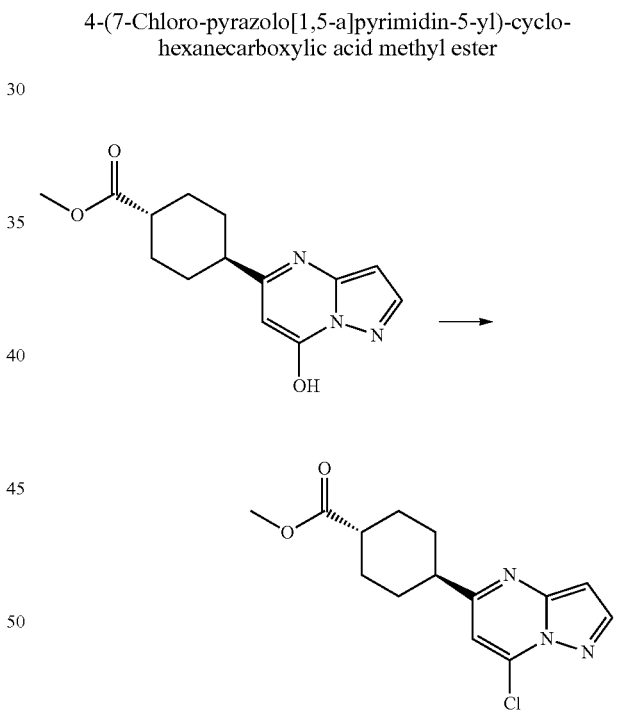

4-(7-Hydroxy-pyrazolo[1,5-a]pyrimidin-5-yl)-cyclohexanecarboxylic acid methyl ester (10.6 g), N,N-dimethylaniline (15.0 ml) and $POCl_3$ (120 mL) were mixed and stirred at room temperature for 18 hours. The solution is reduced in vacuo and cooled to 0° C. in ice bath. The reaction is then quenched with sat. $NaHCO_{3(aq)}$ and extracted with DCM (100 mL×3). The combined organics are dried with $Na_2SO_4$ and the solvent removed in vacuo. The resulting oil was purified via silica gel column on 20% to 100% ethyl acetate in

4-(7-Amino-pyrazolo[1,5-a]pyrimidin-5-yl)-cyclohexanecarboxylic acid methyl ester

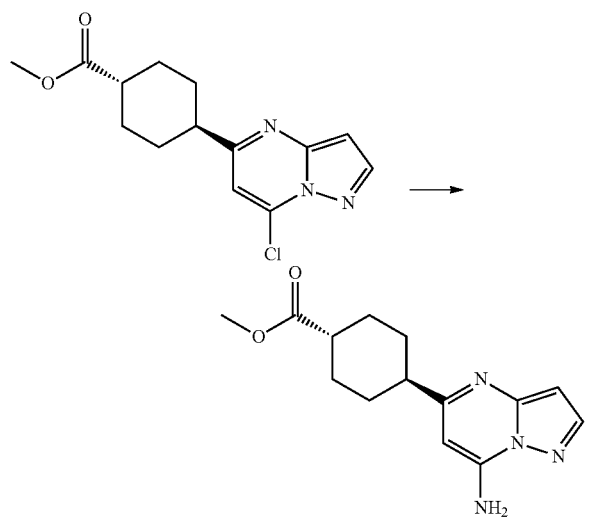

4-(7-Chloro-pyrazolo[1,5-a]pyrimidin-5-yl)-cyclohexanecarboxylic acid methyl ester (2.5 g, 8.51 mmol) was dissolved in 15 mL ~7N ammonia in methanol in a sealed vessel. The reaction mixture was heated at 80° C. for 16 hours. After 16 hours, the reaction mixture is cooled to room temperature and concentrated in vacuo to yield a brown solid (2.58 g). The title compound was used in the next step without further purification. LC-MS: 275 [M+H].

4-{7-[Bis-(2-trimethylsilanyl-ethoxymethyl)-amino]-pyrazolo[1,5-a]pyrimidin-5-yl}-cyclohexanecarboxylic acid methyl ester

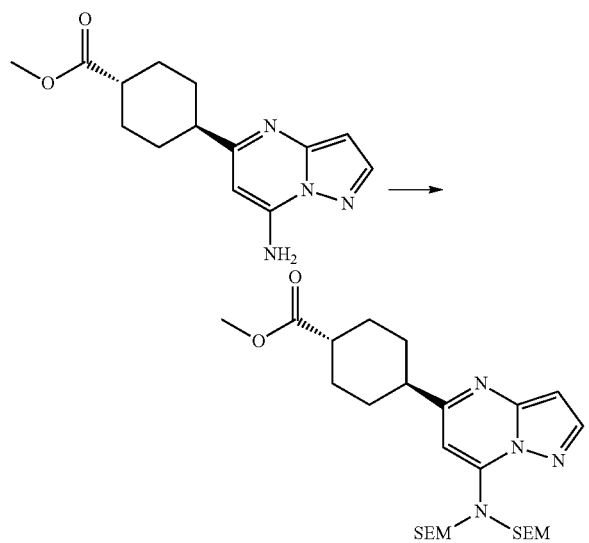

4-(7-Amino-pyrazolo[1,5-a]pyrimidin-5-yl)-cyclohexanecarboxylic acid methyl ester (2.58 g, 9.4 mmol) was dissolved in 1,2-dichloroethane (20 mL). To this solution was added N,N'-diisopropylethylamine (65.8 mmol, 11.5 mL). The resulting solution was stirred at room temperature while 2-(trimethylsilyl)ethoxymethyl chloride (SEM-Cl, 5.8 mL, 33.0 mmol) was added dropwise. After the addition was completed, the reaction mixture was stirred at 90° C. for 2 h. The solvent is removed in vacuo and the residue is purified on silica gel column (0% to 60% ethyl acetate in hexanes gradient) to yield the title compound (2.05 g, 41% yield over two steps) as pale yellow oil. LC-MS: 535 [M+H].

4-{7-[Bis-(2-trimethylsilanyl-ethoxymethyl)-amino]-3-iodo-pyrazolo[1,5-a]pyrimidin-5-yl}-cyclohexanecarboxylic acid methyl ester

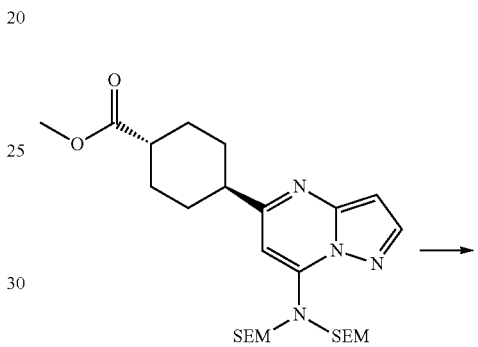

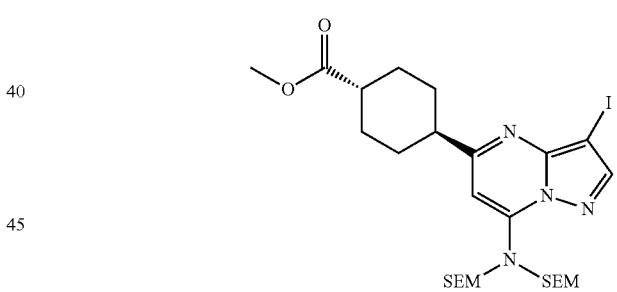

N-Iodosuccinimide (811 mg, 3.6 mmol) was added into a solution of 4-{7-[bis-(2-trimethylsilanyl-ethoxymethyl)-amino]-pyrazolo[1,5-a]pyrimidin-5-yl}-cyclohexanecarboxylic acid methyl ester (1.75 g, 3.27 mmol) in acetonitrile (25 mL). The resulting reaction mixture was stirred at room temperature for 16 hours. The reaction mixture was concentrated in vacuo and purified via silica gel chromatography (0% to 30% ethyl acetate in hexanes gradient) to yield the title compound (1.79 g, 82.8% yield) at clear oil. LC-MS: 661 [M+H].

717

4-{7-[Bis-(2-trimethylsilanyl-ethoxymethyl)-amino]-3-quinolin-3-yl-pyrazolo[1,5-a]pyrimidin-5-yl}-cyclohexanecarboxylic acid methyl ester

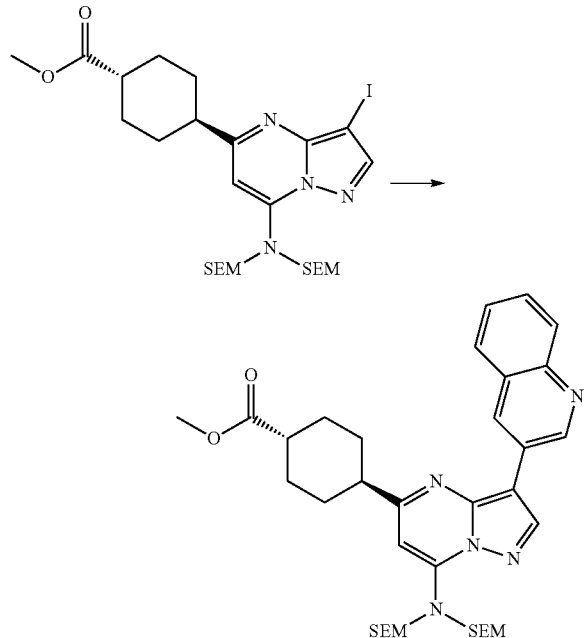

3-Quinoline boronic acid (2.42 mmol, 420 mg), $K_3PO_4$ (3.63 mmol, 771 mg), and $PdCl_2(dppf)\cdot CH_2Cl_2$ (0.121 mmol, 100 mg) was added to a solution of 4-{7-[Bis-(2-trimethylsilanyl-ethoxymethyl)-amino]-3-iodo-pyrazolo[1,5-a]pyrimidin-5-yl}-cyclohexanecarboxylic acid methyl ester (1.21 mmol, 800 mg) in dioxane (10 mL). To this suspension was added distilled $H_2O$ (1.0 mL). The resulting reaction mixture was stirred at 100° C. under an argon atmosphere for 18 hours. The reaction mixture was concentrated in vacuo and then purified via silica gel chromatography (0% to 60% ethyl acetate in hexanes gradient) to yield the title compound (630 mg, 79% yield) as yellow oil. LC-MS: 662 [M+H].

4-{7-[Bis-(2-trimethylsilanyl-ethoxymethyl)-amino]-6-bromo-3-quinolin-3-yl-pyrazolo[1,5-a]pyrimidin-5-yl}-cyclohexanecarboxylic acid methyl ester

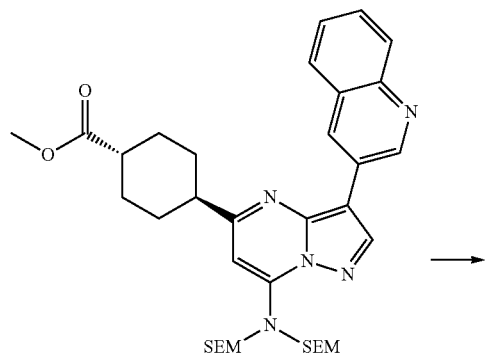

718

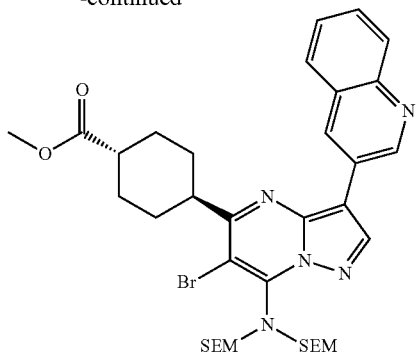

N-bromosuccinimide (148 mg, 0.832 mmol) was added to a solution of 4-{7-[bis-(2-trimethylsilanyl-ethoxymethyl)-amino]-3-quinolin-3-yl-pyrazolo[1,5-a]pyrimidin-5-yl}-cyclohexanecarboxylic acid methyl ester (500 mg, 0.756 mmol) in acetonitrile (10 mL). The reaction mixture was stirred at room temperature for 1 hour. The reaction mixture was concentrated in vacuo and the resulting oil is then purified via silica gel chromatography (0% to 30% ethyl acetate in hexanes gradient) to yield the title compound (530 mg, 95% yield) as yellow oil. LC-MS: 740 [M+H].

4-(7-Amino-6-bromo-3-quinolin-3-yl-pyrazolo[1,5-a]pyrimidin-5-yl)-cyclohexanecarboxylic acid

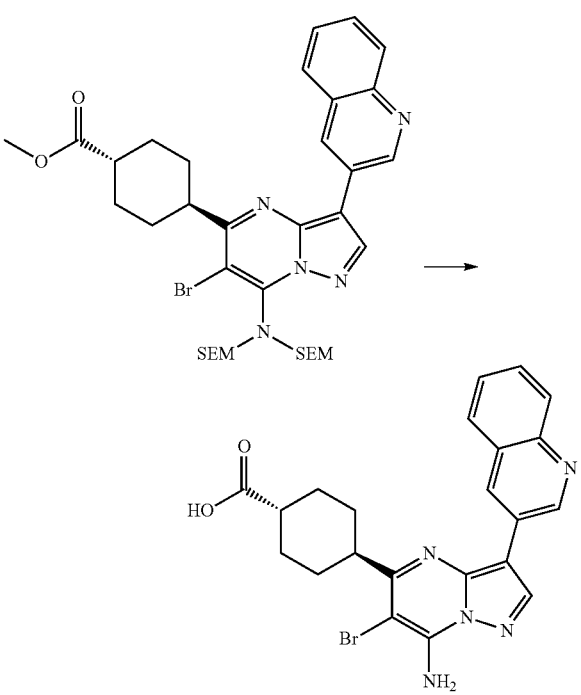

4-{7-[Bis-(2-trimethylsilanyl-ethoxymethyl)-amino]-6-bromo-3-quinolin-3-yl-pyrazolo[1,5-a]pyrimidin-5-yl}-cyclohexanecarboxylic acid methyl ester (100 mg, 0.135 mmol) in 2:1 MeOH:$H_2O$ (3 mL) was treated with 2N $NaOH_{(aq)}$ (0.5 mL). The reaction mixture was stirred at room temperature for 18 hours. The reaction mixture was treated with 1N hydrochloride solution (2 ml) at 65° C. for 4 h. The reaction mixture was concentrated and purified by prep-LC to afford the title compound (21.8 mg): LC/MS RT=3.57 min. Mass calculated for, M+H 466.08, observed 466.08.

By essentially the same procedure given in Scheme 5, the compounds listed in Table 4 can be prepared.

TABLE 4

| Compound ID | Structures | M + H (calc.) | M + H (observed) | Retention Time, (min) |
|---|---|---|---|---|
| 4.1 | 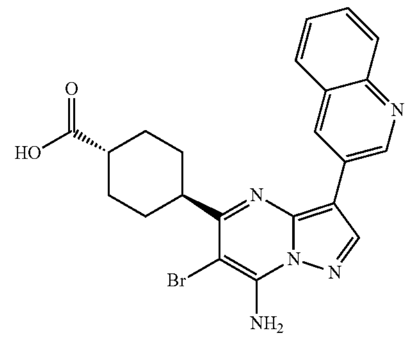 [SMILES: Nc1c(Br)c([C@H]2CC[C@H](C(=O)O)CC2)nc2c(-c3cnc4ccccc4c3)cnn12] | 466.08 | 466.08 | 3.57 |
| 4.2 | 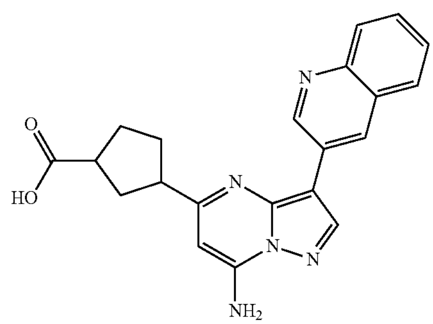 [SMILES: Nc1cc(C2CCC(C(=O)O)C2)nc2c(-c3cnc4ccccc4c3)cnn12] | 374.15 | 374.15 | 2.83 |
| 4.3 | 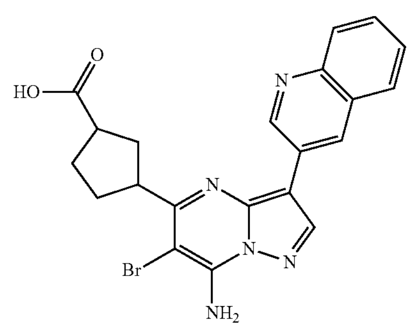 [SMILES: Nc1c(Br)c(C2CCC(C(=O)O)C2)nc2c(-c3cnc4ccccc4c3)cnn12] | 452.06 | 452.08 | 3.4 |
| 4.4 | 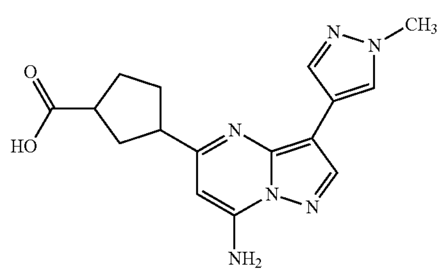 [SMILES: Cn1cc(-c2cnn3c(N)cc(C4CCC(C(=O)O)C4)nc23)cn1] | 327.1 | 327.1 | 2.04 |

TABLE 4-continued

| Compound ID | Structures | M + H (calc.) | M + H (observed) | Retention Time, (min) |
|---|---|---|---|---|
| 4.5 | 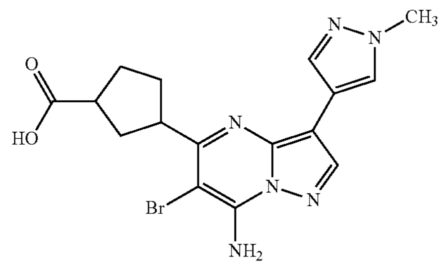 [SMILES: Cn1cc(-c2cnn3c(N)c(Br)c(C4CCC(C(=O)O)C4)nc23)cn1] | 405.1 | 405.1 | 3.65 |
| 4.6 | 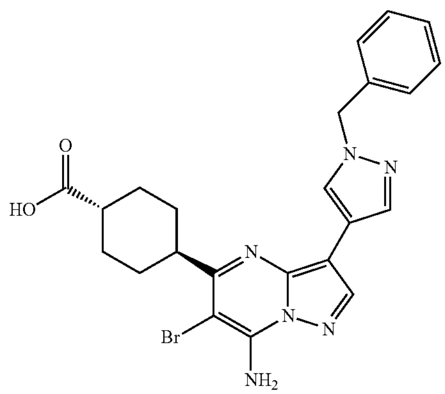 [SMILES: Nc1c(Br)c([C@H]2CC[C@H](C(=O)O)CC2)nc2c(-c3cnn(Cc4ccccc4)c3)cnn12] | 494.11 | 495.11 | 4.59 |
| 4.7 | 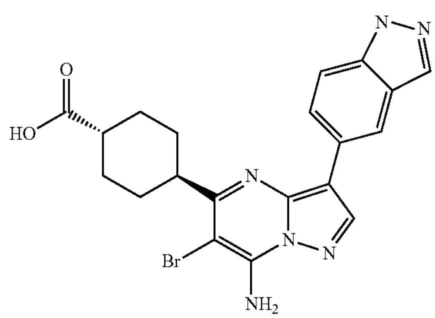 [SMILES: Nc1c(Br)c([C@H]2CC[C@H](C(=O)O)CC2)nc2c(-c3ccc4[nH]ncc4c3)cnn12] | 454.08 | 455.08 | 4.0 |
| 4.8 | 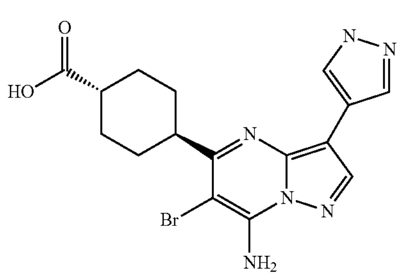 [SMILES: Nc1c(Br)c([C@H]2CC[C@H](C(=O)O)CC2)nc2c(-c3cn[nH]c3)cnn12] | 405.06 | 405.06 | 3.3 |

TABLE 4-continued
| Compound ID | Structures | M + H (calc.) | M + H (observed) | Retention Time, (min) |
|---|---|---|---|---|
| 4.9 | 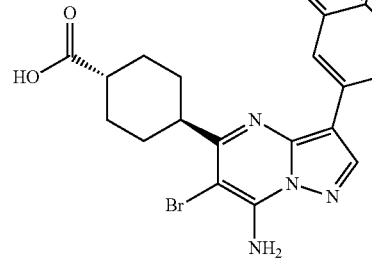 | 466.08 | 466.08 | 3.36 |
| 4.10 | 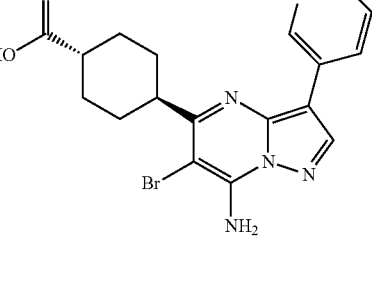 | 434.06 | 434.06 | 3.89 |
| 4.11 | 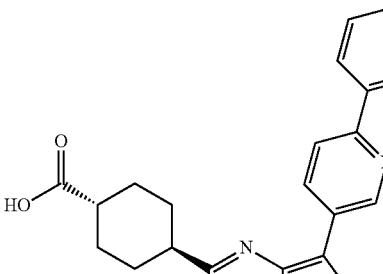 | 493.0 | 493.0 | 3.65 |
| 4.12 | 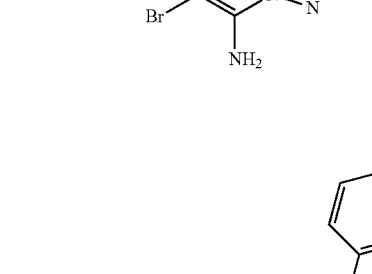 | 493.0 | 493.0 | 3.69 |

Following additional compounds in table-4a were synthesized following the general experimental procedures described in scheme-5
TABLE 4A
| Compound ID | Structures | M + H (calc.) | M + H (observed) | LC/MS retention time (10 min method) |
|---|---|---|---|---|
| 4.13 | 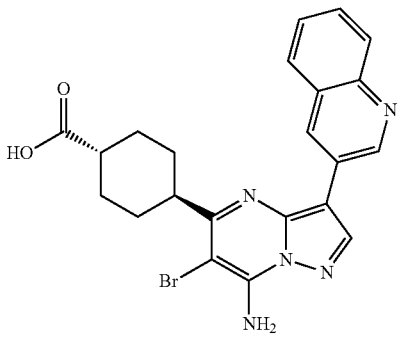 [SMILES: Nc1c(Br)c([C@H]2CC[C@H](C(=O)O)CC2)nc2c(-c3cnc4ccccc4c3)cnn12] | 466.08 | 466.08 | 3.57 |
| 4.14 | 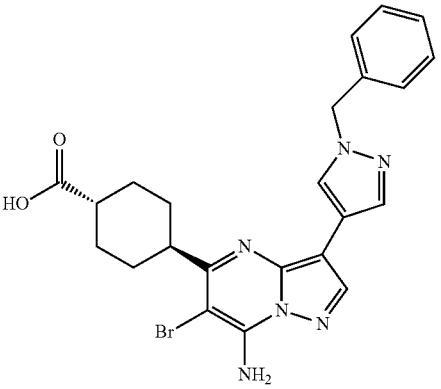 [SMILES: Nc1c(Br)c([C@H]2CC[C@H](C(=O)O)CC2)nc2c(-c3cnn(Cc4ccccc4)c3)cnn12] | 495.11 | 495.11 | 4.59 |
| 4.15 | 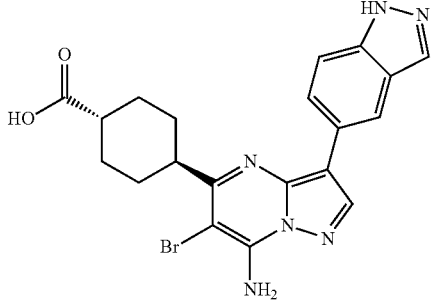 [SMILES: Nc1c(Br)c([C@H]2CC[C@H](C(=O)O)CC2)nc2c(-c3ccc4[nH]ncc4c3)cnn12] | 455.08 | 455.08 | 4.00 |
| 4.16 | 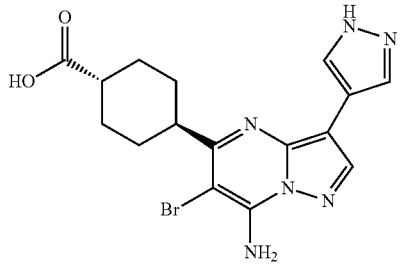 [SMILES: Nc1c(Br)c([C@H]2CC[C@H](C(=O)O)CC2)nc2c(-c3cn[nH]c3)cnn12] | 405.06 | 405.06 | 3.30 |

TABLE 4A-continued
| Compound ID | Structures | M + H (calc.) | M + H (observed) | LC/MS retention time (10 min method) |
|---|---|---|---|---|
| 4.17 | 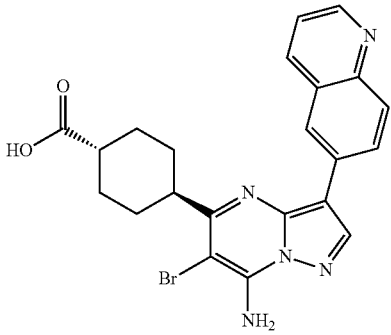 [SMILES: Nc1c(Br)c([C@H]2CC[C@H](C(=O)O)CC2)nc2c(-c3ccc4ncccc4c3)cnn12] | 466.08 | 466.08 | 3.36 |
| 4.18 | 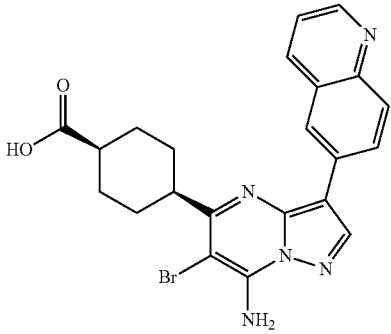 [SMILES: Nc1c(Br)c([C@H]2CC[C@@H](C(=O)O)CC2)nc2c(-c3ccc4ncccc4c3)cnn12] | 466.08 | 466.08 | 3.70 |
| 4.19 | 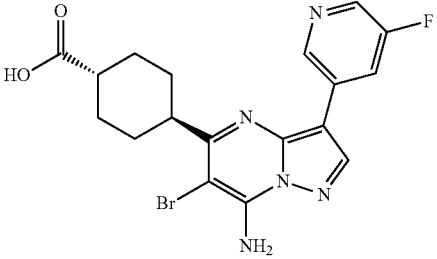 [SMILES: Nc1c(Br)c([C@H]2CC[C@H](C(=O)O)CC2)nc2c(-c3cncc(F)c3)cnn12] | 434.06 | 434.06 | 3.89 |
| 4.20 | 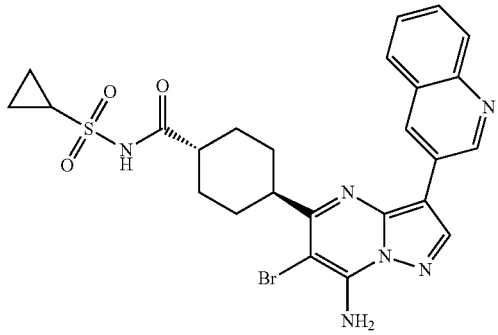 [SMILES: Nc1c(Br)c([C@H]2CC[C@H](C(=O)NS(=O)(=O)C3CC3)CC2)nc2c(-c3cnc4ccccc4c3)cnn12] | 569.09 | 569.09 | 3.82 |

TABLE 4A-continued
| Compound ID | Structures | M + H (calc.) | M + H (observed) | LC/MS retention time (10 min method) |
|---|---|---|---|---|
| 4.21 | 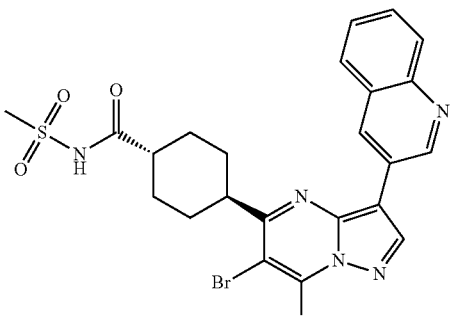 | 543.07 | 543.07 | 3.56 |
| 4.22 | 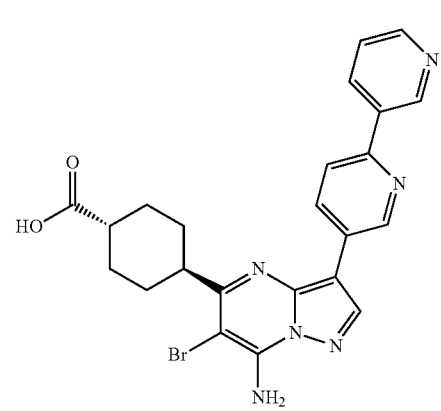 [SMILES: Nc1c(Br)c([C@H]2CC[C@H](C(=O)O)CC2)nc2c(-c3ccc(-c4cccnc4)nc3)cnn12] | 493.09 | 493.09 | 3.37 |
| 4.23 | 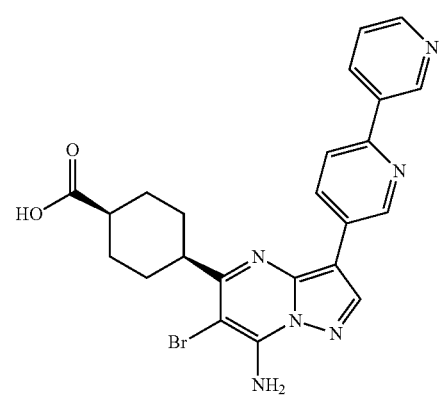 [SMILES: Nc1c(Br)c([C@H]2CC[C@@H](C(=O)O)CC2)nc2c(-c3ccc(-c4cccnc4)nc3)cnn12] | 493.09 | 493.09 | 3.69 |
| 4.24 | 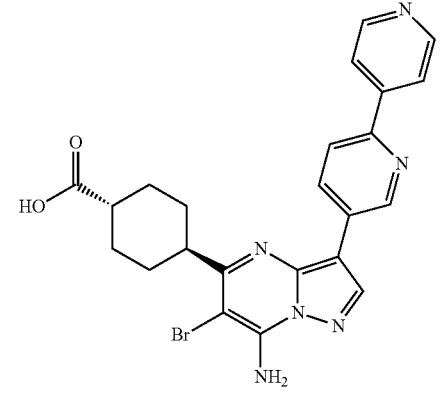 [SMILES: Nc1c(Br)c([C@H]2CC[C@H](C(=O)O)CC2)nc2c(-c3ccc(-c4ccncc4)nc3)cnn12] | 493.09 | 493.09 | 3.36 |

TABLE 4A-continued

| Compound ID | Structures | M + H (calc.) | M + H (observed) | LC/MS retention time (10 min method) |
|---|---|---|---|---|
| 4.25 | 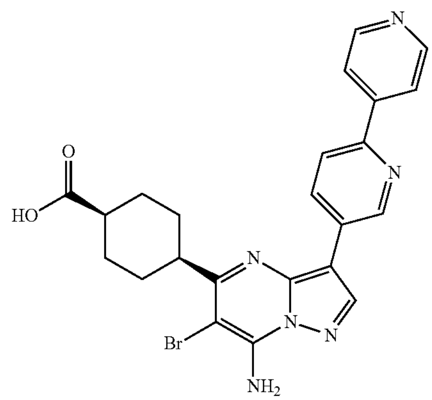 [SMILES: Nc1c(Br)c([C@H]2CC[C@@H](C(=O)O)CC2)nc2c(-c3ccc(-c4ccncc4)nc3)cnn12] | 493.09 | 493.09 | 3.65 |
| 4.26 | 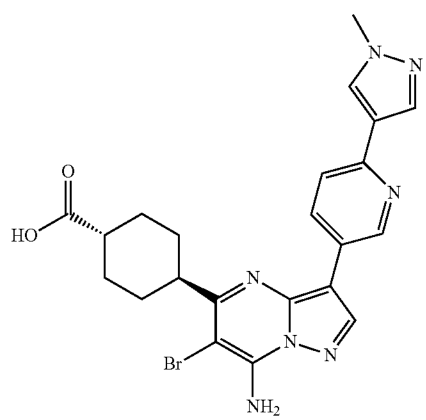 [SMILES: Cn1cc(-c2ccc(-c3cnn4c(N)c(Br)c([C@H]5CC[C@H](C(=O)O)CC5)nc34)cn2)cn1] | 496.10 | 496.10 | 3.26 |
| 4.27 | 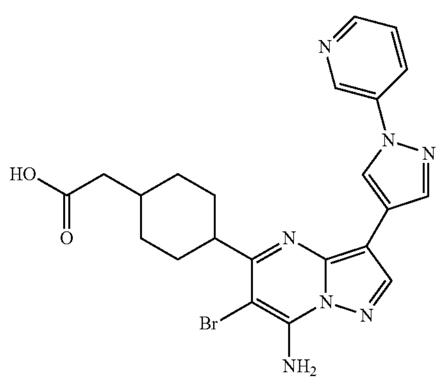 [SMILES: Nc1c(Br)c(C2CCC(CC(=O)O)CC2)nc2c(-c3cnn(-c4cccnc4)c3)cnn12] | 496.10 | 496.10 | 4.13 |

TABLE 4A-continued
| Compound ID | Structures | M + H (calc.) | M + H (observed) | LC/MS retention time (10 min method) |
|---|---|---|---|---|
| 4.28 | 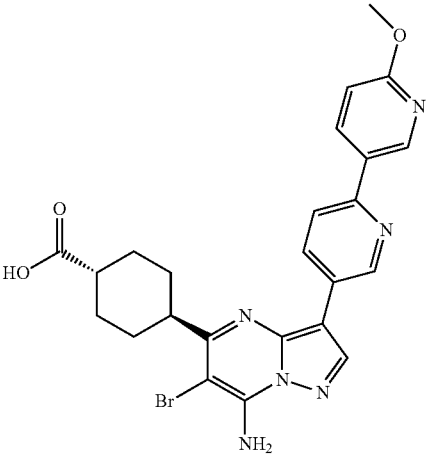 [SMILES: COc1ccc(-c2ccc(-c3cnn4c(N)c(Br)c([C@H]5CC[C@H](C(=O)O)CC5)nc34)cn2)cn1] | 523.10 | 523.10 | 4.12 |
| 4.29 | 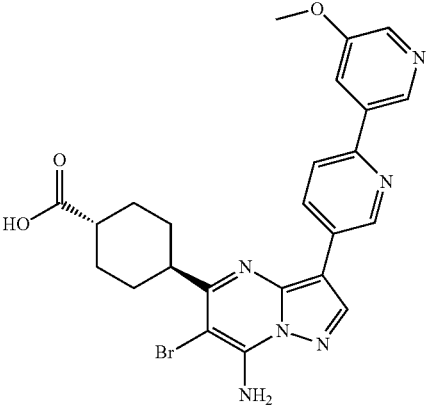 [SMILES: COc1cncc(-c2ccc(-c3cnn4c(N)c(Br)c([C@H]5CC[C@H](C(=O)O)CC5)nc34)cn2)c1] | 523.10 | 523.10 | 3.81 |
| 4.30 | 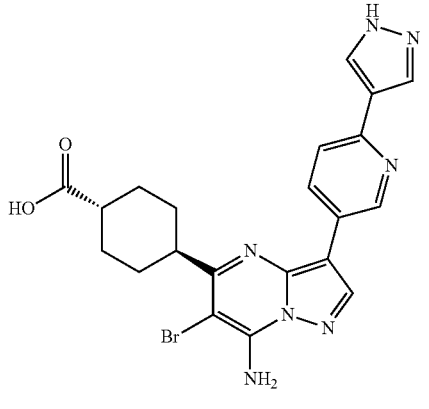 [SMILES: Nc1c(Br)c([C@H]2CC[C@H](C(=O)O)CC2)nc2c(-c3ccc(-c4cn[nH]c4)nc3)cnn12] | 482.09 | 482.09 | 3.12 |

TABLE 4A-continued

| Compound ID | Structures | M + H (calc.) | M + H (observed) | LC/MS retention time (10 min method) |
|---|---|---|---|---|
| 4.31 | 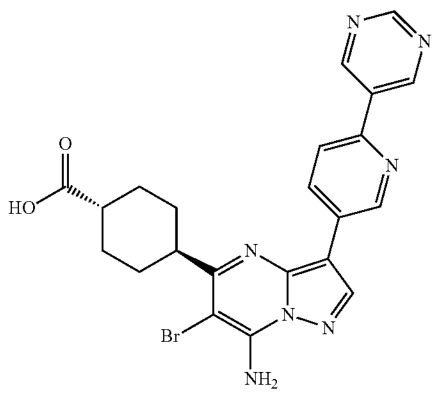 [SMILES: Nc1c(Br)c([C@H]2CC[C@H](C(=O)O)CC2)nc2c(-c3ccc(-c4cncnc4)nc3)cnn12] | 494.09 | 494.09 | 4.12 |
| 4.32 | 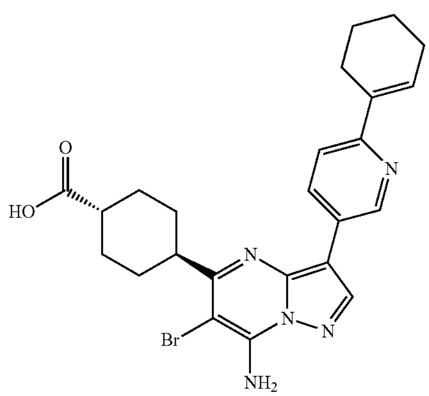 [SMILES: Nc1c(Br)c([C@H]2CC[C@H](C(=O)O)CC2)nc2c(-c3ccc(C4=CCCCC4)nc3)cnn12] | 496.13 | 496.13 | 3.96 |
| 4.33 | 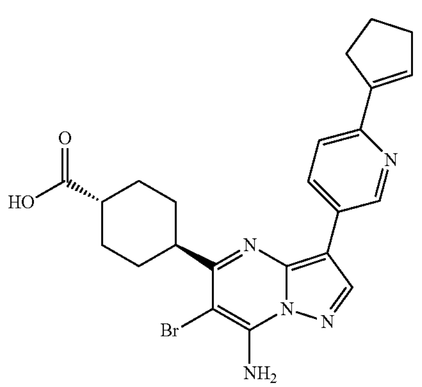 [SMILES: Nc1c(Br)c([C@H]2CC[C@H](C(=O)O)CC2)nc2c(-c3ccc(C4=CCCC4)nc3)cnn12] | 482.11 | 482.11 | 3.79 |

TABLE 4A-continued
| Compound ID | Structures | M + H (calc.) | M + H (observed) | LC/MS retention time (10 min method) |
|---|---|---|---|---|
| 4.34 | 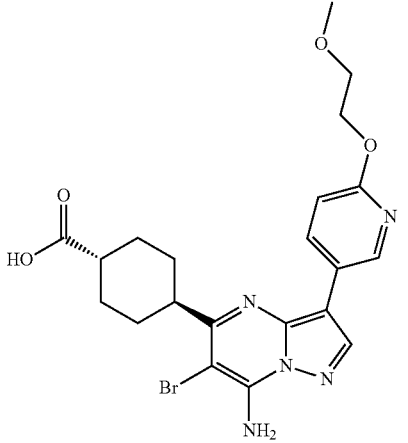 [SMILES: COCCOc1ccc(-c2cnn3c(N)c(Br)c([C@H]4CC[C@H](C(=O)O)CC4)nc23)cn1] | 490.10 | 490.10 | 4.19 |
| 4.35 | 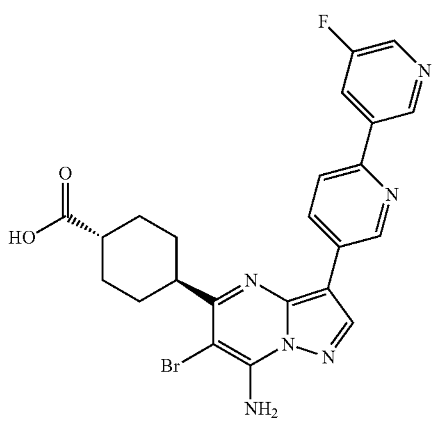 [SMILES: Nc1c(Br)c([C@H]2CC[C@H](C(=O)O)CC2)nc2c(-c3ccc(-c4cncc(F)c4)nc3)cnn12] | 511.08 | 511.08 | 4.38 |
| 4.36 | 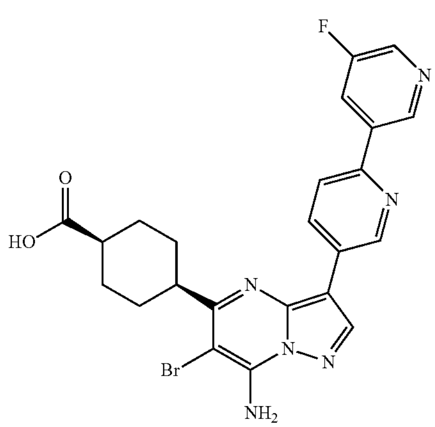 [SMILES: Nc1c(Br)c([C@H]2CC[C@@H](C(=O)O)CC2)nc2c(-c3ccc(-c4cncc(F)c4)nc3)cnn12] | 511.08 | 511.08 | 4.56 |

TABLE 4A-continued

| Compound ID | Structures | M + H (calc.) | M + H (observed) | LC/MS retention time (10 min method) |
| --- | --- | --- | --- | --- |
| 4.37 | 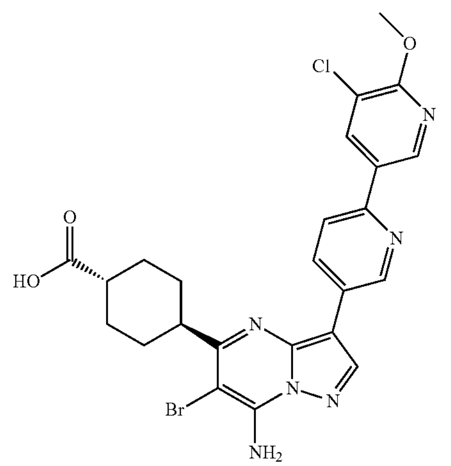 [SMILES: COc1ncc(-c2ccc(-c3cnn4c(N)c(Br)c([C@H]5CC[C@H](C(=O)O)CC5)nc34)cn2)cc1Cl] | 557.06 | 557.06 | 4.89 |
| 4.38 | 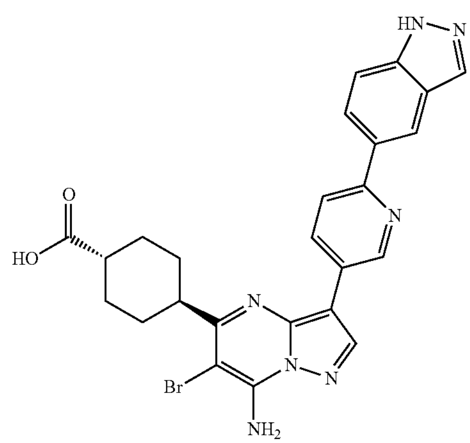 [SMILES: Nc1c(Br)c([C@H]2CC[C@H](C(=O)O)CC2)nc2c(-c3ccc(-c4ccc5[nH]ncc5c4)nc3)cnn12] | 532.10 | 532.10 | 3.57 |
| 4.39 | 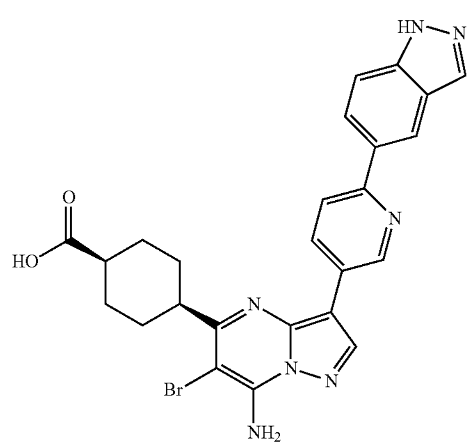 [SMILES: Nc1c(Br)c([C@H]2CC[C@@H](C(=O)O)CC2)nc2c(-c3ccc(-c4ccc5[nH]ncc5c4)nc3)cnn12] | 532.10 | 532.10 | 3.88 |

TABLE 4A-continued
| Compound ID | Structures | M + H (calc.) | M + H (observed) | LC/MS retention time (10 min method) |
|---|---|---|---|---|
| 4.40 | 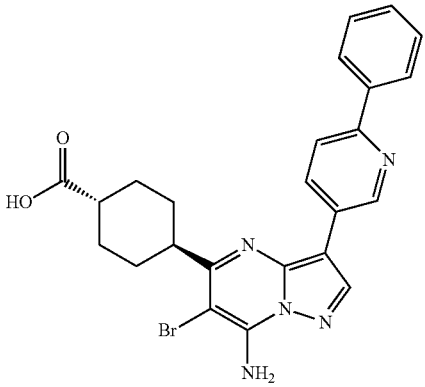 [SMILES: Nc1c(Br)c([C@H]2CC[C@H](C(=O)O)CC2)nc2c(-c3ccc(-c4ccccc4)nc3)cnn12] | 492.10 | 492.10 | 3.91 |
| 4.41 | 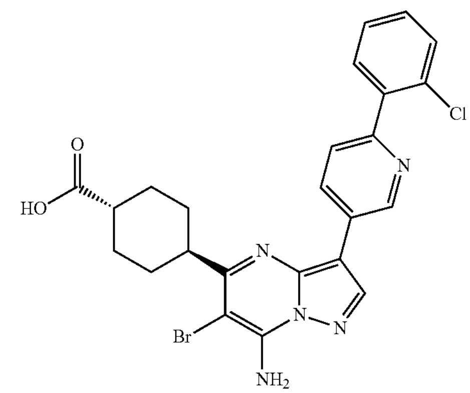 [SMILES: Nc1c(Br)c([C@H]2CC[C@H](C(=O)O)CC2)nc2c(-c3ccc(-c4ccccc4Cl)nc3)cnn12] | 526.06 | 526.06 | 4.18 |
| 4.42 | 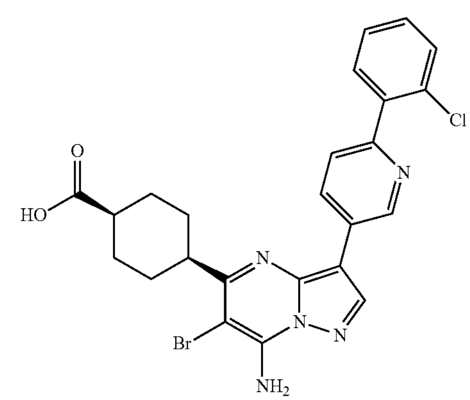 [SMILES: Nc1c(Br)c([C@H]2CC[C@@H](C(=O)O)CC2)nc2c(-c3ccc(-c4ccccc4Cl)nc3)cnn12] | 526.06 | 526.06 | 4.39 |

TABLE 4A-continued

| Compound ID | Structures | M + H (calc.) | M + H (observed) | LC/MS retention time (10 min method) |
|---|---|---|---|---|
| 4.43 | 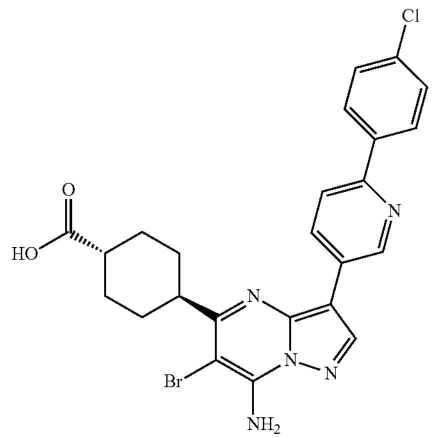 [SMILES: Nc1c(Br)c([C@H]2CC[C@H](C(=O)O)CC2)nc2c(-c3ccc(-c4ccc(Cl)cc4)nc3)cnn12] | 526.06 | 526.06 | 4.56 |
| 4.44 | 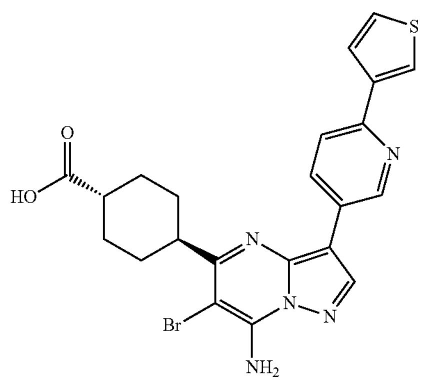 [SMILES: Nc1c(Br)c([C@H]2CC[C@H](C(=O)O)CC2)nc2c(-c3ccc(-c4ccsc4)nc3)cnn12] | 498.05 | 498.05 | 3.79 |
| 4.45 | 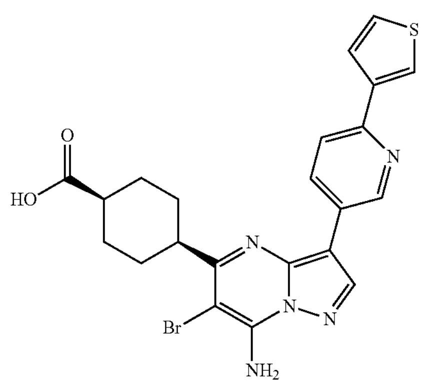 [SMILES: Nc1c(Br)c([C@H]2CC[C@@H](C(=O)O)CC2)nc2c(-c3ccc(-c4ccsc4)nc3)cnn12] | 498.05 | 498.05 | 3.81 |
| 4.46 | 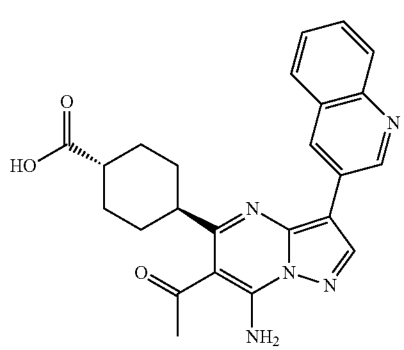 [SMILES: CC(=O)c1c(N)n2ncc(-c3cnc4ccccc4c3)c2nc1[C@H]1CC[C@H](C(=O)O)CC1] | 430.18 | 430.18 | 3.40 |

TABLE 4A-continued

| Compound ID | Structures | M + H (calc.) | M + H (observed) | LC/MS retention time (10 min method) |
|---|---|---|---|---|
| 4.47 | 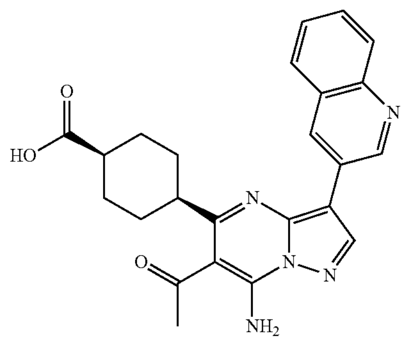 [SMILES: CC(=O)c1c(N)n2ncc(-c3cnc4ccccc4c3)c2nc1[C@H]1CC[C@@H](C(=O)O)CC1] | 430.18 | 430.18 | 3.58 |
| 4.48 | 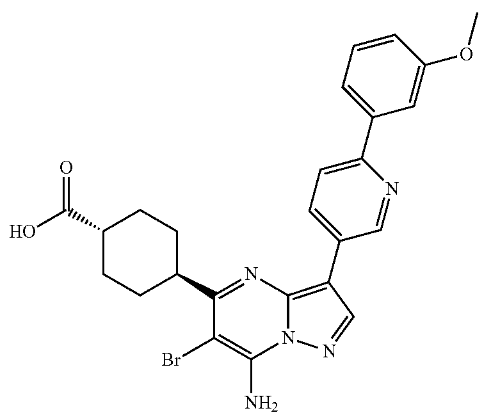 [SMILES: COc1cccc(-c2ccc(-c3cnn4c(N)c(Br)c([C@H]5CC[C@H](C(=O)O)CC5)nc34)cn2)c1] | 522.11 | 522.11 | 4.23 |
| 4.49 | 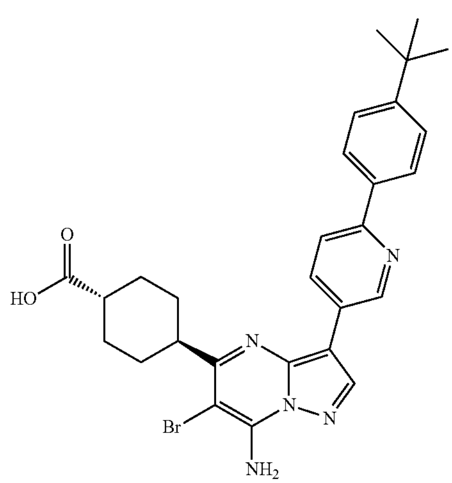 [SMILES: CC(C)(C)c1ccc(-c2ccc(-c3cnn4c(N)c(Br)c([C@H]5CC[C@H](C(=O)O)CC5)nc34)cn2)cc1] | 548.16 | 548.16 | 4.68 |

TABLE 4A-continued

| Compound ID | Structures | M + H (calc.) | M + H (observed) | LC/MS retention time (10 min method) |
|---|---|---|---|---|
| 4.50 | 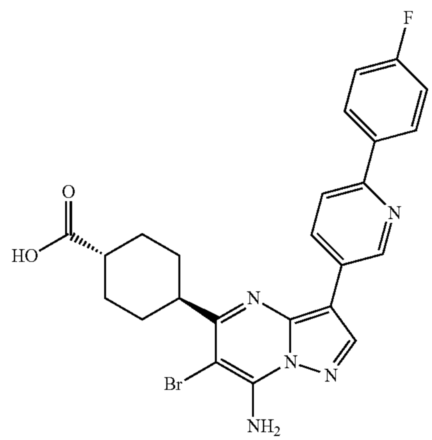 [SMILES: Nc1c(Br)c([C@H]2CC[C@H](C(=O)O)CC2)nc2c(-c3ccc(-c4ccc(F)cc4)nc3)cnn12] | 510.09 | 510.09 | 3.44 |
| 4.51 | 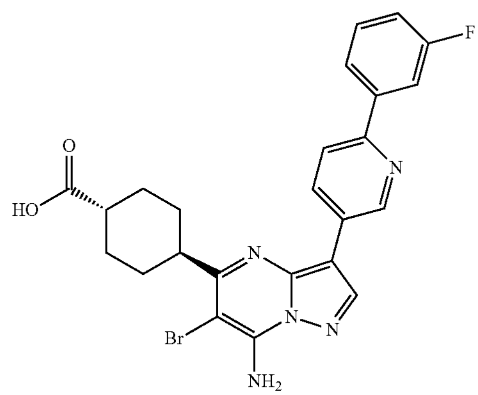 [SMILES: Nc1c(Br)c([C@H]2CC[C@H](C(=O)O)CC2)nc2c(-c3ccc(-c4cccc(F)c4)nc3)cnn12] | 510.09 | 510.09 | 3.60 |
| 4.52 | 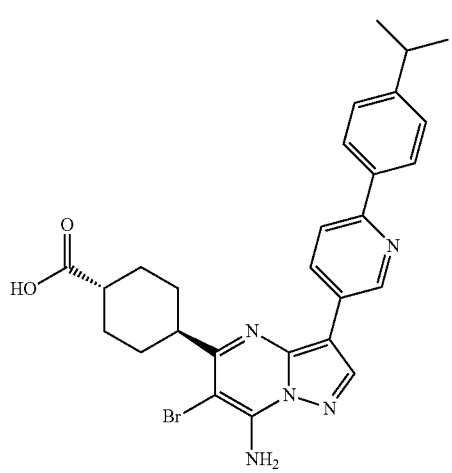 [SMILES: CC(C)c1ccc(-c2ccc(-c3cnn4c(N)c(Br)c([C@H]5CC[C@H](C(=O)O)CC5)nc34)cn2)cc1] | 534.14 | 534.14 | 4.55 |

TABLE 4A-continued

| Compound ID | Structures | M + H (calc.) | M + H (observed) | LC/MS retention time (10 min method) |
|---|---|---|---|---|
| 4.53 | 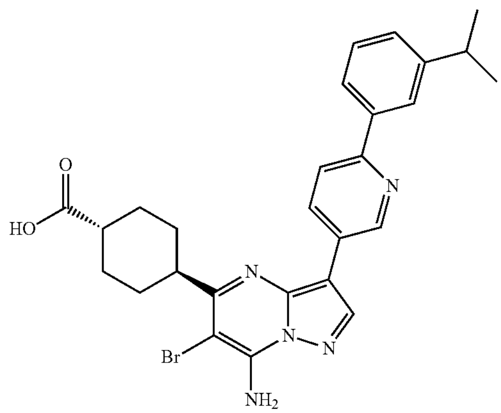 [SMILES: CC(C)c1cccc(-c2ccc(-c3cnn4c(N)c(Br)c([C@H]5CC[C@H](C(=O)O)CC5)nc34)cn2)c1] | 534.14 | 534.14 | 4.55 |
| 4.54 | 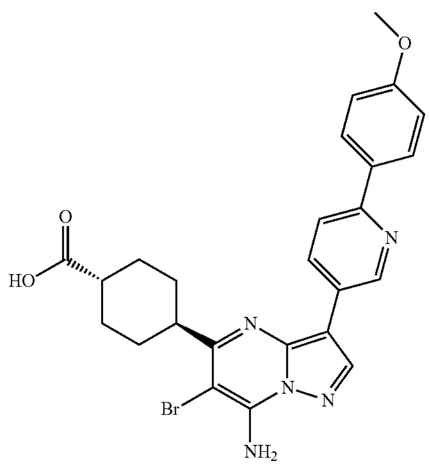 [SMILES: COc1ccc(-c2ccc(-c3cnn4c(N)c(Br)c([C@H]5CC[C@H](C(=O)O)CC5)nc34)cn2)cc1] | 522.11 | 522.11 | 3.85 |
| 4.55 | 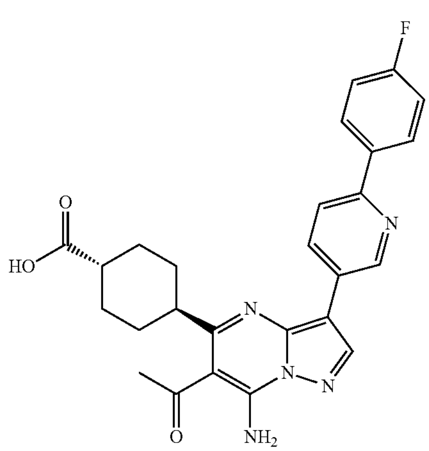 [SMILES: CC(=O)c1c(N)n2ncc(-c3ccc(-c4ccc(F)cc4)nc3)c2nc1[C@H]1CC[C@H](C(=O)O)CC1] | 474.19 | 474.19 | 3.81 |

TABLE 4A-continued

| Compound ID | Structures | M + H (calc.) | M + H (observed) | LC/MS retention time (10 min method) |
| --- | --- | --- | --- | --- |
| 4.56 | 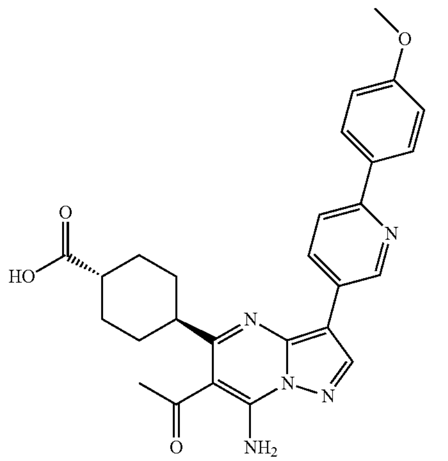 [SMILES: COc1ccc(-c2ccc(-c3cnn4c(N)c(C(C)=O)c([C@H]5CC[C@H](C(=O)O)CC5)nc34)cn2)cc1] | 486.21 | 486.21 | 4.06 |
| 4.57 | 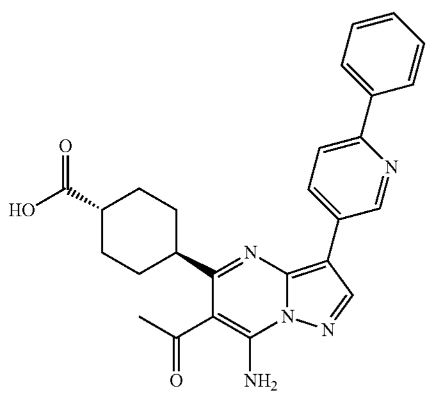 [SMILES: CC(=O)c1c(N)n2ncc(-c3ccc(-c4ccccc4)nc3)c2nc1[C@H]1CC[C@H](C(=O)O)CC1] | 456.20 | 456.20 | 3.88 |
| 4.58 | 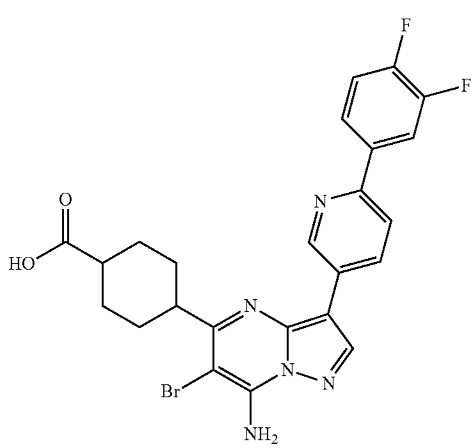 [SMILES: Nc1c(Br)c(C2CCC(C(=O)O)CC2)nc2c(-c3ccc(-c4ccc(F)c(F)c4)nc3)cnn12] | 528.0 | 528.0 | 4.77 |

TABLE 4A-continued

| Compound ID | Structures | M + H (calc.) | M + H (observed) | LC/MS retention time (10 min method) |
|---|---|---|---|---|
| 4.59 | 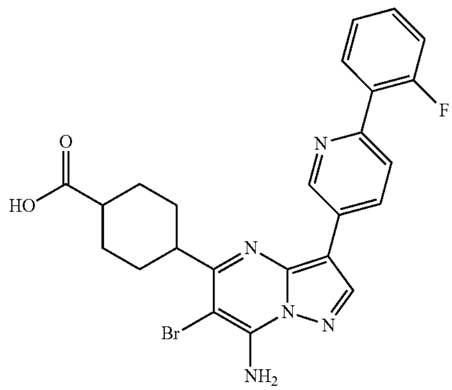 [SMILES: Nc1c(Br)c(C2CCC(C(=O)O)CC2)nc2c(-c3ccc(-c4ccccc4F)nc3)cnn12] | 510.0 | 510.0 | 4.15 |
| 4.60 | 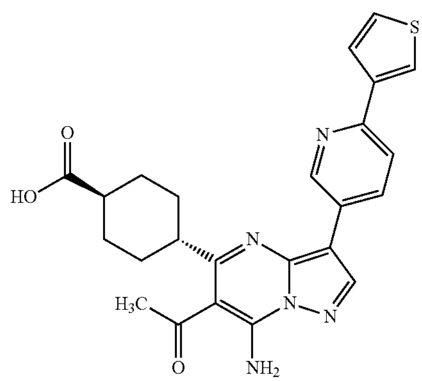 [SMILES: CC(=O)c1c(N)n2ncc(-c3ccc(-c4ccsc4)nc3)c2nc1[C@H]1CC[C@H](C(=O)O)CC1] | 462.1 | 462.1 | 1.68 (5 min) |
| 4.61 | 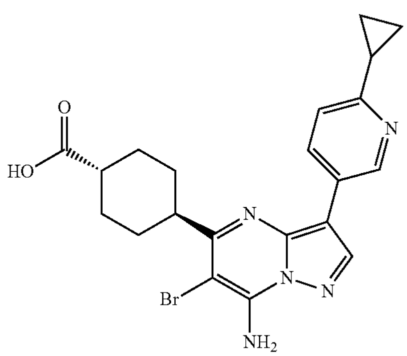 [SMILES: Nc1c(Br)c([C@H]2CC[C@H](C(=O)O)CC2)nc2c(-c3ccc(C4CC4)nc3)cnn12] | 456.10 | 456.10 | 3.27 |
| 4.62 | 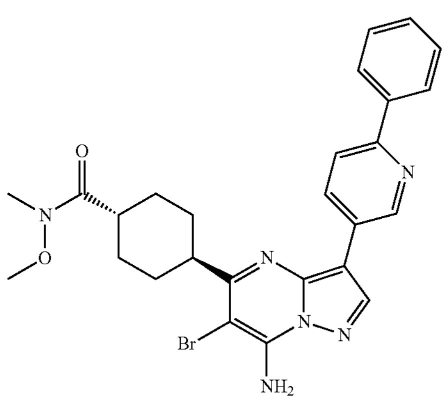 [SMILES: CON(C)C(=O)[C@H]1CC[C@H](c2nc3c(-c4ccc(-c5ccccc5)nc4)cnn3c(N)c2Br)CC1] | 535.14 | 535.14 | 4.07 |

TABLE 4A-continued

| Compound ID | Structures | M + H (calc.) | M + H (observed) | LC/MS retention time (10 min method) |
| --- | --- | --- | --- | --- |
| 4.63 | 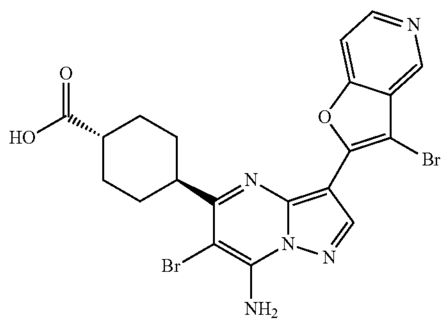 [SMILES: Nc1c(Br)c([C@H]2CC[C@H](C(=O)O)CC2)nc2c(-c3oc4ccncc4c3Br)cnn12] | 533.97 | 533.97 | 3.22 |
| 4.64 | 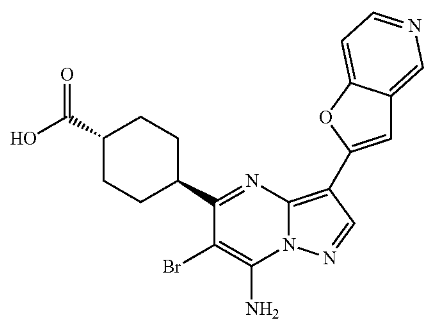 [SMILES: Nc1c(Br)c([C@H]2CC[C@H](C(=O)O)CC2)nc2c(-c3cc4cnccc4o3)cnn12] | 456.06 | 456.06 | 3.36 |
| 4.65 | 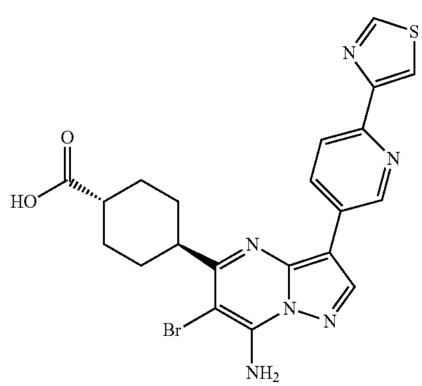 [SMILES: Nc1c(Br)c([C@H]2CC[C@H](C(=O)O)CC2)nc2c(-c3ccc(-c4cscn4)nc3)cnn12] | 499.05 | 499.05 | 2.99 |
| 4.66 | 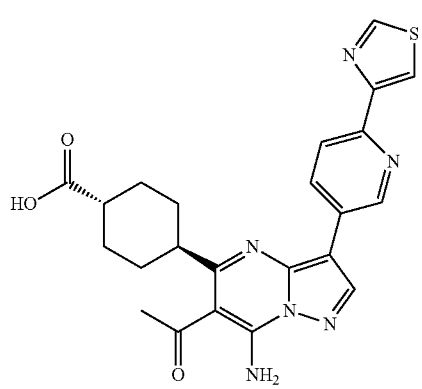 [SMILES: CC(=O)c1c(N)n2ncc(-c3ccc(-c4cscn4)nc3)c2nc1[C@H]1CC[C@H](C(=O)O)CC1] | 463.15 | 463.15 | 3.47 |

TABLE 4A-continued

| Compound ID | Structures | M + H (calc.) | M + H (observed) | LC/MS retention time (10 min method) |
|---|---|---|---|---|
| 4.67 | 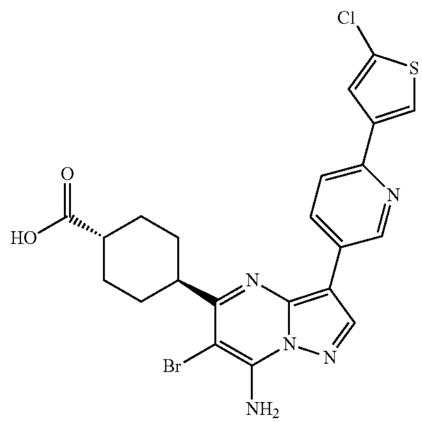 [SMILES: Nc1c(Br)c([C@H]2CC[C@H](C(=O)O)CC2)nc2c(-c3ccc(-c4csc(Cl)c4)nc3)cnn12] | 532.01 | 532.01 | 4.45 |
| 4.68 | 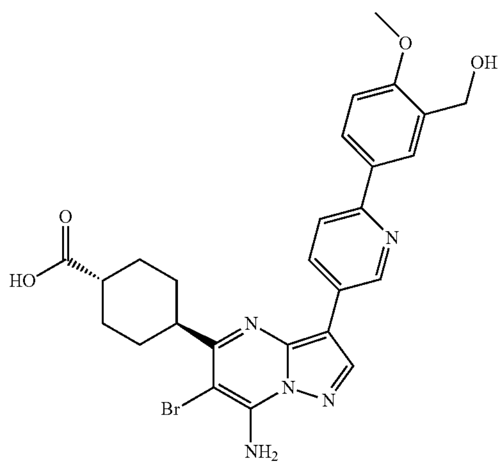 [SMILES: COc1ccc(-c2ccc(-c3cnn4c(N)c(Br)c([C@H]5CC[C@H](C(=O)O)CC5)nc34)cn2)cc1CO] | 552.12 | 552.12 | 3.60 |
| 4.69 | 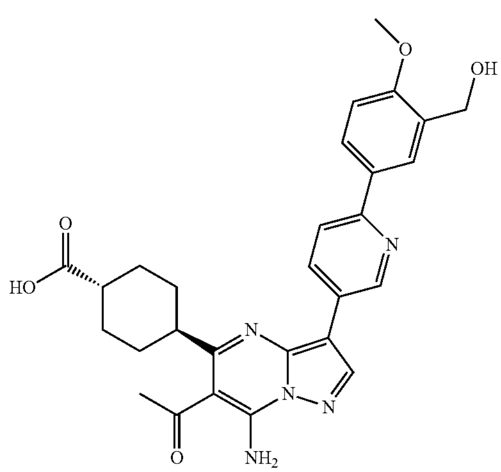 [SMILES: COc1ccc(-c2ccc(-c3cnn4c(N)c(C(C)=O)c([C@H]5CC[C@H](C(=O)O)CC5)nc34)cn2)cc1CO] | 516.22 | 516.22 | 3.47 |

TABLE 4A-continued

| Compound ID | Structures | M + H (calc.) | M + H (observed) | LC/MS retention time (10 min method) |
|---|---|---|---|---|
| 4.70 | 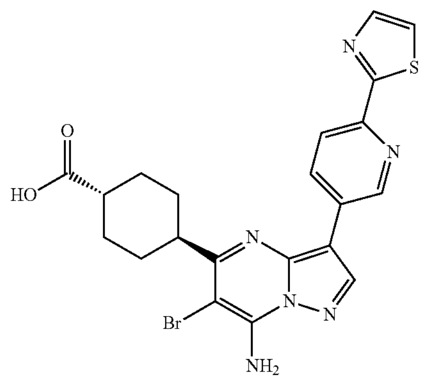 [SMILES: Nc1c(Br)c([C@H]2CC[C@H](C(=O)O)CC2)nc2c(-c3ccc(-c4nccs4)nc3)cnn12] | 499.05 | 499.05 | 1.81 (5 min) |
| 4.71 | 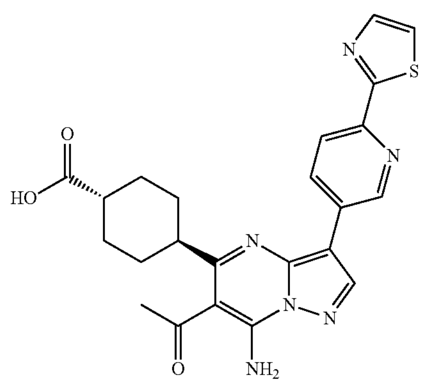 [SMILES: CC(=O)c1c(N)n2ncc(-c3ccc(-c4nccs4)nc3)c2nc1[C@H]1CC[C@H](C(=O)O)CC1] | 463.15 | 463.15 | 3.31 |
| 4.72 | 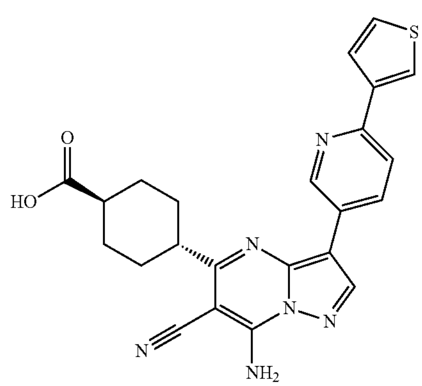 [SMILES: N#Cc1c(N)n2ncc(-c3ccc(-c4ccsc4)nc3)c2nc1[C@H]1CC[C@H](C(=O)O)CC1] | 444.1 | 445.0 | 1.68 (5 min) |
| 4.73 | 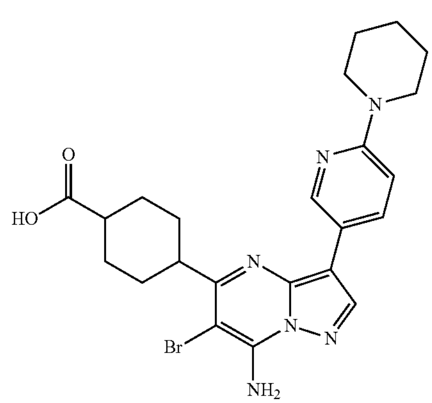 [SMILES: Nc1c(Br)c(C2CCC(C(=O)O)CC2)nc2c(-c3ccc(N4CCCCC4)nc3)cnn12] | 498.1 | 499.0 | 3.80 (10 min) |

TABLE 4A-continued

| Compound ID | Structures | M + H (calc.) | M + H (observed) | LC/MS retention time (10 min method) |
|---|---|---|---|---|
| 4.74 | 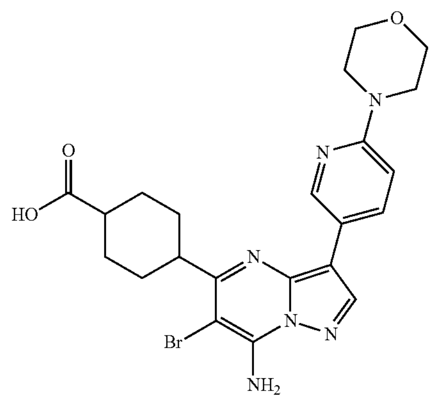 [SMILES: Nc1c(Br)c(C2CCC(C(=O)O)CC2)nc2c(-c3ccc(N4CCOCC4)nc3)cnn12] | 500.1 | 501.1 | 3.30 (10 min) |
| 4.75 | 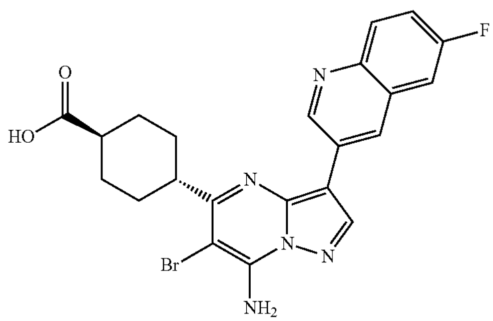 [SMILES: Nc1c(Br)c([C@H]2CC[C@H](C(=O)O)CC2)nc2c(-c3cnc4ccc(F)cc4c3)cnn12] | 483.1 | 484.0 | 1.66 (5 min) |
| 4.76 | 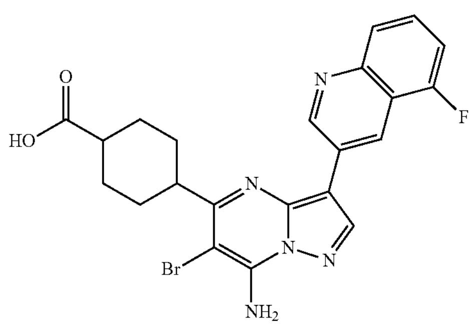 [SMILES: Nc1c(Br)c(C2CCC(C(=O)O)CC2)nc2c(-c3cnc4cccc(F)c4c3)cnn12] | 483.1 | 484.0 | 4.79 (10 min) |
| 4.77 | 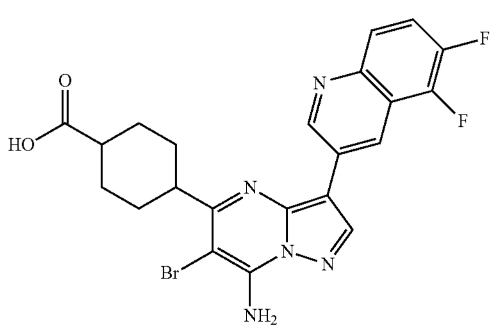 [SMILES: Nc1c(Br)c(C2CCC(C(=O)O)CC2)nc2c(-c3cnc4ccc(F)c(F)c4c3)cnn12] | 501.1 | 502.0 | 5.16 (10 min) |

TABLE 4A-continued

| Compound ID | Structures | M + H (calc.) | M + H (observed) | LC/MS retention time (10 min method) |
|---|---|---|---|---|
| 4.78 | 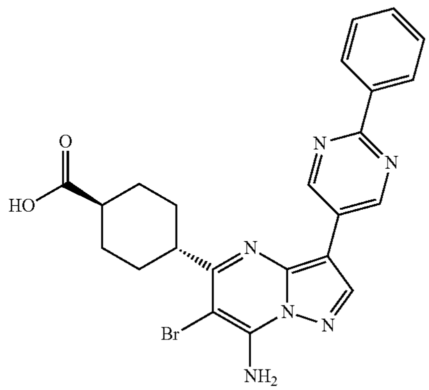 [SMILES: Nc1c(Br)c([C@H]2CC[C@H](C(=O)O)CC2)nc2c(-c3cnc(-c4ccccc4)nc3)cnn12] | 492.1 | 493.1 | 1.98 (5 min) |
| 4.79 | 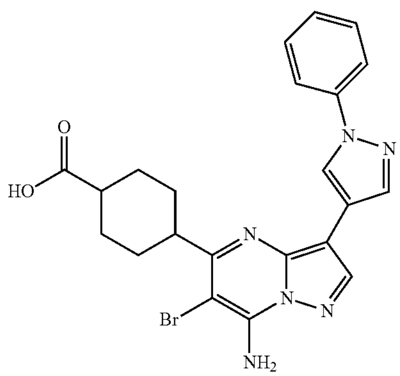 [SMILES: Nc1c(Br)c(C2CCC(C(=O)O)CC2)nc2c(-c3cnn(-c4ccccc4)c3)cnn12] | 480.1 | 481.0 | 4.96 (10 min) |
| 4.80 | 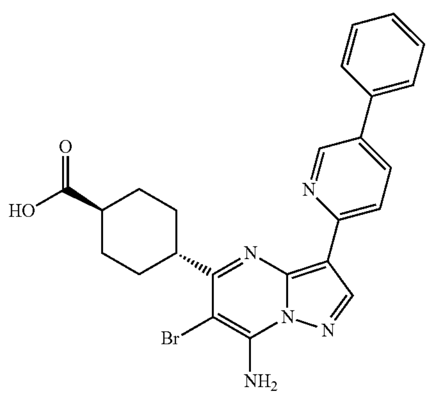 [SMILES: Nc1c(Br)c([C@H]2CC[C@H](C(=O)O)CC2)nc2c(-c3ccc(-c4ccccc4)cn3)cnn12] | 491.1 | 492 | 3.89 (10 min) |
| 4.81 | 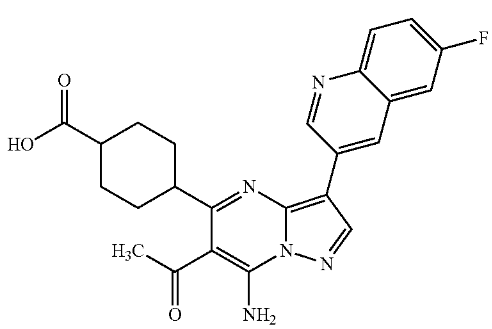 [SMILES: CC(=O)c1c(C2CCC(C(=O)O)CC2)nc2c(-c3cnc4ccc(F)cc4c3)cnn2c1N] | 447.2 | 448.1 | 1.61 (5 min) |

TABLE 4A-continued

| Compound ID | Structures | M + H (calc.) | M + H (observed) | LC/MS retention time (10 min method) |
|---|---|---|---|---|
| 4.82 | 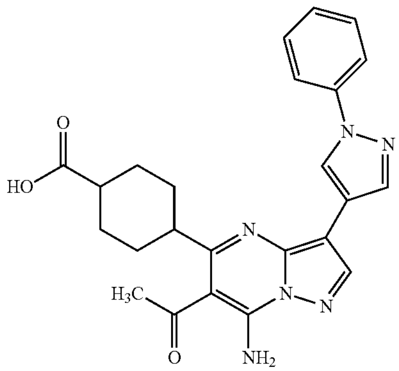 [SMILES: CC(=O)c1c(C2CCC(C(=O)O)CC2)nc2c(-c3cnn(-c4ccccc4)c3)cnn2c1N] | 444.2 | 445.1 | 4.85 (10 min) |
| 4.83 | 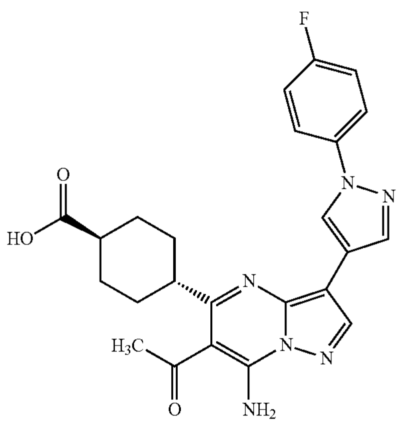 [SMILES: CC(=O)c1c(N)n2ncc(-c3cnn(-c4ccc(F)cc4)c3)c2nc1[C@H]1CC[C@H](C(=O)O)CC1] | 462.2 | 463.1 | 2.01 (5 min) |
| 4.84 | 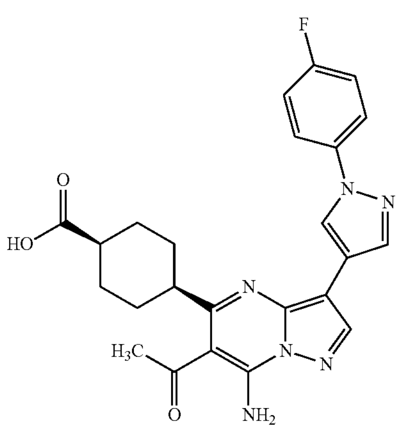 [SMILES: CC(=O)c1c(N)n2ncc(-c3cnn(-c4ccc(F)cc4)c3)c2nc1[C@H]1CC[C@@H](C(=O)O)CC1] | 462.2 | 463.1 | 2.01 (5 min) |

TABLE 4A-continued

| Compound ID | Structures | M + H (calc.) | M + H (observed) | LC/MS retention time (10 min method) |
|---|---|---|---|---|
| 4.85 | 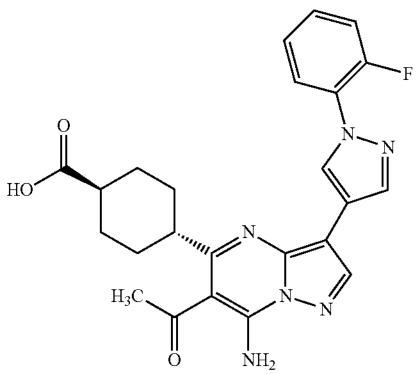 [SMILES: CC(=O)c1c(N)n2ncc(-c3cnn(-c4ccccc4F)c3)c2nc1[C@H]1CC[C@H](C(=O)O)CC1] | 462.2 | 463.1 | 1.97 (5 min) |
| 4.86 | 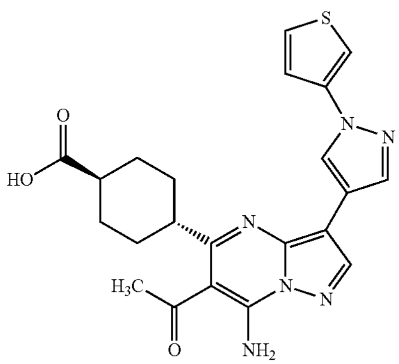 [SMILES: CC(=O)c1c(N)n2ncc(-c3cnn(-c4ccsc4)c3)c2nc1[C@H]1CC[C@H](C(=O)O)CC1] | 450.1 | 451.1 | 1.90 (5 min) |

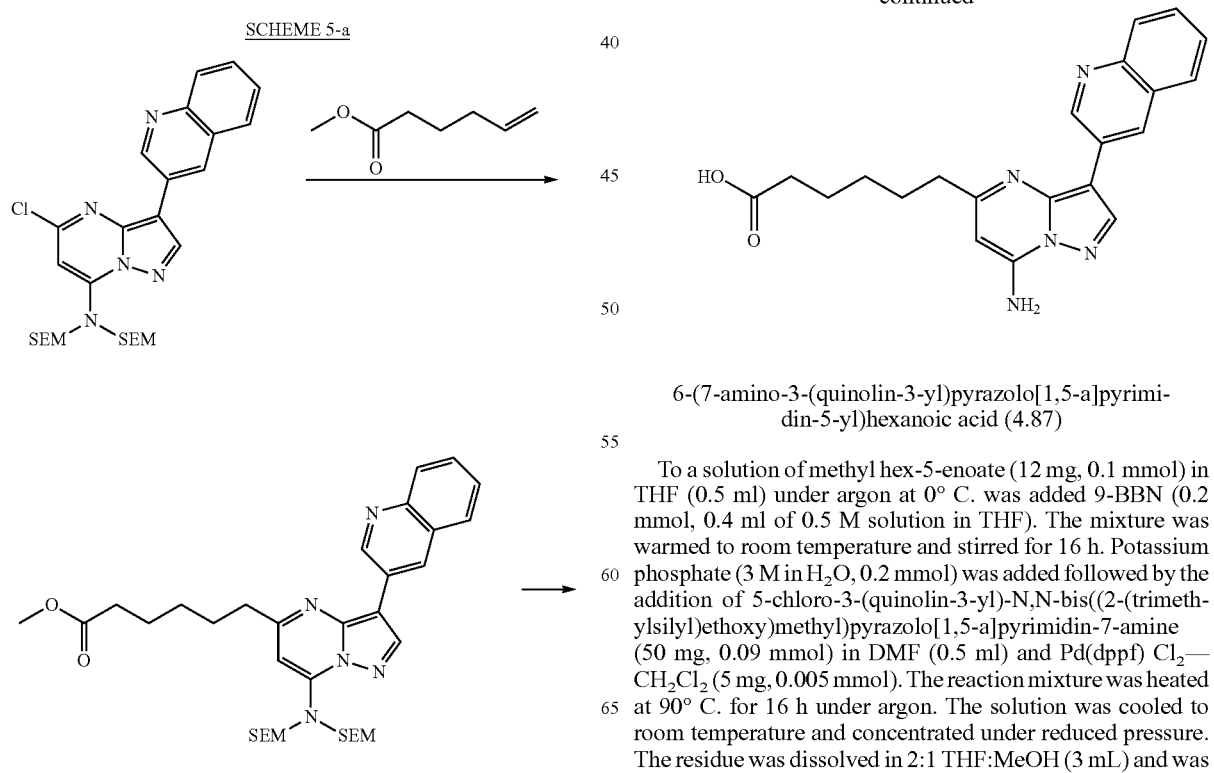

6-(7-amino-3-(quinolin-3-yl)pyrazolo[1,5-a]pyrimidin-5-yl)hexanoic acid (4.87)

To a solution of methyl hex-5-enoate (12 mg, 0.1 mmol) in THF (0.5 ml) under argon at 0° C. was added 9-BBN (0.2 mmol, 0.4 ml of 0.5 M solution in THF). The mixture was warmed to room temperature and stirred for 16 h. Potassium phosphate (3 M in H₂O, 0.2 mmol) was added followed by the addition of 5-chloro-3-(quinolin-3-yl)-N,N-bis((2-(trimethylsilyl)ethoxy)methyl)pyrazolo[1,5-a]pyrimidin-7-amine (50 mg, 0.09 mmol) in DMF (0.5 ml) and Pd(dppf) Cl₂—CH₂Cl₂ (5 mg, 0.005 mmol). The reaction mixture was heated at 90° C. for 16 h under argon. The solution was cooled to room temperature and concentrated under reduced pressure. The residue was dissolved in 2:1 THF:MeOH (3 mL) and was treated with 2N NaOH$_{(aq)}$ (0.25 mL). The resulting solution was stirred at room temperature for 4 hours followed by the addition of 2N hydrochloride solution (1.0 ml). The solution was heated at 65° C. for 2 h, cooled to room temperature, concentrated and purified by prep-LC to afford the title compound (8.2 mg): LC/MS RT=2.74 min. Mass calculated for, M+H 376.17, observed 376.17.

Analogues to the compound 4.87, following compounds in the table-4C can be synthesized as described above in the scheme-5a

TABLE 4C

| Compound ID | Structures | M + H (calc.) | M + H (observed) | LC/MS retention time (10 min method) |
|---|---|---|---|---|
| 4.88 | 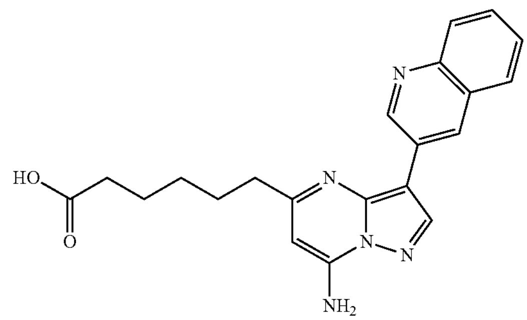 [SMILES: Nc1cc(CCCCCC(=O)O)nc2c(-c3cnc4ccccc4c3)cnn12] | 376.17 | 376.17 | 2.74 |
| 4.89 | 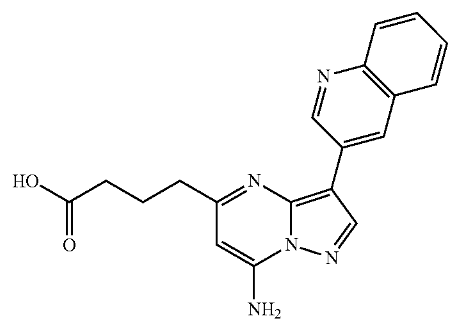 [SMILES: Nc1cc(CCCC(=O)O)nc2c(-c3cnc4ccccc4c3)cnn12] | 348.14 | 348.14 | 2.41 |
| 4.90 | 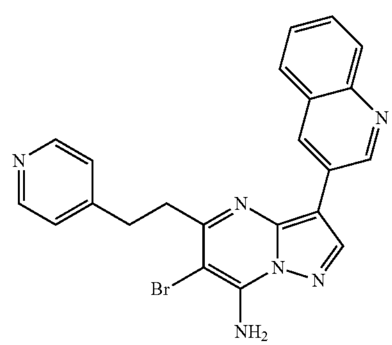 | 445.07 | 445.07 | 2.62 |
| 4.91 | 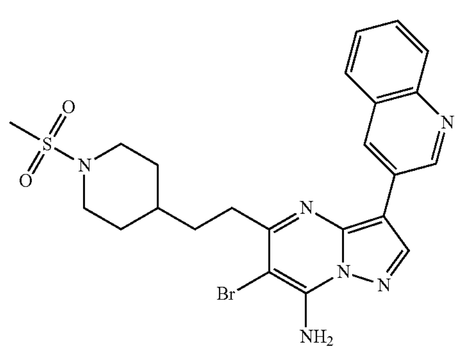 [SMILES: CS(=O)(=O)N1CCC(CCc2nc3c(-c4cnc5ccccc5c4)cnn3c(N)c2Br)CC1] | 529.10 | 529.10 | 3.90 |

TABLE 4C-continued

| Compound ID | Structures | M + H (calc.) | M + H (observed) | LC/MS retention time (10 min method) |
| --- | --- | --- | --- | --- |
| 4.91 | 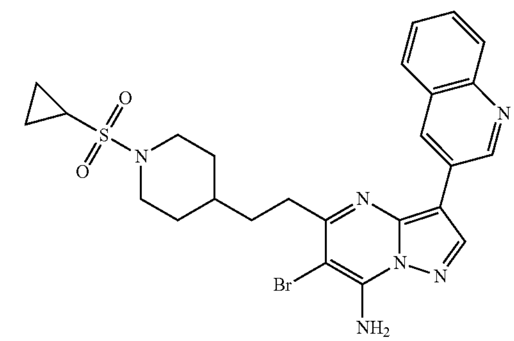 [SMILES: Nc1c(Br)c(CCC2CCN(S(=O)(=O)C3CC3)CC2)nc2c(-c3cnc4ccccc4c3)cnn12] | 555.11 | 555.11 | 4.21 |
| 4.92 | 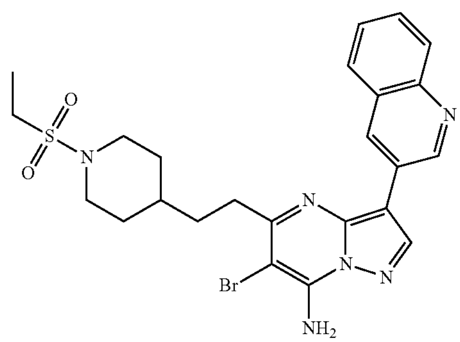 [SMILES: CCS(=O)(=O)N1CCC(CCc2nc3c(-c4cnc5ccccc5c4)cnn3c(N)c2Br)CC1] | 543.11 | 543.11 | 4.11 |
| 4.93 | 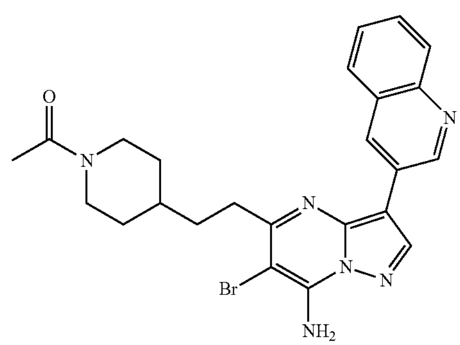 [SMILES: CC(=O)N1CCC(CCc2nc3c(-c4cnc5ccccc5c4)cnn3c(N)c2Br)CC1] | 493.13 | 499.13 | 3.75 |
| 4.94 | 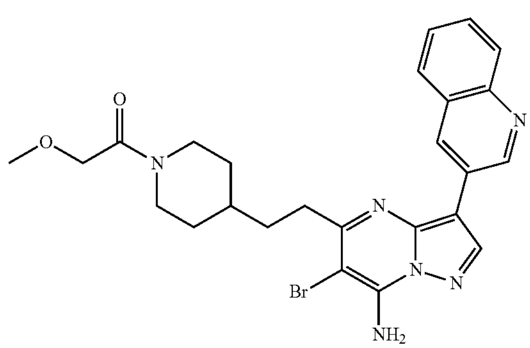 [SMILES: COCC(=O)N1CCC(CCc2nc3c(-c4cnc5ccccc5c4)cnn3c(N)c2Br)CC1] | 523.14 | 523.14 | 3.72 |

TABLE 4C-continued

| Compound ID | Structures | M + H (calc.) | M + H (observed) | LC/MS retention time (10 min method) |
| --- | --- | --- | --- | --- |
| 4.95 | 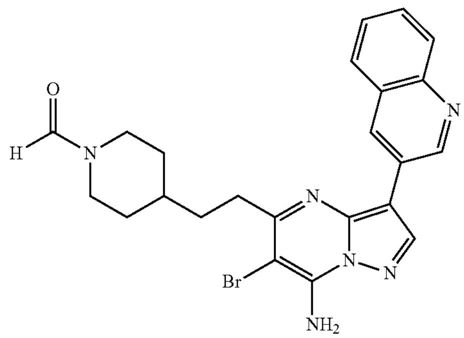 [SMILES: Nc1c(Br)c(CCC2CCN(C=O)CC2)nc2c(-c3cnc4ccccc4c3)cnn12] | 479.11 | 479.11 | 3.63 |
| 4.96 | 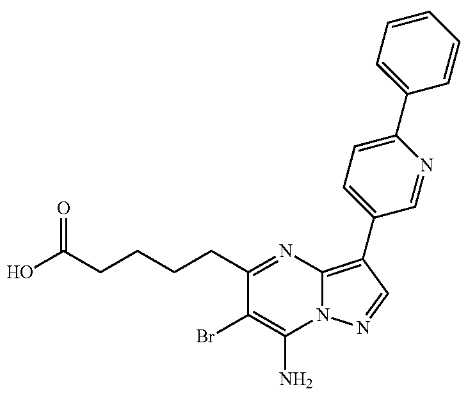 [SMILES: Nc1c(Br)c(CCCCC(=O)O)nc2c(-c3ccc(-c4ccccc4)nc3)cnn12] | 466.08 | 466.08 | 3.68 |
| 4.97 | 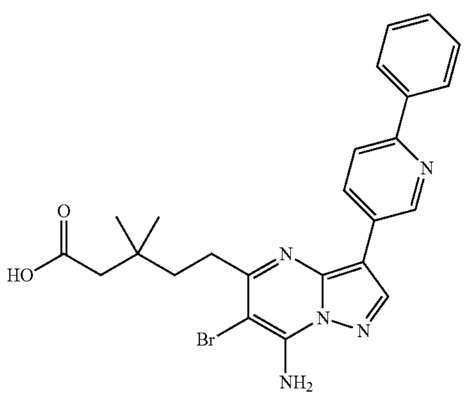 [SMILES: CC(C)(CCc1nc2c(-c3ccc(-c4ccccc4)nc3)cnn2c(N)c1Br)CC(=O)O] | 494.11 | 494.11 | 4.12 |
| 4.98 | 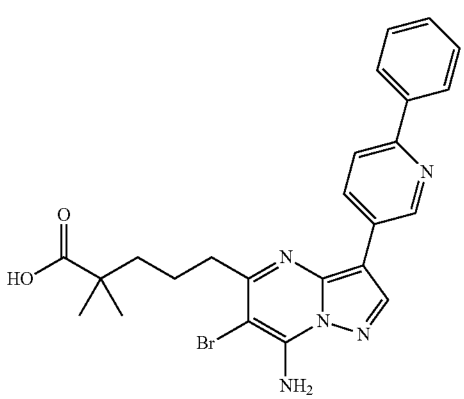 [SMILES: CC(C)(CCCc1nc2c(-c3ccc(-c4ccccc4)nc3)cnn2c(N)c1Br)C(=O)O] | 494.11 | 494.11 | 4.26 |

Following nucleophilic displacement reaction of 5-chloro-3-(quinolin-3-yl)-N,N-bis((2-(trimethylsilyl)ethoxy)methyl)pyrazolo[1,5-a]pyrimidin-7-amine with appropriate amine or alcohol (experimental procedure described in Scheme-5a, compounds in the table-4C can be synthesized.

Synthesis of 2-methyl-6-(4,4,5,5-tetramethyl-1,3,2-dioxaborolan-2-yl)thieno[3,2-b]pyridine

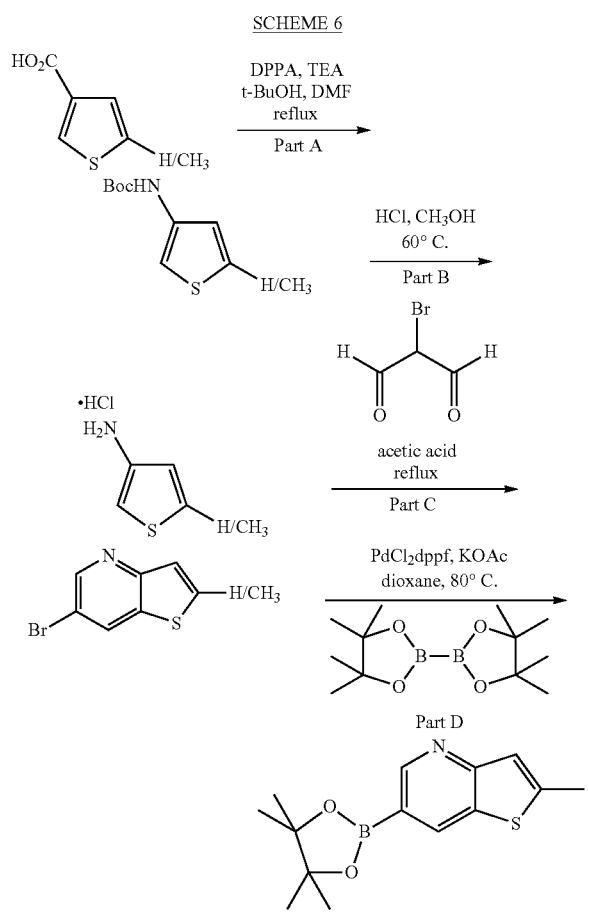

Part A:
To a stirring solution of thiophenecarboxylic acid (1 equiv) in DMF and t-BuOH at 0° C. was added the DPPA (1 equiv) and TEA (1 equiv). The reaction was then stirred at room temperature for 1 hour, then warmed to reflux and stirred for 15 hours. The reaction was allowed to cool to room temperature, and then evaporated to dryness. The resulting residue was dissolved in EtOAc then washed with sat. aq. NH$_4$Cl, sat. aq. NaHCO$_3$, and brine, dried over sodium sulfate, filtered, and purified on silica gel to afford the product.

Part B:
A solution of HCl in dioxane was added to a stirring solution of the product from Part A in methanol at 0° C. The reaction was then stirred at reflux for 1 hour, then allowed to cool to room temperature and concentrated to afford the product.

Part C:
Bromomalonaldehyde (1 equiv) was added to a solution of the product from Part B (1 equiv) in glacial acetic acid at room temperature. The mixture was stirred at reflux for 1 hour, then allowed to cool to room temperature, then evaporated to dryness. The residue was dissolved in methanol, filtered through a pad of celite, concentrated, and purified on silica gel to afford the product.

Part D:
A mixture of the product from Part C (1 equiv), bispinacolatodiboron (1.2 equiv), PdCl$_2$dppf (0.1 equiv), and potassium acetate (3 equiv) in dioxane was heated at 85° C. until the reaction was deemed complete by TLC, HPLC, or LC-MS analysis. The reaction was allowed to cool to room temperature, filtered through a pad of celite, concentrated to dryness, treated with diethyl ether, filtered through a pad of celite, then concentrated to afford the desired product, 2-methyl-6-(4,4,5,5-tetramethyl-1,3,2-dioxaborolan-2-yl)thieno[3,2-b]pyridine.

Synthesis of 6-(4,4,5,5-tetramethyl-1,3,2-dioxaborolan-2-yl)thieno[3,2-b]pyridine Essentially utilizing the procedure described above scheme—the title compound 6-(4,4,5,5-tetramethyl-1,3,2-dioxaborolan-2-yl)thieno[3,2-b]pyridine can be synthesized

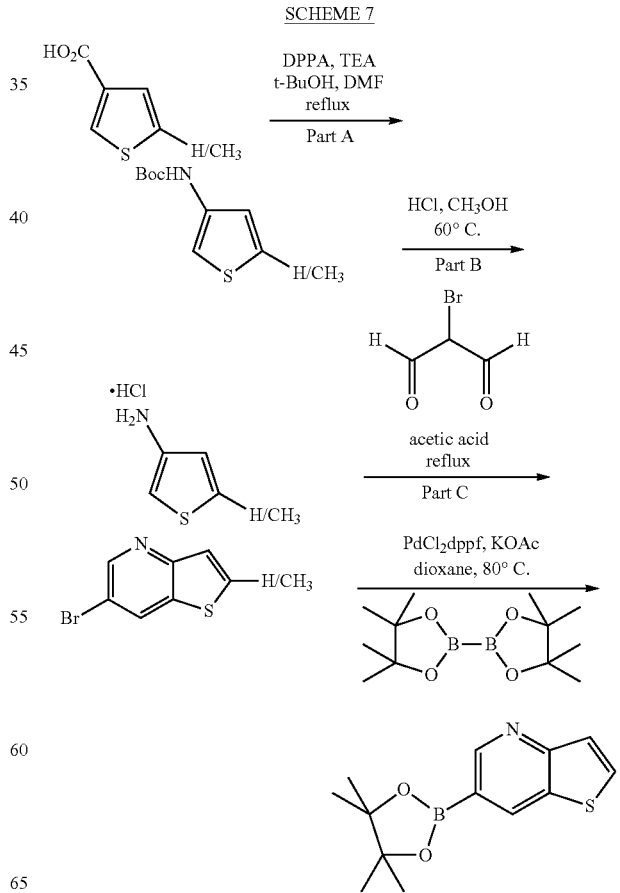

Synthesis of 5-(4,4,5,5-tetramethyl-1,3,2-dioxaborolan-2-yl)furo[2,3-b]pyridine (modified procedure from the patent # GB2289276A)

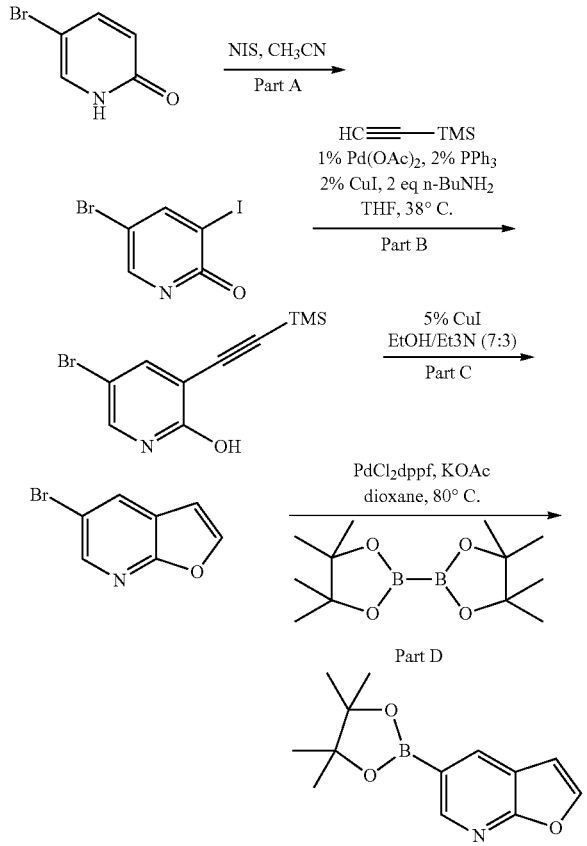

Part A:
To a solution of 5-bromo-2-(1H)-pyridone (18.8 g, 10.8 mmol) in dry toluene (400 mL) was added N-iodosuccinimide (24.3 g, 10.8 mmol) under nitrogen. The reaction mixture was stirred at 90° C. for 20 minutes then cooled to 25° C. The precipitate was filtered off and washed with methanol, dried under vacuum to give the pink-orange color solid 28.0 g (86%). $^1$H NMR (300 MHz, CDCl$_3$) δ 8.1 (s, 1H), 7.6 (s, 1H). Mass calculated for formula C$_5$H$_3$BrINO 298.84, observe MS ES+: 300.0/302.0.

Part B:
The iodide (6.0 g, 20.0 mmol), Pd(OAc)$_2$ (45 mg, 0.2 mmol), PPh$_3$ (105 mg, 0.4 mmol), CuI (76 mg, 0.4 mmol) were added to a round bottom flask under nitrogen. Dry THF (30 mL) was added and the solution was degassed 2 minutes with nitrogen. TMS-acetylene (2.9 g, 30 mmol) was added followed with n-BuNH$_2$ (2.9 g, 40 mmol). The homogeneous green solution was heated to 38° C. for 4 hours. The reaction mixture was cool to 25° C., concentrated to dryness and then dissolved in EtOAc (100 mL). The solution was washed with saturated sodium potassium tartrate (50 mL), followed with 0.1 N HCl (50 mL), saturated NaHCO$_3$ (50 mL), and brine (50 mL), dried over Na$_2$SO$_4$, Purification by column chromatography (SiO$_2$, 50% ethyl acetate/hexanes) afforded compound as a green solid 4.40 g (81%). $^1$H NMR (300 MHz, CDCl$_3$) δ 7.85 (s, 1H), 7.5 (s, 1H), 0.2 (s, 9H).

Part C:
To a EtOH (8.0 mL) solution of compound from Part B (1.12 g, 4.1 mmol) was added CuI (39 mg, 0.2 mmol) and followed with Et$_3$N (3.5 mL) the resulting mixture was stirred at 70° C. for 3 hours. The reaction mixture was allowed to cool to 25° C., concentrated to dryness and then dissolved in toluene (30 mL). The solution was washed with 0.1 N HCl (20 mL), saturated NaHCO$_3$ (20 mL), and brine (30 mL), dried over Na$_2$SO$_4$. Purification by column chromatography (SiO$_2$, 20% ethyl acetate/hexanes) afforded compound as a white solid 0.26 g (32%). $^1$H NMR (300 MHz, CDCl$_3$) δ 8.4 (s, 1H), 8.1 (s, 1H), 7.7 (s, 1H), 6.8 (s, 1H).

Part D:
A mixture of the product from Part C (1 equiv), bispinacolatodiboron (1.2 equiv), PdCl$_2$dppf (0.1 equiv), and potassium acetate (3 equiv) in dioxane was heated at 85° C. until the reaction was deemed complete by TLC, HPLC, or LC-MS analysis. The reaction was allowed to cool to room temperature, filtered through a pad of celite, concentrated to dryness, treated with diethyl ether, filtered through a pad of celite, then concentrated to afford the desired product, 5-(4,4,5,5-tetramethyl-1,3,2-dioxaborolan-2-yl)furo[2,3-b]pyridine.

2-methyl-5-(4,4,5,5-tetramethyl-1,3,2-dioxaborolan-2-yl)furo[2,3-b]pyridine

SCHEME-8

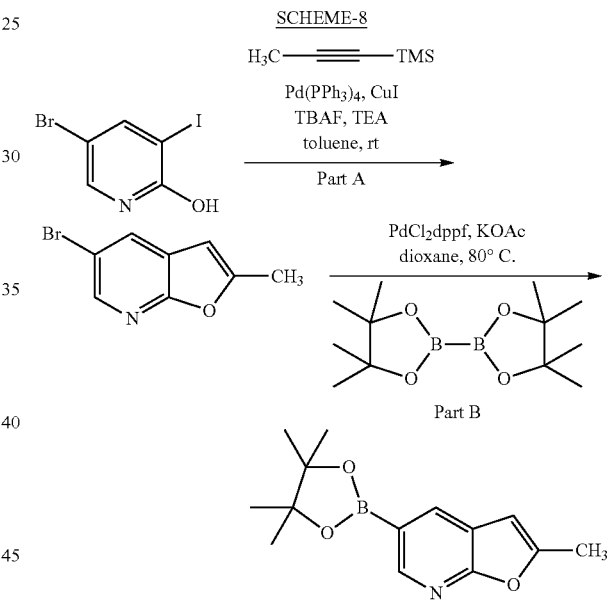

Part A:
A mixture of 5-bromo-3-iodopyridin-2-ol (1 equiv), copper iodide (3 equiv), palladium catalyst (0.05 equiv), TBAF (1 equiv), triethylamine (3.3 equiv) and alkyne (1 equiv) in toluene was stirred at room temperature until the reaction was deemed complete by TLC analysis. The reaction mixture was diluted with dichloromethane, washed with water, saturated sodium bicarbonate, and brine, dried over sodium bicarbonate, filtered through celite, concentrated, and purified on silica gel to give the product, 5-bromo-2-methylfuro[2,3-b]pyridine.

Part B:
A mixture of the product, 5-bromo-2-methylfuro[2,3-b]pyridine, from Part A (1 equiv), bispinacolatodiboron (1.2 equiv), PdCl$_2$dppf (0.1 equiv), and potassium acetate (3 equiv) in dioxane was heated at 85° C. until the reaction was deemed complete by TLC, HPLC, or LC-MS analysis. The reaction was allowed to cool to room temperature, filtered through a pad of celite, concentrated to dryness, treated with diethyl ether, filtered through a pad of celite, and then concentrated to afford the desired product, 2-methyl-5-(4,4,5,5-tetramethyl-1,3,2-dioxaborolan-2-yl)furo[2,3-b]pyridine.

Synthesis of 5-(4,4,5,5-tetramethyl-1,3,2-dioxaborolan-2-yl)thieno[2,3-b]pyridine

SCHEME-9

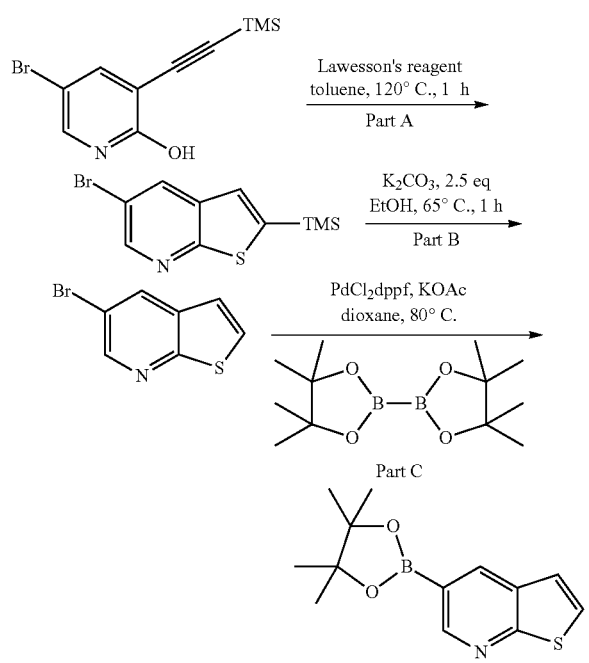

Part A:

To a solution of 5-bromo-3-((trimethylsiyl)ethynyl)pyridin-2-ol (10.63 g, 39.5 mmol) in toluene (195 mL) was added Lawesson's reagent (8.00 g, 19.8 mmol) under nitrogen. The reaction mixture was stirred at 120° C. for 1 hour, and then allowed to cool to 25° C. Purification by column chromatography (SiO$_2$, 20% ethyl acetate/hexanes) afforded compound as a white solid, 5-bromo-2-(trimethylsilyl)thieno[2,3-b]pyridine, 8.99 g (79%). $^1$H NMR (300 MHz, CDCl$_3$) δ 8.57 (d, J=2.2 Hz, 1H), 8.16 (d, J=2.2 Hz 1H), 7.30 (s, 1H), 0.39 (s, 9H).

Part B:

The 5-bromo-2-(trimethylsilyl)thieno[2,3-b]pyridine from Part A (8.99 g, 31.4 mmol) was dissolved in ethanol (70 mL), followed by addition of K$_2$CO$_3$ (10.85 g, 78.5 mmol). Reaction was stirred at 65° C. for 1 hour. The reaction mixture was allowed to cool to 25° C., concentrated to dryness, and dissolved in EtOAc (150 mL). The solution was washed with H$_2$O (80 mL), and brine (150 mL), dried over Na$_2$SO$_4$, filtered, and concentrated to yield white solid, 5-bromothieno[2,3-b]pyridine, 6.57 g (98%). $^1$H NMR (300 MHz, CDCl$_3$) δ 8.60 (d, J≤2.2 Hz, 1H), 8.16 (d, J=2.2 Hz 1H), 7.57 (d, J=6.0 Hz 1H), 7.21 (d, J=6.0 Hz, 1H).

Part C:

A mixture of the product, 5-bromothieno[2,3-b]pyridine, from Part B (1 equiv), bispinacolatodiboron (1.2 equiv), PdCl$_2$dppf (0.1 equiv), and potassium acetate (3 equiv) in dioxane was heated at 85° C. until the reaction was deemed complete by TLC, HPLC, or LC-MS analysis. The reaction was allowed to cool to room temperature, filtered through a pad of celite, concentrated to dryness, treated with diethyl ether, filtered through a pad of celite, and then concentrated to afford the desired product, 5-(4,4,5,5-tetramethyl-1,3,2-dioxaborolan-2-yl)thieno[2,3-b]pyridine.

General Synthesis of (1r,4r)-4-(7-amino-3-Aryl,6-substituted pyrazolo[1,5-a]pyrimidin-5-yl)cyclohexanecarboxylic acid

SCHEME-10

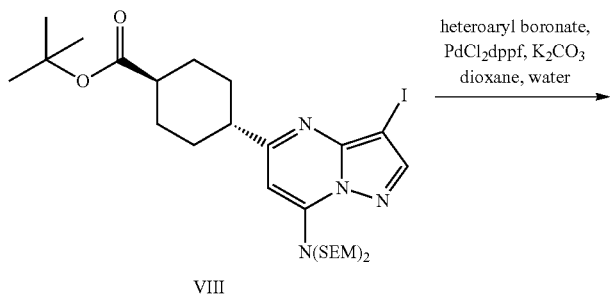

VIII

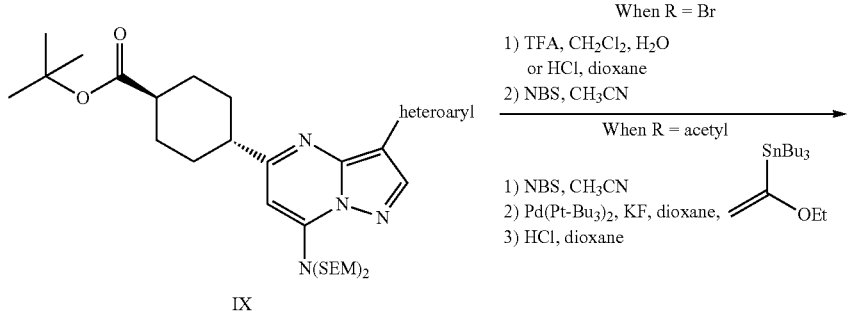

IX

-continued

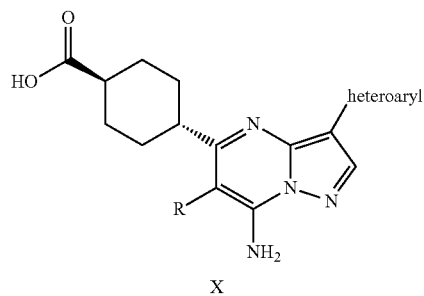

X

A mixture of compound (1r,4r)-tert-butyl 4-(7-(bis((2-(trimethylsilyl)ethoxy)methyl)amino)-3-iodopyrazolo[1,5-a]pyrimidin-5-yl)cyclohexanecarboxylate (1 equiv), boronate (1.75 equiv), palladium catalyst (0.1 equiv), and potassium carbonate (3 equiv) in water and dioxane was stirred at 40° C. until the reaction was deemed complete by HPLC, LC-MS, or TLC analysis. The mixture was allowed to cool to room temperature, diluted with water and extracted three times with dichloromethane. The combined organics were dried over sodium sulfate, filtered, concentrated, and purified on silica gel to afford compound (1r,4r)-tert-butyl 4-(7-(bis((2-(trimethylsilyl)ethoxy)methyl)amino)-3-aryl-pyrazolo[1,5-a]pyrimidin-5-yl)cyclohexanecarboxylate.

When R=Br:

Compound, (1r,4r)-tert-butyl 4-(7-(bis((2-(trimethylsilyl)ethoxy)methyl)amino)-3-aryl-pyrazolo[1,5-a]pyrimidin-5-yl)cyclohexanecarboxylate, was stirred in a mixture of dichloromethane, water, and TFA until the reaction was deemed complete by HPLC, LC-MS, or TLC analysis. The reaction was concentrated and purified on prep-HPLC. The resulting material was stirred with NBS (1.05 equiv) in acetonitrile and DMF at room temperature until the reaction was deemed complete by HPLC, LC-MS, or TLC analysis. The mixture was concentrated, purified on prep-HPLC, and freeze-dried to afford compound, (1r,4r)-4-(7-amino-6-bromo-3-aryl-pyrazolo[1,5-a]pyrimidin-5-yl)cyclohexanecarboxylic acid.

When R=acetyl: Compound, (1r,4r)-tert-butyl 4-(7-(bis((2-(trimethylsilyl)ethoxy)methyl)amino)-3-aryl-pyrazolo[1,5-a]pyrimidin-5-yl)cyclohexanecarboxylate, (1 equiv) was stirred with NBS (1.05 equiv) in DMF at room temperature until the reaction was deemed complete by HPLC, LC-MS, or TLC analysis. The reaction was diluted with ethyl acetate, washed three times with brine, dried over sodium sulfate, filtered, concentrated, and purified on silica gel. The resulting material was stirred with a mixture of vinyl stannane (2 equiv), palladium catalyst (0.1 equiv), and potassium fluoride (3 equiv) in dioxane at 85° C. until the reaction was deemed complete by HPLC, LC-MS, or TLC analysis. The mixture was allowed to cool to room temperature, diluted with 10% aqueous potassium fluoride, and extracted three times with ethyl acetate. The combined organics were dried over sodium sulfate, filtered, concentrated, and purified on silica gel. The resulting material was stirred with a mixture of HCl in methanol and water at 60° C. until the reaction was deemed complete by HPLC, LC-MS, or TLC analysis. The mixture was then allowed to cool to room temperature, concentrated, purified by prep-HPLC, and freeze-dried to afford compound (1r,4r)-4-(6-acetyl-7-amino-3-aryl-pyrazolo[1,5-a]pyrimidin-5-yl)cyclohexanecarboxylic acid.

Essentially using the general procedure described above the compounds in the table 4-D can be synthesized.

TABLE 4D

| Example | Column 2 | M.Wt.(Cacld) | M.Wt (Observed) MH+ m/z | HPLC $t_R$ |
|---|---|---|---|---|
| 4.99 | | 455.06 | 456 | 8.02 |

TABLE 4D-continued

| Example | Column 2 | M.Wt.(Cacld) | M.Wt (Observed) MH+ m/z | HPLC $t_R$ |
|---|---|---|---|---|
| 4.100 | | 471.04 | 472.4 | 4.55 |
| 4.101 | | 471.04 | 472.2 | 8.23 |
| 4.102 | | 471.04 | 472.2 | 8.58 |
| 4.103 | | 469.07 | 470 | 6.93 |
| 4.104 | | 435.14 | 436.4 | 7.73 |

TABLE 4D-continued

| Example | Column 2 | M.Wt.(Cacld | M.Wt (Observed) MH+ m/z | HPLC $t_R$ |
|---|---|---|---|---|
| 4.105 | | 449.15 | 450.2 | 5.77 |
| 4.106 | | 455.06 | 456.3 | 5.49 |

6-Bromo-5-((1-(cyclopropylsulfonyl)piperidin-4-yl)methoxy)-3-(quinolin-3-yl)pyrazolo[1,5-a]pyrimidin-7-amine

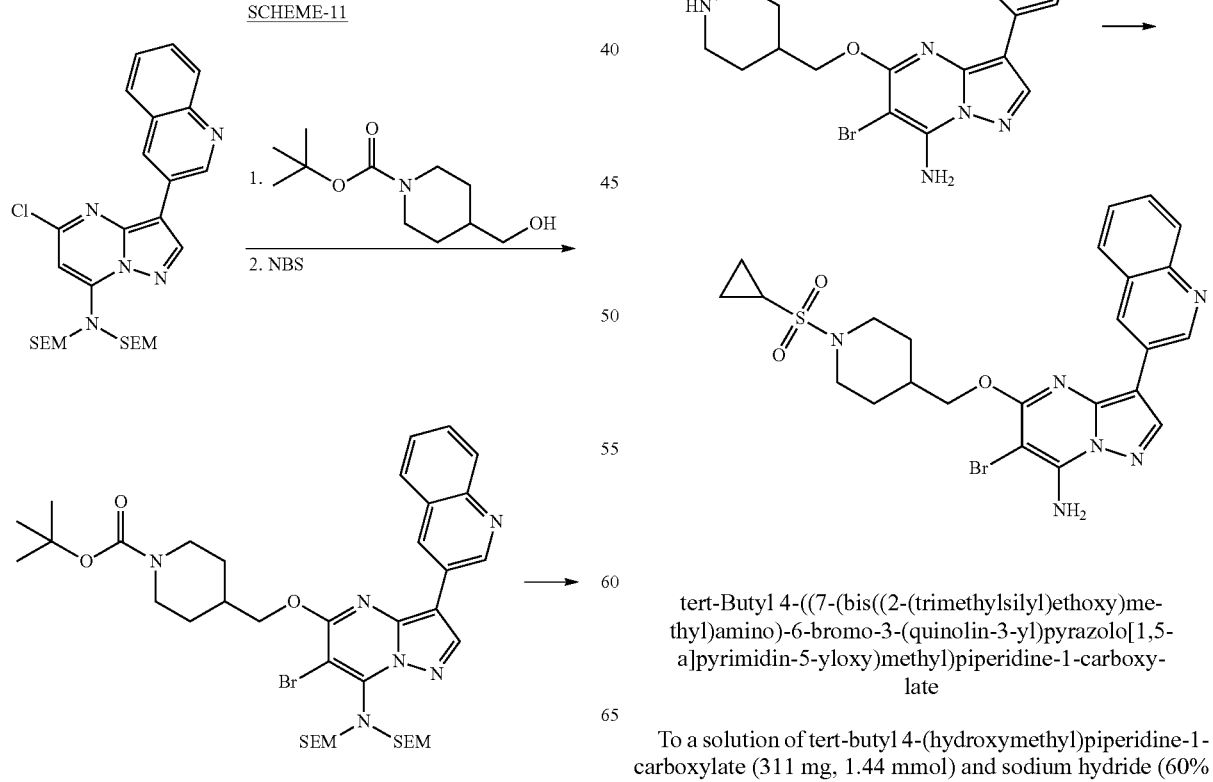

SCHEME-11 tert-Butyl 4-((7-(bis((2-(trimethylsilyl)ethoxy)methyl)amino)-6-bromo-3-(quinolin-3-yl)pyrazolo[1,5-a]pyrimidin-5-yloxy)methyl)piperidine-1-carboxylate To a solution of tert-butyl 4-(hydroxymethyl)piperidine-1-carboxylate (311 mg, 1.44 mmol) and sodium hydride (60% in mineral oil, 58 mg, 1.44 mmol) in THF (2 ml) under argon at room temperature was added 5-chloro-3-(quinolin-3-yl)-N,N-bis((2(trimethylsilyl)ethoxy)methyl)pyrazolo[1,5-a]pyrimidin-7-amine (400 mg, 0.72 mmol). The mixture was heated at 100° C. for 30 min in microwave. Ethyl acetate (50 ml) was added and the mixture was washed with brine and water, dried over $Na_2SO_4$, and concentrated in vacuo. The crude product was dissolved in acetonitrile, followed by the addition of N-bromosuccinimide (193 mg, 1.08 mmol). The reaction mixture was stirred at room temperature for 2 h, concentrated in vacuo and purified via silica gel chromatography (10% to 50% ethyl acetate in hexanes gradient) to yield the title compound (0.56 g, 95% yield). LC-MS: 813 [M+H].

6-Bromo-5-(piperidin-4-ylmethoxy)-3-(quinolin-3-yl)pyrazolo[1,5-a]pyrimidin-7-amine tert-Butyl 4-((7-(bis((2-(trimethylsilyl)ethoxy)methyl)amino)-6-bromo-3-(quinolin-3-yl)pyrazolo[1,5-a]pyrimidin-5-yloxy)methyl)piperidine-1-carboxylate (0.56 g, 68.9 mmol) was dissolved in methanol (6 ml) and treated with 4N hydrochloride solution in dioxane (4 ml) at 65° C. for 30 min. The reaction solution was concentrated and the crude product (0.48 g) was used in the next step without further purification. LC-MS: 453 [M+H].

6-Bromo-5-((1-(cyclopropylsulfonyl)piperidin-4-yl)methoxy)-3-(quinolin-3-yl)pyrazolo[1,5-a]pyrimidin-7-amine Cyclopropanesulfonyl chloride (24 mg, 0.167 mmol) was added into a solution of 6-bromo-5-(piperidin-4-ylmethoxy)-3-(quinolin-3-yl)pyrazolo[1,5-a]pyrimidin-7-amine (50 mg, 0.111 mmol) and triethylamine (56 mg, 0.553 mmol) in DMF at room temperature. The resulting reaction mixture was stirred at room temperature for 16 h, concentrated and purified by prep-LC to afford the title compound (21.5 mg): LC/MS RT=4.17 min. Mass calculated for, M+H 557.09, observed 557.09.

Compounds in the table-4-E can be synthesized as described following general procedure described above scheme (11)

TABLE 4E

| Compound ID | Structures | M + H (calc.) | M + H (observed) | LC/MS retention time (10 min method) |
|---|---|---|---|---|
| 4.107 | 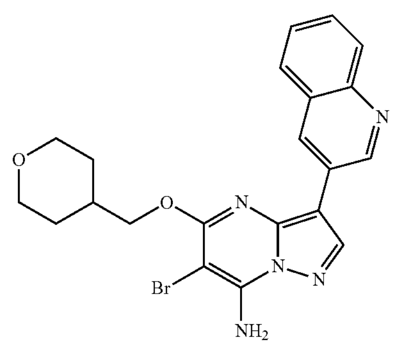 [SMILES: Nc1c(Br)c(OCC2CCOCC2)nc2c(-c3cnc4ccccc4c3)cnn12] | 454.08 | 454.08 | 3.96 |
| 4.108 | 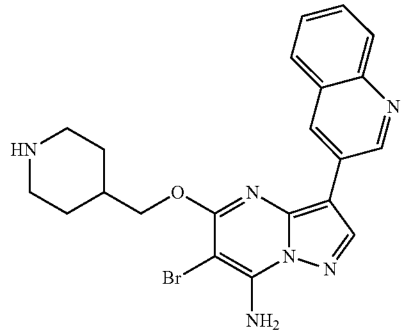 [SMILES: Nc1c(Br)c(OCC2CCNCC2)nc2c(-c3cnc4ccccc4c3)cnn12] | 453.10 | 453.10 | 2.66 |

TABLE 4E-continued
| Compound ID | Structures | M + H (calc.) | M + H (observed) | LC/MS retention time (10 min method) |
|---|---|---|---|---|
| 4.109 | 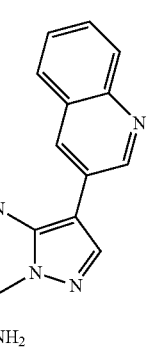 | 502.05 | 502.05 | 3.35 |
| 4.110 | 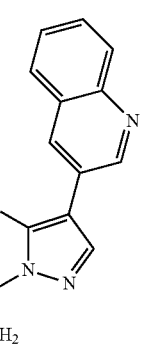 | 557.09 | 557.09 | 4.17 |
| 4.111 | 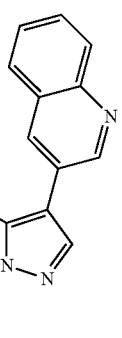 | 525.12 | 525.12 | 3.61 |
| 4.112 | 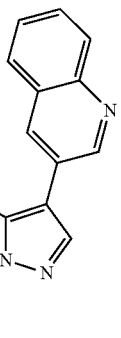 | 481.09 | 481.09 | 3.54 |

TABLE 4E-continued

| Compound ID | Structures | M + H (calc.) | M + H (observed) | LC/MS retention time (10 min method) |
|---|---|---|---|---|
| 4.113 | 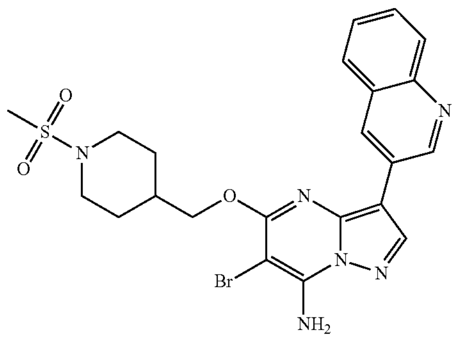 [SMILES: CS(=O)(=O)N1CCC(COc2nc3c(-c4cnc5ccccc5c4)cnn3c(N)c2Br)CC1] | 531.07 | 531.07 | 3.82 |
| 4.114 | 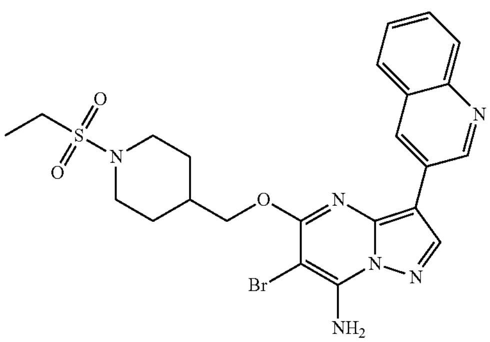 [SMILES: CCS(=O)(=O)N1CCC(COc2nc3c(-c4cnc5ccccc5c4)cnn3c(N)c2Br)CC1] | 545.09 | 545.09 | 4.07 |
| 4.115 | 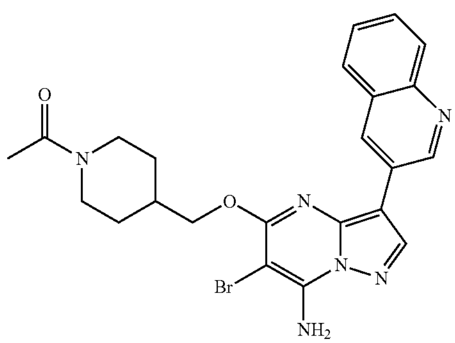 [SMILES: CC(=O)N1CCC(COc2nc3c(-c4cnc5ccccc5c4)cnn3c(N)c2Br)CC1] | 495.11 | 495.11 | 3.65 |
| 4.116 | 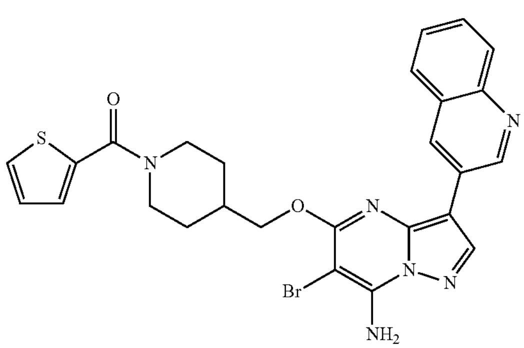 [SMILES: Nc1c(Br)c(OCC2CCN(C(=O)c3cccs3)CC2)nc2c(-c3cnc4ccccc4c3)cnn12] | 563.08 | 563.08 | 4.30 |

TABLE 4E-continued

| Compound ID | Structures | M + H (calc.) | M + H (observed) | LC/MS retention time (10 min method) |
|---|---|---|---|---|
| 4.117 | 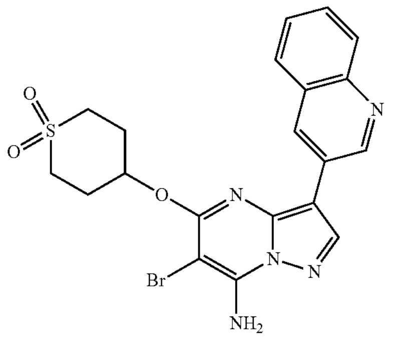 [SMILES: Nc1c(Br)c(OC2CCS(=O)(=O)CC2)nc2c(-c3cnc4ccccc4c3)cnn12] | 488.03 | 488.03 | 3.30 |
| 4.118 | 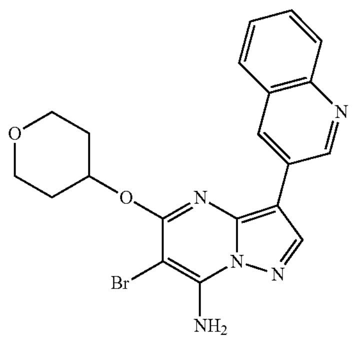 [SMILES: Nc1c(Br)c(OC2CCOCC2)nc2c(-c3cnc4ccccc4c3)cnn12] | 440.07 | 440.07 | 3.84 |
| 4.119 | 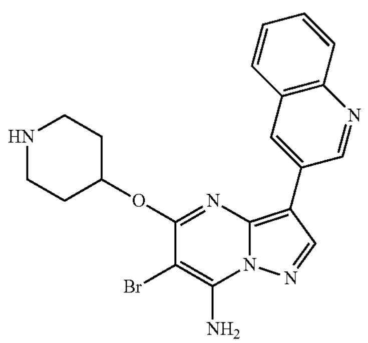 [SMILES: Nc1c(Br)c(OC2CCNCC2)nc2c(-c3cnc4ccccc4c3)cnn12] | 439.08 | 439.08 | 2.57 |
| 4.120 | 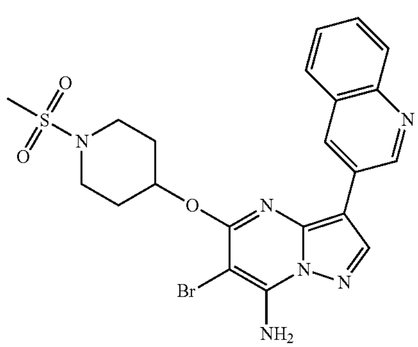 [SMILES: CS(=O)(=O)N1CCC(Oc2nc3c(-c4cnc5ccccc5c4)cnn3c(N)c2Br)CC1] | 517.06 | 517.06 | 3.68 |

TABLE 4E-continued
| Compound ID | Structures | M + H (calc.) | M + H (observed) | LC/MS retention time (10 min method) |
|---|---|---|---|---|
| 4.121 | 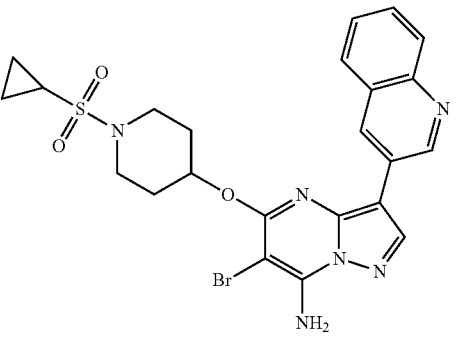 [SMILES: Nc1c(Br)c(OC2CCN(S(=O)(=O)C3CC3)CC2)nc2c(-c3cnc4ccccc4c3)cnn12] | 543.07 | 543.07 | 4.02 |
| 4.122 | 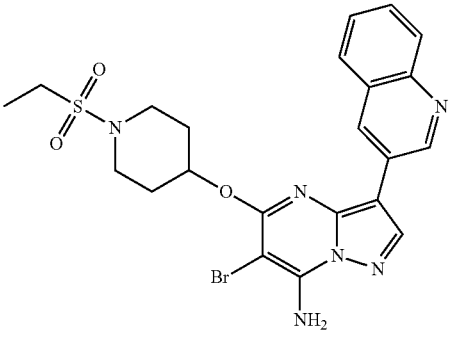 [SMILES: CCS(=O)(=O)N1CCC(Oc2nc3c(-c4cnc5ccccc5c4)cnn3c(N)c2Br)CC1] | 531.07 | 531.07 | 3.90 |
| 4.123 | 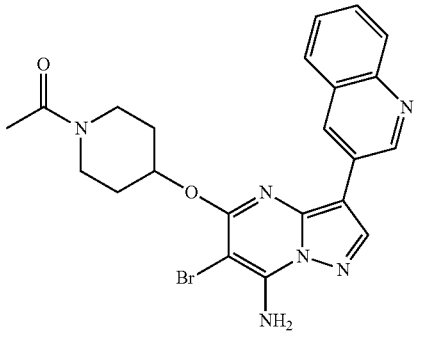 [SMILES: CC(=O)N1CCC(Oc2nc3c(-c4cnc5ccccc5c4)cnn3c(N)c2Br)CC1] | 481.09 | 481.09 | 3.48 |
| 4.124 | 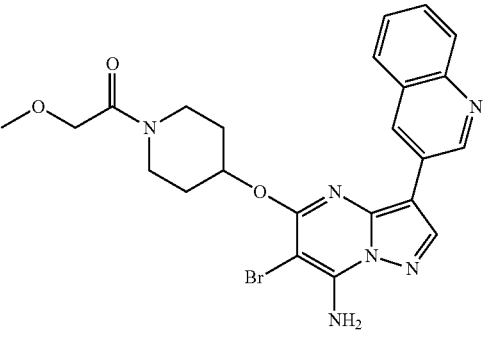 [SMILES: COCC(=O)N1CCC(Oc2nc3c(-c4cnc5ccccc5c4)cnn3c(N)c2Br)CC1] | 511.10 | 511.10 | 3.46 |

TABLE 4E-continued

| Compound ID | Structures | M + H (calc.) | M + H (observed) | LC/MS retention time (10 min method) |
| --- | --- | --- | --- | --- |
| 4.125 | 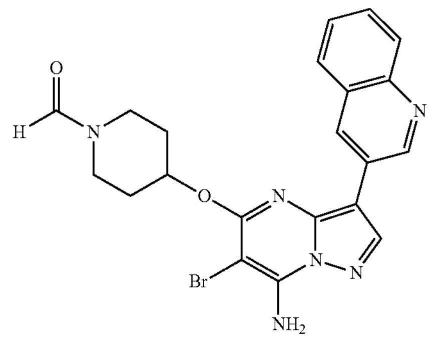 [SMILES: Nc1c(Br)c(OC2CCN(C=O)CC2)nc2c(-c3cnc4ccccc4c3)cnn12] | 467.08 | 467.08 | 3.37 |
| 4.126 | 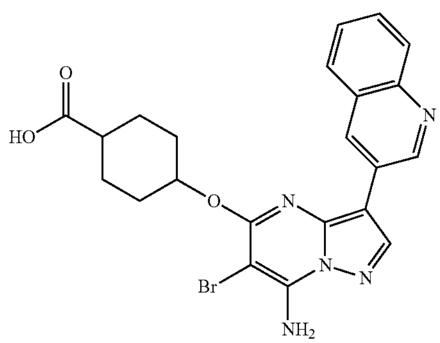 [SMILES: Nc1c(Br)c(OC2CCC(C(=O)O)CC2)nc2c(-c3cnc4ccccc4c3)cnn12] | 482.08 | 482.08 | 3.65 |
| 4.127 | 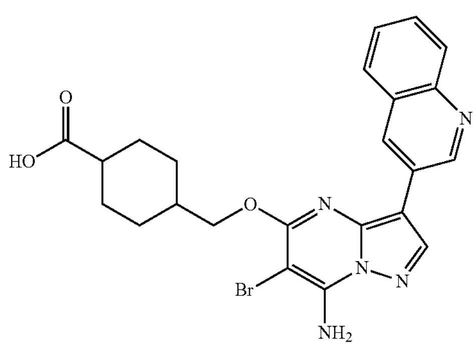 [SMILES: Nc1c(Br)c(OCC2CCC(C(=O)O)CC2)nc2c(-c3cnc4ccccc4c3)cnn12] | 496.09 | 496.09 | 3.89 |

By essentially using the similar experimental conditions used in the scheme 11, compounds in the table 4F can be synthesized.
TABLE 4F
| Compound ID | Structures | M + H (calc.) | M + H (observed) | LC/MS retention time (10 min method) |
|---|---|---|---|---|
| 4.128 | 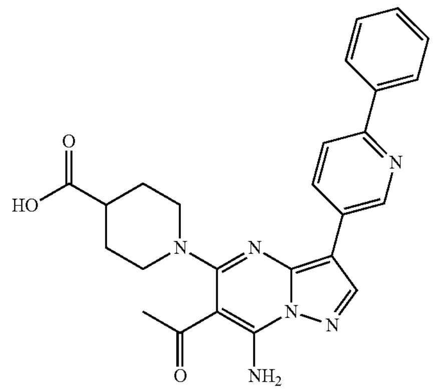 [SMILES: CC(=O)c1c(N2CCC(C(=O)O)CC2)nc2c(-c3ccc(-c4ccccc4)nc3)cnn2c1N] | 457.19 | 457.19 | 3.65 |
| 4.129 | 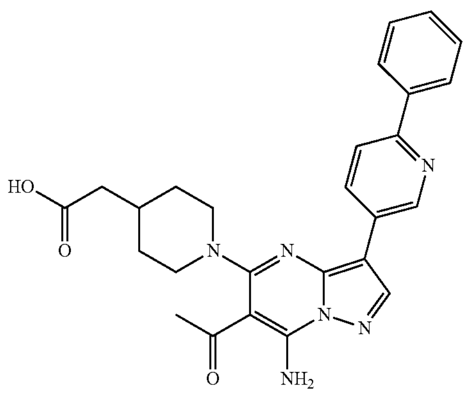 [SMILES: CC(=O)c1c(N2CCC(CC(=O)O)CC2)nc2c(-c3ccc(-c4ccccc4)nc3)cnn2c1N] | 471.21 | 471.21 | 3.55 |
2-(4-(7-amino-6-bromo-3-(quinolin-3-yl) pyrazolo[1,5-a]pyrimidin-5-yloxy)phenyl)acetic acid
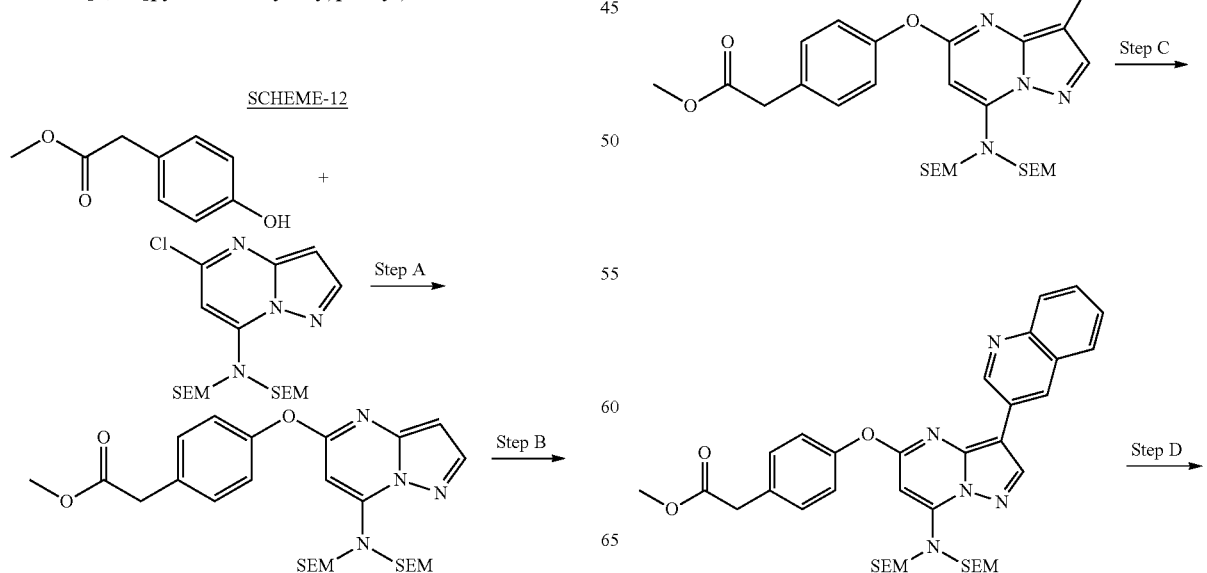

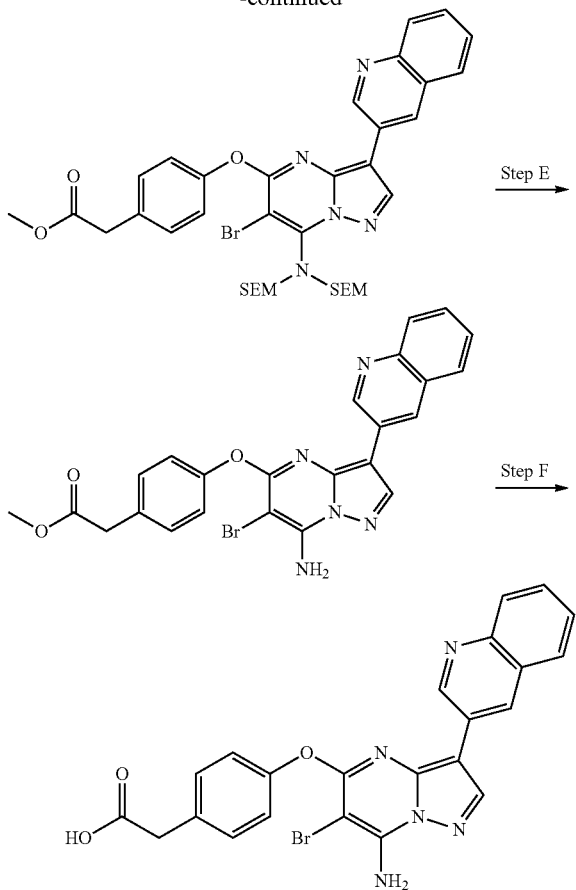

Part A:

Methyl 2-(4-(7-(bis((2-(trimethylsilyl)ethoxy)methyl)amino)pyrazolo[1,5-a]pyrimidin-5-yloxy)phenyl)acetate The compound methyl 2-(4-hydroxyphenyl)acetate (330 mg, 0.2 mmol) was dissolved in dry DMF (3 mL) and NaH (80 mg, 60% in oil, 0.2 mmol) was added and the mixture was stirred at room temperature for 5 min. Then, 5-chloro-N,N-bis((2-(trimethylsilyl)ethoxy)methyl)pyrazolo[1,5-a]pyrimidin-7-amine (430 mg, 0.1 mmol) was added and the resulting mixture was heated up to 130° C. with microwave and stirred for 30 min. After cooling to room temperature, NH$_4$Cl (aq) was added to quench the reaction and extracted with EtOAc (50 mL×3). The combined organics were washed with water and brine and dried over Na$_2$SO$_4$. After concentration, the residue was purified with column (silica gel, 20% EtOAc/Hexane) gave the product, methyl 2-(4-(7-(bis((2-(trimethylsilyl)ethoxy)methyl)amino)pyrazolo[1,5-a]pyrimidin-5-yloxy)phenyl)acetate, (490 mg) as clear oil. HPLC-MS $t_R$=2.77 min (UV$_{254\ nm}$); mass calculated for formula C$_{27}$H$_{42}$N$_4$O$_5$Si$_2$ 558.3, observed LCMS m/z 559.3 (M+H).

Part B:

Methyl 2-(4-(7-(bis((2-(trimethylsilyl)ethoxy)methyl)amino)-3-iodopyrazolo[1,5-a]pyrimidin-5-yloxy)phenyl)acetate Methyl 2-(4-(7-(bis((2-(trimethylsilyl)ethoxy)methyl)amino)pyrazolo[1,5-a]pyrimidin-5-yloxy)phenyl)acetate (450 mg, 0.81 mmol) was dissolved in ACN (15 mL) and NIS (200 mg, 0.88 mmol) was added. The resulting mixture was stirred at room temperature for 2 h and then the solvent was removed under reduced pressure. The residue was purified with column (silica gel, 10% EtOAc/Hexane) gave the product, methyl 2-(4-(7-(bis((2-(trimethylsilyl)ethoxy)methyl)amino)-3-iodopyrazolo[1,5-a]pyrimidin-5-yloxy)phenyl)acetate (541 mg) as yellowish oil. HPLC-MS $t_R$=2.96 min (UV$_{254\ nm}$); mass calculated for formula C$_{27}$H$_{41}$IN$_4$O$_5$Si$_2$ 684.2, observed LCMS m/z 685.2 (M+H).

Part C:

Methyl 2-(4-(7-(bis((2-(trimethylsilyl)ethoxy)methyl)amino)-3-(quinolin-3-yl)pyrazolo[1,5-a]pyrimidin-5-yloxy)phenyl)acetate Under Ar, compound, methyl 2-(4-(7-(bis((2-(trimethylsilyl)ethoxy)methyl)amino)-3-iodopyrazolo[1,5-a]pyrimidin-5-yloxy)phenyl)acetate (180 mg, 0.26 mmol) was mixed with Pd(dppf)Cl$_2$ (21 mg, 0.26 mmol, K$_3$PO$_4$ (106 mg, 0.5 mmol), 3-quinoline bornic acid (55 mg, 0.31 mmol) and dioxane (10 mL with 1 ml water). The resulting mixture was heated at 90° C. and stirred over night. After cooled to room temperature, the mixture was diluted with EtOAc (60 mL) and filtered through celite. After concentration, the crude was purified with column (silica gel, 0~30% EtOAc/Hexane) gave the product, methyl 2-(4-(7-(bis((2-(trimethylsilyl)ethoxy)methyl)amino)-3-(quinolin-3-yl)pyrazolo[1,5-a]pyrimidin-5-yloxy)phenyl)acetate (150 mg). HPLC-MS $t_R$=2.60 min (UV$_{254\ nm}$); mass calculated for formula C$_{36}$H$_{47}$N$_5$O$_5$Si$_2$ 685.3, observed LCMS m/z 686.3 (M+H).

Part D:

methyl 2-(4-(7-(bis((2-(trimethylsilyl)ethoxy)methyl)amino)-6-bromo-3-(quinolin-3-yl)pyrazolo[1,5-a]pyrimidin-5-yloxy)phenyl)acetate Compound, methyl 2-(4-(7-(bis((2-(trimethylsilyl)ethoxy)methyl)amino)-3-(quinolin-3-yl)pyrazolo[1,5-a]pyrimidin-5-yloxy)phenyl)acetate (150 mg, 0.22 mmol) was dissolved in ACN (10 mL). NBS (40 mg, 0.22 mmol) was added and the mixture was stirred at room temperature for 1 h. After concentration, the product, methyl 2-(4-(7-(bis((2-(trimethylsilyl)ethoxy)methyl)amino)-6-bromo-3-(quinolin-3-yl)pyrazolo[1,5-a]pyrimidin-5-yloxy)phenyl)acetate was used in the next step without further purification. HPLC-MS $t_R$=2.70 min (UV$_{254\ nm}$); mass calculated for formula C$_{36}$H$_{46}$BrN$_5$O$_5$Si$_2$ 763.2, observed LCMS m/z 764.2 (M+H).

Part E:

methyl 2-(4-(7-amino-6-bromo-3-(quinolin-3-yl)pyrazolo[1,5-a]pyrimidin-5-yloxy)phenyl)acetate The crude methyl 2-(4-(7-(bis((2-(trimethylsilyl)ethoxy)methyl)amino)-6-bromo-3-(quinolin-3-yl)pyrazolo[1,5-a]pyrimidin-5-yloxy)phenyl)acetate from above step D was treated with 50% TFA/H$_2$O (3 mL) and stirred at room temperature for 1 h. Solvent was removed to yield thick oil, methyl 2-(4-(7-amino-6-bromo-3-(quinolin-3-yl)pyrazolo[1,5-a]pyrimidin-5-yloxy)phenyl)acetate, which was used in the next step directly without further purification. HPLC-MS $t_R$=1.60 min (UV$_{254\ nm}$); Mass calculated for formula C$_{24}$H$_{18}$BrN$_5$O$_3$, 503.1, observed LCMS m/z 504.1 (M+Na).

Part F:

2-(4-(7-amino-6-bromo-3-(quinolin-3-yl)pyrazolo[1,5-a]pyrimidin-5-yloxy)phenyl)acetic acid Crude compound, methyl 2-(4-(7-amino-6-bromo-3-(quinolin-3-yl)pyrazolo[1,5-a]pyrimidin-5-yloxy)phenyl)

acetate from step E was dissolved in THF (5 mL) and LiOH (1N, 1 mL) was added. The mixture was stirred at room temperature overnight. The solvent was removed under vacuo, and the resulting residue was taken over with water and the pH value was adjusted to 5~6. The solid was collected with filtration and purified with HPLC gave the product, 2-(4-(7-amino-6-bromo-3-(quinolin-3-yl)pyrazolo[1,5-a]pyrimidin-5-yloxy)phenyl)acetic acid. HPLC-MS tR=1.53 min (UV254 nm); Mass calculated for formula $C_{23}H_{16}BrN_5O_3$, 489.0, observed LCMS m/z 490.0 (M+H).

By essentially the same procedure given in Preparative Example given above, compounds 4.130-4.144 given in Column 2 of Table 4G can be prepared.

TABLE 4G

| Example | Column 2 | MS Exact mass | MS m/z (M + H) | HPLC MS $t_R$ |
|---|---|---|---|---|
| 4.130 | 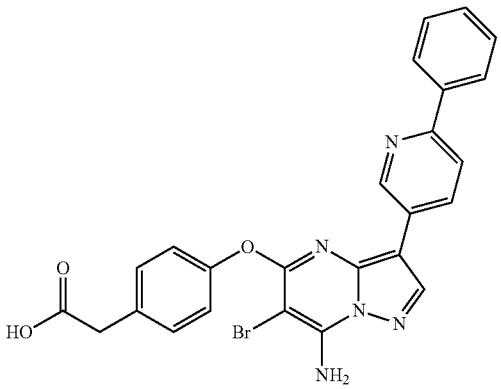 | 515.1 | 516.0 | 1.64 |
| 4.131 | 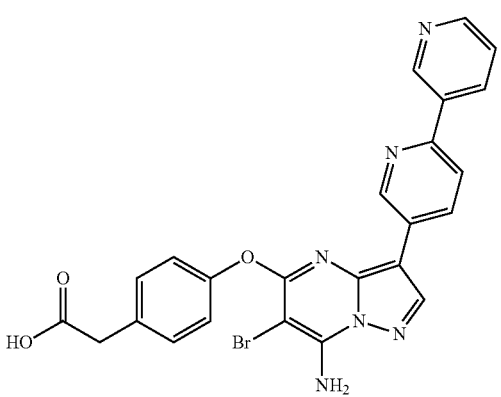 [SMILES: Nc1c(Br)c(Oc2ccc(CC(=O)O)cc2)nc2c(-c3ccc(-c4ccccc4)nc3)cnn12] | 516.1 | 517.0 | 1.49 |
| 4.132 | 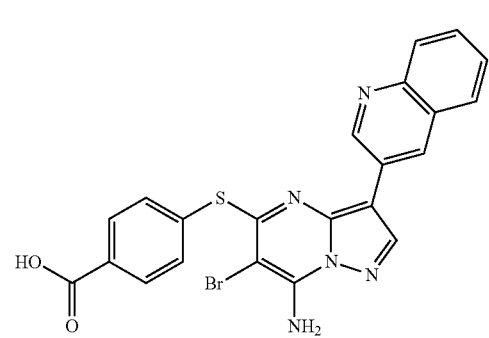 | 491.0 | 492.1 | 1.48 |

TABLE 4G-continued
| Example | Column 2 | Exact mass | MS m/z (M + H) | HPLC MS $t_R$ |
|---|---|---|---|---|
| 4.133 | 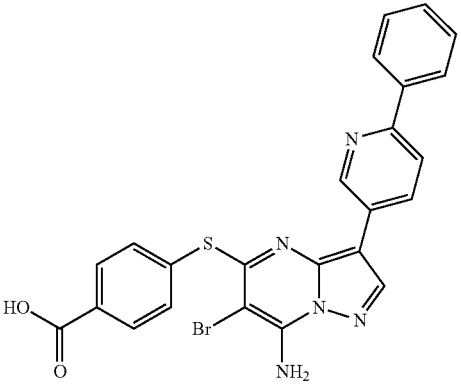 | 517.0 | 518.0 | 1.62 |
| 4.134 | 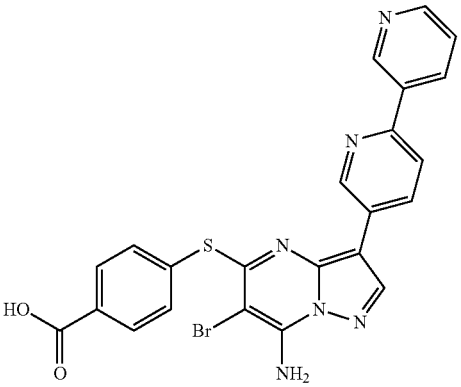 [SMILES: Nc1c(Br)c(Sc2ccc(C(=O)O)cc2)nc2c(-c3ccc(-c4cccnc4)nc3)cnn12] | 518.0 | 519.1 | 1.49 |
| 4.135 | 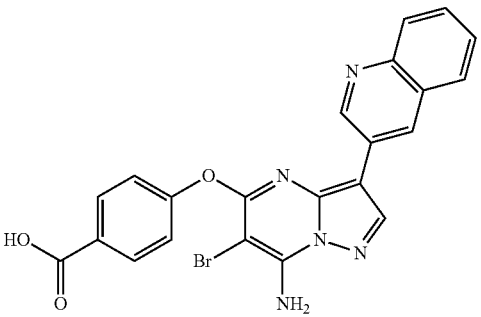 [SMILES: Nc1c(Br)c(Oc2ccc(C(=O)O)cc2)nc2c(-c3cnc4ccccc4c3)cnn12] | 475.0 | 475.9 | 1.49 |
| 4.136 | 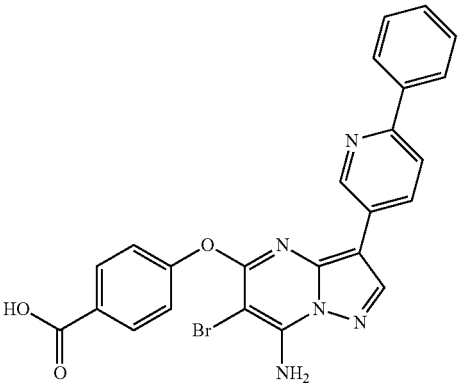 [SMILES: Nc1c(Br)c(Oc2ccc(C(=O)O)cc2)nc2c(-c3ccc(-c4ccccc4)nc3)cnn12] | 501.0 | 502.0 | 1.60 |

TABLE 4G-continued

| Example | Column 2 | Exact mass | MS m/z (M + H) | HPLC MS $t_R$ |
|---|---|---|---|---|
| 4.137 | | 502.0 | 502.9 | 1.45 |
| 4.138 | | 505.0 | 505.9 | 1.65 |
| 4.139 | | 531.0 | 532.0 | 1.76 |
| 4.140 | | 532.0 | 532.9 | 1.61 |

TABLE 4G-continued

| Example | Column 2 | Exact mass | MS m/z (M + H) | HPLC MS $t_R$ |
|---|---|---|---|---|
| 4.141 | | 502.0 | 503.0 | 1.90 |
| 4.142 | | 490.0 | 491.0 | 1.84 |
| 4.143 | | 502.0 | 503.1 | 1.28 |
| 4.144 | | 503.0 | 504.1 | 1.14 |

811

Synthesis of 4-(7-amino-6-bromo-3-(6-phenylpyridin-3-yl)pyrazolo[1,5-a]pyrimidin-5-yl)benzoic acid

SCHEME-13

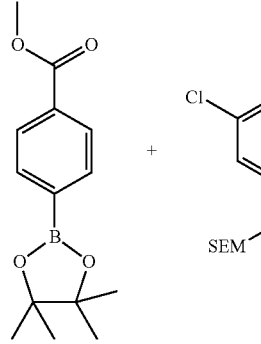

Step A

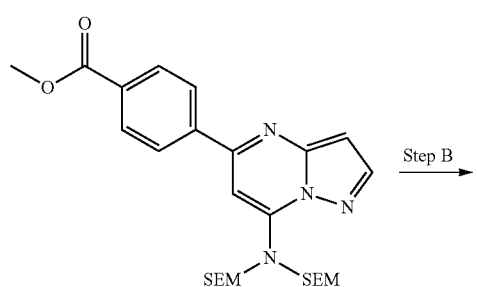

Step B

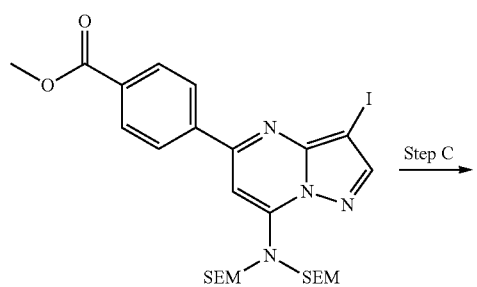

Step C

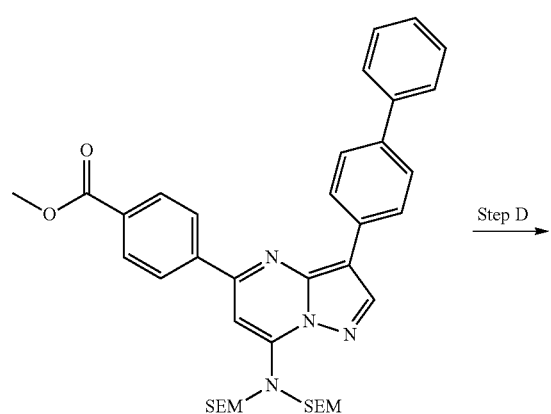

Step D

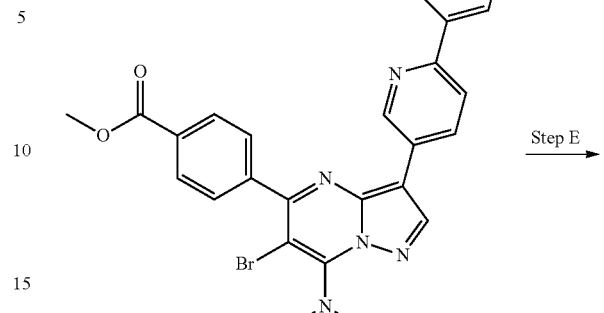

Step E

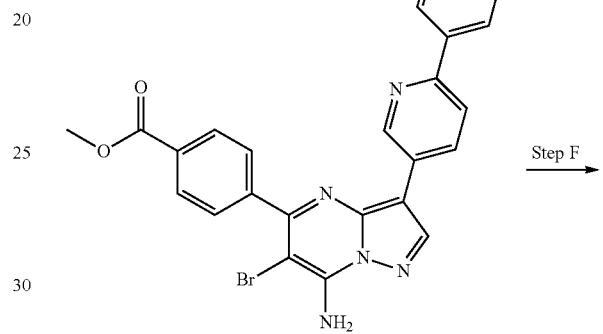

Step F

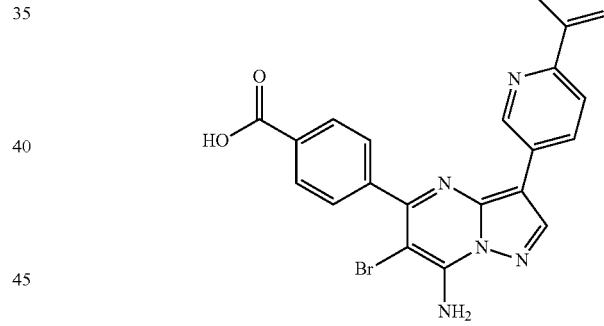

Part A:

Synthesis of methyl 4-(7-(bis((2-(trimethylsilyl)ethoxy)methyl)amino)pyrazolo[1,5-a]pyrimidin-5-yl)benzoate Under Ar, compound, 5-chloro-N,N-bis((2-(trimethylsilyl)ethoxy)methyl)pyrazolo[1,5-a]pyrimidin-7-amine, (430 mg, 1.0 mmol) was mixed with Pd(dppf)Cl$_2$ (82 mg, 0.1 mmol), K$_3$PO$_4$ (636 mg, 3.0 mmol), methyl 4-(4,4,5,5-tetramethyl-1,3,2-dioxaborolan-2-yl)benzoate (200 mg, 1.1 mmol) and dioxane (20 mL with 1 ml water). The resulting mixture was heated at 90° C. and stirred over night. After cooled to room temperature, the mixture was diluted with EtOAc (60 mL) and filtered through celite. After concentration, the crude was purified with column (silica gel, 0-30% EtOAc/Hexane) gave the product, methyl 4-(7-(bis((2-(trimethylsilyl)ethoxy)methyl)amino)pyrazolo[1,5-a]pyrimidin-5-yl)benzoate (459 mg). HPLC-MS $t_R$=2.89 min (UV$_{254\ nm}$); mass calculated for formula $C_{26}H_{40}N_4O_4Si_2$ 528.3, observed LCMS m/z 529.2 (M+H).

Part B:

Synthesis of methyl 4-(7-(bis((2-(trimethylsilyl)ethoxy)methyl)amino)-3-iodopyrazolo[1,5-a]pyrimidin-5-yl)benzoate Compound, methyl 4-(7-(bis((2-(trimethylsilyl)ethoxy)methyl)amino)-3-iodopyrazolo[1,5-a]pyrimidin-5-yl)benzoate was prepared with the same iodonation condition described in scheme-12 Part B. HPLC-MS $t_R$=3.09 min (UV$_{254\ nm}$); mass calculated for formula C26H39IN4O4Si2 654.2, observed LCMS m/z 655.2 (M+H).

Part C:

Synthesis of methyl 4-(3-(biphenyl-4-yl)-7-(bis((2-(trimethylsilyl)ethoxy) methyl)amino)pyrazolo[1,5-a]pyrimidin-5-yl)benzoate Title Compound, methyl 4-(3-(biphenyl-4-yl)-7-(bis((2-(trimethylsilyl)ethoxy)methyl)amino)pyrazolo[1,5-a]pyrimidin-5-yl)benzoate was prepared with the same coupling condition described in the scheme-12 Part C. HPLC-MS $t_R$=2.98 min (UV$_{254\ nm}$); mass calculated for formula C37H47N5O4Si2 681.3, observed LCMS m/z 682.2 (M+H).

Part D:

Synthesis of methyl 4-(7-(bis((2-(trimethylsilyl)ethoxy)methyl)amino)-6-bromo-3-(6-phenylpyridin-3-yl)pyrazolo[1,5-a]pyrimidin-5-yl)benzoate Title Compound was prepared with the same bromonation condition described in Scheme-12, Part D. HPLC-MS $t_R$=3.11 min (UV$_{254\ nm}$); mass calculated for formula $C_{37}H_{46}BrN_5O_4Si_2$ 759.2, observed LCMS m/z 760.2 (M+H).

Part E:

Synthesis of methyl 4-(7-amino-6-bromo-3-(6-phenylpyridin-3-yl)pyrazolo[1,5-a]pyrimidin-5-yl)benzoate Title compound, methyl 4-(7-amino-6-bromo-3-(6-phenylpyridin-3-yl)pyrazolo[1,5-a]pyrimidin-5-yl)benzoate was prepared with the same deprotection condition described in Scheme-12 Part E. HPLC-MS $t_R$=1.88 min (UV$_{254\ nm}$); mass calculated for formula $C_{25}H_{18}BrN_5O_2$ 499.1, observed LCMS m/z 500.1 (M+H).

Part F:

4-(7-amino-6-bromo-3-(6-phenylpyridin-3-yl)pyrazolo[1,5-a]pyrimidin-5-yl)benzoic acid Compound, 4-(7-amino-6-bromo-3-(6-phenylpyridin-3-yl)pyrazolo[1,5-a]pyrimidin-5-yl)benzoic acid was prepared with the same hydrolysis condition described in Scheme-12 Part E. HPLC-MS $t_R$=1.44 min (UV$_{254\ nm}$); mass calculated for formula $C_{24}H_{16}BrN_5O_2$ 485.0, observed LCMS m/z 486.1 (M+H).

By essentially the same procedure given in Preparative scheme-13 above, compound 4.145-4.166 given in Column 2 of Table 4 H can be prepared from compound 2.

TABLE 4H

| Example | Column 2 | Exact mass | MS m/z (M + H) | HPLC MS $t_R$ |
|---|---|---|---|---|
| 4.145 | | 508.1 | 509.0 | 1.91 |

TABLE 4H-continued

| Example | Column 2 | Exact mass | MS m/z (M + H) | HPLC MS $t_R$ |
|---------|----------|-----------|----------------|---------------|
| 4.146 | | 509.1 | 510.1 | 1.50 |
| 4.147 | | 499.1 | 500.1 | 1.48 |
| 4.148 | | 500.1 | 501.1 | 1.23 |
| 4.149 | | 488.1 | 489.1 | 1.81 |

TABLE 4H-continued
| Example | Column 2 | MS Exact mass | MS m/z (M + H) | HPLC MS $t_R$ |
|---|---|---|---|---|
| 4.150 | 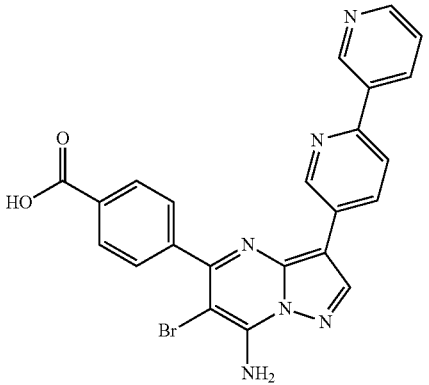 [SMILES: Nc1c(Br)c(-c2ccc(C(=O)O)cc2)nc2c(-c3ccc(-c4cccnc4)nc3)cnn12] | 486.0 | 487.0 | 1.24 |
| 4.151 | 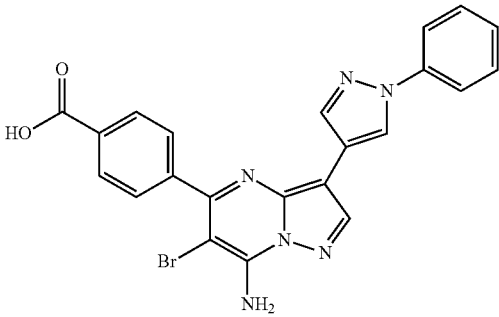 | 474.0 | 475.1 | 1.80 |
| 4.152 | 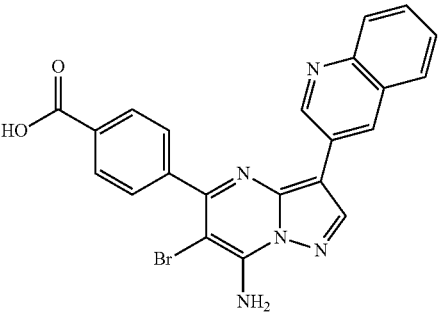 [SMILES: Nc1c(Br)c(-c2ccc(C(=O)O)cc2)nc2c(-c3cnc4ccccc4c3)cnn12] | 459.0 | 460.0 | 1.41 |
| 4.153 | 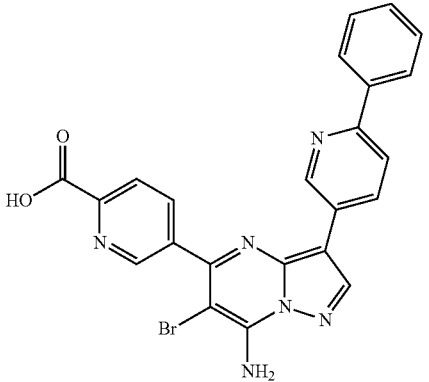 [SMILES: Nc1c(Br)c(-c2ccc(C(=O)O)nc2)nc2c(-c3ccc(-c4ccccc4)nc3)cnn12] | 486.0 | 487.0 | 1.40 |

TABLE 4H-continued

| Example | Column 2 | Exact mass | MS m/z (M + H) | HPLC MS $t_R$ |
|---|---|---|---|---|
| 4.154 | | 475.0 | 476.0 | 1.75 |
| 4.155 | | 486.0 | 487.1 | 1.26 |
| 4.156 | | 528.1 | 529.0 | 1.51 |
| 4.157 | | 475.0 | 476.0 | 1.36 |

TABLE 4H-continued

| Example | Column 2 | Exact mass | MS m/z (M + H) | HPLC MS $t_R$ |
|---|---|---|---|---|
| 4.158 | | 474.0 | 475.0 | 1.40 |
| 4.159 | | 491.0 | 492.0 | 1.47 |
| 4.160 | | 489.1 | 490.1 | 1.24 |
| 4.161 | | 485.0 | 486.1 | 1.44 |

TABLE 4H-continued

| Example | Column 2 | Exact mass | MS m/z (M + H) | HPLC MS $t_R$ |
|---|---|---|---|---|
| 4.162 | | 501.0 | 502.1 | 1.30 |
| 4.163 | | 486.0 | 487.1 | 1.25 |
| 4.164 | | 516.1 | 517.0 | 1.32 |

TABLE 4H-continued
| Example | Column 2 | Exact mass | MS m/z (M + H) | HPLC MS $t_R$ |
|---|---|---|---|---|
| 4.165 | | 546.0 | 547.0 | 1.27 |
| 4.166 | | 546.0 | 547.0 | 1.25 |
Synthesis of 4-(6-acetyl-7-amino-3-(6-phenylpyridin-3-yl)pyrazolo[1,5-a]pyrimidin-5-yl)benzoic acid
SCHEME-14
-continued
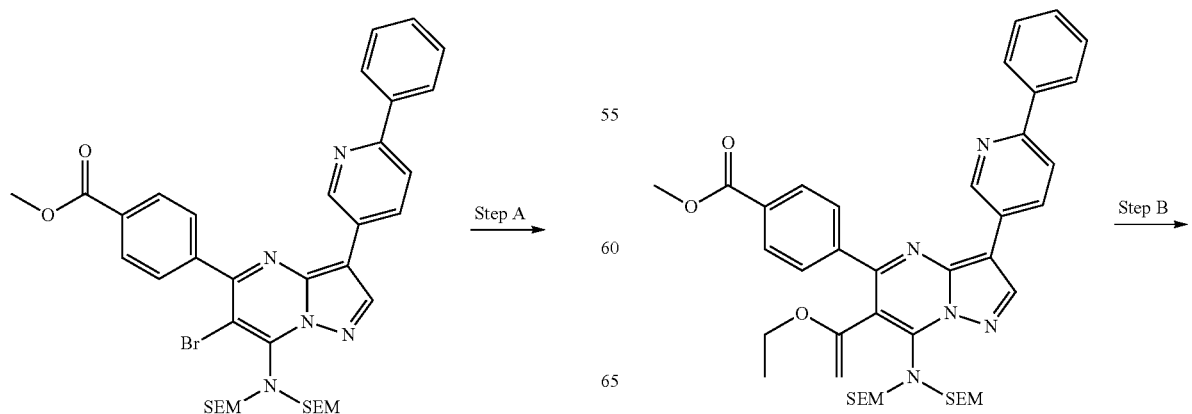

-continued

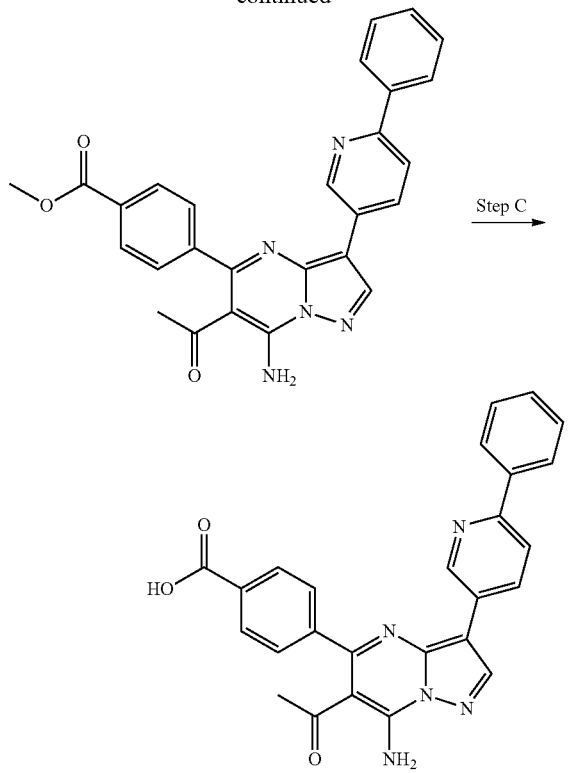

Step C

Part A methyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)benzoate Compound, methyl 4-(7-(bis((2-(trimethylsilyl)ethoxy)methyl)amino)-6-bromo-3-(6-phenylpyridin-3-yl)pyrazolo[1,5-a]pyrimidin-5-yl)benzoate (40 mg, 0.053 mmol) under Argon, was mixed with Pd(PPh$_3$)$_4$ (12 mg, 0.01 mmol, (1-ethoxyvinyl)tributylstannane (85 uL, 0.25 mmol) and dioxane (3 mL). The resulting mixture was heated at 100° C. and stirred over night. After cooled to room temperature, the mixture was filtered through 10% KF on silica gel and washed with EtOAc. After concentration, the crude product, methyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)benzoate was used in the next step directly without further purification. HPLC-MS $t_R$=3.18 min (UV$_{254\ nm}$); mass calculated for formula C$_{41}$H$_{53}$N$_5$O$_5$Si$_2$ 751.4, observed LCMS m/z 752.3 (M+H).

Part B

Methyl 4-(6-acetyl-7-amino-3-(6-phenylpyridin-3-yl)pyrazolo[1,5-a]pyrimidin-5-yl)benzoate Compound, methyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)benzoate was treated with 4N HCl in dioxane for 2 hrs to result in the product, methyl 4-(6-acetyl-7-amino-3-(6-phenylpyridin-3-yl)pyrazolo[1,5-a]pyrimidin-5-yl)benzoate purified by prep. HPLC. HPLC-MS $t_R$=1.85 min (UV$_{254\ nm}$); mass calculated for formula C$_{27}$H$_{21}$N$_5$O$_3$ 463.2, observed LCMS m/z 464.0 (M+H).

Part C:

4-(6-acetyl-7-amino-3-(6-phenylpyridin-3-yl)pyrazolo[1,5-a]pyrimidin-5-yl)benzoic acid Compound methyl 4-(6-acetyl-7-amino-3-(6-phenylpyridin-3-yl)pyrazolo[1,5-a]pyrimidin-5-yl)benzoate was treated with 2 equivalents of LiOH and stirred at room temperature for 4 hrs. Neutralization with dil.HCl and extraction in to organic layer, gave the product, 4-(6-acetyl-7-amino-3-(6-phenylpyridin-3-yl)pyrazolo[1,5-a]pyrimidin-5-yl)benzoic acid in quantitative yield. The compound dissolved in to water-acetonitrile and lyophilized to give a white powder. HPLC-MS $t_R$=1.49 min (UV$_{254\ nm}$); mass calculated for formula C$_{26}$H$_{19}$N$_5$O$_3$ 449.1, observed LCMS m/z 450.2 (M+H).

By essentially the same procedure given in above preparative example, compounds 4.167-4.171 given in Column 2 of Table 41 can be prepared.

TABLE 4I

| Compound ID | Column 2 | Exact mass | MS m/z (M + H) | HPLC MS $t_R$ |
|---|---|---|---|---|
| 4.167 | | 492.2 | 493.1 | 1.68 |

TABLE 4I-continued

| Compound ID | Column 2 | Exact mass | MS m/z (M + H) | HPLC MS $t_R$ |
|---|---|---|---|---|
| 4.168 | | 449.1 | 450.2 | 1.44 |
| 4.169 | | 450.1 | 451.1 | 1.25 |
| 4.170 | | 510.1 | 511.1 | 1.22 |
| 4.171 | | 499.1 | 500.1 | 1.58 |

831

Synthesis of 6-bromo-5-(4-(methylsulfonyl)phenoxy)-3-(quinolin-3-yl)pyrazolo[1,5-a]pyrimidin-7-amine

SCHEME-15

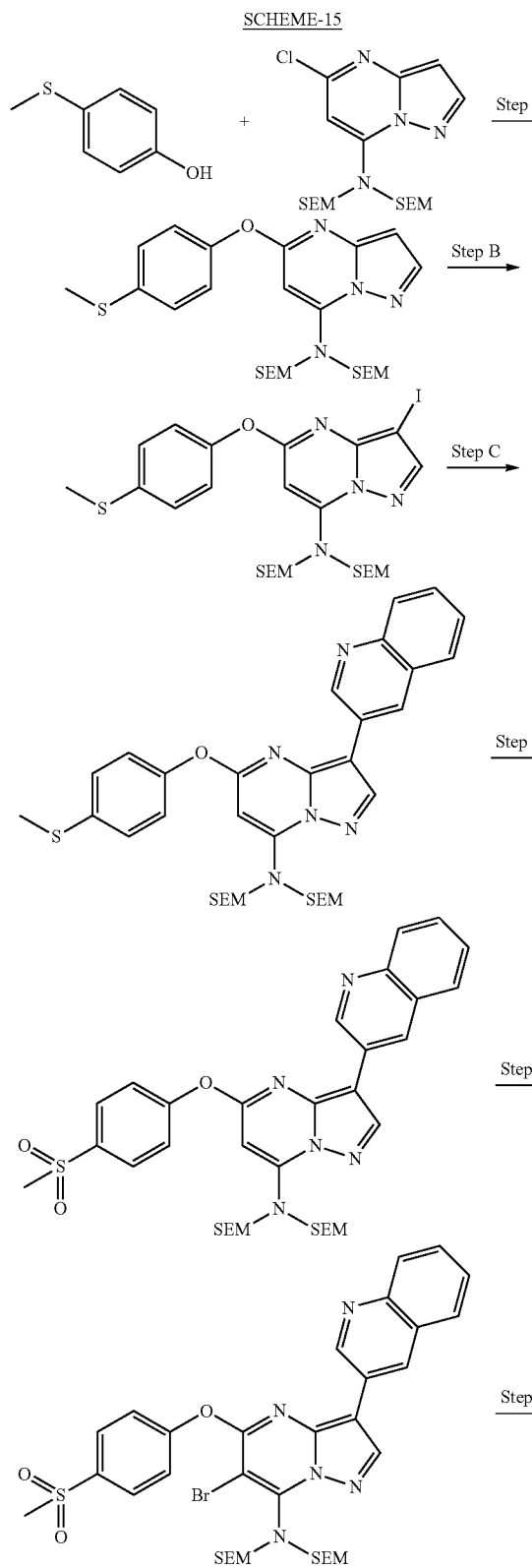

832

-continued

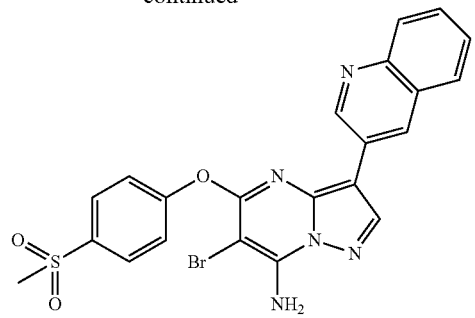

Part A:

5-(4-(methylthio)phenoxy)-N,N-bis((2-(trimethylsilyl)ethoxy)methyl)pyrazolo[1,5-a]pyrimidin-7-amine The 4-(methylthio)phenol (280 mg, 2.0 mmol) was dissolved in dry DMF (3 mL) and NaH (88 mg, 60% in oil, 2.2 mmol) was added and the mixture was stirred at room temperature for 5 min. Then, 5-chloro-N,N-bis((2-(trimethylsilyl)ethoxy)methyl)pyrazolo[1,5-a]pyrimidin-7-amine (430 mg, 0.1 mmol) was added and the resulting mixture was heated up to 130° C. with Microwave and stirred for 30 min. After cooling to room temperature, NH4Cl (aq) was added to quench the reaction and extracted with EtOAc (50 mL×3). The combined organics were washed with water and brine and dried over $Na_2SO_4$. After concentration, the residue was purified with column (silica gel, 20% EtOAc/Hexane) gave the product 5-(4-(methylthio)phenoxy)-N,N-bis((2-(trimethylsilyl)ethoxy)methyl)pyrazolo[1,5-a]pyrimidin-7-amine (490 mg) HPLC-MS $t_R$=2.98 min ($UV_{254\ nm}$); mass calculated for formula $C_{25}H_{40}N_4O_3SSi_2$ 532.2, observed LCMS m/z 533.2 (M+H).

Part B:

3-iodo-5-(4-(methylthio)phenoxy)-N,N-bis((2-(trimethylsilyl)ethoxy)methyl)pyrazolo[1,5-a]pyrimidin-7-amine 5-(4-(methylthio)phenoxy)-N,N-bis((2-(trimethylsilyl)ethoxy)methyl)pyrazolo[1,5-a]pyrimidin-7-amine (490 mg, 0.81 m) was dissolved in ACN (15 mL) and NIS (200 mg, 0.88 mmol) was added. The resulting mixture was stirred at room temperature for 2 h and then the solvent was removed under reduced pressure. The residue was purified with column (silica gel, 10% EtOAc/Hexane) gave the product, 3-iodo-5-(4-(methylthio)phenoxy)-N,N-bis((2-(trimethylsilyl)ethoxy)methyl)pyrazolo[1,5-a]pyrimidin-7-amine (541 mg) as yellowish oil. HPLC-MS $t_R$=3.18 min ($UV_{254\ nm}$); mass calculated for formula C25H39IN4O3SSi2 658.1, observed LCMS m/z 659.2 (M+H).

Part C:

5-(4-(methylthio)phenoxy)-3-(quinolin-3-yl)-N,N-bis((2-(trimethylsilyl)ethoxy)methyl)pyrazolo[1,5-a]pyrimidin-7-amine 3-iodo-5-(4-(methylthio)phenoxy)-N,N-bis((2-(trimethylsilyl)ethoxy)methyl)pyrazolo[1,5-a]pyrimidin-7-amine (180 mg, 0.26 mmol) under Argon, was mixed with Pd(dppf)Cl₂ (21 mg, 0.26 mmol, $K_3PO_4$ (106 mg, 0.5 mmol), 3-quinoline bornic acid (55 mg, 0.31 mmol) and dioxane (10 mL with 1 ml water). The resulting mixture was heated at 90° C. and stirred over night. After cooled to room temperature, the mixture was diluted with EtOAc (60 mL) and filtered through celite. After concentration, the crude was purified with column (silica gel, 0~30% EtOAc/Hexane) gave the product 5-(4-(methylthio)phenoxy)-3-(quinolin-3-yl)-N,N-bis((2-(trimethylsilyl)ethoxy)methyl)pyrazolo[1,5-a]pyrimidin-7-amine (150 mg). HPLC-MS $t_R$=2.85 min (UV$_{254\ nm}$); mass calculated for formula $C_{34}H_{45}N_5O_3SSi_2$ 659.3, observed LCMS m/z 660.1 (M+H).

Part D:

5-(4-(methylsulfonyl)phenoxy)-3-(quinolin-3-yl)-N,N-bis((2-(trimethylsilyl)ethoxy)methyl)pyrazolo[1,5-a]pyrimidin-7-amine Compound, 5-(4-(methylthio)phenoxy)-3-(quinolin-3-yl)-N,N-bis((2-(trimethylsilyl)ethoxy)methyl)pyrazolo[1,5-a]pyrimidin-7-amine (87 mg, 0.132 mmol) was dissolved in DCM (5 mL) and m-CPBA (66 mg, ~70%, 0.27 mmol) was added. The result mixture was stirred at room temperature for 1 h. NaHCO3 (aq.) was added and the water was extracted with DCM. The combined organics was dried over Na2SO4 and concentrated. The crude was purified with column (silica gel, 0~30% EtOAc/Hexane) gave the product, 5-(4-(methylsulfonyl)phenoxy)-3-(quinolin-3-yl)-N,N-bis((2-(trimethylsilyl)ethoxy)methyl)pyrazolo[1,5-a]pyrimidin-7-amine (89 mg). HPLC-MS $t_R$=2.37 min (UV$_{254\ nm}$); mass calculated for formula $C_{34}H_{45}N_5O_5SSi_2$ 691.3, observed LCMS m/z 692.2 (M+H).

Part E:

6-Bromo-5-(4-(methylsulfonyl)phenoxy)-3-(quinolin-3-yl)-N,N-bis((2-(trimethylsilyl)ethoxy)methyl)pyrazolo[1,5-a]pyrimidin-7-amine Compound, 5-(4-(methylsulfonyl)phenoxy)-3-(quinolin-3-yl)-N,N-bis((2-(trimethylsilyl)ethoxy)methyl)pyrazolo[1,5-a]pyrimidin-7-amine (150 mg, 0.22 mmol) was dissolved in ACN (10 mL). NBS (40 mg, 0.22 mmol) was added and the mixture was stirred at room temperature for 1 h. After concentration, the residue, 6-bromo-5-(4-(methylsulfonyl)phenoxy)-3-(quinolin-3-yl)-N,N-bis((2-(trimethylsilyl)ethoxy)methyl)pyrazolo[1,5-a]pyrimidin-7-amine was used in the next step without further purification. HPLC-MS $t_R$=2.66 min (UV$_{254\ nm}$); mass calculated for formula $C_{34}H_{44}BrN_5O_5SSi_2$ 769.2, observed LCMS m/z 770.0 (M+H).

Part F:

6-bromo-5-(4-(methylsulfonyl)phenoxy)-3-(quinolin-3-yl)pyrazolo[1,5-a]pyrimidin-7-amine The crude, 6-bromo-5-(4-(methylsulfonyl)phenoxy)-3-(quinolin-3-yl)-N,N-bis((2-(trimethylsilyl)ethoxy)methyl)pyrazolo[1,5-a]pyrimidin-7-amine from above step E was treated with 50% TFA/H$_2$O (3 mL) and stirred at room temperature for 1 h. Solvent was removed to yield thick oil which was purified by prep HPLC to give the final product. 6-bromo-5-(4-(methylsulfonyl)phenoxy)-3-(quinolin-3-yl)pyrazolo[1,5-a]pyrimidin-7-amine. HPLC-MS $t_R$=1.37 min (UV$_{254\ nm}$); mass calculated for formula $C_{22}H_{16}BrN_5O_3S_2$ 509.0, observed LCMS m/z 510.0 (M+H).

By essentially the same procedure given in Preparative above Example, compounds 4.172-4.174 given in Column 2 of Table 4J can be prepared.

TABLE 4-J

| Example | Column 2 | Exact mass | MS m/z (M + H) | HPLC MS $t_R$ |
|---|---|---|---|---|
| 4.172 | | 493.0 | 494.0 | 1.28 |
| 4.173 | | 535.0 | 536.0 | 1.52 |

TABLE 4-J-continued
| Example | Column 2 | Exact mass | MS m/z (M + H) | HPLC MS $t_R$ |
|---|---|---|---|---|
| 4.174 | | 536.0 | 537.0 | 1.44 |
Synthesis of 2-(4-((7-amino-6-bromo-3-(quinolin-3-yl)pyrazolo[1,5-a]pyrimidin-5-yl)methyl)phenyl)acetic acid
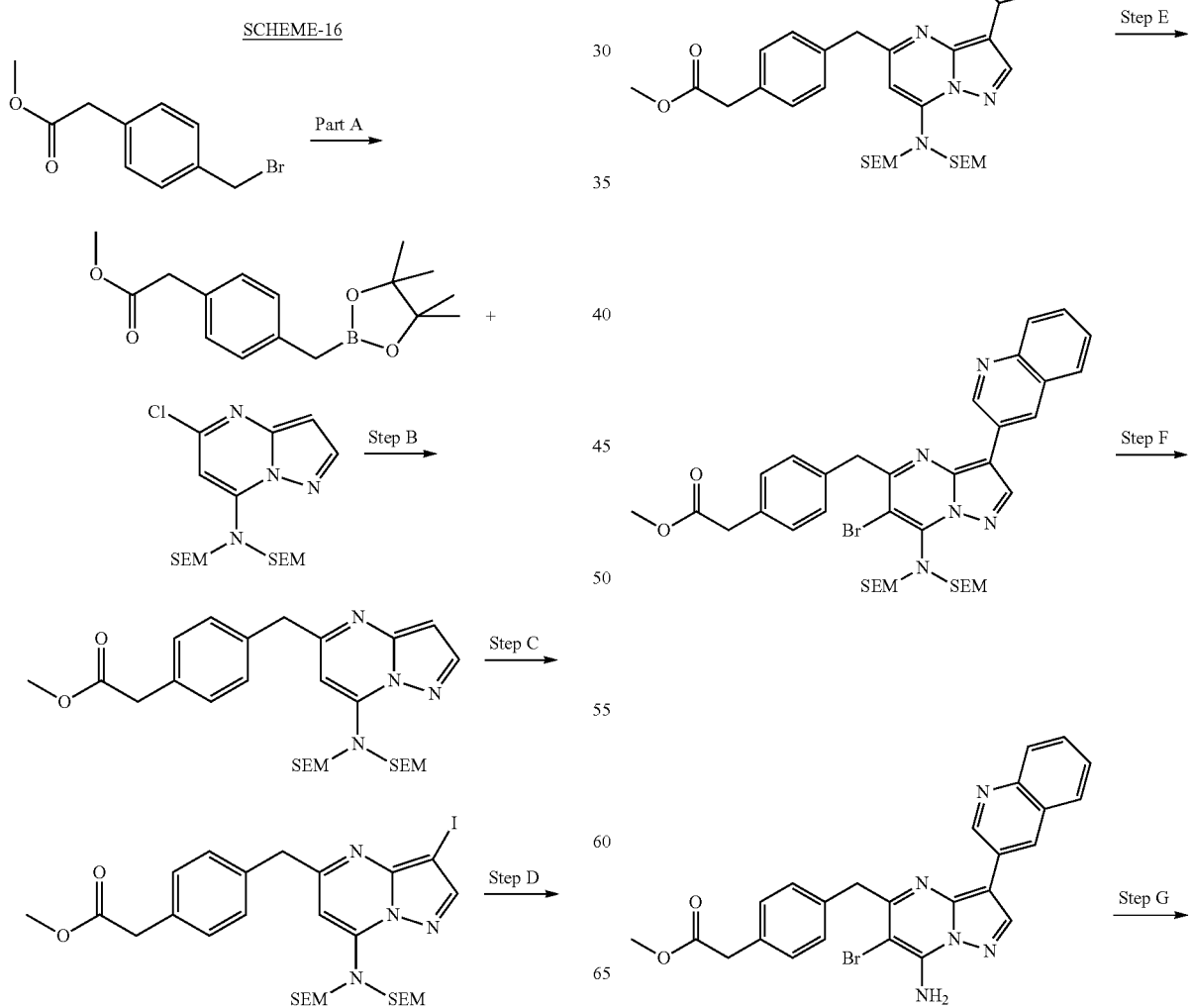
SCHEME-16

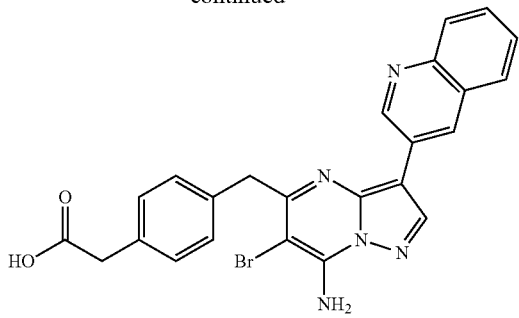

Part A:

Methyl 2-(4-((4,5,5-tetramethyl-1,3,2-dioxaborolan-2-yl)methyl)phenyl)acetate Methyl 2-(4-(bromomethyl)phenyl)acetate (1.03 g, 4.24 mmol) was mixed with Pd(PPh3)4 (500 mg, 0.4 mmol, 4,4,4',4',5,5,5',5'-octamethyl-2,2'-bi(1,3,2-dioxaborolane) (1.27 g, 5 mmol), K2CO3 (1.75 g, 12.7 mmol) and dioxane (20 mL) under inert Argon atmosphere. The resulting mixture was heated at 80° C. and stirred over night. After cooled to room temperature, the mixture was diluted with EtOAc (100 mL) and filtered through celite. After concentration, the crude was purified with column (silica gel, 10~30% EA/hexane) gave the product, methyl 2-(4-((4,4,5,5-tetramethyl-1,3,2-dioxaborolan-2-yl)methyl)phenyl)acetate (721 mg) as semi-solid. HPLC-MS $t_R$=2.17 min ($UV_{254\ nm}$); mass calculated for formula $C_{16}H_{23}BO_4$ 290.2, observed LCMS m/z 291.3 (M+H).

Part B:

Methyl 2-(4-((7-(bis((2-(trimethylsilyl)ethoxy)methyl)amino)pyrazolo[1,5-a]pyrimidin-5-yl)methyl)phenyl)acetate Under Ar, 5-chloro-N,N-bis((2-(trimethylsilyl)ethoxy)methyl)pyrazolo[1,5-a]pyrimidin-7-amine (429 mg, 1.0 mmol) was mixed with Pd(dppf)Cl2 (82 mg, 0.1 mmol, boronate, methyl 2-(4-((4,4,5,5-tetramethyl-1,3,2-dioxaborolan-2-yl)methyl)phenyl)acetate (480 mg, 1.65 mmol, not very pure), K3PO4 (424 mg, 2.0 mmol) and dioxane (10 mL). The resulting mixture was heated at 100° C. and stirred over night. After cooled to room temperature, the mixture was diluted with EtOAc (100 mL) and filtered through celite. After concentration, the crude was purified with column (silica gel, 10~30% EA/hexane) gave the product, methyl 2-(4-((7-(bis((2-(trimethylsilyl)ethoxy)methyl)amino)pyrazolo[1,5-a]pyrimidin-5-yl)methyl)phenyl)acetate (188 mg) and recovered the starting material 5-chloro-N,N-bis((2-(trimethylsilyl)ethoxy)methyl)pyrazolo[1,5-a]pyrimidin-7-amine (289 mg). HPLC-MS $t_R$=2.50 min ($UV_{254\ nm}$); mass calculated for formula $C_{28}H_{44}N_4O_4Si_2$ 556.3, observed LCMS m/z 557.3 (M+H).

Part C:

Methyl 2-(4-((7-(bis((2-(trimethylsilyl)ethoxy)methyl)amino)-3-iodopyrazolo[1,5-a]pyrimidin-5-yl)methyl)phenyl)acetate methyl 2-(4-((7-(bis((2-(trimethylsilyl)ethoxy)methyl)amino)pyrazolo[1,5-d]pyrimidin-5-yl)methyl)phenyl)acetate (450 mg, 0.81 mmol) was dissolved in ACN (15 mL) and NIS (200 mg, 0.88 mmol) was added. The resulting mixture was stirred at room temperature for 2 h and then the solvent was removed under reduced pressure. The residue was purified with column (silica gel, 10% EtOAc/Hexane) gave the product methyl 2-(4-((7-(bis((2-(trimethylsilyl)ethoxy)methyl)amino)-3-iodopyrazolo[1,5-a]pyrimidin-5-yl)methyl)phenyl)acetate (541 mg) as yellowish oil. HPLC-MS $t_R$=2.97 min ($UV_{254\ nm}$); mass calculated for formula $C_{28}H_{43}IN_4O_4Si_2$ 682.2, observed LCMS m/z 683.2 (M+H).

Part D:

Methyl 2-(4-((7-(bis((2-(trimethylsilyl)ethoxy)methyl)amino)-3-(quinolin-3-yl)pyrazolo[1,5-a]pyrimidin-5-yl)methyl)phenyl)acetate Under Ar, methyl 2-(4-((7-(bis((2-(trimethylsilyl)ethoxy)methyl)amino)-3-iodopyrazolo[1,5-a]pyrimidin-5-yl)methyl)phenyl)acetate (180 mg, 0.26 mmol) was mixed with Pd(dppf)Cl2 (21 mg, 0.26 mmol, K3PO4 (106 mg, 0.5 mmol), 3-quinoline bornic acid (55 mg, 0.31 mmol) and dioxane (10 mL with 1 ml water). The resulting mixture was heated at 90° C. and stirred over night. After cooled to room temperature, the mixture was diluted with EtOAc (60 mL) and filtered through celite. After concentration, the crude was purified with column (silica gel, 0~30% EtOAc/Hexane) gave the product methyl 2-(4-((7-(bis((2-(trimethylsilyl)ethoxy)methyl)amino)-3-(quinolin-3-yl)pyrazolo[1,5-a]pyrimidin-5-yl)methyl)phenyl)acetate (150 mg). HPLC-MS $t_R$=2.50 min ($UV_{254\ nm}$); mass calculated for formula $C_{37}H_{49}N_5O_4Si_2$ 683.3, observed LCMS m/z 684.4 (M+H).

Part E:

Methyl 2-(4-((7-(bis((2-(trimethylsilyl)ethoxy)methyl)amino)-6-bromo-3-(quinolin-3-yl)pyrazolo[1,5-a]pyrimidin-5-yl)methyl)phenyl)acetate Methyl 2-(4-((7-(bis((2-(trimethylsilyl)ethoxy)methyl)amino)-3-(quinolin-3-yl)pyrazolo[1,5-a]pyrimidin-5-yl)methyl)phenyl)acetate (150 mg, 0.22 mmol) was dissolved in ACN (10 mL). NBS (40 mg, 0.22 mmol) was added and the mixture was stirred at room temperature for 1 h. After concentration, the product that resulted, methyl 2-(4-((7-(bis((2-(trimethylsilyl)ethoxy)methyl)amino)-6-bromo-3-(quinolin-3-yl)pyrazolo[1,5-a]pyrimidin-5-yl)methyl)phenyl)acetate was used in the next step without further purification HPLC-MS $t_R$=2.66 min ($UV_{254\ nm}$); mass calculated for formula $C_{37}H_{48}BrN_5O_4Si_2$ 761.2, observed LCMS m/z 762.2 (M+H).

Part F:

Methyl 2-(4-((7-amino-6-bromo-3-(quinolin-3-yl)pyrazolo[1,5-a]pyrimidin-5-yl)methyl)phenyl)acetate The crude methyl 2-(4-((7-(bis((2-(trimethylsilyl)ethoxy)methyl)amino)-6-bromo-3-(quinolin-3-yl)pyrazolo[1,5-a]pyrimidin-5-yl)methyl)phenyl)acetate from above step E was treated with 50% TFA/H2O (3 mL) and stirred at room temperature for 1 h. Solvent was removed to yield thick oil, Methyl 2-(4-((7-amino-6-bromo-3-(quinolin-3-yl)pyrazolo[1,5-a]pyrimidin-5-yl)methyl)phenyl)acetate which was used in the next step directly without further purification. HPLC-MS $t_R$=1.72 min ($UV_{254\ nm}$); mass calculated for formula $C_{25}H_{20}BrN_5O_2$ 501.1, observed LCMS m/z 502.0 (M+H).

Part G:

2-(4-((7-amino-6-bromo-3-(quinolin-3-yl)pyrazolo[1,5-a]pyrimidin-5-yl)methyl)phenyl)acetic acid Crude Methyl 2-(4-((7-amino-6-bromo-3-(quinolin-3-yl)pyrazolo[1,5-a]pyrimidin-5-yl)methyl)phenyl)acetate from step F was dissolved in THF (5 mL) and LiOH (1N, 1 mL) was added. The mixture was stirred at room temperature overnight. The solvent was removed under vacuo, and the resulting residue was taken over with water and the pH value was adjusted to 5~6. The solid was collected with filtration and purified with HPLC gave the product 2-(4-((7-amino-6-bromo-3-(quinolin-3-yl)pyrazolo[1,5-a]pyrimidin-5-yl)methyl)phenyl)acetic acid. HPLC-MS $t_R$=1.53 min ($UV_{254\ nm}$); mass calculated for formula $C_{24}H_{18}BrN_5O_2$ 487.1, observed LCMS m/z 487.9 (M+H).

By essentially same procedure given, in preparative above example, compounds 4.175 & 4.176 given in Column 2 of Table 4K can be prepared.

Synthesis of 6-bromo-5-(4-(methylsulfonyl)benzyl)-3-(quinolin-3-yl)pyrazolo[1,5-a]pyrimidin-7-amine

SCHEME-17

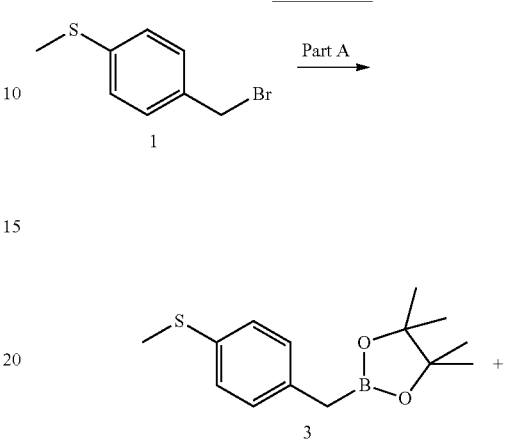

TABLE 4 K

| Example | Column 2 | Exact mass | MS m/z (M + H) | HPLC MS $t_R$ |
|---|---|---|---|---|
| 4.175 | | 513.1 | 514.0 | 1.66 |
| 4.176 | | 514.1 | 515.0 | 1.46 |

841
-continued

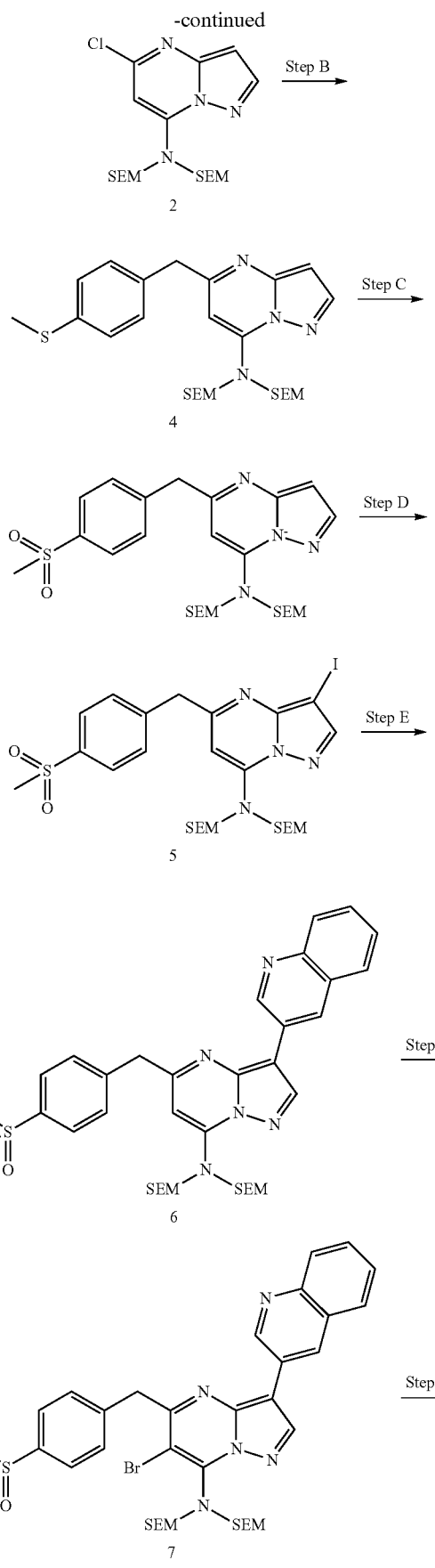

842
-continued

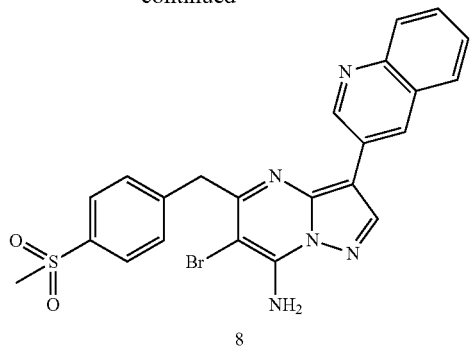
8

Essentially the steps from A through G described in the example, synthesis of 2-(4-((7-amino-6-bromo-3-(quinolin-3-yl)pyrazolo[1,5-a]pyrimidin-5-yl)methyl)phenyl)acetic acid can be used for this synthesis of 6-bromo-5-(4-(methyl-sulfonyl)benzyl)-3-(quinolin-3-yl)pyrazolo[1,5-a]pyrimidin-7-amine Part A:

4,4,5,5-tetramethyl-2-(4-(methylthio)benzyl)-1,3,2-dioxaborolane 4,4,5,5-tetramethyl-2-(4-(methylthio)benzyl)-1,3,2-dioxaborolane prepared with the same condition described in above example Part A. HPLC-MS $t_R$=2.23 min ($UV_{254\ nm}$); mass calculated for formula $C_{14}H_{21}BO_2S$ 264.1, observed LCMS m/z 265.2 (M+H).

Part B:

5-(4-(methylthio)benzyl)-N,N-bis((2-(trimethylsilyl)ethoxy)methyl)pyrazolo[1,5-a]pyrimidin-7-amine Compound, 5-(4-(methylthio)benzyl)-N,N-bis((2-(trimethylsilyl)ethoxy)methyl)pyrazolo[1,5-a]pyrimidin-7-amine was prepared with the same coupling condition described in above example Part B. HPLC-MS $t_R$=2.74 min ($UV_{254\ nm}$); mass calculated for formula $C_{26}H_{42}N_4O_2SSi_2$ 530.3, observed LCMS m/z 531.2 (M+H).

Part C:

5-(4-(methylsulfonyl)benzyl)-N,N-bis((2-(trimethylsilyl)ethoxy)methyl)pyrazolo[1,5-a]pyrimidin-7-amine Compound, 5-(4-(methylthio)benzyl)-N,N-bis((2-(trimethylsilyl)ethoxy)methyl)pyrazolo[1,5-a]pyrimidin-7-amine (87 mg, 0.132 mmol) was dissolved in DCM (5 mL) and m-CPBA (66 mg, ~70%, 0.27 mmol) was added. The result mixture was stirred at room temperature for 1 h. NaHCO3 (aq.) was added and the water was extracted with DCM. The combined organics was dried over Na2SO4 and concentrated. The crude was purified with column (silica gel, 0~30% EtOAc/Hexane) gave the product 5-(4-(methylsulfonyl)benzyl)-N,N-bis((2-(trimethylsilyl)ethoxy)methyl)pyrazolo[1,5-a]pyrimidin-7-amine (89 mg). HPLC-MS $t_R$=2.52 min ($UV_{254\ nm}$); mass calculated for formula $C_{26}H_{42}N_4O_4SSi_2$ 562.2, observed LCMS m/z 563.3 (M+H).

Part D:

3-iodo-5-(4-(methylsulfonyl)benzyl)-N,N-bis((2-(trimethylsilyl)ethoxy)methyl)pyrazolo[1,5-a]-pyrimidin-7-amine Compound, 3-iodo-5-(4-(methylsulfonyl)benzyl)-N,N-bis((2-(trimethylsilyl)ethoxy)methyl)pyrazolo[1,5-a]pyrimidin-7-amine was prepared with the same iodonation condition described in above example part C. HPLC-MS $t_R$=2.81 min (UV$_{254\ nm}$); mass calculated for formula C$_{26}$H$_{41}$IN$_4$O$_4$SSi$_2$ 688.1, observed LCMS m/z 689.2 (M+H).

Part E:

5-(4-(methyl)sulfonyl)benzyl)-3-(quinolin-3-yl)-N,N-bis((2-(trimethylsilyl)ethoxy)methyl)pyrazolo[1,5-a]pyrimidin-7-amine Compound, 5-(4-(methylsulfonyl)benzyl)-3-(quinolin-3-yl)-N,N-bis((2-(trimethylsilyl)ethoxy)methyl)pyrazolo[1,5-a]pyrimidin-7-amine was prepared with the same coupling condition described in the above example Part D. HPLC-MS $t_R$=2.35 min (UV$_{254\ nm}$); mass calculated for formula C$_{35}$H$_{47}$N$_5$O$_4$SSi$_2$ 689.3, observed LCMS m/z 690.3 (M+H).

Part F:

6-bromo-5-(4-(methylsulfonyl)benzyl)-3-(quinolin-3-yl)-N,N-bis((2-(trimethylsilyl)ethoxy)methyl)pyrazolo[1,5-a]pyrimidin-7-amine Compound, 6-bromo-5-(4-(methylsulfonyl)benzyl)-3-(quinolin-3-yl)-N,N-bis((2-(trimethylsilyl)ethoxy)methyl) pyrazolo[1,5-a]pyrimidin-7-amine was prepared with the same bromonation condition described in the above example 1 Part E. HPLC-MS $t_R$=2.52 min (UV$_{254\ nm}$); mass calculated for formula C$_{35}$H$_{46}$BrN$_5$O$_4$SSi$_2$ 767.2, observed LCMS m/z 768.2 (M+H).

Part G:

6-bromo-5-(4-(methylsulfonyl)benzyl)-3-(quinolin-3-yl)pyrazolo[1,5-a]pyrimidin-7-amine Title compound, 6-bromo-5-(4-(methylsulfonyl)benzyl)-3-(quinolin-3-yl)pyrazolo[1,5-a]pyrimidin-7-amine was prepared with the same deprotection condition described in example 1 Part F. HPLC-MS $t_R$=1.49 min (UV$_{254\ nm}$); mass calculated for formula C$_{23}$H$_{18}$BrN$_5$O$_2$S 507.0, observed LCMS m/z 508.0 (M+H).

By essentially the same procedure given in preparative above example, compound 4.177-4.178 given in Column 2 of Table 4L can be prepared.

TABLE 4L

| Example | Column 2 | Exact mass | MS m/z (M + H) | HPLC MS $t_R$ |
|---|---|---|---|---|
| 4.177 | | 533.10 | 534.10 | 1.65 |
| 4.178 | | 534.10 | 535.10 | 1.41 |

845
Synthesis of 4-(6-acetyl-7-amino-3-(6-phenylpyridin-3-yl)pyrazolo[1,5-a]pyrimidin-5-yloxy)benzoic acid
SCHEME-18
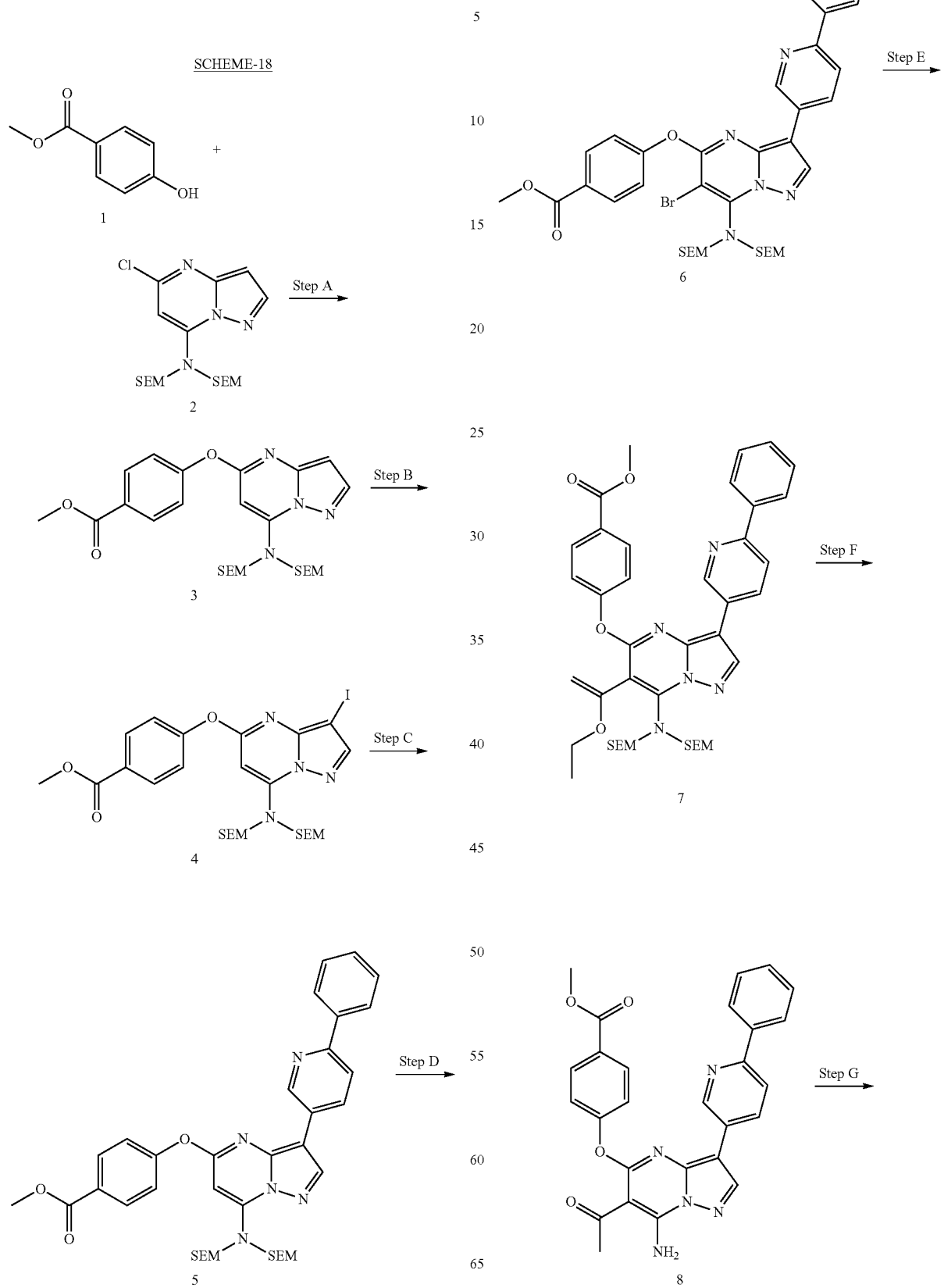

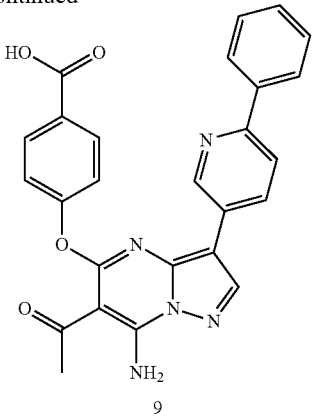

9

Part A:

Methyl 4-(7-(bis((2-(trimethylsilyl)ethoxy)methyl)amino)pyrazolo[1,5-a]pyrimidin-5-yloxy)benzoate The methyl 4-hydroxybenzoate (330 mg, 0.2 mmol) was dissolved in dry DMF (3 mL) and NaH (8 mg, 60% in oil, 0.2 mmol) was added and the mixture was stirred at room temperature for 5 min. Then, 5-chloro-N,N-bis((2-(trimethylsilyl)ethoxy)methyl)pyrazolo[1,5-a]pyrimidin-7-amine (430 mg, 0.1 mmol) was added and the resulting mixture was heated up to 130° C. with Microwave and stirred for 30 min. After cooling to room temperature, NH4Cl (aq) was added to quench the reaction and extracted with EtOAc (50 mL×3). The combined organics were washed with water and brine and dried over Na$_2$SO4. After concentration, the residue was purified with column (silica gel, 20% EtOAc/Hexane) gave the product, methyl 4-(7-(bis((2-(trimethylsilyl)ethoxy)methyl)amino)pyrazolo[1,5-a]pyrimidin-5-yloxy)benzoate (490 mg) as clear oil. HPLC-MS $t_R$=2.84 min (UV$_{254\ nm}$); mass calculated for formula $C_{26}H_{40}N_4O_5Si_2$ 544.3, observed LCMS m/z 545.3 (M+H).

Part B:

Methyl 4-(7-(bis((2-(trimethylsilyl)ethoxy)methyl)amino)-3-iodopyrazolo[1,5-a]pyrimidin-5-yloxy)benzoate Methyl 4-(7-(bis((2-(trimethylsilyl)ethoxy)methyl)amino)pyrazolo[1,5-a]pyrimidin-5-yloxy)benzoate (450 mg, 0.81 mmol) was dissolved in ACN (15 mL) and NIS (200 mg, 0.88 mmol) was added. The resulting mixture was stirred at room temperature for 2 h and then the solvent was removed under reduced pressure. The residue was purified with column (silica gel, 10% EtOAc/Hexane) gave the product, methyl 4-(7-(bis((2-(trimethylsilyl)ethoxy)methyl)amino)-3-iodopyrazolo[1,5-a]pyrimidin-5-yloxy)benzoate (541 mg) as yellowish oil. HPLC-MS $t_R$=3.10 min (UV$_{254\ nm}$); mass calculated for formula $C_{26}H_{39}IN_4O_5Si_2$ 670.2, observed LCMS m/z 671.2 (M+H).

Part C:

Methyl 4-(7-(bis((2-(trimethylsilyl)ethoxy)methyl)amino)-3-(6-phenylpyridin-3-yl)pyrazolo[1,5-a]pyrimidin-5-yloxy)benzoate Under Ar, methyl 4-(7-(bis((2-(trimethylsilyl)ethoxy)methyl)amino)-3-iodopyrazolo[1,5-a]pyrimidin-5-yloxy)benzoate (180 mg, 0.26 mmol) was mixed with Pd(dppf)Cl$_2$ (21 mg, 0.26 mmol, K$_3$PO$_4$ (106 mg, 0.5 mmol), 3-quinoline bornic acid (55 mg, 0.31 mmol) and dioxane (10 mL with 1 ml water). The resulting mixture was heated at 90° C. and stirred over night. After cooled to room temperature, the mixture was diluted with EtOAc (60 mL) and filtered through celite. After concentration, the crude was purified with column (silica gel, 0~30% EtOAc/Hexane) gave the product methyl 4-(7-(bis((2-(trimethylsilyl)ethoxy)methyl)amino)-3-(6-phenylpyridin-3-yl)pyrazolo[1,5-a]pyrimidin-5-yloxy)benzoate. HPLC-MS $t_R$=2.77 min (UV$_{254\ nm}$); mass calculated for formula $C_{37}H_{47}N_5O_5Si_2$ 697.3, observed LCMS m/z 698.2 (M+H).

Part D:

Methyl 4-(7-(bis((2-(trimethylsilyl)ethoxy)methyl)amino)-6-bromo-3-(6-phenylpyridin-3-yl)pyrazolo[1,5-a]pyrimidin-5-yloxy)benzoate Compound, methyl 4-(7-(bis((2-(trimethylsilyl)ethoxy)methyl)amino)-3-(6-phenylpyridin-3-yl)pyrazolo[1,5-a]pyrimidin-5-yloxy)benzoate (150 mg, 0.22 mmol) was dissolved in ACN (10 mL). NBS (40 mg, 0.22 mmol) was added and the mixture was stirred at room temperature for 1 h. After concentration, the residue, methyl 4-(7-(bis((2-(trimethylsilyl)ethoxy)methyl)amino)-6-bromo-3-(6-phenylpyridin-3-yl)pyrazolo[1,5-a]pyrimidin-5-yloxy)benzoate was used in the next step without further purification. HPLC-MS $t_R$=3.06 min (UV$_{254\ nm}$); mass calculated for formula C37H46BrN5O5Si2 775.2, observed LCMS m/z 776.0 (M+H).

Part E:

Methyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yloxy)benzoate Under Ar, methyl 4-(7-(bis((2-(trimethylsilyl)ethoxy)methyl)amino)-6-bromo-3-(6-phenylpyridin-3-yl)pyrazolo[1,5-a]pyrimidin-5-yloxy)benzoate (180 mg, 0.26 mmol) was mixed with Pd(dppf)Cl$_2$ (21 mg, 0.26 mmol, K$_3$PO$_4$ (106 mg, 0.5 mmol), 3-phenyl pyridyl bornic acid (75 mg, 0.31 mmol) and dioxane (10 mL with 1 ml water). The resulting mixture was heated at 90° C. and stirred over night. After cooled to room temperature, the mixture was diluted with EtOAc (60 mL) and filtered through celite. After concentration, the crude was purified with column (silica gel, 0~30% EtOAc/Hexane) gave the product 5 (150 mg), which was used in the next step directly without further purification. HPLC-MS $t_R$=2.96 min (UV$_{254\ nm}$); mass calculated for formula $C_{41}H_{53}N_5O_6Si_2$ 767.4, observed LCMS m/z 768.4 (M+H).

Part F:

Methyl 4-(6-acetyl-7-amino-3-(6-phenylpyridin-3-yl)pyrazolo[1,5-a]pyrimidin-5-yloxy)benzoate The crude from above step E was treated with 50% TFA/H$_2$O (3 mL) and stirred at room temperature for 1 h. Solvent was removed to yield thick oil, methyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yloxy)benzoate. HPLC-MS $t_R$=1.84 min (UV$_{254\ nm}$); mass calculated for formula $C_{27}H_{21}N_5O_4$ 479.2, observed LCMS m/z 480.2 (M+H).

Part G:

4-(6-acetyl-7-amino-3-(6-phenylpyridin-3-yl)pyrazolo[1,5-a]pyrimidin-5-yloxy)benzoic acid Crude from step F was dissolved in THF (5 mL) and LiOH (1N, 1 mL) was added. The mixture was stirred at room temperature overnight. The solvent was removed under vacuo, and the resulting residue was taken over with water and the pH value was adjusted to 5~6. The solid was collected with filtration and purified with HPLC gave the product 4-(6-acetyl-7-amino-3-(6-phenylpyridin-3-yl)pyrazolo[1,5-a]pyrimidin-5-yloxy)benzoic acid. HPLC-MS $t_R$=1.49 min ($UV_{254\,nm}$); mass calculated for formula $C_{26}H_{19}N_5O_4$ 465.1, observed LCMS m/z 466.2 (M+H).

By essentially the same procedure given in preparative above example (scheme-18), compound 4.179 given in Column 2 of Table 4M can be prepared.

TABLE 4M

| Example | Column 2 | Exact mass | MS m/z (M + H) | HPLC MS $t_R$ |
|---|---|---|---|---|
| 4.179 | (structure shown) | 457.1 | 458.2 | 1.52 |

Synthesis of 4-(7-amino-6-cyano-3-(6-phenylpyridin-3-yl)pyrazolo[1,5-a]pyrimidin-5-yl)benzoic acid

SCHEME-19

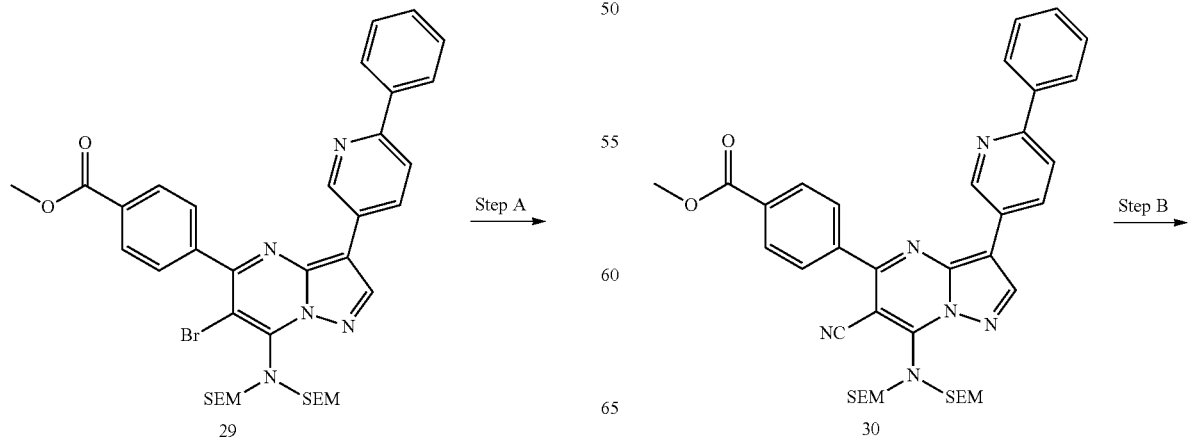

-continued

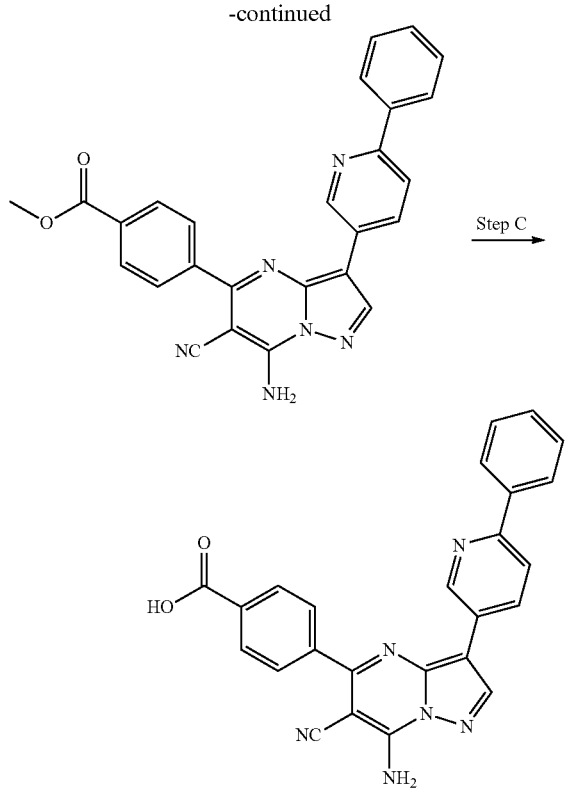

Part A

Methyl 4-(7-(bis((2-(trimethylsilyl)ethoxy)methyl)amino)-6-cyano-3-(6-phenylpyridin-3-yl)pyrazolo[1,5-a]pyrimidin-5-yl)benzoate Under Ar, compound, methyl 4-(7-(bis((2-(trimethylsilyl)ethoxy)methyl)amino)-6-bromo-3-(6-phenylpyridin-3-yl)pyrazolo[1,5-a]pyrimidin-5-yl)benzoate (80 mg, 0.1 mmol) was mixed with Pd(PPh3)$_4$ (12 mg, 0.01 mmol, Pd(t-Bu3P)3 (5 mg, 0.01 mmol), cyanotributylstannane (85 uL, 0.3 mmol) and dioxane (3 mL) in sealed tube. The resulting mixture was heated at 160° C. and stirred 2 hrs. After cooled to room temperature, the mixture was filtered through 10% KF on silica gel and washed with EtOAc. After concentration, the crude was used in the next step directly without further purification. HPLC-MS $t_R$=3.18 min (UV$_{254\ nm}$); mass calculated for formula $C_{38}H_{46}N_6O_4Si_2$ 706.3, observed LCMS m/z 707.2 (M+H).

Part B

Methyl 4-(7-amino-6-cyano-3-(6-phenylpyridin-3-yl)pyrazolo[1,5-a]pyrimidin-5-yl)benzoate The crude from above step A was treated with 50% TFA/H2O (3 mL) and stirred at room temperature for 1 h. Solvent was removed to yield thick oil which was used in the next step directly without further purification. HPLC-MS $t_R$=2.15 min (UV$_{254\ nm}$); mass calculated for formula $C_{26}H_{18}N_6O_2$ 446.1, observed LCMS m/z 447.1 (M+H).

Part C:

4-(7-amino-6-cyano-3-(6-phenylpyridin-3-yl)pyrazolo[1,5-a]pyrimidin-5-yl)benzoic acid Crude compound from step B was dissolved in THF (5 mL) and LiOH (1N, 1 mL) was added. The mixture was stirred at room temperature overnight. The solvent was removed under vacuo, and the resulting residue was taken over with water and the pH value was adjusted to 5-6. The solid was collected with filtration and purified with HPLC gave the product 4-(7-amino-6-cyano-3-(6-phenylpyridin-3-yl)pyrazolo[1,5-a]pyrimidin-5-yl)benzoic acid. HPLC-MS $t_R$=1.40 min (UV$_{254\ nm}$); mass calculated for formula $C_{25}H_{16}N_6O_2$ 432.1, observed LCMS m/z 433.1 (M+H).

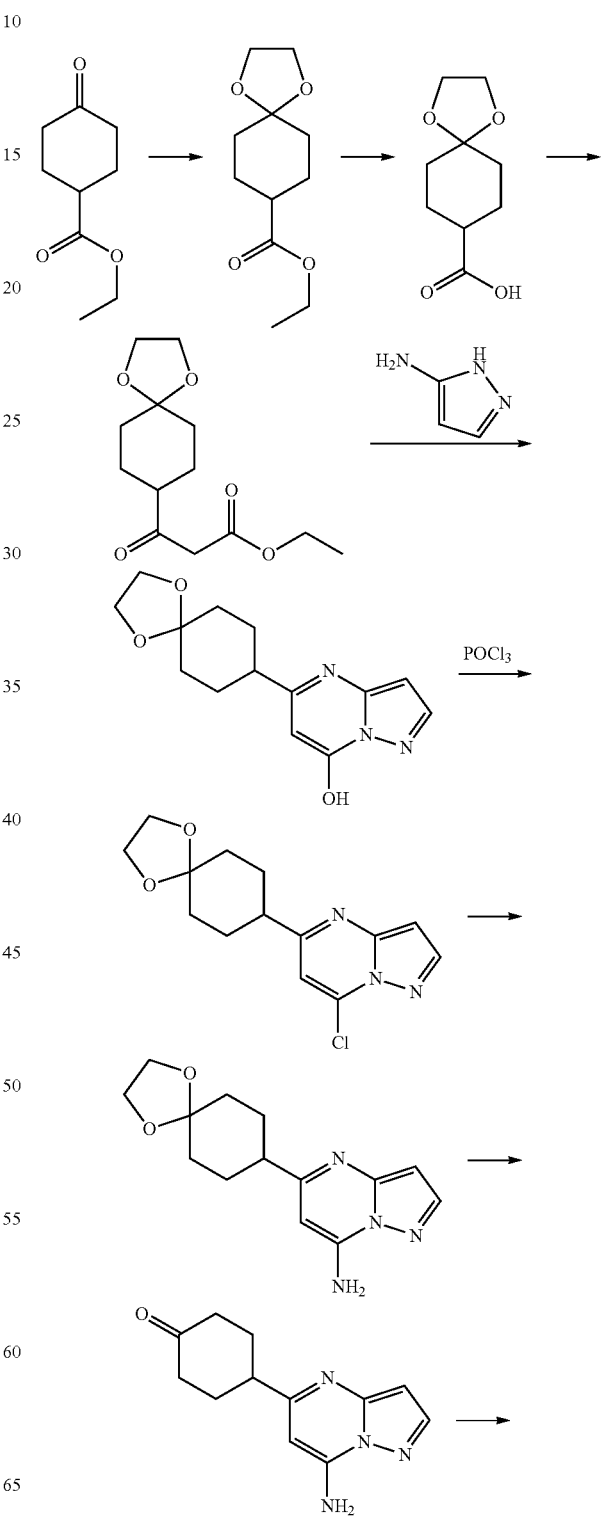

853
-continued

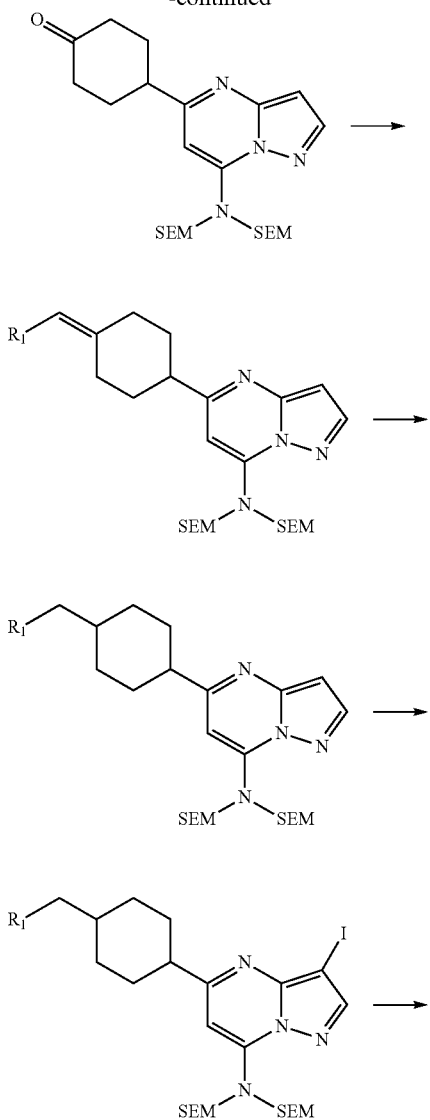

854
Scheme-20

Synthesis of Ethyl 1,4-dioxaspiro[4.5]decane-8-carboxylate

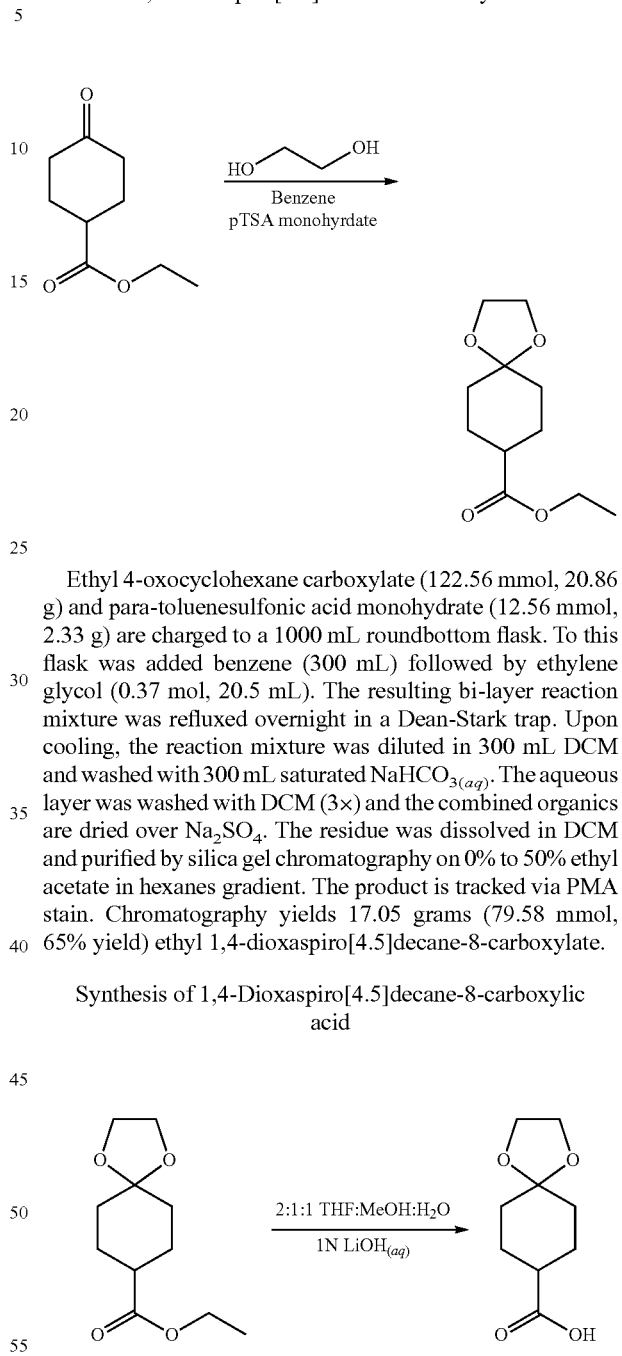

Ethyl 4-oxocyclohexane carboxylate (122.56 mmol, 20.86 g) and para-toluenesulfonic acid monohydrate (12.56 mmol, 2.33 g) are charged to a 1000 mL roundbottom flask. To this flask was added benzene (300 mL) followed by ethylene glycol (0.37 mol, 20.5 mL). The resulting bi-layer reaction mixture was refluxed overnight in a Dean-Stark trap. Upon cooling, the reaction mixture was diluted in 300 mL DCM and washed with 300 mL saturated $NaHCO_{3(aq)}$. The aqueous layer was washed with DCM (3×) and the combined organics are dried over $Na_2SO_4$. The residue was dissolved in DCM and purified by silica gel chromatography on 0% to 50% ethyl acetate in hexanes gradient. The product is tracked via PMA stain. Chromatography yields 17.05 grams (79.58 mmol, 65% yield) ethyl 1,4-dioxaspiro[4.5]decane-8-carboxylate.

Synthesis of 1,4-Dioxaspiro[4.5]decane-8-carboxylic acid

Ethyl 1,4-dioxaspiro[4.5]decane-8-carboxylate (79.58 mmol, 17.05 g) is taken up in 300 mL 2:1 THF:$H_2O$ in 500 mL roundbottom flask. Lithium hydroxide monohydrate (120 mmol, 5.01 g) and 100 mL MeOH were added to this solution. The reaction mixture was allowed to stir overnight at room temperature. The reaction mixture was acidified to pH 3 with 1N $HCl_{(aq)}$ and extracted with 100 mL DCM (×5). The combined organics were combined and then dried over $Na_2SO_4$, and the solvent was removed in vacuo to yield 1,4-dioxaspiro[4.5]decane-8-carboxylic acid (14.96 g, 100% yield) as white solid.

Synthesis of Ethyl 3-oxo-3-(1,4-dioxaspiro[4.5]decan-8-yl)propanoate

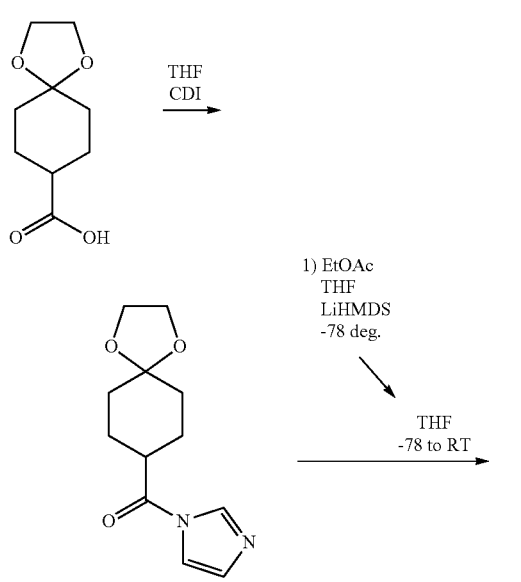

1,4-Dioxaspiro[4.5]decane-8-carboxylic acid (80.34 mmol, 14.96 g) is charged to a 500 mL roundbottom flask. To this flask is added anhydrous THF (200 mL), followed by N,N'-carbonyldiimidazole (96.41 mmol, 15.63 g). After vigorous release of $CO_2$ gas, the solution was flushed with argon, sealed, and allowed to stir overnight at room temperature under argon.

After 18 hours, in a separate, sealed and argon-flushed 1000 mL roundbottom flask, LiHMDS (1.0 M in THF, 168.7 mmol) is added to 200 mL anhydrous THF stirring at −78° C. To this solution is added dropwise anhydrous ethyl acetate (173 mmol, 16.9 mL). This solution is allowed to stir at −78° C. for 1 hour prior to dropwise addition of original CDI/acid solution that has been stirred overnight. The reaction mixture was allowed to stir and warm to room temperature overnight.

The reaction was then quenched with saturated $NH_4Cl_{(aq)}$ (500 mL) and extracted with $Et_2O$ (×2). The combined organics are then washed with $H_2O$, saturated brine, and dried over $Na_2SO_4$. The solvent is removed in vacuo and the residue is taken up in DCM. The reaction mixture was purified with silica gel chromatography (0% to 60% ethyl acetate in hexanes gradient) to yield ethyl 3-oxo-3-(1,4-dioxaspiro[4.5]decan-8-yl)propanoate (11.26 g, 55% yield) as pale yellow oil.

Synthesis of 5-(1,4-dioxaspiro[4.5]decan-8-yl)pyrazolo[1,5-a]pyrimidin-7-ol

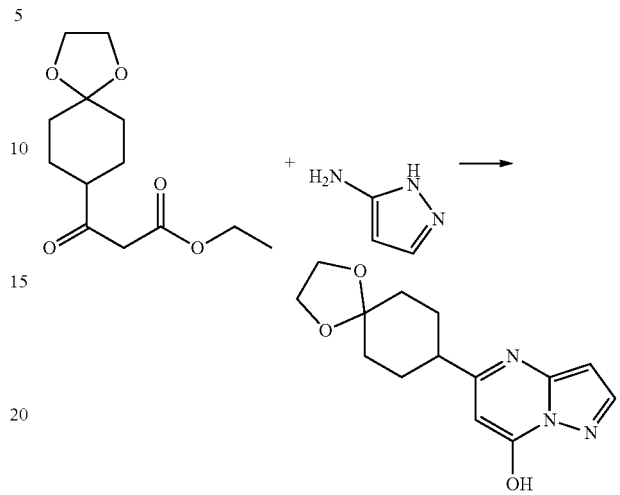

To a 20 mL scintillation vial containing ethyl 3-oxo-3-(1,4-dioxaspiro[4.5]decan-8-yl)propanoate (11.7 mmol, 3.00 g) is added 3-amino-1H-pyrazole (11.7 mmol, 973 mg). The two oils were mixed and heated neat at 100° C. for 3 hours. The resulting off-white solid was dissolved up in EtOH (100 mL) and reduced in vacuo to remove water formed during cyclization. This solid was used in the next step without further purification.

Synthesis of 7-chloro-5-(1,4-dioxaspiro[4.5]decan-8-yl)pyrazolo[1,5-a]pyrimidine

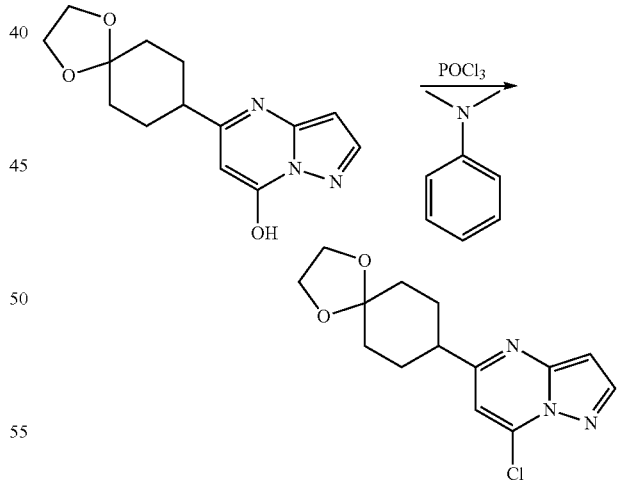

5-(1,4-dioxaspiro[4.5]decan-8-yl)pyrazolo[1,5-a]pyrimidin-7-ol (11.7 mmol) is charged to 250 mL roundbottom flask. To this flask is added 4 mL N,N-dimethylaniline, followed by 40 mL $POCl_3$. This suspension was sonicated to break up the starting material and stirred at room temperature for 18 hours. After 18 hours, a solution formed. The solution was reduced in vacuo and cooled to 0° C. in ice bath. The reaction is then quenched with sat. $NaHCO_{3(aq)}$ and extracted with DCM (×3). The combined organics are dried with Na₂SO₄ and the solvent was removed in vacuo. The resulting oil was purified via silica gel column on 20% to 100% ethyl acetate in hexanes gradient to yield 7-chloro-5-(1,4-dioxaspiro[4.5]decan-8-yl)pyrazolo[1,5-a]pyrimidine (2.65 grams, 77% across 2 steps) as white solid.

Synthesis of 5-(1,4-dioxaspiro[4.5]decan-8-yl)pyrazolo[1,5-a]pyrimidin-7-amine

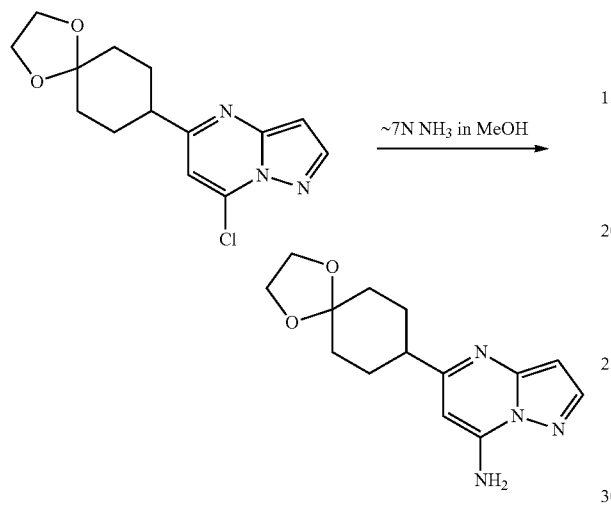

7-chloro-5-(1,4-dioxaspiro[4.5]decan-8-yl)pyrazolo[1,5-a]pyrimidine (5.58 mmol, 1.64 g) is charged to 10-20 mL microwave vessel. To this vessel is added 10 mL ~7N NH₃ in methanol. The vessel was sealed and heated at 100° C. for 18 hours. After 18 hours, the reaction mixture was cooled to room temperature and diluted with 100 mL DCM. The resulting solution is washed with saturated NaHCO₃(aq) and extracted with DCM twice more. The combined organics were dried over Na₂SO₄ and the solvent removed in vacuo to yield 5-(1,4-dioxaspiro[4.5]decan-8-yl)pyrazolo[1,5-a]pyrimidin-7-amine (1.52 g, 99% yield) as pale orange solid.

Synthesis of 4-(7-aminopyrazolo[1,5-a]pyrimidin-5-yl)cyclohexanone

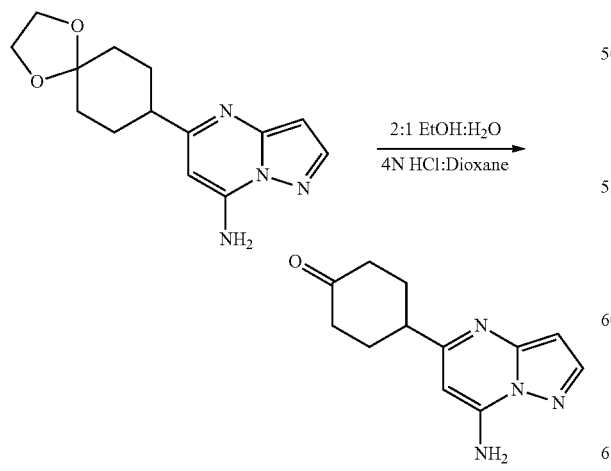

In a 40 mL scintillation vial is combined 5-(1,4-dioxaspiro[4.5]decan-8-yl)pyrazolo[1,5-a]pyrimidin-7-amine (5.54 mmol, 1.52 g), EtOH (10 mL), H2O (4 mL) and 4N HCL:dioxane (4 mL). The vial was capped, sealed and the reaction was heated to 80° C. overnight. After 18 hours, the reaction mixture was cooled to room temperature and diluted with DCM (100 mL). The solution was washed with saturated NaHCO₃(aq) and extracted with DCM twice more. The combined organics are dried over Na₂SO₄ and the solvent removed in vacuo to yield 4-(7-aminopyrazolo[1,5-a]pyrimidin-5-yl)cyclohexanone (1.18 g, 93% yield) as pale orange solid.

Synthesis of 4-(7-(bis((2-(trimethylsilyl)ethoxy)methyl)amino)pyrazolo[1,5-a]pyrimidin-5-yl)cyclohexanone

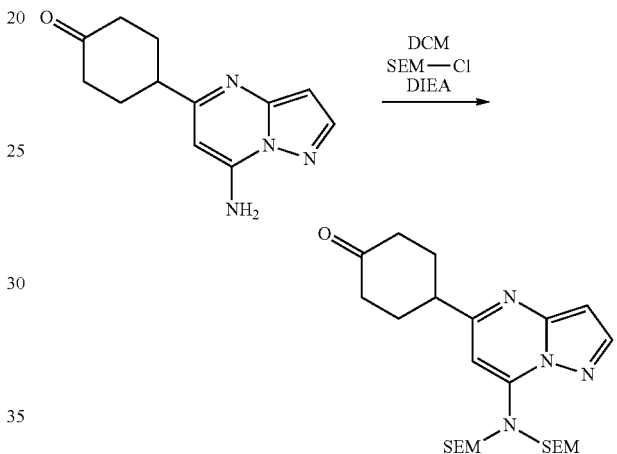

4-(7-aminopyrazolo[1,5-a]pyrimidin-5-yl)cyclohexanone (5.12 mmol, 1.18 g) was dissolved in DCM (15 mL). To this solution was added N,N'-diisopropylethylamine (17.94 mmol, 3.13 mL). The resulting solution was stirred at room temperature while 2-(trimethylsilyl)ethoxymethyl chloride (SEM-Cl, 17.94 mL, 3.17 mL) in DCM (5 mL) was added dropwise. After the addition was completed, the reaction mixture was stirred at 50° C. for 10 minutes. The solvent was removed in vacuo, and the residue was purified on silica gel column (0% to 60% ethyl acetate in hexanes gradient) to yield 4-(7-(bis((2-(trimethylsilyl)ethoxy)methyl)amino)pyrazolo[1,5-a]pyrimidin-5-yl)cyclohexanone (1.87 g, 74% yield) as pale yellow oil.

Synthesis of Ethyl 2-(4-(7-(bis((2-(trimethylsilyl)ethoxy)methyl)amino)pyrazolo[1,5-a]pyrimidin-5-yl)cyclohexylidene)acetate

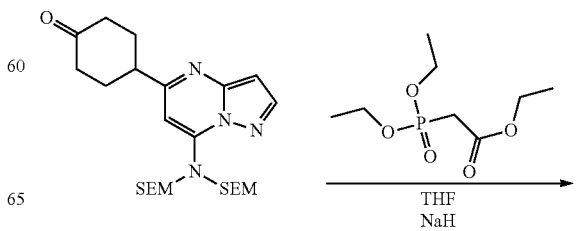

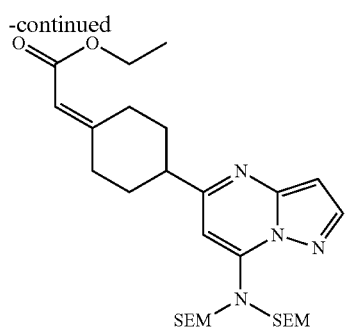

A 20 mL scintillation vial containing 5 mL THF was charged sodium hydride (60% w/w in mineral oil, 448 µmol, 18 mg). This suspension was broken up via sonication. Triethyl phosphonoacetate (448 µmol, 89.3 µL) in THF (2 mL) was added dropwise. The resulting solution was stirred at room temperature for 10 minutes. To this solution was slowly added a solution of 4-(7-(bis((2-(trimethylsilyl)ethoxy)methyl)amino)pyrazolo[1,5-a]pyrimidin-5-yl)cyclohexanone (408 µmol, 200 mg) in THF (2 mL). The reaction mixture was stirred for 18 hours at room temperature. After 18 hours, the reaction mixture was diluted with DCM (25 mL) and washed with H$_2$O. The aqueous phase was washed with DCM (×2), and the combined organics was dried over Na$_2$SO$_4$. The solvent was removed in vacuo to yield ethyl 2-(4-(7-(bis((2-(trimethylsilyl)ethoxy)methyl)amino)pyrazolo[1,5-a]pyrimidin-5-yl)cyclohexylidene)acetate (222 mg, 97% yield) as pale yellow oil.

Synthesis of 2-(4-(7-(Bis((2-(trimethylsilyl)ethoxy)methyl)amino)pyrazolo[1,5-a]pyrimidin-5-yl)cyclohexylidene)acetonitrile

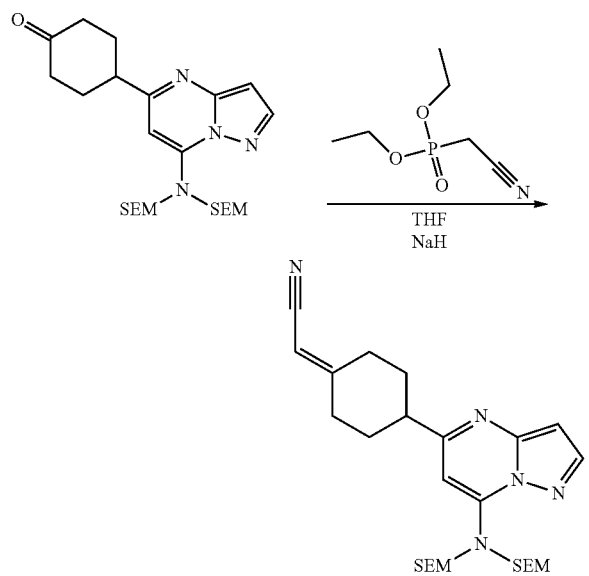

2-(4-(7-(Bis((2-(trimethylsilyl)ethoxy)methyl)amino)pyrazolo[1,5-a]pyrimidin-5-yl)cyclohexylidene)acetonitrile was synthesized in a manner similar to the synthesis of ethyl 2-(4-(7-(bis((2-(trimethylsilyl)ethoxy)methyl)amino)pyrazolo[1,5-a]pyrimidin-5-yl)cyclohexylidene)acetate, but with diethyl cyanomethylphosphonate substituted for triethyl phosphonoacetate.

Synthesis of ethyl 2-(4-(7-(bis((2-(trimethylsilyl)ethoxy)methyl)amino)pyrazolo[1,5-a]pyrimidin-5-yl)cyclohexyl)acetate

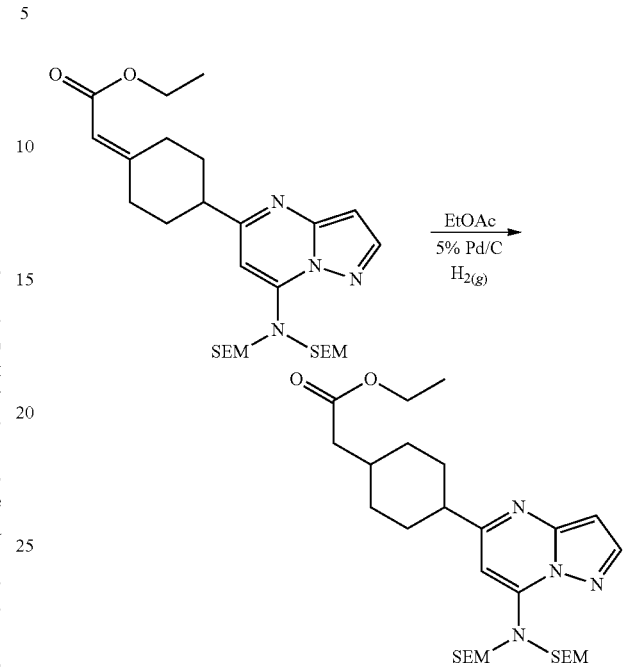

To a 50 mL roundbottom flask was charged ethyl 2-(4-(7-(bis((2-(trimethylsilyl)ethoxy)-methyl)amino)pyrazolo[1,5-a]pyrimidin-5-yl)cyclohexylidene)acetate (800 mg, 1.43 mmol) and ethyl acetate (15 mL). The flask was flushed with argon, and 5% palladium on carbon (100 mg) was added. The flask was sealed and degassed under vacuum. Hydrogen gas was then added via balloon. The reaction was stirred under a hydrogen atmosphere for 18 hours. The reaction was then filtered through celite to yield ethyl 2-(4-(7-(bis((2-(trimethylsilyl)ethoxy)methyl)amino)pyrazolo[1,5-a]pyrimidin-5-yl)cyclohexyl)acetate (761 mg, 1.35 mmol, 95% yield) as pale yellow oil.

Synthesis of 2-(4-(7-(bis((2-(trimethylsilyl)ethoxy)methyl)amino)pyrazolo[1,5-a]pyrimidin-5-yl)cyclohexyl)acetonitrile

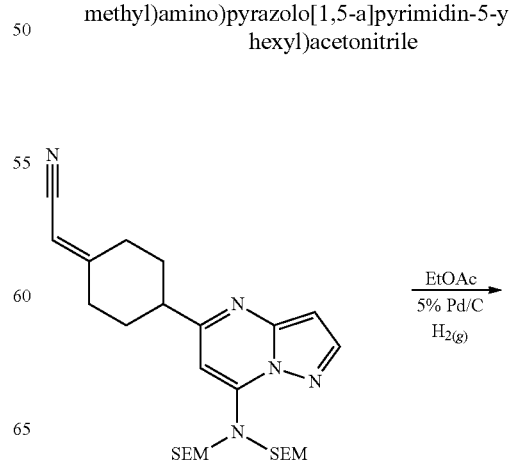

861

-continued

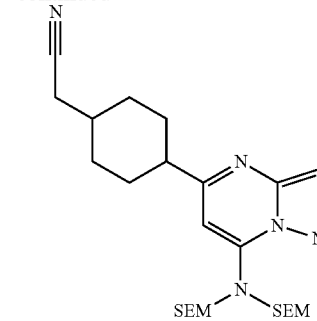

2-(4-(7-(Bis((2-(trimethylsilyl)ethoxy)methyl)amino)
pyrazolo[1,5-a]pyrimidin-5-yl)cyclohexyl)acetonitrile was
synthesized in a manner similar to the synthesis of ethyl
2-(4-(7-(bis((2-(trimethylsilyl)ethoxy)methyl)amino)pyrazolo[1,5-a]pyrimidin-5-yl)cyclohexyl)acetate, but with 2-(4-(7-(bis((2-(trimethylsilyl)ethoxy)methyl)amino)pyrazolo[1,5-a]pyrimidin-5-yl)cyclohexylidene)acetonitrile substituted for ethyl 2-(4-(7-(bis((2-(trimethylsilyl)ethoxy)methyl)amino)pyrazolo[1,5-a]pyrimidin-5-yl)cyclohexylidene)acetate.

Synthesis of ethyl 2-(4-(7-(bis((2-(trimethylsilyl)ethoxy)methyl)amino)-3-iodopyrazolo[1,5-a]pyrimidin-5-yl)cyclohexyl)acetate A 50 mL roundbottom flask was charged ethyl 2-(4-(7-(bis((2-(trimethylsilyl)ethoxy)-methyl)amino)pyrazolo[1,5-a]pyrimidin-5-yl)cyclohexyl)acetate (381 mg, 0.68 mmol) and acetonitrile (10 mL). To this solution was added N-Iodosuccinimide (167 mg, 0.74 mmol). The reaction mixture was stirred at room temperature for 18 hours. The reaction mixture was concentrated in vacuo and the crude oil was purified via silica gel chromatography (0% to 30% ethyl acetate in hexanes gradient) to yield ethyl 2-(4-(7-(bis((2-(trimethylsilyl)ethoxy)methyl)amino)-3-iodopyrazolo[1,5-a]pyrimidin-5-yl)cyclohexyl)acetate (335 mg, 0.49 mmol, 72% yield) as clear oil.

862

Synthesis of 2-(4-(7-(bis((2-(trimethylsilyl)ethoxy)methyl)amino)-3-iodopyrazolo[1,5-a]pyrimidin-5-yl)cyclohexyl)acetonitrile 2-(4-(7-(bis((2-(trimethylsilyl)ethoxy)methyl)amino)-3-iodopyrazolo[1,5-a]pyrimidin-5-yl)cyclohexyl)acetonitrile was synthesized in a manner similar to the synthesis of ethyl 2-(4-(7-(bis((2-(trimethylsilyl)ethoxy)methyl)amino)-3-iodopyrazolo[1,5-a]pyrimidin-5-yl)cyclohexyl)acetate, but with 2-(4-(7-(bis((2-(trimethylsilyl)ethoxy)methyl)amino)pyrazolo[1,5-a]pyrimidin-5-yl)cyclohexyl)acetonitrile substituted for ethyl 2-(4-(7-(bis((2-(trimethylsilyl)ethoxy)methyl)amino)pyrazolo[1,5-a]pyrimidin-5-yl)cyclohexyl)acetate.

Synthesis of ethyl 2-(4-(7-(bis((2-(trimethylsilyl)ethoxy)methyl)amino)-3-(quinolin-3-yl)pyrazolo[1,5-a]pyrimidin-5-yl)cyclohexyl)acetate

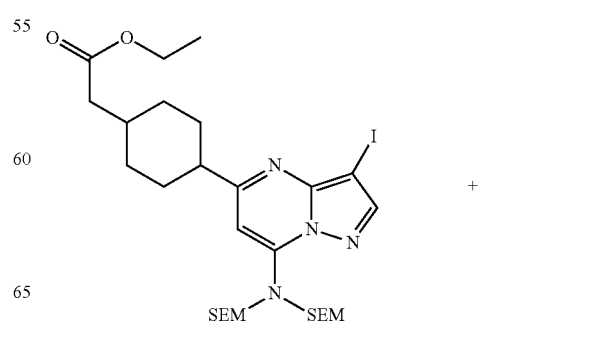

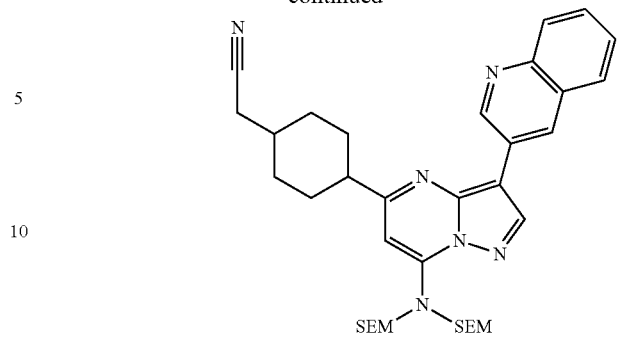

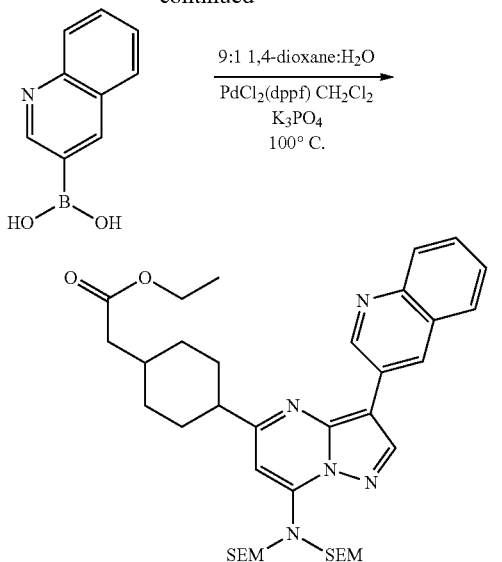

To a 40 mL scintillation vial was charged 3-quinoline boronic acid (0.73 mmol, 127 mg), K$_3$PO$_4$ (1.46 mmol, 310 mg) and PdCl$_2$(dppf).CH$_2$Cl$_2$ (0.049 mmol, 40 mg). To this mixture was added a solution of ethyl 2-(4-(7-(bis((2-(trimethylsilyl)ethoxy)methyl)amino)-3-iodopyrazolo[1,5-a]pyrimidin-5-yl)cyclohexyl)acetate (335 mg, 0.49 mmol) in dioxane (9 mL). To this suspension was added distilled H$_2$O (1 mL). The resulting solution was stirred at 100° C. for 18 hours. The reaction was concentrated in vacuo and then purified via silica gel chromatography (0% to 60% ethyl acetate in hexanes gradient) to yield ethyl 2-(4-(7-(bis((2-(trimethylsilyl)ethoxy)methyl)amino)-3-(quinolin-3-yl)pyrazolo[1,5-a]pyrimidin-5-yl)cyclohexyl)acetate (198 mg, 287 µmol, 59% yield) as yellow oil.

Synthesis of 2-(4-(7-(bis((2-(trimethylsilyl)ethoxy)methyl)amino)-3-(quinolin-3-yl)pyrazolo[1,5-a]pyrimidin-5-yl)cyclohexyl)acetonitrile

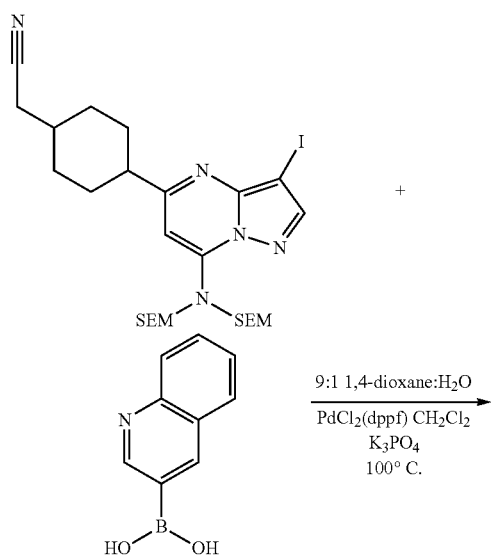

2-(4-(7-(bis((2-(trimethylsilyl)ethoxy)methyl)amino)-3-(quinolin-3-yl)pyrazolo[1,5-a]pyrimidin-5-yl)cyclohexyl)acetonitrile was synthesized in a manner similar to the synthesis of ethyl 2-(4-(7-(bis((2-(trimethylsilyl)ethoxy)methyl)amino)-3-(quinolin-3-yl)pyrazolo[1,5-a]pyrimidin-5-yl)cyclohexyl)acetate, but with 2-(4-(7-(bis((2-(trimethylsilyl)ethoxy)methyl)amino)-3-iodopyrazolo[1,5-a]pyrimidin-5-yl)cyclohexyl)acetonitrile substituted for ethyl 2-(4-(7-(bis((2-(trimethylsilyl)ethoxy)methyl)amino)-3-iodopyrazolo[1,5-a]pyrimidin-5-yl)cyclohexyl)acetate.

Synthesis of ethyl 2-(4-(7-(bis((2-(trimethylsilyl)ethoxy)methyl)amino)-6-bromo-3-(quinolin-3-yl)pyrazolo[1,5-a]pyrimidin-5-yl)cyclohexyl)acetate

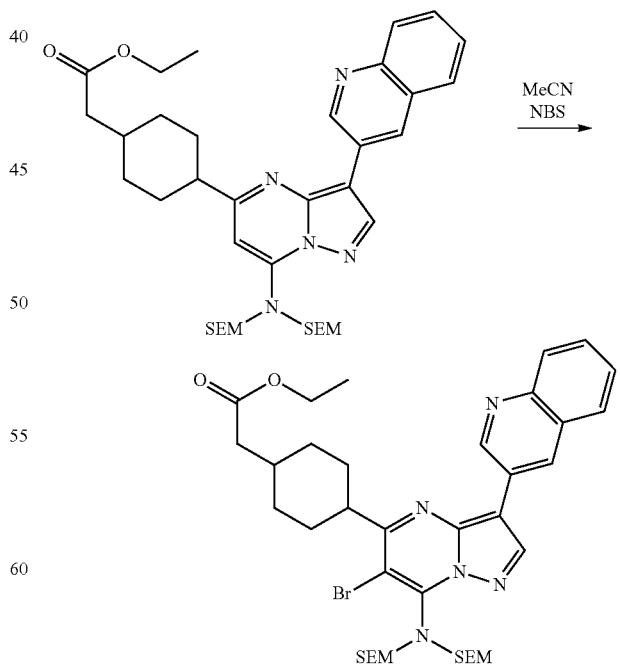

To a 25 mL roundbottom flask was charged ethyl 2-(4-(7-(bis((2-(trimethylsilyl)ethoxy)-methyl)amino)-3-(quinolin- 3-yl)pyrazolo[1,5-a]pyrimidin-5-yl)cyclohexyl)acetate (198 mg, 287 µmol) and acetonitrile (10 mL). To this solution was added N-bromosuccinimide (56 mg, 316 µmol). The resulting reaction mixture was stirred at room temperature for 1 hour. The reaction mixture was concentrated in vacuo and the resulting oil was then purified via silica gel chromatography (0% to 30% ethyl acetate in hexanes gradient) to yield ethyl 2-(4-(7-(bis((2-(trimethylsilyl)ethoxy)methyl)amino)-6-bromo-3-(quinolin-3-yl)pyrazolo[1,5-a]pyrimidin-5-yl)cyclohexyl)acetate (205 mg, 266 µmol, 93% yield) as yellow oil.

Synthesis of 2-(4-(7-(bis((2-(trimethylsilyl)ethoxy)methyl)amino)-6-bromo-3-(quinolin-3-yl)pyrazolo[1,5-a]pyrimidin-5-yl)cyclohexyl)acetonitrile

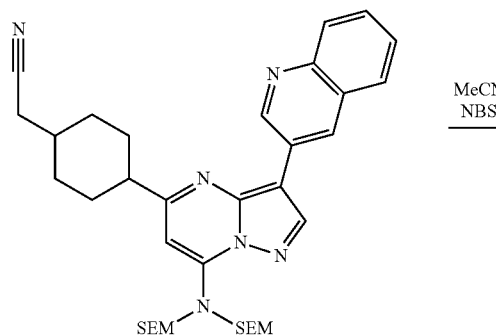

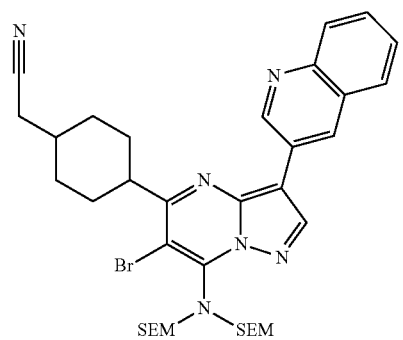

2-(4-(7-(bis((2-(trimethylsilyl)ethoxy)methyl)amino)-6-bromo-3-(quinolin-3-yl)pyrazolo[1,5-a]pyrimidin-5-yl)cyclohexyl)acetonitrile was synthesized in a manner similar to the synthesis of ethyl 2-(4-(7-(bis((2-(trimethylsilyl)ethoxy)methyl)amino)-6-bromo-3-(quinolin-3-yl)pyrazolo[1,5-a]pyrimidin-5-yl)cyclohexyl)acetate, but with 2-(4-(7-(bis((2-(trimethylsilyl)ethoxy)methyl)amino)-3-(quinolin-3-yl)pyrazolo[1,5-a]pyrimidin-5-yl)cyclohexyl)acetonitrile substituted ethyl 2-(4-(7-(bis((2-(trimethylsilyl)ethoxy)methyl)amino)-3-(quinolin-3-yl)pyrazolo[1,5-a]pyrimidin-5-yl)cyclohexyl)acetate.

Synthesis of 2-(4-(7-amino-6-bromo-3-(quinolin-3-yl)pyrazolo[1,5-a]pyrimidin-5-yl)cyclohexyl)acetic acid

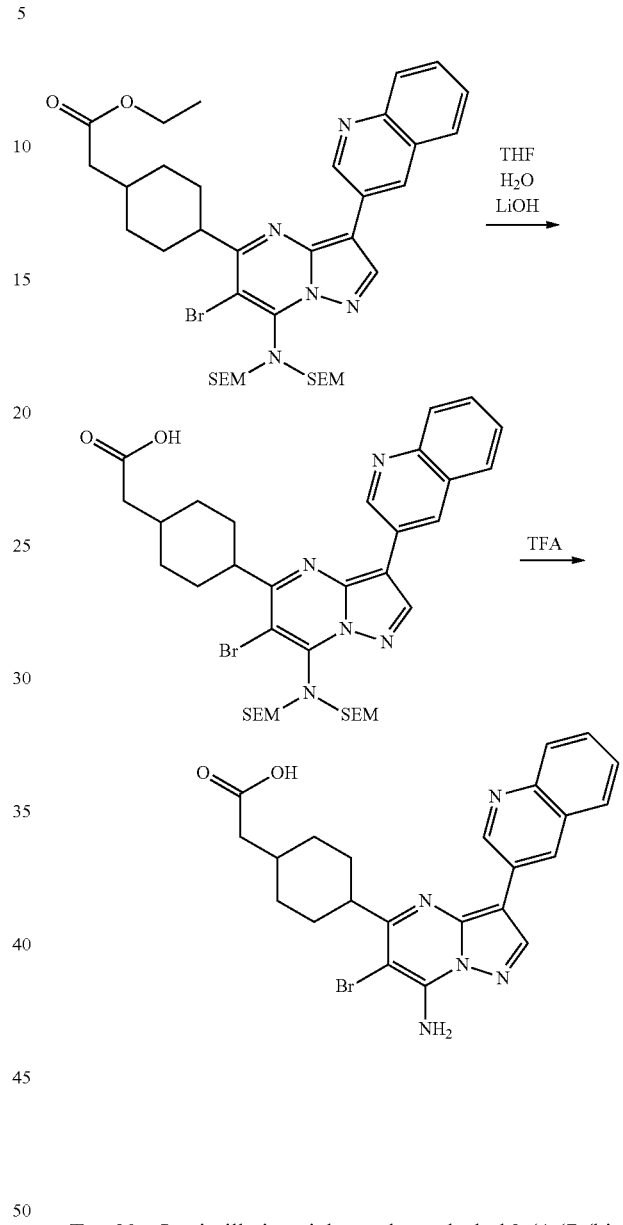

To a 20 mL scintillation vial was charged ethyl 2-(4-(7-(bis((2-(trimethylsilyl)ethoxy)-methyl)amino)-6-bromo-3-(quinolin-3-yl)pyrazolo[1,5-a]pyrimidin-5-yl)cyclohexyl)acetate (100 mg, 130 µmol) and 2:1 THF:H$_2$O (10 mL). To this solution was added 1N LiOH$_{(aq)}$ (200 µL). The resulting reaction mixture was stirred at room temperature for 18 hours. The reaction mixture was concentrated in vacuo and the resulting residue was dissolved in TFA and stirred at room temperature for 1 hour. This solution was concentrated in vacuo and the residue was dissolved in 3:1 DMSO:MeCN. The crude product was purified via reverse-phase preparatory HPLC to yield 2-(4-(7-amino-6-bromo-3-(quinolin-3-yl)pyrazolo[1,5-a]pyrimidin-5-yl)cyclohexyl)acetic acid (m+H=480.1, retention time=3.95 min (isomer 1) and 4.03 min (isomer 2))

867

Synthesis of trans-2-(4-(7-amino-6-bromo-3-(quinolin-3-yl)pyrazolo[1,5-a]pyrimidin-5-yl)cyclohexyl)acetic acid and cis-2-(4-(7-amino-6-bromo-3-(quinolin-3-yl)pyrazolo[1,5-a]pyrimidin-5-yl)cyclohexyl)acetic acid

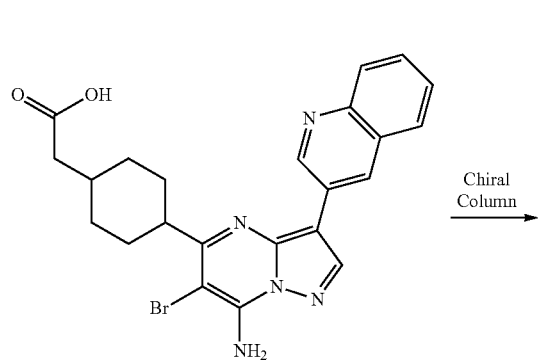

Chiral Column →

+

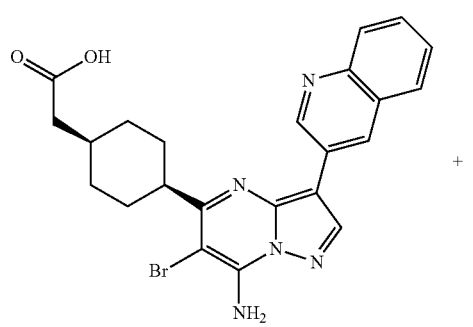

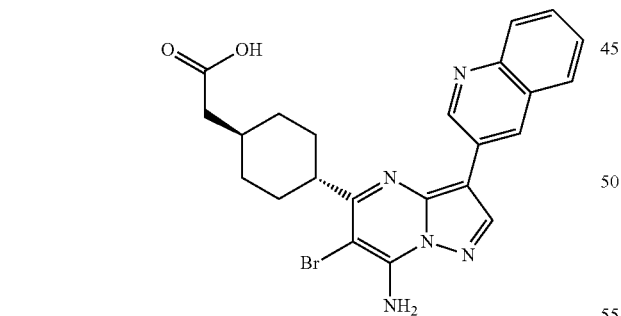

2-(4-(7-amino-6-bromo-3-(quinolin-3-yl)pyrazolo[1,5-a]pyrimidin-5-yl)cyclohexyl)acetic acid is taken up in 9:1 MeOH:TFA. The mixture is eluted through chiral column to yield two single isomers. (m+H=480.1, 10 min. RP HPLC Ret$_{(iso1)}$: 4.03 min., 10 min. RP HPLC Ret$_{(iso2)}$: 3.95 min.)

868

Synthesis of 2-(4-(7-amino-6-bromo-3-(quinolin-3-yl)pyrazolo[1,5-a]pyrimidin-5-yl)cyclohexyl)acetonitrile

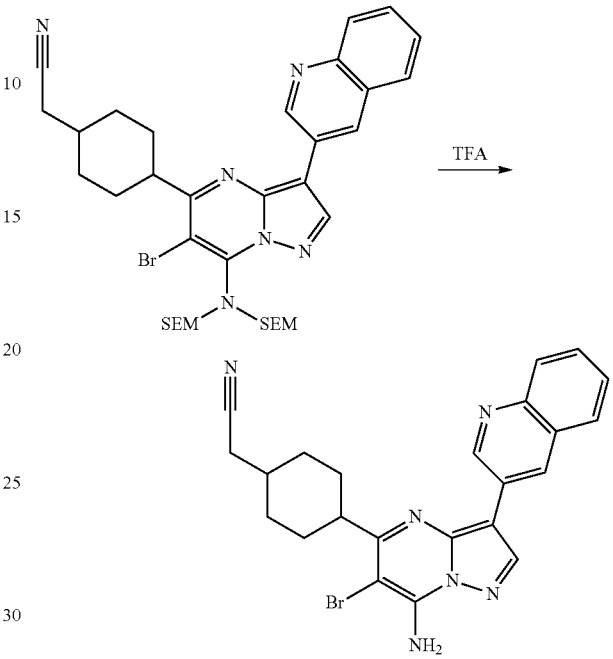

TFA →

2-(4-(7-amino-6-bromo-3-(quinolin-3-yl)pyrazolo[1,5-a]pyrimidin-5-yl)cyclohexyl)acetonitrile (44 μmol, 32 mg) is dissolved in 1 mL TFA in a 20 mL scintillation vial. The reaction mixture is allowed to stir 1 hour at room temperature. The reaction mixture is concentrated in vacuo and purified via reverse-phase preparatory HPLC to yield 2-(4-(7-amino-6-bromo-3-(quinolin-3-yl)pyrazolo[1,5-a]pyrimidin-5-yl)cyclohexyl)acetonitrile as a two-isomer mixture. (m+H=461.2, retention time=4.13 min (isomer 1) and 4.18 min (isomer 2))

5-Trans-4-((1H-tetrazol-5-yl)methyl)cyclohexyl)-6-bromo-3-(quinolin-3-yl)pyrazolo[1,5-a]pyrimidin-7-amine and 5-cis-4-((1H-tetrazol-5-yl)methyl)cyclohexyl)-6-bromo-3-(quinolin-3-yl)pyrazolo[1,5-a]pyrimidin-7-amine

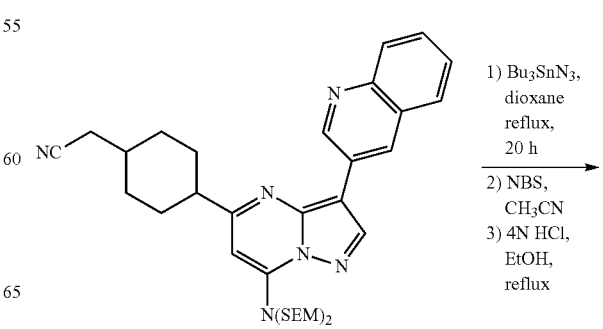

1) Bu$_3$SnN$_3$, dioxane reflux, 20 h
2) NBS, CH$_3$CN
3) 4N HCl, EtOH, reflux

-continued

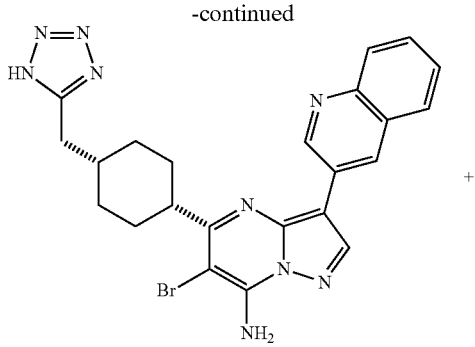

+

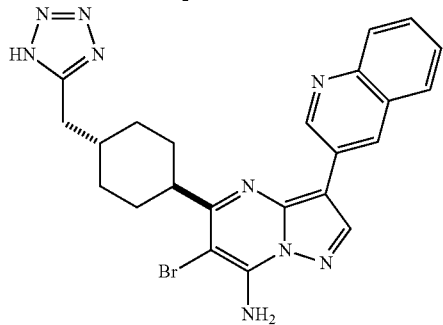

To a solution of 2-(4-(7-(bis((2-(trimethylsilyl)ethoxy)methyl)amino)-3-(quinolin-3-yl)pyrazolo[1,5-a]pyrimidin-5-yl)cyclohexyl)acetonitrile (28 mg, 0.044 mmol) in dioxane (0.50 mL) was added azotributyltin azide (22 mg, 0.066 mmol). The mixture was heated at 105° C. for 20 h. The tin reagent was removed by a short column and the fraction containing the desired product was collected and concentrated in vacuo. The residue was dissolved in $CH_3CN$ and NBS (2.0 mg) was added. The mixture was stirred at rt for 1 h and concentrated in vacuo. The residue was purified by prep-LC to give the Iran-isomer and the cis-isomer of the title compounds.

LC/MS RT=3.53 min (trans), 3.73 min (cis). Mass calculated for, M+H 504.12, observed 504.12.

By essentially the same procedures given in the complete synthesis of 2-(4-(7-amino-6-bromo-3-(quinolin-3-yl)pyrazolo[1,5-a]pyrimidin-5-yl)cyclohexyl)acetonitrile, but with cis/trans isomers separated on silica gel after hydrogen reduction. By essentially the same procedure given in Scheme 6, the compounds listed in Table 5 can be prepared.

TABLE 5

| Compound ID | Structures | M + H (Cal.) | M + H (observed) | Retention Time, (min) |
|---|---|---|---|---|
| 5.1 | 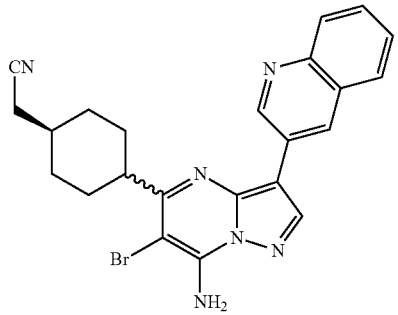 | 461.4 | 461.2 | 4.24 |
| 5.2 | 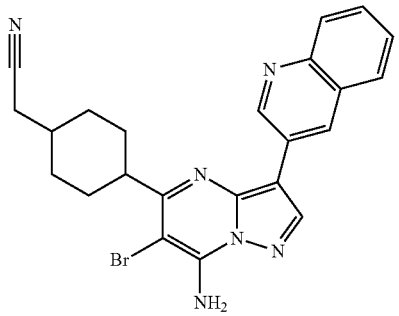 [SMILES: N#CCC1CCC(c2nc3c(-c4cnc5ccccc5c4)cnn3c(N)c2Br)CC1] | 461.10 | 461.2 | 4.24 |

TABLE 5-continued
| Compound ID | Structures | M + H (Cal.) | M + H (observed) | Retention Time, (min) |
|---|---|---|---|---|
| 5.3 | 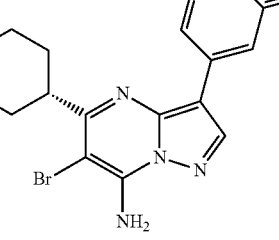 | 504.12 | 504.12 | 3.73 |
| 5.4 | 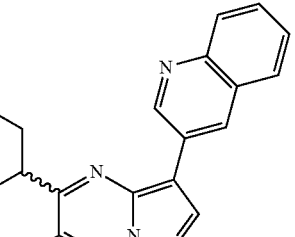 | 480.4 | 480.1 | 3.95 |
| 5.5 | 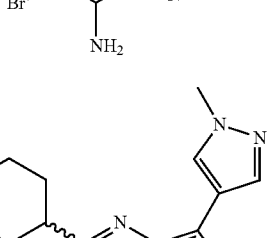 | 433.3 | 433.2 | 4.08 |
| 5.6 | 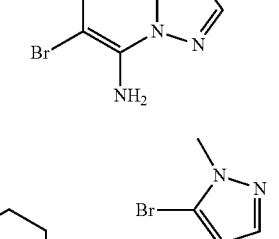 | 513.2 | 513.2 | 4.60 |
| 5.7 | 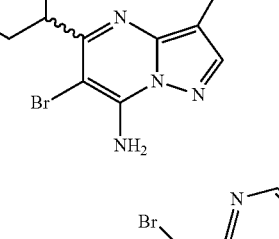 | 558.01 | 558.01 | 4.49 |

TABLE 5-continued

| Compound ID | Structures | M + H (Cal.) | M + H (observed) | Retention Time, (min) |
|---|---|---|---|---|
| 5.8 | 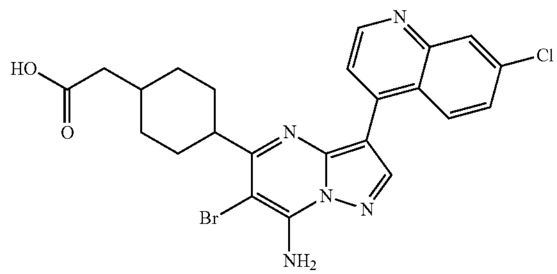 [SMILES: Nc1c(Br)c(C2CCC(CC(=O)O)CC2)nc2c(-c3ccnc4cc(Cl)ccc34)cnn12] | 514.06 | 514.06 | 3.95 |
| 5.9 | 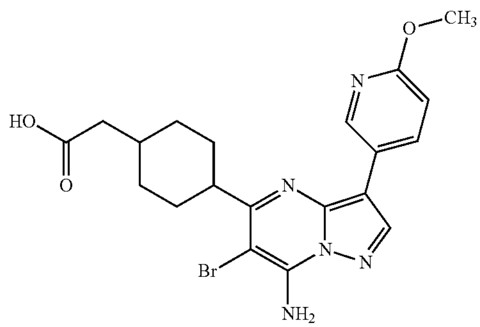 [SMILES: COc1ccc(-c2cnn3c(N)c(Br)c(C4CCC(CC(=O)O)CC4)nc23)cn1] | 460.09 | 460.09 | 4.69 |
| 5.10 | 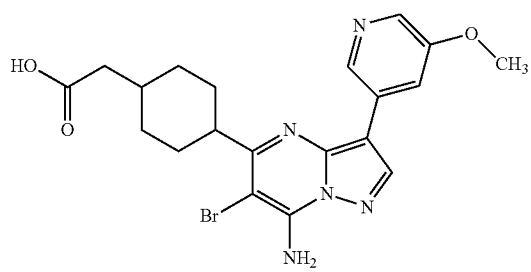 [SMILES: COc1cncc(-c2cnn3c(N)c(Br)c(C4CCC(CC(=O)O)CC4)nc23)c1] | 459.09 | 460.09 | 3.44 |
| 5.11 | 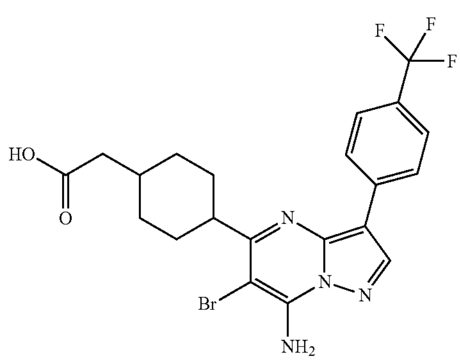 [SMILES: Nc1c(Br)c(C2CCC(CC(=O)O)CC2)nc2c(-c3ccc(C(F)(F)F)cc3)cnn12] | 496.07 | 497.07 | 6.08 |
| 5.12 | 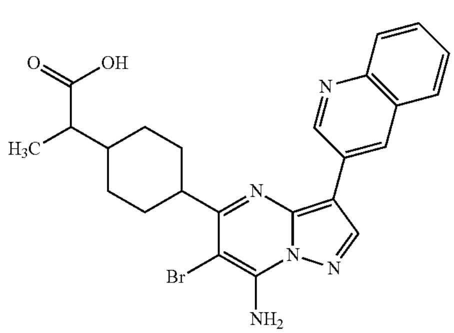 [SMILES: CC(C(=O)O)C1CCC(c2nc3c(-c4cnc5ccccc5c4)cnn3c(N)c2Br)CC1] | 494.11 | 494.2 | 4.05 |

TABLE 5-continued

| Compound ID | Structures | M + H (Cal.) | M + H (observed) | Retention Time, (min) |
|---|---|---|---|---|
| 5.13 | 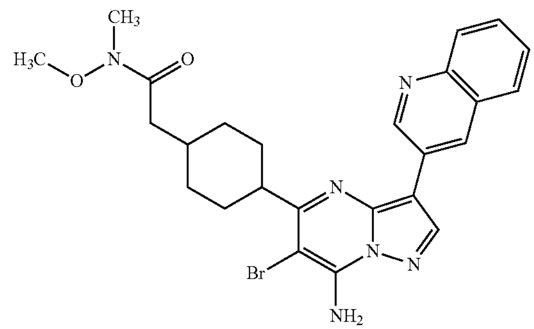 [SMILES: CON(C)C(=O)CC1CCC(c2nc3c(-c4cnc5ccccc5c4)cnn3c(N)c2Br)CC1] | 523.14 | 523.25 | 4.18 |
| 5.14 | 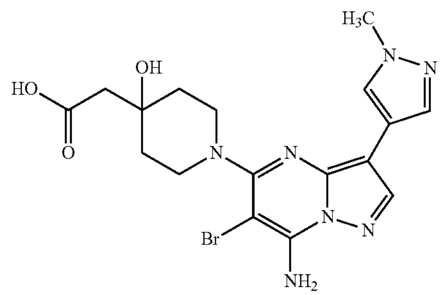 [SMILES: Cn1cc(-c2cnn3c(N)c(Br)c(N4CCC(O)(CC(=O)O)CC4)nc23)cn1] | 386.19 | 386.19 | 2.73 |

[4-(7-Amino-6-pyridin-4-yl-3-quinolin-3-yl-pyrazolo[1,5-a]pyrimidin-5-yl)-cyclohexyl]-acetic acid

SCHEME-21

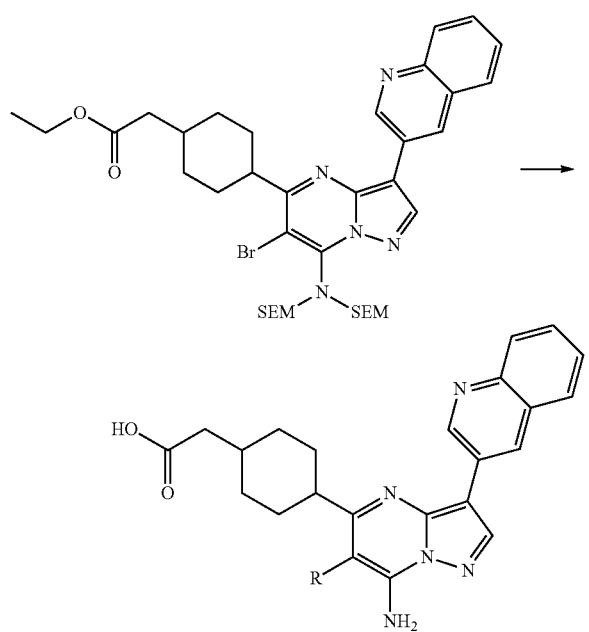

4-Pyridine boronic acid (0.156 mmol, 20 mg), K₂CO₃ (0.234 mmol, 33 mg), and Pd(PPh₃)₄ (0.008 mmol, 10 mg) was added to a solution of (4-{7-[bis-(2-trimethylsilanyl-ethoxymethyl)-amino]-6-bromo-3-quinolin-3-yl-pyrazolo[1,5-a]pyrimidin-5-yl}-cyclohexyl)-acetic acid ethyl ester (0.078 mmol, 60 mg) in dioxane (1 mL). To this suspension was added distilled H₂O (0.2 mL). The resulting reaction mixture was stirred at 100° C. under argon for 18 hours. The reaction mixture was concentrated in vacuo. The crude mixture was dissolved in 2:1 MeOH:H₂O (1.5 mL) and was treated with 2N NaOH$_{(aq)}$ (0.5 mL). The resulting reaction mixture was stirred at room temperature for 18 hours. Aqueous hydrochloride solution (1.0 N, 2 ml) was added to the reaction mixture and the resulting solution was stirred at 65° C. for 2 h. The solution was concentrated in vacuo and purified by prep-LC to afford the title compound (3.6 mg) as a mixture of cis and trans isomers: LC/MS RT=2.84 min. Mass calculated for, M+H 479.21, observed 479.21.

[4-(7-Amino-6-cyano-3-quinolin-3-yl-pyrazolo[1,5-a]pyrimidin-5-yl)-cyclohexyl]-acetic acid A degassed mixture of (4-{7-[bis-(2-trimethylsilanyl-ethoxymethyl)-amino]-6-bromo-3-quinolin-3-yl-pyrazolo[1,5-a]pyrimidin-5-yl}-cyclohexyl)-acetic acid ethyl ester (0.078 mmol, 60 mg), Bu₃SnCN (50 mg, 0.156 mmoL), Pd[P(t-Bu)₃]₂ (8.3 mg, 0.016 mmoL) in Dioxane (1 mL) was heated at 100° C. for 18 h. The reaction mixture was concentrated in vacuo. The crude mixture was dissolved in 2:1 MeOH:H₂O (1.5 mL) and was treated with 2N NaOH$_{(aq)}$ (0.5 mL). The resulting reaction mixture was stirred at room temperature for 18 hours. Aqueous hydrochloride solution (1.0 N, 2 ml) was added to the reaction mixture and the resulting solution was stirred at 65° C. for 2 h. The solution was concentrated and purified by prep-LC to afford the title compound (8.8 mg) as a mixture of cis and trans isomers: LC/MS RT=3.88 min. Mass calculated for, M+H 427.18, observed 427.18.

By essentially the same procedure given in Scheme 7, the compounds listed in Table 6 can be prepared.

TABLE 6

| Compound ID | Structures | M + H (calc.) | M + H (observed) | Retention Time, (min) |
| --- | --- | --- | --- | --- |
| 6.1 | 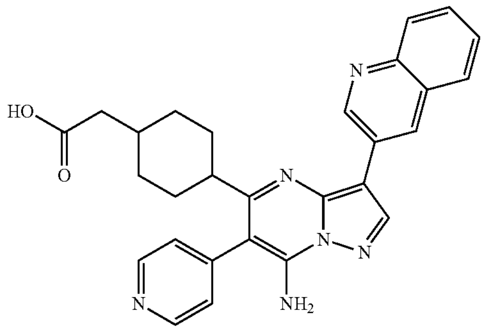 [SMILES: Nc1c(-c2ccncc2)c(C2CCC(CC(=O)O)CC2)nc2c(-c3cnc4ccccc4c3)cnn12] | 479.21 | 479.21 | 2.84 |
| 6.2 | 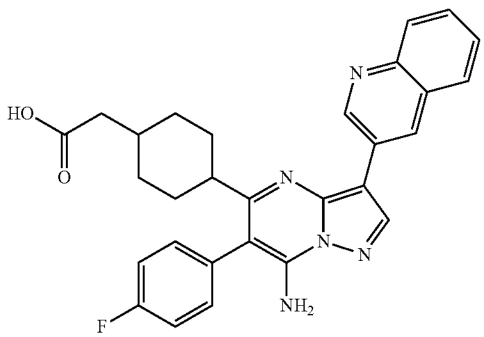 [SMILES: Nc1c(-c2ccc(F)cc2)c(C2CCC(CC(=O)O)CC2)nc2c(-c3cnc4ccccc4c3)cnn12] | 496.21 | 496.21 | 4.32 |
| 6.3 | 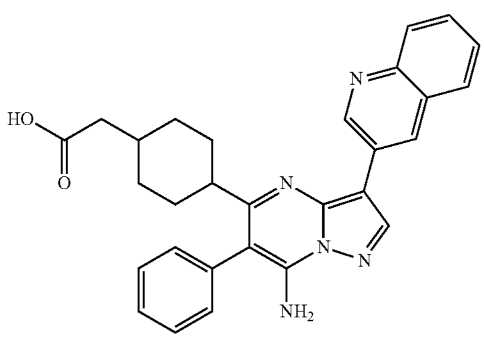 [SMILES: Nc1c(-c2ccccc2)c(C2CCC(CC(=O)O)CC2)nc2c(-c3cnc4ccccc4c3)cnn12] | 478.22 | 478.22 | 4.12 |
| 6.4 | 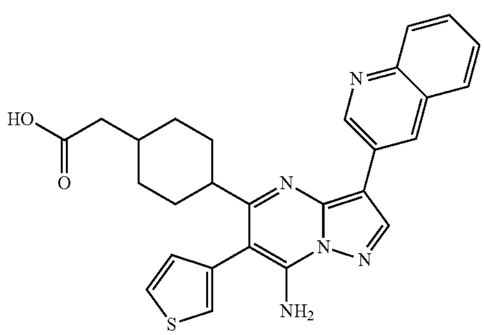 [SMILES: Nc1c(-c2ccsc2)c(C2CCC(CC(=O)O)CC2)nc2c(-c3cnc4ccccc4c3)cnn12] | 484.17 | 484.17 | 4.02 |

TABLE 6-continued

| Compound ID | Structures | M + H (calc.) | M + H (observed) | Retention Time, (min) |
|---|---|---|---|---|
| 6.5 | 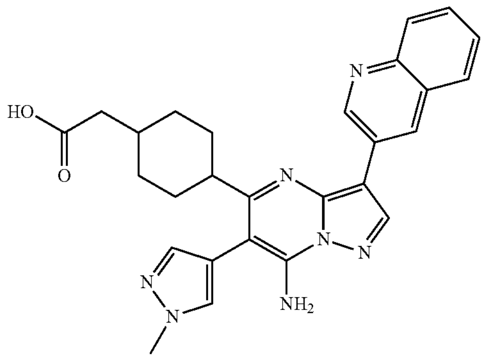 [SMILES: Cn1cc(-c2c(C3CCC(CC(=O)O)CC3)nc3c(-c4cnc5ccccc5c4)cnn3c2N)cn1] | 482.22 | 482.22 | 3.40 |
| 6.6 | 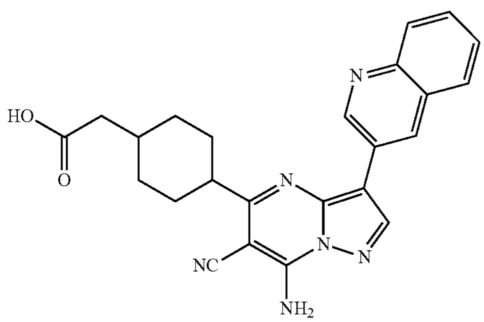 | 427.18 | 427.18 | 3.49 |
| 6.7 | 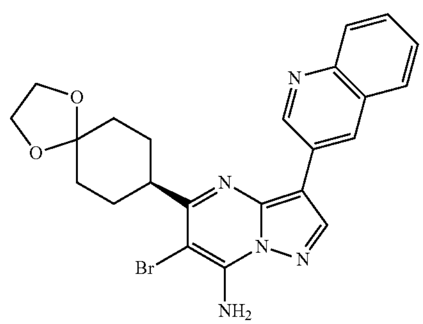 | | | |

2-(4-(7-amino-6-bromo-3-(quinolin-3-yl)pyrazolo[1,5-a]pyrimidin-5-yl)cyclohexyl)-N-(methylsulfonyl)acetamide

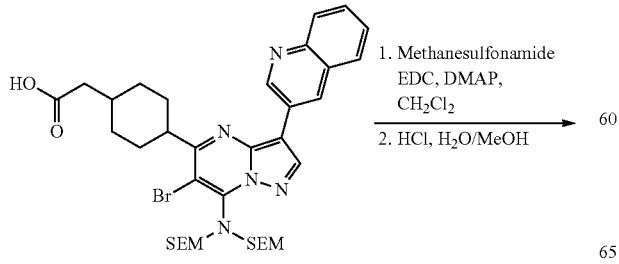

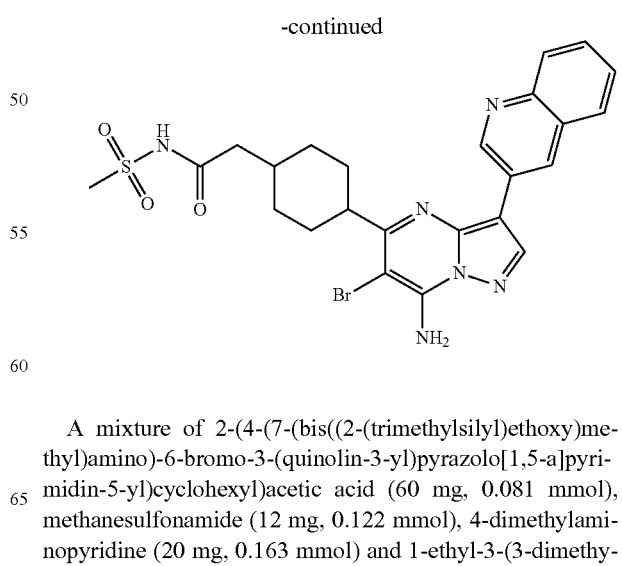

A mixture of 2-(4-(7-(bis((2-(trimethylsilyl)ethoxy)methyl)amino)-6-bromo-3-(quinolin-3-yl)pyrazolo[1,5-a]pyrimidin-5-yl)cyclohexyl)acetic acid (60 mg, 0.081 mmol), methanesulfonamide (12 mg, 0.122 mmol), 4-dimethylaminopyridine (20 mg, 0.163 mmol) and 1-ethyl-3-(3-dimethylaminopropyl)carbodiimide hydrochloride (32 mg, 0.163 mmol) in dichloromethane (2.0 ml) was stirred at room temperature for 16 h. The reaction mixture was concentrated in vacuo. The crude mixture was dissolved in methanol (2 ml) and treated with 1N hydrochloride solution (2 ml) at 65° C. for 2 h. The reaction solution was concentrated and purified by prep-LC to afford the title compound (two isomers, cis and trans). Isomer 1: LC/MS RT=3.63 min. Mass calculated for, M+H 557.09, observed 557.09. Isomer 2: LC/MS RT=3.88 min. Mass calculated for, M+H 557.09, observed 557.09.

By essentially the same procedure given in Scheme 22, the compounds listed in Table 7 can be prepared.

TABLE 7

| Compound ID | Structures | M + H (calc.) | M + H (observed) | Retention Time, (min) |
|---|---|---|---|---|
| 7.1 | 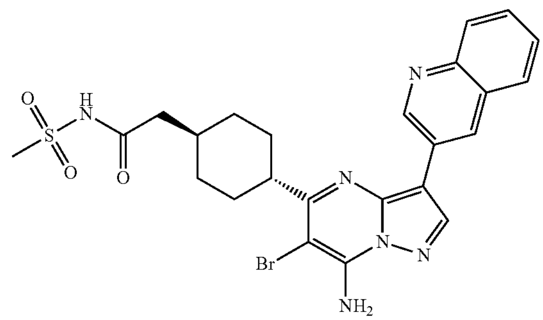 [SMILES: CS(=O)(=O)NC(=O)C[C@H]1CC[C@H](c2nc3c(-c4cnc5ccccc5c4)cnn3c(N)c2Br)CC1] | 557.09 | 557.09 | 3.63 |
| 7.2 | 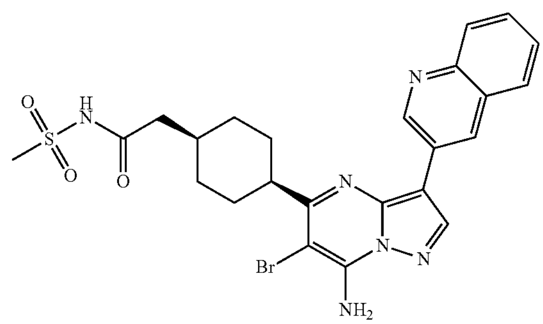 [SMILES: CS(=O)(=O)NC(=O)C[C@H]1CC[C@@H](c2nc3c(-c4cnc5ccccc5c4)cnn3c(N)c2Br)CC1] | 557.09 | 557.09 | 3.88 |
| 7.3 | 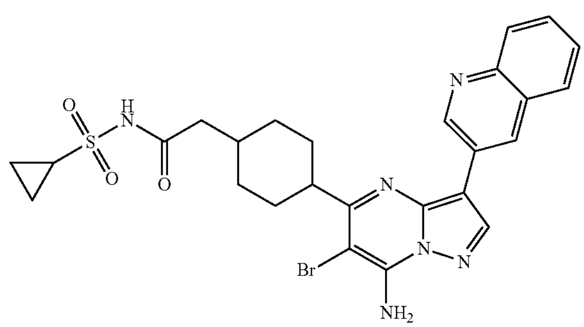 [SMILES: Nc1c(Br)c(C2CCC(CC(=O)NS(=O)(=O)C3CC3)CC2)nc2c(-c3cnc4ccccc4c3)cnn12] | 583.11 | 583.11 | 4.07 |
| 7.4 | 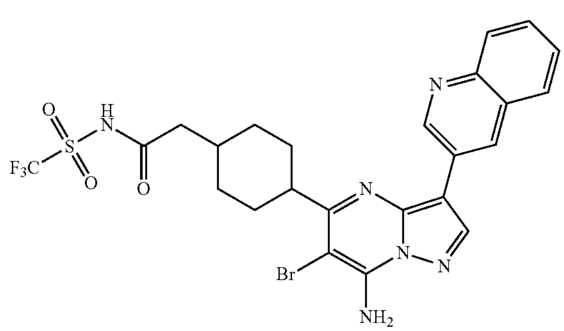 [SMILES: Nc1c(Br)c(C2CCC(CC(=O)NS(=O)(=O)C(F)(F)F)CC2)nc2c(-c3cnc4ccccc4c3)cnn12] | 611.06 | 611.06 | Isomer 1: 4.33<br>Isomer 2: 4.55 |

TABLE 7-continued

| Compound ID | Structures | M + H (calc.) | M + H (observed) | Retention Time, (min) |
|---|---|---|---|---|
| 7.5 | 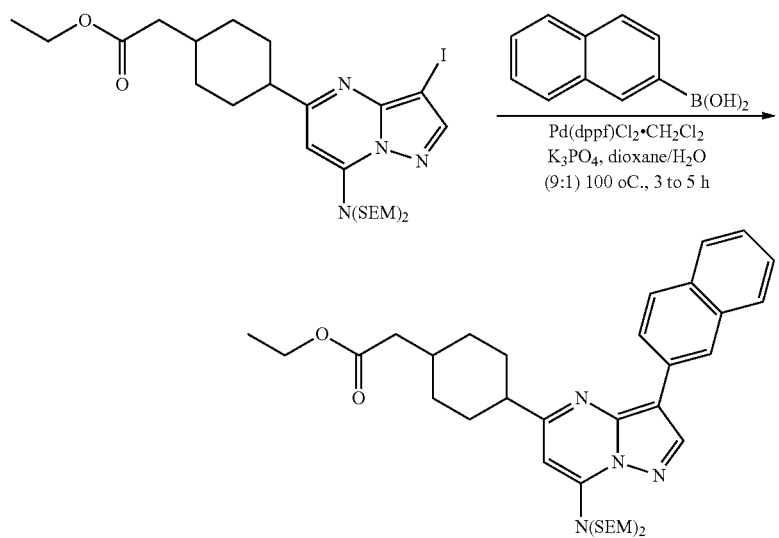 | 557.0 | 557.0 | 3.88 |

Ethyl 2-(4-(7-(bis((2-(trimethylsilyl)ethoxy)methyl) amino)-3-(naphthalen-2-yl)pyrazolo[1,5-a]pyrimidin-5-yl) cyclohexyl)acetate. LC/MS RT=3.40 min (5 min method). Mass calculated for, M+H 689.38, observed 689.38.

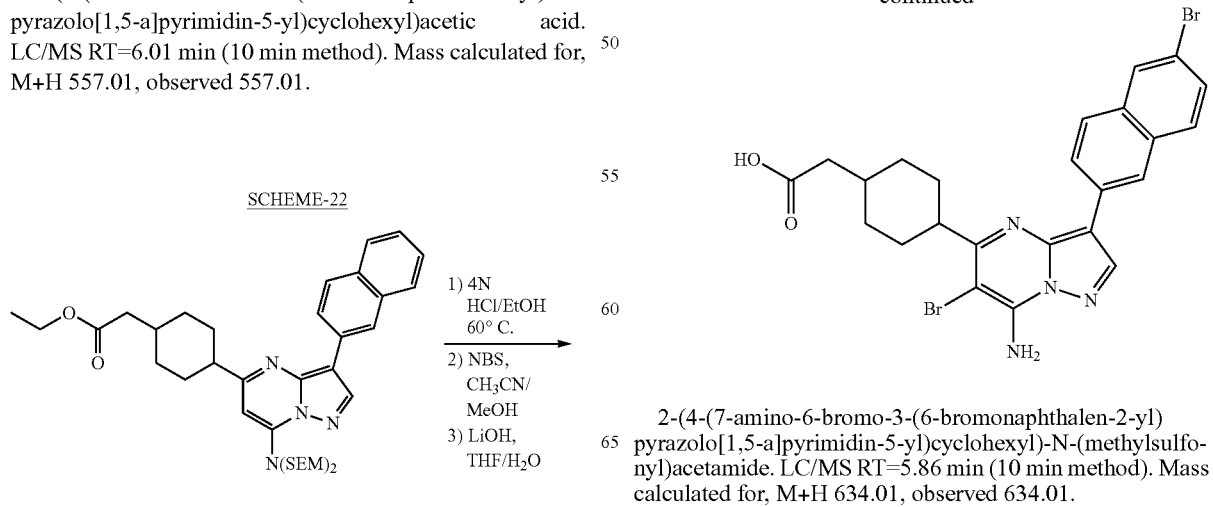

2-(4-(7-Amino-6-bromo-3-(6-bromonaphthalen-2-yl) pyrazolo[1,5-a]pyrimidin-5-yl)cyclohexyl)acetic acid. LC/MS RT=6.01 min (10 min method). Mass calculated for, M+H 557.01, observed 557.01.

2-(4-(7-amino-6-bromo-3-(6-bromonaphthalen-2-yl) pyrazolo[1,5-a]pyrimidin-5-yl)cyclohexyl)-N-(methylsulfonyl)acetamide. LC/MS RT=5.86 min (10 min method). Mass calculated for, M+H 634.01, observed 634.01.

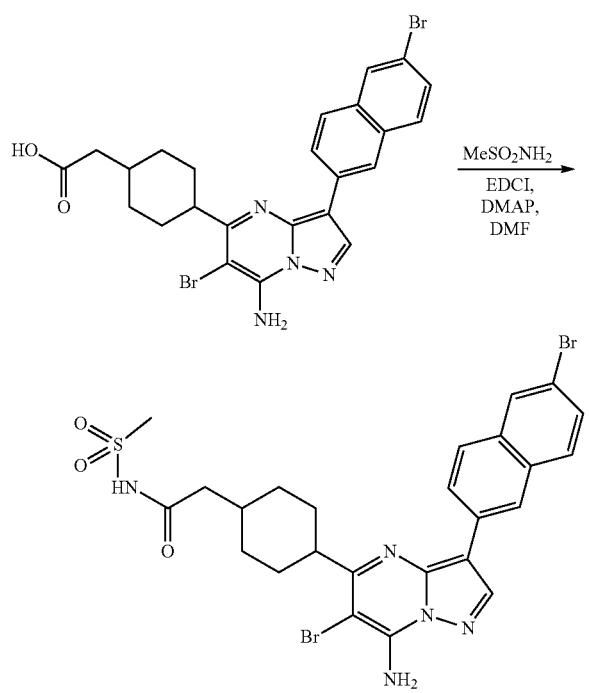

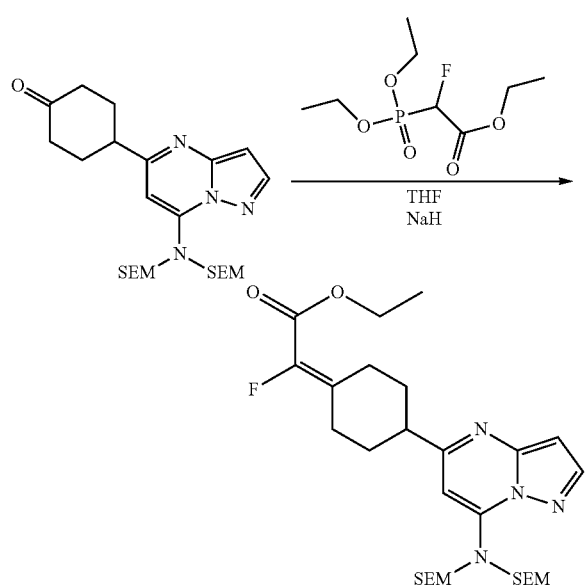

(S)-2-((1s,4R)-4-(7-amino-6-bromo-3-(6-phenylpyridin-3-yl)pyrazolo[1,5-a]pyrimidin-5-yl)cyclohexyl)-2-fluoroacetic acid Part-A Ethyl 2-(4-(7-(bis((2-(trimethylsilyl)ethoxy)methyl)amino)pyrazolo[1,5-a]pyrimidin-5-yl)cyclohexylidene)-2-fluoroacetate To a 250 mL roundbottom flask containing 80 mL THF was charged sodium hydride (60% w/w in mineral oil, 12.86 mmol, 515 mg). This suspension was broken up in the sonic-aid and then cooled to 0° C. in icebath. Triethyl 2-fluoro-2-phosphonoacetate (12.86 mmol, 3.12 g) was taken up in THF (10 mL) and added dropwise to stirring NaH suspension. The resulting solution was allowed to stir at 0° C. for 10 minutes. 4-(7-(bis((2-(trimethylsilyl)ethoxy)methyl)amino)pyrazolo[1,5-a]pyrimidin-5-yl)cyclohexanone (6.43 mmol, 3.16 g) was taken up in THF (10 mL) and added dropwise to the stirring solution. The reaction was allowed to warm to room temperature and stir 18 hours. At 18 hours, the reaction was diluted with DCM (400 mL) and washed with H₂O. The organic layer was collected and dried over Na₂SO₄. This solution was reduced in vacuo and purified via flash chromatography to yield the title compound (3.43 g, 5.92 mmol).

Part-B

Ethyl 2-(4-(7-(bis((2-(trimethylsilyl)ethoxy)methyl)amino)pyrazolo[1,5-a]pyrimidin-5-yl)cyclohexylidene)-2-fluoroacetate

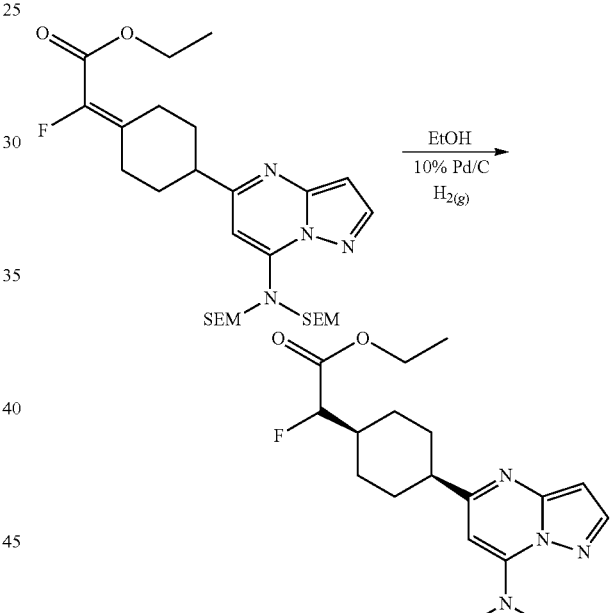

To a 50 mL roundbottom flask was charged ethanol (20 mL), ethyl 2-(4-(7-(bis((2-(trimethylsilyl)ethoxy)methyl)amino)pyrazolo[1,5-a]pyrimidin-5-yl)cyclohexylidene)-2-fluoroacetate (1.99 mmol, 1.15 g), and 10% palladium on carbon (200 mg). The flask was sealed and degassed under vacuum. Hydrogen gas was then added via balloon and the reaction was allowed to stir at room temperature for 18 hours. At 18 hours the reaction was filtered through celite and the solvent reduced in vacuo. The title compound was then purified via flash chromatography on high-performance silica (829 mg).

887

Part-C

(S)-ethyl 2-((1s,4R)-4-(7-(bis((2-(trimethylsilyl)ethoxy)methyl)amino)-3-iodopyrazolo[1,5-a]pyrimidin-5-yl)cyclohexyl)-2-fluoroacetate

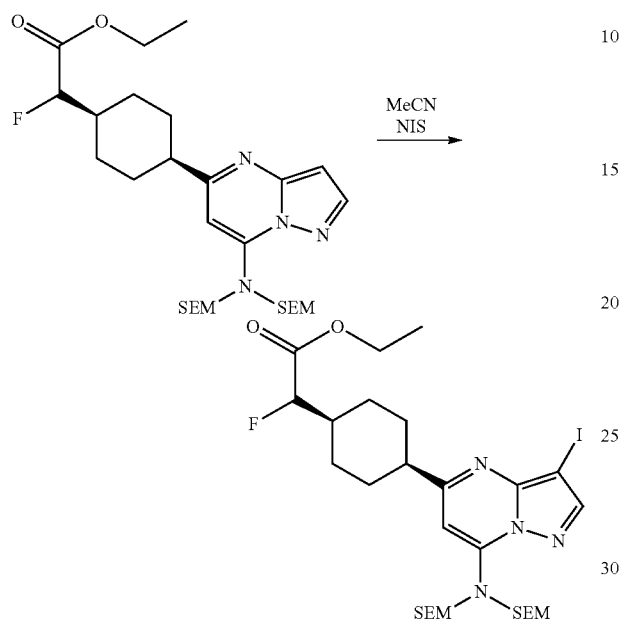

To a 50 mL roundbottom flask was charged acetonitrile (20 mL), ethyl 2-(4-(7-(bis((2-(trimethylsilyl)ethoxy)methyl)amino)pyrazolo[1,5-a]pyrimidin-5-yl)cyclohexylidene)-2-fluoroacetate (1.43 mmol, 828 mg), and N-Iodosuccinimide (1.57 mmol, 353 mg). The resulting solution was allowed to stir at room temperature for 18 hours. At 18 hours, the reaction was reduced in vacuo and purified via flash chromatography to yield the title compound (995 mg, 1.41 mmol).

Part-D

(S)-ethyl 2-((1s,4R)-4-(7-(bis((2-(trimethylsilyl)ethoxy)methyl)amino)-3-(6-phenylpyridin-3-yl)pyrazolo[1,5-a]pyrimidin-5-yl)cyclohexyl)-2-fluoroacetate

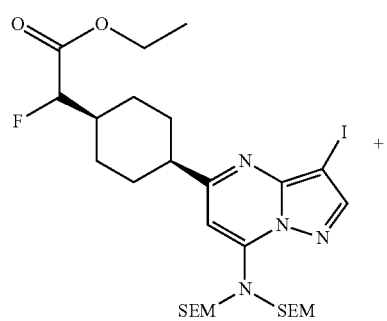

888

-continued

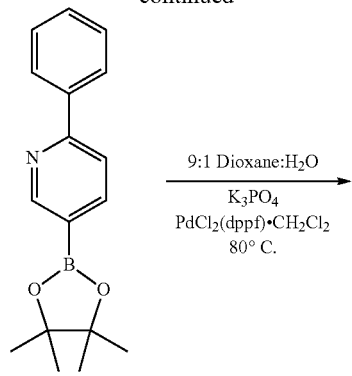

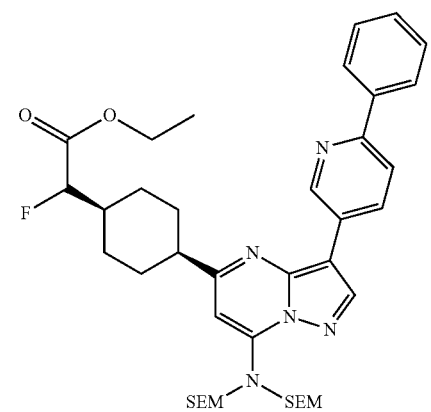

A pressure vial was charged with (S)-ethyl 2-((1s,4R)-4-(7-(bis((2-(trimethylsilyl)ethoxy)methyl)amino)-3-iodopyrazolo[1,5-a]pyrimidin-5-yl)cyclohexyl)-2-fluoroacetate (4.26 mmol, 3.01 g), 6-phenylpyridine-3-boronic acid pinacol ester (5.54 mmol, 1.56 g), potassium phosphate (12.78 mmol, 2.71 g), $PdCl_2(dppf) \cdot CH_2Cl_2$ (0.43 mmol, 348 mg), and a solution of 9:1 1,4-dioxane:$H_2O$ (45 mL). The flask was flushed with argon and sealed. The reaction was stirred at 80° C. for 18 hours. At 18 hours, the reaction was diluted with DCM (200 mL) and washed with $H_2O$. The organic layer was collected and dried over $Na_2SO_4$. The resulting residue was purified via flash chromatography to yield the title compound (3.79 mmol, 2.78 g)

Part-E (S)-ethyl 2-((1s,4R)-4-(7-(bis((2-(trimethylsilyl)ethoxy)methyl)amino)-6-bromo-3-(6-phenylpyridin-3-yl)pyrazolo[1,5-a]pyrimidin-5-cyclohexyl)-2-fluoroacetate Part-F (S)-ethyl 2-((1s,4R)-4-(7-amino-6-bromo-3-(6-phenylpyridin-3-yl)pyrazolo[1,5-a]pyrimidin-5-yl)cyclohexyl)-2-fluoroacetate

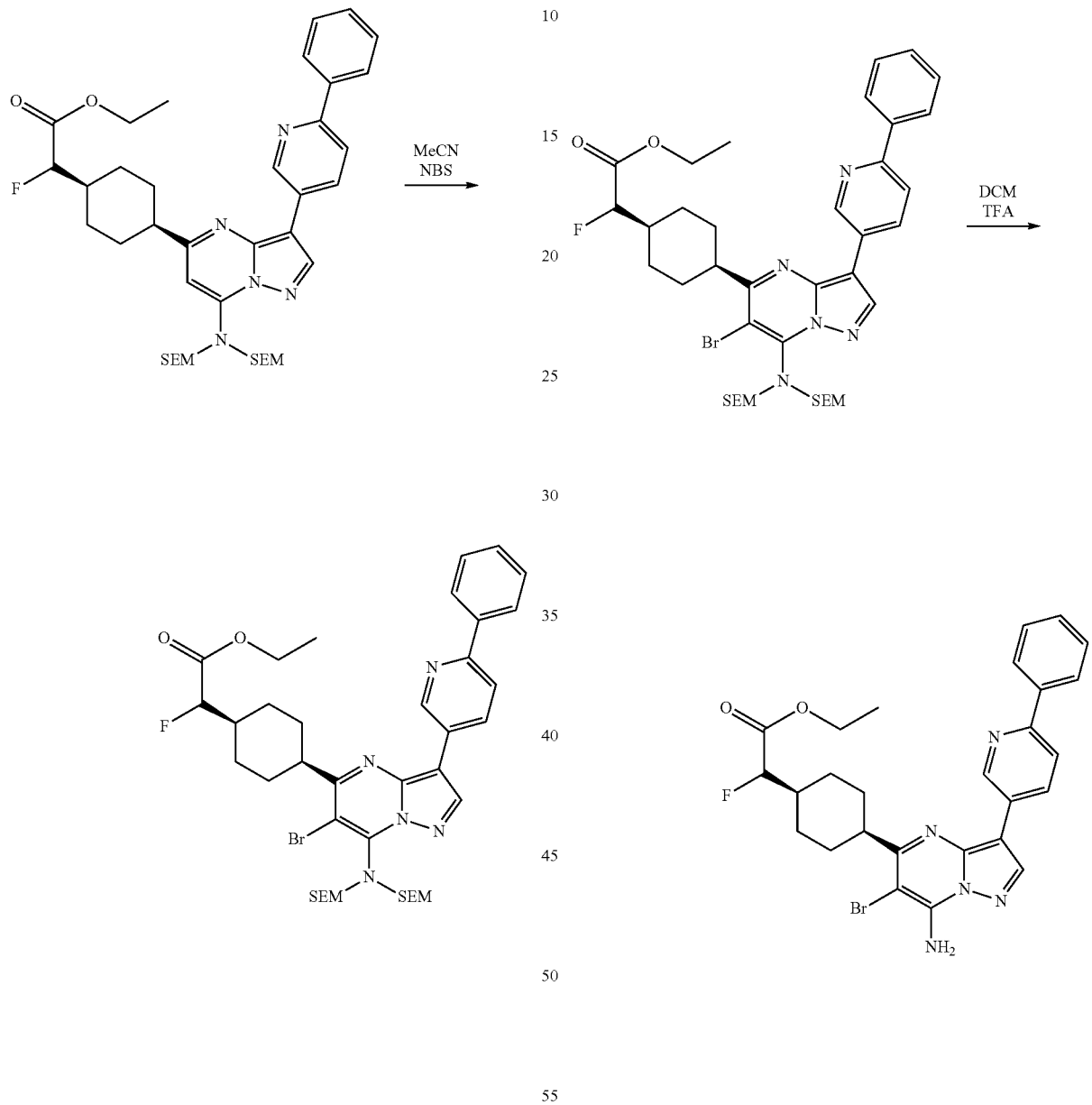

To a 100 mL roundbottom flask was charged (S)-ethyl 2-((1s,4R)-4-(7-(bis((2-(trimethylsilyl)ethoxy)methyl)amino)-3-(6-phenylpyridin-3-yl)pyrazolo[1,5-a]pyrimidin-5-yl)cyclohexyl)-2-fluoroacetate (3.51 mmol, 2.58 g), acetonitrile (40 mL) and N-bromosuccinimide (3.87 mmol, 688 mg). The resulting solution was stirred at room temperature for 18 hours. At 18 hours, the solvent was removed in vacuo and the residue was purified via flash chromatography to yield the title compound (3.21 mmol, 2.61 g)

To a 50 mL roundbottom flask was charged (S)-ethyl 2-((1s,4R)-4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)-2-fluoroacetate (0.62 mmol, 500 mg), DCM (10 mL), and TFA (10 mL). The resulting solution was stirred at room temperature for 30 minutes. At 30 minutes, the solvent was removed in vacuo and the title compound was purified by reverse-phase preparatory HPLC (m+H=552.20, retention time=3.46 min).

Part-G (S)-2-((1s,4R)-4-(7-amino-6-bromo-3-(6-phenylpyridin-3-yl)pyrazolo[1,5-a]pyrimidin-5-yl)cyclohexyl)-2-fluoroacetic acid

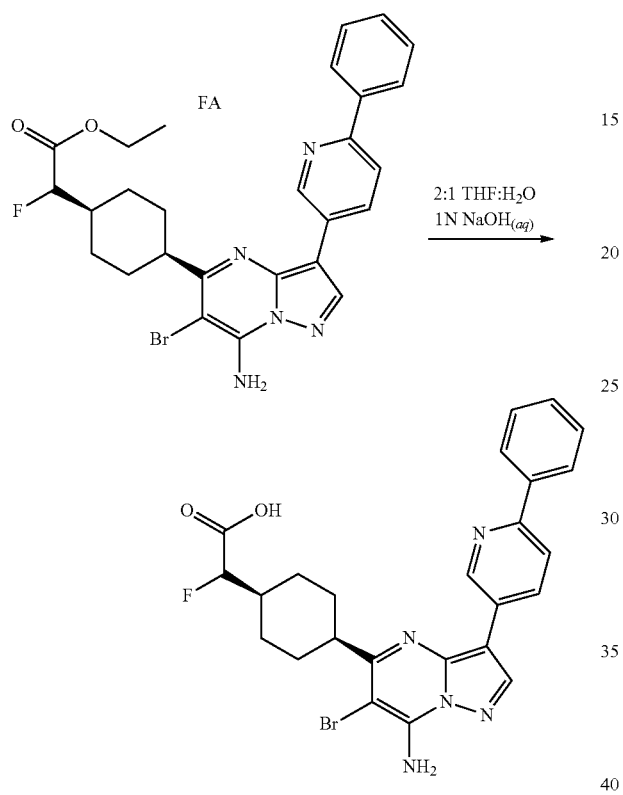

To a 20 mL scintillation vial was charged (S)-ethyl 2-((1s,4R)-4-(7-amino-6-bromo-3-(6-phenylpyridin-3-yl)pyrazolo[1,5-a]pyrimidin-5-yl)cyclohexyl)-2-fluoroacetate as a formic acid salt (0.25 mmol, 150 mg), a solution of 2:1 THF:H$_2$O (9 mL), and 1N NaOH$_{(aq)}$ (0.50 mmol, 0.50 mL). This solution was stirred at room temperature for 2 hours. At 2 hours, the solvent was removed in vacuo and the residue was taken up in 2 mL 1:1 MeCN:H$_2$O. This solution was frozen in liquid nitrogen and then pumped dry on lyophilizer to yield (S)-2-((1s,4R)-4-(7-amino-6-bromo-3-(6-phenylpyridin-3-yl)pyrazolo[1,5-a]pyrimidin-5-yl)cyclohexyl)-2-fluoroacetic acid as a sodium salt (m+H=524.08, retention time=4.16 min).

The following compounds (Table-7A) were synthesized using essentially the same procedures used for the total synthesis of (S)-2-((1s,4R)-4-(7-amino-6-bromo-3-(6-phenylpyridin-3-yl)pyrazolo[1,5-a]pyrimidin-5-yl)cyclohexyl)-2-fluoroacetic acid:

TABLE 7A

| Compound ID | Structures | M + H (calc.) | M + H (observed) | Retention Time, (min) |
|---|---|---|---|---|
| 7.1.1 | 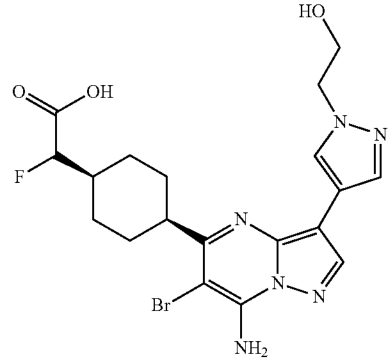 [SMILES: Nc1c(Br)c([C@H]2CC[C@@H](C(F)C(=O)O)CC2)nc2c(-c3cnn(CCO)c3)cnn12] | 480.09 | 481.54 | 3.47 |

TABLE 7A-continued

| Compound ID | Structures | M + H (calc.) | M + H (observed) | Retention Time, (min) |
|---|---|---|---|---|
| 7.1.2 | 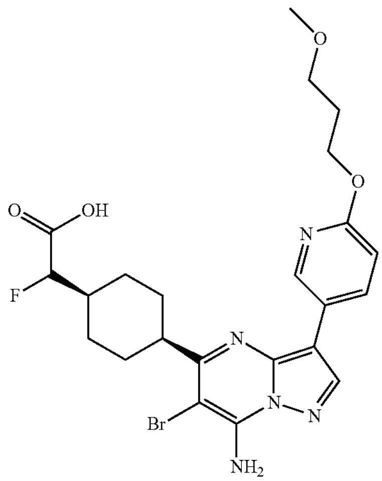 [SMILES: COCCCOc1ccc(-c2cnn3c(N)c(Br)c([C@H]4CC[C@@H](C(F)C(=O)O)CC4)nc23)cn1] | 535.12 | 535.85 | 4.79 |

Ethyl 7-(bis((2-(trimethylsilyl)ethoxy)methyl) amino)-5-((1R,4s)-4-((S)-2-ethoxy-1-fluoro-2-oxoethyl)cyclohexyl)-3-(6-phenylpyridin-3-yl)pyrazolo[1,5-a]pyrimidine-6-carboxylate To a pressure vial was charged (S)-ethyl 2-((1s,4R)-4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)-2-fluoroacetate (0.32 mmol, 263 mg), tetrakis(triphenylphosphine)palladium(0) (0.032 mmol, 37 mg), 1,4-dioxane (5 mL), and tributyl(1-ethoxyvinyl)tin (0.97 mmol, 329 μL). The vessel was flushed with argon, sealed, and the reaction stirred at 100° C. for 18 hours. At 18 hours, the solvent was removed in vacuo and the residue purified via flash chromatography to yield the title compound.

(S)-2-(1s,4R)-4-(6-acetyl-7-amino-3-(6-phenylpyridin-3-yl)pyrazolo[1,5-a]pyrimidin-5-yl)cyclohexyl)-2-fluoroacetic acid

895

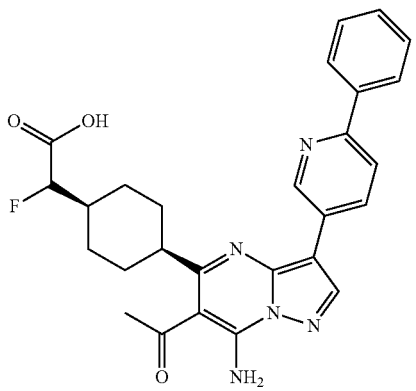

To a 50 mL roundbottom flask is charged ethyl 7-(bis((2-(trimethylsilyl)ethoxy)methyl)amino)-5-((1R,4s)-4-((S)-2-ethoxy-1-fluoro-2-oxoethyl)cyclohexyl)-3-(6-phenylpyridin-3-yl)pyrazolo[1,5-a]pyrimidine-6-carboxylate (0.29 mmol, 236 mg), a solution of 2:1 THF:H$_2$O (9 mL), and 1N LiOH$_{(aq)}$ (0.59 mmol, 0.59 mL). The resulting solution was stirred at room temperature for 2 hours. The reaction was then acidified to pH ~4 with 1N HCl$_{(aq)}$ and the solvent removed in vacuo. This residue was dissolved in 10 mL 1,4-dioxane. To this solution was added H$_2$O (3 mL) followed by 4N HCl:dioxane (5 mL). This solution was stirred at room temperature for 18 hours. After 18 hours, the solvent was removed in vacuo and the residue purified via reverse-phase HPLC to yield (S)-2-((1s,4R)-4-(6-acetyl-7-amino-3-(6-phenylpyridin-3-yl)pyrazolo[1,5-a]pyrimidin-5-yl)cyclohexyl)-2-fluoroacetic acid (m+H=488.62, retention time=3.71 min).

(S)-2-(1s,4R)-4-(6-acetyl-7-amino-3-(6-(1-(2-hydroxyethyl)-1H-pyrazol-4-yl)pyridin-3-yl)pyrazolo[1,5-a]pyrimidin-5-yl)cyclohexyl)-2-fluoroacetic acid

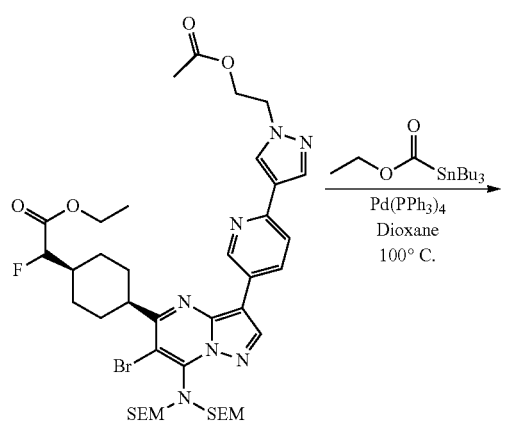

896

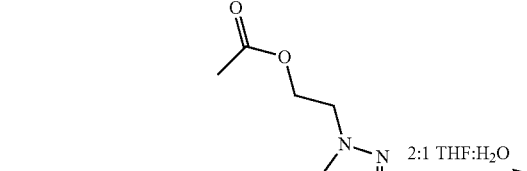

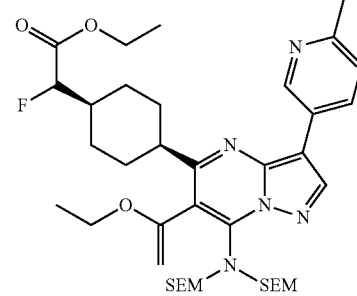

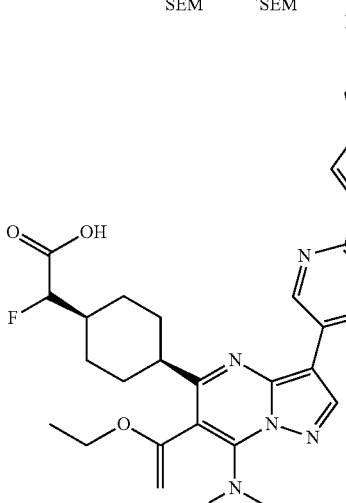

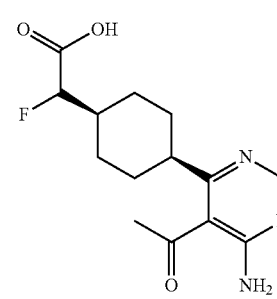

(S)-2-((1s,4R)-4-(6-acetyl-7-amino-3-(6-(1-(2-hydroxyethyl)-1H-pyrazol-4-yl)pyridin-3-yl)pyrazolo[1,5-a]pyrimidin-5-yl)cyclohexyl)-2-fluoroacetic acid was synthesized in the manner previously described. (m+H=521.22, retention time=3.01 min).

897

(S)-2-(1s,4R)-4-(7-amino-3-(6-phenylpyridin-3-yl)pyrazolo[1,5-a]pyrimidin-5-yl)cyclohexyl)-2-fluoroacetic acid

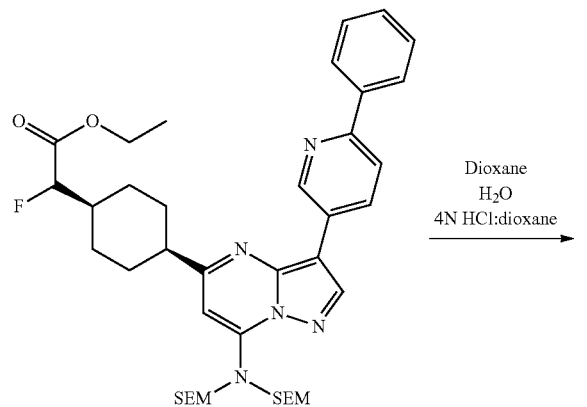

To a 50 mL roundbottom flask was charged (S)-ethyl 2-((1s,4R)-4-(7-(bis((2-(trimethylsilyl)ethoxy)methyl)amino)-3-(6-phenylpyridin-3-yl)pyrazolo[1,5-a]pyrimidin-5-yl)cyclohexyl)-2-fluoroacetate (0.27 mmol, 200 mg), 1,4-dioxane (5 mL), H$_2$O (1 mL), and 4N HCl in 1,4-dioxane. The resulting solution was stirred at room temperature for 5 days. At day 5, the solvent was removed in vacuo and the residue taken on without further purification.

(S)-2-(1s,4R)-4-(7-amino-6-chloro-3-(6-phenylpyridin-3-yl)pyrazolo[1,5-a]pyrimidin-5-yl)cyclohexyl)-2-fluoroacetic acid

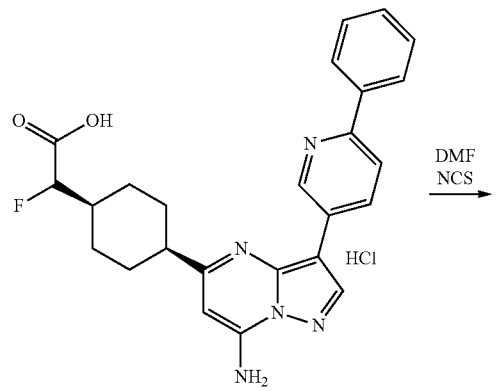

898

-continued

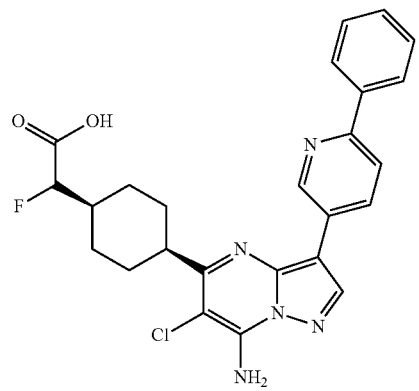

To a 50 mL roundbottom flask was charged (S)-2-((1s,4R)-4-(7-amino-3-(6-phenylpyridin-3-yl)pyrazolo[1,5-a]pyrimidin-5-yl)cyclohexyl)-2-fluoroacetic acid hydrochloride (0.27 mmol), DMF (8 mL), and N-chlorosuccinimide (0.30 mmol, 40 mg). The resulting solution was stirred at room temperature for 18 hours. At 18 hours, the solvent was removed in vacuo. The resulting residue was purified via reverse-phase HPLC to yield (S)-2-((1s,4R)-4-(7-amino-6-chloro-3-(6-phenylpyridin-3-yl)pyrazolo[1,5-a]pyrimidin-5-yl)cyclohexyl)-2-fluoroacetic acid (m+H=480.02, retention time=4.02 min).

(S)-ethyl 2-((1s,4R)-4-(7-(bis((2-(trimethylsilyl)ethoxy)methyl)amino)-3-(6-chloropyridin-3-yl)pyrazolo[1,5-a]pyrimidin-5-yl)cyclohexyl)-2-fluoroacetate

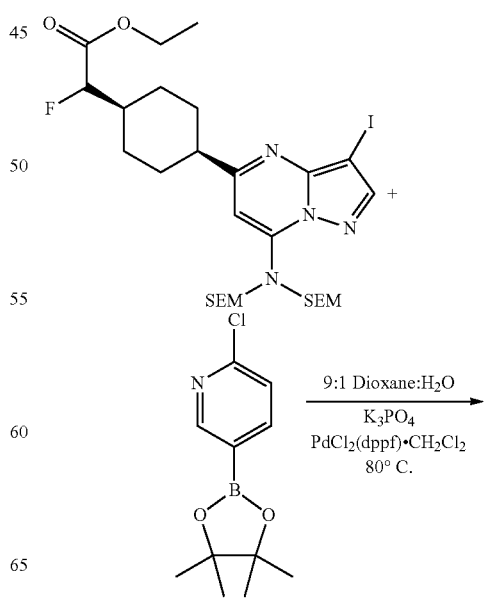

899
-continued

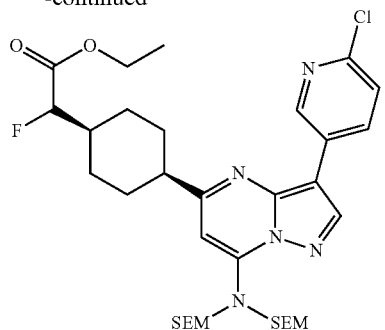

(S)-ethyl 2-((1s,4R)-4-(7-(bis((2-(trimethylsilyl)ethoxy)methyl)amino)-3-(6-chloropyridin-3-yl)pyrazolo[1,5-a]pyrimidin-5-yl)cyclohexyl)-2-fluoroacetate is synthesized in a manner similar to the synthesis of (S)-ethyl 2-((1s,4R)-4-(7-(bis((2-(trimethylsilyl)ethoxy)methyl)amino)-3-(6-phenylpyridin-3-yl)pyrazolo[1,5-a]pyrimidin-5-yl)cyclohexyl)-2-fluoroacetate, but with 6-chloropyridine-3-boronic acid pinacol ester substituted for 6-phenylpyridine-3-boronic acid pinacol ester.

(S)-ethyl 2-((1s,4R)-4-(7-(bis((2-(trimethylsilyl)ethoxy)methyl)amino)-3-(6-(pyrimidin-2-yl)pyridin-3-yl)pyrazolo[1,5-a]pyrimidin-5-yl)cyclohexyl)-2-fluoroacetate

900

To a 2-5 mL microwave vessel was charged (S)-ethyl 2-((1s,4R)-4-(7-(bis((2-(trimethylsilyl)ethoxy)methyl)amino)-3-(6-chloropyridin-3-yl)pyrazolo[1,5-a]pyrimidin-5-yl)cyclohexyl)-2-fluoroacetate (0.22 mmol, 150 mg), acetonitrile (3 mL), 2-(tributylstannyl)pyrimidine (0.65 mmol, 240 mg), and tetrakis(triphenylphosphine)palladium (0) (0.02 mmol, 25 mg). The vessel was flushed with argon, sealed and heated to 150° C. for 40 minutes in microwave synthesizer. Upon completion, the solvent was removed in vacuo and the residue purified by flash chromatography to yield the title compound.

(S)-2-(1s,4R)-4-(7-amino-6-bromo-3-(6-(pyrimidin-2-yl)pyridin-3-yl)pyrazolo[1,5-a]pyrimidin-5-yl)cyclohexyl)-2-fluoroacetic acid

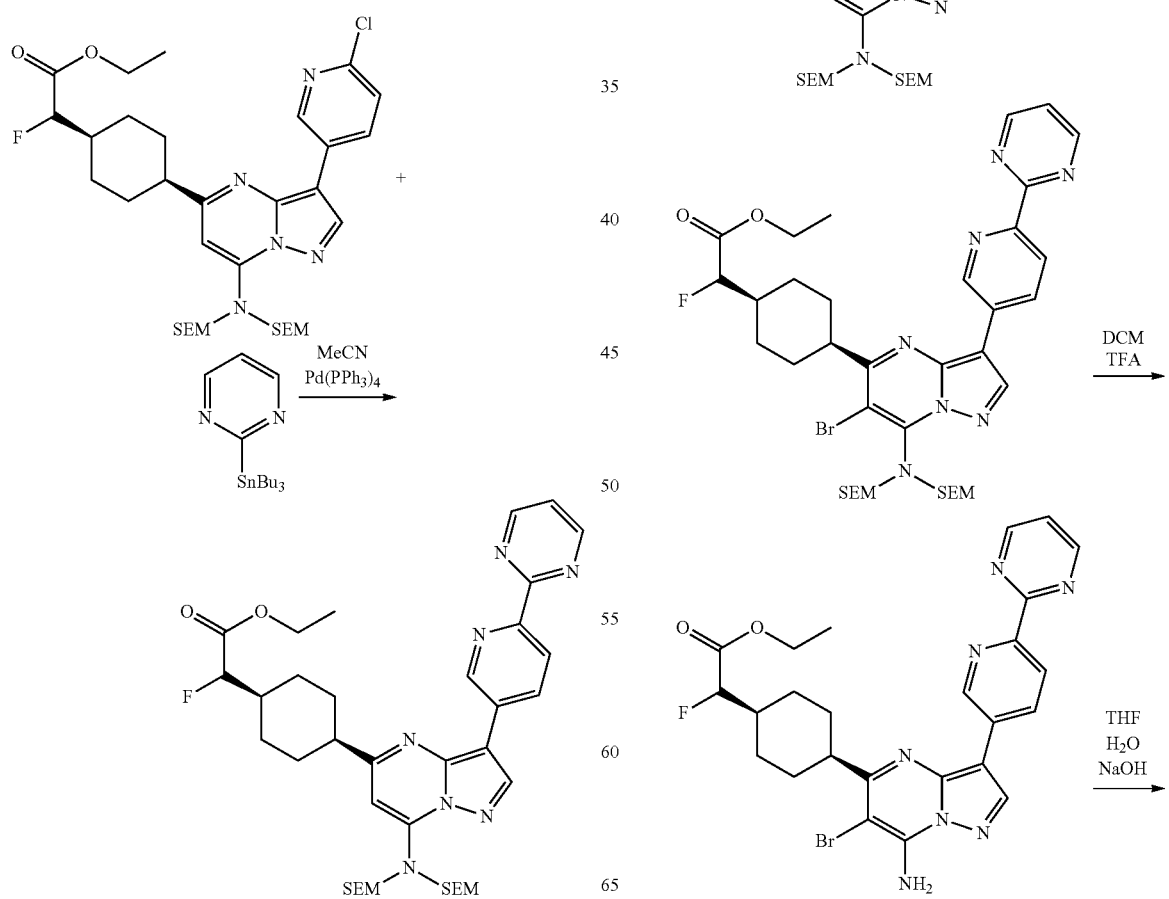

901
-continued

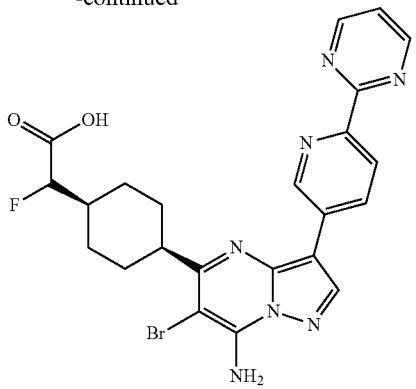

902

(S)-2-((1s,4R)-4-(7-amino-6-bromo-3-(6-(pyrimidin-2-yl)pyridin-3-yl)pyrazolo[1,5-a]pyrimidin-5-yl)cyclohexyl)-2-fluoroacetic acid is synthesized in a manner similar to the synthesis of (S)-2-((1s,4R)-4-(7-amino-6-bromo-3-(6-phenylpyridin-3-yl)pyrazolo[1,5-a]pyrimidin-5-yl)cyclohexyl)-2-fluoroacetic acid (m+H=524.80, retention time=3.70 min).

The following compounds (Table-7B) were synthesized using essentially the same procedures used for the total synthesis of (S)-2-((1s,4R)-4-(7-amino-6-bromo-3-(6-(pyrimidin-2-yl)pyridin-3-yl)pyrazolo[1,5-a]pyrimidin-5-yl)cyclohexyl)-2-fluoroacetic acid:

TABLE 7B

| Compound ID | Structures | M + H (calc.) | M + H (observed) | Retention Time, (min) |
|---|---|---|---|---|
| 7.2.1 | 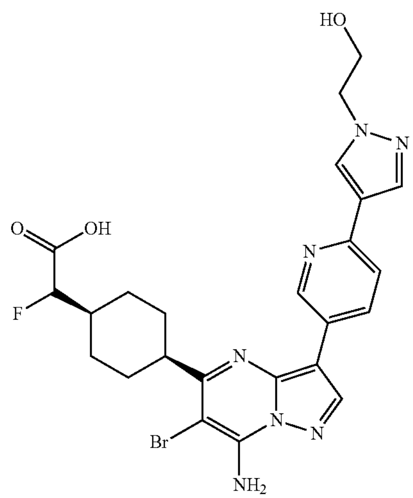 [SMILES: Nc1c(Br)c([C@H]2CC[C@@H](C(F)C(=O)O)CC2)nc2c(-c3ccc(-c4cnn(CCO)c4)nc3)cnn12] | 557.12 | 558.52 | 3.34 |
| 7.2.2 | 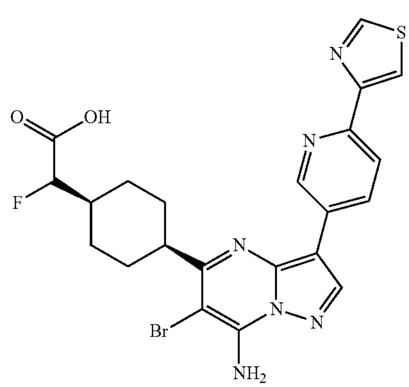 [SMILES: Nc1c(Br)c([C@H]2CC[C@@H](C(F)C(=O)O)CC2)nc2c(-c3ccc(-c4cscn4)nc3)cnn12] | 530.06 | 530.82 | 3.81 |

TABLE 7B-continued
| Compound ID | Structures | M + H (calc.) | M + H (observed) | Retention Time, (min) |
|---|---|---|---|---|
| 7.2.3 | 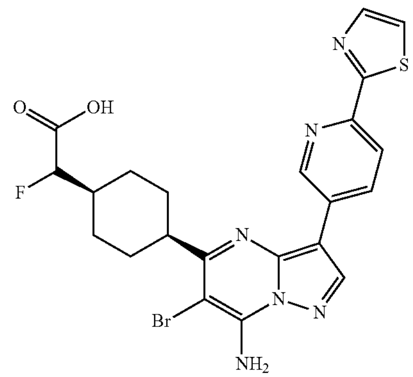 [SMILES: Nc1c(Br)c([C@H]2CC[C@@H](C(F)C(=O)O)CC2)nc2c(-c3ccc(-c4nccs4)nc3)cnn12] | 530.06 | 530.78 | 5.22 |
| 7.2.4 | 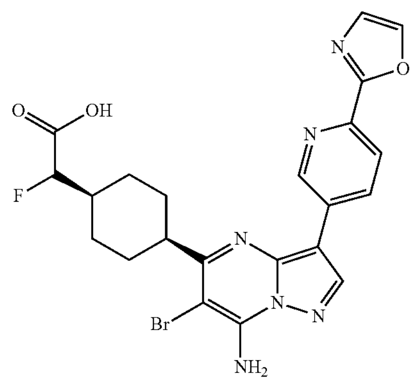 [SMILES: Nc1c(Br)c([C@H]2CC[C@@H](C(F)C(=O)O)CC2)nc2c(-c3ccc(-c4ncco4)nc3)cnn12] | 514.08 | 514.81 | 4.66 |
| 7.2.5 | 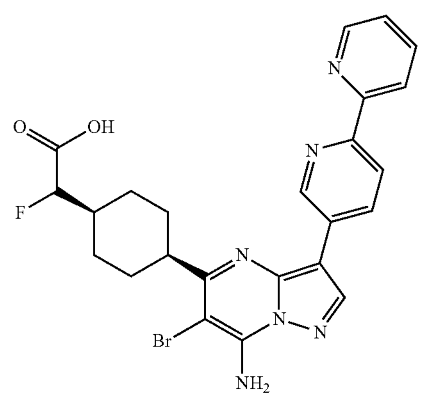 [SMILES: Nc1c(Br)c([C@H]2CC[C@@H](C(F)C(=O)O)CC2)nc2c(-c3ccc(-c4ccccn4)nc3)cnn12] | 524.10 | 524.78 | 3.71 |
| 7.2.6 | 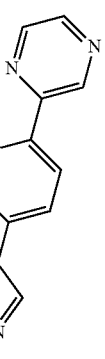 | 525.10 | 525.83 | 4.29 |

TABLE 7B-continued

| Compound ID | Structures | M + H (calc.) | M + H (observed) | Retention Time, (min) |
|---|---|---|---|---|
| 7.2.7 | 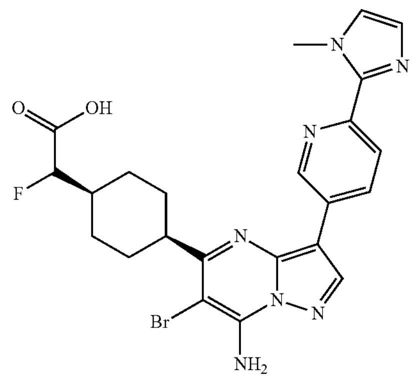 [SMILES: Cn1ccnc1-c1ccc(-c2cnn3c(N)c(Br)c([C@H]4CC[C@@H](C(F)C(=O)O)CC4)nc23)cn1] | 527.11 | 528.08 | 3.31 |
| 7.2.8 | 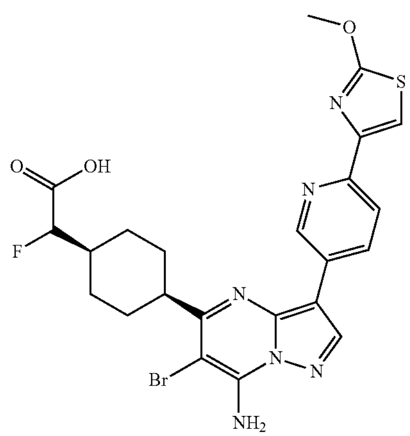 [SMILES: COc1nc(-c2ccc(-c3cnn4c(N)c(Br)c([C@H]5CC[C@@H](C(F)C(=O)O)CC5)nc34)cn2)cs1] | 560.06 | 560.74 | 4.55 |
| 7.2.9 | 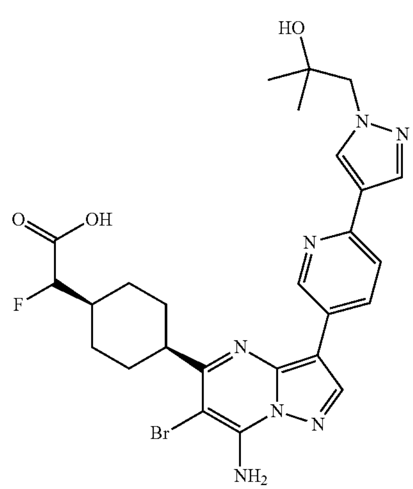 [SMILES: CC(C)(O)Cn1cc(-c2ccc(-c3cnn4c(N)c(Br)c([C@H]5CC[C@@H](C(F)C(=O)O)CC5)nc34)cn2)cn1] | 585.15 | 585.90 | 3.55 |

TABLE 7B-continued
| Compound ID | Structures | M + H (calc.) | M + H (observed) | Retention Time, (min) |
|---|---|---|---|---|
| 7.2.10 | 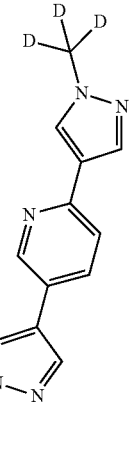 | 530.13 >95% D | 530.85 >95% D | 3.49 |
| 7.2.11 | 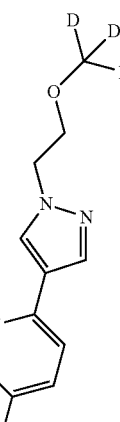 | 574.15 >95% D | 574.87 >95% D | 3.59 |
| 7.2.12 | 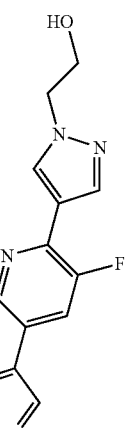 | 575.11 | 576.10 | 3.13 |

TABLE 7B-continued

| Compound ID | Structures | M + H (calc.) | M + H (observed) | Retention Time, (min) |
|---|---|---|---|---|
| 7.2.13 | 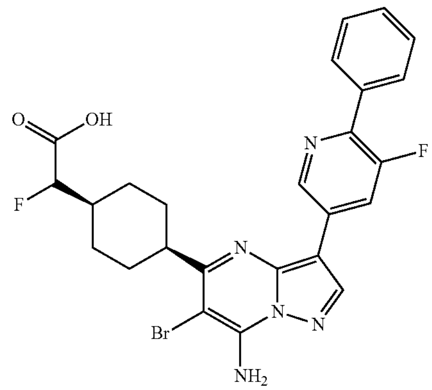 [SMILES: Nc1c(Br)c([C@H]2CC[C@@H](C(F)C(=O)O)CC2)nc2c(-c3cnc(-c4ccccc4)c(F)c3)cnn12] | 541.09 | 542.59 | 4.96 |
| 7.2.14 | 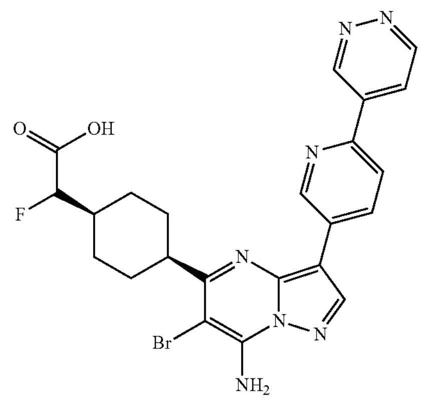 [SMILES: Nc1c(Br)c([C@H]2CC[C@@H](C(F)C(=O)O)CC2)nc2c(-c3ccc(-c4ccnnc4)nc3)cnn12] | 525.09 | 526.06 | 4.09 |

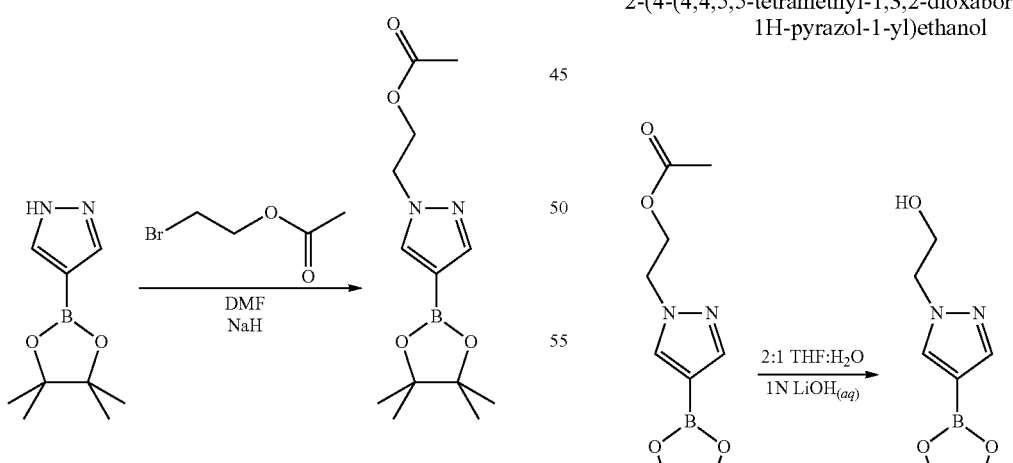

2-(4-(4,4,5,5-tetramethyl-1,3,2-dioxaborolan-2-yl)-1H-pyrazol-1-yl)ethyl acetate To a 20 mL pressure vial was charged pyrazole-4-boronic acid pinacol ester (5.15 mmol, 1.00 g) and DMF (10 mL). NaH (60% w/w in mineral oil, 5.67 mmol, 227 mg) was then added portion-wise. The resulting solution was stirred at room temperature for 10 minutes. 2-bromoethyl acetate (5.67 mmol, 623 µL) was then added dropwise. The vial was flushed with argon, sealed, and the reaction was stirred at 60° C. for 18 hours. At 18 hours, the DMF was removed in vacuo, and the residue taken up in DCM. This suspension was filtered through celite and then purified via flash chromatography to yield the title compound.

2-(4-(4,4,5,5-tetramethyl-1,3,2-dioxaborolan-2-yl)-1H-pyrazol-1-yl)ethanol

To a 50 mL roundbottom flask was charged 2-(4-(4,4,5,5-tetramethyl-1,3,2-dioxaborolan-2-yl)-1H-pyrazol-1-yl)ethyl acetate (2.11 mmol, 591 mg), a solution of 2:1 THF:H$_2$O (15 mL), and 1N LiOH$_{(aq)}$ (4.82 mmol, 4.82 mL). The resulting solution was stirred at room temperature for 48 hours. At 48 hours, the reaction was quenched with 1N HCl$_{(aq)}$ (4.82 mmol, 4.82 mL) and the solvent removed in vacuo. The product was taken forward without further purification.

1-(2-trideuteromethoxyethyl)-4-(4,4,5,5-tetramethyl-1,3,2-dioxaborolan-2-yl)-1H-pyrazole

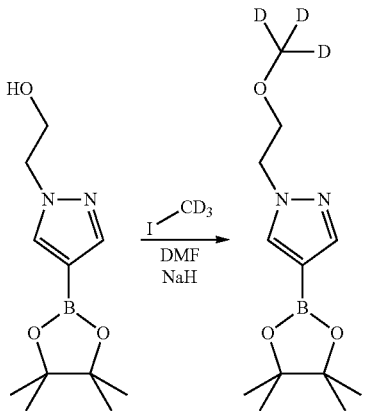

To a 20 mL pressure vial was 2-(4-(4,4,5,5-tetramethyl-1,3,2-dioxaborolan-2-yl)-1H-pyrazol-1-yl)ethanol (2.11 mmol) and DMF (10 mL). NaH (60% w/w in mineral oil, 4.22 mmol, 169 mg) was added portion-wise and the resulting solution was allowed to stir at room temperature for 10 minutes. At 10 minutes, iodomethane-d$_3$ (4.22 mmol, 263 µL) was added dropwise. The vial was sealed and the reaction was stirred at 80° C. for 48 hours. At 48 hours, the solvent was removed in vacuo. The residue was taken up in DCM and filtered through celite. The title compound was then purified via flash chromatography.

2-methyl-1-(4-(4,4,5,5-tetramethyl-1,3,2-dioxaborolan-2-yl)-1H-pyrazol-1-yl)propan-2-ol

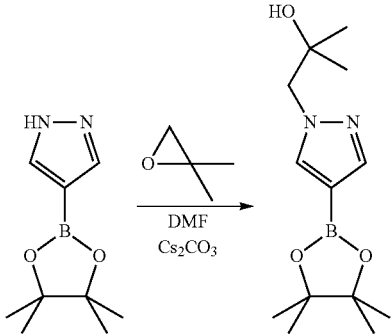

To a 20 mL pressure vial was charged pyrazole-4-boronic acid pinacol ester (5.15 mmol, 1.00 g), DMF (10 mL), and Cs$_2$CO$_3$ (5.67 mmol, 1.85 g). To this suspension was added isobutylene oxide (15.45 mmol, 1.38 mL). The vial was flushed with argon and sealed. The reaction was stirred 18 hours at 80° C. After 18 hours, the reaction was filtered through celite and the solvent removed in vacuo. This residue was pumped dry under high vacuum and then purified via flash chromatography to yield the title compound.

1-trideuteromethyl-4-(4,4,5,5-tetramethyl-1,3,2-dioxaborolan-2-yl)-1H-pyrazole

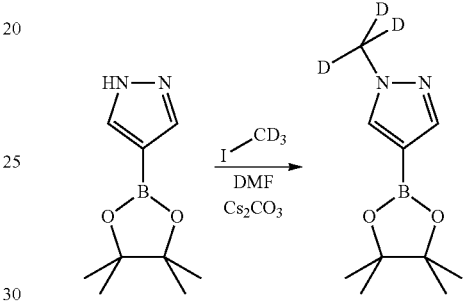

1-trideuteromethyl-4-(4,4,5,5-tetramethyl-1,3,2-dioxaborolan-2-yl)-1H-pyrazole was synthesized in the manner previously described.

3-(6-phenylpyridin-3-yl)-5-(1H-pyrazol-4-yl)-N,N-bis((2-(trimethylsilyl)ethoxy)methyl)pyrazolo[1,5-a]pyrimidin-7-amine

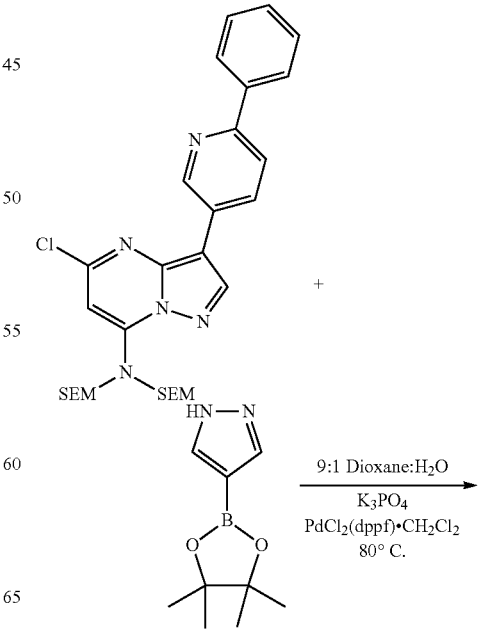

913
-continued

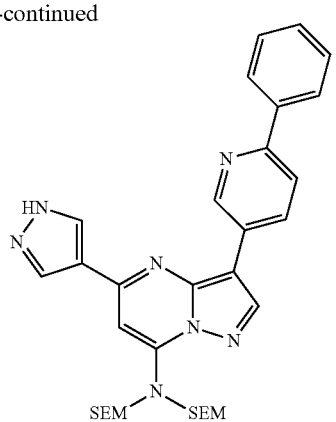

3-(6-phenylpyridin-3-yl)-5-(1H-pyrazol-4-yl)-N,N-bis((2-(trimethylsilyl)ethoxy)methyl)pyrazolo[1,5-a]pyrimidin-7-amine was synthesized in a manner similar to the synthesis of (S)-ethyl 2-((1s,4R)-4-(7-(bis((2-(trimethylsilyl)ethoxy)methyl)amino)-3-(6-phenylpyridin-3-yl)pyrazolo[1,5-a]pyrimidin-5-yl)cyclohexyl)-2-fluoroacetate.

2-(4-(7-(bis((2-(trimethylsilyl)ethoxy)methyl)amino)-3-(6-phenylpyridin-3-yl)pyrazolo[1,5-a]pyrimidin-5-yl)-1H-pyrazol-1-yl)ethyl acetate

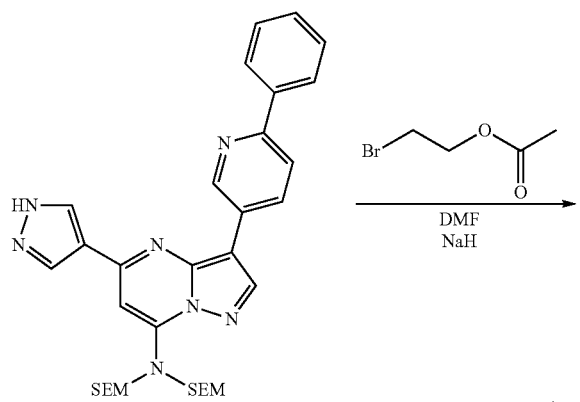

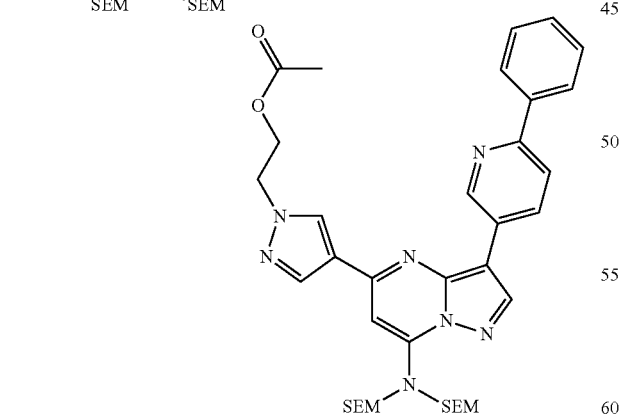

To a 2-5 mL pressure vial was charged 3-(6-phenylpyridin-3-yl)-5-(1H-pyrazol-4-yl)-N,N-bis((2-(trimethylsilyl)ethoxy)methyl)pyrazolo[1,5-a]pyrimidin-7-amine (0.38

914 mmol, 230 mg), DMF (4 mL), and sodium hydride (40% w/w in mineral oil, 0.56 mmol, 23 mg). This suspension was sonicaided and allowed to stir at room temperature for 15 minutes. At 15 minutes, 2-bromoethyl acetate (0.56 mmol, 62 µL). The vial was then sealed and the reaction was stirred at 80° C. for 18 hours. After 18 hours, the solvent was removed in vacuo, and the resulting residue was purified by flash chromatography to yield the title compound.

1-(7-amino-5-(1-(2-hydroxyethyl)-1H-pyrazol-4-yl)-3-(6-phenylpyridin-3-yl)pyrazolo[1,5-a]pyrimidin-6-yl)ethanone

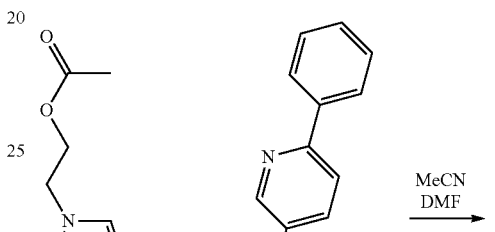

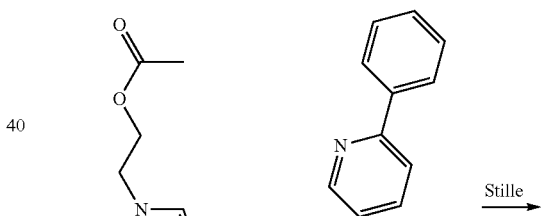

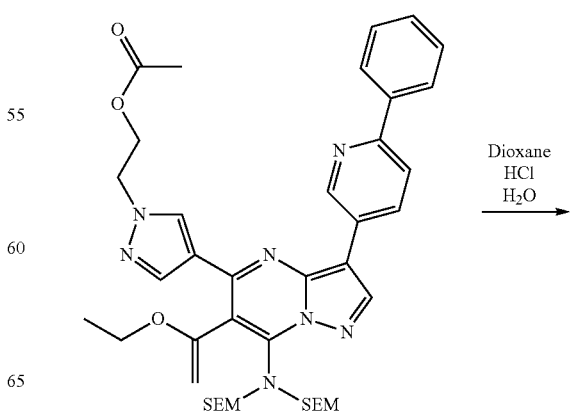

915
-continued

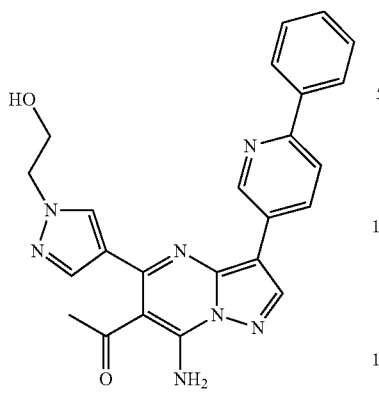

1-(7-amino-5-(1-(2-hydroxyethyl)-1H-pyrazol-4-yl)-3-(6-phenylpyridin-3-yl)pyrazolo[1,5-a]pyrimidin-6-yl)ethanone was synthesized in a manner similar to the synthesis of (S)-2-((1s,4R)-4-(6-acetyl-7-amino-3-(6-phenylpyridin-3-yl)pyrazolo[1,5-a]pyrimidin-5-yl)cyclohexyl)-2-fluoroacetic acid (m+H=440.64, retention time=2.95 min).

Ethyl 2-(4-(7-(bis((2-(trimethylsilyl)ethoxy)methyl)amino)-3-(1-phenyl-1H-pyrazol-4-yl)pyrazolo[1,5-a]pyrimidin-5-yl)cyclohexyl)acetate

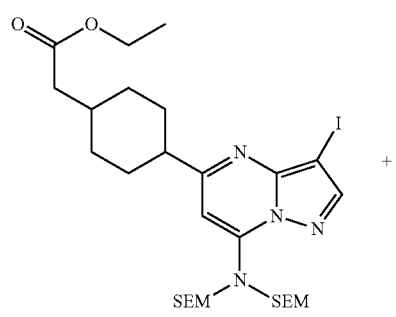

916
-continued

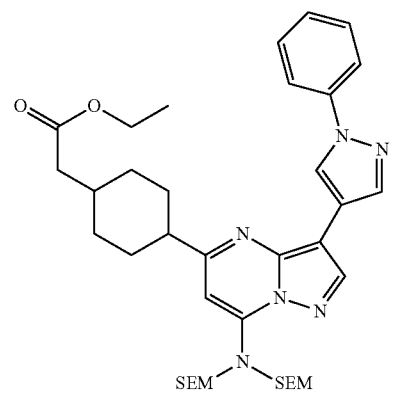

Ethyl 2-(4-(7-(bis((2-(trimethylsilyl)ethoxy)methyl)amino)-3-(1-phenyl-1H-pyrazol-4-yl)pyrazolo[1,5-a]pyrimidin-5-yl)cyclohexyl)acetate was synthesized in a manner similar to the synthesis of (S)-ethyl 2-((1s,4R)-4-(7-(bis((2-(trimethylsilyl)ethoxy)methyl)amino)-3-(6-phenylpyridin-3-yl)pyrazolo[1,5-a]pyrimidin-5-yl)cyclohexyl)-2-fluoroacetate.

2-(4-(7-amino-6-bromo-3-(1-phenyl-1H-pyrazol-4-yl)pyrazolo[1,5-a]pyrimidin-5-yl)cyclohexyl)acetic acid

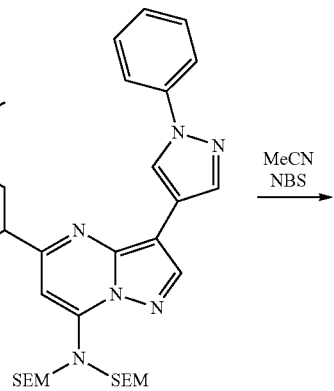

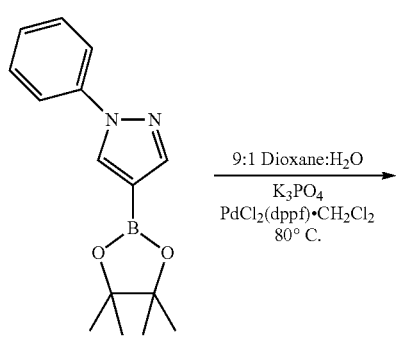

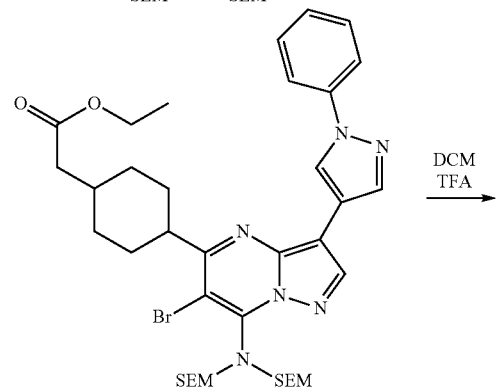

917
-continued

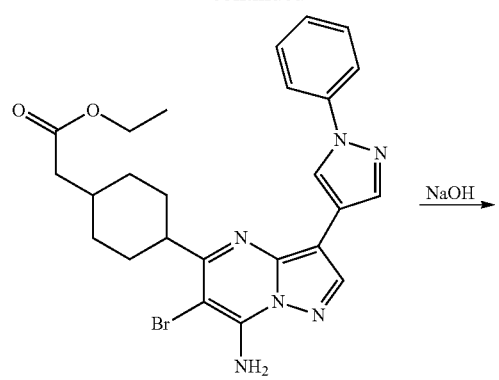

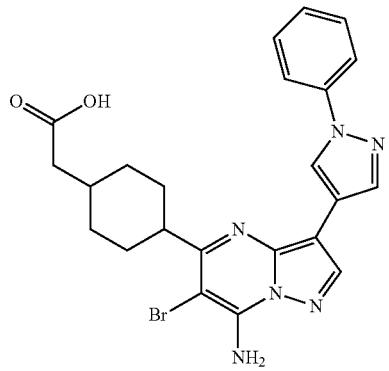

2-(4-(7-amino-6-bromo-3-(1-phenyl-1H-pyrazol-4-yl)pyrazolo[1,5-a]pyrimidin-5-yl)cyclohexyl)acetic acid was synthesized in the manner previously described. (m+H=495.57, retention time=4.78 min (isomer1) and 4.84 min (isomer 2)).

(S)-2-(1s,4R)-4-(7-amino-6-bromo-3-(1-phenyl-1H-pyrazol-4-yl)pyrazolo[1,5-a]pyrimidin-5-yl)cyclohexyl)-2-fluoroacetic acid

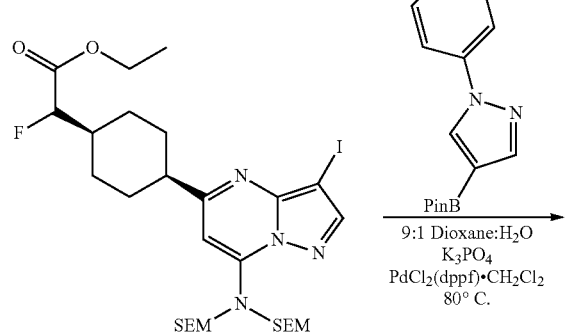

918
-continued

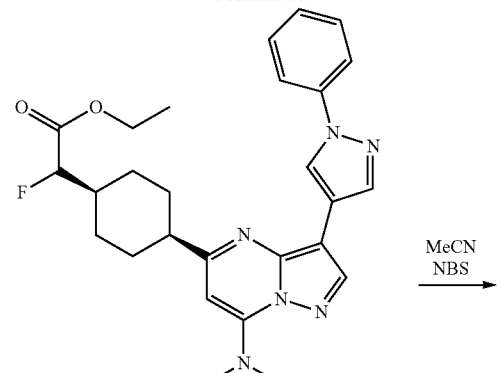

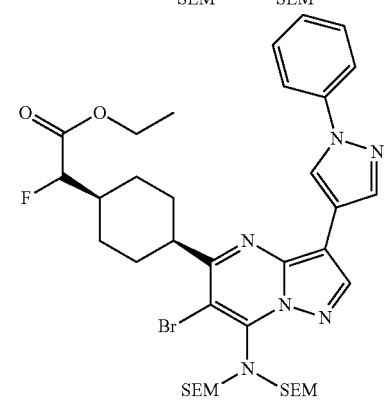

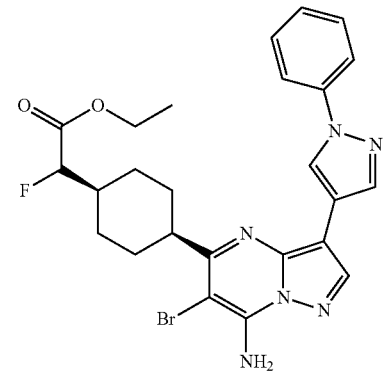 [SMILES: Nc1c(Br)c([C@H]2CC[C@@H](C(F)C(=O)O)CC2)nc2c(-c3cnn(-c4ccccc4)c3)cnn12]

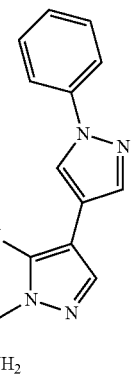

(S)-2-((1s,4R)-4-(7-amino-6-bromo-3-(1-phenyl-1H-pyrazol-4-yl)pyrazolo[1,5-a]pyrimidin-5-yl)cyclohexyl)-2-fluoroacetic acid was synthesized in the manner similar to the synthesis of 2-(4-(7-amino-6-bromo-3-(1-phenyl-1H-pyrazol-4-yl)pyrazolo[1,5-a]pyrimidin-5-yl)cyclohexyl)acetic acid. (m+H=513.54, retention time=4.81 min).

919
2-(4-(6-acetyl-7-amino-3-(1-phenyl-1H-pyrazol-4-yl)pyrazolo[1,5-a]pyrimidin-5-yl)cyclohexyl)acetic acid
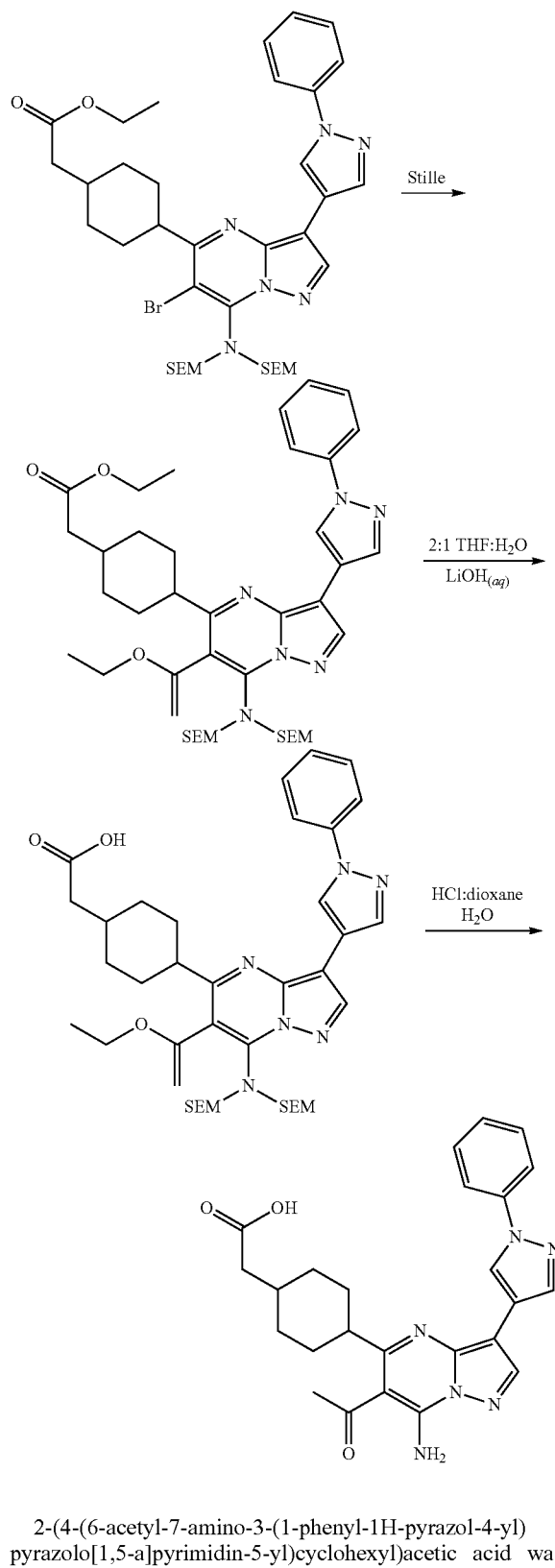
2-(4-(6-acetyl-7-amino-3-(1-phenyl-1H-pyrazol-4-yl)pyrazolo[1,5-a]pyrimidin-5-yl)cyclohexyl)acetic acid was
920
synthesized in the manner previously described. (m+H=459.66, retention time=4.58 min).
(S)-2-(1s,4R)-4-(6-acetyl-7-amino-3-(1-phenyl-1H-pyrazol-4-yl)pyrazolo[1,5-a]pyrimidin-5-yl)cyclohexyl)-2-fluoroacetic acid
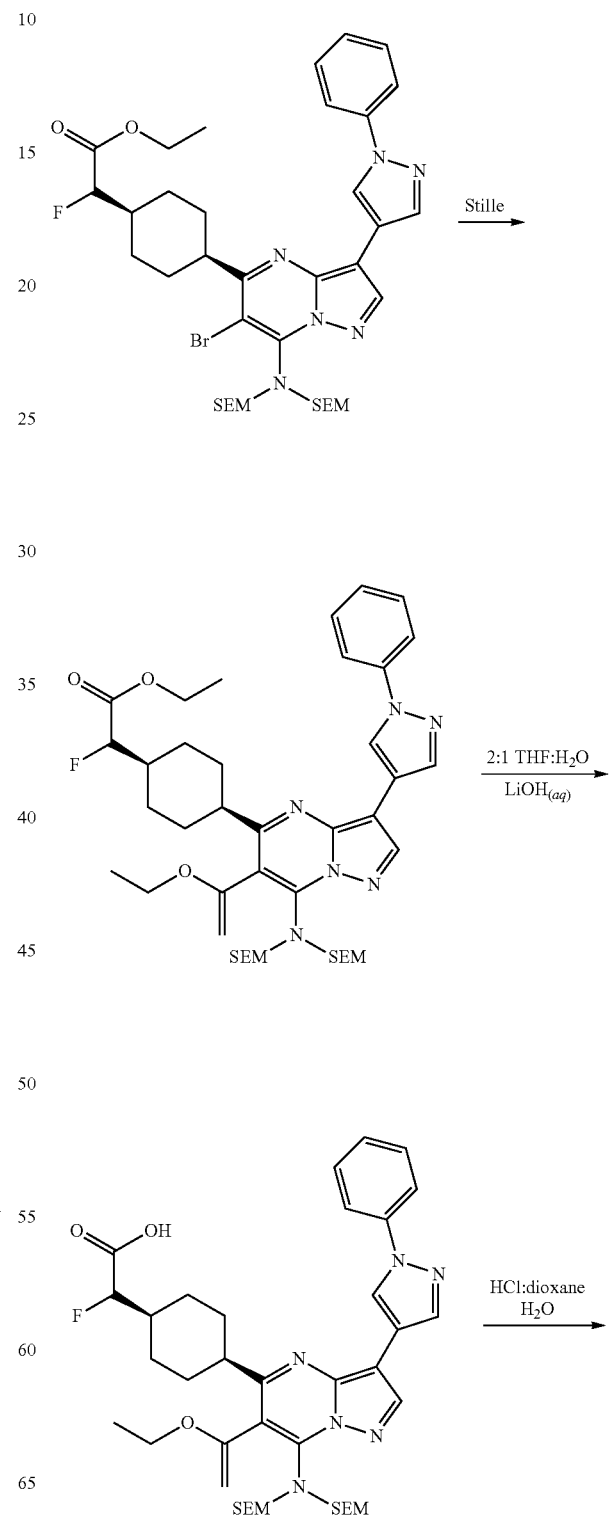

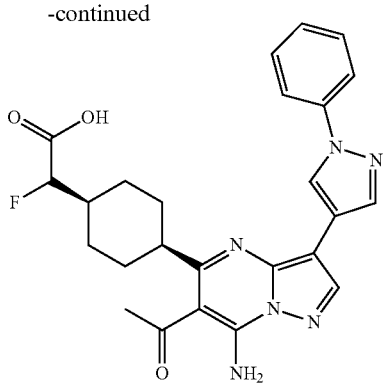

(S)-2-((1s,4R)-4-(6-acetyl-7-amino-3-(1-phenyl-1H-pyrazol-4-yl)pyrazolo[1,5-a]pyrimidin-5-yl)cyclohexyl)-2-fluoroacetic acid was synthesized in the manner similar to the synthesis of 2-(4-(6-acetyl-7-amino-3-(1-phenyl-1H-pyrazol-4-yl)pyrazolo[1,5-a]pyrimidin-5-yl)cyclohexyl)acetic acid. (m+H=477.64, retention time=4.53 min).

Ethyl 6-(7-(bis((2-(trimethylsilyl)ethoxy)methyl)amino)pyrazolo[1,5-a]pyrimidin-5-yl)spiro[2.5]octane-1-carboxylate

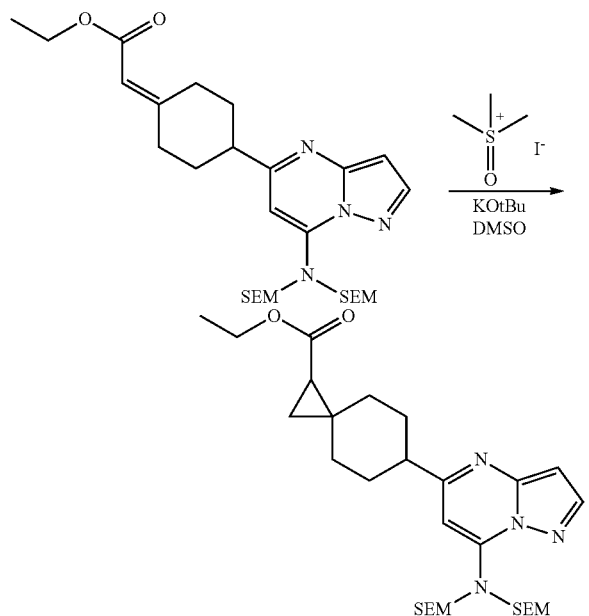

To 50 mL roundbottom flask containing trimethylsulfoxonium iodide (3.57 mmol, 785 mg) in DMSO (8 mL) was added potassium tert-butoxide (3.57 mmol, 401 mg). This suspension was allowed to stir at room temperature for 3 hours. After 3 hours, ethyl 2-(4-(7-(bis((2-(trimethylsilyl)ethoxy)methyl)amino)pyrazolo[1,5-a]pyrimidin-5-yl)cyclohexylidene)acetate (1.78 mmol, 1.00 g) was added in 2 mL DMSO. The resulting solution was stirred at room temperature for 18 hours. After 18 hours, the reaction was diluted with saturated NaCl$_{(aq)}$ (30 mL). The pH was adjusted to ~7 with saturated NH$_4$Cl$_{(aq)}$ and extracted with DCM (50 mL) 4 times. The combined organics are dried over Na$_2$SO$_4$ and reduced in vacuo. The resulting residue was purified via flash chromatography to yield the title compound.

Ethyl 6-(7-(bis((2-(trimethylsilyl)ethoxy)methyl)amino)pyrazolo[1,5-a]pyrimidin-5-yl)-1-fluorospiro[2.5]octane-1-carboxylate

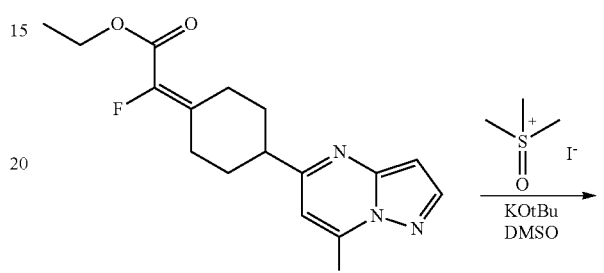

Ethyl 6-(7-(bis((2-(trimethylsilyl)ethoxy)methyl)amino)pyrazolo[1,5-a]pyrimidin-5-yl)-1-fluorospiro[2.5]octane-1-carboxylate was synthesized in the manner similar to the synthesis of ethyl 6-(7-(bis((2-(trimethylsilyl)ethoxy)methyl)amino)pyrazolo[1,5-a]pyrimidin-5-yl)spiro[2.5]octane-1-carboxylate.

6-(7-amino-6-bromo-3-(6-phenylpyridin-3-yl)pyrazolo[1,5-a]pyrimidin-5-yl)spiro[2.5]octane-1-carboxylic acid

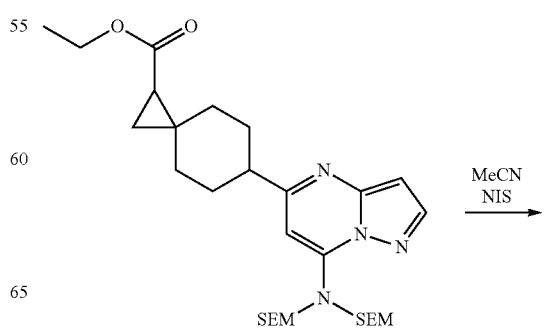

923
-continued
924
-continued
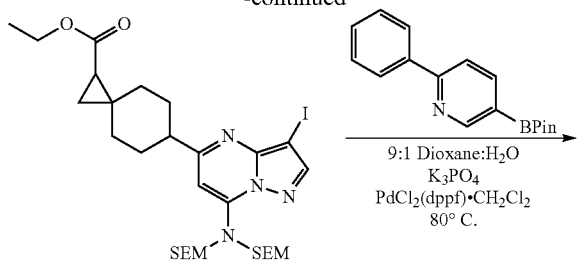
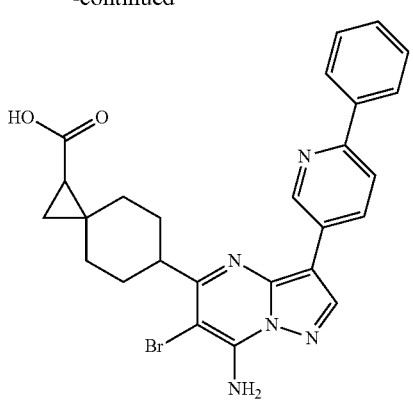
6-(7-amino-6-bromo-3-(6-phenylpyridin-3-yl)pyrazolo[1,5-a]pyrimidin-5-yl)spiro[2,5]octane-1-carboxylic acid was synthesized in the manner previously described. (m+H=417.86, retention time=4.41 min).
6-(7-amino-6-bromo-3-(6-phenylpyridin-3-yl)pyrazolo[1,5-a]pyrimidin-5-yl)-1-fluorospiro[2,5]octane-1-carboxylic acid
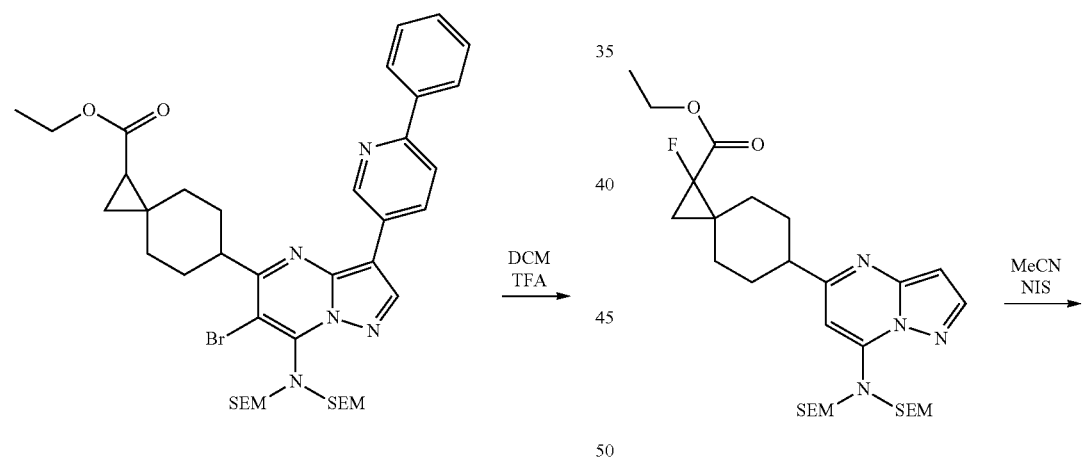
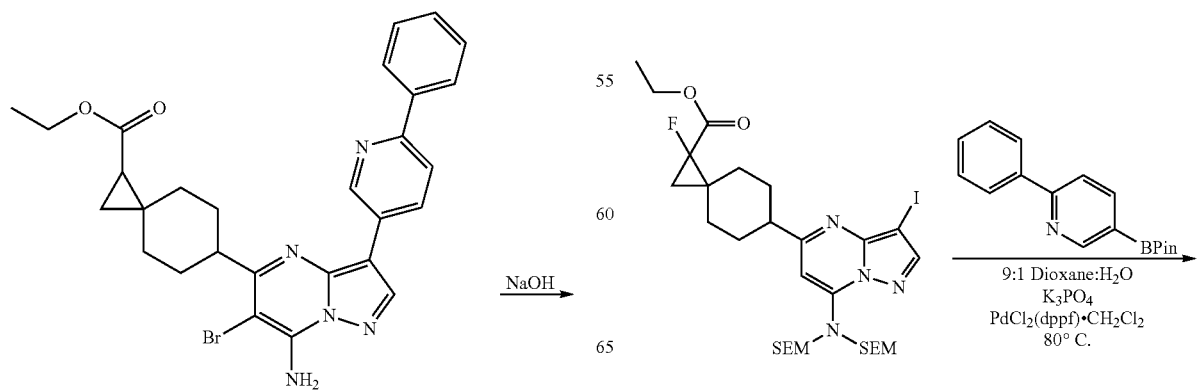

925
-continued

926
ethyl 2-acetoxy-2-(4-(7-(bis((2-(trimethylsilyl)ethoxy)methyl)amino)pyrazolo[1,5-a]pyrimidin-5-yl)cyclohexylidene)acetate

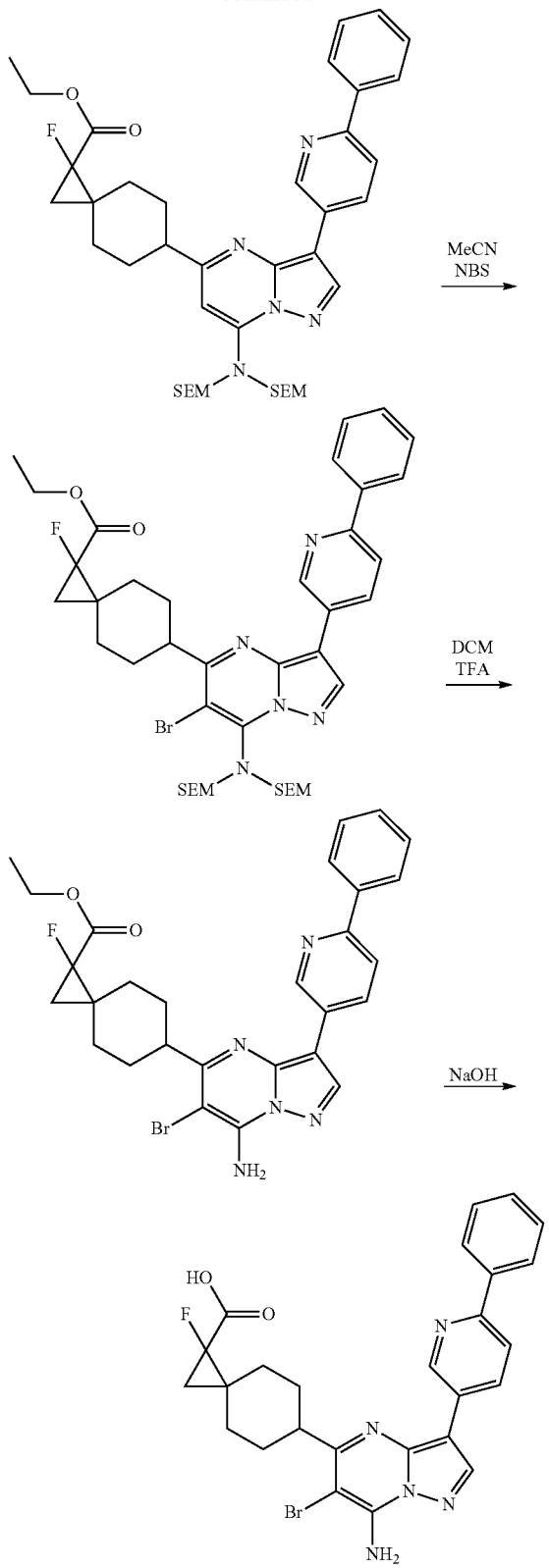

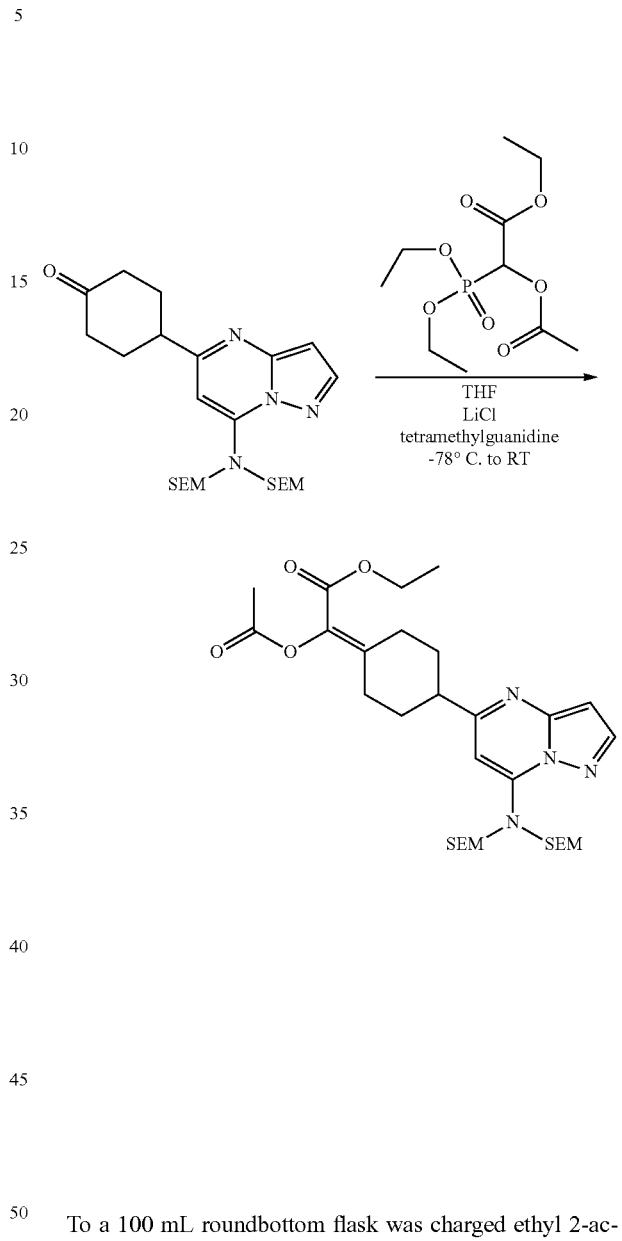

6-(7-amino-6-bromo-3-(6-phenylpyridin-3-yl)pyrazolo[1,5-a]pyrimidin-5-yl)-1-fluorospiro[2.5]octane-1-carboxylic acid was synthesized in the manner previously described. (m+H=435.86, retention time=4.40 min).

To a 100 mL roundbottom flask was charged ethyl 2-acetoxy-2-(diethoxyphosphoryl)acetate (1121 mmol, 3.16 g), LiCl (11.21 mmol, 475 mg), and THF (25 mL). The flask was then flushed with argon, sealed, and cooled to −78° C. in a dry ice/IPA bath. Added dropwise to this solution was a solution of 1,1,3,3-tetramethylguanidine (11.21 mmol. 1.41 g) in THF (5 mL). The resulting solution was allowed to stir at −78° C. for 30 minutes. At 30 minutes, 4-(7-(bis((2-(trimethylsilyl)ethoxy)methyl)amino)pyrazolo[1,5-a]pyrimidin-5-yl)cyclohexanone (5.09 mmol, 2.50 g) was added in THF (3 mL). The reaction was then allowed to slowly warm to room temperature and then stirred for 48 hours. After 48 hours, the reaction was diluted with DCM (100 mL) and washed with H₂O (50 mL). The organic layer was collected, dried over Na₂SO₄, and reduced in vacuo. The resulting residue was purified via flash chromatography to yield the title compound.

927
Ethyl 2-acetoxy-2-(4-(7-(bis((2-(trimethylsilyl)
ethoxy)methyl)amino)-6-bromo-3-(6-phenylpyridin-
3-yl)pyrazolo[1,5-a]pyrimidin-5-yl)cyclohexylidene)
acetate

928
2-(4-(7-(bis((2-(trimethylsilyl)ethoxy)methyl)
amino)-6-bromo-3-(6-phenylpyridin-3-yl)pyrazolo
[1,5-a]pyrimidin-5-yl)cyclohexyl)-2-oxoacetic acid

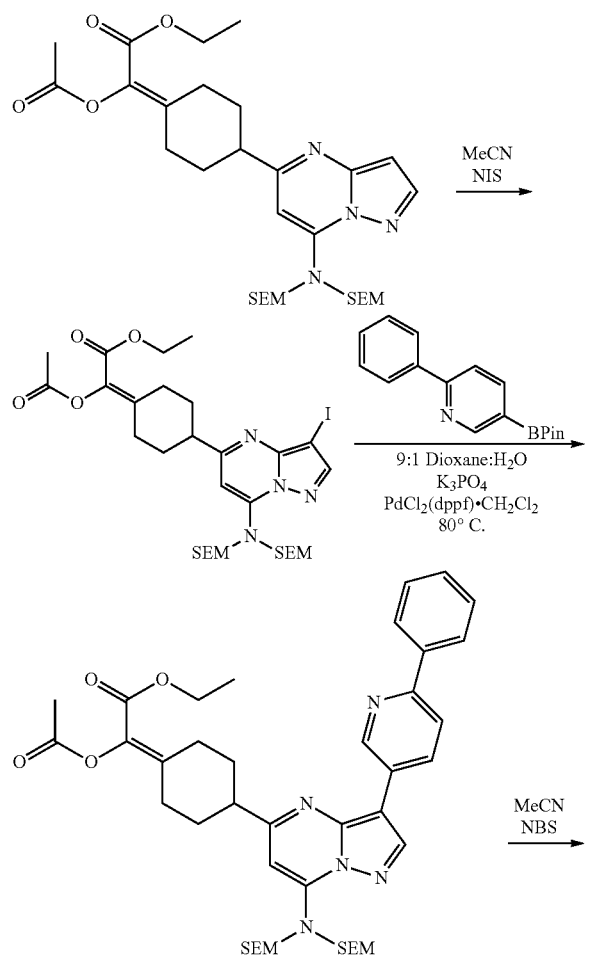

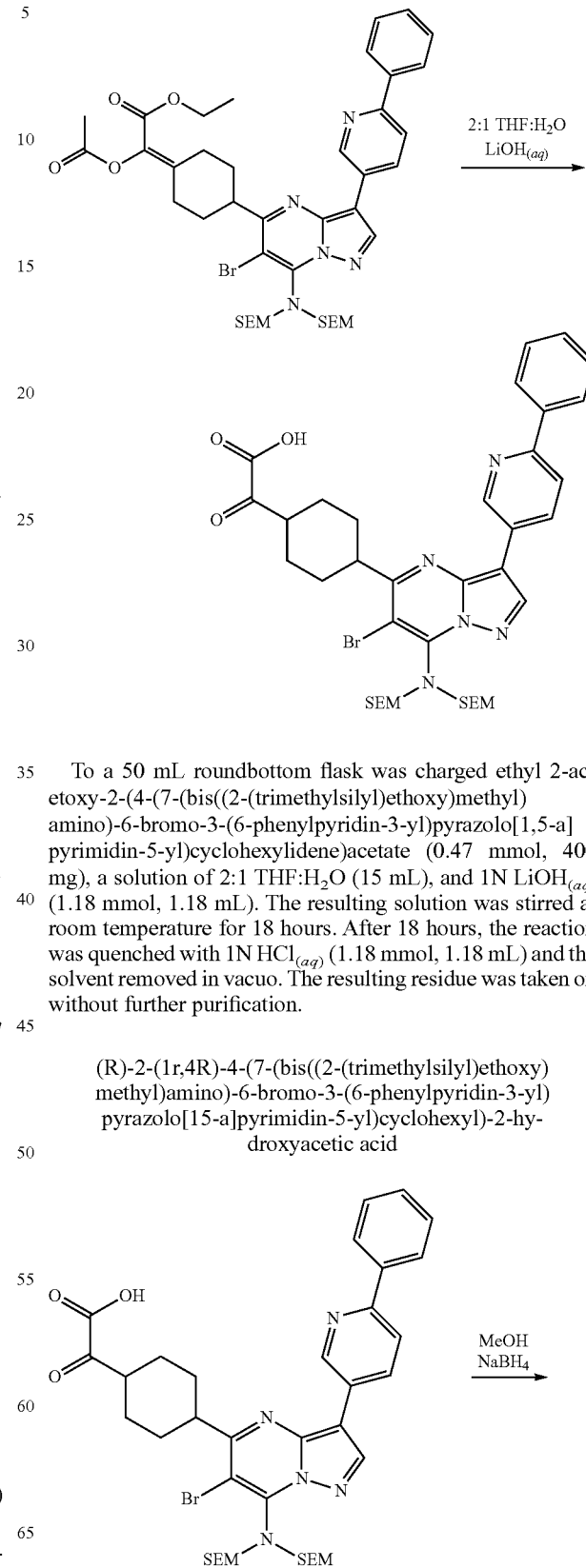

To a 50 mL roundbottom flask was charged ethyl 2-acetoxy-2-(4-(7-(bis((2-(trimethylsilyl)ethoxy)methyl)amino)-6-bromo-3-(6-phenylpyridin-3-yl)pyrazolo[1,5-a]pyrimidin-5-yl)cyclohexylidene)acetate (0.47 mmol, 400 mg), a solution of 2:1 THF:H$_2$O (15 mL), and 1N LiOH$_{(aq)}$ (1.18 mmol, 1.18 mL). The resulting solution was stirred at room temperature for 18 hours. After 18 hours, the reaction was quenched with 1N HCl$_{(aq)}$ (1.18 mmol, 1.18 mL) and the solvent removed in vacuo. The resulting residue was taken on without further purification.

(R)-2-(1r,4R)-4-(7-(bis((2-(trimethylsilyl)ethoxy)
methyl)amino)-6-bromo-3-(6-phenylpyridin-3-yl)
pyrazolo[15-a]pyrimidin-5-yl)cyclohexyl)-2-hy-
droxyacetic acid Ethyl 2-acetoxy-2-(4-(7-(bis((2-(trimethylsilyl)ethoxy)methyl)amino)-6-bromo-3-(6-phenylpyridin-3-yl)pyrazolo[1,5-a]pyrimidin-5-yl)cyclohexylidene)acetate was synthesized in the manner previously described.

929
-continued

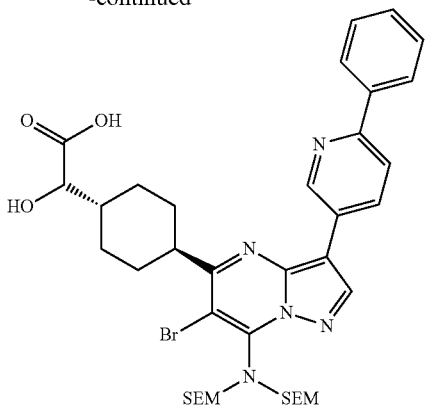

To a 50 mL roundbottom flask was charged 2-(4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)-2-oxoacetic acid (0.47 mmol) and MeOH (10 mL). To this solution was charged NaBH₄ (0.71 mmol, 27 mg). This solution was allowed to stir at room temperature for 18 hours. After 18 hours, the reaction was quenched with saturated NH₄Cl$_{(aq)}$ (10 mL) and extracted with DCM twice. The combined organics were dried over Na₂SO₄, and the solvent removed in vacuo. The compound was taken on without further purification.

(R)-1-((1r,4R)-4-(7-(bis((2-(trimethylsilyl)ethoxy)methyl)amino)-3-(6-phenylpyridin-3-yl)pyrazolo[1,5-a]pyrimidin-5-yl)cyclohexyl)ethane-1,2-diol

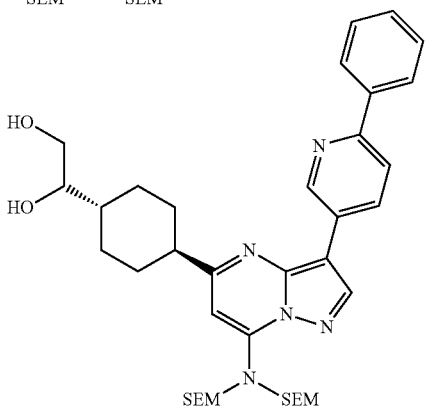

To a 50 mL roundbottom flask was charged (R)-2-((1r,4R)-4-(7-(bis((2-(trimethylsilyl)ethoxy)methyl)amino)-6-

930 bromo-3-(6-phenylpyridin-3-yl)pyrazolo[1,5-a]pyrimidin-5-yl)cyclohexyl)-2-hydroxyacetic acid (0.47 mmol) and THF (20 mL). This solution was cooled to 0° C. in an ice bath. Lithium aluminum hydride (1.0 M in hexanes, 2.06 mmol, 2.06 mL) was added dropwise. The reaction is then allowed to slowly warm to room temperature and then stirred for 30 hours. After 30 hours, the reaction was quenched with EtOAc (20 mL) and washed with H₂O. The organic layer was dried over Na₂SO₄, and the solvent removed in vacuo. The product was taken on without further purification.

(R)-1-((1r,4R)-4-(7-amino-6-bromo-3-(6-phenylpyridin-3-yl)pyrazolo[1,5-a]pyrimidin-5-yl)cyclohexyl)ethane-1,2-diol

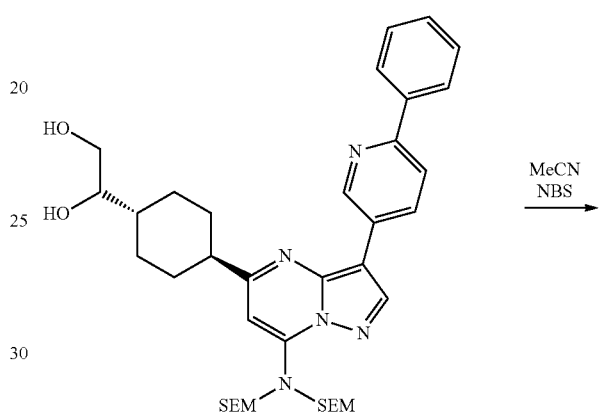

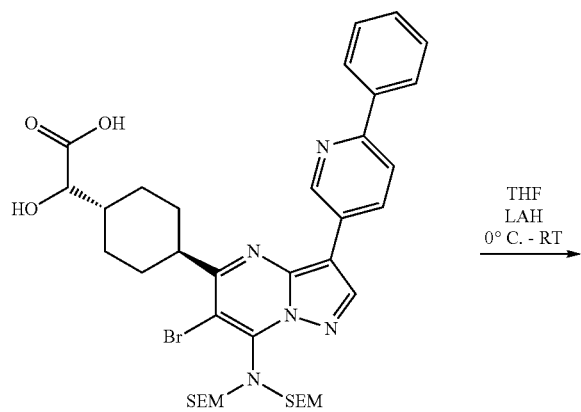

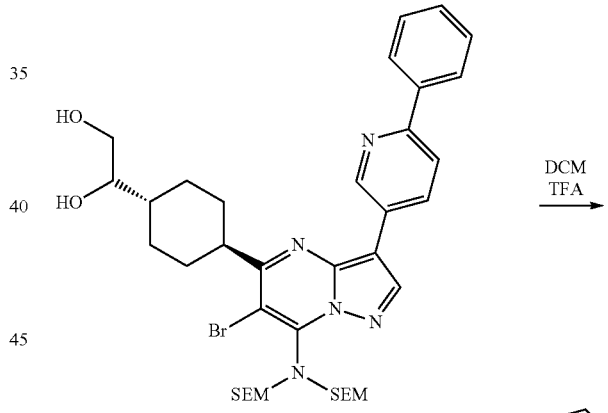

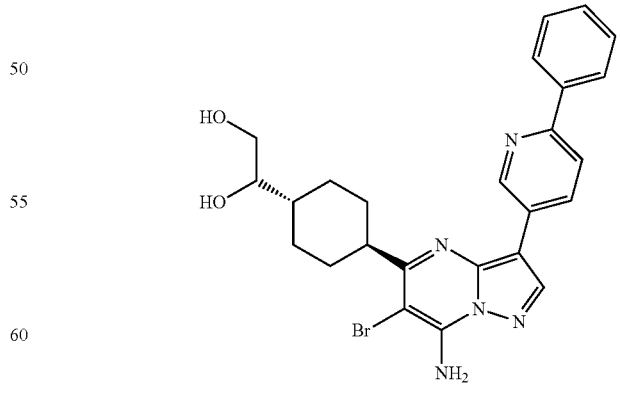

(R)-1-((1r,4R)-4-(7-amino-6-bromo-3-(6-phenylpyridin-3-yl)pyrazolo[1,5-a]pyrimidin-5-yl)cyclohexyl)ethane-1,2-diol was synthesized in the manner previously described. (m+H=507.84, retention time=3.56 min).

931

1-(7-amino-5-((1R,4r)-4-((R)-1,2-dihydroxyethyl)
cyclohexyl)-3-(6-phenylpyridin-3-yl)pyrazolo[1,5-a]
pyrimidin-6-yl)ethanone

932

(R)-2-((1r,4R)-4-(7-amino-6-bromo-3-(6-phenylpyri-
din-3-yl)pyrazolo[1,5-a]pyrimidin-5-yl)cyclohexyl)-
2-hydroxyacetic acid

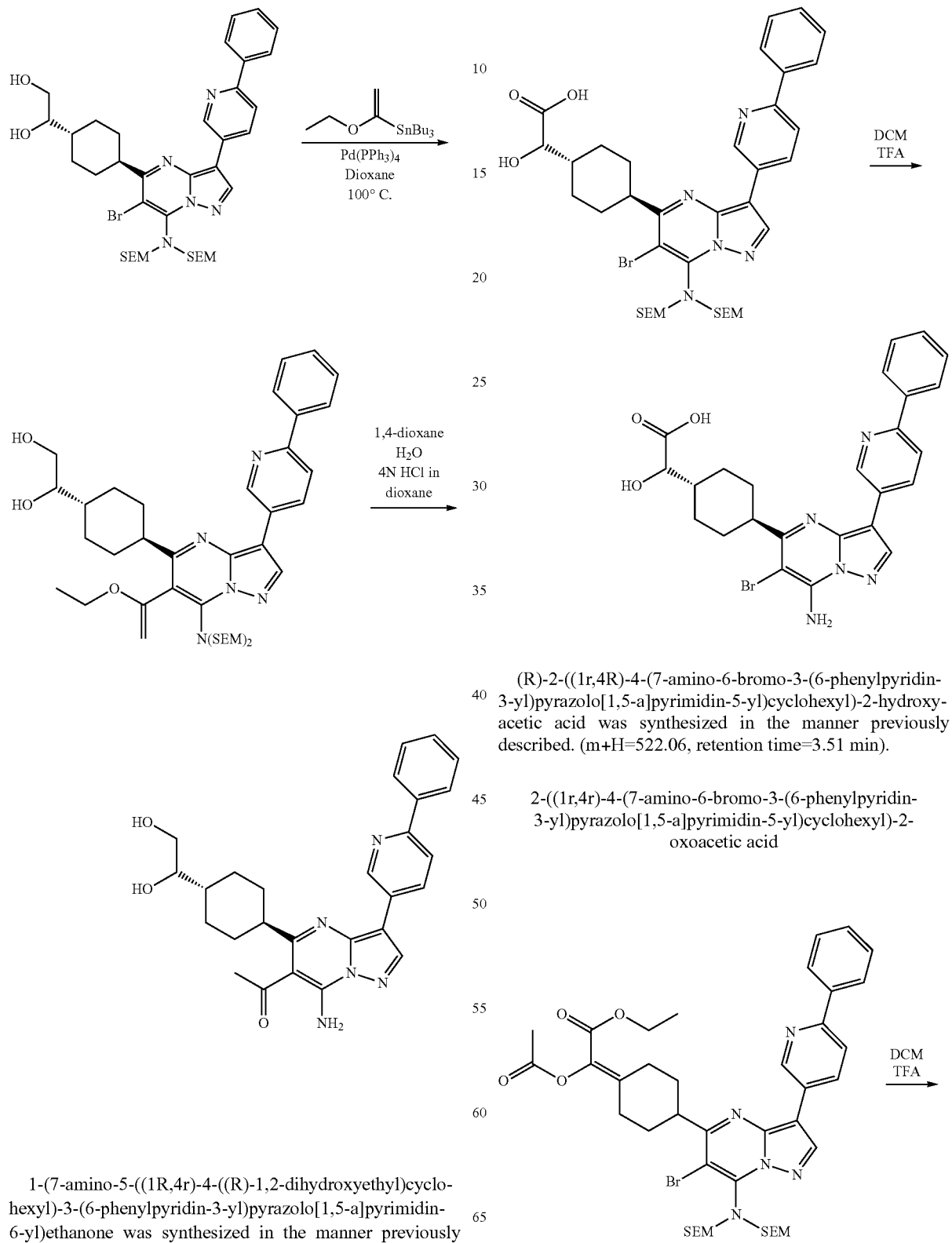

(R)-2-((1r,4R)-4-(7-amino-6-bromo-3-(6-phenylpyridin-
3-yl)pyrazolo[1,5-a]pyrimidin-5-yl)cyclohexyl)-2-hydroxy-
acetic acid was synthesized in the manner previously
described. (m+H=522.06, retention time=3.51 min).

2-((1r,4r)-4-(7-amino-6-bromo-3-(6-phenylpyridin-
3-yl)pyrazolo[1,5-a]pyrimidin-5-yl)cyclohexyl)-2-
oxoacetic acid 1-(7-amino-5-((1R,4r)-4-((R)-1,2-dihydroxyethyl)cyclo-
hexyl)-3-(6-phenylpyridin-3-yl)pyrazolo[1,5-a]pyrimidin-
6-yl)ethanone was synthesized in the manner previously
described. (m+H=471.98, retention time=3.45 min).

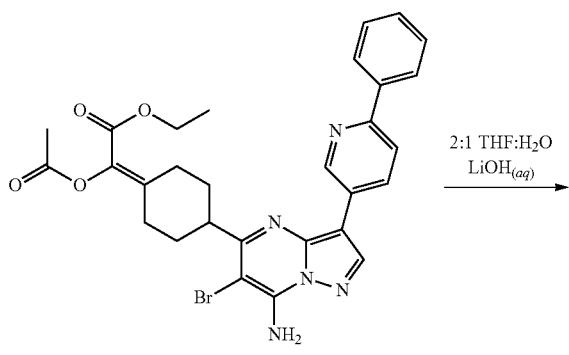

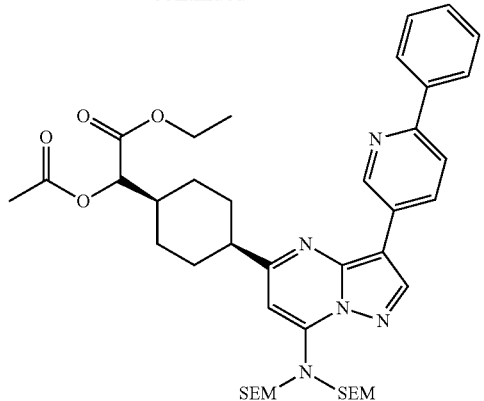

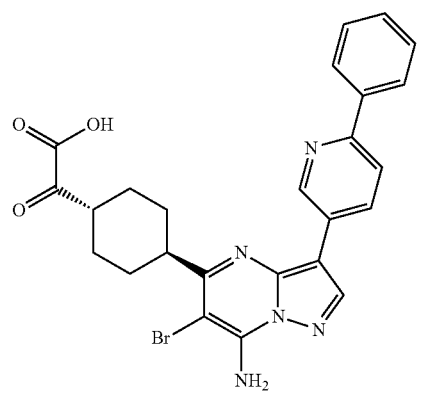

2-((1r,4r)-4-(7-amino-6-bromo-3-(6-phenylpyridin-3-yl)pyrazolo[1,5-a]pyrimidin-5-yl)cyclohexyl)-2-oxoacetic acid was synthesized in the manner previously described. (m+H=520.05, retention time=3.79 min).

(S)-ethyl 2-acetoxy-2-((1s,4R)-4-(7-(bis((2-(trimethylsilyl)ethoxy)methyl)amino)-3-(6-phenylpyridin-3-yl)pyrazolo[1,5-a]pyrimidin-5-yl)cyclohexyl)acetate

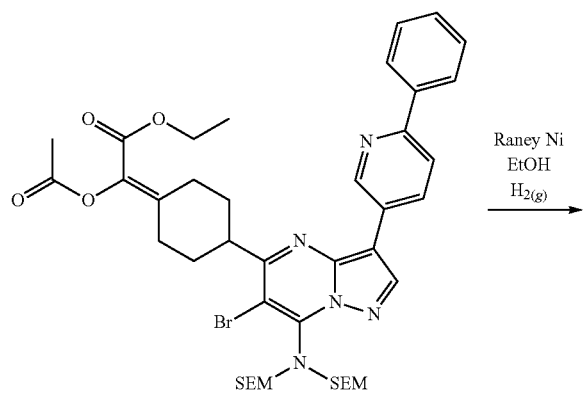

To a 50 mL roundbottom flask was charged ethyl 2-acetoxy-2-(4-(7-(bis((2-(trimethylsilyl)ethoxy)methyl)amino)-6-bromo-3-(6-phenylpyridin-3-yl)pyrazolo[1,5-a]pyrimidin-5-yl)cyclohexylidene)acetate (0.47 mmol, 400 mg), ethanol (15 mL), di-isopropylethyl amine (0.50 mmol, 88 µL), and Raney 2800 nickel (slurry in H$_2$O, 100 mg). The flask was sealed and degassed under vacuum for 15 minutes. After 15 minutes, the hydrogen gas was added in balloon and the reaction stirred at room temperature for 18 hours. After 18 hours, the reaction was filtered through celite, being careful to not dry out Raney nickel. The filtrate was reduced in vacuo and the resulting residue was purified via flash chromatography to yield the title compound.

(S)-2-((1s,4R)-4-(7-amino-6-bromo-3-(6-phenylpyridin-3-yl)pyrazolo[1,5-a]pyrimidin-5-yl)cyclohexyl)-2-hydroxyacetic acid

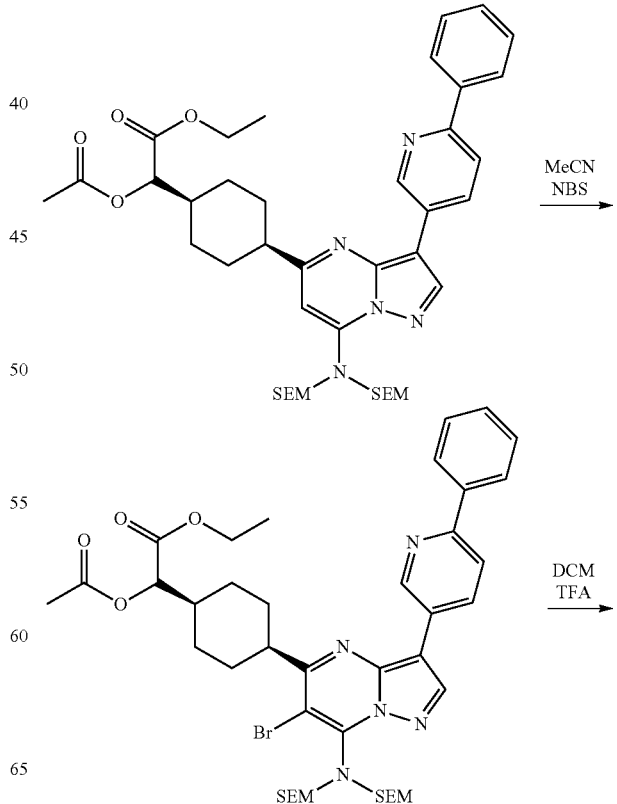

935
-continued

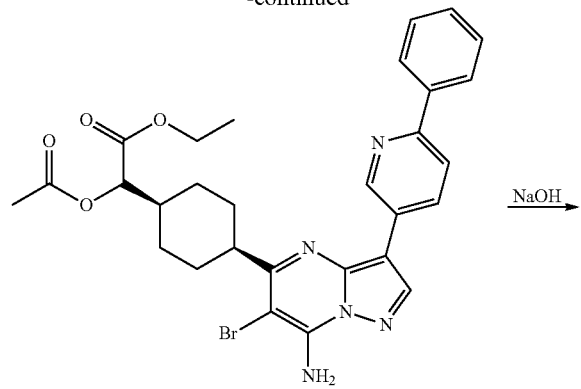

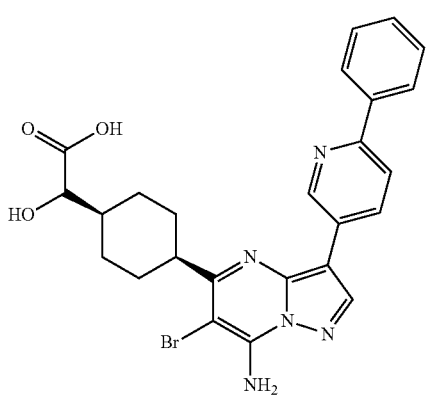

(S)-2-((1s,4R)-4-(7-amino-6-bromo-3-(6-phenylpyridin-3-yl)pyrazolo[1,5-a]pyrimidin-5-yl)cyclohexyl)-2-hydroxyacetic acid was synthesized in the manner previously described. (m+H=522.10, retention time=2.68 min).

(R)-methyl 2-((1r,4R)-4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)-2-methoxyacetate

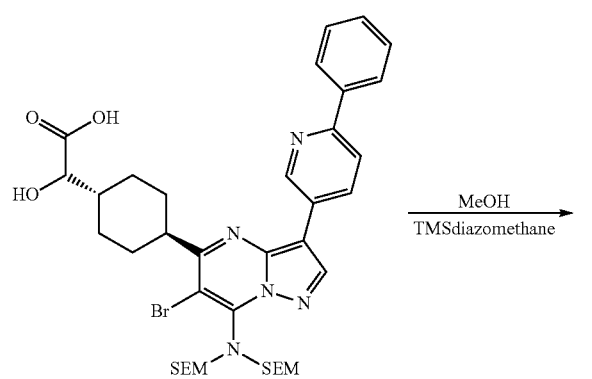

936
-continued

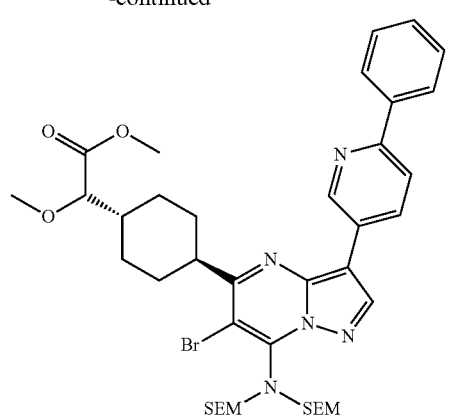

To a 50 mL roundbottom flask was charged (R)-2-((1r,4R)-4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)-2-hydroxyacetic acid (0.40 mmol), MeOH (15 mL), and TMS diazomethane (2.0 M in hexanes, 40 mmol, 20 mL). This solution was allowed to stir at room temperature for 72 hours. After 72 hours, the solvent was removed in vacuo and the residue was purified via flash chromatography to yield the title compound.

(R)-2-((1r,4R)-4-(7-amino-6-bromo-3-(6-phenylpyridin-3-yl)pyrazolo[1,5-a]pyrimidin-5-yl)cyclohexyl)-2-methoxyacetic acid

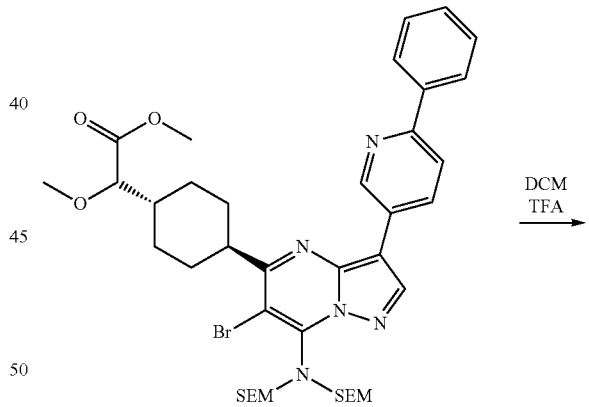

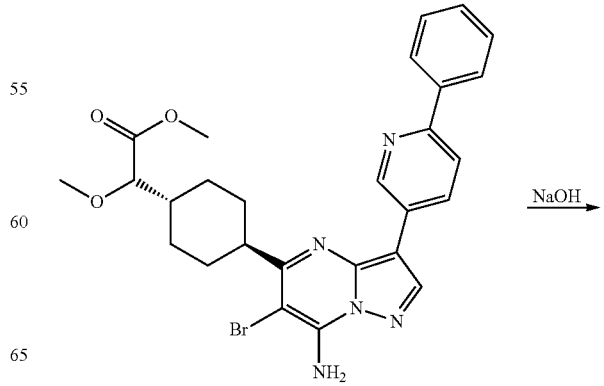

937

-continued

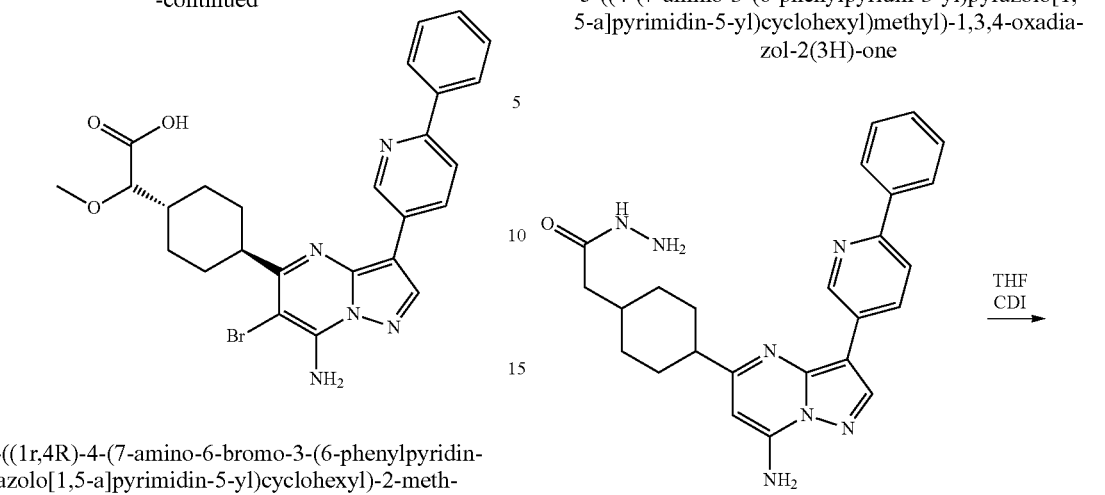

(R)-2-((1r,4R)-4-(7-amino-6-bromo-3-(6-phenylpyridin-3-yl)pyrazolo[1,5-a]pyrimidin-5-yl)cyclohexyl)-2-methoxyacetic acid was synthesized in the manner previously described. (m+H=536.56, retention time=3.84 min).

2-(4-(7-amino-3-(6-phenylpyridin-3-yl)pyrazolo[1,5-a]pyrimidin-5-yl)cyclohexyl)acetohydrazide

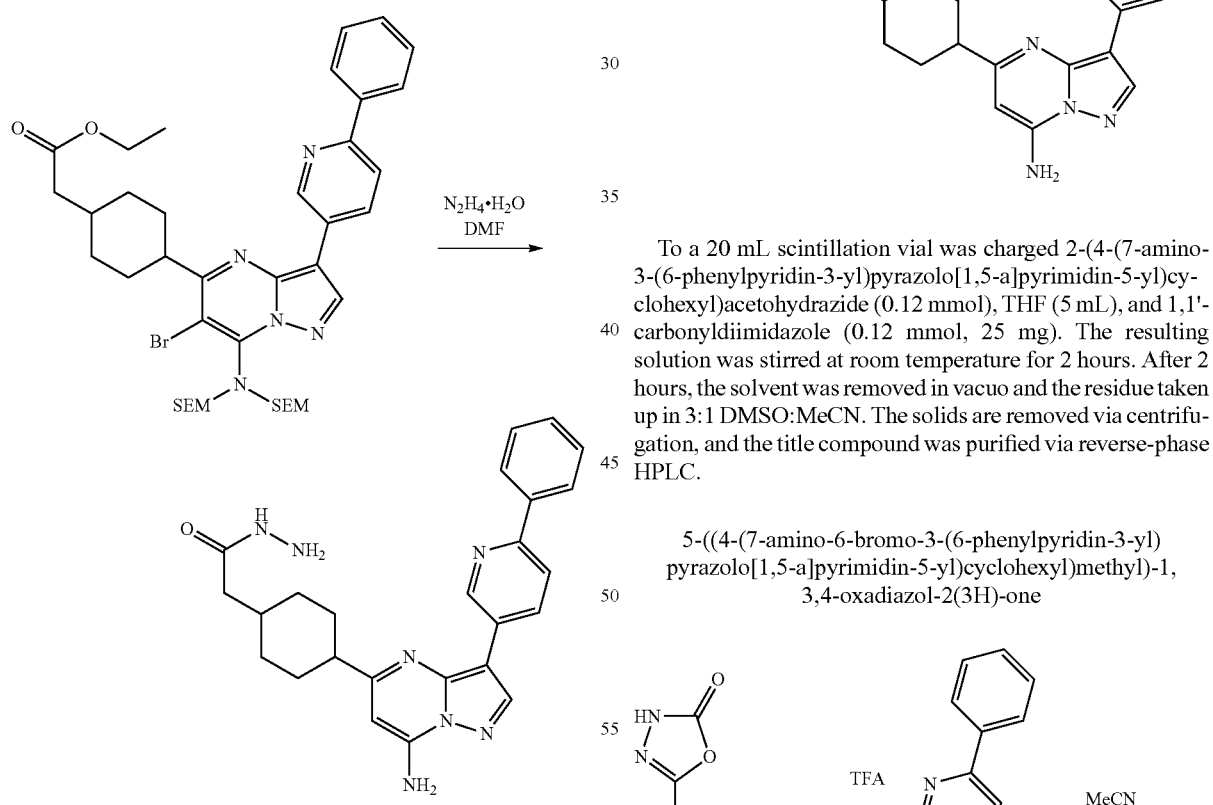

To a 2-5 mL pressure vial was charged ethyl 2-(4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)acetate (0.12 mmol, 95 mg), DMF (1 mL), and hydrazine monohydrate (1 mL). The pressure vial was sealed and heated to 80° C. for 18 hours. After 18 hours, the solvents were removed in vacuo and the product taken on without further purification.

938

5-((4-(7-amino-3-(6-phenylpyridin-3-yl)pyrazolo[1,5-a]pyrimidin-5-yl)cyclohexyl)methyl)-1,3,4-oxadiazol-2(3H)-one To a 20 mL scintillation vial was charged 2-(4-(7-amino-3-(6-phenylpyridin-3-yl)pyrazolo[1,5-a]pyrimidin-5-yl)cyclohexyl)acetohydrazide (0.12 mmol), THF (5 mL), and 1,1'-carbonyldiimidazole (0.12 mmol, 25 mg). The resulting solution was stirred at room temperature for 2 hours. After 2 hours, the solvent was removed in vacuo and the residue taken up in 3:1 DMSO:MeCN. The solids are removed via centrifugation, and the title compound was purified via reverse-phase HPLC.

5-((4-(7-amino-6-bromo-3-(6-phenylpyridin-3-yl)pyrazolo[1,5-a]pyrimidin-5-yl)cyclohexyl)methyl)-1,3,4-oxadiazol-2(3H)-one

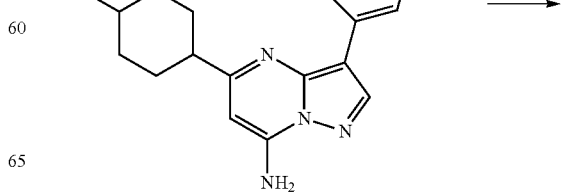

939
-continued

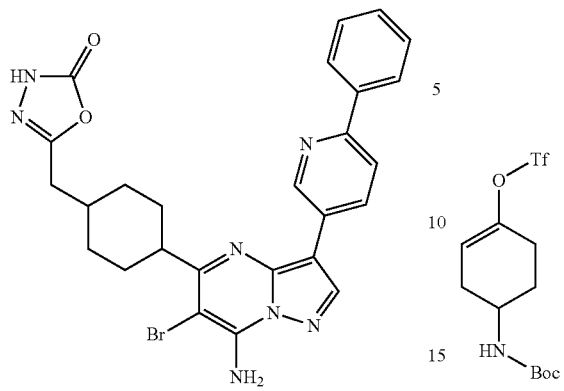

To a 20 mL scintillation vial was charged 5-((4-(7-amino-3-(6-phenylpyridin-3-yl)pyrazolo[1,5-a]pyrimidin-5-yl)cyclohexyl)methyl)-1,3,4-oxadiazol-2(3H)-one as a trifluoroacetate salt (0.035 mmol, 20 mg), MeCN (2 mL) and N-bromosuccinimide (0.035 mmol, 6.3 mg). The resulting solution was stirred at room temperature for 1 hour. After 1 hour, the solvent was removed in vacuo and the resulting residue was purified via reverse-phase HPLC to yield 5-((4-(7-amino-6-bromo-3-(6-phenylpyridin-3-yl)pyrazolo[1,5-a]pyrimidin-5-yl)cyclohexyl)methyl)-1,3,4-oxadiazol-2(3H)-one (m+H=546.57, retention time=4.07 min).

4-(tert-butoxycarbonylamino)cyclohex-1-enyl trifluoromethanesulfonate

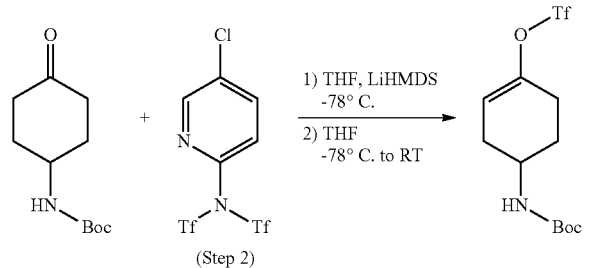

To a 100 mL roundbottom flask was charged 4-N-Boc-aminocyclohexanone (4.69 mmol, 1.00 g) and THF (15 mL). The flask was flushed with argon and sealed with a rubber septum. The solution was then cooled to −78° C. in a dry ice/isopropanol bath. LiHMDS (1.0 M in hexanes, 9.61 mmol, 9.61 mL) was then added dropwise. After addition, the resulting solution was stirred at −78° C. for 45 minutes. At this point, 2-[N,N-Bis(trifluoromethanesulfonyl)amino]-5-chloropyridine (5.16 mmol, 2.03 g) was taken up in THF (5 mL) and added dropwise to stirring solution at −78° C. The resulting solution was allowed to gently warm to room temperature over 1 hour. At 1 hour, the reaction was quenched with H₂O and extracted with DCM (×2). The combined organics were dried over Na₂SO₄ and the solvent them removed in vacuo. The residue was then purified via flash chromatography to yield the title compound.

940
4-(tert-butoxycarbonylamino)cyclohex-1-enyl trifluoromethanesulfonate

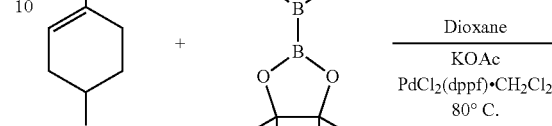

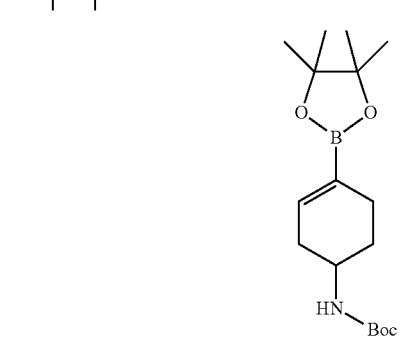

To a 10-20 mL pressure vial was charged 4-(tert-butoxycarbonylamino)cyclohex-1-enyl trifluoromethanesulfonate (1.15 mmol, 397 mg), 1,4-dioxane (8 mL), bis(pinacolato)diboron (1.72 mmol, 438 mg), potassium acetate (3.45 mmol, 339 mg), and PdCl₂(dppf).CH₂Cl₂ (115 μmol, 94 mg). The vial was flushed with argon, sealed, and heated to 80° C. for 5 hours. After 5 hours, the solvent removed in vacuo and the residue was taken up in DCM. This suspension was filtered through celite and then purified via flash chromatography to yield the title compound.

tert-butyl 4-(7-(bis((2-(trimethylsilyl)ethoxy)methyl)amino)pyrazolo[1,5-a]pyrimidin-5-yl)cyclohex-3-enylcarbamate

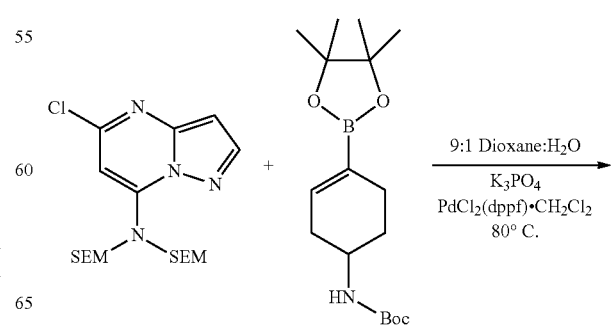

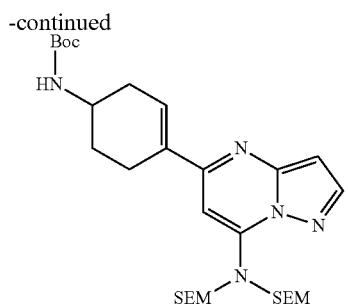

tert-butyl 4-(7-(bis((2-(trimethylsilyl)ethoxy)methyl)amino)pyrazolo[1,5-a]pyrimidin-5-yl)cyclohex-3-enylcarbamate was synthesized in the manner previously described.

tert-butyl (1s,4s)-4-(7-(bis((2-(trimethylsilyl)ethoxy)methyl)amino)pyrazolo[1,5-a]pyrimidin-5-yl)cyclohexylcarbamate and tert-butyl (1r,4r)-4-(7-(bis((2-(trimethylsilyl)ethoxy)methyl)amino)pyrazolo[1,5-a]pyrimidin-5-yl cyclohexylcarbamate

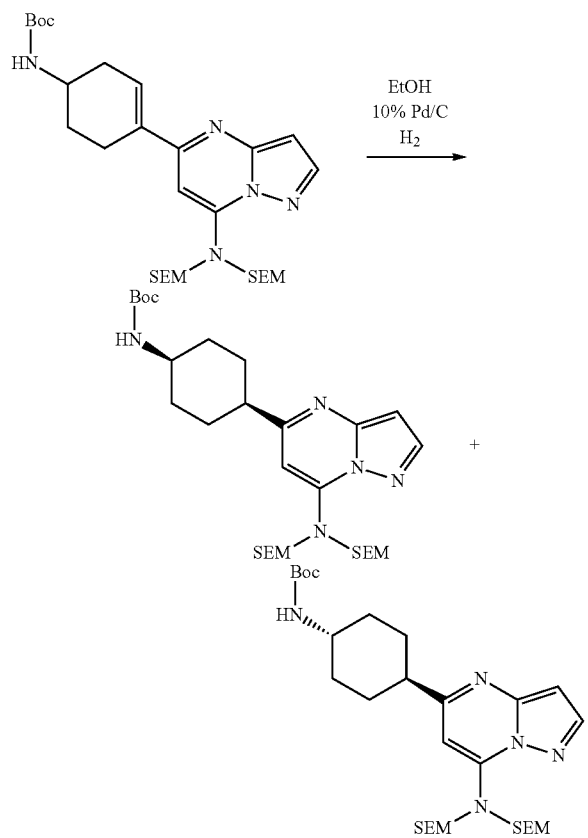

To a 50 mL roundbottom flask was charged tert-butyl 4-(7-(bis((2-(trimethylsilyl)ethoxy)methyl)amino)pyrazolo[1,5-a]pyrimidin-5-yl)cyclohex-3-enylcarbamate (0.67 mmol, 396 mg), ethanol (15 mL), and 10% palladium on carbon (100 mg). The flask was flushed with argon, sealed, and degassed under vacuum. Hydrogen gas was added in a balloon and the reaction was allowed to stir at room temperature under a hydrogen atmosphere for 18 hours. After 18 hours, the reaction was filtered though celite. The solvent was removed in vacuo and the resulting residue was purified to yield the title compounds (isomer 1=cis, isomer 2=trans).

5-((1s,4s)-4-aminocyclohexyl)-6-bromo-3-(6-phenylpyridin-3-yl)pyrazolo[1,5-a]pyrimidin-7-amine

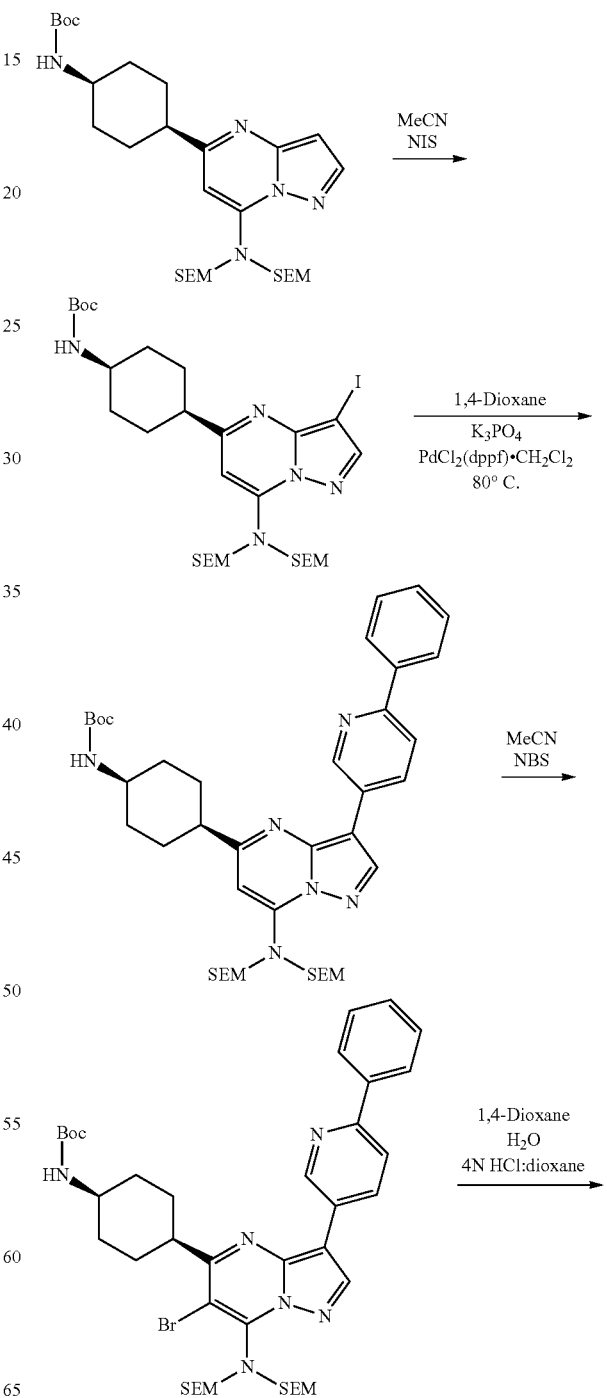

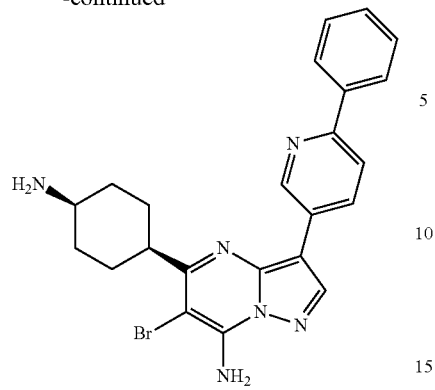

5-((1s,4s)-4-aminocyclohexyl)-6-bromo-3-(6-phenylpyridin-3-yl)pyrazolo[1,5-a]pyrimidin-7-amine was synthesized in the manner previously described.

(R)-N-((1s,4S)-4-(7-amino-6-bromo-3-(6-phenylpyridin-3-yl)pyrazolo[1,5-a]pyrimidin-5-yl)cyclohexyl)-2-hydroxypropanamide

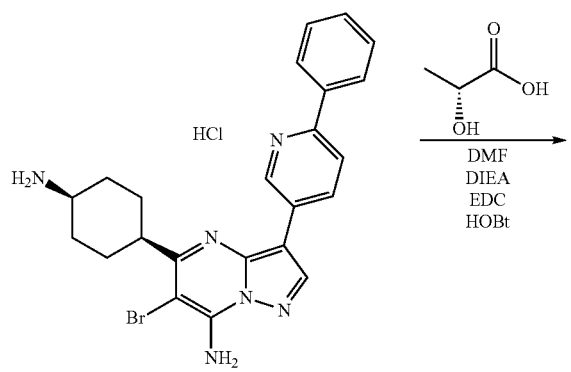

To a 20 mL scintillation vial was charged 5-((1s,4s)-4-aminocyclohexyl)-6-bromo-3-(6-phenylpyridin-3-yl)pyrazolo[1,5-a]pyrimidin-7-amine as a hydrochloride salt (37 μmol), DMF (2 mL), D-lactic acid (0.08 mmol, 7.2 mg), EDC (0.08 mmol, 15.4 mg), HOBt (0.08 mmol, 10.8 mg), and DIEA (0.15 mmol, 26 μL). The resulting solution was stirred at room temperature for 4 hours. After 4 hours, the solvent was removed in vacuo and the residue purified via reverse-phase HPLC to yield (R)-N-((1s,4S)-4-(7-amino-6-bromo-3-(6-phenylpyridin-3-yl)pyrazolo[1,5-a]pyrimidin-5-yl)cyclohexyl)-2-hydroxypropanamide (m+H=534.74, retention time=3.82 min).

The following compound (Table-7C) was synthesized using essentially the same procedures used for the total synthesis of (R)-N-((1s,4S)-4-(7-amino-6-bromo-3-(6-phenylpyridin-3-yl)pyrazolo[1,5-a]pyrimidin-5-yl)cyclohexyl)-2-hydroxypropanamide:

TABLE-7C

| Compound ID | Structures | M + H (calc.) | M + H (observed) | Retention Time, (min) |
|---|---|---|---|---|
| 7.3.1 | 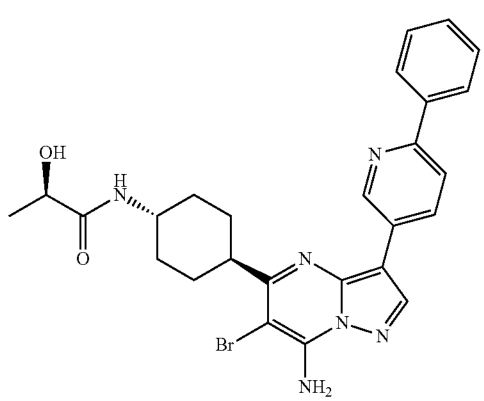 [SMILES: C[C@@H](O)C(=O)N[C@H]1CC[C@H](c2nc3c(-c4ccc(-c5ccccc5)nc4)cnn3c(N)c2Br)CC1] | 534.14 | 534.83 | 3.60 |

945

(R)-N-((1s,4S)-4-(6-acetyl-7-amino-3-(6-phenylpyridin-3-yl)pyrazolo[1,5-a]pyrimidin-5-yl)cyclohexyl)-2-hydroxypropanamide

946

-continued

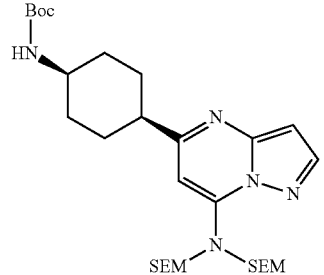

MeCN
NIS
→

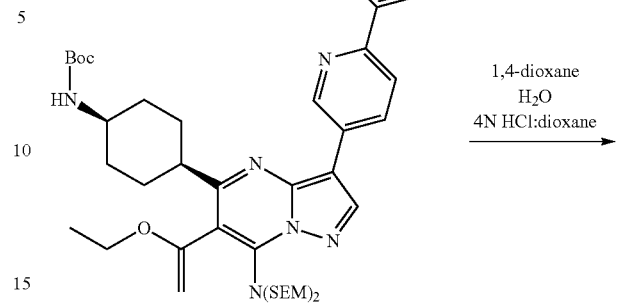

1,4-dioxane
H₂O
4N HCl:dioxane
→

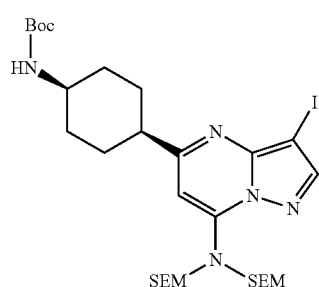

1,4-Dioxane
K₃PO₄
PdCl₂(dppf)·CH₂Cl₂
80° C.
→

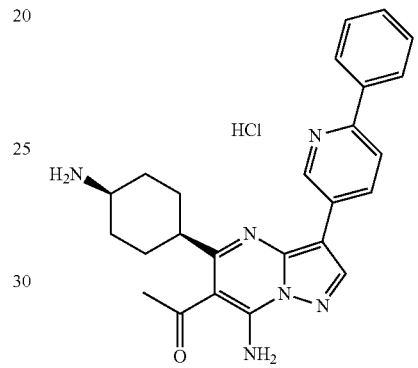

DMF
DIEA
EDC
HOBt
→

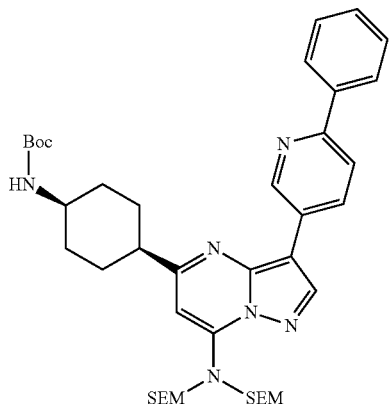

MeCN
NBS
→

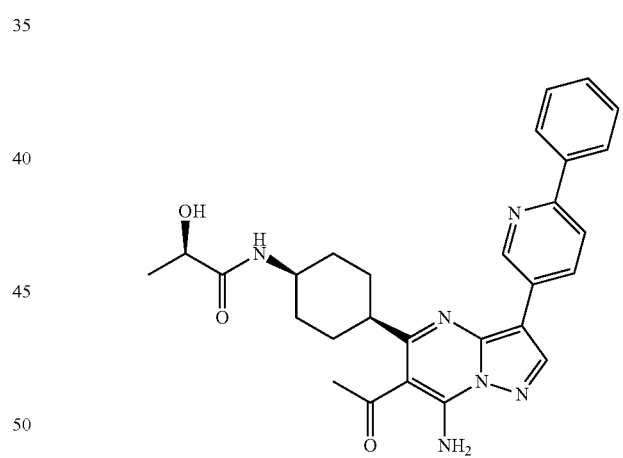

Stille
→

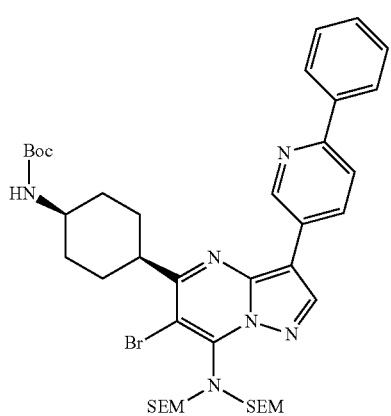

(R)-N-((1s,4S)-4-(6-acetyl-7-amino-3-(6-phenylpyridin-3-yl)pyrazolo[1,5-a]pyrimidin-5-yl)cyclohexyl)-2-hydroxypropanamide was synthesized in the manner previously described (m+H=499.11, retention time=3.68 min).

The following compounds (Table-7D) were synthesized using essentially the same procedures used for the total synthesis of (R)-N-((1s,4S)-4-(6-acetyl-7-amino-3-(6-phenylpyridin-3-yl)pyrazolo[1,5-a]pyrimidin-5-yl)cyclohexyl)-2-hydroxypropanamide:

TABLE-7D
| Compound ID | Structures | M + H (calc.) | M + H (observed) | Retention Time, (min) |
|---|---|---|---|---|
| 7.4.1 | 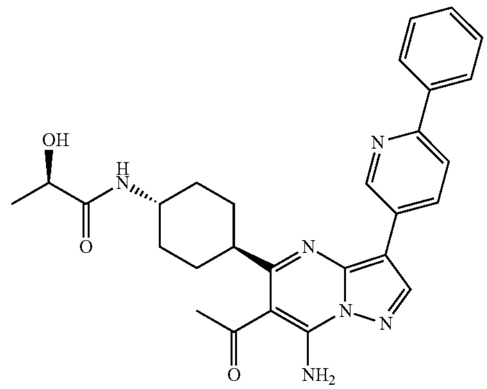 [SMILES: CC(=O)c1c(N)n2ncc(-c3ccc(-c4ccccc4)nc3)c2nc1[C@H]1CC[C@H](N(C)C(=O)[C@@H](C)O)CC1] | 498.24 | 498.99 | 3.48 |
| 7.4.2 | 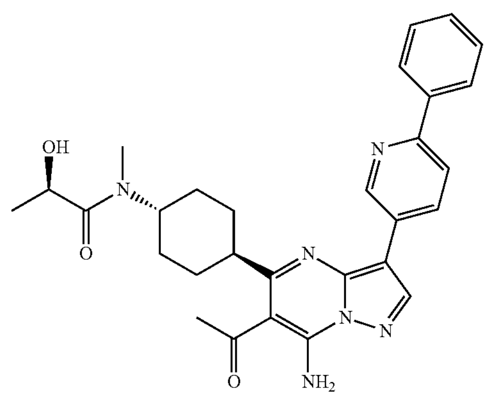 | 512.25 | 513.16 | 2.56 (new purity check method) |
Synthesis of 1-(7-amino-5-((1r,4r)-4-(methylsulfonylmethyl)cyclohexyl)-3-(1-phenyl-1H-pyrazol-4-yl)pyrazolo[1,5-a]pyrimidin-6-yl)ethanone
-continued
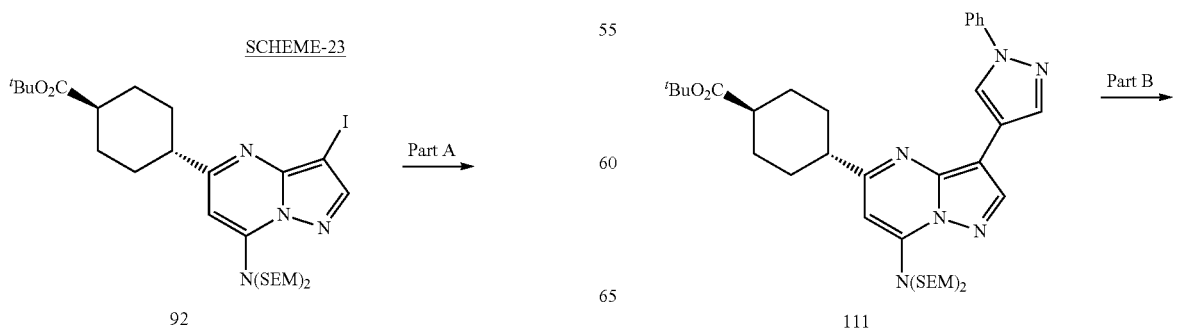
SCHEME-23

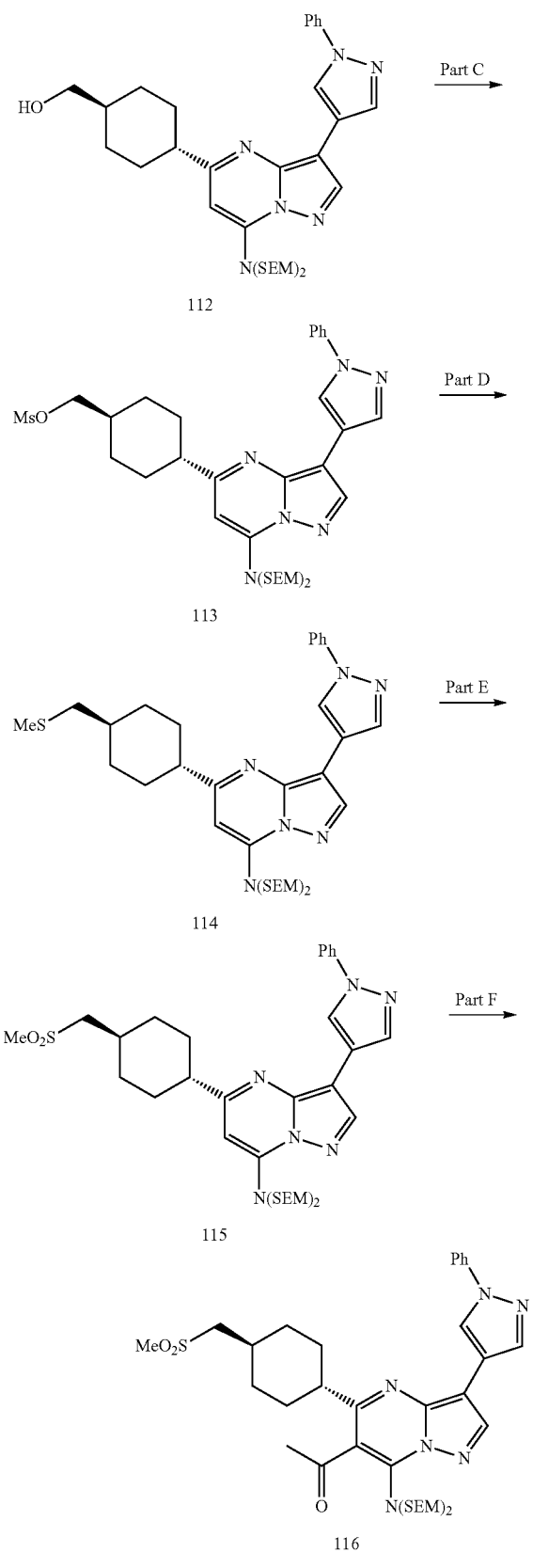

Part A:

(1r,4r)-tert-butyl 4-(7-(bis((2-(trimethylsilyl)ethoxy)methyl)amino)-3-(1-phenyl-1H-pyrazol-4-1)pyrazolo[1,5-a]pyrimidin-5-yl)cyclohexanecarboxylate Compound, (1r,4r)-tert-butyl 4-(7-(bis((2-(trimethylsilyl)ethoxy)methyl)amino)-3-(1-phenyl-1H-pyrazol-4-yl)pyrazolo[1,5-a]pyrimidin-5-yl)cyclohexanecarboxylate was prepared from compound (1r,4r)-tert-butyl 4-(7-(bis((2-(trimethylsilyl)ethoxy)methyl)amino)-3-iodopyrazolo[1,5-a]pyrimidin-5-yl)cyclohexanecarboxylate and 1-phenyl-4-(4,4,5,5-tetramethyl-1,3,2-dioxaborolan-2-yl)-1H-pyrazole using the coupling conditions described in Part G of Example 8 (68%). HPLC-MS $T_R$=3.13 min (UV 254 nm, 5 min method); mass calculated for formula $C_{38}H_{58}N_6O_4Si_2$ 718.4, observed LCMS m/z 719.3 (M+H).

Part B:

((1r,4r)-4-(7-(bis((2-(trimethylsilyl)ethoxy)methyl)amino)-3-(1-phenyl-1H-pyrazol-4-yl)pyrazolo[1,5-a]pyrimidin-5-yl)cyclohexyl)methanol To a solution of compound (1r,4r)-tert-butyl 4-(7-(bis((2-(trimethylsilyl)ethoxy)methyl)amino)-3-(1-phenyl-1H-pyrazol-4-yl)pyrazolo[1,5-a]pyrimidin-5-yl)cyclohexanecarboxylate (1.68 mmol, 1.21 g) in THF (20 mL) at 0° C. was added lithium aluminum hydride solution (1.68 mL, 2.0 M in THF). The resulting reaction mixture was slowly warmed to rt and stirred for 1 h. The reaction quenched with 3 N NaOH and filtered. The filtrate and washes were combined and concentrated. The crude product was purified by a $SiO_2$ column (0-40% EtOAc/Hexanes, $R_f$=0.7 in 50% EtOAc) to afford compound, ((1r,4r)-4-(7-(bis((2-(trimethylsilyl)ethoxy)methyl)amino)-3-(1-phenyl-1H-pyrazol-4-yl)pyrazolo[1,5-a]pyrimidin-5-yl)cyclohexyl)methanol, as a pale yellow solid (923 mg, 85%). HPLC-MS $T_R$=3.08 min (UV 254 nm, 5 min method); mass calculated for formula $C_{34}H_{52}N_6O_3Si_2$ 648.4, observed LCMS m/z 649.3 (M+H).

Part C:

((1r,4r)-4-(7-(bis((2-(trimethylsilyl)ethoxy)methyl)amino)-3-(1-phenyl-1H-pyrazol-4-yl)pyrazolo[1,5-a]pyrimidin-5-yl)cyclohexyl)methyl methanesulfonate To a solution of compound, ((1r,4r)-4-(7-(bis((2-(trimethylsilyl)ethoxy)methyl)amino)-3-(1-phenyl-1H-pyrazol-4-yl)pyrazolo[1,5-a]pyrimidin-5-yl)cyclohexyl)methanol (1.42 mmol, 920 mg) in DCM (10 mL) was added TEA (4.26 mmol, 0.594 mL), followed by MsCl (2.13 mmol, 0.165 mL) at 0° C. and stirred for 1 h. The reaction mixture was washed with $H_2O$ and brine, dried over $Na_2SO_4$, and concentrated. The crude product was purified by a $SiO_2$ column (0-30% EtOAc/Hexanes, $R_f$=0.8 in 50% EtOAc) to afford compound, ((1r,4r)-4-(7-(bis((2-(trimethylsilyl)ethoxy)methyl)amino)-3-(1-phenyl-1H-pyrazol-4-yl)pyrazolo[1,5-a]pyrimidin-5-yl)cyclohexyl)methyl methanesulfonate, as a pale yellow oil (949 mg, 92%).

Part D:

5-((1r,4r)-4-(methylthiomethyl)cyclohexyl)-3-(1-phenyl-1H-pyrazol-4-yl)-N,N-bis((2-(trimethylsilyl)ethoxy)methyl)pyrazolo[1,5-a]pyrimidin-7-amine A mixture compound ((1r,4r)-4-(7-(bis((2-(trimethylsilyl)ethoxy)methyl)amino)-3-(1-phenyl-1H-pyrazol-4-yl)pyrazolo[1,5-a]pyrimidin-5-yl)cyclohexyl)methyl methanesulfonate (1.31 mmol, 949 mg) and NaSMe (2.61 mmol, 183 mg) in DMF (5 mL) was heated at 80° C. for 3 d. The reaction mixture was diluted with EtOAc, washed with H₂O and brine, dried over Na₂SO₄, and concentrated. The crude product was purified by a SiO₂ column (0-20% EtOAc/Hexanes, $R^f$=0.5 in 20% EtOAc) to afford compound, 5-((1r,4r)-4-(methylthiomethyl)cyclohexyl)-3-(1-phenyl-1H-pyrazol-4-yl)-N,N-bis((2-(trimethylsilyl)ethoxy)methyl)pyrazolo[1,5-a]pyrimidin-7-amine, as a pale yellow oil (804 mg, 90%). HPLC-MS $T_R$=3.59 min (UV 254 nm, 5 min method); mass calculated for formula $C_{35}H_{54}N_6O_2SSi_2$ 678.4, observed LCMS m/z 679.3 (M+H).

Part E:

5-((1r,4r)-4-(methylsulfonylmethyl)cyclohexyl)-3-(1-phenyl-1H-pyrazol-4-yl)-N,N-bis((2-(trimethylsilyl)ethoxy)methyl)pyrazolo[1,5-a]pyrimidin-7-amine To a solution of compound, 5-((1r,4r)-4-(methylthiomethyl)cyclohexyl)-3-(1-phenyl-1H-pyrazol-4-yl)-N,N-bis((2-(trimethylsilyl)ethoxy)methyl)pyrazolo[1,5-a]pyrimidin-7-amine (1.18 mmol, 804 mg) in DCM (10 mL) was added mCPBA (2.83 mmol, 699 mg) and the resulting mixture was stirred at rt for overnight. The reaction was quenched with Na₂S₂O₃ (aq.) and diluted with DCM (10 mL). The separated organic layer was washed with NaHCO₃ (2*) and brine, dried over Na₂SO₄, and concentrated. The crude product was purified by a SiO₂ column (0-40% EtOAc/Hexanes, $R_f$=0.45 in 50% EtOAc) to afford compound, 5-((1r,4r)-4-(methylsulfonylmethyl)cyclohexyl)-3-(1-phenyl-1H-pyrazol-4-yl)-N,N-bis((2-(trimethylsilyl)ethoxy)methyl)pyrazolo[1,5-a]pyrimidin-7-amine, as a pale yellow oil (446 mg, 53%). HPLC-MS $T_R$=2.99 min (UV 254 nm, 5 min method); mass calculated for formula $C_{35}H_{54}N_6O_4SSi_2$ 710.3, observed LCMS m/z 711.2 (M+H).

Part F:

1-(7-amino-5-((1r,4r)-4-(methylsulfonylmethyl)cyclohexyl)-3-(1-phenyl-1H-pyrazol-4-yl)pyrazolo[1,5-a]pyrimidin-6-yl)ethanone By essentially the same procedures given in Preparative earlier Example compound, 1-(7-amino-5-((1r,4r)-4-(methylsulfonylmethyl)cyclohexyl)-3-(1-phenyl-1H-pyrazol-4-yl)pyrazolo[1,5-a]pyrimidin-6-yl)ethanone was prepared from compound, 5-((1r,4r)-4-(methylsulfonylmethyl)cyclohexyl)-3-(1-phenyl-1H-pyrazol-4-yl)-N,N-bis((2-(trimethylsilyl)ethoxy)methyl)pyrazolo[1,5-a]pyrimidin-7-amine. HPLC-MS $T_R$=4.64 min (UV 254 nm, 10 min method); mass calculated for formula $C_{25}H_{28}N_6O_3S$, 492.2, observed LCMS m/z 493.1 (M+H).

SCHEME-24

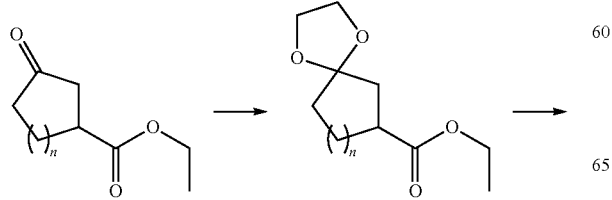

-continued

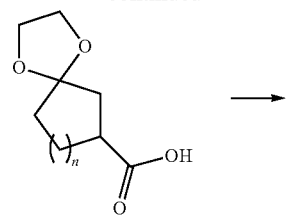

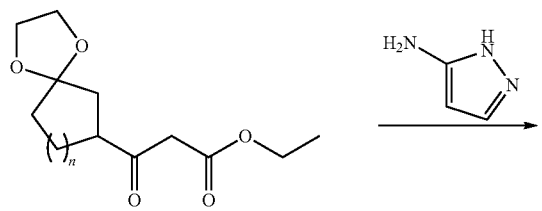

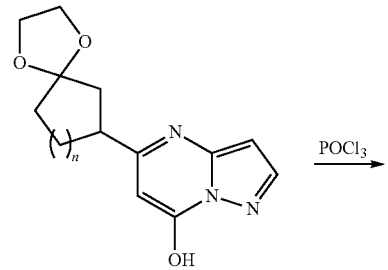

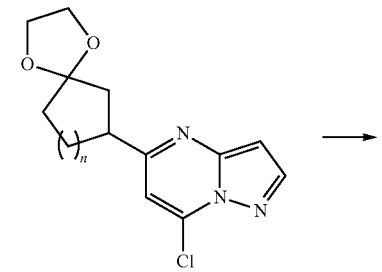

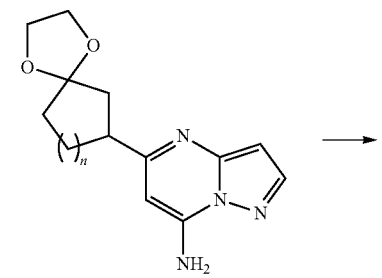

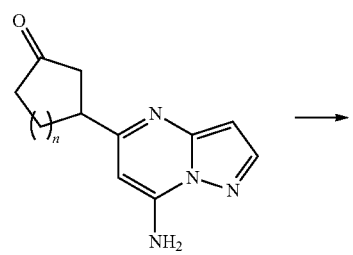

953
-continued

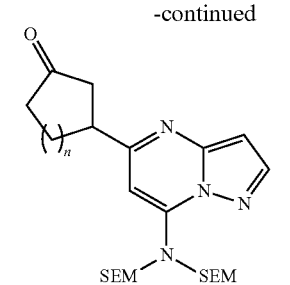

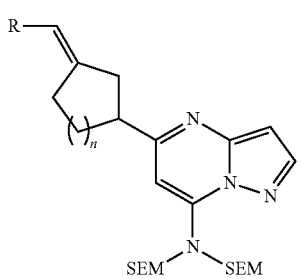

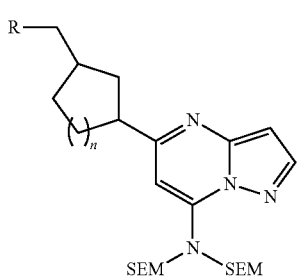

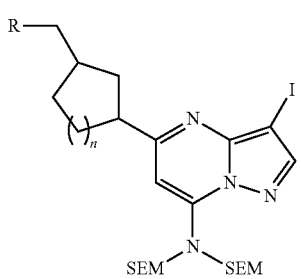

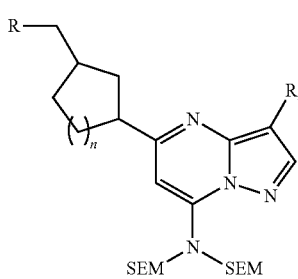

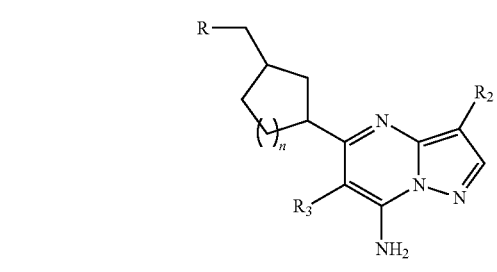

954

Synthesis of ethyl 1,4-dioxaspiro[4.5]decane-7-carboxylate

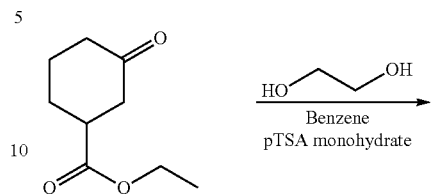

Ethyl 1,4-dioxaspiro[4.5]decane-7-carboxylate was synthesized in a manner similar to the synthesis of ethyl 1,4-dioxaspiro[4.5]decane-8-carboxylate, but with ethyl 3-oxo-cyclohexanecarboxylate substituted for ethyl 4-oxocyclohexanecarboxylate.

Synthesis of ethyl 1,4-dioxaspiro[4.4]nonane-7-carboxylate

Ethyl 1,4-dioxaspiro[4.4]nonane-7-carboxylate was synthesized in a manner similar to the synthesis of ethyl 1,4-dioxaspiro[4.5]decane-8-carboxylate, but with ethyl 3-oxo-cyclopentanecarboxylate substituted for ethyl 4-oxocyclohexanecarboxylate.

Synthesis of 1,4-dioxaspiro[4.5]decane-7-carboxylic acid

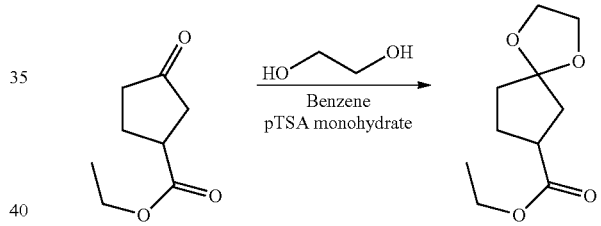

1,4-Dioxaspiro[4.5]decane-7-carboxylic acid was synthesized in a manner similar to the synthesis of 1,4-dioxaspiro[4.5]decane-8-carboxylic acid, but with ethyl 1,4-dioxaspiro[4.5]decane-7-carboxylate substituted for ethyl 1,4-dioxaspiro[4.5]decane-8-carboxylate.

955
Synthesis of 1,4-dioxaspiro[4.4]nonane-7-carboxylic acid

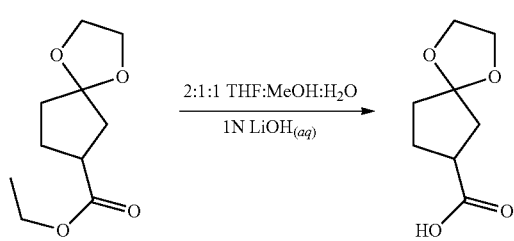

1,4-dioxaspiro[4.4]nonane-7-carboxylic acid was synthesized in a manner similar to the synthesis of 1,4-dioxaspiro[4.5]decane-8-carboxylic acid, but with ethyl 1,4-dioxaspiro[4.4]nonane-7-carboxylate substituted for ethyl 1,4-dioxaspiro[4.5]decane-8-carboxylate.

Synthesis of ethyl 3-oxo-3-(1,4-dioxaspiro[4.5]decan-7-yl)propanoate

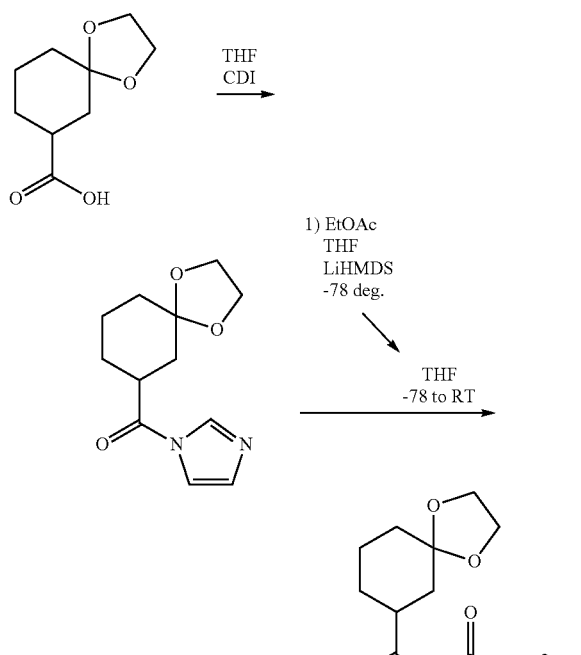

Ethyl 3-oxo-3-(1,4-dioxaspiro[4.5]decan-7-yl)propanoate was synthesized in a manner similar to the synthesis of ethyl 3-oxo-3-(1,4-dioxaspiro[4.5]decan-8-yl)propanoate, but with 1,4-dioxaspiro[4.5]decane-7-carboxylic acid substituted for 1,4-dioxaspiro[4.5]decane-8-carboxylic acid.

956
Synthesis of ethyl 3-oxo-3-(1,4-dioxaspiro[4.4]nonan-7-yl)propanoate

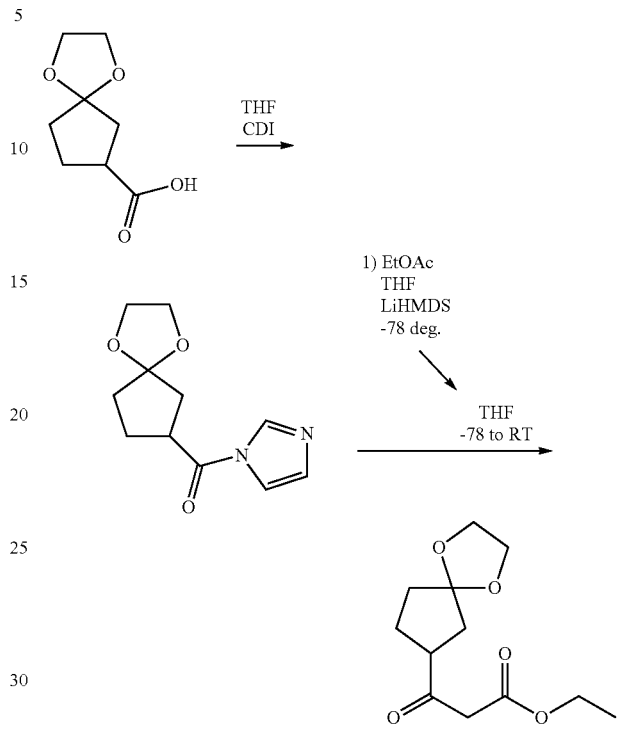

Ethyl 3-oxo-3-(1,4-dioxaspiro[4.4]nonan-7-yl)propanoate was synthesized in a manner similar to the synthesis of ethyl 3-oxo-3-(1,4-dioxaspiro[4.5]decan-8-yl)propanoate, but with 1,4-dioxaspiro[4.4]nonane-7-carboxylic acid substituted for 1,4-dioxaspiro[4.5]decane-8-carboxylic acid.

Synthesis of 5-(1,4-dioxaspiro[4.5]decan-7-yl)pyrazolo[1,5-a]pyrimidin-7-ol

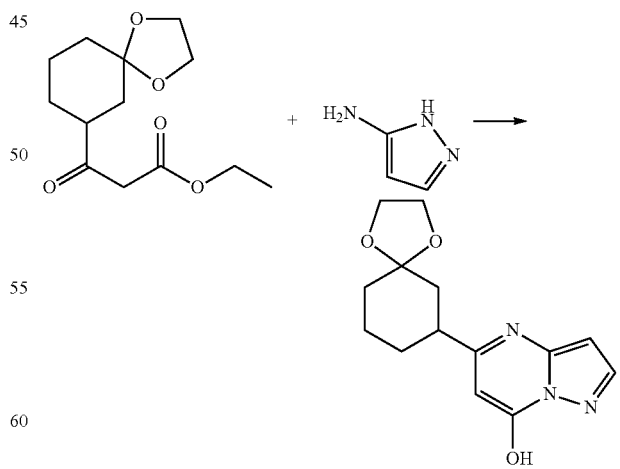

5-(1,4-dioxaspiro[4.5]decan-7-yl)pyrazolo[1,5-a]pyrimidin-7-ol was synthesized in a manner similar to the synthesis of 5-(1,4-dioxaspiro[4.5]decan-8-yl)pyrazolo[1,5-a]pyrimidin-7-ol, but with ethyl 3-oxo-3-(1,4-dioxaspiro[4.5]decan-

Synthesis of 5-(1,4-dioxaspiro[4.4]nonan-7-yl)pyrazolo[1,5-a]pyrimidin-7-ol

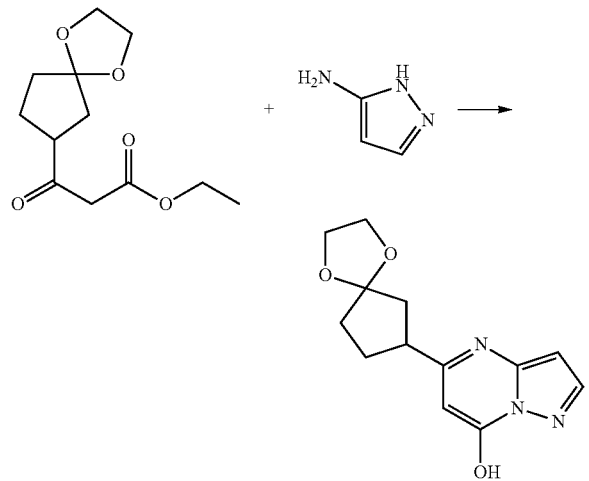

5-(1,4-dioxaspiro[4.4]nonan-7-yl)pyrazolo[1,5-a]pyrimidin-7-ol was synthesized in a manner similar to the synthesis of 5-(1,4-dioxaspiro[4.5]decan-8-yl)pyrazolo[1,5-a]pyrimidin-7-ol, but with ethyl 3-oxo-3-(1,4-dioxaspiro[4.4]nonan-7-yl)propanoate substituted for ethyl 3-oxo-3-(1,4-dioxaspiro[4.5]decan-8-yl)propanoate.

Synthesis of 7-chloro-5-(1,4-dioxaspiro[4.5]decan-7-yl)pyrazolo[1,5-a]pyrimidine

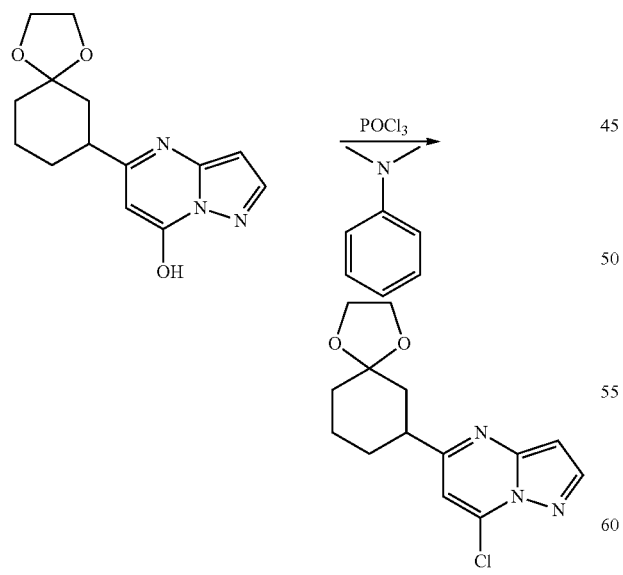

7-Chloro-5-(1,4-dioxaspiro[4.5]decan-7-yl)pyrazolo[1,5-a]pyrimidine is synthesized in a manner similar to the synthesis of 7-chloro-5-(1,4-dioxaspiro[4.5]decan-8-yl)pyrazolo[1,5-a]pyrimidine, but with 5-(1,4-dioxaspiro[4.5]decan-7-yl)pyrazolo[1,5-a]pyrimidin-7-ol substituted for 5-(1,4-dioxaspiro[4.5]decan-8-yl)pyrazolo[1,5-a]pyrimidin-7-ol.

Synthesis of 7-chloro-5-(1,4-dioxaspiro[4.4]nonan-7-yl)pyrazolo[1,5-a]pyrimidine

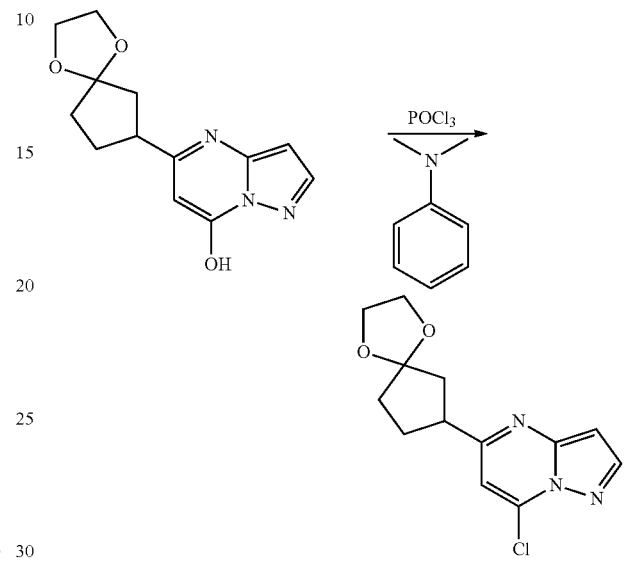

7-Chloro-5-(1,4-dioxaspiro[4.4]nonan-7-yl)pyrazolo[1,5-a]pyrimidine is synthesized in a manner similar to the synthesis of 7-chloro-5-(1,4-dioxaspiro[4.5]decan-8-yl)pyrazolo[1,5-a]pyrimidine, but with 5-(1,4-dioxaspiro[4.4]nonan-7-yl)pyrazolo[1,5-a]pyrimidin-7-ol substituted for 5-(1,4-dioxaspiro[4.5]decan-8-yl)pyrazolo[1,5-a]pyrimidin-7-ol.

Synthesis of 5-(1,4-dioxaspiro[14.5]decan-7-yl)pyrazolo[1,5-a]pyrimidin-7-amine

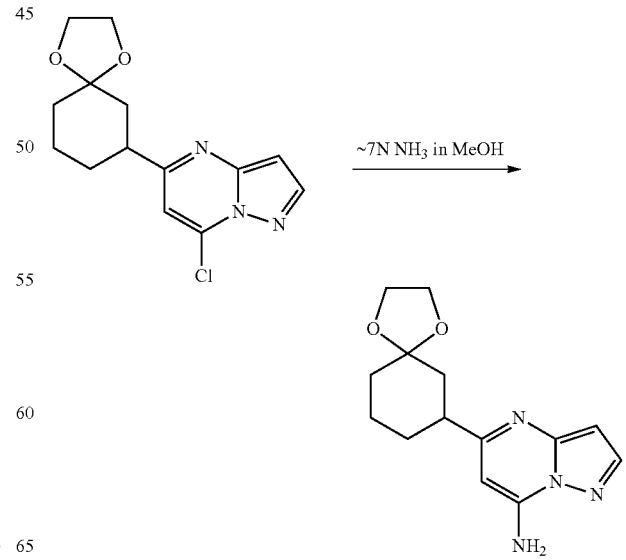

5-(1,4-Dioxaspiro[4.5]decan-7-yl)pyrazolo[1,5-a]pyrimidin-7-amine is synthesized in a manner similar to the synthesis of 5-(1,4-dioxaspiro[4.5]decan-8-yl)pyrazolo[1,5-a]pyrimidin-7-amine, but with 7-chloro-5-(1,4-dioxaspiro[4.5]decan-7-yl)pyrazolo[1,5-a]pyrimidine substituted for 7-chloro-5-(1,4-dioxaspiro[4.5]decan-8-yl)pyrazolo[1,5-a]pyrimidine.

Synthesis of 5-(1,4-dioxaspiro[4.4]nonan-7-yl)pyrazolo[1,5-a]pyrimidin-7-amine

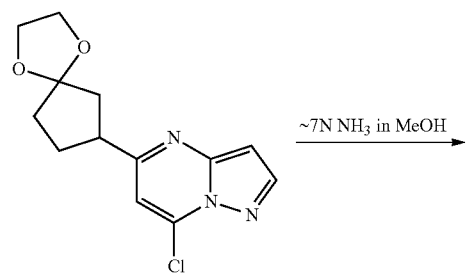

~7N NH$_3$ in MeOH

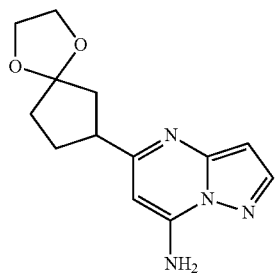

5-(1,4-Dioxaspiro[4.4]nonan-7-yl)pyrazolo[1,5-a]pyrimidin-7-amine was synthesized in a manner similar to the synthesis of 5-(1,4-dioxaspiro[4.5]decan-8-yl)pyrazolo[1,5-a]pyrimidin-7-amine, but with 7-chloro-5-(1,4-dioxaspiro[4.4]nonan-7-yl)pyrazolo[1,5-a]pyrimidine substituted for 7-chloro-5-(1,4-dioxaspiro[4.5]decan-8-yl)pyrazolo[1,5-a]pyrimidine.

Synthesis of 3-(7-aminopyrazolo[1,5-a]pyrimidin-5-yl)cyclohexanone

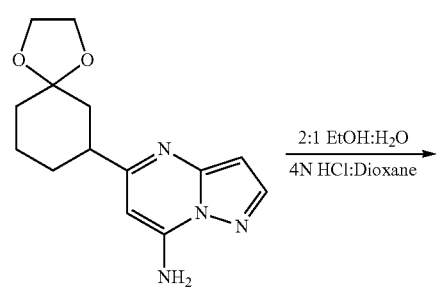

2:1 EtOH:H$_2$O
4N HCl:Dioxane

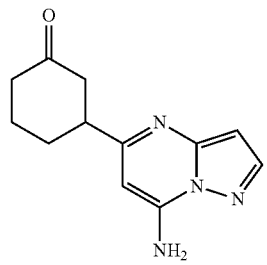

3-(7-Aminopyrazolo[1,5-a]pyrimidin-5-yl)cyclohexanone was synthesized in a manner similar to the synthesis of 4-(7-aminopyrazolo[1,5-a]pyrimidin-5-yl)cyclohexanone, but 5-(1,4-dioxaspiro[4.5]decan-7-yl)pyrazolo[1,5-a]pyrimidin-7-amine substituted for 5-(1,4-dioxaspiro[4.5]decan-8-yl)pyrazolo[1,5-a]pyrimidin-7-amine.

Synthesis of 3-(7-aminopyrazolo[1,5-a]pyrimidin-5-yl)cyclopentanone

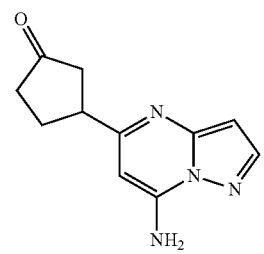

2:1 EtOH:H$_2$O
4N HCl:Dioxane 3-(7-Aminopyrazolo[1,5-a]pyrimidin-5-yl)cyclopentanone was synthesized in a manner similar to the synthesis of 4-(7-aminopyrazolo[1,5-a]pyrimidin-5-yl)cyclohexanone, but 5-(1,4-dioxaspiro[4.4]nonan-7-yl)pyrazolo[1,5-a]pyrimidin-7-amine substituted for 5-(1,4-dioxaspiro[4.5]decan-8-yl)pyrazolo[1,5-a]pyrimidin-7-amine.

961

Synthesis of 3-(7-(bis((2-(trimethylsilyl)ethoxy)methyl)amino)pyrazolo[1,5-a]pyrimidin-5-yl)cyclohexanone

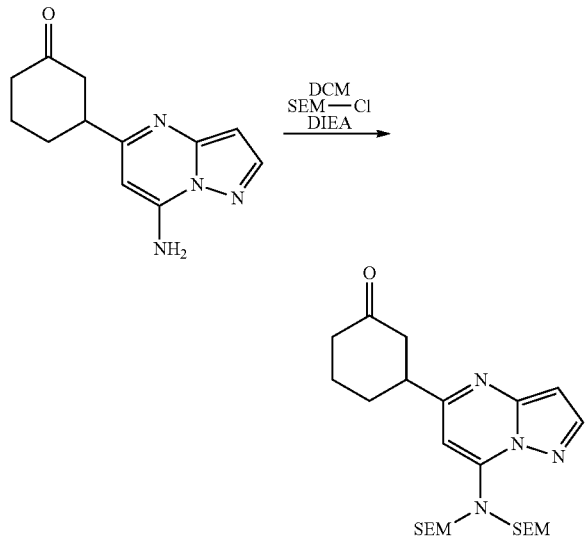

3-(7-(Bis((2-(trimethylsilyl)ethoxy)methyl)amino)pyrazolo[1,5-a]pyrimidin-5-yl)cyclohexanone was synthesized in a manner similar to the synthesis of 4-(7-(bis((2-(trimethylsilyl)ethoxy)methyl)amino)pyrazolo[1,5-a]pyrimidin-5-yl)cyclohexanone, but 3-(7-aminopyrazolo[1,5-a]pyrimidin-5-yl)cyclohexanone substituted for 4-(7-aminopyrazolo[1,5-a]pyrimidin-5-yl)cyclohexanone.

Synthesis of 3-(7-(bis((2-(trimethylsilyl)ethoxy)methyl)amino)pyrazolo[1,5-a]pyrimidin-5-yl)cyclopentanone

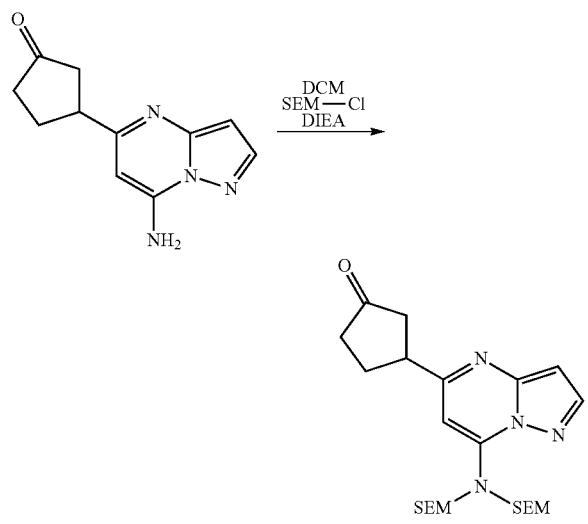

3-(7-(Bis((2-(trimethylsilyl)ethoxy)methyl)amino)pyrazolo[1,5-a]pyrimidin-5-yl)cyclopentanone was synthesized in a manner similar to the synthesis of 4-(7-(bis((2-(trimethylsilyl)ethoxy)methyl)amino)pyrazolo[1,5-a]pyrimidin-5-yl)cyclohexanone, but 3-(7-aminopyrazolo[1,5-a]pyrimidin-5-yl)cyclopentanone substituted for 4-(7-aminopyrazolo[1,5-a]pyrimidin-5-yl)cyclohexanone.

962

Synthesis of ethyl 2-(3-(7-(bis((2-(trimethylsilyl)ethoxy)methyl)amino)pyrazolo[1,5-a]pyrimidin-5-yl)cyclohexylidene)acetate

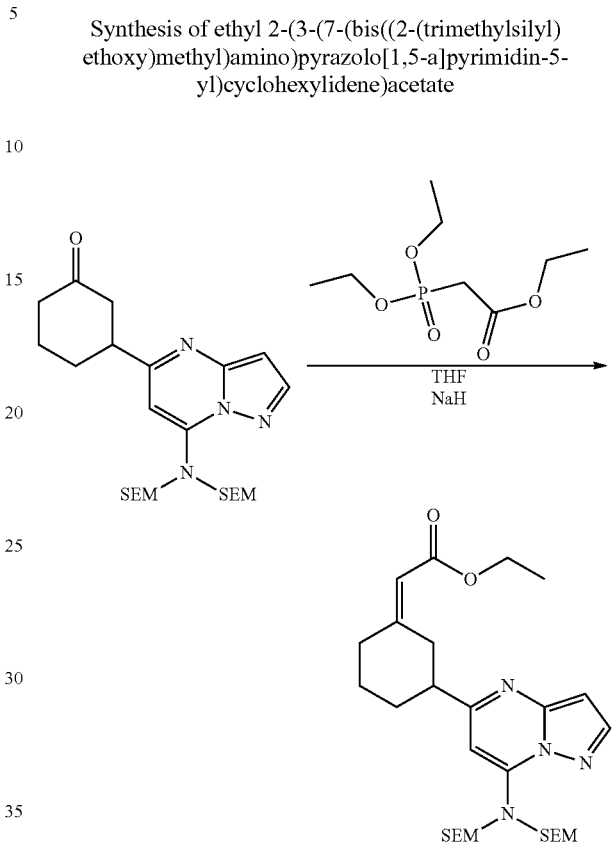

Ethyl 2-(3-(7-(bis((2-(trimethylsilyl)ethoxy)methyl)amino)pyrazolo[1,5-a]pyrimidin-5-yl)cyclohexylidene)acetate was synthesized in a manner similar to the synthesis of ethyl 2-(4-(7-(bis((2-(trimethylsilyl)ethoxy)methyl)amino)pyrazolo[1,5-a]pyrimidin-5-yl)cyclohexylidene)acetate, but with 3-(7-(bis((2-(trimethylsilyl)ethoxy)methyl)amino)pyrazolo[1,5-a]pyrimidin-5-yl)cyclohexanone substituted for 4-(7-(bis((2-(trimethylsilyl)ethoxy)methyl)amino)pyrazolo[1,5-a]pyrimidin-5-yl)cyclohexanone.

Synthesis of 2-(3-(7-(bis-((2-(trimethylsilyl)ethoxy)methyl)amino)pyrazolo[1,5-a]pyrimidin-5-yl)cyclopentylidene)acetonitrile

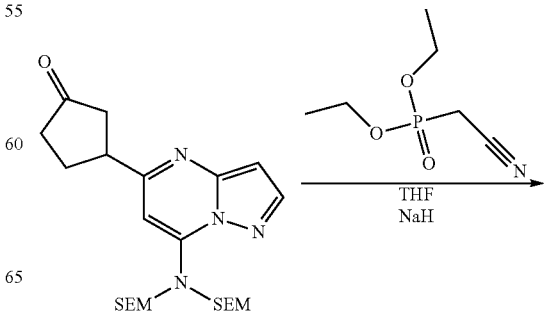

963
-continued

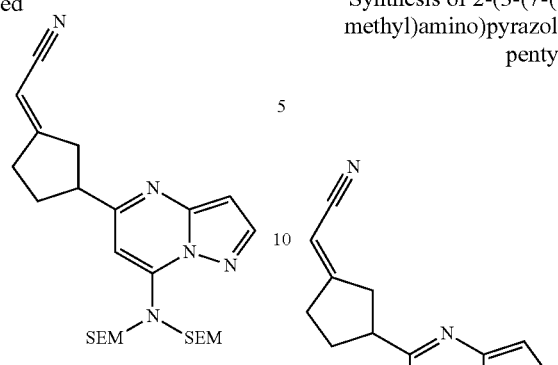

2-(3-(7-(bis((2-(trimethylsilyl)ethoxy)methyl)amino)pyrazolo[1,5-a]pyrimidin-5-yl)cyclopentylidene)acetonitrile was synthesized in a manner similar to the synthesis of 2-(4-(7-(Bis((2-(trimethylsilyl)ethoxy)methyl)amino)pyrazolo[1,5-a]pyrimidin-5-yl)cyclohexylidene)acetonitrile, but with 3-(7-(bis((2-(trimethylsilyl)ethoxy)methyl)amino)pyrazolo[1,5-a]pyrimidin-5-yl)cyclopentanone substituted for 4-(7-(bis((2-(trimethylsilyl)ethoxy)methyl)amino)pyrazolo[1,5-a]pyrimidin-5-yl)cyclohexanone.

Synthesis of ethyl 2-(3-(7-(bis-((2-(trimethylsilyl)ethoxy)methyl)amino)pyrazolo[1,5-a]pyrimidin-5-yl)cyclohexyl)acetate

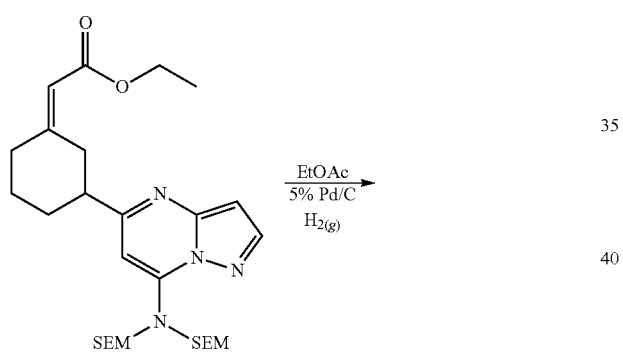

Ethyl 2-(3-(7-(bis((2-(trimethylsilyl)ethoxy)methyl)amino)pyrazolo[1,5-a]pyrimidin-5-yl)cyclohexyl)acetate was synthesized in a manner similar to the synthesis of ethyl 2-(4-(7-(bis((2-(trimethylsilyl)ethoxy)methyl)amino)pyrazolo[1,5-a]pyrimidin-5-yl)cyclohexyl)acetate, but with ethyl 2-(3-(7-(bis((2-(trimethylsilyl)ethoxy)methyl)amino)pyrazolo[1,5-a]pyrimidin-5-yl)cyclohexylidene)acetate substituted for ethyl 2-(4-(7-(bis((2-(trimethylsilyl)ethoxy)methyl) amino)pyrazolo[1,5-a]pyrimidin-5-yl)cyclohexylidene)acetate.

964
Synthesis of 2-(3-(7-(bis((2-(trimethylsilyl)ethoxy)methyl)amino)pyrazolo[1,5-a]pyrimidin-5-yl)cyclopentyl)acetonitrile

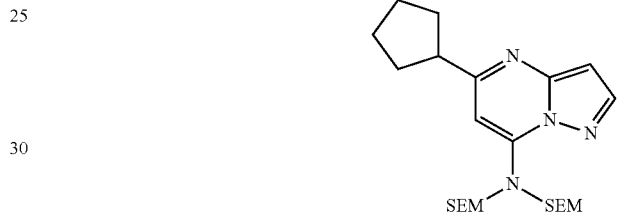

2-(3-(7-(Bis((2-(trimethylsilyl)ethoxy)methyl)amino)pyrazolo[1,5-a]pyrimidin-5-yl)cyclopentyl)acetonitrile was synthesized in a manner similar to the synthesis of ethyl 2-(4-(7-(bis((2-(trimethylsilyl)ethoxy)methyl)amino)pyrazolo[1,5-a]pyrimidin-5-yl)cyclohexyl)acetate, but 2-(3-(7-(bis((2-(trimethylsilyl)ethoxy)methyl)amino)pyrazolo[1,5-a]pyrimidin-5-yl)cyclopentylidene)acetonitrile substituted for ethyl 2-(4-(7-(bis((2-(trimethylsilyl)ethoxy)methyl)amino)pyrazolo[1,5-a]pyrimidin-5-yl)cyclohexylidene)acetate.

Synthesis of ethyl 2-(3-(7-(bis((2-(trimethylsilyl)ethoxy)methyl)amino)-3-iodopyrazolo[1,5-a]pyrimidin-5-yl)cyclohexyl)acetate

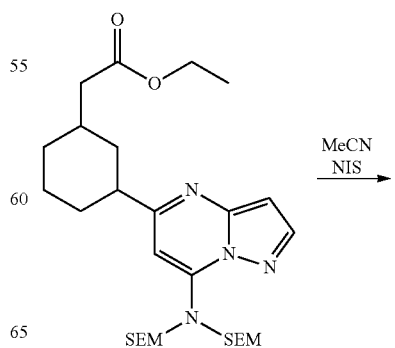

965

-continued

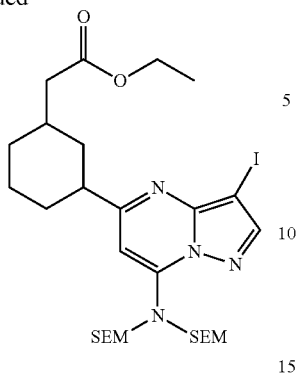

Ethyl 2-(3-(7-(bis((2-(trimethylsilyl)ethoxy)methyl)amino)-3-iodopyrazolo[1,5-a]pyrimidin-5-yl)cyclohexyl)acetate was synthesized in a manner similar to the synthesis of ethyl 2-(4-(7-(bis((2-(trimethylsilyl)ethoxy)methyl)amino)-3-iodopyrazolo[1,5-a]pyrimidin-5-yl)cyclohexyl)acetate, but with 2-(3-(7-(bis((2-(trimethylsilyl)ethoxy)methyl)amino)pyrazolo[1,5-a]pyrimidin-5-yl)cyclopentyl)acetonitrile substituted for ethyl 2-(4-(7-(bis((2-(trimethylsilyl)ethoxy)methyl)amino)pyrazolo[1,5-a]pyrimidin-5-yl)cyclohexyl)acetate.

Synthesis of 2-(3-(7-(bis((2-(trimethylsilyl)ethoxy)methyl)amino)-3-iodopyrazolo[1,5-a]pyrimidin-5-yl)cyclopentyl)acetonitrile

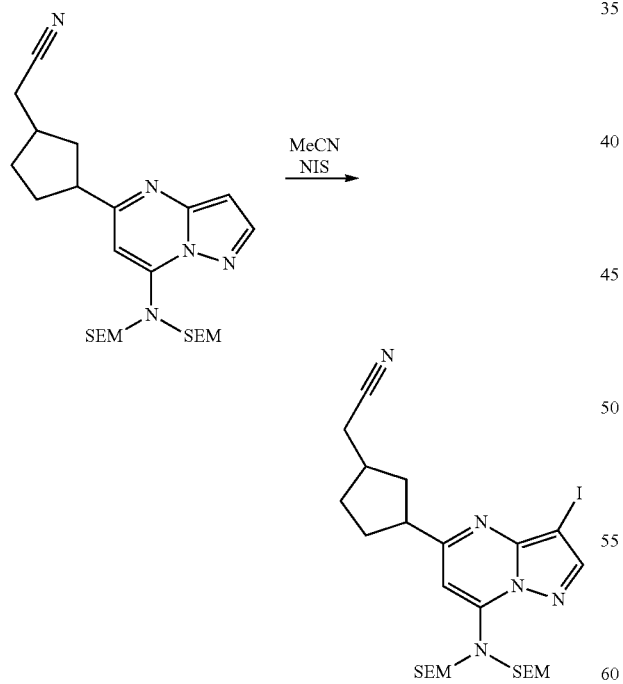

2-(3-(7-(Bis((2-(trimethylsilyl)ethoxy)methyl)amino)-3-iodopyrazolo[1,5-a]pyrimidin-5-yl)cyclopentyl)acetonitrile was synthesized in a manner similar to the synthesis of ethyl

966

2-(4-(7-(bis((2-(trimethylsilyl)ethoxy)methyl)amino)-3-iodopyrazolo[1,5-a]pyrimidin-5-yl)cyclohexyl)acetate, but with ethyl 2-(3-(7-(bis((2-(trimethylsilyl)ethoxy)methyl)amino)pyrazolo[1,5-a]pyrimidin-5-yl)cyclohexyl)acetate substituted for ethyl 2-(4-(7-(bis((2-(trimethylsilyl)ethoxy)methyl)amino)pyrazolo[1,5-a]pyrimidin-5-yl)cyclohexyl)acetate.

Synthesis of ethyl 2-(3-(7-(bis((2-(trimethylsilyl)ethoxy)methyl)amino)-3-(quinolin-3-yl)pyrazolo[1,5-a]pyrimidin-5-yl)cyclohexyl)acetate

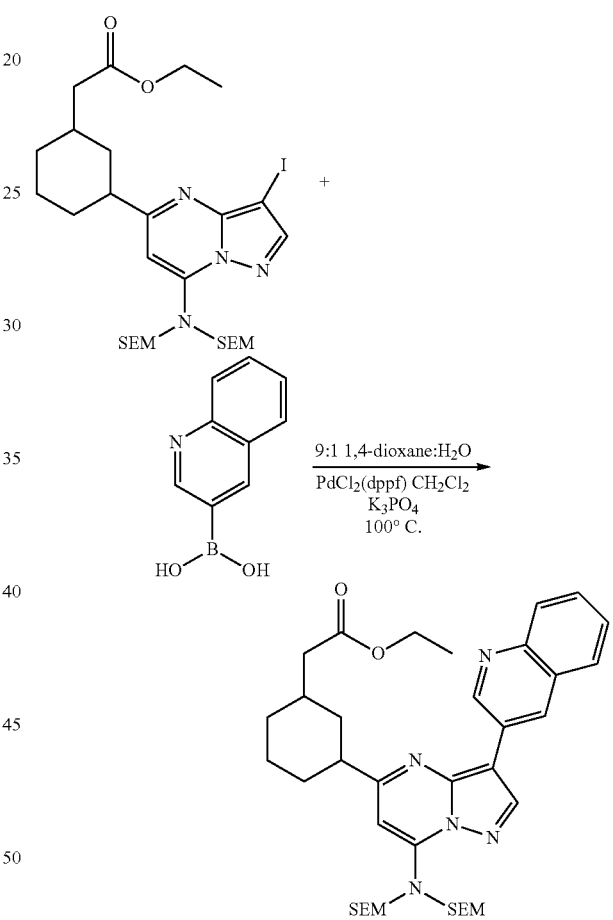

Ethyl 2-(3-(7-(bis((2-(trimethylsilyl)ethoxy)methyl)amino)-3-(quinolin-3-yl)pyrazolo[1,5-a]pyrimidin-5-yl)cyclohexyl)acetate was synthesized in a manner similar to the synthesis of ethyl 2-(4-(7-(bis((2-(trimethylsilyl)ethoxy)methyl)amino)-3-(quinolin-3-yl)pyrazolo[1,5-a]pyrimidin-5-yl)cyclohexyl)acetate, but with ethyl 2-(3-(7-(bis((2-(trimethylsilyl)ethoxy)methyl)amino)-3-iodopyrazolo[1,5-a]pyrimidin-5-yl)cyclohexyl)acetate substituted for ethyl 2-(4-(7-(bis((2-(trimethylsilyl)ethoxy)methyl)amino)-3-iodopyrazolo[1,5-a]pyrimidin-5-yl)cyclohexyl)acetate.

967
Synthesis of 2-(3-(7-(bis((2-(trimethylsilyl)ethoxy) methyl)amino)-3-(quinolin-3-yl)pyrazolo[1,5-a]pyrimidin-5-yl)cyclopentyl)acetonitrile

968
Synthesis of ethyl 2-(4-(7-(bis((2-(trimethylsilyl) ethoxy)methyl)amino)-3-(1-methyl-1H-pyrazol-4-yl) pyrazolo[1,5-a]pyrimidin-5-yl)cyclohexyl)acetate

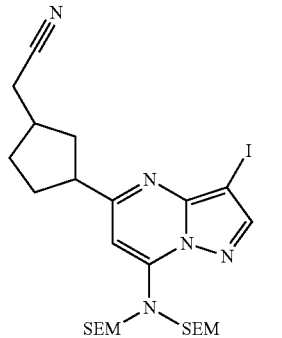

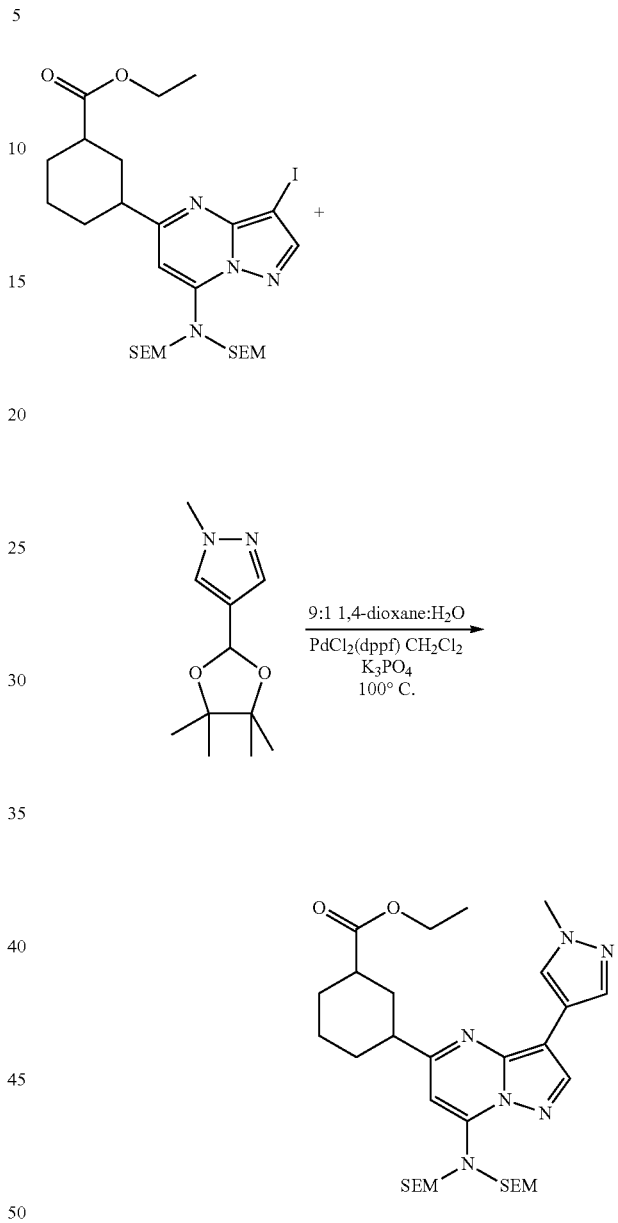

2-(3-(7-(Bis((2-(trimethylsilyl)ethoxy)methyl)amino)-3-(quinolin-3-yl)pyrazolo[1,5-a]pyrimidin-5-yl)cyclopentyl) acetonitrile was synthesized in a manner similar to the synthesis of ethyl 2-(4-(7-(bis((2-(trimethylsilyl)ethoxy)methyl) amino)-3-(quinolin-3-yl)pyrazolo[1,5-a]pyrimidin-5-yl) cyclohexyl)acetate, but with 2-(3-(7-(bis((2-(trimethylsilyl) ethoxy)methyl)amino)-3-iodopyrazolo[1,5-a]pyrimidin-5-yl)cyclopentyl)acetonitrile substituted for ethyl 2-(4-(7-(bis ((2-(trimethylsilyl)ethoxy)methyl)amino)-3-iodopyrazolo [1,5-a]pyrimidin-5-yl)cyclohexyl)acetate.

Ethyl 2-(4-(7-(bis((2-(trimethylsilyl)ethoxy)methyl) amino)-3-(1-methyl-1H-pyrazol-4-yl)pyrazolo[1,5-a]pyrimidin-5-yl)cyclohexyl)acetate was synthesized in a manner similar to the synthesis of ethyl 2-(4-(7-(bis((2-(trimethylsilyl)ethoxy)methyl)amino)-3-(quinolin-3-yl)pyrazolo[1,5-a] pyrimidin-5-yl)cyclohexyl)acetate, but with N-methyl pyrazole-4-boronic acid pinacol ester substituted for quinoline-3-boronic acid.

969

Synthesis of 2-(3-(7-amino-6-bromo-3-(quinolin-3-yl)pyrazolo[1,5-a]pyrimidin-5-yl)cyclohexyl)acetic acid

970

Synthesis of 2-(3-(7-amino-6-bromo-3-(quinolin-3-yl)pyrazolo[1,5-a]pyrimidin-5-yl)cyclopentyl)acetonitrile

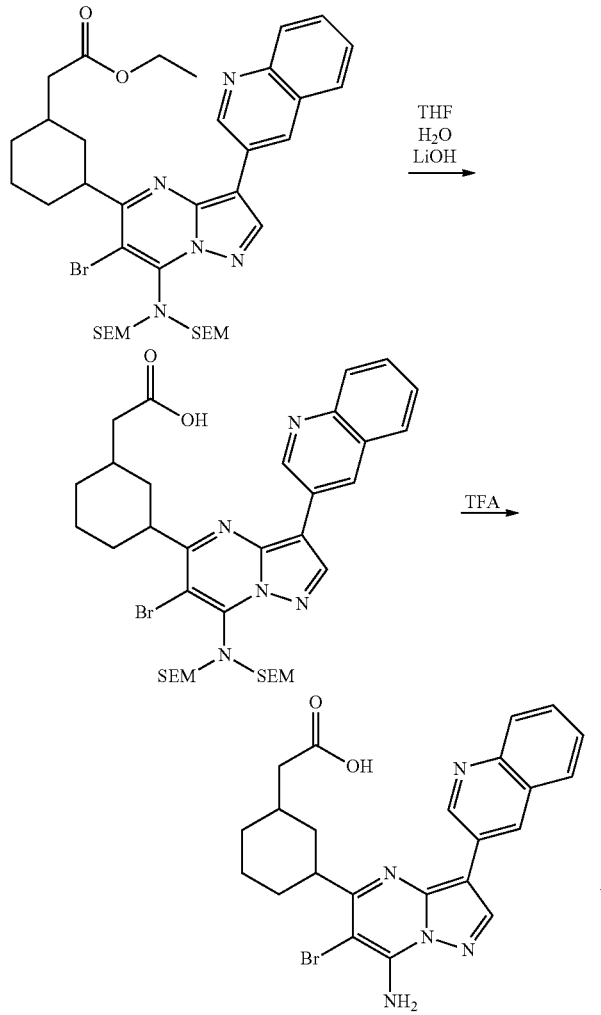

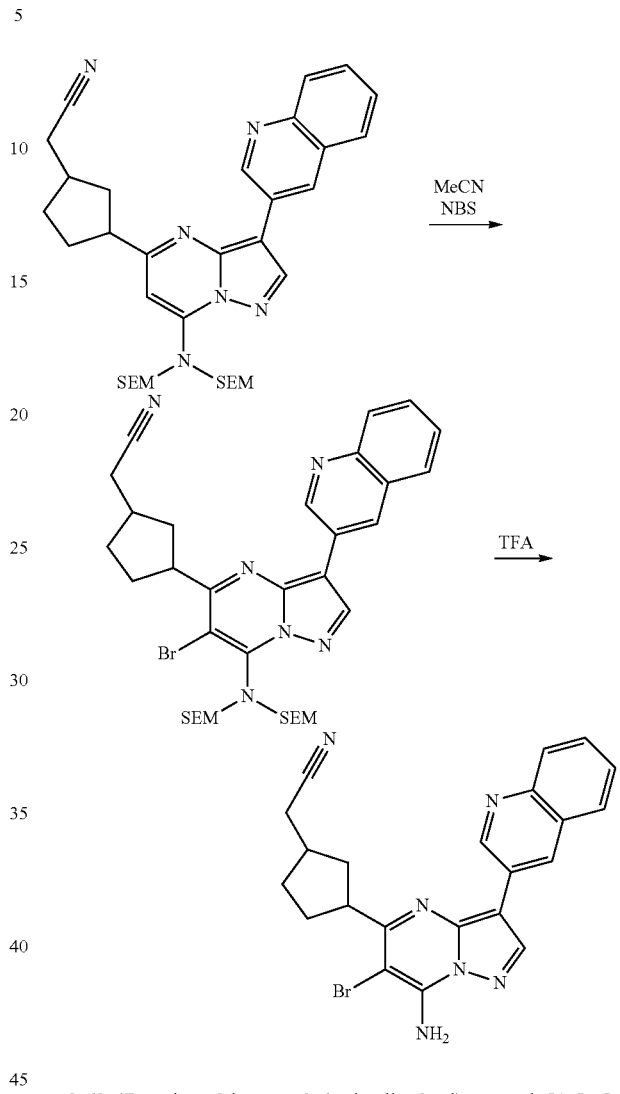

2-(3-(7-Amino-6-bromo-3-(quinolin-3-yl)pyrazolo[1,5-a]pyrimidin-5-yl)cyclohexyl)acetic acid was synthesized in a manner similar to the synthesis of 2-(4-(7-amino-6-bromo-3-(quinolin-3-yl)pyrazolo[1,5-a]pyrimidin-5-yl)cyclohexyl)acetic acid, but with ethyl 2-(3-(7-(bis((2-(trimethylsilyl)ethoxy)methyl)amino)-3-(quinolin-3-yl)pyrazolo[1,5-a]pyrimidin-5-yl)cyclohexyl)acetate substituted for ethyl 2-(4-(7-(bis((2-(trimethylsilyl)ethoxy)methyl)amino)-3-(quinolin-3-yl)pyrazolo[1,5-a]pyrimidin-5-yl)cyclohexyl)acetate. The reaction was concentrated in vacuo and purified via reverse-phase preparatory HPLC to yield 2-(4-(7-amino-6-bromo-3-(quinolin-3-yl)pyrazolo[1,5-a]pyrimidin-5-yl)cyclohexyl)acetonitrile as a four-isomer mixture. (m+H=480.1, retention time=3.51 min)

2-(3-(7-amino-6-bromo-3-(quinolin-3-yl)pyrazolo[1,5-a]pyrimidin-5-yl)cyclopentyl)acetonitrile was synthesized in a manner similar to the synthesis of 2-(4-(7-amino-6-bromo-3-(quinolin-3-yl)pyrazolo[1,5-a]pyrimidin-5-yl)piperidin-1-yl)acetic acid, but with 2-(3-(7-(bis((2-(trimethylsilyl)ethoxy)methyl)amino)-3-(quinolin-3-yl)pyrazolo[1,5-a]pyrimidin-5-yl)cyclopentyl)acetonitrile substituted for tert-butyl 2-(4-(7-amino-3-(quinolin-3-yl)pyrazolo[1,5-a]pyrimidin-5-yl)piperidin-1-yl)acetate. The reaction was concentrated in vacuo and purified via reverse-phase preparatory HPLC to yield 2-(3-(7-amino-6-bromo-3-(quinolin-3-yl)pyrazolo[1,5-a]pyrimidin-5-yl)cyclopentyl)acetonitrile as a yellow solid. (m+H=447.22, retention time=3.99 min).

SCHEME-6

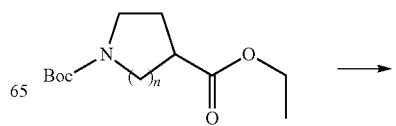

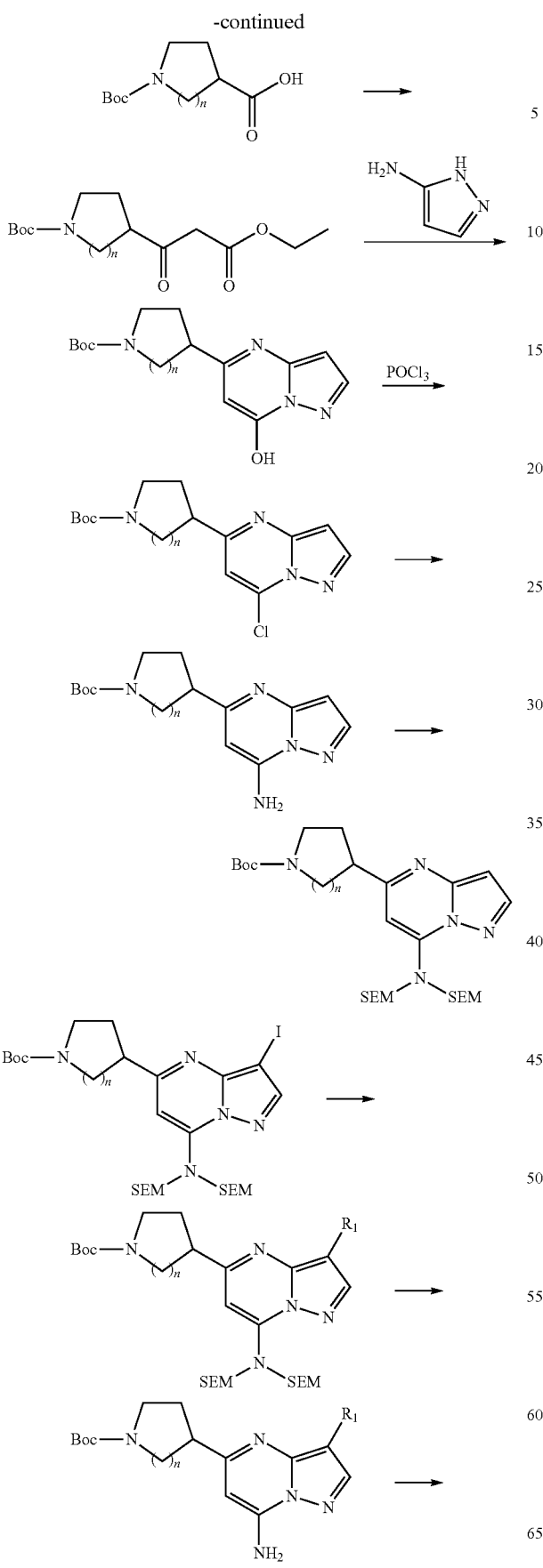
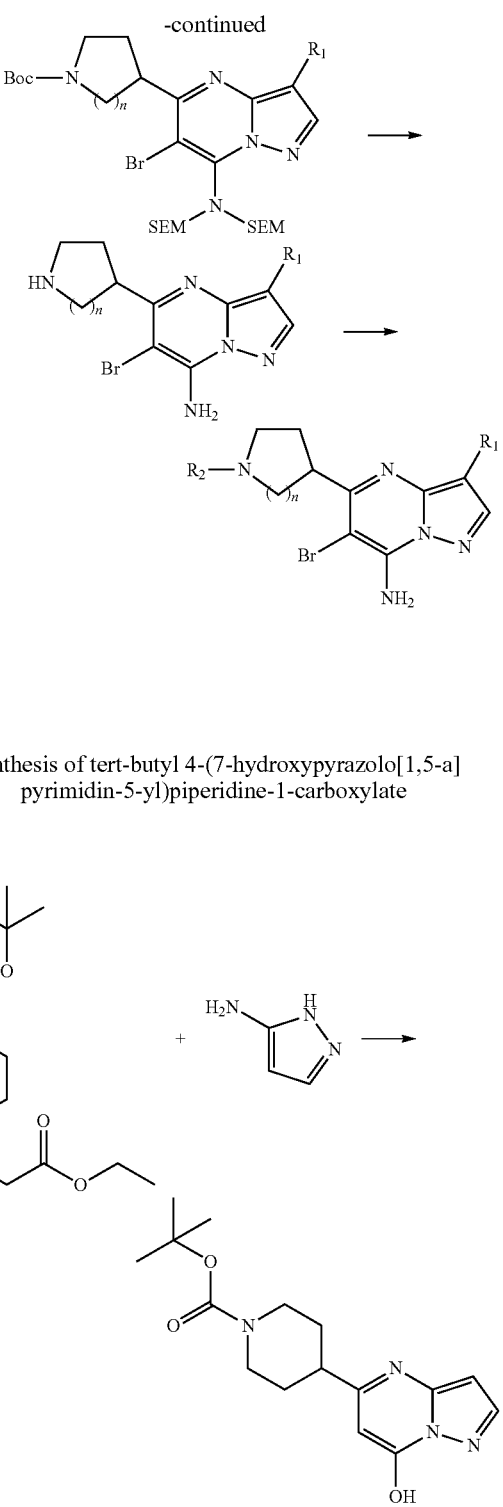

Synthesis of tert-butyl 4-(7-hydroxypyrazolo[1,5-a]pyrimidin-5-yl)piperidine-1-carboxylate tert-Butyl 4-(7-hydroxypyrazolo[1,5-a]pyrimidin-5-yl)piperidine-1-carboxylate was synthesized in a manner similar to the synthesis of 5-(1,4-dioxaspiro[4.5]decan-8-yl)pyrazolo[1,5-a]pyrimidin-7-ol, but with tert-butyl 4-(3-ethoxy-3-oxopropanoyl)piperidine-1-carboxylate substituted for ethyl 3-oxo-3-(1,4-dioxaspiro[4.5]decan-8-yl)propanoate.

973

Synthesis of tert-butyl 4-(7-chloropyrazolo[1,5-a]pyrimidin-5-yl)piperidine-1-carboxylate

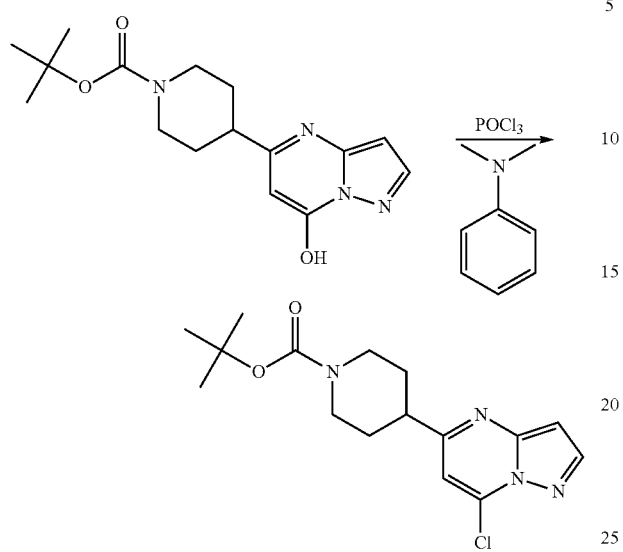

tert-Butyl 4-(7-chloropyrazolo[1,5-a]pyrimidin-5-yl)piperidine-1-carboxylate was synthesized in a manner similar to the synthesis of 7-chloro-5-(1,4-dioxaspiro[4.5]decan-8-yl)pyrazolo[1,5-a]pyrimidine, but with tert-butyl 4-(7-hydroxypyrazolo[1,5-a]pyrimidin-5-yl)piperidine-1-carboxylate substituted for 5-(1,4-dioxaspiro[4.5]decan-8-yl)pyrazolo[1,5-a]pyrimidin-7-ol.

Synthesis of tert-butyl 4-(7-aminopyrazolo[1,5-a]pyrimidin-5-yl)piperidine-1-carboxylate

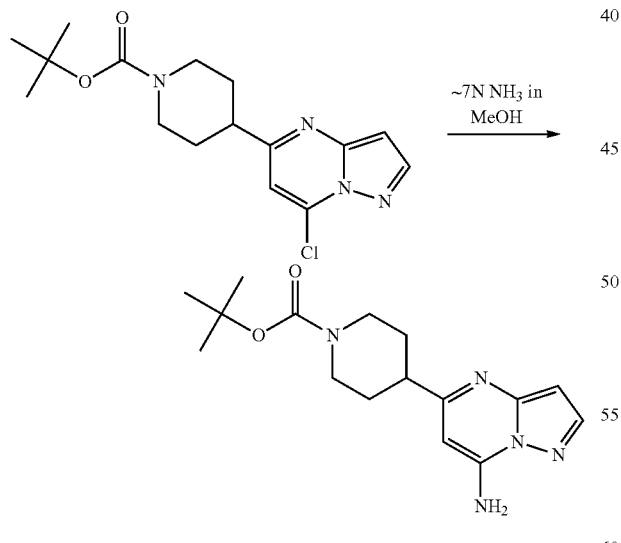

tert-Butyl 4-(7-aminopyrazolo[1,5-a]pyrimidin-5-yl)piperidine-1-carboxylate was synthesized in a manner similar to the synthesis of 5-(1,4-dioxaspiro[4.5]decan-8-yl)pyrazolo[1,5-a]pyrimidin-7-amine, but tert-butyl 4-(7-chloropyrazolo[1,5-a]pyrimidin-5-yl)piperidine-1-carboxylate substituted for 7-chloro-5-(1,4-dioxaspiro[4.5]decan-8-yl)pyrazolo[1,5-a]pyrimidine.

974

Synthesis of tert-butyl 4-(7-(bis((2-(trimethylsilyl)ethoxy)methyl)amino)pyrazolo[1,5-a]pyrimidin-5-yl)piperidine-1-carboxylate

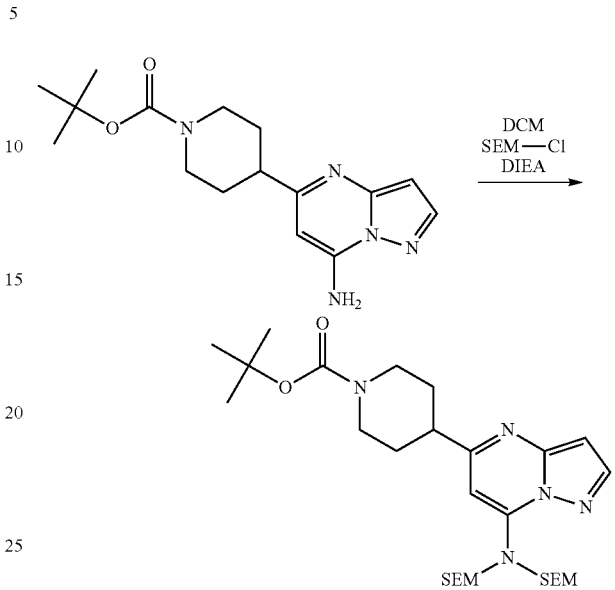

tert-Butyl 4-(7-(bis((2-(trimethylsilyl)ethoxy)methyl)amino)pyrazolo[1,5-a]pyrimidin-5-yl)piperidine-1-carboxylate was synthesized in a manner similar to the synthesis of 4-(7-(bis((2-(trimethylsilyl)ethoxy)methyl)amino)pyrazolo[1,5-a]pyrimidin-5-yl)cyclohexanone, but with tert-butyl 4-(7-aminopyrazolo[1,5-a]pyrimidin-5-yl)piperidine-1-carboxylate substituted for 4-(7-aminopyrazolo[1,5-a]pyrimidin-5-yl)cyclohexanone.

Synthesis of tert-butyl 4-(7-(bis((2-(trimethylsilyl)ethoxy)methyl)amino)-3-iodopyrazolo[1,5-a]pyrimidin-5-yl)piperidine-1-carboxylate

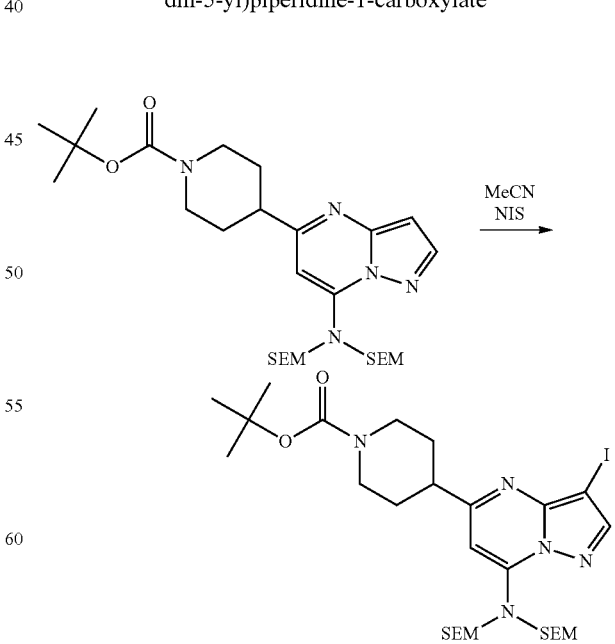

tert-Butyl 4-(7-(bis((2-(trimethylsilyl)ethoxy)methyl)amino)-3-iodopyrazolo[1,5-a]pyrimidin-5-yl)piperidine-1- carboxylate was synthesized in a manner similar to the synthesis of ethyl 2-(4 7-(bis((2-(trimethylsilyl)ethoxy)methyl)amino)-3-iodopyrazolo[1,5-a]pyrimidin-5-yl)cyclohexyl)acetate, but with tert-butyl 4-(7-(bis((2-(trimethylsilyl)ethoxy)methyl)amino)pyrazolo[1,5-a]pyrimidin-5-yl)piperidine-1-carboxylate substituted for ethyl 2-(4-(7-(bis((2-(trimethylsilyl)ethoxy)methyl)amino)pyrazolo[1,5-a]pyrimidin-5-yl)cyclohexyl)acetate.

Synthesis of tert-butyl 4-(7-(bis((2-(trimethylsilyl)ethoxy)methyl)amino)-3-(quinolin-3-yl)pyrazolo[1,5-a]pyrimidin-5-yl)piperidine-1-carboxylate

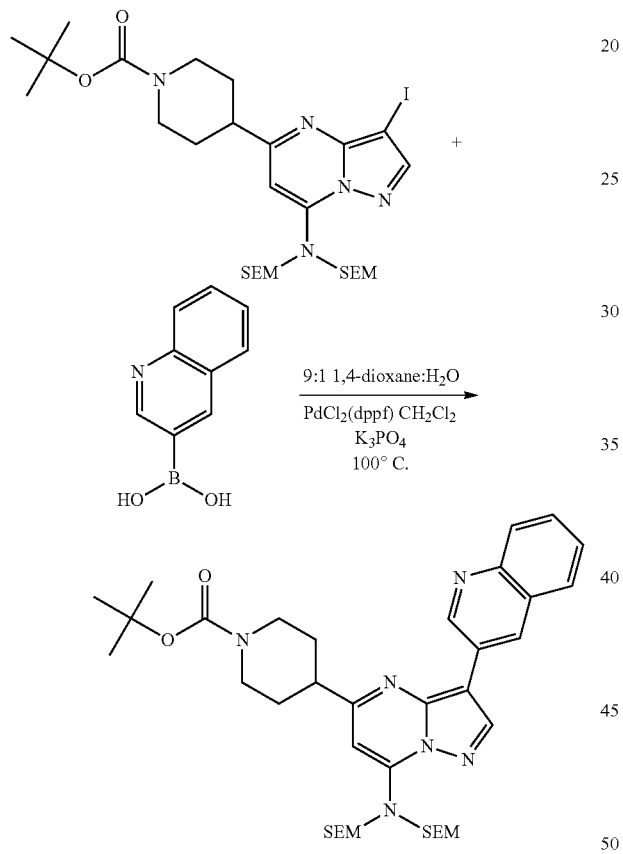

tert-Butyl 4-(7-(bis((2-(trimethylsilyl)ethoxy)methyl)amino)-3-(quinolin-3-yl)pyrazolo[1,5-a]pyrimidin-5-yl)piperidine-1-carboxylate was synthesized in a manner similar to the synthesis of ethyl 2-(4-(7-(bis((2-(trimethylsilyl)ethoxy)methyl)amino)-3-(quinolin-3-yl)pyrazolo[1,5-a]pyrimidin-5-yl)cyclohexyl)acetate, but with tert-butyl 4-(7-(bis((2-(trimethylsilyl)ethoxy)methyl)amino)-3-iodopyrazolo[1,5-a]pyrimidin-5-yl)piperidine-1-carboxylate substituted for ethyl 2-(4-(7-(bis((2-(trimethylsilyl)ethoxy)methyl)amino)-3-iodopyrazolo[1,5-a]pyrimidin-5-yl)cyclohexyl)acetate.

Synthesis of tert-butyl 4-(7-(bis((2-(trimethylsilyl)ethoxy)methyl)amino)-3-(1-methyl-1H-pyrazol-4-yl)pyrazolo[1,5-a]pyrimidin-5-yl)piperidine-1-carboxylate

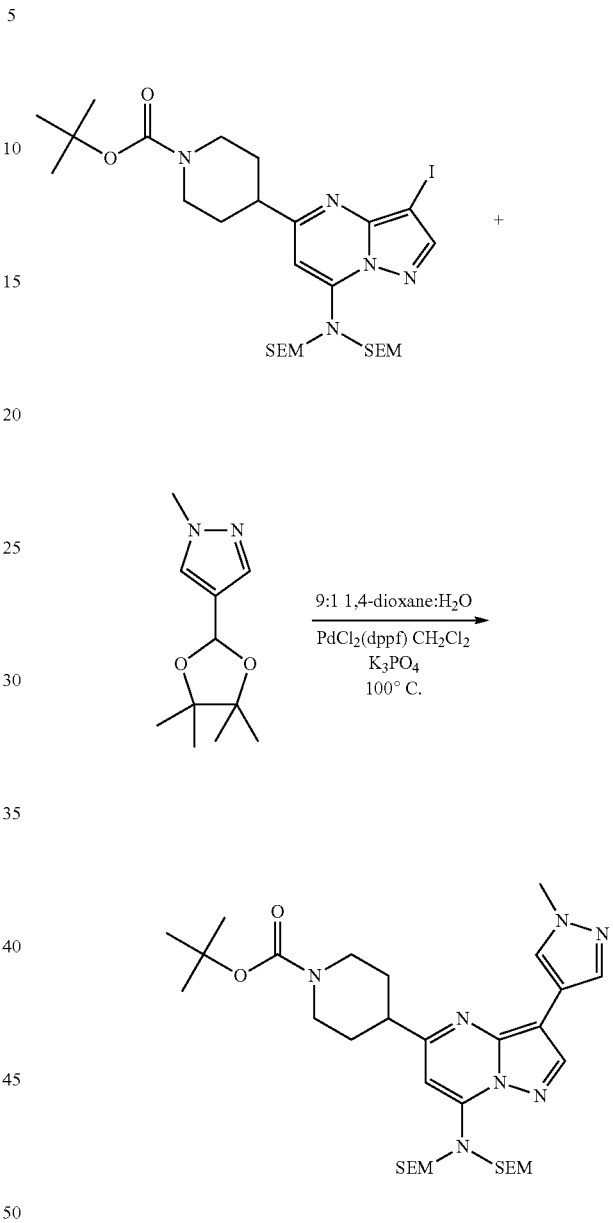

tert-Butyl 4-(7-(bis((2-(trimethylsilyl)ethoxy)methyl)amino)-3-(1-methyl-1H-pyrazol-4-yl)pyrazolo[1,5-a]pyrimidin-5-yl)piperidine-1-carboxylate was synthesized in a manner similar to the synthesis of ethyl 2-(4-(7-(bis((2-(trimethylsilyl)ethoxy)methyl)amino)-3-(1-methyl-1H-pyrazol-4-yl)pyrazolo[1,5-a]pyrimidin-5-yl)cyclohexyl)acetate, but with tert-butyl 4-(7-(bis((2-(trimethylsilyl)ethoxy)methyl)amino)-3-iodopyrazolo[1,5-a]pyrimidin-5-yl)piperidine-1-carboxylate substituted for ethyl 2-(4-(7-(bis((2-(trimethylsilyl)ethoxy)methyl)amino)-3-iodopyrazolo[1,5-a]pyrimidin-5-yl)cyclohexyl)acetate.

977

Synthesis of 5-(piperidin-4-yl)-3-(quinolin-3-yl) pyrazolo[1,5-a]pyrimidin-7-amine

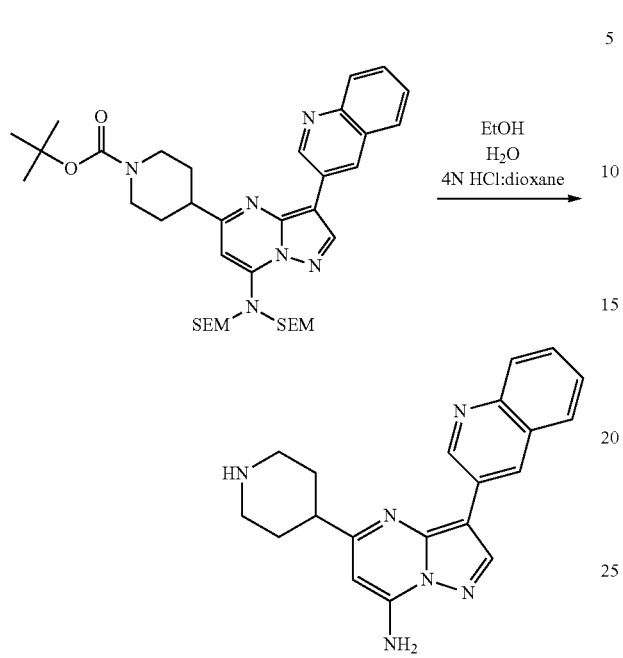

To a 20 mL scintillation vial was charged tert-butyl 4-(7-(bis((2-(trimethylsilyl)ethoxy)methyl)-amino)-3-(quinolin-3-yl)pyrazolo[1,5-a]pyrimidin-5-yl)piperidine-1-carboxylate (80 μmol, 56 mg) followed by ethanol (2 mL) and H₂O (500 μL). To this solution was added 2 mL of 4N HCl in 1,4-dioxane. This solution was heated to 60° C. for 2 hours. Upon completion, the reaction mixture was diluted with DCM (10 mL) and washed with NaHCO₃(aq) and extracted with DCM twice more. The combined organics were then dried over Na₂SO₄ and the solvent was removed in vacuo to yield 5-(piperidin-4-yl)-3-(quinolin-3-yl)pyrazolo[1,5-a]pyrimidin-7-amine (20.3 mg, 59 umol) as cream-colored solid

Synthesis of tert-butyl 2-(4-(7-amino-3-(quinolin-3-yl)pyrazolo[1,5-a]pyrimidin-5-yl)piperidin-1-yl) acetate

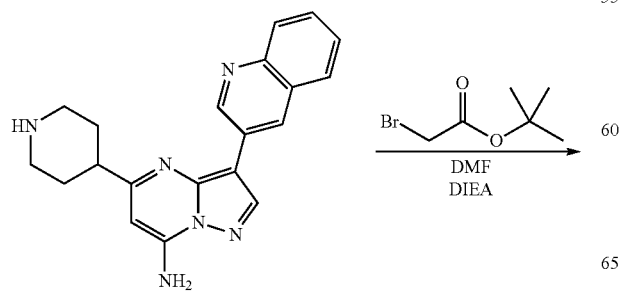

978

-continued

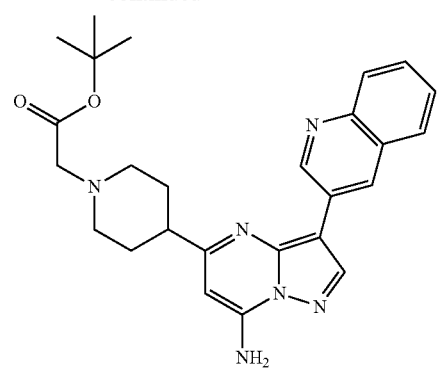

To a 20 mL scintillation vial was charged tert-butyl 2-(4-(7-amino-3-(quinolin-3-yl)pyrazolo[1,5-a]pyrimidin-5-yl) piperidin-1-yl)acetate (100 μmol, 34 mg) followed by a solution of N,N-diisopropylethylamine (150 μmol, 26 μL) in DMF (2 mL). To the resulting solution was added tert-butyl 2-bromoacetate (120 μmol, 18 μL). The reaction mixture was stirred at 60° C. for 18 hours. After 18 hours, the reaction mixture was concentrated in vacuo and purified via silica gel chromatography (0% to 20% MeOH in DCM) to yield tert-butyl 2-(4-(7-amino-3-(quinolin-3-yl)pyrazolo[1,5-a]pyrimidin-5-yl)piperidin-1-yl)acetate (41 mg, 90 μmol).

Synthesis of 2-(4-(7-amino-6-bromo-3-(quinolin-3-yl)pyrazolo[1,5-a]pyrimidin-5-yl)piperidin-1-yl) acetic acid

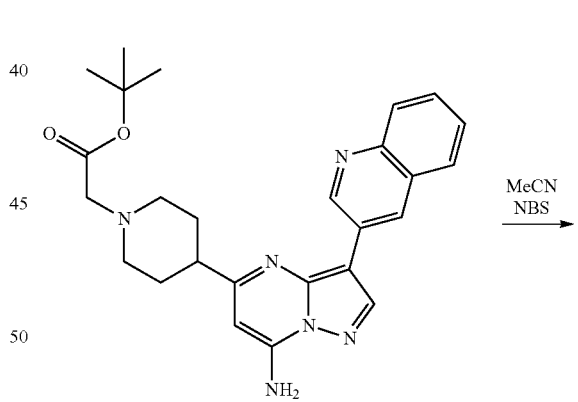

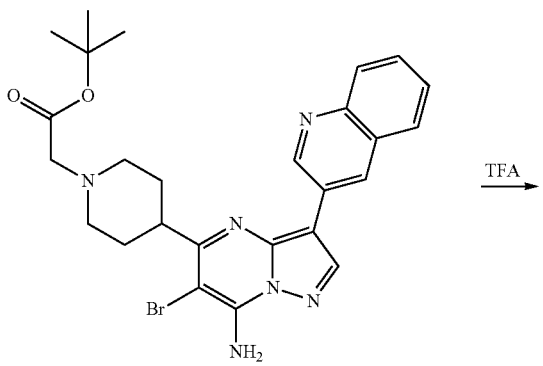

-continued

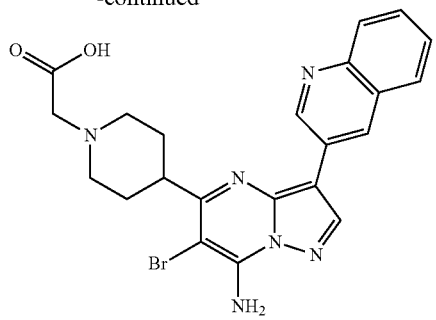

To a 20 mL scintillation vial was charged 2-(4-(7-amino-6-bromo-3-(quinolin-3-yl)pyrazolo[1,5-a]pyrimidin-5-yl)piperidin-1-yl)acetic acid (41 mg, 90 µmol) plus acetonitrile (2 mL). To this solution was added N-bromosuccinimide (90 µmol, 16 mg). This solution was allowed to stir at room temperature for 1 hour. The reaction was concentrated in vacuo and dissolved in TFA (2 mL). The reaction mixture was stirred at room temperature for 1 hour. The reaction mixture was concentrated in vacuo and purified via reverse-phase preparatory HPLC to yield 2-(4-(7-amino-6-bromo-3-(quinolin-3-yl)pyrazolo[1,5-a]pyrimidin-5-yl)piperidin-1-yl)acetic acid as yellow solid. (m+H=481.22, retention time=2.32 min)

Synthesis of 3-(1-methyl-1H-pyrazol-4-yl)-5-(piperidin-4-yl)pyrazolo[1,5-a]pyrimidin-7-amine

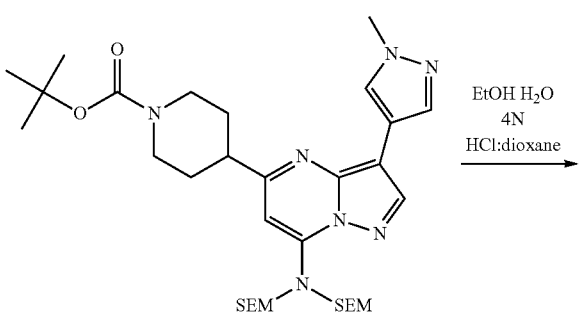

3-(1-Methyl-1H-pyrazol-4-yl)-5-(piperidin-4-yl)pyrazolo[1,5-a]pyrimidin-7-amine was synthesized in a manner similar to the synthesis of 5-(piperidin-4-yl)-3-(quinolin-3-yl)pyrazolo[1,5-a]pyrimidin-7-amine, but with tert-butyl 4-(7-(bis((2-(trimethylsilyl)ethoxy)methyl)amino)-3-(1-methyl-1H-pyrazol-4-yl)pyrazolo[1,5-a]pyrimidin-5-yl)piperidine-1-carboxylate substituted for tert-butyl 4-(7-(bis((2-(trimethylsilyl)ethoxy)methyl)amino)-3-(quinolin-3-yl)pyrazolo[1,5-a]pyrimidin-5-yl)piperidine-1-carboxylate.

Synthesis of tert-butyl 2-(4-(7-amino-3-(1-methyl-1H-pyrazol-4-yl)pyrazolo[1,5-a]pyrimidin-5-yl)piperidin-1-yl)acetate

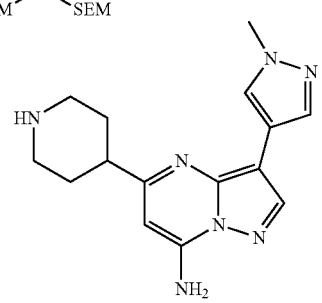

tert-Butyl 2-(4-(7-amino-3-(1-methyl-1H-pyrazol-4-yl)pyrazolo[1,5-a]pyrimidin-5-yl)piperidin-1-yl)acetate was synthesized in a manner similar to the synthesis of tert-butyl 2-(4-(7-amino-3-(quinolin-3-yl)pyrazolo[1,5-a]pyrimidin-5-yl)piperidin-1-yl)acetate, but with 3-(1-methyl-1H-pyrazol-4-yl)-5-(piperidin-4-yl)pyrazolo[1,5-a]pyrimidin-7-amine substituted for 5-(piperidin-4-yl)-3-(quinolin-3-yl)pyrazolo[1,5-a]pyrimidin-7-amine.

Synthesis of 2-(4-(7-amino-6-bromo-3-(1-methyl-1H-pyrazol-4-yl)pyrazolo[1,5-a]pyrimidin-5-yl)piperidin-1-yl)acetic acid

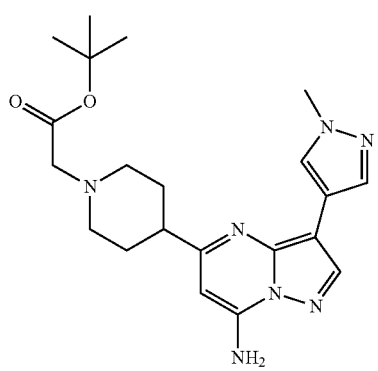

-continued

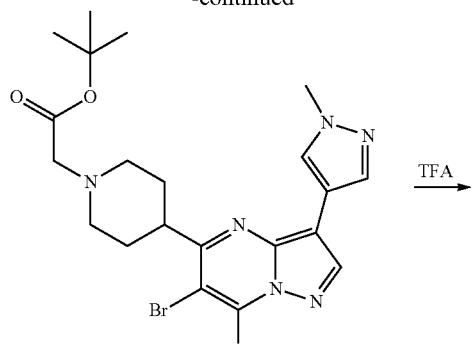

2-(4-(7-amino-6-bromo-3-(1-methyl-1H-pyrazol-4-yl)pyrazolo[1,5-a]pyrimidin-5-yl)piperidin-1-yl)acetic acid was synthesized in a manner similar to the synthesis of 2-(4-(7-amino-6-bromo-3-(quinolin-3-yl)pyrazolo[1,5-a]pyrimidin-5-yl)piperidin-1-yl)acetic acid, but with tert-butyl 2-(4-(7-amino-3-(1-methyl-1H-pyrazol-4-yl)pyrazolo[1,5-a]pyrimidin-5-yl)piperidin-1-yl)acetate substituted for tert-butyl 2-(4-(7-amino-3-(quinolin-3-yl)pyrazolo[1,5-a]pyrimidin-5-yl)piperidin-1-yl)acetate. The reaction mixture was reduced in vacuo and purified via reverse-phase preparatory HPLC to yield 2-(4-(7-amino-6-bromo-3-(1-methyl-1H-pyrazol-4-yl)pyrazolo[1,5-a]pyrimidin-5-yl)piperidin-1-yl)acetic acid as off-yellow solid. (m+H=434.19, retention time=2.25 min)

tert-butyl 3-(7-hydroxypyrazolo[1,5-a]pyrimidin-5-yl)pyrrolidine-1-carboxylate

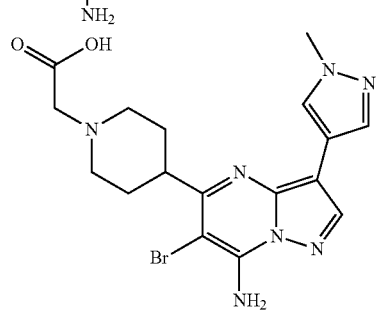

A mixture of tert-butyl 3-(3-ethoxy-3-oxopropanoyl)pyrrolidine-1-carboxylate (7.00 g, 25 mmol) and 1H-pyrazol-3-amine (2.08 g, 25 mmol) in toluene 30 mL) was heated at 110° C. under argon for 18 h and concentrated in vacuo. The residue was triturated with EtOAc and the solid was collected by filtration and dried in high vacuum to give 6.84 g (90%) of the title compound as a white solid. LC/MS RT=1.40 min (5 min method). Mass calculated for, M+H 305.15, observed 305.15.

tert-butyl 3-(7-chloropyrazolo[1,5-a]pyrimidin-5-yl)pyrrolidine-1-carboxylate

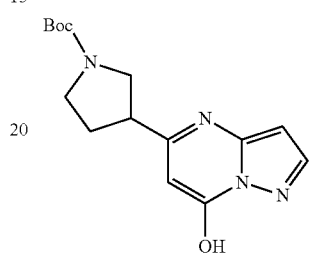

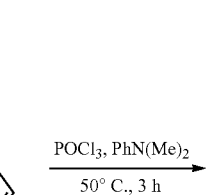

To a mixture of tert-butyl 3-(7-hydroxypyrazolo[1,5-a]pyrimidin-5-yl)pyrrolidine-1-carboxylate (3.70 g, 12.0 mmol) and dimethylaniline (4.0 mL, 30 mml) was added phosphoryl trichloride (40 mL). The mixture was heated at 50° C. for 5 h and concentrated in vacuo. The residue was diluted with methylene chloride (100 mL) and quenched with saturated NaHCO$_3$ (100 mL). The mixture was separated and the aqueous layer was extracted with chloride (100 mL×2). The combined organic layers were dried over Na$_2$SO$_4$, filtered and concentrated in vacuo. The residue was purified by Biotage (CH$_2$Cl$_2$/EtOAc, 20:1 to 4:1). LC/MS RT=2.09 min (5 min method). Mass calculated for, M+H 322.12, observed 337.14.

tert-butyl 3-(7-aminopyrazolo[1,5-a]pyrimidin-5-yl)pyrrolidine-1-carboxylate

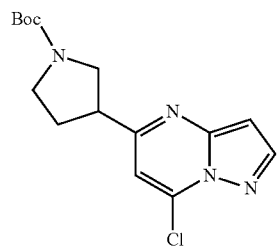

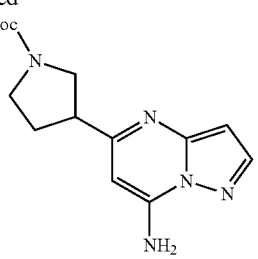

A mixture of tert-butyl 3-(7-chloropyrazolo[1,5-a]pyrimidin-5-yl)pyrrolidine-1-carboxylate (3.40 g, 10.5 mmol) in a solution of ammonia in MeOH (7N, 20 mL) was heated in sealed vessel at 80° C. for 5 h. The reaction mixture was cooled down and concentrated in vacuo. The residue was dried in high vacuum and used for the next step without further purification. LC/MS RT=1.30 min (5 min method). Mass calculated for, M+H 303.17, observed 318.19.

tert-butyl 3-(7-(bis((2-(trimethylsilyl)ethoxy)methyl)amino)pyrazolo[1,5-a]pyrimidin-5-yl)pyrrolidine-1-carboxylate

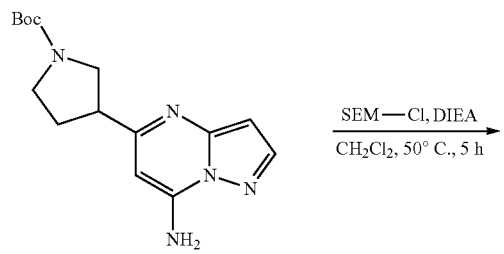

To a mixture of tert-butyl 3-(7-aminopyrazolo[1,5-a]pyrimidin-5-yl)pyrrolidine-1-carboxylate (10.5 mmol) in CH$_2$Cl$_2$ was added DIEA (10.8 mL, 63 mmol) and SEM-Cl (5.6 mL, 32 mmol). The mixture was heated at 50° C. for 5 h under an argon atmosphere. The mixture was cooled, and the reaction was quenched with saturated NaHCO$_3$ (100 mL) and extracted with CH$_2$Cl$_2$ (50 mL×3). The combined organic layers were dried over Na$_2$SO$_4$, filtered and concentrated in vacuo. The residue was purified by Biotage (CH$_2$Cl$_2$/EtOAc, 20:1 to 5:1) to give the title compound as a light brown oil. LC/MS RT=2.90 min (5 min method). Mass calculated for, M+H 563.33, observed 578.35.

tert-butyl 3-(7-(bis((2-(trimethylsilyl)ethoxy)methyl)amino)-3-iodopyrazolo[1,5-a]pyrimidin-5-yl)pyrrolidine-1-carboxylate

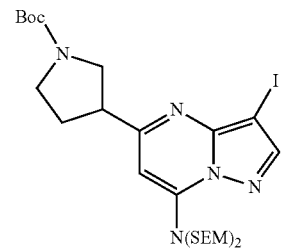

To a solution of tert-butyl 3-(7-(bis((2-(trimethylsilyl)ethoxy)methyl)amino)pyrazolo[1,5-a]pyrimidin-5-yl)pyrrolidine-1-carboxylate 3.95 g, 7.0 mmol) in CH$_3$CN (30 mL) was added NIS (1.65 mg, 7.0 mmol). The mixture was stirred at rt for 2 h and diluted with EtOAC (50 mL) and washed with saturated sodium thiosulfate, dried over Na$_2$SO$_4$, filtered and concentrated in vacuo. The residue was purified by Biotage (CH$_2$Cl$_2$/EtOAc, 100:1 to 10:1) to the title compound as a light brown oil. LC/MS RT=2.49 min. Mass calculated for, M+H 689.23, observed 389.17.

tert-butyl 3-(7-(bis((2-(trimethylsilyl)ethoxy)methyl)amino)-3-(quinolin-3-yl)pyrazolo[1,5-a]pyrimidin-5-yl)pyrrolidine-1-carboxylate

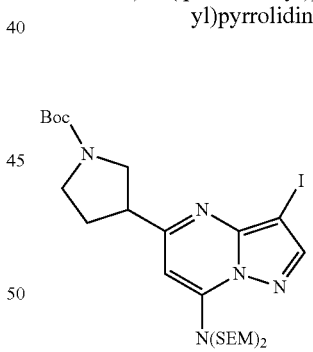

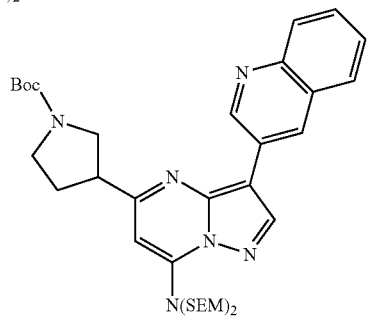

A mixture of tert-butyl 3-(7-(bis((2-(trimethylsilyl)ethoxy)methyl)amino)-3-iodopyrazolo[1,5-a]pyrimidin-5- yl)pyrrolidine-1-carboxylate (703 mol), quinolin-3-ylboronic acid (350 mg, 2.00 mmol), Pd(dppf)Cl$_2$—CH$_2$Cl$_2$ (82 mg, 0.10 mmol) and potassium phosphate (636 mg, 3.0 mmol) in a mixture of dioxane/H$_2$O (9:1, 20 mL) was heated at 100° C. for 5 h under argon. The reaction mixture was cooled down and diluted with EtOAC, washed with Brine, dried over Na$_2$SO$_4$, filtered and concentrated. The residue was purified by Biotage (CH$_2$Cl$_2$/EtOAc, 10:1 to 3:1) to give the title compound as brown solid. LC/MS RT=2.49 min. Mass calculated for, M+H 690.37, observed 389.17.

tert-butyl 3-(7-(bis((2-(trimethylsilyl)ethoxy)methyl)amino)-6-bromo-3-(quinolin-3-yl)pyrazolo[1,5-a]pyrimidin-5-yl)piperidine-1-carboxylate

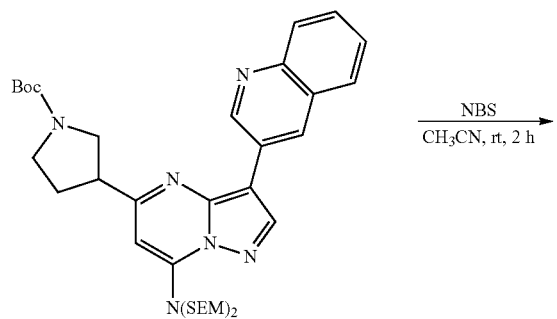

To a solution of tert-butyl 3-(7-(bis((2-(trimethylsilyl)ethoxy)methyl)amino)-3-(quinolin-3-yl)pyrazolo[1,5-a]pyrimidin-5-yl)piperidine-1-carboxylate (350 mg, 0.50 mmol) in CH$_3$CN (5.0 mL) was added NBS (90 mg, 0.50 mmol). The mixture was stirred at it for 3 h and concentrated in vacuo. The residue was purified by Biotage (CH$_2$Cl$_2$/EtOAc, 100:1 to 10:1) to give the title compound as light yellow solid. LC/MS RT=2.49 min. Mass calculated for, M+H 768.29, observed 389.17.

6-bromo-5-(piperidin-3-yl)-3-(quinolin-3-yl)pyrazolo[1,5]pyrimidin-7-amine

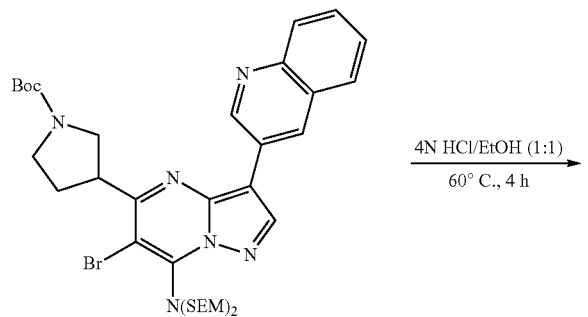

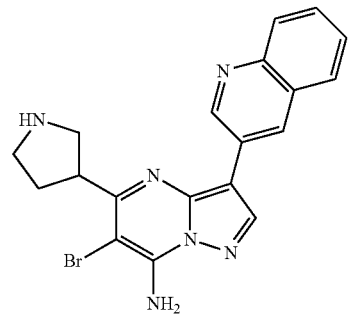

To a solution of tert-butyl 3-(7-(bis((2-(trimethylsilyl)ethoxy)methyl)amino)-6-bromo-3-(quinolin-3-yl)pyrazolo[1,5-a]pyrimidin-5-yl)piperidine-1-carboxylate (196 mg, 0.40 mmol) in EtOH (5.0 mL) was added 4 N HCl (5.0 mL). The mixture was heated at 60° C. for 4 h under argon, cooled down and concentrated in vacuo. The residue was dried in high vacuum to give the title compound as yellow solid (HCl salt). LC/MS RT=2.49 min. Mass calculated for, M+H 408.07, observed 389.17.

6-bromo-5-(1-(methylsulfonyl)piperidin-3-yl)-3-(quinolin-3-yl)pyrazolo[1,5-a]pyrimidin-7-amine

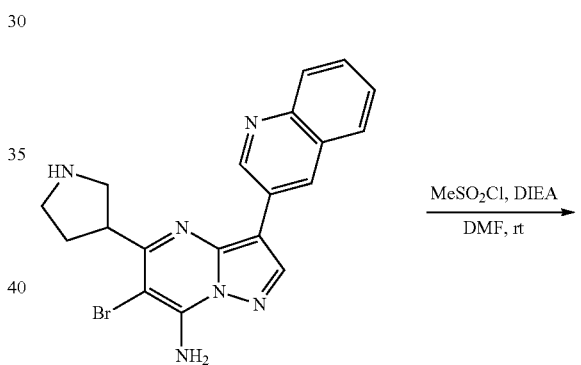

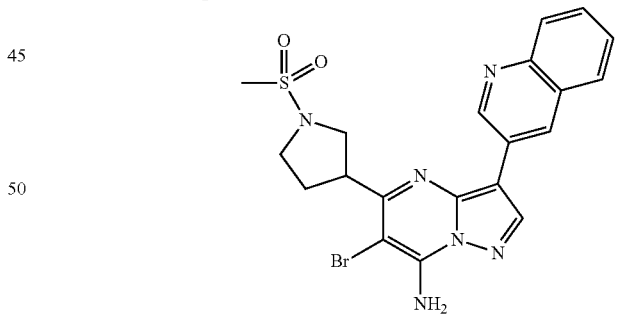

To a mixture of 6-bromo-5-(piperidin-3-yl)-3-(quinolin-3-yl)pyrazolo[1,5-a]pyrimidin-7-amine (HCl salt, 46 mg, 0.10 mmol) in DMF (2.0 mL) was added DIEA (0.10 mL, 0.30 mmol) and methylsulfonyl chloride (14 mg, 0.12 mmol). The reaction mixture was stirred at rt for 3 h and concentrated in vacuo. The residue was purified by prep-LC to give the title compound. LC/MS RT=2.49 min. Mass calculated for, M+H 486.05, observed 389.17.

By essentially the same procedure given in Schemes 25, the compounds listed in Table 8 can be prepared.

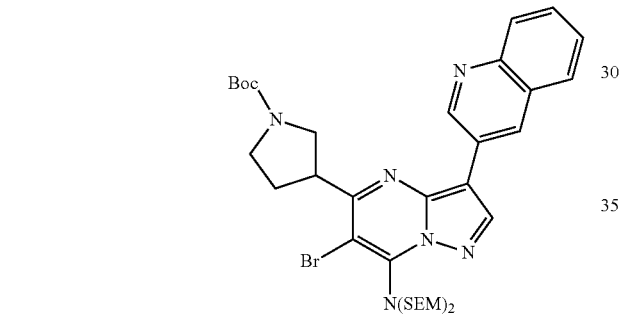

TABLE 8

| Compound ID | Structures | M + H (calc.) | M + H (observed) | Retention Time, (min) |
|---|---|---|---|---|
| 8.1 | 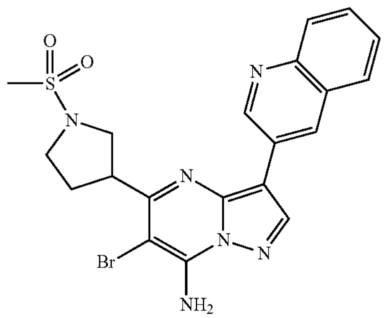 [SMILES: CS(=O)(=O)N1CCC(c2nc3c(-c4cnc5ccccc5c4)cnn3c(N)c2Br)C1] | 487.05 | 487.05 | 2.49 |
| 8.2 | 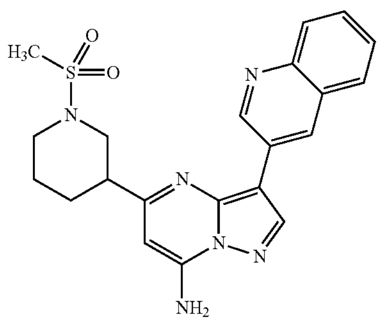 [SMILES: CS(=O)(=O)N1CCCC(c2cc(N)n3ncc(-c4cnc5ccccc5c4)c3n2)C1] | 423.15 | 423.15 | 3.12 |
| 8.3 | 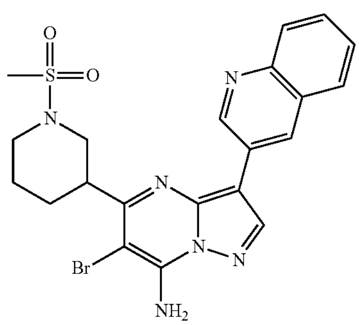 [SMILES: CS(=O)(=O)N1CCCC(c2nc3c(-c4cnc5ccccc5c4)cnn3c(N)c2Br)C1] | 501.07 | 501.06 | 3.42 |
| 8.4 | 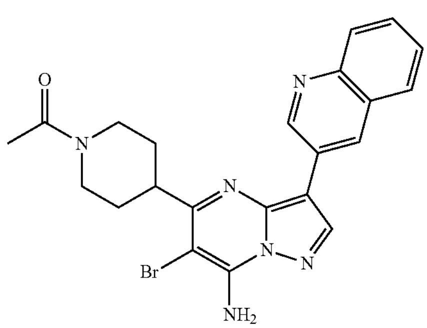 [SMILES: CC(=O)N1CCC(c2nc3c(-c4cnc5ccccc5c4)cnn3c(N)c2Br)CC1] | 465.10 | 465.10 | 3.26 |

TABLE 8-continued

| Compound ID | Structures | M + H (calc.) | M + H (observed) | Retention Time, (min) |
| --- | --- | --- | --- | --- |
| 8.5 | 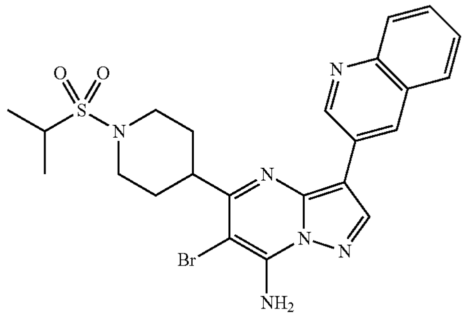 [SMILES: CC(C)S(=O)(=O)N1CCC(c2nc3c(-c4cnc5ccccc5c4)cnn3c(N)c2Br)CC1] | 529.09 | 529.09 | 3.84 |
| 8.6 | 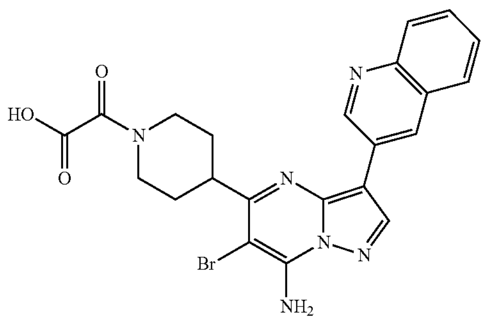 [SMILES: Nc1c(Br)c(C2CCN(C(=O)C(=O)O)CC2)nc2c(-c3cnc4ccccc4c3)cnn12] | 495.07 | 495.07 | 2.84 |
| 8.7 | 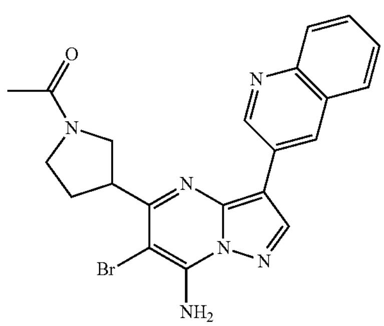 [SMILES: CC(=O)N1CCC(c2nc3c(-c4cnc5ccccc5c4)cnn3c(N)c2Br)C1] | 451.08 | 451.08 | 3.12 |
| 8.8 | 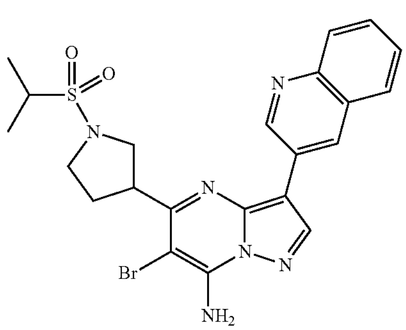 [SMILES: CC(C)S(=O)(=O)N1CCC(c2nc3c(-c4cnc5ccccc5c4)cnn3c(N)c2Br)C1] | 515.08 | 515.08 | 3.82 |

TABLE 8-continued

| Compound ID | Structures | M + H (calc.) | M + H (observed) | Retention Time, (min) |
|---|---|---|---|---|
| 8.9 | 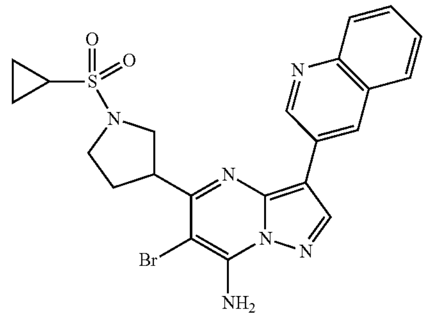 [SMILES: Nc1c(Br)c(C2CCN(S(=O)(=O)C3CC3)C2)nc2c(-c3cnc4ccccc4c3)cnn12] | 513.06 | 513.06 | 3.44 |
| 8.10 | 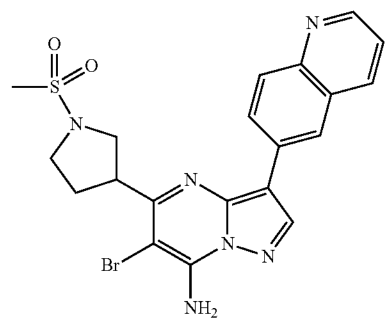 | 487.05 | 487.05 | 3.06 |
| 8.11 | 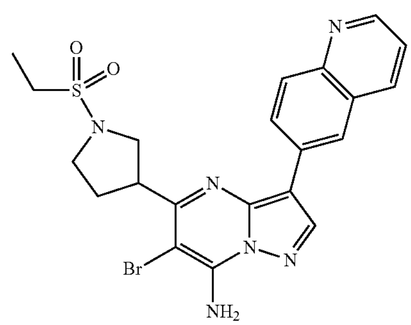 [SMILES: CCS(=O)(=O)N1CCC(c2nc3c(-c4ccc5ncccc5c4)cnn3c(N)c2Br)C1] | 501.06 | 501.06 | 3.53 |
| 8.12 | 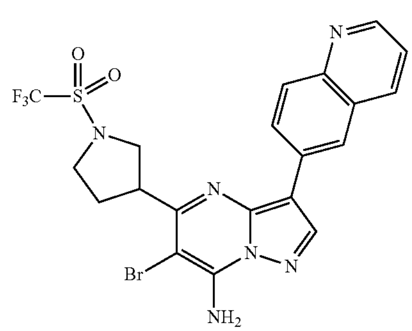 [SMILES: Nc1c(Br)c(C2CCN(S(=O)(=O)C(F)(F)F)C2)nc2c(-c3ccc4ncccc4c3)cnn12] | 541.02 | 541.02 | 4.44 |

TABLE 8-continued

| Compound ID | Structures | M + H (calc.) | M + H (observed) | Retention Time, (min) |
| --- | --- | --- | --- | --- |
| 8.13 | 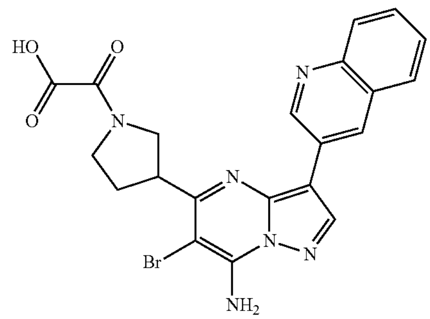 [SMILES: Nc1c(Br)c(C2CCN(C(=O)C(=O)O)C2)nc2c(-c3cnc4ccccc4c3)cnn12] | 481.06 | 481.06 | 2.79 |
| 8.14 | 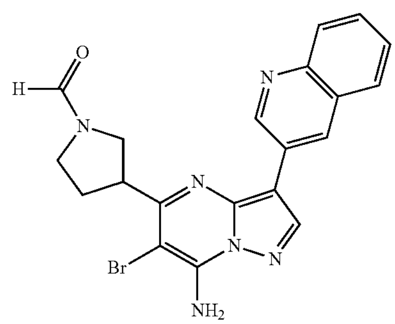 [SMILES: Nc1c(Br)c(C2CCN(C=O)C2)nc2c(-c3cnc4ccccc4c3)cnn12] | 437.06 | 437.06 | 3.04 |
| 8.15 | 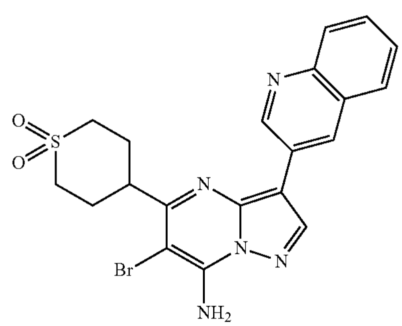 [SMILES: Nc1c(Br)c(C2CCS(=O)(=O)CC2)nc2c(-c3cnc4ccccc4c3)cnn12] | 471.04 | 471.04 | 3.05 |
| 8.16 | 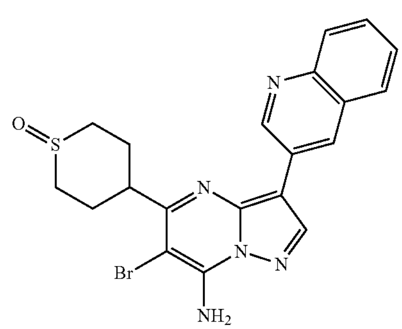 [SMILES: Nc1c(Br)c(C2CCS(=O)CC2)nc2c(-c3cnc4ccccc4c3)cnn12] | 456.04 | 456.04 | 2.97 |

TABLE 8-continued

| Compound ID | Structures | M + H (calc.) | M + H (observed) | Retention Time, (min) |
|---|---|---|---|---|
| 8.17 | 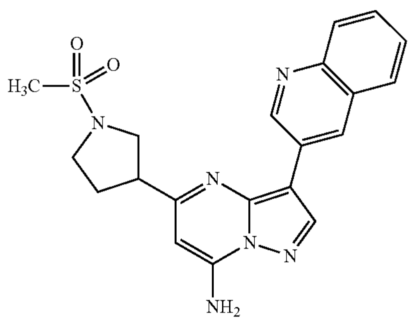 [SMILES: CS(=O)(=O)N1CCC(c2cc(N)n3ncc(-c4cnc5ccccc5c4)c3n2)C1] | 409.0 | 409.0 | 2.9 |
| 8.18 | 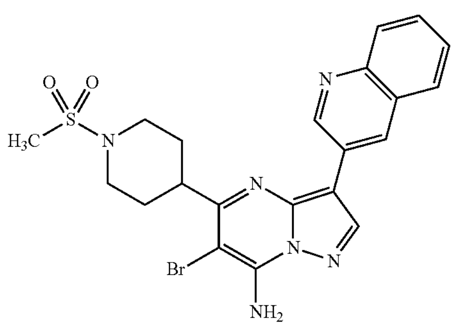 [SMILES: CS(=O)(=O)N1CCC(c2nc3c(-c4cnc5ccccc5c4)cnn3c(N)c2Br)CC1] | 501.0 | 501.0 | 3.53 |
| 8.19 | 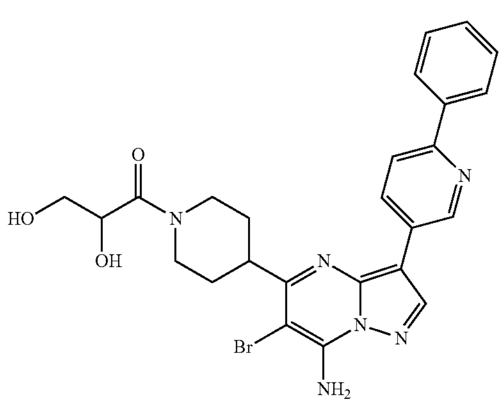 [SMILES: Nc1c(Br)c(C2CCN(C(=O)C(O)CO)CC2)nc2c(-c3ccc(-c4ccccc4)nc3)cnn12] | 537.1 | 537.0 | 3.13 |

Alternative to the described procedure in the Scheme-14, these compounds can also be made by the scheme 25 given below.

7-Amino-3-(6-phenylpyridin-3-yl)pyrazolo[1,5-a]pyrimidin-5-yl)piperidine-1-carboxylate

SCHEME-26

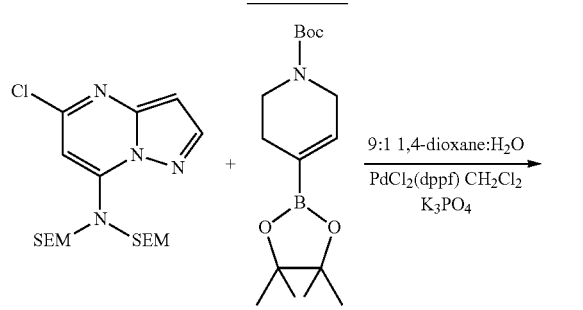

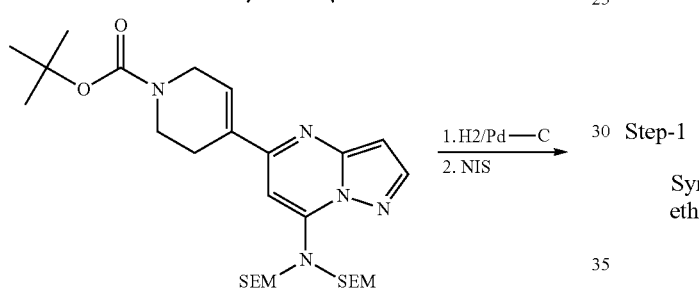

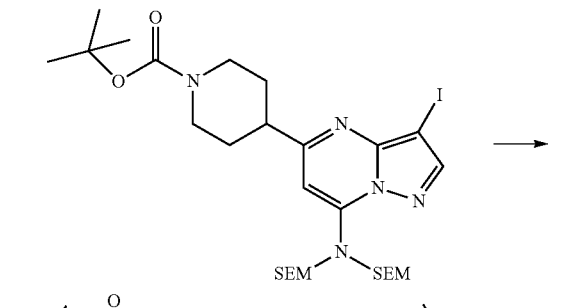

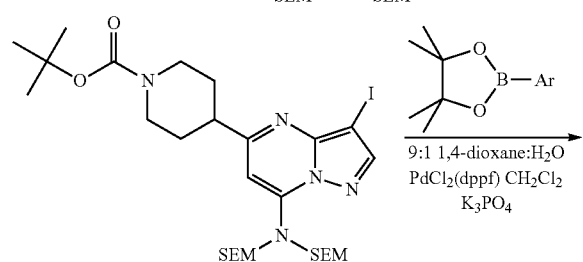

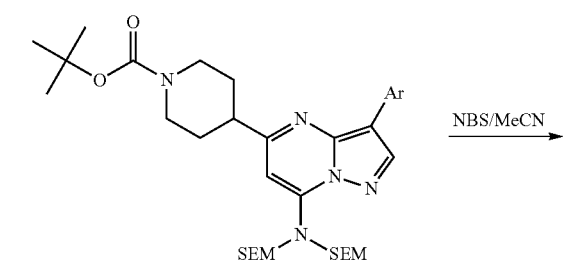

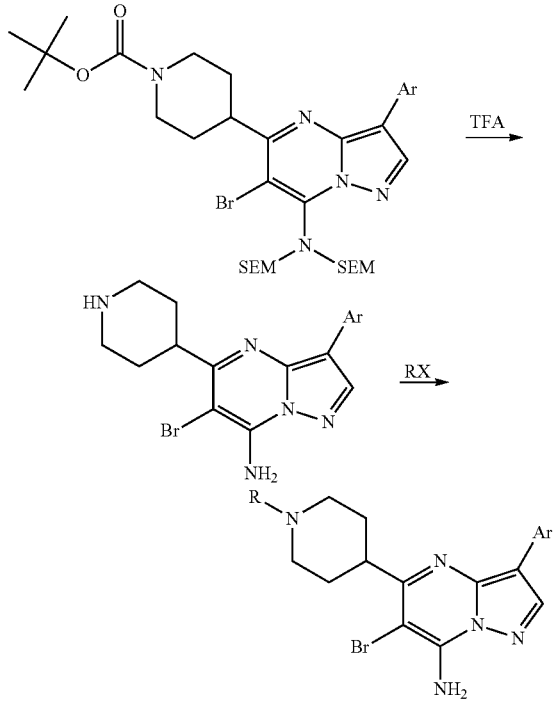

Step-1

Synthesis of tert-butyl 4-(7-(bis((2-(trimethylsilyl)ethoxy)methyl)amino)pyrazolo[1,5-a]pyrimidin-5-yl)-5,6-dihydropyridine-1(2H)-carboxylate

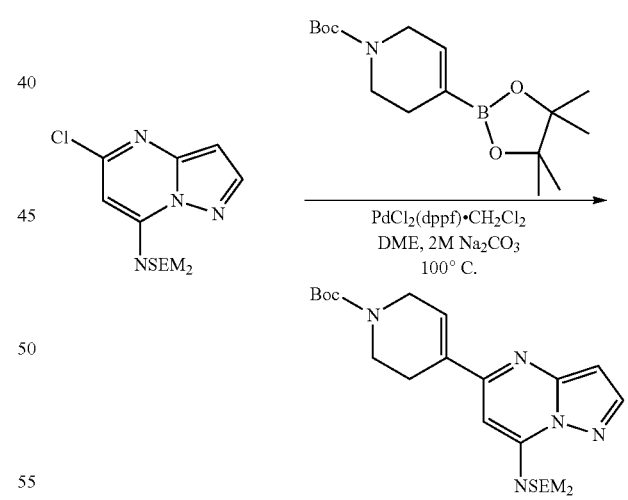

To a pressure tube were charged 5-chloro-N,N-bis((2-(trimethylsilyl)ethoxy)methyl)pyrazolo[1,5-a]pyrimidin-7-amine (5.36 g, 12.5 mmols), tert-butyl 4-(4,4,5,5-tetramethyl-1,3,2-dioxaborolan-2-yl)-5,6-dihydropyridine-1(2H)-carboxylate (4.26 g, 13.8 mmols), PdCl$_2$(dppf).CH$_2$Cl$_2$ ([1,1'-bis(diphenylphosphino)ferrocene]dichloropalladium(II) complex with dichloromethane (1:1)) (510 mg, 0.62 mmol), 2M Na$_2$CO$_3$ (30 mL) and DME (60 mL). The tube was degassed with Ar briefly, capped and heated at 100° C. with stirring overnight. After cooling, the reaction mixture was diluted with EtOAc and water, organic layer was isolated, washed with brine and dried (MgSO$_4$). After solvent was removed under reduced pressure, the residue was purified on silica. Elution with EtOAc in hexanes (0-25%) gave tert-butyl 4-(7-(bis((2-(trimethylsilyl)ethoxy)methyl)amino)pyrazolo [1,5-a]pyrimidin-5-yl)-5,6-dihydropyridine-1(2H)-carboxylate (5.76 g, 80%).

Step 2

Synthesis of tert-butyl 4-(7-(bis((2-(trimethylsilyl)ethoxy)methyl)amino)pyrazolo[1,5-a]pyrimidin-5-yl)piperidine-1-carboxylate

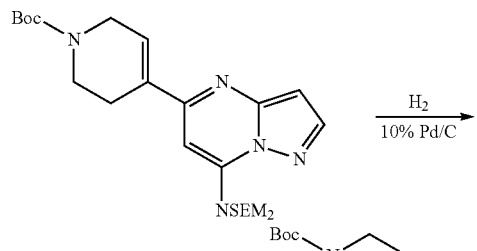

A mixture of tert-butyl 4-(7-(bis((2-(trimethylsilyl)ethoxy)methyl)amino)pyrazolo[1,5-a]pyrimidin-5-yl)-5,6-dihydropyridine-1(2H)-carboxylate (5.05 g, 8.78 mmol) and 10% Pd/C (100 mg) in EtOAc was stirred at 45° C. under hydrogen (balloon pressure) for three hours. After filtration, washing with EtOAc (3×) and concentration, tert-butyl 4-(7-(bis((2-(trimethylsilyl)ethoxy)methyl)amino)pyrazolo[1,5-a]pyrimidin-5-yl)piperidine-1-carboxylate (5.1 g, 99.5%) was obtained as oil.

Step 3

Synthesis of tert-butyl 4-(7-(bis((2-(trimethylsilyl)ethoxy)methyl)amino)-3-iodopyrazolo[1,5-a]pyrimidin-5-yl)piperidine-1-carboxylate

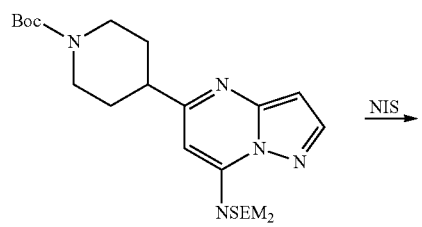

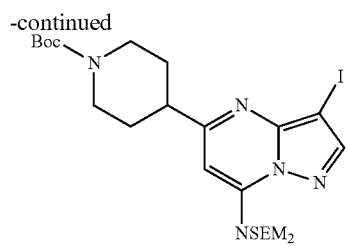

To a mixture of tert-butyl 4-(7-(bis((2-(trimethylsilyl)ethoxy)methyl)amino)pyrazolo[1,5-a]pyrimidin-5-yl)piperidine-1-carboxylate (5 g, 8.65 mmol) in DMF (15 mL) was added N-iodosuccinimide (1.86 g, 8.27 mmol) and the resulting mixture was allowed to stir at room temperature for 1 hour. The mixture diluted with EtOAc (100 mL), washed with water (20 mL). The aqueous layer was extracted with EtOAc (20 mL) once, and combined organic layer was washed with water (20 mL) three times, brine once and dried (MgSO$_4$). After concentration, the residue was purified by column chromatography on silica gel. Elution with EtOAc/Hex (0-30%) gave tert-butyl 4-(7-(bis((2-(trimethylsilyl)ethoxy)methyl)amino)-3-iodopyrazolo[1,5-a]pyrimidin-5-yl)piperidine-1-carboxylate (4.55 g, 75%). (Note: DMF could be replaced by acetonitrile.)

Step 4

Synthesis of tert-butyl 4-(7-(bis((2-(trimethylsilyl)ethoxy)methyl)amino)-3-(6-phenylpyridin-3-yl)pyrazolo[1,5-a]pyrimidin-5-yl)piperidine-1-carboxylate

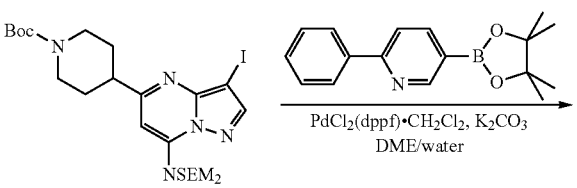

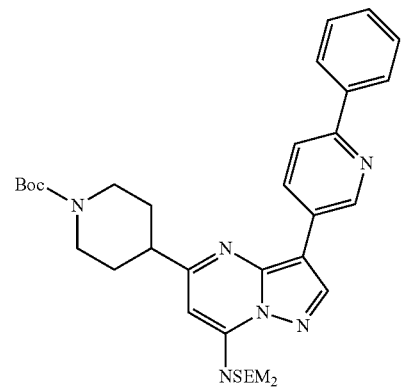

To a pressure tube were charged tert-butyl 4-(7-(bis((2-(trimethylsilyl)ethoxy)methyl)amino)-3-iodopyrazolo[1,5-a]pyrimidin-5-yl)piperidine-1-carboxylate (4.2 g, 5.97 mmol), 2-phenyl-5-(4,4,5,5-tetramethyl-1,3,2-dioxaborolan-2-yl)pyridine (2 g, 7.1 mmol), PdCl$_2$(dppf).CH$_2$Cl$_2$ (240 mg, 0.33 mmol), DME (16 mL) and 2M Na$_2$CO$_3$ (8 mL). The mixture was briefly degassed with Argon and the tube was capped and heated at 100° C. for 15 hours. On cooling, H$_2$O (20 mL) and EtOAc (40 mL) and aqueous layer was extracted with EtOAc (3×) and combined organic layers were washed with brine once and dried (MgSO$_4$). After concentration in vacuo the residue was purified on silica gel. Elution with EtOAc/Hexanes (0-40%) gave the title compound (3.24 g, 74%).

Step 5

Preparation of tert-butyl 4-(7-(bis((2-(trimethylsilyl)ethoxy)methyl)amino)-6-bromo-3-(6-phenylpyridin-3-yl)pyrazolo[1,5-a]pyrimidin-5-yl)piperidine-1-carboxylate

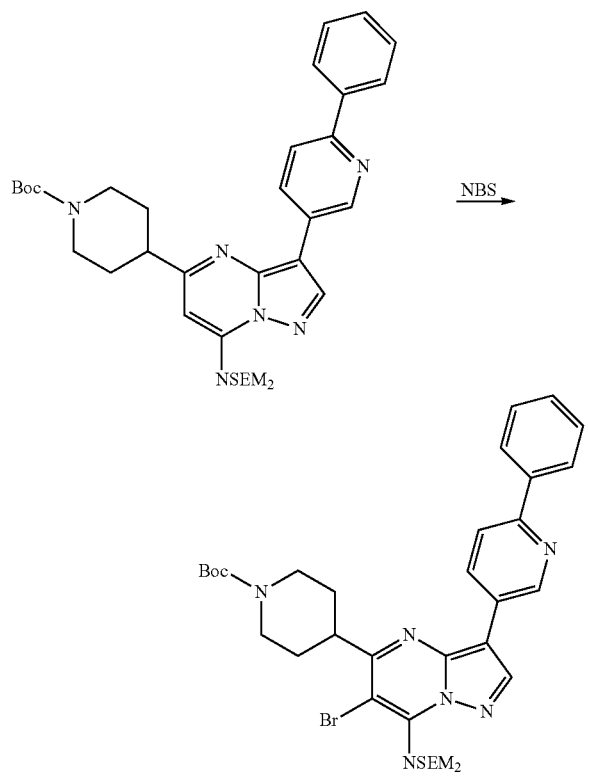

To a solution of tert-butyl 4-(7-(bis((2-(trimethylsilyl)ethoxy)methyl)amino)-3-(6-phenylpyridin-3-yl)pyrazolo[1,5-a]pyrimidin-5-yl)piperidine-1-carboxylate (3.24 g, 4.44 mmol) in DMF (20 mL) was added NBS (750 mg, 4.21 mmol). After stirring at rt for one hour, NBS (75 mg 0.42 mmol) was added and the resulting mixture was stirred for another 40 minutes to complete the reaction. The reaction mixture was diluted with EtOAc (200 mL), washed with water (2×50 mL), brine (20 mL) and dried (MgSO$_4$). After concentration in vacuo the residue was purified on silica gel. Elution with EtOAc/Hexanes (0-40%) gave the title compound (3 g, 83%).

Step-6

General Method:

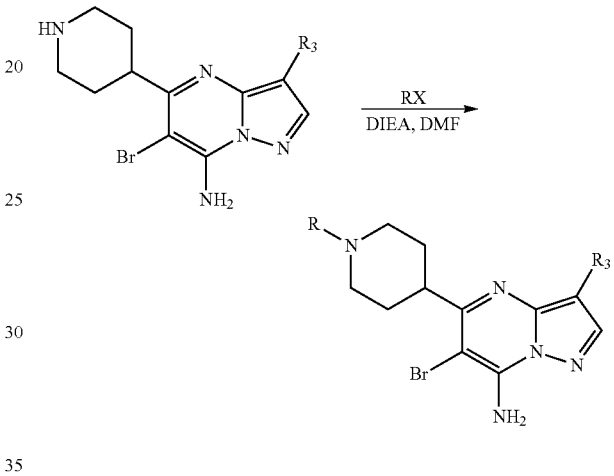

To a solution of the piperidine derivative (1 eq), DIEA (4 eq) in DMF was added appropriate coupling reagent (1 eq): chloroformate to form carbamate; isocyanate to provide urea; sulfonyl chloride to form sulfonamide; and carboxylic acid/EDCI/HOBt to yield the corresponding amide. The reaction was monitored by HPLC. Once the reaction was complete, the reaction mixture was directly purified by HPLC to furnish the corresponding product.

TABLE-8A

| Cpd ID | Structures | M + H (calculated) | M + H (observed) | Retention Time(min) |
|---|---|---|---|---|
| 8.20 | 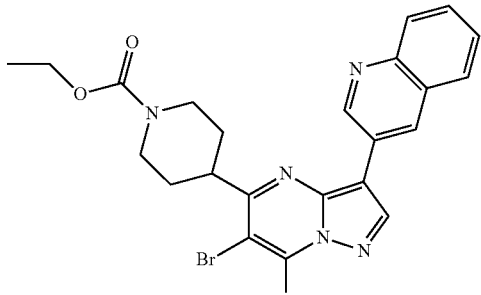 | 495.1 | 495.2 | 4.16 |

TABLE-8A-continued
| Cpd ID | Structures | M + H (calculated) | M + H (observed) | Retention Time(min) |
|---|---|---|---|---|
| 8.21 | 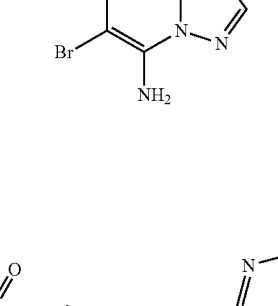 | 481.1 | 481.1 | 3.84 |
| 8.22 | 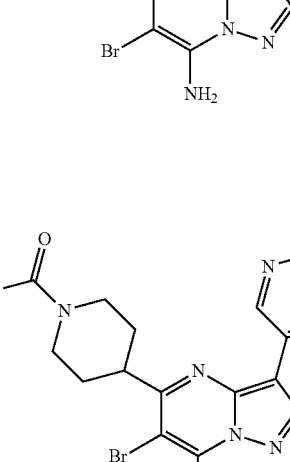 | 529.1 | 529.1 | 4.03 |
| 8.23 | 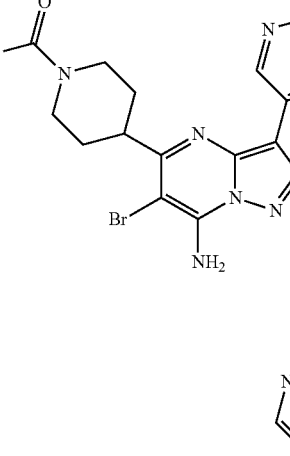 | 494.1 | 494.3 | 3.44 |
| 8.24 | 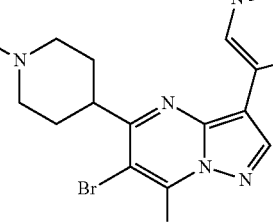 | 521.1 | 521.2 | 2.80 |

TABLE-8A-continued

| Cpd ID | Structures | M + H (calculated) | M + H (observed) | Retention Time(min) |
|---|---|---|---|---|
| 8.25 | 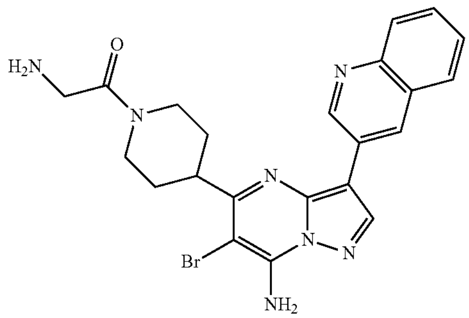 [SMILES: NCC(=O)N1CCC(c2nc3c(-c4cnc5ccccc5c4)cnn3c(N)c2Br)CC1] | 480.1 | 480.2 | 2.52 |
| 8.26 | 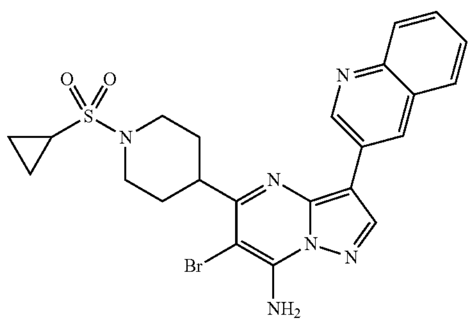 [SMILES: Nc1c(Br)c(C2CCN(S(=O)(=O)C3CC3)CC2)nc2c(-c3cnc4ccccc4c3)cnn12] | 527.1 | 527.0 | 3.96 |
| 8.27 | 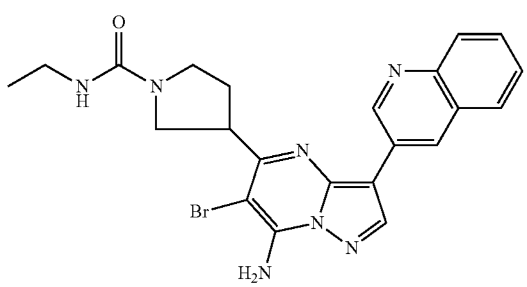 [SMILES: CCNC(=O)N1CCC(c2nc3c(-c4cnc5ccccc5c4)cnn3c(N)c2Br)C1] | 480.1 | 480.1 | 2.85 |
| 8.28 | 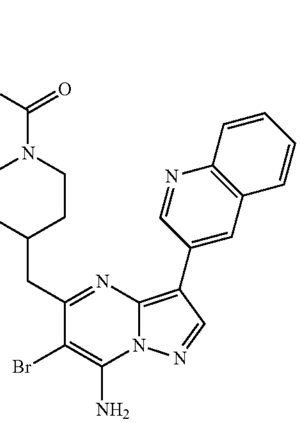 | 508.1 | 508.1 | 3.54 |

TABLE-8A-continued
| Cpd ID | Structures | M + H (calculated) | M + H (observed) | Retention Time(min) |
|---|---|---|---|---|
| 8.29 | 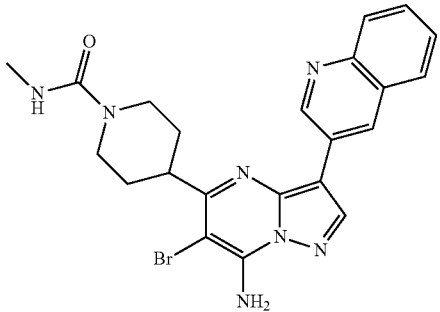 [SMILES: CNC(=O)N1CCC(c2nc3c(-c4cnc5ccccc5c4)cnn3c(N)c2Br)CC1] | 480.1 | 480.1 | 2.88 |
| 8.30 | 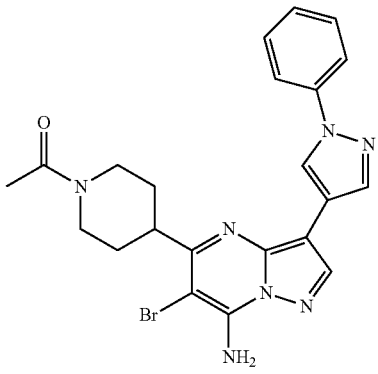 [SMILES: CC(=O)N1CCC(c2nc3c(-c4cnn(-c5ccccc5)c4)cnn3c(N)c2Br)CC1] | 480.1 | 480.0 | 4.60 |
| 8.31 | 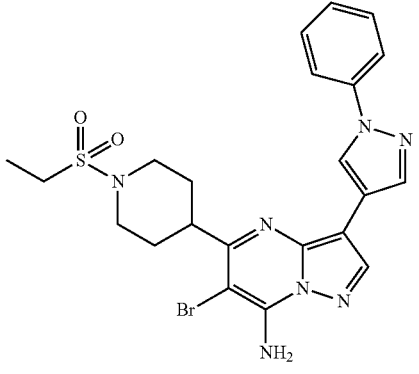 [SMILES: CCS(=O)(=O)N1CCC(c2nc3c(-c4cnn(-c5ccccc5)c4)cnn3c(N)c2Br)CC1] | 530.1 | 529.7 | 5.01 |
| 8.32 | 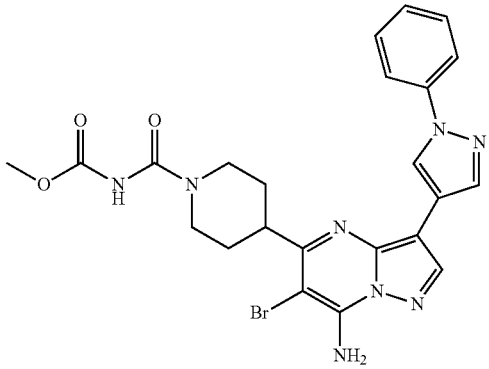 [SMILES: COC(=O)NC(=O)N1CCC(c2nc3c(-c4cnn(-c5ccccc5)c4)cnn3c(N)c2Br)CC1] | 539.1 | 539.1 | 4.31 |

TABLE-8A-continued

| Cpd ID | Structures | M + H (calculated) | M + H (observed) | Retention Time(min) |
|---|---|---|---|---|
| 8.33 | 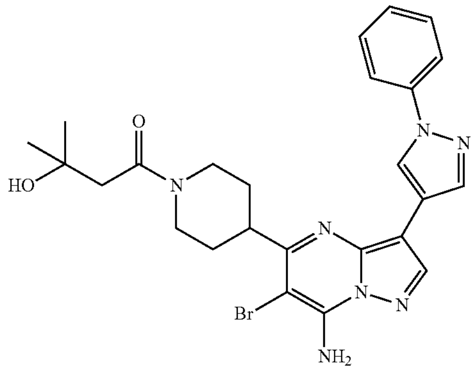 [SMILES: CC(C)(O)CC(=O)N1CCC(c2nc3c(-c4cnn(-c5ccccc5)c4)cnn3c(N)c2Br)CC1] | 538.1 | 538.4 | 4.77 |
| 8.34 | 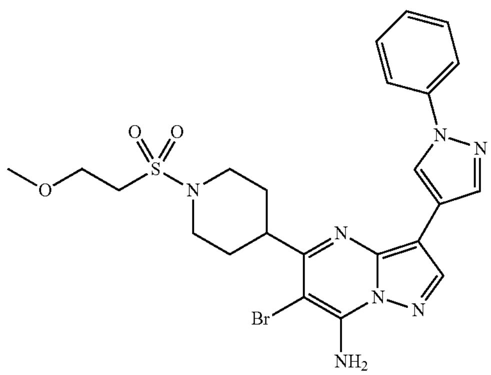 [SMILES: COCCS(=O)(=O)N1CCC(c2nc3c(-c4cnn(-c5ccccc5)c4)cnn3c(N)c2Br)CC1] | 560.1 | 560.1 | 4.96 |
| 8.35 | 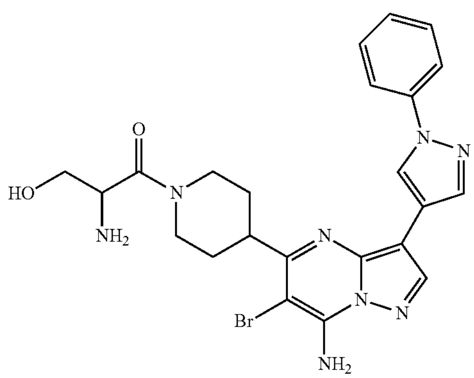 [SMILES: Nc1c(Br)c(C2CCN(C(=O)C(N)CO)CC2)nc2c(-c3cnn(-c4ccccc4)c3)cnn12] | 525.1 | 525.2 | 2.86 |
| 8.36 | 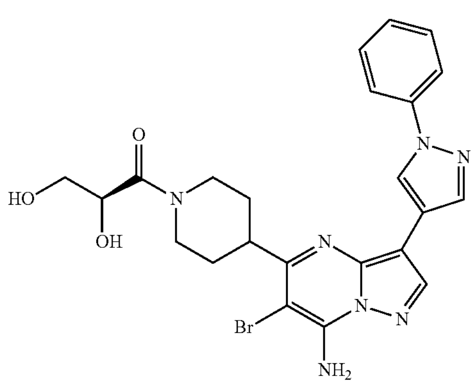 [SMILES: Nc1c(Br)c(C2CCN(C(=O)[C@@H](O)CO)CC2)nc2c(-c3cnn(-c4ccccc4)c3)cnn12] | 526.1 | 526.5 | 3.96 |

TABLE-8A-continued
| Cpd ID | Structures | M + H (calculated) | M + H (observed) | Retention Time(min) |
|---|---|---|---|---|
| 8.37 | 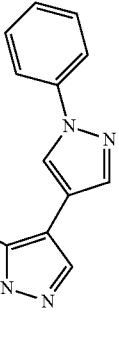 | 509.1 | 509.4 | 4.62 |
| 8.38 | 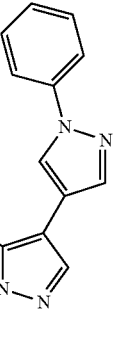 | 495.1 | 495.1 | 4.37 |
| 8.39 | 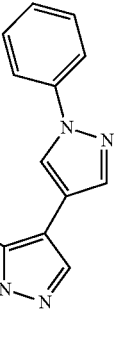 | 542.1 | 542.3 | 5.11 |
| 8.40 | 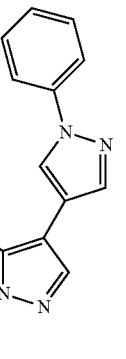 | 495.1 | 495.2 | 2.93 |

TABLE-8A-continued

| Cpd ID | Structures | M + H (calculated) | M + H (observed) | Retention Time(min) |
|---|---|---|---|---|
| 8.41 | 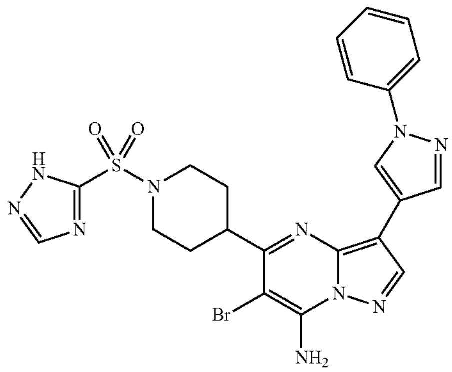 [SMILES: Nc1c(Br)c(C2CCN(S(=O)(=O)c3ncn[nH]3)CC2)nc2c(-c3cnn(-c4ccccc4)c3)cnn12] | 569.1 | 569.4 | 4.42 |
| 8.42 | 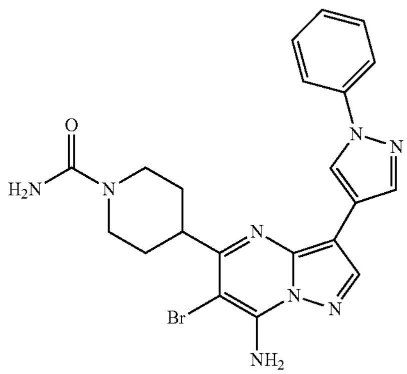 [SMILES: NC(=O)N1CCC(c2nc3c(-c4cnn(-c5ccccc5)c4)cnn3c(N)c2Br)CC1] | 481.1 | 481.1 | 4.13 |
| 8.43 | 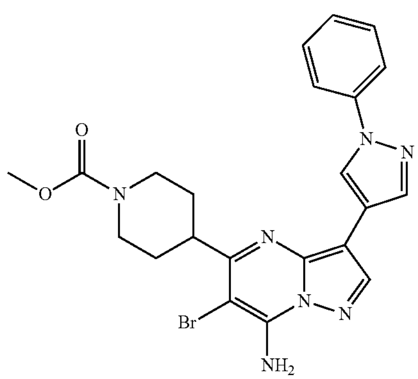 [SMILES: COC(=O)N1CCC(c2nc3c(-c4cnn(-c5ccccc5)c4)cnn3c(N)c2Br)CC1] | 496.1 | 496.1 | 5.19 |
| 8.44 | 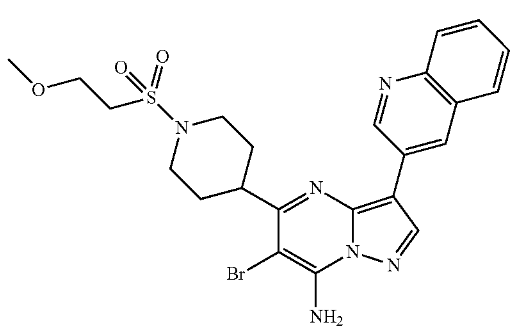 [SMILES: COCCS(=O)(=O)N1CCC(c2nc3c(-c4cnc5ccccc5c4)cnn3c(N)c2Br)CC1] | 545.1 | 545.1 | 3.61 |

TABLE-8A-continued
| Cpd ID | Structures | M + H (calculated) | M + H (observed) | Retention Time(min) |
|---|---|---|---|---|
| 8.45 | 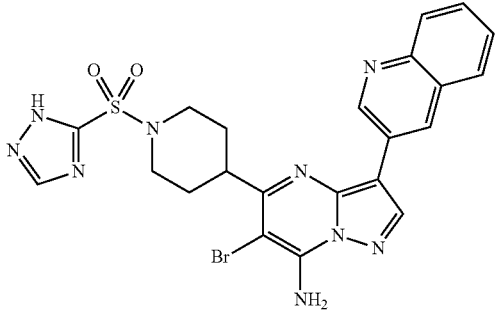 [SMILES: Nc1c(Br)c(C2CCN(S(=O)(=O)c3ncn[nH]3)CC2)nc2c(-c3cnc4ccccc4c3)cnn12] | 554.1 | 554.1 | 3.23 |
| 8.46 | 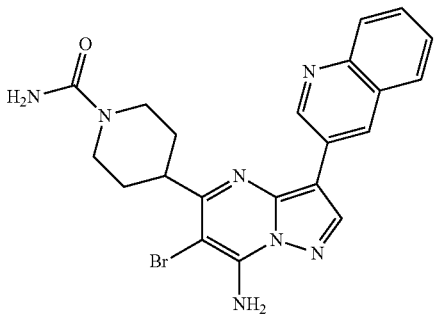 [SMILES: NC(=O)N1CCC(c2nc3c(-c4cnc5ccccc5c4)cnn3c(N)c2Br)CC1] | 466.1 | 466.3 | 3.00 |
| 8.47 | 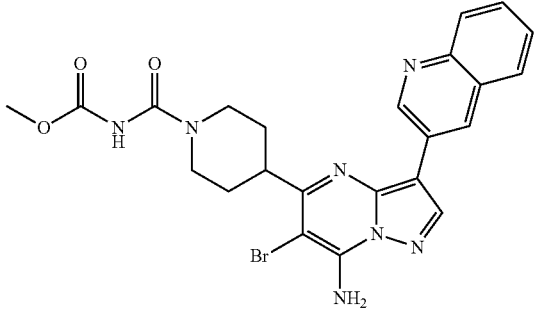 [SMILES: COC(=O)NC(=O)N1CCC(c2nc3c(-c4cnc5ccccc5c4)cnn3c(N)c2Br)CC1] | 524.1 | 524.1 | 3.14 |
| 8.48 | 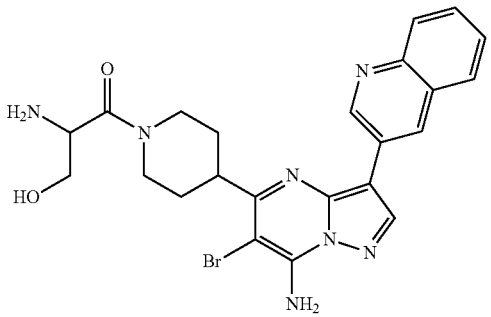 [SMILES: Nc1c(Br)c(C2CCN(C(=O)C(N)CO)CC2)nc2c(-c3cnc4ccccc4c3)cnn12] | 510.1 | 510.1 | 1.92 |

TABLE-8A-continued
| Cpd ID | Structures | M + H (calculated) | M + H (observed) | Retention Time(min) |
|---|---|---|---|---|
| 8.49 | 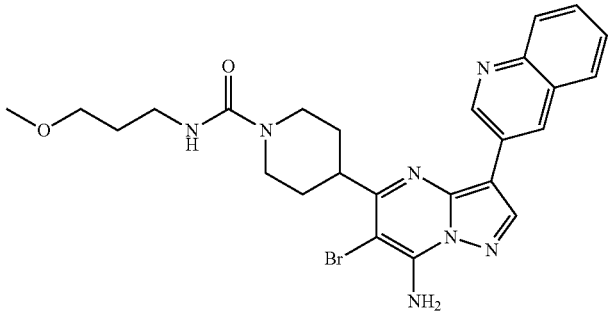 [SMILES: COCCCNC(=O)N1CCC(c2nc3c(-c4cnc5ccccc5c4)cnn3c(N)c2Br)CC1] | 538.1 | 538.1 | 3.42 |
| 8.50 | 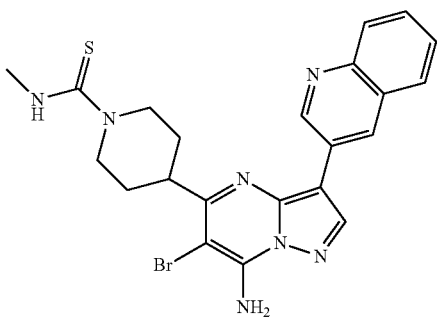 [SMILES: CNC(=S)N1CCC(c2nc3c(-c4cnc5ccccc5c4)cnn3c(N)c2Br)CC1] | 496.1 | 496.0 | 2.89 |
| 8.51 | 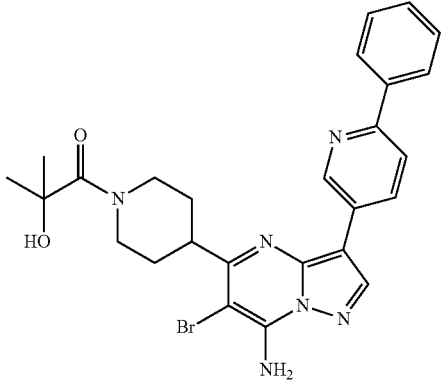 [SMILES: CC(C)(O)C(=O)N1CCC(c2nc3c(-c4ccc(-c5ccccc5)nc4)cnn3c(N)c2Br)CC1] | 535.1 | 535.0 | 3.42 |
| 8.52 | 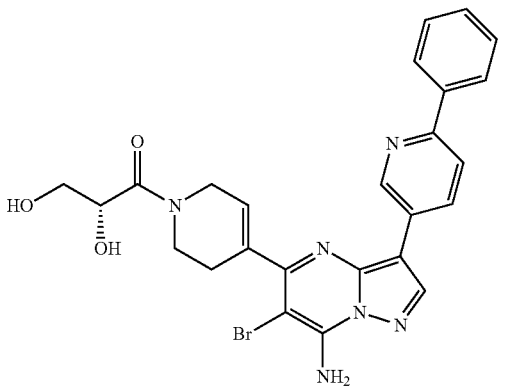 [SMILES: Nc1c(Br)c(C2=CCN(C(=O)[C@H](O)CO)CC2)nc2c(-c3ccc(-c4ccccc4)nc3)cnn12] | 535.1 | 535.2 | 2.47 |

TABLE-8A-continued

| Cpd ID | Structures | M + H (calculated) | M + H (observed) | Retention Time(min) |
|---|---|---|---|---|
| 8.53 | 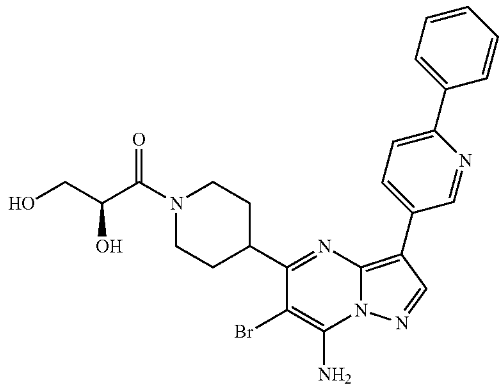 [SMILES: Nc1c(Br)c(C2CCN(C(=O)[C@@H](O)CO)CC2)nc2c(-c3ccc(-c4ccccc4)nc3)cnn12] | 537.1 | 537.2 | 3.11 |
| 8.54 | 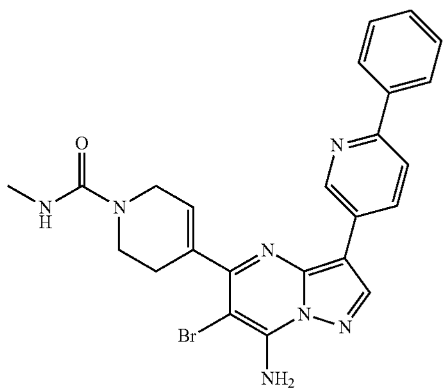 [SMILES: CNC(=O)N1CC=C(c2nc3c(-c4ccc(-c5ccccc5)nc4)cnn3c(N)c2Br)CC1] | 504.1 | 504.0 | 3.48 |
| 8.55 | 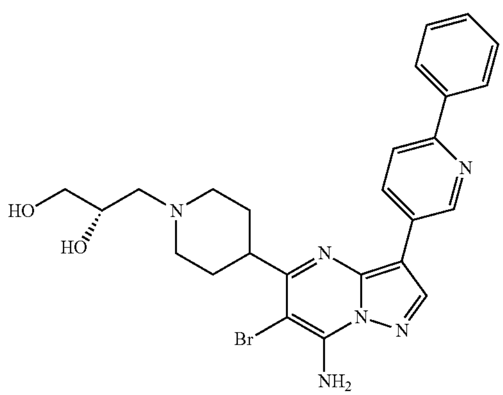 [SMILES: Nc1c(Br)c(C2CCN(C[C@H](O)CO)CC2)nc2c(-c3ccc(-c4ccccc4)nc3)cnn12] | 523.2 | 523.2 | 2.13 |
| 8.56 | 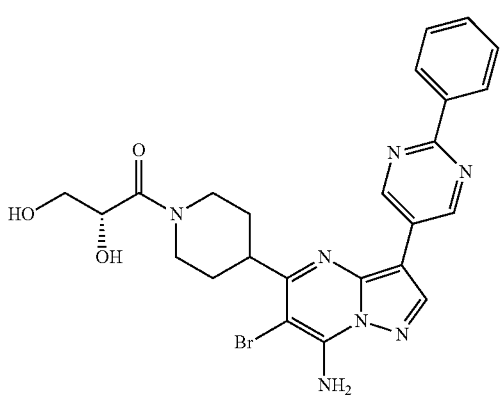 [SMILES: Nc1c(Br)c(C2CCN(C(=O)[C@H](O)CO)CC2)nc2c(-c3cnc(-c4ccccc4)nc3)cnn12] | 538.1 | 538.0 | 4.21 |

TABLE-8A-continued

| Cpd ID | Structures | M + H (calculated) | M + H (observed) | Retention Time(min) |
|---|---|---|---|---|
| 8.57 | 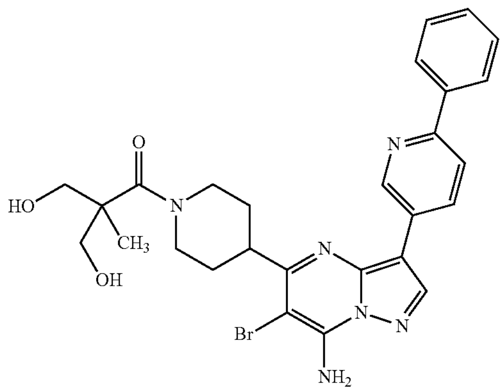 [SMILES: CC(CO)(CO)C(=O)N1CCC(c2nc3c(-c4ccc(-c5ccccc5)nc4)cnn3c(N)c2Br)CC1] | 565.1 | 565.6 | 3.36 |
| 8.58 | 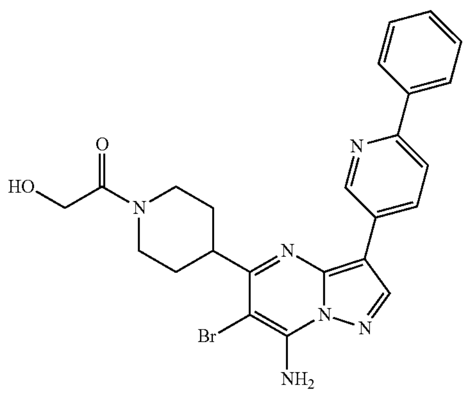 [SMILES: Nc1c(Br)c(C2CCN(C(=O)CO)CC2)nc2c(-c3ccc(-c4ccccc4)nc3)cnn12] | 507.1 | 507.6 | 3.29 |
| 8.59 | 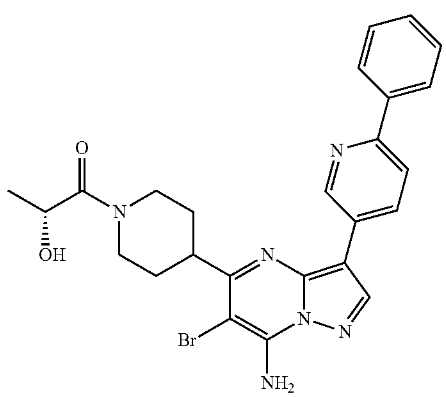 [SMILES: C[C@@H](O)C(=O)N1CCC(c2nc3c(-c4ccc(-c5ccccc5)nc4)cnn3c(N)c2Br)CC1] | 521.1 | 521.2 | 2.78 |
| 8.60 | 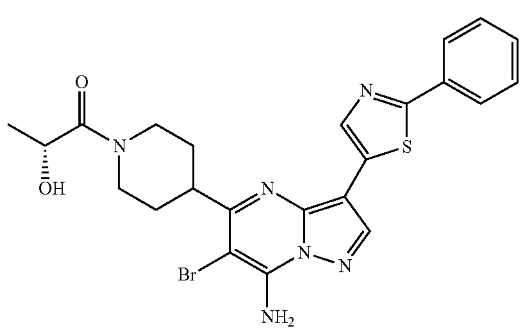 [SMILES: C[C@@H](O)C(=O)N1CCC(c2nc3c(-c4cnc(-c5ccccc5)s4)cnn3c(N)c2Br)CC1] | 527.1 | 527.6 | 4.58 |

TABLE-8A-continued
| Cpd ID | Structures | M + H (calculated) | M + H (observed) | Retention Time(min) |
|---|---|---|---|---|
| 8.61 | 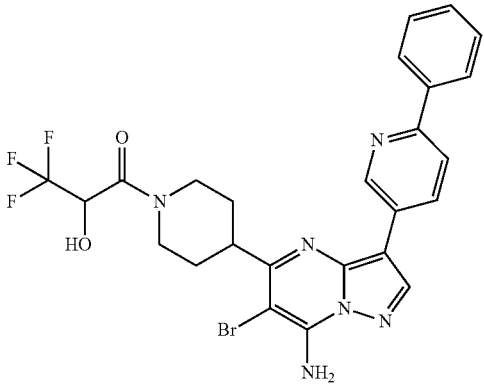 [SMILES: Nc1c(Br)c(C2CCN(C(=O)C(O)C(F)(F)F)CC2)nc2c(-c3ccc(-c4ccccc4)nc3)cnn12] | 575.1 | 575.6 | 2.79 |
| 8.62 | 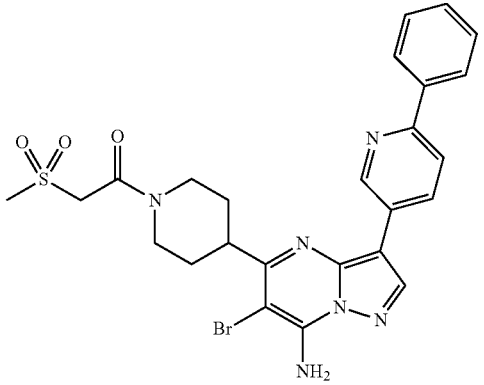 [SMILES: CS(=O)(=O)CC(=O)N1CCC(c2nc3c(-c4ccc(-c5ccccc5)nc4)cnn3c(N)c2Br)CC1] | 568.08 | 569.35 | 3.34 |
| 8.63 | 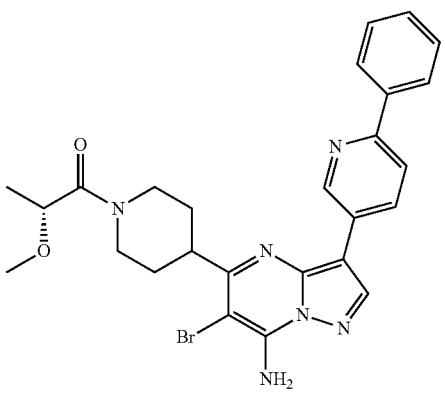 [SMILES: CO[C@H](C)C(=O)N1CCC(c2nc3c(-c4ccc(-c5ccccc5)nc4)cnn3c(N)c2Br)CC1] | 534.13 | 535.60 | 3.69 |
| 8.64 | 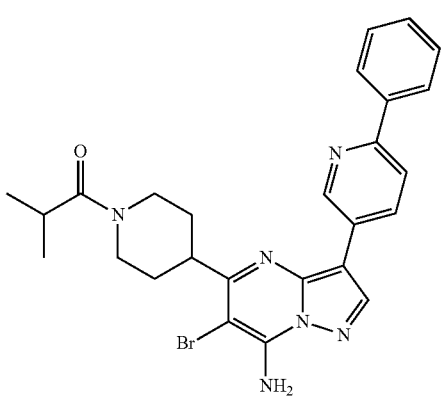 [SMILES: CC(C)C(=O)N1CCC(c2nc3c(-c4ccc(-c5ccccc5)nc4)cnn3c(N)c2Br)CC1] | 518.14 | 519.57 | 4.05 |

TABLE-8A-continued
| Cpd ID | Structures | M + H (calculated) | M + H (observed) | Retention Time(min) |
| --- | --- | --- | --- | --- |
| 8.65 | 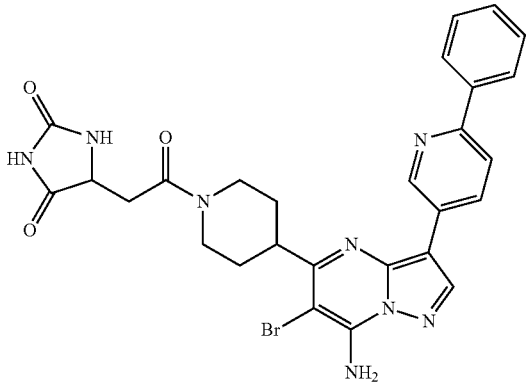 [SMILES: Nc1c(Br)c(C2CCN(C(=O)CC3NC(=O)NC3=O)CC2)nc2c(-c3ccc(-c4ccccc4)nc3)cnn12] | 588.12 | 589.62 | 3.12 |
| 8.66 | 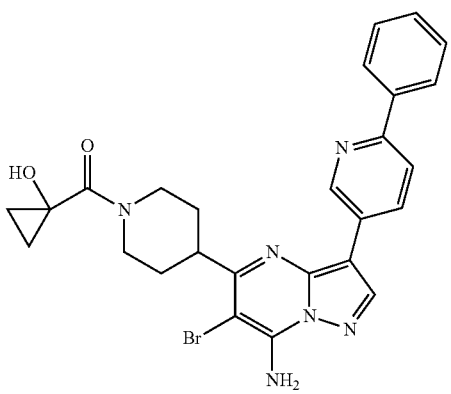 [SMILES: Nc1c(Br)c(C2CCN(C(=O)C3(O)CC3)CC2)nc2c(-c3ccc(-c4ccccc4)nc3)cnn12] | 532.12 | 533.57 | 3.53 |
| 8.67 | 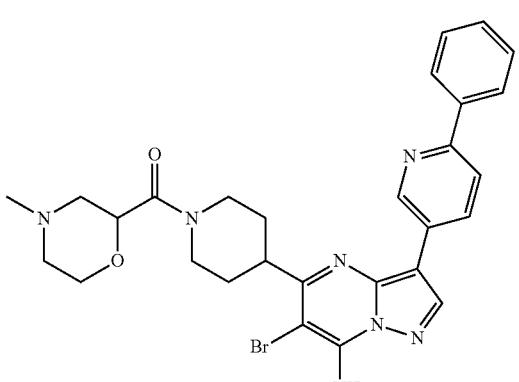 | 575.16 | 576.64 | 3.00 |
| 8.68 | 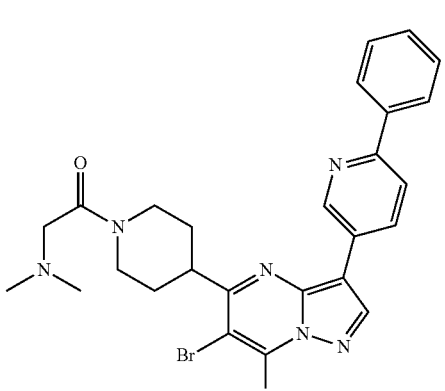 | 533.15 | 534.60 | 2.90 |

TABLE-8A-continued

| Cpd ID | Structures | M + H (calculated) | M + H (observed) | Retention Time(min) |
|---|---|---|---|---|
| 8.69 | 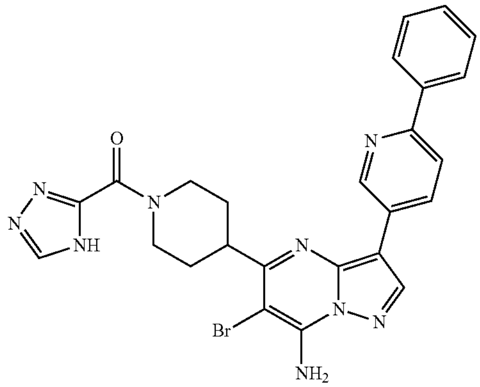 [SMILES: Nc1c(Br)c(C2CCN(C(=O)c3nnc[nH]3)CC2)nc2c(-c3ccc(-c4ccccc4)nc3)cnn12] | 543.11 | 544.52 | 3.25 |
| 8.70 | 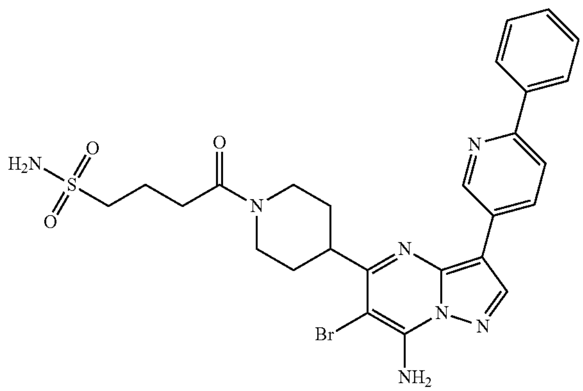 [SMILES: Nc1c(Br)c(C2CCN(C(=O)CCCS(N)(=O)=O)CC2)nc2c(-c3ccc(-c4ccccc4)nc3)cnn12] | 597.11 | 598.61 | 3.23 |
| 8.71 | 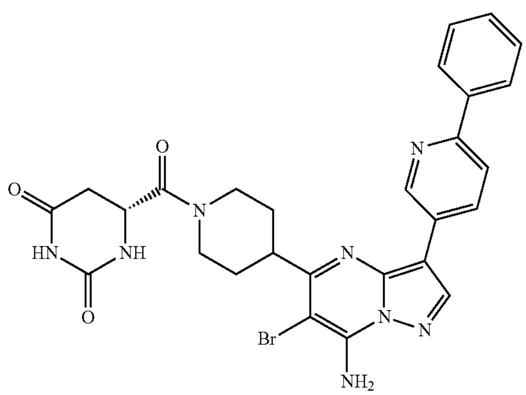 [SMILES: Nc1c(Br)c(C2CCN(C(=O)[C@H]3CC(=O)NC(=O)N3)CC2)nc2c(-c3ccc(-c4ccccc4)nc3)cnn12] | 588.12 | 589.60 | 3.03 |
| 8.72 | 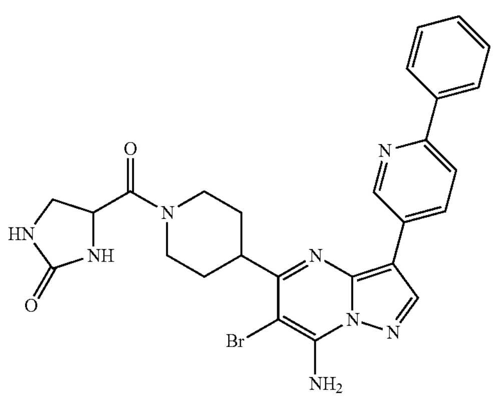 [SMILES: Nc1c(Br)c(C2CCN(C(=O)C3CNC(=O)N3)CC2)nc2c(-c3ccc(-c4ccccc4)nc3)cnn12] | 560.12 | 561.60 | 3.09 |

TABLE-8A-continued
| Cpd ID | Structures | M + H (calculated) | M + H (observed) | Retention Time(min) |
|---|---|---|---|---|
| 8.73 | 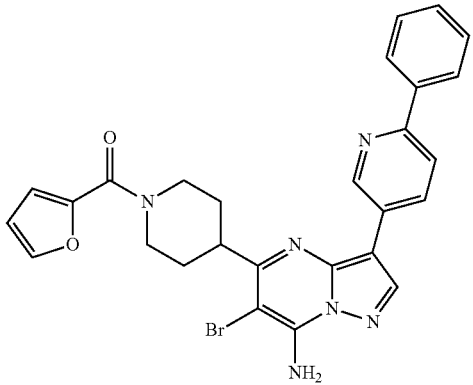 [SMILES: Nc1c(Br)c(C2CCN(C(=O)c3ccco3)CC2)nc2c(-c3ccc(-c4ccccc4)nc3)cnn12] | 542.10 | 543.56 | 3.95 |
| 8.74 | 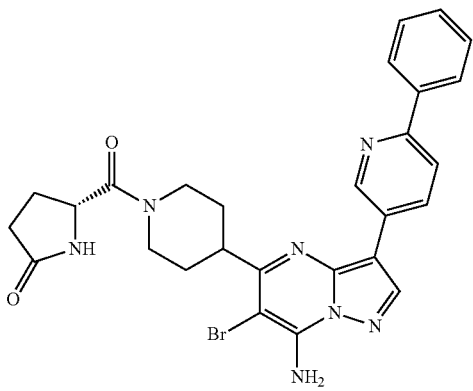 [SMILES: Nc1c(Br)c(C2CCN(C(=O)[C@H]3CCC(=O)N3)CC2)nc2c(-c3ccc(-c4ccccc4)nc3)cnn12] | 559.13 | 560.61 | 3.26 |
| 8.75 | 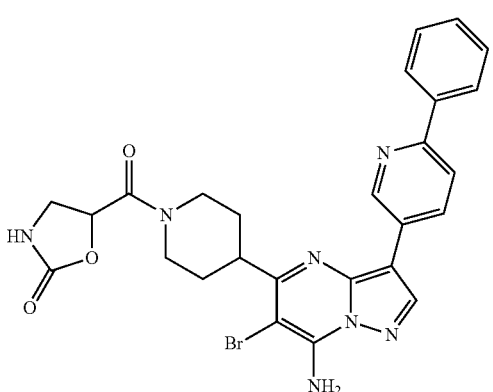 | 561.11 | 562.59 | 3.27 |
| 8.76 | 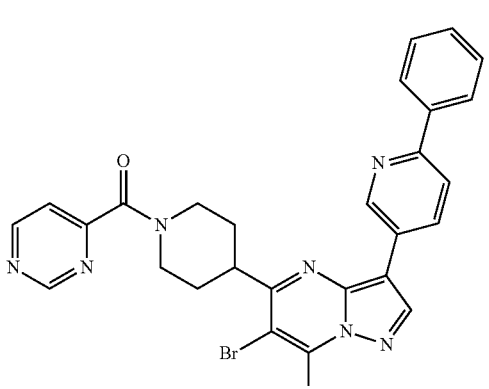 | 554.11 | 555.60 | 3.63 |

TABLE-8A-continued

| Cpd ID | Structures | M + H (calculated) | M + H (observed) | Retention Time(min) |
|---|---|---|---|---|
| 8.77 | 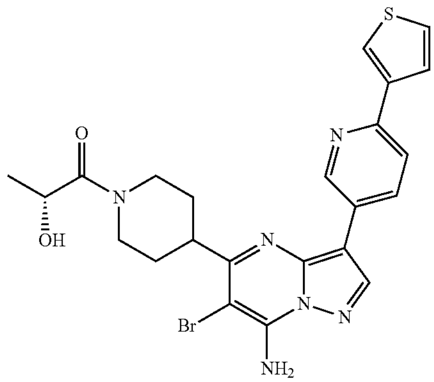 [SMILES: C[C@@H](O)C(=O)N1CCC(c2nc3c(-c4ccc(-c5ccsc5)nc4)cnn3c(N)c2Br)CC1] | 526.07 | 527.51 | 3.31 |
| 8.78 | 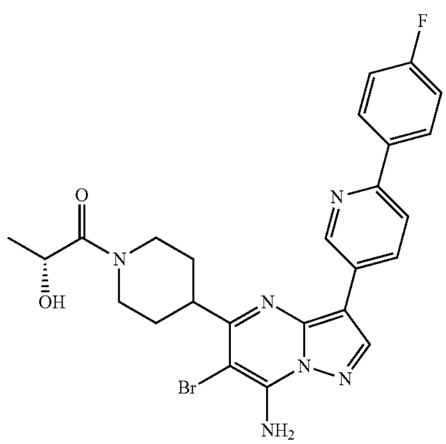 [SMILES: C[C@@H](O)C(=O)N1CCC(c2nc3c(-c4ccc(-c5ccc(F)cc5)nc4)cnn3c(N)c2Br)CC1] | 538.11 | 539.55 | 3.52 |
| 8.79 | 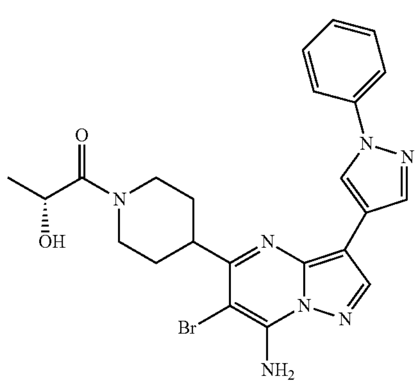 [SMILES: C[C@@H](O)C(=O)N1CCC(c2nc3c(-c4cnn(-c5ccccc5)c4)cnn3c(N)c2Br)CC1] | 509.11 | 510.52 | 4.29 |

TABLE-8A-continued

| Cpd ID | Structures | M + H (calculated) | M + H (observed) | Retention Time(min) |
|---|---|---|---|---|
| 8.80 | 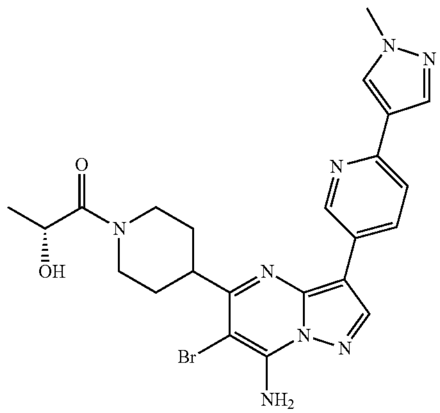 [SMILES: C[C@@H](O)C(=O)N1CCC(c2nc3c(-c4ccc(-c5cnn(C)c5)nc4)cnn3c(N)c2Br)CC1] | 524.12 | 525.57 | 3.03 |
| 8.81 | 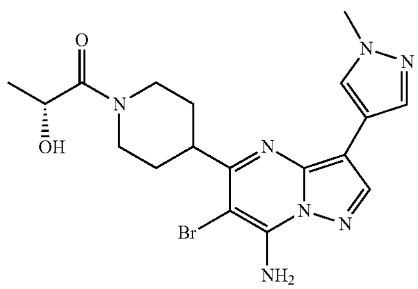 [SMILES: C[C@@H](O)C(=O)N1CCC(c2nc3c(-c4cnn(C)c4)cnn3c(N)c2Br)CC1] | 447.10 | 448.53 | 3.22 |
| 8.82 | 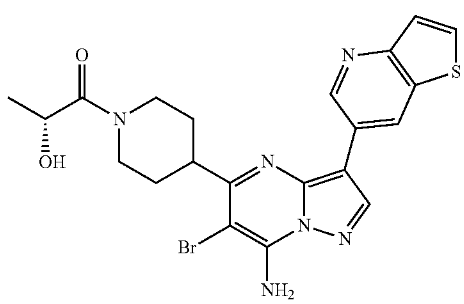 [SMILES: C[C@@H](O)C(=O)N1CCC(c2nc3c(-c4cnc5ccsc5c4)cnn3c(N)c2Br)CC1] | 484.08 | 485.52 | 3.00 |
| 8.83 | 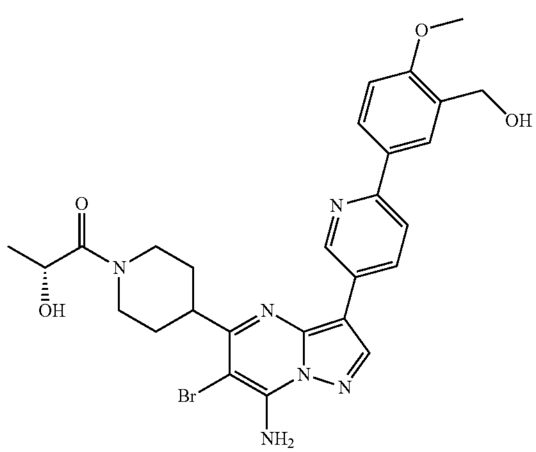 [SMILES: COc1ccc(-c2ccc(-c3cnn4c(N)c(Br)c(C5CCN(C(=O)[C@@H](C)O)CC5)nc34)cn2)cc1CO] | 580.14 | 581.63 | 3.25 |

TABLE-8A-continued
| Cpd ID | Structures | M + H (calculated) | M + H (observed) | Retention Time(min) |
|---|---|---|---|---|
| 8.84 | 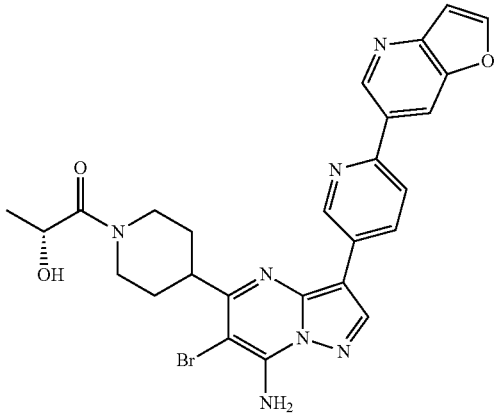 [SMILES: C[C@@H](O)C(=O)N1CCC(c2nc3c(-c4ccc(-c5cnc6ccoc6c5)nc4)cnn3c(N)c2Br)CC1] | 561.11 | 562.58 | 3.51 |
| 8.85 | 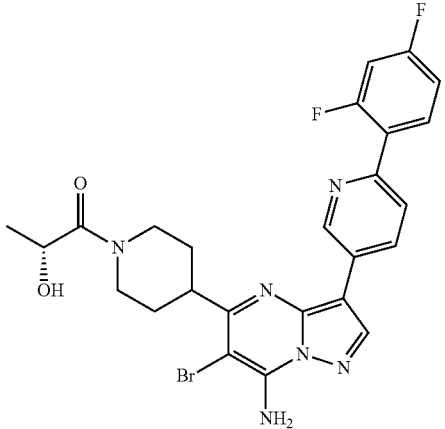 [SMILES: C[C@@H](O)C(=O)N1CCC(c2nc3c(-c4ccc(-c5ccc(F)cc5F)nc4)cnn3c(N)c2Br)CC1] | 556.10 | 557.56 | 3.77 |
| 8.86 | 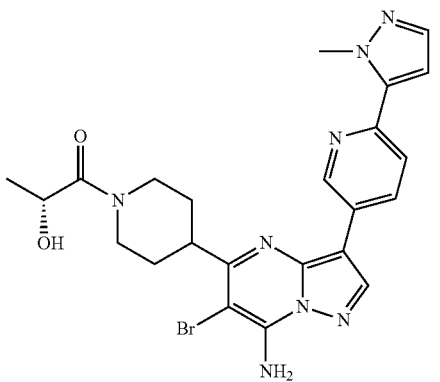 [SMILES: C[C@@H](O)C(=O)N1CCC(c2nc3c(-c4ccc(-c5ccnn5C)nc4)cnn3c(N)c2Br)CC1] | 524.12 | 525.59 | 3.58 |

TABLE-8A-continued
| Cpd ID | Structures | M + H (calculated) | M + H (observed) | Retention Time(min) |
|---|---|---|---|---|
| 8.87 | 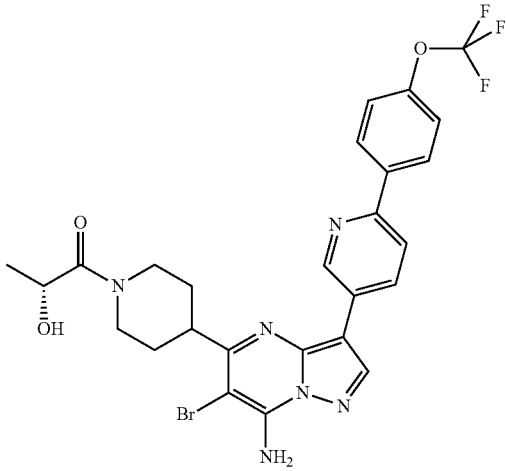 [SMILES: C[C@@H](O)C(=O)N1CCC(c2nc3c(-c4ccc(-c5ccc(OC(F)(F)F)cc5)nc4)cnn3c(N)c2Br)CC1] | 604.10 | 605.60 | 4.24 |
| 8.88 | 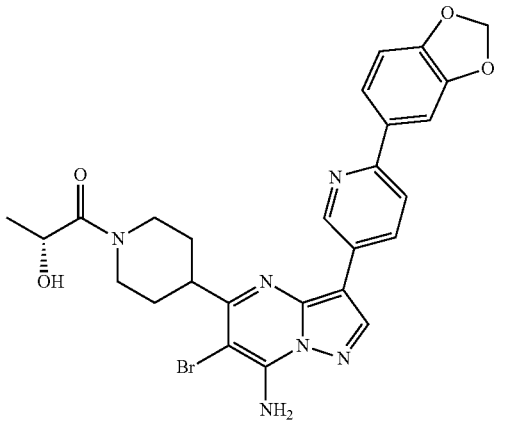 [SMILES: C[C@@H](O)C(=O)N1CCC(c2nc3c(-c4ccc(-c5ccc6c(c5)OCO6)nc4)cnn3c(N)c2Br)CC1] | 564.11 | 565.56 | 3.45 |
| 8.89 | 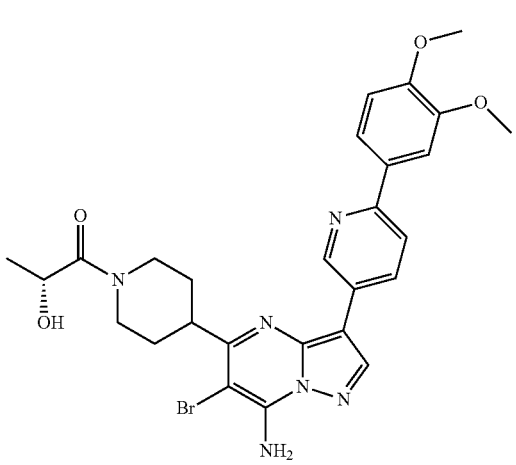 [SMILES: COc1ccc(-c2ccc(-c3cnn4c(N)c(Br)c(C5CCN(C(=O)[C@@H](C)O)CC5)nc34)cn2)cc1OC] | 580.14 | 581.60 | 3.46 |

1039

Synthesis of (R)-1-(4-(6-acetyl-7-amino-3-(6-phenylpyridin-3-yl)pyrazolo[1,5-a]pyrimidin-5-yl)piperidin-1-yl)-2-hydroxypropan-1-one

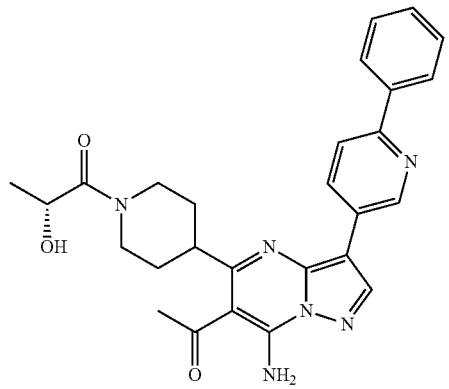 [SMILES: CC(=O)c1c(C2CCN(C(=O)[C@@H](C)O)CC2)nc2c(-c3ccc(-c4ccccc4)nc3)cnn2c1N]

Step 6

Preparation of tert-butyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)piperidine-1-carboxylate

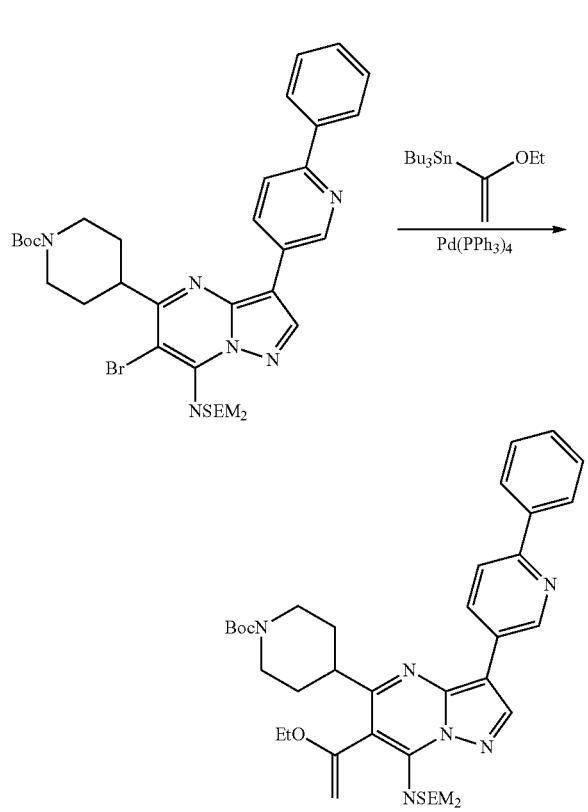

To a pressure flask were charged compound tert-butyl 4-(7-(bis((2-(trimethylsilyl)ethoxy)methyl)amino)-6-bromo-3-(6-phenylpyridin-3-yl)pyrazolo[1,5-a]pyrimidin-5-yl)piperidine-1-carboxylate (intermediate from Scheme-10A) (13.66 g, 16.86 mmol), tributyl (1-ethoxyvinyl)tin (11.4 mL, 33.74 mmols) and dioxane (150 ml). The flask was degassed with Ar briefly, capped and heated at 100 C with stirring overnight. After cooling, the reaction mixture was concentrated. The residue was taken into ether (200 ml), washed with 0.5 M KF (50 ml), brine and dried (MgSO$_4$). After solvent was removed under reduced pressure, the residue was purified on silica. Elution with EtOAc in hexanes (0-30%) gave compound tert-butyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)piperidine-1-carboxylate (11.55 g, 85%) as yellow form.

Step 7

Preparation of 1-(7-amino-3-(6-phenylpyridin-3-yl)-5-(piperidin-4-yl)pyrazolo[1,5-a]pyrimidin-6-yl)ethanone

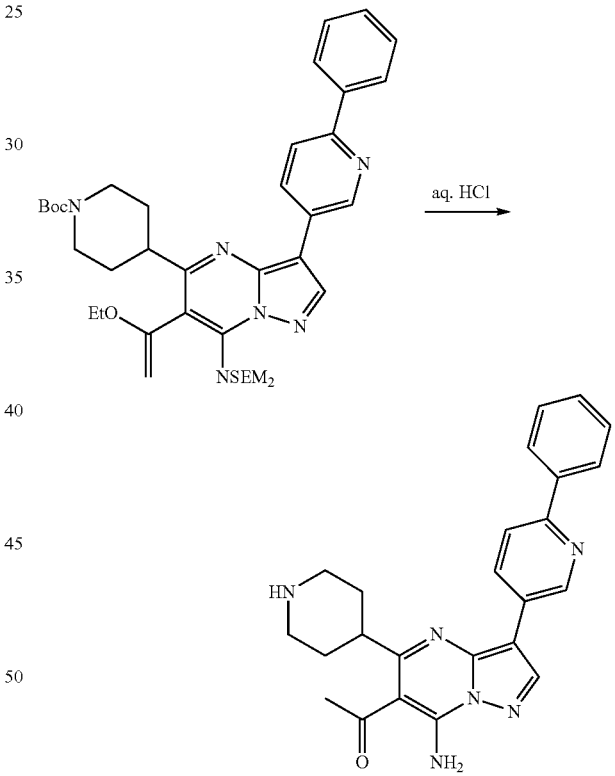

To a solution of tert-butyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)piperidine-1-carboxylate (11.5 g, 14.4 mmol) in dioxane (60 mL) was added 4M HCl in water (14.4 mL) at 0° C. After stirring for 30 min at 0° C., the reaction mixture was allowed to warm to rt in 1.5 hours. 4M HCl in dioxane (10 mL) was added. The reaction mixture was stirred at rt overnight. Solvent was removed in vacuo to get the desired product as an HCl salt (6.97 g).

Step 8

Preparation of (R)-1-(4-(6-acetyl-7-amino-3-(6-phenylpyridin-3-yl)pyrazolo[1,5-a]pyrimidin-5-yl)piperidin-1-yl)-2-hydroxypropan-1-one

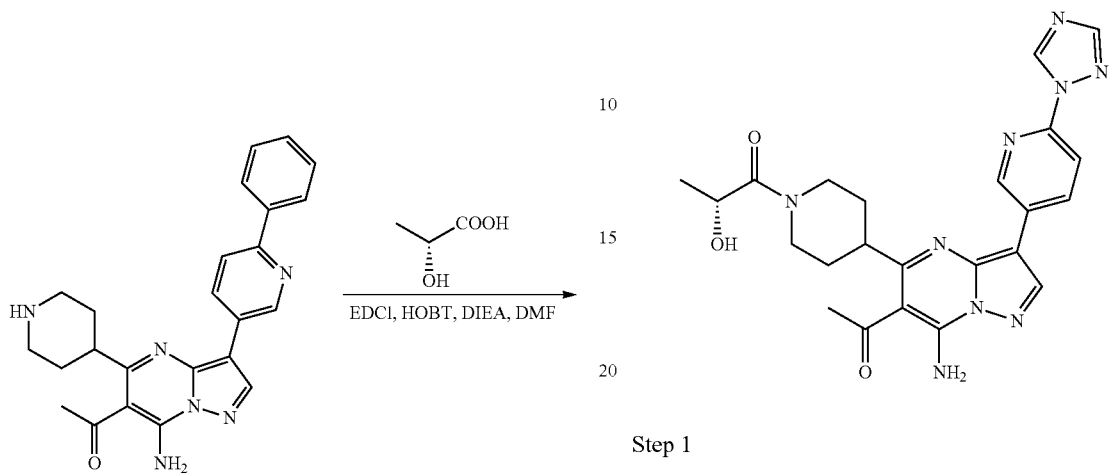

To a solution of 1-(7-amino-3-(6-phenylpyridin-3-yl)-5-(piperidin-4-yl)pyrazolo[1,5-a]pyrimidin-6-yl)ethanone hydrochloride (0.5 mmol), DIEA (350 µL, 2 mmol) in DMF (5 mL) was added a solution of D-lactic acid (45 mg, 0.5 mmol), HOBt (68 mg, 0.5 mmol), EDCI (144 mg, 0.75 mmol) in DMF (1 mL). The reaction was stirred at rt for 20 min. Another solution of solution of D-lactic acid (45 mg, 0.5 mmol), HOBt (68 mg, 0.5 mmol), EDCI (144 mg, 0.75 mmol) in DMF (2 mL) was added and stirred for 5 minutes. LC-MS indicated the reaction was complete and reaction mixture was directly purified by HPLC to furnish the title compound.

LC/MS RT=3.22 min. Mass calculated for M+H 485.2, observed 485.4.

Synthesis of (R)-1-(4-(3-(6-(1H-1,2,4-triazol-1-yl)pyridin-3-yl)-6-acetyl-7-aminopyrazolo[1,5-a]pyrimidin-5-yl)piperidin-1-yl)-2-hydroxypropan-1-one

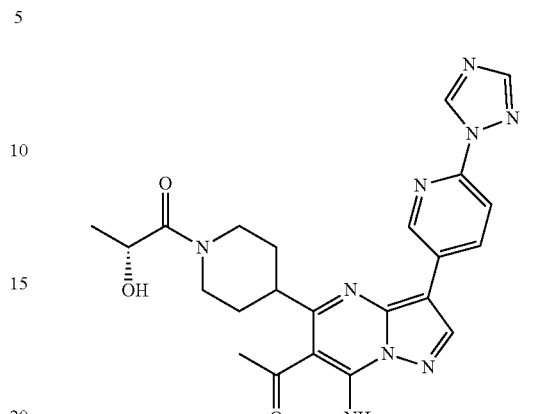

Step 1

Preparation of 5-bromo-2-(1H-1,2,4-triazol-1-yl)pyridine

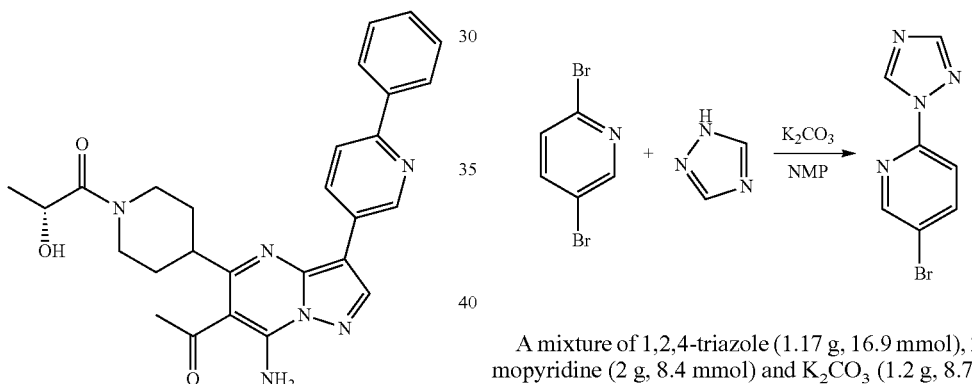

A mixture of 1,2,4-triazole (1.17 g, 16.9 mmol), 2,5-dibromopyridine (2 g, 8.4 mmol) and K₂CO₃ (1.2 g, 8.7 mmol) in NMP (20 mL) was heated at 100° C. with stirring for 5 hours. After cooling, the reaction mixture was poured into water (100 mL) and solid was collected by filtration and further purified by column chromatography on silica gel. Elution with EtOAc/Hexanes (0-50%) provided the title compound (250 mg, 13%).

Step 2

Preparation of 5-(4,4,5,5-tetramethyl-1,3,2-dioxaborolan-2-yl)-2-(1H-1,2,4-triazol-1-yl)pyridine

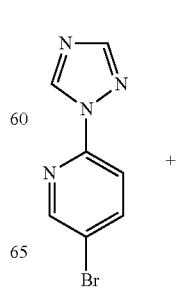

+

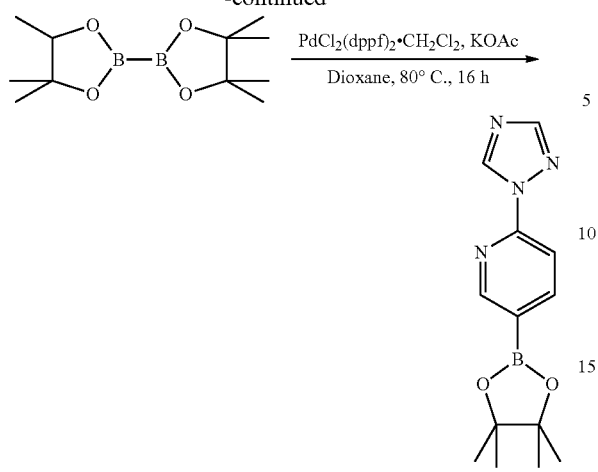

A mixture of 5-bromo-2-(1H-1,2,4-triazol-1-yl)pyridine (248 mg, 1.1 mmol), bis(pinacolato)diboron (337 mg, 1.4 mmol), KOAc (324 mg, 3.3 mmol), PdCl$_2$(dppf)$_2$·CH$_2$Cl$_2$ (45 mg, 0.06 mmol) in dioxane (4 mL) was flushed with Argon and stirred at 80° C. for 16 h. On cooling, the solvent was rotoevaporated, and the crude was redissolved in dichloromethane (20 mL), washed with water (3×10 ml), brine (1×101 ml), and dried over MgSO$_4$. Solvent was removed in vacuo and the residue was triturated with hexanes to provide the title compound (287 mg, 96%).

Step 3

Preparation of tert-butyl 4-(3-(6-(1H-1,2,4-triazol-1-yl)pyridin-3-yl)-7-(bis((2-(trimethylsilyl)ethoxy)methyl)amino)pyrazolo[1,5-a]pyrimidin-5-yl)piperidine-1-carboxylate

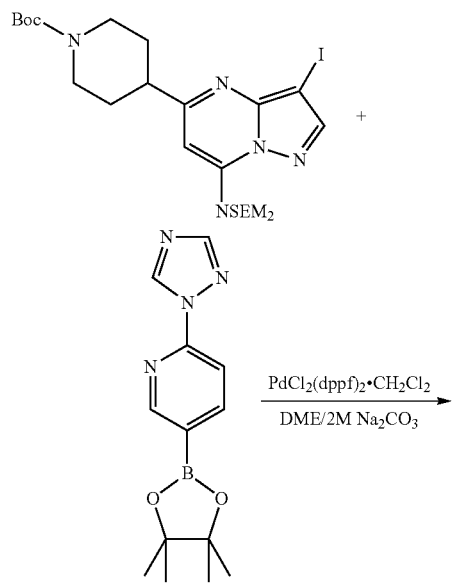

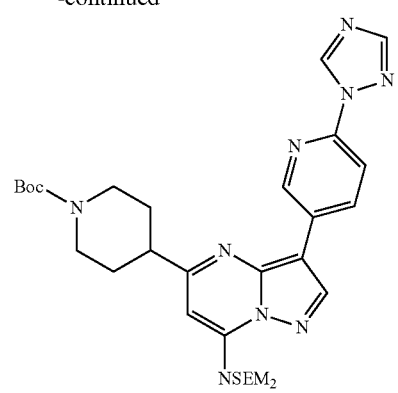

To a pressure tube were charged tert-butyl 4-(7-(bis((2-(trimethylsilyl)ethoxy)methyl)amino)-3-iodopyrazolo[1,5-a]pyrimidin-5-yl)piperidine-1-carboxylate (563 mg, 0.8 mmol), 5-(4,4,5,5-tetramethyl-1,3,2-dioxaborolan-2-yl)-2-(1H-1,2,4-triazol-1-yl)pyridine (287 mg, 1.1 mmol), PdCl$_2$(dppf)$_2$·CH$_2$Cl$_2$ (29 mg, 0.04 mmol), DME (6 mL) and 2M Na$_2$CO$_3$ (2 mL). The resulting mixture was briefly degassed with Argon; the tube was capped, and heated with stirring under 80° C. overnight. After cooling, solvent was removed. The residue was diluted with EtOAc (20 ml), and organic layer was isolated, washed with brine and dried (MgSO$_4$). After concentration under reduced pressure, the residue was purified on silica gel eluting with EtOAc/Hexanes (0-50%) to provide the title compound (370 mg, 64%).

Step 4

Synthesis of (R)-1-(4-(3-(6-(1H-1,2,4-triazol-1-yl)pyridin-3-yl)-6-acetyl-7-aminopyrazolo[1,5-a]pyrimidin-5-yl)piperidin-1-yl)-2-hydroxypropan-1-one The rest of the synthesis is similar to the synthesis of (R)-1-(4-(6-acetyl-7-amino-3-(6-phenylpyridin-3-yl)pyrazolo[1,5-a]pyrimidin-5-yl)piperidin-1-yl)-2-hydroxypropan-1-one.

Synthesis of 1-(7-amino-5-(1-methylpiperidin-4-yl)-3-(6-phenylpyridin-3-yl)pyrazolo[1,5-a]pyrimidin-6-yl)ethanone

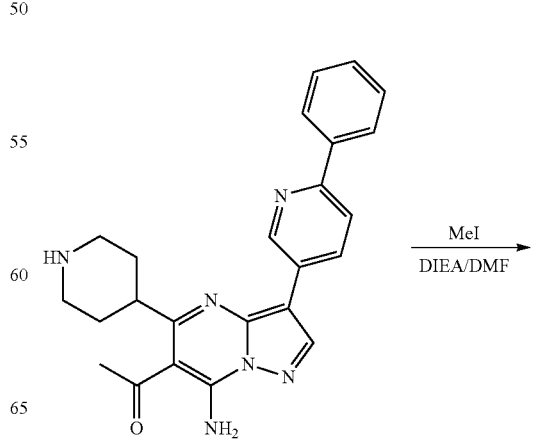

1045
-continued

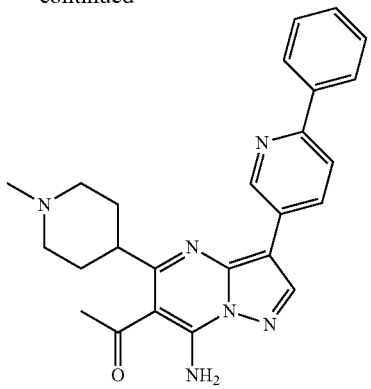

1046

To a solution of 1-(7-amino-3-(6-phenylpyridin-3-yl)-5-(piperidin-4-yl)pyrazolo[1,5-a]pyrimidin-6-yl)ethanone (25 mg, 0.06 mmol), DEA (52 μL, 0.3 mmol) in DMF (1 mL) was added MeI (15 μL, 0.24 mmol). The reaction mixture was stirred for one hour and directly purified by HPLC to provide the title compound. LC/MS RT=2.76 min. Mass calculated for M+H 427.2, observed 427.3.

General methods described above, compounds in the table 8-B can be synthesized.

TABLE- 8B

| Compound ID | Structures | M + H (calculated) | M + H (observed) | Retention Time(min) |
|---|---|---|---|---|
| 8.90 | 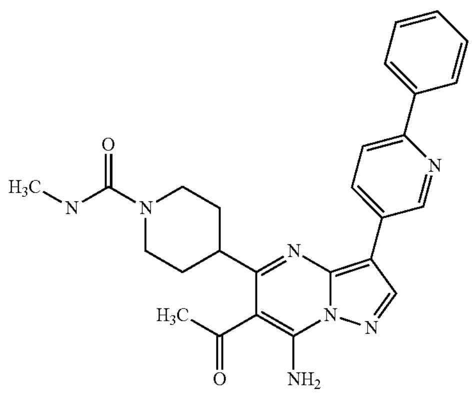 [SMILES: CNC(=O)N1CCC(c2nc3c(-c4ccc(-c5ccccc5)nc4)cnn3c(N)c2C(C)=O)CC1] | 470.2 | 470.2 | 3.37 |
| 8.91 | 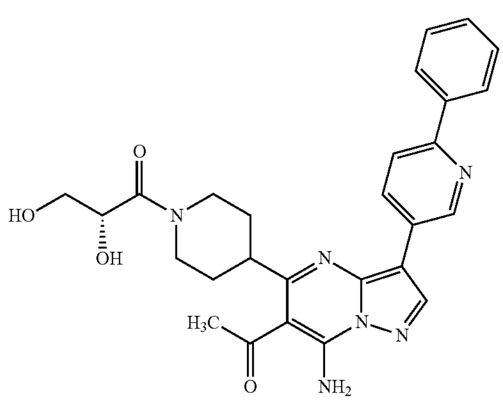 [SMILES: CC(=O)c1c(C2CCN(C(=O)[C@H](O)CO)CC2)nc2c(-c3ccc(-c4ccccc4)nc3)cnn2c1N] | 501.2 | 501.3 | 2.95 |

TABLE- 8B-continued

| Compound ID | Structures | M + H (calculated) | M + H (observed) | Retention Time(min) |
|---|---|---|---|---|
| 8.92 | 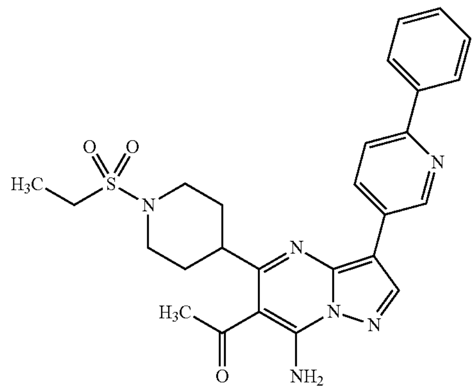 [SMILES: CCS(=O)(=O)N1CCC(c2nc3c(-c4ccc(-c5ccccc5)nc4)cnn3c(N)c2C(C)=O)CC1] | 505.2 | 505.2 | 3.78 |
| 8.93 | 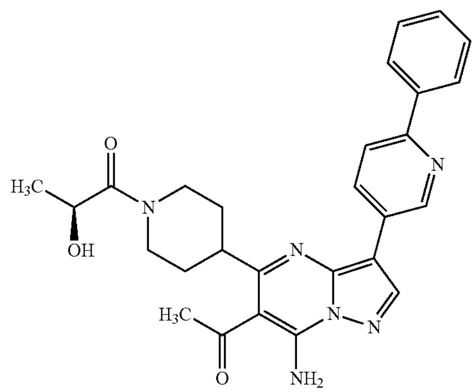 [SMILES: CC(=O)c1c(C2CCN(C(=O)[C@H](C)O)CC2)nc2c(-c3ccc(-c4ccccc4)nc3)cnn2c1N] | 485.2 | 485.3 | 3.24 |
| 8.94 | 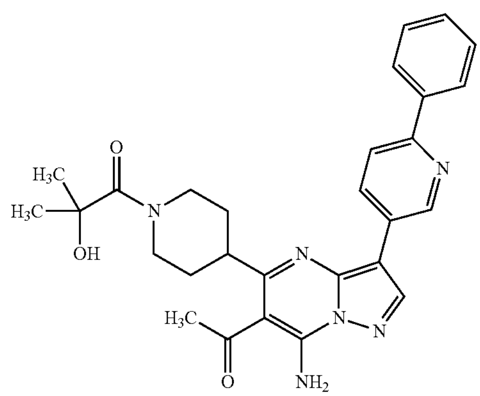 [SMILES: CC(=O)c1c(C2CCN(C(=O)C(C)(C)O)CC2)nc2c(-c3ccc(-c4ccccc4)nc3)cnn2c1N] | 499.2 | 499.3 | 3.48 |
| 8.95 | 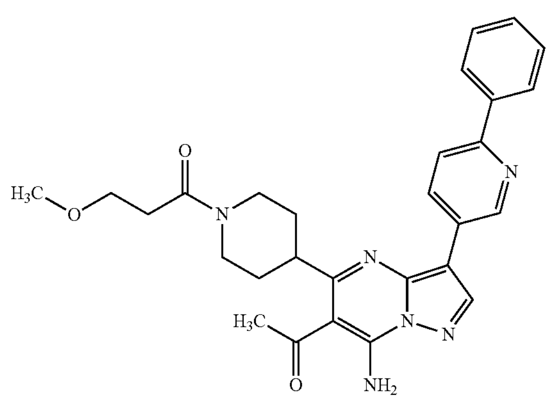 [SMILES: COCCC(=O)N1CCC(c2nc3c(-c4ccc(-c5ccccc5)nc4)cnn3c(N)c2C(C)=O)CC1] | 499.2 | 499.3 | 3.49 |

TABLE- 8B-continued

| Compound ID | Structures | M + H (calculated) | M + H (observed) | Retention Time(min) |
|---|---|---|---|---|
| 8.96 | 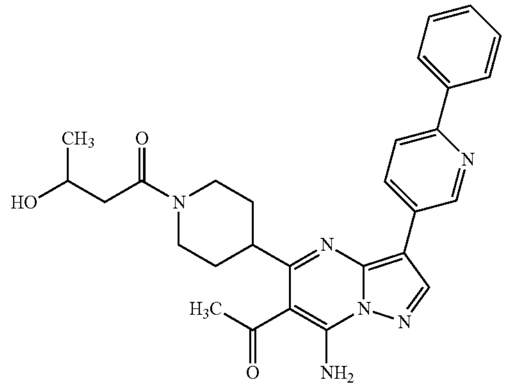 [SMILES: CC(=O)c1c(C2CCN(C(=O)CC(C)O)CC2)nc2c(-c3ccc(-c4ccccc4)nc3)cnn2c1N] | 499.2 | 499.3 | 3.30 |
| 8.97 | 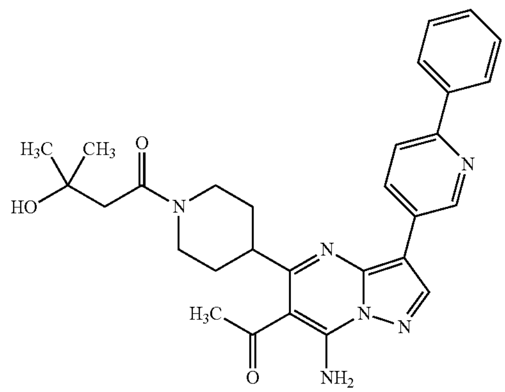 [SMILES: CC(=O)c1c(C2CCN(C(=O)CC(C)(C)O)CC2)nc2c(-c3ccc(-c4ccccc4)nc3)cnn2c1N] | 513.3 | 513.1 | 3.31 |
| 8.98 | 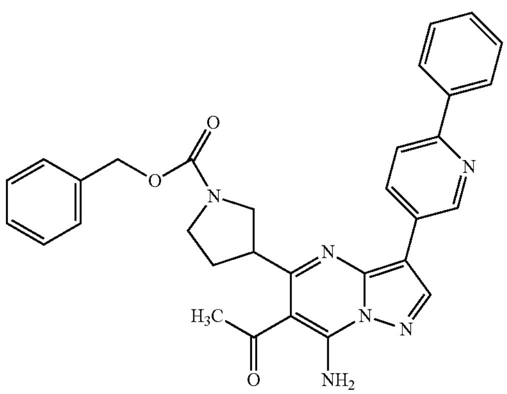 [SMILES: CC(=O)c1c(C2CCN(C(=O)OCc3ccccc3)C2)nc2c(-c3ccc(-c4ccccc4)nc3)cnn2c1N] | 533.2 | 533.7 | 4.42 |
| 8.99 | 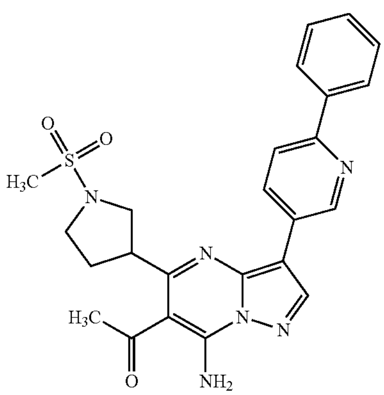 [SMILES: CC(=O)c1c(C2CCN(S(C)(=O)=O)C2)nc2c(-c3ccc(-c4ccccc4)nc3)cnn2c1N] | 477.2 | 477.6 | 3.42 |

TABLE- 8B-continued

| Compound ID | Structures | M + H (calculated) | M + H (observed) | Retention Time(min) |
|---|---|---|---|---|
| 8.100 | 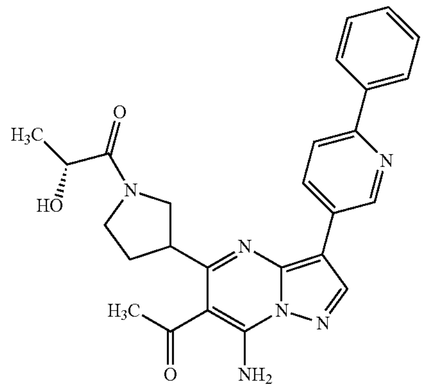 [SMILES: CC(=O)c1c(C2CCN(C(=O)[C@@H](C)O)C2)nc2c(-c3ccc(-c4ccccc4)nc3)cnn2c1N] | 471.2 | 471.6 | 3.14 |
| 8.101 | 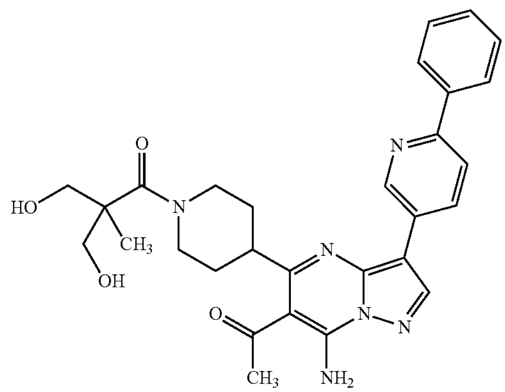 [SMILES: CC(=O)c1c(C2CCN(C(=O)C(C)(CO)CO)CC2)nc2c(-c3ccc(-c4ccccc4)nc3)cnn2c1N] | 529.2 | 529.7 | 3.14 |
| 8.102 | 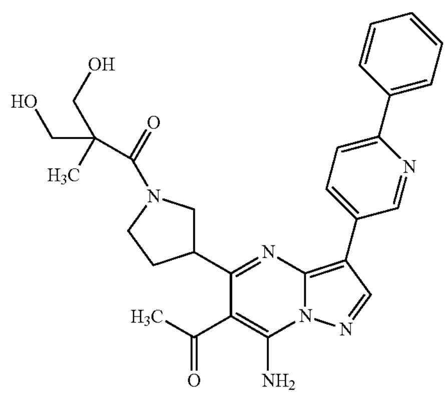 [SMILES: CC(=O)c1c(C2CCN(C(=O)C(C)(CO)CO)C2)nc2c(-c3ccc(-c4ccccc4)nc3)cnn2c1N] | 515.2 | 515.7 | 2.98 |
| 8.103 | 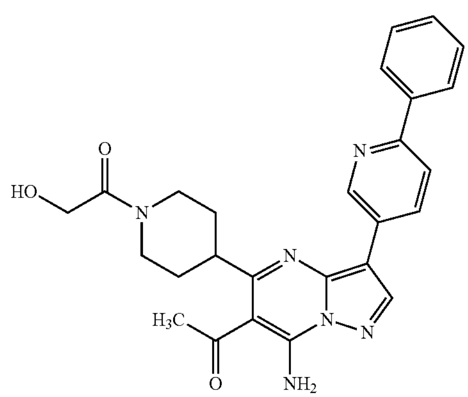 [SMILES: CC(=O)c1c(C2CCN(C(=O)CO)CC2)nc2c(-c3ccc(-c4ccccc4)nc3)cnn2c1N] | 471.2 | 471.7 | 3.07 |

TABLE- 8B-continued
| Compound ID | Structures | M + H (calculated) | M + H (observed) | Retention Time(min) |
|---|---|---|---|---|
| 8.104 | 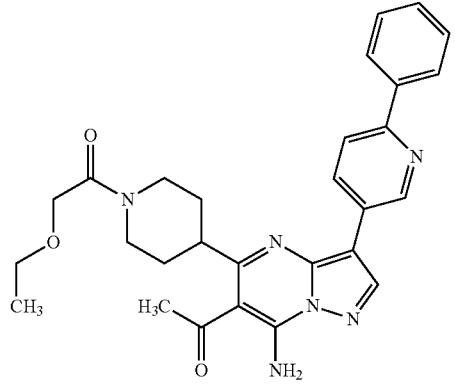 [SMILES: CCOCC(=O)N1CCC(c2nc3c(-c4ccc(-c5ccccc5)nc4)cnn3c(N)c2C(C)=O)CC1] | 499.2 | 499.7 | 3.50 |
| 8.105 | 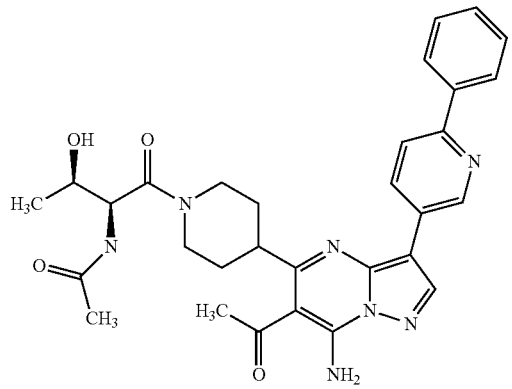 [SMILES: CC(=O)N[C@H](C(=O)N1CCC(c2nc3c(-c4ccc(-c5ccccc5)nc4)cnn3c(N)c2C(C)=O)CC1)[C@@H](C)O] | 556.3 | 556.7 | 3.08 |
| 8.106 | 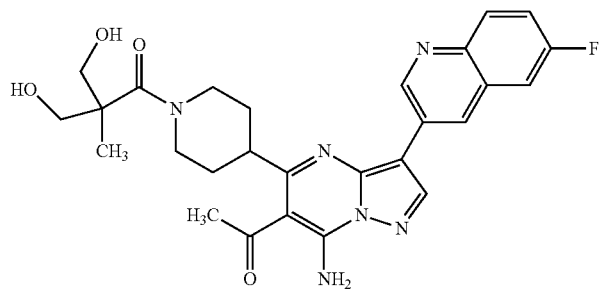 [SMILES: CC(=O)c1c(C2CCN(C(=O)C(C)(CO)CO)CC2)nc2c(-c3cnc4ccc(F)cc4c3)cnn2c1N] | 521.2 | 521.2 | 1.22 |
| 8.107 | 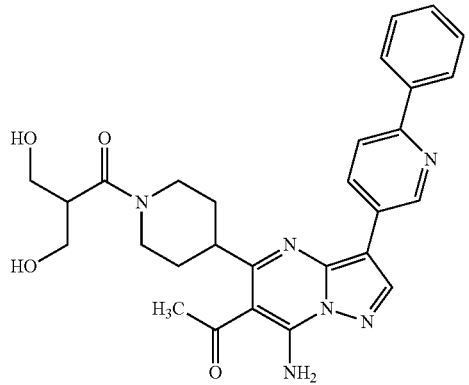 [SMILES: CC(=O)c1c(C2CCN(C(=O)C(CO)CO)CC2)nc2c(-c3ccc(-c4ccccc4)nc3)cnn2c1N] | 515.2 | 515.2 | 2.92 |

TABLE- 8B-continued

| Compound ID | Structures | M + H (calculated) | M + H (observed) | Retention Time(min) |
|---|---|---|---|---|
| 8.108 | 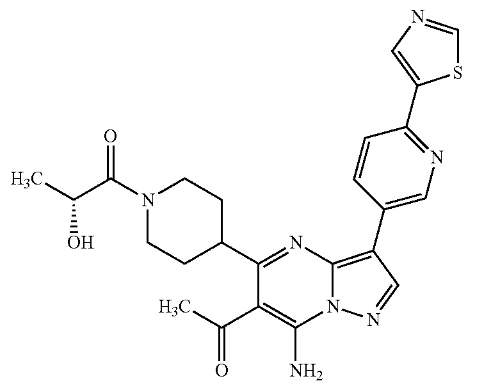 [SMILES: CC(=O)c1c(C2CCN(C(=O)[C@@H](C)O)CC2)nc2c(-c3ccc(-c4cncs4)nc3)cnn2c1N] | 492.2 | 492.6 | 3.48 |
| 8.109 | 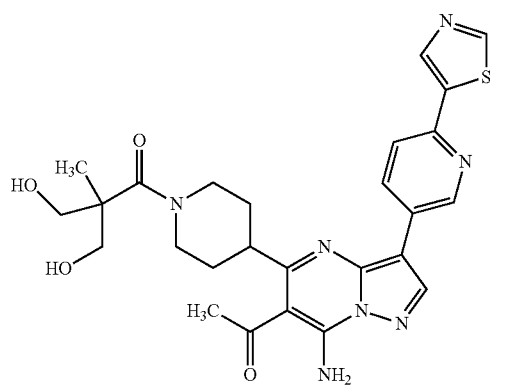 [SMILES: CC(=O)c1c(C2CCN(C(=O)C(C)(CO)CO)CC2)nc2c(-c3ccc(-c4cncs4)nc3)cnn2c1N] | 536.2 | 536.2 | 2.75 |
| 8.110 | 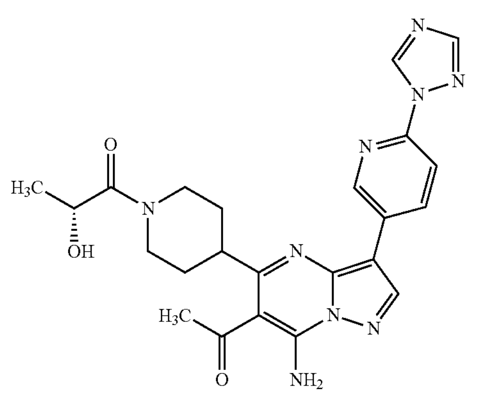 [SMILES: CC(=O)c1c(C2CCN(C(=O)[C@@H](C)O)CC2)nc2c(-c3ccc(-n4cncn4)nc3)cnn2c1N] | 476.2 | 476.2 | 3.50 |
| 8.111 | 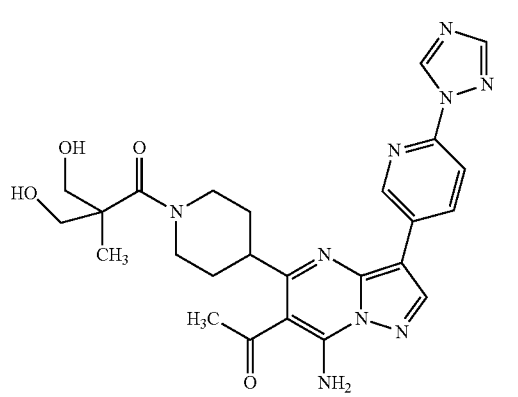 [SMILES: CC(=O)c1c(C2CCN(C(=O)C(C)(CO)CO)CC2)nc2c(-c3ccc(-n4cncn4)nc3)cnn2c1N] | 520.2 | 520.3 | 2.70 |

TABLE- 8B-continued
| Compound ID | Structures | M + H (calculated) | M + H (observed) | Retention Time(min) |
|---|---|---|---|---|
| 8.112 | 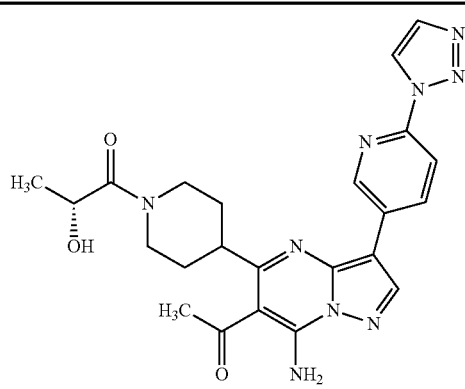 | 476.2 | 476.2 | 2.70 |
| 8.113 | 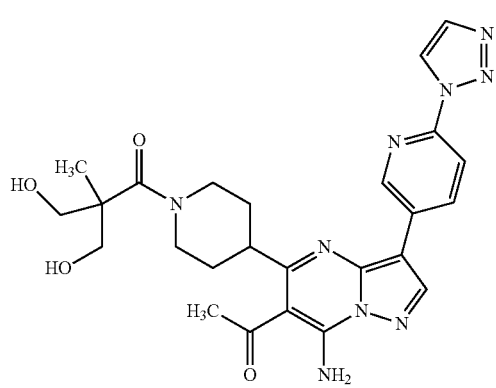 [SMILES: CC(=O)c1c(C2CCN(C(=O)C(C)(CO)CO)CC2)nc2c(-c3ccc(-n4ccnn4)nc3)cnn2c1N] | 520.2 | 520.3 | 2.64 |
| 8.114 | 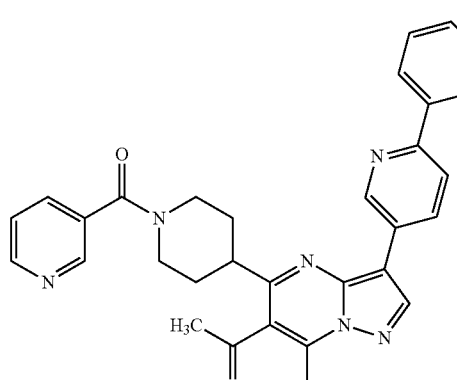 | 518.2 | 518 | 3.27 |
| 8.115 | 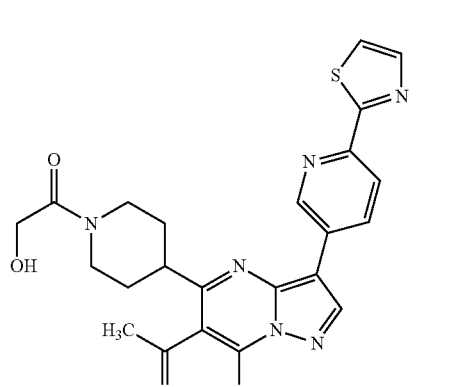 | 478.2 | 477.9 | 4.03 |

TABLE- 8B-continued
| Compound ID | Structures | M + H (calculated) | M + H (observed) | Retention Time(min) |
|---|---|---|---|---|
| 8.116 | 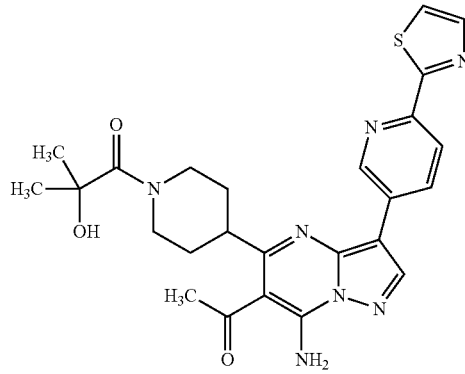 | 506.2 | 505.8 | 4.50 |
| 8.117 | 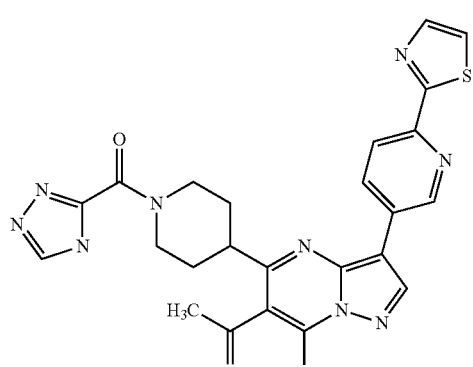 | 515.2 | 514.9 | 3.79 |
| 8.118 | 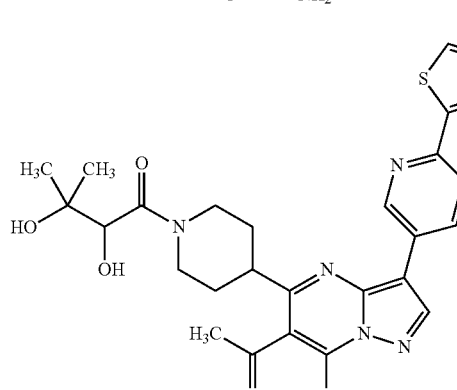 | 536.2 | 535.9 | 4.07 |
| 8.119 | 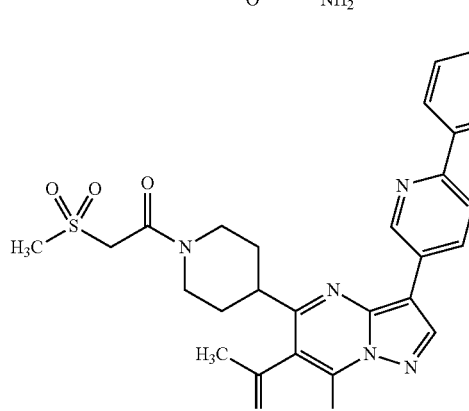 | 532.18 | 533.67 | 3.18 |

TABLE- 8B-continued

| Compound ID | Structures | M + H (calculated) | M + H (observed) | Retention Time(min) |
| --- | --- | --- | --- | --- |
| 8.120 | 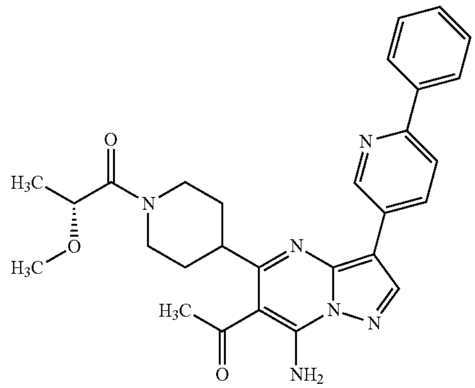 [SMILES: CO[C@H](C)C(=O)N1CCC(c2nc3c(-c4ccc(-c5ccccc5)nc4)cnn3c(N)c2C(C)=O)CC1] | 498.23 | 499.68 | 3.53 |
| 8.121 | 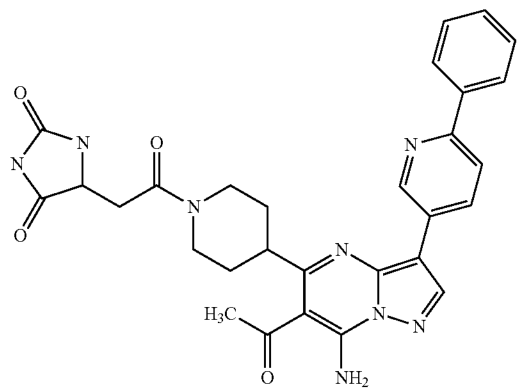 [SMILES: CC(=O)c1c(C2CCN(C(=O)CC3NC(=O)NC3=O)CC2)nc2c(-c3ccc(-c4ccccc4)nc3)cnn2c1N] | 552.22 | 553.69 | 2.96 |
| 8.122 | 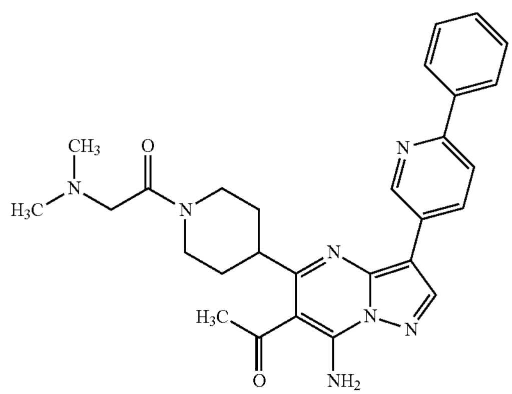 [SMILES: CC(=O)c1c(C2CCN(C(=O)CN(C)C)CC2)nc2c(-c3ccc(-c4ccccc4)nc3)cnn2c1N] | 497.25 | 498.1 | 3.09 |
| 8.123 | 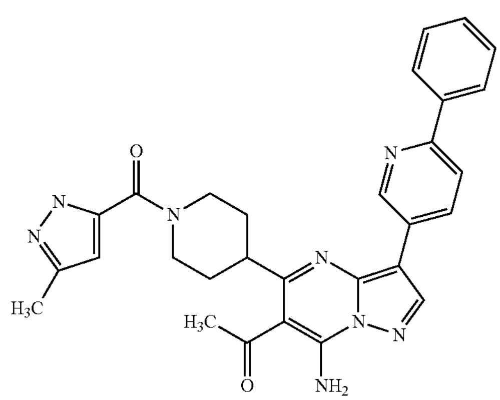 | 520.23 | 521.70 | 3.38 |

TABLE-8B-continued

| Compound ID | Structures | M + H (calculated) | M + H (observed) | Retention Time(min) |
|---|---|---|---|---|
| 8.124 | 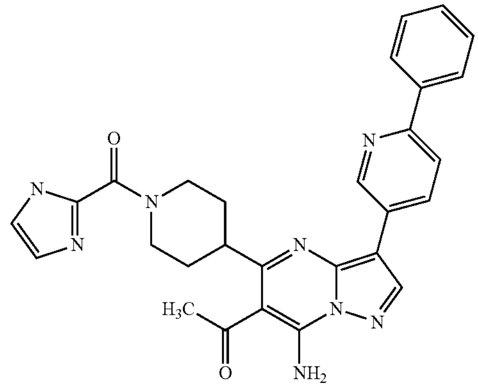 [SMILES: CC(=O)c1c(C2CCN(C(=O)c3ncc[nH]3)CC2)nc2c(-c3ccc(-c4ccccc4)nc3)cnn2c1N] | 506.21 | 507.68 | 3.01 |
| 8.125 | 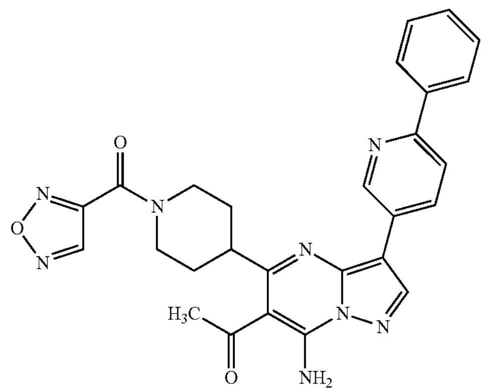 [SMILES: CC(=O)c1c(C2CCN(C(=O)c3cnon3)CC2)nc2c(-c3ccc(-c4ccccc4)nc3)cnn2c1N] | 508.19 | 509.65 | 3.46 |
| 8.126 | 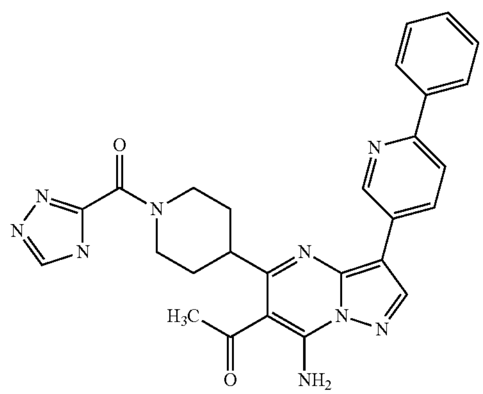 [SMILES: CC(=O)c1c(C2CCN(C(=O)c3nnc[nH]3)CC2)nc2c(-c3ccc(-c4ccccc4)nc3)cnn2c1N] | 507.21 | 508.68 | 3.01 |
| 8.127 | 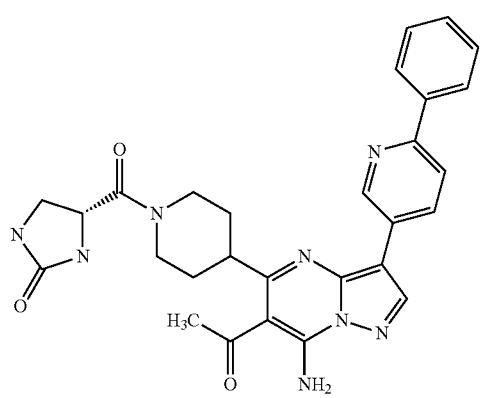 | 524.22 | 525.69 | 2.89 |

TABLE-8B-continued

| Compound ID | Structures | M + H (calculated) | M + H (observed) | Retention Time(min) |
|---|---|---|---|---|
| 8.128 | 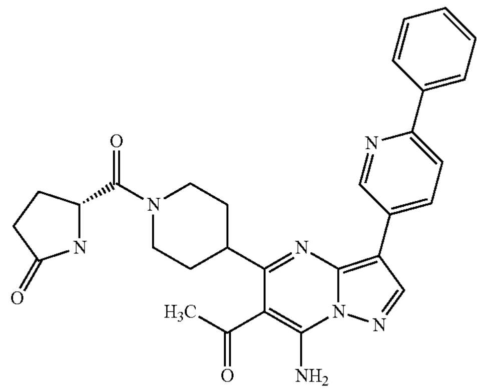 [SMILES: CC(=O)c1c(C2CCN(C(=O)[C@H]3CCC(=O)N3)CC2)nc2c(-c3ccc(-c4ccccc4)nc3)cnn2c1N] | 523.23 | 524.69 | 3.05 |
| 8.129 | 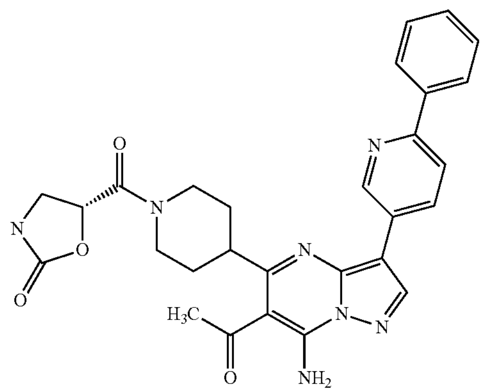 | 525.21 | 526.66 | 3.05 |
| 8.130 | 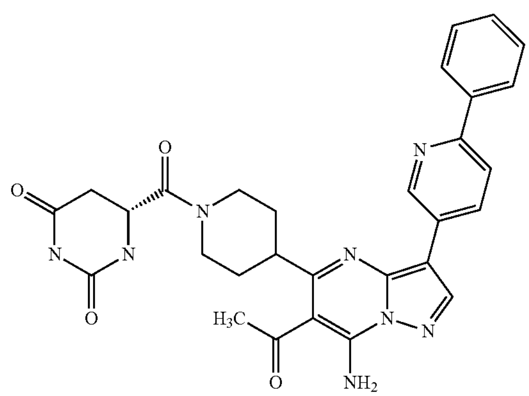 [SMILES: CC(=O)c1c(C2CCN(C(=O)[C@H]3CC(=O)NC(=O)N3)CC2)nc2c(-c3ccc(-c4ccccc4)nc3)cnn2c1N] | 552.22 | 553.69 | 2.85 |
| 8.131 | 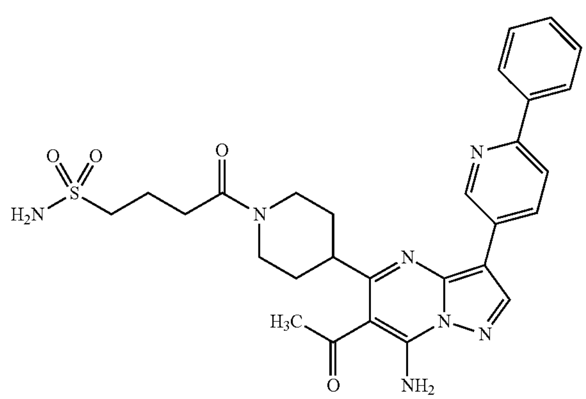 [SMILES: CC(=O)c1c(C2CCN(C(=O)CCCS(N)(=O)=O)CC2)nc2c(-c3ccc(-c4ccccc4)nc3)cnn2c1N] | 561.21 | 562.70 | 3.03 |

TABLE- 8B-continued
| Compound ID | Structures | M + H (calculated) | M + H (observed) | Retention Time(min) |
|---|---|---|---|---|
| 8.132 | 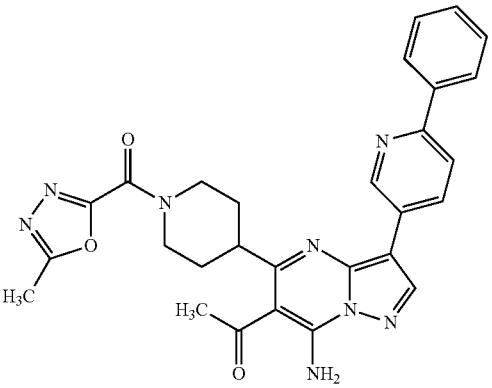 [SMILES: CC(=O)c1c(C2CCN(C(=O)c3nnc(C)o3)CC2)nc2c(-c3ccc(-c4ccccc4)nc3)cnn2c1N] | 522.21 | 523.69 | 3.39 |
| 8.133 | 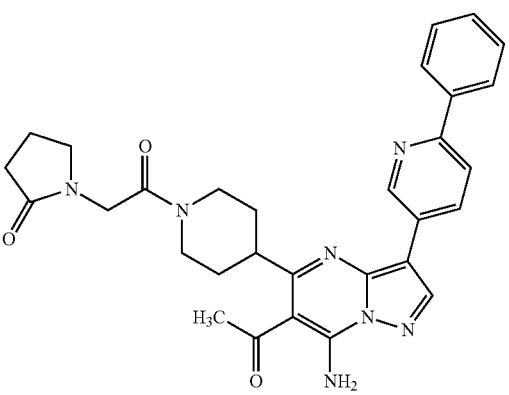 [SMILES: CC(=O)c1c(C2CCN(C(=O)CN3CCCC3=O)CC2)nc2c(-c3ccc(-c4ccccc4)nc3)cnn2c1N] | 537.24 | 538.71 | 3.46 |
| 8.134 | 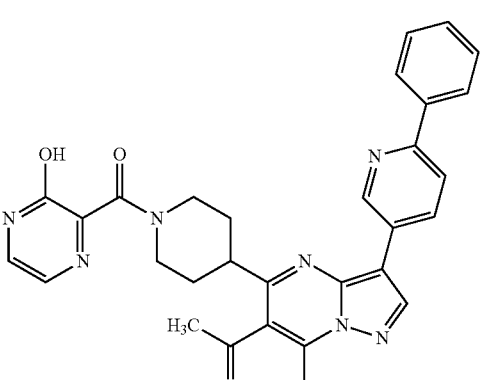 | 534.21 | 535.66 | 2.98 |
| 8.135 | 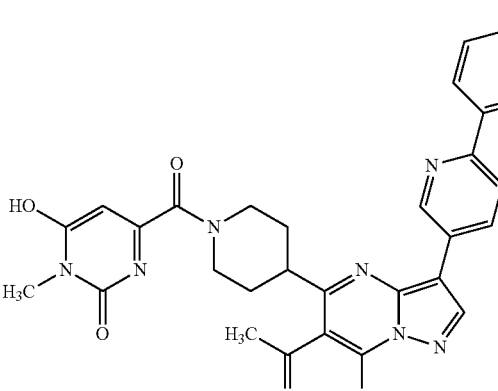 | 564.22 | 565.70 | 3.18 |

TABLE- 8B-continued

| Compound ID | Structures | M + H (calculated) | M + H (observed) | Retention Time(min) |
|---|---|---|---|---|
| 8.136 | 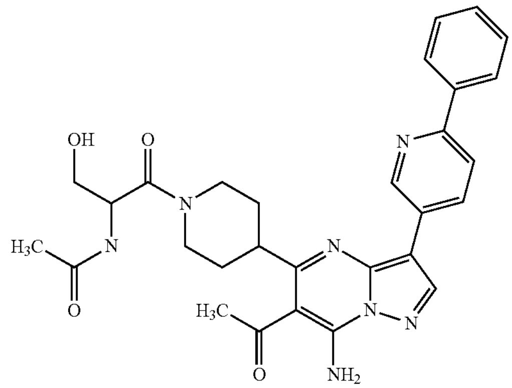 [SMILES: CC(=O)NC(CO)C(=O)N1CCC(c2nc3c(-c4ccc(-c5ccccc5)nc4)cnn3c(N)c2C(C)=O)CC1] | 541.24 | 542.67 | 2.98 |
| 8.137 | 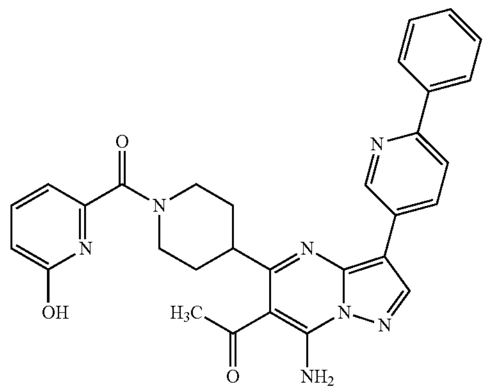 [SMILES: CC(=O)c1c(C2CCN(C(=O)c3cccc(O)n3)CC2)nc2c(-c3ccc(-c4ccccc4)nc3)cnn2c1N] | 533.21 | 534.67 | 3.18 |
| 8.138 | 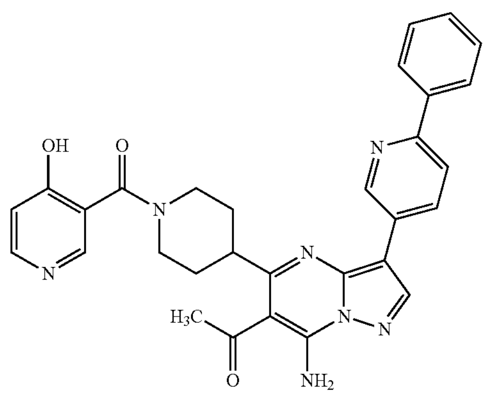 | 533.21 | 534.68 | 2.97 |
| 8.139 | 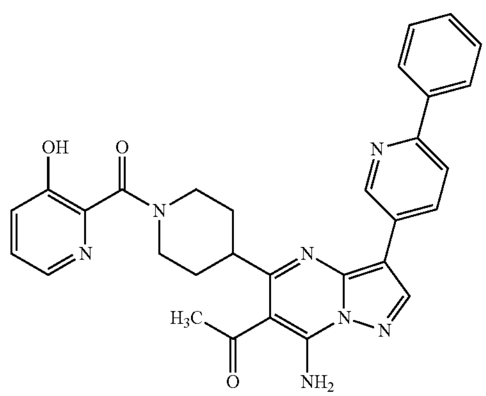 [SMILES: CC(=O)c1c(C2CCN(C(=O)c3ncccc3O)CC2)nc2c(-c3ccc(-c4ccccc4)nc3)cnn2c1N] | 533.21 | 534.59 | 3.28 |

TABLE- 8B-continued
| Compound ID | Structures | M + H (calculated) | M + H (observed) | Retention Time(min) |
|---|---|---|---|---|
| 8.140 | 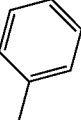 | 533.21 | 534.67 | 2.84 |
| 8.141 | 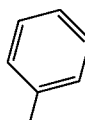 | 522.22 | 523.65 | 2.79 |
| 8.142 | 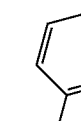 | 539.26 | 540.78 | 2.75 |
| 8.143 | 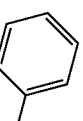 | 532.23 | 533.63 | 3.15 |

TABLE- 8B-continued

| Compound ID | Structures | M + H (calculated) | M + H (observed) | Retention Time(min) |
|---|---|---|---|---|
| 8.144 | 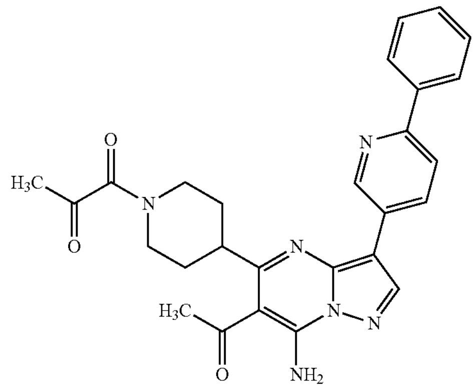 [SMILES: CC(=O)C(=O)N1CCC(c2nc3c(-c4ccc(-c5ccccc5)nc4)cnn3c(N)c2C(C)=O)CC1] | 482.20 | 482.94 | 3.68 |
| 8.145 | 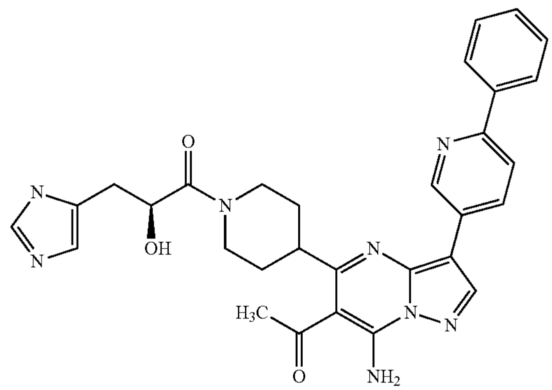 [SMILES: CC(=O)c1c(C2CCN(C(=O)[C@@H](O)Cc3cnc[nH]3)CC2)nc2c(-c3ccc(-c4ccccc4)nc3)cnn2c1N] | 550.24 | 550.98 | 2.67 |
| 8.146 | 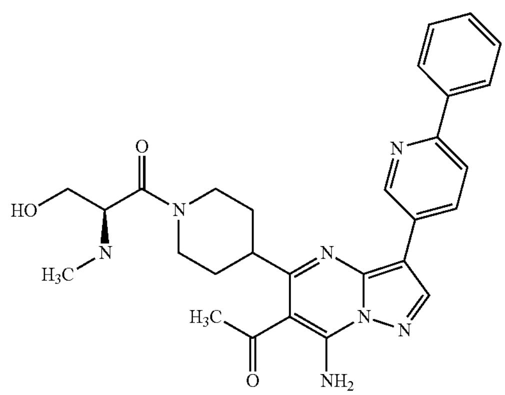 [SMILES: CN[C@@H](CO)C(=O)N1CCC(c2nc3c(-c4ccc(-c5ccccc5)nc4)cnn3c(N)c2C(C)=O)CC1] | 513.24 | 514.01 | 2.65 |
| 8.147 | 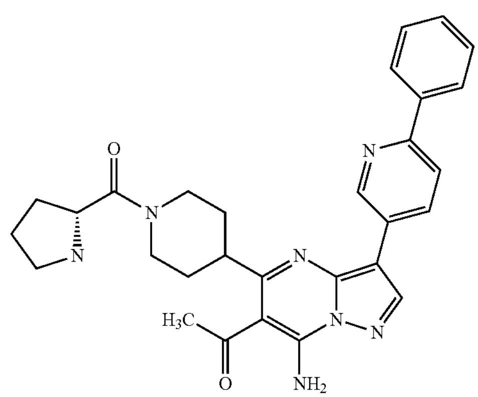 [SMILES: CC(=O)c1c(C2CCN(C(=O)[C@H]3CCCN3)CC2)nc2c(-c3ccc(-c4ccccc4)nc3)cnn2c1N] | 509.25 | 510.01 | 2.83 |

TABLE- 8B-continued

| Compound ID | Structures | M + H (calculated) | M + H (observed) | Retention Time(min) |
| --- | --- | --- | --- | --- |
| 8.148 | 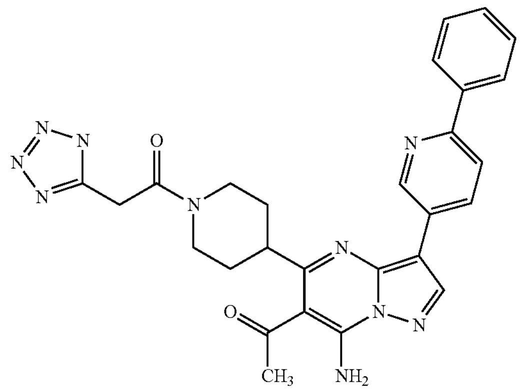 [SMILES: CC(=O)c1c(C2CCN(C(=O)Cc3nnn[nH]3)CC2)nc2c(-c3ccc(-c4ccccc4)nc3)cnn2c1N] | 522.22 | 523.21 | 3.18 |
| 8.149 | 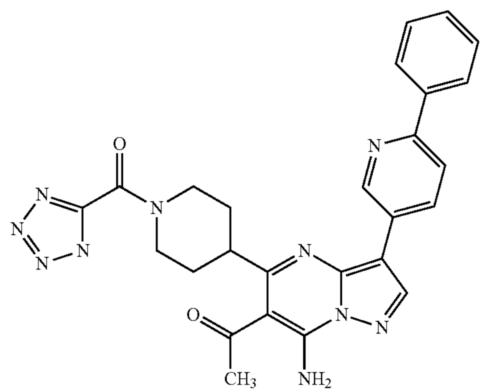 [SMILES: CC(=O)c1c(C2CCN(C(=O)c3nnn[nH]3)CC2)nc2c(-c3ccc(-c4ccccc4)nc3)cnn2c1N] | 508.20 | 509.2 | 3.86 |
| 8.150 | 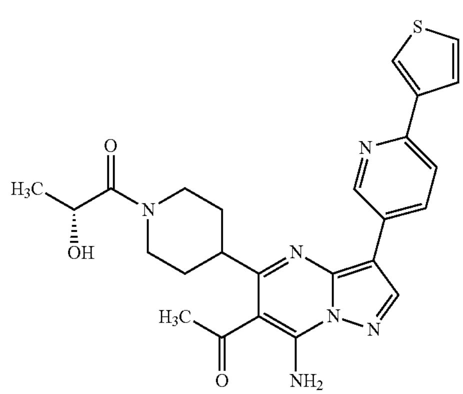 [SMILES: CC(=O)c1c(C2CCN(C(=O)[C@@H](C)O)CC2)nc2c(-c3ccc(-c4ccsc4)nc3)cnn2c1N] | 490.17 | 491.61 | 3.14 |

TABLE-8B-continued

| Compound ID | Structures | M + H (calculated) | M + H (observed) | Retention Time(min) |
|---|---|---|---|---|
| 8.151 | 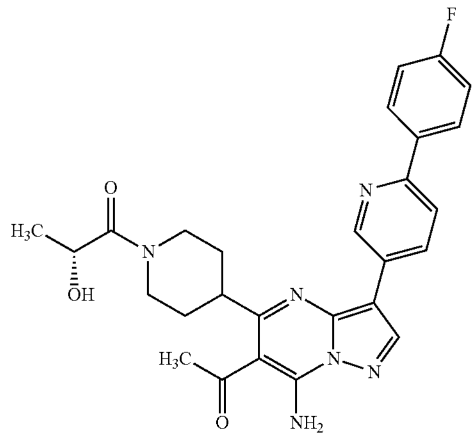 [SMILES: CC(=O)c1c(C2CCN(C(=O)[C@@H](C)O)CC2)nc2c(-c3ccc(-c4ccc(F)cc4)nc3)cnn2c1N] | 502.21 | 503.66 | 3.51 |
| 8.152 | 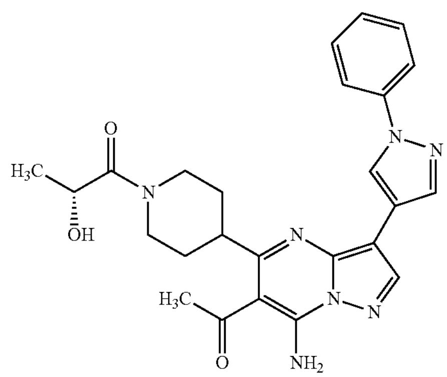 [SMILES: CC(=O)c1c(C2CCN(C(=O)[C@@H](C)O)CC2)nc2c(-c3cnn(-c4ccccc4)c3)cnn2c1N] | 473.21 | 474.67 | 4.09 |
| 8.153 | 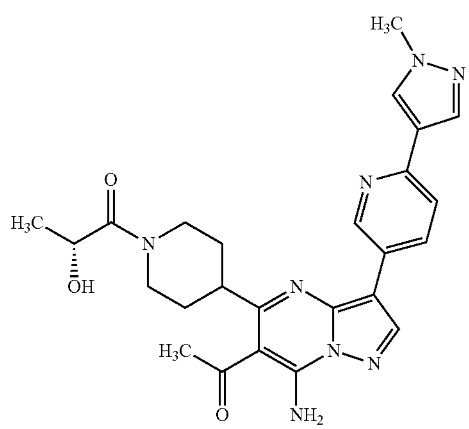 [SMILES: CC(=O)c1c(C2CCN(C(=O)[C@@H](C)O)CC2)nc2c(-c3ccc(-c4cnn(C)c4)nc3)cnn2c1N] | 488.22 | 489.67 | 2.79 |
| 8.154 | 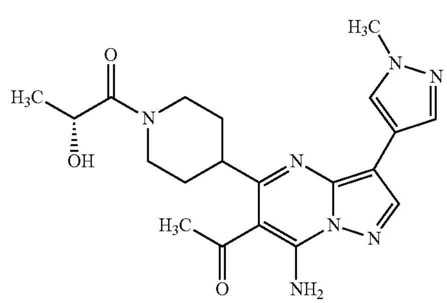 [SMILES: CC(=O)c1c(C2CCN(C(=O)[C@@H](C)O)CC2)nc2c(-c3cnn(C)c3)cnn2c1N] | 411.20 | 412.64 | 2.97 |

TABLE- 8B-continued
| Compound ID | Structures | M + H (calculated) | M + H (observed) | Retention Time(min) |
|---|---|---|---|---|
| 8.155 | 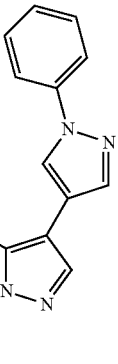 | 517.24 | 518.68 | 3.95 |
| 8.156 | 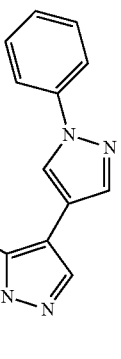 | 487.23 | 488.68 | 4.32 |
| 8.157 | 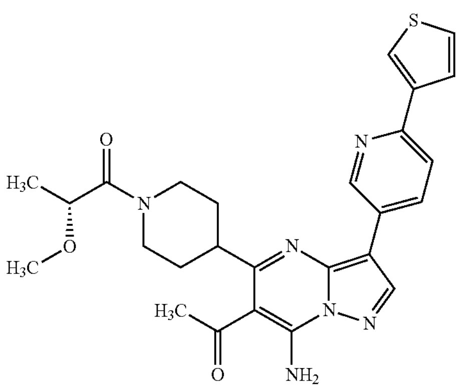 [SMILES: CO[C@H](C)C(=O)N1CCC(c2nc3c(-c4ccc(-c5ccsc5)nc4)cnn3c(N)c2C(C)=O)CC1] | 504.19 | 505.66 | 3.34 |
| 8.158 | 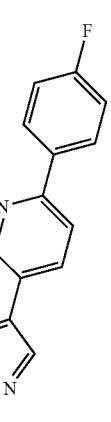 | 546.23 | 547.71 | 3.28 |

TABLE- 8B-continued
| Compound ID | Structures | M + H (calculated) | M + H (observed) | Retention Time(min) |
|---|---|---|---|---|
| 8.159 | 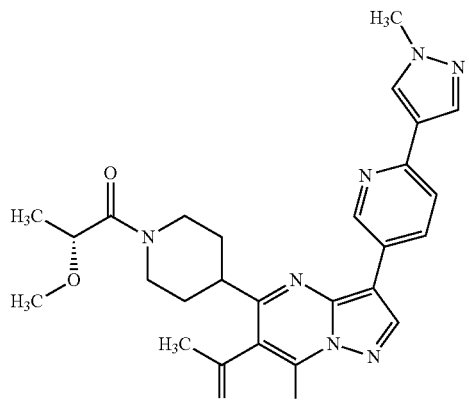 | 502.24 | 503.70 | 2.99 |
| 8.160 | 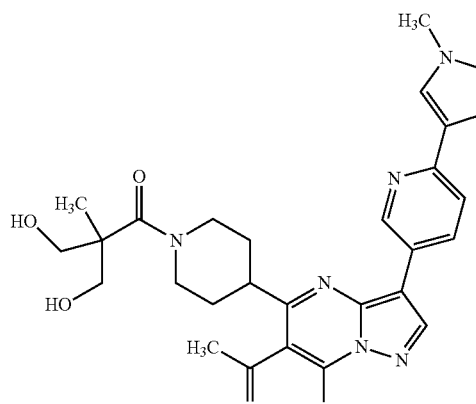 | 532.25 | 533.71 | 2.74 |
| 8.161 | 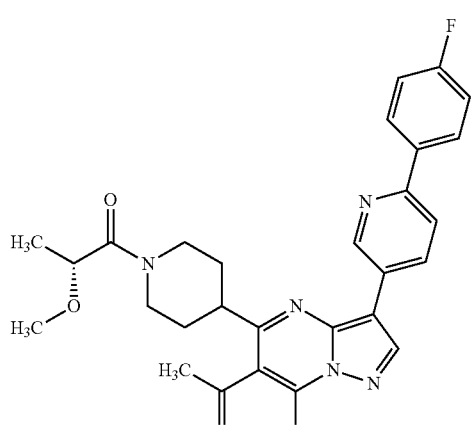 | 516.22 | 517.68 | 3.65 |

TABLE- 8B-continued

| Compound ID | Structures | M + H (calculated) | M + H (observed) | Retention Time(min) |
|---|---|---|---|---|
| 8.162 | 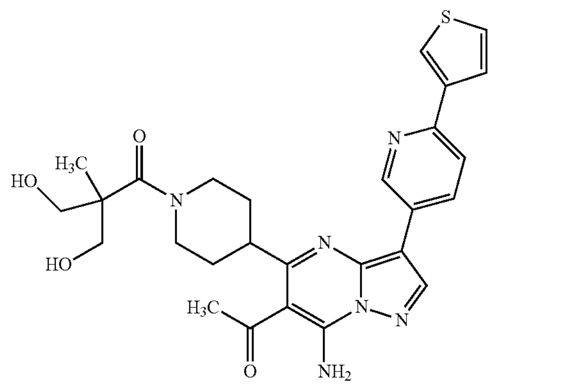 [SMILES: CC(=O)c1c(C2CCN(C(=O)C(C)(CO)CO)CC2)nc2c(-c3ccc(-c4ccsc4)nc3)cnn2c1N] | 534.20 | 535.66 | 3.03 |
| 8.163 | 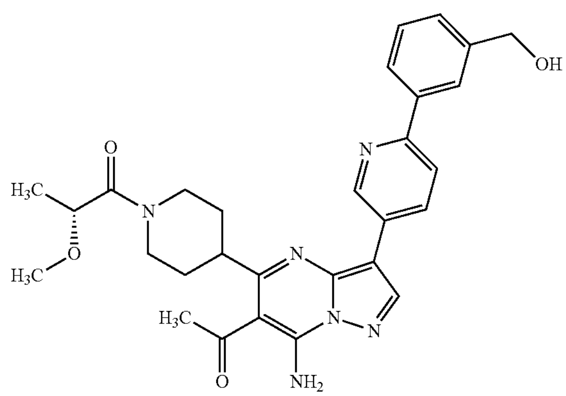 [SMILES: CO[C@H](C)C(=O)N1CCC(c2nc3c(-c4ccc(-c5cccc(CO)c5)nc4)cnn3c(N)c2C(C)=O)CC1] | 528.24 | 529.70 | 3.11 |
| 8.164 | 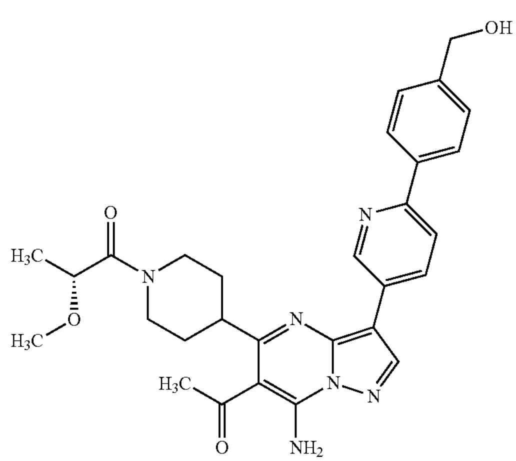 [SMILES: CO[C@H](C)C(=O)N1CCC(c2nc3c(-c4ccc(-c5ccc(CO)cc5)nc4)cnn3c(N)c2C(C)=O)CC1] | 528.24 | 529.70 | 3.07 |

TABLE- 8B-continued
| Compound ID | Structures | M + H (calculated) | M + H (observed) | Retention Time(min) |
|---|---|---|---|---|
| 8.165 | 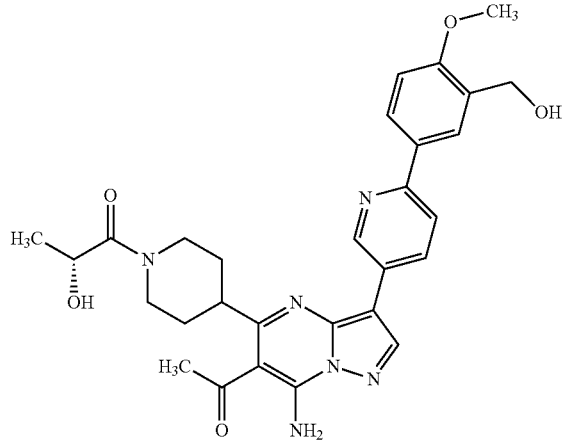 [SMILES: COc1ccc(-c2ccc(-c3cnn4c(N)c(C(C)=O)c(C5CCN(C(=O)[C@@H](C)O)CC5)nc34)cn2)cc1CO] | 544.24 | 545.71 | 2.98 |
| 8.166 | 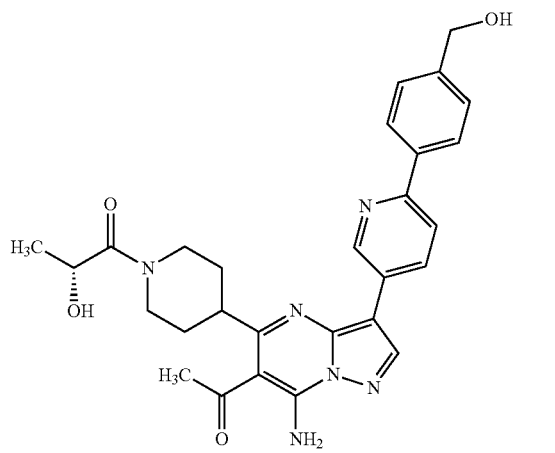 [SMILES: CC(=O)c1c(C2CCN(C(=O)[C@@H](C)O)CC2)nc2c(-c3ccc(-c4ccc(CO)cc4)nc3)cnn2c1N] | 514.23 | 515.68 | 2.83 |
| 8.167 | 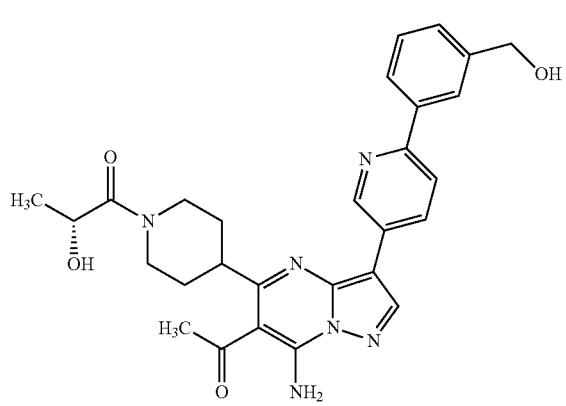 [SMILES: CC(=O)c1c(C2CCN(C(=O)[C@@H](C)O)CC2)nc2c(-c3ccc(-c4cccc(CO)c4)nc3)cnn2c1N] | 514.23 | 515.68 | 2.86 |

TABLE- 8B-continued
| Compound ID | Structures | M + H (calculated) | M + H (observed) | Retention Time(min) |
|---|---|---|---|---|
| 8.168 | 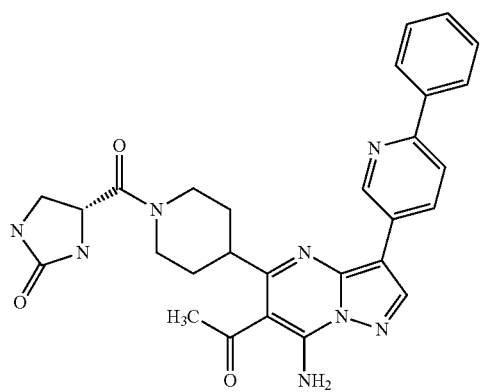 [SMILES: CC(=O)c1c(C2CCN(C(=O)[C@H]3CNC(=O)N3)CC2)nc2c(-c3ccc(-c4ccccc4)nc3)cnn2c1N] | 524.22 | 525.69 | 2.89 |
| 8.169 | 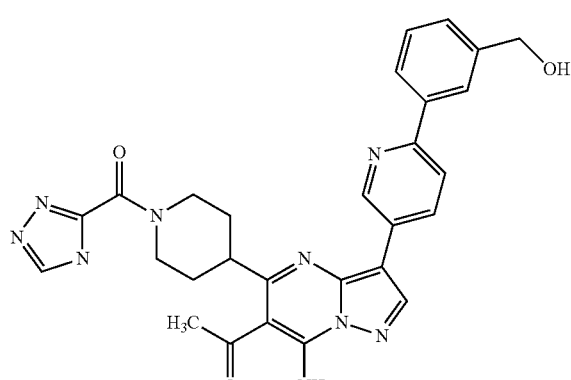 | 537.22 | 538.71 | 2.75 |
| 8.170 | 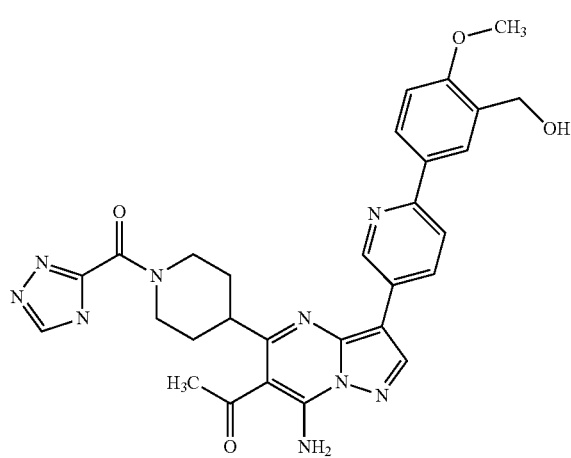 [SMILES: COc1ccc(-c2ccc(-c3cnn4c(N)c(C(C)=O)c(C5CCN(C(=O)c6nnc[nH]6)CC5)nc34)cn2)cc1CO] | 567.23 | 568.71 | 2.90 |

TABLE- 8B-continued

| Compound ID | Structures | M + H (calculated) | M + H (observed) | Retention Time(min) |
|---|---|---|---|---|
| 8.171 | 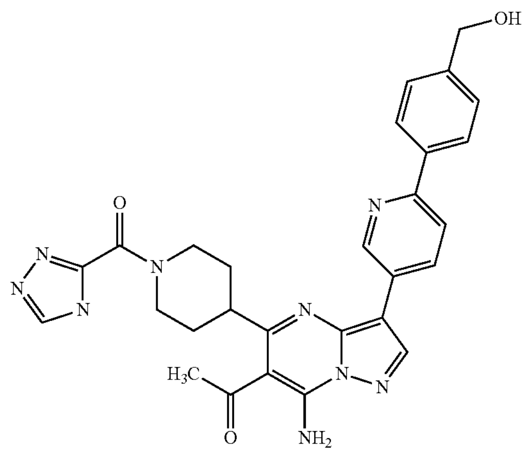 [SMILES: CC(=O)c1c(C2CCN(C(=O)c3nnc[nH]3)CC2)nc2c(-c3ccc(-c4ccc(CO)cc4)nc3)cnn2c1N] | 537.22 | 538.67 | 2.73 |
| 8.172 | 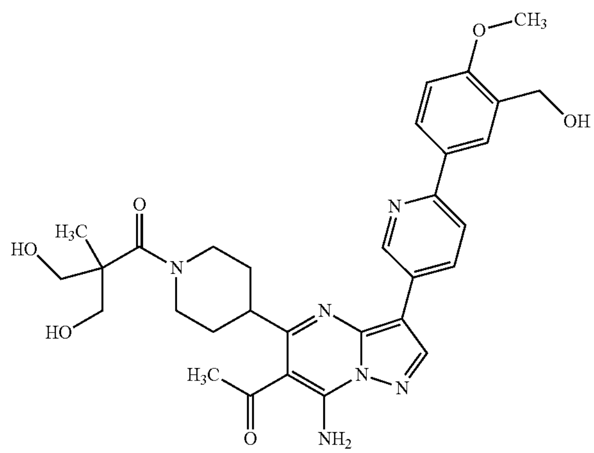 [SMILES: COc1ccc(-c2ccc(-c3cnn4c(N)c(C(C)=O)c(C5CCN(C(=O)C(C)(CO)CO)CC5)nc34)cn2)cc1CO] | 588.26 | 589.74 | 2.98 |
| 8.173 | 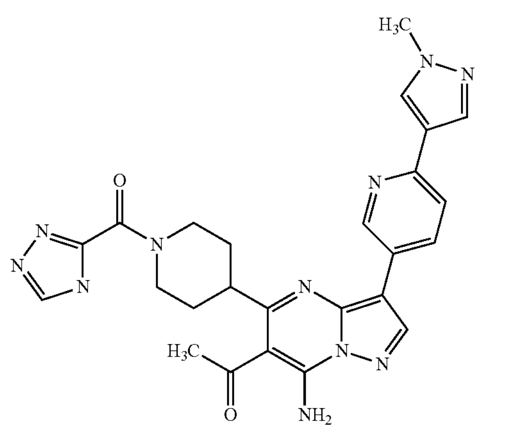 [SMILES: CC(=O)c1c(C2CCN(C(=O)c3nnc[nH]3)CC2)nc2c(-c3ccc(-c4cnn(C)c4)nc3)cnn2c1N] | 511.21 | 512.65 | 2.67 |

TABLE- 8B-continued
| Compound ID | Structures | M + H (calculated) | M + H (observed) | Retention Time(min) |
|---|---|---|---|---|
| 8.174 | 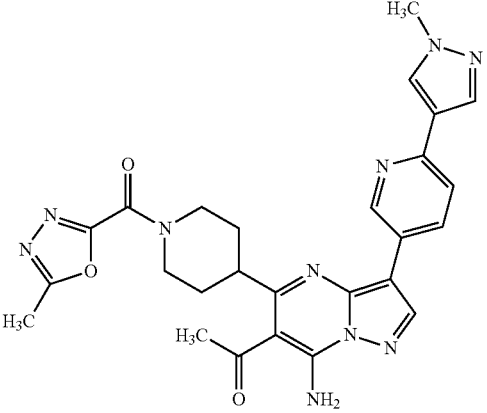 [SMILES: CC(=O)c1c(C2CCN(C(=O)c3nnc(C)o3)CC2)nc2c(-c3ccc(-c4cnn(C)c4)nc3)cnn2c1N] | 526.21 | 527.65 | 2.96 |
| 8.175 | 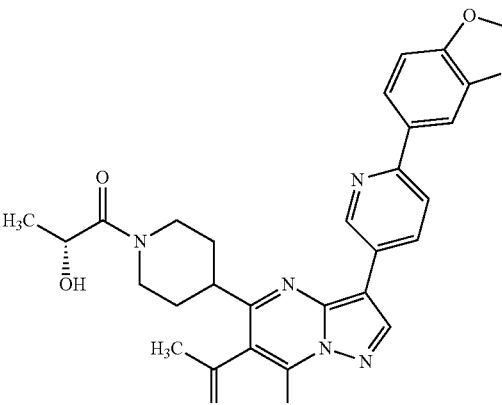 | 528.21 | 529.67 | 3.23 |
| 8.176 | 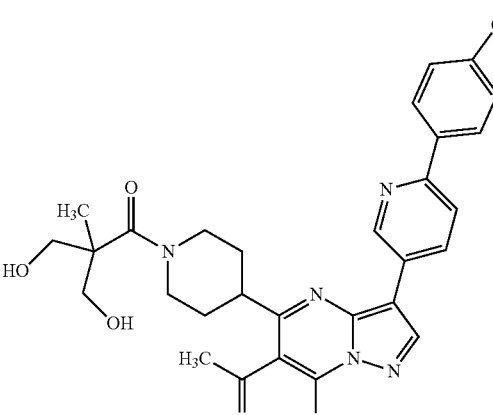 | 572.23 | 573.69 | 3.18 |

TABLE- 8B-continued

| Compound ID | Structures | M + H (calculated) | M + H (observed) | Retention Time(min) |
|---|---|---|---|---|
| 8.177 | 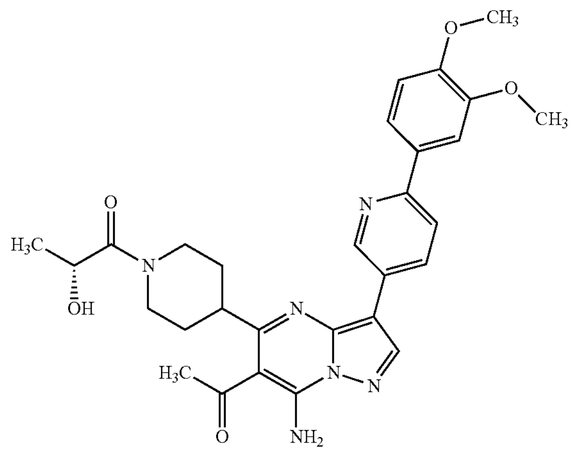 [SMILES: COc1ccc(-c2ccc(-c3cnn4c(N)c(C(C)=O)c(C5CCN(C(=O)[C@@H](C)O)CC5)nc34)cn2)cc1OC] | 544.24 | 545.71 | 3.23 |
| 8.178 | 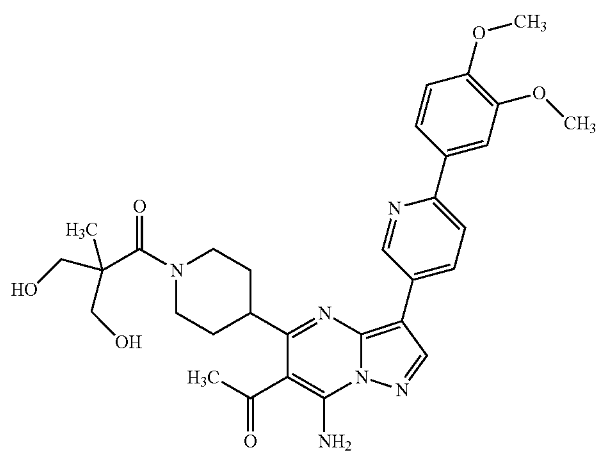 [SMILES: COc1ccc(-c2ccc(-c3cnn4c(N)c(C(C)=O)c(C5CCN(C(=O)C(C)(CO)CO)CC5)nc34)cn2)cc1OC] | 588.26 | 589.77 | 3.20 |
| 8.179 | 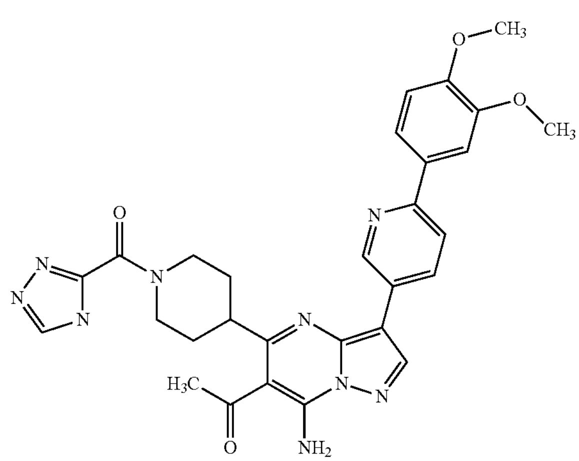 [SMILES: COc1ccc(-c2ccc(-c3cnn4c(N)c(C(C)=O)c(C5CCN(C(=O)c6nnc[nH]6)CC5)nc34)cn2)cc1OC] | 567.23 | 568.67 | 3.11 |

TABLE- 8B-continued

| Compound ID | Structures | M + H (calculated) | M + H (observed) | Retention Time(min) |
|---|---|---|---|---|
| 8.180 | 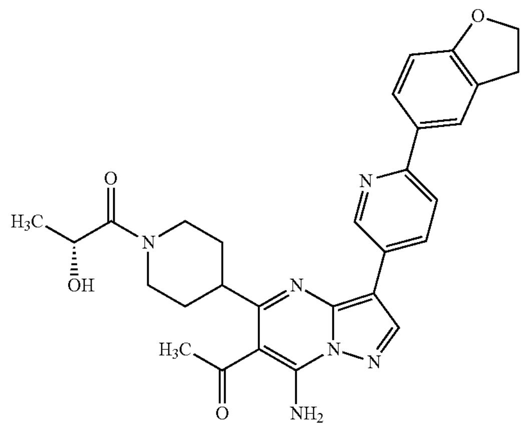 [SMILES: CC(=O)c1c(C2CCN(C(=O)[C@@H](C)O)CC2)nc2c(-c3ccc(-c4ccc5c(c4)CCO5)nc3)cnn2c1N] | 526.23 | 527.69 | 3.28 |
| 8.181 | 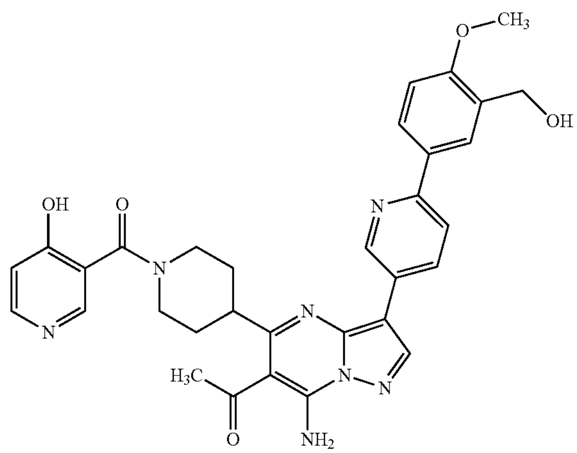 [SMILES: COc1ccc(-c2ccc(-c3cnn4c(N)c(C(C)=O)c(C5CCN(C(=O)c6cnccc6O)CC5)nc34)cn2)cc1CO] | 593.23 | 594.63 | 2.87 |
| 8.182 | 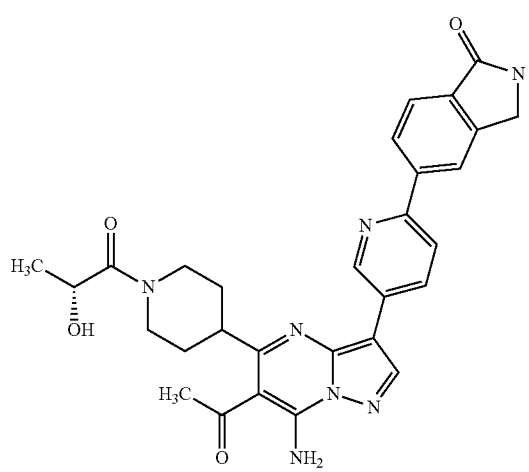 [SMILES: CC(=O)c1c(C2CCN(C(=O)[C@@H](C)O)CC2)nc2c(-c3ccc(-c4ccc5c(c4)CNC5=O)nc3)cnn2c1N] | 539.22 | 540.64 | 2.89 |

TABLE- 8B-continued

| Compound ID | Structures | M + H (calculated) | M + H (observed) | Retention Time(min) |
|---|---|---|---|---|
| 8.183 | 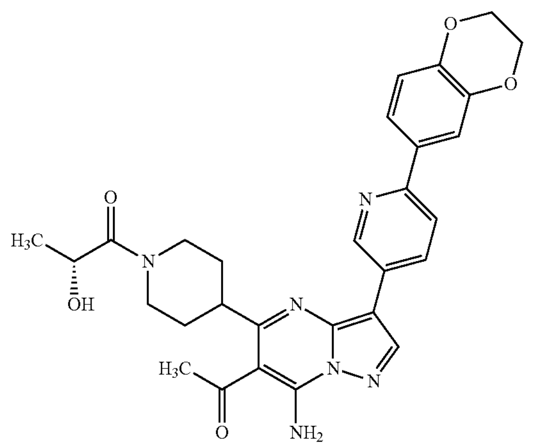 [SMILES: CC(=O)c1c(C2CCN(C(=O)[C@@H](C)O)CC2)nc2c(-c3ccc(-c4ccc5c(c4)OCCO5)nc3)cnn2c1N] | 542.22 | 543.65 | 3.28 |
| 8.184 | 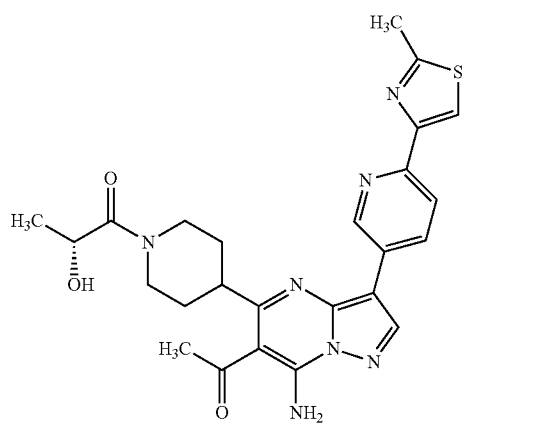 [SMILES: CC(=O)c1c(C2CCN(C(=O)[C@@H](C)O)CC2)nc2c(-c3ccc(-c4csc(C)n4)nc3)cnn2c1N] | 505.18 | 506.1 | 3.34 |
| 8.185 | 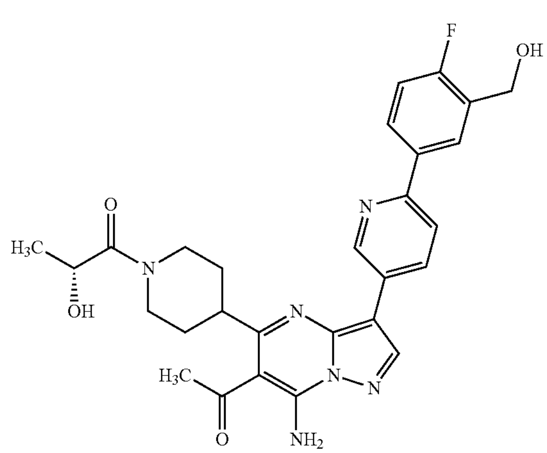 [SMILES: CC(=O)c1c(C2CCN(C(=O)[C@@H](C)O)CC2)nc2c(-c3ccc(-c4ccc(F)c(CO)c4)nc3)cnn2c1N] | 532.22 | 533.64 | 2.93 |

TABLE- 8B-continued
| Compound ID | Structures | M + H (calculated) | M + H (observed) | Retention Time(min) |
|---|---|---|---|---|
| 8.186 | 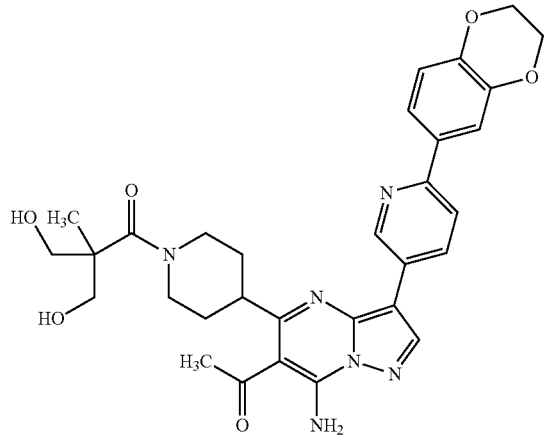 [SMILES: CC(=O)c1c(C2CCN(C(=O)C(C)(CO)CO)CC2)nc2c(-c3ccc(-c4ccc5c(c4)OCCO5)nc3)cnn2c1N] | 586.25 | 587.73 | 3.25 |
| 8.187 | 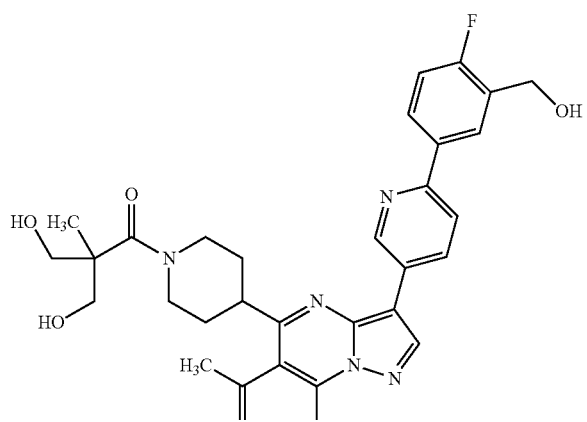 | 576.24 | 577.76 | 2.92 |
| 8.188 | 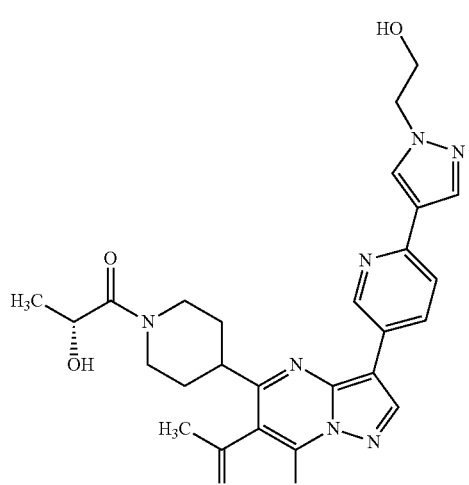 | 518.23 | 519.69 | 2.58 |

TABLE- 8B-continued
| Compound ID | Structures | M + H (calculated) | M + H (observed) | Retention Time(min) |
|---|---|---|---|---|
| 8.189 | 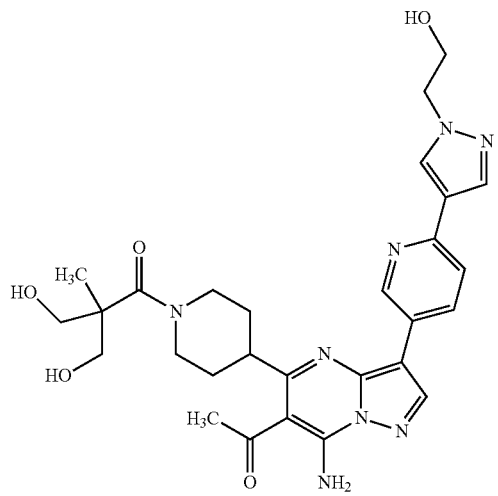 [SMILES: CC(=O)c1c(C2CCN(C(=O)C(C)(CO)CO)CC2)nc2c(-c3ccc(-c4cnn(CCO)c4)nc3)cnn2c1N] | 562.26 | 563.74 | 2.58 |
| 8.190 | 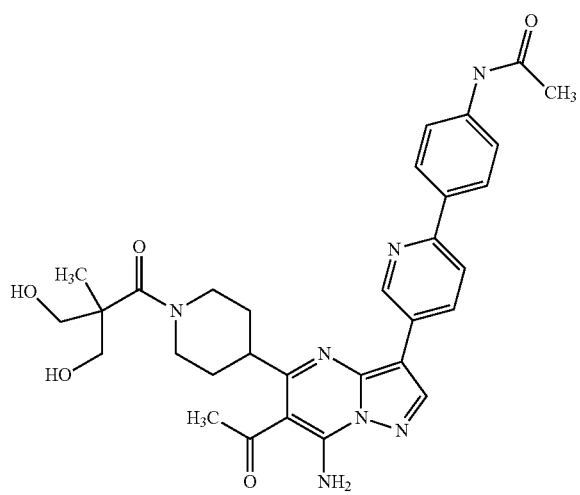 [SMILES: CC(=O)Nc1ccc(-c2ccc(-c3cnn4c(N)c(C(C)=O)c(C5CCN(C(=O)C(C)(CO)CO)CC5)nc34)cn2)cc1] | 585.27 | 586.75 | 2.98 |
| 8.191 | 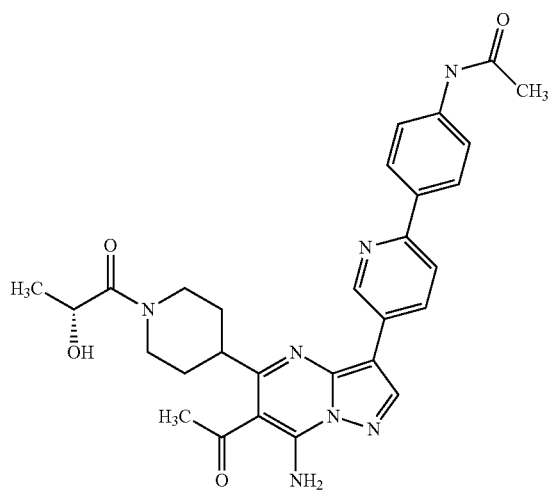 [SMILES: CC(=O)Nc1ccc(-c2ccc(-c3cnn4c(N)c(C(C)=O)c(C5CCN(C(=O)[C@@H](C)O)CC5)nc34)cn2)cc1] | 541.24 | 542.72 | 2.96 |

TABLE- 8B-continued
| Compound ID | Structures | M + H (calculated) | M + H (observed) | Retention Time(min) |
|---|---|---|---|---|
| 8.192 | 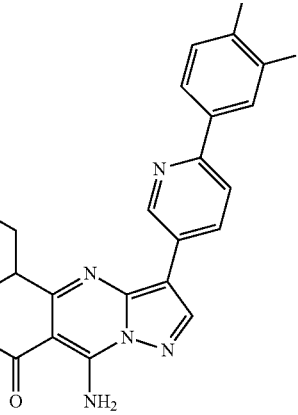 | 555.25 | 556.72 | 2.96 |
| 8.193 | 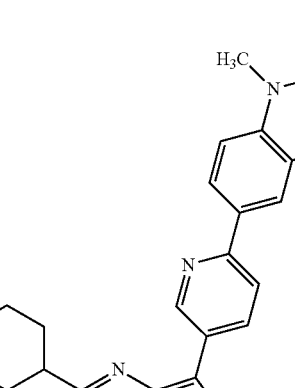 | 599.28 | 600.84 | 3.15 |
| 8.194 | 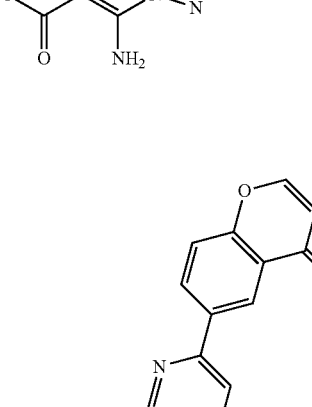 | 552.21 | 553.65 | 3.32 |

TABLE- 8B-continued

| Compound ID | Structures | M + H (calculated) | M + H (observed) | Retention Time(min) |
|---|---|---|---|---|
| 8.195 | 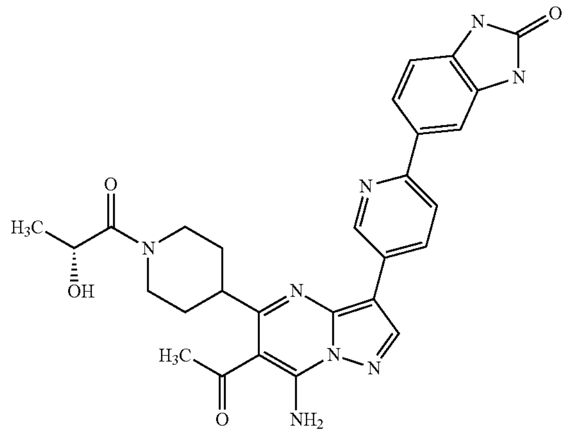 [SMILES: CC(=O)c1c(C2CCN(C(=O)[C@@H](C)O)CC2)nc2c(-c3ccc(-c4ccc5[nH]c(=O)[nH]c5c4)nc3)cnn2c1N] | 540.22 | 541.73 | 2.74 |
| 8.196 | 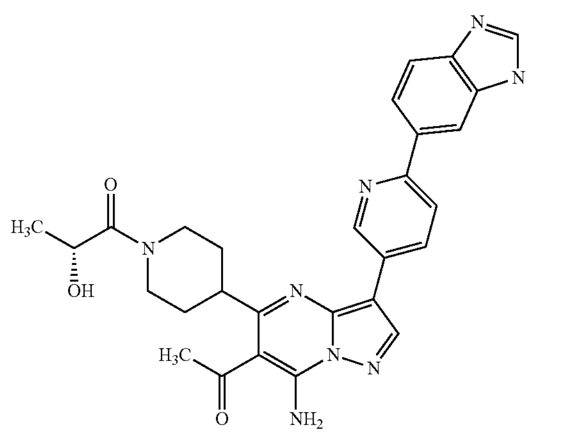 [SMILES: CC(=O)c1c(C2CCN(C(=O)[C@@H](C)O)CC2)nc2c(-c3ccc(-c4ccc5nc[nH]c5c4)nc3)cnn2c1N] | 524.22 | 525.62 | 2.61 |
| 8.197 | 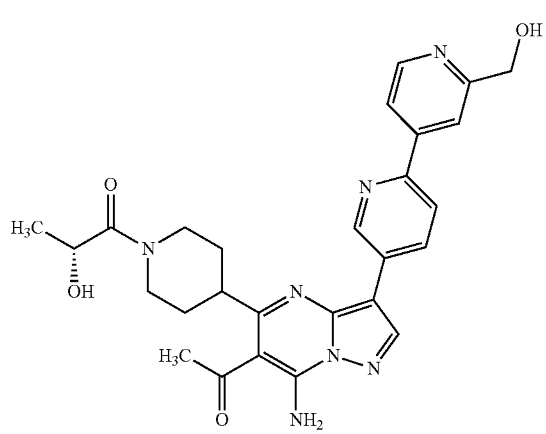 [SMILES: CC(=O)c1c(C2CCN(C(=O)[C@@H](C)O)CC2)nc2c(-c3ccc(-c4ccnc(CO)c4)nc3)cnn2c1N] | 515.22 | 516.70 | 2.77 |

TABLE-8B-continued

| Compound ID | Structures | M + H (calculated) | M + H (observed) | Retention Time(min) |
|---|---|---|---|---|
| 8.198 | 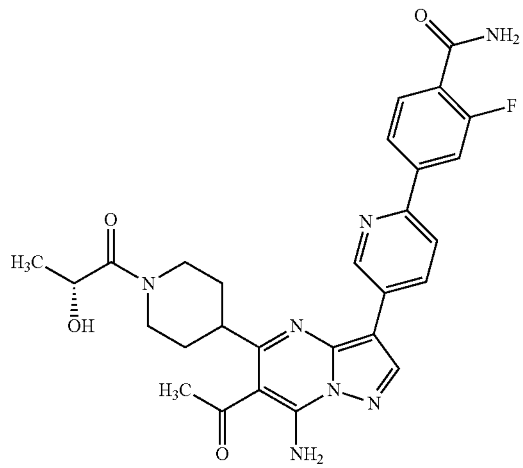 [SMILES: CC(=O)c1c(C2CCN(C(=O)[C@@H](C)O)CC2)nc2c(-c3ccc(-c4ccc(C(N)=O)c(F)c4)nc3)cnn2c1N] | 545.21 | 546.71 | 3.10 |
| 8.199 | 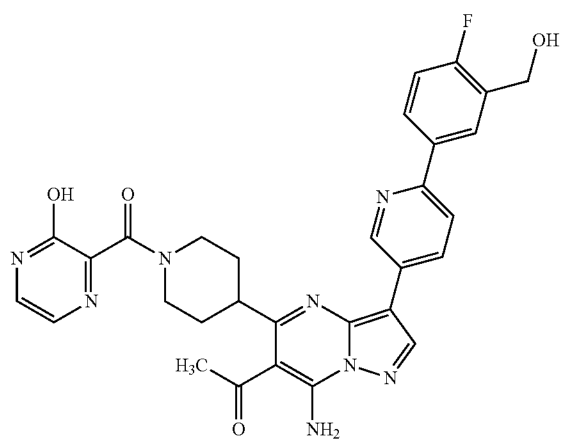 [SMILES: CC(=O)c1c(C2CCN(C(=O)c3nccnc3O)CC2)nc2c(-c3ccc(-c4ccc(F)c(CO)c4)nc3)cnn2c1N] | 582.21 | 583.70 | 2.77 |
| 8.200 | 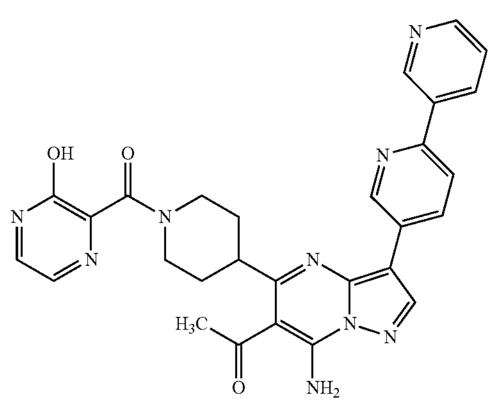 [SMILES: CC(=O)c1c(C2CCN(C(=O)c3nccnc3O)CC2)nc2c(-c3ccc(-c4cccnc4)nc3)cnn2c1N] | 535.20 | 536.05 | 2.64 |

TABLE- 8B-continued
| Compound ID | Structures | M + H (calculated) | M + H (observed) | Retention Time(min) |
|---|---|---|---|---|
| 8.201 | 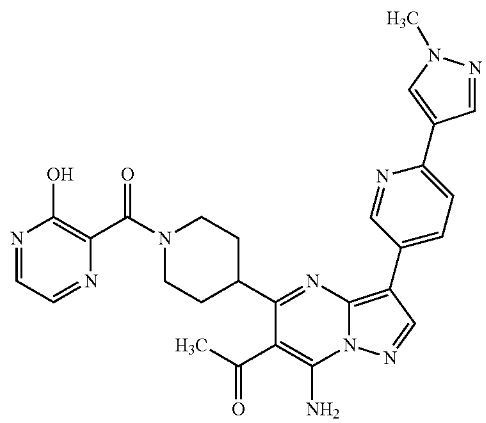 [SMILES: CC(=O)c1c(C2CCN(C(=O)c3nccnc3O)CC2)nc2c(-c3ccc(-c4cnn(C)c4)nc3)cnn2c1N] | 538.21 | 539.1 | 2.52 |
| 8.202 | 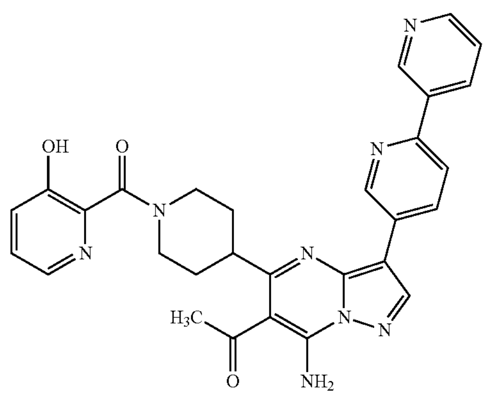 | 534.21 | 535.2 | 2.93 |
| 8.203 | 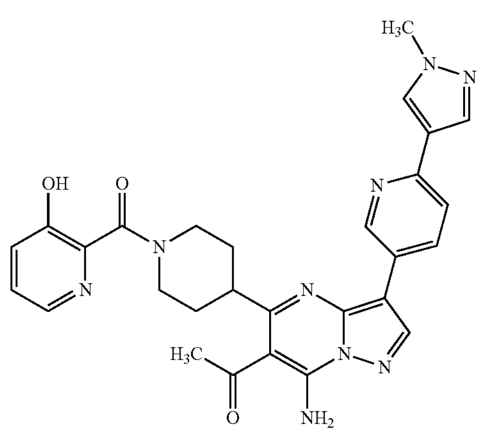 [SMILES: CC(=O)c1c(C2CCN(C(=O)c3ncccc3O)CC2)nc2c(-c3ccc(-c4cnn(C)c4)nc3)cnn2c1N] | 537.22 | 538.03 | 2.86 |

TABLE- 8B-continued

| Compound ID | Structures | M + H (calculated) | M + H (observed) | Retention Time(min) |
|---|---|---|---|---|
| 8.204 | 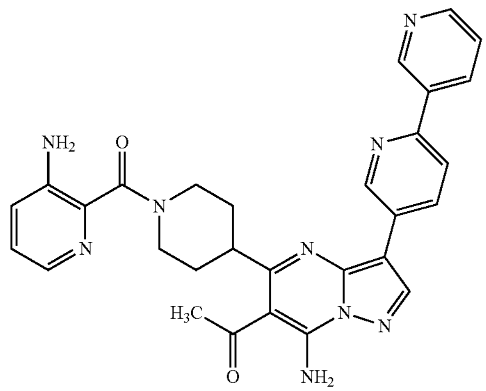 | 533.22 | 534.1 | 2.73 |
| 8.205 | 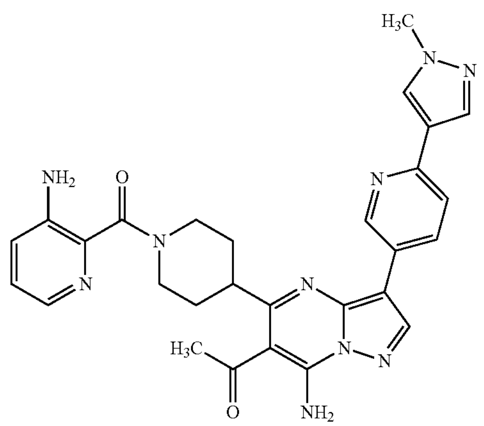 | 536.24 | 537.05 | 2.75 |
| 8.206 | 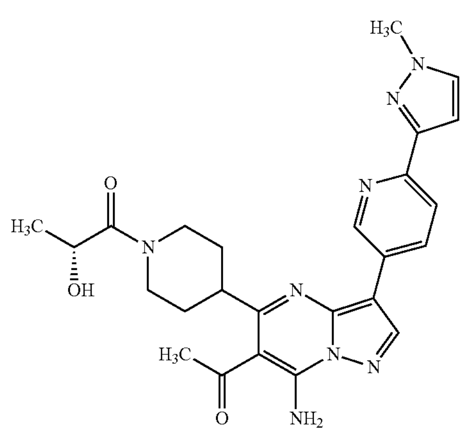 [SMILES: CC(=O)c1c(C2CCN(C(=O)[C@@H](C)O)CC2)nc2c(-c3ccc(-c4ccn(C)n4)nc3)cnn2c1N] | 488.22 | 488.96 | 2.89 |

TABLE-8B-continued

| Compound ID | Structures | M + H (calculated) | M + H (observed) | Retention Time(min) |
|---|---|---|---|---|
| 8.207 | 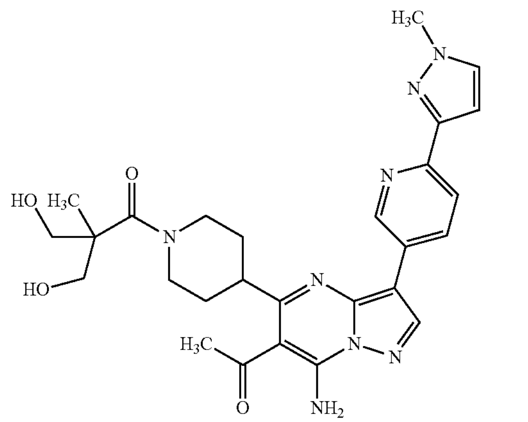 [SMILES: CC(=O)c1c(C2CCN(C(=O)C(C)(CO)CO)CC2)nc2c(-c3ccc(-c4ccn(C)n4)nc3)cnn2c1N] | 532.25 | 533.2 | 2.94 |
| 8.208 | 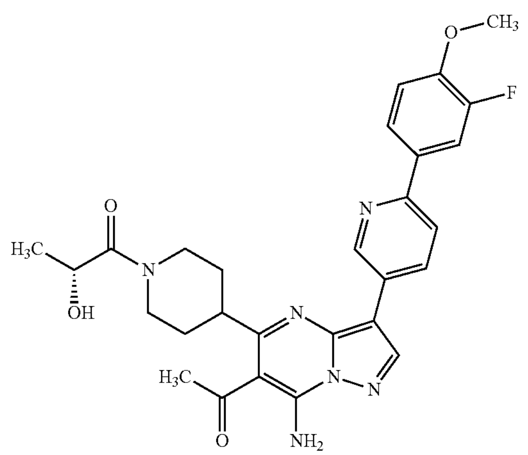 [SMILES: COc1ccc(-c2ccc(-c3cnn4c(N)c(C(C)=O)c(C5CCN(C(=O)[C@@H](C)O)CC5)nc34)cn2)cc1F] | 532.22 | 533.04 | 3.39 |
| 8.209 | 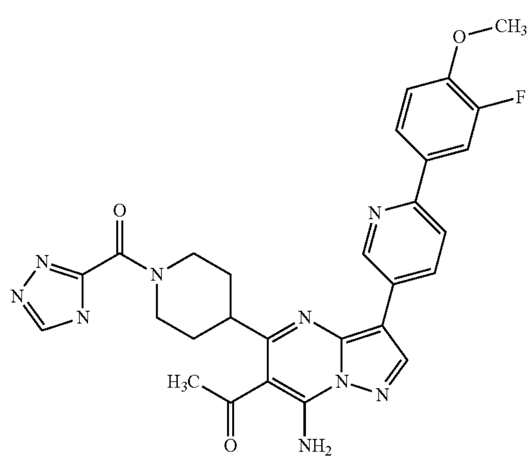 [SMILES: COc1ccc(-c2ccc(-c3cnn4c(N)c(C(C)=O)c(C5CCN(C(=O)c6nnc[nH]6)CC5)nc34)cn2)cc1F] | 555.21 | 556.1 | 3.35 |

TABLE- 8B-continued
| Compound ID | Structures | M + H (calculated) | M + H (observed) | Retention Time(min) |
|---|---|---|---|---|
| 8.210 | 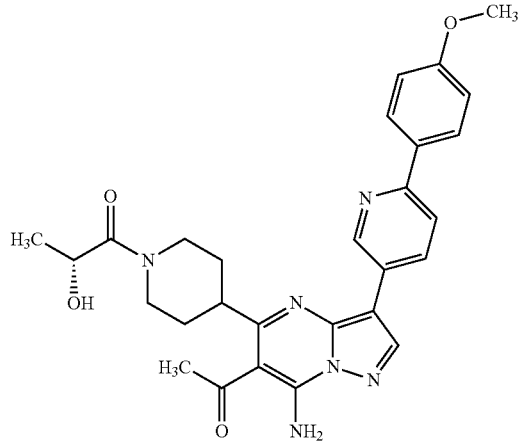 [SMILES: COc1ccc(-c2ccc(-c3cnn4c(N)c(C(C)=O)c(C5CCN(C(=O)[C@@H](C)O)CC5)nc34)cn2)cc1] | 514.23 | 515.06 | 3.24 |
| 8.211 | 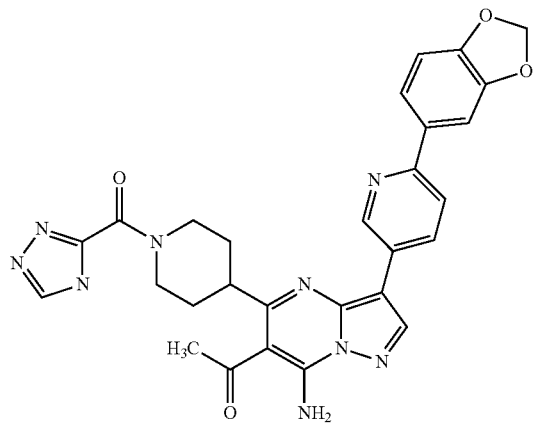 [SMILES: CC(=O)c1c(C2CCN(C(=O)c3nnc[nH]3)CC2)nc2c(-c3ccc(-c4ccc5c(c4)OCO5)nc3)cnn2c1N] | 551.20 | 552.1 | 3.17 |
| 8.212 | 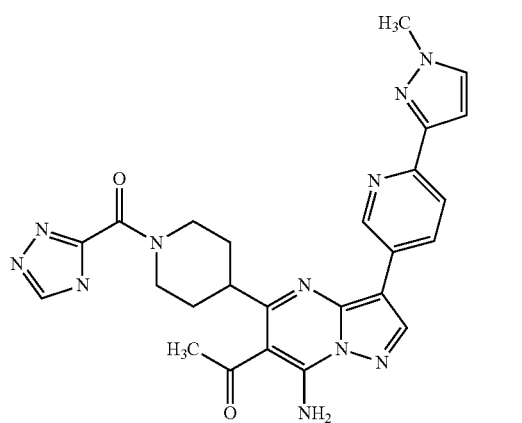 [SMILES: CC(=O)c1c(C2CCN(C(=O)c3nnc[nH]3)CC2)nc2c(-c3ccc(-c4ccn(C)n4)nc3)cnn2c1N] | 511.21 | 512.1 | 2.83 |

TABLE- 8B-continued

| Compound ID | Structures | M + H (calculated) | M + H (observed) | Retention Time(min) |
|---|---|---|---|---|
| 8.213 | 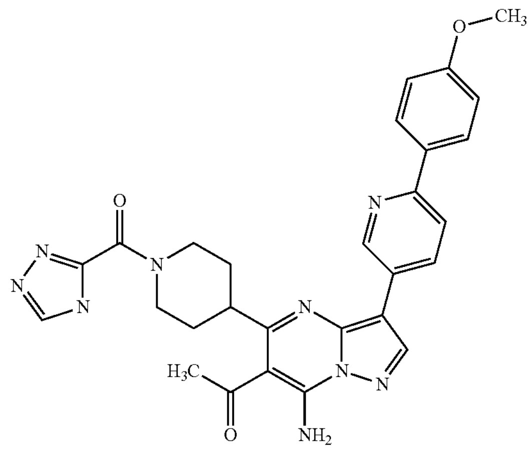 [SMILES: COc1ccc(-c2ccc(-c3cnn4c(N)c(C(C)=O)c(C5CCN(C(=O)c6nnc[nH]6)CC5)nc34)cn2)cc1] | 537.22 | 538.2 | 3.21 |
| 8.214 | 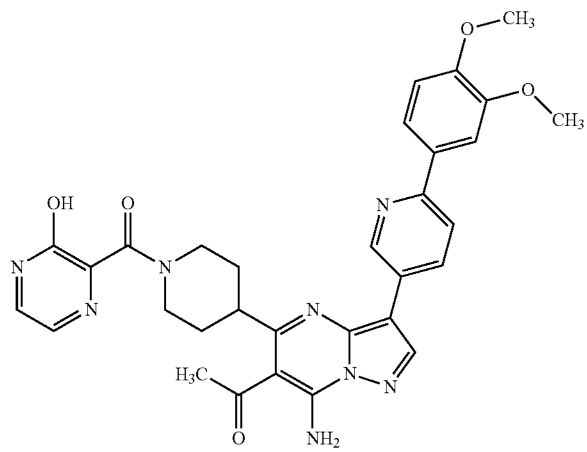 [SMILES: COc1ccc(-c2ccc(-c3cnn4c(N)c(C(C)=O)c(C5CCN(C(=O)c6nccnc6O)CC5)nc34)cn2)cc1OC] | 594.23 | 595.2 | 2.99 |
| 8.215 | 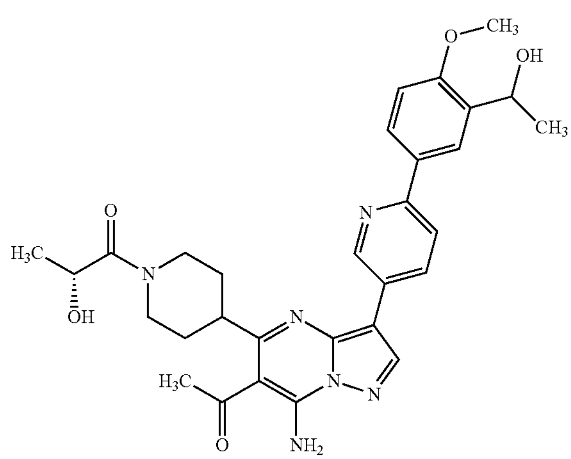 [SMILES: COc1ccc(-c2ccc(-c3cnn4c(N)c(C(C)=O)c(C5CCN(C(=O)[C@@H](C)O)CC5)nc34)cn2)cc1C(C)O] | 558.25 | 559.06 | 3.15 |

TABLE- 8B-continued

| Compound ID | Structures | M + H (calculated) | M + H (observed) | Retention Time(min) |
|---|---|---|---|---|
| 8.216 | 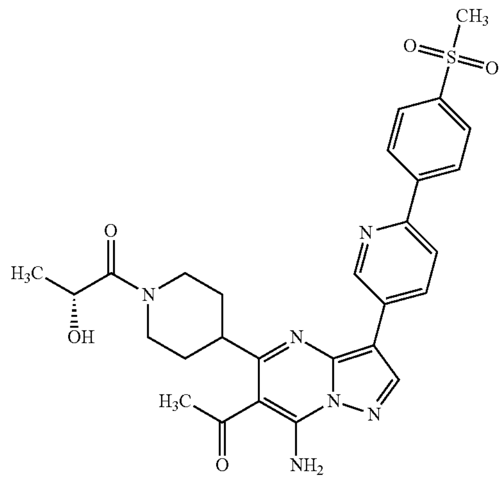 [SMILES: CC(=O)c1c(C2CCN(C(=O)[C@@H](C)O)CC2)nc2c(-c3ccc(-c4ccc(S(C)(=O)=O)cc4)nc3)cnn2c1N] | 562.20 | 562.97 | 3.57 |
| 8.217 | 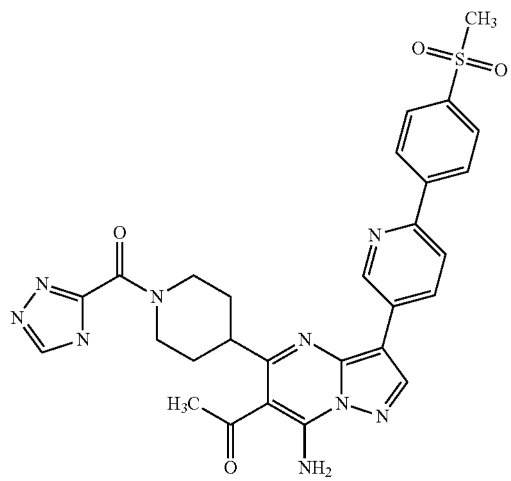 [SMILES: CC(=O)c1c(C2CCN(C(=O)c3nnc[nH]3)CC2)nc2c(-c3ccc(-c4ccc(S(C)(=O)=O)cc4)nc3)cnn2c1N] | 585.19 | 585.87 | 3.27 |
| 8.218 | 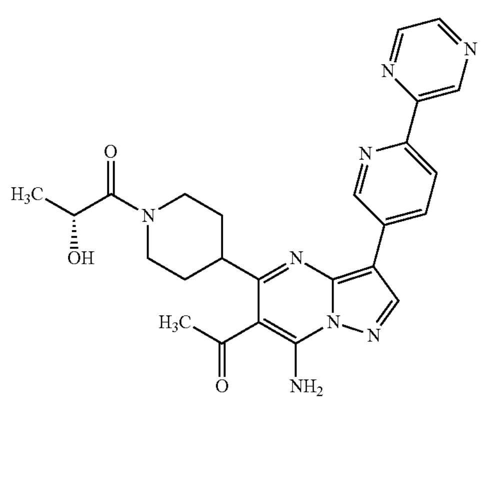 [SMILES: CC(=O)c1c(C2CCN(C(=O)[C@@H](C)O)CC2)nc2c(-c3ccc(-c4cnccn4)nc3)cnn2c1N] | 486.21 | 486.93 | 3.41 |

TABLE- 8B-continued

| Compound ID | Structures | M + H (calculated) | M + H (observed) | Retention Time(min) |
|---|---|---|---|---|
| 8.219 | 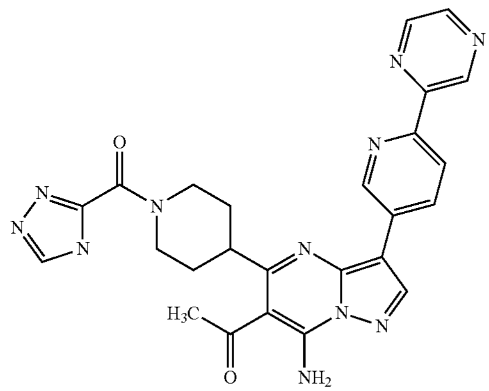 [SMILES: CC(=O)c1c(C2CCN(C(=O)c3nnc[nH]3)CC2)nc2c(-c3ccc(-c4cnccn4)nc3)cnn2c1N] | 509.20 | 509.92 | 3.09 |
| 8.220 | 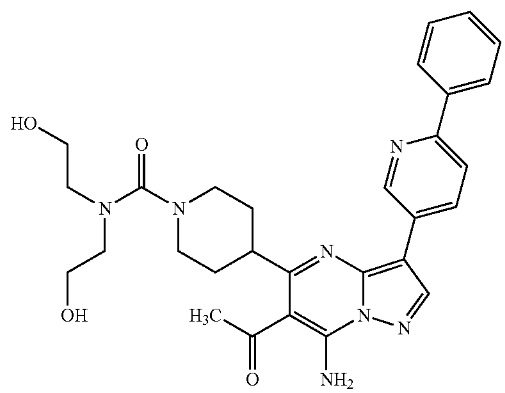 [SMILES: CC(=O)c1c(C2CCN(C(=O)N(CCO)CCO)CC2)nc2c(-c3ccc(-c4ccccc4)nc3)cnn2c1N] | 543.63 | 544.72 | 3.05 |
| 8.221 | 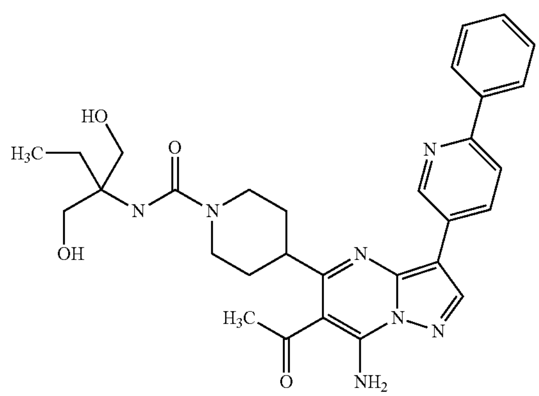 [SMILES: CCC(CO)(CO)NC(=O)N1CCC(c2nc3c(-c4ccc(-c5ccccc5)nc4)cnn3c(N)c2C(C)=O)CC1] | 557.65 | 558.76 | 3.26 |
| 8.222 | 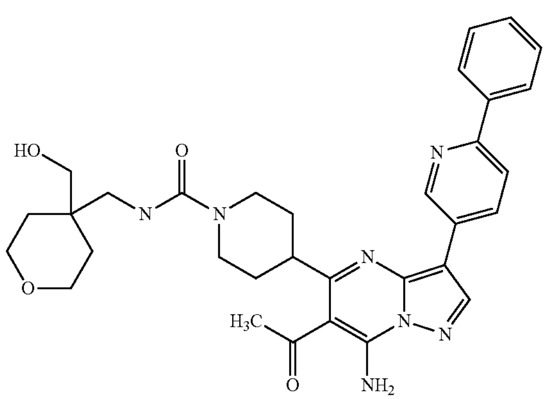 [SMILES: CC(=O)c1c(C2CCN(C(=O)NCC3(CO)CCOCC3)CC2)nc2c(-c3ccc(-c4ccccc4)nc3)cnn2c1N] | 583.69 | 584.76 | 3.28 |

TABLE- 8B-continued

| Compound ID | Structures | M + H (calculated) | M + H (observed) | Retention Time(min) |
|---|---|---|---|---|
| 8.223 | 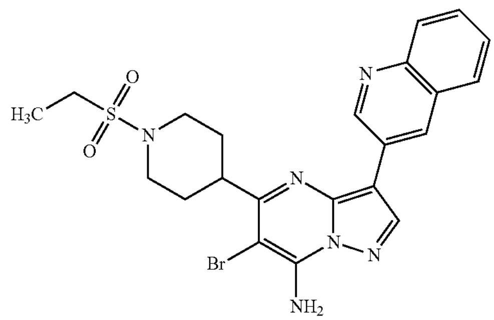 [SMILES: CCS(=O)(=O)N1CCC(c2nc3c(-c4cnc5ccccc5c4)cnn3c(N)c2Br)CC1] | 514.07 | 515 | 3.82 |
| 8.224 | 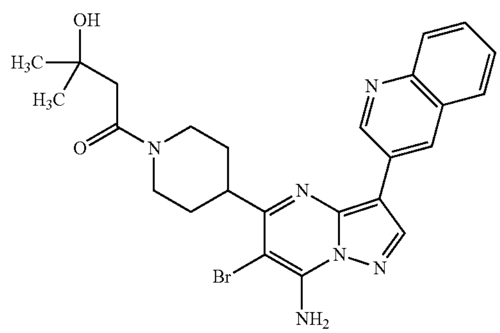 [SMILES: CC(C)(O)CC(=O)N1CCC(c2nc3c(-c4cnc5ccccc5c4)cnn3c(N)c2Br)CC1] | 522.13 | 523.2 | 3.02 |
| 8.225 | 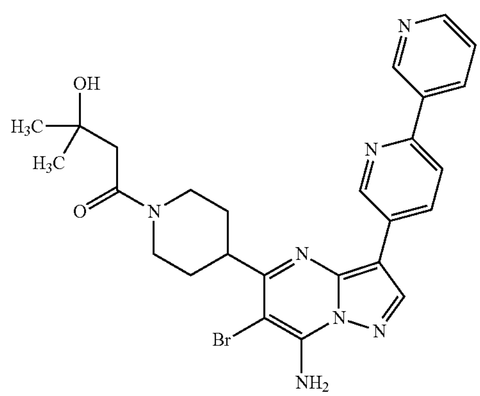 [SMILES: CC(C)(O)CC(=O)N1CCC(c2nc3c(-c4ccc(-c5cccnc5)nc4)cnn3c(N)c2Br)CC1] | 549.14 | 550 | 3.44 |
| 8.226 | 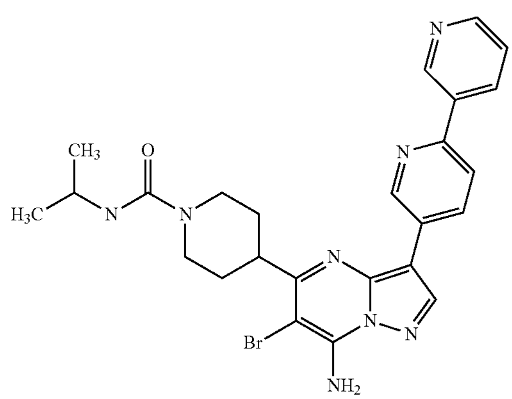 [SMILES: CC(C)NC(=O)N1CCC(c2nc3c(-c4ccc(-c5cccnc5)nc4)cnn3c(N)c2Br)CC1] | 534.14 | 535 | 3.56 |

TABLE-8B-continued

| Compound ID | Structures | M + H (calculated) | M + H (observed) | Retention Time(min) |
|---|---|---|---|---|
| 8.227 | 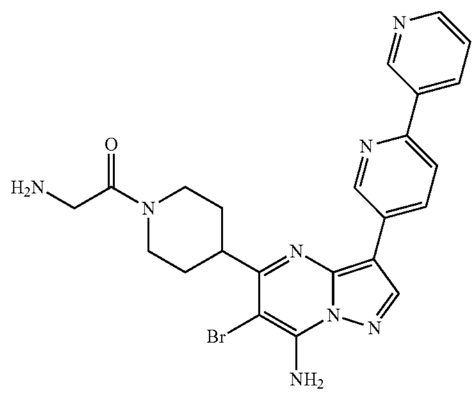 [SMILES: NCC(=O)N1CCC(c2nc3c(-c4ccc(-c5cccnc5)nc4)cnn3c(N)c2Br)CC1] | 506.11 | 507 | 2.52 |
| 8.228 | 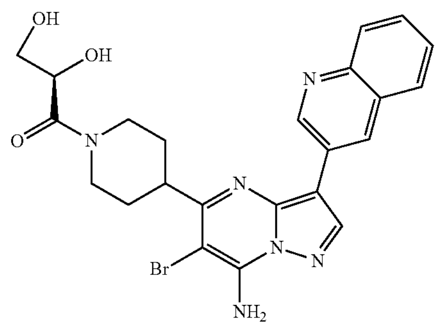 [SMILES: Nc1c(Br)c(C2CCN(C(=O)[C@H](O)CO)CC2)nc2c(-c3cnc4ccccc4c3)cnn12] | 510.1 | 511 | 2.9 |
| 8.229 | 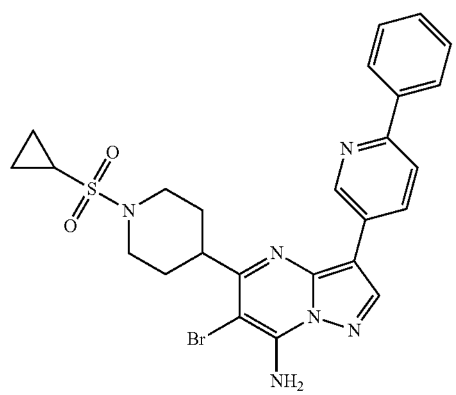 [SMILES: Nc1c(Br)c(C2CCN(S(=O)(=O)C3CC3)CC2)nc2c(-c3ccc(-c4ccccc4)nc3)cnn12] | 552.09 | 553 | 4.3 |
| 8.230 | 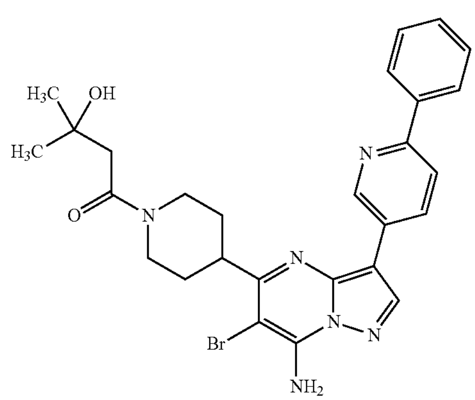 [SMILES: CC(C)(O)CC(=O)N1CCC(c2nc3c(-c4ccc(-c5ccccc5)nc4)cnn3c(N)c2Br)CC1] | 548.15 | 549 | 3.82 |

TABLE- 8B-continued

| Compound ID | Structures | M + H (calculated) | M + H (observed) | Retention Time(min) |
| --- | --- | --- | --- | --- |
| 8.231 | 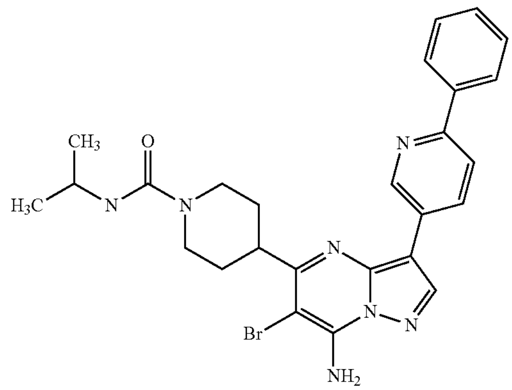 [SMILES: CC(C)NC(=O)N1CCC(c2nc3c(-c4ccc(-c5ccccc5)nc4)cnn3c(N)c2Br)CC1] | 533.15 | 534 | 3.99 |
| 8.232 | 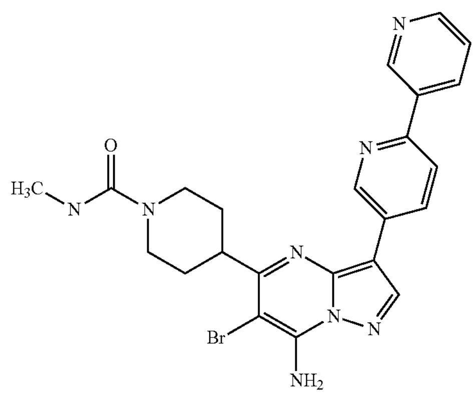 | 506.11 | 507 | 3.09 |
| 8.233 | 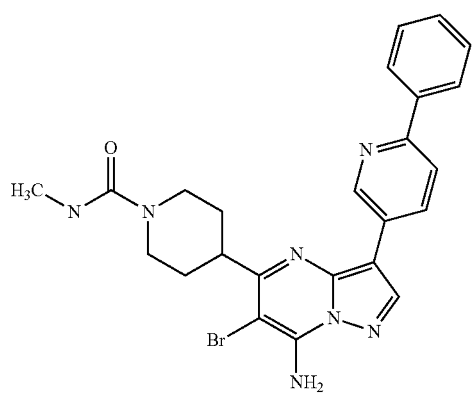 | 505.12 | 506 | 3.50 |
| 8.234 | 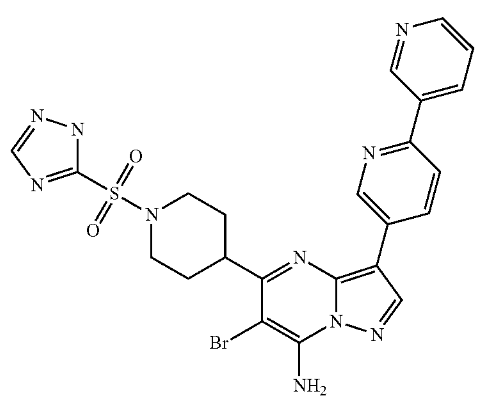 | 580.07 | 581 | 3.11 |

TABLE- 8B-continued

| Compound ID | Structures | M + H (calculated) | M + H (observed) | Retention Time(min) |
|---|---|---|---|---|
| 8.235 | 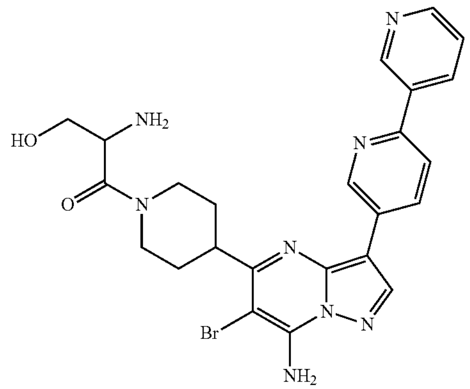 [SMILES: Nc1c(Br)c(C2CCN(C(=O)C(N)CO)CC2)nc2c(-c3ccc(-c4cccnc4)nc3)cnn12] | 536.12 | 537.1 | 2.18 |
| 8.236 | 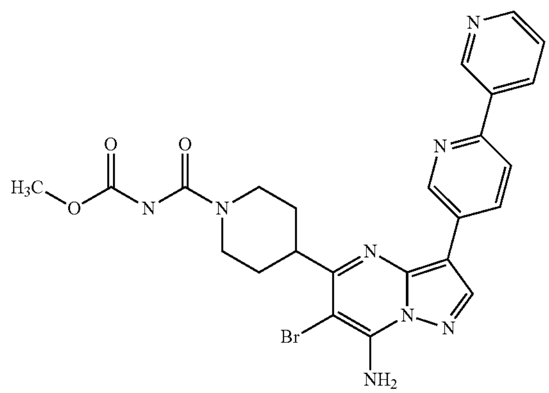 | 550.1 | 551 | 3.04 |
| 8.237 | 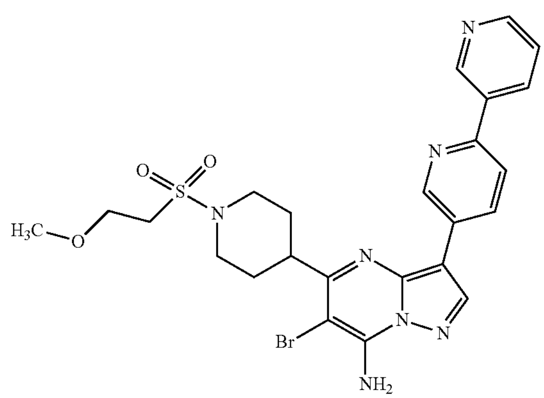 [SMILES: COCCS(=O)(=O)N1CCC(c2nc3c(-c4ccc(-c5cccnc5)nc4)cnn3c(N)c2Br)CC1] | 571.1 | 572 | 3.49 |
| 8.238 | 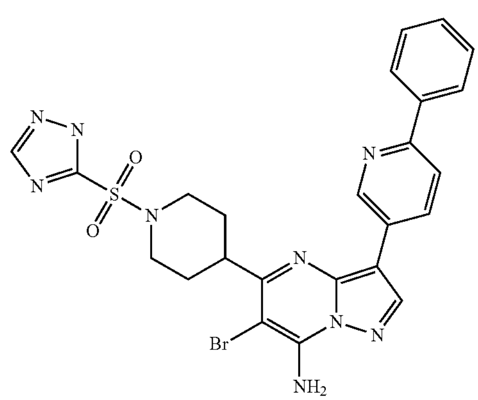 [SMILES: Nc1c(Br)c(C2CCN(S(=O)(=O)c3ncn[nH]3)CC2)nc2c(-c3ccc(-c4ccccc4)nc3)cnn12] | 579.08 | 580 | 3.6 |

TABLE-8B-continued

| Compound ID | Structures | M + H (calculated) | M + H (observed) | Retention Time(min) |
|---|---|---|---|---|
| 8.239 | 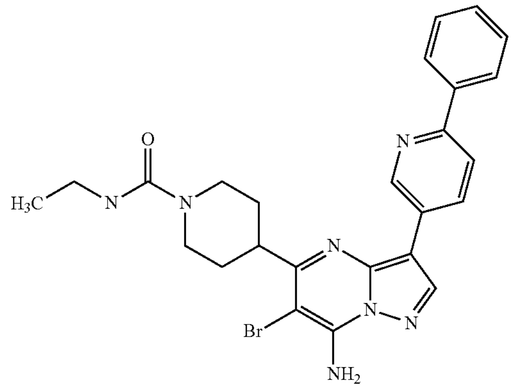 [SMILES: CCNC(=O)N1CCC(c2nc3c(-c4ccc(-c5ccccc5)nc4)cnn3c(N)c2Br)CC1] | 519.13 | 520 | 3.7 |
| 8.240 | 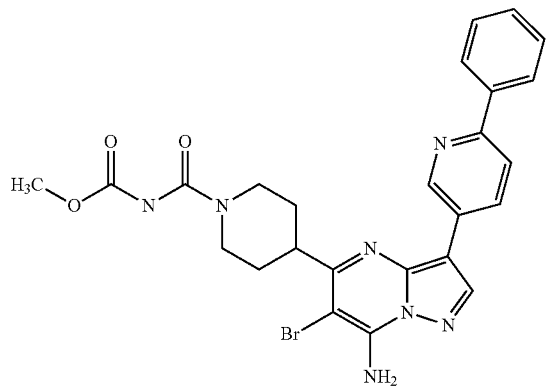 [SMILES: COC(=O)NC(=O)N1CCC(c2nc3c(-c4ccc(-c5ccccc5)nc4)cnn3c(N)c2Br)CC1] | 549.11 | 550 | 3.43 |
| 8.241 | 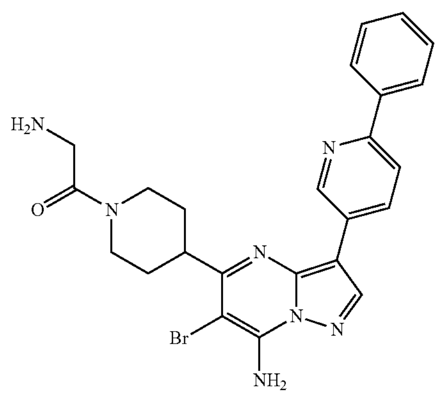 [SMILES: NCC(=O)N1CCC(c2nc3c(-c4ccc(-c5ccccc5)nc4)cnn3c(N)c2Br)CC1] | 505.12 | 506 | 2.77 |
| 8.242 | 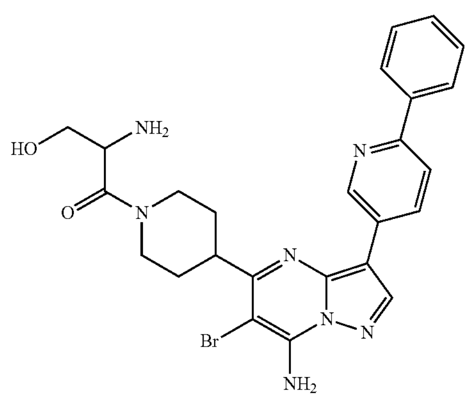 [SMILES: Nc1c(Br)c(C2CCN(C(=O)C(N)CO)CC2)nc2c(-c3ccc(-c4ccccc4)nc3)cnn12] | 535.13 | 536 | 2.73 |

TABLE-8B-continued

| Compound ID | Structures | M + H (calculated) | M + H (observed) | Retention Time(min) |
|---|---|---|---|---|
| 8.243 | 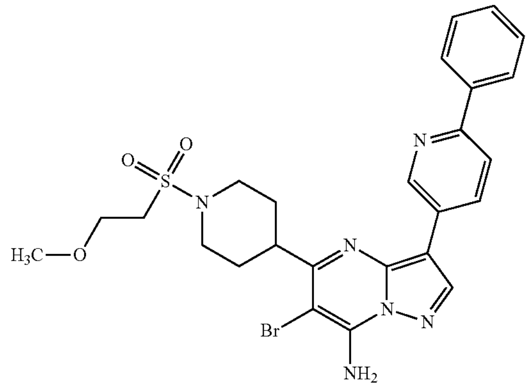 [SMILES: COCCS(=O)(=O)N1CCC(c2nc3c(-c4ccc(-c5ccccc5)nc4)cnn3c(N)c2Br)CC1] | 570.1 | 571 | 4.17 |
| 8.244 | 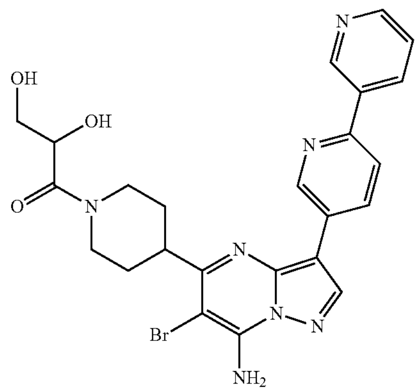 [SMILES: Nc1c(Br)c(C2CCN(C(=O)C(O)CO)CC2)nc2c(-c3ccc(-c4cccnc4)nc3)cnn12] | 537.11 | 538 | 2.78 |
| 8.245 | 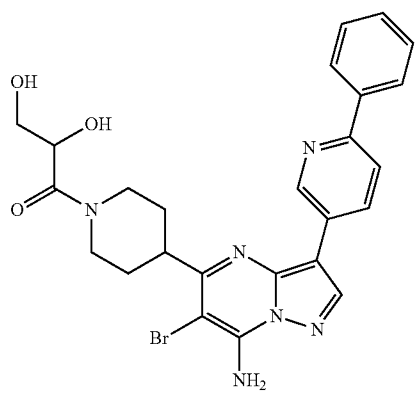 [SMILES: Nc1c(Br)c(C2CCN(C(=O)C(O)CO)CC2)nc2c(-c3ccc(-c4ccccc4)nc3)cnn12] | 536.11 | 537 | 3.13 |
| 8.246 | 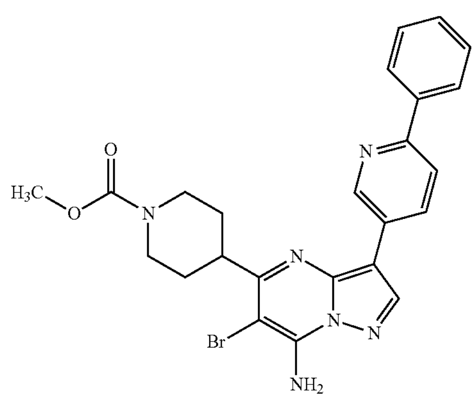 | 506.1 | 507 | 4.14 |

TABLE- 8B-continued

| Compound ID | Structures | M + H (calculated) | M + H (observed) | Retention Time(min) |
|---|---|---|---|---|
| 8.247 | 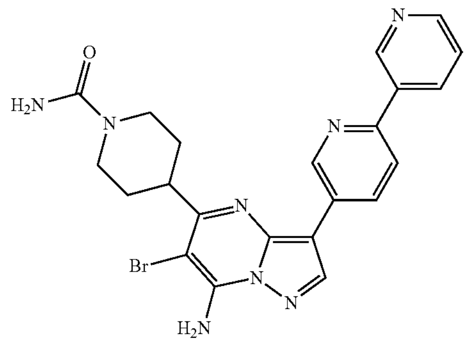 [SMILES: NC(=O)N1CCC(c2nc3c(-c4ccc(-c5cccnc5)nc4)cnn3c(N)c2Br)CC1] | 492.1 | 493 | 2.91 |
| 8.248 | 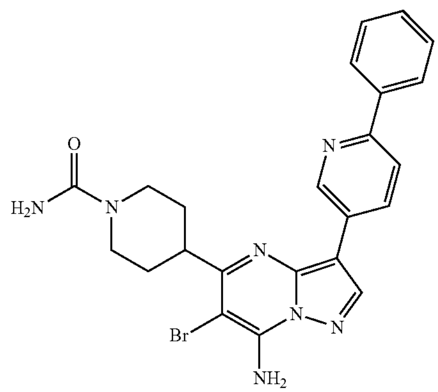 [SMILES: NC(=O)N1CCC(c2nc3c(-c4ccc(-c5ccccc5)nc4)cnn3c(N)c2Br)CC1] | 491.1 | 492.1 | 2.77 |
| 8.249 | 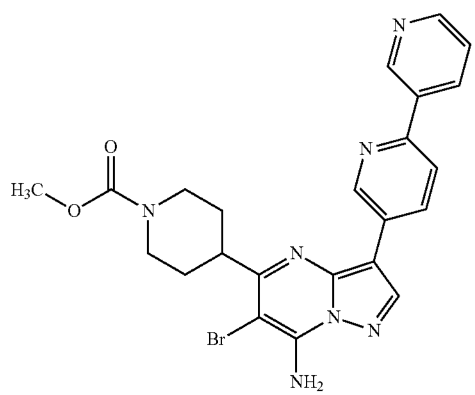 [SMILES: COC(=O)N1CCC(c2nc3c(-c4ccc(-c5cccnc5)nc4)cnn3c(N)c2Br)CC1] | 507.1 | 508 | 3.67 |
| 8.250 | 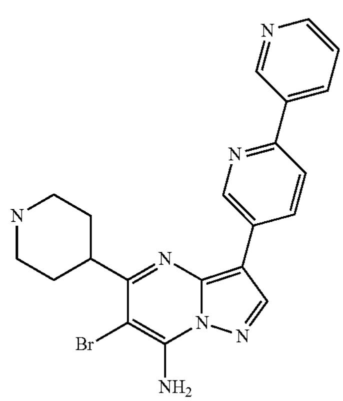 [SMILES: Nc1c(Br)c(C2CCNCC2)nc2c(-c3ccc(-c4cccnc4)nc3)cnn12] | 449.09 | 450 | 2.27 |

TABLE- 8B-continued
| Compound ID | Structures | M + H (calculated) | M + H (observed) | Retention Time(min) |
|---|---|---|---|---|
| 8.251 | 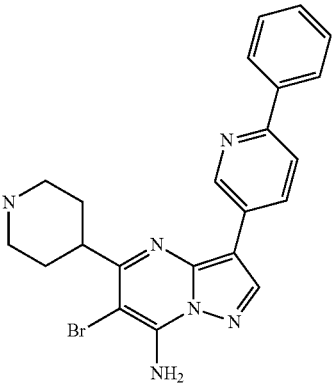 | 448.1 | 449 | 2.7 |
| 8.252 | 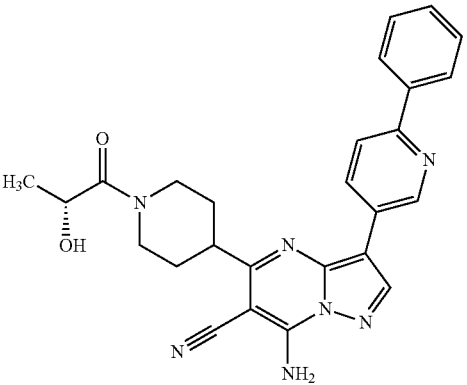 [SMILES: C[C@@H](O)C(=O)N1CCC(c2nc3c(-c4ccc(-c5ccccc5)nc4)cnn3c(N)c2C#N)CC1] | 467.2 | 468.2 | 2.59 |
| 8.253 | 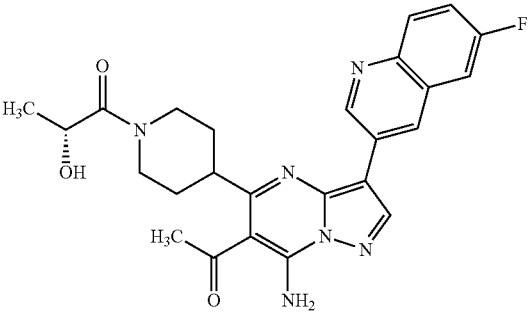 [SMILES: CC(=O)c1c(C2CCN(C(=O)[C@@H](C)O)CC2)nc2c(-c3cnc4ccc(F)cc4c3)cnn2c1N] | 476.19 | 478 | 3.25 |
| 8.254 | 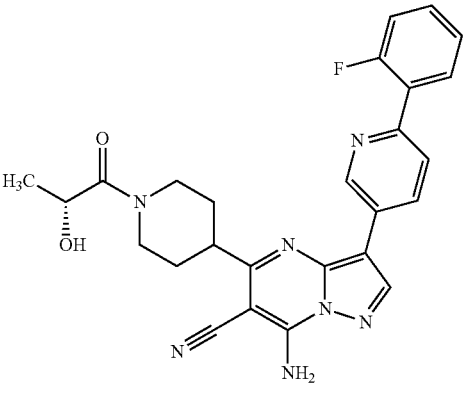 [SMILES: C[C@@H](O)C(=O)N1CCC(c2nc3c(-c4ccc(-c5ccccc5F)nc4)cnn3c(N)c2C#N)CC1] | 485.19 | 486 | 3.41 |

TABLE- 8B-continued
| Compound ID | Structures | M + H (calculated) | M + H (observed) | Retention Time(min) |
|---|---|---|---|---|
| 8.255 | 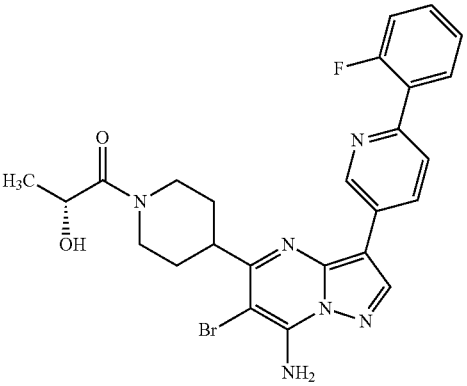 [SMILES: C[C@@H](O)C(=O)N1CCC(c2nc3c(-c4ccc(-c5ccccc5F)nc4)cnn3c(N)c2Br)CC1] | 538.11 | 539 | 3.85 |
| 8.256 | 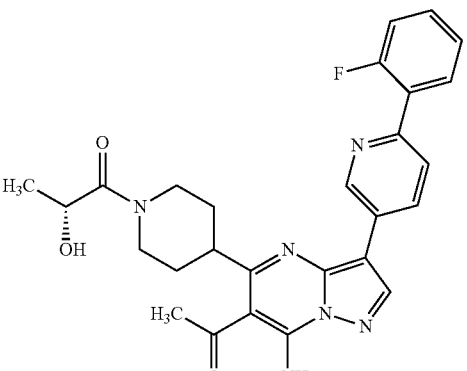 | 502.21 | 503.2 | 2.81 |
| 8.257 | 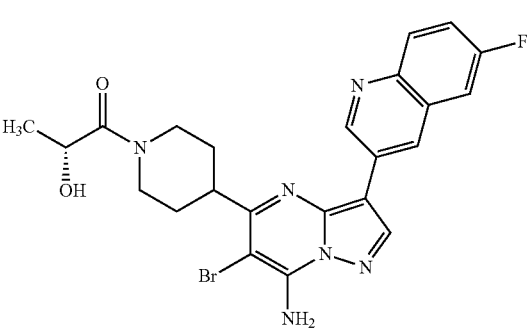 [SMILES: C[C@@H](O)C(=O)N1CCC(c2nc3c(-c4cnc5ccc(F)cc5c4)cnn3c(N)c2Br)CC1] | 512.09 | 513 | 3.52 |
| 8.258 | 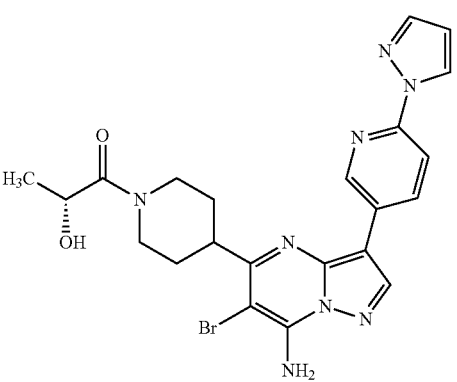 [SMILES: C[C@@H](O)C(=O)N1CCC(c2nc3c(-c4ccc(-n5cccn5)nc4)cnn3c(N)c2Br)CC1] | 510.11 | 511 | 4.16 |

TABLE- 8B-continued
| Compound ID | Structures | M + H (calculated) | M + H (observed) | Retention Time(min) |
|---|---|---|---|---|
| 8.259 | 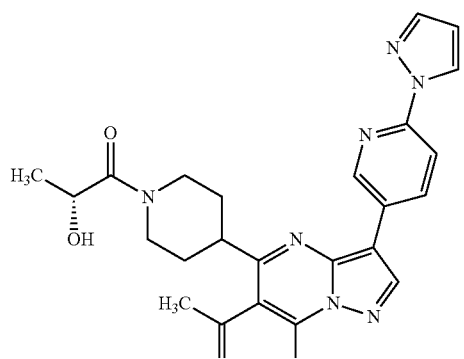 | 474.21 | 475 | 3.9 |
| 8.260 | 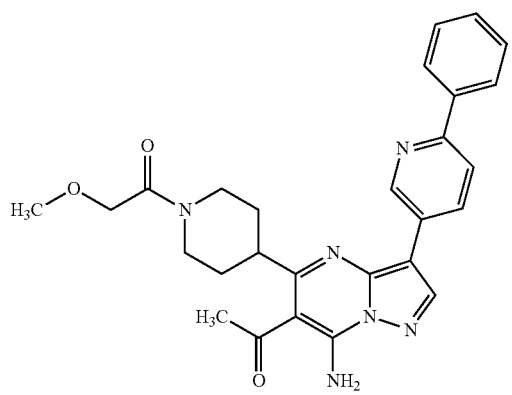 [SMILES: COCC(=O)N1CCC(c2nc3c(-c4ccc(-c5ccccc5)nc4)cnn3c(N)c2C(C)=O)CC1] | 484.22 | 485 | 3.3 |
| 8.261 | 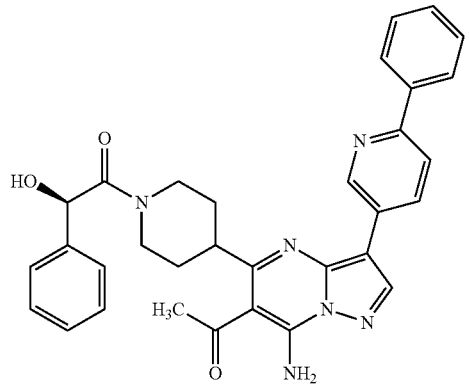 [SMILES: CC(=O)c1c(C2CCN(C(=O)[C@H](O)c3ccccc3)CC2)nc2c(-c3ccc(-c4ccccc4)nc3)cnn2c1N] | 546.23 | 547 | 3.68 |
| 8.265 | 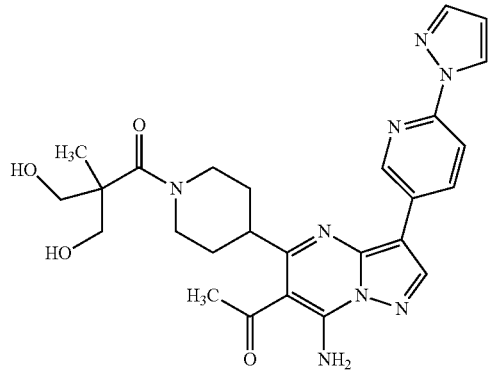 [SMILES: CC(=O)c1c(C2CCN(C(=O)C(C)(CO)CO)CC2)nc2c(-c3ccc(-n4cccn4)nc3)cnn2c1N] | 518.23 | 519.1 | 3.91 |

TABLE- 8B-continued
| Compound ID | Structures | M + H (calculated) | M + H (observed) | Retention Time(min) |
|---|---|---|---|---|
| 8.266 | 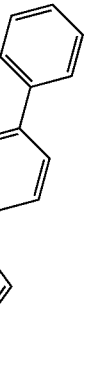 | 497.25 | 498.2 | 2.22 |
| 8.267 | 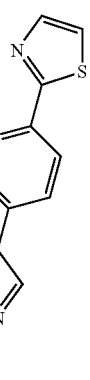 | 535.2 | 536.2 | 2.92 |
| 8.268 | 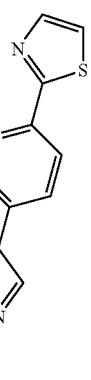 | 491.17 | 492 | 3.76 |
| 8.269 | 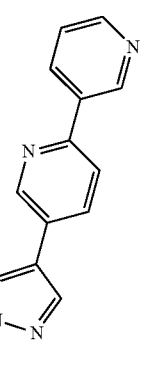 | 529.24 | 530.2 | 2.34 |

TABLE-8B-continued

| Compound ID | Structures | M + H (calculated) | M + H (observed) | Retention Time(min) |
|---|---|---|---|---|
| 8.270 | 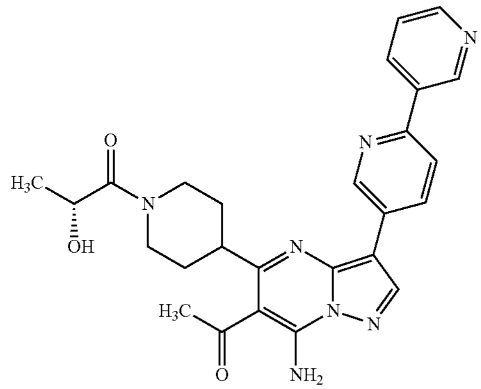 [SMILES: CC(=O)c1c(C2CCN(C(=O)[C@@H](C)O)CC2)nc2c(-c3ccc(-c4cccnc4)nc3)cnn2c1N] | 485.21 | 486.1 | 2.89 |
| 8.271 | 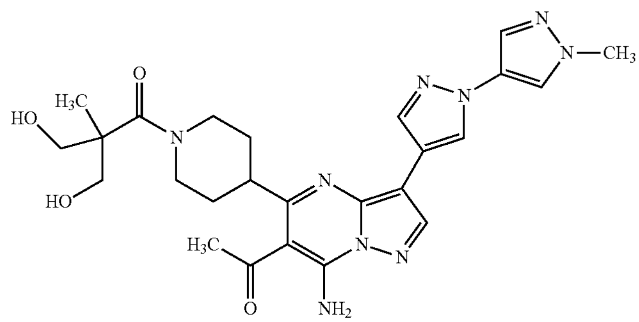 [SMILES: CC(=O)c1c(C2CCN(C(=O)C(C)(CO)CO)CC2)nc2c(-c3cnn(-c4cnn(C)c4)c3)cnn2c1N] | 521.25 | 522.2 | 2.59 |
| 8.272 | 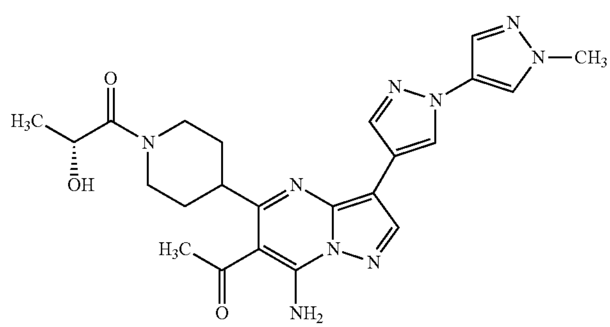 [SMILES: CC(=O)c1c(C2CCN(C(=O)[C@@H](C)O)CC2)nc2c(-c3cnn(-c4cnn(C)c4)c3)cnn2c1N] | 477.22 | 478.1 | 3.38 |
| 8.273 | 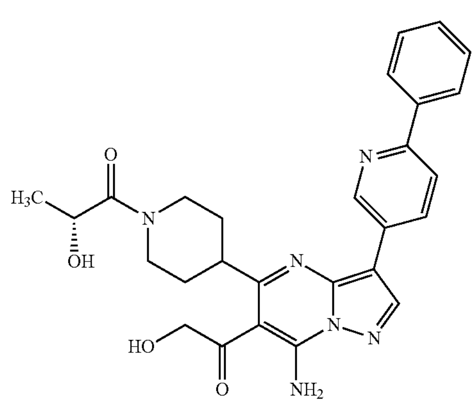 [SMILES: C[C@@H](O)C(=O)N1CCC(c2nc3c(-c4ccc(-c5ccccc5)nc4)cnn3c(N)c2C(=O)CO)CC1] | 500.21 | 501 | 3.27 |

TABLE- 8B-continued
| Compound ID | Structures | M + H (calculated) | M + H (observed) | Retention Time(min) |
|---|---|---|---|---|
| 8.274 | 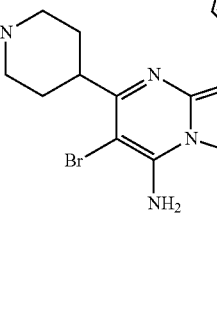 | 494.11 | 496 + 498 | 3.20 |
| 8.275 | 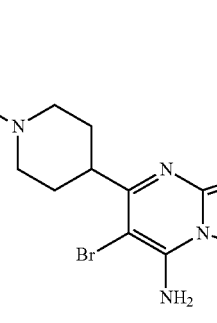 | 517.09 | 519 + 521 | 3.37 |
| 8.276 | 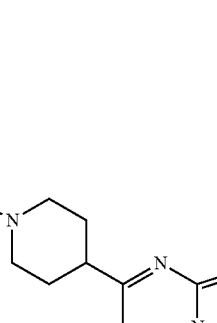 | 517.09 | 519 + 521 | 3.48 |
| 8.277 | 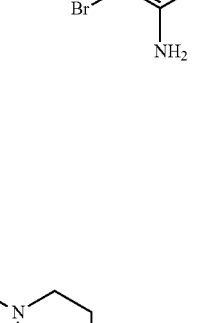 | 517.09 | 519 + 521 | 3.31 |

TABLE- 8B-continued

| Compound ID | Structures | M + H (calculated) | M + H (observed) | Retention Time(min) |
|---|---|---|---|---|
| 8.278 | 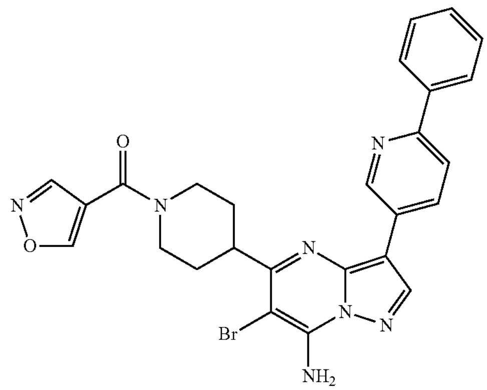 [SMILES: Nc1c(Br)c(C2CCN(C(=O)c3cnoc3)CC2)nc2c(-c3ccc(-c4ccccc4)nc3)cnn12] | 543.10 | 545 + 547 | 3.63 |
| 8.279 | 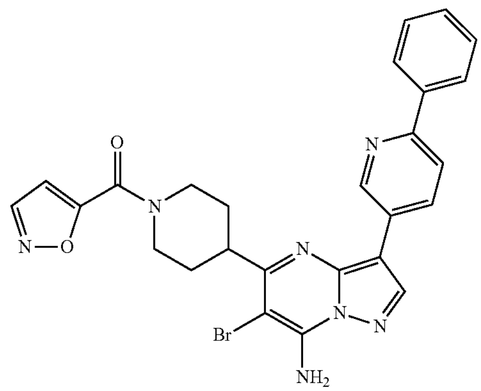 [SMILES: Nc1c(Br)c(C2CCN(C(=O)c3ccno3)CC2)nc2c(-c3ccc(-c4ccccc4)nc3)cnn12] | 543.10 | 545 + 547 | 3.72 |
| 8.280 | 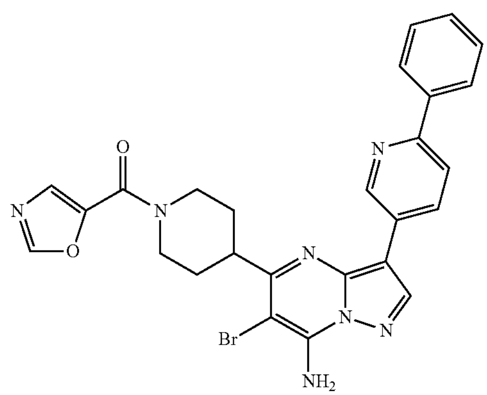 [SMILES: Nc1c(Br)c(C2CCN(C(=O)c3cnco3)CC2)nc2c(-c3ccc(-c4ccccc4)nc3)cnn12] | 543.10 | 545 + 547 | 3.53 |
| 8.281 | 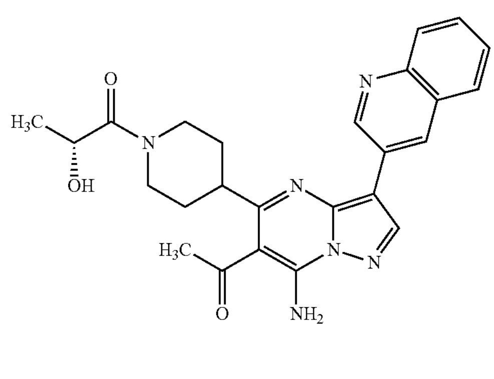 [SMILES: CC(=O)c1c(C2CCN(C(=O)[C@@H](C)O)CC2)nc2c(-c3cnc4ccccc4c3)cnn2c1N] | 458.21 | 460 | 2.92 |

TABLE- 8B-continued

| Compound ID | Structures | M + H (calculated) | M + H (observed) | Retention Time(min) |
|---|---|---|---|---|
| 8.282 | 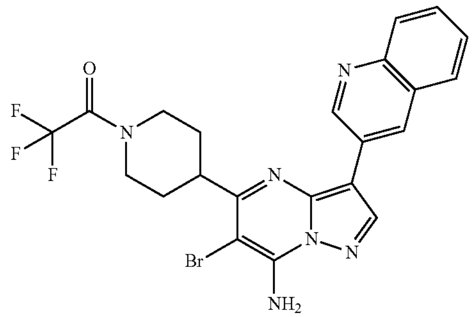 [SMILES: Nc1c(Br)c(C2CCN(C(=O)C(F)(F)F)CC2)nc2c(-c3cnc4ccccc4c3)cnn12] | 518.07 | 520 + 522 | 3.98 |
| 8.283 | 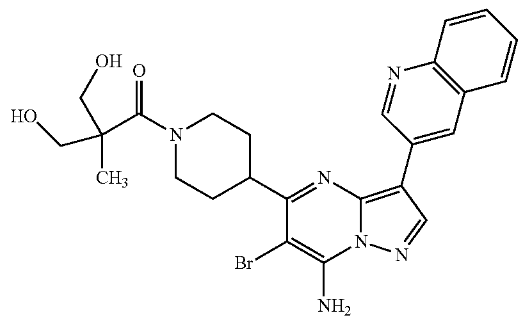 [SMILES: CC(CO)(CO)C(=O)N1CCC(c2nc3c(-c4cnc5ccccc5c4)cnn3c(N)c2Br)CC1] | 538.13 | 539 + 541 | 1.33 |
| 8.284 | 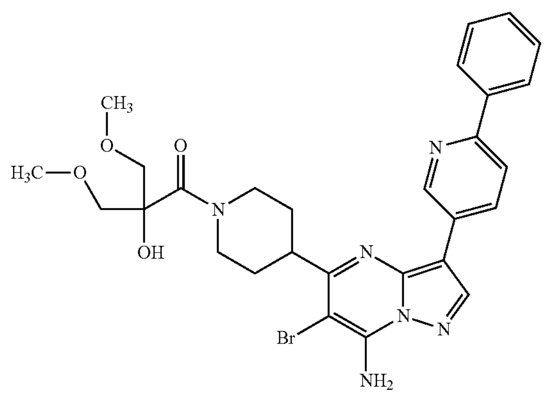 [SMILES: COCC(O)(COC)C(=O)N1CCC(c2nc3c(-c4ccc(-c5ccccc5)nc4)cnn3c(N)c2Br)CC1] | 594.16 | 596 + 598 | 3.61 |
| 8.285 | 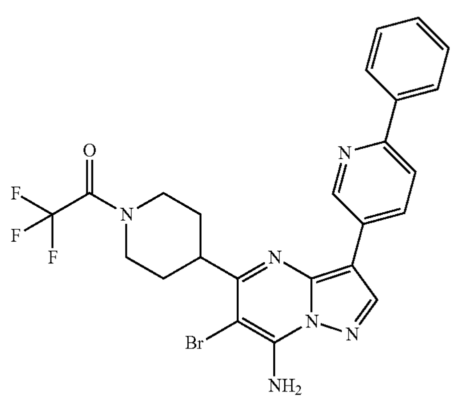 [SMILES: Nc1c(Br)c(C2CCN(C(=O)C(F)(F)F)CC2)nc2c(-c3ccc(-c4ccccc4)nc3)cnn12] | 544.08 | 546 + 548 | 4.20 |

TABLE- 8B-continued
| Compound ID | Structures | M + H (calculated) | M + H (observed) | Retention Time(min) |
|---|---|---|---|---|
| 8.286 | 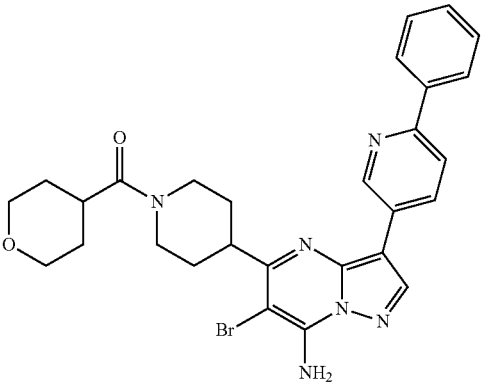 [SMILES: Nc1c(Br)c(C2CCN(C(=O)C3CCOCC3)CC2)nc2c(-c3ccc(-c4ccccc4)nc3)cnn12] | 560.15 | 562 + 564 | 3.66 |
| 8.287 | 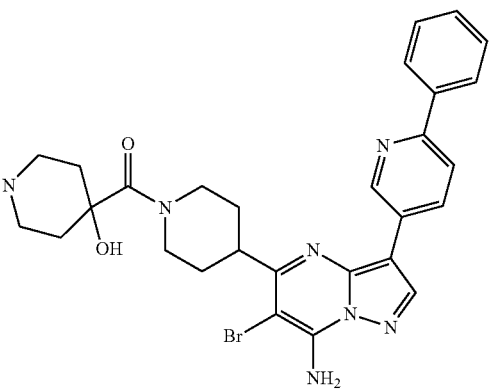 [SMILES: Nc1c(Br)c(C2CCN(C(=O)C3(O)CCNCC3)CC2)nc2c(-c3ccc(-c4ccccc4)nc3)cnn12] | 575.16 | 576 + 578 | 1.20 |
| 8.288 | 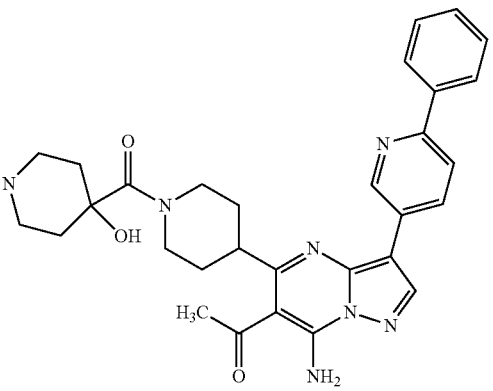 [SMILES: CC(=O)c1c(C2CCN(C(=O)C3(O)CCNCC3)CC2)nc2c(-c3ccc(-c4ccccc4)nc3)cnn2c1N] | 539.26 | 540 | 1.31 |
| 8.289 | 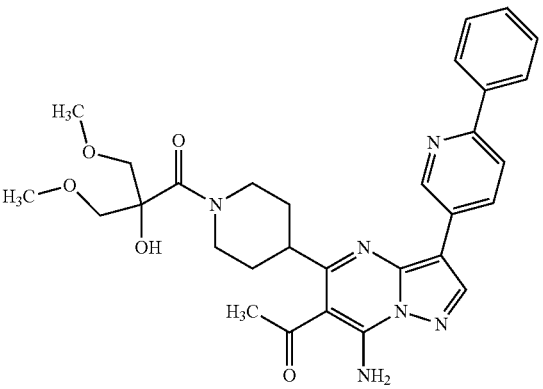 [SMILES: COCC(O)(COC)C(=O)N1CCC(c2nc3c(-c4ccc(-c5ccccc5)nc4)cnn3c(N)c2C(C)=O)CC1] | 558.26 | 559 | 3.41 |

TABLE- 8B-continued

| Compound ID | Structures | M + H (calculated) | M + H (observed) | Retention Time(min) |
|---|---|---|---|---|
| 8.290 | 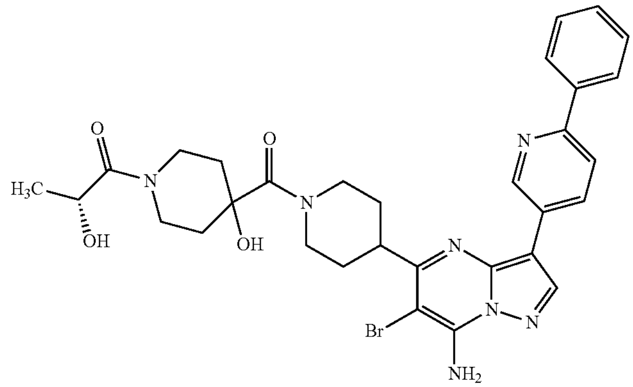 [SMILES: C[C@@H](O)C(=O)N1CCC(O)(C(=O)N2CCC(c3nc4c(-c5ccc(-c6ccccc6)nc5)cnn4c(N)c3Br)CC2)CC1] | 647.19 | 648 + 650 | 2.74 |
| 8.291 | 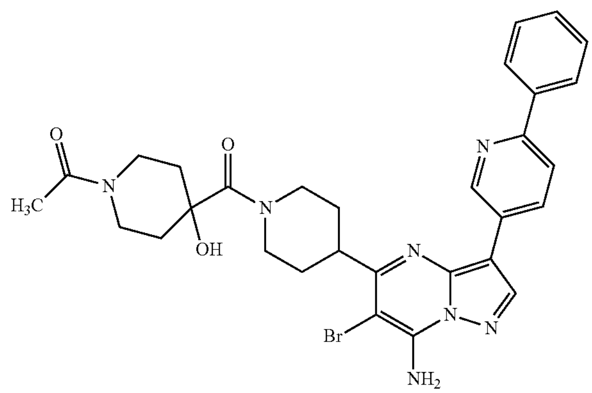 [SMILES: CC(=O)N1CCC(O)(C(=O)N2CCC(c3nc4c(-c5ccc(-c6ccccc6)nc5)cnn4c(N)c3Br)CC2)CC1] | 617.18 | 518 + 520 | 3.58 |
| 8.292 | 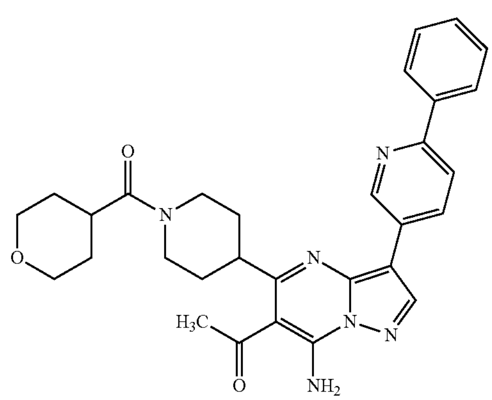 [SMILES: CC(=O)c1c(C2CCN(C(=O)C3CCOCC3)CC2)nc2c(-c3ccc(-c4ccccc4)nc3)cnn2c1N] | 524.25 | 525 | 3.41 |

TABLE-8B-continued
| Compound ID | Structures | M + H (calculated) | M + H (observed) | Retention Time(min) |
|---|---|---|---|---|
| 8.293 | 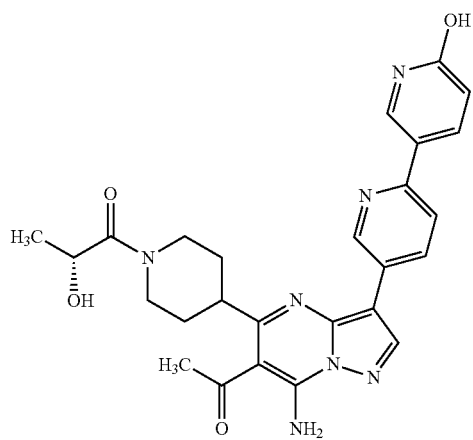 [SMILES: CC(=O)c1c(C2CCN(C(=O)[C@@H](C)O)CC2)nc2c(-c3ccc(-c4ccc(O)nc4)nc3)cnn2c1N] | 501.21 | 502 | 2.64 |
| 8.294 | 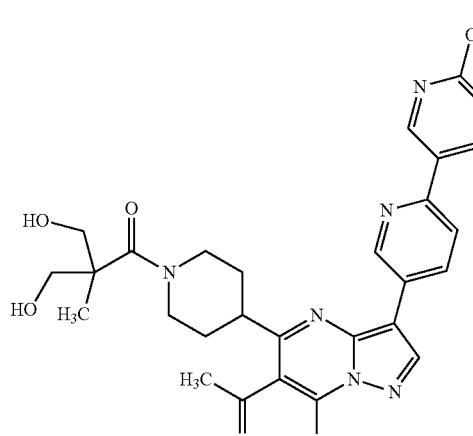 | 545.24 | 546 | 2.62 |
| 8.295 | 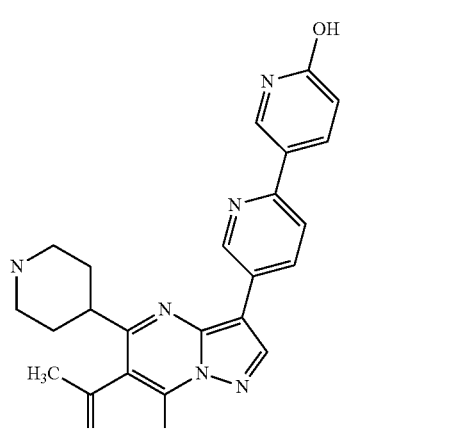 | 429.19 | 430 | 2.07 |

TABLE- 8B-continued

| Compound ID | Structures | M + H (calculated) | M + H (observed) | Retention Time(min) |
| --- | --- | --- | --- | --- |
| 8.296 | 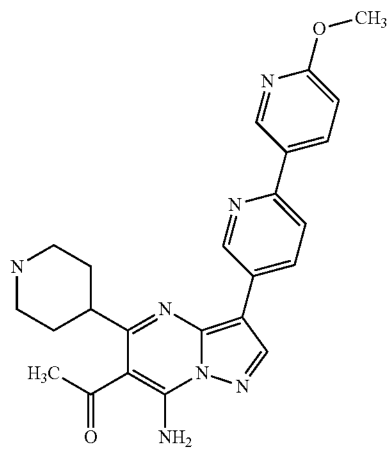 [SMILES: COc1ccc(-c2ccc(-c3cnn4c(N)c(C(C)=O)c(C5CCNCC5)nc34)cn2)cn1] | 443.21 | 444 | 2.74 |
| 8.297 | 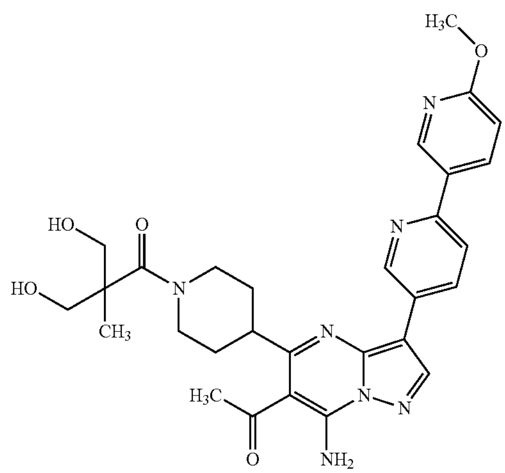 [SMILES: COc1ccc(-c2ccc(-c3cnn4c(N)c(C(C)=O)c(C5CCN(C(=O)C(C)(CO)CO)CC5)nc34)cn2)cn1] | 559.25 | 560 | 3.37 |
| 8.298 | 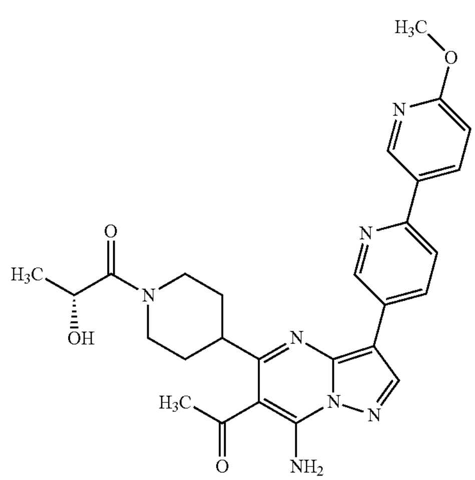 [SMILES: COc1ccc(-c2ccc(-c3cnn4c(N)c(C(C)=O)c(C5CCN(C(=O)[C@@H](C)O)CC5)nc34)cn2)cn1] | 515.23 | 516 | 3.51 |

TABLE- 8B-continued

| Compound ID | Structures | M + H (calculated) | M + H (observed) | Retention Time(min) |
|---|---|---|---|---|
| 8.299 | 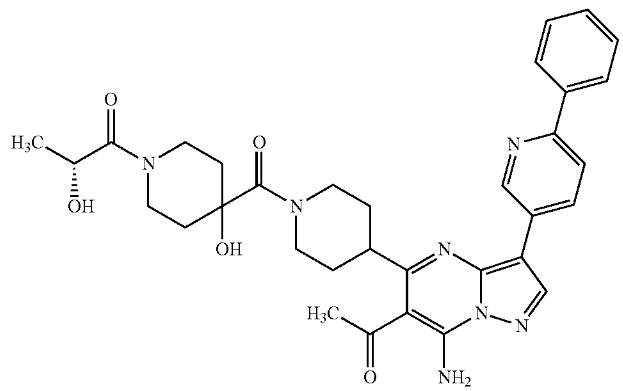 [SMILES: CC(=O)c1c(C2CCN(C(=O)C3(O)CCN(C(=O)[C@@H](C)O)CC3)CC2)nc2c(-c3ccc(-c4ccccc4)nc3)cnn2c1N] | 611.29 | 612 | 3.33 |
| 8.300 | 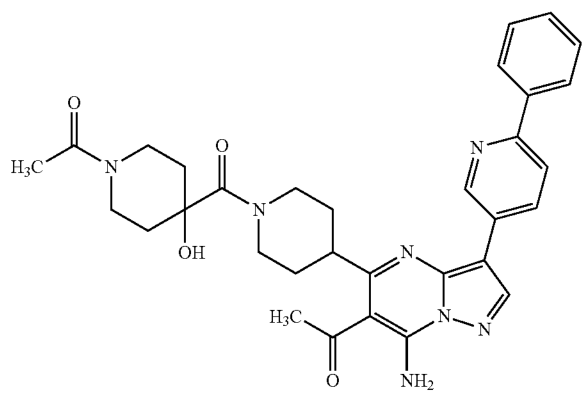 [SMILES: CC(=O)c1c(C2CCN(C(=O)C3(O)CCN(C(C)=O)CC3)CC2)nc2c(-c3ccc(-c4ccccc4)nc3)cnn2c1N] | 581.28 | 582 | 3.36 |
| 8.301 | 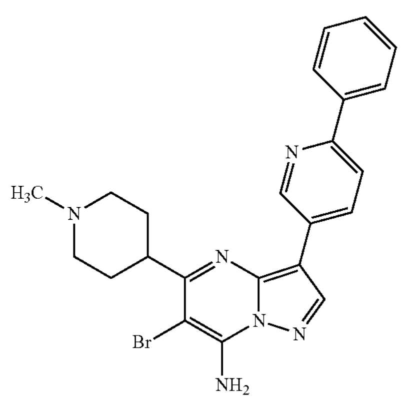 [SMILES: CN1CCC(c2nc3c(-c4ccc(-c5ccccc5)nc4)cnn3c(N)c2Br)CC1] | 462.12 | 463 + 465 | 2.80 |

TABLE- 8B-continued

| Compound ID | Structures | M + H (calculated) | M + H (observed) | Retention Time(min) |
|---|---|---|---|---|
| 8.302 | 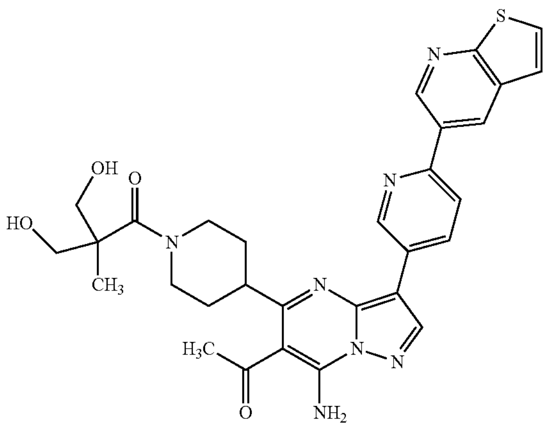 [SMILES: CC(=O)c1c(C2CCN(C(=O)C(C)(CO)CO)CC2)nc2c(-c3ccc(-c4cnc5sccc5c4)nc3)cnn2c1N] | 585.22 | 586 | 3.75 |
| 8.303 | 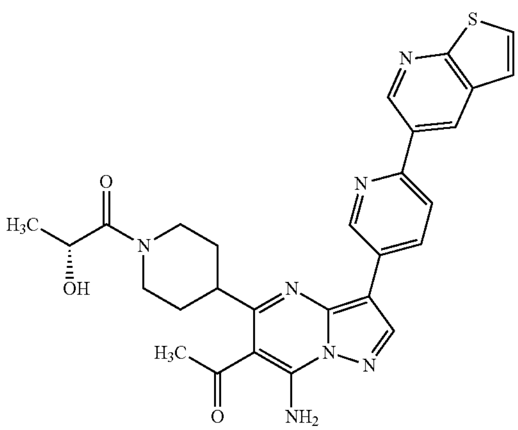 | 541.19 | 542 | 3.90 |
| 8.304 | 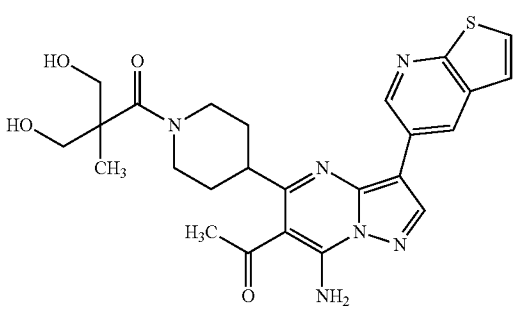 [SMILES: CC(=O)c1c(C2CCN(C(=O)C(C)(CO)CO)CC2)nc2c(-c3cnc4sccc4c3)cnn2c1N] | 508.19 | 509 | 1.57 |
| 8.305 | 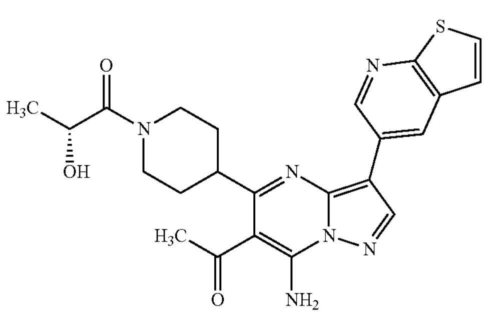 [SMILES: CC(=O)c1c(C2CCN(C(=O)[C@@H](C)O)CC2)nc2c(-c3cnc4sccc4c3)cnn2c1N] | 464.16 | 465 | 4.05 |

1165

Synthesis of tert-butyl 4-(3-(6-(1H-pyrazol-1-yl)pyridin-3-yl)-7-(bis((2-(trimethylsilyl)ethoxy)methyl) amino)pyrazolo[1,5-a]pyrimidin-5-yl)piperidine-1-carboxylate

1166

Synthesis of tert-butyl 4-(3-(6-(1H-pyrazol-1-yl)pyridin-3-yl)-7-(bis((2-(trimethylsilyl)ethoxy)methyl)amino)pyrazolo[1,5-a]pyrimidin-5-yl)piperidine-1-carboxylate

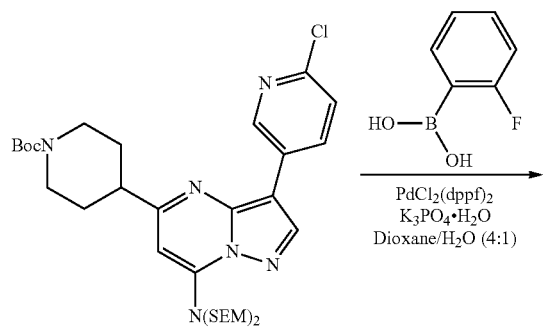

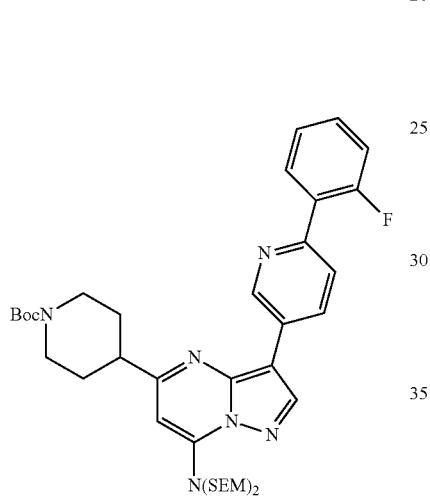

By essentially the same procedure as above, tert-butyl 4-(3-(6-(1H-pyrazol-1-yl)pyridin-3-yl)-7-(bis((2-(trimethylsilyl)ethoxy)methyl)amino)pyrazolo[1,5-a]pyrimidin-5-yl)piperidine-1-carboxylate is prepared.

To tert-butyl 4-(7-(bis((2-(trimethylsilyl)ethoxy)methyl)amino)-3-(6-chloropyridin-3-yl)pyrazolo[1,5-a]pyrimidin-5-yl)piperidine-1-carboxylate (2.25 g, 3.3 mmol) in Dioxane (24 ml) and H$_2$O (6 ml) was added the 2-fluorophenylboronic acid (0.92 g, 6.6 mmol), PdCl$_2$(dppf)$_2$.CH$_2$Cl$_2$ (0.32 g, 0.39 mmol) and K$_3$PO$_4$.H$_2$O (1.7 g, 8.2 mmol). The reaction was heated at 100° C. for 16 hours, at which time LC/MS analysis confirmed full consumption of starting material. On cooling, H$_2$O (100 ml) and EtOAc (100 ml) were added and organics were extracted with EtOAc (4×50 ml), dried (Na$_2$SO$_4$) and concentrated in vacuo to give a crude product. Gradient column chromatography on silica eluting with 0% to 100% EtOAc/hexanes gave tert-butyl 4-(7-(bis((2-(trimethylsilyl)ethoxy)methyl)amino)-3-(6-(2-fluorophenyl)pyridin-3-yl)pyrazolo[1,5-a]pyrimidin-5-yl)piperidine-1-carboxylate (2.3 g, 95%).

By essentially the same procedure as to other related compound, different derivatives of above compound is prepared (Table-8B).

Synthesis of (R)-1-(4-(7-amino-6-(2-hydroxyacetyl)-3-(6-phenylpyridin-3-yl)pyrazolo[1,5-a]pyrimidin-5-yl)piperidin-1-yl)-2-hydroxypropan-1-one

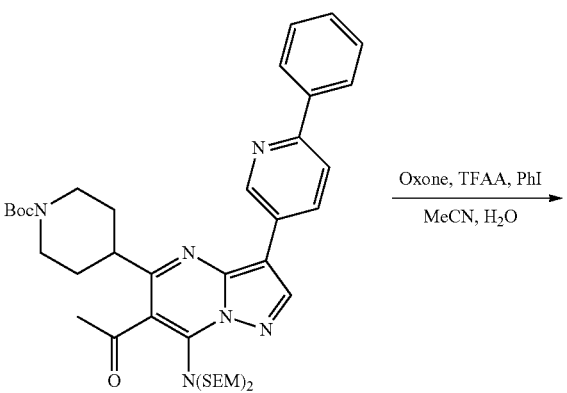

1167

-continued

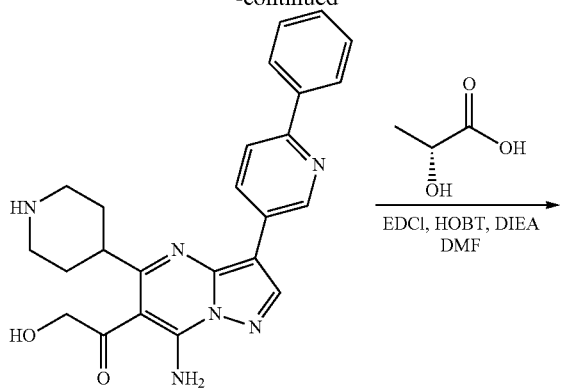

EDCl, HOBT, DIEA
DMF

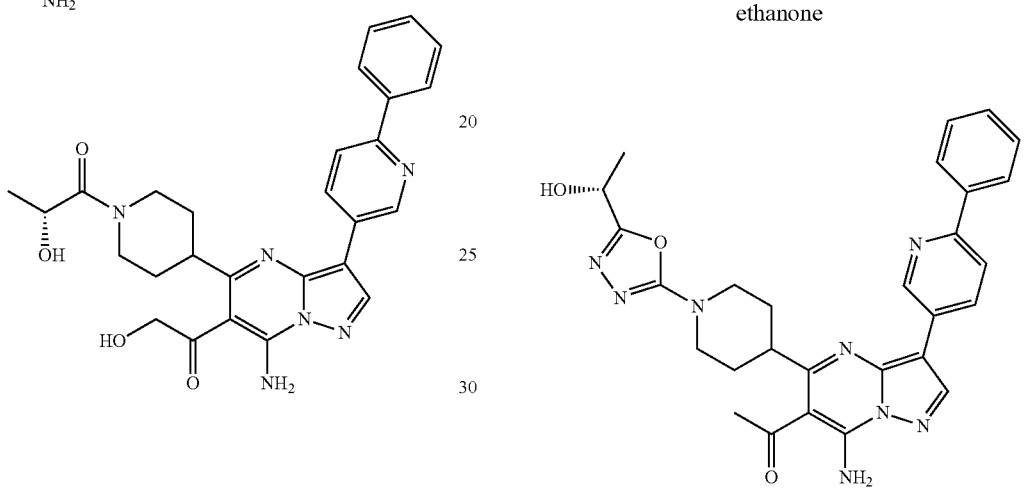

Step-1

Synthesis of 1-(7-amino-3-(6-phenylpyridin-3-yl)-5-(piperidin-4-yl)pyrazolo[1,5-a]pyrimidin-6-yl)-2-hydroxyethanone A solution of oxone (1.9 g, 3.1 mmol), trifluoroacetic anhydride (1.1 ml, 7.9 mmol) and H₂O (5.7 ml) was stirred at 40° C. for 7 h, and then cooled to room temperature. To this a solution of tert-butyl 4-(6-acetyl-7-(bis((2-(trimethylsilyl)ethoxy)methyl)amino)-3-(6-phenylpyridin-3-yl)pyrazolo[1,5-a]pyrimidin-5-yl)piperidine-1-carboxylate (0.87 g, 1.13 mmol) and PhI (0.03 ml, 0.23 mmol) in acetonitrile (17 ml) was added. The resulting solution was stirred at 90° C. for 15 h. On cooling, the reaction mixture was filtered and solids were washed with DCM. It was then concentrated in vacuo to give a crude product which was submitted to the analytical group for purification to afford the desired 1-(7-amino-3-(6-phenylpyridin-3-yl)-5-(piperidin-4-yl)pyrazolo[1,5-a]pyrimidin-6-yl)-2-hydroxyethanone (94.2 mg, 17%).

Step-2:

Synthesis of (R)-1-(4-(7-amino-6-(2-hydroxyacetyl)-3-(6-phenylpyridin-3-yl)pyrazolo[1,5-a]pyrimidin-5-yl)piperidin-1-yl)-2-hydroxypropan-1-one A mixture of (R)-2-hydroxypropanoic acid (13.8 mg, 0.16 mmol), EDCI (46 mg, 0.24 mmol), and 1-hydroxybenzotriazole (16.22 mg, 0.12 mmol) in DMF (2 ml) was stirred at room temperature for 10 min. To this 1-(7-amino-3-(6-phe-

1168 nylpyridin-3-yl)-5-(piperidin-4-yl)pyrazolo[1,5-a]pyrimidin-6-yl)-2-hydroxyethanone (58.77 mg, 0.12 mmol) was added followed by N,N-diisopropylethylamine (0.1 ml, 0.6 mmol). It was stirred further for 20 min at room temperature at which time LC/MS analysis confirmed full consumption of starting material. This crude compound was submitted to the analytical group for purification to afford the desired (R)-1-(4-(7-amino-6-(2-hydroxyacetyl)-3-(6-phenylpyridin-3-yl)pyrazolo[1,5-a]pyrimidin-5-yl)piperidin-1-yl)-2-hydroxypropan-1-one. LCMS: 3.27 mins, m/z=501.0 (MH⁺).

Synthesis of (R)-1-(7-amino-5-(1-(5-(1-hydroxyethyl)-1,3,4-oxadiazol-2-yl)piperidin-4-yl)-3-(6-phenylpyridin-3-yl)pyrazolo[1,5-a]pyrimidin-6-yl)ethanone

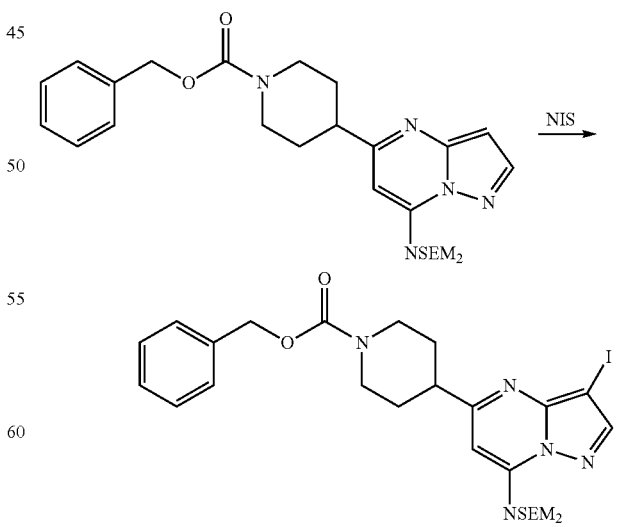

Step 1

Preparation of benzyl 4-(7-(bis((2-(trimethylsilyl)ethoxy)methyl)amino)-3-iodopyrazolo[1,5-a]pyrimidin-5-yl)piperidine-1-carboxylate To a solution of benzyl 4-(7-(bis((2-(trimethylsilyl)ethoxy)methyl)amino)pyrazolo[1,5-a]pyrimidin-5-yl)piperidine-1-carboxylate (2.27 g, 3.7 mmol) in acetonitrile (15 mL) was added NIS (833 mg, 1 eq). After stirring 1.5 hour, solvent was removed and the residue was purified on silica gel. Elution with EtOAc/Hexanes (0-50%) gave the title compound (2.38 g, 86%) as gum.

Step 2

Preparation of benzyl 4-(7-(bis((2-(trimethylsilyl)ethoxy)methyl)amino)-3-(6-phenylpyridin-3-yl)pyrazolo[1,5-a]pyrimidin-5-yl)piperidine-1-carboxylate

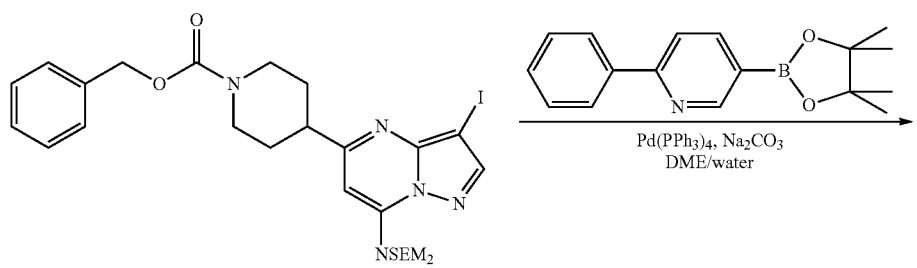

To a pressure tube were charged benzyl 4-(7-(bis((2-(trimethylsilyl)ethoxy)methyl)amino)-3-iodopyrazolo[1,5-a]pyrimidin-5-yl)piperidine-1-carboxylate (1 g, 2.85 mmol), 2-phenyl-5-(4,4,5,5-tetramethyl-1,3,2-dioxaborolan-2-yl)pyridine (1.2 g, 4.1 mmol), Pd(PPh$_3$)$_4$ (164 mg, 0.14 mmol), DME (20 mL) and 2 M Na$_2$CO$_3$ (10 mL). The mixture was briefly degassed with Argon and the tube was capped and heated at 80° C. for 15 hours. On cooling, H$_2$O (40 mL) and EtOAc (100 mL) and aqueous layer was extracted with EtOAc (3×) and combined organic layers were washed with brine once and dried (MgSO$_4$). After concentration in vacuo the residue was purified on silica gel. Elution with EtOAc/Hexanes (0-30%) gave the title compound (1.33 g, 61%).

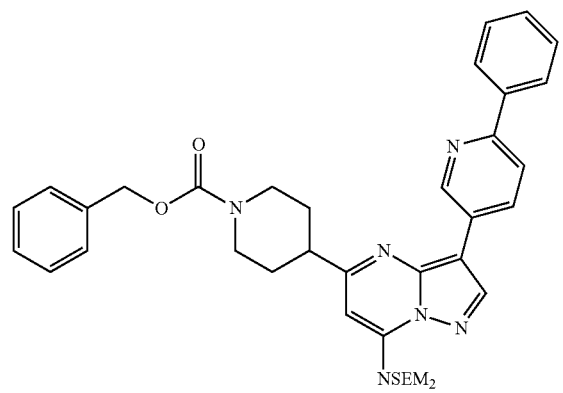

Step 3

Preparation of 3-(6-phenyl)pyridin-3-yl)-5-(piperidin-4-yl)-N,N-bis((2-(trimethylsilyl)ethoxy)methyl)pyrazolo[1,5-a]pyrimidin-7-amine

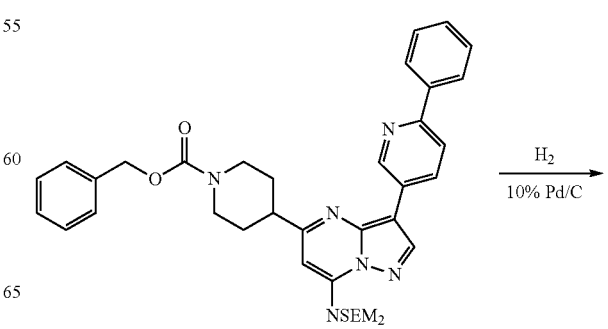

-continued

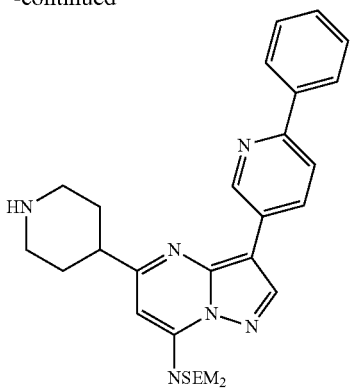

A mixture of benzyl 4-(7-(bis((2-(trimethylsilyl)ethoxy)methyl)amino)-3-(6-phenylpyridin-3-yl)pyrazolo[1,5-a]pyrimidin-5-yl)piperidine-1-carboxylate (1.33 g, 1.77 mmol), 10% Pd/C (170 mg) in EtOAc (10 mL) was stirred under hydrogen (balloon pressure) for two days, and then at 45° C. for 15 hours. After filtration and washing with EtOAc 4 times the title product (1 g, 93%) was obtained.

Step 4

Preparation of (R)-2-(benzyloxy)propanehydrazide

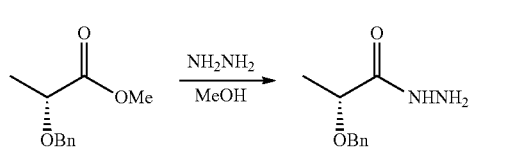

A mixture of (R)-methyl 2-(benzyloxy)propanoate (1 g, 5.15 mmol), hydrazine monohydrate (250 ul) in MeOH (14 mL) was refluxed 3 hours. Solvent was removed under reduced pressure and the residue was purified on silica gel. Elution with EtOAc yielded title compound (640 mg, 64%).

Step 5

Preparation of (R)-5-(1-(benzyloxy)ethyl)-1,3,4-oxadiazol-2(3H)-one

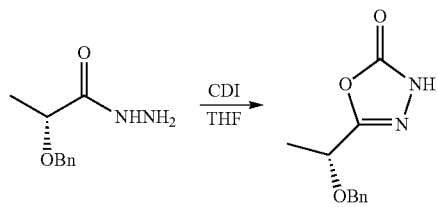 [SMILES: C[C@@H](OCc1ccccc1)C(=O)NN ; "CDI" ; C[C@@H](OCc1ccccc1)c1n[nH]c(=O)o1 ; "THF"]

To a solution of (R)-2-(benzyloxy)propanehydrazide (194 mg, 1 mmol) in anhydrous THF (2 mL) was added CDI (178 mg, 1.1 mmol) and the resulting mixture was allowed to stir one hour. Solvent was removed under reduced pressure and the residue was purified on silica gel. Elution with EtOAc yielded title product.

Step 6

Preparation of (R)-5-(1-(5-(1-(benzyloxy)ethyl)-1,3,4-oxadiazol-2-yl)piperidin-4-yl)-3-(6-phenylpyridin-3-yl)-N,N-bis((2-(trimethylsilyl)ethoxy)methyl)pyrazolo[1,5-a]pyrimidin-7-amine

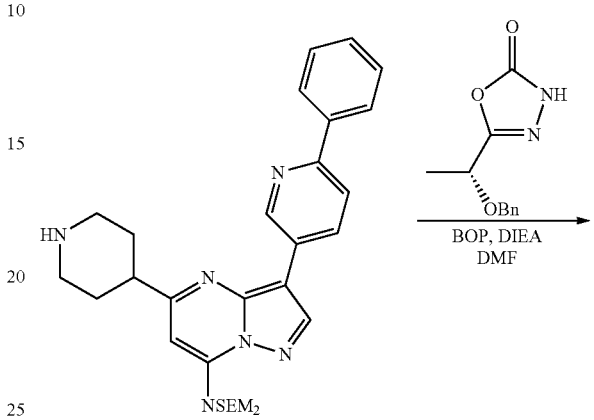

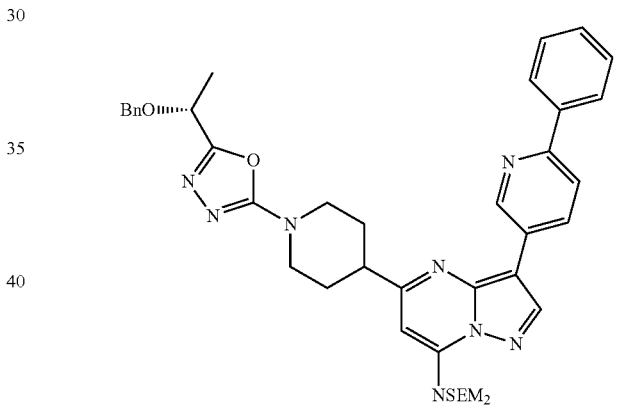

To a stirred solution of (R)-5-(1-(benzyloxy)ethyl)-1,3,4-oxadiazol-2(3H)-one (44 mg, 0.2 mmol), 3-(6-phenylpyridin-3-yl)-5-(piperidin-4-yl)-N,N-bis((2-(trimethylsilyl)ethoxy)methyl)pyrazolo[1,5-a]pyrimidin-7-amine (150 mg, 0.24 mmol) and DIEA (70 ul, 0.4 mmol) in DMF (1.4 mL) was added BOP (97 mg, 0.22 mmol) and the resulting solution was allowed to stir overnight. Water was added and was extracted with EtOAc (3×) and combined organic layers were washed with water (3×), brine once and dried (MgSO$_4$). After concentration in vacuo the residue was purified on silica gel. Elution with EtOAc/Hexanes (0-10%) gave the title compound (142 mg, 85%).

1173

Step 7

Preparation of (R)-1-(5-(4-(7-(bis((2-(trimethylsilyl)ethoxy)methyl)amino)-3-(6-phenylpyridin-3-yl)pyrazolo[1,5-a]pyrimidin-5-yl)piperidin-1-yl)-1,3,4-oxadiazol-2-yl)ethanol

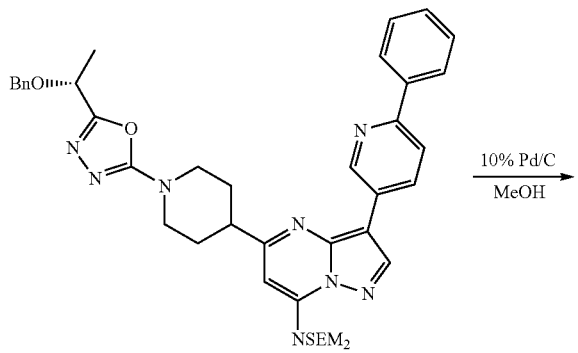

A mixture of (R)-5-(1-(5-(1-(benzyloxy)ethyl)-1,3,4-oxadiazol-2-yl)piperidin-4-yl)-3-(6-phenylpyridin-3-yl)-N,N-bis((2-(trimethylsilyl)ethoxy)methyl)pyrazolo[1,5-a]pyrimidin-7-amine (105 mg), 20% Pd(OH)$_2$/C (150 mg) in MeOH (4 mL) was stirred under hydrogen (60 psi) overnight. After filtration, washing with EtOAc 4 times and concentration in vacuo the residue was purified on silica gel. Elution with EtOAc/Hexanes (0-100%) gave the title compound (32 mg, 43%).

1174

Step 8

Preparation of (R)-1-(5-(4-(7-(bis((2-(trimethylsilyl)ethoxy)methyl)amino)-6-bromo-3-(6-phenylpyridin-3-yl)pyrazolo[1,5-a]pyrimidin-5-yl)piperidin-1-yl)-1,3,4-oxadiazol-2-yl)ethanol

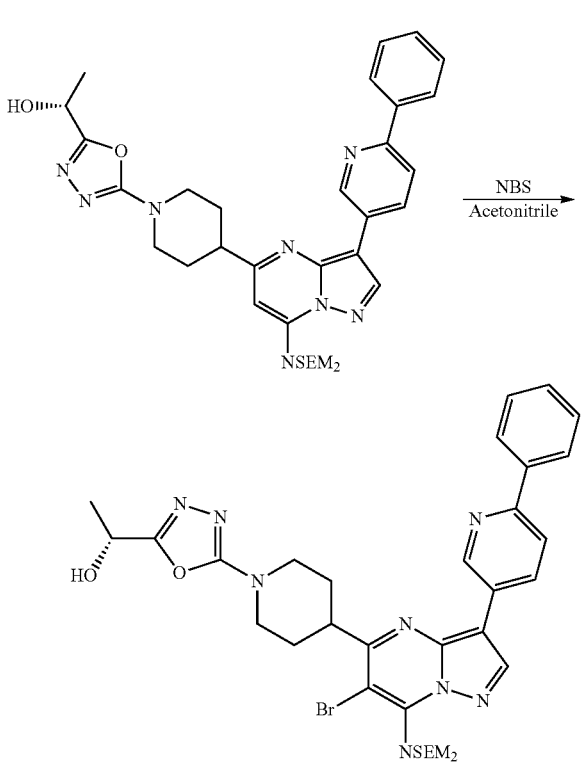

To a solution of (R)-1-(5-(4-(7-(bis((2-(trimethylsilyl)ethoxy)methyl)amino)-3-(6-phenylpyridin-3-yl)pyrazolo[1,5-a]pyrimidin-5-yl)piperidin-1-yl)-1,3,4-oxadiazol-2-yl)ethanol (32 mg, 0.04 mmol) in acetonitrile (1 mL) was added NBS (7 mg, 0.04 mmol) and the resulting solution was stirred for 10 minutes and concentrated. The residue was purified on silica gel. Elution with EtOAc provided a relatively pure product (9 mg).

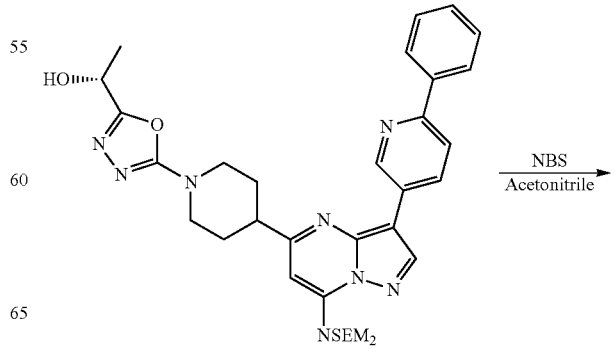

-continued

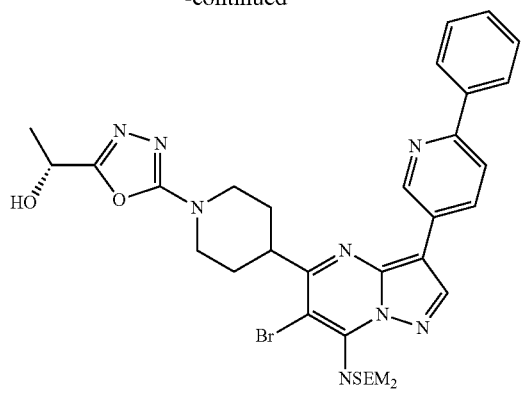

Step 9

Preparation of (R)-1-(7-amino-5-(1-(5-(1-hydroxy-ethyl)-1,3,4-oxadiazol-2-yl)piperidin-4-yl)-3-(6-phenylpyridin-3-yl)pyrazolo[1,5-a]pyrimidin-6-yl)ethanone

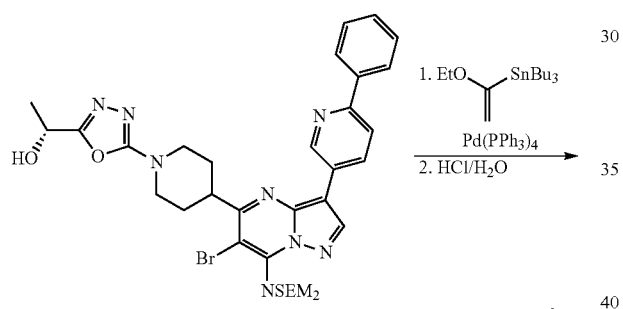

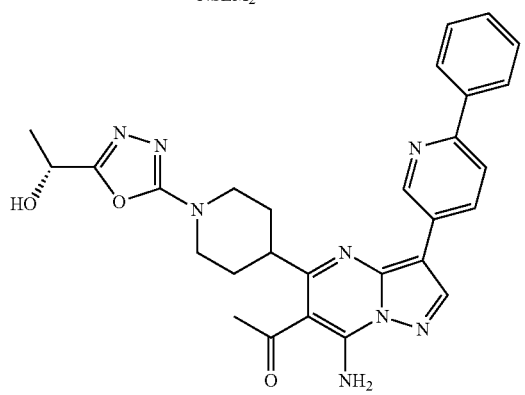

To a pressure tube were charged (R)-1-(5-(4-(7-(bis((2-(trimethylsilyl)ethoxy)methyl)amino)-6-bromo-3-(6-phenylpyridin-3-yl)pyrazolo[1,5-a]pyrimidin-5-yl)piperidin-1-yl)-1,3,4-oxadiazol-2-yl)ethanol (9 mg, ~0.01 mmol), Pd(PPh₃)₄ (10 mg, 0.087 mmol), tributyl(-ethoxy-vinyl)tin (8 ul, 0.02 mmol) and dioxane (2 mL). The resulting mixture was degassed with Argon briefly, capped with a Teflon cap and stirred at 100° C. overnight. On cooling, the solvent was rotoevaporated, and the crude was redissolved in EtOAc (10 ml), washed with 0.5 M KF solution (1×2 ml), water (1×3 ml), brine (1×3 ml), and dried over MgSO₄. Solvent was removed in vacuo and the residue was purified by column chromatography on silica gel. Elution with EtOAc/Hexanes (0-100%) gave the intermediate enol ether which was re-dissolve in dioxane (2 mL) and cooled to 0° C. and treated aqueous 4N HCl (0.2 mL). After the reaction mixture was warmed up to room temperature and stirred for 4 hours, solvents were removed and the residue was directly purified by HPLC to provide the title compound.

Synthesis of (R)-7-amino-5-(1-(2,3-dihydroxypropanoyl)piperidin-4-yl)-3-(6-phenylpyridin-3-yl)pyrazolo[1,5-a]pyrimidine-6-carbonitrile

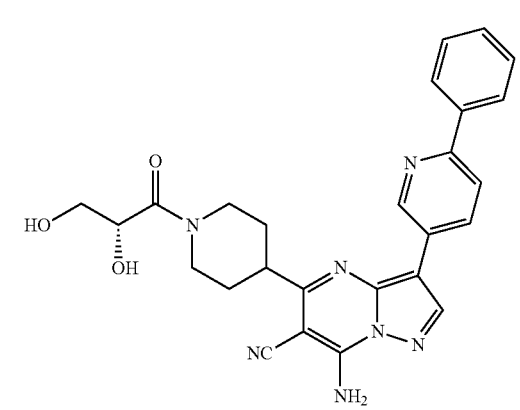 [SMILES: N#Cc1c(C2CCN(C(=O)[C@H](O)CO)CC2)nc2c(-c3ccc(-c4ccccc4)nc3)cnn2c1N]

Step 1

Preparation of tert-butyl 4-(7-(bis((2-(trimethylsilyl)ethoxy)methyl)amino)-6-cyano-3-(6-phenylpyridin-3-yl)pyrazolo[1,5-a]pyrimidin-5-yl)piperidine-1-carboxylate

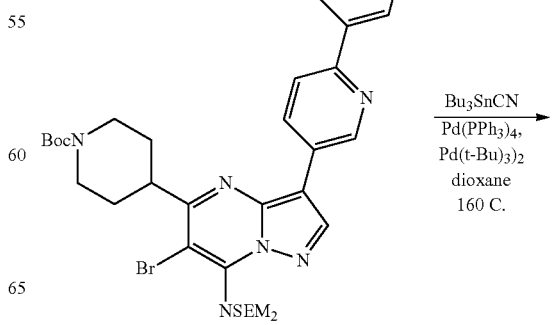

1177
-continued

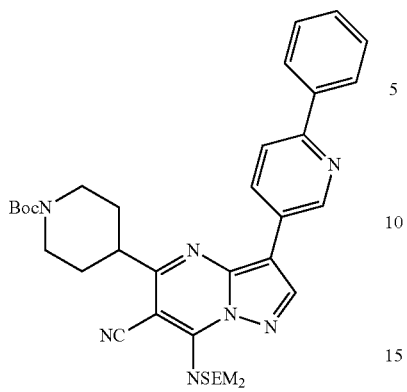

To a Schenk tube were charged compound tert-butyl 4-(7-(bis((2-(trimethylsilyl)ethoxy)methyl)amino)-6-bromo-3-(6-phenylpyridin-3-yl)pyrazolo[1,5-a]pyrimidin-5-yl)piperidine-1-carboxylate (81 mg, 0.1 mmol), Bu$_3$SnCN (47 mg, 1.5 eq.), Pd(PPh$_3$)$_4$ (23 mg, 0.2 eq.), Bis(tri-t-butylphosphine)palladium (0) (10 mg, O$_2$ eq.). The tube was evacuated and charged with Ar for three cycles. Dioxane (3 ml) was added; the tube was capped and heated at 160 C with stirring for one hour. After cooling, the mixture was diluted with EtOAc and washed with brine once. Organic layer separated, dried over MgSO$_4$ and concentrated. The residue was purified on silica gel. Elution with EtOAc/hexane (0-25%) gave the desired title product (63 mg, 84%).

Step 2

Preparation of 7-amino-3-(6-phenylpyridin-3-yl)-5-(piperidin-4-yl)pyrazolo[1,5-a]pyrimidine-6-carbonitrile

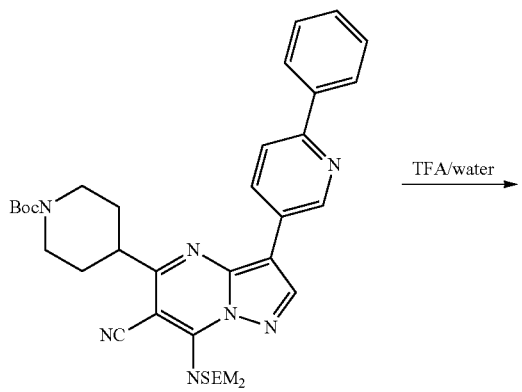

1178
-continued

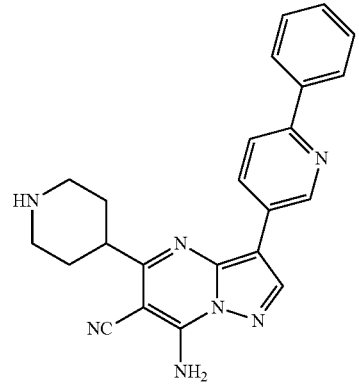

Tert-butyl 4-(7-(bis((2-(trimethylsilyl)ethoxy)methyl)amino)-6-cyano-3-(6-phenylpyridin-3-yl)pyrazolo[1,5-a]pyrimidin-5-yl)piperidine-1-carboxylate (190 mg) was treated with TFA/water (95:5, 3 ml) with stirring for 10 minutes. The reaction mixture was concentrated and lyophilized to yield the title compound as TFA salt.

Step 3

Preparation of (R)-7-amino-5-(1-(2,3-dihydroxypropanoyl)piperidin-4-yl)-3-(6-phenylpyridin-3-yl)pyrazolo[1,5-a]pyrimidine-6-carbonitrile

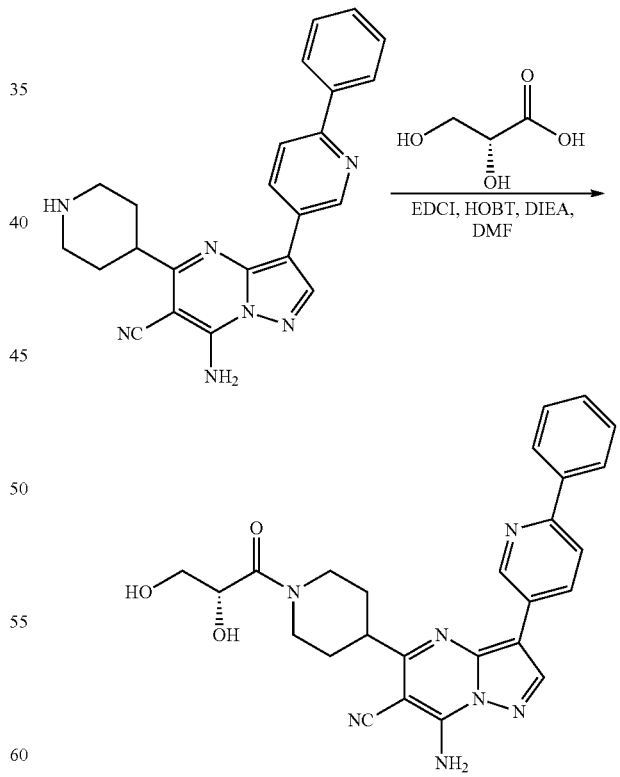

To a solution of 7-amino-3-(6-phenylpyridin-3-yl)-5-(piperidin-4-yl)pyrazolo[1,5-a]pyrimidine-6-carbonitrile TFA salt (0.1 mmol), DIEA (87 μL, 0.5 mmol) in DMF (2 mL) was added a solution of (R)-2,3-dihydroxypropanoic acid (11 mg, 0.1 mmol), HOBt (14 mg, 0.1 mmol), EDCI (29 mg, 0.15 mmol) in DMF (1 mL). The reaction was stirred at rt for 2.5 hour and the mixture was directly purified by HPLC to furnish the title compound. LC/MS RT=2.86 min. Mass calculated for M+H 484.2, observed 484.3.

Scheme 27

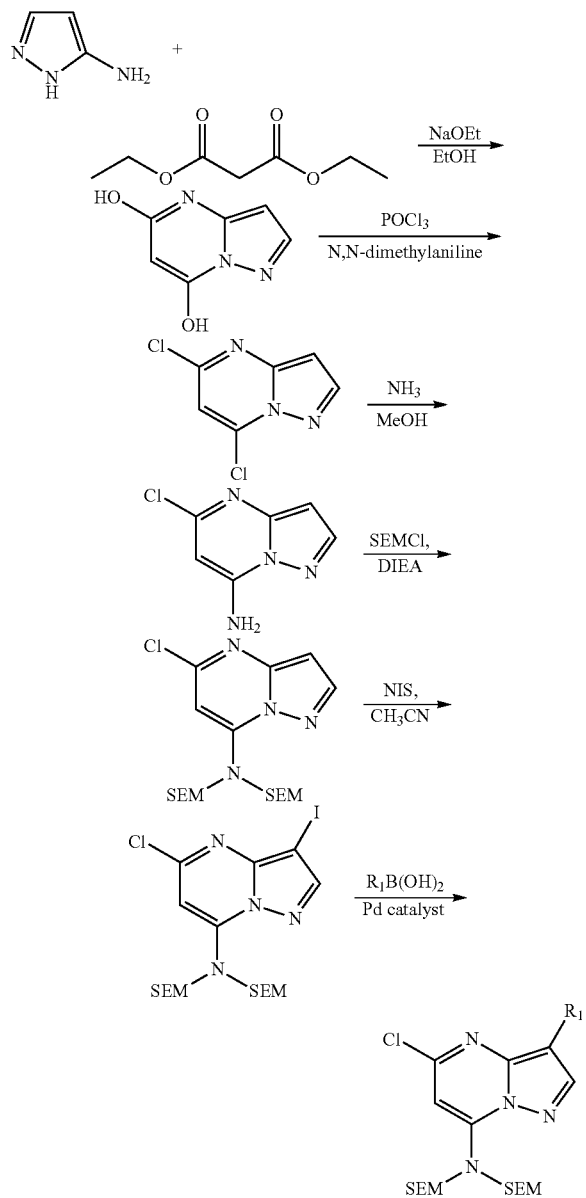

Synthesis of pyrazolo[1,5-a]pyrimidine-5,7-diol

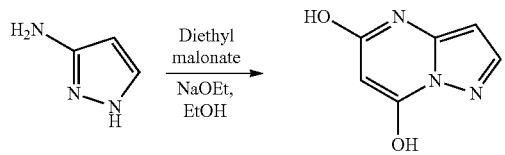 [SMILES: Nc1cc[nH]n1 ; Oc1cc(O)n2nccc2n1]

To 1H-pyrazol-3-amine (12.3 g, 148.0 mmol) in EtOH (50 mL) was added diethyl malonate (25.0 mL, 164.7 mmol), 21 wt % NaOEt in EtOH (110 mL, 294.6 mmol) and additional EtOH (50 mL). The resulting reaction mixture was then heated at 80° C. under an atmosphere of argon for 16 hours, at which time the reaction was allowed to cool to room temperature. The reaction mixture was then concentrated in vacuo until almost dry, before H₂O (500 mL) was added. Vigorous stirring aided the dissolution of solids, at which time conc. HCl was added until pH~2 was attained (precipitate formed). The precipitate was collected and dried by vacuum filtration giving pyrazolo[1,5-a]pyrimidine-5,7-diol as a tan solid (17.13 g, 113.4 mmol, 77%).

Synthesis of 5,7-dichloropyrazolo[1,5-a]pyrimidine

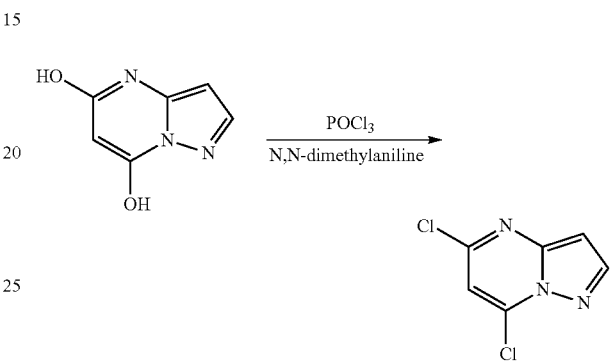

To pyrazolo[1,5-a]pyrimidine-5,7-diol (9.6 g, 63.5 mmol) in a 500 mL flask was added POCl₃ (125 mL, 1341.1 mmol). The flask was then cooled to 0° C. and N,N-dimethylaniline (22 mL, 173.6 mmol) was carefully added. On warming to room temperature, the reaction mixture was then heated at 60° C. under an atmosphere of argon for 16 hours. On cooling, the reaction mixture was concentrated in vacuo to give a brown viscous liquid. This brown viscous liquid was carefully poured onto ice and allowed to warm to room temperature overnight. To the brown solution was carefully added saturated NaHCO₃ solution until no further effervescence was observed and pH ~8 was attained. Organics were then extracted with CH₂Cl₂ (4×50 mL), dried (Na₂SO₄) and concentrated in vacuo to give a brown liquid (29.8 g). Gradient column chromatography on silica eluting with 50% CH₂Cl₂/hexanes (to elute aniline) followed by 75% CH₂Cl₂/hexanes (to elute product) gave 5,7-dichloropyrazolo[1,5-a]pyrimidine as a white solid (7.7 g, 40.8 mmol, 64%).

Synthesis of 5-chloropyrazolo[1,5-a]pyrimidin-7-amine

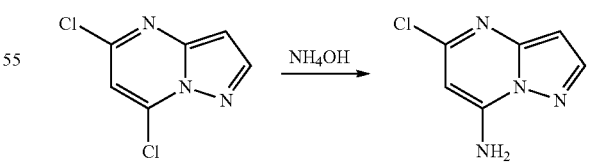

To 5,7-dichloropyrazolo[1,5-a]pyrimidine (7.6 g, 40.4 mmol) in a sealed vessel was added NH₄OH (100 mL). The vessel was then sealed and heated at 85° C. for 2.5 hours, at which time the consistency of the white solid had changed (from foamy white solid to free-flowing white solid). The vessel was removed from the heat source and allowed to cool to room temperature overnight. On cooling, the contents of the vessel were collected and dried by vacuum filtration giving 5-chloropyrazolo[1,5-a]pyrimidin-7-amine as a yellow-tinged white solid (6.8 g, 40.3 mmol, 100%).

Synthesis of 5-chloro-N,N-bis((2-(trimethylsilyl)ethoxy)methyl)pyrazolo[1,5-a]pyrimidin-7-amine

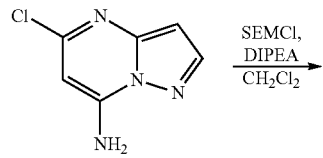

To 5-chloropyrazolo[1,5-a]pyrimidin-7-amine (6.7 g, 39.7 mmol) in CH$_2$Cl$_2$ (30 mL) was added N,N-diisopropylethylamine (48.0 mL, 275.6 mmol) followed by 2-(Trimethylsilyl)ethoxymethyl chloride (25.0 mL, 141.7 mmol). The reaction mixture was heated at 45° C. for 3 hours before being allowed to cool to room temperature. The reaction mixture was then poured into a separatory funnel containing ~100 mL saturated NaHCO$_3$ solution and CH$_2$Cl$_2$ (50 mL). Organics were then extracted with CH$_2$Cl$_2$ (4×50 mL), dried (Na$_2$SO$_4$) and concentrated in vacuo to give a thick orange liquid (33.8 g). Gradient column chromatography on silica eluting with 5% to 15% EtOAc/hexanes gave crude 5-chloro-N,N-bis((2-(trimethylsilyl)ethoxy)methyl)pyrazolo[1,5-a]pyrimidin-7-amine as a colorless liquid (18.7 g).

Synthesis of 5-chloro-3-iodo-N,N-bis((2-(trimethylsilyl)ethoxy)methyl)pyrazolo[1,5-a]pyrimidin-7-amine

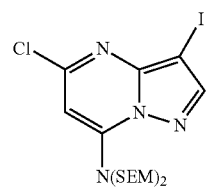

To crude 5-chloro-N,N-bis((2-(trimethylsilyl)ethoxy)methyl)pyrazolo[1,5-a]pyrimidin-7-amine (7.9 g) in CH$_3$CN (100 mL) was added N-iodosuccinimide (4.3 g, 19.2 mmol) and the resulting mixture was stirred at room temperature for 30 mins, at which time LC/MS confirmed full conversion of starting material to product. Saturated sodium thiosulfate solution (~20 mL) was added and stirring continued for 5 minutes before the mixture was transferred to a separatory funnel using CH$_2$Cl$_2$ (30 mL) and H$_2$O (30 mL). Brine (50 mL) was added and organics were extracted with CH$_2$Cl$_2$ (4×40 mL), dried (Na$_2$SO$_4$) and concentrated in vacuo to give crude 5-chloro-3-iodo-N,N-bis((2-(trimethylsilyl)ethoxy)methyl)pyrazolo[1,5-a]pyrimidin-7-amine as a light brown liquid (10.4 g). LCMS: 2.95 mins, m/z=555.1 (MH$^+$).

Synthesis of 5-chloro-3-(quinolin-3-yl)-N,N-bis((2-(trimethylsilyl)ethoxy)methyl)pyrazolo[1,5-a]pyrimidin-7-amine

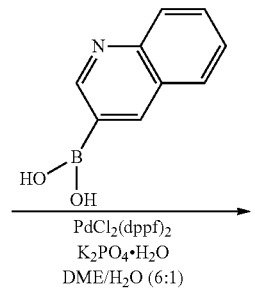

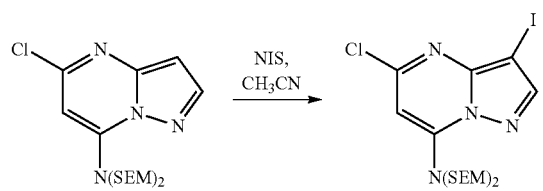

To crude 5-chloro-3-iodo-N,N-bis((2-(trimethylsilyl)ethoxy)methyl)pyrazolo[1,5-a]pyrimidin-7-amine (7.1 g) in DME (120 mL) and H$_2$O (15 mL) was added the quinoline boronic acid (2.4 g, 14.1 mmol), PdCl$_2$(dppf)$_2$ (1.0 g, 1.2 mmol) and K$_3$PO$_4$.H$_2$O (5.4 g, 25.6 mmol). The reaction mixture was heated at 60° C. for 2 hours, at which time LC/MS analysis confirmed full consumption of starting material. On cooling, H$_2$O (40 mL) and EtOAc (100 mL) were added and organics were extracted with EtOAc (4×50 mL), dried (Na$_2$SO$_4$) and concentrated in vacuo to give a brown oil. Gradient column chromatography on silica eluting with 10% to 60% EtOAc/hexanes gave 5-chloro-3-(quinolin-3-yl)-N,N-bis((2-(trimethylsilyl)ethoxy)methyl)pyrazolo[1,5-a]pyrimidin-7-amine as a light yellow solid (4.1 g, 7.4 mmol, 65% over three steps). LCMS: 2.62 mins, m/z=556.2 (MH$^+$).

SCHEME-28

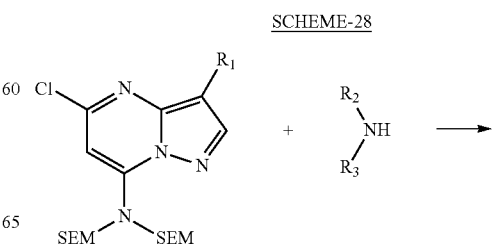

1183

-continued

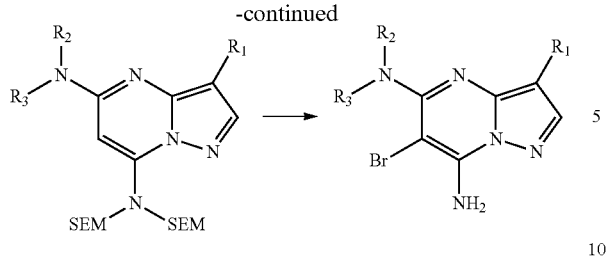

Synthesis of 5-morpholino-3-(quinolin-3-yl)pyrazolo[1,5-a]pyrimidin-7-amine

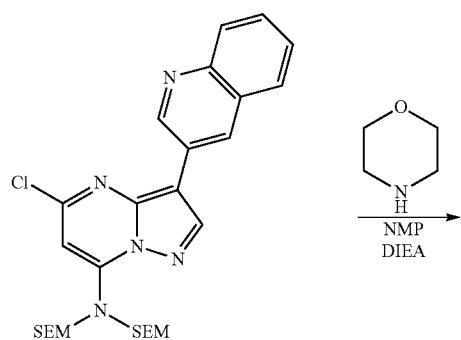

1184

-continued

To a 2-5 mL microwave vessel is charged 5-chloro-3-(quinolin-3-yl)-N,N-bis((2-(trimethylsilyl)ethoxy)methyl)pyrazolo[1,5-a]pyrimidin-7-amine (72 µmol, 40 mg), N,N-diisopropylethylamine (220 µmol, 38 µL), NMP (2 mL), and morpholine (220 µmol, 19 µL). The reaction vessel is flushed with agron and sealed. The reaction mixture was heated to 200° C. in microwave synthesizer for 30 minutes. Upon completion, the NMP was removed in vacuo as an azeotropic using chlorobenzene. The crude product was purified via reverse-phase preparatory HPLC to yield 5-morpholino-3-(quinolin-3-yl)pyrazolo[1,5-a]pyrimidin-7-amine as brown-yellow solid. (m+H=347.31, retention time=2.97 min).

By essentially the same procedure given in the synthesis of 5-morpholino-3-(quinolin-3-yl)pyrazolo[1,5-a]pyrimidin-7-amine, Schemes 27 & 28, the compounds listed in Table 9 can be prepared.

TABLE 9

| Compound ID | Structures | M + H (calc.) | M + H (observed) | Retention Time, (min) |
|---|---|---|---|---|
| 9.1 | 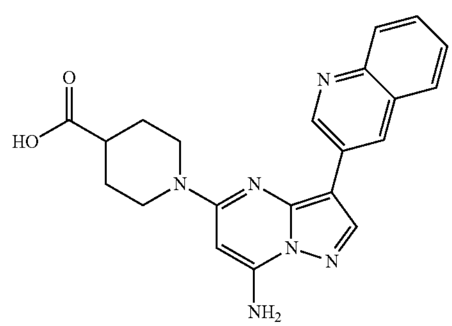 [SMILES: Nc1cc(N2CCC(C(=O)O)CC2)nc2c(-c3cnc4ccccc4c3)cnn12] | 389.17 | 389.17 | 2.86 |
| 9.2 | 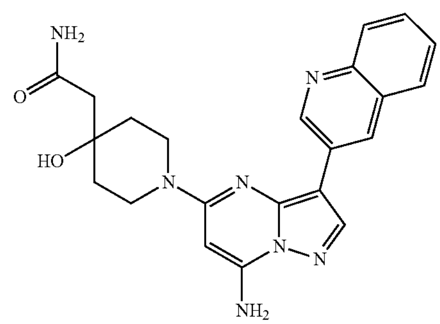 | 418.5 | 418.3 | 2.37 |

TABLE 9-continued
| Compound ID | Structures | M + H (calc.) | M + H (observed) | Retention Time, (min) |
|---|---|---|---|---|
| 9.3 | 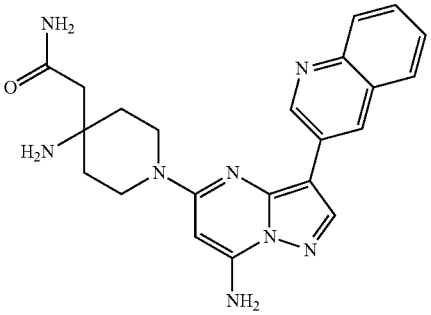 [SMILES: NC(=O)CC1(N)CCN(c2cc(N)n3ncc(-c4cnc5ccccc5c4)c3n2)CC1] | 417.5 | 417.3 | 2.08 |
| 9.4 | 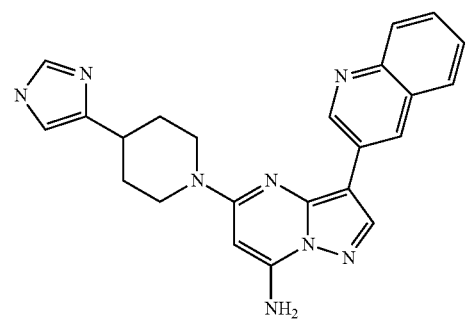 [SMILES: Nc1cc(N2CCC(c3c[nH]cn3)CC2)nc2c(-c3cnc4ccccc4c3)cnn12] | 411.5 | 411.2 | 2.42 |
| 9.5 | 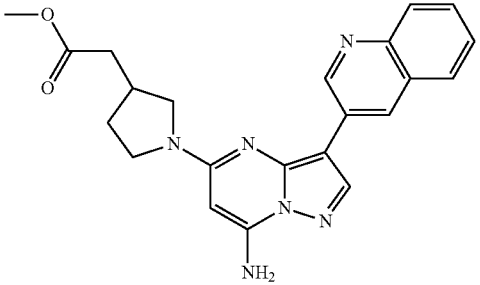 [SMILES: COC(=O)CC1CCN(c2cc(N)n3ncc(-c4cnc5ccccc5c4)c3n2)C1] | 403.19 | 403.18 | 3.46 |
| 9.6 | 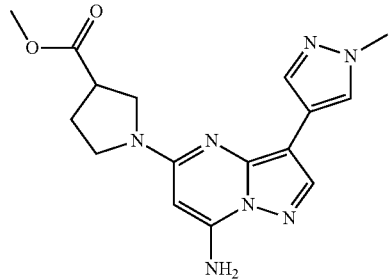 | 342.17 | 342.16 | 2.36 |
| 9.7 | 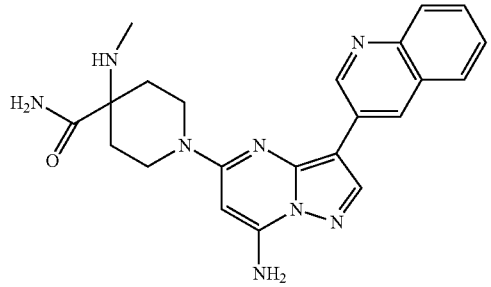 [SMILES: CNC1(C(N)=O)CCN(c2cc(N)n3ncc(-c4cnc5ccccc5c4)c3n2)CC1] | 417.22 | 417.21 | 2.10 |

TABLE 9-continued

| Compound ID | Structures | M + H (calc.) | M + H (observed) | Retention Time, (min) |
|---|---|---|---|---|
| 9.8 | 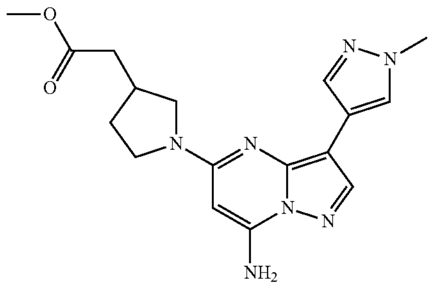 | 356.19 | 356.18 | 2.51 |
| 9.9 | 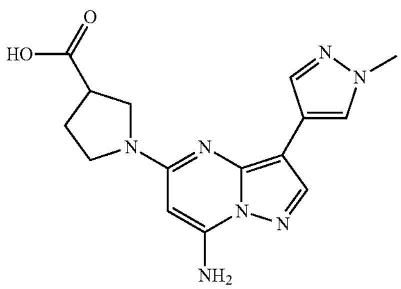 [SMILES: Cn1cc(-c2cnn3c(N)cc(N4CCC(C(=O)O)C4)nc23)cn1] | 375.16 | 375.15 | 2.8 |
| 9.10 | 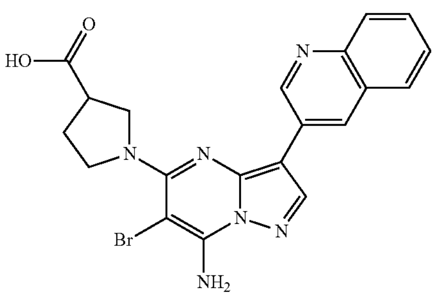 [SMILES: Nc1c(Br)c(N2CCC(C(=O)O)C2)nc2c(-c3cnc4ccccc4c3)cnn12] | 453.07 | 453.07 | 3.27 |
| 9.11 | 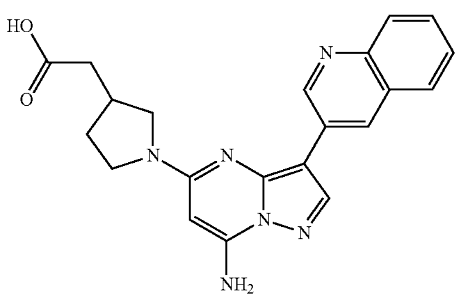 [SMILES: Nc1cc(N2CCC(CC(=O)O)C2)nc2c(-c3cnc4ccccc4c3)cnn12] | 389.17 | 389.16 | 2.93 |
| 9.12 | 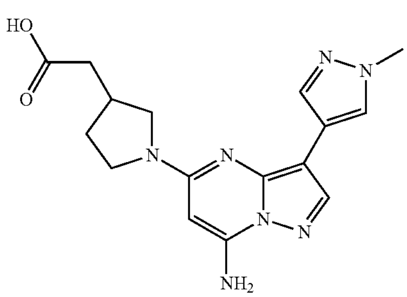 [SMILES: Cn1cc(-c2cnn3c(N)cc(N4CCC(CC(=O)O)C4)nc23)cn1] | 342.16 | 342.16 | 2.09 |

TABLE 9-continued

| Compound ID | Structures | M + H (calc.) | M + H (observed) | Retention Time, (min) |
|---|---|---|---|---|
| 9.13 | 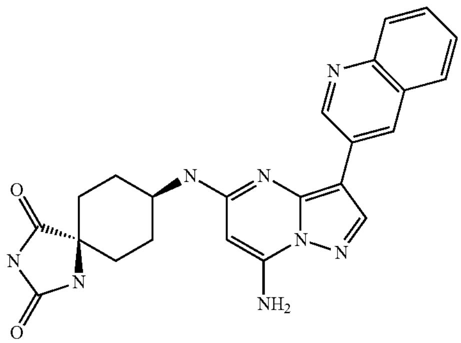 [SMILES: Nc1cc(N[C@H]2CC[C@]3(CC2)NC(=O)NC3=O)nc2c(-c3cnc4ccccc4c3)cnn12] | 442.5 | 443.20 | 2.70 |

Synthesis of 1-(7-amino-3-(quinolin-3-yl)pyrazolo[1,5-a]pyrimidin-5-yl)-1,4-diazepan-5-one Synthesis of 1-(7-amino-6-bromo-3-(quinolin-3-yl)pyrazolo[1,5-a]pyrimidin-5-yl)-1,4-diazepan-5-one A mixture of 5-chloro-3-(quinolin-3-yl)-N,N-bis((2-(trimethylsilyl)ethoxy)methyl)-pyrazolo-[1,5-a]pyrimidin-7-amine (50 mg, 0.09 mmoL), 1,4-diazepan-5-one (36 mg, 0.32 mmoL), EtN(iPr)$_2$ (110 uL, 0.63 mmoL) in NMP (0.8 mL) was heated at 185° C. under microwave condition for 45 min. Purification by prep-LC afforded titled compound (32.3 mg, 85%) as its formic acid salt. LCMS $t_R$=2.49 Min. Mass calculated for, M+ 373.1, observed LC/MS m/z 374.1 (M+H).

A solution of NBS (14.6 mg, 0.082 mmoL) in CH$_3$CN (0.5 mL) was added to a mixture of 1-(7-amino-3-(quinolin-3-yl)pyrazolo[1,5-a]pyrimidin-5-yl)-1,4-diazepan-5-one formic acid salt (32.3 mg, 0.077 mmoL) in CH$_3$CN (3 mL). After stirring at room temperature for 10 min, the solvent was evaporated and the residue was purified by prep-LC to afford titled compound (22.6 mg, 59%). LCMS $t_R$=2.78 Min. Mass calculated for, M+ 451.0, observed LC/MS m/z 452.0 (M+H).

1191

Methyl 1-(7-amino-3-(quinolin-3-yl)pyrazolo[1,5-a]pyrimidin-5-yl)pyrrolidine-3-carboxylate

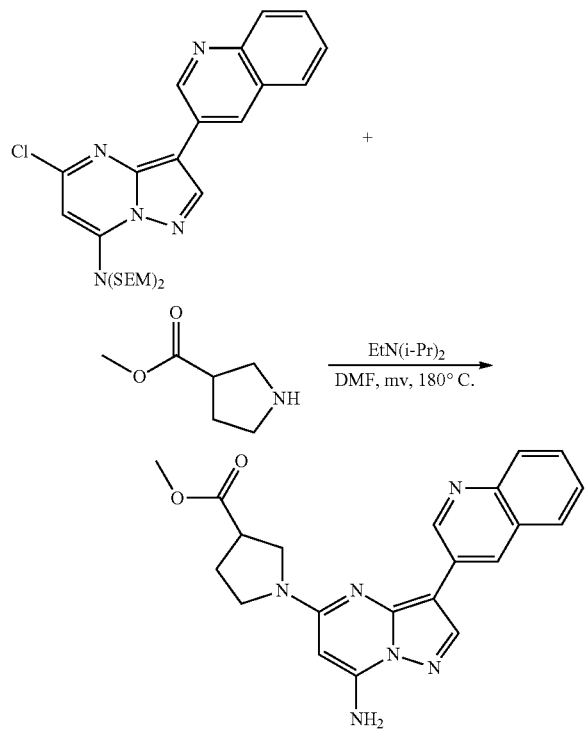

A mixture of 5-chloro-3-(quinolin-3-yl)-N,N-bis((2-(trimethylsilyl)ethoxy)methyl)-pyrazolo-[1,5-a]pyrimidin-7-amine (55 mg, 0.10 mmoL), methylpyrrolidine-3-carboxylate (52 mg, 0.30 mmoL) and EtN(iPr)$_2$ (86 uL, 0.50 mmoL) in DMF (1.0 mL) was heated at 180° C. under microwave condition for 45 min. The mixture was purified by prep-LC to afford the title compound. LC/MS RT=3.30 min. Mass calculated for, M+H 389.17, observed 389.17.

1-(7-Amino-3-(quinolin-3-yl)pyrazolo[1,5-a]pyrimidin-5-yl)pyrrolidine-3-carboxylic acid

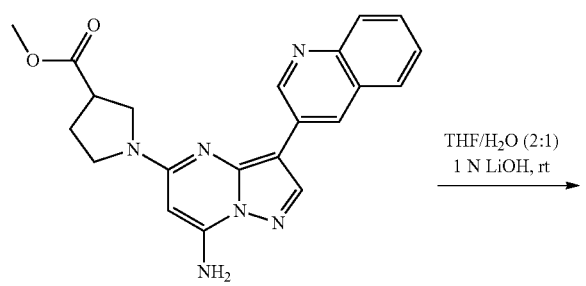

1192

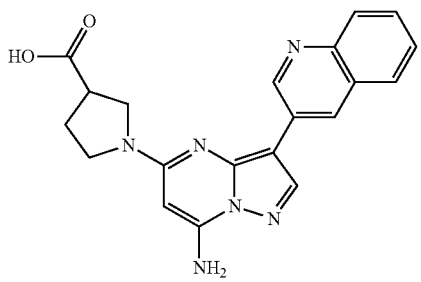

To a solution of methyl 1-(7-amino-3-(quinolin-3-yl)pyrazolo[1,5-a]pyrimidin-5-yl)pyrrolidine-3-carboxylate (19 mg, 0.050 mmol) in a 2:1 mixture of THF and H$_2$O (3 mL) was added 1 N LiOH solution (0.25 mL). The reaction mixture was stirred at rt overnight and concentrated in vacuo. The residue was purified by prep-LC to afford the title compound. LC/MS RT=2.80 min. Mass calculated for, M+H 375.16, observed 375.15.

1-(7-Amino-6-bromo-3-(quinolin-3-yl)pyrazolo[1,5-a]pyrimidin-5-yl)pyrrolidine-3-carboxylic acid

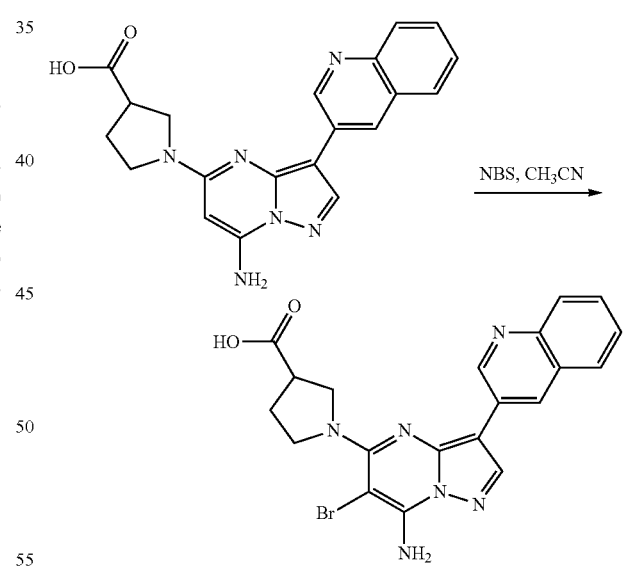

To a solution of 1-(7-amino-3-(quinolin-3-yl)pyrazolo[1,5-a]pyrimidin-5-yl)pyrrolidine-3-carboxylic acid (17 mg, 0.033 mmol) in a 2:1 mixture of CH$_3$CN/MeOH (1.0 mL) was added NBS (6.2 mg, 0.033 mmol). The mixture was stirred at it for 1 h then concentrated in vacuo. The residue was purified by prep-LC to afford the title compound. LC/MS RT=3.27 min. Mass calculated for, M+H 453.07, observed 453.07

Synthesis of tetrahydro-imidazo[1,5-a]pyrazine-1,3-dione

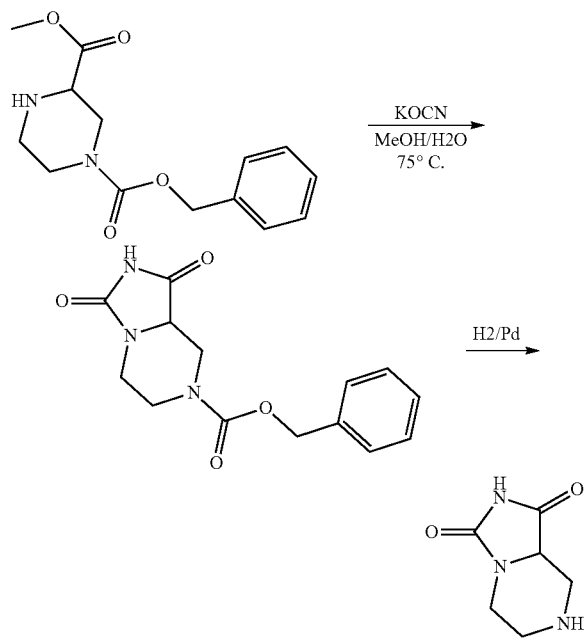

Step 1:

Potassium cyanate (10 mmol, 811 mg) was added to 1-benzyl-3-methyl piperazine-1,3-dicarboxylate (2 mmol, 556 mg) dissolved in methanol-water, and the reaction mixture heated at 75° C. for 2 hrs until LCMS showed the completion of the reaction. The solvent was evaporated in vacuo and the crude product was purified by silica gel column chromatography to yield the product, benzyl 1,3-dioxohexahydroimidazo[1,5-a]pyrazine-7(1H)-carboxylate, (290 mg, 50%). LCMS $t_R$=2.50 min. Mass calculated for, M+ 289.11, observed LC/MS m/z 288.20 (M−H negative ion mode).

Step 2;

To benzyl 1,3-dioxohexahydroimidazo[1,5-a]pyrazine-7(1H)-carboxylate (1.0 mmol, 290 mg) in methanol was added 50 mg of Pd/C (10%). The solution was kept under hydrogen atmospheric by a balloon for 14 hrs at which time LCMS showed the completion of the reaction. The solution was filtered through celite and the solvent was evaporated in vacuo to dryness to yield, tetrahydroimidazo[1,5-a]pyrazine-1,3(2H,5H)-dione. LCMS $t_R$=1.00 min. Mass calculated for, M+ 155.07, observed LC/MS m/z 156 (M+H).

By essentially the same procedure given in Scheme 28, the compounds listed in Table 10 can be prepared.

TABLE 10

| Compound ID | Structures | M + H (calc.) | M + H (observed) | Retention Time, (min) |
|---|---|---|---|---|
| 10.1 | 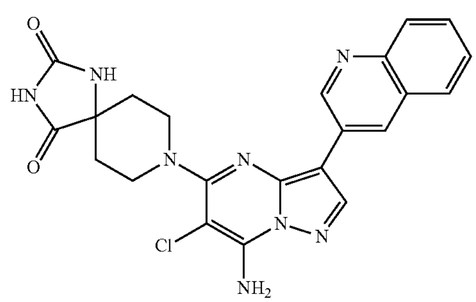 [SMILES: Nc1c(Cl)c(N2CCC3(CC2)NC(=O)NC3=O)nc2c(-c3cnc4ccccc4c3)cnn12] | 463.14 | 463.13 | 2.83 |
| 10.2 | 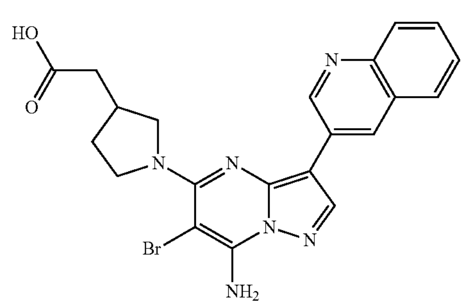 [SMILES: Nc1c(Br)c(N2CCC(CC(=O)O)C2)nc2c(-c3cnc4ccccc4c3)cnn12] | 403.19 | 403.18 | 2.15 |

TABLE 10-continued

| Compound ID | Structures | M + H (calc.) | M + H (observed) | Retention Time, (min) |
|---|---|---|---|---|
| 10.3 | 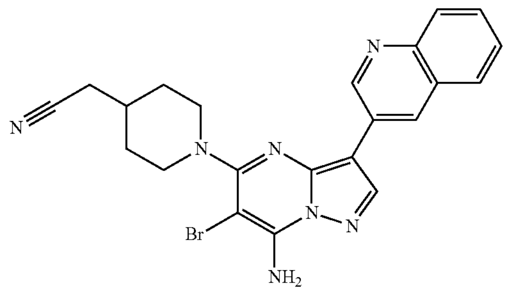 [SMILES: N#CCC1CCN(c2nc3c(-c4cnc5ccccc5c4)cnn3c(N)c2Br)CC1] | 462.11 | 462.10 | 3.84 |
| 10.4 | 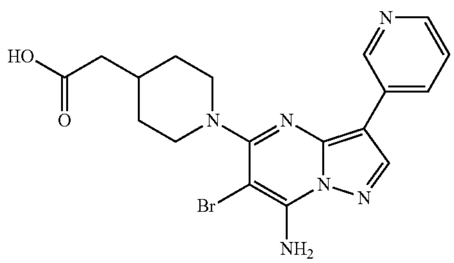 [SMILES: Nc1c(Br)c(N2CCC(CC(=O)O)CC2)nc2c(-c3cccnc3)cnn12] | 431.09 | 431.08 | 2.92 |
| 10.5 | 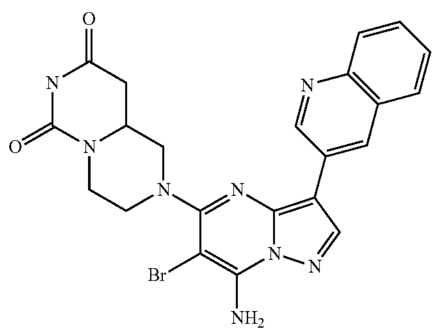 [SMILES: Nc1c(Br)c(N2CCN3C(=O)NC(=O)CC3C2)nc2c(-c3cnc4ccccc4c3)cnn12] | 507.4 | 507.0 | 3.0 |
| 10.6 | 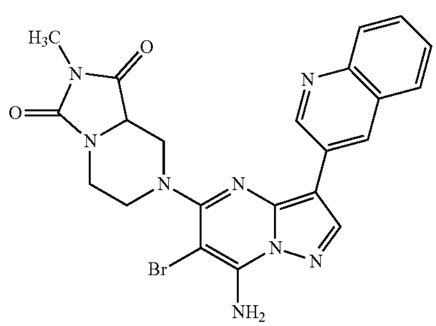 [SMILES: CN1C(=O)C2CN(c3nc4c(-c5cnc6ccccc6c5)cnn4c(N)c3Br)CCN2C1=O] | 507.4 | 507.0 | 3.3 |
| 10.7 | 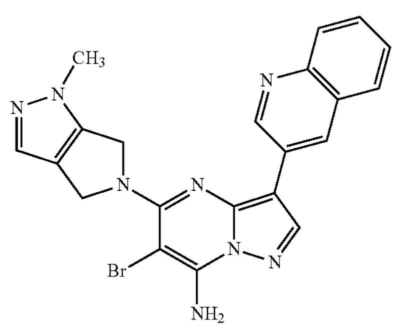 [SMILES: Cn1ncc2c1CN(c1nc3c(-c4cnc5ccccc5c4)cnn3c(N)c1Br)C2] | 461.3 | 461.0 | 3.6 |

TABLE 10-continued

| Compound ID | Structures | M + H (calc.) | M + H (observed) | Retention Time, (min) |
|---|---|---|---|---|
| 10.8 | 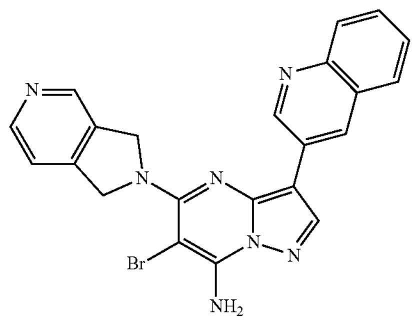 [SMILES: Nc1c(Br)c(N2Cc3ccncc3C2)nc2c(-c3cnc4ccccc4c3)cnn12] | 458.3 | 458.0 | 3.3 |
| 10.9 | 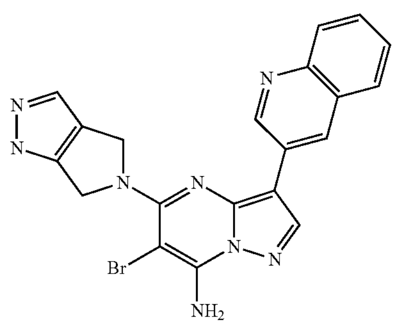 [SMILES: Nc1c(Br)c(N2Cc3cn[nH]c3C2)nc2c(-c3cnc4ccccc4c3)cnn12] | 447.3 | 447.0 | 3.3 |
| 10.10 | 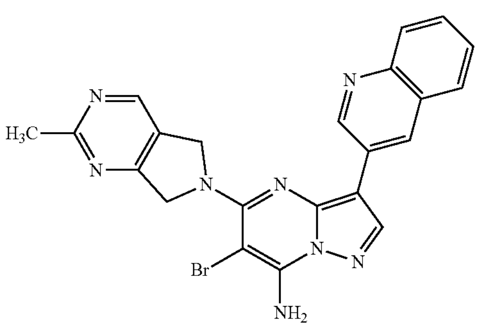 [SMILES: Cc1ncc2c(n1)CN(c1nc3c(-c4cnc5ccccc5c4)cnn3c(N)c1Br)C2] | 473.3 | 473.0 | 3.4 |
| 10.11 | 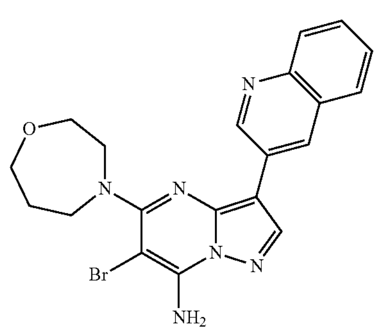 [SMILES: Nc1c(Br)c(N2CCCOCC2)nc2c(-c3cnc4ccccc4c3)cnn12] | 439.3 | 439.0 | 3.4 |

TABLE 10-continued

| Compound ID | Structures | M + H (calc.) | M + H (observed) | Retention Time, (min) |
|---|---|---|---|---|
| 10.12 | 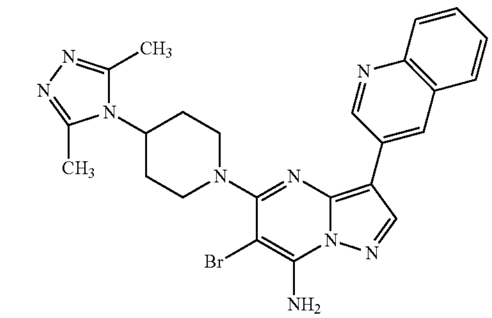 [SMILES: Cc1nnc(C)n1C1CCN(c2nc3c(-c4cnc5ccccc5c4)cnn3c(N)c2Br)CC1] | 518.4 | 518.1 | 2.6 |
| 10.13 | 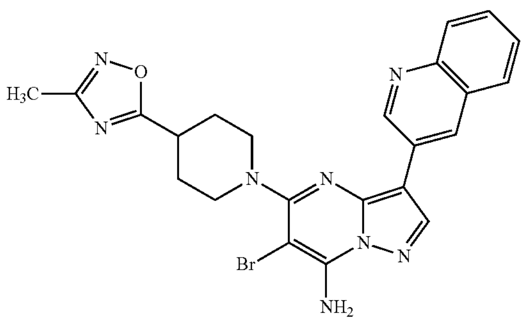 [SMILES: Cc1noc(C2CCN(c3nc4c(-c5cnc6ccccc6c5)cnn4c(N)c3Br)CC2)n1] | 505.4 | 5.05.1 | 3.8 |
| 10.14 | 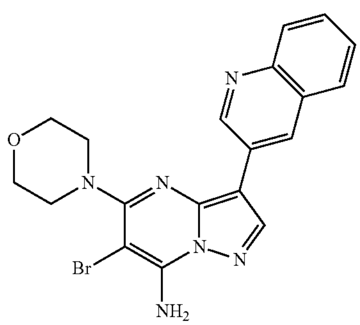 [SMILES: Nc1c(Br)c(N2CCOCC2)nc2c(-c3cnc4ccccc4c3)cnn12] | 425.3 | 425.0 | 3.2 |
| 10.15 | 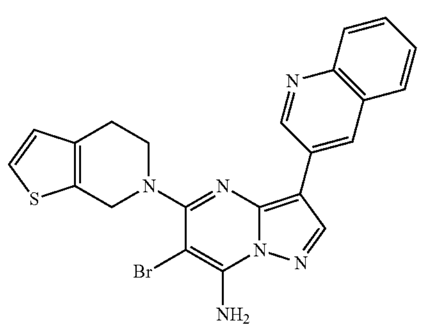 [SMILES: Nc1c(Br)c(N2CCc3ccsc3C2)nc2c(-c3cnc4ccccc4c3)cnn12] | 477.4 | 477.0 | 4.3 |

TABLE 10-continued

| Compound ID | Structures | M + H (calc.) | M + H (observed) | Retention Time, (min) |
|---|---|---|---|---|
| 10.16 | 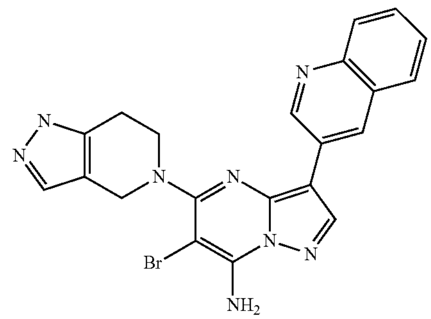 [SMILES: Nc1c(Br)c(N2CCc3[nH]ncc3C2)nc2c(-c3cnc4ccccc4c3)cnn12] | 461.3 | 461.0 | 2.8 |
| 10.17 | 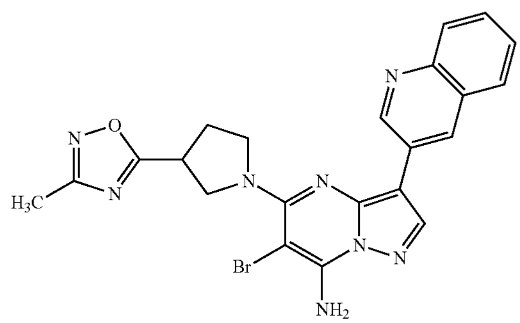 [SMILES: Cc1noc(C2CCN(c3nc4c(-c5cnc6ccccc6c5)cnn4c(N)c3Br)C2)n1] | 491.4 | 491.0 | 3.6 |
| 10.18 | 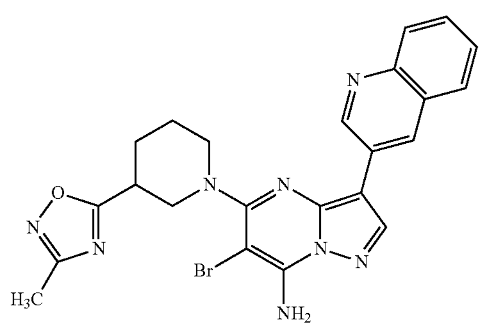 [SMILES: Cc1noc(C2CCCN(c3nc4c(-c5cnc6ccccc6c5)cnn4c(N)c3Br)C2)n1] | 505.4 | 505.1 | 3.9 |
| 10.19 | 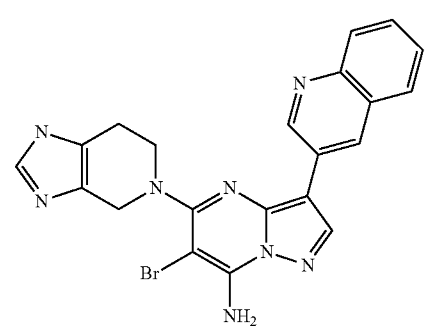 [SMILES: Nc1c(Br)c(N2CCc3[nH]cnc3C2)nc2c(-c3cnc4ccccc4c3)cnn12] | 461.3 | 461.0 | 2.4 |

TABLE 10-continued

| Compound ID | Structures | M + H (calc.) | M + H (observed) | Retention Time, (min) |
|---|---|---|---|---|
| 10.20 | 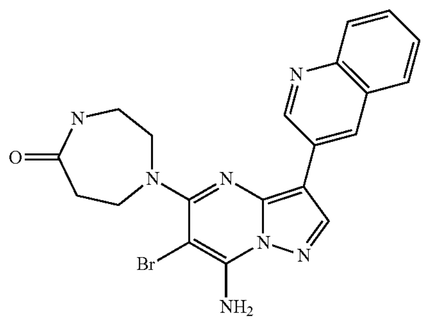 [SMILES: Nc1c(Br)c(N2CCNC(=O)CC2)nc2c(-c3cnc4ccccc4c3)cnn12] | 452.3 | 452.0 | 2.8 |
| 10.21 | 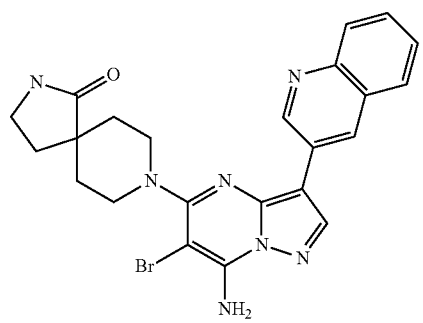 [SMILES: Nc1c(Br)c(N2CCC3(CCNC3=O)CC2)nc2c(-c3cnc4ccccc4c3)cnn12] | 492.4 | 492.0 | 3.3 |
| 10.22 | 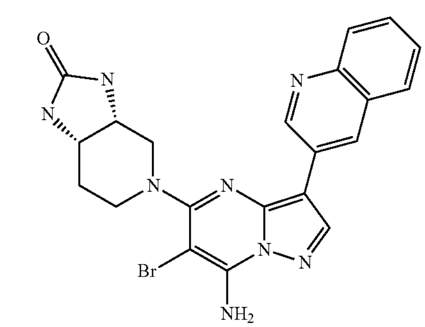 [SMILES: Nc1c(Br)c(N2CC[C@@H]3NC(=O)N[C@@H]3C2)nc2c(-c3cnc4ccccc4c3)cnn12] | 479.3 | 479.0 | 2.8 |
| 10.23 | 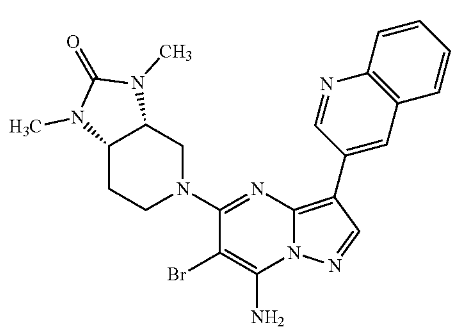 [SMILES: CN1C(=O)N(C)[C@H]2CCN(c3nc4c(-c5cnc6ccccc6c5)cnn4c(N)c3Br)C[C@H]21] | 507.4 | 507.1 | 3.3 |

TABLE 10-continued

| Compound ID | Structures | M + H (calc.) | M + H (observed) | Retention Time, (min) |
|---|---|---|---|---|
| 10.24 | 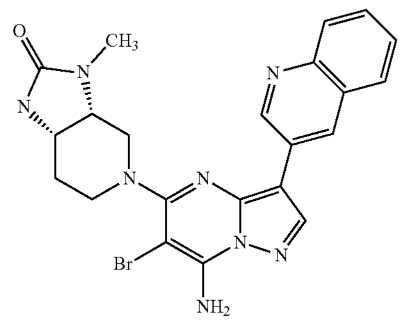 | 493.4 | 493.2 | 4.0 |
| 10.25 | 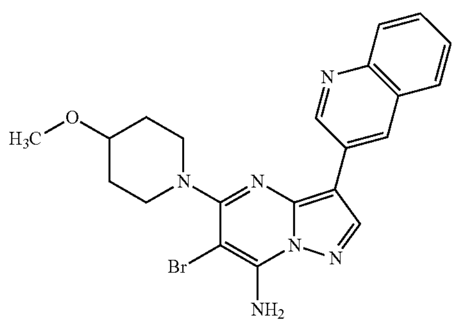 [SMILES: COC1CCN(c2nc3c(-c4cnc5ccccc5c4)cnn3c(N)c2Br)CC1] | 453.3 | 453.0 | 3.8 |
| 10.26 | 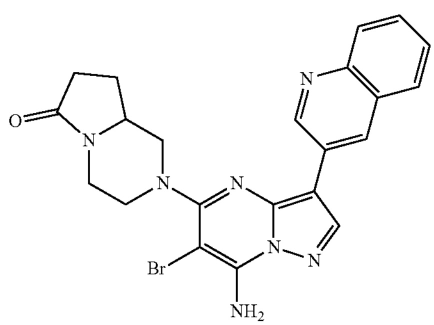 [SMILES: Nc1c(Br)c(N2CCN3C(=O)CCC3C2)nc2c(-c3cnc4ccccc4c3)cnn12] | 478.4 | 478.0 | 3.2 |
| 10.27 | 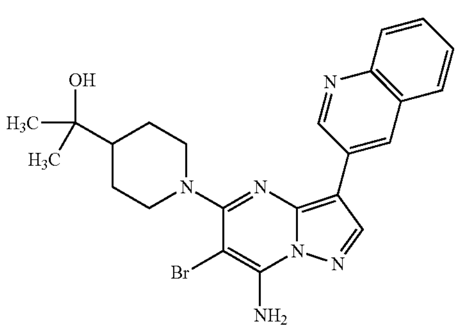 [SMILES: CC(C)(O)C1CCN(c2nc3c(-c4cnc5ccccc5c4)cnn3c(N)c2Br)CC1] | 481.4 | 481.1 | 3.7 |

TABLE 10-continued
| Compound ID | Structures | M + H (calc.) | M + H (observed) | Retention Time, (min) |
|---|---|---|---|---|
| 10.28 | 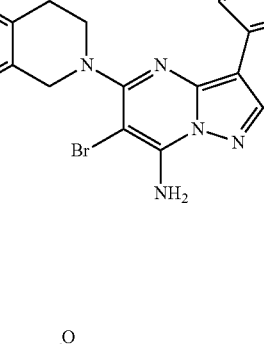 | 489.3 | 489.0 | 3.0 |
| 10.29 | 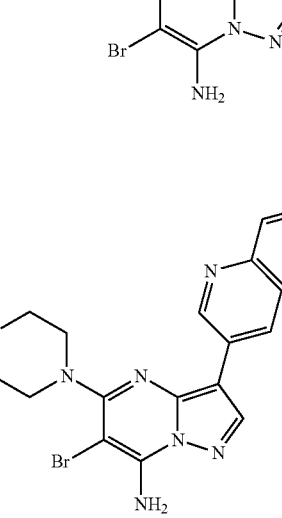 | 509.4 | 509.1 | 4.7 |
| 10.30 | 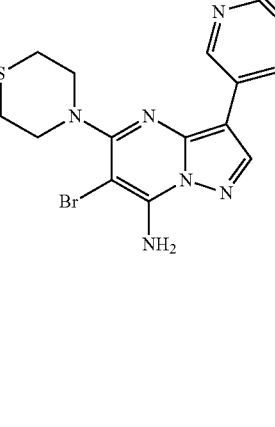 | 441.4 | 441.0 | 4.2 |
| 10.31 | 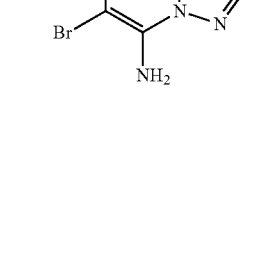 | 473.4 | 473.0 | 3.0 |

TABLE 10-continued

| Compound ID | Structures | M + H (calc.) | M + H (observed) | Retention Time, (min) |
|---|---|---|---|---|
| 10.32 | 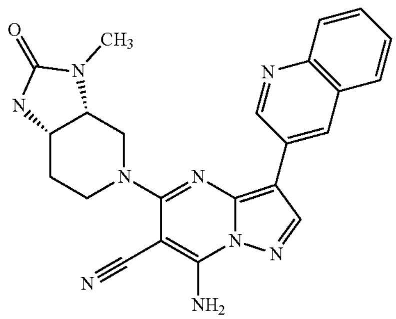 [SMILES: CN1C(=O)N[C@H]2CCN(c3nc4c(-c5cnc6ccccc6c5)cnn4c(N)c3C#N)C[C@H]21] | 440.1 | 440.1 | 2.76 |
| 10.33 | 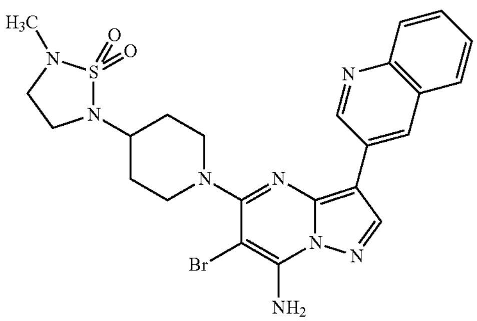 [SMILES: CN1CCN(C2CCN(c3nc4c(-c5cnc6ccccc6c5)cnn4c(N)c3Br)CC2)S1(=O)=O] | 557.1 | 557.1 | 3.69 |
| 10.34 | 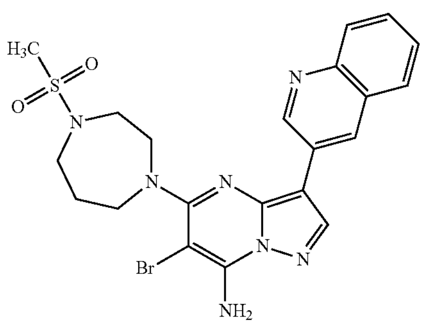 [SMILES: CS(=O)(=O)N1CCCN(c2nc3c(-c4cnc5ccccc5c4)cnn3c(N)c2Br)CC1] | 516 | 516 | 3.47 |
| 10.35 | 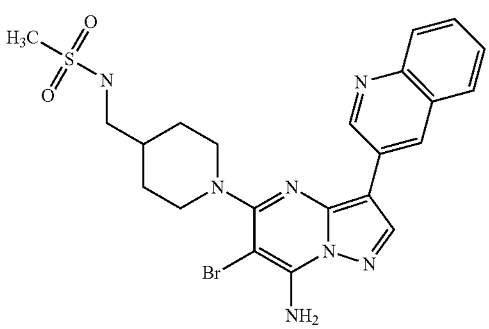 [SMILES: CS(=O)(=O)NCC1CCN(c2nc3c(-c4cnc5ccccc5c4)cnn3c(N)c2Br)CC1] | 530 | 530 | 3.51 |

TABLE 10-continued

| Compound ID | Structures | M + H (calc.) | M + H (observed) | Retention Time, (min) |
|---|---|---|---|---|
| 10.36 | 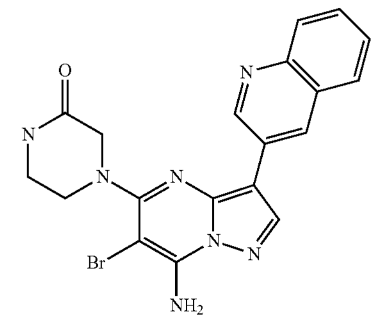 [SMILES: Nc1c(Br)c(N2CCNC(=O)C2)nc2c(-c3cnc4ccccc4c3)cnn12] | 438 | 438 | 2.78 |
| 10.37 | 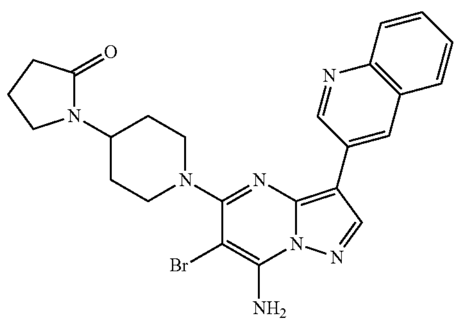 [SMILES: Nc1c(Br)c(N2CCC(N3CCCC3=O)CC2)nc2c(-c3cnc4ccccc4c3)cnn12] | 506.1 | 506.1 | 3.58 |
| 10.38 | 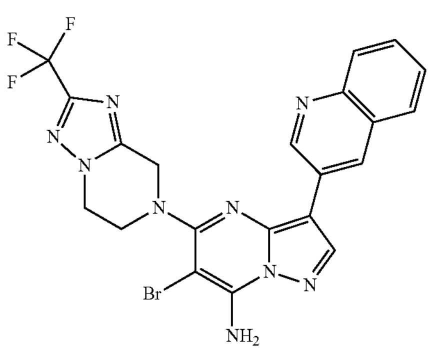 [SMILES: Nc1c(Br)c(N2CCn3nc(C(F)(F)F)nc3C2)nc2c(-c3cnc4ccccc4c3)cnn12] | 530 | 530 | 3.97 |
| 10.39 | 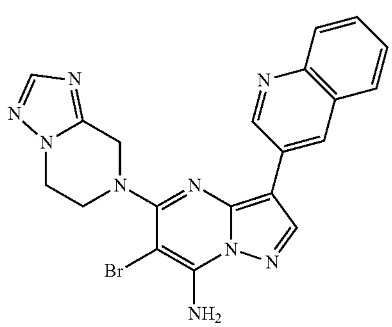 [SMILES: Nc1c(Br)c(N2CCn3ncnc3C2)nc2c(-c3cnc4ccccc4c3)cnn12] | 462 | 462 | 3.01 |

TABLE 10-continued

| Compound ID | Structures | M + H (calc.) | M + H (observed) | Retention Time, (min) |
| --- | --- | --- | --- | --- |
| 10.39a | 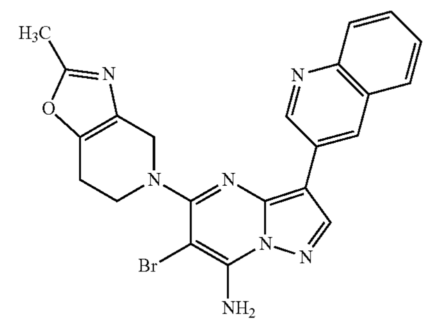 [SMILES: Cc1nc2c(o1)CCN(c1nc3c(-c4cnc5ccccc5c4)cnn3c(N)c1Br)C2] | 476.33 | 476.11 | 3.91 |
| 10.40 | 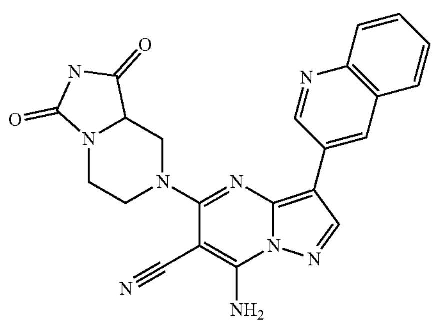 [SMILES: N#Cc1c(N2CCN3C(=O)NC(=O)C3C2)nc2c(-c3cnc4ccccc4c3)cnn2c1N] | 440.1 | 440.1 | 2.71 |
| 10.41 | 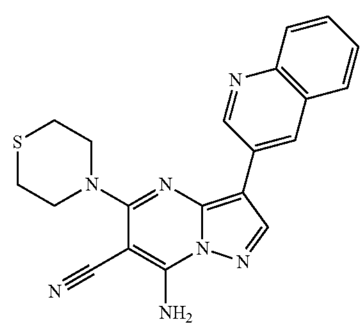 [SMILES: N#Cc1c(N2CCSCC2)nc2c(-c3cnc4ccccc4c3)cnn2c1N] | 388.1 | 388.1 | 3.63 |
| 10.42 | 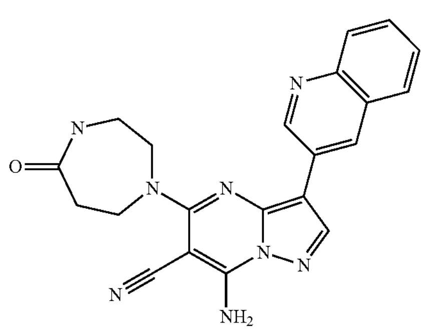 [SMILES: N#Cc1c(N2CCNC(=O)CC2)nc2c(-c3cnc4ccccc4c3)cnn2c1N] | 399.1 | 399.1 | 2.64 |

TABLE 10-continued

| Compound ID | Structures | M + H (calc.) | M + H (observed) | Retention Time, (min) |
|---|---|---|---|---|
| 10.43 | 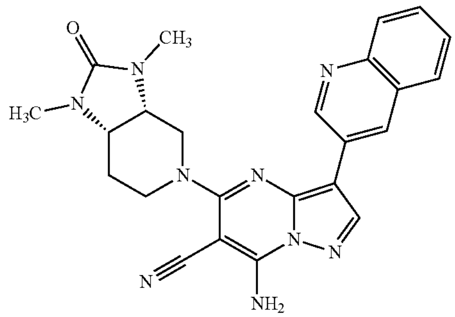 [SMILES: CN1C(=O)N(C)[C@H]2CCN(c3nc4c(-c5cnc6ccccc6c5)cnn4c(N)c3C#N)C[C@H]21] | 454.2 | 454.2 | 2.99 |
| 10.44 | 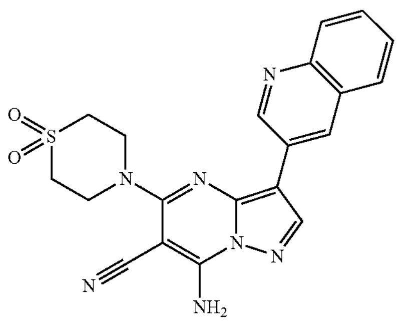 [SMILES: N#Cc1c(N2CCS(=O)(=O)CC2)nc2c(-c3cnc4ccccc4c3)cnn2c1N] | 420.1 | 420.1 | 2.79 |
| 10.45 | 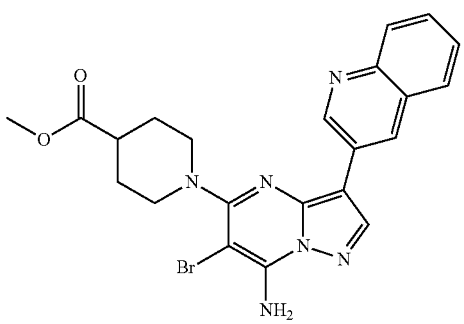 [SMILES: COC(=O)C1CCN(c2nc3c(-c4cnc5ccccc5c4)cnn3c(N)c2Br)CC1] | 481.09 | 481.09 | 4.00 |
| 10.46 | 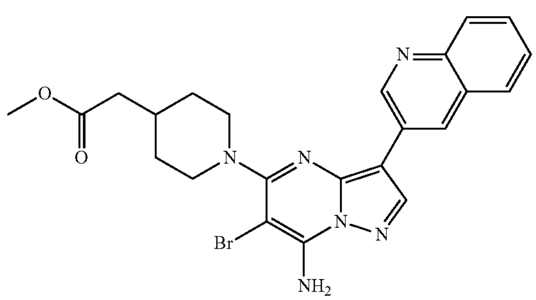 [SMILES: COC(=O)CC1CCN(c2nc3c(-c4cnc5ccccc5c4)cnn3c(N)c2Br)CC1] | 495.11 | 495.10 | 4.23 |

TABLE 10-continued

| Compound ID | Structures | M + H (calc.) | M + H (observed) | Retention Time, (min) |
|---|---|---|---|---|
| 10.47 | 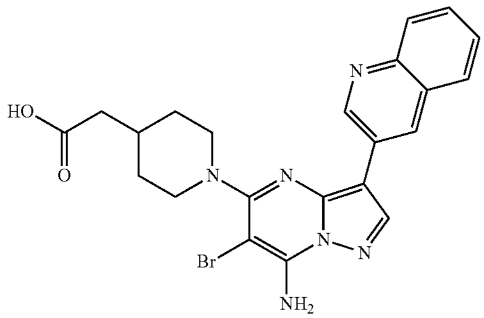 [SMILES: Nc1c(Br)c(N2CCC(CC(=O)O)CC2)nc2c(-c3cnc4ccccc4c3)cnn12] | 481.09 | 481.09 | 3.46 |
| 10.48 | 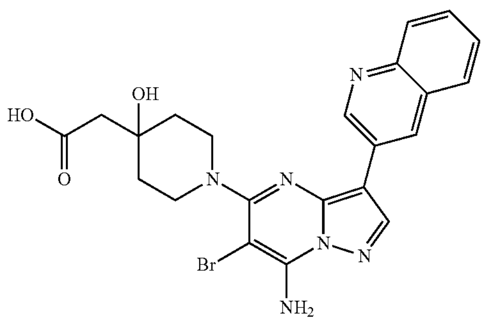 | 497.09 | 497.09 | 2.99 |
| 10.49 | 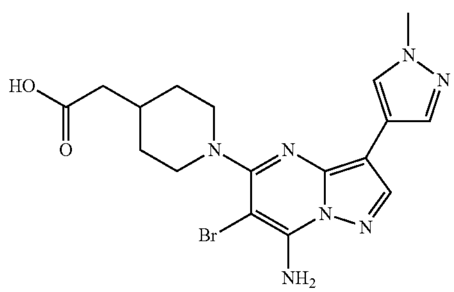 [SMILES: Cn1cc(-c2cnn3c(N)c(Br)c(N4CCC(CC(=O)O)CC4)nc23)cn1] | 434.09 | 434.09 | 3.41 |
| 10.50 | 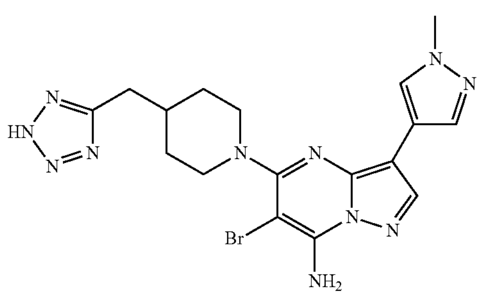 [SMILES: Cn1cc(-c2cnn3c(N)c(Br)c(N4CCC(Cc5nn[nH]n5)CC4)nc23)cn1] | 458.11 | 458.11 | 3.23 |
| 10.51 | 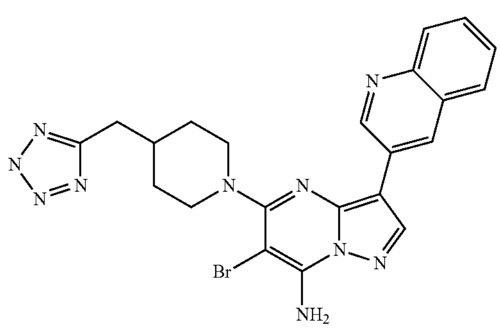 [SMILES: Nc1c(Br)c(N2CCC(Cc3nn[nH]n3)CC2)nc2c(-c3cnc4ccccc4c3)cnn12] | 505.11 | 505.11 | 3.30 |

TABLE 10-continued

| Compound ID | Structures | M + H (calc.) | M + H (observed) | Retention Time, (min) |
|---|---|---|---|---|
| 10.52 | 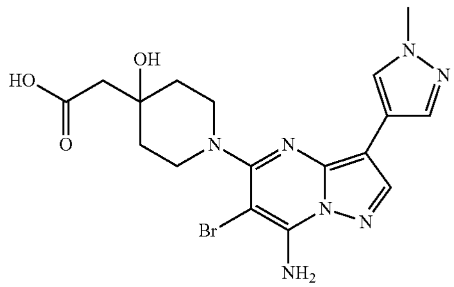 [SMILES: Cn1cc(-c2cnn3c(N)c(Br)c(N4CCC(O)(CC(=O)O)CC4)nc23)cn1] | 450.08 | 450.08 | 2.99 |
| 10.53 | 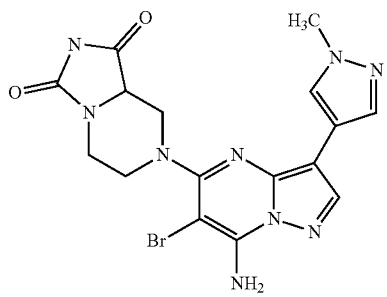 [SMILES: Cn1cc(-c2cnn3c(N)c(Br)c(N4CCN5C(=O)NC(=O)C5C4)nc23)cn1] | 446.3 | 446.10 | 2.89 |
| 10.54 | 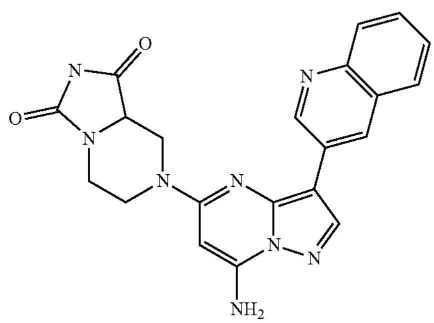 [SMILES: Nc1cc(N2CCN3C(=O)NC(=O)C3C2)nc2c(-c3cnc4ccccc4c3)cnn12] | 415.4 | 415.20 | 2.64 |
| 10.55 | 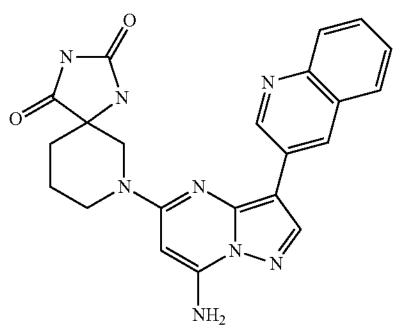 [SMILES: Nc1cc(N2CCCC3(C2)NC(=O)NC3=O)nc2c(-c3cnc4ccccc4c3)cnn12] | 429.5 | 429.2 | 2.61 |
| 10.58 | 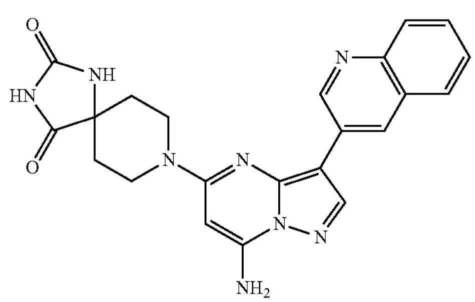 [SMILES: Nc1cc(N2CCC3(CC2)NC(=O)NC3=O)nc2c(-c3cnc4ccccc4c3)cnn12] | 429.18 | 429.17 | 2.57 |

TABLE 10-continued

| Compound ID | Structures | M + H (calc.) | M + H (observed) | Retention Time, (min) |
|---|---|---|---|---|
| 10.59 | 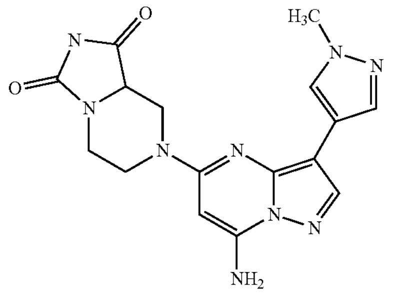 [SMILES: Cn1cc(-c2cnn3c(N)cc(N4CCN5C(=O)NC(=O)C5C4)nc23)cn1] | 368.4 | 368.10 | 2.30 |
| 10.60 | 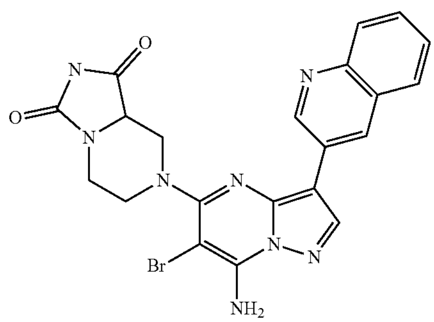 [SMILES: Nc1c(Br)c(N2CCN3C(=O)NC(=O)C3C2)nc2c(-c3cnc4ccccc4c3)cnn12] | 493.00 | 493 | 2.92 |
| 10.61 | 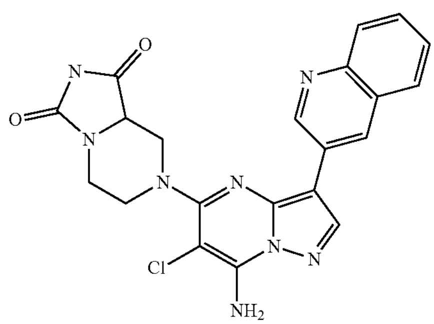 [SMILES: Nc1c(Cl)c(N2CCN3C(=O)NC(=O)C3C2)nc2c(-c3cnc4ccccc4c3)cnn12] | 449.10 | 449.1 | 3.32 |
| 10.62 | 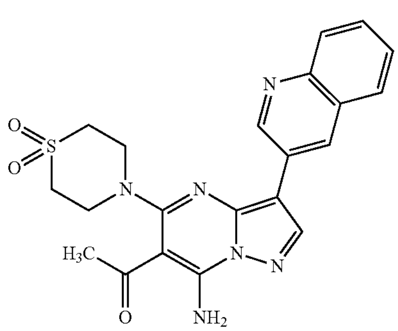 [SMILES: CC(=O)c1c(N2CCS(=O)(=O)CC2)nc2c(-c3cnc4ccccc4c3)cnn2c1N] | 437.0 | 437.0 | 2.88 |

TABLE 10-continued

| Compound ID | Structures | M + H (calc.) | M + H (observed) | Retention Time, (min) |
|---|---|---|---|---|
| 10.63 | 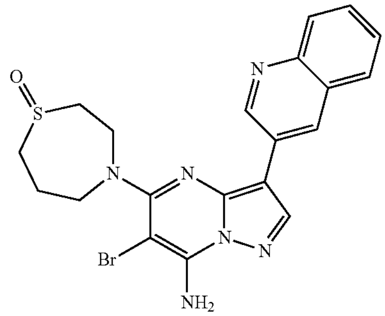 [SMILES: Nc1c(Br)c(N2CCCS(=O)CC2)nc2c(-c3cnc4ccccc4c3)cnn12] | 471.0 | 471.0 | 2.95 |
| 10.64 | 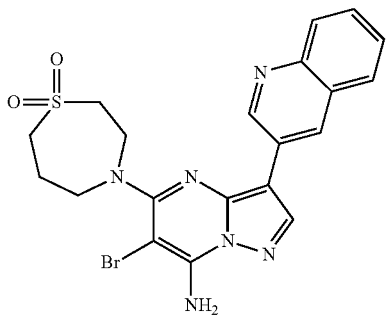 [SMILES: Nc1c(Br)c(N2CCCS(=O)(=O)CC2)nc2c(-c3cnc4ccccc4c3)cnn12] | 487.0 | 487.0 | 3.12 |
| 10.64.1 | 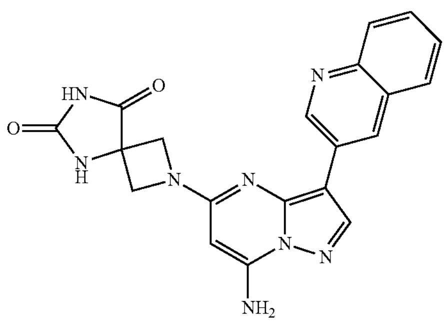 [SMILES: Nc1cc(N2CC3(C2)NC(=O)NC3=O)nc2c(-c3cnc4ccccc4c3)cnn12] | 400.1 | 401.1 | 1.09 |
| 10.64.2 | 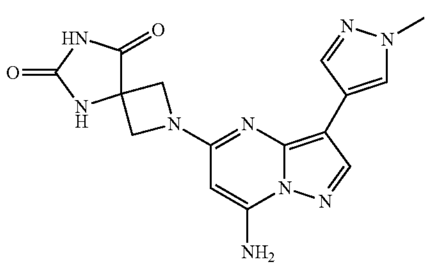 [SMILES: Cn1cc(-c2cnn3c(N)cc(N4CC5(C4)NC(=O)NC5=O)nc23)cn1] | 353.1 | 354.1 | 0.68 |
| 10.64.3 | 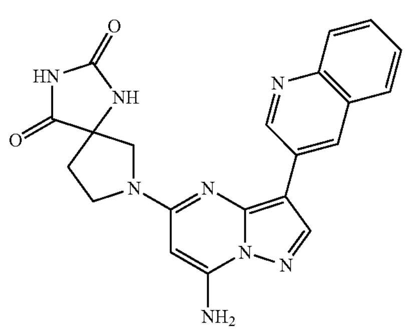 [SMILES: Nc1cc(N2CCC3(C2)NC(=O)NC3=O)nc2c(-c3cnc4ccccc4c3)cnn12] | 414.16 | 415.20 | 2.46 |

TABLE 10-continued

| Compound ID | Structures | M + H (calc.) | M + H (observed) | Retention Time, (min) |
|---|---|---|---|---|
| 10.64.4 | 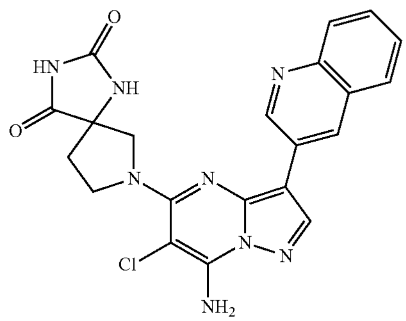 [SMILES: Nc1c(Cl)c(N2CCC3(C2)NC(=O)NC3=O)nc2c(-c3cnc4ccccc4c3)cnn12] | 448.12 | 449.20 | 2.80 |
| 10.64.5 | 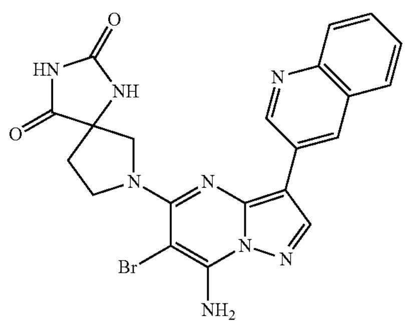 | 492.07 | 493.10 | 2.85 |
| 10.64.6 | 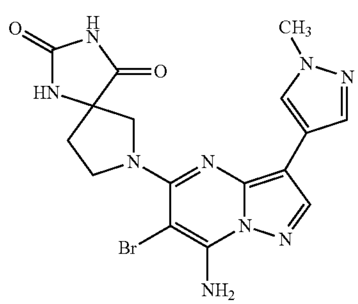 [SMILES: Cn1cc(-c2cnn3c(N)c(Br)c(N4CCC5(C4)NC(=O)NC5=O)nc23)cn1] | 367.15 | 368.20 | 1.84 |
| 10.64.7 | 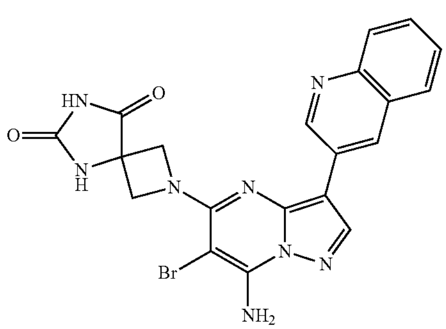 [SMILES: Nc1c(Br)c(N2CC3(C2)NC(=O)NC3=O)nc2c(-c3cnc4ccccc4c3)cnn12] | 478.05 | 479.20 | 2.59 |

TABLE 10-continued

| Compound ID | Structures | M + H (calc.) | M + H (observed) | Retention Time, (min) |
|---|---|---|---|---|
| 10.64.8 | 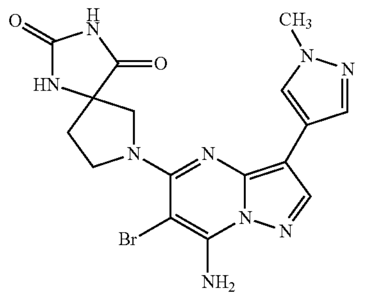 [SMILES: Cn1cc(-c2cnn3c(N)c(Br)c(N4CCC5(C4)NC(=O)NC5=O)nc23)cn1] | 445.06 | 446.20 | 2.80 |

6-bromo-5-morpholino-3-(quinolin-3-yl)-N,N-bis((2-(trimethylsilyl)ethoxy)methyl)pyrazolo[1,5-a]pyrimidin-7-amine Synthesis of 7-(bis((2-(trimethylsilyl)ethoxy)methyl)amino)-5-morpholino-3-(quinolin-3-yl)pyrazolo[1,5-a]pyrimidine-6-carbonitrile

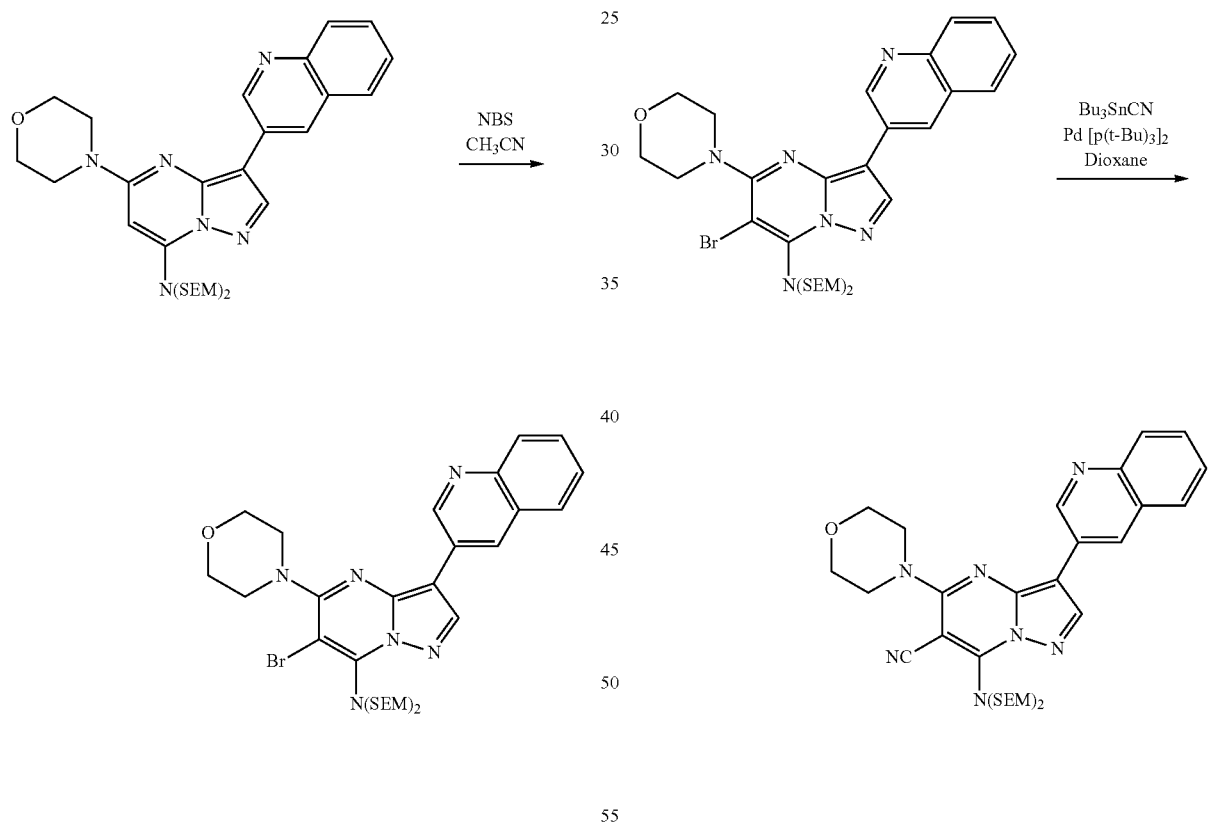

A solution of NBS (20.6 mg, 0.116 mmoL) in $CH_3CN$ (1 mL) was added to a mixture of 5-morpholino-3-(quinolin-3-yl)-N,N-bis((2-(trimethylsilyl)ethoxy)methyl)pyrazolo[1,5-a]pyrimidin-7-amine (70.0 mg, 0.116 mmoL) in $CH_3CN$ (6 mL). After stirring at room temperature for 10 min, the reaction mixture was concentrated and purified by column chromatography to afford the desired compound. LCMS $t_R$=2.91 Min (5 min run, $UV_{254nm}$). Mass calculated for, M+ 684.2, observed LC/MS m/z 685.2 (M+H).

A degassed mixture of 6-bromo-5-morpholino-3-(quinolin-3-yl)-N,N-bis((2-(trimethylsilyl)ethoxy)methyl)pyrazolo[1,5-a]pyrimidin-7-amine (35 mg, 0.051 mmoL), $Bu_3SnCN$ (32.3 mg, 0.10 mmoL), $Pd[P(t-Bu)_3]_2$ (5.2 mg, 0.010 mmoL) in Dioxane (3 mL) was heated at 100° C. overnight. The mixture was cooled to room temperature and the solvent was evaporated in vacuo. Purification by column chromatography afforded the titled compound. LCMS $t_R$=2.76 Min (5 min run, $UV_{254nm}$). Mass calculated for, M+ 631.3, observed LC/MS m/z 632.2 (M+H).

Synthesis of 7-amino-5-morpholino-3-(quinolin-3-yl)pyrazolo[1,5-a]pyrimidine-6-carbonitrile

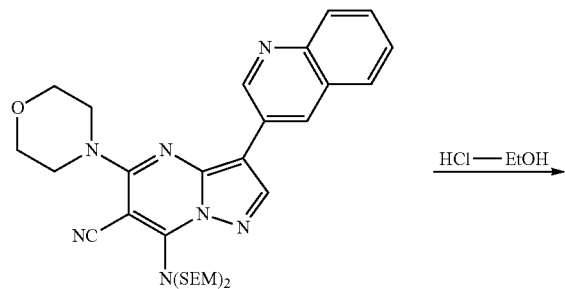

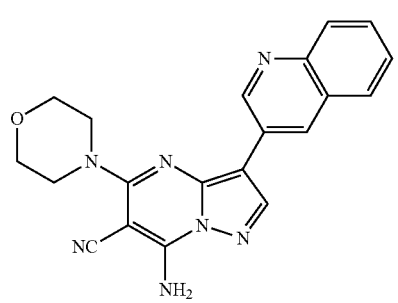

A mixture of 7-(bis((2-(trimethylsilyl)ethoxy)methyl)amino)-5-morpholino-3-(quinolin-3-yl)pyrazolo[1,5-a]pyrimidine-6-carbonitrile (5 mg), EtOH (1 mL) and 3N HCl (1 mL) was heated at 60° C. until LCMS indicated the completed reaction. The mixture was cooled to room temperature and the solvent was evaporated in vacuo. Purification by prep-LC afforded the desired compound. LCMS $t_R$=3.12 Min ($UV_{254nm}$). Mass calculated for, M+ 371.1, observed LC/MS m/z 372.2 (M+H).

Synthesis of 5-morpholino-3-(quinolin-3-yl)-N,N-bis((2-(trimethylsilyl)ethoxy)methyl)pyrazolo[1,5-a]pyrimidin-7-amine

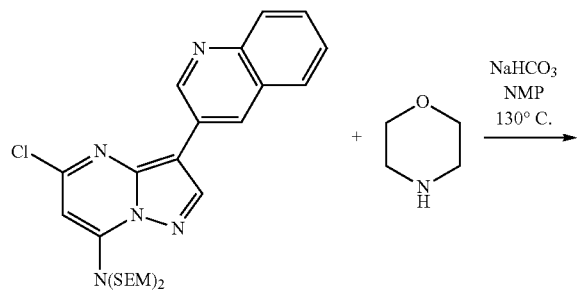

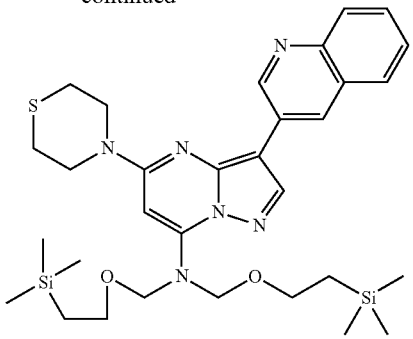

A mixture of 5-chloro-3-(quinolin-3-yl)-N,N-bis((2-(trimethylsilyl)ethoxy)methyl)pyrazolo[1,5-a]pyrimidin-7-amine (77.9 mg, 0.14 mmoL), morpholine (36.7 mg, 0.42 mmoL), NaHCO₃ (53 mg, 0.63 mmoL) in NMP (3 mL) was heated at 130° C. overnight. The mixture was cooled to room temperature and diluted with H₂O and then extracted with ethyl acetate (×2). The combined organic layers were washed with brine and dried with Na₂SO₄. Evaporation of solvent afforded the crude displacement compound. Purification by column chromatography afforded 5-morpholino-3-(quinolin-3-yl)-N,N-bis((2-(trimethylsilyl)ethoxy)methyl)pyrazolo[1,5-a]pyrimidin-7-amine (70 mg, 82%). LCMS $t_R$=2.72 Min (5 min run, $UV_{254nm}$). Mass calculated for, M+ 606.3, observed LC/MS m/z 607.2 (M+H).

Synthesis of 5-thiomorpholinodioxo-3-(quinolin-3-yl)-N,N-bis((2-(trimethylsilyl)ethoxy)methyl)pyrazolo[1,5-a]pyrimidin-7-amine

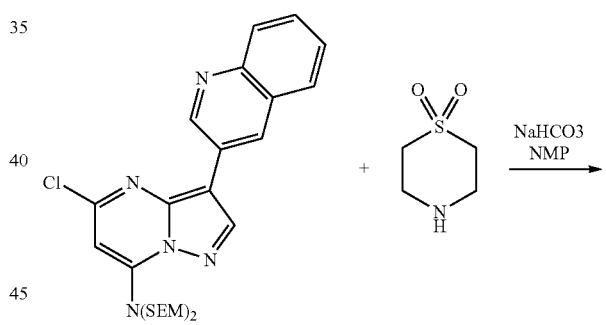

A mixture of 5-chloro-3-(quinolin-3-yl)-N,N-bis((2-(trimethylsilyl)ethoxy)methyl)pyrazolo[1,5-a]pyrimidin-7-amine (503.0 mg, 0.91 mmoL), thiomorpholine 1,1-dioxide (367.1 mg, 2.72 mmoL), NaHCO₃ (533.0 mg, 6.34 mmoL) in NMP (8 mL) was heated at 130° C. overnight. The mixture was cooled to room temperature and diluted with H₂O and then extracted with ethyl acetate (×2). The combined organic layers were washed with brine and dried with Na₂SO₄. Evaporation of solvent afforded the crude displacement compound. Purification by column chromatography afforded compound 5-thiomorpholinodioxo-3-(quinolin-3-yl)-N,N-bis((2-(trimethylsilyl)ethoxy)methyl)pyrazolo[1,5-a]pyrimidin-7-amine LCMS $t_R$=2.52 Min (5 min run, $UV_{254nm}$). Mass calculated for, M+ 654.2, observed m/z 655.2 (M+H).

Synthesis of 5-morpholino-3-(quinolin-3-yl)-N,N-bis((2-(trimethylsilyl)ethoxy)methyl)pyrazolo[1,5-a]pyrimidin-6-bromo-7-amine

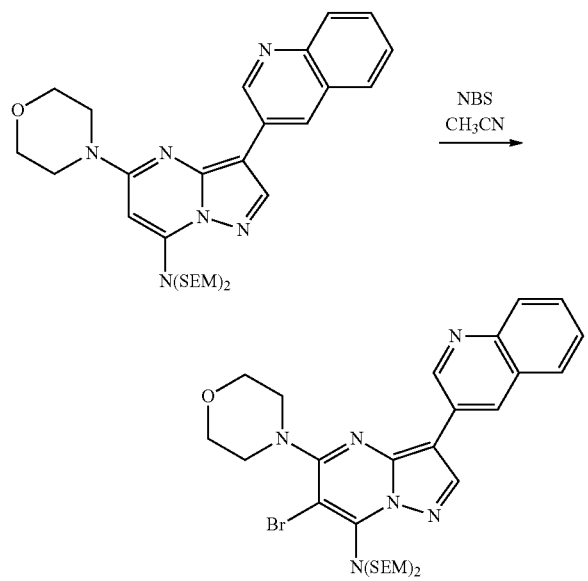

A solution of NBS (20.6 mg, 0.116 mmoL) in CH$_3$CN (1 mL) was added to a mixture of 5-morpholino-3-(quinolin-3-yl)-N,N-bis((2-(trimethylsilyl)ethoxy)methyl)pyrazolo[1,5-a]pyrimidin-7-amine (70.0 mg, 0.116 mmoL) in CH$_3$CN (6 mL). After stirring at room temperature for 10 min, the reaction mixture was concentrated and purified by column chromatography to afford 6-bromo-5-morpholino-3-(quinolin-3-yl)-N,N-bis((2-(trimethylsilyl)ethoxy)methyl)pyrazolo[1,5-a]pyrimidin-7-amine. LCMS $t_R$=2.91 Min (5 min run, $UV_{254nm}$). Mass calculated for, M+ 684.2, observed LC/MS m/z 685.2 (M+H).

Synthesis of 5-thiomoroholinodioxo-3-(quinolin-3-yl)-N,N-bis((2-(trimethylsilyl)ethoxy)methyl)pyrazolo[1,5-a]pyrimidin-6-bromo-7-amine

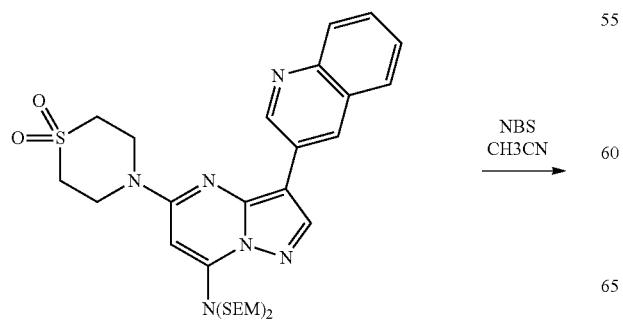

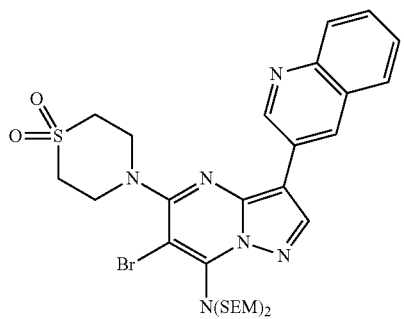

By essentially the same procedure given in Preparative Example 3-1, 6-bromo-3-(quinolin-3-yl)-5-thiomorpholino-1',1'-dioxide-N,N-bis((2-(trimethylsilyl)ethoxy) methyl) pyrazolo[1,5-a]pyrimidin-7-amine can be prepared. LCMS $t_R$=2.90 Min (5 min run, $UV_{254nm}$). Mass calculated for, M+ 732.2, observed LC/MS m/z 733.2 (M+H).

Synthesis of 6-bromo-3-(6-fluoroquinolin-3-yl)-5-thiomorpholin-dioxo-pyrazolo[1,5-a]pyrimidin-7-amine Scheme-29

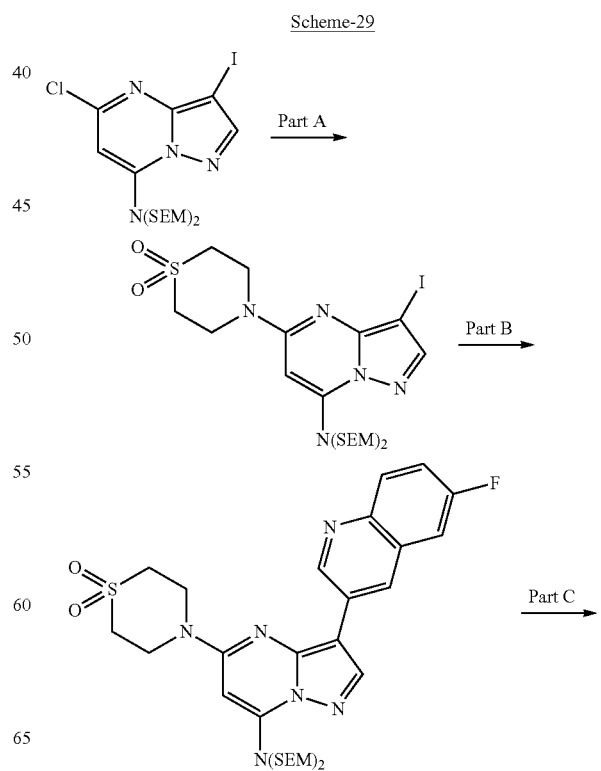

1233

-continued

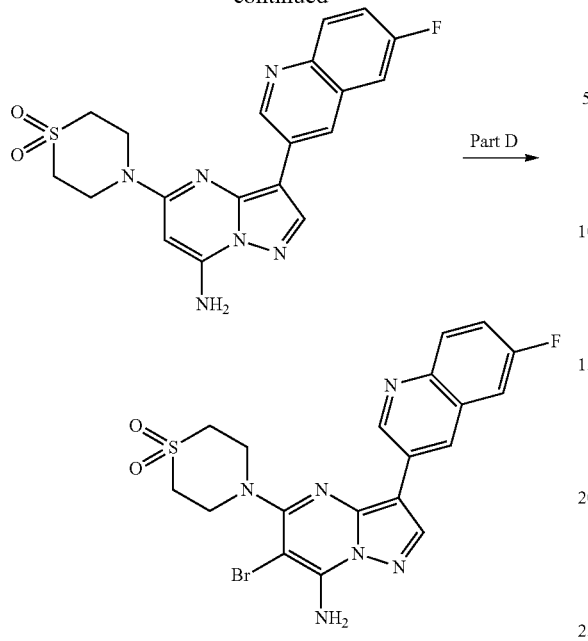

Part A:

Synthesis of 3-iodo-5-thiomorpholin-4-dioxo-N,N-bis((2-(trimethylsilyl)ethoxy)methyl)pyrazolo[1,5-a]pyrimidin-7-amine A mixture of compound 5-chloro-3-iodo-N,N-bis((2-(trimethylsilyl)ethoxy)methyl)pyrazolo[1,5-a]pyrimidin-7-amine (10.8 mmol, 6.00 g, preparation reported previously), thiomorpholine 1,1-dioxide (32.4 mmol, 4.38 g), and NaHCO₃ (48.6 mmol, 4.08 g) in NMP (50 mL) was heated at 130° C. for 28 h. LCMS showed nearly complete consumption of A. The reaction mixture was diluted with EtOAc, washed with H₂O and brine, dried over Na2SO4, and concentrated. The crude product was purified by a SiO₂ column (0-30% EtOAc/Hexanes) to afford compound 3-iodo-5-thiomorpholin-4-dioxo-N,N-bis((2-(trimethylsilyl)ethoxy)methyl)pyrazolo[1,5-a]pyrimidin-7-amine as a pale yellow solid (6.15 g, 87%). HPLC-MS $T_R$=2.70 min (UV 254 nm, 5 min method); mass calculated for formula $C_{22}H_{40}IN_5O_4SSi_2$ 653.1, observed LCMS m/z 654.1 (M+H).

Part B:

Synthesis of 3-(6-fluoroquinolin-3-yl)-5-thiomorpholin-4'-dioxo-N,N-bis((2-(trimethylsilyl)ethoxy)methyl)pyrazolo[1,5-a]pyrimidin-7-amine A mixture of compound 3-iodo-5-thiomorpholin-4-dioxo-N,N-bis((2-(trimethylsilyl)ethoxy)methyl)pyrazolo[1,5-a]pyrimidin-7-amine (0.551 mmol, 360 mg), boronate 7 (0.827 mmol, prepared in situ, see below), PdCl₂(dppf)CH₂Cl₂ (0.055 mmol, 45.0 mg), and K₂CO₃ (1.65 mmol, 229 mg) in DME/H₂O (5/1 mL) was degassed and then heated at 90° C. for 24 h. The reaction mixture was diluted with EtOAc and filtered. The filtrate was concentrated and purified by a SiO₂ column (0-50% EtOAc/Hexanes) to afford compound 3-(6-fluoroquinolin-3-yl)-5-thiomorpholin-4'-dioxo-N,N-bis((2-(trimethylsilyl)ethoxy)methyl)pyrazolo[1,5-a]pyrimidin-7-amine as a yellow solid (260 mg, 70%). HPLC-MS $T_R$=2.39 min (UV 254 nm, 5 min method); mass calculated for formula $C_{31}H_{45}FN_6O_4SSi_2$ 672.3, observed LCMS m/z 673.2 (M+H).

1234

Synthesis of 6-fluoro-3-(4,4,5,5-tetramethyl-1,3,2-dioxaborolan-2-yl)quinoline

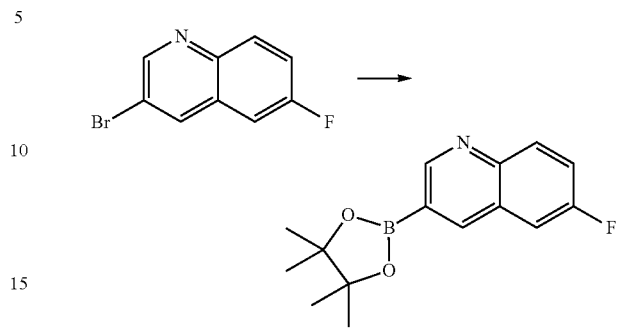

A mixture of the corresponding 3-bromo-6-fluoro quinoline (0.827 mmol, 187 mg, 1.0 eq), bis(pinacolato)diboron (1.2 eq), PdCl₂(dppf)CH₂Cl₂ (0.1 eq), and KOAc (3.0 eq) in dioxane (5 mL) was degassed and then heated at 80° C. for 16 h. All the volatiles were removed under reduced pressure and the crude product 6-fluoro-3-(4,4,5,5-tetramethyl-1,3,2-dioxaborolan-2-yl)quinoline was used without further purification.

Part C:

3-(6-fluoroquinolin-3-yl)-5-thiomorpholin-4'-dioxo-pyrazolo[1,5-a]pyrimidin-7-amine To a solution of compound 3-(6-fluoroquinolin-3-yl)-5-thiomorpholin-4'-dioxo-N,N-bis((2-(trimethylsilyl)ethoxy)methyl)pyrazolo[1,5-a]pyrimidin-7-amine (0.169 mmol, 156 mg) in EtOH (4 mL) was added 4 N HCl in dioxane (1 mL) and the resulting mixture was heated at 65° C. for 1 h. All the volatiles were removed under reduced pressure. The residue, which has a very poor solubility in DMSO, was diluted with a small amount of DMSO and basicified with NaHCO₃. The resulting slurry was stirred vigorously overnight and filtered. The precipitates were washed with H₂O and MeOH to afford compound 3-(6-fluoroquinolin-3-yl)-5-thiomorpholin-4'-dioxo-pyrazolo[1,5-a]pyrimidin-7-amine as a pale yellow solid (60.1 mg, 86%). HPLC-MS $T_R$=1.17 min (UV 254 nm, 5 min method); mass calculated for formula $C_{19}H_{17}FN_6O_2S$ 412.1, observed LCMS m/z 413.0 (M+H).

Part D:

3-(6-fluoroquinolin-3-yl)-5-thiomorpholin-4'-dioxo-6-bromo-pyrazolo[1,5-a]pyrimidin-7-amine To a slurry of compound 3-(6-fluoroquinolin-3-yl)-5-thiomorpholin-4'-dioxo-pyrazolo[1,5-a]pyrimidin-7-amine (0.0659 mmol, 27.2 mg) in CH₃CN was added NBS (1.0 eq, in a stock solution in CH₃CN) and the resulting mixture was stirred at rt for 1 h. The reaction solution was concentrated and purified by prep-HPLC to afford compound 3-(6-fluoroquinolin-3-yl)-5-thiomorpholin-4'-dioxo-6-bromo-pyrazolo[1,5-a]pyrimidin-7-amine as a pale yellow solid (6.1 mg, 19%). HPLC-MS $T_R$=1.56 min (UV 254 nm, 5 min method); mass calculated for formula $C_{19}H_{16}BrFN_6O_2S$ 490.0, observed LCMS m/z 491.0 (M+H).

By essentially the same procedures given in Preparative Example (scheme-29) Part B, Part C and Part D, compounds 10.65-10.85 given in Table 10A can be prepared.

TABLE-10A

| Compound | Structure | M.Wt. (Calcd) | MS m/z (M + H) | HPLC-MS T$_R$ (Method) |
|---|---|---|---|---|
| 10.65 | 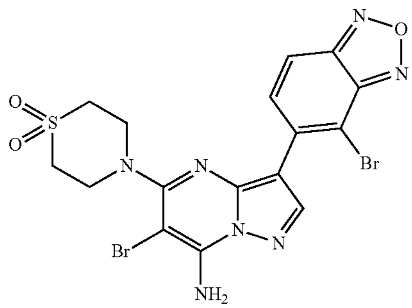 [SMILES: Nc1c(Br)c(N2CCS(=O)(=O)CC2)nc2c(-c3ccc4nonc4c3Br)cnn12] | 540.9 | 542 | 4.78 (10 min) |
| 10.66 | 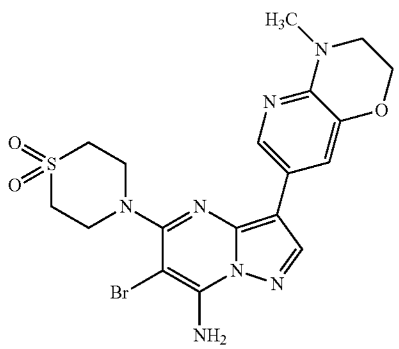 [SMILES: CN1CCOc2cc(-c3cnn4c(N)c(Br)c(N5CCS(=O)(=O)CC5)nc34)cnc21] | 493.0 | 494 | 2.67 (10 min) |
| 10.67 | 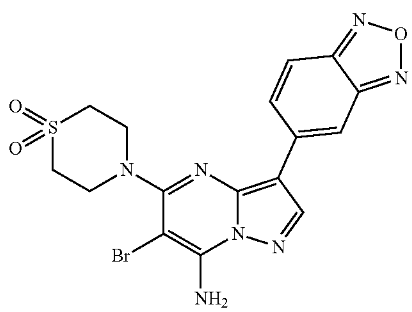 [SMILES: Nc1c(Br)c(N2CCS(=O)(=O)CC2)nc2c(-c3ccc4nonc4c3)cnn12] | 463.0 | 464.0 | 1.87 (5 min) |
| 10.68 | 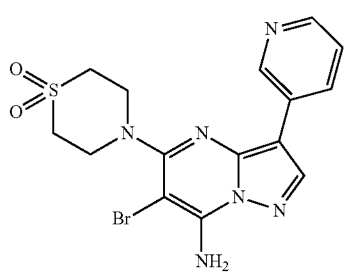 [SMILES: Nc1c(Br)c(N2CCS(=O)(=O)CC2)nc2c(-c3cccnc3)cnn12] | 422.0 | 423.0 | 0.89 (5 min) |
| 10.69 | 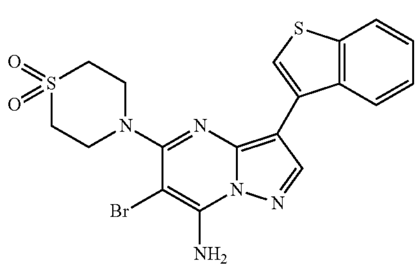 [SMILES: Nc1c(Br)c(N2CCS(=O)(=O)CC2)nc2c(-c3csc4ccccc34)cnn12] | 477.0 | 478.9 | 2.06 (5 min) |

TABLE-10A-continued
| Compound | Structure | M.Wt. (Calcd) | MS m/z (M + H) | HPLC-MS T$_R$ (Method) |
|---|---|---|---|---|
| 10.70 | 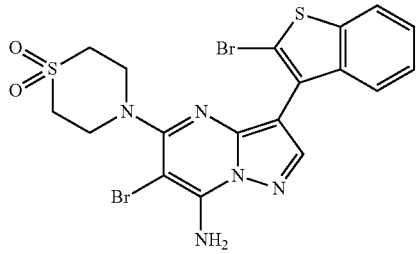 [SMILES: Nc1c(Br)c(N2CCS(=O)(=O)CC2)nc2c(-c3c(Br)sc4ccccc34)cnn12] | 554.9 | 555.8 | 2.21 (5 min) |
| 10.71 | 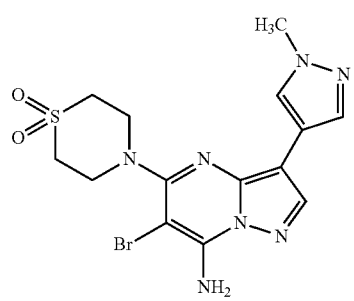 [SMILES: Cn1cc(-c2cnn3c(N)c(Br)c(N4CCS(=O)(=O)CC4)nc23)cn1] | 425.0 | 426.0 | 1.37 (5 min) |
| 10.72 | 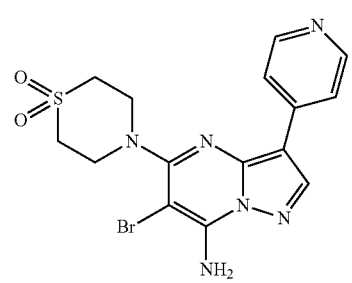 [SMILES: Nc1c(Br)c(N2CCS(=O)(=O)CC2)nc2c(-c3ccncc3)cnn12] | 422.0 | 423.0 | 1.06 (5 min) |
| 10.73 | 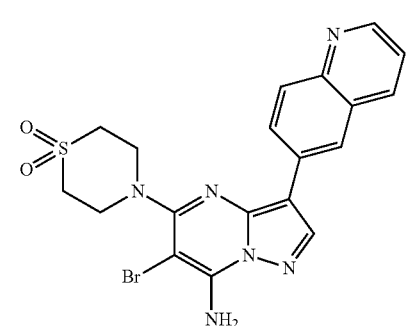 | 472.0 | 473.0 | 1.22 (5 min) |
| 10.74 | 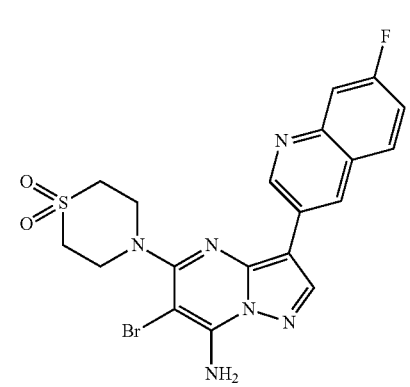 [SMILES: Nc1c(Br)c(N2CCS(=O)(=O)CC2)nc2c(-c3cnc4cc(F)ccc4c3)cnn12] | 490.0 | 491.0 | 1.57 (5 min) |

TABLE-10A-continued

| Compound | Structure | M.Wt. (Calcd) | MS m/z (M + H) | HPLC-MS T$_R$ (Method) |
|---|---|---|---|---|
| 10.75 | 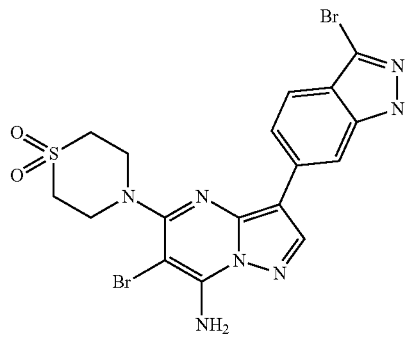 [SMILES: Nc1c(Br)c(N2CCS(=O)(=O)CC2)nc2c(-c3ccc4c(Br)n[nH]c4c3)cnn12] | 538.9 | 540.0 | 1.41 (5 min) |
| 10.76 | 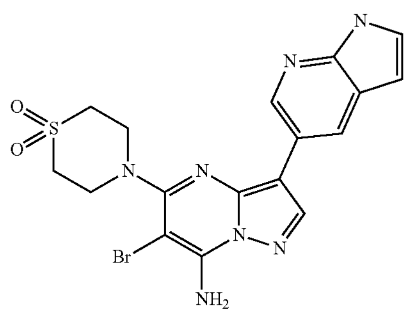 [SMILES: Nc1c(Br)c(N2CCS(=O)(=O)CC2)nc2c(-c3cnc4[nH]ccc4c3)cnn12] | 461.0 | 462.0 | 0.98 (5 min) |
| 10.77 | 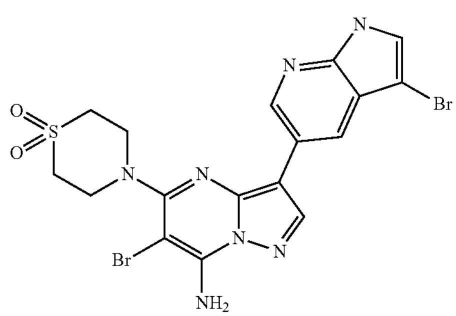 [SMILES: Nc1c(Br)c(N2CCS(=O)(=O)CC2)nc2c(-c3cnc4[nH]cc(Br)c4c3)cnn12] | 538.9 | 540.0 | 1.08 (5 min) |
| 10.78 | 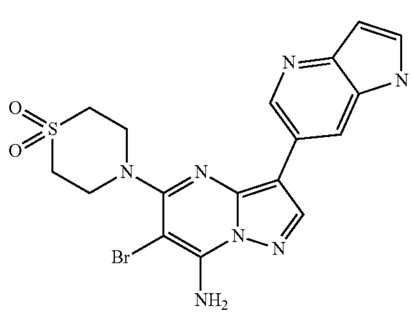 [SMILES: Nc1c(Br)c(N2CCS(=O)(=O)CC2)nc2c(-c3cnc4cc[nH]c4c3)cnn12] | 461.0 | 462 | 3.45 (10 min) |

TABLE-10A-continued

| Compound | Structure | M.Wt. (Calcd) | MS m/z (M + H) | HPLC-MS T$_R$ (Method) |
|---|---|---|---|---|
| 10.79 | 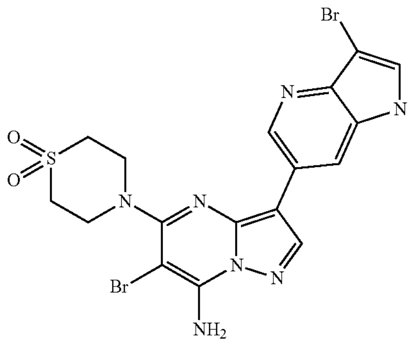 [SMILES: Nc1c(Br)c(N2CCS(=O)(=O)CC2)nc2c(-c3cnc4c(Br)c[nH]c4c3)cnn12] | 538.9 | 540.0 | 1.52 (5 min) |
| 10.80 | 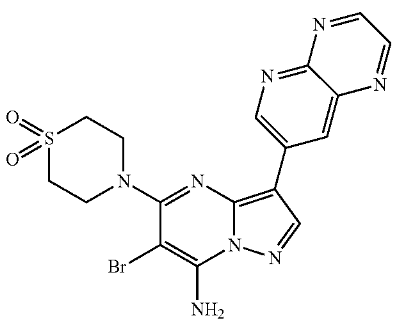 | 474.0 | 475 | 3.13 (10 min) |
| 10.81 | 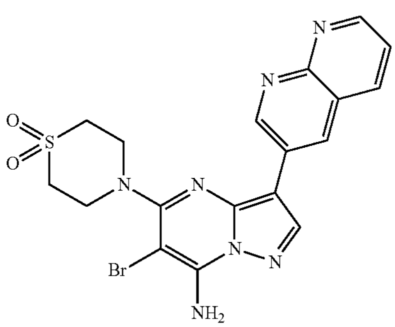 | 473.0 | 474 | 2.81 (10 min) |
| 10.82 | 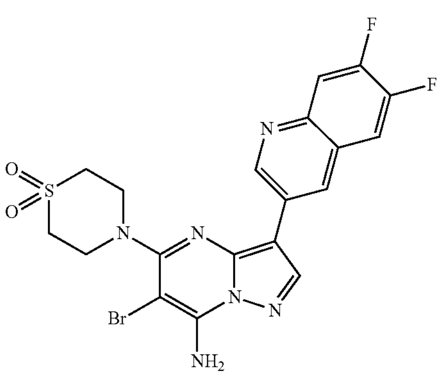 [SMILES: Nc1c(Br)c(N2CCS(=O)(=O)CC2)nc2c(-c3cnc4cc(F)c(F)cc4c3)cnn12] | 508.0 | 509 | 4.06 (10 min) |

TABLE-10A-continued
| Compound | Structure | M.Wt. (Calcd) | MS m/z (M + H) | HPLC-MS T_R (Method) |
|---|---|---|---|---|
| 10.83 | 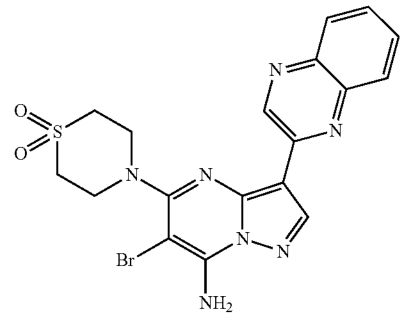 [SMILES: Nc1c(Br)c(N2CCS(=O)(=O)CC2)nc2c(-c3cnc4ccccc4n3)cnn12] | 473.0 | 474 | 4.04 (10 min) |
| 10.84 | 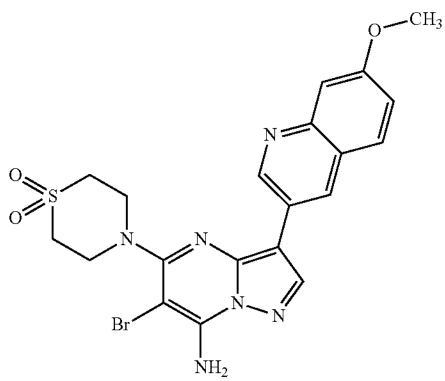 [SMILES: COc1ccc2cc(-c3cnn4c(N)c(Br)c(N5CCS(=O)(=O)CC5)nc34)cnc2c1] | 502.0 | 503 | 3.21 (10 min) |
| 10.85 | 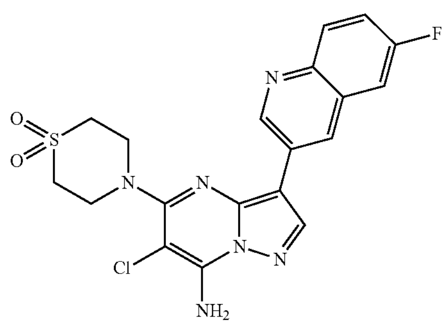 [SMILES: Nc1c(Cl)c(N2CCS(=O)(=O)CC2)nc2c(-c3cnc4ccc(F)cc4c3)cnn12] | 446.1 | 447.1 | 1.35 (5 min) |
Synthesis of 3-(2,3'-bipyridin-5-yl)-5-thiomorpholino-4-dioxo-N,N-bis((2-(trimethylsilyl)ethoxy)methyl)pyrazolo[1,5-a]pyrimidin-7-amine
SCHEME-30
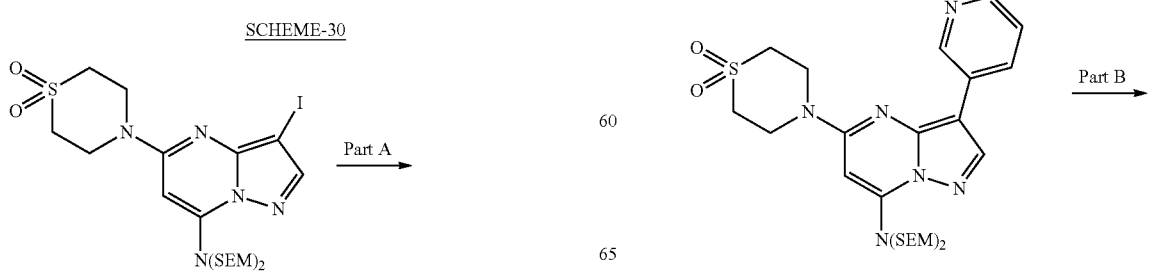
-continued

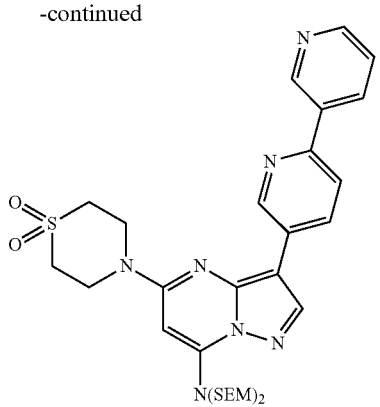

N(SEM)₂

Part A:

3-(6-chloropyridin-3-yl)-5-thiomorpholino-4-dioxo-N,N-bis((2-(trimethylsilyl)ethoxy)methyl)pyrazolo[1,5-a]pyrimidin-7-amine Title compound was prepared from compound 3-iodo-5-thiomorpholino-4'-dioxo-N,N-bis((2-(trimethylsilyl)ethoxy)methyl)pyrazolo[1,5-a]pyrimidin-7-amine and 6-chloro-3-pyridineboronic acid pinacol ester using the coupling conditions described in Part B of Example 1. HPLC-MS $T_R$=2.89 min (UV 254 nm, 5 min method); mass calculated for formula $C_{27}H_{43}ClN_6O_4SSi_2$ 638.2, observed LCMS m/z 639.1 (M+H).

Part B:

3-(2,3'-bipyridin-5-yl)-5-thiomorpholino-4-dioxo-N,N-bis((2-(trimethylsilyl)ethoxy)methyl)pyrazolo[1,5-a]pyrimidin-7-amine A mixture of 3-(6-chloropyridin-3-yl)-5-thiomorpholino-4-dioxo-N,N-bis((2-(trimethylsilyl)ethoxy)methyl)pyrazolo[1,5-a]pyrimidin-7-amine (0.258 mmol, 165 mg), pyridine-3-ylboronic acid (0.516 mmol, 63.4 mg), PdCl₂(dppf)·CH₂Cl₂ (0.026 mmol, 21.2 mg), and K₂CO₃ (0.774 mmol, 107 mg) in DME/H₂O (2/0.4 mL) was degassed and then heated at 150° C. under microwave radiation for 1 h. The reaction mixture was diluted with EtOAc and filtered. The filtrate was concentrated and purified by a SiO₂ column (20-100% EtOAc/Hexanes) to afford compound 3-(2,3'-bipyridin-5-yl)-5-thiomorpholino-4-dioxo-N,N-bis((2-(trimethylsilyl)ethoxy)methyl)pyrazolo[1,5-a]pyrimidin-7-amine as a pale yellow solid (161 mg, 91%). HPLC-MS $T_R$=2.15 min (UV 254 nm, 5 min method); mass calculated for formula $C_{32}H_{47}N_7O_4SSi_2$ 681.3, observed LCMS m/z 682.3 (M+H).

By essentially the same procedures given in Preparative above Example (scheme-30) Compounds given in Table 10B can be prepared.

TABLE 10B

| Compound | Structure | Exact Mass | MS m/z (M + H) | HPLC-MS $T_R$ (Method) |
|---|---|---|---|---|
| 10.86 | 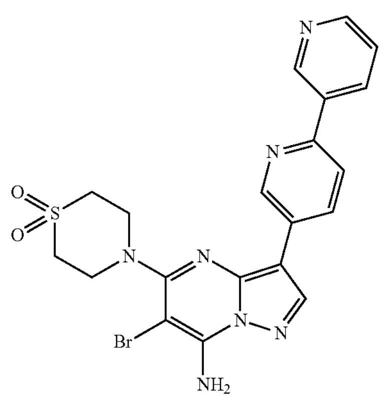 [SMILES: Nc1c(Br)c(N2CCS(=O)(=O)CC2)nc2c(-c3ccc(-c4cccnc4)nc3)cnn12] | 499.0 | 500.10 | 2.83 (10 min) |
| 10.87 | 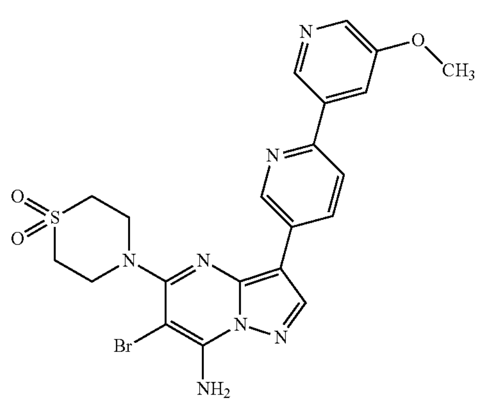 [SMILES: COc1cncc(-c2ccc(-c3cnn4c(N)c(Br)c(N5CCS(=O)(=O)CC5)nc34)cn2)c1] | 529.0 | 530.10 | 3.14 (10 min) |

TABLE 10B-continued
| Compound | Structure | Exact Mass | MS m/z (M + H) | HPLC-MS T_R (Method) |
|---|---|---|---|---|
| 10.88 | 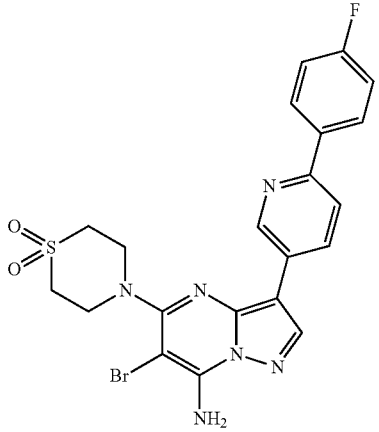 [SMILES: Nc1c(Br)c(N2CCS(=O)(=O)CC2)nc2c(-c3ccc(-c4ccc(F)cc4)nc3)cnn12] | 516.0 | 517.10 | 3.81 (10 min) |
| 10.89 | 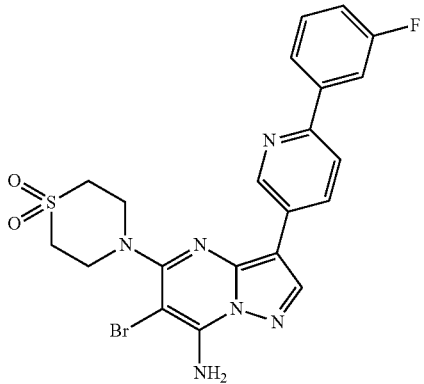 [SMILES: Nc1c(Br)c(N2CCS(=O)(=O)CC2)nc2c(-c3ccc(-c4cccc(F)c4)nc3)cnn12] | 516.0 | 517.10 | 3.56 (10 min) |
| 10.90 | 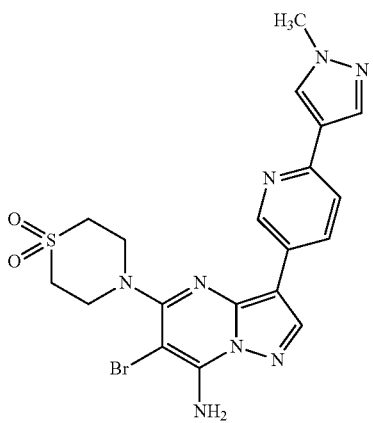 [SMILES: Cn1cc(-c2ccc(-c3cnn4c(N)c(Br)c(N5CCS(=O)(=O)CC5)nc34)cn2)cn1] | 502.0 | 503.10 | 2.77 (10 min) |

Synthesis of 3-(3,3'-bipyridin-5-yl)-5-thiomorpholin-4'-dioxo-N,N-bis((2-(trimethylsilyl)ethoxy)methyl)pyrazolo[2,5-a]pyrimidin-7-amine

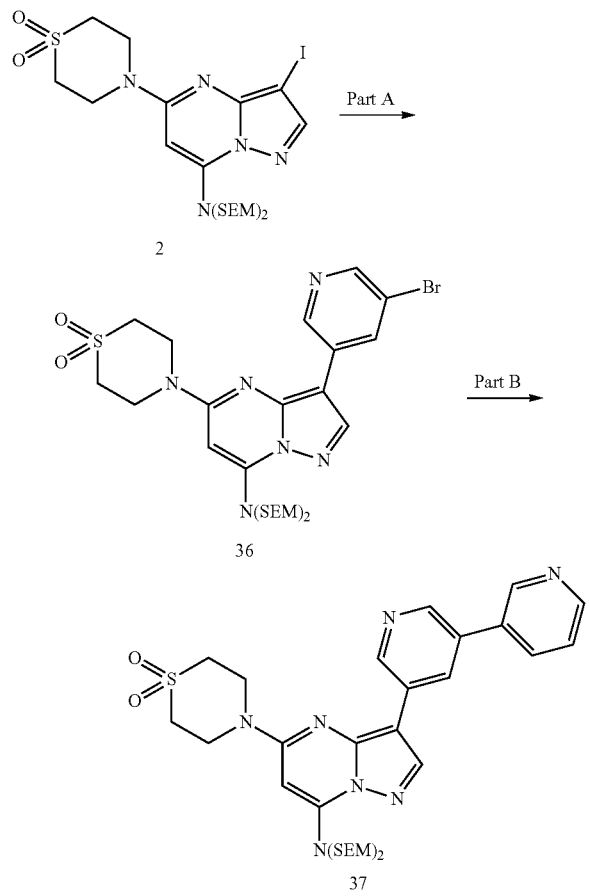

Part A:

3-(5-bromopyridin-3-yl)-5-thiomorpholin-4'-dioxo-N,N-bis((2-(trimethylsilyl)ethoxy)methyl)pyrazolo[1,5-a]pyrimidin-7-amine Compound 3-(5-bromopyridin-3-yl)-5-thiomorpholin-4'-dioxo-N,N-bis((2-(trimethylsilyl)ethoxy)methyl)pyrazolo[1,5-a]pyrimidin-7-amine was prepared from compound 3-iodo-5-thiomorpholino-4'-dioxo-N,N-bis((2-(trimethylsilyl)ethoxy)methyl)pyrazolo[1,5-a]pyrimidin-7-amine and 5-bromo-3-pyridineboronic acid pinacol ester using the coupling conditions described in Part B of Example 1. HPLC-MS $T_R$=2.62 min (UV 254 nm, 5 min method); mass calculated for formula $C_{27}H_{43}BrN_6O_4SSi_2$ 682.2, observed LCMS m/z 683.0 (M+H).

Part B:

3-(3,3'-bipyridin-5-yl)-5-thiomorpholin-4'-dioxo-N,N-bis((2-(trimethylsilyl)ethoxy)methyl)pyrazolo[1,5-a]pyrimidin-7-amine Compound, 3-(3,3'-bipyridin-5-yl)-5-thiomorpholin-4'-dioxo-N,N-bis((2-(trimethylsilyl)ethoxy)methyl)pyrazolo[1,5-a]pyrimidin-7-amine was prepared from 3-(5-bromopyridin-3-yl)-5-thiomorpholin-4'-dioxo-N,N-bis((2-(trimethylsilyl)ethoxy)methyl)pyrazolo[1,5-a]pyrimidin-7-amine using the coupling conditions described in Part B of Preparative Example 3. HPLC-MS $T_R$=2.50 min (UV 254 nm, 5 min method); mass calculated for formula $C_{27}H_{43}BrN_6O_4SSi_2$ 681.3, observed LCMS m/z 682.2 (M+H).

By essentially the same procedures given in Preparative Example above (Scheme-31), compounds given in Table-10C can be prepared

TABLE 10C

| Compound Structure | Exact Mass | MS m/z (M + H) | HPLC-MS $T_R$ (Method) |
|---|---|---|---|
| 10.91 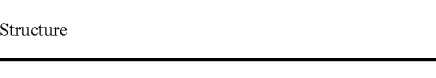 | 499.0 | 500 | 2.36 (10 min) |

TABLE 10C-continued

| Compound Structure | Exact Mass | MS m/z (M + H) | HPLC-MS $T_R$ (Method) |
|---|---|---|---|
| 10.92 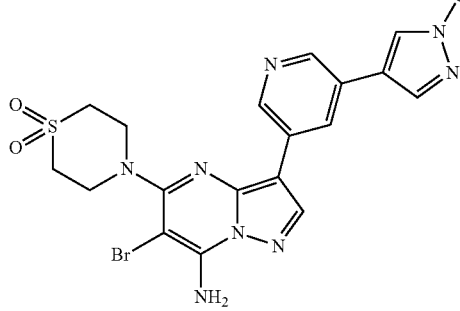 | 502.0 | 503 | 2.71 (10 min) |

1-(7-amino-5-morpholino-3-(quinolin-3-yl)pyrazolo[1,5-a]pyrimidin-6-yl)ethanone

SCHEME-32

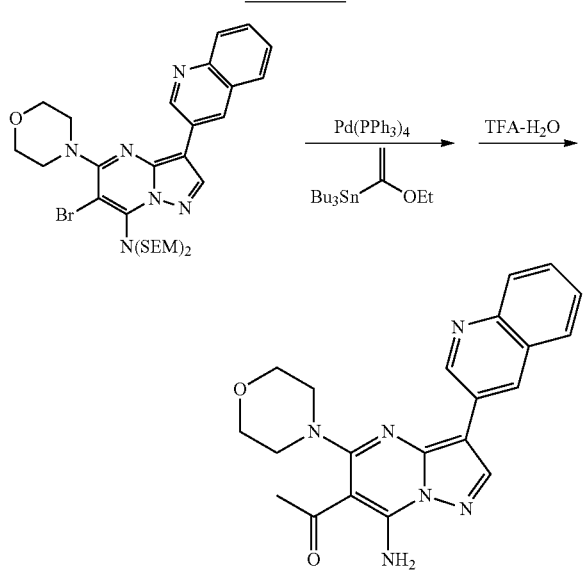

A degassed mixture of 6-bromo-5-morpholino-3-(quinolin-3-yl)-N,N-bis((2-(trimethylsilyl)ethoxy)methyl)pyrazolo[1,5-a]pyrimidin-7-amine (141 mg, 0.20 mmoL), tributyl(1-ethoxyvinyl)tin (112 mg, 0.31 mmoL), Pd(PPh$_3$)$_4$ (24 mg, 0.02 mmoL) in Dioxane (4 mL) was heated at 100° C. for 2 days. The mixture was cooled to room temperature and filtered through short plug of 10% KF/SiO$_2$. The crude Stille coupling product obtained after concentrating the filtrate was then treated with 3 mL of 1:1 mixture of TFA and H$_2$O at room temperature for 30 min. Concentration and purification by prep-LC afforded 1-(7-amino-5-morpholino-3-(quinolin-3-yl)pyrazolo[1,5-a]pyrimidin-6-yl)ethanone. LCMS $t_R$=3.32 Min. Mass calculated for, M+ 388.1, observed LC/MS m/z 389.1 (M+H).

By essentially the same procedure given in Preparative above (Scheme-32), compounds in the table-10-D can be synthesized.

TABLE-10D

| Compound ID | Structures | M.Wt (calc.) | M + H (observed) | Retention Time, 10 min method (min) |
|---|---|---|---|---|
| 10.93 | 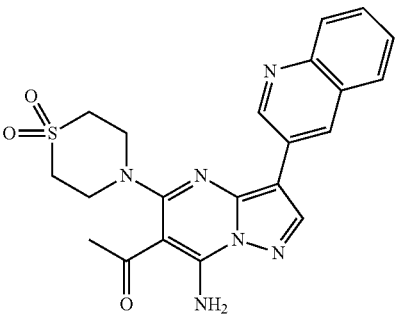 [SMILES: CC(=O)c1c(N2CCS(=O)(=O)CC2)nc2c(-c3cnc4ccccc4c3)cnn2c1N] | 436.1 | 437.1 | 2.88 |

TABLE-10D-continued

| Compound ID | Structures | M.Wt (calc.) | M + H (observed) | Retention Time, 10 min method (min) |
|---|---|---|---|---|
| 10.94 | 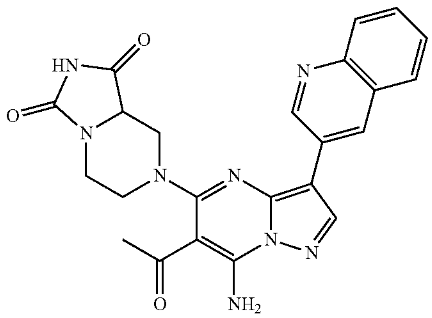 [SMILES: CC(=O)c1c(N2CCN3C(=O)NC(=O)C3C2)nc2c(-c3cnc4ccccc4c3)cnn2c1N] | 456.16 | 457.26 | 2.83 |
| 10.95 | 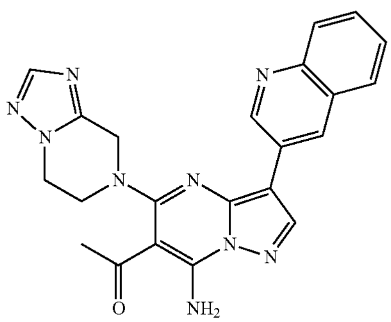 [SMILES: CC(=O)c1c(N2CCn3ncnc3C2)nc2c(-c3cnc4ccccc4c3)cnn2c1N] | 425.17 | 426.23 | 2.90 |
| 10.96 | 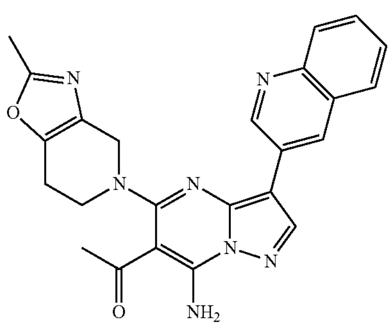 [SMILES: CC(=O)c1c(N2CCc3oc(C)nc3C2)nc2c(-c3cnc4ccccc4c3)cnn2c1N] | 439.17 | 440.47 | 3.57 |
| 10.97 | 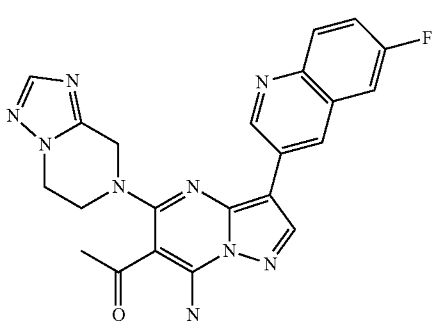 [SMILES: CC(=O)c1c(N2CCn3ncnc3C2)nc2c(-c3cnc4ccc(F)cc4c3)cnn2c1N] | 443.16 | 444.13 | 3.27 |

TABLE-10D-continued
| Compound ID | Structures | M.Wt (calc.) | M + H (observed) | Retention Time, 10 min method (min) |
|---|---|---|---|---|
| 10.98 | 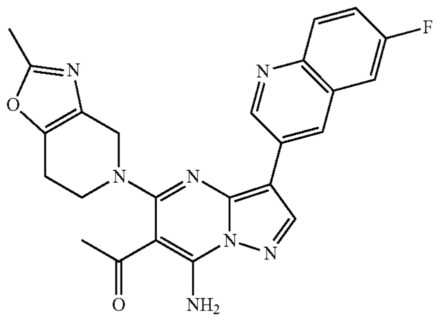 [SMILES: CC(=O)c1c(N2CCc3oc(C)nc3C2)nc2c(-c3cnc4ccc(F)cc4c3)cnn2c1N] | 457.16 | 458.13 | 3.98 |
| 10.99 | 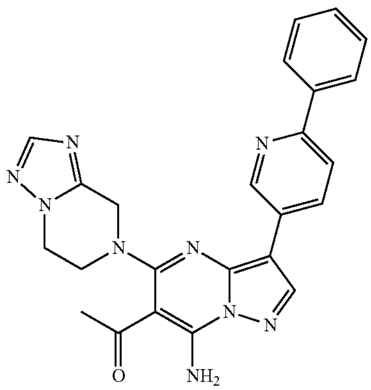 [SMILES: CC(=O)c1c(N2CCn3ncnc3C2)nc2c(-c3ccc(-c4ccccc4)nc3)cnn2c1N] | 451.18 | 452.63 | 3.16 |
Synthesis of 1-(7-amino-3-(1-phenyl-1H-pyrazol-4-yl)-5-thiomorpholin-4'-dioxo-pyrazolo[1,5-a]pyrimidin-6-yl)ethanone
SCHEME-33
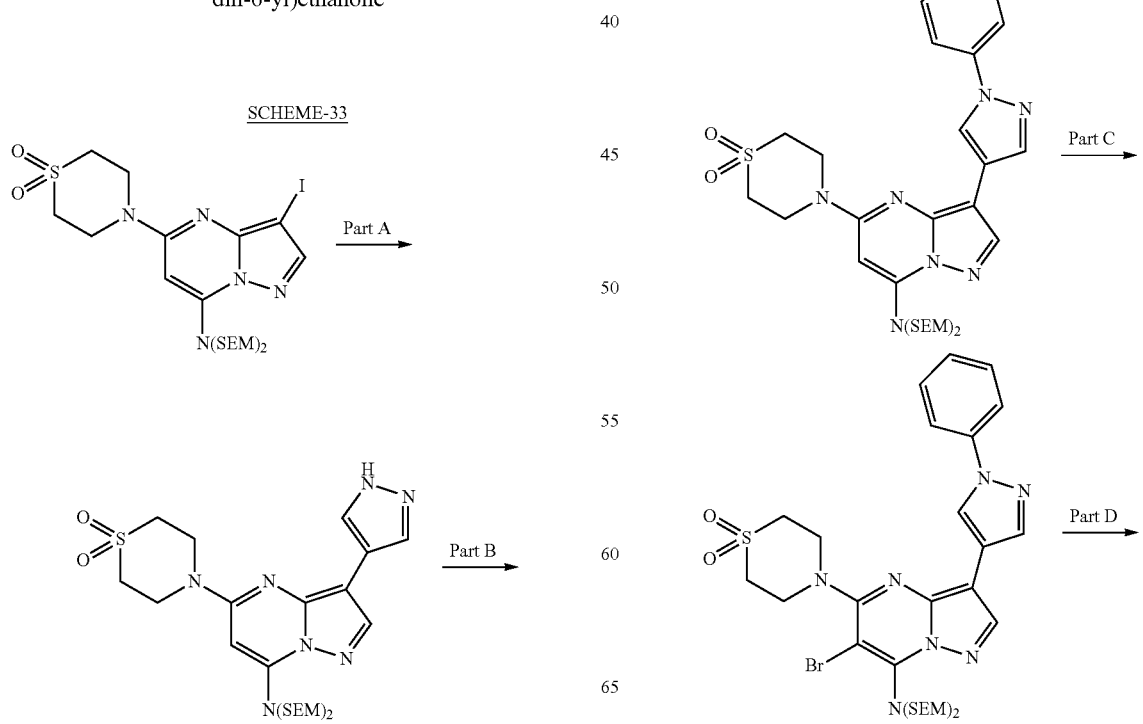
-continued

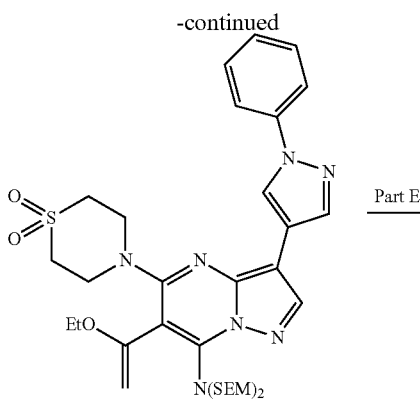

→ Part E

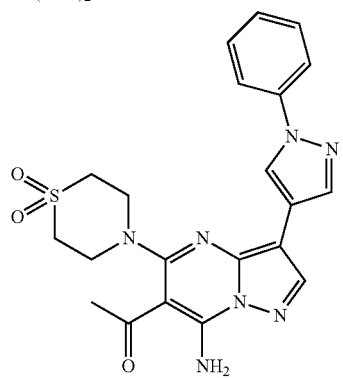

Part A:

3-(1H-pyrazol-4-yl)-5-thiomorpholin-4'-dioxo-N,N-bis((2-(trimethylsilyl)ethoxy)methyl)pyrazolo[1,5-a]pyrimidin-7-amine A mixture of compound, 3-(5-bromopyridin-3-yl)-5-thiomorpholin-4'-dioxo-N,N-bis((2-(trimethylsilyl)ethoxy)methyl)pyrazolo[1,5-a]pyrimidin-7-amine (1.90 mmol, 1.24 g) 1-Boc-pyrazole-4-boronic acid pinacol ester (2.85 mmol, 838 mg), Pd(PPh$_3$)$_4$ (0.19 mmol, 220 mg), and K$_2$CO$_3$ (5.70 mmol, 788 mg) in dioxane/H$_2$O (20/5 mL) was degassed and heated at 80° C. overnight using an oil bath. Then the reaction mixture was heated at 150° C. under microwave radiation for 1 h. After cooling to rt, the reaction mixture was diluted with EtOAc, washed with H$_2$O and brine, dried over Na$_2$SO$_4$, and concentrated. The residue was purified by a SiO$_2$ column (20-100% EtOAc/Hexanes, R$_f$=0.5 in 100% EtOAc/Hexanes) to afford compound, 3-(1H-pyrazol-4-yl)-5-thiomorpholin-4'-dioxo-N,N-bis((2-(trimethylsilyl)ethoxy)methyl)pyrazolo[1,5-a]pyrimidin-7-amine as a brown solid (358 mg, 32%). HPLC-MS T$_R$=2.39 min (UV 254 nm, 5 min method); mass calculated for formula C$_{25}$H$_{43}$N$_7$O$_4$SSi$_2$ 593.3, observed LCMS m/z 594.2 (M+H).

Part B:

3-(1-phenyl-1H-pyrazol-4-yl)-5-thiomorpholin-4'-dioxo-N,N-bis((2-(trimethylsilyl)ethoxy)methyl)pyrazolo[1,5-a]pyrimidin-7-amine A mixture compound, 3-(1H-pyrazol-4-yl)-5-thiomorpholin-4'-dioxo-N,N-bis((2-(trimethylsilyl)ethoxy)methyl)pyrazolo[1,5-a]pyrimidin-7-amine (0.603 mmol, 358 mg), iodobenzene (0.904 mmol, 101 μL), CuI (0.0603 mmol, 11.5 mg), N,N'-dimethyl-ethylenediamine (0.241 mmol, 25.9 μL) and K$_3$PO$_4$ (1.27 mmol, 269 mg) in toluene (6 mL) was stirred at 110° C. under Ar$_2$ for 24 h. After cooling to rt, the crude mixture was diluted with EtOAc and filtered. The filtrate was concentrated and purified by a SiO$_2$ column (0-50% EtOAc/Hexanes, R$_f$=0.7 in 50% EtOAc/Hexanes) to afford the compound, 3-(1-phenyl-1H-pyrazol-4-yl)-5-thiomorpholin-4'-dioxo-N,N-bis((2-(trimethylsilyl)ethoxy)methyl)pyrazolo[1,5-a]pyrimidin-7-amine, as a pale yellow solid (365 mg, 90%). HPLC-MS T$_R$=2.77 min (UV 254 nm, 5 min method); mass calculated for formula C$_{31}$H$_{47}$N$_7$O$_4$SSi$_2$ 669.3, observed LCMS m/z 670.3 (M+H).

Part C:

6-bromo-3-(1-phenyl-1H-pyrazol-4-yl)-5-thiomorpholin-4'-dioxo-N,N-bis((2-(trimethylsilyl)ethoxy)methyl)pyrazolo[1,5-a]pyrimidin-7-amine To a solution of compound 3-(1-phenyl-1H-pyrazol-4-yl)-5-thiomorpholin-4'-dioxo-N,N-bis((2-(trimethylsilyl)ethoxy)methyl)pyrazolo[1,5-a]pyrimidin-7-amine (0.545 mmol, 365 mg) in CH$_3$CN/DCM (3/3 mL) was added NBS (0.545 mmol, 97 mg) and stirred at rt for 1 h. All the volatiles were removed under reduced pressure and the residue was purified by a SiO2 column (0-50% EtOAc/Hexanes, R$_f$=0.8 in 50% EtOAc) to afford compound, 6-Bromo-3-(1-phenyl-1H-pyrazol-4-yl)-5-thiomorpholin-4'-dioxo-1-N,N-bis((2-(trimethylsilyl)ethoxy)methyl)pyrazolo[1,5-a]pyrimidin-7-amine, as a yellow forming solid (224 mg, 55%). HPLC-MS T$_R$=3.01 min (UV 254 nm, 5 min method); mass calculated for formula C$_{31}$H$_{46}$BrN$_7$O$_4$SSi$_2$ 747.2, observed LCMS m/z 748.0 (M+H).

Part D:

6-(1-ethoxyvinyl)-3-(1-phenyl-1H-pyrazol-4-yl)-5-thiomorpholin-4'-dioxo-N,N-bis((2-(trimethylsilyl)ethoxy)methyl)pyrazolo[1,5-a]pyrimidin-7-amine A mixture of compound 6-Bromo-3-(1-phenyl-1H-pyrazol-4-yl)-5-thiomorpholin-4'-dioxo-1-N,N-bis((2-(trimethylsilyl)ethoxy)methyl)pyrazolo[1,5-a]pyrimidin-7-amine (0.299 mmol, 224 mg), tributyl(1-ethoxyvinyl)tin (0.897 mmol, 0.303 mL), Pd(PPh$_3$)$_4$ (0.030 mmol, 34.6 mg) in dioxane (5 mL) was stirred at 100° C. under Ar$_2$ for 16 h. After cooling to rt, the reaction mixture was passed through a short SiO$_2$/KF (9:1) plug to removed majority of the Sn species, and then purified by a SiO$_2$ column (0-40% EtOAc/Hexanes, R$_f$=0.7 in 50% EtOAc) to afford compound, 6-(1-ethoxyvinyl)-3-(1-phenyl-1H-pyrazol-4-yl)-5-thiomorpholin-4'-dioxo-N,N-bis((2-(trimethylsilyl)ethoxy)methyl)pyrazolo[1,5-a]pyrimidin-7-amine as a pale yellow oil (185 mg, 84%). HPLC-MS T$_R$=3.06 min (UV 254 nm, 5 min method); mass calculated for formula C$_{35}$H$_{53}$N$_7$O$_5$SSi$_2$ 739.3, observed LCMS m/z 622.2 (M− 117).

Part E:

1-(7-amino-3-(1-phenyl-1H-pyrazol-4-yl)-5-thiomorpholin-4'-dioxo-pyrazolo[1,5-a]pyrimidin-6-yl)ethanone Compound, 6-(1-ethoxyvinyl)-3-(1-phenyl-1H-pyrazol-4-yl)-5-thiomorpholin-4'-dioxo-N,N-bis((2-(trimethylsilyl)ethoxy)methyl)pyrazolo[1,5-a]pyrimidin-7-amine, (0.250 mmol, 185 mg) was treated with a mixture of TFA/H$_2$O (2/2 mL) at rt for 30 min. All the volatiles were removed under reduced pressure. The residue was dissolved in 3.0 mL of DMSO and purified by a reverse phase HPLC (H$_2$O/CH$_3$CN, 0.1% TFA). The product fraction was concentrated to dryness and converted to HCl salt by adding 1 N HCl (aq) solution to its slurry in MeOH, and then concentrated to dryness. Compound, 1-(7-amino-3-(1-phenyl-1H-pyrazol-4-yl)-5-thiomorpholin-4'-dioxo-pyrazolo[1,5-a]pyrimidin-6-yl)ethanone (HCl salt) was obtained as a pale yellow solid (16.4 mg, 38%). HPLC-MS $T_R$=1.86 min (UV 254 nm, 5 min method); mass calculated for formula $C_{21}H_{21}N_7O_3S$ 451.1, observed LCMS m/z 452.0 (M+H).

By essentially the same procedures given in Preparative Example above (Scheme-33), compounds given in Table-10E can be prepared.

TABLE-10E

| Compound | Structure | Exact Mass | MS m/z (M + H) | HPLC-MS $T_R$ (Method) |
|---|---|---|---|---|
| 10.100 | 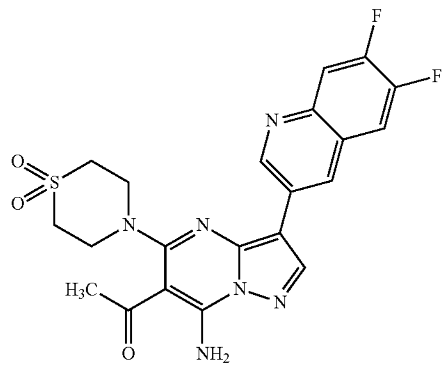 [SMILES: CC(=O)c1c(N2CCS(=O)(=O)CC2)nc2c(-c3cnc4cc(F)c(F)cc4c3)cnn2c1N] | 472.1 | 473 | 4.01 (10 min) |
| 10.101 | 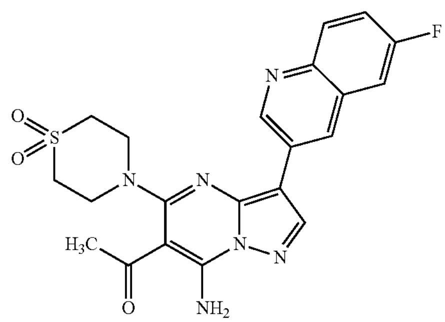 [SMILES: CC(=O)c1c(N2CCS(=O)(=O)CC2)nc2c(-c3cnc4ccc(F)cc4c3)cnn2c1N] | 454.1 | 455 | 3.35 (10 min) |
| 10.102 | 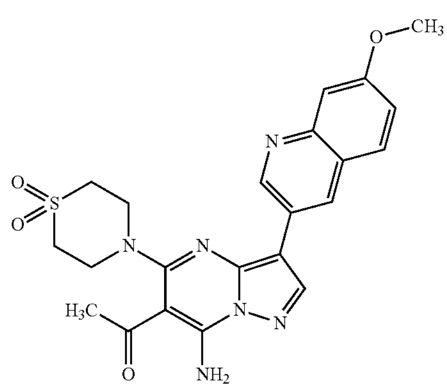 [SMILES: COc1ccc2cc(-c3cnn4c(N)c(C(C)=O)c(N5CCS(=O)(=O)CC5)nc34)cnc2c1] | 466.1 | 467 | 3.03 (10 min) |

TABLE-10E-continued

| Compound | Structure | Exact Mass | MS m/z (M + H) | HPLC-MS T_R (Method) |
|---|---|---|---|---|
| 10.103 | 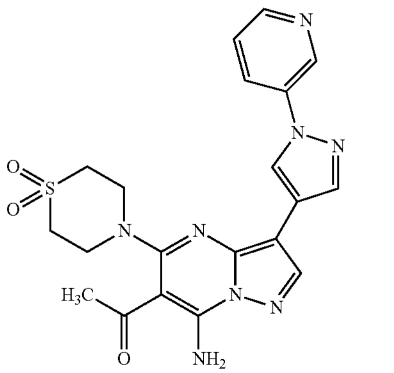 | 452.1 | 453 | 2.94 (10 min) |
| 10.104 | 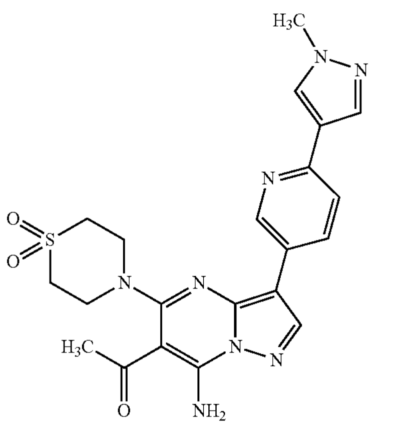 [SMILES: CC(=O)c1c(N2CCS(=O)(=O)CC2)nc2c(-c3ccc(-c4cnn(C)c4)nc3)cnn2c1N] | 466.2 | 467.2 | 1.13 (5 min) |
| 10.105 | 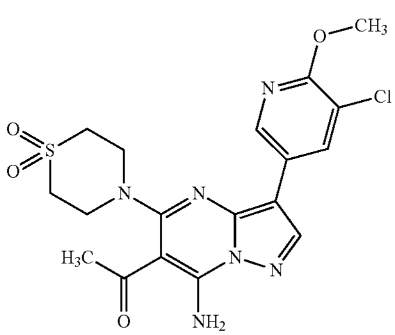 [SMILES: COc1ncc(-c2cnn3c(N)c(C(C)=O)c(N4CCS(=O)(=O)CC4)nc23)cc1Cl] | 450.1 | 451 | 4.46 (10 min) |
| 10.106 | 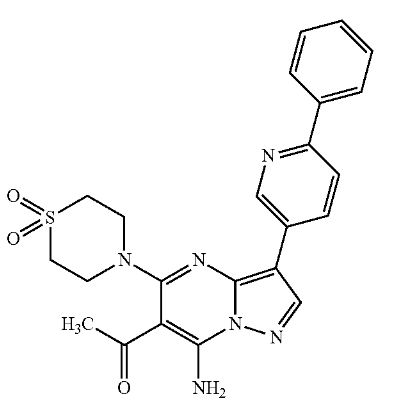 [SMILES: CC(=O)c1c(N2CCS(=O)(=O)CC2)nc2c(-c3ccc(-c4ccccc4)nc3)cnn2c1N] | 462.2 | 463 | 3.24 (10 min) |

TABLE-10E-continued
| Compound | Structure | Exact Mass | MS m/z (M + H) | HPLC-MS $T_R$ (Method) |
|---|---|---|---|---|
| 10.107 | 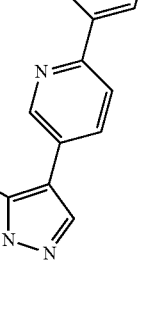 | 463.1 | 464 | 2.68 (10 min) |
| 10.108 | 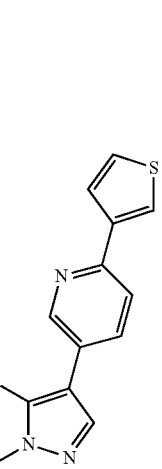 | 468.1 | 469 | 3.09 (10 min) |
| 10.109 | 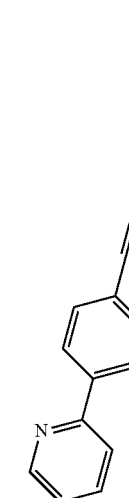 | 487.1 | 488.2 | 1.68 (5 min) |

TABLE-10E-continued

| Compound | Structure | Exact Mass | MS m/z (M + H) | HPLC-MS T$_R$ (Method) |
|---|---|---|---|---|
| 10.110 | 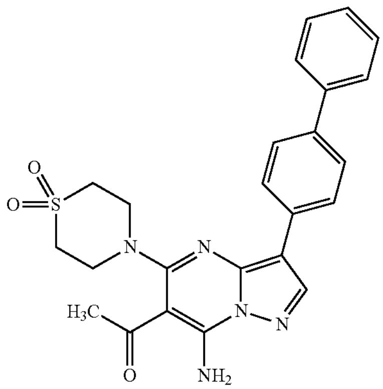 [SMILES: CC(=O)c1c(N2CCS(=O)(=O)CC2)nc2c(-c3ccc(-c4ccccc4)cc3)cnn2c1N] | 461.2 | 462.1 | 2.23 (5 min) |
| 10.111 | 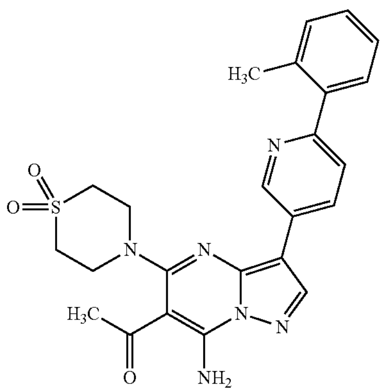 [SMILES: CC(=O)c1c(N2CCS(=O)(=O)CC2)nc2c(-c3ccc(-c4ccccc4C)nc3)cnn2c1N] | 476.2 | 477.1 | 1.53 (5 min) |
| 10.112 | 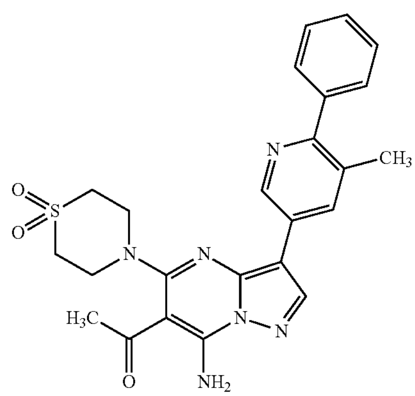 [SMILES: CC(=O)c1c(N2CCS(=O)(=O)CC2)nc2c(-c3cnc(-c4ccccc4)c(C)c3)cnn2c1N] | 476.2 | 477.1 | 1.37 (5 min) |
| 10.113 | 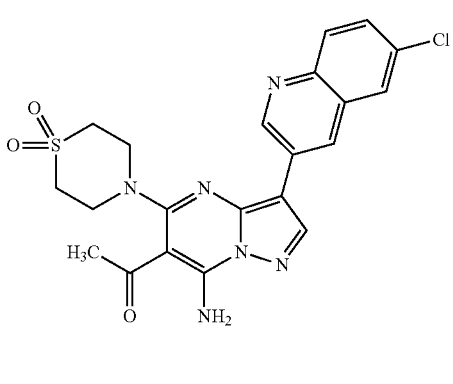 [SMILES: CC(=O)c1c(N2CCS(=O)(=O)CC2)nc2c(-c3cnc4ccc(Cl)cc4c3)cnn2c1N] | 470.1 | 471.0 | 1.85 (5 min) |

TABLE-10E-continued
| Compound | Structure | Exact Mass | MS m/z (M + H) | HPLC-MS T$_R$ (Method) |
|---|---|---|---|---|
| 10.114 | 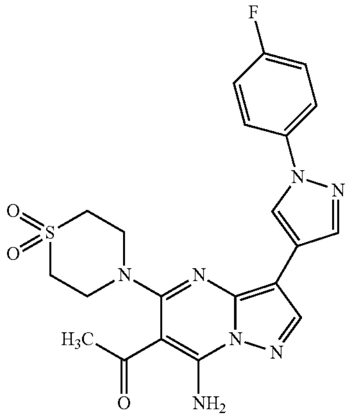 [SMILES: CC(=O)c1c(N2CCS(=O)(=O)CC2)nc2c(-c3cnn(-c4ccc(F)cc4)c3)cnn2c1N] | 469.1 | 470.0 | 1.86 (5 min) |
| 10.115 | 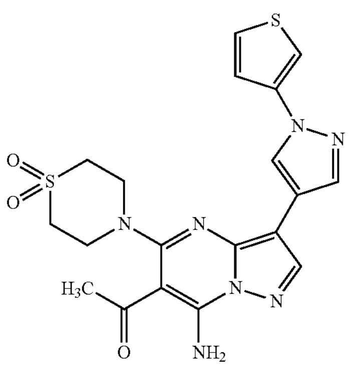 [SMILES: CC(=O)c1c(N2CCS(=O)(=O)CC2)nc2c(-c3cnn(-c4ccsc4)c3)cnn2c1N] | 457.1 | 458.0 | 1.75 (5 min) |
Synthesis of 1-(7-amino-3-(quinolin-3-yl)-5-thio-morpholino-1',1'-dioxide-pyrazolo[1,5-a]pyrimidin-6-yl)propan-1-one
-continued
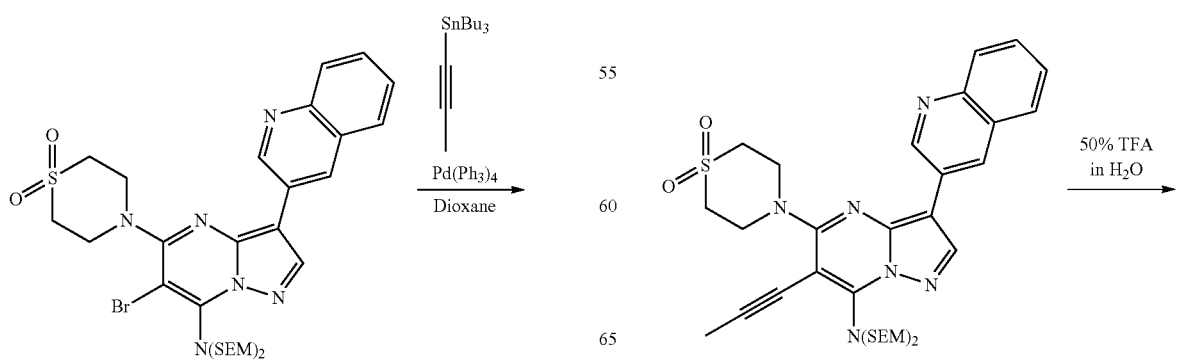

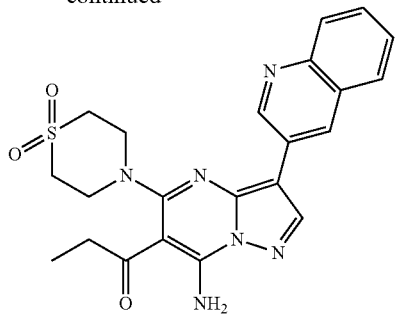

A degassed mixture of 6-bromo-3-(quinolin-3-yl)-5-thiomorpholino-1',1'-dioxide-N,N-bis((2-(trimethylsilyl)ethoxy)methyl)pyrazolo[1,5-a]pyrimidin-7-amine (16 mg, 0.022 mmoL), tributyl(prop-1-ynyl)stannane (22 mg, 0.067 mmoL), Pd(PPh$_3$)$_4$ (2.6 mg, 0.002 mmoL) in Dioxane (3 mL) was heated at 100° C. overnight. The mixture was cooled to room temperature and filtered through short plug of 10% KF/SiO$_2$. The crude Stille coupling product obtained after concentrating the filtrate was then treated with 1:1 mixture of TFA and H$_2$O at room temperature for 30 min. Concentration and purification by prep-LC afforded 1-(7-amino-3-(quinolin-3-yl)-5-thiomorpholino-1',1'-dioxide-pyrazolo[1,5-a]pyrimidin-6-yl)propan-1-one. LCMS t$_R$=3.20 Min (10 min run, UV$_{254nm}$). Mass calculated for, M+ 450.1, observed LC/MS m/z 451.1 (M+H).

7-(7-amino-6-propionyl-3-(quinolin-3-yl)pyrazolo[1,5-a]pyrimidin-5-yl)tetrahydroimidazo[1,5-a]pyrazine-1,3(2H,5H)-dione

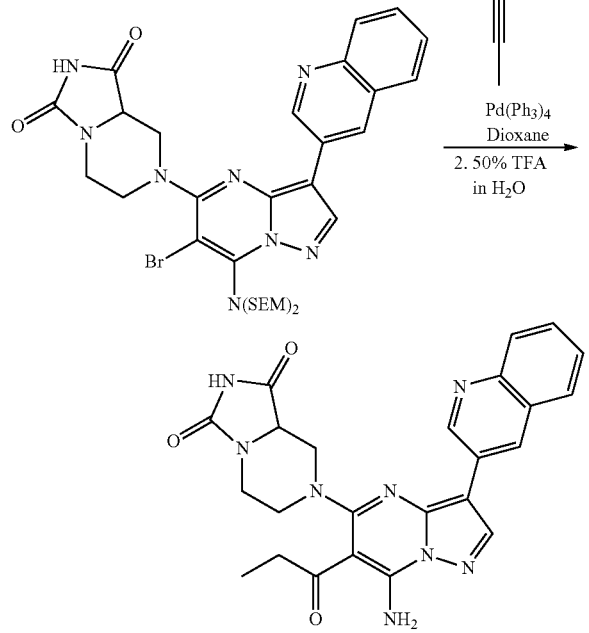

By essentially the same procedure given in Preparative Example above, 7-(7-amino-6-propionyl-3-(quinolin-3-yl)pyrazolo[1,5-a]pyrimidin-5-yl)tetrahydroimidazo[1,5-a]pyrazine-1,3(2H,5H)-dione can be prepared from 7-(7-(bis((2-(trimethylsilyl)ethoxy)methyl)amino)-6-bromo-3-(quinolin-3-yl)pyrazolo[1,5-a]pyrimidin-5-yl)tetrahydroimidazo[1,5-a]pyrazine-1,3(2H,5H)-dione. LCMS t$_R$=3.14 Min (10 min run, UV$_{254nm}$). Mass calculated for, M+ 470.18, observed LC/MS m/z 471.28 (M+H).

Synthesis of 1-(7-amino-3-(quinolin-3-yl)-5-thiomorpholino-1',1'-dioxide-pyrazolo[1,5-a]pyrimidin-6-yl)-2-phenylethanone

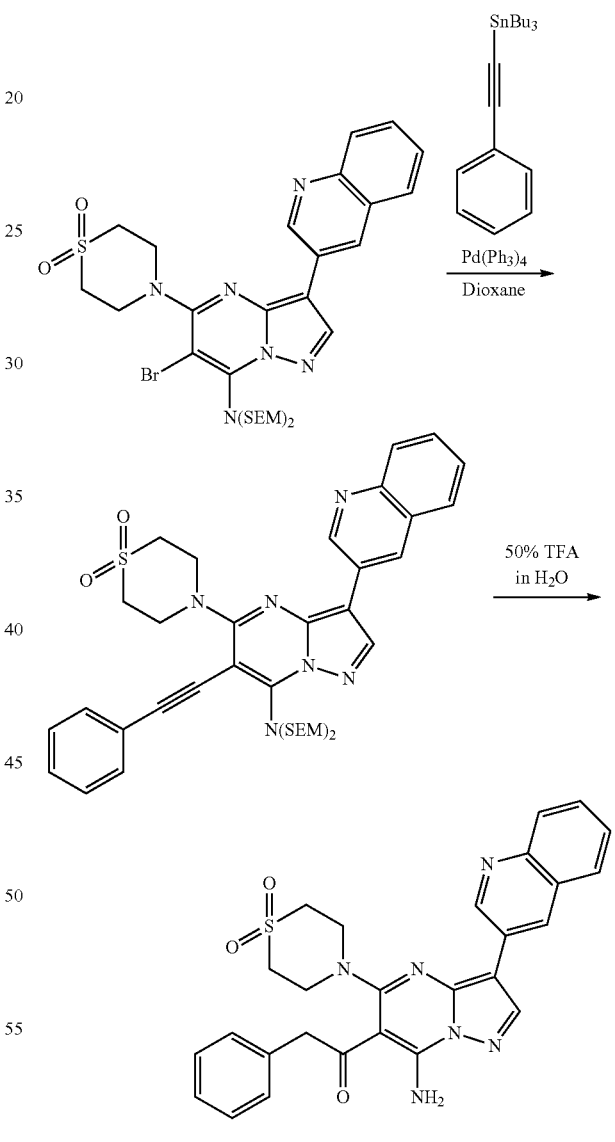

By essentially the same procedure given in Preparative Example above, 1-(7-amino-3-(quinolin-3-yl)-5-thiomorpholino-1',1'-dioxide-pyrazolo[1,5-a]pyrimidin-6-yl)-2-phenylethanone can be prepared using tributyl(phenylethynyl)stannane instead of tributyl(prop-1-ynyl)stannane. LCMS t$_R$=3.74 Min (10 min run, UV$_{254nm}$). Mass calculated for, M+ 512.16, observed LC/MS m/z 513.18 (M+H).

1271

Synthesis of 1-(7-amino-5-(3-methylthiomorpholin-4'dioxo)-3-(1-phenyl-1H-pyrazol-4-yl)pyrazolo[1,5-a]pyrimidin-6-yl)ethanone

SCHEME-34

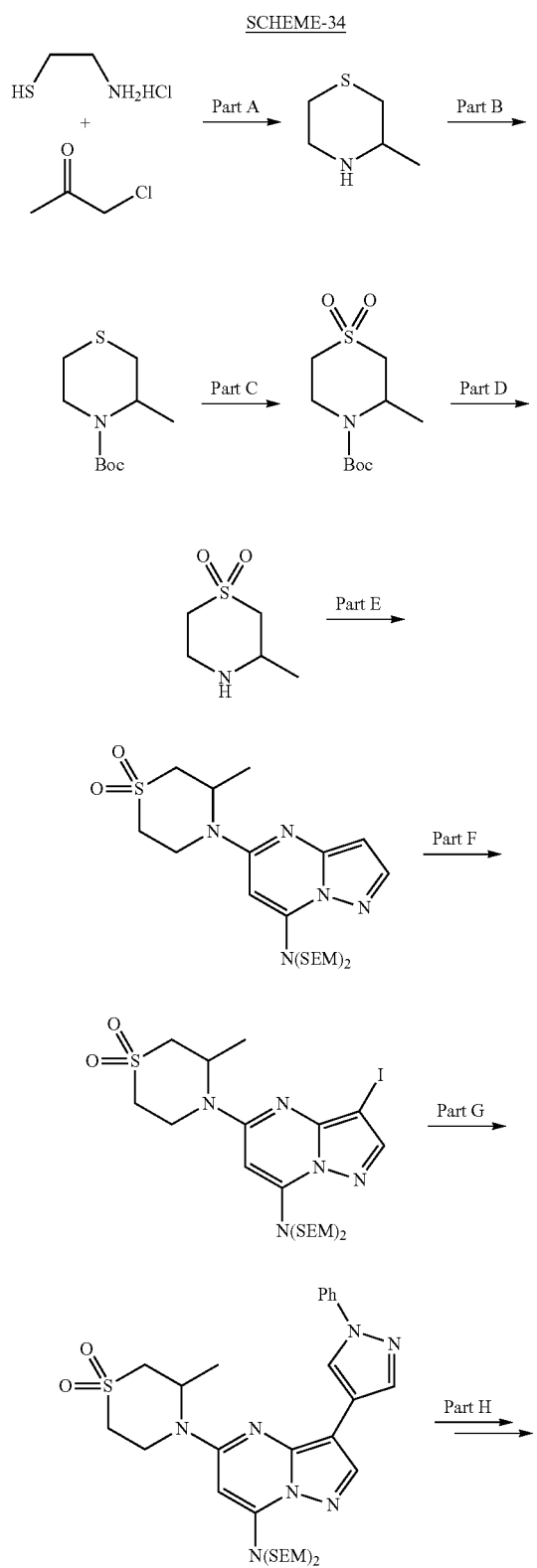

-continued

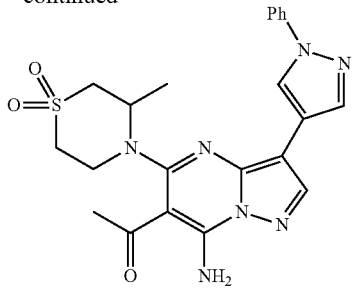

Part A:

Synthesis of 3-methylthiomorpholine

To a solution of KOH (331 mmol, 21.9 g, 85%) in 250 mL of MeOH was added cystamine hydrochloride (158 mmol, 17.9 g), in small portions, followed by a solution of chloroacetone (158 mmol, 12.6 mL) in 100 mL of MeOH at 0-5° C. After being stirred for 90 min at 0° C.; the reaction was acidified with 350 mL of 1.25 M HCl in MeOH at 0-5° C. and stirred for 1 h. NaBH$_4$ was then added in small portions at below 5° C. and the mixture was stirred for 30 min. The reaction was quenched with 1 N HCl (aq) and filtered. The filtrate was concentrated and then dissolved in H$_2$O and extracted with DCM (*8). The organic layers were discarded and the aqueous phase was carefully neutralized with NaOH first, and then Na$_2$CO$_3$. The aqueous phase was extracted with DCM, dried over Na$_2$SO$_4$ and concentrated to afford compound, 3-methylthiomorpholine (7.69 g, 42%), which slowly turned into a sticky solid and was used without further purification. HPLC-MS T$_R$=0.19 min (UV 254 nm, 5 min method); mass calculated for formula C$_5$H$_{11}$NS 117.1, observed LCMS m/z 118.2 (M+H).

Part B:

Synthesis of tert-butyl 3-methylthiomorpholine-4-carboxylate

To a solution of compound, 3-methylthiomorpholine (65.6 mmol, 7.69 g) and TEA (131 mmol, 18.3 mL) in THF (200 mL) was added (Boc)$_2$O (98.4 mmol, 21.5 g), followed by DMAP (13.1 mmol, 1.60 g). The resulting reaction mixture was stirred at rt overnight. THF was removed and the residue was dissolved in DCM and directly purified by a SiO$_2$ column (0-15% EtOAc/Hexanes, R$_f$=0.55 in 20% EtOAc, KMnO$_4$ staining) to afford compound tert-butyl 3-methylthiomorpholine-4-carboxylate as a white sticky solid (7.31 g, 51%).

Part C:

Synthesis of tert-butyl 3-methylthiomorpholine-4'-dioxo-4-carboxylate

To a solution of compound, tert-butyl 3-methylthiomorpholine-4-carboxylate (33.6 mmol, 7.31 g) in DCM (170 mL) at 0° C. was added mCPBA (101 mmol, 24.0 g) in small portions. The reaction mixture was warmed to rt and stirred for 1 h. DCM was removed and the residue was then partitioned between EtOAc and NaHCO3 (aq). The aqueous layer was extracted with EtOAc (*3). The combined organic layers were washed with brine, dried over Na$_2$SO$_4$, and concentrated. The crude product was purified by a SiO$_2$ column (0-50% EtOAc/Hexanes, R$_f$=0.6 in 50% EtOAc) to afford compound, tert-butyl 3-methylthiomorpholine-4'-dioxo-4-carboxylate as a white solid (6.51 g, 78%).

Part D:

Synthesis of 3-methylthiomorpholine-4'-dioxide

Compound tert-butyl 3-methylthiomorpholine-4'-dioxo-4-carboxylate (20.1 mmol, 5.00 g) was treated with TFA/DCM (25/25 mL) at rt for 1 h. The reaction mixture was evaporated to afford compound, 3-methylthiomorpholine-4'-dioxide as a white solid (TFA salt MW: 263.23, 5.18 g, 98%), which was used without further purification. HPLC-MS $T_R$=0.18 min (UV 254 nm, 5 min method); mass calculated for formula $C_5H_{11}NO_2S$ 149.1, observed LCMS m/z 150.1 (M+H).

Part E:

Synthesis of 5-(3-methylthiomorpholin-4'-dioxo)-N,N-bis((2-(trimethylsilyl)ethoxy)methyl)pyrazolo[1,5-a]pyrimidin-7-amine A mixture of compound, 3-methylthiomorpholine-4'-dioxide (1.00 mmol, 263 mg), 5-chloro-N,N-bis[(2-trimethylsilylethoxy)methyl]-pyrazolo[1,5-a]pyrimidin-7-amine (0.667 mmol, 286 mg, preparation was reported previously), Pd(OAc)$_2$ and Cs$_2$CO$_3$ in dioxane (3 mL) was heated at 110° C. for 24 h. The reaction mixture was diluted with EtOAc and washed with H$_2$O and brine, dried over Na$_2$SO$_4$, and concentrated. The crude product was purified by a SiO$_2$ column (0-40% EtOAc/Hexanes, R$_f$=0.5 in 50% EtOAc) to afford compound, 5-(3-methylthiomorpholin-4'-dioxo)-N,N-bis((2-(trimethylsilyl)ethoxy)methyl)pyrazolo[1,5-a]pyrimidin-7-amine, as a colorless oil (145 mg, 40%). HPLC-MS $T_R$=2.75 min (UV 254 nm, 5 min method); mass calculated for formula $C_{23}H_{43}N_5O_4SSi_2$ 541.3, observed LCMS m/z 542.2 (M+H).

Part F:

Synthesis of 3-iodo-5-(3-methylthiomorpholin-4'-dioxo)-N,N-bis((2-(trimethylsilyl)ethoxy)methyl)pyrazolo[1,5-a]pyrimidin-7-amine To a solution of compound, 5-(3-methylthiomorpholin-4'-dioxo)-N,N-bis((2-(trimethylsilyl)ethoxy)methyl)pyrazolo[1,5-a]pyrimidin-7-amine (0.268 mmol, 145 mg) in CH$_3$CN (5 mL) was added NIS (0.294 mmol, 66.2 mg). The resulting solution was stirred at rt for 30 min. The reaction mixture was evaporated and directly purified by a SiO$_2$ column (0-1.5% EtOAc/Hexanes, R$_f$=0.55 in 20% EtOAc) to afford compound, 3-iodo-5-(3-methylthiomorpholin-4'-dioxo)-N,N-bis((2-(trimethylsilyl)ethoxy)methyl)pyrazolo[1,5-a]pyrimidin-7-amine, as a pale yellow oil (161 mg, 90.0%). HPLC-MS $T_R$=7.29 min (UV 254 nm, 10 min method); mass calculated for formula $C_{23}H_{42}IN_5O_4SSi_2$ 667.2, observed LCMS m/z 668.0 (M+H).

Part G:

Synthesis of 5-(3-methylthiomorpholin-4'dioxo)-3-(1-phenyl-1H-pyrazol-4-yl)-N,N-bis((2-(trimethylsilyl)ethoxy)methyl)pyrazolo[1,5-a]pyrimidin-7-amine A mixture of compound, 3-iodo-5-(3-methylthiomorpholin-4'-dioxo)-N,N-bis((2-(trimethylsilyl)ethoxy)methyl)pyrazolo[1,5-a]pyrimidin-7-amine (0.428 mmol, 286 mg), 1-phenyl-4-(4,4,5,5-tetramethyl-1,3,2-dioxaborolan-2-yl)-1H-pyrazole (0.557 mmol, 150 mg), PdCl$_2$(dppf)CH$_2$Cl$_2$, and K$_3$PO$_4$ in dioxane/H$_2$O (4/0.4 mL) was degassed and then heated at 100° C. for 16 h. After cooling to r.t., the reaction mixture was diluted with EtOAc and filtered. The filtrate was concentrated and purified by a SiO$_2$ column (0-40% EtOAc/Hexanes, R$_f$=0.6 in 50% EtOAc/Hexanes) to afford compound, 5-(3-methylthiomorpholin-4'-dioxo)-3-(1-phenyl-1H-pyrazol-4-yl)-N,N-bis((2-(trimethylsilyl)ethoxy)methyl)pyrazolo[1,5-a]pyrimidin-7-amine, as a pale yellow oil (142 mg, 48%). HPLC-MS $T_R$=2.92 min (UV 254 nm, 5 min method); mass calculated for formula $C_{32}H_{49}N_7O_4SSi_2$ 683.3, observed LCMS m/z 684.2 (M+H).

Part H:

1-(7-amino-5-(3-methylthiomorpholin-4'dioxo)-3-(1-phenyl-1H-pyrazol-4-yl)pyrazolo[1,5-a]pyrimidin-6-yl)ethanone compound, 5-(3-methylthiomorpholin-4'-dioxo)-3-(1-phenyl-1H-pyrazol-4-yl)-N,N-bis((2-(trimethylsilyl)ethoxy)methyl)pyrazolo[1,5-a]pyrimidin-7-amine, bromination with NBS, followed by on stifle reaction with Vinyl triflate and treatment with 4N HCl in dioxane as described in the above example (scheme-???) resulted in a compound, 5-(3-methylthiomorpholin-4'-dioxo)-3-(1-phenyl-1H-pyrazol-4-yl)pyrazolo[1,5-a]pyrimidin-7-amine as HCl salt. Evaporation of dioxane and lyophilization of the product resulted in 5-(3-methylthiomorpholin-4'-dioxo)-3-(1-phenyl-1H-pyrazol-4-yl)pyrazolo[1,5-a]pyrimidin-7-amine as white powder. HPLC-MS $T_R$=4.93 min (UV 254 nm, 10 min method); mass calculated for formula $C_{32}H_{49}N_7O_4S$ 465.16, observed LCMS m/z 466.10 (M+H).

Synthesis of 6-bromo-3-(6-phenylpyridin-3-yl)-5-(tetrahydro-2H-thiopyran-4-yl-1',1'-dioxide)-methyl)pyrazolo[1,5-a]pyrimidin-7-amine

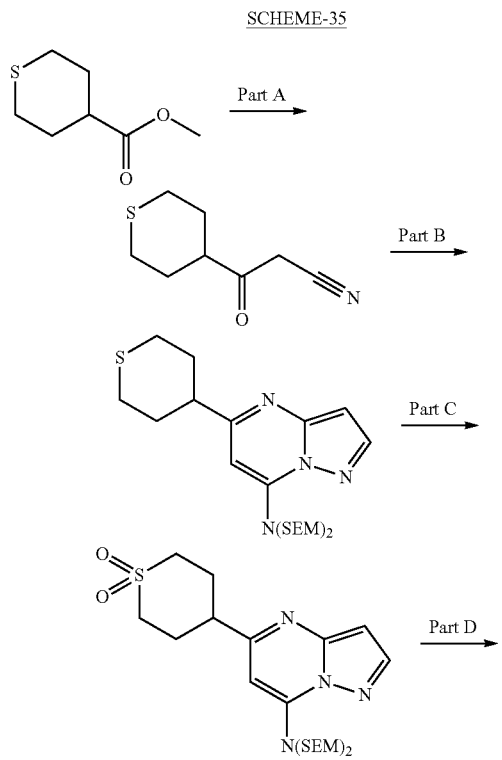

SCHEME-35

-continued

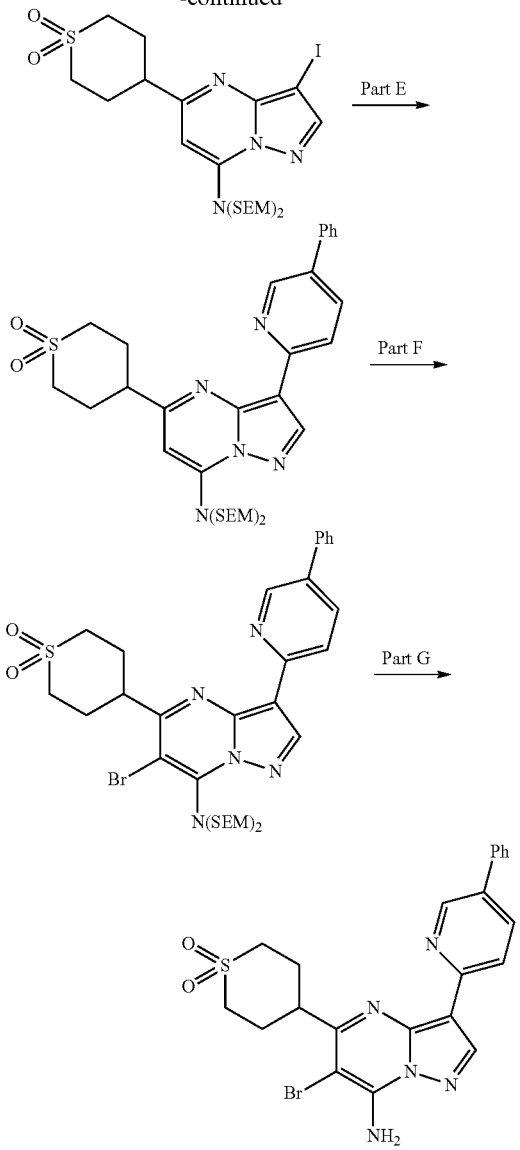

Part A:

3-oxo-3-(tetrahydro-2H-thiopyran-4-yl)propanenitrile

A solution of $CH_3CN$ (48.7 mmol, 2.54 mL) in 10 mL of THF was added dropwise to a solution of "BuLi (48.7 mmol) in 15 mL of THF at −78° C. After stirring for 1 h at −78° C., a solution of methyl tetrahydro-2H-thiopyran-4-carboxylate (24.3 mmol, 3.90 g) in 10 mL of THF was added dropwise and the resulting reaction mixture was stirred at −78° C. for 1 h, then slowly warmed to −40° C. in 2 h. The reaction was quench with 1 N HCl (pH<1). THF was removed and the residue was extracted with EtOAC, washed with brine, dried over $Na_2SO_4$, and concentrated. The crude product was purified by a $SiO_2$ column (0-50% EtOAc/Hexanes, $R_f$=0.45 in 50% EtOAc) to afford compound 3-oxo-3-(tetrahydro-2H-thiopyran-4-yl)propanenitrile (3.60 g, 87.5%) as a light brownish oil. HPLC-MS $T_R$=1.15 min (UV 254 nm, 5 min method); mass calculated for formula $C_8H_{11}NOS$ 169.1 observed LCMS m/z 170.1 (M+H).

Part B:

5-(tetrahydro-2H-thiopyran-4-yl)-N,N-bis((2-(trimethylsilyl)ethoxy)methyl)pyrazolo[1,5-a]pyrimidin-7-amine A mixture of 3-aminopyrazole (19.3 mmol, 1.61 g) and compound 3-oxo-3-(tetrahydro-2H-thiopyran-4-yl)propanenitrile (21.3 mmol, 3.60 g) in acetic acid (40 mL) was heated at 100° C. in a sealed tube overnight. After cooling to rt, all the volatiles were removed under reduced pressure to afford a light brownish oil. This brownish oil was dissolve in DCM (60 mL), and then SEMCl (67.6 mmol, 11.9 mL) and DIPEA (135 mmol, 23.5 mL) were added. The resulting reaction mixture was stirred at 45° C. for 1 h. After cooling to rt, all the volatiles were removed under reduced pressure. The residue was diluted with EtOAc (300 mL), filtered and washed with EtOAc. The filtrate was concentrated and the crude product was purified by a $SiO_2$ column (0-30%) to afford compound, 5-(tetrahydro-2H-thiopyran-4-yl)-N,N-bis((2-(trimethylsilyl)ethoxy)methyl)pyrazolo[1,5-a]pyrimidin-7-amine as a light brownish oil (9.23 g, 97%). HPLC-MS $T_R$=3.09 min (UV 254 nm, 5 min method); mass calculated for formula $C_{23}H_{42}N_4O_2SSi_2$ 494.3, observed LCMS m/z 495.1 (M+H).

Part C:

5-(tetrahydro-2H-thiopyran-4-yl-1',1'-dioxide)-)-N,N-bis((2-(trimethylsilyl)ethoxy)methyl)pyrazolo[1,5-a]pyrimidin-7-amine To a solution of compound, 5-(tetrahydro-2H-thiopyran-4-yl)-N,N-bis((2-(trimethylsilyl)ethoxy)methyl)pyrazolo[1,5-a]pyrimidin-7-amine (18.7 mmol, 9.23 g) DCM (100 mL) was added mCPBA and stirred at rt for 1 h. The reaction was quenched with $Na_2S_2O_3$ (aq.) and diluted with DCM (100 mL). The separated organic layer was washed with $NaHCO_3$ (2*) and brine, dried over $Na_2SO_4$, and concentrated to afford crude compound, 5-(tetrahydro-2H-thiopyran-4-yl-1',1'-dioxide)-)-N,N-bis((2-(trimethylsilyl)ethoxy)methyl)pyrazolo[1,5-a]pyrimidin-7-amine as a purple oil, which was used without further purification. HPLC-MS $T_R$=2.72 min (UV 254 nm, 5 min method); mass calculated for formula $C_{23}H_{42}N_4O_4SSi_2$ 526.2, observed LCMS m/z 527.2 (M+H).

Part D:

3-iodo-5-(tetrahydro-2H-thiopyran-4-yl-1,1-dioxide)-N,N-bis((2-(trimethylsilyl)ethoxy)methyl)pyrazolo[1,5-a]pyrimidin-7-amine To a solution of all crude compound, 5-(tetrahydro-2H-thiopyran-4-yl-1',1'-dioxide)-)-N,N-bis((2-(trimethylsilyl)ethoxy)methyl)pyrazolo[1,5-a]pyrimidin-7-amine from Part C (18.7 mmol) in $CH_3CN$ (100 mL) was added NIS (20.6 mmol, 4.63 g). The resulting solution was stirred at rt for 30 min. TLC (50% EtOAc/Hexanes) indicated complete conversion to a new spot ($R_f$=0.5, less polar than SM $R_f$=0.3). The reaction was quenched with $Na_2S_2O_3$. $CH_3CN$ was removed under reduced pressure. The residue was dissolved in DCM, washed with $H_2O$ and brine, dried over $Na_2SO_4$, and concentrated. The crude product was purified by a $SiO_2$ column (0-50% EtOAc/Hexanes) to afford compound, 3-iodo-5-(tetrahydro-2H-thiopyran-4-yl-1,1-dioxide)-N,N-bis((2-(trimethylsilyl)ethoxy)methyl)pyrazolo[1,5-a]pyrimidin-7-amine: as a pale yellow oil (6.82 g, 56%).

Part E:

3-(5-phenylpyridin-2-yl)-5-(tetrahydro-2H-thiopyran-4-yl-1,1-dioxide)-N,N-bis((2-(trimethylsilyl)ethoxy)methyl)pyrazolo[1,5-a]pyrimidin-7-amine To a solution of 2-bromo-5-phenylpyridine (0.400 mmol, 93.6 mg) and triisopropyl borate (0.440 mmol, 0.102 mL) in a mixed solvent of toluene/THF (1.6/0.4 mL) was added dropwise "BuLi (0.440 mmol) at −78° C., then kept at −78° C. for 30 min (sticky mixture, stopped stirring after 5 min). The reaction mixture was allowed to warm to rt and stirred for 4 h. All the volatiles were removed under reduced pressure from rt to 90° C. The thus formed crude lithium borate was used without further purification. A mixture of the crude lithium borate (0.400 mmol), compound, 3-iodo-5-(tetrahydro-2H-thiopyran-4-yl-1,1-dioxide)-N,N-bis((2-(trimethylsilyl)ethoxy)methyl)pyrazolo[1,5-a]pyrimidin-7-amine (0.267 mmol, 174 mg), PdCl$_2$(dppf)CH$_2$Cl$_2$ (0.027 mmol, 22.0 mg), and KF (0.800 mmol, 46.5 mg) in dioxane (2 mL) was degassed and then heated at 90° C. for 16 h. The reaction mixture was diluted with EtOAc and filtered. The filtrate was concentrated and purified by a SiO$_2$ column (0-40% EtOAc/Hexanes, R$_f$=0.5 in 50% EtOAc/Hexanes) to afford compound, 3-(5-phenylpyridin-2-yl)-5-(tetrahydro-2H-thiopyran-4-yl-1,1-dioxide)-N,N-bis((2-(trimethylsilyl)ethoxy)methyl)pyrazolo[1,5-a]pyrimidin-7-amine as a pale yellow solid (32 mg, 18%). HPLC-MS T$_R$=2.62 min (UV 254 nm, 5 min method); mass calculated for formula C$_{34}$H$_{49}$N$_5$O$_4$SSi$_2$ 679.3, observed LCMS m/z 680.2 (M+H).

Part-F:

6-bromo-3-(6-phenylpyridin-3-yl)-5-(tetrahydro-2H-thiopyran-4-yl-1',1'-dioxide)-N,N-bis((2-(trimethylsilyl)ethoxy)methyl)pyrazolo[1,5-a]pyrimidin-7-amine NBS (176 mg, 0.99 mmoL) was added to a solution of 3-(6-phenylpyridin-3-yl)-5-(tetrahydro-2H-thiopyran-4-yl-1',1'-dioxide)-N,N-bis((2-(trimethylsilyl)ethoxy)methyl)pyrazolo[1,5-a]pyrimidin-7-amine (679 mg, 0.94 mmoL) in CH$_3$CN (10 mL). The mixture was stirred at room temperature for 1 h. Concentration and purification by column chromatography afforded 6-bromo-3-(6-phenylpyridin-3-yl)-5-(tetrahydro-2H-thiopyran-4-yl-1',1'-dioxide)-N,N-bis((2-(trimethylsilyl)ethoxy)methyl)pyrazolo[1,5-a]pyrimidin-7-amine. LCMS t$_R$=2.87 Min (5 min run, UV$_{254nm}$). Mass calculated for, M+ 757, observed LC/MS m/z 758.2 (M+H).

Part G:

6-bromo-3-(6-phenylpyridin-3-yl)-5-(tetrahydro-2H-thiopyran-4-yl-1',1'-dioxide)-methyl)pyrazolo[1,5-a]pyrimidin-7-amine 6-bromo-3-(6-phenylpyridin-3-yl)-5-(tetrahydro-2H-thiopyran-4-yl-1',1'-dioxide)-N,N-bis((2-(trimethylsilyl)ethoxy)methyl)pyrazolo[1,5-a]pyrimidin-7-amine was treated with 4NHCl in dioxane at room temperature for 1 hr and reaction evaporated to dry ness and lyophilized under vacuo to give product in powder form, 6-bromo-3-(6-phenylpyridin-3-yl)-5-(tetrahydro-2H-thiopyran-4-yl-1',1'-dioxide)-methyl)pyrazolo[1,5-a]pyrimidin-7-amine as HCl salt. LCMS t$_R$=1.27 Min (5 min run, UV$_{254nm}$). Mass calculated for, M+ 497.10, observed LC/MS m/z 498.20 (M+H).

By essentially the same procedure given in Preparative above (Scheme-35), compounds 10.116 to 10.133 given in the table (10-F) can be prepared.

TABLE-10-F

| Compound No. | Structures | M.Wt (calc.) | M + H (observed) | Retention Time, 10 min method (min) |
|---|---|---|---|---|
| 10.116 | 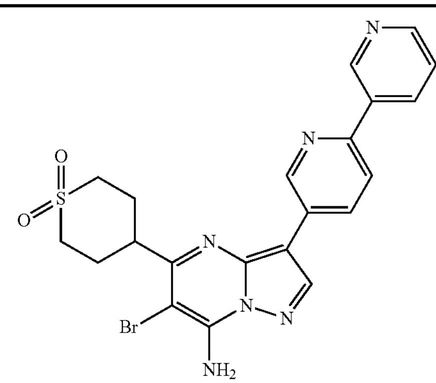 | 498.05 | 499.10 | 1.65 (5 min) |
| 10.117 | 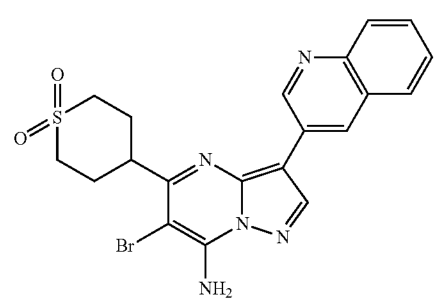 [SMILES: Nc1c(Br)c(C2CCS(=O)(=O)CC2)nc2c(-c3cnc4ccccc4c3)cnn12] | 471.04 | 472.10 | 2.00 (5 min) |

TABLE-10-F-continued

| Compound No. | Structures | M.Wt (calc.) | M + H (observed) | Retention Time, 10 min method (min) |
|---|---|---|---|---|
| 10.118 | 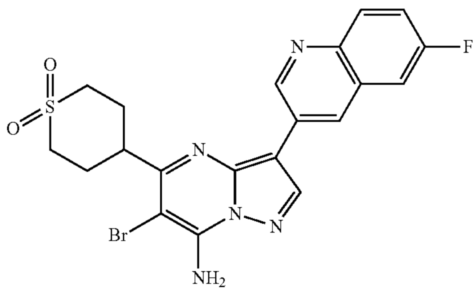 [SMILES: Nc1c(Br)c(C2CCS(=O)(=O)CC2)nc2c(-c3cnc4ccc(F)cc4c3)cnn12] | 489.03 | 491.20 | 2.10 (5 min) |
| 10.119 | 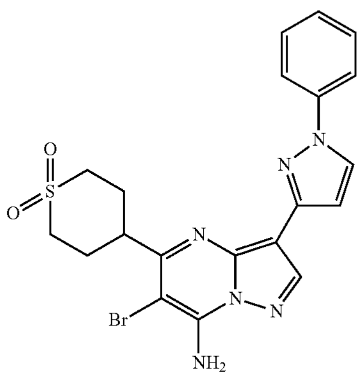 [SMILES: Nc1c(Br)c(C2CCS(=O)(=O)CC2)nc2c(-c3ccn(-c4ccccc4)n3)cnn12] | 486.05 | 487.10 | 1.80 (5 min) |
| 10.120 | 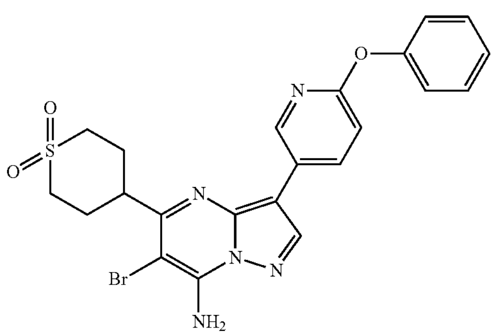 [SMILES: Nc1c(Br)c(C2CCS(=O)(=O)CC2)nc2c(-c3ccc(Oc4ccccc4)nc3)cnn12] | 513.10 | 514.20 | 1.80 (5 min) |
| 10.121 | 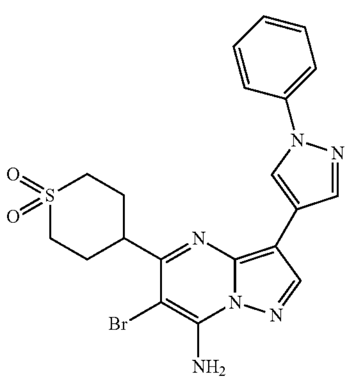 [SMILES: Nc1c(Br)c(C2CCS(=O)(=O)CC2)nc2c(-c3cnn(-c4ccccc4)c3)cnn12] | 486.0 | 487.1 | 1.77 (5 min) |

TABLE-10-F-continued

| Compound No. | Structures | M.Wt (calc.) | M + H (observed) | Retention Time, 10 min method (min) |
|---|---|---|---|---|
| 10.122 | 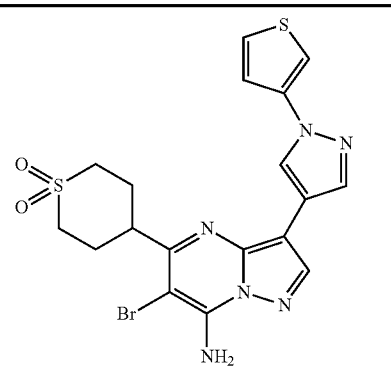 | 492.0 | 493.0 | 1.67 (5 min) |
| 10.123 | 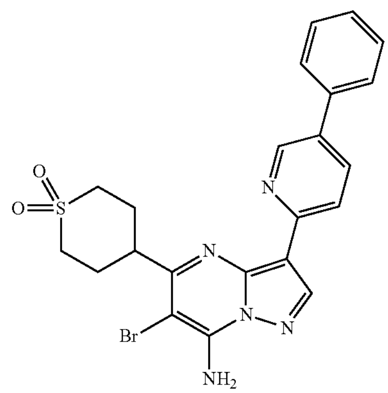 | 497.0 | 498.1 | 1.27 (5 min) |
| 10.124 | 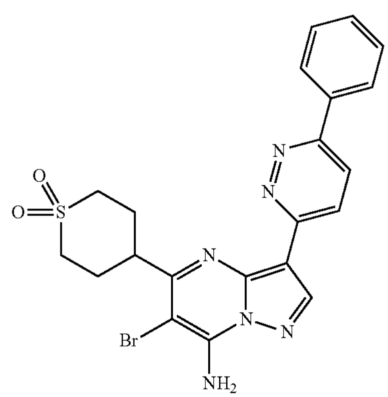 [SMILES: Nc1c(Br)c(C2CCS(=O)(=O)CC2)nc2c(-c3ccc(-c4ccccc4)nn3)cnn12] | 498.0 | 499.0 | 1.70 (5 min) |
| 10.125 | 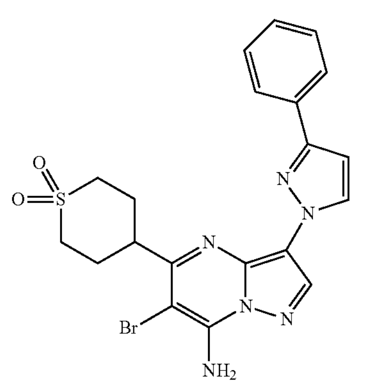 [SMILES: Nc1c(Br)c(C2CCS(=O)(=O)CC2)nc2c(-n3ccc(-c4ccccc4)n3)cnn12] | 486.0 | 487.1 | 1.82 (5 min) |

TABLE-10-F-continued

| Compound No. | Structures | M.Wt (calc.) | M + H (observed) | Retention Time, 10 min method (min) |
|---|---|---|---|---|
| 10.126 | 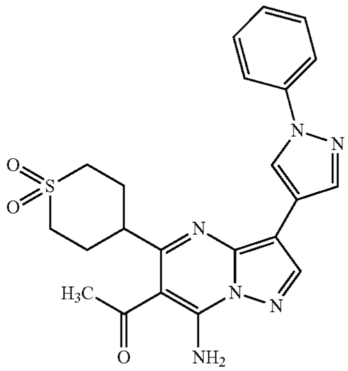 [SMILES: CC(=O)c1c(C2CCS(=O)(=O)CC2)nc2c(-c3cnn(-c4ccccc4)c3)cnn2c1N] | 450.1 | 451.1 | 1.71 (5 min) |
| 10.127 | 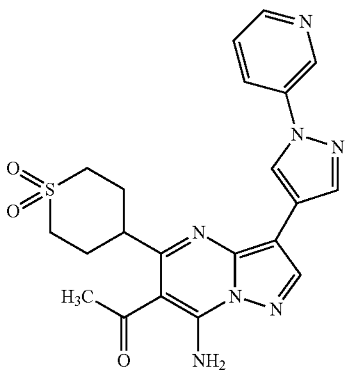 [SMILES: CC(=O)c1c(C2CCS(=O)(=O)CC2)nc2c(-c3cnn(-c4cccnc4)c3)cnn2c1N] | 451.1 | 452.2 | 1.29 (5 min) |
| 10.128 | 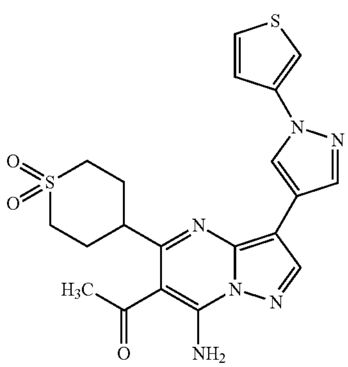 [SMILES: CC(=O)c1c(C2CCS(=O)(=O)CC2)nc2c(-c3cnn(-c4ccsc4)c3)cnn2c1N] | 456.1 | 457.0 | 1.77 (5 min) |
| 10.129 | 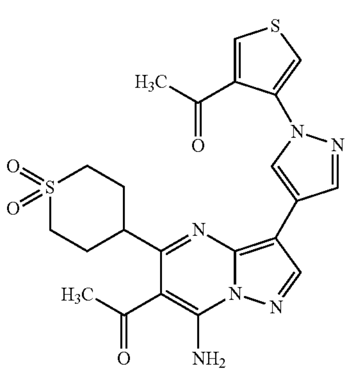 [SMILES: CC(=O)c1cscc1-n1cc(-c2cnn3c(N)c(C(C)=O)c(C4CCS(=O)(=O)CC4)nc23)cn1] | 498.1 | 499.0 | 1.65 (5 min) |

TABLE-10-F-continued

| Compound No. | Structures | M.Wt (calc.) | M + H (observed) | Retention Time, 10 min method (min) |
|---|---|---|---|---|
| 10.130 | 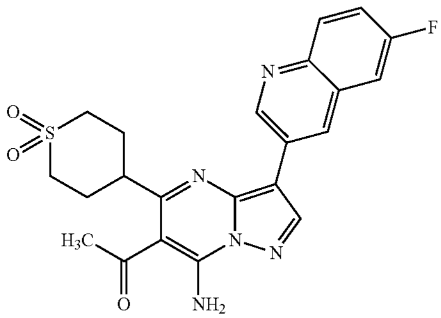 | 453.1 | 454.1 | 1.48 (5 min) |
| 10.131 | 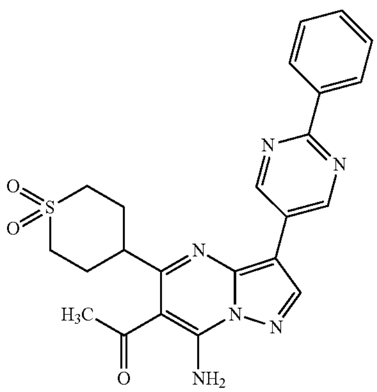 [SMILES: CC(=O)c1c(C2CCS(=O)(=O)CC2)nc2c(-c3cnc(-c4ccccc4)nc3)cnn2c1N] | 462.1 | 463.1 | 1.80 (5 min) |
| 10.132 | 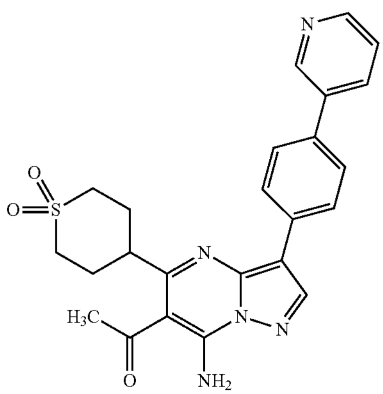 [SMILES: CC(=O)c1c(C2CCS(=O)(=O)CC2)nc2c(-c3ccc(-c4cccnc4)cc3)cnn2c1N] | 461.2 | 462.3 | 1.12 (5 min) |
| 10.133 | 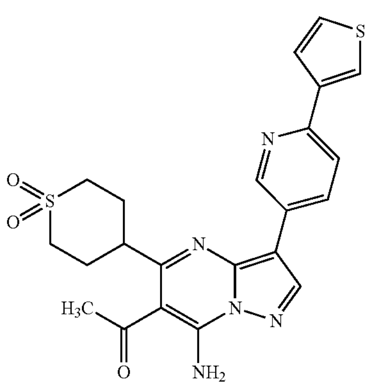 [SMILES: CC(=O)c1c(C2CCS(=O)(=O)CC2)nc2c(-c3ccc(-c4ccsc4)nc3)cnn2c1N] | 467.1 | 468.1 | 1.35 (5 min) |

Synthesis of 3-(6-phenylpyridin-3-yl)-5-(tetrahydro-2H-thiopyran-4-yl-1',1'-dioxide)-N,N-bis((2-(trimethylsilyl)ethoxy)methyl)-6-vinylpyrazolo[1,5-a]pyrimidin-7-amine

SCHEME-36

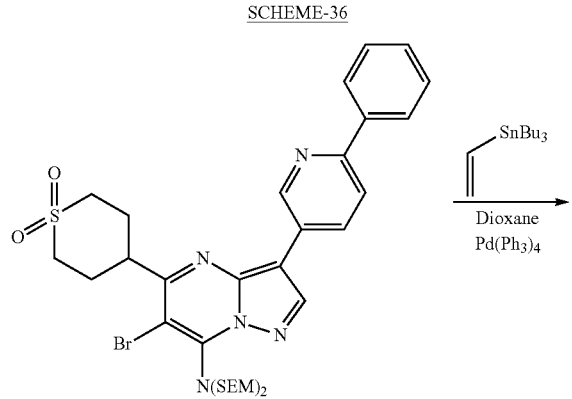

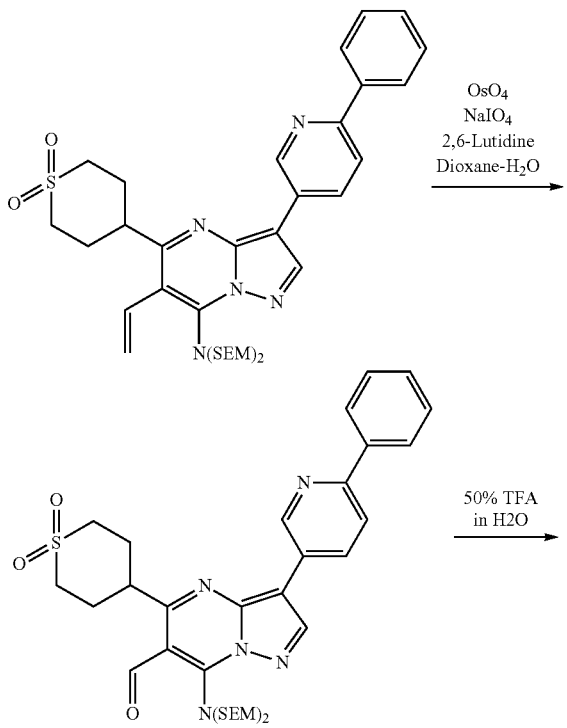

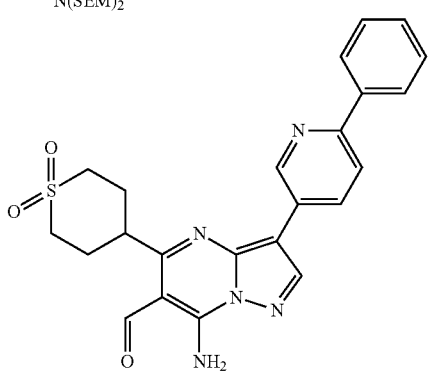

Part A

3-(6-phenylpyridin-3-yl)-5-(tetrahydro-2H-thiopyran-4-yl-1',1'-dioxide)-N,N-bis((2-(trimethylsilyl)ethoxy)methyl)-6-vinylpyrazolo[1,5-a]pyrimidin-7-amine A degassed mixture of 6-bromo-3-(6-phenylpyridin-3-yl)-5-(tetrahydro-2H-thiopyran-4-yl-1',1'-dioxide)-N,N-bis((2-(trimethylsilyl)ethoxy)methyl)pyrazolo[1,5-a]pyrimidin-7-amine (203 mg, 0.27 mmol), Pd(PPh$_3$)$_4$ (31 mg, 0.027 mmoL), tributyl(vinyl)stannane (255 mg, 0.80 mmoL) in CH$_3$CN (6 mL) was heated at 150° C. under microwave condition for 60 min. The reaction mixture was cooled to room temperature, filtered through 9:1 SiO$_2$:KF plug and concentrated in vacuo. Purification by column chromatography afforded 3-(6-phenylpyridin-3-yl)-5-(tetrahydro-2H-thiopyran-4-yl-1',1'-dioxide)-N,N-bis((2-(trimethylsilyl)ethoxy)methyl)-6-vinylpyrazolo[1,5-a]pyrimidin-7-amine: LCMS $t_R$=2.82 mM (5 min run, UV$_{254nm}$). Mass calculated for, M+ 705.3, observed LC/MS m/z 706.3 (M+H).

Part B

7-(bis((2-(trimethylsilyl)ethoxy)methyl)amino)-3-(6-phenylpyridin-3-yl)-5-(tetrahydro-2H-thiopyran-4-yl-1',1'-dioxide)pyrazolo[1,5-a]pyrimidine-6-carbaldehyde To 3-(6-phenylpyridin-3-yl)-5-(tetrahydro-2H-thiopyran-4-yl-1',1'-dioxide)-N,N-bis((2-(trimethylsilyl)ethoxy)methyl)-6-vinylpyrazolo[1,5-a]pyrimidin-7-amine (189 mg, 0.26 mmol) in 1,4-dioxide (3 mL) was added 2.5 wt % OsO$_4$ in 1,4-dioxane (168 uL, 0.013 mmol), 2,6-lutidine (265 uL, 2.68 mmol) and H$_2$O (1 mL) and the resulting mixture was stirred at room temperature for 20 minutes. NaIO$_4$ (287 mg, 1.34 mmol) was then added and stirring at room temperature continued for 4 days. Saturated Na$_2$S$_2$O$_3$ solution (5 mL) was added and the mixture stirred for 10 minutes. Organics were then extracted with CH$_2$Cl$_2$ (2×), dried (Na$_2$SO$_4$) and concentrated in vacuo to 7-(bis((2-(trimethylsilyl)ethoxy)methyl)amino)-3-(6-phenylpyridin-3-yl)-5-(tetrahydro-2H-thiopyran-4-yl-1',1'-dioxide)pyrazolo[1,5-a]pyrimidine-6-carbaldehyde, which was used without further purification: LCMS $t_R$=2.87 Min (5 min run, UV$_{254nm}$). Mass calculated for, M+ 707.2, observed. LC/MS m/z 708.3 (M+H).

Part C

7-amino-3-(6-phenylpyridin-3-yl)-5-(tetrahydro-2H-thiopyran-4-yl-1',1'-dioxide)pyrazolo[1,5-a]pyrimidine-6-carbaldehyde The crude 7-(bis((2-(trimethylsilyl)ethoxy)methyl)amino)-3-(6-phenylpyridin-3-yl)-5-(tetrahydro-2H-thiopyran-4-yl-1',1'-dioxide)pyrazolo[1,5-a]pyrimidine-6-carbaldehyde (150 mg, 0.21 mmoL) was treated with 50% TFA in H$_2$O (4 mL) until the disappearance of starting material in LCMS. Concentration and purification by prep-LC afforded 7-amino-3-(6-phenylpyridin-3-yl)-5-(tetrahydro-2H-thiopyran-4-yl-1',1'-dioxide)pyrazolo[1,5-a]pyrimidine-6-carbaldehyde, LCMS $t_R$=3.10 Min (10 min run, UV$_{254nm}$). Mass calculated for, M+ 447.1, observed LC/MS m/z 448.1 (M+H).

By essentially the same procedure given in Preparative Example (Scheme-36) compounds 10.134-10.137 (Table-10-G) can be prepared.

TABLE-10 G

| Compound ID | Structures | M.Wt (calc.) | M + H (observed) | Retention Time, 10 min method (min) |
|---|---|---|---|---|
| 10.134 | 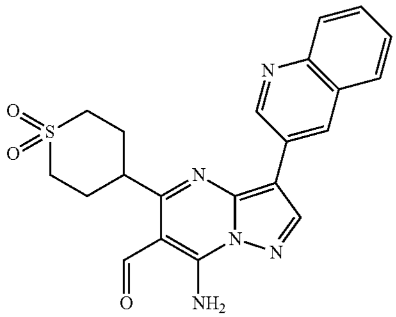 [SMILES: Nc1c(C=O)c(C2CCS(=O)(=O)CC2)nc2c(-c3cnc4ccccc4c3)cnn12] | 421.12 | 422.17 | 2.75 |
| 10.135 | 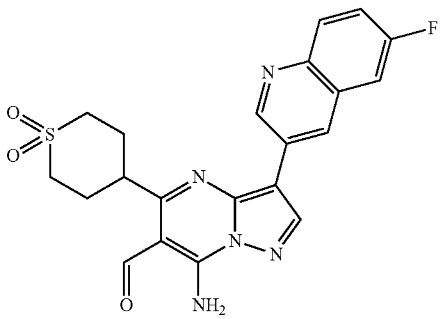 [SMILES: Nc1c(C=O)c(C2CCS(=O)(=O)CC2)nc2c(-c3cnc4ccc(F)cc4c3)cnn12] | 439.11 | 440.0 | 3.14 |
| 10.136 | 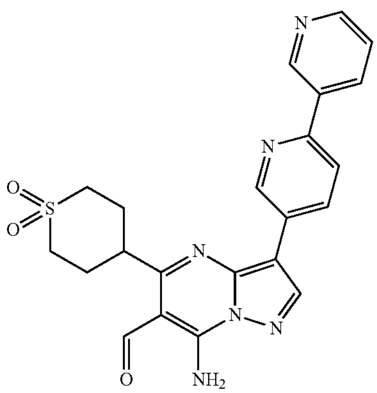 [SMILES: Nc1c(C=O)c(C2CCS(=O)(=O)CC2)nc2c(-c3ccc(-c4cccnc4)nc3)cnn12] | 448.13 | 449.0 | 2.22 |
| 10.137 | 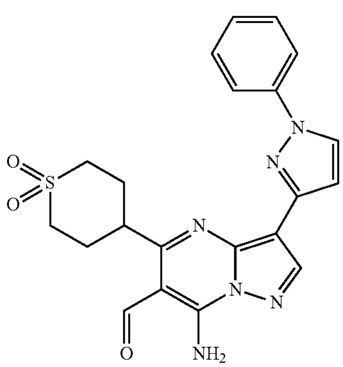 [SMILES: Nc1c(C=O)c(C2CCS(=O)(=O)CC2)nc2c(-c3ccn(-c4ccccc4)n3)cnn12] | 436.13 | 437.0 | 4.28 |

1291

Synthesis of 1-(7-amino-3-(6-phenylpyridin-3-yl)-5-(tetrahydro-2H-thiopyran-4-yl-1',1'-dioxide)pyrazolo[1,5-a]pyrimidin-6-yl)propan-1-one

1292

Synthesis of 1-(7-amino-3-(6-phenylpyridin-3-yl)-5-(tetrahydro-2H-thiopyran-4-yl)-1',1'-dioxide)pyrazolo[1,5-a]pyrimidin-6-yl)ethanone

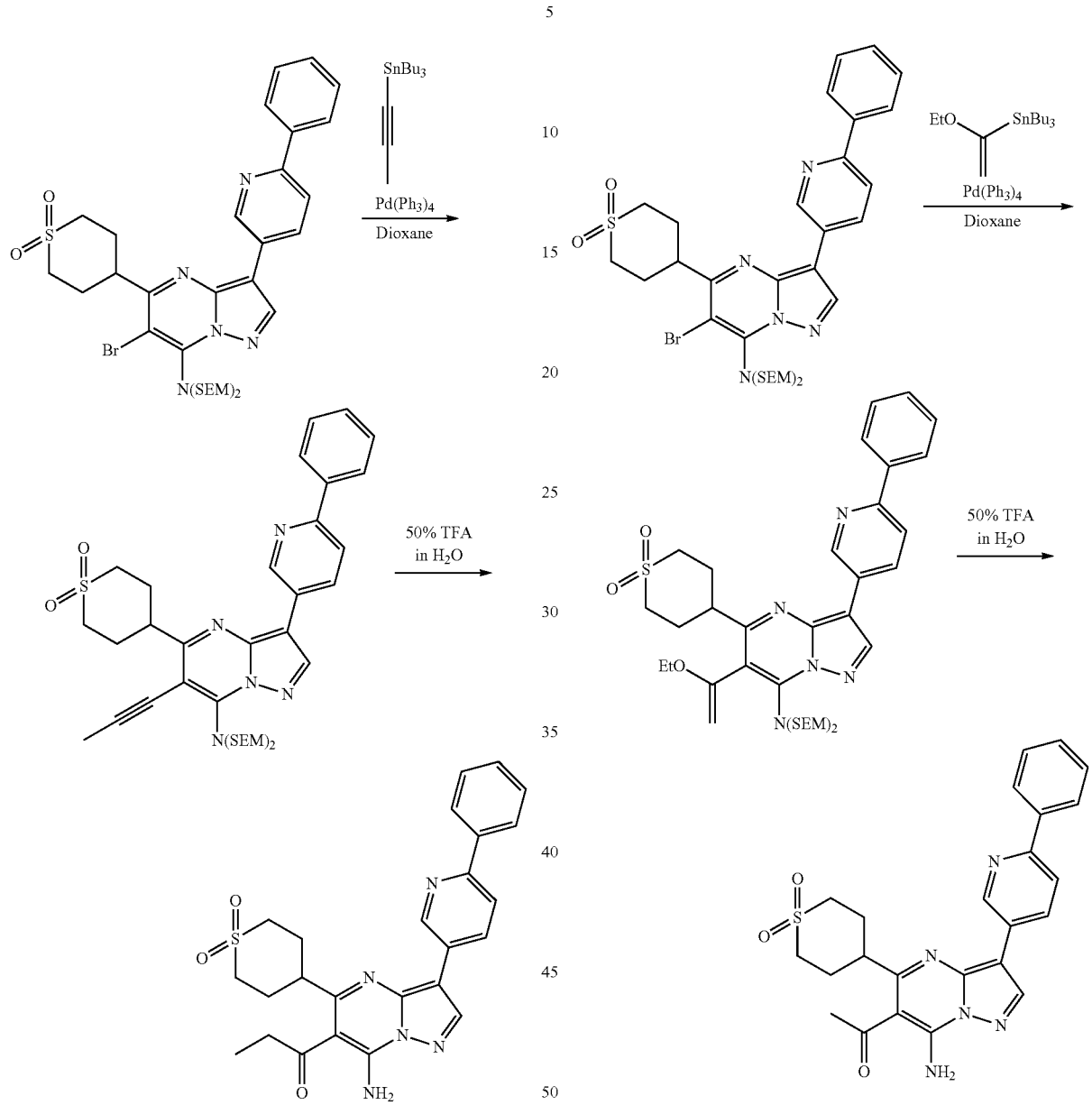

By essentially the same procedure given in Preparative Example above (Scheme-36), 1-(7-amino-3-(6-phenylpyridin-3-yl)-5-(tetrahydro-2H-thiopyran-4-yl-1',1'-dioxide)pyrazolo[1,5-a]pyrimidin-6-yl)propan-1-one can be prepared from 6-bromo-3-(6-phenylpyridin-3-yl)-5-(tetrahydro-2H-thiopyran-4-yl-1',1'-dioxide)-N,N-bis((2-trimethylsilyl)ethoxy)methyl)pyrazolo[1,5-a]pyrimidin-7-amine. LCMS $t_R$=3.13 Min (10 min run, $UV_{254}$ nm). Mass calculated for, 449.15, observed LC/MS m/z 450.40 (M+H).

A degassed mixture of 6-bromo-3-(6-phenylpyridin-3-yl)-5-(tetrahydro-2H-thiopyran-4-yl-1',1'-dioxide)-N,N-bis((2-(trimethylsilyl)ethoxy)methyl)pyrazolo[1,5-a]pyrimidin-7-amine (203 mg, 0.27 mmol), Pd(PPh$_3$)$_4$ (31 mg, 0.027 mmoL), tributyl(vinyl)stannane (255 mg, 0.80 mmoL) in CH$_3$CN (6 mL) was heated at 150° C. under microwave condition for 60 min. The reaction mixture was cooled to room temperature, filtered through 9:1 SiO$_2$:KF plug and concentrated in vacuo. The crude 6-(1-ethoxyvinyl)-3-(6-phenylpyridin-3-yl)-5-(tetrahydro-2H-thiopyran-4-yl-1',1'-dioxide)-N,N-bis((2-(trimethylsilyl)ethoxy)methyl)pyrazolo[1,5-a]pyrimidin-7-amine was treated with 50% TFA in H$_2$O (2 mL) for 1 h. Concentration and purification afforded 1-(7-amino-3-(6-phenylpyridin-3-yl)-5-(tetrahydro-2H-thiopyran-4-yl-1',1'-dioxide)pyrazolo[1,5-a]pyrimidin-6-yl)ethanone: LCMS $t_R$=3.18 Min (10 min run, $UV_{254nm}$). Mass calculated for, M+ 461.1, observed LC/MS m/z 462.1 (M+H).

1293

6-(methylsulfonyl-3-(quinolin-3-yl)-5-thiomorpholino-1',1'-dioxide-pyrazolo[1,5-a]pyrimidin-7-amine

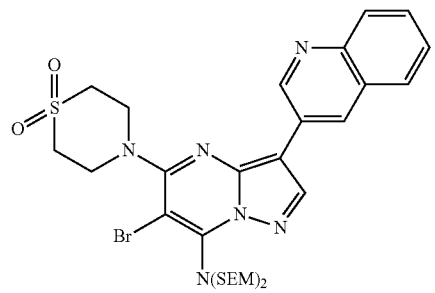

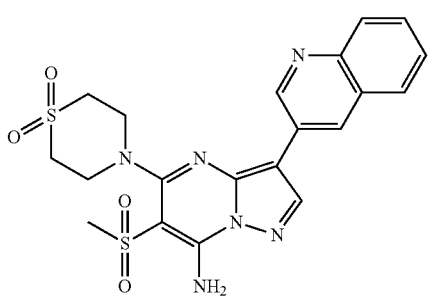

A mixture of 6-bromo-3-(quinolin-3-yl)-5-thiomorpholino-1',1'-dioxide-N,N-bis((2-(trimethylsilyl)ethoxy)methyl)pyrazolo[1,5-a]pyrimidin-7-amine (0.061 mmol, 45 mg), CuI (0.49 mmol, 94 mg) and NaSO₂Me (0.49 mmol, 50 mg) in NMP (2 mL) was heated at 120° C. for 1 h and then 130° C. for 1 h under microwave condition. Purification by prep-LC afforded 6-(methylsulfonyl)-3-(quinolin-3-yl)-5-thiomorpholino-1',1'-dioxide-pyrazolo[1,5-a]pyrimidin-7-amine: LCMS $t_R$=2.94 Min (10 min run, $UV_{254nm}$). Mass calculated for, M+ 472.0, observed LC/MS m/z 473.0 (M+H).

1294

-continued

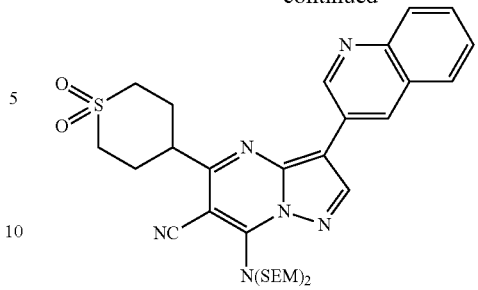

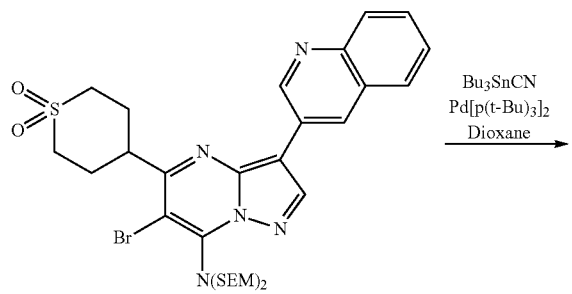

A degassed mixture of 6-bromo-5-thiomorpholinodioxo-3-(quinolin-3-yl)-N,N-bis((2-(trimethylsilyl)ethoxy)methyl)pyrazolo[1,5-a]pyrimidin-7-amine (35 mg, 0.051 mmoL), Bu₃SnCN (32.3 mg, 0.10 mmoL), Pd[P(t-Bu)₃]₂ (5.2 mg, 0.010 mmoL) in Dioxane (3 mL) was heated at 100° C. overnight. The mixture was cooled to room temperature and the solvent was evaporated. Purification by column chromatography afforded 7-(bis((2-(trimethylsilyl)ethoxy)methyl)amino)-5-thiomorpholinodioxo-3-(quinolin-3-yl)pyrazolo[1,5-a]pyrimidine-6-carbonitrile. LCMS $t_R$=2.76 Min (5 min run, $UV_{254nm}$). Mass calculated for, M+ 678.28, observed LC/MS m/z 679.20 (M+H).

A mixture of 7-(bis((2-(trimethylsilyl)ethoxy)methyl)amino)-5-thiomorpholinodioxo-3-(quinolin-3-yl)pyrazolo[1,5-a]pyrimidine-6-carbonitrile (5 mg), EtOH (1 mL) and 3N HCl (1 mL) was heated at 60° C. until LCMS indicated complete reaction. The mixture was cooled to room temperature and the solvent was evaporated. Purification by prep-LC afforded 7-amino-5-thiomorpholinodioxo-3-(quinolin-3-yl)pyrazolo[1,5-a]pyrimidine-6-carbonitrile. LCMS $t_R$=3.12 Min (10 min run, $UV_{254nm}$). Mass calculated for, M+ 418.12, observed LC/MS m/z 419.2 (M+H).

Following the examples described above, the compounds (Scheme-36)) given in the Table-10-H can be synthesized

TABLE-10-H

| Compound ID | Structures | M.Wt (calc.) | M + H (observed) | Retention Time, 10 min method (min) |
|---|---|---|---|---|
| 10.138 | 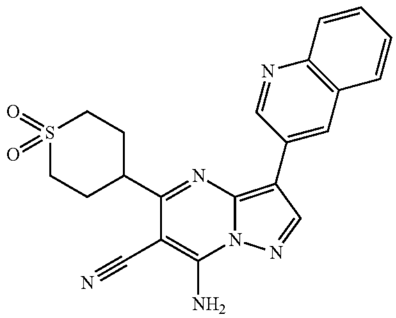 [SMILES: N#Cc1c(C2CCS(=O)(=O)CC2)nc2c(-c3cnc4ccccc4c3)cnn2c1N] | 418.12 | 419.14 | 2.70 |
| 10.139 | 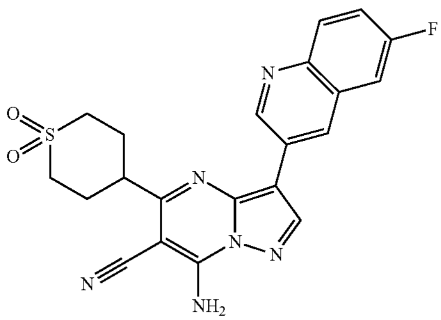 [SMILES: N#Cc1c(C2CCS(=O)(=O)CC2)nc2c(-c3cnc4ccc(F)cc4c3)cnn2c1N] | 436.11 | 437.1 | 2.85 |
| 10.140 | 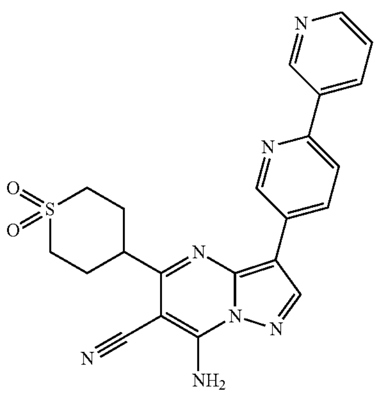 [SMILES: N#Cc1c(C2CCS(=O)(=O)CC2)nc2c(-c3ccc(-c4cccnc4)nc3)cnn2c1N] | 445.13 | 446.44 | 2.52 |
| 10.141 | 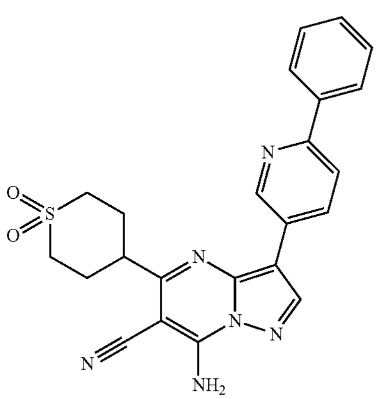 [SMILES: N#Cc1c(C2CCS(=O)(=O)CC2)nc2c(-c3ccc(-c4ccccc4)nc3)cnn2c1N] | 444.13 | 445.15 | 3.15 |

Synthesis of 7-amino-3-(quinolin-3-yl)-5-(tetrahydro-2H-thiopyran-4-yl-1',1'-dioxide)pyrazolo[1,5-a]pyrimidine-6-carboxamide

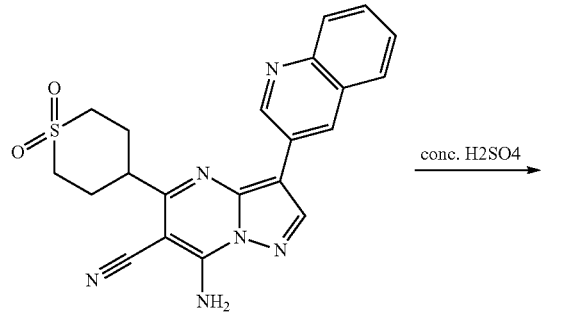

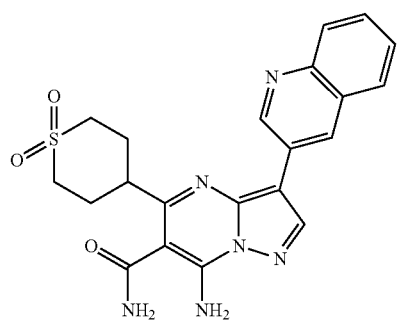

The 7-amino-3-(quinolin-3-yl)-5-(tetrahydro-2H-thiopyran-4-yl-1',1'-dioxide)pyrazolo[1,5-a]pyrimidine-6-carbonitrile was stirred in conc. $H_2SO_4$ (1 mL) at 60° C. until LCMS indicated complete conversion. The reaction was quenched with ice and the pH was adjusted to ~8 by 6 N NaOH. The mixture was extracted by 15% i-PrOH/$CH_2Cl_2$ (×3). The combined organic layers were dried with $Na_2SO_4$. Evaporation of solvent afforded the crude displacement compound. Purification by prep-LC afforded 7-amino-3-(quinolin-3-yl)-5-(tetrahydro-2H-thiopyran-4-yl-1',1'-dioxide)pyrazolo[1,5-a]pyrimidine-6-carboxamide. LCMS $t_R$=2.27 Min (10 min run, $UV_{254nm}$). Mass calculated for, M+ 436.13, observed LC/MS m/z 437.23 (M+H).

Synthesis of 7-amino-3-(quinolin-3-yl)-5-(tetrahydro-2H-thiopyran-4-yl)pyrazolo[1,5-a]pyrimidine-6-carboxamide

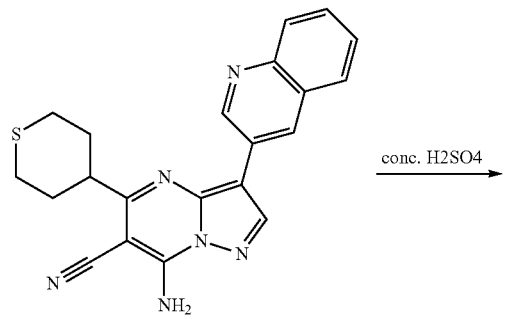

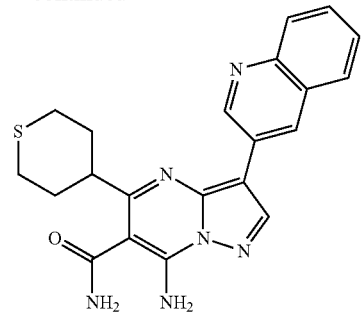

By essentially the same procedure given in Preparative above, 7-amino-3-(quinolin-3-yl)-5-(tetrahydro-2H-thiopyran-4-yl)pyrazolo[1,5-a]pyrimidine-6-carboxamide can be prepared. LCMS $t_R$=3.21 Min (10 min run, $UV_{254nm}$). Mass calculated for, M+ 405.13, observed LC/MS m/z 406.15 (M+H).

Synthesis of 1-(7-amino-3-(6-phenylpyridin-3-yl)-5-(tetrahydro-2H-thiopyran-4-yl-1',1'-dioxide)pyrazolo[1,5-a]pyrimidin-6-yl)ethanone oxime

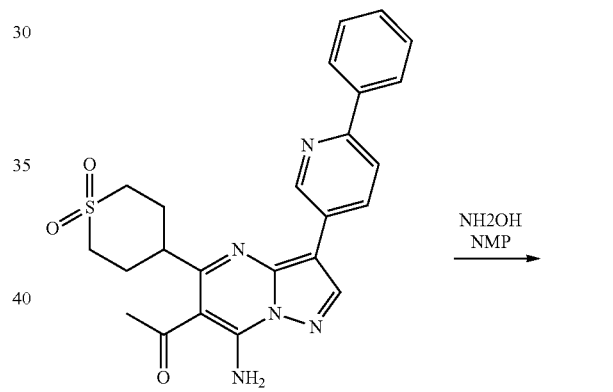

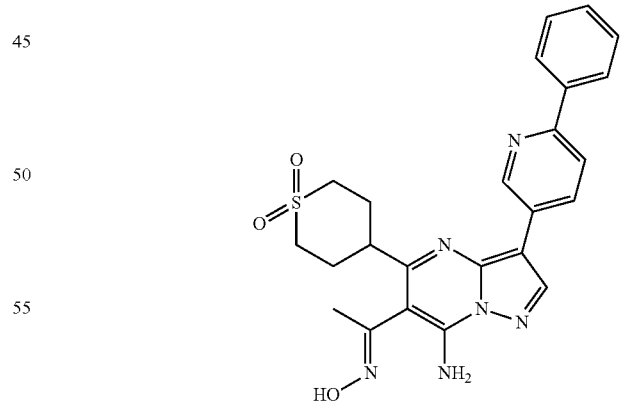

A mixture of 1-(7-amino-3-(6-phenylpyridin-3-yl)-5-(tetrahydro-2H-thiopyran-4-yl-1',1'-dioxide)pyrazolo[1,5-a]pyrimidin-6-yl)ethanone (4 mg) and 50% NH2OH (120 uL) in NMP (1 mL) was heated at 100° C. for 30 min under microwave condition. Purification by prep-LC afforded 1-(7-amino-3-(6-phenylpyridin-3-yl)-5-(tetrahydro-2H-thiopyran-4-yl-1',1'-dioxide)pyrazolo[1,5-a]pyrimidin-6-yl)

ethanone oxime: LCMS $t_R$=3.04 Min (10 min run, $UV_{254nm}$). Mass calculated for, M+ 476.16, observed LC/MS m/z 477.59 (M+H).

Synthesis of 1-amino-3-(6-phenylpyridin-3-yl)-5-(tetrahydro-2H-thiopyran-4-yl-1',1'-dioxide)pyrazolo[1,5-a]pyrimidine-6-carbaldehyde oxime $t_R$=3.15 Min (10 min run, $UV_{254nm}$). Mass calculated for, M+ 462.14, observed LC/MS m/z 463.57 (M+H).

Synthesis of 1-(7-amino-3-(quinolin-3-yl)-5-thiomorpholinopyrazolo-1',1'-dioxide-[1,5-a]pyrimidin-6-yl)ethanol

SCHEME-37

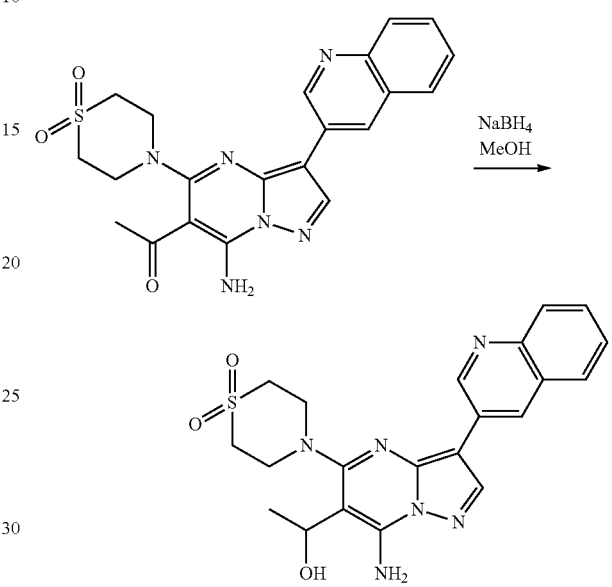

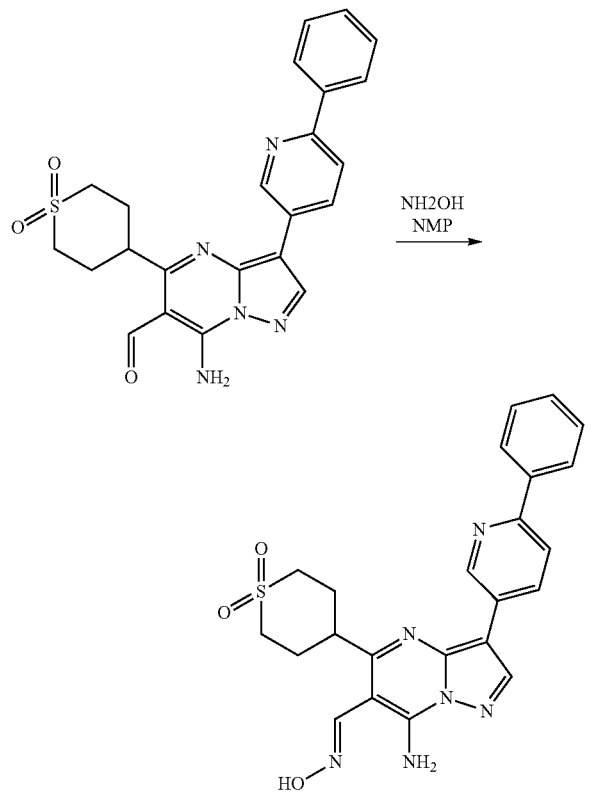

By essentially the same procedure given in Preparative Example given above 1-amino-3-(6-phenylpyridin-3-yl)-5-(tetrahydro-2H-thiopyran-4-yl-1',1'-dioxide) pyrazolo[1,5-a]pyrimidine-6-carbaldehyde oxime can be prepared. LCMS NaBH₄ (10 mg) was added to a solution of 1-(7-amino-3-(quinolin-3-yl)-5-thiomorpholino-1',1'-dioxide-pyrazolo[1,5-a]pyrimidin-6-yl)ethanone (10 mg, 0.023 mmoL) in MeOH (1 mL). After stirring at room temperature for 1 h, the mixture was concentrated to dry. Purification by prep-TLC afforded 1-(7-amino-3-(quinolin-3-yl)-5-thiomorpholinopyrazolo-1',1'-dioxide-[1,5-a]pyrimidin-6-yl)ethanol: LCMS $t_R$=2.44 Min (5 min run, $UV_{254nm}$). Mass calculated for, M+ 438.1, observed LC/MS m/z 439.1 (M+H).

By essentially the same procedure given in Preparative Example described above (Scheme-37), following compounds 10.142-10.148 in table-10-I can be prepared,

TABLE-10-I

| Compound ID | Structures | M.Wt (calc.) | M + H (observed) | Retention Time, 10 min method (min) |
|---|---|---|---|---|
| 10.142 | 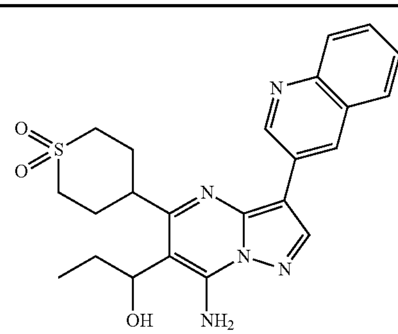 | 452.16 | 453.3 | 2.69 |

TABLE-10-I-continued

| Compound ID | Structures | M.Wt (calc.) | M + H (observed) | Retention Time, 10 min method (min) |
|---|---|---|---|---|
| 10.143 | 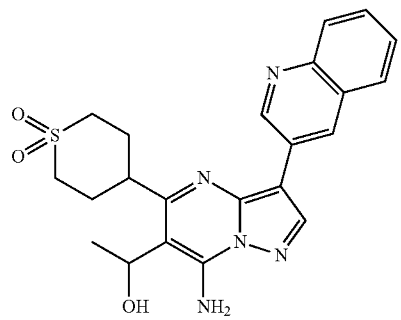 [SMILES: CCC(O)c1c(C2CCS(=O)(=O)CC2)nc2c(-c3cnc4ccccc4c3)cnn2c1N] | 437.15 | 438.1 | 2.94 |
| 10.144 | 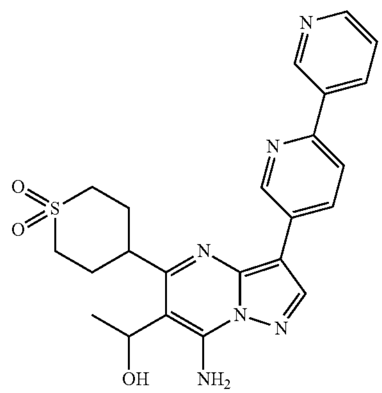 [SMILES: CC(O)c1c(C2CCS(=O)(=O)CC2)nc2c(-c3ccc(-c4cccnc4)nc3)cnn2c1N] | 464.16 | 465.1 | 2.68 |
| 10.145 | 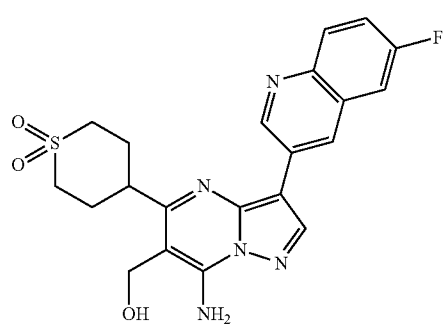 | 441.12 | 442.0 | 1.23 |
| 10.146 | 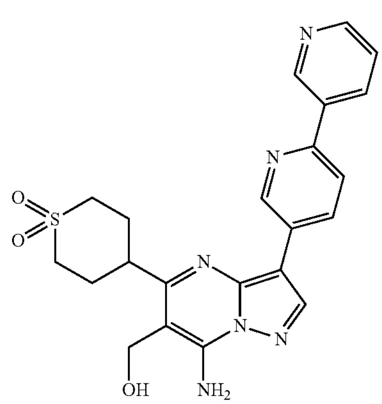 [SMILES: Nc1c(CO)c(C2CCS(=O)(=O)CC2)nc2c(-c3ccc(-c4cccnc4)nc3)cnn12] | 450.14 | 451.1 | 2.41 |

TABLE-10-I-continued
| Compound ID | Structures | M.Wt (calc.) | M + H (observed) | Retention Time, 10 min method (min) |
|---|---|---|---|---|
| 10.147 | 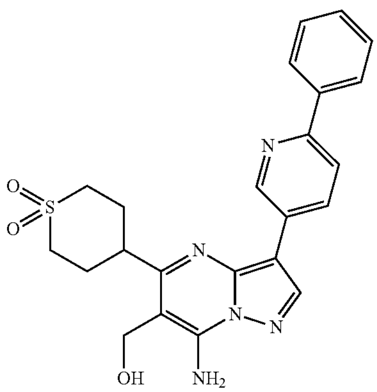 | 449.15 | 450.1 | 3.08 |
| 10.148 | 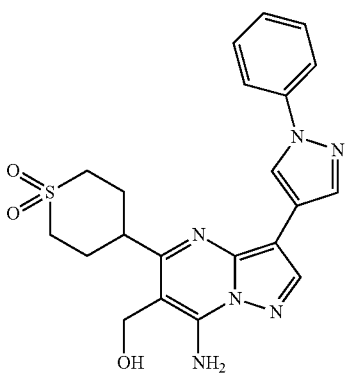 [SMILES: Nc1c(CO)c(C2CCS(=O)(=O)CC2)nc2c(-c3cnn(-c4ccccc4)c3)cnn12] | 438.14 | 439.1 | 2.90 |
Synthesis of 3-(6-phenylpyridin-3-yl)-5-(tetrahydro-2H-thiopyran-4-yl-1',1'-dioxide)-6-(thiophen-2-yl)pyrazolo[1,5-a]pyrimidin-7-amine
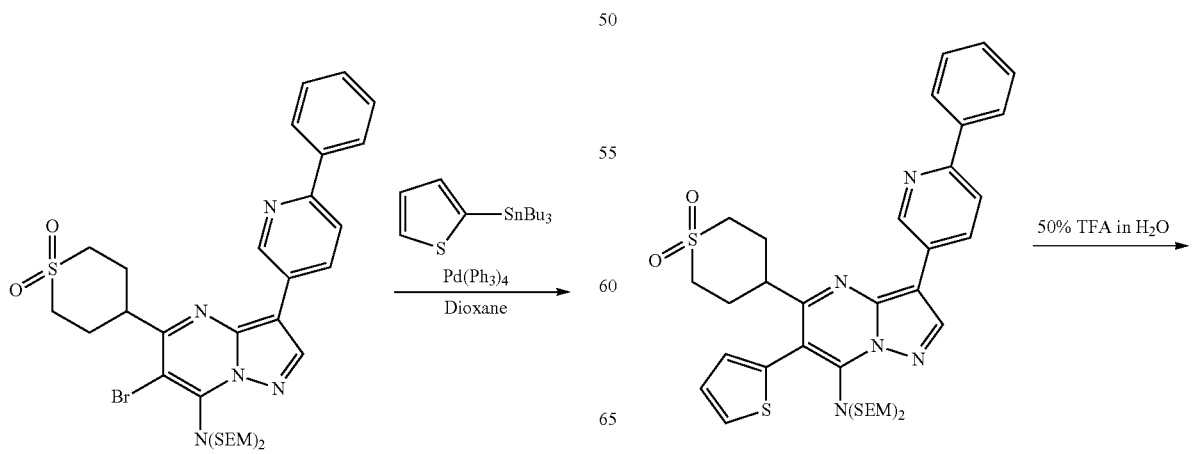

1305

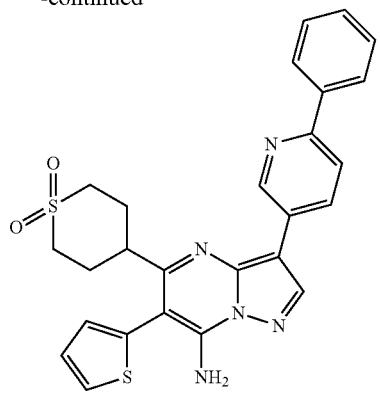

1306

By essentially the same procedure given in Preparative Example described above (Scheme-36), 3-(6-phenylpyridin-3-yl)-5-(tetrahydro-2H-thiopyran-4-yl-1',1'-dioxide)-6-(thiophen-2-yl)pyrazolo[1,5-a]pyrimidin-7-amine be prepared. LCMS $t_R$=4.18 Min (10 min run, $UV_{254nm}$). Mass calculated for, M+ 501.12, observed LC/MS m/z 502.0 (M+H).

By essentially the same procedure given in Preparative Example above (36), compounds in table 10-J (10.149-10.151) can be prepared.

TABLE-10-J

| Compound ID | Structures | M.Wt (calc.) | M + H (observed) | Retention Time, 10 min method (min) |
|---|---|---|---|---|
| 10.149 | 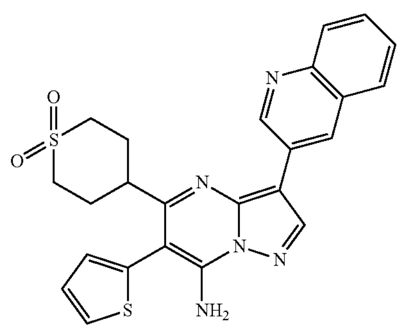 [SMILES: Nc1c(-c2cccs2)c(C2CCS(=O)(=O)CC2)nc2c(-c3cnc4ccccc4c3)cnn12] | 475.1 | 476.0 | 1.48 (5 min run) |
| 10.150 | 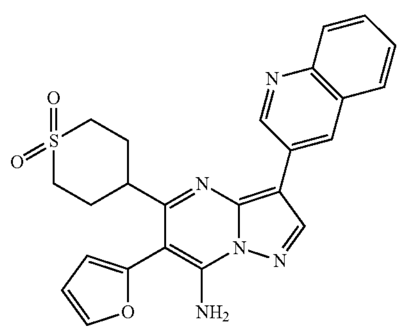 [SMILES: Nc1c(-c2ccco2)c(C2CCS(=O)(=O)CC2)nc2c(-c3cnc4ccccc4c3)cnn12] | 459.13 | 460.21 | 3.25 |
| 10.151 | 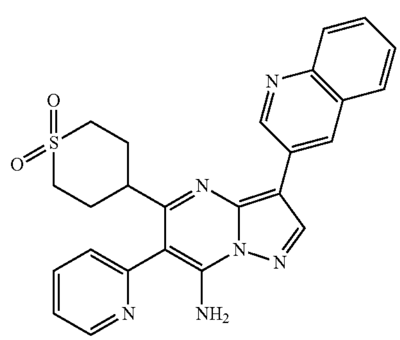 [SMILES: Nc1c(-c2ccccn2)c(C2CCS(=O)(=O)CC2)nc2c(-c3cnc4ccccc4c3)cnn12] | 470.15 | 471.03 | 2.67 |

1307

Synthesis of 6-cyclopropyl-3-(6-phenylpyridin-3-yl)-5-(tetrahydro-2H-thiopyran-4-yl-1',1'-dioxide)pyrazolo[1,5-a]pyrimidin-7-amine

SCHEME-38

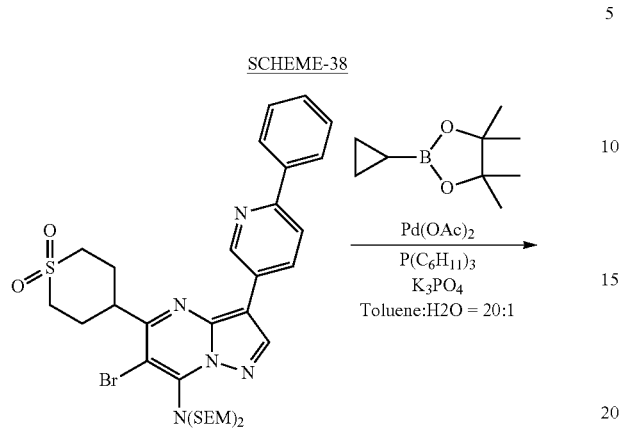

A degassed mixture of 6-bromo-3-(6-phenylpyridin-3-yl)-5-(tetrahydro-2H-thiopyran-4-yl-1',1'-dioxide)-N,N-bis((2-(trimethylsilyl)ethoxy)methyl)pyrazolo[1,5-a]pyrimidin-7-amine (53 mg, 0.07 mmol), Pd(OAc)$_2$ (3.1 mg, 0.014 mmoL), P(C6H11)$_3$ (7.9 mg, 0.028 mmoL), 2-cyclopropyl-4,4,5,5-tetramethyl-1,3,2-dioxaborolane (23.5 mg, 0.14 mmoL), K3PO4 (53 mg, 0.25 mmoL) in Toluene (0.4 mL) and H2O (0.02 mL) was heated at 100° C. overnight. The reaction mixture was cooled to room temperature, filtered through celite and concentrated in vacuo. The crude coupling product was treated with 50% TFA in H$_2$O (4 mL) for 1 h. The reaction mixture was concentrated in vacuo. Concentration and purification afforded 6-cyclopropyl-3-(6-phenylpyridin-3-yl)-5-(tetrahydro-2H-thiopyran-4-yl-1',1'-dioxide)pyrazolo[1,5-a]pyrimidin-7-amine: LCMS t$_R$=3.49 Min (10 min run, UV$_{254nm}$). Mass calculated for, M+ 459.17, observed LC/MS m/z 460.22 (M+H).

By essentially the same procedure given in Preparative Example above (Scheme-38), compounds 10.152-10.154 can be prepared are given in Table-10-K

TABLE-10-K

| Compound ID | Structures | M.Wt (calc.) | M + H (observed) | Retention Time, 10 min method (min) |
|---|---|---|---|---|
| 10.152 | 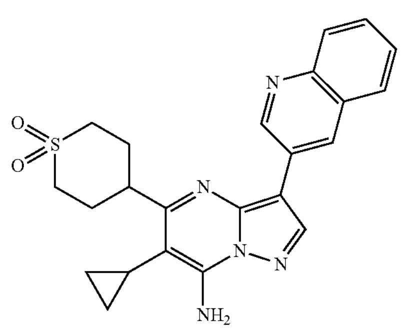 [SMILES: Nc1c(C2CC2)c(C2CCS(=O)(=O)CC2)nc2c(-c3cnc4ccccc4c3)cnn12] | 433.15 | 434.18 | 3.24 |

TABLE-10-K-continued
| Compound ID | Structures | M.Wt (calc.) | M + H (observed) | Retention Time, 10 min method (min) |
|---|---|---|---|---|
| 10.153 | 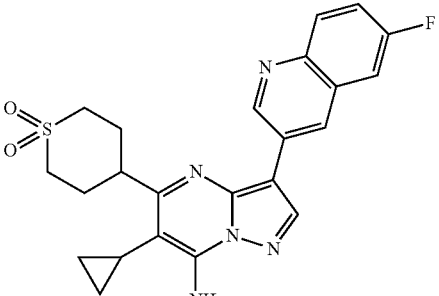 | 451.1 | 452.0 | 4.04 |
| 10.154 | 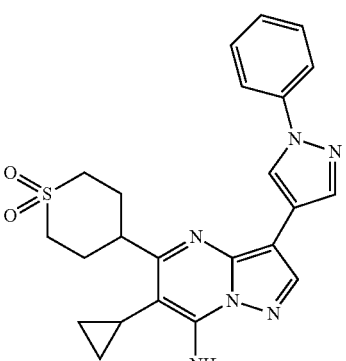 | 449.16 | 449.25 | 4.29 |

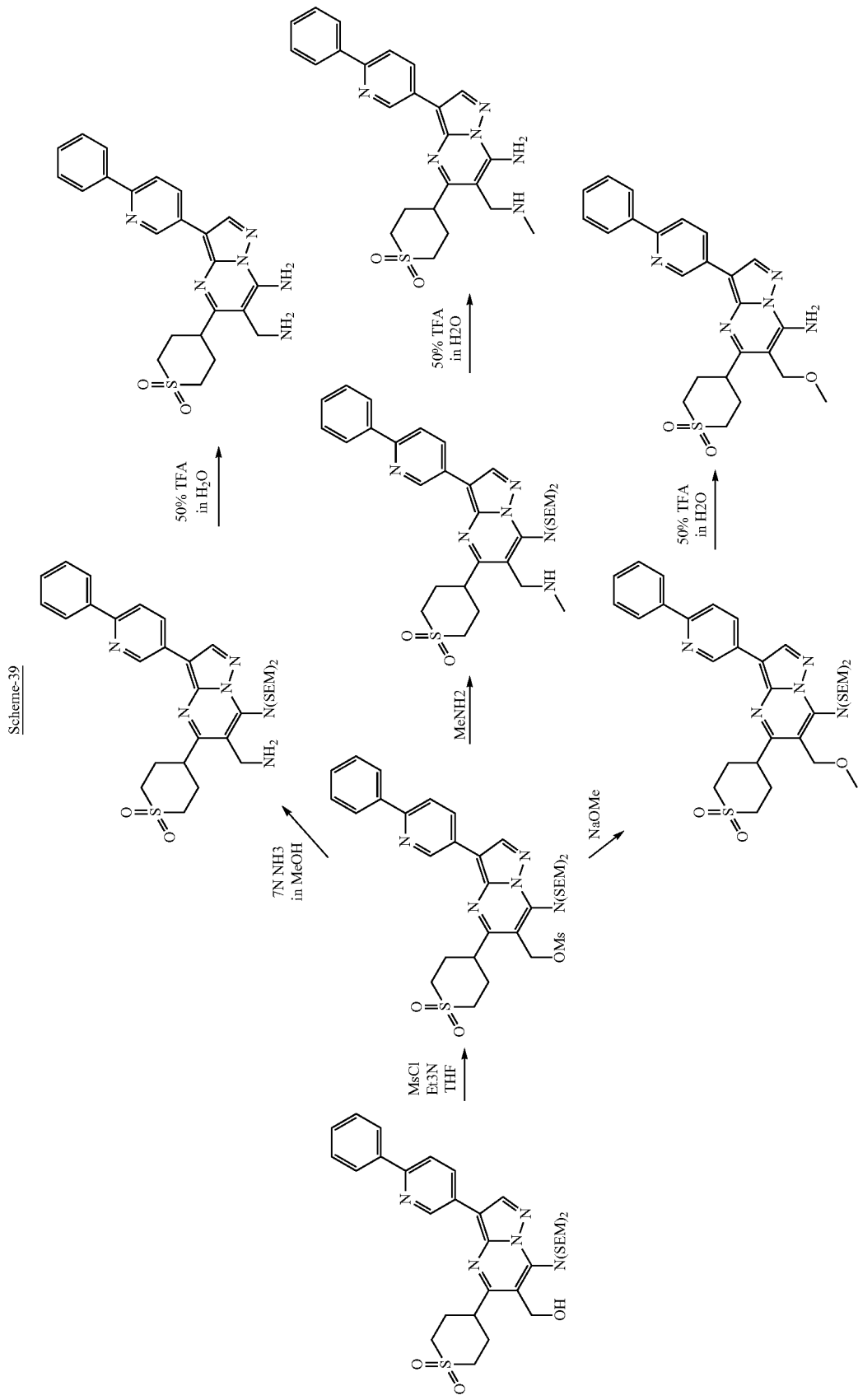
Scheme-39

Part A:

(7-(bis((2-(trimethylsilyl)ethoxy)methyl)amino)-3-(6-phenylpyridin-3-yl)-5-(tetrahydro-2H-thiopyran-4-yl-1',1'-dioxide) pyrazolo[1,5-a]pyrimidin-6-yl) methyl methanesulfonate At 0° C., Et$_3$N (41.7 uL, 0.29 mmol) and MsCl (17.4 uL, 0.22 mmol) were added to a solution of (7-(bis((2-(trimethylsilyl)ethoxy)methyl)amino)-3-(6-phenylpyridin-3-yl)-5-(tetrahydro-2H-thiopyran-4-yl-1',1'-dioxide)pyrazolo[1,5-a]pyrimidin-6-yl)methanol (53 mg, 0.75 mmol) in THF (3 mL). After stirring at room temperature for 1 h, the compound, (7-(bis((2-(trimethylsilyl)ethoxy)methyl)amino)-3-(6-phenylpyridin-3-yl)-5-(tetrahydro-2H-thiopyran-4-yl-1',1'-dioxide)pyrazolo[1,5-a]pyrimidin-6-yl)methyl methanesulfonate was evenly transferred to three vials.

Part B:

6-(aminomethyl)-3-(6-phenylpyridin-3-yl)-5-(tetrahydro-2H-thiopyran-4-yl-1',1'-dioxide) pyrazolo[1,5-a]pyrimidin-7-amine 7N NH$_3$ in MeOH (1 mL) added was added to vial 1. 6-(aminomethyl)-3-(6-phenylpyridin-3-yl)-5-(tetrahydro-2H-thiopyran-4-yl-1',1'-dioxide) pyrazolo[1,5-a]pyrimidin-7-amine was obtained after concentration and deprotection by treating with 50% TFA in H2O and then prep-LC purification to give the product, 6-(aminomethyl)-3-(6-phenylpyridin-3-yl)-5-(tetrahydro-2H-thiopyran-4-yl-1',1'-dioxide) pyrazolo[1,5-a]pyrimidin-7-amine. LCMS t$_R$=1.97 Min (10 min run, UV$_{254nm}$). Mass calculated for, M+ 448.16, observed LC/MS m/z 449.2 (M+H).

Part C:

6-((methylamino)methyl)-3-(6-phenylpyridin-3-yl)-5-(tetrahydro-2H-thiopyran-4-yl-1',1'-dioxide)pyrazolo[1,5-a]pyrimidin-7-amine 2 N MeNH$_2$ in THF (1 mL) added was added to vial 2. 6-((methylamino)methyl)-3-(6-phenylpyridin-3-yl)-5-(tetrahydro-2H-thiopyran-4-yl-1',1'-dioxide)pyrazolo[1,5-a]pyrimidin-7-amine was obtained after concentration and deprotection by treating with 50% TFA in H2O and then prep-LC purification resulted in pure 6-((methylamino)methyl)-3-(6-phenylpyridin-3-yl)-5-(tetrahydro-2H-thiopyran-4-yl-1',1'-dioxide) pyrazolo[1,5-a]pyrimidin-7-amine as TFA salt. LCMS t$_R$=2.12 Min (10 min run, UV$_{254nm}$). Mass calculated for, M+ 462.18, observed LC/MS m/z 463.3 (M+H).

Part D:

6-(methoxymethyl)-3-(6-phenylpyridin-3-yl)-5-(tetrahydro-2H-thiopyran-4-yl)pyrazolo[1,5-a]pyrimidin-7-amine 0.5 M NaOMe in MeOH (1 mL) added was added to vial 3. 6-(methoxymethyl)-3-(6-phenylpyridin-3-yl)-5-(tetrahydro-2H-thiopyran-4-yl-1',1'-dioxide)pyrazolo[1,5-a]pyrimidin-7-amine was obtained after concentration and deprotection by treating with 50% TFA in H2O and then prep-LC purification provided pure compound, 6-(methoxymethyl)-3-(6-phenylpyridin-3-yl)-5-(tetrahydro-2H-thiopyran-4-yl-1',1'-dioxide)pyrazolo[1,5-a]pyrimidin-7-amine. LCMS t$_R$=2.66 Min (10 min run, UV$_{254nm}$). Mass calculated for, M+ 463.1, observed LC/MS m/z 464.1 (M+H).

By essentially the same procedure given in Scheme-39, following compounds 10.155 to 10.161 can be prepared. (Table-10-L)

TABLE-10-L

| Compound ID | Structures | M.Wt (calc.) | M + H (observed) | Retention Time, 10 min method (min) |
|---|---|---|---|---|
| 10.155 | 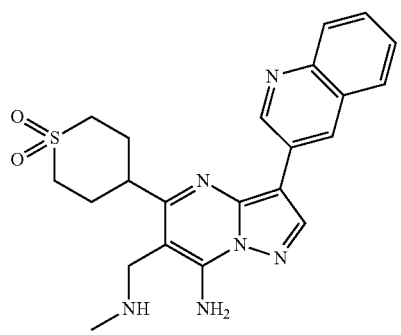 [SMILES: CNCc1c(C2CCS(=O)(=O)CC2)nc2c(-c3cnc4ccccc4c3)cnn2c1N] | 436.16 | 437.0 | 2.12 |

TABLE-10-L-continued

| Compound ID | Structures | M.Wt (calc.) | M + H (observed) | Retention Time, 10 min method (min) |
|---|---|---|---|---|
| 10.156 | 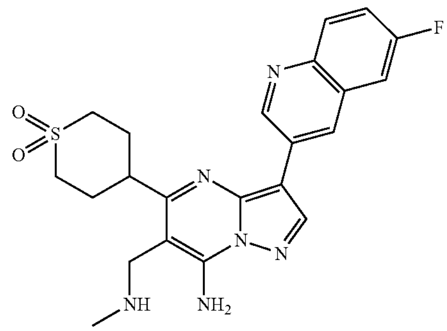 [SMILES: CNCc1c(C2CCS(=O)(=O)CC2)nc2c(-c3cnc4ccc(F)cc4c3)cnn2c1N] | 454.15 | 455.0 | 2.67 |
| 10.157 | 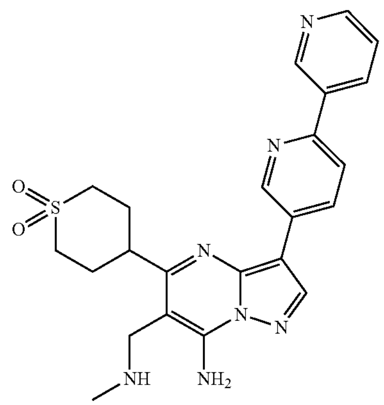 [SMILES: CNCc1c(C2CCS(=O)(=O)CC2)nc2c(-c3ccc(-c4cccnc4)nc3)cnn2c1N] | 463.17 | 464.2 | 1.67 |
| 10.158 | 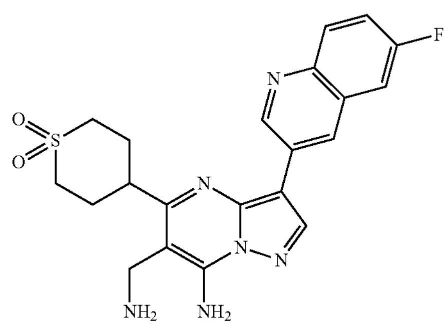 [SMILES: NCc1c(C2CCS(=O)(=O)CC2)nc2c(-c3cnc4ccc(F)cc4c3)cnn2c1N] | 440.14 | 441.1 | 2.62 |
| 10.159 | 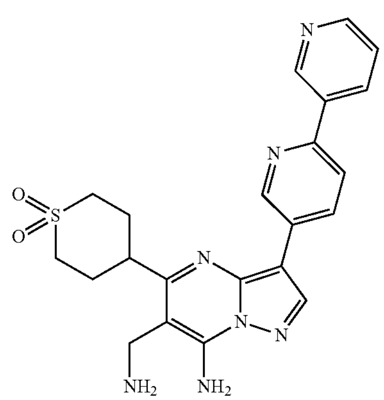 [SMILES: NCc1c(C2CCS(=O)(=O)CC2)nc2c(-c3ccc(-c4cccnc4)nc3)cnn2c1N] | 449.16 | 450.2 | 1.67 |

TABLE-10-L-continued

| Compound ID | Structures | M.Wt (calc.) | M + H (observed) | Retention Time, 10 min method (min) |
|---|---|---|---|---|
| 10.160 | 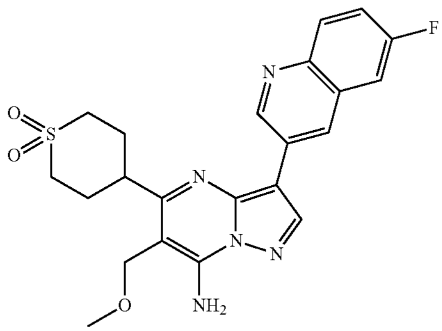 [SMILES: COCc1c(C2CCS(=O)(=O)CC2)nc2c(-c3cnc4ccc(F)cc4c3)cnn2c1N] | 455.1 | 456.1 | 3.57 |
| 10.161 | 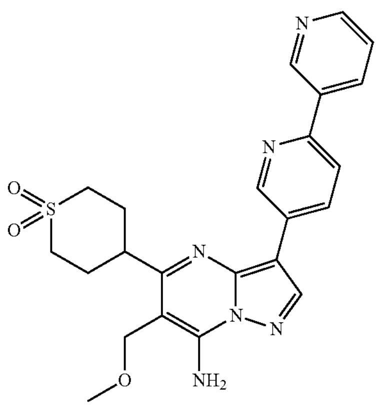 [SMILES: COCc1c(C2CCS(=O)(=O)CC2)nc2c(-c3ccc(-c4cccnc4)nc3)cnn2c1N] | 464.16 | 465.1 | 2.34 |

Synthesis of tert-butyl 2-(7-(bis((2-(trimethylsilyl)ethoxy)methyl)amino)-3-(6-phenylpyridin-3-yl)pyrazolo[1,5-a]pyrimidin-5-yl)-5-methoxy-1H-indole-1-carboxylate

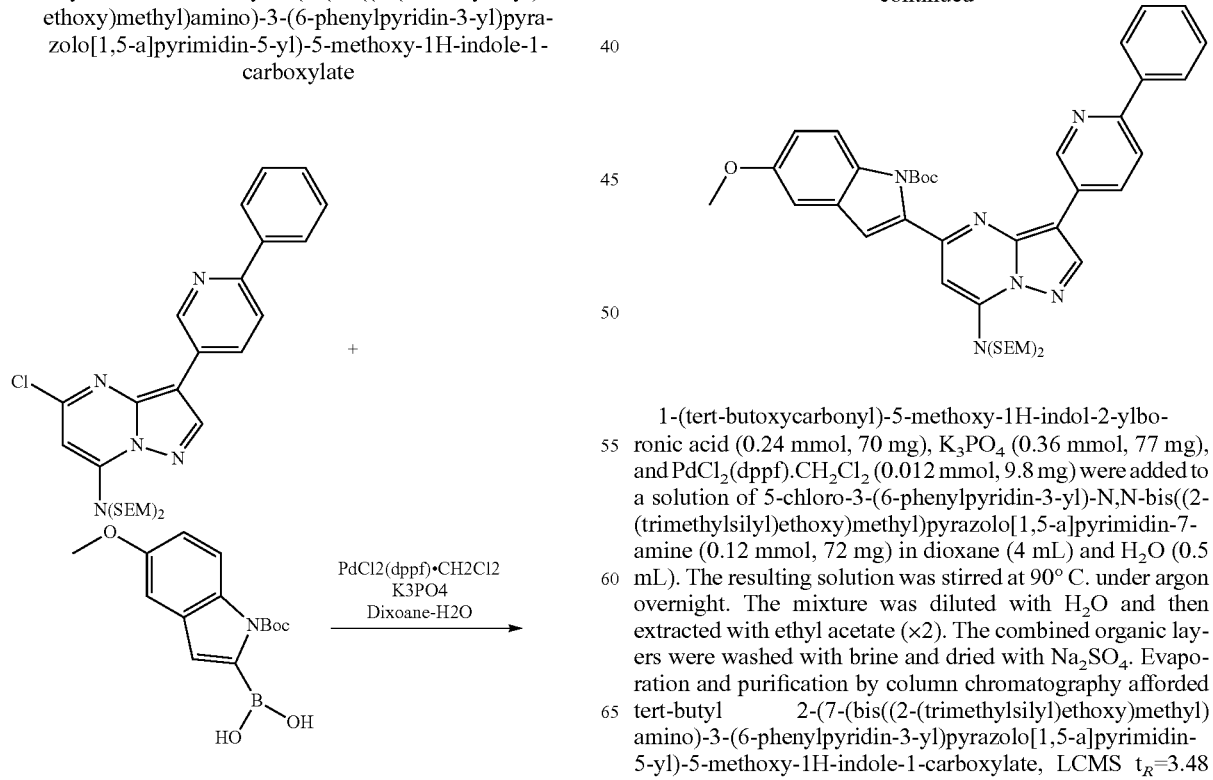

1-(tert-butoxycarbonyl)-5-methoxy-1H-indol-2-ylboronic acid (0.24 mmol, 70 mg), K₃PO₄ (0.36 mmol, 77 mg), and PdCl₂(dppf).CH₂Cl₂ (0.012 mmol, 9.8 mg) were added to a solution of 5-chloro-3-(6-phenylpyridin-3-yl)-N,N-bis((2-(trimethylsilyl)ethoxy)methyl)pyrazolo[1,5-a]pyrimidin-7-amine (0.12 mmol, 72 mg) in dioxane (4 mL) and H₂O (0.5 mL). The resulting solution was stirred at 90° C. under argon overnight. The mixture was diluted with H₂O and then extracted with ethyl acetate (×2). The combined organic layers were washed with brine and dried with Na₂SO₄. Evaporation and purification by column chromatography afforded tert-butyl 2-(7-(bis((2-(trimethylsilyl)ethoxy)methyl)amino)-3-(6-phenylpyridin-3-yl)pyrazolo[1,5-a]pyrimidin-5-yl)-5-methoxy-1H-indole-1-carboxylate, LCMS $t_R$=3.48

1319

Min (5 min run, UV$_{254nm}$). Mass calculated for, M+ 792.3, observed LC/MS m/z 793.2 (M+H).

6-bromo-5-(5-methoxy-1H-indol-2-yl)-3-(6-phenylpyridin-3-yl)pyrazolo[1,5-a]pyrimidin-7-amine

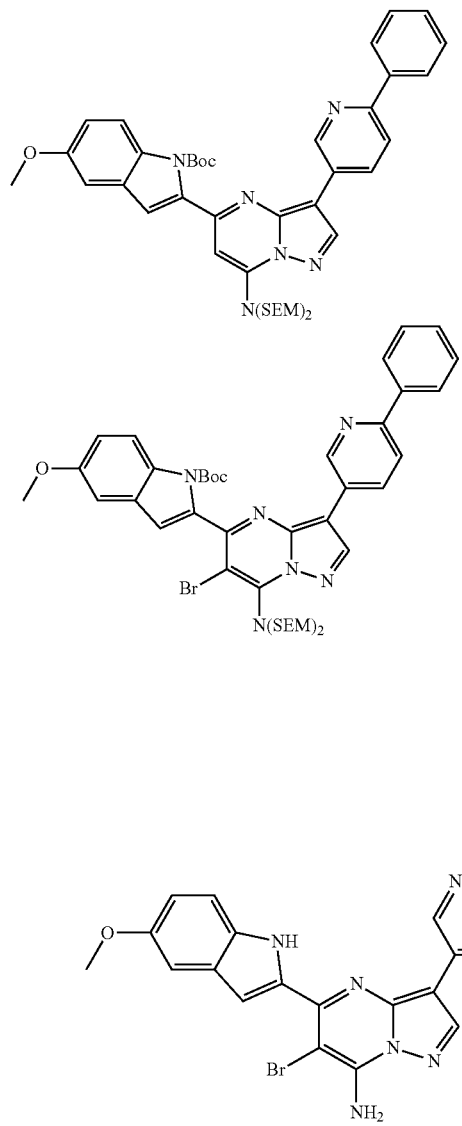

By essentially the same procedure given in Preparative Examples above, 6-bromo-5-(5-methoxy-1H-indol-2-yl)-3-(6-phenylpyridin-3-yl)pyrazolo[1,5-a]pyrimidin-7-amine can be prepared. LCMS t$_R$=4.59 Min (10 min run, UV$_{254nm}$). Mass calculated for, M+ 510.08, observed LC/MS m/z 511.50 (M+H).

1320

Synthesis of 5-chloro-3-(6-phenylpyridin-3-yl)-N,N-bis((2-(trimethylsilyl)ethoxy)methyl)pyrazolo[1,5-a]pyrimidin-7-amine

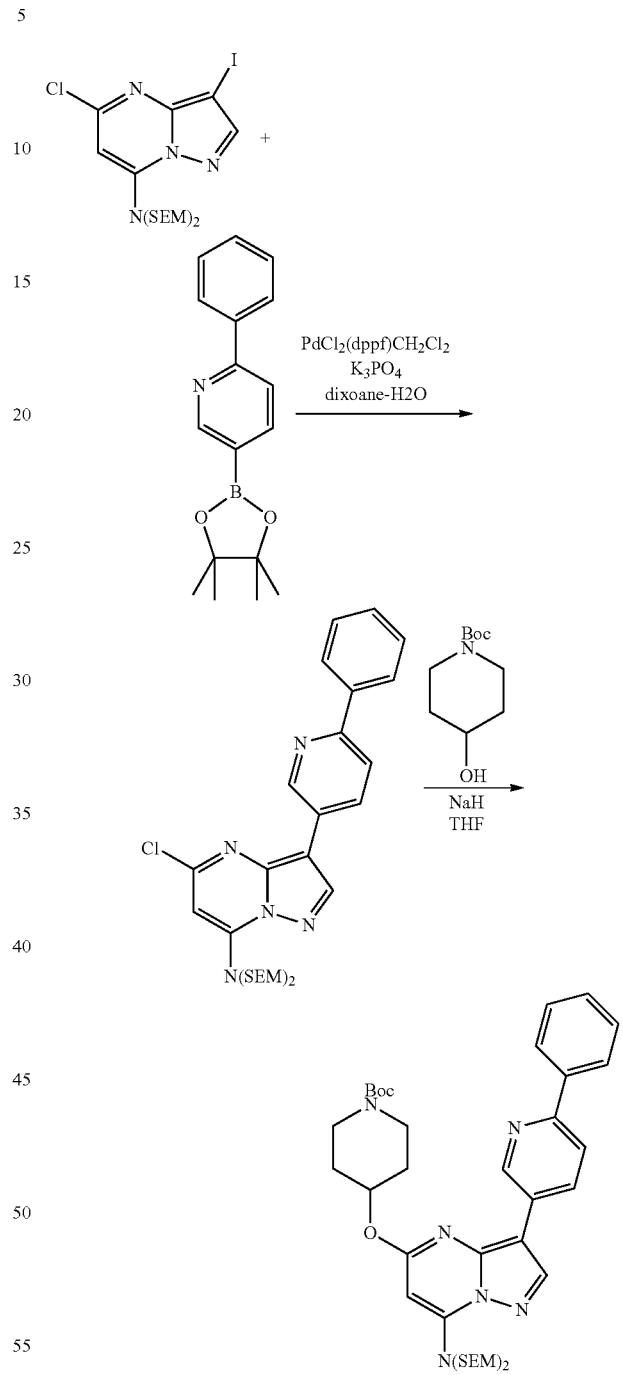

2-phenyl-5-(4,4,5,5-tetramethyl-1,3,2-dioxaborolan-2-yl)pyridine (2.38 mmol, 675 mg), K$_3$PO$_4$ (5.96 mmol, 1264 mg), and PdCl$_2$(dppf).CH$_2$Cl$_2$ (0.20 mmol, 162 mg) were added to a solution of 5-chloro-3-iodo-N,N-bis((2-(trimethylsilyl)ethoxy)methyl)pyrazolo[1,5-a]pyrimidin-7-amine (1.98 mmol, 1101 mg) in dioxane (18 mL) and H$_2$O (3 mL). The resulting solution was stirred at 70° C. under argon overnight. The mixture was diluted with H$_2$O and then extracted with ethyl acetate (×2). The combined organic layers were washed with brine and dried with Na$_2$SO$_4$. Evaporation and purification by column chromatography afforded 5-chloro-3-(6-phenylpyridin-3-yl)-N,N-bis((2 trimethylsilyl)ethoxy)methyl)pyrazolo[1,5-a]pyrimidin-7-amine: LCMS $t_R$=3.36 Min (5 min run, $UV_{254nm}$). Mass calculated for, M+ 581.2, observed LC/MS m/z 582.2 (M+H).

Synthesis of tert-butyl 4-(7-(bis((2-(trimethylsilyl)ethoxy)methyl)amino)-3-(6-phenylpyridin-3-yl)pyrazolo[1,5-a]pyrimidin-5-yloxy)piperidine-1-carboxylate NaH (120 mg, 3 mmoL) was added to a solution of tert-butyl 4-hydroxypiperidine-1-carboxylate (522 mg, 2.60 mmoL) in THF (8 mL). After stirring at room temperature for 5 min, 5-chloro-3-(6-phenylpyrimidin-3-yl)-N,N-bis((2-(trimethylsilyl)ethoxy)methyl)pyrazolo[1,5-a]pyrimidin-7-amine (755 mg, 1.30 mmoL) in THF (4 mL) was added dropwise. The mixture was heated under microwave condition at 100° C. for 30 min, diluted with $H_2O$ and then extracted with ethyl acetate (×2). The combined organic layers were washed with brine and dried with $Na_2SO_4$. Evaporation and purification by column chromatography afforded tert-butyl 4-(7-(bis((2-(trimethylsilyl)ethoxy)methyl)amino)-3-(6-phenylpyridin-3-yl)pyrazolo[1,5-a]pyrimidin-5-yloxy)piperidine-1-carboxylate: LCMS $t_R$=3.53 Min (5 min run, $UV_{254nm}$). Mass calculated for, M+ 746.4, observed LC/MS m/z 747.2 (M+H).

Synthesis of tert-butyl 4-(7-(bis((2-(trimethylsilyl)ethoxy)methyl)amino)-6-bromo-3-(6-phenylpyridin-3-yl)pyrazolo[1,5-a]pyrimidin-5-yloxy)piperidine-1-carboxylate

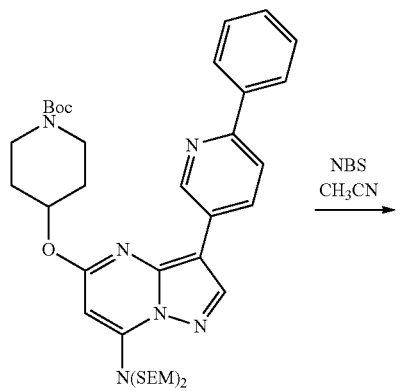

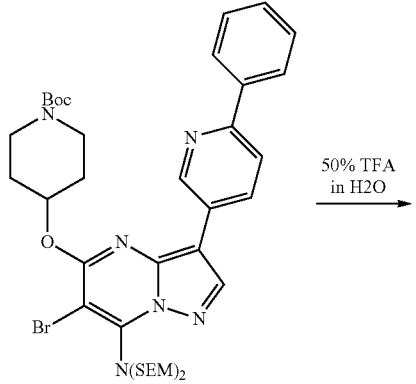

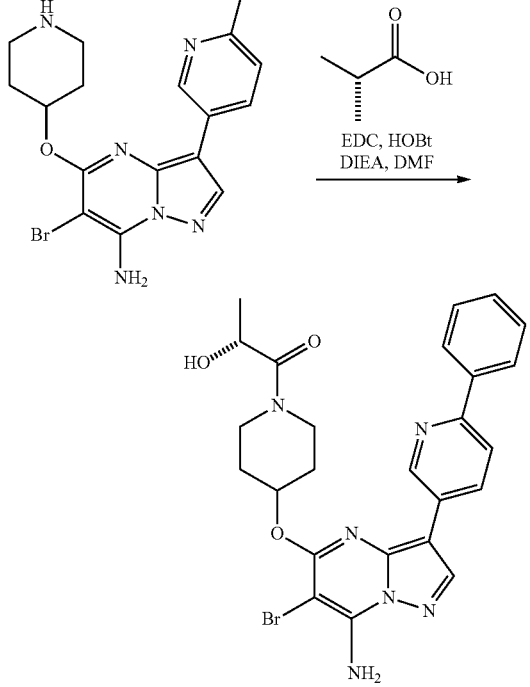

NBS (246 mg, 1.38 mmoL) was added to a solution of tert-butyl 4-(7-(bis((2-(trimethylsilyl)ethoxy)methyl)amino)-3-(6-phenylpyridin-3-yl)pyrazolo[1,5-a]pyrimidin-5-yloxy)piperidine-1-carboxylate (1022 mg, 1.38 mmoL) in $CH_3CN$ (15 mL). After stirring at room temperature for 30 min, the mixture was concentrated in vacuo. Purification by column chromatography afforded tert-butyl 4-(7-(bis((2-(trimethylsilyl)ethoxy)methyl)amino)-6-bromo-3-(6-phenylpyridin-3-yl)pyrazolo[1,5-a]pyrimidin-5-yloxy)piperidine-1-carboxylate: LCMS $t_R$=3.59 Min (5 min run, $UV_{254nm}$). Mass calculated for, M+ 824.3, observed LC/MS m/z 825.1 (M+H).

The tert-butyl 4-(7-(bis((2-(trimethylsilyl)ethoxy)methyl)amino)-6-bromo-3-(6-phenylpyridin-3-yl)pyrazolo[1,5-a]pyrimidin-5-yloxy)piperidine-1-carboxylate (143 mg, 0.17 mmoL) was treated with 50% TFA in $H_2O$ (6 mL) and stirred overnight. The reaction mixture was concentrated in vacuo.

(R)-1-(4-(7-amino-6-bromo-3-(6-phenylpyridin-3-yl)pyrazolo[1,5-a]pyrimidin-5-yloxy)piperidin-1-yl)-2-hydroxypropan-1-one A mixture of the crude 6-bromo-3-(6-phenylpyridin-3-yl)-5-(piperidin-4-yloxy)pyrazolo[1,5-a]pyrimidin-7-amine, D-(−)-lactic acid (18.5 mg, 0.20 mmoL), EDC (78.7 mg, 0.41 mmoL), HOBt (27.7 mg, 0.20 mmoL) and DIEA (238 uL, 1.37 mmoL) in DMF (4 mL) was stirred at room temperature for 2 hr. Purification with prep-LC provided (R)-1-(4-(7-amino-6-bromo-3-(6-phenylpyridin-3-yl)pyrazolo[1,5-a]pyrimidin-5-yloxy)piperidin-1-yl)-2-hydroxypropan-1-one, LCMS $t_R$=4.39 Min (10 min run, $UV_{254nm}$). Mass calculated for, M+ 513.0, observed LC/MS m/z 514.43 (M+H).

1323

Synthesis of 1-(7-amino-3-(6-phenylpyridin-3-yl)-5-(piperidin-4-yloxy)pyrazolo[1,5-a]pyrimidin-6-yl)ethanone

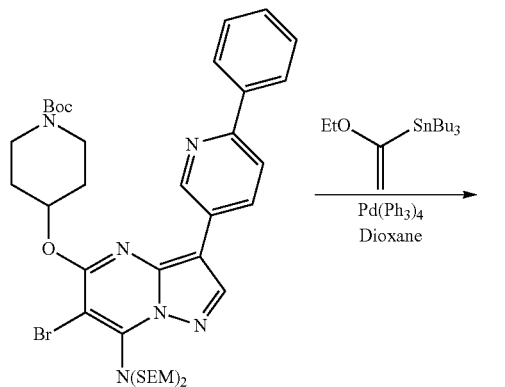

1324

A degassed mixture of tert-butyl 4-(7-(bis((2-(trimethylsilyl)ethoxy)methyl)amino)-6-bromo-3-(6-phenylpyridin-3-yl)pyrazolo[1,5-a]pyrimidin-5-yloxy)piperidine-1-carboxylate (0.57 mmol, 486 mg), Pd(PPh$_3$)$_4$ (66 mg, 0.056 mmoL), tributyl(1-ethoxyvinyl)stannane (410 mg, 1.13 mmoL) in Dioxane (6 mL) was heated at 100° C. overnight. The reaction mixture was cooled to room temperature, filtered through 9:1 SiO$_2$:KF plug and concentrated in vacuo.

The crude tert-butyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yloxy)piperidine-1-carboxylate was treated with 50% TFA in H$_2$O (6 mL) and stirred overnight. The reaction mixture was concentrated in vacuo. Purification with prep-LC provided 1-(7-amino-3-(6-phenylpyridin-3-yl)-5-(piperidin-4-yloxy)pyrazolo[1,5-a]pyrimidin-6-yl)ethanone: LCMS t$_R$=1.11 Min (5 min run, UV$_{254nm}$). Mass calculated for, M+ 428.1, observed LC/MS m/z 429.1 (M+H).

(R)-1-(4-(6-acetyl-7-amino-3-(6-phenylpyridin-3-yl)pyrazolo[1,5-a]pyrimidin-5-yloxy)piperidin-1-yl)-2-hydroxypropan-1-one A mixture of 1-(7-amino-3-(6-phenylpyridin-3-yl)-5-(piperidin-4-yloxy)pyrazolo[1,5-a]pyrimidin-6-yl)ethanone (211 mg, 0.49 mmoL), D-(−)-lactic acid (53.3 mg, 0.59 mmoL), EDC (189.0 mg, 0.99 mmoL), HOBt (132.0 mg, 0.99 mmoL) and DIEA (514 uL, 2.96 mmoL) in DMF (5 mL) was stirred at room temperature for 2 hr. Purification with prep-LC provided (R)-1-(4-(6-acetyl-7-amino-3-(6-phenylpyridin-3-yl)pyrazolo[1,5-a]pyrimidin-5-yloxy)piperidin-1-yl)-2-hydroxypropan-1-one: LCMS t$_R$=3.53 Min (10 min run, UV$_{254nm}$). Mass calculated for, M+ 500.21, observed LC/MS m/z 501.62 (M+H).

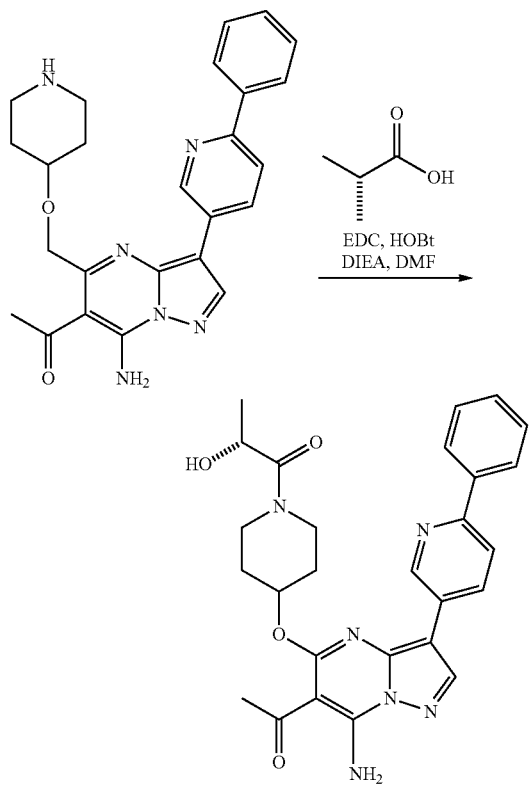

SCHEME-40

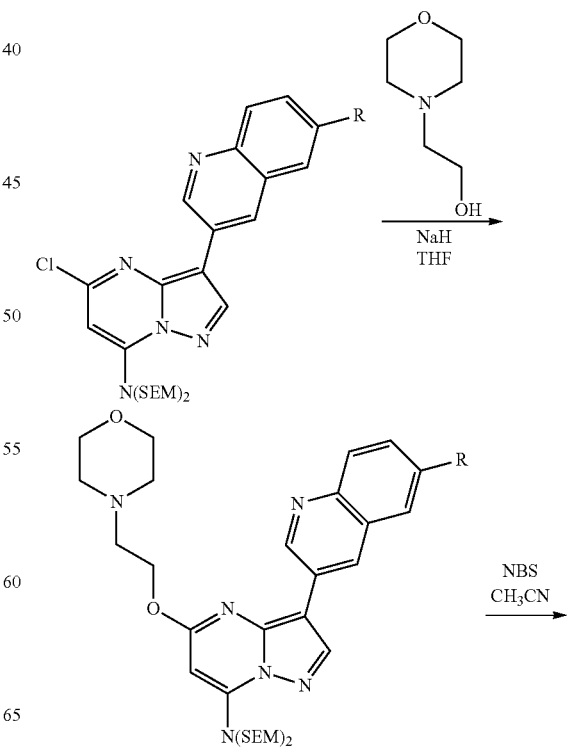

1325
-continued
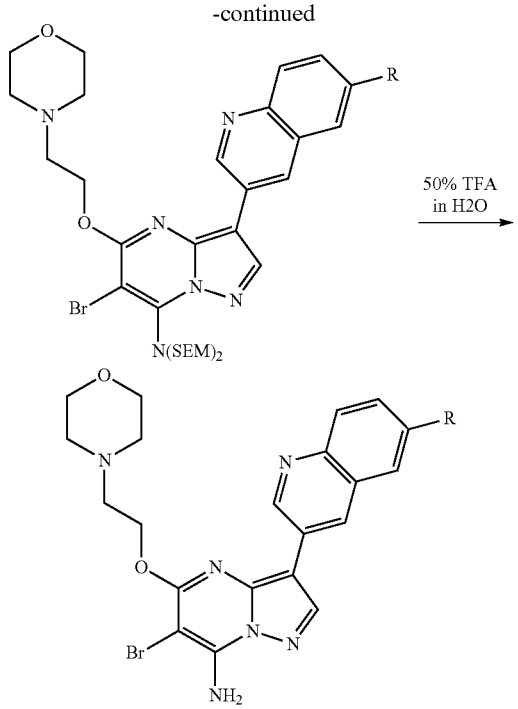
R = H or F
By essentially the same procedure given in Preparative Examples above and scheme-40, compounds 10.162 and 10.163 can be prepared (Table-10-M).
1326
SCHEME-41
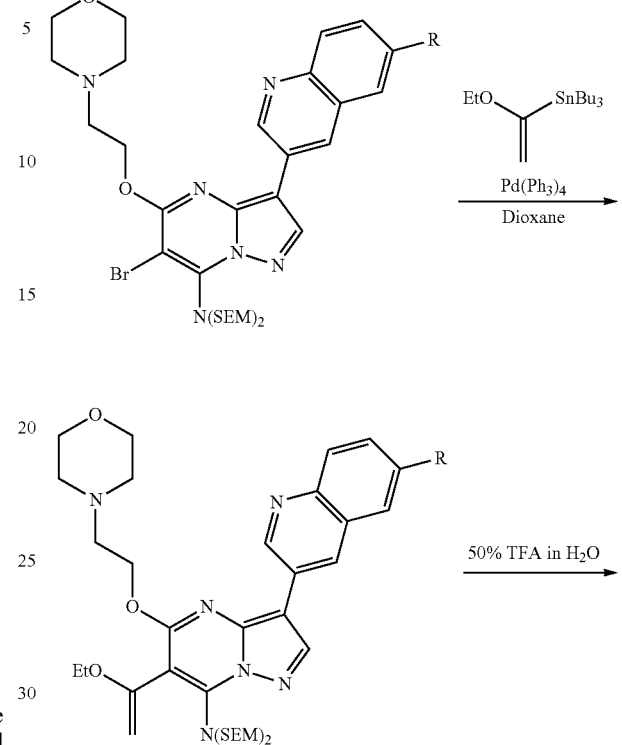
TABLE-10-M
| Compound No. | Structures | FW | M + H | Retention Time, 5 min method (min) |
|---|---|---|---|---|
| 10.162 | 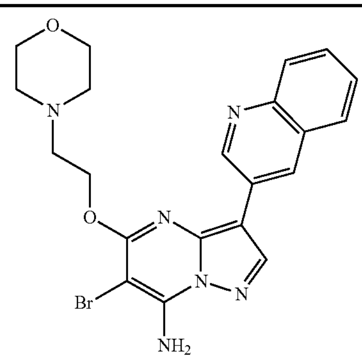 | 468.0 | 469.1 | 2.02 |
| 10.163 | 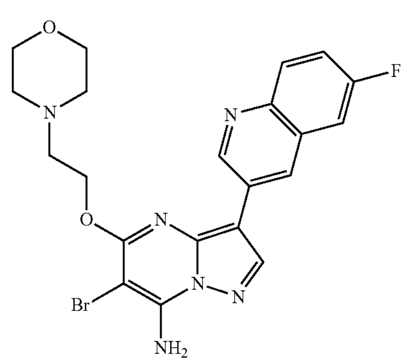 [SMILES: Nc1c(Br)c(OCCN2CCOCC2)nc2c(-c3cnc4ccc(F)cc4c3)cnn12] | 486.0 | 487.0 | 2.88 |

1327
-continued

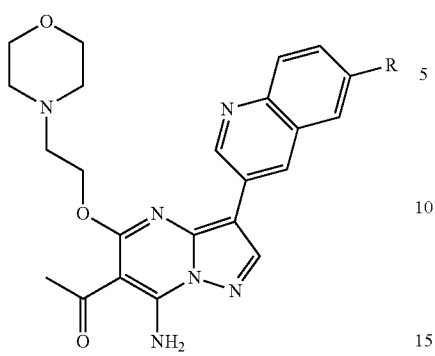

By essentially the same procedure given in Preparative Example (Scheme-41), 10.164 and 10.165 can be prepared. (Table-10-N)

1328
Synthesis of tert-butyl 4-(2-methoxy-2-oxoethyl)piperidine-1-carboxylate

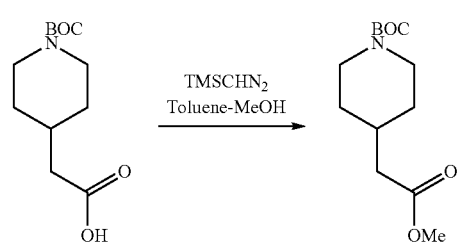

At 0° C., TMSCHN$_2$ (2.0 M in ether, 15 mL) was added dropwise to a mixture of 2-(1-(tert-butoxycarbonyl)piperidin-4-yl)acetic acid (6272 mg, 25.78 mmoL) in Toluene (60 mL) and MeOH (60 mL). After stirring at room temperature for 1 h, the mixture was concentrated. The crude tert-butyl

TABLE-10-N

| Compound No. | Structures | FW | M + H | Retention Time, 5 min method (min) |
|---|---|---|---|---|
| 10.164 | 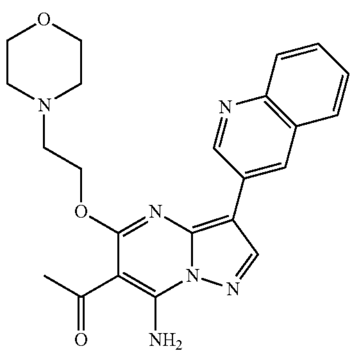 [SMILES: CC(=O)c1c(OCCN2CCOCC2)nc2c(-c3cnc4ccccc4c3)cnn2c1N] | 432.1 | 433.1 | 2.45 |
| 10.165 | 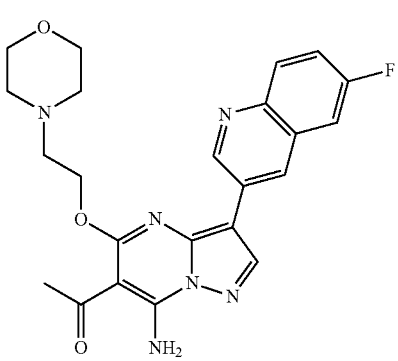 [SMILES: CC(=O)c1c(OCCN2CCOCC2)nc2c(-c3cnc4ccc(F)cc4c3)cnn2c1N] | 450.1 | 451.1 | 2.84 |

4-(2-methoxy-2-oxoethyl)piperidine-1-carboxylate was used as it is without further purification.

tert-butyl 4-((7-(bis((2-(trimethylsilyl)ethoxy)methyl)amino)pyrazolo[1,5-a]pyrimidin-5-yl)methyl)piperidine-1-carboxylate

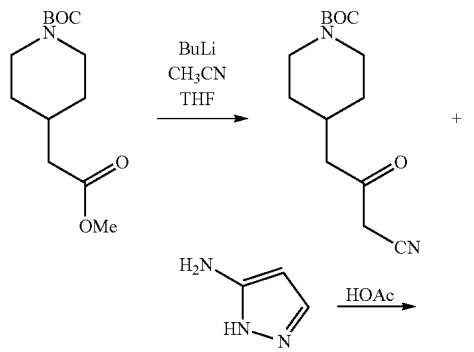

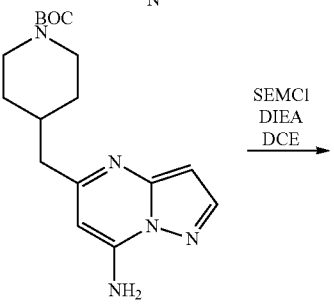

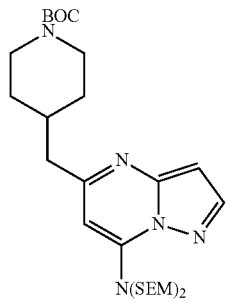

tert-butyl 4-(3-cyano-2-oxopropyl)piperidine-1-carboxylate

At −78° C., CH₃CN in THF (1505 uL, 28.82 mmoL) was added dropwise to BuLi (2.5 M in hexane, 11.52 mL) in THF (40 mL). After stirring at −78° C. for 1 h, tert-butyl 4-(2-methoxy-2-oxoethyl)piperidine-1-carboxylate (3708 mg, 14.41 mmoL) in THF (10 mL) was added dropwise in 5 min. The mixture was stirred at −78° C. for 1 h and −45° C. for 1 h. At 0° C., 1N HCl was added carefully to adjust the pH to about 7. The mixture was then extracted with ethyl acetate (×2). The combined organic layers were washed with brine and dried with Na₂SO₄. Evaporation afforded tert-butyl 4-(3-cyano-2-oxopropyl)piperidine-1-carboxylate.

tert-butyl 4-((7-aminopyrazolo[1,5-a]pyrimidin-5-yl)methyl)piperidine-1-carboxylate The crude tert-butyl 4-(3-cyano-2-oxopropyl)piperidine-1-carboxylate was then heated at 100° C. overnight with 1H-pyrazol-5-amine (1197 mg, 14.41 mmoL) in HOAc (25 mL). Concentration provided crude tert-butyl 4-((7-aminopyrazolo[1,5-a]pyrimidin-5-yl)methyl)piperidine-1-carboxylate.

tert-butyl 4-((7-(bis((2-(trimethylsilyl)ethoxy)methyl)amino)pyrazolo[1,5-a]pyrimidin-5-yl)methyl)piperidine-1-carboxylate The amino analog was treated with SEMCl (72.05 mmoL, 12.71 mL) and DIEA (144.4 mmoL, 25.05 mL) in DCE (100 mL) at 50° C. for 1 h. The mixture was diluted with H₂O and then extracted with CH₂Cl₂ (×2). The combined organic layers were washed with brine and dried with Na₂SO₄. Evaporation and purification by column chromatography afforded tert-butyl 4-((7-(bis((2-(trimethylsilyl)ethoxy)methyl)amino)pyrazolo[1,5-a]pyrimidin-5-yl)methyl)piperidine-1-carboxylate: LCMS $t_R$=3.05 Min (5 min run, $UV_{254nm}$). Mass calculated for, M+ 591.3, observed LC/MS m/z 592.3 (M+H).

Synthesis of tert-butyl 4-((7-(bis((2-(trimethylsilyl)ethoxy)methyl)amino)-3-(6-phenylpyridin-3-yl)pyrazolo[1,5-a]pyrimidin-5-yl)methyl)piperidine-1-carboxylate

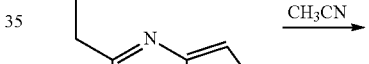
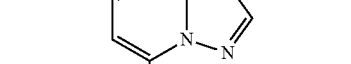
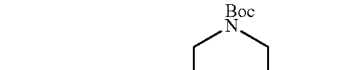
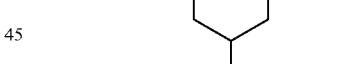
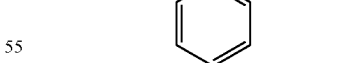
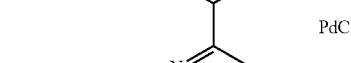
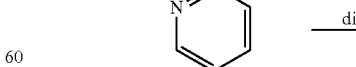
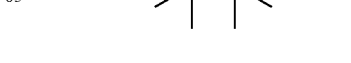

1331

-continued tert-butyl 4-((7-(bis((2-(trimethylsilyl)ethoxy)methyl)amino)-3-iodopyrazolo[1,5-a]pyrimidin-5-yl)methyl)piperidine-1-carboxylate NIS (288 mg, 1.28 mmoL) as added to a solution of tert-butyl 4-((7-(bis((2-(trimethylsilyl)ethoxy)methyl)amino)pyrazolo[1,5-a]pyrimidin-5-yl)methyl)piperidine-1-carboxylate (741.6 mg, 1.25 mmoL) in $CH_3CN$ (10 mL). The mixture was stirred at room temperature for 1 h. Purification by column chromatography afforded tert-butyl 4-((7-(bis((2-(trimethylsilyl)ethoxy)methyl)amino)-3-iodopyrazolo[1,5-a]pyrimidin-5-yl)methyl)piperidine-1-carboxylate: LCMS $t_R$=3.02 Min (5 min run, $UV_{254nm}$). Mass calculated for, M+ 717.2, observed LC/MS m/z 718.3 (M+H).

tert-butyl 4-((7-(bis((2-(trimethylsilyl)ethoxy)methyl)amino)-3-(6-phenylpyridin-3-yl)pyrazolo[1,5-a]pyrimidin-5-yl)methyl)piperidine-1-carboxylate 2-phenyl-5-(4,4,5,5-tetramethyl-1,3,2-dioxaborolan-2-yl)pyridine (1.32 mmol, 370 mg), $K_3PO_4$ (3.04 mmol, 644 mg), and $PdCl_2(dppf).CH_2Cl_2$ (0.10 mmol, 83 mg) were added to a solution of tert-butyl 4-((7-(bis((2-(trimethylsilyl)ethoxy)methyl)amino)-3-iodopyrazolo[1,5-a]pyrimidin-5-yl)methyl)piperidine-1-carboxylate (1.02 mmol, 726 mg) in dioxane (6 mL) and $H_2O$ (1 mL). The resulting solution was stirred at 100° C. under argon for 18 hours. The mixture was diluted with $H_2O$ and then extracted with ethyl acetate (×2). The combined organic layers were washed with brine and dried with $Na_2SO_4$. Evaporation and purification by column chromatography afforded tert-butyl 4-((7-(bis((2-(trimethylsilyl)ethoxy)methyl)amino)-3-(6-phenylpyridin-3-yl)pyrazolo[1,5-a]pyrimidin-5-yl)methyl)piperidine-1-carboxylate: LCMS $t_R$=3.47 Min (5 min run, $UV_{254nm}$). Mass calculated for, M+ 744.2, observed LC/MS m/z 745.2 (M+H).

1332

(R)-1-(4-((7-amino-6-bromo-3-(6-phenylpyridin-3-yl) pyrazolo[1,5-a]pyrimidin-5-yl)methyl)piperidin-1-yl)-2-hydroxypropan-1-one

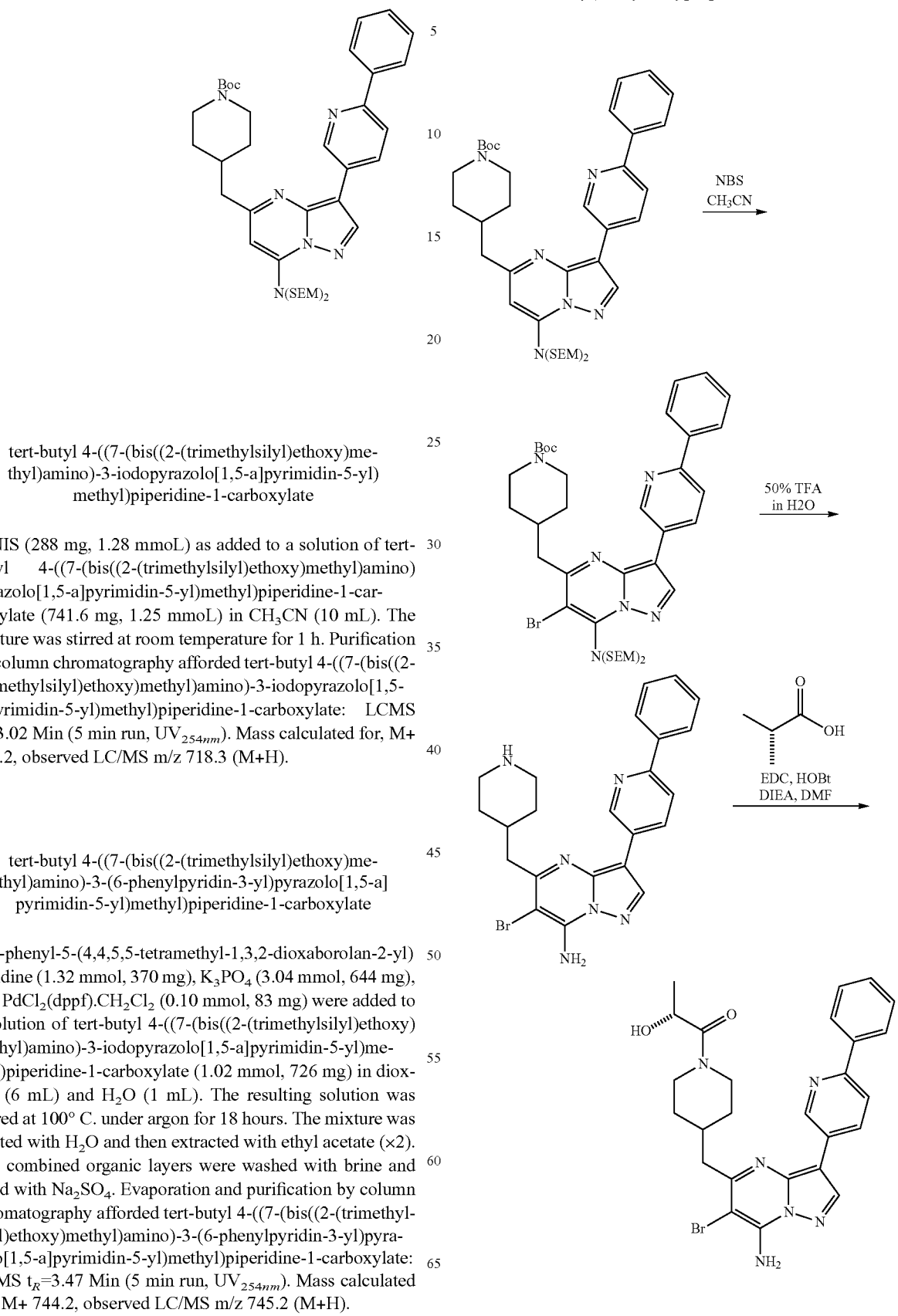

1333

By essentially the same procedure given in Preparative Example above, (R)-1-(4-((7-amino-6-bromo-3-(6-phenylpyridin-3-yl)pyrazolo[1,5-a]pyrimidin-5-yl)methyl)piperidin-1-yl)-2-hydroxypropan-1-one can be prepared. LCMS $t_R$=3.58 Min (10 min run, $UV_{254nm}$). Mass calculated for, M+ 534.13, observed LC/MS m/z 535.55 (M+H).

(R)-1-(4-((6-acetyl-7-amino-3-(6-phenylpyridin-3-yl)pyrazolo[1,5-a]pyrimidin-5-yl)methyl)piperidin-1-yl)-2-hydroxypropan-1-one

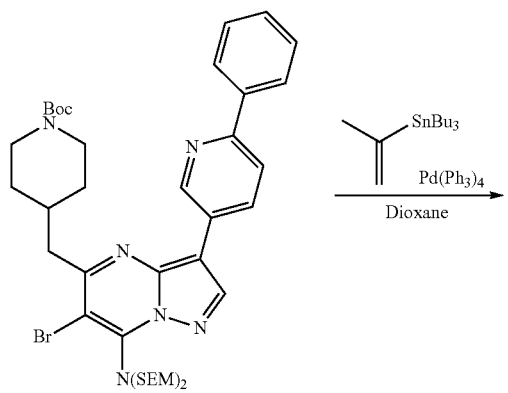

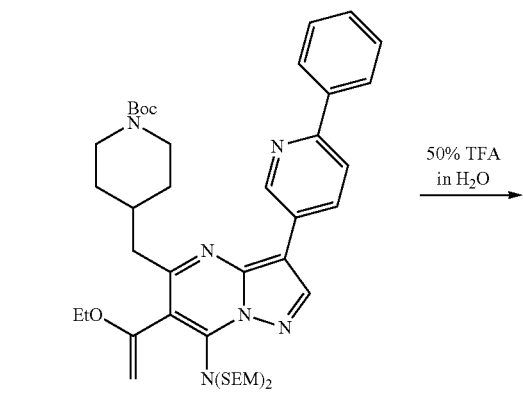

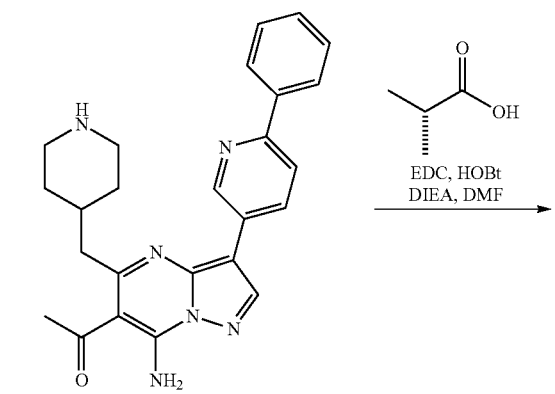

1334

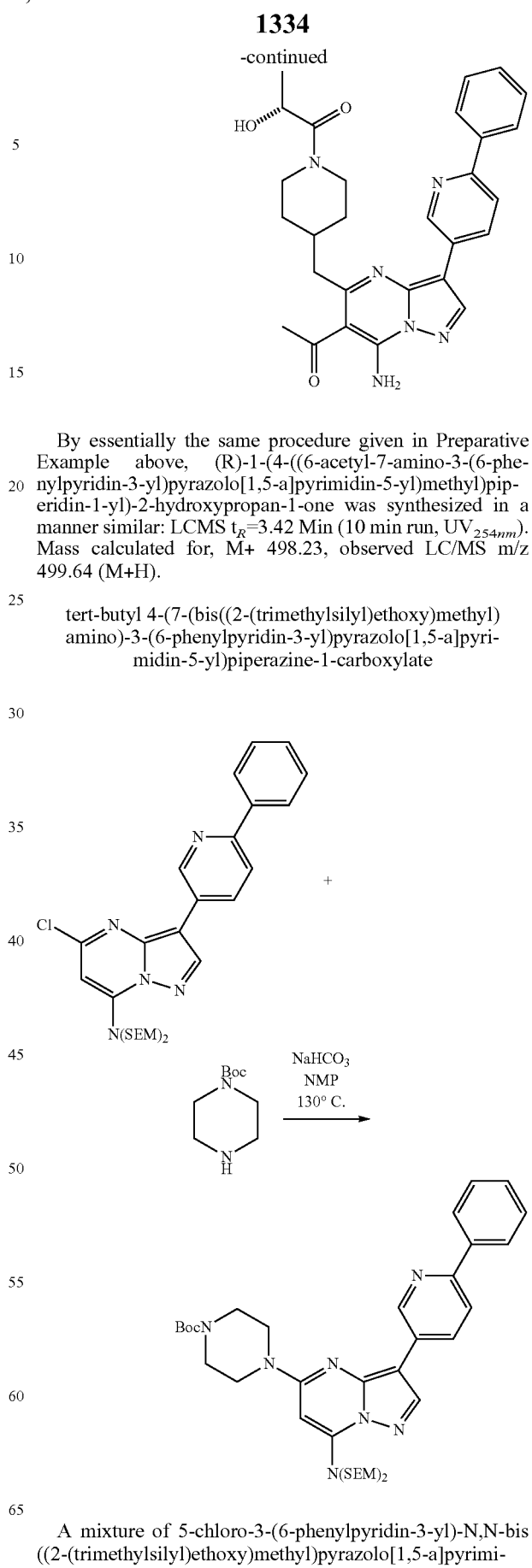

By essentially the same procedure given in Preparative Example above, (R)-1-(4-((6-acetyl-7-amino-3-(6-phenylpyridin-3-yl)pyrazolo[1,5-a]pyrimidin-5-yl)methyl)piperidin-1-yl)-2-hydroxypropan-1-one was synthesized in a manner similar: LCMS $t_R$=3.42 Min (10 min run, $UV_{254nm}$). Mass calculated for, M+ 498.23, observed LC/MS m/z 499.64 (M+H).

tert-butyl 4-(7-(bis((2-(trimethylsilyl)ethoxy)methyl)amino)-3-(6-phenylpyridin-3-yl)pyrazolo[1,5-a]pyrimidin-5-yl)piperazine-1-carboxylate A mixture of 5-chloro-3-(6-phenylpyridin-3-yl)-N,N-bis((2-(trimethylsilyl)ethoxy)methyl)pyrazolo[1,5-a]pyrimidin-7-amine (200 mg, 0.34 mmoL), tert-butyl piperazine-1-carboxylate (224 mg, 1.20 mmoL) and NaHCO3 (116 mg, 1.38 mmoL) in NMP (5 mL) was heated at 130° C. overnight. The mixture was diluted with $H_2O$ and then extracted with ethyl acetate (×2). The combined organic layers were washed with brine and dried with $Na_2SO_4$. Evaporation and purification by column chromatography afforded tert-butyl 4-(7-(bis((2-(trimethylsilyl)ethoxy)methyl)amino)-3-(6-phenylpyridin-3-yl)pyrazolo[1,5-a]pyrimidin-5-yl)piperazine-1-carboxylate: LCMS $t_R$=3.04 Min (5 min run, $UV_{254nm}$). Mass calculated for, M+ 731.4, observed LC/MS m/z 732.4 (M+H).

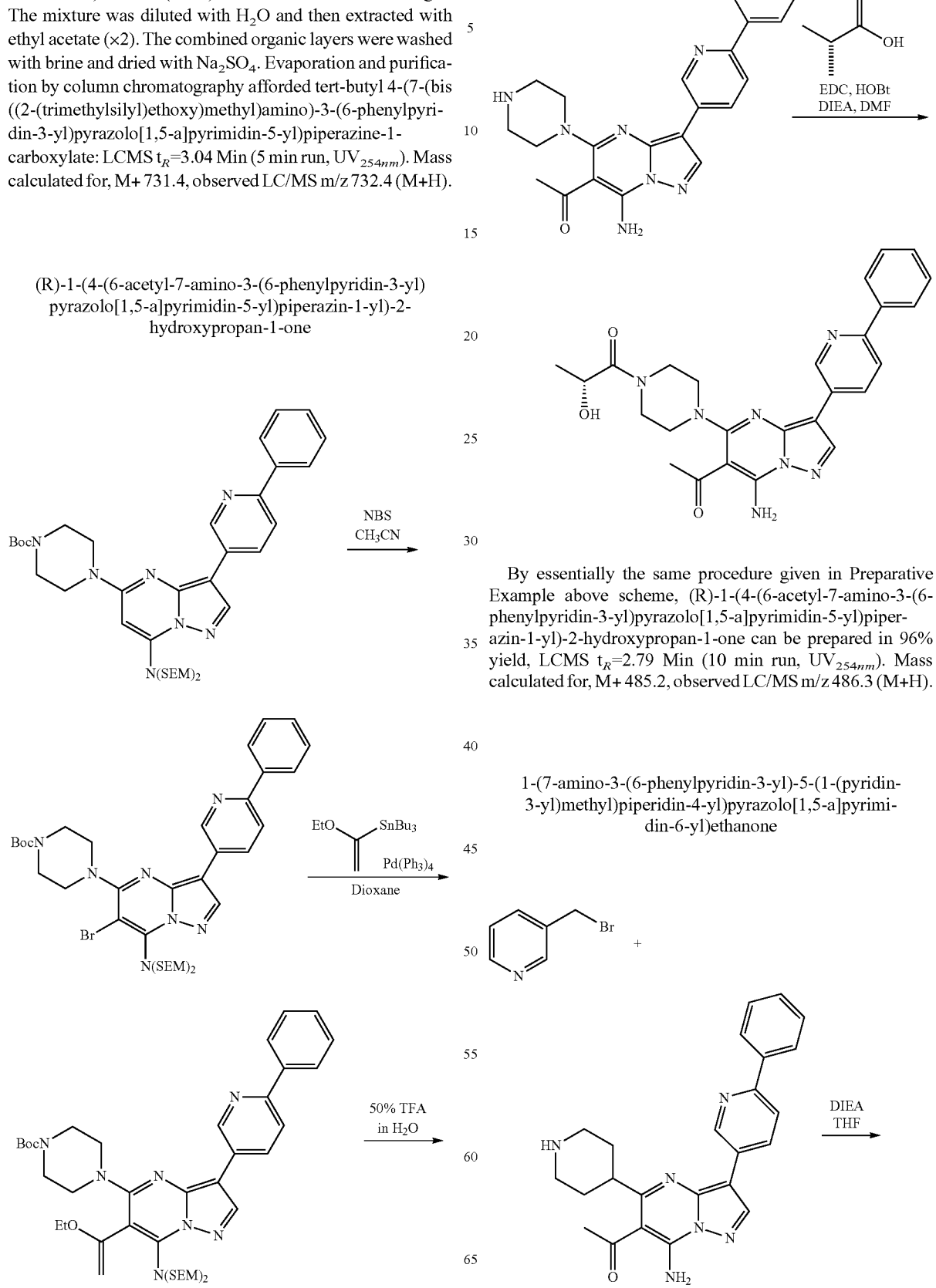

By essentially the same procedure given in Preparative Example above scheme, (R)-1-(4-(6-acetyl-7-amino-3-(6-phenylpyridin-3-yl)pyrazolo[1,5-a]pyrimidin-5-yl)piperazin-1-yl)-2-hydroxypropan-1-one can be prepared in 96% yield, LCMS $t_R$=2.79 Min (10 min run, $UV_{254nm}$). Mass calculated for, M+ 485.2, observed LC/MS m/z 486.3 (M+H).

1-(7-amino-3-(6-phenylpyridin-3-yl)-5-(1-(pyridin-3-yl)methyl)piperidin-4-yl)pyrazolo[1,5-a]pyrimidin-6-yl)ethanone

1337

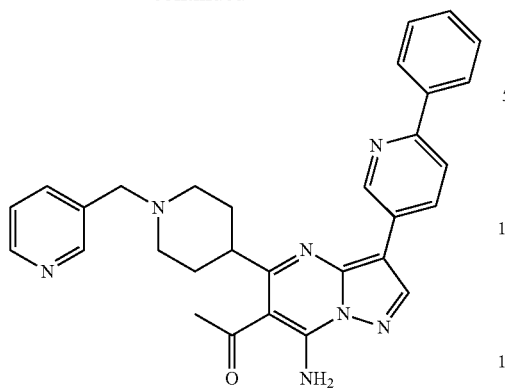

A mixture of 1-(7-amino-3-(6-phenylpyridin-3-yl)-5-(piperidin-4-yl)pyrazolo[1,5-a]pyrimidin-6-yl)ethanone (0.049 mmol, 20 mg), 3-(bromomethyl)pyridine (0.049 mmol, 12 mg) and DIEA (0.29 mmol, 37 mg) in THF (2 mL) was stirred at room temperature overnight. Concentration and purification by prep-LC afforded 1-(7-amino-3-(6-phenylpyridin-3-yl)-5-(1-(pyridin-3-ylmethyl)piperidin-4-yl)pyrazolo[1,5-a]pyrimidin-6-yl)ethanone: LCMS $t_R$=2.71 Min (10 min run, $UV_{254nm}$). Mass calculated for, M+ 503.24, observed LC/MS m/z 503.99 (M+H).

1-(7-amino-5-(1-(morpholinosulfonyl)piperidin-4-yl)-3-(6-phenylpyridin-3-yl)pyrazolo[1,5a]pyrimidin-6-yl)ethanone

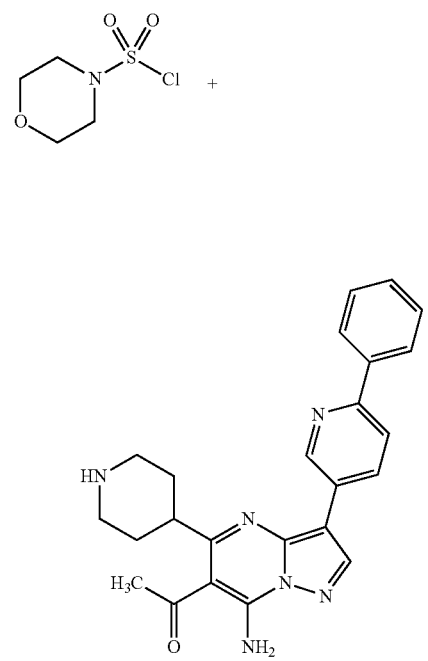

1338

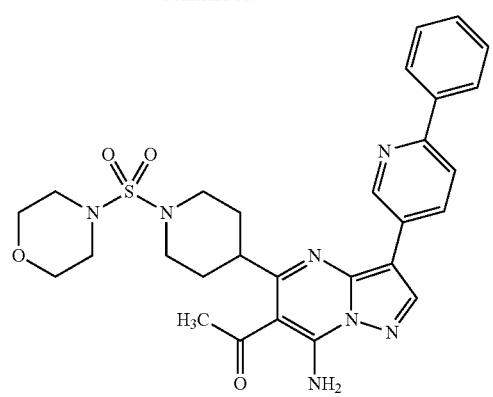

DIEA (121 mg, 0.94 mmoL) was added to at 0° C. a mixture of 1-(7-amino-3-(6-phenylpyridin-3-yl)-5-(piperidin-4-yl)pyrazolo[1,5-a]pyrimidin-6-yl)ethanone (64.3 mg, 0.15 mmoL) and morpholine-4-sulfonyl chloride (28.9 mg, 0.15 mmol) in DMF (3 mL). After stirring at 0° C. for 0.5 h and then room temperature for 2 h, the mixture was purified by prep-LC to afford 1-(7-amino-5-(1-(morpholinosulfonyl)piperidin-4-yl)-3-(6-phenylpyridin-3-yl)pyrazolo[1,5-a]pyrimidin-6-yl)ethanone, LCMS $t_R$=3.83 Min (5 min run, $UV_{254nm}$). Mass calculated for, M+ 561.66, observed LC/MS m/z 567.66 (M+H).

Synthesis of tert-butyl 4-(7-amino-6-bromo-3-(quinolin-3-yl)pyrazolo[1,5-a]pyrimidin-5-yl)piperazine-1-carboxylate

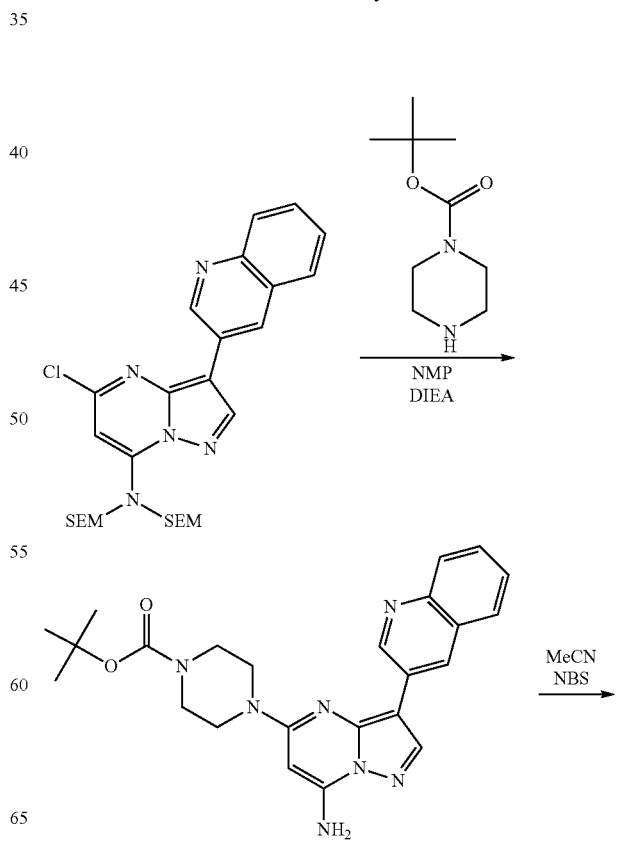

1339

-continued

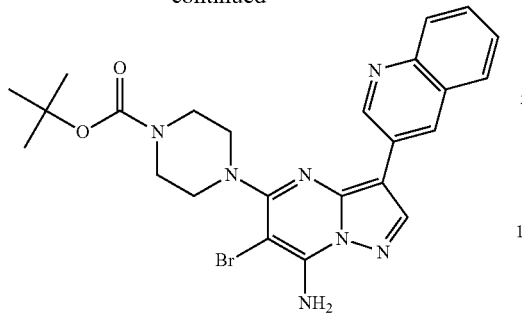

To a 20 mL scintillation vial was charged 5-chloro-3-(quinolin-3-yl)-N,N-bis((2-(trimethylsilyl)-ethoxy)methyl)pyrazolo[1,5-a]pyrimidin-7-amine (0.09 mmol, 50 mg), NMP (1 mL), N,N-diisopropylethylamine (0.36 mmol, 63 µL), and 4-N-Boc-piperazine (0.27 mmol, 50 mg). The resulting solution was heated to 200° C. in microwave synthesizer for 30 minutes. Upon completion, the NMP was removed in vacuo as an azeotrope using chlorobenzene. This residue was dissolved in acetonitrile (1 mL) to which N-bromosuccinimide (0.10 mmol, 17.7 mg) was added. This reaction mixture was allowed to stir at room temperature for 2 hours. The reaction mixture was concentrated in vacuo and tert-butyl 4-(7-amino-6-bromo-3-(quinolin-3-yl)pyrazolo[1,5-a]pyrimidin-5-yl)piperazine-1-carboxylate used without further purification.

Synthesis of 6-chloro-5-(piperazin-1-yl)-3-(quinolin-3-yl)pyrazolo[1,5-a]pyrimidin-7-amine

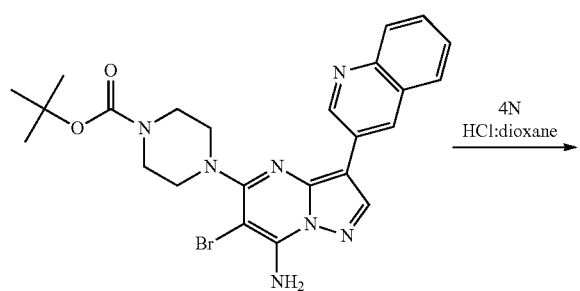

tert-Butyl 4-(7-amino-6-bromo-3-(quinolin-3-yl)pyrazolo[1,5-a]pyrimidin-5-yl)piperazine-1-carboxylate (0.09 mmol) was charged to a 20 mL scintillation vial. To this vial was added 4N HCl in 1,4-dioxane. The reaction mixture was stirred at room temperature for 1 hour. The reaction mixture was concentrated in vacuo and 6-chloro-5-(piperazin-1-yl)-3-(quinolin-3-yl)pyrazolo[1,5-a]pyrimidin-7-amine was used without further purification.

1340

Synthesis of (4-(7-amino-6-chloro-3-(quinolin-3-yl)pyrazolo[1,5-a]pyrimidin-5-yl)piperazin-1-yl)(thiophen-2-yl)methanone

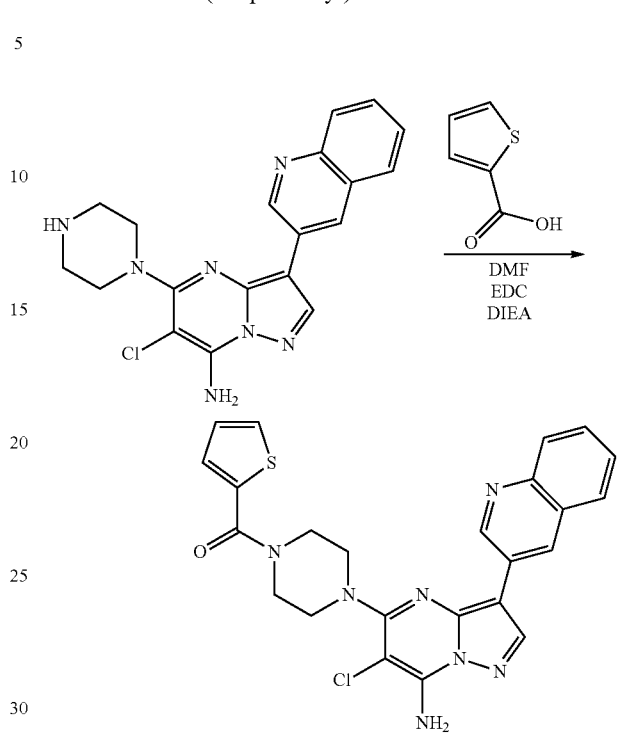

(4-(7-Amino-6-chloro-3-(quinolin-3-yl)pyrazolo[1,5-a]pyrimidin-5-yl)piperazin-1-yl)(thiophen-2-yl)methanone was synthesized in a manner similar to the synthesis of (4-(7-amino-6-bromo-3-(quinolin-3-yl)pyrazolo[1,5-a]pyrimidin-5-yl)-5,6-dihydropyridin-1(2H)-yl)(thiophen-2-yl)methanone, but with 6-chloro-5-(piperazin-1-yl)-3-(quinolin-3-yl)pyrazolo[1,5-a]pyrimidin-7-amine substituted for 6-bromo-3-(quinolin-3-yl)-5-(1,2,3,6-tetrahydropyridin-4-yl)pyrazolo[1,5-a]pyrimidin-7-amine. The reaction was purified via reverse-phase preparatory HPLC to yield (4-(7-amino-6-chloro-3-(quinolin-3-yl)pyrazolo[1,5-a]pyrimidin-5-yl)piperazin-1-yl)(thiophen-2-yl)methanone as yellow solid. (M+H=490.19, retention time=3.75 min).

Scheme-42

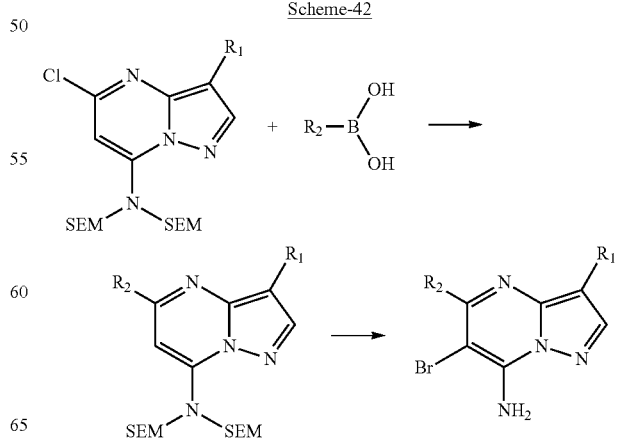

[4-(7-Amino-3-quinolin-3-yl-pyrazolo[1,5-a]pyrimidin-5-yl)-phenyl]-acetic acid

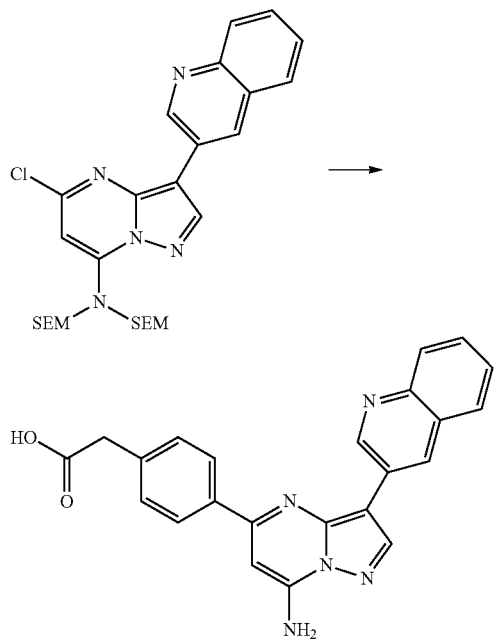

[4-(4,4,5,5-Tetramethyl-[1,3,2]dioxaborolan-2-yl)-phenyl]-acetic acid methyl ester (0.576 mmol, 160 mg), $K_3PO_4$ (0.864 mmol, 183 mg), and $PdCl_2(dppf) \cdot CH_2Cl_2$ (0.029 mmol, 24 mg) was added to a solution of (5-Chloro-3-quinolin-3-yl-pyrazolo[1,5-a]pyrimidin-7-yl)-bis-(2-trimethylsilanyl-ethoxymethyl)-amine (0.288 mmol, 160 mg) in dioxane (2 mL). To this suspension was added distilled $H_2O$ (0.2 mL). The resulting solution was stirred at 100° C. under an argon atmosphere for 18 hours. The reaction mixture was concentrated in vacuo. The crude mixture was dissolved in 2:1 MeOH:$H_2O$ (1.5 mL) and was treated with 2N NaOH$_{(aq)}$ (1.0 mL). The resulting solution was stirred at room temperature for 18 hours. Aqueous hydrochloride solution (1.0 N, 4 ml) was added to the reaction mixture and the resulting solution was stirred at 65° C. for 2 h. The reaction mixture was concentrated and purified by prep-LC to afford the title compound (70 mg, 62% yield): LC/MS RT=3.21 min. Mass calculated for, M+H 396.14, observed 396.14.

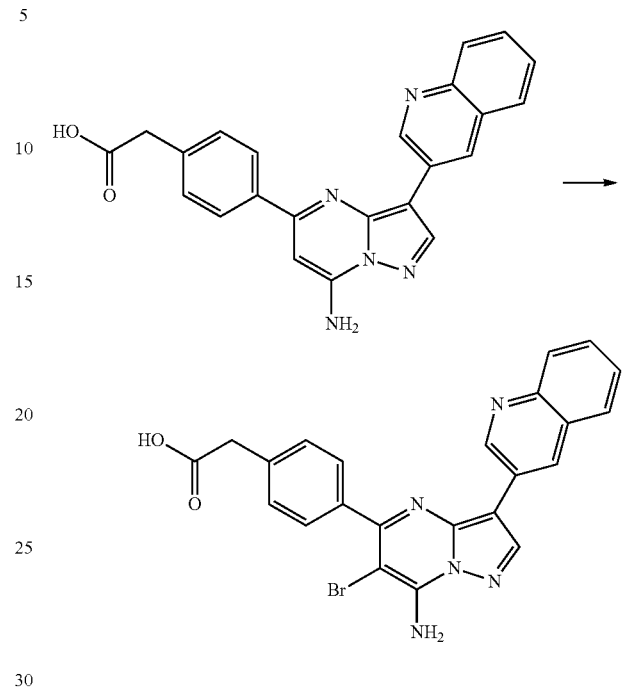

[4-(7-Amino-6-bromo-3-quinolin-3-yl-pyrazolo[1,5-a]pyrimidin-5-yl)-phenyl]-acetic acid A solution of NBS (32 mg, 0.179 mmol) in $CH_3CN$ (1 mL) was added to a mixture of [4-(7-amino-3-quinolin-3-yl-pyrazolo[1,5-a]pyrimidin-5-yl)-phenyl]-acetic acid (70 mg, 0.179 mmol) in $CH_3CN$ (3 mL). After stirring at room temperature for 1 h, the solvent was evaporated in vacuo and the residue was purified by prep-LC to afford titled compound (22.9 mg, 27%). LC/MS RT=3.44 min. Mass calculated for, M+H 474.05, observed 474.05.

By essentially the same procedure given in Scheme 42, the compounds listed in Table 11 can be prepared.

TABLE 11

| Compound ID | Structures | M + H (calc.) | M + H (observed) | Retention Time, (min) |
|---|---|---|---|---|
| 11.1 | 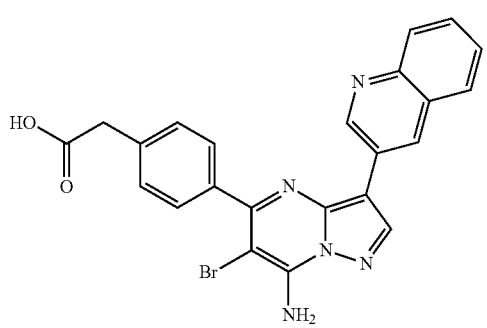 [SMILES: Nc1c(Br)c(-c2ccc(CC(=O)O)cc2)nc2c(-c3cnc4ccccc4c3)cnn12] | 474.05 | 474.05 | 3.44 |

TABLE 11-continued

| Compound ID | Structures | M + H (calc.) | M + H (observed) | Retention Time, (min) |
|---|---|---|---|---|
| 11.2 | 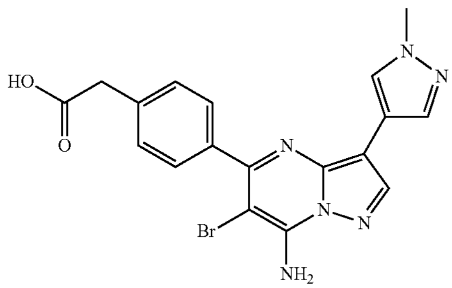 [SMILES: Cn1cc(-c2cnn3c(N)c(Br)c(-c4ccc(CC(=O)O)cc4)nc23)cn1] | 427.04 | 427.04 | 3.61 |
| 11.3 | 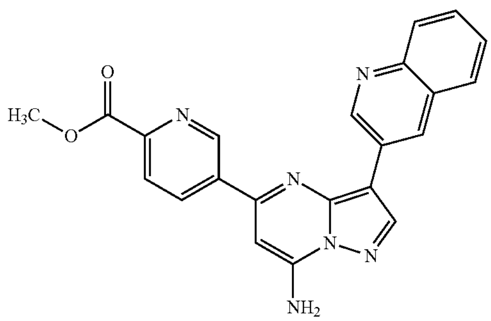 [SMILES: COC(=O)c1ccc(-c2cc(N)n3ncc(-c4cnc5ccccc5c4)c3n2)cn1] | 397.13 | 397.13 | 3.2 |
| 11.4 | 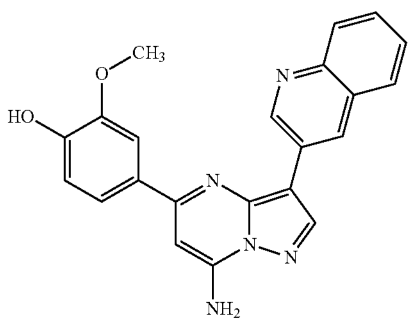 [SMILES: COc1cc(-c2cc(N)n3ncc(-c4cnc5ccccc5c4)c3n2)ccc1O] | 384.14 | 384.14 | 3.18 |
| 11.5 | 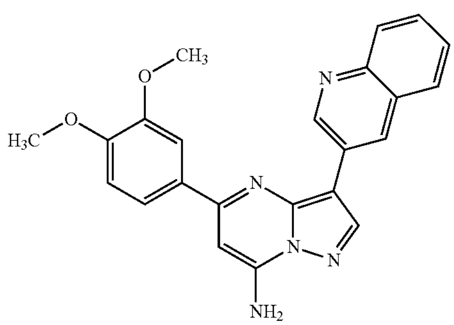 [SMILES: COc1ccc(-c2cc(N)n3ncc(-c4cnc5ccccc5c4)c3n2)cc1OC] | 398.15 | 398.15 | 3.57 |
| 11.6 | 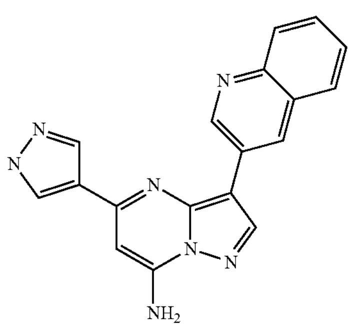 [SMILES: Nc1cc(-c2cn[nH]c2)nc2c(-c3cnc4ccccc4c3)cnn12] | 328.12 | 328.12 | 2.53 |

TABLE 11-continued

| Compound ID | Structures | M + H (calc.) | M + H (observed) | Retention Time, (min) |
| --- | --- | --- | --- | --- |
| 11.7 | 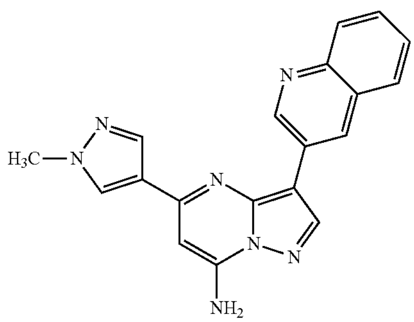 [SMILES: Cn1cc(-c2cc(N)n3ncc(-c4cnc5ccccc5c4)c3n2)cn1] | 342.14 | 342.14 | 2.83 |
| 11.8 | 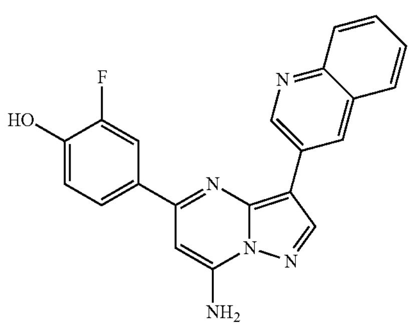 [SMILES: Nc1cc(-c2ccc(O)c(F)c2)nc2c(-c3cnc4ccccc4c3)cnn12] | 372.12 | 372.12 | 3.2 |
| 11.9 | 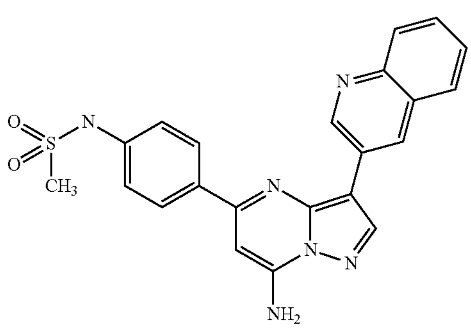 [SMILES: CS(=O)(=O)Nc1ccc(-c2cc(N)n3ncc(-c4cnc5ccccc5c4)c3n2)cc1] | 431.12 | 431.12 | 3.15 |
| 11.10 | 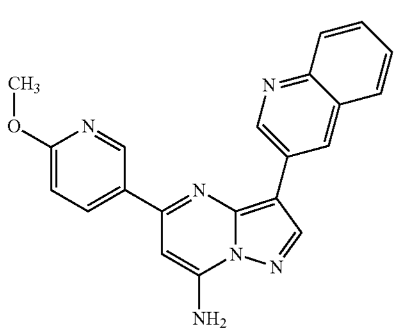 [SMILES: COc1ccc(-c2cc(N)n3ncc(-c4cnc5ccccc5c4)c3n2)cn1] | 369.14 | 369.14 | 3.49 |

TABLE 11-continued

| Compound ID | Structures | M + H (calc.) | M + H (observed) | Retention Time, (min) |
|---|---|---|---|---|
| 11.11 | 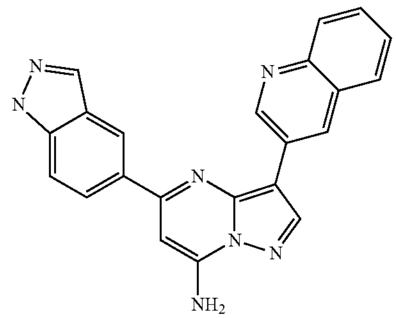 [SMILES: Nc1cc(-c2ccc3[nH]ncc3c2)nc2c(-c3cnc4ccccc4c3)cnn12] | 378.14 | 378.14 | 3.09 |

Synthesis of tert-butyl 4-(7-(bis((2-(trimethylsilyl)ethoxy)methyl)amino)-3-(quinolin-3-yl)pyrazolo[1,5-a]pyrimidin-5-yl)-5,6-dihydropyridine-1(2H)-carboxylate

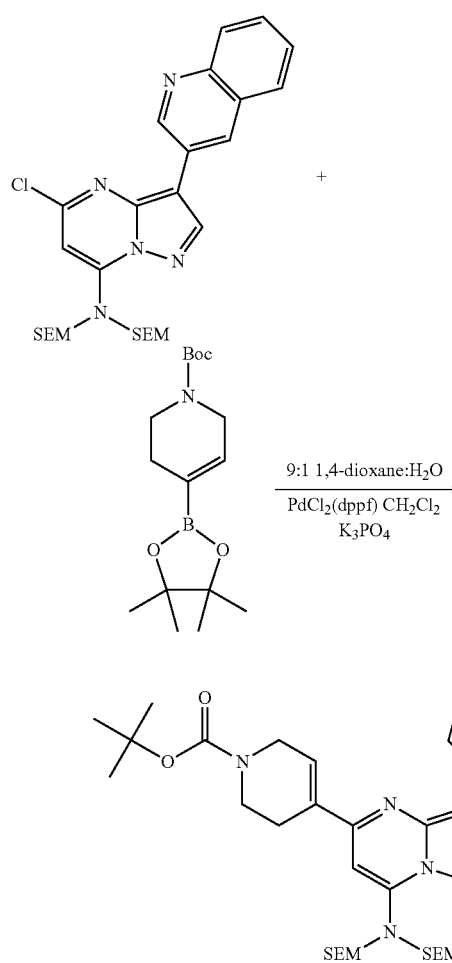

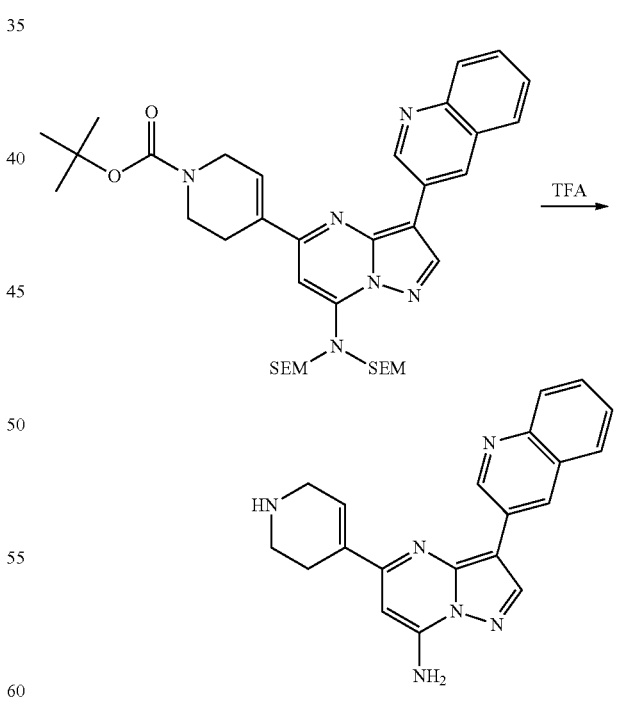

To a 40 mL scintillation vial was charged 5-chloro-3-(quinolin-3-yl)-N,N-bis((2-(trimethylsilyl)-ethoxy)methyl) pyrazolo[1,5-a]pyrimidin-7-amine (0.86 mmol, 480 mg), tert-butyl 4-(4,4,5,5-tetramethyl-1,3,2-dioxaborolan-2-yl)-5, 6-dihydropyridine-1(2H)-carboxylate (1.30 mmol, 400 mg), $K_3PO_4$ (2.60 mmol, 550 mg), and $PdCl_2(dppf).CH_2Cl_2$ (0.086 mmol, 70 mg). To this reaction mixture was added a 9:1 solution of 1,4-dioxane:$H_2O$ (10 mL). The vial was flushed with argon, sealed with Teflon tape, and stirred at 100° C. 18 hours. After 18 hours, the reaction was concentrated in vacuo and the residue purified via silica gel chromatography to yield tert-butyl 4-(7-(bis((2-(trimethylsilyl)ethoxy)methyl)amino)-3-(quinolin-3-yl)pyrazolo[1,5-a]pyrimidin-5-yl)-5,6-dihydropyridine-1(2H)-carboxylate (586 mg, 833 mmol, 97% yield) as yellow solid.

Synthesis of 3-(quinolin-3-yl)-5-(1,2,3,6-tetrahydropyridin-4-yl)pyrazolo[1,5-a]pyrimidin-7-amine tert-Butyl 4-(7-(bis((2-(trimethylsilyl)ethoxy)methyl)amino)-3-(quinolin-3-yl)pyrazolo[1,5-a]pyrimidin-5-yl)-5,6-dihydropyridine-1(2H)-carboxylate (0.057 mmol, 40 mg) was charged to a 20 mL scintillation vial containing 1 mL TFA. The reaction mixture was stirred at room temperature. The reaction mixture was concentrated in vacuo and purified

1349 via reverse-phase preparatory HPLC to yield 3-(quinolin-3-yl)-5-(1,2,3,6-tetrahydropyridin-4-yl)pyrazolo[1,5-a]pyrimidin-7-amine (m+H=343.31, retention time=2.05 min)

Synthesis of 6-bromo-3-(quinolin-3-yl)-5-(1,2,3,6-tetrahydropyridin-4-yl)pyrazolo[1,5-a]pyrimidin-7-amine

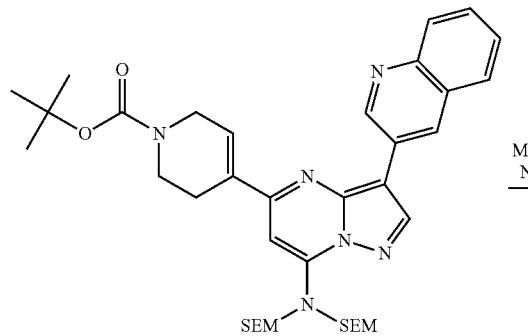

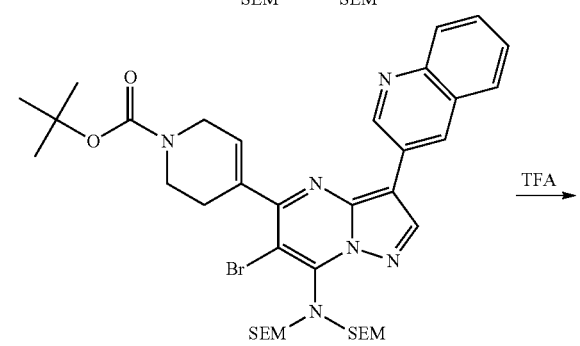

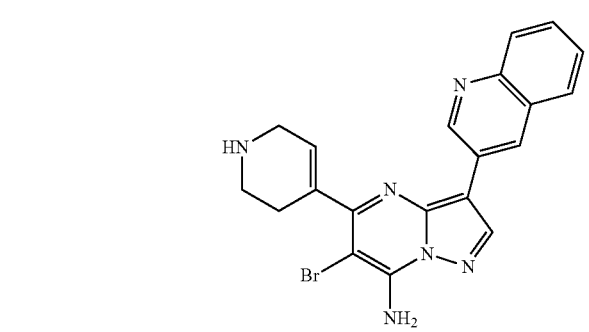

tert-Butyl 4-(7-(bis((2-(trimethylsilyl)ethoxy)methyl)amino)-3-(quinolin-3-yl)pyrazolo[1,5-a]pyrimidin-5-yl)-5,6-dihydropyridine-1(2H)-carboxylate (0.071 mmol, 50 mg) was charged to a 20 mL scintillation vial containing 1 mL acetonitrile. To this solution was added N-bromosuccinimide (0.078 mmol, 14 mg). The reaction mixture was allowed to stir at room temperature for 1 hour. After 1 hour, the reaction was concentrated in vacuo and the crude intermediate was dissolved in 1 mL TFA. The reaction mixture was stirred for 1 hour at room temperature and concentrated in vacuo to yield 6-bromo-3-(quinolin-3-yl)-5-(1,2,3,6-tetrahydropyridin-4-yl)pyrazolo[1,5-a]pyrimidin-7-amine as yellow solid.

1350

Synthesis of 6-chloro-3-(quinolin-3-yl)-5-(1,2,3,6-tetrahydropyridin-4-yl)pyrazolo[1,5-a]pyrimidin-7-amine

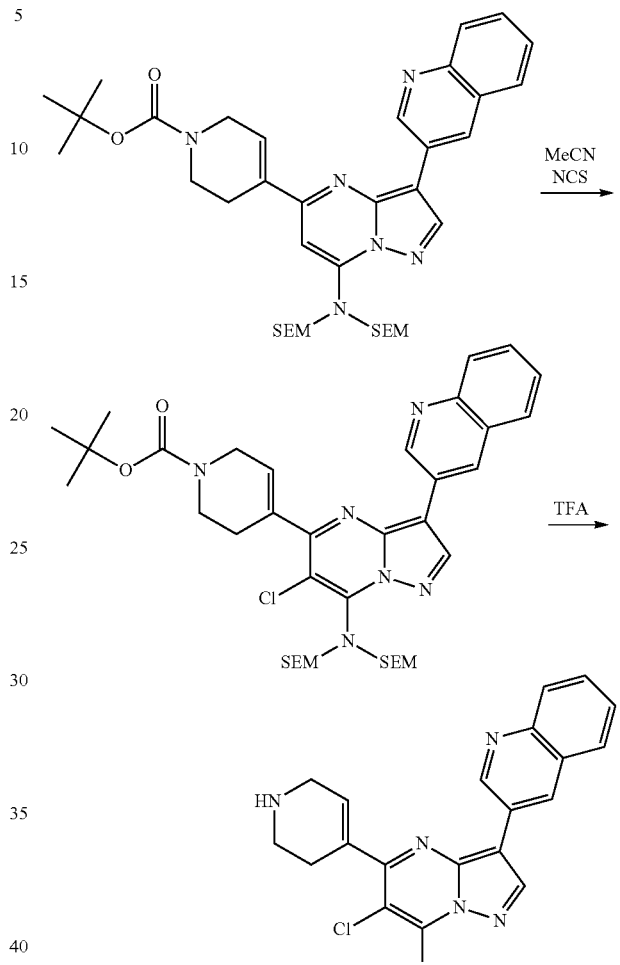

6-Chloro-3-(quinolin-3-yl)-5-(1,2,3,6-tetrahydropyridin-4-yl)pyrazolo[1,5-a]pyrimidin-7-amine was synthesized in a manner similar to the synthesis of 6-bromo-3-(quinolin-3-yl)-5-(1,2,3,6-tetrahydropyridin-4-yl)pyrazolo[1,5-a]pyrimidin-7-amine, but with N-chlorosuccinimide substituted for N-bromosuccinimide.

Synthesis of 2-(4-(7-amino-6-bromo-3-(quinolin-3-yl)pyrazolo[1,5-a]pyrimidin-5-yl)-5,6-dihydropyridin-1(2H)-yl)acetic acid

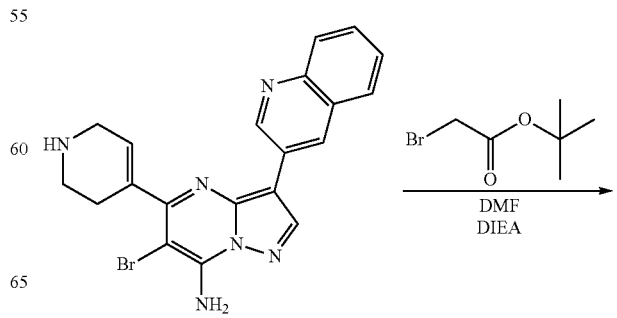

1351
-continued

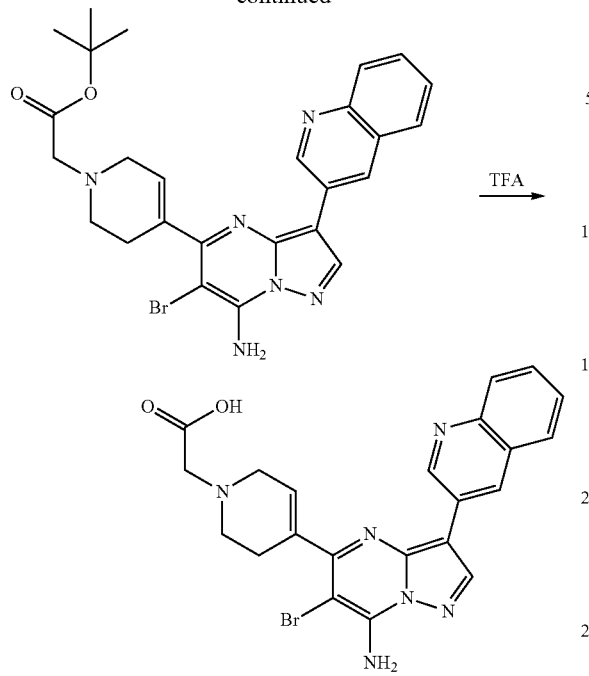

1352
-continued

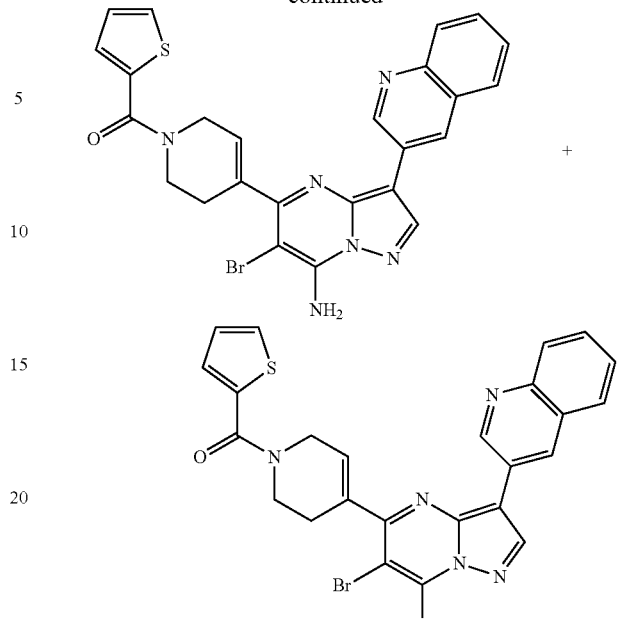

6-Bromo-3-(quinolin-3-yl)-5-(1,2,3,6-tetrahydropyridin-4-yl)pyrazolo[1,5-a]pyrimidin-7-amine (0.035 mmol) was charged to a 20 mL scintillation vial. Then DMF (1 ml), N,N-diisopropylethylamine (0.14 mmol, 25 µL), and tert-butyl 2-bromoacetate (0.035 mmol, 5.2 µL) were added, respectively. The resulting reaction mixture was stirred at 50° C. 18 hours. After 18 hours, the reaction was concentrated in vacuo and treated with 1 mL TFA. This reaction mixture was stirred at room temperature for 2 hours. The reaction mixture was concentrated in vacuo and purified via reverse-phase preparatory HPLC to yield 2-(4-(7-amino-6-bromo-3-(quinolin-3-yl)pyrazolo[1,5-a]pyrimidin-5-yl)-5,6-dihydropyridin-1(2H)-yl)acetic acid as yellow solid. (m+H=479.17, retention time=2.09 min)

Synthesis of (4-(7-amino-6-bromo-3-(quinolin-3-yl)pyrazolo[1,5-a]pyrimidin-5-yl)-5,6-dihydropyridin-1(2H)-yl)(thiophen-2-yl)methanone and (4-(7-amino-3-(quinolin-3-yl)pyrazolo[1,5-a]pyrimidin-5-yl)-5,6-dihydropyridin-1(2H)-yl)(thiophen-2-yl)methanone 6-Bromo-3-(quinolin-3-yl)-5-(1,2,3,6-tetrahydropyridin-4-yl)pyrazolo[1,5-a]pyrimidin-7-amine (0.035 mmol) was charged to a 20 mL scintillation vial. Then DMF (1 ml), N,N-diisopropylethylamine (0.14 mmol, 25 µL), thiophene-2-carboxylic acid (0.039 mmol, 5 mg), and EDC (0.039 mmol, 7.4 mg) were added, respectively. The resulting reaction mixture was stirred at room temperature for 18 hours. Upon completion, the reaction mixture was concentrated in vacuo and purified via reverse-phase preparatory HPLC to yield (4-(7-amino-6-bromo-3-(quinolin-3-yl)pyrazolo[1,5-a]pyrimidin-5-yl)-5,6-dihydropyridin-1(2H)-yl)(thiophen-2-yl)methanone (m+H=531.06, retention time=3.74 min). Also recovered was the dehalogenated product, (4-(7-amino-3-(quinolin-3-yl)pyrazolo[1,5-a]pyrimidin-5-yl)-5,6-dihydropyridin-1(2H)-yl)(thiophen-2-yl)methanone (m+H=453.24, retention time=3.51 min).

Synthesis of (4-(7-amino-6-chloro-3-(quinolin-3-yl)pyrazolo[1,5-a]pyrimidin-5-yl)-5,6-dihydropyridin-1(2H)-yl)(thiophen-2-yl)methanone

SCHEME-43

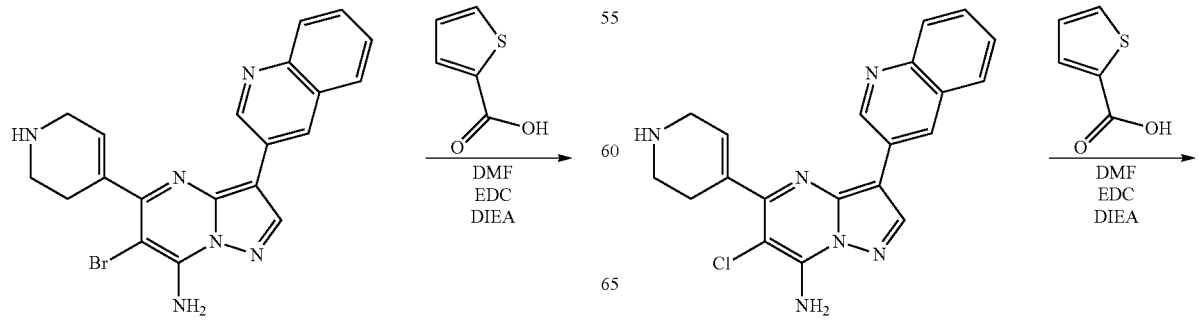

-continued

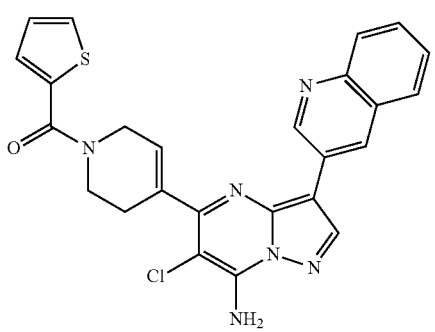

(4-(7-amino-6-chloro-3-(quinolin-3-yl)pyrazolo[1,5-a]pyrimidin-5-yl)-5,6-dihydropyridin-1(2H)-yl)(thiophen-2-yl)methanone was synthesized in a manner similar to the synthesis of (4-(7-amino-6-bromo-3-(quinolin-3-yl)pyrazolo[1,5-a]pyrimidin-5-yl)-5,6-dihydropyridin-1(2H)-yl)(thiophen-2-yl)methanone, but with 6-chloro-3-(quinolin-3-yl)-5-(1,2,3,6-tetrahydropyridin-4-yl)pyrazolo[1,5-a]pyrimidin-7-amine substituted for 6-bromo-3-(quinolin-3-yl)-5-(1,2,3,6-tetrahydropyridin-4-yl)pyrazolo[1,5-a]pyrimidin-7-amine. The reaction mixture was purified via reverse-phase preparatory HPLC to yield (4-(7-amino-6-chloro-3-(quinolin-3-yl)pyrazolo[1,5-a]pyrimidin-5-yl)-5,6-dihydropyridin-1(2H)-yl)(thiophen-2-yl)methanone as yellow solid. (m+H=487.17, retention time=3.73 min)

Synthesis of 4-bromo-1-((2-(trimethylsilyl)ethoxy)methyl)-1H-pyrazole

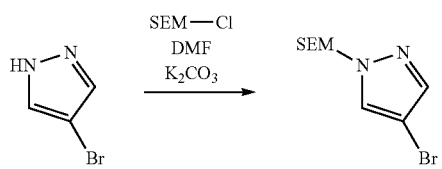 [SMILES: C[Si](C)(C)CCOCCl ; Brc1cn[nH]c1 ; C[Si](C)(C)CCOCn1cc(Br)cn1]

To a 100 mL roundbottom flask was charged 4-bromopyrazole (13.6 mmol, 2.00 g), K$_2$CO$_3$ (20.4 mmol, 2.82 g), and DMF (20 mL). To this suspension was added 2-(trimethylsilyl)ethoxymethyl chloride (15.0 mmol, 2.64 mL). This suspension was allowed to stir at room temperature 18 hours. The reaction mixture was then concentrated in vacuo, dissolved in 20 mL DCM, and filtered through celite. The crude mixture was purified via silica gel chromatography (0% to 80% ethyl acetate in hexanes gradient) to yield 4-bromo-1-((2-(trimethylsilyl)ethoxy)methyl)-1H-pyrazole (2.53 g, 9.12 mmol, 67% yield) as clear oil.

Synthesis of 4-(1,4-dioxaspiro[4.5]dec-7-en-8-yl)-1-(2-(trimethylsilyl)ethoxy)methyl)-1H-pyrazole

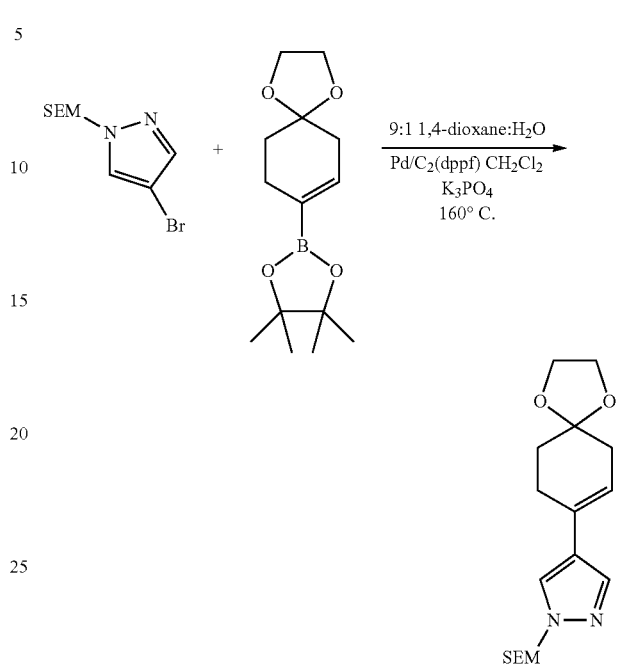

To a 10-20 mL microwave vessel was charged 4-bromo-1-((2-(trimethylsilyl)ethoxy)methyl)-1H-pyrazole (0.60 mmol, 166 mg), 4,4,5,5-tetramethyl-2-(1,4-dioxaspiro[4.5]dec-7-en-8-yl)-1,3,2-dioxaborolane (0.84 mmol, 224 mg), K$_3$PO$_4$ (1.80 mmol, 382 mg), PdCl$_2$(dppf).CH$_2$Cl$_2$ (0.06 mmol, 50 mg) and 9:1 Dioxane:H$_2$O (15 mL). The suspension was sonicated to break up salts, flushed with argon, sealed, and heated to 160° C. for 45 minutes in microwave synthesizer. The reaction was concentrated in vacuo, and the residue purified via silica gel chromatography (0% to 60% ethyl acetate in hexanes) to yield 4-(1,4-dioxaspiro[4.5]dec-7-en-8-yl)-1-((2-(trimethylsilyl)ethoxy)methyl)-1H-pyrazole (115 mg, 0.34 mmol, 57% yield) as clear oil.

Synthesis of 4-(1,4-dioxaspiro[4.5]decan-8-yl)-1-((2-(trimethylsilyl)ethoxy)methyl)-1H-pyrazole

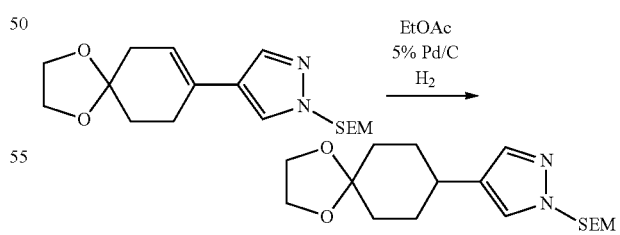

4-(1,4-Dioxaspiro[4.5]dec-7-en-8-yl)-1-((2-(trimethylsilyl)ethoxy)methyl)-1H-pyrazole (505 µmol, 170 mg) was dissolved in 10 mL EtOAc in a 50 mL roundbottom flask. The flask was flushed with argon and 5% palladium on carbon (50 mg) was added. The flask was sealed, degassed under vacuum, and hydrogen gas was added with a balloon. The reaction mixture was stirred at room temperature under hydrogen atmosphere for 18 hours. The reaction was then filtered through celite to yield 4-(1,4-dioxaspiro[4.5]decan-8-yl)-1-((2-(trimethylsilyl)ethoxy)methyl)-1H-pyrazole (165 mg, 487 µmol, 97% yield) as a clear oil.

Synthesis of 4-(1-((2-(trimethylsilyl)ethoxy)methyl)-1H-pyrazol-4-yl)cyclohexanone

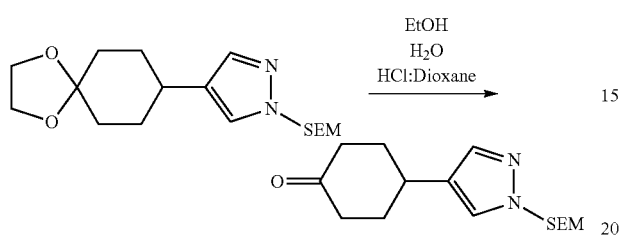

4-(1,4-dioxaspiro[4.5]decan-8-yl)-1-((2-(trimethylsilyl) ethoxy)methyl)-1H-pyrazole (487 µmol, 165 mg) was dissolved in EtOH (10 mL) in a 20 mL scintillation vial. To this solution was added H$_2$O (3 mL) followed by 4N HCl in 1,4-dioxane. The resulting reaction mixture was stirred at room temperature for 60 hours. At this point, the reaction was quenched with saturated NaHCO$_{3(aq)}$ and extracted with DCM (×3). The combined organics were dried over Na$_2$SO$_4$ to yield 4-(1-((2-(trimethylsilyl)ethoxy)methyl)-1H-pyrazol-4-yl)cyclohexanone (141 mg, 480 µmol, 98% yield) as white solid.

Synthesis of 4-(1-((2-(trimethylsilyl)ethoxy)methyl)-1H-pyrazol-4-yl)cyclohex-1-enyl trifluoromethanesulfonate

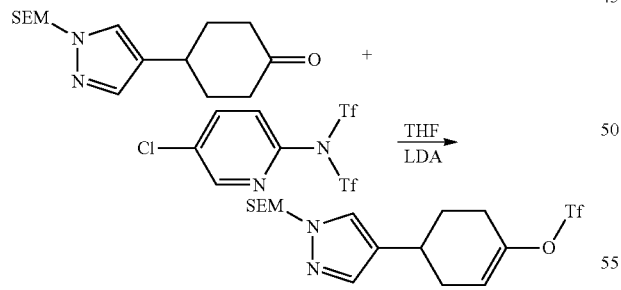

4-(1-((2-(trimethylsilyl)ethoxy)methyl)-1H-pyrazol-4-yl)cyclohexanone (480 µmol, 141 mg) was added to a 50 mL roundbottom flask containing anhydrous THF (5 mL). The flask was flushed with argon, sealed, and cooled to −78° C. in dry ice/isopropanol bath. To this solution was added dropwise LDA (1.5 M is cyclohexane, 0.72 mmol, 480 µL). This solution was stirred at −78° C. for 30 minutes. To this solution was added 2-[N,N-bis(trifluoromethylsulfonyl)amino]-5-chloropyridine (0.72 mmol, 282 mg). The resulting reaction mixture was allowed to gradually warm to room temperature as it stirs for 18 hours. After 18 hours, the reaction mixture was concentrated in vacuo and purified via silica gel chromatography to yield 4-(1-((2-(trimethylsilyl)ethoxy)methyl)-1H-pyrazol-4-yl)cyclohex-1-enyl trifluoromethanesulfonate (115 mg, 270 µmol, 56% yield) as clear oil.

Synthesis of 4-(4-(4,4,5,5-tetramethyl-1,3,2-dioxaborolan-2-yl)cyclohex-3-enyl)-1-((2-(trimethylsilyl)ethoxy)methyl)-1H-pyrazole

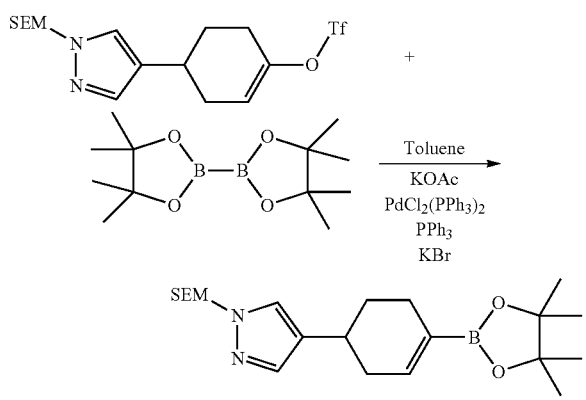

To a 20 mL scintillation vial was charged 4-(1-((2-(trimethylsilyl)ethoxy)methyl)-1H-pyrazol-4-yl)cyclohex-1-enyl trifluoromethanesulfonate (0.047 mmol, 20 mg), bis(pinacolato)diboron (0.070 mmol, 18 mg), potassium acetate (0.094 mmol, 9.2 mg), PdCl$_2$(PPh$_3$)$_2$ (0.0014 mmol, 1 mg), triphenylphosphine (0.0028 mmol, 0.8 mg), KBr (0.07 mmol, 8.4 mg), and toluene (0.5 mL). The vial was flushed with argon and sealed. The reaction was then stirred at 60° C. for 18 hours. After 18 hours, the reaction was filtered through celite, and 4-(4-(4,4,5,5-tetramethyl-1,3,2-dioxaborolan-2-yl)cyclohex-3-enyl)-1-((2-(trimethylsilyl)ethoxy)methyl)-1H-pyrazole was used without further purification.

Synthesis of 5-(4-(1H-pyrazol-4-yl)cyclohex-1-enyl)-3-(quinolin-3-yl)pyrazolo[1,5-a]pyrimidin-7-amine

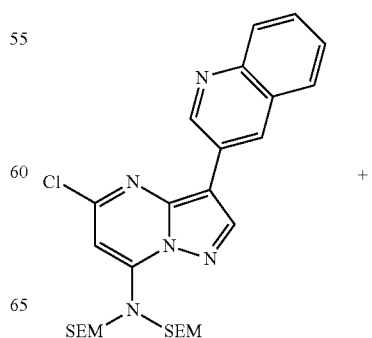

1357

-continued

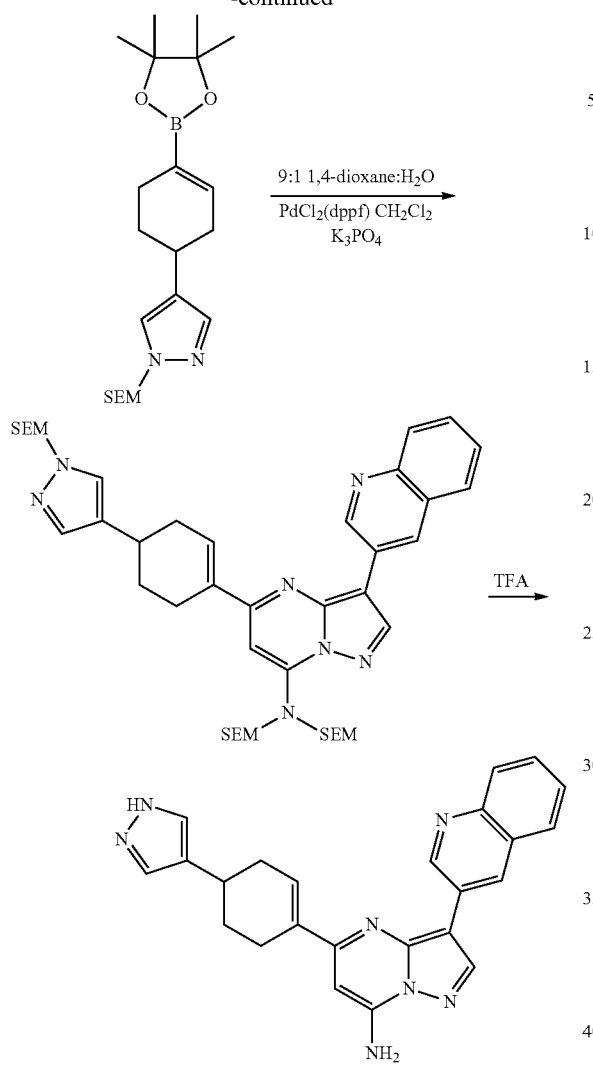

1358

Synthesis of 5-(4-(1H-pyrazol-4-yl)cyclohex-1-enyl)-6-bromo-3-(quinolin-3-yl)pyrazolo[1,5-a]pyrimidin-7-amine

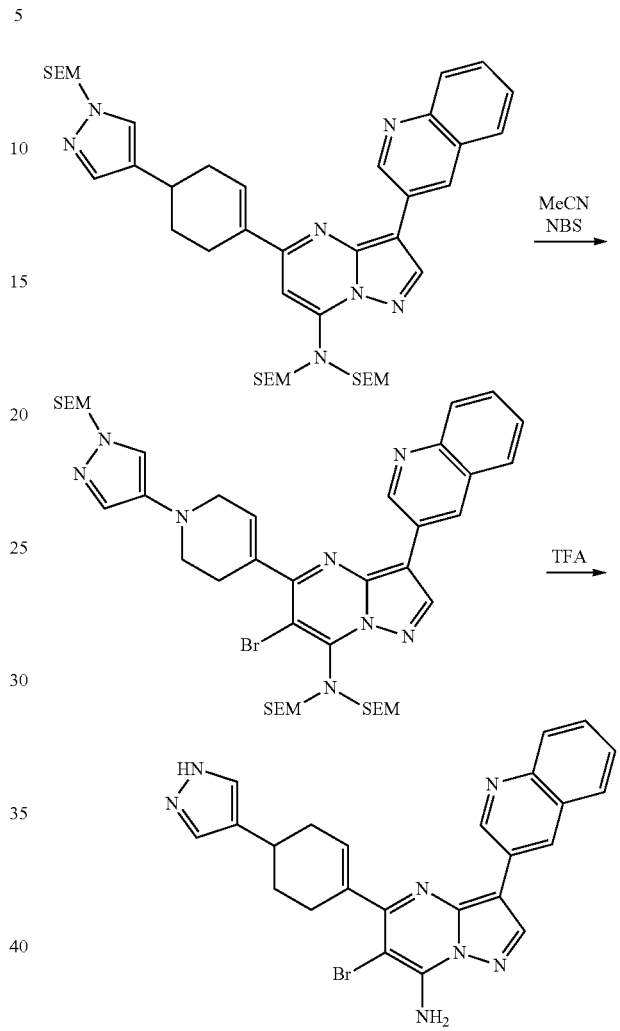

To a 2 mL microwave vessel was charged 5-chloro-3-(quinolin-3-yl)-N,N-bis((2-(trimethylsilyl)ethoxy)methyl) pyrazolo[1,5-a]pyrimidin-7-amine (0.043 mmol, 23.5 mg), 4-(4-(4,4,5,5-tetramethyl-1,3,2-dioxaborolan-2-yl)cyclohex-3-enyl)-1-((2-(trimethylsilyl)ethoxy)methyl)-1H-pyrazole (0.047 mmol), $K_3PO_4$ (130 mmol, 27 mg), and $PdCl_2$(dppf).$CH_2Cl_2$ (0.0043 mmol, 3.5 mg). To this mixture was added 9:1 dioxane:H2O (1 mL). The vessel was flushed with argon and heated to 160° C. for 30 minutes in microwave synthesizer. Upon completion, the reaction was concentrated in vacuo and the residue was dissolved in 1 mL TFA. This reaction mixture was stirred at room temperature for 1 hour. The reaction mixture was concentrated in vacuo and purified via reverse-phase preparatory HPLC to yield 5-(4-(1H-pyrazol-4-yl)cyclohex-1-enyl)-3-(quinolin-3-yl)pyrazolo[1,5-a]pyrimidin-7-amine as yellow solid. (m+H=408.30, retention time=3.16 min)

5-(4-(1H-pyrazol-4-yl)cyclohex-1-enyl)-6-bromo-3-(quinolin-3-yl)pyrazolo[1,5-a]pyrimidin-7-amine was synthesized in a manner similar to the synthesis of 6-bromo-3-(quinolin-3-yl)-5-(1,2,3,6-tetrahydropyridin-4-yl)pyrazolo[1,5-a]pyrimidin-7-amine, but with 6-bromo-3-(quinolin-3-yl)-N,N-bis((2-(trimethylsilyl)ethoxy)methyl)-5-(4-(1-((2-(trimethylsilyl)ethoxy)methyl)-1H-pyrazol-4-yl)cyclohex-1-enyl)pyrazolo[1,5-a]pyrimidin-7-amine substituted for tert-Butyl 4-(7-(bis((2-(trimethylsilyl)ethoxy)methyl)amino)-3-(quinolin-3-yl)pyrazolo[1,5-a]pyrimidin-5-yl)-5,6-dihydropyridine-1(2H)-carboxylate. The reaction mixture was purified via reverse-phase preparatory HPLC to yield 5-(4-(1'-1-pyrazol-4-yl)cyclohex-1-enyl)-3-(quinolin-3-yl)pyrazolo[1,5-a]pyrimidin-7-amine as yellow solid. (M+H=486.12, retention time=3.43 min.

By essentially the same procedure given in Scheme 43, the compounds listed in Table 12 can be prepared.

TABLE 12

| Compound ID | Structures | M + H (calc.) | M + H (observed) | Retention Time, (min) |
|---|---|---|---|---|
| 12.1 | 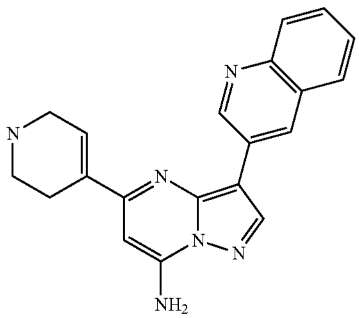 [SMILES: Nc1cc(C2=CCNCC2)nc2c(-c3cnc4ccccc4c3)cnn12] | 343.15954 | 343.3 | 2.05 |
| 12.2 | 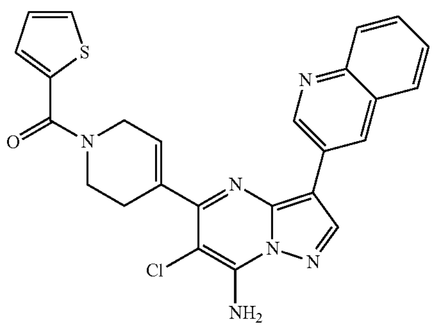 [SMILES: Nc1c(Cl)c(C2=CCN(C(=O)c3cccs3)CC2)nc2c(-c3cnc4ccccc4c3)cnn12] | 487.10327 | 487.2 | 3.73 |
| 12.3 | 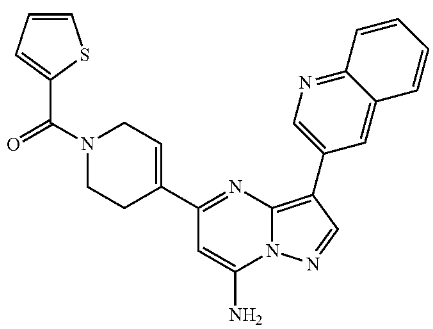 [SMILES: Nc1cc(C2=CCN(C(=O)c3cccs3)CC2)nc2c(-c3cnc4ccccc4c3)cnn12] | 453.1422 | 453.2 | 3.51 |
| 12.4 | 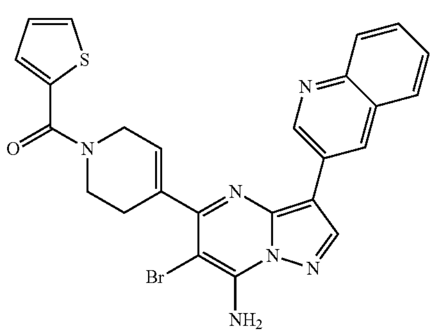 | 531.05 | 531.1 | 3.74 |

TABLE 12-continued
| Compound ID | Structures | M + H (calc.) | M + H (observed) | Retention Time, (min) |
|---|---|---|---|---|
| 12.5 | 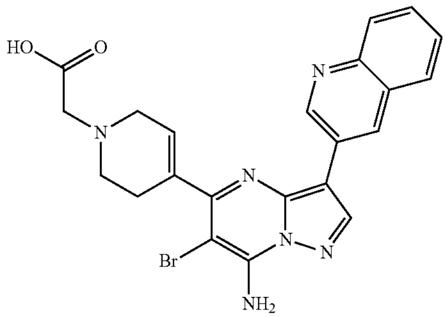 [SMILES: Nc1c(Br)c(C2=CCN(CC(=O)O)CC2)nc2c(-c3cnc4ccccc4c3)cnn12] | 479.07 | 499.1 | 2.09 |
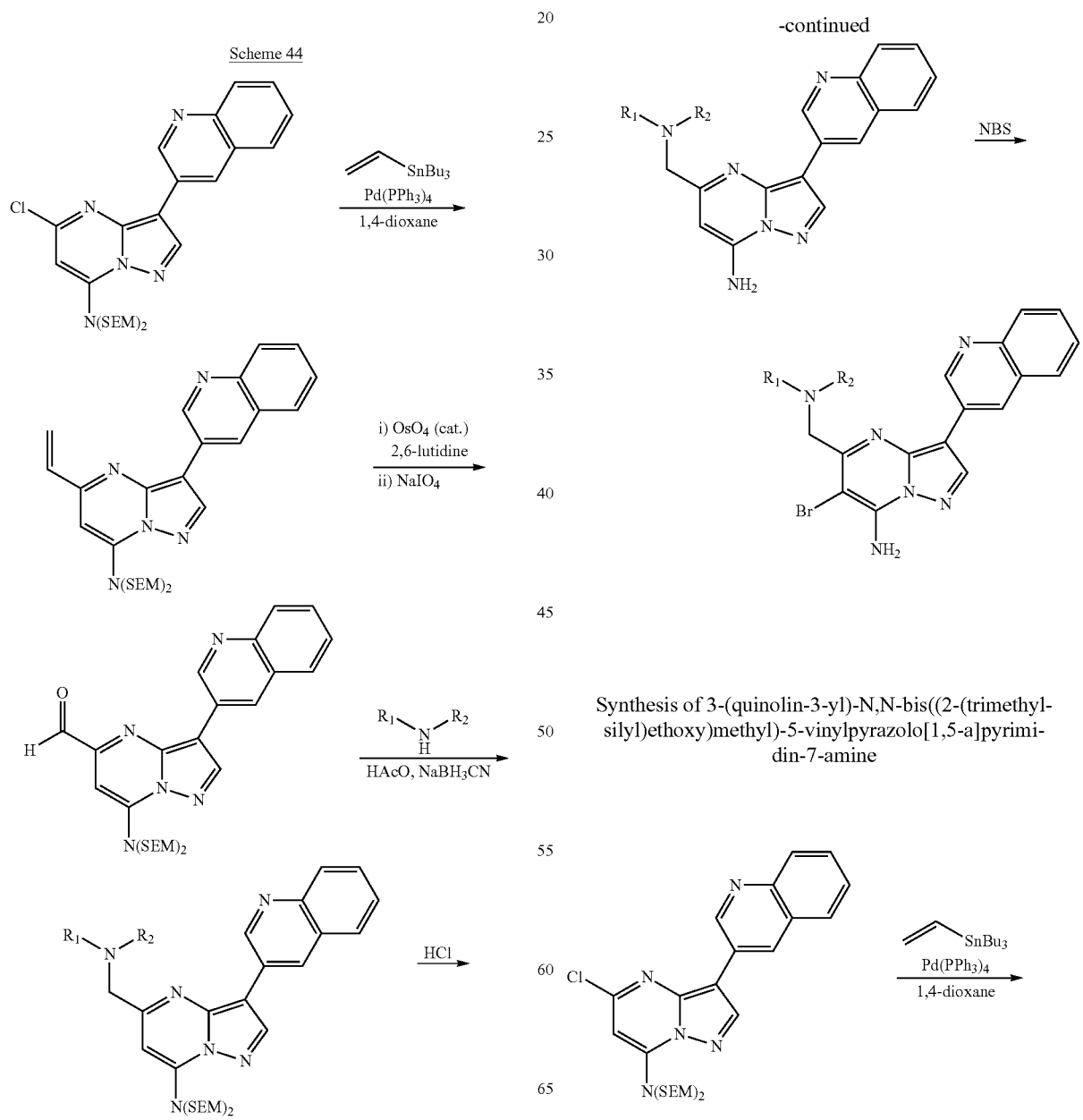
Scheme 44
Synthesis of 3-(quinolin-3-yl)-N,N-bis((2-(trimethylsilyl)ethoxy)methyl)-5-vinylpyrazolo[1,5-a]pyrimidin-7-amine

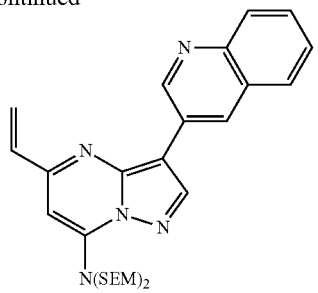

To 5-chloro-3-(quinolin-3-yl)-N,N-bis((2-(trimethylsilyl)ethoxy)methyl)pyrazolo[1,5-a]pyrimidin-7-amine (0.9 g, 1.64 mmol) in a 20 mL vials was added 1,4-dioxane (10 mL), tributyl(vinyl)tin (0.5 mL, 1.71 mmol) and Pd(PPh₃)₄ (0.1 g, 0.08 mmol). The vial was flushed with argon, sealed and heated at 100° C. for 16 hours, at which time LC/MS analysis confirmed full conversion of the starting material to the product. The reaction mixture was filtered through a mixture of silica (8 g) and KF (2 g), and EtOAc was used to wash the filter pad. Concentration of the filtrate gave a brown oil (1.4 g). Further purification via gradient column chromatography on silica eluting with 5% to 40% EtOAc/hexanes gave 3-(quinolin-3-yl)-N,N-bis((2-(trimethylsilyl)ethoxy)methyl)-5-vinylpyrazolo[1,5-a]pyrimidin-7-amine as a yellow oil (0.7 g, 1.3 mmol, 78%). LCMS: 2.55 mins, m/z=548.2 (MH⁺).

Synthesis of 7-(bis((2-(trimethylsilyl)ethoxy)methyl)amino)-3-(quinolin-3-yl)pyrazolo[1,5-a]pyrimidine-5-carbaldehyde

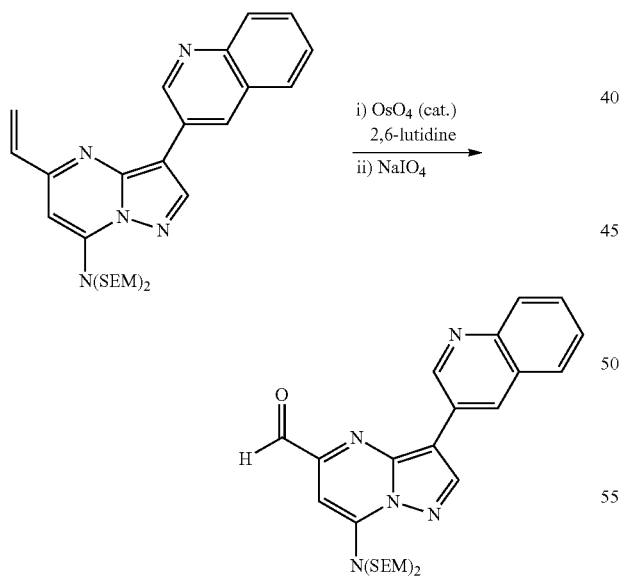

To 3-(quinolin-3-yl)-N,N-bis((2-(trimethylsilyl)ethoxy)methyl)-5-vinylpyrazolo[1,5-a]pyrimidin-7-amine (0.7 g, 1.3 mmol) in 1,4-dioxide (10 mL) was added 2.5 wt % OsO₄ in 1,4-dioxane (1.0 g, 0.02 mmol), 2,6-lutidine (0.6 mL, 5.2 mmol) and H₂O (2 mL), and the resulting mixture was stirred at room temperature for 20 minutes. NaIO₄ (0.8 g, 3.81 mmol) was then added and the reaction mixture was stirred at room temperature for 16 hours. LC/MS analysis at that time showed the diol intermediate still present. Therefore, more NaIO₄ (0.3 g, 1.3 mmol) was added, and the reaction mixture was stirred for 12 hours for full conversion to the product. Saturated Na₂S₂O₃ solution (10 mL) was added and the mixture was stirred for 10 minutes. Organics were then extracted with CH₂Cl₂ (4×40 mL), dried (Na₂SO₄) and concentrated in vacuo to give 7-(bis((2-(trimethylsilyl)ethoxy)methyl)amino)-3-(quinolin-3-yl)pyrazolo[1,5-a]pyrimidine-5-carbaldehyde as a yellow solid (0.6 g, 1.2 mmol, 92%). LCMS: 2.67 mins, m/z=550.0 (MH⁺).

Synthesis of 5-(morpholinomethyl)-3-(quinolin-3-yl)-N,N-bis((2-(trimethylsilyl)-ethoxy)methyl)pyrazolo[1,5-a]pyrimidin-7-amine

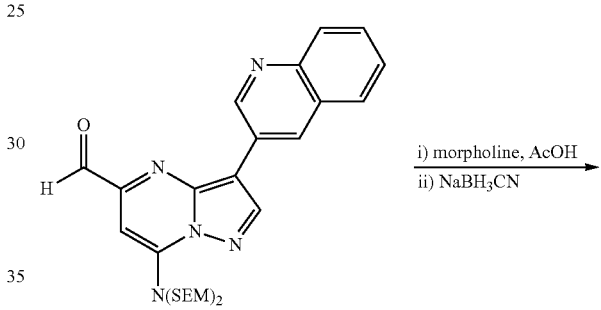

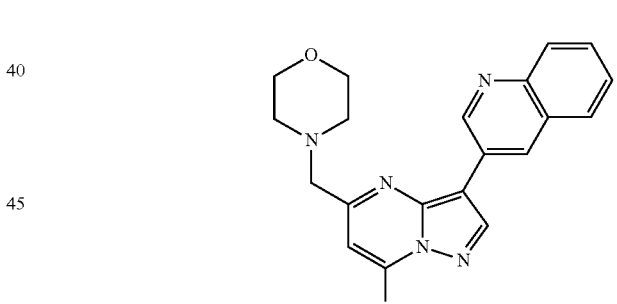

To 7-(bis((2-(trimethylsilyl)ethoxy)methyl)amino)-3-(quinolin-3-yl)pyrazolo[1,5-a]pyrimidine-5-carbaldehyde (0.15 g, 0.3 mmol) in EtOH (10 mL) was added morpholine (0.12 mL, 1.4 mmol) and AcOH (0.2 mL), and the resulting mixture was stirred at room temperature for 15 minutes. NaBH₃CN (0.12 g, 2.0 mmol) in EtOH (1.5 mL total) was then added and the reaction mixture was stirred at room temperature for 16 hours, at which time LC/MS analysis confirmed full consumption of starting material. Saturated NaHCO₃ solution (~20 mL) was added and the mixture was stirred for 30 minutes. The mixture was transferred to a separatory funnel with CH₂Cl₂ (30 mL) and H₂O (10 mL) and brine (20 mL) was then added. Organics were extracted with CH₂Cl₂ (4×30 mL), dried (Na₂SO₄) and concentrated in vacuo to give crude 5-(morpholinomethyl)-3-(quinolin-3-yl)-N,N-bis((2-(trimethylsilyl)ethoxy)methyl)pyrazolo[1,5-a]pyrimidin-7-amine as a brown oil (0.2 g). LCMS: 2.01 mins, m/z=621.3 (MH⁺).

Synthesis of 5-(morpholinomethyl)-3-(quinolin-3-yl)pyrazolo[1,5-a]pyrimidin-7-amine

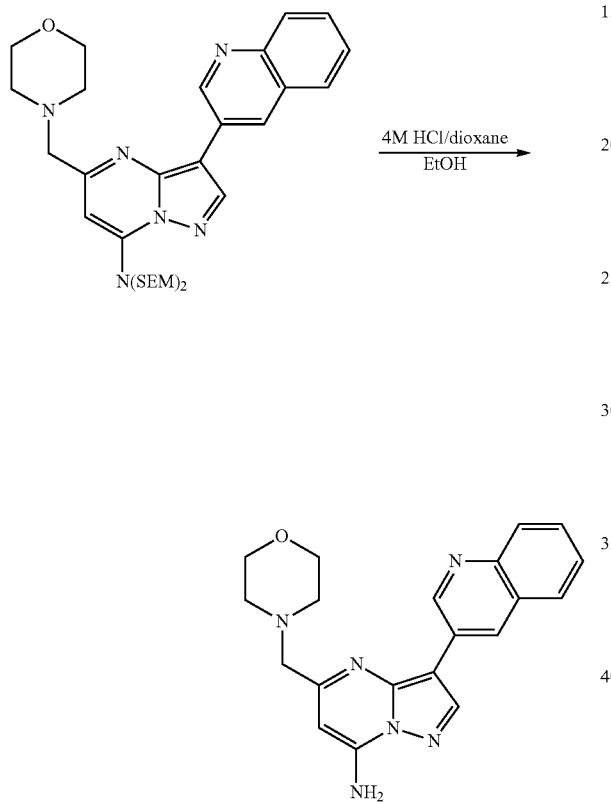

To crude 5-(morpholinomethyl)-3-(quinolin-3-yl)-N,N-bis((2-(trimethylsilyl)-ethoxy)methyl)pyrazolo[1,5-a]pyrimidin-7-amine (0.2 g) in a 20 mL vial was added EtOH (4 mL) and then 4M HCl/dioxane (1.5 mL, 6.0 mmol). The vial was capped and heated at 85° C. for 16 hours. On cooling, saturated NaHCO₃ solution (~0.5 mL) was added, and the reaction mixture was stirred for 30 minutes. The reaction mixture was then transferred to a separatory funnel using CH₂Cl₂ (20 mL) and H₂O (20 mL) and saturated NaHCO₃ solution (20 mL) and brine (20 mL) were added. Organics were extracted with CH₂Cl₂ (4×30 mL), dried (Na₂SO₄) and concentrated in vacuo to give crude 5-(morpholinomethyl)-3-(quinolin-3-yl)pyrazolo[1,5-a]pyrimidin-7-amine as a brown solid (0.04 g). LCMS: 0.78 mins, m/z=361.1 (MH⁺).

Synthesis of 6-bromo-5-(morpholinomethyl)-3-(quinolin-3-yl)pyrazolo[1,5-a]pyrimidin-7-amine

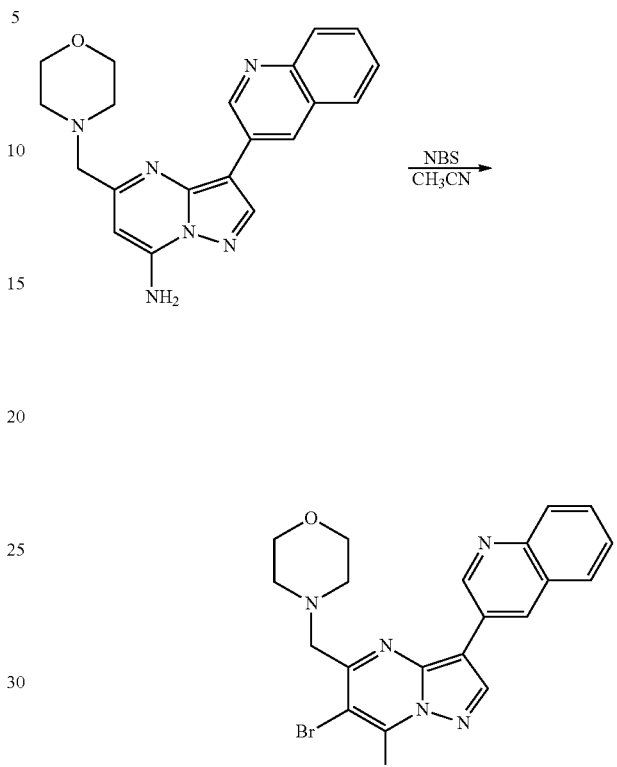

To crude 5-(morpholinomethyl)-3-(quinolin-3-yl)pyrazolo[1,5-a]pyrimidin-7-amine (44 mg) in CH₃CN (8 mL) was added N-bromosuccinimide (22 mg, 0.12 mmol), followed by additional CH₃CN (4 mL). The reaction was then stirred at room temperature for 30 minutes, at which time LC/MS analysis confirmed full conversion of the starting material to the product. The reaction mixture was concentrated in vacuo and purified by preparative HPLC to give 6-bromo-5-(morpholinomethyl)-3-(quinolin-3-yl)pyrazolo[1,5-a]pyrimidin-7-amine as a yellow solid (8.7 mg, 0.02 mmol, 7% over three steps). LCMS: 0.82 mins, m/z=439.0 and 441.0 (MH⁺).

Related reductive amination analogs were prepared as described in Preparative Example included in the following table. In most cases, reduction of the aldehyde to the primary alcohol was a competing reaction to the desired reductive amination. Generally, reactions giving >80% reductive amination product progressed without purification whereas those with >20% primary alcohol were purified by silica gel column chromatography before continuing to the de-SEM reaction.

By essentially the same procedure given in Scheme 44, the compounds listed in Table 13 can be prepared.

TABLE 13

| Compound ID | Structures | M + H (Calc.) | M + H (Observed) | Retention Time, (min) |
|---|---|---|---|---|
| 13.1 | 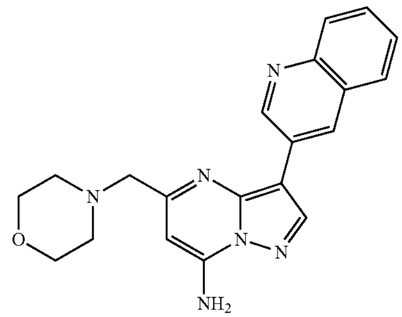 [SMILES: Nc1cc(CN2CCOCC2)nc2c(-c3cnc4ccccc4c3)cnn12] | 361.4 | 361 | 2.02 |
| 13.2 | 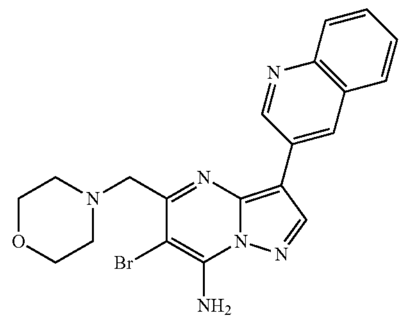 [SMILES: Nc1c(Br)c(CN2CCOCC2)nc2c(-c3cnc4ccccc4c3)cnn12] | 439.3 | 439 + 441 | 2.26 |
| 13.3 | 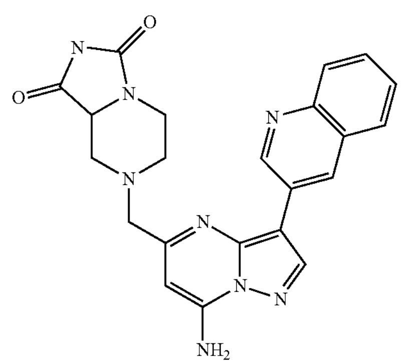 [SMILES: Nc1cc(CN2CCN3C(=O)NC(=O)C3C2)nc2c(-c3cnc4ccccc4c3)cnn12] | 429.5 | 429 | 2.06 |
| 13.4 | 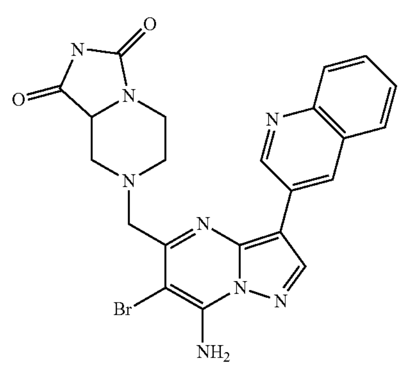 [SMILES: Nc1c(Br)c(CN2CCN3C(=O)NC(=O)C3C2)nc2c(-c3cnc4ccccc4c3)cnn12] | 507.4 | 507 + 509 | 2.37 |

TABLE 13-continued

| Compound ID | Structures | M + H (Calc.) | M + H (Observed) | Retention Time, (min) |
|---|---|---|---|---|
| 13.5 | 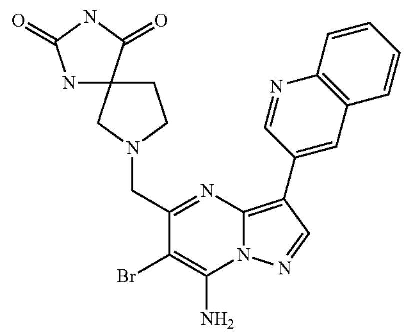 [SMILES: Nc1c(Br)c(CN2CCC3(C2)NC(=O)NC3=O)nc2c(-c3cnc4ccccc4c3)cnn12] | 507.4 | 507 + 509 | 2.00 |
| 13.6 | 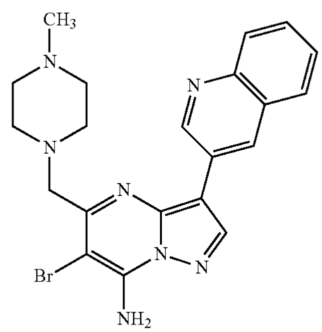 [SMILES: CN1CCN(Cc2nc3c(-c4cnc5ccccc5c4)cnn3c(N)c2Br)CC1] | 452.4 | 452 + 454 | 2.26 |
| 13.7 | 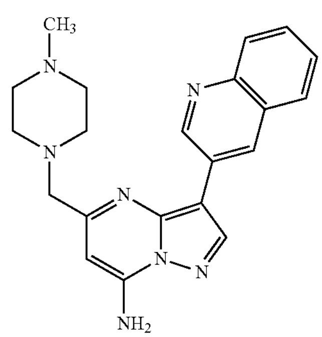 [SMILES: CN1CCN(Cc2cc(N)n3ncc(-c4cnc5ccccc5c4)c3n2)CC1] | 373.5 | 374 | 2.00 |
| 13.8 | 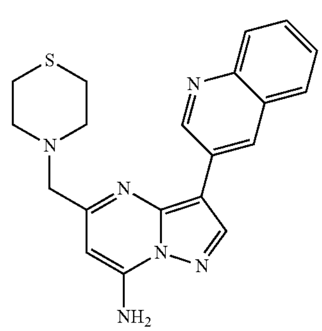 [SMILES: Nc1cc(CN2CCSCC2)nc2c(-c3cnc4ccccc4c3)cnn12] | 377.15 | 377 | 2.12 |

TABLE 13-continued
| Compound ID | Structures | M + H (Calc.) | M + H (Observed) | Retention Time, (min) |
| --- | --- | --- | --- | --- |
| 13.9 | 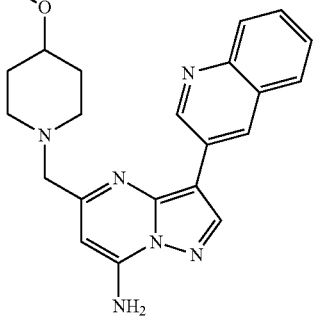 | 389.20 | 389 | 2.14 |
| 13.10 | 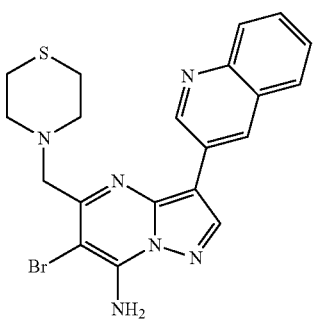 [SMILES: Nc1c(Br)c(CN2CCSCC2)nc2c(-c3cnc4ccccc4c3)cnn12] | 455.06 | 455 | 2.32 |
| 13.11 | 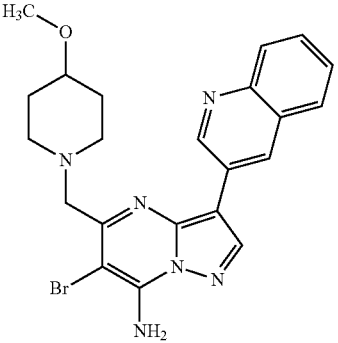 [SMILES: COC1CCN(Cc2nc3c(-c4cnc5ccccc5c4)cnn3c(N)c2Br)CC1] | 467.11 | 467 | 2.36 |
| 13.12 | 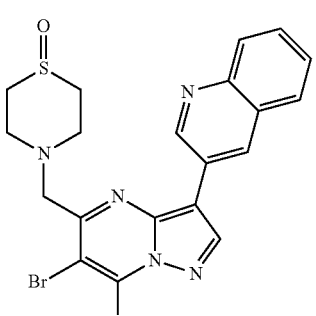 | 471.05 | 471 | 2.03 |

TABLE 13-continued

| Compound ID | Structures | M + H (Calc.) | M + H (Observed) | Retention Time, (min) |
|---|---|---|---|---|
| 13.13 | 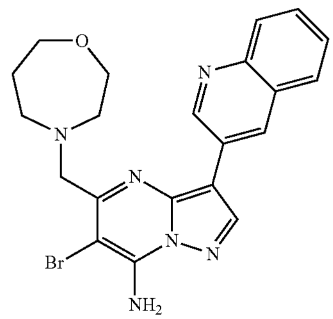 [SMILES: Nc1c(Br)c(CN2CCCOCC2)nc2c(-c3cnc4ccccc4c3)cnn12] | 453.10 | 453 | 2.15 |
| 13.14 | 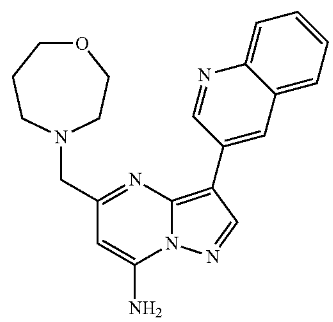 [SMILES: Nc1cc(CN2CCCOCC2)nc2c(-c3cnc4ccccc4c3)cnn12] | 375.19 | 375 | 2.07 |
| 13.15 | 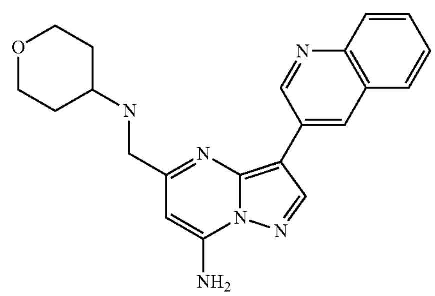 [SMILES: Nc1cc(CNC2CCOCC2)nc2c(-c3cnc4ccccc4c3)cnn12] | 375.19 | 375 | 2.02 |
| 13.16 | 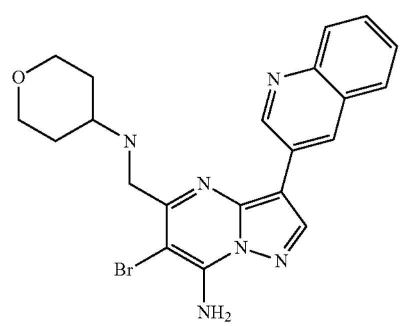 [SMILES: Nc1c(Br)c(CNC2CCOCC2)nc2c(-c3cnc4ccccc4c3)cnn12] | 453.1 | 453 | 2.12 |
| 13.17 | 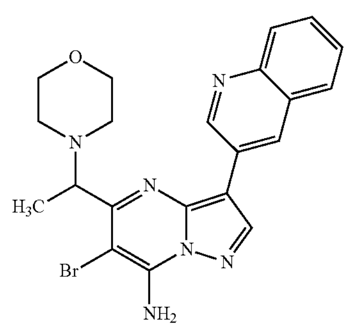 [SMILES: CC(c1nc2c(-c3cnc4ccccc4c3)cnn2c(N)c1Br)N1CCOCC1] | 453.1 | 453 | 2.26 |

TABLE 13-continued

| Compound ID | Structures | M + H (Calc.) | M + H (Observed) | Retention Time, (min) |
|---|---|---|---|---|
| 13.18 | 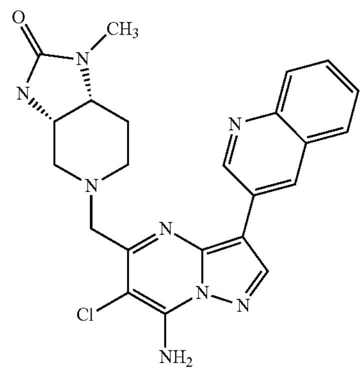 [SMILES: CN1C(=O)N[C@H]2CN(Cc3nc4c(-c5cnc6ccccc6c5)cnn4c(N)c3Cl)CC[C@H]21] | 463.17 | 463 | 1.89 |
| 13.19 | 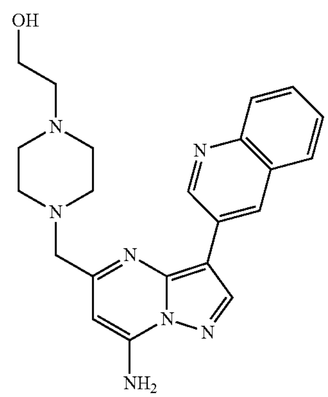 [SMILES: Nc1cc(CN2CCN(CCO)CC2)nc2c(-c3cnc4ccccc4c3)cnn12] | 404.21 | 404 | 1.92 |
| 13.20 | 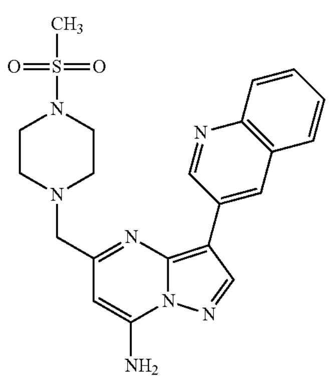 [SMILES: CS(=O)(=O)N1CCN(Cc2cc(N)n3ncc(-c4cnc5ccccc5c4)c3n2)CC1] | 438.16 | 438 | 2.12 |
| 13.21 | 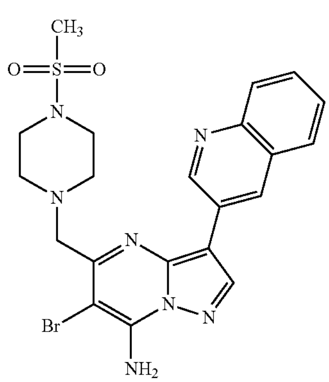 [SMILES: CS(=O)(=O)N1CCN(Cc2nc3c(-c4cnc5ccccc5c4)cnn3c(N)c2Br)CC1] | 516.07 | 516 + 518 | 2.22 |

TABLE 13-continued

| Compound ID | Structures | M + H (Calc.) | M + H (Observed) | Retention Time, (min) |
| --- | --- | --- | --- | --- |
| 13.22 | 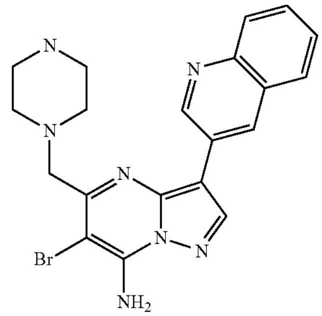 [SMILES: Nc1c(Br)c(CN2CCNCC2)nc2c(-c3cnc4ccccc4c3)cnn12] | 438.10 | 438 + 440 | 2.10 |
| 13.23 | 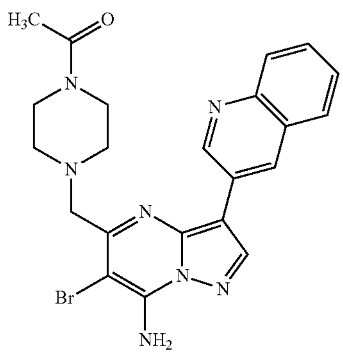 [SMILES: CC(=O)N1CCN(Cc2nc3c(-c4cnc5ccccc5c4)cnn3c(N)c2Br)CC1] | 480.11 | 480 + 482 | 2.05 |
| 13.24 | 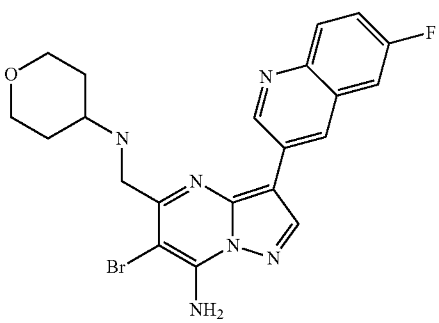 [SMILES: Nc1c(Br)c(CNC2CCOCC2)nc2c(-c3cnc4ccc(F)cc4c3)cnn12] | 471.1 | 471.0 | 2.67 |
| 13.25 | 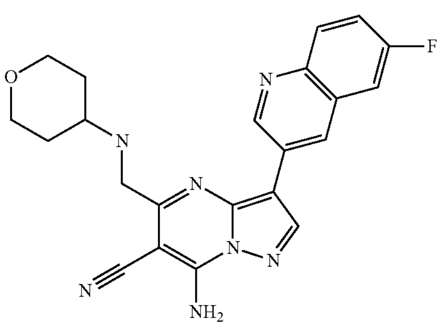 [SMILES: N#Cc1c(CNC2CCOCC2)nc2c(-c3cnc4ccc(F)cc4c3)cnn2c1N] | 417.13 | 418.30 | 2.70 |

TABLE 13-continued
| Compound ID | Structures | M + H (Calc.) | M + H (Observed) | Retention Time, (min) |
|---|---|---|---|---|
| 13.26 | 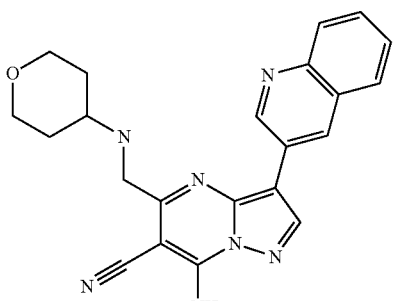 | 399.18 | 400.31 | 2.27 |
| 13.27 | 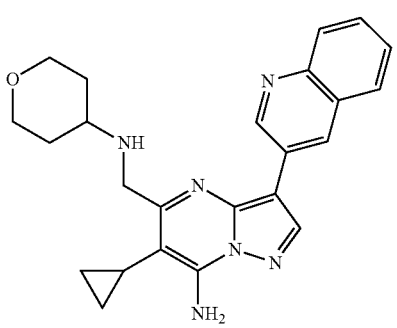 [SMILES: Nc1c(C2CC2)c(CNC2CCOCC2)nc2c(-c3cnc4ccccc4c3)cnn12] | 414.20 | 415.32 | 2.34 |
| 13.28 | 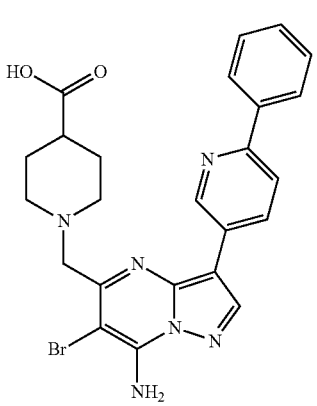 [SMILES: Nc1c(Br)c(CN2CCC(C(=O)O)CC2)nc2c(-c3ccc(-c4ccccc4)nc3)cnn12] | 506.10 | 507.17 | 2.52 |
| 13.29 | 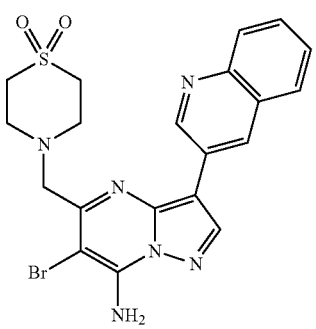 [SMILES: Nc1c(Br)c(CN2CCS(=O)(=O)CC2)nc2c(-c3cnc4ccccc4c3)cnn12] | 487.08 | 487.20 | 2.75 |

TABLE 13-continued

| Compound ID | Structures | M + H (Calc.) | M + H (Observed) | Retention Time, (min) |
|---|---|---|---|---|
| 13.30 | 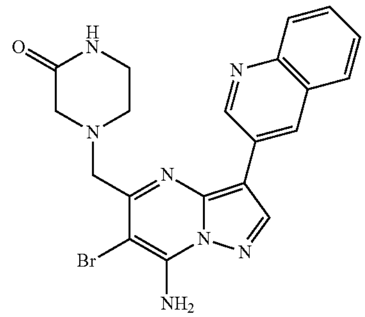 [SMILES: Nc1c(Br)c(CN2CCNC(=O)C2)nc2c(-c3cnc4ccccc4c3)cnn12] | 452.08 | 453.20 | 2.13 |
| 13.31 | 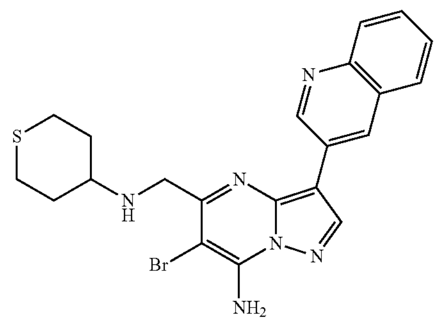 [SMILES: Nc1c(Br)c(CNC2CCSCC2)nc2c(-c3cnc4ccccc4c3)cnn12] | 485.07 | 486.20 | 1.10 |
| 13.32 | 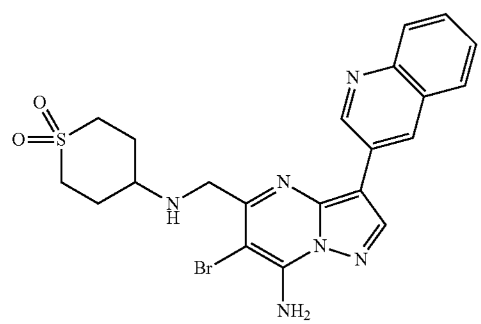 [SMILES: Nc1c(Br)c(CNC2CCS(=O)(=O)CC2)nc2c(-c3cnc4ccccc4c3)cnn12] | 501.06 | 502.20 | 1.99 |
| 13.33 | 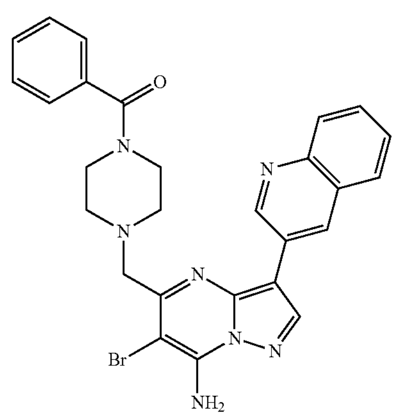 [SMILES: Nc1c(Br)c(CN2CCN(C(=O)c3ccccc3)CC2)nc2c(-c3cnc4ccccc4c3)cnn12] | 542.12 | 543.20 | 2.78 |

TABLE 13-continued

| Compound ID | Structures | M + H (Calc.) | M + H (Observed) | Retention Time, (min) |
|---|---|---|---|---|
| 13.34 | 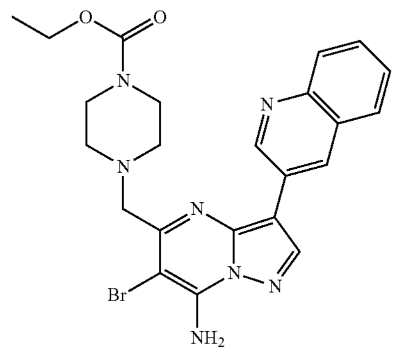 [SMILES: CCOC(=O)N1CCN(Cc2nc3c(-c4cnc5ccccc5c4)cnn3c(N)c2Br)CC1] | 509.12 | 510.20 | 2.61 |
| 13.35 | 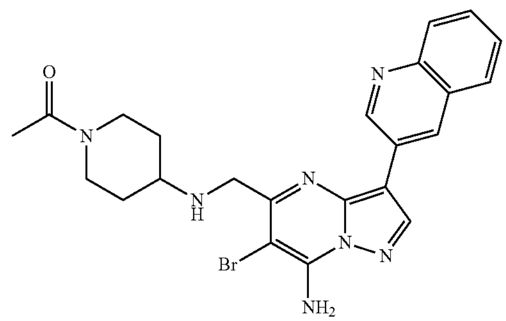 [SMILES: CC(=O)N1CCC(NCc2nc3c(-c4cnc5ccccc5c4)cnn3c(N)c2Br)CC1] | 494.12 | 495.20 | 2.15 |
| 13.36 | 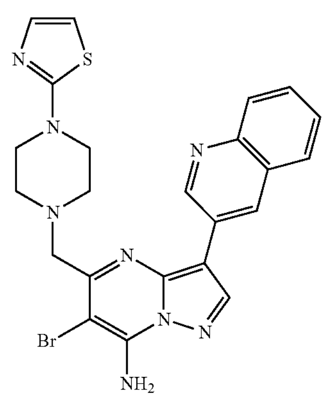 [SMILES: Nc1c(Br)c(CN2CCN(c3nccs3)CC2)nc2c(-c3cnc4ccccc4c3)cnn12] | 520.08 | 521.20 | 2.52 |
| 13.37 | 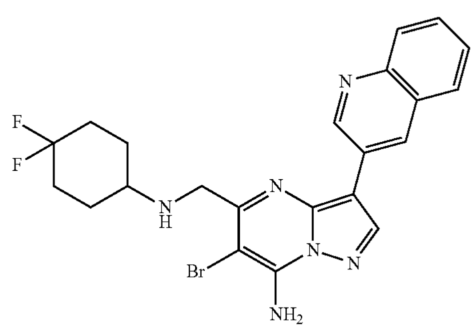 [SMILES: Nc1c(Br)c(CNC2CCC(F)(F)CC2)nc2c(-c3cnc4ccccc4c3)cnn12] | 486.10 | 487.20 | 2.71 |

TABLE 13-continued

| Compound ID | Structures | M + H (Calc.) | M + H (Observed) | Retention Time, (min) |
|---|---|---|---|---|
| 13.38 | 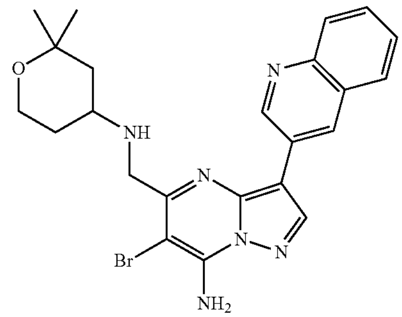 [SMILES: CC1(C)CC(NCc2nc3c(-c4cnc5ccccc5c4)cnn3c(N)c2Br)CCO1] | 480.13 | 481.20 | 1.23 |
| 13.39 | 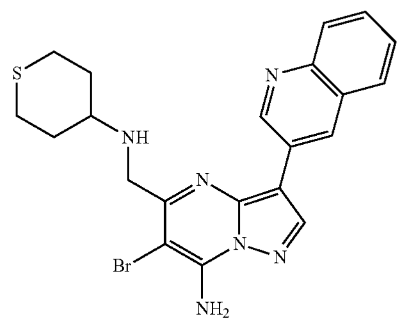 [SMILES: Nc1c(Br)c(CNC2CCSCC2)nc2c(-c3cnc4ccccc4c3)cnn12] | 468.07 | 469.20 | 2.56 |
| 13.40 | 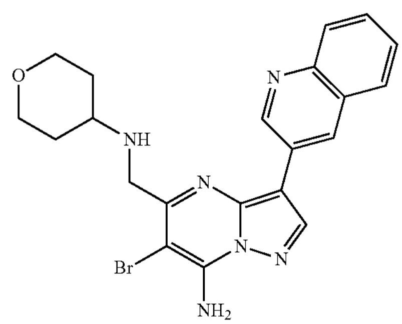 [SMILES: Nc1c(Br)c(CNC2CCOCC2)nc2c(-c3cnc4ccccc4c3)cnn12] | 470.09 | 471.20 | 2.52 |
| 13.41 | 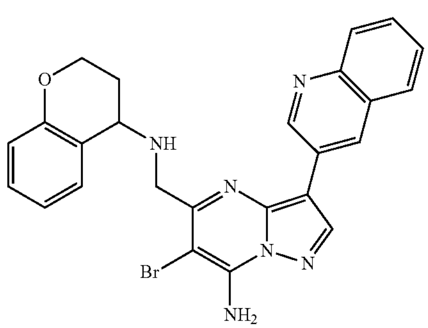 [SMILES: Nc1c(Br)c(CNC2CCOc3ccccc32)nc2c(-c3cnc4ccccc4c3)cnn12] | 500.10 | 501.20 | 2.90 |

TABLE 13-continued

| Compound ID | Structures | M + H (Calc.) | M + H (Observed) | Retention Time, (min) |
| --- | --- | --- | --- | --- |
| 13.42 | 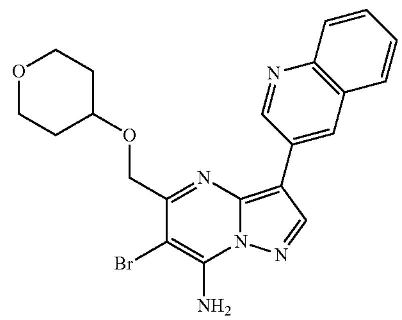 | 453.10 | 454.20 | 2.48 |
| 13.43 | 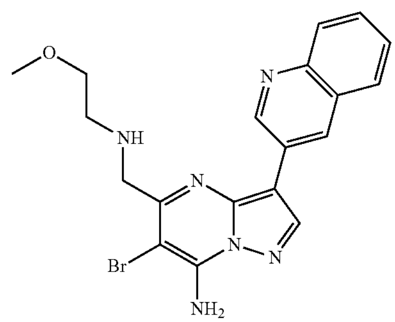 [SMILES: COCCNCc1nc2c(-c3cnc4ccccc4c3)cnn2c(N)c1Br] | 426.08 | 427.20 | 2.19 |
| 13.44 | 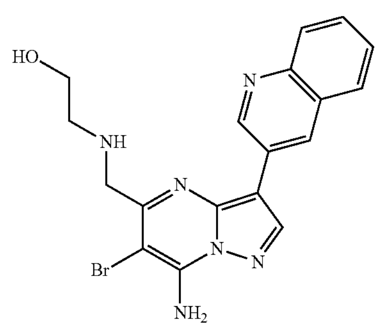 [SMILES: Nc1c(Br)c(CNCCO)nc2c(-c3cnc4ccccc4c3)cnn12] | 412.10 | 413.20 | 1.88 |
| 13.45 | 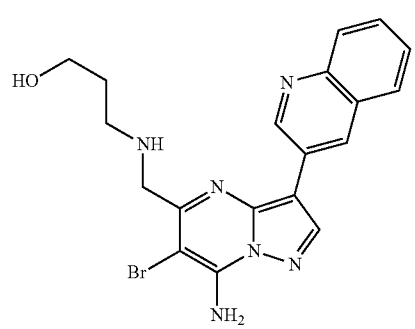 [SMILES: Nc1c(Br)c(CNCCCO)nc2c(-c3cnc4ccccc4c3)cnn12] | 426.10 | 427.20 | 1.99 |

TABLE 13-continued

| Compound ID | Structures | M + H (Calc.) | M + H (Observed) | Retention Time, (min) |
| --- | --- | --- | --- | --- |
| 13.45 | 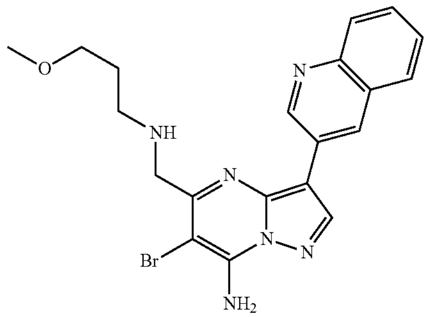 [SMILES: COCCCNCc1nc2c(-c3cnc4ccccc4c3)cnn2c(N)c1Br] | 440.10 | 441.20 | 2.29 |
| 13.46 | 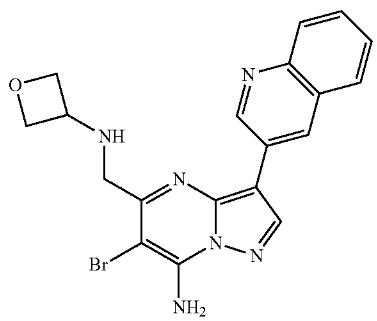 [SMILES: Nc1c(Br)c(CNC2COC2)nc2c(-c3cnc4ccccc4c3)cnn12] | 442.10 | 443.20 | 2.12 |
| 13.47 | 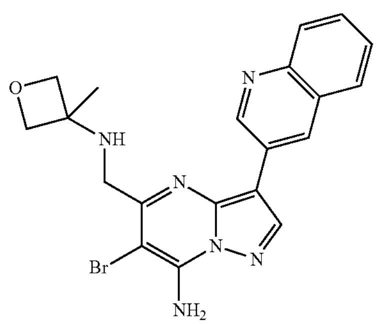 [SMILES: CC1(NCc2nc3c(-c4cnc5ccccc5c4)cnn3c(N)c2Br)COC1] | 456.10 | 457.20 | 2.36 |
| 13.48 | 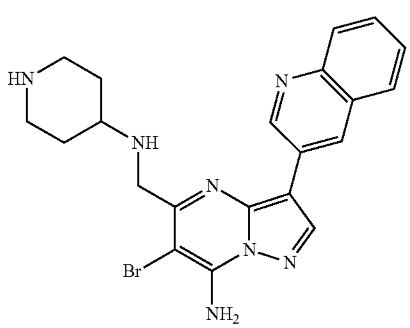 [SMILES: Nc1c(Br)c(CNC2CCNCC2)nc2c(-c3cnc4ccccc4c3)cnn12] | 451.11 | 452.20 | 1.71 |

TABLE 13-continued

| Compound ID | Structures | M + H (Calc.) | M + H (Observed) | Retention Time, (min) |
|---|---|---|---|---|
| 13.49 | 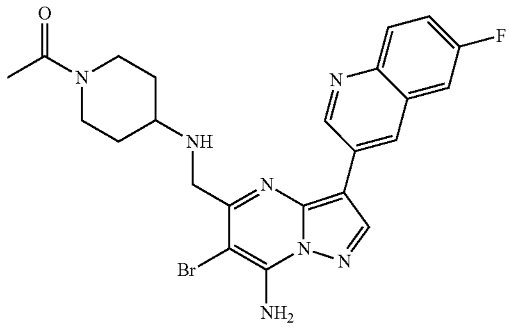 [SMILES: CC(=O)N1CCC(NCc2nc3c(-c4cnc5ccc(F)cc5c4)cnn3c(N)c2Br)CC1] | 511.10 | 512.20 | 2.46 |
| 13.50 | 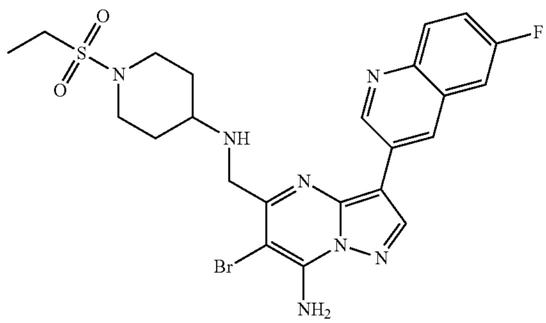 [SMILES: CCS(=O)(=O)N1CCC(NCc2nc3c(-c4cnc5ccc(F)cc5c4)cnn3c(N)c2Br)CC1] | 561.10 | 562.20 | 2.68 |
| 13.51 | 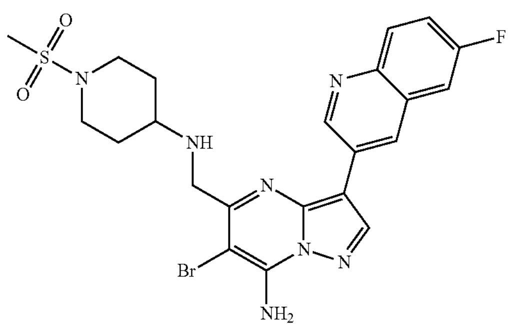 [SMILES: CS(=O)(=O)N1CCC(NCc2nc3c(-c4cnc5ccc(F)cc5c4)cnn3c(N)c2Br)CC1] | 547.10 | 548.20 | 2.67 |
| 13.52 | 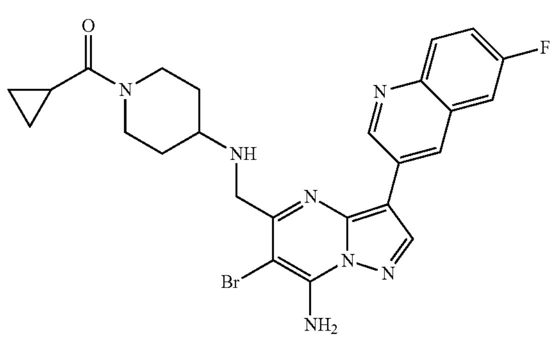 [SMILES: Nc1c(Br)c(CNC2CCN(C(=O)C3CC3)CC2)nc2c(-c3cnc4ccc(F)cc4c3)cnn12] | 537.10 | 538.20 | 2.03 |

TABLE 13-continued
| Compound ID | Structures | M + H (Calc.) | M + H (Observed) | Retention Time, (min) |
|---|---|---|---|---|
| 13.53 | 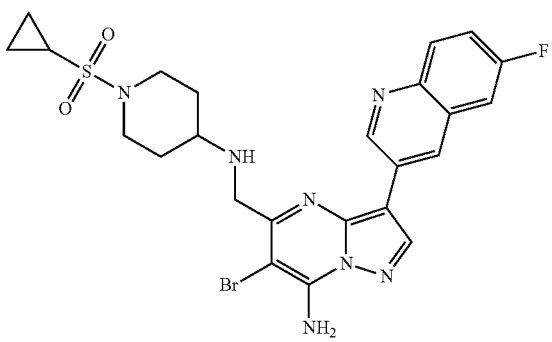 [SMILES: Nc1c(Br)c(CNC2CCN(S(=O)(=O)C3CC3)CC2)nc2c(-c3cnc4ccc(F)cc4c3)cnn12] | 573.10 | 574.20 | 3.07 |
| 13.54 | 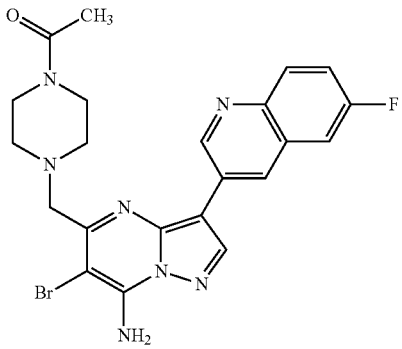 [SMILES: CC(=O)N1CCN(Cc2nc3c(-c4cnc5ccc(F)cc5c4)cnn3c(N)c2Br)CC1] | 497.10 | 498.20 | 2.58 |
| 13.55 | 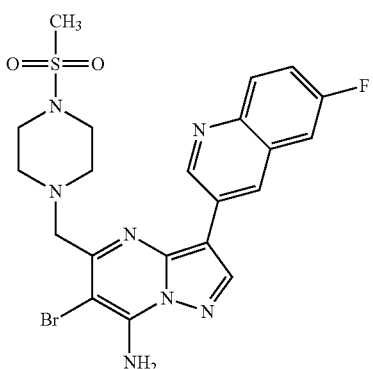 | 533.10 | 534.20 | 2.85 |
| 13.56 | 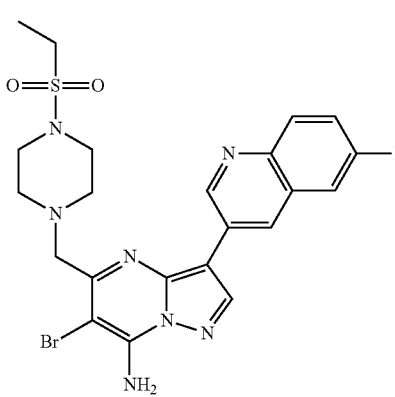 | 547.10 | 548.20 | 2.93 |

TABLE 13-continued

| Compound ID | Structures | M + H (Calc.) | M + H (Observed) | Retention Time, (min) |
|---|---|---|---|---|
| 13.57 | 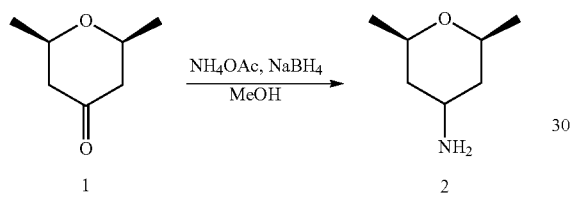 | 483.10 | 484.20 | 2.16 |

Synthesis of 6-bromo-5-(((2R,6S)-2,6-dimethyltetrahydro-2H-pyran-4-ylamino)methyl)-3-(6-fluoroquinolin-3-yl)pyrazolo[1,5-a]pyrimidin-7-amine Part A

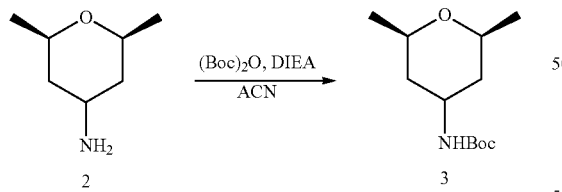

To a solution of (2R,6S)-2,6-dimethyldihydro-2H-pyran-4 (3H)-one (0.22 g, 1.7 mmol) in MeOH (11.5 ml) at room temperature was added ammonium acetate (1.3 g, 16.9 mmol) and sodium borohydride (0.07 g, 1.8 mmol) slowly and the reaction mixture was stirred for 216 h, at which time LC/MS analysis confirmed full consumption of starting material. The mixture was transferred to a separatory funnel with $CH_2Cl_2$ (30 ml) and $H_2O$ (10 ml) and brine (20 ml) was then added. Organics were extracted with $CH_2Cl_2$ (4×30 ml), dried ($Na_2SO_4$) and concentrated in vacuo to give crude product 2R,6S)-2,6-dimethyltetrahydro-2H-pyran-4-amine.

Part B:

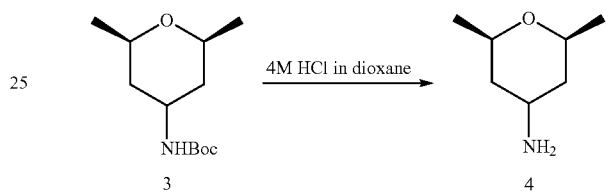

To 2R,6S)-2,6-dimethyltetrahydro-2H-pyran-4-amine (crude) in $CH_3CN$ (3.2 ml) was added N,N-diisopropylethylamine (0.9 ml) followed by di-tert-butyl dicarbonate (1.9 g) and the resulting mixture was stirred at room temperature for 1 h, at which time LC/MS confirmed full conversion of starting material to product. Solvent was removed in vacuo and the crude was redissolved in DCM (20 ml), washed with water (1×5 ml), brine (1×5 ml), dried over $MgSO_4$. Solvent was removed in vacuo to give tert-butyl (2R,6S)-2,6-dimethyltetrahydro-2H-pyran-4-ylcarbamate as a crude product which was used for the next step without any purification.

Part C:

To tert-butyl (2R,6S)-2,6-dimethyltetrahydro-2H-pyran-4-ylcarbamate (crude, 0.6 g) was added 4M HCl in 1,4-dioxane (15 ml) at r.t. It was stirred further at room temperature for 2 h, at which time LC/MS analysis confirmed full consumption of starting material. Solvent was removed in vacuo to get the desired (2R,6S)-2,6-dimethyltetrahydro-2H-pyran-4-amine as an HCl salt.

Part D:

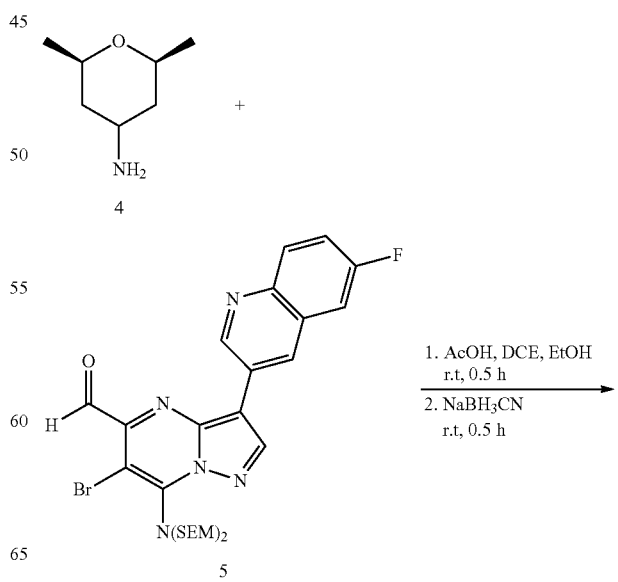

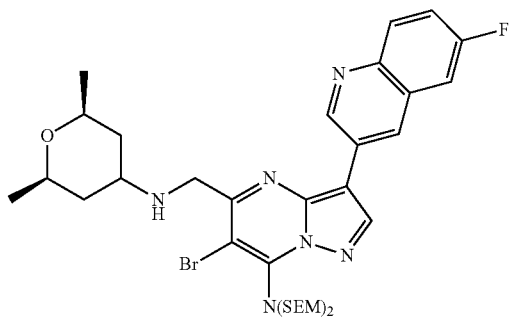

6

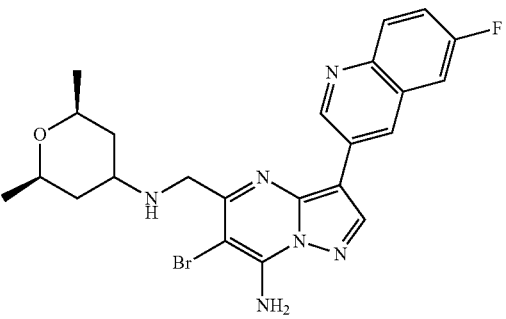

7

To crude (2R,6S)-2,6-dimethyltetrahydro-2H-pyran-4-amine (0.18 g) in DCE (4.2 ml) and Ethanol (4.2 ml) was added 7-(bis((2-(trimethylsilyl)ethoxy)methyl)amino)-6-bromo-3-(6-fluoroquinolin-3-yl)pyrazolo[1,5-a]pyrimidine-5-carbaldehyde (0.19 g, 0.3 mmol) followed by AcOH (0.03 ml, 0.6 mmol). After stirring for 30 minutes at room temperature, NaBH₃CN (37.8 mg, 0.6 mmol) was added and stirring was continued further for 30 minutes more. LC/MS showed no starting material remaining. After the solvent was rotoevaporated, the crude was dissolved with DCM (20 ml), washed with sat. NaHCO₃ (1×5 ml), water (1×5 ml), brine (1×5 ml), dried over MgSO₄. Solvent was removed in vacuo and the residue was purified by column chromatography on silica gel. Elution with EtOAc/Hexanes (0-60%) gave desired 6-bromo-5-(((2R,6S)-2,6-dimethyltetrahydro-2H-pyran-4-ylamino)methyl)-3-(6-fluoroquinolin-3-yl)-N,N-bis((2-(trimethylsilyl)ethoxy)methyl)pyrazolo[1,5-a]pyrimidin-7-amine (68 mg, 30%).

Part E 6-bromo-5-(((2R,6S)-2,6-dimethyltetrahydro-2H-pyran-4-ylamino)methyl)-3-(6-fluoroquinolin-3-yl)pyrazolo[1,5-a]pyrimidin-7-amine

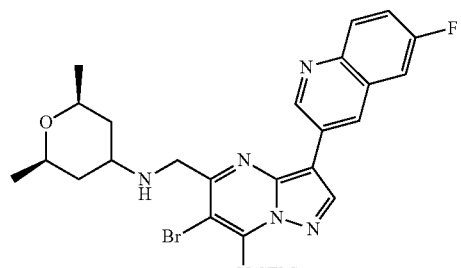

6

To a 6-bromo-5-(((2R,6S)-2,6-dimethyltetrahydro-2H-pyran-4-ylamino)methyl)-3-(6-fluoroquinolin-3-yl)-N,N-bis((2-(trimethylsilyl)ethoxy)methyl)pyrazolo[1,5-a]pyrimidin-7-amine (69.3 mg, 0.09 mmol) in TFA (2 ml) was added few drops of water and stirring continued for 2 h at room temperature. LC/MS showed no starting material remaining. TFA along with water was rotoevaporated. This crude compound was submitted to the analytical group for purification to afford the desired 6-bromo-5-(((2R,6S)-2,6-dimethyltetrahydro-2H-pyran-4-ylamino)methyl)-3-(6-fluoroquinolin-3-yl)pyrazolo[1,5-a]pyrimidin-7-amine. LCMS: 3.157 mins, m/z=499.0 (MH⁺).

Synthesis of 6-bromo-3-(6-fluoroquinolin-3-yl)-5-((3-methoxytetrahydro-2H-pyran-4-ylamino)methyl)pyrazolo[1,5-a]pyrimidin-7-amine

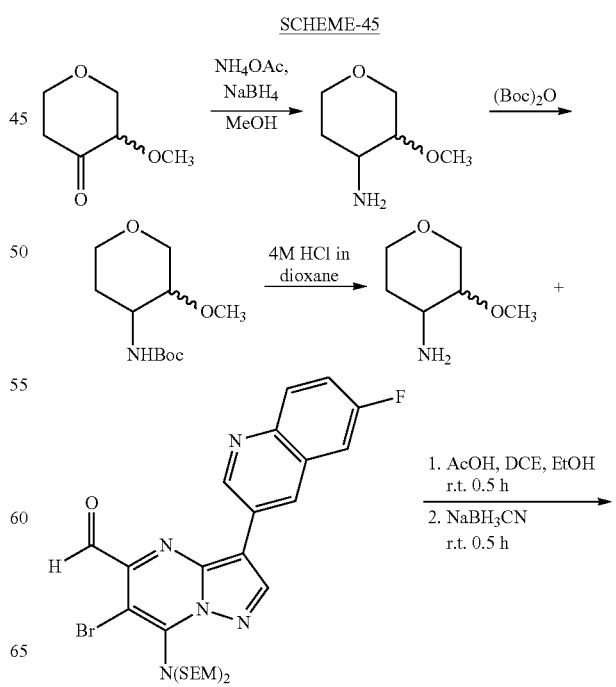

1399

-continued

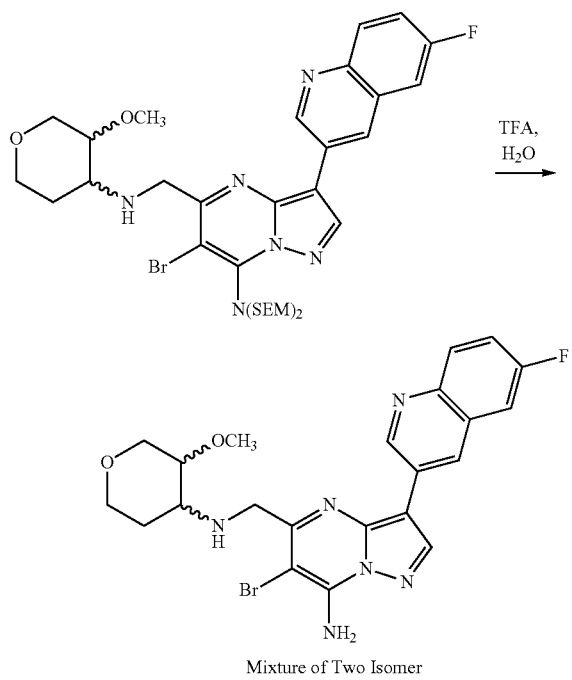

Mixture of Two Isomer

Above compound was prepared by essentially the same procedure (1) as to compound 7 is prepared. However exact configuration has not been determined.

Isomer 1: LCMS: 1.942 mins, m/z=501.1 (MH+)
Isomer 2: LCMS: 2.706 mins, m/z=501.0 (MH+)

Synthesis of 6-bromo-3-(6-fluoroquinolin-3-yl)-5-((1-(methylsulfonylmethyl)cyclopropylamino)methyl)pyrazolo[1,5-a]pyrimidin-7-amine

SCHEME-46

1.

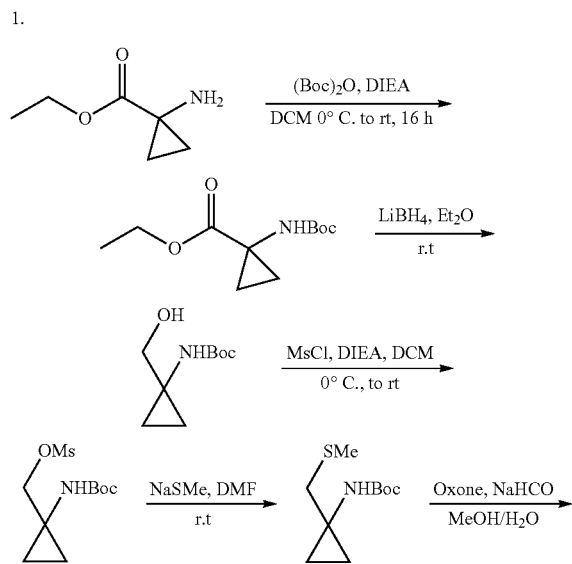

1400

-continued

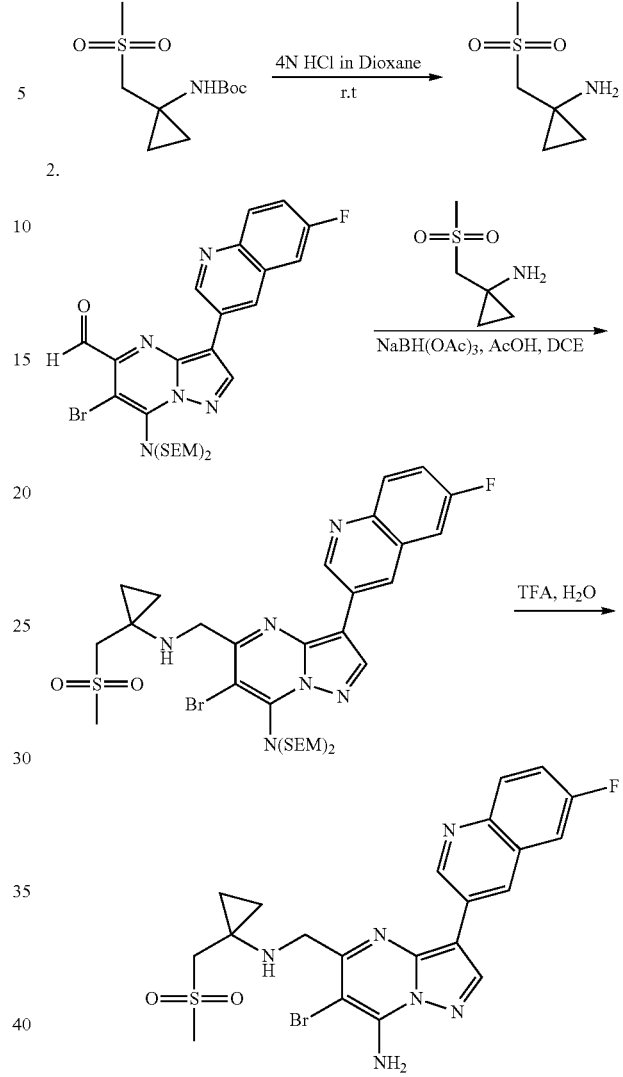

Synthesis of ethyl 1-(tert-butoxycarbonylamino)cyclopropanecarboxylate

To ethyl 1-aminocyclopropane-1-carboxylic acid ethyl ester hydrochloride (7.9 g, 48 mmol) in DCM (400 ml) was added N,N-diisopropylethylamine (21.7 ml, 124.7 mmol) followed by di-tert-butyl dicarbonate (11.5 g, 52.8 mmol) at 0° C., and the resulting mixture was stirred at room temperature for 16 h, at which time LC/MS confirmed full conversion of starting material to product. Reaction mixture was transferred in to the seperatory funnel and washed with water (1×75 ml), brine (1×75 ml), dried over MgSO$_4$. Solvent was removed in vacuo to get desired ethyl 1-(tert-butoxycarbonylamino)cyclopropanecarboxylate as a crude product which was used for the next step without any purification.

Synthesis of tert-butyl 1-(hydroxymethyl)cyclopropylcarbamate

While under argon atmosphere, LiBH$_4$ (0.73 g, 33.6 mmol) was suspended in Et$_2$O (18 ml). To this mixture was added dropwise a solution of ethyl 1-(tert-butoxycarbonylamino) cyclopropane carboxylate (5 g, 21.8 mmol) in Et$_2$O (18 ml).

The reaction mixture was stirred at room temperature for 2 h and then quenched by slow addition of MeOH (18 ml). After being stirred overnight, the reaction mixture was poured into an equal volume of sat. NH₄Cl (54 ml). The Et₂O layer was separated, and the aqueous layer was extracted four times with Et₂O. Solvent was removed in vacuo and the residue was purified by column chromatography on silica gel. Elution with EtOAc/Hexanes (50-100%) gave desired tert-butyl 1-(hydroxymethyl)cyclopropyl carbamate as a white solid (3.14 g, 77%).

Synthesis of (1-(tert-butoxycarbonylamino)cyclopropyl)methylmethanesulfonate

To tert-butyl 1-(hydroxymethyl)cyclopropylcarbamate (1.1 g, 5.83 mmol) in DCM (47 ml) was added N,N-diisopropylethylamine (1.3 ml, 7.67 mmol) followed by methanesulfonylchloride (0.5 ml, 6.4 mmol) at 0° C., and the resulting mixture was stirred at room temperature for 16 h, at which time LC/MS confirmed full conversion of starting material to product. Reaction mixture was transferred in to the seperatory funnel and washed with sat. NaHCO₃ (1×10 ml), water (1×10 ml), brine (1×10 ml), dried over MgSO₄. Solvent was removed in vacuo to get desired (1-(tert-butoxycarbonylamino)cyclopropyl)methylmethanesulfonate as a crude product (1.38 g) which was used for the next step without any purification.

Synthesis of tert-butyl 1-(methylthiomethyl)cyclopropylcarbamate

A mixture of (1-(tert-butoxycarbonylamino)cyclopropyl)methylmethanesulfonate (1.38 g, 5.2 mmol), and NaSCH₃ (0.48 g, 6.8 mmol) in DMF (21 ml) was stirred at room temperature for 2 h, at which time LC/MS confirmed full conversion of starting material to product (No Starting material is present). Reaction mixture was diluted with EtOAc (250 ml), and, washed with water (3×60 ml), brine (1×60 ml) and dried over MgSO₄. Solvent was removed to give the tert-butyl 1-(methylthiomethyl)cyclopropylcarbamate as a crude product which was used for the next step without any purification.

Synthesis of tert-butyl 1-(methylsulfonylmethyl)cyclopropylcarbamate

A mixture of tert-butyl 1-(methylthiomethyl)cyclopropylcarbamate (crude), Oxone (4.8 g, 7.8 mmol) and NaHCO₃ (2.6 g, 31.3 mmol) in MeOH (28 ml) and Water (7 ml) was stirred at room temperature for 1.5 h, at which time LC/MS analysis confirmed full consumption of starting material. Solvent was removed in vacuo and the crude was redissolved in EtOAc (100 ml), washed with water (1×20 ml), brine (1×20 ml), dried over MgSO₄. Solvent was removed in vacuo to give tert-butyl 1-(methylsulfonylmethyl)cyclopropylcarbamate as a crude product (white solid, 1.1 g) which was used for the next step without any purification.

Synthesis of 1-(methylsulfonylmethyl)cyclopropanamine

To tert-butyl 1-(methylsulfonylmethyl)cyclopropylcarbamate (crude, 1.05 g) in DCM (7 ml) was added 4M HCl in 1,4-dioxane (16 ml) at r.t. It was stirred further at room temperature for 1 h, at which time LC/MS analysis confirmed full consumption of starting material. Solvent was removed in vacuo and the solid was washed with ether to get the desired 1-(methylsulfonylmethyl)cyclopropanamine as an HCl salt.

Synthesis of 6-bromo-3-(6-fluoroquinolin-3-yl)-5-((1-(methylsulfonylmethyl)cyclo propylamino)methyl)pyrazolo[1,5-a]pyrimidin-7-amine 6-bromo-3-(6-fluoroquinolin-3-yl)-5-((1-(methylsulfonylmethyl)cyclo propylamino)methyl)pyrazolo[1,5-a]pyrimidin-7-amine was prepared by essentially the same procedure (1) as to compound 7 is prepared. LCMS: 2.52 mins, m/z=519.0 (MH⁺).

Synthesis of (1-((7-(bis((2-(trimethylsilyl)ethoxy)methyl)amino)-6-bromo-3-(6-fluoroquinolin-3-yl)pyrazolo[1,5-a]pyrimidin-5-yl)methylamino)cyclopropyl)methanol

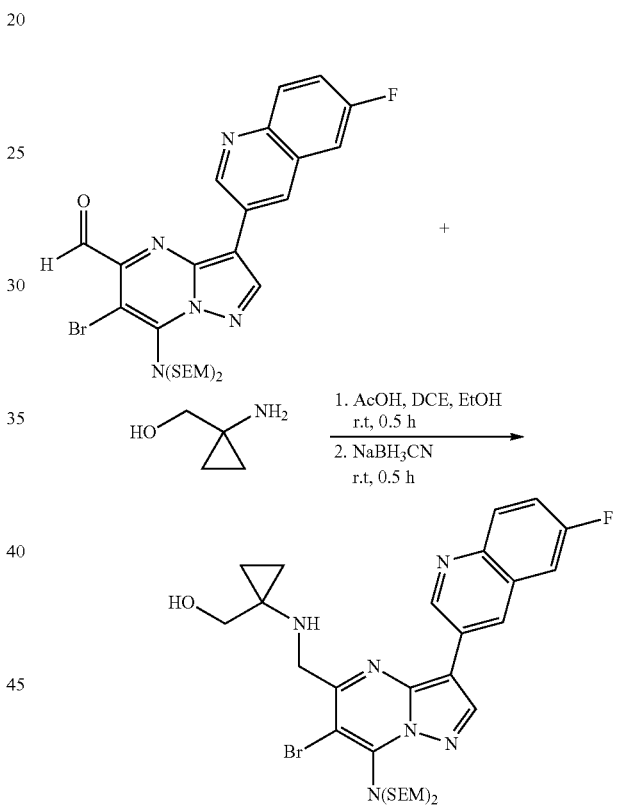

To 1-aminocyclopropyl)methanol (0.22 g, 2.5 mmol) in DCE (7 ml) and Ethanol (7 ml) was added -(bis((2-(trimethylsilyl)ethoxy)methyl)amino)-6-bromo-3-(6-fluoroquinolin-3-yl)pyrazolo[1,5-a]pyrimidine-5-carbaldehyde (0.32 g, 0.5 mmol) followed by AcOH (0.064 ml, 1 mmol). After stirring for 30 minutes at room temperature, NaBH₃CN (63 mg, 1 mmol) was added and stirring was continued further for 30 minutes more. After the solvent was rotoevaporated, the crude was dissolved with DCM (40 ml), washed with sat. NaHCO₃ (1×10 ml), water (1×10 ml), brine (1×10 ml), dried over MgSO₄. Solvent was removed in vacuo and the residue was purified by column chromatography on silica gel. Elution with EtOAc/Hexanes (0-100%) gave slightly impure desired (1-((7-(bis((2-(trimethylsilyl)ethoxy)methyl)amino)-6-bromo-3-(6-fluoroquinolin-3-yl)pyrazolo[1,5-a]pyrimidin-5-yl)methylamino)cyclopropyl)methanol (320 mg).

1403

Synthesis of tert-butyl (7-(bis((2-(trimethylsilyl)ethoxy)methy)amino)-6-bromo-3-(6-fluoroquinolin-3-yl)pyrazolo[1,5-a]pyrimidin-5-yl)methyl(1-(hydroxymethyl)cyclopropyl)carbamate

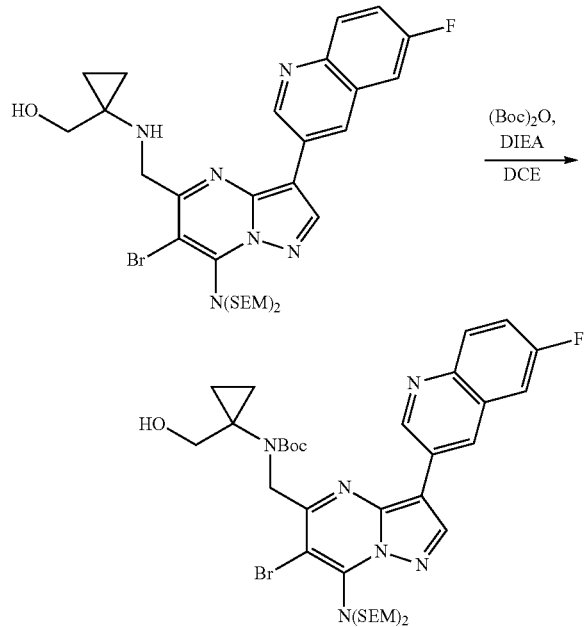

To (1-((7-(bis((2-(trimethylsilyl)ethoxy)methyl)amino)-6-bromo-3-(6-fluoroquinolin-3-yl)pyrazolo[1,5-a]pyrimidin-5-yl)methylamino)cyclopropyl)methanol (0.17 g, 0.24 mmol) in dichloroethane (2 ml) was added N,N-diisopropylethylamine (0.09 ml, 0.49 mmol) followed by di-tert-butyl dicarbonate (0.16 g, 0.73 mmol) and the resulting mixture was stirred at room temperature for 16 h, at which time LC/MS confirmed full conversion of starting material to product. The mixture was diluted with DCM (20 ml), washed with water (1×5 ml), brine (1×5 ml), dried over MgSO₄. Solvent was removed in vacuo and the residue was purified by column chromatography on silica gel. Elution with EtOAc/Hexanes (0-60%) gave desired tert-butyl (7-(bis((2-(trimethylsilyl)ethoxy)methyl)amino)-6-bromo-3-(6-fluoroquinolin-3-yl)pyrazolo[1,5-a]pyrimidin-5-yl)methyl(1-(hydroxymethyl)cyclopropyl)carbamate (0.19 g, 95%).

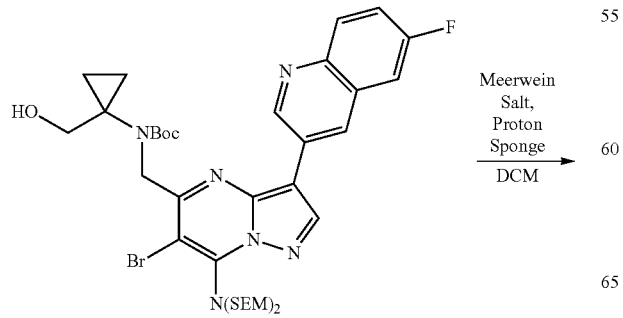

1404

-continued

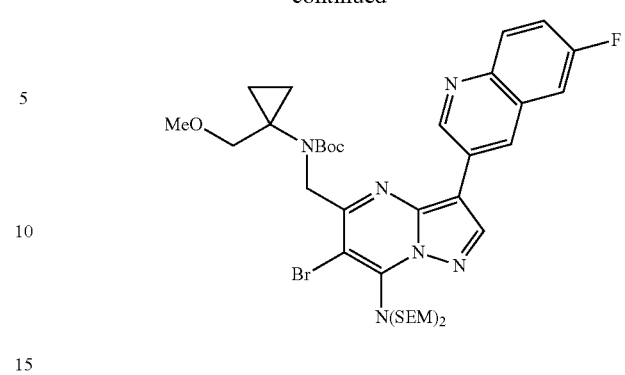

To tert-butyl (7-(bis((2-(trimethylsilyl)ethoxy)methyl)amino)-6-bromo-3-(6-fluoroquinolin-3-yl)pyrazolo[1,5-a]pyrimidin-5-yl)methyl(1-(hydroxymethyl)cyclopropyl)carbamate (0.19 g, 0.23 mmol) in DCM (2.5 ml) was added protonsponge (70 mg, 0.33 mmol) followed by trimethyloxoniumtetrafluoroborate (48.2 mg, 0.33 mmol) at room temperature and the resulting mixture was stirred at room temperature for 16 h, at which time LC/MS confirmed full conversion of starting material to product. Reaction mixture was quenched with sat. NH₄Cl and diluted with DCM (25 ml). Organics were separated and washed with brine (5 ml) and dried over MgSO₄. Solvent was removed in vacuo and the residue was purified by column chromatography on silica gel. Elution with DCM/MeOH (0-50%) gave slightly impure desired tert-butyl (7-(bis((2-(trimethylsilyl)ethoxy)methyl)amino)-6-bromo-3-(6-fluoroquinolin-3-yl)pyrazolo[1,5-a]pyrimidin-5-yl)methyl(1-(methoxymethyl)cyclopropyl)carbamate (97 mg, 50%).

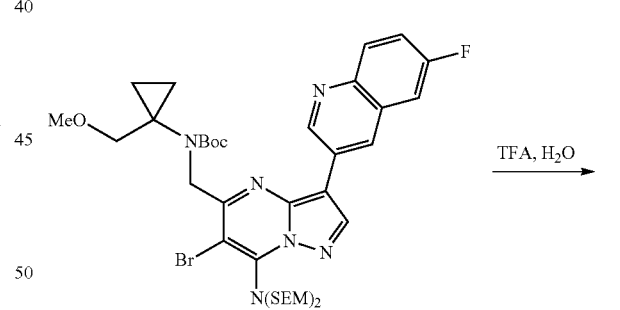

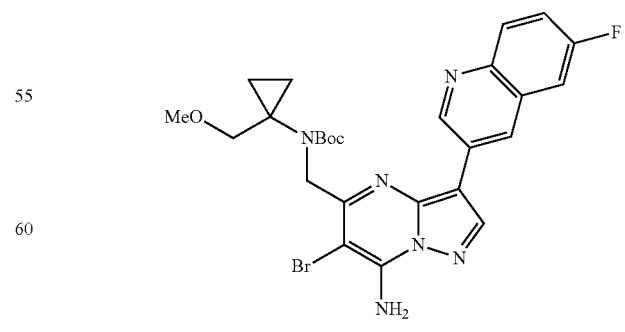

By essentially following the same procedure above compounds prepared. LCMS: 1.87 mins, m/z=471.0 (MH⁺).

1405

Synthesis of 4-(methoxymethyl)tetrahydro-2H-pyran-4-amine

Synthesis of benzyl 4-(methoxymethyl)tetrahydro-2H-pyran-4-ylcarbamate

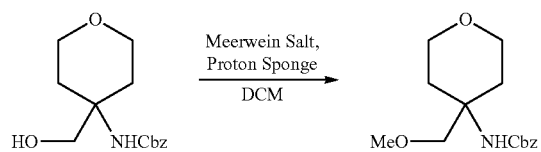 [SMILES: O=C(NC1(CO)CCOCC1)OCc1ccccc1 ; COCC1(NC(=O)OCc2ccccc2)CCOCC1]

To benzyl 4-(hydroxymethyl)tetrahydro-2H-pyran-4-yl-carbamate (0.59 g, 2.23 mmol) in DCM (24 ml) was added protonsponge (0.53 g, 2.5 mmol) followed by trimethyloxo-niumtetrafluoroborate (0.36 g, 2.5 mmol) at 0° C. After 20 min at 0° C., reaction mixture was warmed up to room temperature and stirred further for 16 h, at which time LC/MS confirmed full conversion of starting material to product. Reaction mixture was quenched with sat. NH₁Cl and with DCM (75 ml). Organics were separated and washed with brine (20 ml) and dried over MgSO₄. Solvent was removed in vacuo and the residue was purified by column chromatography on silica gel. Elution with EtOAc/Hexanes (66%-100%) gave slightly impure desired benzyl 4-(methoxymethyl)tetrahydro-2H-pyran-4-ylcarbamate (0.31 g, 50%).

Synthesis of 4-(methoxymethyl)tetrahydro-2H-pyran-4-amine

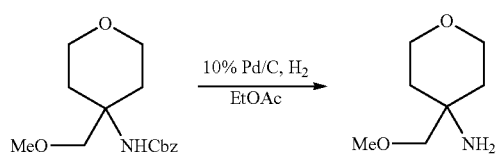

A mixture of benzyl 4-(methoxymethyl)tetrahydro-2H-pyran-4-ylcarbamate (0.86 g, 3.1 mmol), 10% Pd/C (0.21 g) in EtOAc (25 ml) was stirred at room temperature under hydrogen (balloon pressure) for 16 hours. It was then filtered and concentrated to get the desired 4-ethoxy methyl)tetrahydro-2H-pyran-4-amine.

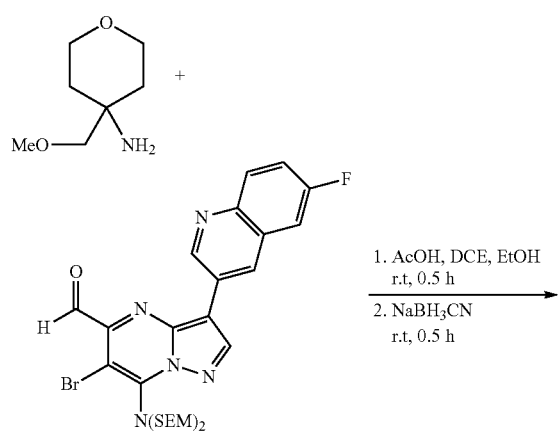

1406

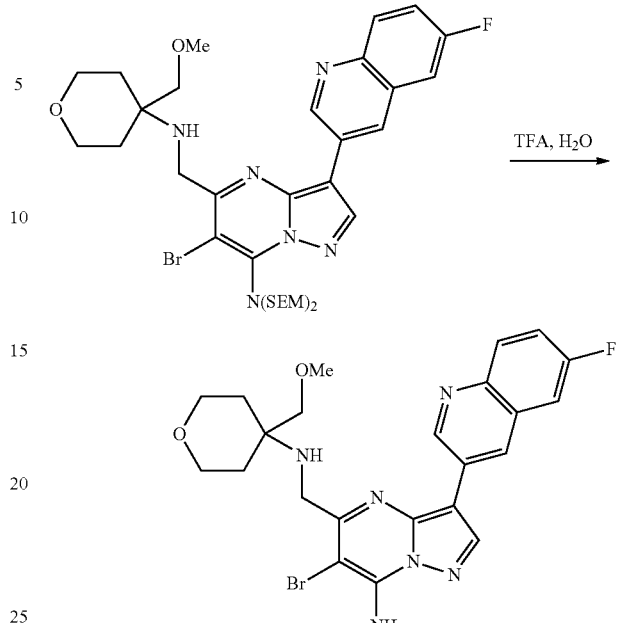

By essentially the same procedure as to compounds above is prepared. LCMS: 2.173 mins, m/z=515.2 (MH⁺).

Synthesis of 7-(bis((2-(trimethylsilyl)ethoxy)methyl)amino)pyrazolo[1,5-a]pyrimidine-5-carbonitrile

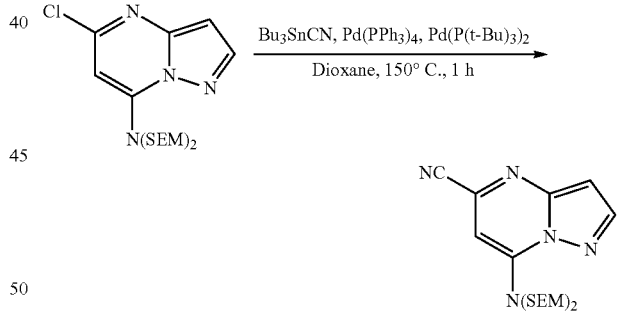

5-chloro-N,N-bis((2-(trimethyl silyl)ethoxy)methyl)pyrazolo[1,5-a]pyrimidin-7-amine (1.5 g, 3.5 mmol), tributyltin cyanide (1.7 g, 5.3 mmol), tetrakis(triphenylphosphine) palladium (0.8 g, 0.7 mmol), bis(tri-t-butylphosphine) palladium (0.4 g, 0.7 mmol) were charged in a pressure tube. The tube was evacuated and charged with argon for three cycles. Dioxane (20 ml) was added, and the tube was capped and heated at 150° C. with stirring for one hour. After cooling, the mixture was diluted with EtOAc (100 ml) and washed with brine (1×20 ml), dried over MgSO₄. Solvent was removed in vacuo and the residue was purified by column chromatography on silica gel. Elution with EtOAc/Hexanes (0-35%) gave desired product, 7-(bis((2-(trimethylsilyl)ethoxy)methyl)amino) pyrazolo[1,5-a]pyrimidine-5-carbonitrile (1.3 g, 90%).

1407

Synthesis of 5-(1-aminoethyl)-N,N-bis((2-(trimethylsilyl)ethoxy)methyl)pyrazolo[1,5-a]pyrimidin-7-amine

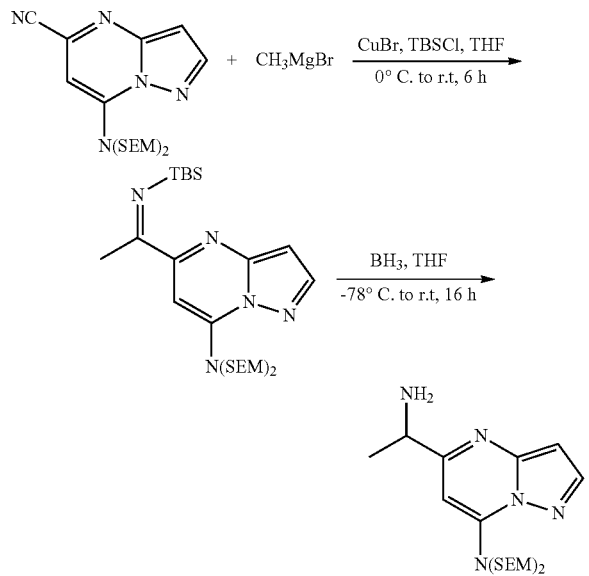

To a solution 7-(bis((2-(trimethylsilyl)ethoxy)methyl)amino)pyrazolo[1,5-a]pyrimidine-5-carbonitrile (0.6 g, 1.4 mmol), copper bromide (42 mg, 0.3 mmol), and TBSCl (0.2 g, 1.4 mmol) in THF (14 ml) at 0° C. was added methyl magnesium bromide (3M in ether, 0.47 ml, 1.4 mmol) dropwise. Reaction mixture was warmed up to room temperature and stirred further for 6 h. LC/MS showed no starting material (M.W=419) remaining. A borane.THF solution (1M in THF, 2.8 ml, 2.8 mmol) was then added to the reaction mixture at −78° C., and the resulting solution was stirred for 4 h and allowed to warm at room temperature overnight. Distilled water (0.5 ml) was cautiously added to the solution cooled at −20° C., followed by sat. NH₄Cl (0.5 ml). After the THF was rotoevaporated, the aqueous phase was extracted with DCM (60 ml), washed with water (1×5 ml), brine (1×5 ml), dried over MgSO₄. Solvent was removed in vacuo and the crude was used for the next step without any further purification.

Alternatively, the 5-(1-aminoethyl)-N,N-bis((2-(trimethylsilyl)ethoxy)methyl)pyrazolo[1,5-a]pyrimidin-7-amine can also be synthesized by the following procedure.

Synthesis of 5-(1-aminoethyl)-N,N-bis((2-(trimethylsilyl)ethoxy)methyl)pyrazolo[1,5-a]pyrimidin-7-amine can Also be Synthesized by the Following Procedure

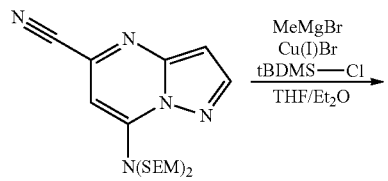

1408

-continued

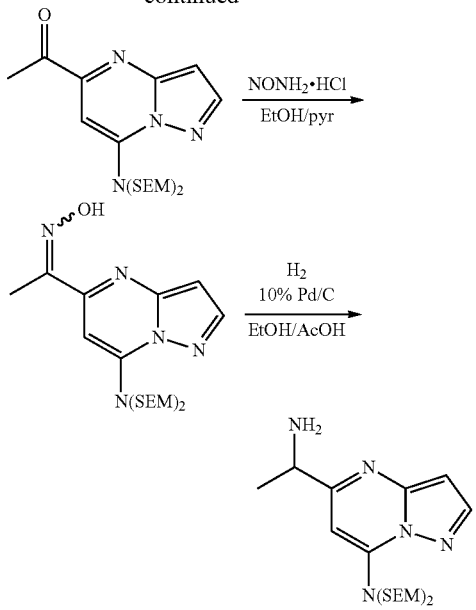

Part A

Synthesis of 1-(7-(bis((2-(trimethylsilyl)ethoxy)methyl)amino)pyrazolo[1,5-a]pyrimidin-5-yl)ethanone An oven-dried 250 mL 3-neck round-bottom flask fitted with a pressure-equalizing addition funnel, temperature probe and septum was charged with 7-(bis{[2-(trimethylsilyl)ethoxy]methyl}amino)pyrazolo[1,5-a]pyrimidine-5-carbonitrile (7.10 g, 16.9 mmol) in dry THF (59 mL), copper(I) bromide (120 mg, 0.84 mmol) and tert-butyldimethylsilyl chloride (2.80 g, 18.6 mmol), and the stirred mixture was cooled in an ice-brine bath. 3M MeMgBr in ether (9.59 mL, 28.8 mmol) was added dropwise over 10 min via the addition funnel, and the resulting heterogeneous mixture was stirred at −5-0° C. for 1.5 h and quenched carefully by the dropwise addition of water until gas evolution ceased. The mixture was diluted with additional water (100 mL) and extracted with diethyl ether (2×150 mL), and the combined organic phase was washed with brine (100 mL), dried over Na₂SO₄ and concentrated under reduced pressure. Purification by chromatography on silica gel (120 g), eluting with 0-20% EtOAc/hexanes, afforded the title compound, 1-(7-(bis((2-(trimethylsilyl)ethoxy)methyl)amino)pyrazolo[1,5-a]pyrimidin-5-yl)ethanone (4.34 g, 59% yield) as a light yellow oil: MS (ESI+) for $C_{20}H_{36}N_4O_3Si_2$ m/z 437 (M+H)⁺; $R_f$=0.70 (25% EtOAc/hexanes).

Part B

Synthesis of 1-(7-(bis((2-(trimethylsilyl)ethoxy)methyl)amino)pyrazolo[1,5-a]pyrimidin-5-yl)ethanone oxime A solution of 1-[7-(bis{[2-(trimethylsilyl)ethoxy]methyl}amino)pyrazolo[1,5-a]pyrimidin-5-yl]ethanone (4.34 g, 9.94 mmol) in 1:1 EtOH/pyridine (50 mL) was treated with hydroxylamine hydrochloride (3.45 g, 49.7 mmol). The resulting mixture was stirred at room temperature for 1.5 h and then concentrated under reduced pressure to remove most solvent. The residue was partitioned between EtOAc (100 mL) and water (60 mL), the layers were separated, and the organic phase was washed with water (60 mL) and brine (20 mL), dried over $Na_2SO_4$ and concentrated under reduced pressure to give the title compound, 1-(7-(bis((2-(trimethylsilyl)ethoxy)methyl)amino)pyrazolo[1,5-a]pyrimidin-5-yl)ethanone oxime (4.90 g, 85% purity, 93% yield) as an off-white semisolid: MS (ESI+) for $C_{20}H_{37}N_5O_3Si_2$ m/z 452 (M+H)⁺.

Part C

Synthesis of 5-(1-aminoethyl)-N,N-bis((2-(trimethylsilyl)ethoxy)methyl)pyrazolo[1,5-a]pyrimidin-7-amine A solution of 1-[7-(bis{[2-(trimethylsilyl)ethoxy]methyl}amino)pyrazolo[1,5-a]pyrimidin-5-yl]ethanone oxime (4.50 g, 8.77 mmol) in 4:1 EtOH/AcOH (90 mL) under nitrogen in a Parr bottle was treated with 10% Pd on carbon (933 mg, 0.877 mmol), and the mixture was shaken on the Parr apparatus under 45 psi hydrogen for 23 h. The catalyst was removed by filtration through Celite, and the filtrate was concentrated under reduced pressure, azeotroping with toluene at 40-45° C. to remove most AcOH. The oily residue was taken up in EtOAc (~100 mL), washed with saturated aqueous $NaHCO_3$ (2×50 mL) and brine (20 mL), dried over $Na_2SO_4$, and concentrated under reduced pressure to give the title compound, 5-(1-aminoethyl)-N,N-bis((2-(trimethylsilyl)ethoxy)methyl)pyrazolo[1,5-a]pyrimidin-7-amine (4.02 g, 91% purity, 95% yield) as an oil: MS (ESI+) for $C_{20}H_{39}N_5O_2Si_2$ m/z 438 (M+H)⁺.

Synthesis of 5-(1-aminoethyl)-3-(6-fluoroquinolin-3-yl)-N,N-bis((2-(trimethylsilyl)ethoxy)methyl)pyrazolo[1,5-a]pyrimidin-7-amine

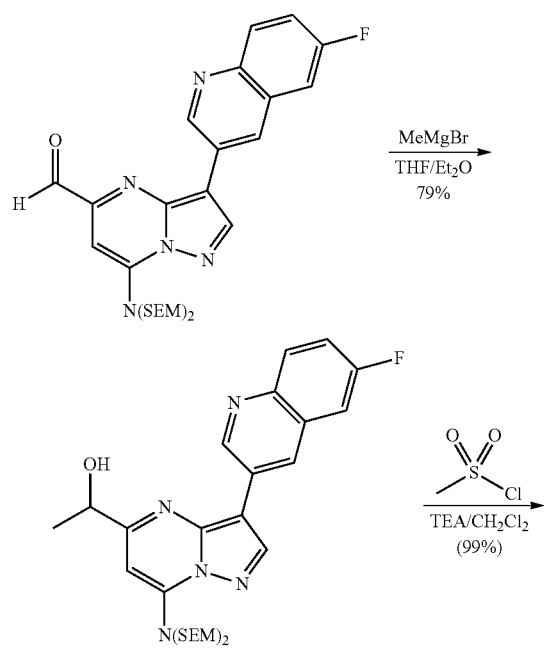

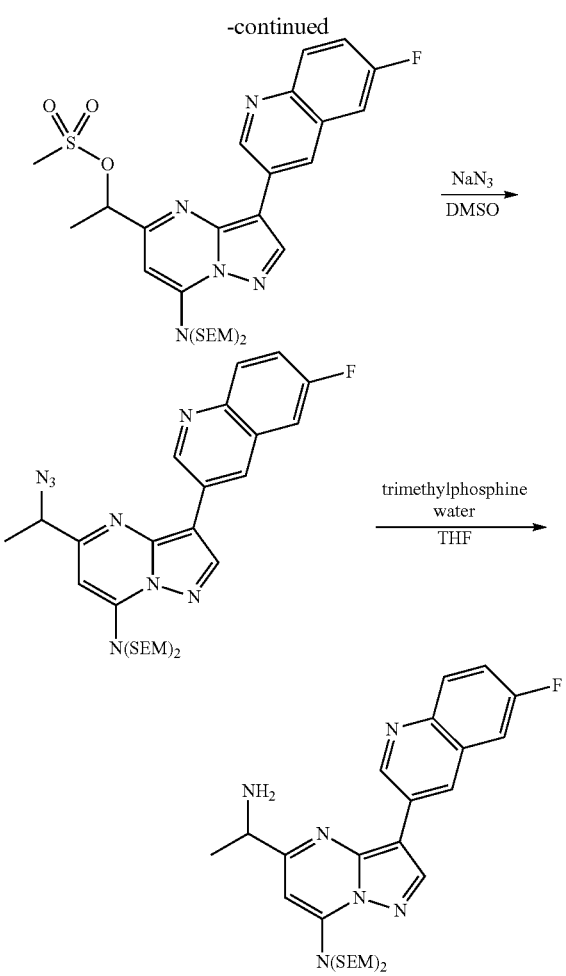

Part A

Synthesis of 1-(7-(bis((2-(trimethylsilyl)ethoxy)methyl)amino)-3-(6-fluoroquinolin-3-yl)pyrazolo[1,5-a]pyrimidin-5-yl)ethanol To a solution of 7-(bis((2-(trimethylsilyl)ethoxy)methyl)amino)-3-(6-fluoroquinolin-3-yl)pyrazolo[1,5-a]pyrimidine-5-carbaldehyde (11.0 g, 19.4 mmol) in anhydrous THF (200 mL, 2 mol) under nitrogen at 0° C. was added 3M methylmagnesium bromide in ether (9.69 mL, 29.0 mmol) dropwise. After 1 hour the reaction was complete by HPLC. Water (10 mL) was added over a 15 minute period to quench the reaction. Removed the flask from the ice bath and concentrated in vacuo. Dissolved the remaining residue in ethyl acetate, washed three times with water and then twice with brine. The organics were dried over sodium sulfate, filtered and concentrated in vacuo. Purified the remaining crude material by flash chromatography (5-40% EtOAc/hex) to afford 1-(7-(bis((2-(trimethylsilyl)ethoxy)methyl)amino)-3-(6-fluoroquinolin-3-yl)pyrazolo[1,5-a]pyrimidin-5-yl)ethanol (6.8 g; 60% yield) as a yellow solid. HPLC: 7.54 min (Method C). LCMS: ESI+ m/z of 584 (M+H)

Part B

Synthesis of 1-(7-(bis((2-(trimethylsilyl)ethoxy)methyl)amino)-3-(6-fluoroquinolin-3-yl)pyrazolo[1,5-a]pyrimidin-5-yl)ethyl methanesulfonate To a solution of 1-(7-(bis((2-(trimethylsilyl)ethoxy)methyl)amino)-3-(6-fluoroquinolin-3-yl)pyrazolo[1,5-a]pyrimidin-5-yl)ethanol (6.1 g, 10.4 mmol) in methylene chloride (100 mL) and triethylamine (7.1 mL, 50.9 mmol) under nitrogen was added methanesulfonyl chloride (2.4 mL, 31.0 mmol) dropwise. After 15 minutes the reaction was complete by HPLC. The contents of the flask were transferred to a separatory funnel, washed twice with water and twice with brine. The organics were dried over sodium sulfate, filtered and concentrated in vacuo to afford 1-(7-(bis((2-(trimethylsilyl)ethoxy)methyl)amino)-3-(6-fluoroquinolin-3-yl)pyrazolo[1,5-a]pyrimidin-5-yl)ethyl methanesulfonate (6.8 g; 98% yield) as a dark yellow oil that was used as is for the following step. HPLC: 6.18 min (Method D). LCMS: ESI+ m/z of 662 (M+H)

Part C

Synthesis of 5-(1-azidoethyl)-3-(6-fluoroquinolin-3-yl)-N,N-bis((2-(trimethylsilyl)ethoxy)methyl)pyrazolo[1,5-a]pyrimidin-7-amine To a solution of 1-(7-(bis((2-(trimethylsilyl)ethoxy)methyl)amino)-3-(6-fluoroquinolin-3-yl)pyrazolo[1,5-a]pyrimidin-5-yl)ethyl methanesulfonate (6.8 g, 10.3 mmol) in DMSO (100 mL) and N,N-diisopropyl-ethylamine (8.95 mL, 51.4 mmol) was added sodium azide (2.0 g, 30.8 mmol). After 4 hours the reaction was complete by HPLC. The contents of the flask were transferred to a separatory funnel, washed twice with water and twice with brine. The organics were dried over sodium sulfate, filtered and concentrated in vacuo to afford 5-(1-azidoethyl)-3-(6-fluoroquinolin-3-yl)-N,N-bis((2-(trimethylsilyl)ethoxy)methyl)pyrazolo[1,5-a]pyrimidin-7-amine (6.2 g; 99% yield) as a dark yellow oil. HPLC: 6.67 min (Method D). LCMS: No ion detected.

Part D

Synthesis of 5-(1-aminoethyl)-3-(6-fluoroquinolin-3-yl)-N,N-bis((2-(trimethylsilyl)ethoxy)methyl)pyrazolo[1,5-a]pyrimidin-7-amine To a solution of 5-(1-azidoethyl)-3-(6-fluoroquinolin-3-yl)-N,N-bis((2-(trimethylsilyl)ethoxy)methyl)pyrazolo[1,5-a]pyrimidin-7-amine (6.2 g, 10.3 mmol) and THF (90 mL) was added 1M trimethylphosphine in THF (30.8 mL, 30.8 mmol) dropwise. After 30 minutes the reaction was complete by HPLC. Water (30 mL) was therefore added and the reaction stirred an additional hour. The contents of the flask were transferred to a separatory funnel, diluted with 300 mL of EtOAc and washed three times with water and three times with brine. The organics were dried over sodium sulfate, filtered and concentrated in vacuo. Purified the remaining crude material by flash chromatography (0-2% 0.7N NH3 in MeOH/CHCl3) to afford 5-(1-aminoethyl)-3-(6-fluoroquinolin-3-yl)-N,N-bis((2-(trimethylsilyl)ethoxy)methyl)pyrazolo[1,5-a]pyrimidin-7-amine (4.9 g, 82% yield) as a yellow solid. HPLC: 6.62 min (Method C). LCMS: ESI+ m/z of 583 (M+H)

Synthesis of 5-(1-(tetrahydro-2H-pyran-4-ylamino)ethyl)-N,N-bis((2-(trimethylsilyl)ethoxy)methyl)pyrazolo[1,5-a]pyrimidin-7-amine

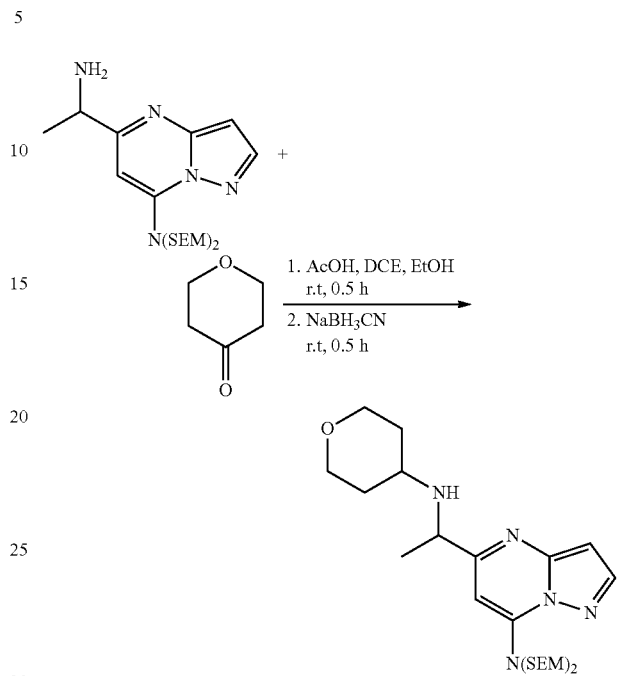

To crude 5-(1-aminoethyl)-N,N-bis((2-(trimethylsilyl)ethoxy)methyl)pyrazolo[1,5-a]pyrimidin-7-amine (0.6 g) in DCE (20 ml) and Ethanol (20 ml) was added tetrahydro-4H-pyran-4-one (0.6 ml, 7 mmol) followed by AcOH (0.08 ml, 1.4 mmol). After stirring for 30 minutes at room temperature, NaBH$_3$CN (0.18 g, 2.8 mmol) was added and stirring was continued further for 30 minutes more. LC/MS showed no starting material (M.W=437) remaining. After the solvent was rotoevaporated, the crude was dissolved with DCM (60 ml), washed with sat. NaHCO$_3$ (1×5 ml), water (1×5 ml), brine (1×5 ml), dried over MgSO$_4$. Solvent was removed in vacuo and the residue was purified by column chromatography on silica gel. Elution with MeOH/EtOAC (0-20%) gave desired product, 5-(1-(tetrahydro-2H-pyran-4-ylamino)ethyl)-N,N-bis((2-(trimethylsilyl)ethoxy)methyl)pyrazolo[1,5-a]pyrimidin-7-amine (0.2 g, 27%).

Synthesis of 3-iodo-5-(1-(tetrahydro-2H-pyran-4-ylamino)ethyl)-N,N-bis((2-(trimethylsilyl)ethoxy)methyl)pyrazolo[1,5-a]pyrimidin-7-amine

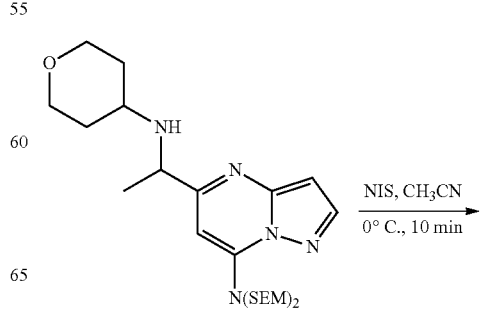

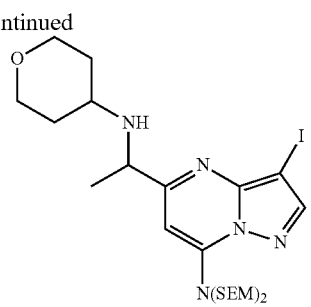

To a solution of 5-(1-(tetrahydro-2H-pyran-4-ylamino)ethyl)-N,N-bis((2-(trimethylsilyl)ethoxy)methyl)pyrazolo[1,5-a]pyrimidin-7-amine (0.17 g, 0.32 mmol) in acetonitrile (15 ml) at 0° C. was added NIS (78 mg, 0.35 mmol) and stirring continued for 10 minutes. LC/MS showed no starting material (M.W=521) remaining. Saturated sodium thiosulfate solution (~0.5 ml) was added and stirring continued for 5 minutes. After the acetonitrile was rotoevaporated, the aqueous phase was extracted with DCM (25 ml), washed with water (1×5 ml), brine (1×5 ml), dried over MgSO₄. Solvent was removed in vacuo and the residue was purified by column chromatography on silica gel. Elution with MeOH/EtOAC (0-20%) gave desired product, 3-iodo-5-(1-(tetrahydro-2H-pyran-4-ylamino)ethyl)-N,N-bis((2-(trimethylsilyl)ethoxy)methyl)pyrazolo[1,5-a]pyrimidin-7-amine (0.14 g, 69%).

Synthesis of 3-(6-fluoroquinolin-3-yl)-5-(1-(tetrahydro-2H-pyran-4-ylamino)ethyl)-N,N-bis((2-(trimethylsilyl)ethoxy)methyl)pyrazolo[1,5-a]pyrimidin-7-amine

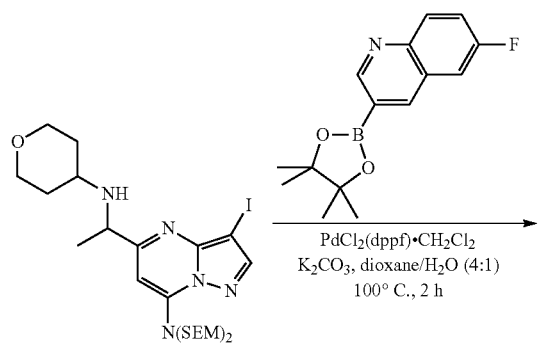

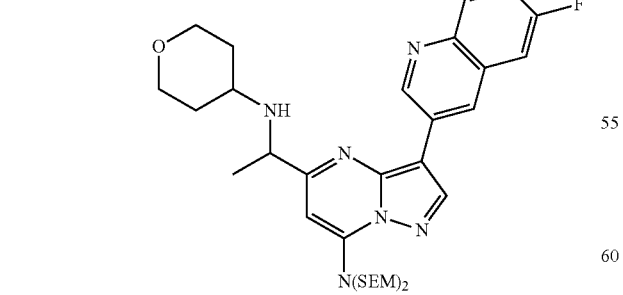

To 3-iodo-5-(1-(tetrahydro-2H-pyran-4-ylamino)ethyl)-N,N-bis((2-(trimethylsilyl)ethoxy)methyl)pyrazolo[1,5-a]pyrimidin-7-amine (0.14 g, 0.21 mmol) was added 6-fluoroquinoline boronate (0.11 g, 0.42 mmol), K₂CO₃ (87 mg, 0.63 mmol), PdCl₂(dppf).CH₂Cl₂ (18 mg, 0.02 mmol), dioxane (4 ml) and H₂O (1 ml). The resulting mixture was heated at 100° C. for 2 hours, at which time LC/MS analysis confirmed full consumption of starting material. On cooling, the solvent was rotoevaporated, and the crude was redissolved in DCM (40 ml), washed with water (1×5 ml), brine (1×5 ml), dried over MgSO₄. Solvent was removed in vacuo and the residue was purified by column chromatography on silica gel. Elution with MeOH/EtOAC (0-20%) gave desired product, 3-(6-fluoroquinolin-3-yl)-5-(1-(tetrahydro-2H-pyran-4-ylamino)ethyl)-N,N-bis((2-(trimethylsilyl)ethoxy)methyl)pyrazolo[1,5-a]pyrimidin-7-amine (84 mg, 60%).

Synthesis of 3-(6-fluoroquinolin-3-yl)-5-(1-(tetrahydro-2H-pyran-4-ylamino)ethyl)pyrazolo[1,5-a]pyrimidin-7-amine

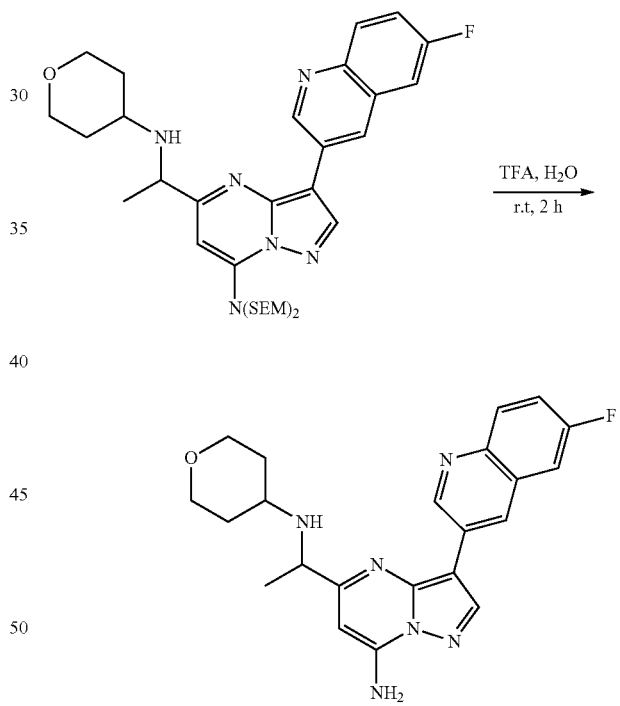

To a solution of 3-(6-fluoroquinolin-3-yl)-5-(1-(tetrahydro-2H-pyran-4-ylamino)ethyl)-N,N-bis((2-(trimethylsilyl)ethoxy)methyl)pyrazolo[1,5-a]pyrimidin-7-amine (84 mg, 0.13 mmol) in TFA (2 ml) was added few drops of water and stirring continued for 2 h at room temperature. LC/MS showed no starting material (M.W=666) remaining. TFA along with water was rotoevaporated, and the crude was dried under the high vacuum for 4 h, which was used without further purification for the next step.

Synthesis of 6-bromo-3-(6-fluoroquinolin-3-yl)-5-(1-(tetrahydro-2H-pyran-4-ylamino)ethyl)pyrazolo[1,5-a]pyrimidin-7-amine

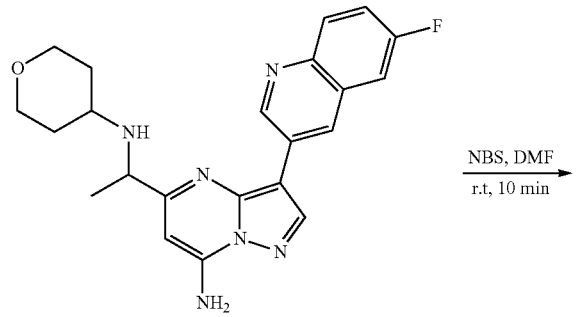

To a solution of 3-(6-fluoroquinolin-3-yl)-5-(1-(tetrahydro-2H-pyran-4-ylamino)ethyl)pyrazolo[1,5-a]pyrimidin-7-amine (Crude, ~0.13 mmol) in DMF (2 ml) at room temperature was added NBS (25 mg, 0.14 mmol) and stirring continued for 10 minutes. LC/MS showed no starting material (M.W=406) remaining. This crude compound was submitted to the analytical group for purification to afford the desired 6-bromo-3-(6-fluoroquinolin-3-yl)-5-(1-(tetrahydro-2H-pyran-4-ylamino)ethyl)pyrazolo[1,5-a]pyrimidin-7-amine.

Synthesis of
1-(4-aminopiperidin-1-yl)-2-methoxyethanone

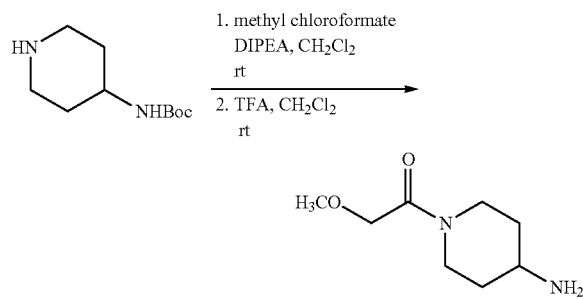

Methyl chloroformate (289 µL, 3.74 mmol) was added to a solution of 4-(N-Boc-amino)-piperidine (500 mg, 2.50 mmol) in methylene chloride (25 mL) at room temperature. N,N-diisopropylethylamine (1.30 mL, 7.49 mmol) was added and the solution was stirred overnight. The reaction mixture was diluted with sat. ammonium chloride (30 mL) and extracted with methylene chloride (3×30 mL). The combined extracts were dried over sodium sulfate and concentrated. The crude material was purified by column chromatography on silica gel (0% to 100% ethyl acetate in methylene chloride) to give 566 mg of a white solid. This solid was taken up in methylene chloride (2 mL) and trifluoroacetic acid (2 mL) was added at room temperature. After 20 min, the solution was concentrated, and then diluted with methylene chloride (2 mL). The solution was basified with sat. sodium carbonate (2 mL) and the mixture was extracted with methylene chloride (5×5 mL) and ethyl acetate (5×5 mL). The combined extracts were concentrated and the resulting solid was freeze dried from acetonitrile and water to give 290 mg of the title compound as a white solid, 1-(4-aminopiperidin-1-yl)-2-methoxyethanone, (73% over two steps). NMR (300 MHz, D$_2$O) δ 4.79 (s, 2H), 4.12 (d, J=13.5 Hz, 2H), 3.72 (s, 3H), 3.28-3.14 (m, 1H), 2.95 (t, J=12.6 Hz, 2H), 1.98 (d, J=12.0 Hz, 2H), 1.54-1.36 (m, 2H).

Synthesis of
1-(4-aminopiperidin-1-yl)-3-methoxypropan-1-one

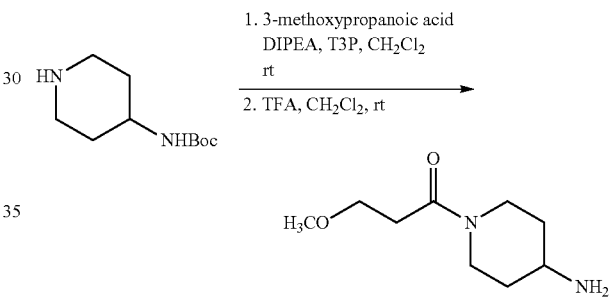

3-Methoxypropanoic acid (225 µL, 2.40 mmol) was added to a solution of 4-(N-Boc-amino)-piperidine (400 mg, 2.00 mmol) in methylene chloride (25 mL) at room temperature. N,N-diisopropylethylamine (1.30 mL, 7.49 mmol) and propylphosphonic anhydride (1.78 mL, 50 wt. % in ethyl acetate, 3.00 mmol) was added, and the solution was stirred for 4.5 h. The reaction mixture was concentrated and partitioned between ethyl acetate (5 mL) and water (5 mL). The organic portion was washed with 0.2M HCl (2 mL), sat. Sodium bicarbonate (5 mL) and brine (5 mL). The solution was then dried over sodium sulfate and concentrated to a white solid. This solid was taken up in methylene chloride (6 mL), and trifluoroacetic acid (3 mL) was added at room temperature. After 1 h the solution was concentrated. The resulting solid was dissolved in methylene chloride (2 mL) and 1M sodium hydroxide (1 mL). This mixture was extracted with methylene chloride (4×2 mL) and ethyl acetate (4×2 mL). The combined organic extracts were dried over sodium sulfate and concentrated to give 135 mg of the title compound, 1-(4-aminopiperidin-1-yl)-3-methoxypropan-1-one (36% over two steps). $^1$H NMR (300 MHz, CD$_3$OD) δ 4.51-4.41 (m, 1H), 4.03-3.93 (m, 1H), 3.64 (d, J=6.3 Hz, 2H), 3.32 (s, 3H), 3.17-3.05 (m, 1H), 2.96-2.83 (m, 1H), 2.75-2.55 (m, 3H), 1.99-1.80 (m, 2H), 1.40-1.14 (m, 2H).

1417
Synthesis of (R)-1-(4-aminopiperidin-1-yl)-2,3-dihydroxy-3-methylbutan-1-one

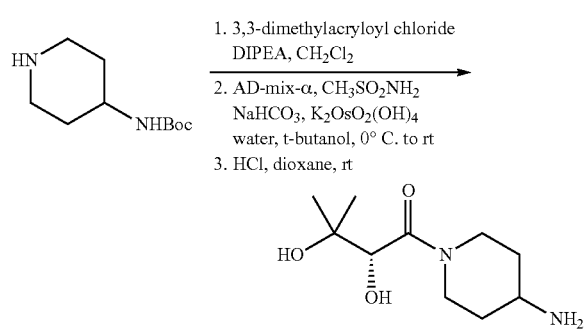

3,3-Dimethylacryloyl chloride (670 µL, 5.99 mmol) was added to a solution of 4-(N-Boc-amino)-piperidine (1.00 g, 4.99 mmol) in methylene chloride (50 mL) at room temperature. N,N-diisopropylethylamine (1.74 mL, 9.99 mmol) was added and the solution was stirred overnight. The reaction mixture was diluted with sat. ammonium chloride (50 mL) and extracted with methylene chloride (3×50 mL). The combined extracts were dried over sodium sulfate and concentrated. The crude material was purified by column chromatography on silica gel (0% to 100% ethyl acetate in methylene chloride) to give 1.39 g of an off white solid. This solid was dissolved in t-butanol (18 mL) and water (18 mL), and the solution was cooled to 0° C. To this mixture were added AD-mix-α (7.50 g), methanesulfonamide (449 mg, 4.72 mmol), sodium bicarbonate (1.13 g, 13.5 mmol), and potassium osmate dihydrate (15 mg 0.0450 mmol). The solution was allowed to warm to room temperature overnight. A 1.9M solution of sodium sulfite (40 mL) was added and the mixture was stirred for 1 h. The resulting aqueous solution was extracted with ethyl acetate (4×100 mL) and dried over sodium sulfate. The solution was concentrated and the crude material was purified by column chromatography on silica gel (0% to 20% methanol in methylene chloride, and 0% to 10% methanol in methylene chloride) to give 670 mg of the diol. A portion of this diol (650 mg, 2.05 mmol) was dissolved in dioxane (10 mL) and HCl in dioxane (5.1 mL, 4M, 20.5 mmol) was added at room temperature. After stirring overnight, the reaction mixture was diluted with ether (20 mL) and filtered to give a white solid. This solid was taken up in methylene chloride (50 mL) and MP-carbonate resin (830 mg, 2.11 mmol) was added. After 1.5 h the solvent was decanted and the resin was washed with methylene chloride (20 mL). Methylene chloride (50 mL) was added to the resin along with additional fresh resin (1.0 g, 2.54 mmol). After stirring for 30 min, the solvent was decanted and the remaining resin was washed with methylene chloride (20 mL). The combined organics were concentrated to 121 mg of the free amine, (R)-1-(4-aminopiperidin-1-yl)-2,3-dihydroxy-3-methylbutan-1-one (13% over three steps). $^1$H NMR (300 MHz, CD$_3$OD) δ 4.54-4.40 (m, 1H), 4.32-4.26 (m, 1H), 4.26-4.13 (m, 1H), 3.16-3.03 (m, 1H), 2.95-2.81 (m, 1H), 2.80-2.69 (m, 1H), 1.94-1.79 (m, 2H), 1.47-1.28 (m, 2H), 1.25 (d, J=5.4 Hz, 3H), 1.17 (d, J=5.1 Hz, 3H).

1418
Synthesis of (R)-1-(4-aminopiperidin-1-yl)-2,3-dihydroxypropan-1-one

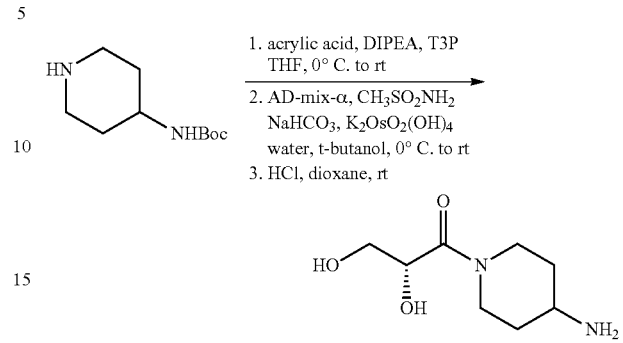

N,N-diisopropylethylamine (2.54 mL, 14.6 mmol) was added to a solution of 4-(N-Boc-amino)-piperidine (1.75 g, 8.75 mmol) in tetrahydrofuran (36 mL) at 0° C. Propylphosphonic anhydride (5.92 mL, 50 wt. % in ethyl acetate, 9.48 mmol) and acrylic acid (500 µL, 7.29 mmol) were added, and the solution was allowed to warm to room temperature overnight. The reaction mixture was partitioned between ethyl acetate (20 mL) and water (20 mL). The organic portion was washed with 0.2M HCl (5 mL), sat. sodium bicarbonate (20 mL), and brine (20 mL). The solution was then dried over sodium sulfate and concentrated to a white solid. A portion of this solid (800 mg, 3.15 mmol) was dissolved in t-butanol (13 mL) and water (13 mL) and cooled to 0° C. To this mixture were added AD-mix-α (5.24 g), methanesulfonamide (314 mg, 3.30 mmol), sodium bicarbonate (793 mg, 9.44 mmol), and potassium osmate dihydrate (52 mg, 0.157 mmol). After 4.5 h, a 0.8M solution of sodium sulfite (100 mL) was added and the mixture was stirred for 1 h at room temperature. The resulting aqueous solution was extracted with ethyl acetate (4×100 mL) and dried over sodium sulfate. The solution was concentrated and the crude material was purified by column chromatography on silica gel (0% to 20% methanol in methylene chloride) to give a clear syrup. A portion of this syrup (790 mg, 2.74 mmol) was dissolved in dioxane (14 mL) and HCl in dioxane (6.8 mL, 4M, 27.4 mmol) was added at room temperature. After 18 h, the solution was concentrated. The resulting white solid was taken up in methylene chloride (50 mL) and MP-carbonate resin (3.2 g, 8.1 mmol) was added. After stirring for 30 min, the solvent was decanted. The resin was washed with ethyl acetate (10 mL) and methylene chloride (10 mL), and the combined organics were discarded. The remaining resin was diluted with methanol (50 mL) and stirred for 30 min. The methanol was decanted and the resin was washed with methanol (10 mL). The combined methanol portions were concentrated to give clear oil, (R)-1-(4-aminopiperidin-1-yl)-2,3-dihydroxypropan-1-one, 382 mg (60% over three steps). $^1$H NMR (300 MHz, CD$_3$OD) δ 4.53-4.40 (m, 2H), 4.14-4.04 (m, 1H), 3.77-3.56 (m, 2H), 3.20-3.05 (m, 1H), 3.04-3.92 (m, 1H), 2.84-2.69 (m, 1H), 2.00-1.82 (m, 2H), 1.48-1.20 (m, 2H).

1419
Synthesis of (4-aminopiperidin-1-yl)(3-methyloxetan-3-yl)ethanone

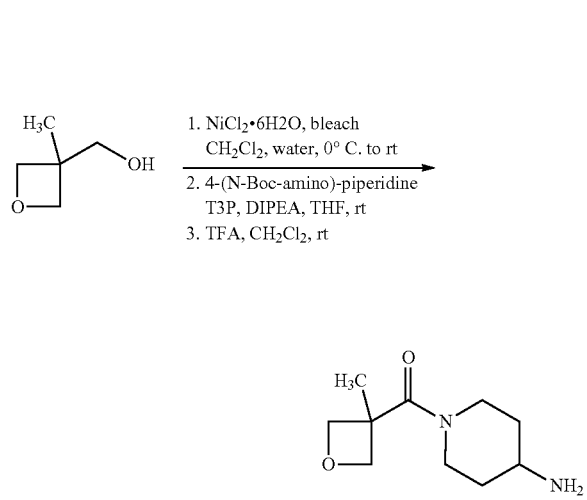

A solution of 3-hydroxymethyl-3-methyloxetane (1.90 mL, 19.1 mmol) in methylene chloride (6 mL) was added to a solution of nickel (II) chloride hexahydrate (113 mg, 0.476 mmol) in water (2 mL). This mixture was cooled to 0° C. and bleach (127 mL) was added over a 30 min period via addition funnel. After 2 h the ice bath was removed and the reaction mixture was stirred at room temperature for an additional 2 h. 2M HCl (120 mL) was added and the solution was extracted with ether (4×200 mL). The combined extracts were dried over sodium sulfate and concentrated to a clear oil. A portion of this oil (1.00 g, 8.61 mmol) was dissolved in tetrahydrofuran (43 mL) and 4-(N-Boc-amino)-piperidine (2.07 g, 10.3 mmol) was added at room temperature. Propylphosphonic anhydride (6.99 mL, 50 wt. % in ethyl acetate, 11.2 mmol) and N,N-diisopropylethylamine (3.00 mL, 17.2 mmol) were added, and the reaction mixture was stirred for 24 h. The solution was partitioned between ethyl acetate (35 mL) and water (35 mL). The organic portion was washed with 0.2M HCl (10 mL), sat. sodium bicarbonate (35 mL), and brine (35 mL). The solution was then dried over sodium sulfate and concentrated. The crude material was purified by column chromatography on silica gel (0% to 100% methylene chloride in ethyl acetate). The resulting amide (213 mg, 0.714 mg) was diluted with methylene chloride (7 mL) and trifluoroacetic acid (1.8 mL) was added at room temperature. After 2 h the solution was concentrated and a 2M sodium hydroxide solution was added. The aqueous solution was extracted with ethyl acetate (3×10 mL). The combined extracts were dried over sodium sulfate and concentrated to give the title compound as a clear oil, (4-aminopiperidin-1-yl)(3-methyloxetan-3-yl)methanone, 68 mg (4% over three steps). $^1$H NMR (300 MHz, CD$_3$OD) δ 4.95-4.88 (m, 2H), 4.48-4.38 (m, 1H), 4.38-4.31 (m, 2H), 3.19-2.96 (m, 2H), 2.94-2.81 (m, 1H), 2.81-2.66 (m, 1H), 1.93-1.81 (m, 2H), 1.67-1.60 (m, 3H), 1.36-1.15 (m, 2H).

1420
Synthesis of (2R,3S)-1-(4-aminopiperidin-1-yl)-2,3-dihydroxybutan-1-one

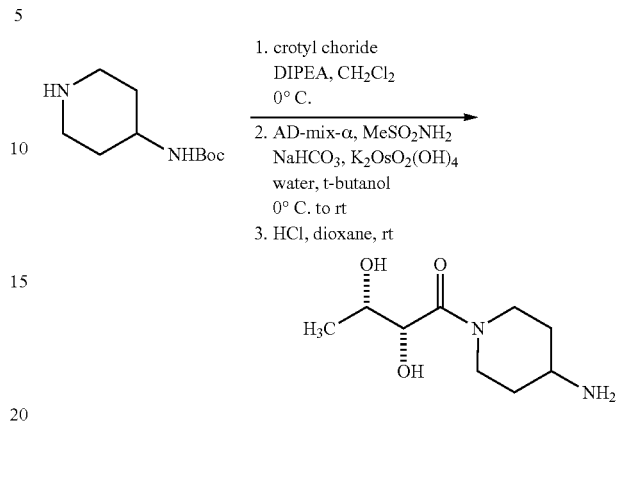

Crotyl chloride (674 μL, 5.99 mmol) was added to a solution of 4-(N-Boc-amino)-piperidine (1.00 g, 4.99 mmol) in methylene chloride (50 mL) at 0° C. N,N-diisopropylethylamine (1.74 mL, 9.99 mmol) was added and the solution was stirred for 21 h. The reaction mixture was diluted with sat. ammonium chloride (50 mL) and extracted with methylene chloride (3×50 mL). The combined extracts were dried over sodium sulfate and concentrated. The residue was dissolved in methylene chloride (10 mL) and was triturated with hexanes (100 mL). The solvent was filtered off to give an off white solid. This solid was dissolved in t-butanol (16 mL) and water (16 mL) and cooled to 0° C. To this mixture were added AD-mix-α (6.83 g), methanesulfonamide (409 mg, 4.30 mmol), sodium bicarbonate (1.03 g, 12.3 mmol), and potassium osmate dihydrate (68 mg, 0.205 mmol). The solution was allowed to warm to room temperature overnight. A 0.5M solution of sodium sulfite (100 mL) was added and the mixture was stirred for 1 h. The resulting aqueous solution was extracted with ethyl acetate (4×100 mL) and dried over sodium sulfate. The solution was concentrated and the crude material was purified by column chromatography on silica gel (0% to 20% methanol in methylene chloride, and 0% to 20% methanol in methylene chloride) to give the diol as a white solid. A portion of the diol (450 mg, 1.49 mmol) was dissolved in dioxane (7 mL) and HCl in dioxane (3.7 mL, 4M, 27.4 mmol) was added at room temperature. After 1.5 h, the solution was concentrated. The resulting white solid was taken up in methylene chloride (30 mL) and MP-carbonate resin (2.0 g, 5.1 mmol) was added. After stirring for 45 min, the solvent was decanted, and the resin was washed with methylene chloride. The remaining resin was washed with methanol (2×30 mL) and the combined methanol portions were concentrated to give a clear oil, (2R,3S)-1-(4-aminopiperidin-1-yl)-2,3-dihydroxybutan-1-one, 160 mg (33% over three steps). $^1$H NMR (300 MHz, CD$_3$OD) δ 4.51-4.35 (m, 1H), 4.32-4.25 (m, 1H), 4.14-4.01 (m, 1H), 3.96-3.84 (m, 1H), 3.19-3.02 (m, 1H), 2.98-2.84 (m, 1H), 2.84-2.67 (m, 1H), 1.97-1.80 (m, 2H), 1.44-1.20 (m, 2H), 1.18 (s, 3H).

Synthesis of 1-(4-amino-4-methyl)piperidin-1-yl)ethanone

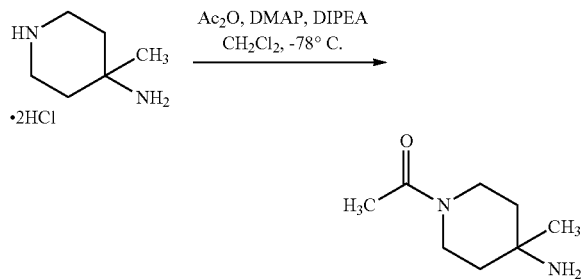

Methylene chloride (53 mL) was added to a mixture of 4-amino-4-methylpiperidine.2HCl (500 mg, 2.67 mmol) and 4-(dimethylamino)pyridine (33 mg, 0.267 mmol). N,N-diisopropylethylamine (4.65 mL, 26.7 mmol) was added and the mixture was cooled to −78° C. Acetic anhydride (126 μL, 1.34 mmol) was added and the solution was allowed to warm to room temperature overnight. 2M sodium hydroxide (10 mL) was added and the mixture was extracted with ethyl acetate (5×20 mL) and methylene chloride (5×20 mL). The combined organic extracts were dried over sodium sulfate and concentrated. The crude material was purified by column chromatography on silica gel (0% to 20% methanol in methylene chloride w/ 0.1% ammonium hydroxide) to give 181 mg of the title compound, 1-(4-amino-4-methylpiperidin-1-yl)ethanone (87%). $^1$H NMR (300 MHz, CD$_3$OD) δ 3.67-3.40 (m, 4H), 2.08 (s, 3H), 1.64-1.38 (m, 4H), 1.18 (s, 3H).

Synthesis of 1-(4-aminopiperidin-1-yl)-3-hydroxy-3-methylbutan-1-one

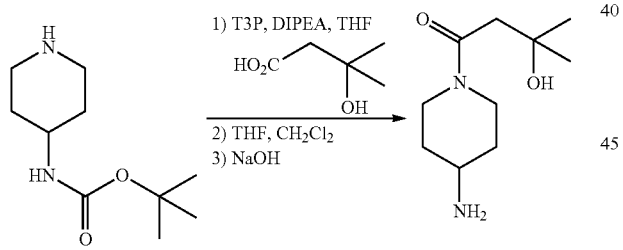

3-hydroxy-3-methyl butyric acid (1.20 equiv), DIPEA (2.00 equiv), and T3P (1.50 equiv) were added to a stirring solution of compound 1 (1.00 equiv) in THF (0.2M) at room temperature under nitrogen. TLC analysis after 2 hours showed almost complete conversion, so reaction was concentrated. Residue was dissolved in ethyl acetate then washed with water, dilute HCl, saturated NaHCO$_3$, and brine. The phases were separated and the organics dried over sodium sulfate, filtered, and concentrated. The resulting residue was purified by flash column chromatography (SiO$_2$, 12 g; 0% to 10% methanol in methylene chloride). The resulting material was dissolved in methylene chloride (0.97M) and TFA (0.97M) was added under nitrogen and the mixture was stirred at room temperature for 1 hour at which time HPLC analysis indicated the reaction was complete. Reaction was concentrated and the resulting residue was dissolved in 1N NaOH and stirred at room temperature for 30 minutes. The aqueous mixture was extracted with methylene chloride. The phases were separated and the organics dried over sodium sulfate, filtered, and concentrated affording the title compound, 1-(4-aminopiperidin-1-yl)-3-hydroxy-3-methylbutan-1-one. $^1$H NMR (300 MHz, CDCl$_3$) δ 4.40 (d, 1H, J$_{Hz}$=13.9), 3.73 (d, 1H, J$_{Hz}$=12.1), 2.99-2.95 (m, 1H), 2.90 (m, 1H), 2.70-2.63 (m, 1H), 2.33 (s, 2H), 1.76 (m, 2H), 1.12 (s, 8H).

General Synthesis of 1-(4-aminopiperidin-1-yl)-acyl Derivatives

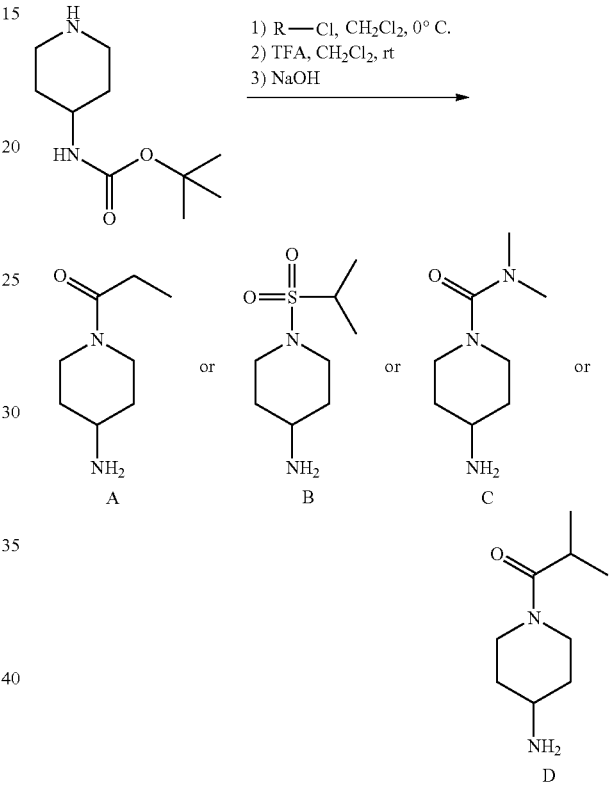

DIPEA (3.00 equiv) and propionyl chloride (compound A), isopropyl sulfonyl chloride (compound B), dimethyl carbamyl chloride (compound C), or isobutyryl chloride (compound D) (1.50 equiv) were added to a stirring solution of tert-butyl piperidin-4-ylcarbamate (1.00 equiv) in methylene chloride (0.1M) at 0° C. Reaction warmed to room temperature. TLC analysis after 16 hours showed no remaining starting material and reaction was diluted in saturated NH$_4$Cl and extracted with methylene chloride. The phases were separated and the organics dried over sodium sulfate, filtered, and concentrated. The resulting residue was purified by flash column chromatography (SiO$_2$, 40 g; 0% to 100% ethyl acetate in hexanes). The resulting material was dissolved in methylene chloride (1.0M) and TFA (1.0M) was added under nitrogen and the mixture was stirred at room temperature for 30 minutes at which time TLC analysis indicated the reaction was complete. Reaction was concentrated and the resulting residue was dissolved in 1N NaOH and stirred at room temperature for 30 minutes. The aqueous mixture was extracted with methylene chloride. The phases were separated and the organics dried over sodium sulfate, filtered, and concentrated affording the title compound.

Compound A: ¹H NMR (300 MHz, CDCl₃) δ 4.53 (d, 1H, $J^{Hz}$=13.2), 3.84 (d, 1H, $J_{Hz}$=13.2), 3.11-3.02 (m, 1H), 2.97-2.87 (m, 1H), 2.76-2.67 (m, 1H), 2.40-2.33 (m, 2H), 1.89-1.83 (m, 2H), 1.37-1.14 (m, 5H);

Compound B: ¹H NMR (300 MHz, CDCl₃) δ 3.82-3.77 (m, 2H), 3.26-3.12 (m, 1H), 3.02-2.93 (m, 2H), 2.90-2.81 (m, 1H), 1.91-1.86 (m, 2H), 1.47-1.33 (m, 8H);

Compound C: ¹H NMR (300 MHz, CDCl₃) δ 3.54 (d, 2H, $J_{Hz}$=14.1), 2.77-2.65 (m, 7H), 1.75-1.70 (m, 2H), 1.30-1.61 (m, 4H);

Compound D: ¹H NMR (300 MHz, CDCl₃) δ 4.50-4.55 (d, J=13.5 Hz, 1H), 3.89-3.92 (d, J=12.3, 1H), 3.03-3.11 (t, J=12.2 Hz, 1H), 2.76-2.95 (m, 2H), 2.64-2.73 (t, J=12.9 Hz, 1H) 1.82-1.90 (m, 2H), 1.32 (s, 2H), 1.19-1.32 (m, 2H), 1.11-1.13 (d, J=6.3 Hz, 6H).

General Synthesis of 3-aryl-6-bromo-5-(1-(disubstitutedamino)ethyl)pyrazolo[1,5-a]pyrimidin-7-amine

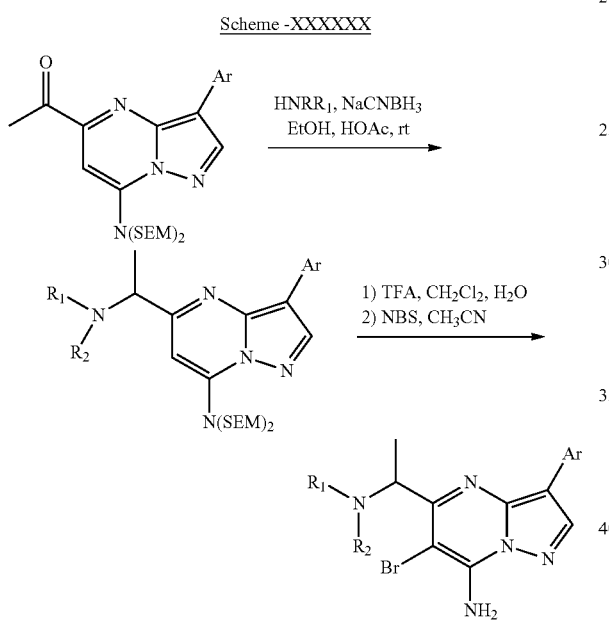

Synthesis of 3-aryl-5-(1-(disubstitutedamino)ethyl)-N,N-bis((2-(trimethylsilyl)ethoxy)methyl)pyrazolo[1,5-a]pyrimidin-7-amine Sodium cyanoborohydride (3.5 equiv) was added to a stirring mixture of ketone, 1-(3-argio-7-(bis((2-(trimethylsilyl)ethoxy)methyl)amino)pyrazolo[1,5-a]pyrimidin-5-yl)ethanone (1 equiv) and amine (2 equiv) in ethanol and acetic acid at room temperature. When the reaction was deemed complete by HPLC, LC-MS, or TLC analysis, the mixture was quenched with saturated aqueous sodium bicarbonate, then extracted with dichloromethane (2×). The combined organics were dried over sodium sulfate, filtered, concentrated to dryness, and purified on silica gel to afford compound 3-aryl-5-(1-(disubstitutedamino)ethyl)-N,N-bis((2-(trimethylsilyl)ethoxy)methyl)pyrazolo[1,5-a]pyrimidin-7-amine.

Synthesis of 3-Aryl-6-bromo-5-(1-(disubstitutedamino)ethyl)pyrazolo[1,5-a]pyrimidin-7-amine Compound, 3-aryl-5-(1-(disubstitutedamino)ethyl)-N,N-bis((2-(trimethylsilyl)ethoxy)methyl)pyrazolo[1,5-a]pyrimidin-7-amine, was stirred in a mixture of TFA, dichloromethane, and water, then concentrated to dryness when the reaction was deemed complete by HPLC, LC-MS, or TLC analysis. This material was then treated with NBS (1.05 equiv) in acetonitrile. When the reaction was deemed complete by HPLC, LC-MS, or TLC analysis, the mixture was concentrated to dryness, purified by prep-HPLC, and freeze-dried to afford compound 3-Aryl-6-bromo-5-(1-(disubstitutedamino)ethyl)pyrazolo[1,5-a]pyrimidin-7-amine.

General Synthesis of 3-aryl-6-acetyl-5-(1-(disubstitutedamino)ethyl)pyrazolo[1,5-a]pyrimidin-7-amine

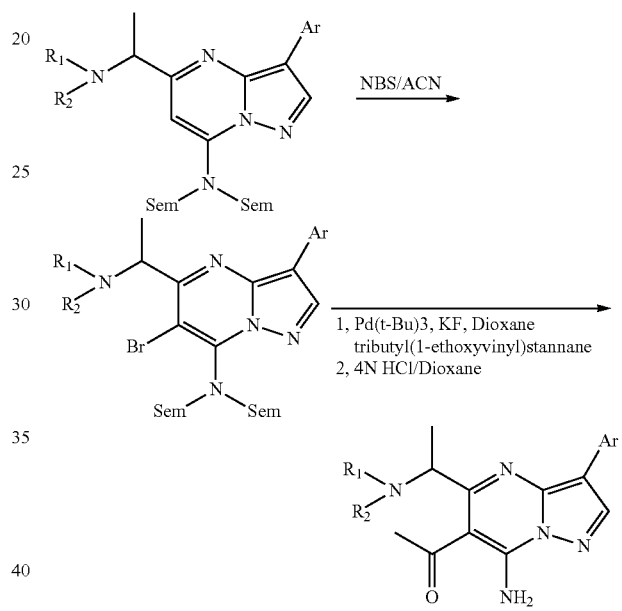

A mixture of compound 3-aryl-5-(1-(disubstitutedamino)ethyl)-N,N-bis((2-(trimethylsilyl)ethoxy)methyl)pyrazolo[1,5-a]pyrimidin-7-amine. (1 equiv) and NBS (1.05 equiv) in acetonitrile was stirred at room temperature until the reaction was deemed complete by HPLC, LC-MS, or TLC analysis. The reaction mixture was concentrated, re-dissolved in dichloromethane, washed with saturated aqueous sodium thiosulfate, dried over sodium sulfate, filtered, concentrated, and purified on silica gel. The resulting material was stirred with a mixture of vinyl stannane (2 equiv), palladium catalyst (0.1 equiv), and potassium fluoride (3 equiv) in dioxane at 85° C. until the reaction was deemed complete by HPLC, LC-MS, or TLC analysis. The mixture was allowed to cool to room temperature, diluted with 10% aqueous potassium fluoride, and extracted three times with ethyl acetate. The combined organics were dried over sodium sulfate, filtered, concentrated, and purified on silica gel. The resulting material was stirred with a mixture of HCl in methanol and water at 60° C. until the reaction was deemed complete by HPLC, LC-MS, or TLC analysis. The mixture was then allowed to cool to room temperature, concentrated, purified by prep-HPLC, and freeze-dried to afford compound 3-aryl-6-acetyl-5-(1-(disubstitutedamino)ethyl)pyrazolo[1,5-a]pyrimidin-7-amine.

1425

4-((7-amino-6-bromo-3-(6-fluoroquinolin-3-yl)pyrazolo[1,5-a]pyrimidin-5-ylamino)methyl)-N-alkylpiperidine-1-carboxamide

SCHEME-47

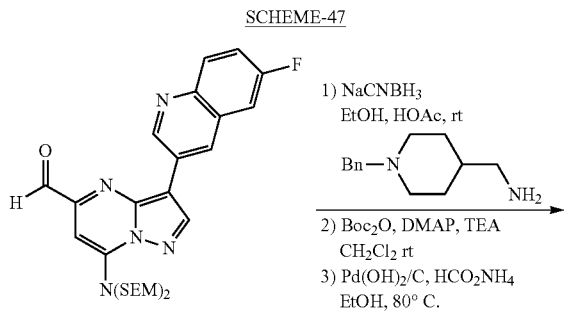

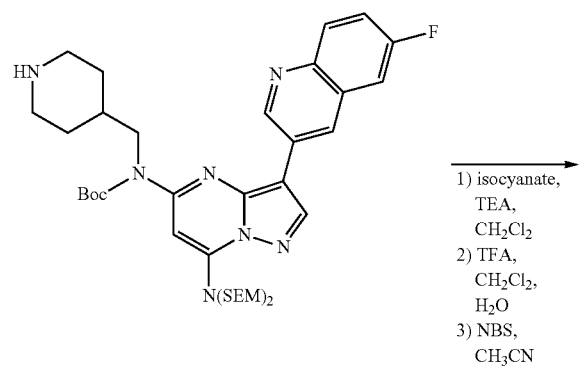

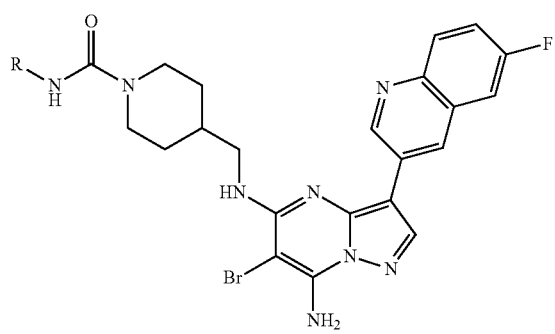

Sodium cyanoborohydride (3.5 equiv) was added to a stirring mixture of aldehyde, 7-(bis((2-(trimethylsilyl)ethoxy)methyl)amino)-3-(6-fluoroquinolin-3-yl)pyrazolo[1,5-a]pyrimidine-5-carbaldehyde (1 equiv) and 1-benzylpiperidin-4-yl)methanamine (2 equiv) in ethanol and acetic acid at room temperature. When the reaction was deemed complete by HPLC, LC-MS, or TLC analysis, the mixture was quenched with saturated aqueous sodium bicarbonate, then extracted with dichloromethane (2×). The combined organics were dried over sodium sulfate, filtered, concentrated to dryness, and purified on silica gel to afford the desired product, N5-

1426

((1-benzylpiperidin-4-yl)methyl)-3-(6-fluoroquinolin-3-yl)-N7,N7-bis((2-(trimethylsilyl)ethoxy)methyl)pyrazolo[1,5-a]pyrimidine-5,7-diamine.

The N5-((1-benzylpiperidin-4-yl)methyl)-3-(6-fluoroquinolin-3-yl)-N7,N7-bis((2-(trimethylsilyl)ethoxy)methyl)pyrazolo[1,5-a]pyrimidine-5,7-diamine (1 equiv), Boc$_2$O (2 equiv), DMAP (0.2 equiv), and triethylamine (3 equiv) in dichloromethane was stirred at room temperature until the reaction was deemed complete by TLC, HPLC, or LC-MS analysis. The mixture was diluted with additional dichloromethane, washed with saturated aqueous ammonium chloride, dried over sodium sulfate, filtered, concentrated, and purified on silica gel to give the product, tert-butyl (1-benzylpiperidin-4-yl)methyl(7-(bis((2-(trimethylsilyl)ethoxy)methyl)amino)-3-(6-fluoroquinolin-3-yl)pyrazolo[1,5-a]pyrimidin-5-yl)carbamate.

This material, tert-butyl (1-benzylpiperidin-4-yl)methyl (7-(bis((2-(trimethylsilyl)ethoxy)methyl)amino)-3-(6-fluoroquinolin-3-yl)pyrazolo[1,5-a]pyrimidin-5-yl)carbamate, was then stirred with Pd(OH)$_2$/C (0.2 equiv) and ammonium formate (20 equiv) in ethanol at 80° C. until the reaction was deemed complete by HPLC, LC-MS, or TLC analysis. The mixture was allowed to cool to room temperature, filtered through a pad of celite, concentrated and purified on silica gel to afford compound tea-butyl 7-(bis((2-(trimethylsilyl)ethoxy)methyl)amino)-3-(6-fluoroquinolin-3-yl)pyrazolo[1,5-a]pyrimidin-5-yl(piperidin-4-ylmethyl)carbamate.

6-bromo-3-(6-fluoroquinolin-3-yl)-N-5-(piperidin-4-ylmethyl)pyrazolo[1,5-a]pyrimidine-5,7-diamine Compound tert-butyl 7-(bis((2-(trimethylsilyl)ethoxy)methyl)amino)-3-(6-fluoroquinolin-3-yl)pyrazolo[1,5-a]pyrimidin-5-yl)piperidin-4-ylmethyl)carbamate was stirred in a mixture of TFA, dichloromethane, and water, then concentrated to dryness when the reaction was deemed complete by HPLC, LC-MS, or TLC analysis. This material Was then treated with NBS (1.05 equiv) in acetonitrile. When the reaction was deemed complete by HPLC, LC-MS, or TLC analysis, the mixture was concentrated to dryness, purified by prep-HPLC, and freeze-dried to afford compound 6-bromo-3-(6-fluoroquinolin-3-yl)-N15-(piperidin-4-ylmethyl)pyrazolo[1,5-a]pyrimidine-5,7-diamine.

Compound, tert-butyl 7-(bis((2-(trimethylsilyl)ethoxy)methyl)amino)-3-(6-fluoroquinolin-3-yl)pyrazolo[1,5-a]pyrimidin-5-yl(piperidin-4-ylmethyl)carbamate (1 equiv) was stirred in a mixture of isocyanate (1.1 equiv), and triethylamine (1.5 equiv) in dichloromethane at 0° C. until the reaction was deemed complete by TLC, HPLC, or LC-MS analysis. The reaction mixture was poured into saturated aqueous ammonium chloride, and then extracted twice with dichloromethane. The combined organics were dried over sodium sulfate, filtered, concentrated, and purified on silica gel to give the desired product. This material was stirred in a mixture of TFA, dichloromethane, and water, and then concentrated to dryness when the reaction was deemed complete by HPLC, LC-MS, or TLC analysis. This material was then treated with NBS (1.05 equiv) in acetonitrile. When the reaction was deemed complete by HPLC, LC-MS, or TLC analysis, the mixture was concentrated to dryness, purified by prep-HPLC, and freeze-dried to afford compound.

1427

Synthesis of 4-((7-amino-6-cyano-3-(6-fluoroquinolin-3-yl)pyrazolo[1,5-a]pyrimidin-5-ylamino)methyl)-N-methylpiperidine-1-carboxamide

SCHEME-48

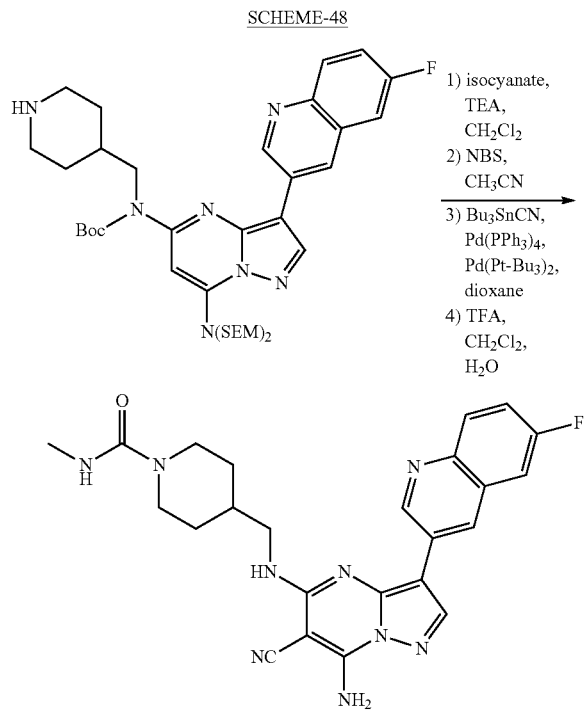

Compound, tert-butyl 7-(bis((2-(trimethylsilyl)ethoxy)methyl)amino)-3-(6-fluoroquinolin-3-yl)pyrazolo[1,5-a]pyrimidin-5-yl(piperidin-4-ylmethyl)carbamate (1 equiv) was stirred in a mixture of methyl isocyanate (1.1 equiv), and triethylamine (1.5 equiv) in dichloromethane at 0° C. until the reaction was deemed complete by TLC, HPLC, or LC-MS analysis. The reaction mixture was poured into saturated aqueous ammonium chloride, and then extracted twice with dichloromethane. The combined organics were dried over sodium sulfate, filtered, concentrated, and purified on silica gel to give the desired product. This material (1 equiv) and NBS (1.05 equiv) in acetonitrile was stirred at room temperature until the reaction was deemed complete by HPLC, LC-MS, or TLC analysis. The reaction mixture was concentrated, re-dissolved in dichloromethane, washed with saturated aqueous sodium thiosulfate, dried over sodium sulfate, filtered, concentrated, and purified on silica gel. The resulting material was stirred with the palladium catalysts (0.2 equiv each) and stannane (1.5 equiv) in dioxane at 160° C. until the reaction was deemed complete by HPLC, LC-MS, or TLC analysis. The reaction was allowed to cool to room temperature, diluted with ethyl acetate, washed with brine, dried over sodium sulfate, filtered, concentrated, and purified in silica gel. The resulting material was stirred in TFA and water at room temperature until the reaction was deemed complete by HPLC, LC-MS, or TLC analysis. The mixture was concen-

1428 trated, purified by prep-HPLC, and freeze-dried to afford compound 4-((7-amino-6-cyano-3-(6-fluoroquinolin-3-yl)pyrazolo[1,5-a]pyrimidin-5-ylamino)methyl)-N-methylpiperidine-1-carboxamide.

General Synthesis of 1-(4-((7-amino-6-bromo-3-(6-fluoroquinolin-3-yl)pyrazolo[1,5-a]pyrimidin-5-ylamino)alkyl)piperidin-1-yl)ethanone

SCHEME-49

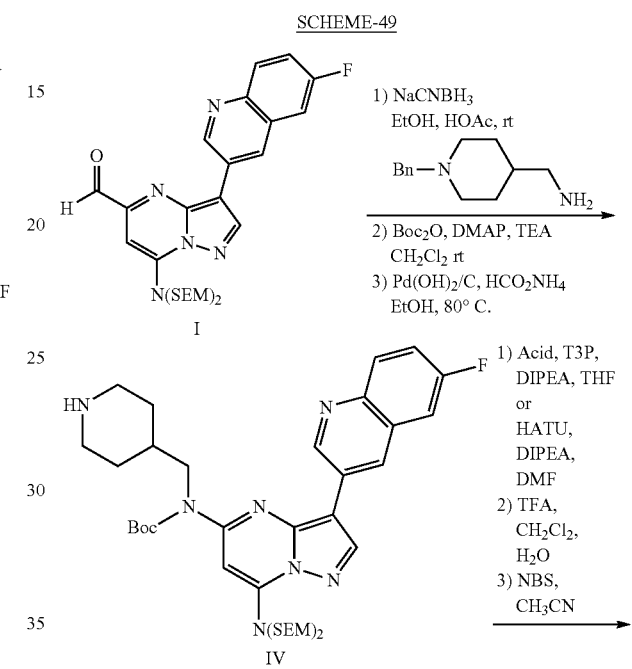

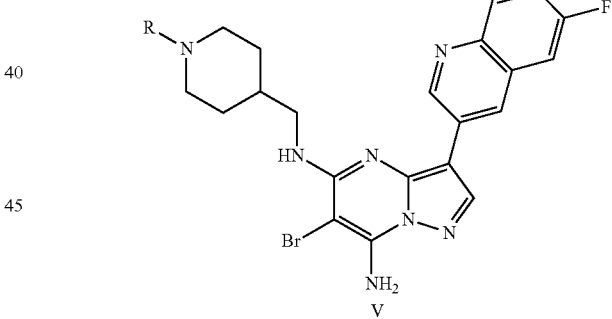

Sodium cyanoborohydride (3.5 equiv) was added to a stirring mixture of 7-(bis((2-(trimethylsilyl)ethoxy)methyl)amino)-3-(6-fluoroquinolin-3-yl)pyrazolo[1,5-a]pyrimidine-5-carbaldehyde (1 equiv) and amine (2 equiv) in ethanol and acetic acid at room temperature. When the reaction was deemed complete by HPLC, LC-MS, or TLC analysis, the mixture was quenched with saturated aqueous sodium bicarbonate, and then extracted with dichloromethane (2×). The combined organics were dried over sodium sulfate, filtered, concentrated to dryness, and purified on silica gel to afford the desired product, N5-((1-benzylpiperidin-4-yl)methyl)-3-(6-fluoroquinolin-3-yl)-N7,N7-bis((2-(trimethylsilyl)ethoxy)methyl)pyrazolo[1,5-a]pyrimidine-5,7-diamine.

This material, (1 equiv), Boc₂O (2 equiv), DMAP (0.2 equiv), and triethylamine (3 equiv) in dichloromethane was stirred at room temperature until the reaction was deemed complete by TLC, HPLC, or LC-MS analysis. The mixture was diluted with additional dichloromethane, washed with saturated aqueous ammonium chloride, dried over sodium sulfate, filtered, concentrated, and purified on silica gel to give the product, tert-butyl (1-benzylpiperidin-4-yl) methyl(7-(bis((2-(trimethylsilyl)ethoxy)methyl)amino)-3-(6-fluoroquinolin-3-yl)pyrazolo[1,5-a]pyrimidin-5-yl)carbamate.

This material was then stirred with Pd(OH)₂/C (0.2 equiv) and ammonium formate (20 equiv) in ethanol at 80° C. until the reaction was deemed complete by HPLC, LC-MS, or TLC analysis. The mixture was allowed to cool to room temperature, filtered through a pad of celite, concentrated and purified on silica gel to afford compound tert-butyl 7-(bis((2-(trimethylsilyl)ethoxy)methyl)amino)-3-(6-fluoroquinolin-3-yl) pyrazolo[1,5-a]pyrimidin-5-yl(piperidin-4-ylmethyl)carbamate.

This material was stirred with carboxylic acid (1.5 equiv), HATU (1.5 equiv), and DIPEA (3 equiv) in DMF until the reaction was deemed complete by TLC, HPLC, or LC-MS analysis. The reaction mixture was concentrated, the resulting residue dissolved in ethyl acetate, washed with water, saturated aqueous sodium bicarbonate, and brine, dried over sodium sulfate, filtered, concentrated, and purified on silica gel to give the product. This material was stirred in a mixture of TFA, dichloromethane, and water, then concentrated to dryness when the reaction was deemed complete by HPLC, LC-MS, or TLC analysis. This material was then treated with NBS (1.05 equiv) in acetonitrile. When the reaction was deemed complete by HPLC, LC-MS, or TLC analysis, the mixture was concentrated to dryness, purified by prep-HPLC, and freeze-dried to afford compound 1-(4-((7-amino-6-bromo-3-(6-fluoroquinolin-3-yl)pyrazolo[1,5-a]pyrimidin-5-ylamino)methyl)piperidin-1-yl)ethanone.

Synthesis of 1-(4-((7-amino-6-bromo-3-(6-fluoroquinolin-3-yl)pyrazolo[1,5-a]pyrimidin-5-yl)methylamino)piperidin-1-yl)-2-methoxypropan-1-one Scheme-49

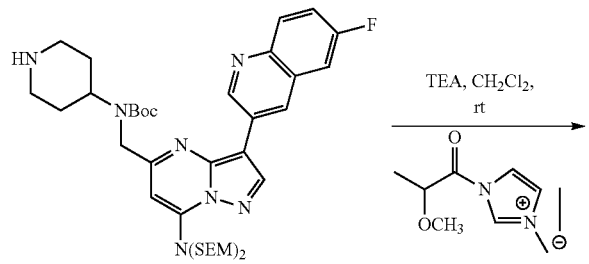

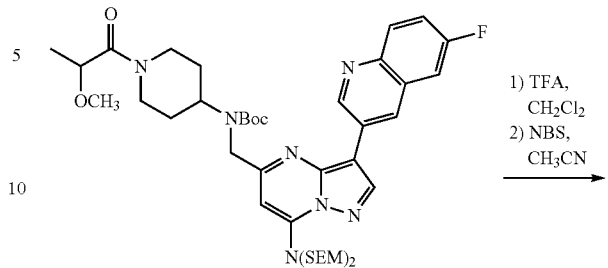

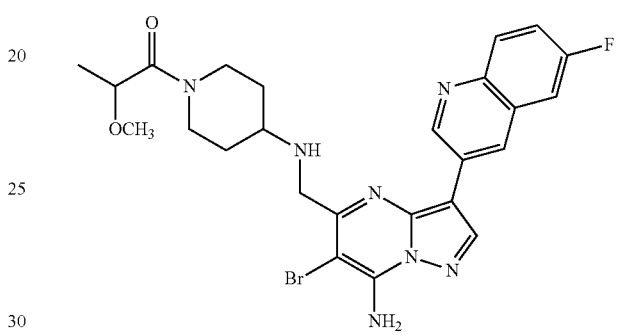

To a solution of tert-butyl (7-(bis((2-(trimethylsilyl) ethoxy)methyl)amino)-3-(6-fluoroquinolin-3-yl)pyrazolo[1, 5-a]pyrimidin-5-yl)methyl(piperidin-4-yl)carbamate (190 mg, 0.25 mmol) in dichloromethane (3 mL) was added imidazolium salt (84 mg, 0.25 mmol) (prepared according to the literature procedure: Grzyb, J. A. et. al. Tetrahedron, 2005, 61, 7153-7175) and Et₃N (35 µL, 0.25 mmol). The resulting mixture was stirred at 25° C. for 16 hours to give. The reaction mixture was diluted with CH₂Cl₂ (50 mL) and was washed with 0.1 N HCl (3 mL), brine (10 mL), dried over Na₂SO₄. LCMS indicated that the crude product, crude tert-butyl (7-(bis((2-(trimethylsilyl)ethoxy)methyl)amino)-3-(6-fluoroquinolin-3-yl)pyrazolo[1,5-a]pyrimidin-5-yl)methyl(1-(2-methoxypropanoyl)piperidin-4-yl)carbamate was clean, This material was then converted to the final compound, by bromination with NBS and followed by treatment with 4NHCl, to give 1-(4-((7-amino-6-bromo-3-(6-fluoroquinolin-3-yl) pyrazolo[1,5-a]pyrimidin-5-yl)methylamino)piperidin-1-yl)-2-methoxypropan-1-one following a similar procedure as that described above schemes: MW: 556.13; MS MH⁺ m/z: 557; HPLC t$_R$: 4.17.

LCMS: 2.67 mins, m/z=485.0 (MH⁺).

By essentially the same procedure given in Schemes 45 through 49, the compounds listed in Table 14 can be prepared

TABLE-14

| Compound ID | Structure | M + H (Calc) | M + H (Observed) | Retention Time(min) |
| --- | --- | --- | --- | --- |
| 14.1 | 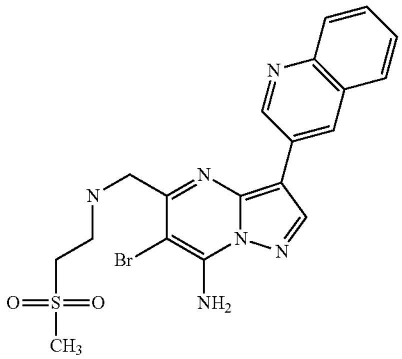 [SMILES: CS(=O)(=O)CCNCc1nc2c(-c3cnc4ccccc4c3)cnn2c(N)c1Br] | 474.04 | 475 | 1.95 |
| 14.2 | 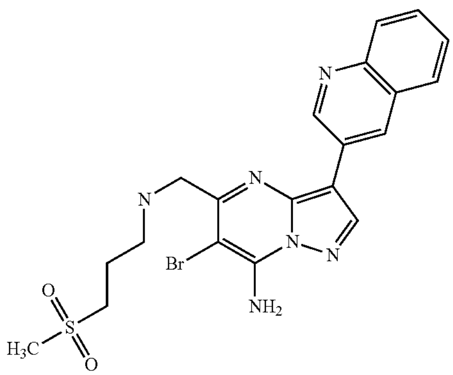 [SMILES: CS(=O)(=O)CCCNCc1nc2c(-c3cnc4ccccc4c3)cnn2c(N)c1Br] | 488.06 | 489 | 2.02 |
| 14.3 | 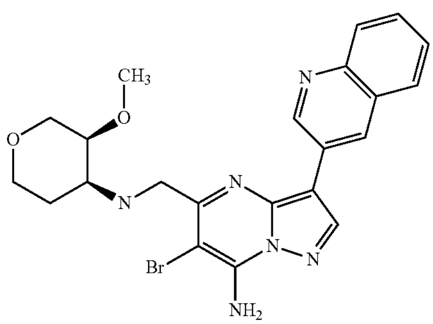 [SMILES: CO[C@@H]1COCC[C@@H]1NCc1nc2c(-c3cnc4ccccc4c3)cnn2c(N)c1Br] | 482.1 | 483 | 2.23 |
| 14.4 | 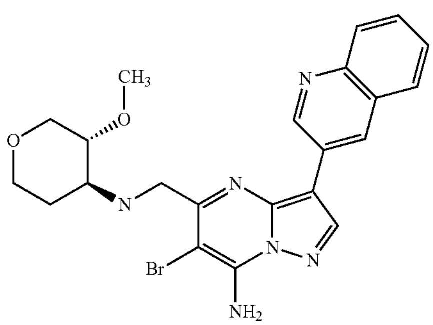 [SMILES: CO[C@H]1COCC[C@@H]1NCc1nc2c(-c3cnc4ccccc4c3)cnn2c(N)c1Br] | 482.1 | 483 | 2.41 |

TABLE-14-continued

| Compound ID | Structure | M + H (Calc) | M + H (Observed) | Retention Time(min) |
|---|---|---|---|---|
| 14.5 | 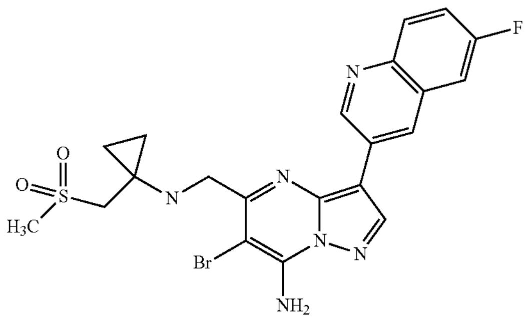 [SMILES: CS(=O)(=O)CC1(NCc2nc3c(-c4cnc5ccc(F)cc5c4)cnn3c(N)c2Br)CC1] | 518.05 | 519 | 2.52 |
| 14.6 | 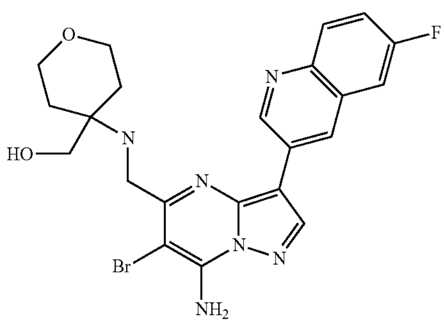 [SMILES: Nc1c(Br)c(CNC2(CO)CCOCC2)nc2c(-c3cnc4ccc(F)cc4c3)cnn12] | 500.09 | 501 | 2.44 |
| 14.7 | 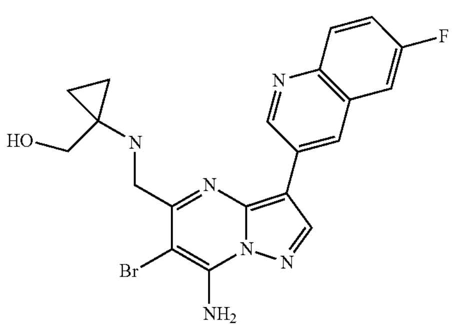 [SMILES: Nc1c(Br)c(CNC2(CO)CC2)nc2c(-c3cnc4ccc(F)cc4c3)cnn12] | 456.07 | 457 | 2.34 |
| 14.8 | 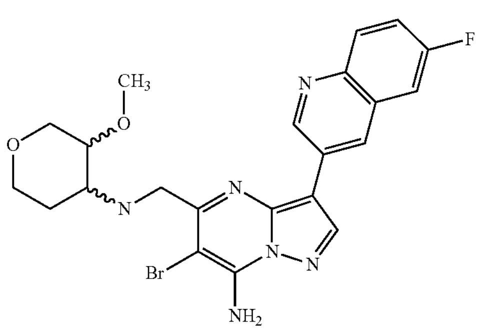 [SMILES: COC1COCCC1NCc1nc2c(-c3cnc4ccc(F)cc4c3)cnn2c(N)c1Br] | 500.09 | 501 | 2.56 |

TABLE-14-continued

| Compound ID | Structure | M + H (Calc) | M + H (Observed) | Retention Time(min) |
|---|---|---|---|---|
| 14.9 | 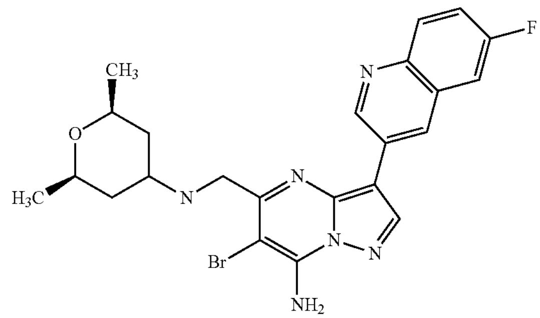 [SMILES: C[C@@H]1CC(NCc2nc3c(-c4cnc5ccc(F)cc5c4)cnn3c(N)c2Br)C[C@H](C)O1] | 498.11 | 499 | 3.15 |
| 14.10 | 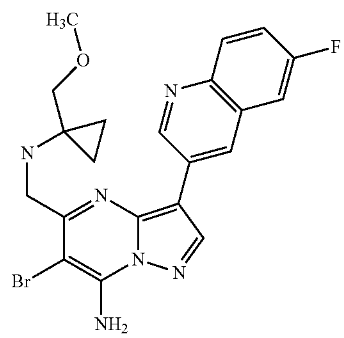 [SMILES: COCC1(NCc2nc3c(-c4cnc5ccc(F)cc5c4)cnn3c(N)c2Br)CC1] | 470.08 | 471 | 1.87 |
| 14.11 | 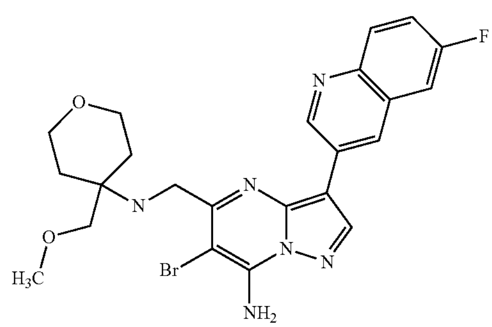 [SMILES: COCC1(NCc2nc3c(-c4cnc5ccc(F)cc5c4)cnn3c(N)c2Br)CCOCC1] | 514.11 | 515.2 | 2.17 |
| 14.12 | 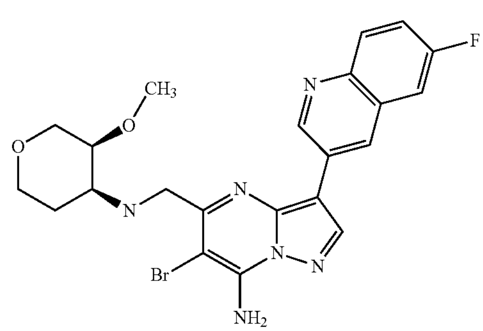 [SMILES: CO[C@@H]1COCC[C@@H]1NCc1nc2c(-c3cnc4ccc(F)cc4c3)cnn2c(N)c1Br] | 500.09 | 501.1 | 1.94 |

TABLE-14-continued

| Compound ID | Structure | M + H (Calc) | M + H (Observed) | Retention Time(min) |
|---|---|---|---|---|
| 14.13 | 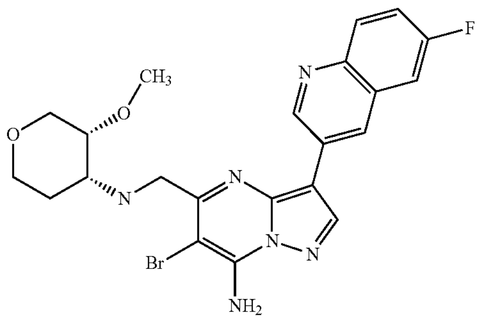 [SMILES: CO[C@H]1COCC[C@H]1NCc1nc2c(-c3cnc4ccc(F)cc4c3)cnn2c(N)c1Br] | 500.09 | 501 | 2.7 |
| 14.14 | 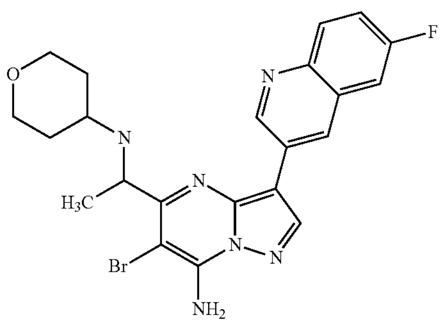 [SMILES: CC(NC1CCOCC1)c1nc2c(-c3cnc4ccc(F)cc4c3)cnn2c(N)c1Br] | 484.1 | 485 | 2.67 |
| 14.15 | 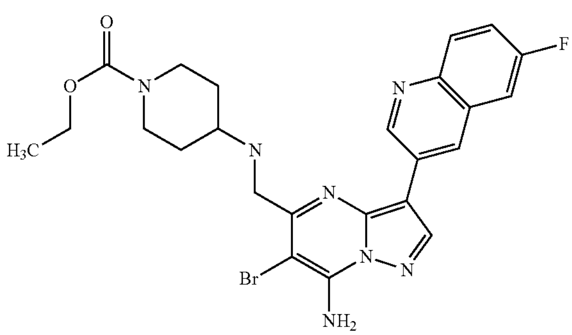 [SMILES: CCOC(=O)N1CCC(NCc2nc3c(-c4cnc5ccc(F)cc5c4)cnn3c(N)c2Br)CC1] | 541.12 | 542.2 | 4.66 |
| 14.16 | 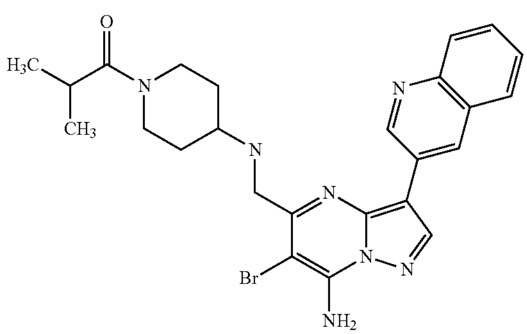 [SMILES: CC(C)C(=O)N1CCC(NCc2nc3c(-c4cnc5ccccc5c4)cnn3c(N)c2Br)CC1] | 521.15 | 522.2 | 3.80 |

TABLE-14-continued

| Compound ID | Structure | M + H (Calc) | M + H (Observed) | Retention Time(min) |
|---|---|---|---|---|
| 14.17 | 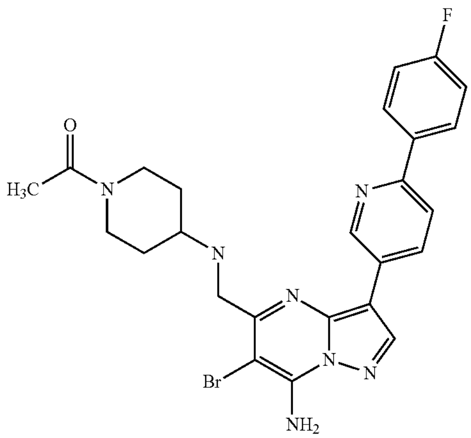 [SMILES: CC(=O)N1CCC(NCc2nc3c(-c4ccc(-c5ccc(F)cc5)nc4)cnn3c(N)c2Br)CC1] | 537.13 | 538 | 3.87 |
| 14.18 | 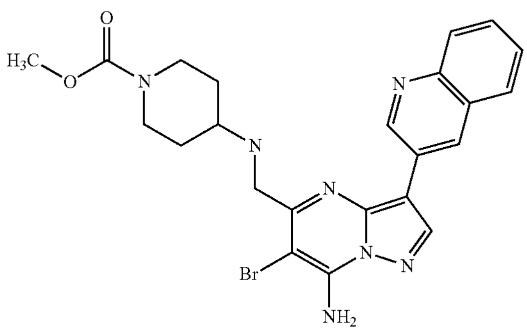 [SMILES: COC(=O)N1CCC(NCc2nc3c(-c4cnc5ccccc5c4)cnn3c(N)c2Br)CC1] | 509.12 | 510 | 3.73 |
| 14.19 | 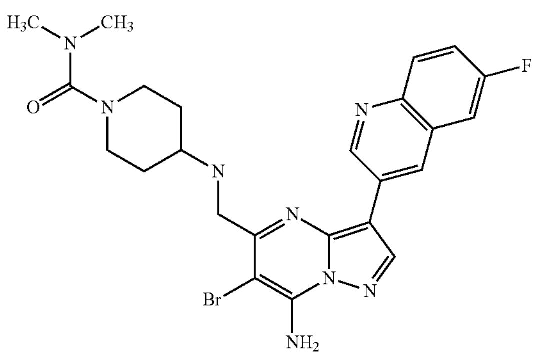 [SMILES: CN(C)C(=O)N1CCC(NCc2nc3c(-c4cnc5ccc(F)cc5c4)cnn3c(N)c2Br)CC1] | 540.14 | 541.3 | 3.93 |
| 14.20 | 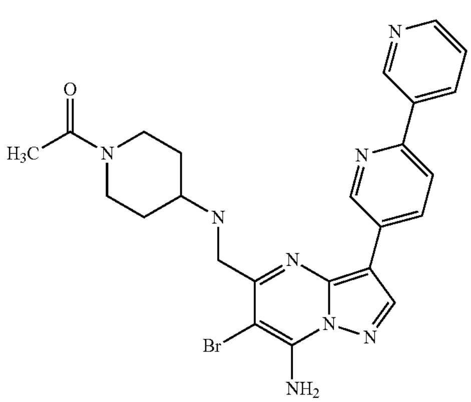 | 520.13 | 521.1 | 3.17 |

TABLE-14-continued

| Compound ID | Structure | M + H (Calc) | M + H (Observed) | Retention Time(min) |
|---|---|---|---|---|
| 14.21 | 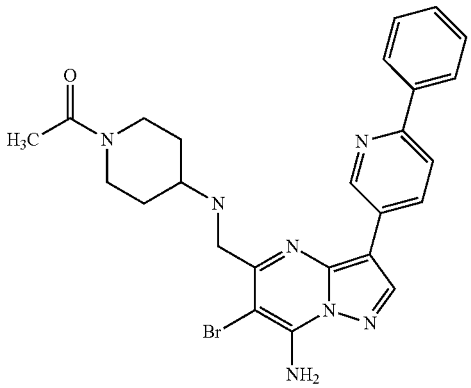 [SMILES: CC(=O)N1CCC(NCc2nc3c(-c4ccc(-c5ccccc5)nc4)cnn3c(N)c2Br)CC1] | 519.14 | 520.8 | 3.79 |
| 14.22 | 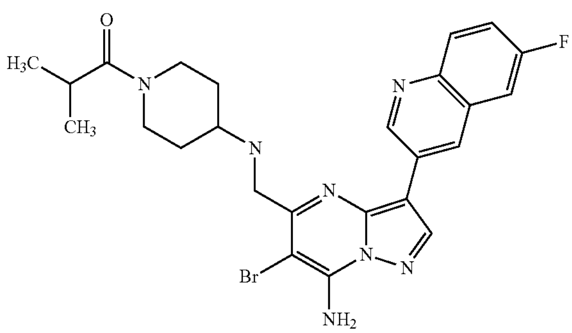 [SMILES: CC(C)C(=O)N1CCC(NCc2nc3c(-c4cnc5ccc(F)cc5c4)cnn3c(N)c2Br)CC1] | 539.14 | 540.2 | 4.21 |
| 14.23 | 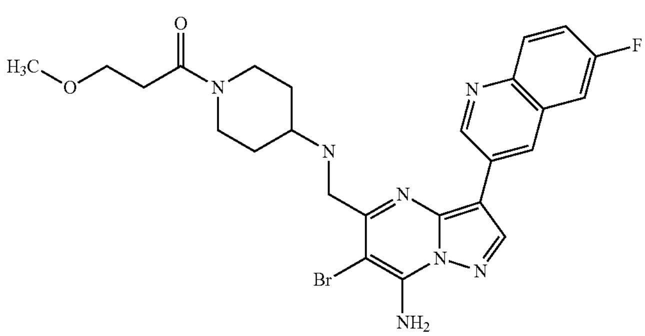 [SMILES: COCCC(=O)N1CCC(NCc2nc3c(-c4cnc5ccc(F)cc5c4)cnn3c(N)c2Br)CC1] | 555.14 | 556 | 3.79 |
| 14.24 | 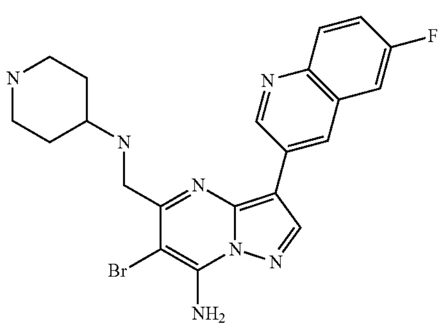 [SMILES: Nc1c(Br)c(CNC2CCNCC2)nc2c(-c3cnc4ccc(F)cc4c3)cnn12] | 469.1 | 470.8 | 3.23 |

TABLE-14-continued

| Compound ID | Structure | M + H (Calc) | M + H (Observed) | Retention Time(min) |
|---|---|---|---|---|
| 14.25 | 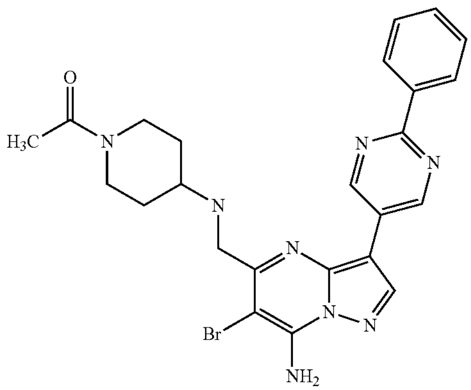 | 520.13 | 521.4 | 5.22 |
| 14.26 | 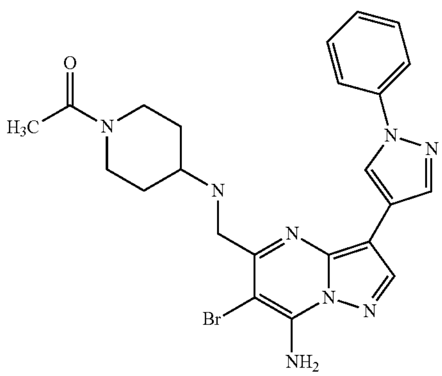 [SMILES: CC(=O)N1CCC(NCc2nc3c(-c4cnn(-c5ccccc5)c4)cnn3c(N)c2Br)CC1] | 508.13 | 509.2 | 4.98 |
| 14.27 | 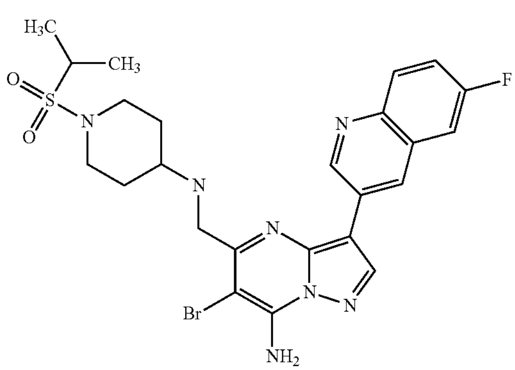 [SMILES: CC(C)S(=O)(=O)N1CCC(NCc2nc3c(-c4cnc5ccc(F)cc5c4)cnn3c(N)c2Br)CC1] | 575.11 | 576.6 | 4.76 |
| 14.28 | 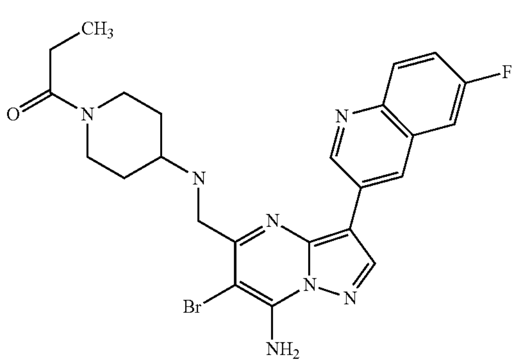 [SMILES: CCC(=O)N1CCC(NCc2nc3c(-c4cnc5ccc(F)cc5c4)cnn3c(N)c2Br)CC1] | 525.13 | 526.5 | 3.96 |

TABLE-14-continued

| Compound ID | Structure | M + H (Calc) | M + H (Observed) | Retention Time(min) |
|---|---|---|---|---|
| 14.29 | 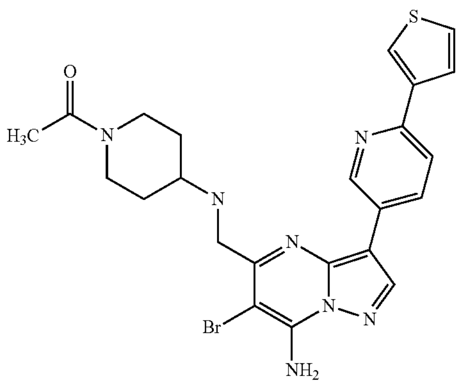 [SMILES: CC(=O)N1CCC(NCc2nc3c(-c4ccc(-c5ccsc5)nc4)cnn3c(N)c2Br)CC1] | 525.09 | 526.1 | 4.04 |
| 14.30 | 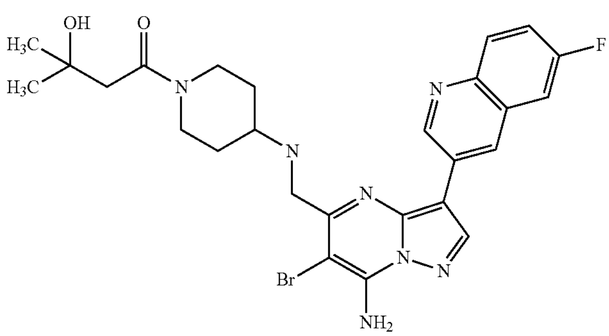 [SMILES: CC(C)(O)CC(=O)N1CCC(NCc2nc3c(-c4cnc5ccc(F)cc5c4)cnn3c(N)c2Br)CC1] | 569.16 | 570.2 | 4.13 |
| 14.31 | 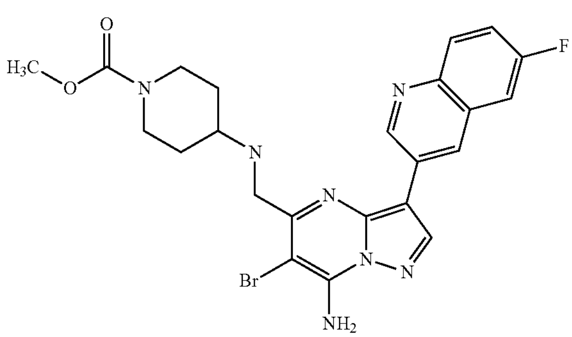 | 527.11 | 528 | 4.30 |
| 14.32 | 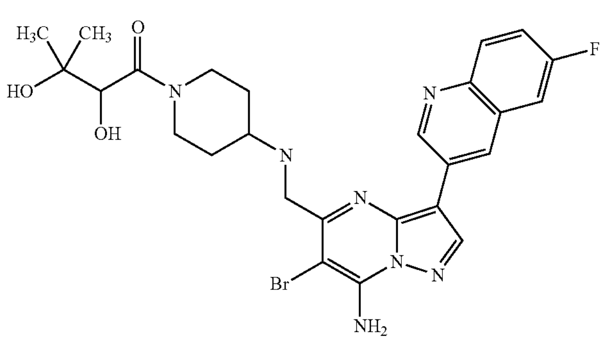 [SMILES: CC(C)(O)C(O)C(=O)N1CCC(NCc2nc3c(-c4cnc5ccc(F)cc5c4)cnn3c(N)c2Br)CC1] | 585.15 | 586 | 3.71 |

TABLE-14-continued
| Compound ID | Structure | M + H (Calc) | M + H (Observed) | Retention Time(min) |
|---|---|---|---|---|
| 14.33 | 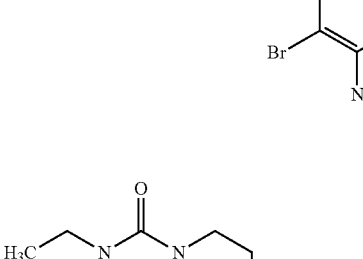 | 557.12 | 558 | 3.44 |
| 14.34 | 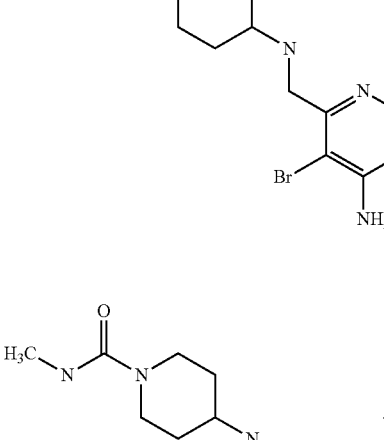 | 540.14 | 541.3 | 3.98 |
| 14.35 | 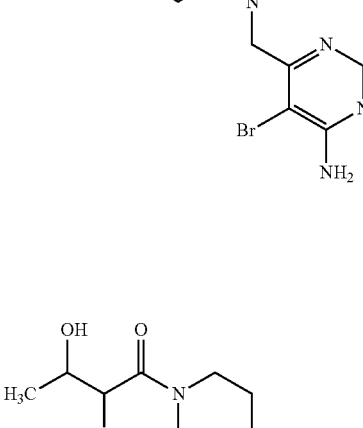 | 526.12 | 527.5 | 3.31 |
| 14.36 | 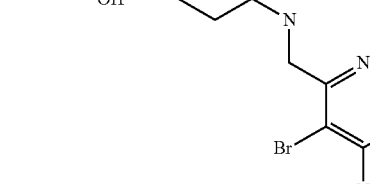 | 571.13 | 572 | 3.89 |

TABLE-14-continued

| Compound ID | Structure | M + H (Calc) | M + H (Observed) | Retention Time(min) |
|---|---|---|---|---|
| 14.37 | 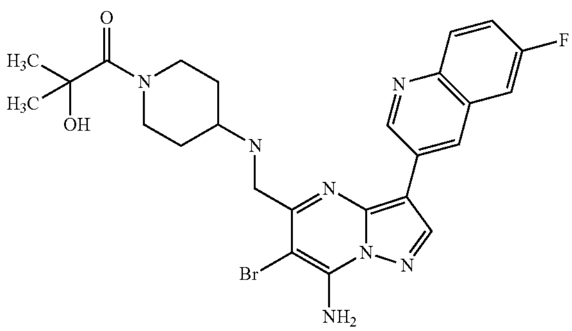 [SMILES: CC(C)(O)C(=O)N1CCC(NCc2nc3c(-c4cnc5ccc(F)cc5c4)cnn3c(N)c2Br)CC1] | 555.14 | 556.2 | 3.49 |
| 14.38 | 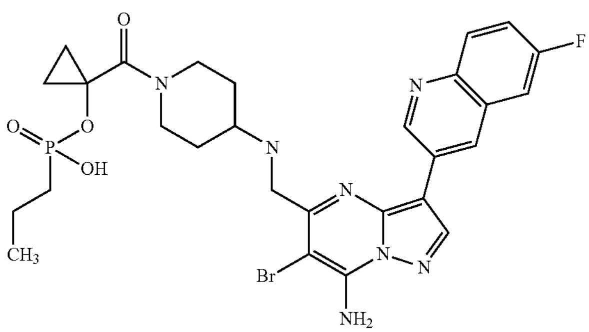 [SMILES: CCCP(=O)(O)OC1(C(=O)N2CCC(NCc3nc4c(-c5cnc6ccc(F)cc6c5)cnn4c(N)c3Br)CC2)CC1] | 659.14 | 661.0 | 4.59 |
| 14.39 | 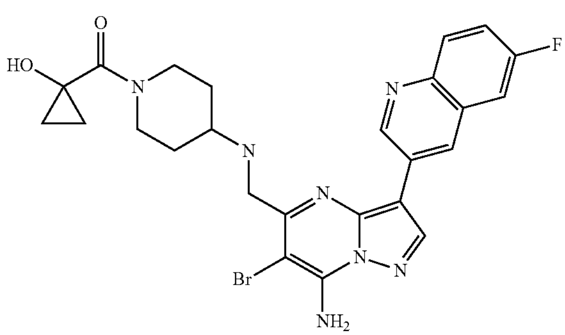 [SMILES: Nc1c(Br)c(CNC2CCN(C(=O)C3(O)CC3)CC2)nc2c(-c3cnc4ccc(F)cc4c3)cnn12] | 553.12 | 554.5 | 4.14 |
| 14.40 | 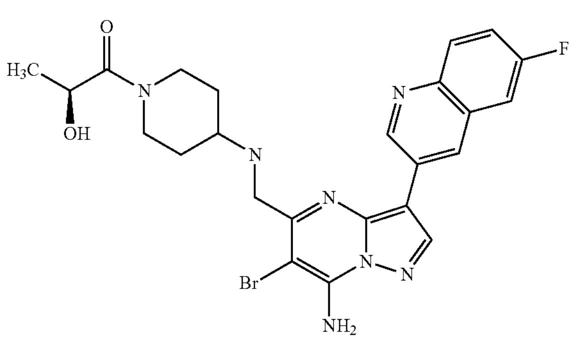 [SMILES: C[C@H](O)C(=O)N1CCC(NCc2nc3c(-c4cnc5ccc(F)cc5c4)cnn3c(N)c2Br)CC1] | 541.12 | 542.1 | 3.83 |

TABLE-14-continued

| Compound ID | Structure | M + H (Calc) | M + H (Observed) | Retention Time(min) |
|---|---|---|---|---|
| 14.41 | 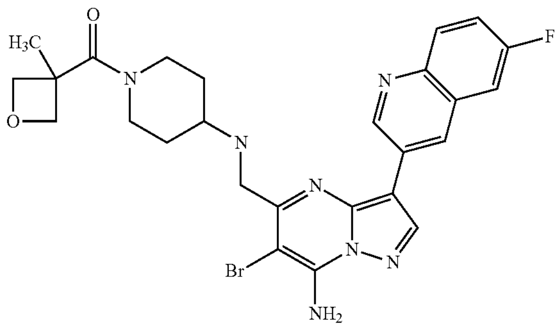 [SMILES: CC1(C(=O)N2CCC(NCc3nc4c(-c5cnc6ccc(F)cc6c5)cnn4c(N)c3Br)CC2)COC1] | 567.14 | 568 | 3.64 |
| 14.42 | 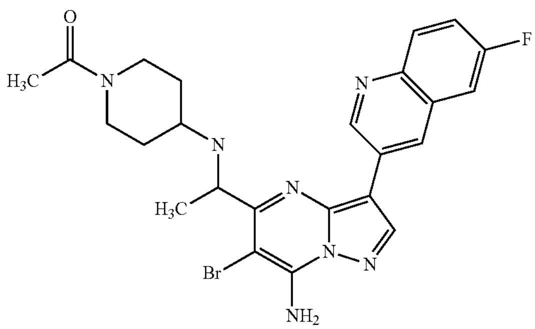 [SMILES: CC(=O)N1CCC(NC(C)c2nc3c(-c4cnc5ccc(F)cc5c4)cnn3c(N)c2Br)CC1] | 525.13 | 526.5 | 4.53 |
| 14.43 | 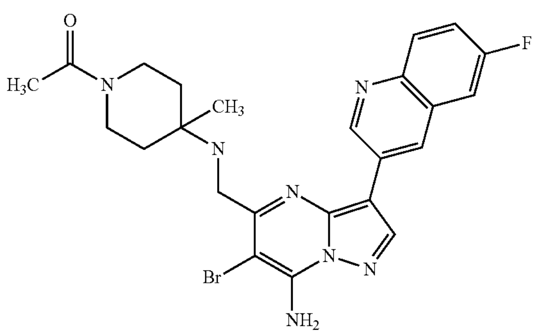 [SMILES: CC(=O)N1CCC(C)(NCc2nc3c(-c4cnc5ccc(F)cc5c4)cnn3c(N)c2Br)CC1] | 525.13 | 526 | 4.11 |
| 14.44 | 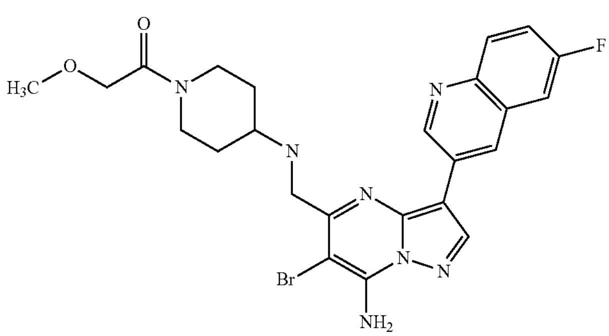 [SMILES: COCC(=O)N1CCC(NCc2nc3c(-c4cnc5ccc(F)cc5c4)cnn3c(N)c2Br)CC1] | 541.12 | 542 | 3.36 |

TABLE-14-continued

| Compound ID | Structure | M + H (Calc) | M + H (Observed) | Retention Time(min) |
|---|---|---|---|---|
| 14.45 | 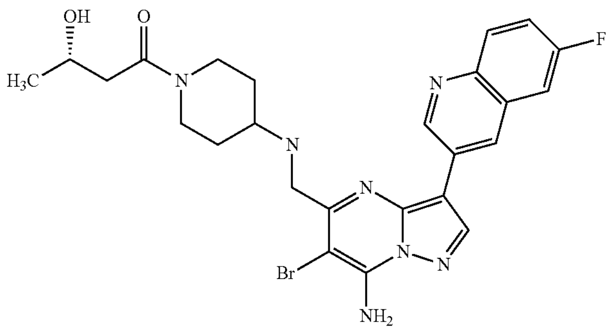 [SMILES: C[C@H](O)CC(=O)N1CCC(NCc2nc3c(-c4cnc5ccc(F)cc5c4)cnn3c(N)c2Br)CC1] | 555.14 | 556.3 | 3.64 |
| 14.46 | 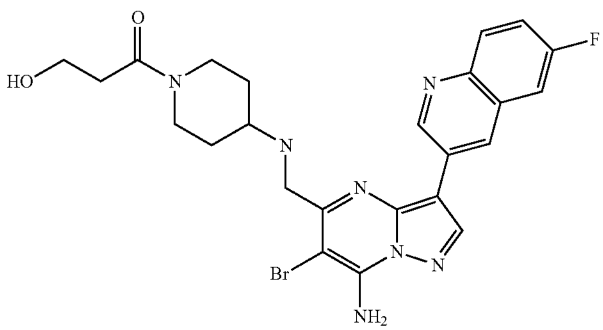 [SMILES: Nc1c(Br)c(CNC2CCN(C(=O)CCO)CC2)nc2c(-c3cnc4ccc(F)cc4c3)cnn12] | 541.12 | 542.3 | 3.56 |
| 14.47 | 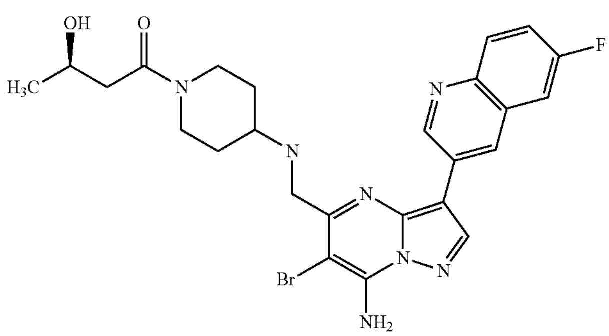 [SMILES: C[C@@H](O)CC(=O)N1CCC(NCc2nc3c(-c4cnc5ccc(F)cc5c4)cnn3c(N)c2Br)CC1] | 555.14 | 556.3 | 3.87 |
| 14.48 | 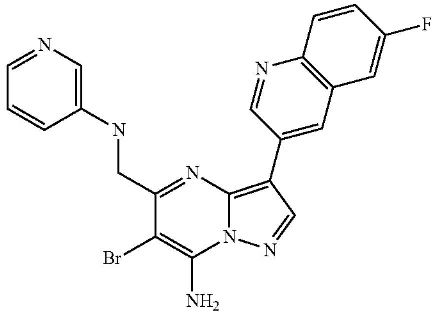 [SMILES: Nc1c(Br)c(CNc2cccnc2)nc2c(-c3cnc4ccc(F)cc4c3)cnn12] | 463.06 | 464.2 | 4.55 |

TABLE-14-continued

| Compound ID | Structure | M + H (Calc) | M + H (Observed) | Retention Time(min) |
|---|---|---|---|---|
| 14.49 | 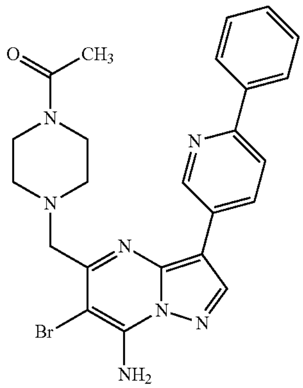 [SMILES: CC(=O)N1CCN(Cc2nc3c(-c4ccc(-c5ccccc5)nc4)cnn3c(N)c2Br)CC1] | 505.12 | 506.2 | 3.32 |
| 14.50 | 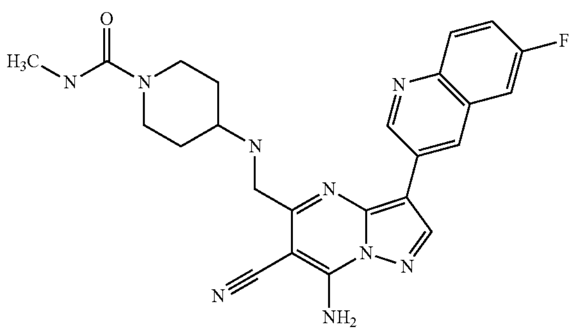 [SMILES: CNC(=O)N1CCC(NCc2nc3c(-c4cnc5ccc(F)cc5c4)cnn3c(N)c2C#N)CC1] | 473.21 | 474.3 | 4.13 |
| 14.51 | 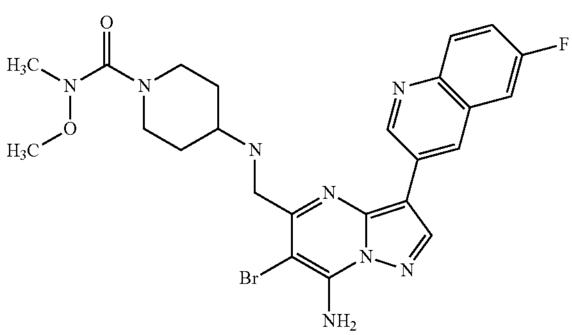 [SMILES: CON(C)C(=O)N1CCC(NCc2nc3c(-c4cnc5ccc(F)cc5c4)cnn3c(N)c2Br)CC1] | 556.13 | 557 | 4.17 |
| 14.52 | 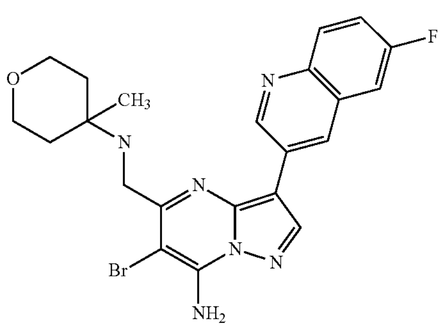 [SMILES: CC1(NCc2nc3c(-c4cnc5ccc(F)cc5c4)cnn3c(N)c2Br)CCOCC1] | 485.36 | 486.10 | 2.31 |

TABLE-14-continued

| Compound ID | Structure | M + H (Calc) | M + H (Observed) | Retention Time(min) |
|---|---|---|---|---|
| 14.53 | 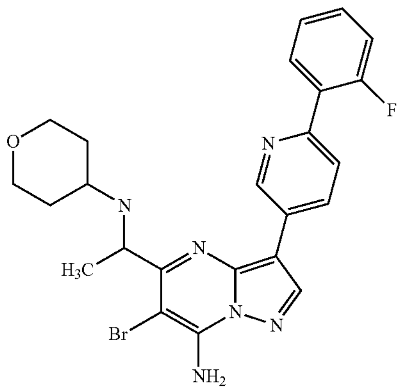 [SMILES: CC(NC1CCOCC1)c1nc2c(-c3ccc(-c4ccccc4F)nc3)cnn2c(N)c1Br] | 511.40 | 512.20 | 2.62 |
| 14.54 | 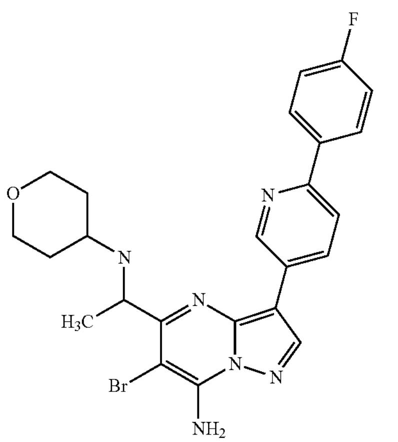 [SMILES: CC(NC1CCOCC1)c1nc2c(-c3ccc(-c4ccc(F)cc4)nc3)cnn2c(N)c1Br] | 511.40 | 512.20 | 2.77 |
| 14.55 | 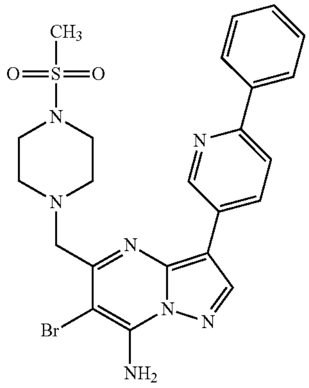 [SMILES: CS(=O)(=O)N1CCN(Cc2nc3c(-c4ccc(-c5ccccc5)nc4)cnn3c(N)c2Br)CC1] | 541.09 | 542.5 | 4.18 |

TABLE-14-continued

| Compound ID | Structure | M + H (Calc) | M + H (Observed) | Retention Time(min) |
|---|---|---|---|---|
| 14.56 | 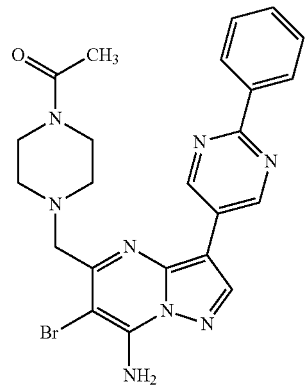 | 506.12 | 507 | 4.62 |
| 14.57 | 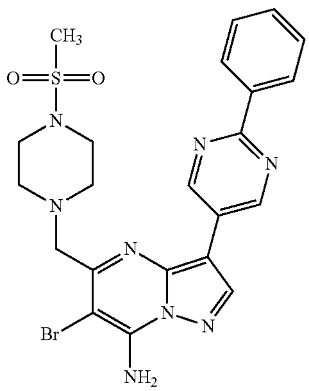 [SMILES: CS(=O)(=O)N1CCN(Cc2nc3c(-c4cnc(-c5ccccc5)nc4)cnn3c(N)c2Br)CC1] | 542.08 | 543 | 5.41 |
| 14.58 | 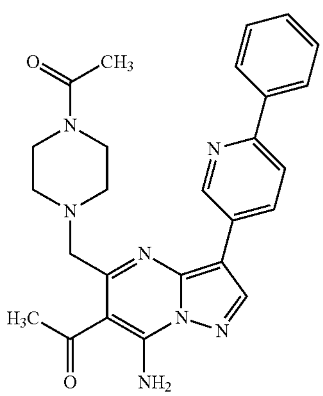 [SMILES: CC(=O)c1c(CN2CCN(C(C)=O)CC2)nc2c(-c3ccc(-c4ccccc4)nc3)cnn2c1N] | 469.22 | 470.8 | 3.58 |
| 14.59 | 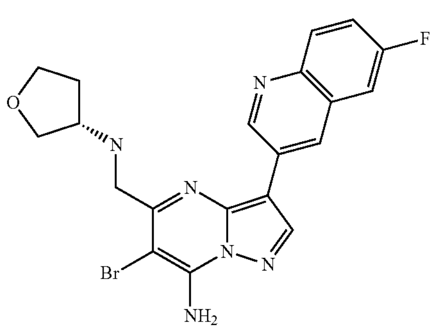 [SMILES: Nc1c(Br)c(CN[C@H]2CCOC2)nc2c(-c3cnc4ccc(F)cc4c3)cnn12] | 457.31 | 458.20 | 2.26 |

TABLE-14-continued

| Compound ID | Structure | M + H (Calc) | M + H (Observed) | Retention Time(min) |
|---|---|---|---|---|
| 14.60 | 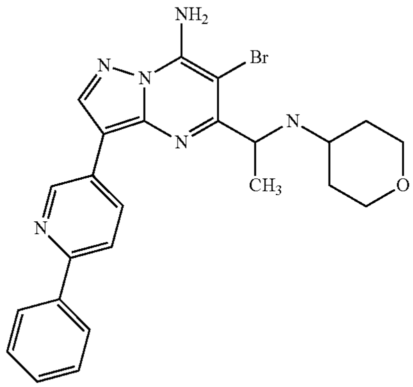 [SMILES: CC(NC1CCOCC1)c1nc2c(-c3ccc(-c4ccccc4)nc3)cnn2c(N)c1Br] | 493.41 | 494.20 | 2.52 |
| 14.61 | 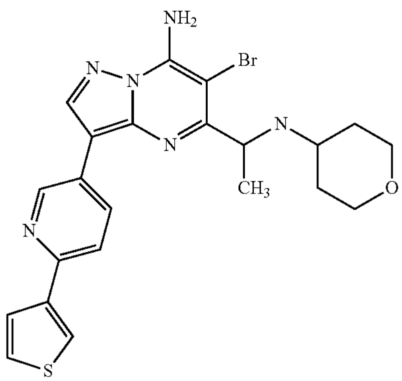 [SMILES: CC(NC1CCOCC1)c1nc2c(-c3ccc(-c4ccsc4)nc3)cnn2c(N)c1Br] | 499.44 | 500.10 | 2.53 |
| 14.62 | 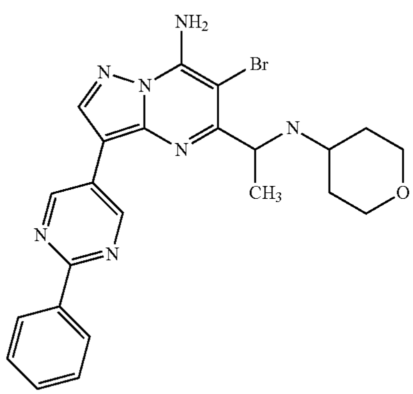 [SMILES: CC(NC1CCOCC1)c1nc2c(-c3cnc(-c4ccccc4)nc3)cnn2c(N)c1Br] | 494.40 | 495.20 | 4.79 |
| 14.63 | 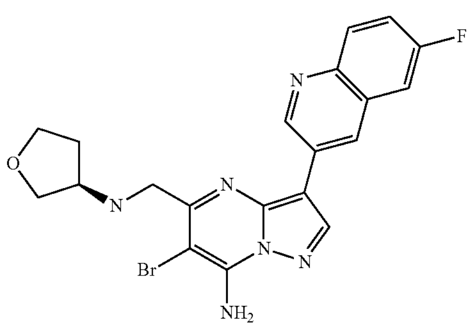 [SMILES: Nc1c(Br)c(CN[C@@H]2CCOC2)nc2c(-c3cnc4ccc(F)cc4c3)cnn12] | 457.31 | 458.10 | 2.29 |

TABLE-14-continued
| Compound ID | Structure | M + H (Calc) | M + H (Observed) | Retention Time(min) |
|---|---|---|---|---|
| 14.64 | 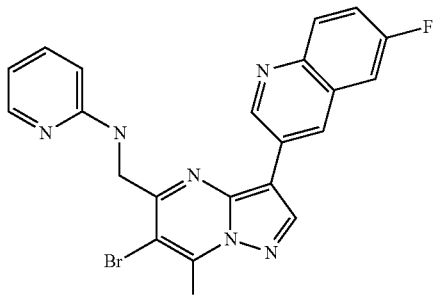 | 464.30 | 465.10 | 2.53 |
| 14.65 | 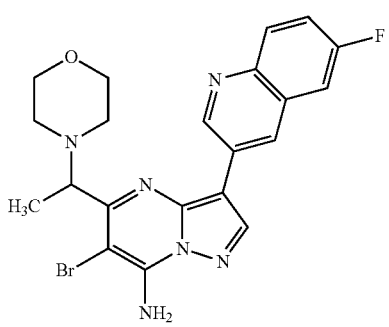 [SMILES: CC(c1nc2c(-c3cnc4ccc(F)cc4c3)cnn2c(N)c1Br)N1CCOCC1] | 471.34 | 472.10 | 2.43 |
| 14.66 | 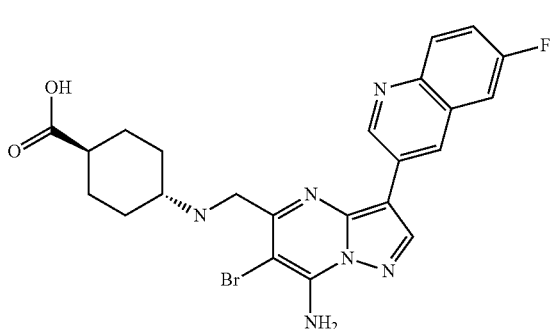 | 513.37 | 514.20 | 2.35 |
| 14.67 | 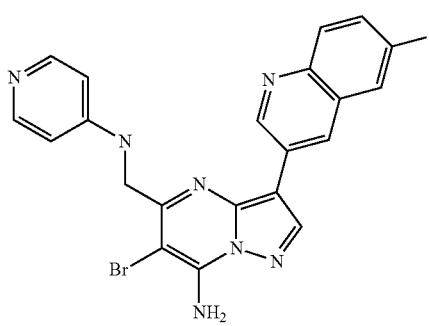 | 464.30 | 465.10 | 2.46 |

TABLE-14-continued

| Compound ID | Structure | M + H (Calc) | M + H (Observed) | Retention Time(min) |
|---|---|---|---|---|
| 14.68 | 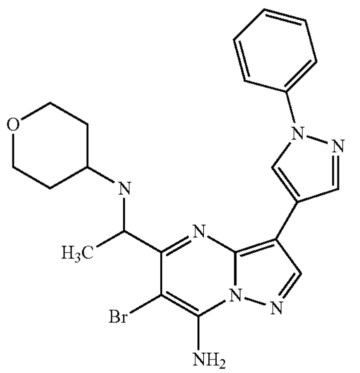 [SMILES: CC(NC1CCOCC1)c1nc2c(-c3cnn(-c4ccccc4)c3)cnn2c(N)c1Br] | 482.39 | 483.20 | 4.81 |
| 14.69 | 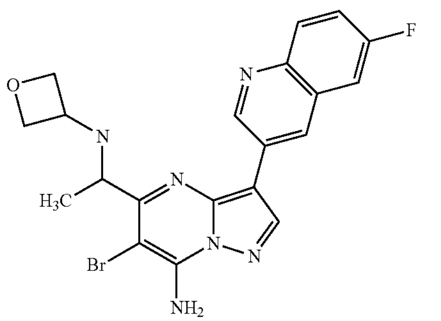 [SMILES: CC(NC1COC1)c1nc2c(-c3cnc4ccc(F)cc4c3)cnn2c(N)c1Br] | 457.31 | 458.10 | 3.82 |
| 14.70 | 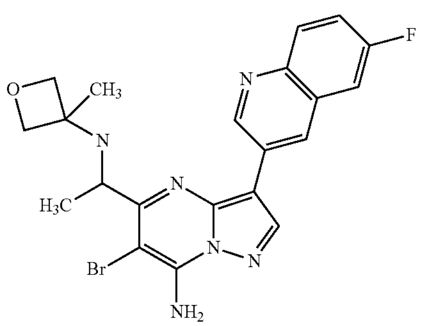 [SMILES: CC(NC1(C)COC1)c1nc2c(-c3cnc4ccc(F)cc4c3)cnn2c(N)c1Br] | 471.34 | 472.10 | 3.91 |
| 14.71 | 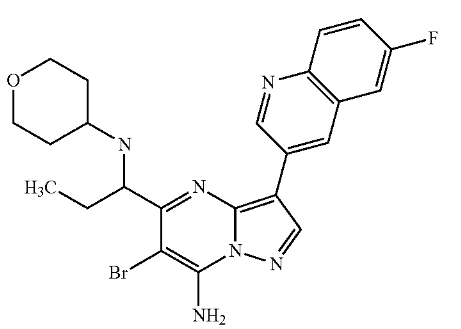 [SMILES: CCC(NC1CCOCC1)c1nc2c(-c3cnc4ccc(F)cc4c3)cnn2c(N)c1Br] | 499.39 | 500.20 | 4.21 |

TABLE-14-continued

| Compound ID | Structure | M + H (Calc) | M + H (Observed) | Retention Time(min) |
|---|---|---|---|---|
| 14.72 | 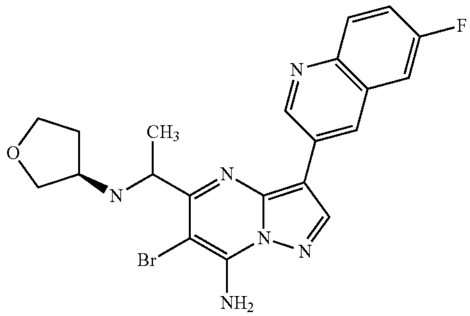 [SMILES: CC(N[C@@H]1CCOC1)c1nc2c(-c3cnc4ccc(F)cc4c3)cnn2c(N)c1Br] | 471.34 | 472.10 | 2.43 |
| 14.73 | 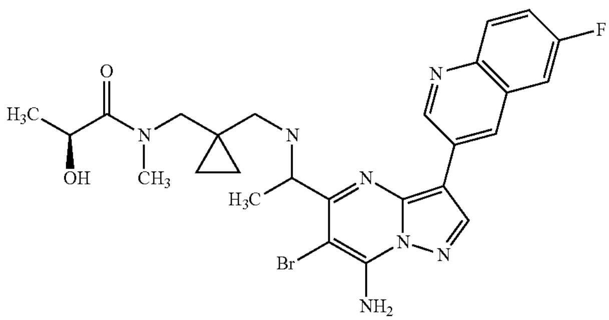 [SMILES: CC(NCC1(CN(C)C(=O)[C@H](C)O)CC1)c1nc2c(-c3cnc4ccc(F)cc4c3)cnn2c(N)c1Br] | 570.47 | 571.20 | 4.22 |
| 14.74 | 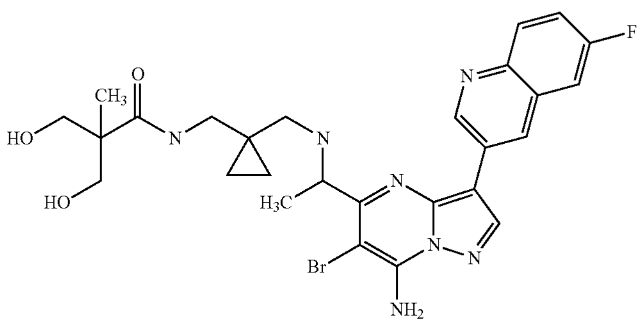 [SMILES: CC(NCC1(CNC(=O)C(C)(CO)CO)CC1)c1nc2c(-c3cnc4ccc(F)cc4c3)cnn2c(N)c1Br] | 600.50 | 601.20 | 2.53 |
| 14.75 | 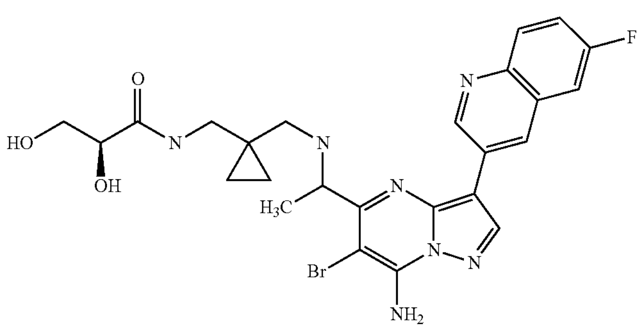 [SMILES: CC(NCC1(CNC(=O)[C@@H](O)CO)CC1)c1nc2c(-c3cnc4ccc(F)cc4c3)cnn2c(N)c1Br] | 572.44 | 573.10 | 2.39 |

TABLE-14-continued

| Compound ID | Structure | M + H (Calc) | M + H (Observed) | Retention Time(min) |
| --- | --- | --- | --- | --- |
| 14.76 | 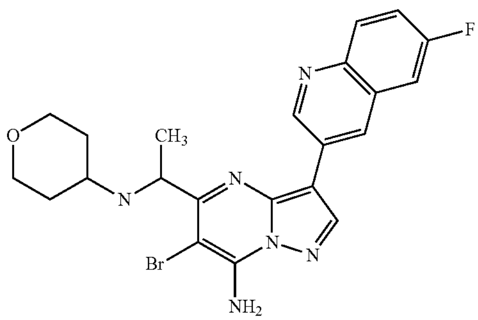 | 485.36 | 486.20 | 2.53 |
| 14.77 | 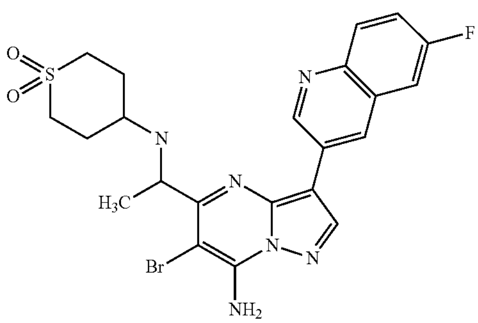 [SMILES: CC(NC1CCS(=O)(=O)CC1)c1nc2c(-c3cnc4ccc(F)cc4c3)cnn2c(N)c1Br] | 533.43 | 534.20 | 3.90 |
| 14.78 | 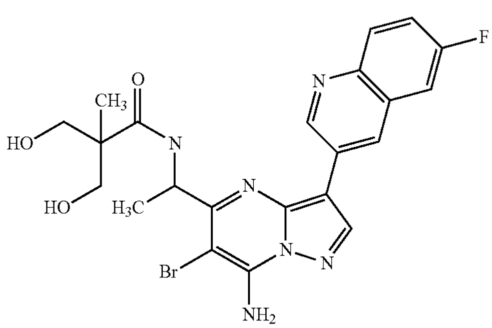 [SMILES: CC(NC(=O)C(C)(CO)CO)c1nc2c(-c3cnc4ccc(F)cc4c3)cnn2c(N)c1Br] | 517.36 | 518.10 | 2.74 |
| 14.79 | 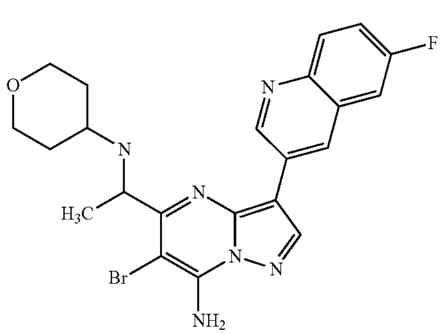 [SMILES: CC(NC1CCOCC1)c1nc2c(-c3cnc4ccc(F)cc4c3)cnn2c(N)c1Br] | 485.36 | 486.20 | 2.55 |

TABLE-14-continued

| Compound ID | Structure | M + H (Calc) | M + H (Observed) | Retention Time(min) |
| --- | --- | --- | --- | --- |
| 14.80 | 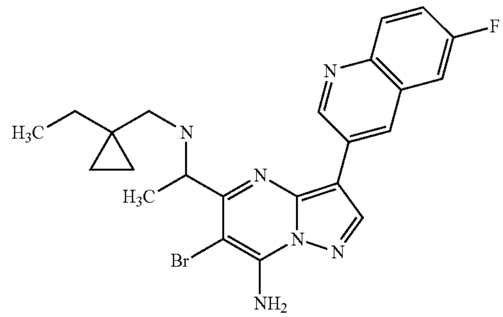 [SMILES: CCC1(CNC(C)c2nc3c(-c4cnc5ccc(F)cc5c4)cnn3c(N)c2Br)CC1] | 485.36 | 486.20 | 2.53 |
| 14.81 | 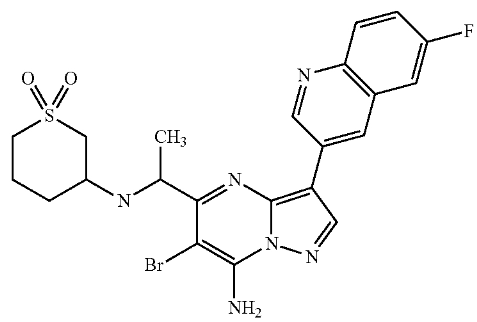 [SMILES: CC(NC1CCCS(=O)(=O)C1)c1nc2c(-c3cnc4ccc(F)cc4c3)cnn2c(N)c1Br] | 533.43 | 534.10 | 2.51 |
| 14.82 | 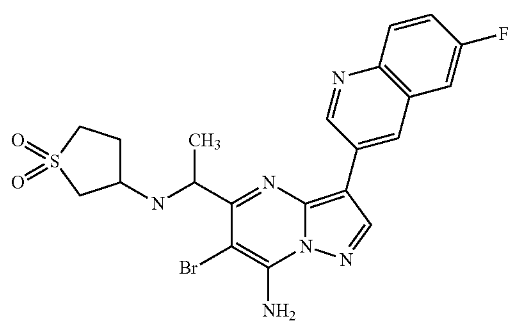 [SMILES: CC(NC1CCS(=O)(=O)C1)c1nc2c(-c3cnc4ccc(F)cc4c3)cnn2c(N)c1Br] | 519.40 | 520.10 | 2.42 |
| 14.83 | 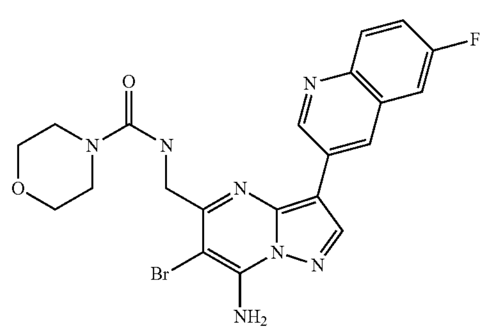 [SMILES: Nc1c(Br)c(CNC(=O)N2CCOCC2)nc2c(-c3cnc4ccc(F)cc4c3)cnn12] | 500.33 | 501.20 | 2.71 |

TABLE-14-continued

| Compound ID | Structure | M + H (Calc) | M + H (Observed) | Retention Time(min) |
|---|---|---|---|---|
| 14.84 | 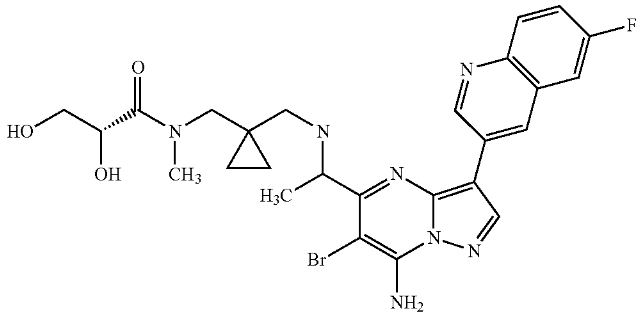 [SMILES: CC(NCC1(CN(C)C(=O)[C@H](O)CO)CC1)c1nc2c(-c3cnc4ccc(F)cc4c3)cnn2c(N)c1Br] | 586.47 | 587.20 | 3.30 |
| 14.85 | 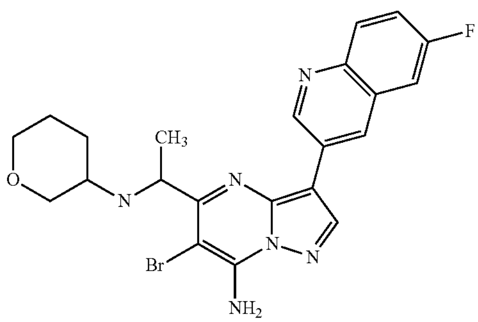 [SMILES: CC(NC1CCCOC1)c1nc2c(-c3cnc4ccc(F)cc4c3)cnn2c(N)c1Br] | 485.36 | 486.20 | 2.60 |
| 14.86 | 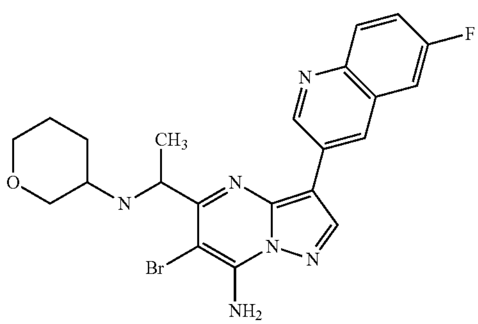 [SMILES: CC(NC1CCCOC1)c1nc2c(-c3cnc4ccc(F)cc4c3)cnn2c(N)c1Br] | 485.36 | 486.20 | 2.55 |
| 14.87 | 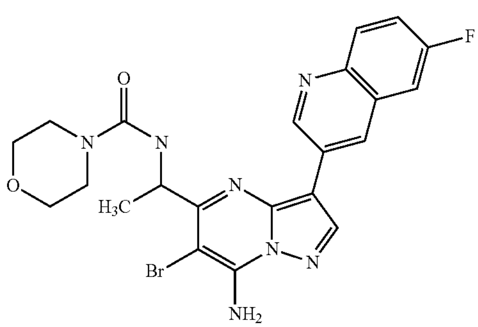 [SMILES: CC(NC(=O)N1CCOCC1)c1nc2c(-c3cnc4ccc(F)cc4c3)cnn2c(N)c1Br] | 514.36 | 515.10 | 4.57 |

TABLE-14-continued

| Compound ID | Structure | M + H (Calc) | M + H (Observed) | Retention Time(min) |
|---|---|---|---|---|
| 14.88 | 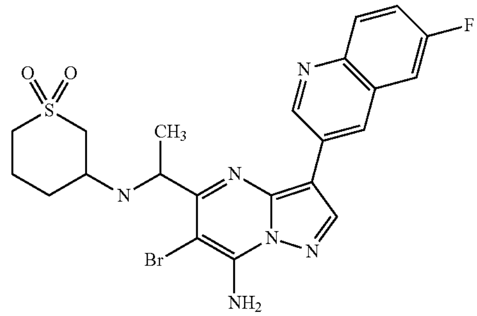 [SMILES: CC(NC1CCCS(=O)(=O)C1)c1nc2c(-c3cnc4ccc(F)cc4c3)cnn2c(N)c1Br] | 533.43 | 534.20 | 2.52 |
| 14.89 | 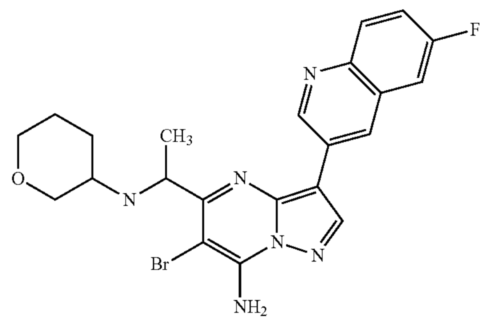 [SMILES: CC(NC1CCCOC1)c1nc2c(-c3cnc4ccc(F)cc4c3)cnn2c(N)c1Br] | 485.36 | 486.10 | 2.60 |
| 14.90 | 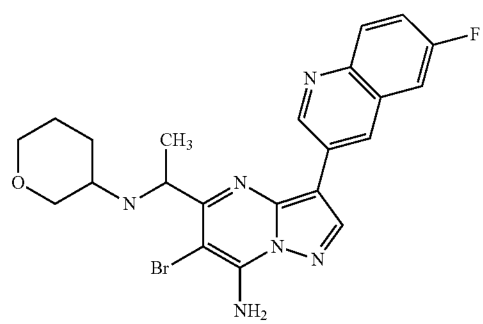 [SMILES: CC(NC1CCCOC1)c1nc2c(-c3cnc4ccc(F)cc4c3)cnn2c(N)c1Br] | 485.36 | 486.10 | 2.60 |
| 14.91 | 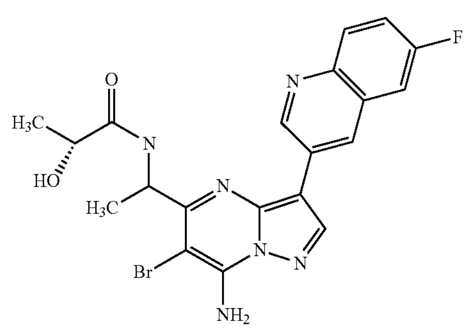 [SMILES: CC(NC(=O)[C@@H](C)O)c1nc2c(-c3cnc4ccc(F)cc4c3)cnn2c(N)c1Br] | 473.31 | 474.20 | 2.79 |

TABLE-14-continued

| Compound ID | Structure | M + H (Calc) | M + H (Observed) | Retention Time(min) |
|---|---|---|---|---|
| 14.92 | 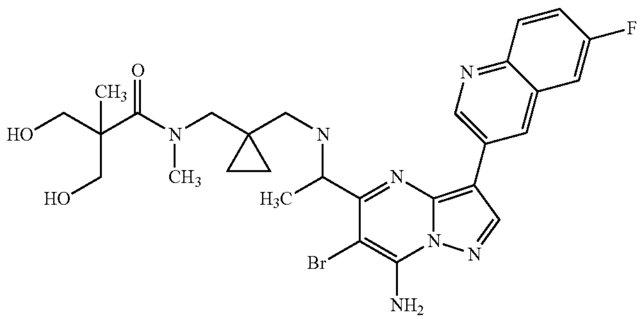 [SMILES: CC(NCC1(CN(C)C(=O)C(C)(CO)CO)CC1)c1nc2c(-c3cnc4ccc(F)cc4c3)cnn2c(N)c1Br] | 614.52 | 615.20 | 2.58 |
| 14.93 | 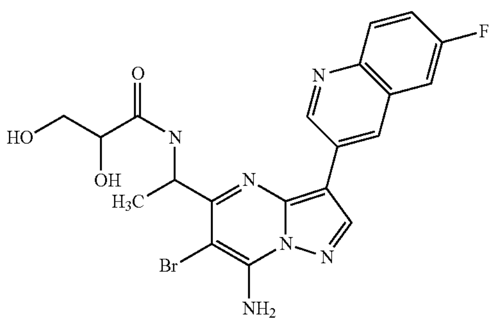 [SMILES: CC(NC(=O)C(O)CO)c1nc2c(-c3cnc4ccc(F)cc4c3)cnn2c(N)c1Br] | 489.31 | 490.10 | 3.44 |
| 14.94 | 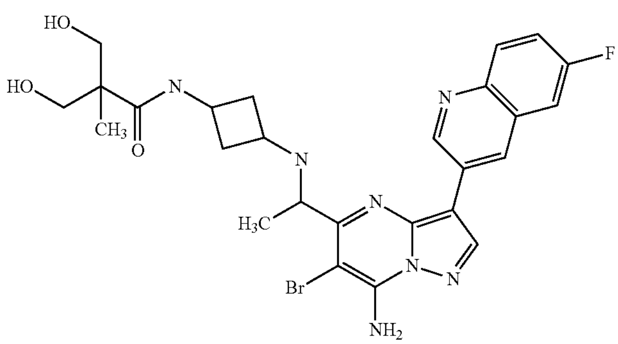 [SMILES: CC(NC1CC(NC(=O)C(C)(CO)CO)C1)c1nc2c(-c3cnc4ccc(F)cc4c3)cnn2c(N)c1Br] | 586.47 | 587.20 | 2.30 |
| 14.95 | 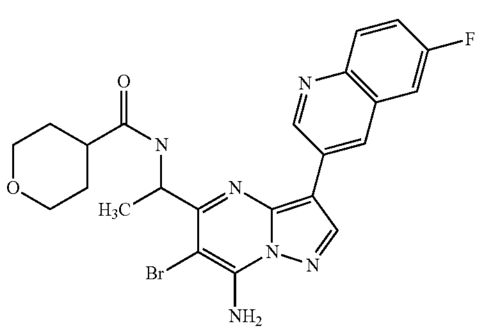 [SMILES: CC(NC(=O)C1CCOCC1)c1nc2c(-c3cnc4ccc(F)cc4c3)cnn2c(N)c1Br] | 513.37 | 514.20 | 2.93 |

TABLE-14-continued

| Compound ID | Structure | M + H (Calc) | M + H (Observed) | Retention Time(min) |
|---|---|---|---|---|
| 14.96 | 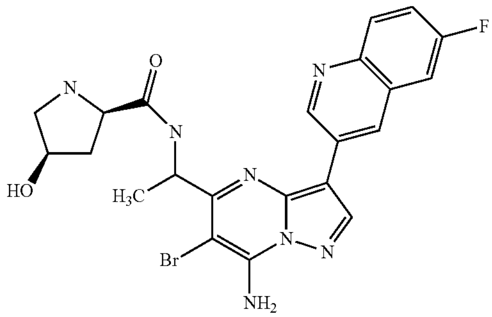 [SMILES: CC(NC(=O)[C@H]1C[C@@H](O)CN1)c1nc2c(-c3cnc4ccc(F)cc4c3)cnn2c(N)c1Br] | 514.36 | 515.10 | 2.56 |
| 14.97 | 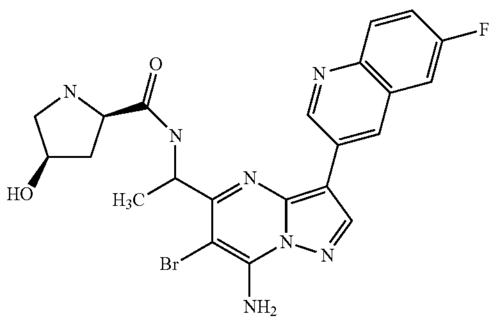 [SMILES: CC(NC(=O)[C@H]1C[C@@H](O)CN1)c1nc2c(-c3cnc4ccc(F)cc4c3)cnn2c(N)c1Br] | 514.36 | 515.20 | 2.51 |
| 14.98 | 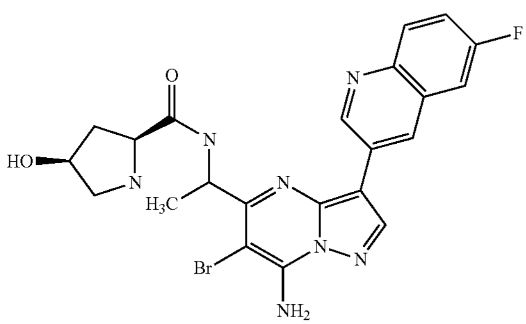 [SMILES: CC(NC(=O)[C@@H]1C[C@H](O)CN1)c1nc2c(-c3cnc4ccc(F)cc4c3)cnn2c(N)c1Br] | 514.36 | 515.20 | 2.49 |
| 14.99 | 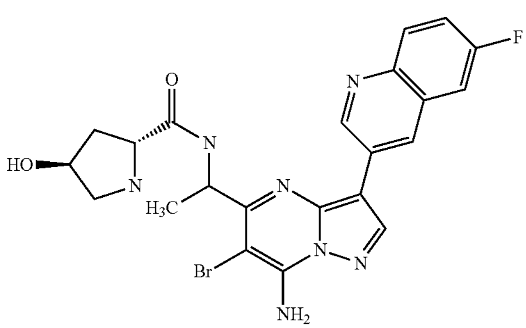 [SMILES: CC(NC(=O)[C@H]1C[C@H](O)CN1)c1nc2c(-c3cnc4ccc(F)cc4c3)cnn2c(N)c1Br] | 514.36 | 515.10 | 2.49 |

TABLE-14-continued

| Compound ID | Structure | M + H (Calc) | M + H (Observed) | Retention Time(min) |
|---|---|---|---|---|
| 14.100 | 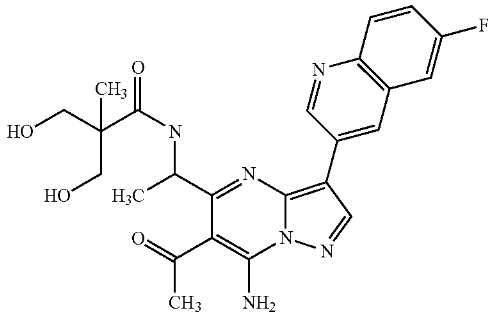 [SMILES: CC(=O)c1c(C(C)NC(=O)C(C)(CO)CO)nc2c(-c3cnc4ccc(F)cc4c3)cnn2c1N] | 480.50 | 481.20 | 2.68 |
| 14.101 | 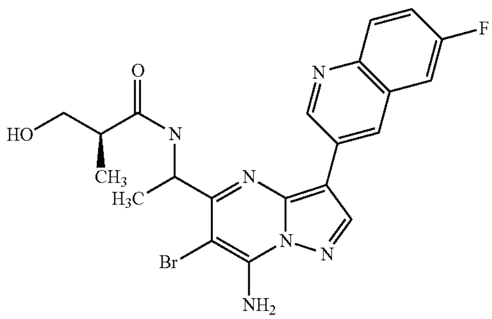 [SMILES: CC(NC(=O)[C@@H](C)CO)c1nc2c(-c3cnc4ccc(F)cc4c3)cnn2c(N)c1Br] | 487.33 | 488.10 | 2.91 |
| 14.102 | 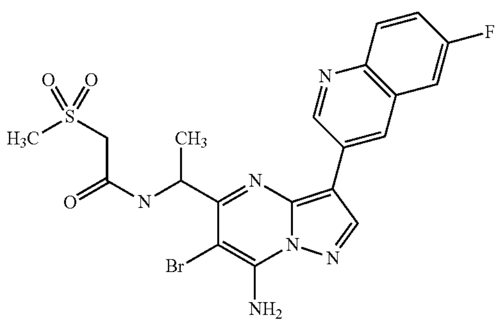 [SMILES: CC(NC(=O)CS(C)(=O)=O)c1nc2c(-c3cnc4ccc(F)cc4c3)cnn2c(N)c1Br] | 521.37 | 522.10 | 2.80 |
| 14.103 | 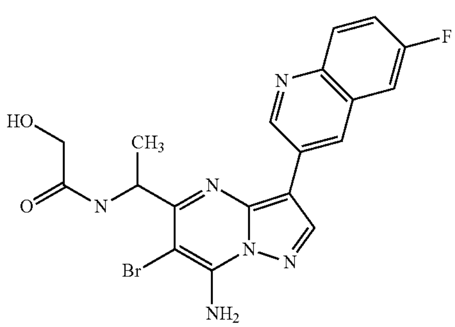 [SMILES: CC(NC(=O)CO)c1nc2c(-c3cnc4ccc(F)cc4c3)cnn2c(N)c1Br] | 459.28 | 460.20 | 2.71 |

TABLE-14-continued

| Compound ID | Structure | M + H (Calc) | M + H (Observed) | Retention Time(min) |
|---|---|---|---|---|
| 14.104 | 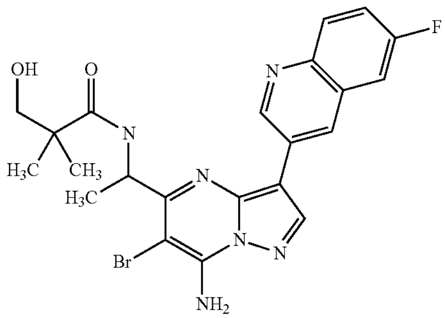 [SMILES: CC(NC(=O)C(C)(C)CO)c1nc2c(-c3cnc4ccc(F)cc4c3)cnn2c(N)c1Br] | 501.36 | 502.10 | 3.01 |
| 14.105 | 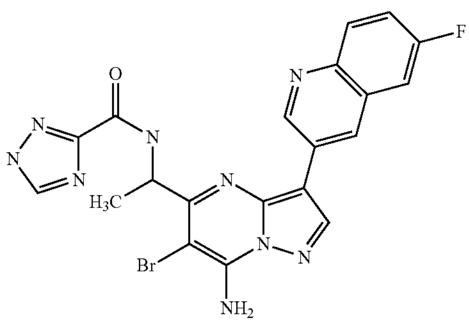 [SMILES: CC(NC(=O)c1nc[nH]n1)c1nc2c(-c3cnc4ccc(F)cc4c3)cnn2c(N)c1Br] | 496.30 | 497.20 | 2.81 |
| 14.106 | 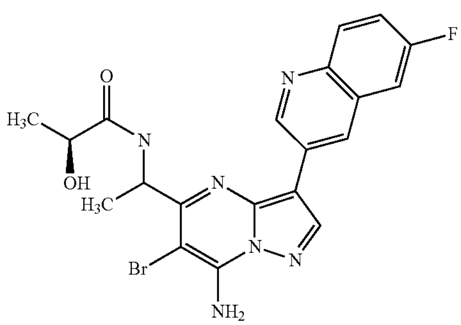 [SMILES: CC(NC(=O)[C@H](C)O)c1nc2c(-c3cnc4ccc(F)cc4c3)cnn2c(N)c1Br] | 473.31 | 474.20 | 2.80 |
| 14.107 | 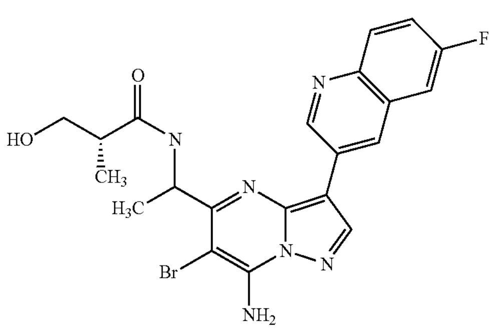 [SMILES: CC(NC(=O)[C@H](C)CO)c1nc2c(-c3cnc4ccc(F)cc4c3)cnn2c(N)c1Br] | 487.33 | 488.20 | 2.91 |

TABLE-14-continued

| Compound ID | Structure | M + H (Calc) | M + H (Observed) | Retention Time(min) |
|---|---|---|---|---|
| 14.108 | 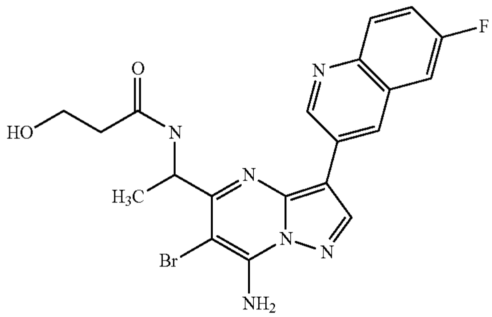 [SMILES: CC(NC(=O)CCO)c1nc2c(-c3cnc4ccc(F)cc4c3)cnn2c(N)c1Br] | 473.31 | 474.10 | 2.81 |
| 14.109 | 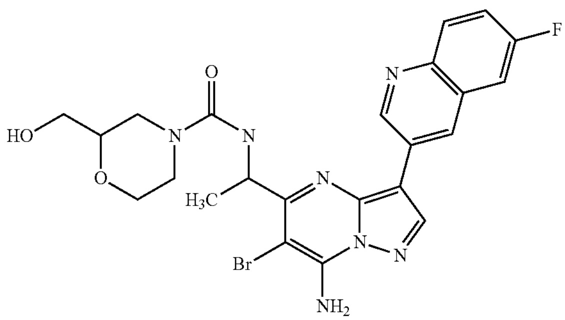 [SMILES: CC(NC(=O)N1CCOC(CO)C1)c1nc2c(-c3cnc4ccc(F)cc4c3)cnn2c(N)c1Br] | 544.39 | 545.10 | 2.73 |
| 14.110 | 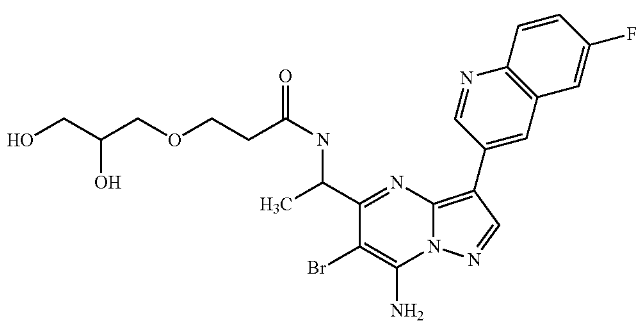 [SMILES: CC(NC(=O)CCOCC(O)CO)c1nc2c(-c3cnc4ccc(F)cc4c3)cnn2c(N)c1Br] | 547.39 | 548.20 | 2.92 |
| 14.111 | 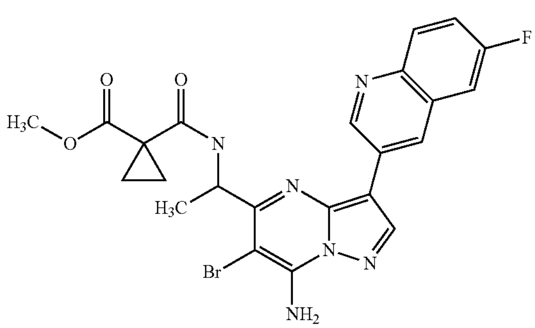 [SMILES: COC(=O)C1(C(=O)NC(C)c2nc3c(-c4cnc5ccc(F)cc5c4)cnn3c(N)c2Br)CC1] | 527.36 | 528.10 | 3.63 |

TABLE-14-continued

| Compound ID | Structure | M + H (Calc) | M + H (Observed) | Retention Time(min) |
|---|---|---|---|---|
| 14.112 | 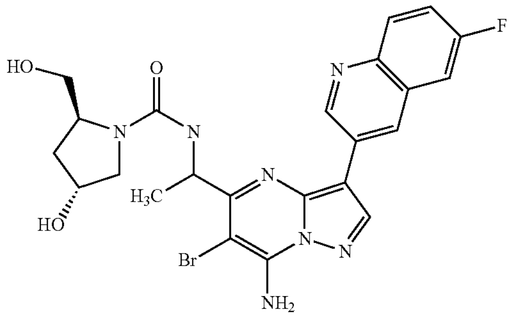 [SMILES: CC(NC(=O)N1C[C@H](O)C[C@H]1CO)c1nc2c(-c3cnc4ccc(F)cc4c3)cnn2c(N)c1Br] | 544.39 | 545.20 | 2.64 |
| 14.113 | 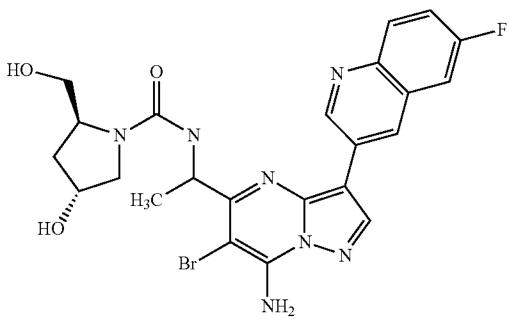 [SMILES: CC(NC(=O)N1C[C@H](O)C[C@H]1CO)c1nc2c(-c3cnc4ccc(F)cc4c3)cnn2c(N)c1Br] | 544.39 | 545.20 | 2.60 |
| 14.114 | 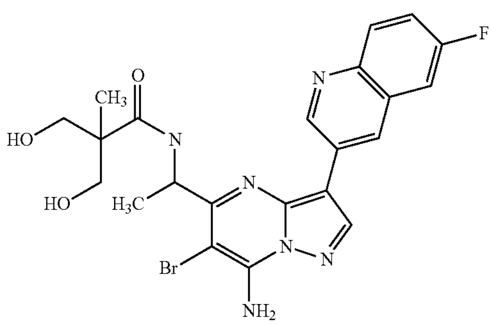 [SMILES: CC(NC(=O)C(C)(CO)CO)c1nc2c(-c3cnc4ccc(F)cc4c3)cnn2c(N)c1Br] | 517.36 | 518.10 | 2.75 |
| 14.115 | 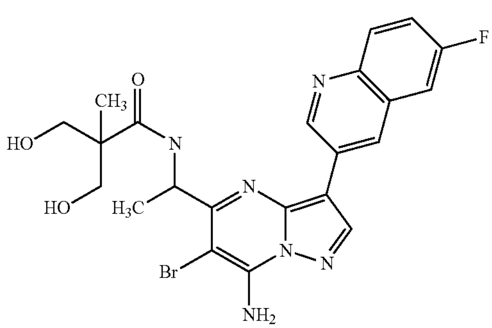 [SMILES: CC(NC(=O)C(C)(CO)CO)c1nc2c(-c3cnc4ccc(F)cc4c3)cnn2c(N)c1Br] | 517.36 | 518.20 | 2.76 |

TABLE-14-continued
| Compound ID | Structure | M + H (Calc) | M + H (Observed) | Retention Time(min) |
|---|---|---|---|---|
| 14.116 | 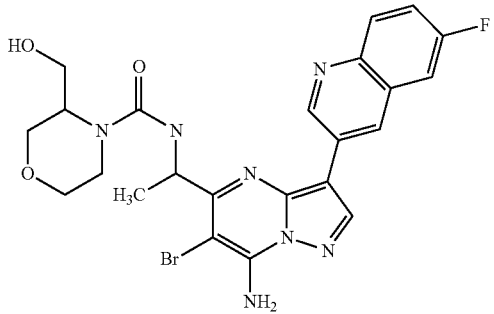 [SMILES: CC(NC(=O)N1CCOCC1CO)c1nc2c(-c3cnc4ccc(F)cc4c3)cnn2c(N)c1Br] | 544.39 | 545.10 | 2.94 |
| 14.117 | 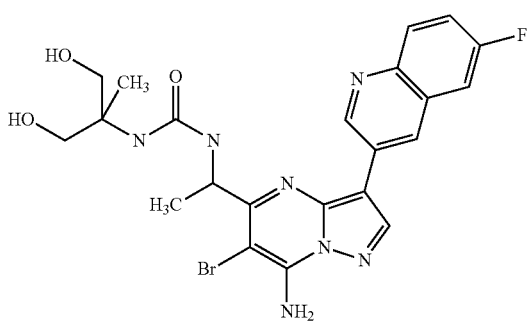 [SMILES: CC(NC(=O)NC(C)(CO)CO)c1nc2c(-c3cnc4ccc(F)cc4c3)cnn2c(N)c1Br] | 532.38 | 533.20 | 2.71 |
| 14.118 | 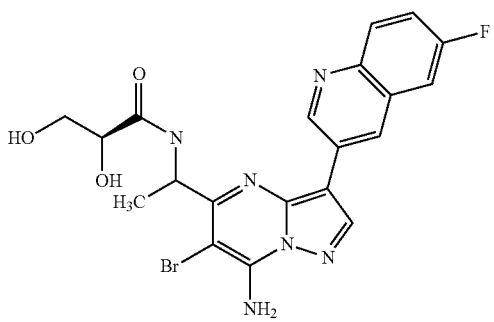 [SMILES: CC(NC(=O)[C@@H](O)CO)c1nc2c(-c3cnc4ccc(F)cc4c3)cnn2c(N)c1Br] | 489.31 | 490.10 | 3.44 |
6-(7-amino-3-(quinolin-3-yl)pyrazolo[1,5-a]pyrimidin-5-yl)hexanoic acid
-continued
Scheme 70
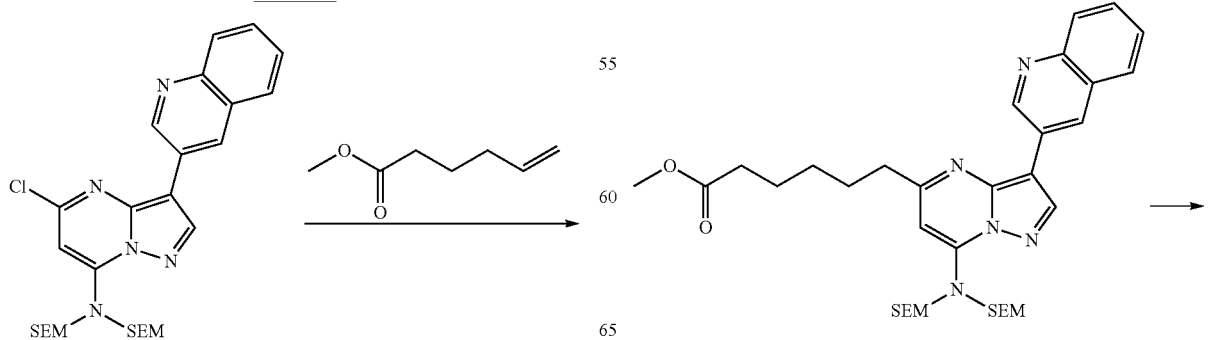

1491 -continued

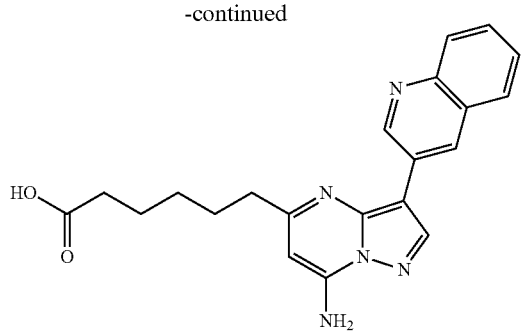

To a solution of methyl hex-5-enoate (12 mg, 0.1 mmol) in THF (0.5 ml) under argon at 0° C. was added 9-BBN (0.2 mmol, 0.4 ml of 0.5 M solution in THF). The mixture was warmed to room temperature and stirred for 16 h. Potassium phosphate (3 M in H₂O, 0.2 mmol) was added followed by the addition of 5-chloro-3-(quinolin-3-yl)-N,N-bis((2-(trimethylsilyl)ethoxy)methyl)pyrazolo[1,5-a]pyrimidin-7-amine (50 mg, 0.09 mmol) in DMF (0.5 ml) and Pd(dppf)Cl₂—CH₂Cl₂ (5 mg, 0.005 mmol). The reaction mixture was heated at 90° C. for 16 h under argon. The solution was cooled to room temperature and concentrated under reduced pressure. The residue was dissolved in 2:1 THF:MeOH (3 mL) and was treated with 2N NaOH$_{(aq)}$ (0.25 mL). The resulting solution was stirred at room temperature for 4 hours followed by the addition of 2N hydrochloride solution (1.0 ml). The solution was heated at 65° C. for 2 h, cooled to room temperature, concentrated in vacuo and purified by prep-LC to afford the title compound (8.2 mg): LC/MS RT=2.74 min. Mass calculated for, M+H 376.17, observed 376.17.

By essentially the same procedure given in Scheme 50, the compounds listed in Table 15 can be prepared.

1492 Incorporation of Deuterium at the 3-Position

Scheme 51

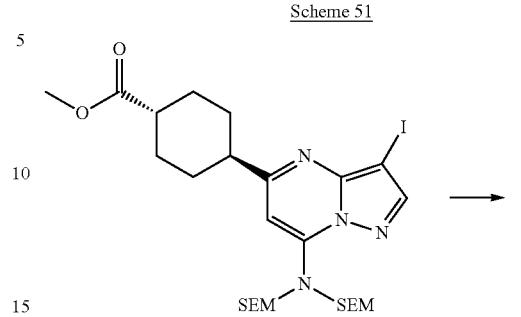

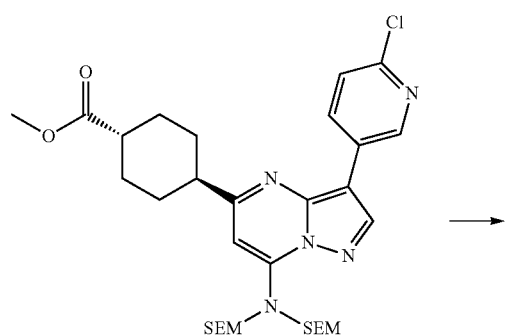

TABLE 15

| Compound ID | Structures | M + H (calc.) | M + H (observed) | Retention Time, (min) |
|---|---|---|---|---|
| 15.1 | ![structure] | 376.17 | 376.17 | 2.74 |
| 15.2 | ![structure] | 348.14 | 348.14 | 2.41 |

-continued

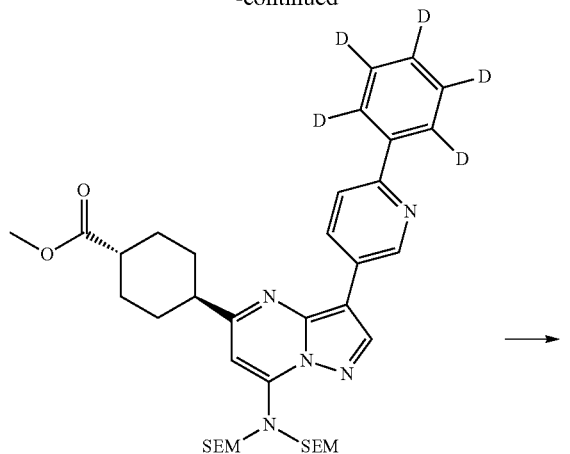

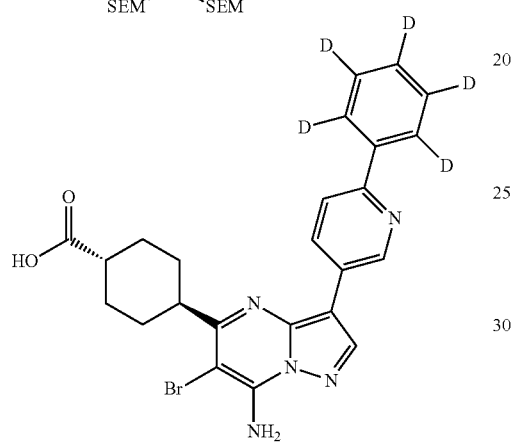

Synthesis of Methyl 4-(7-(bis((2-(trimethylsilyl)ethoxy)methyl)amino)-3-(6-chloropyridin-3-yl)pyrazolo[1,5-a]pyrimidin-5-yl)cyclohexanecarboxylate

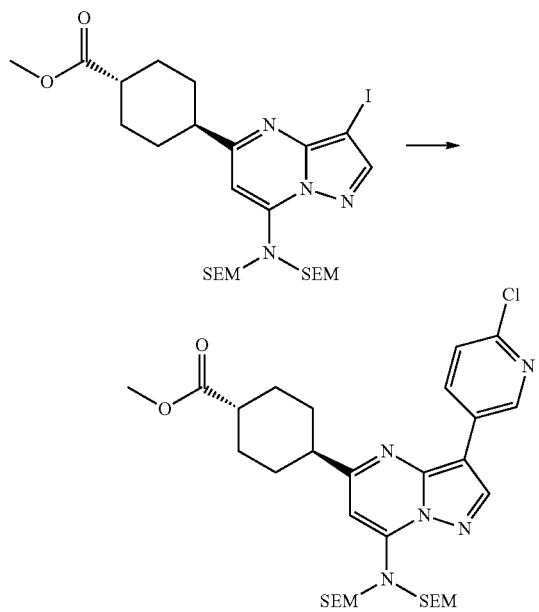

2-Chloro-5-(4,4,5,5-tetramethyl-1,3,2-dioxaborolan-2-yl)pyridine (0.55 mmol, 131 mg), $K_3PO_4$ (1.36 mmol, 290 mg), and $PdCl_2(dppf) \cdot CH_2Cl_2$ (0.045 mmol, 37 mg) is added to a solution of 4-{7-[Bis-(2-trimethylsilanyl-ethoxymethyl)-amino]-3-iodo-pyrazolo[1,5-a]pyrimidin-5-yl}-cyclohexanecarboxylic acid methyl ester (0.45 mmol, 300 mg) in dioxane (3.8 mL). To this suspension is added distilled $H_2O$ (0.38 mL). The resulting solution is stirred at 90° C. under argon for 18 hours. The reaction mixture is concentrated in vacuo and then purified via silica gel chromatography (0% to 60% ethyl acetate in hexanes gradient) to yield the title compound (220 mg, 75% yield) as yellow oil. LC-MS: 646 [M+H].

Synthesis of (1r,4r)-methyl 4-(7-(bis((2-(trimethylsilyl)ethoxy)methyl)amino)-3-(6-phenyl-d5-pyridin-3-yl)pyrazolo[1,5-a]pyrimidin-5-yl)cyclohexanecarboxylate

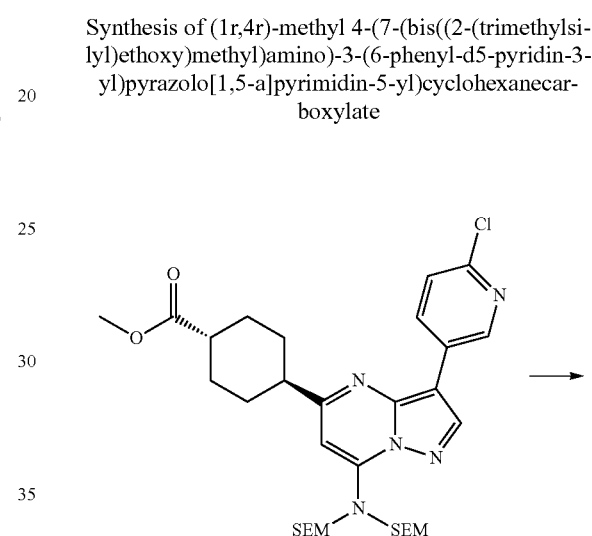

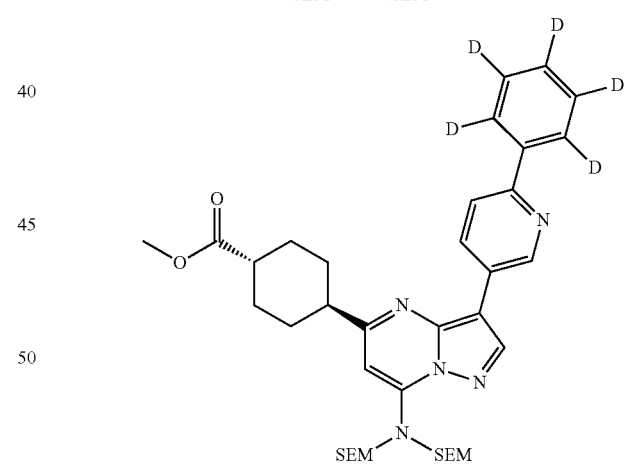

Phenyl-d5-boronic acid (1.08 mmol, 137 mg), $K_3PO_4$ (1.63 mmol, 345 mg), and $PdCl_2(dppf) \cdot CH_2Cl_2$ (0.054 mmol, 45 mg) is added to a solution of methyl 4-(7-(bis((2-(trimethylsilyl)ethoxy)methyl)amino)-3-(6-chloropyridin-3-yl)pyrazolo[1,5-a]pyrimidin-5-yl)cyclohexanecarboxylate (0.54 mmol, 350 mg) in dioxane (6.0 mL). To this suspension is added distilled $H_2O$ (0.6 mL). The resulting solution is stirred at 100° C. under argon for 18 hours. The reaction mixture is concentrated in vacuo and then purified via silica gel chromatography (0% to 60% ethyl acetate in hexanes gradient) to yield the title compound.

1495

Synthesis of (1r,4r)-4-(7-amino-6-bromo-3-(6-phenyl-d5-Pyridin-3-yl)pyrazolo[1,5-a]pyrimidin-5-yl)cyclohexanecarboxylic acid

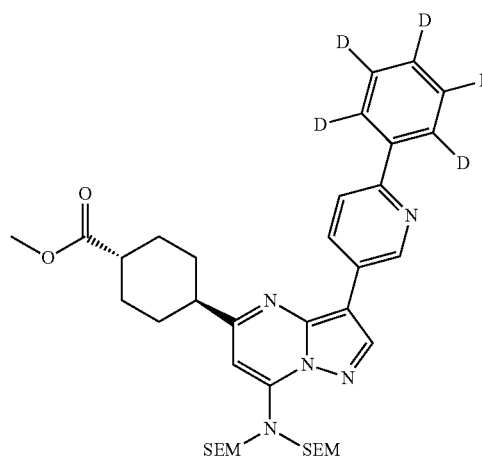

N-bromosuccinimide (73 mg, 0.41 mmol) is added to a solution of (1r,4r)-methyl 4-(7-(bis((2-(trimethylsilyl)ethoxy)methyl)amino)-3-(6-phenyl-d5-pyridin-3-yl)pyrazolo[1,5-a]pyrimidin-5-yl)cyclohexanecarboxylate (284 mg, 0.41 mmol) in acetonitrile (4 mL). The resulting solution is stirred at room temperature for 1 hour. The reaction mixture is concentrated in vacuo and dissolved in 3:3:2 MeOH:THF:H$_2$O (8 mL), followed by the treatment with 3.75 N NaOH$_{(aq)}$ (0.6 mL). The resulting solution is stirred at room temperature for 18 hours. The reaction mixture is treated with 1N hydrochloride solution (4 ml) at 65° C. for 4 h. The reaction solution is concentrated and purified by prep-LC to afford the title compound.

1496

Incorporation of Deuterium at the 5-Position

Scheme 52

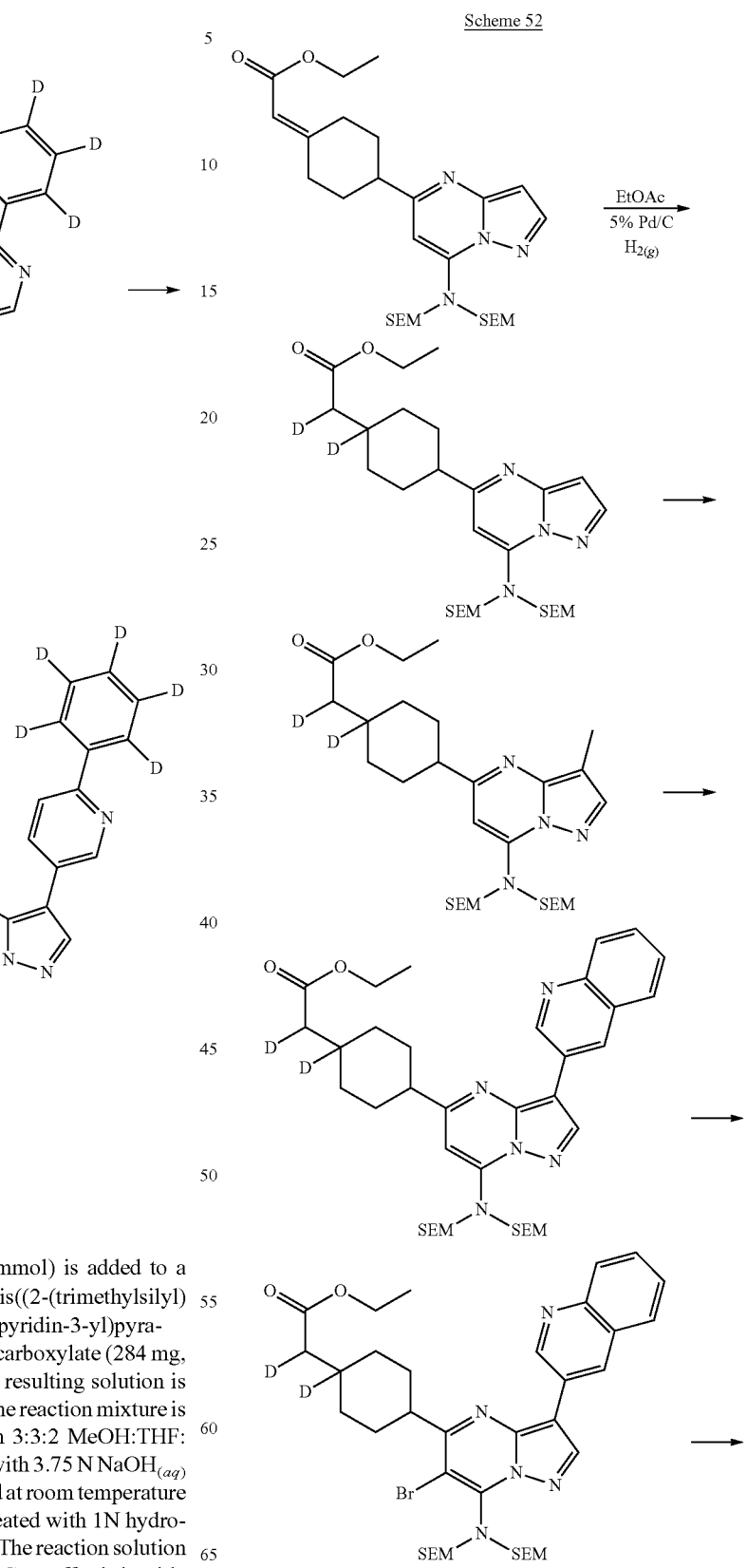

1497
-continued

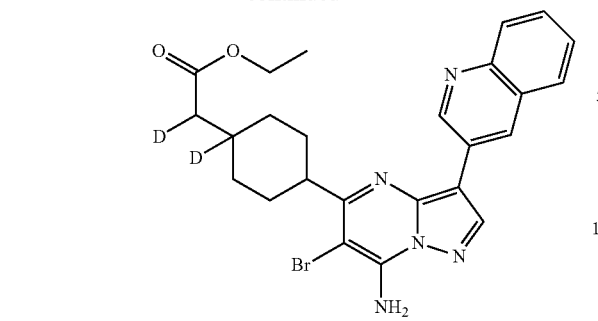

Synthesis of ethyl 2-(4-(7-(bis((2-(trimethylsilyl)ethoxy)methyl)amino)pyrazolo[1,5-a]pyrimidin-5-yl)cyclohexyl)acetate

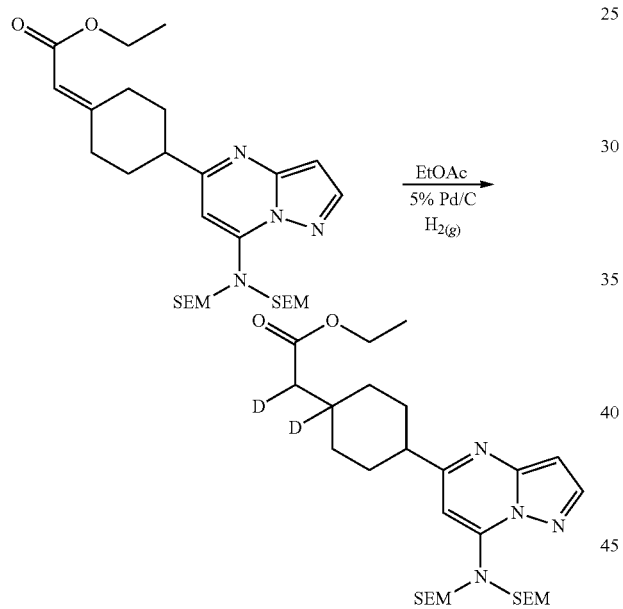

To a 50 mL roundbottom flask is charged ethyl 2-(4-(7-(bis((2-(trimethylsilyl)ethoxy)-methyl)amino)pyrazolo[1,5-a]pyrimidin-5-yl)cyclohexylidene)acetate (800 mg, 1.43 mmol) and ethyl acetate (15 mL). The flask is flushed with argon and 5% palladium on carbon (100 mg) is added. The flask is sealed and degassed under vacuum.

Deuterium gas is then added via balloon. The reaction is stirred under D$_2$ atmosphere 18 hours. The reaction is then filtered through celite to yield deuterated ethyl 2-(4-(7-(bis((2-(trimethylsilyl)ethoxy)methyl)amino)pyrazolo[1,5-a]pyrimidin-5-yl)cyclohexyl)acetate (761 mg, 1.35 mmol, 95% yield) as pale yellow oil.

1498
Incorporate Deuterium at Both 3- and 5-Positions

Scheme 53

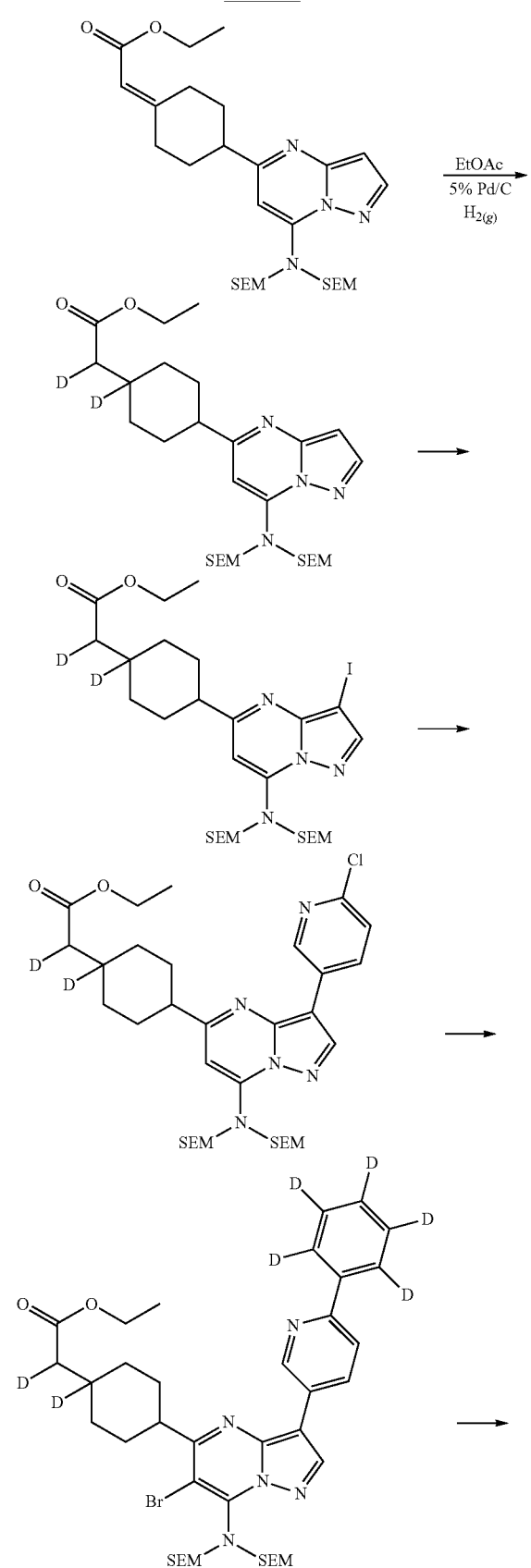

-continued

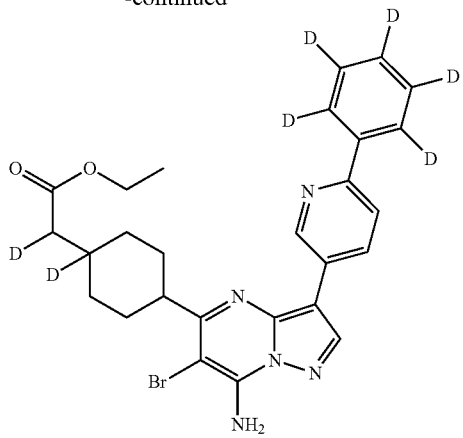

Synthesis of ethyl 2-(4-(7-amino-6-bromo-3-(6-phenylpyridin-3-yl)pyrazolo[1,5-a]pyrimidin-5-yl)cyclohexyl)acetate

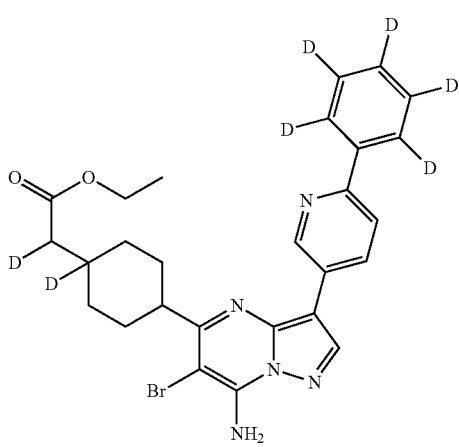 [SMILES: [2H]c1c([2H])c([2H])c(-c2ccc(-c3cnn4c(N)c(Br)c(C5CCC([2H])(C([2H])C(=O)OCC)CC5)nc34)cn2)c([2H])c1[2H]]

By essentially the same procedure given in Schemes 16, 17 and 18, ethyl 2-(4-(7-amino-6-bromo-3-(6-phenylpyridin-3-yl)pyrazolo[1,5-a]pyrimidin-5-yl)cyclohexyl)acetate can be prepared.

Assays:

mTOR Kinase Assay

The mTOR assay buffer contains 10 mM hepes (pH 7.4), 50 mM NaCl, 100 μg/ml BSA, 50 mM B-glycerophosphate, 10 mM MnCl2 and 0.5 mM DTT. 20 ng of mTOR enzyme is preincubated with the compound for 10 minutes. 5 μM ATP and 0.1 μM GSTS6K is added. The reaction is incubated for one hour at 30° C. Anti phospho p70S6K (about 1.7 ng/well) and anti GSTXL665 (1:1 Ratio with the substrate GSTS6K) are added after incubating. The plates are read at least 2 hours after adding the anti phospho p70S6K and the anti GSTXL665.

IC$_{50}$ Determinations:

Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate IC$_{50}$ values, the dose-response curves were then fitted to a standard sigmoidal curve and IC$_{50}$ values were derived by nonlinear regression analysis.

CHK1 In Vitro Kinase Assay

This in vitro assay utilizes recombinant His-CHK1 expressed in the baculovirus expression system as an enzyme source and a biotinylated peptide based on CDC25C as substrate (biotin-RSGLYRSPSMPENLNRPR).

Materials and Reagents:

1) CDC25C Ser 216 C-term Biotinylated peptide substrate (25 mg), stored at −20° C., Custom Synthesis by Research Genetics: biotin-RSGLYRSPSMPENLNRPR 2595.4 MW 2) His-CHK1 In House lot P976, 235 μg/mL, stored at −80° C.

3) D-PBS (without CaCl and MgCl): GIBCO, Cat. #14190-144

4) SPA beads: Amersham, Cat. # SPQ0032: 500 mg/vial
   Add 10 mL of D-PBS to 500 mg of SPA beads to make a working concentration of 50 mg/mL. Store at 4° C. Use within 2 week after hydration.

5) 96-Well White Microplate with Bonded GF/B filter: Packard, Cat. #6005177

6) Top seal-A 96 well Adhesive Film: Perkin Elmer, Cat. #6005185

7) 96-well Non-Binding White Polystyrene Plate: Corning, Cat. #6005177

8) MgCl$_2$: Sigma, Cat. # M-8266

9) DTT: Promega, Cat. # V3155

10) ATP, stored at 4° C.: Sigma, Cat. # A-5394

11) γ$^{33}$P-ATP, 1000-3000 Ci/mMol: Amersham, Cat. # AH9968

12) NaCl: Fisher Scientific, Cat. # BP358-212

13) H$_3$PO$_4$ 85% Fisher, Cat. #A242-500

14) Tris-HCL pH 8.0: Bio-Whittaker, Cat. #16-015V

15) Staurosporine, 100 μg: CALBIOCHEM, Cat. #569397

16) Hypure Cell Culture Grade Water, 500 mL: HyClone, Cat. # SH30529.02

Reaction Mixtures:

1) Kinase Buffer: 50 mM Tris pH 8.0; 10 mM MgCl$_2$; 1 mM DTT

2) His-CHK1, In House Lot P976, MW ~30 KDa, stored at −80° C.

6 nM is required to yield positive controls of ~5,000 CPM. For 1 plate (100 reaction): dilute 8 μL of 235 μg/mL (7.83 μM) stock in 2 mL Kinase Buffer. This makes a 31 nM mixture. Add 20 μL/well. This makes a final reaction concentration of 6 nM.

3) CDC25C Biotinylated peptide.

Dilute CDC25C to 1 mg/mL (385 μM) stock and store at −20° C. For 1 plate (100 reactions): dilute 10 μL of 1 mg/mL peptide stock in 2 mL Kinase Buffer. This gives a 1.925 μM mix. Add 20 μL/reaction. This makes a final reaction concentration of 385 nM.

4) ATP Mix.

For 1 plate (100 reactions): dilute 10 μL of 1 mM ATP (cold) stock and 2 μL fresh P33-ATP (20 μCi) in 5 mL Kinase Buffer. This gives a 2 μM ATP (cold) solution; add 50 μL/well to start the reaction. Final volume is 100 μL/reaction so the final reaction concentrations will be 1 μM ATP (cold) and 0.2 μCi/reaction.

5) Stop Solution:

For 1 plate add: To 10 mL Wash Buffer 2 (2M NaCl 1% H$_3$PO$_4$): 1 mL SPA bead slurry (50 mg); Add 100 μL/well 6) Wash buffer 1: 2 M NaCl 7) Wash buffer 2: 2 M NaCl, 1% H$_3$PO$_4$ Assay Procedure:

| Assay Component | Final Concentration | Volume |
| --- | --- | --- |
| CHK1 | 6 nM | 20 µl/rxn |
| Compound (10% DMSO) | — | 10 µl/rxn |
| CDC25C | 0.385 µM | 20 µl/rxn |
| γ$^{33}$P-ATP | 0.2 µCi/rxn | 50 µl/rxn |
| Cold ATP | 1 µM | |
| Stop solution SPA beads | 0.5 mg/rxn | 100 µl/rxn* |
| | | 200 µl/rxn** |

*Total reaction volume for assay.
**Final reaction volume at termination of reaction (after addition of stop solution).

1) Dilute test compounds to desired concentrations in water/10% DMSO—this will give a final DMSO concentration of 1% in the reaction. Dispense 10 µL/reaction to appropriate wells. Add 10 µL 10% DMSO to positive (CHK1+CDC25C+ATP) and negative (CHK1+ATP only) control wells.
2) Thaw enzyme on ice—dilute enzyme to proper concentration in kinase buffer (see Reaction Mixtures) and dispense 20 µL to each well.
3) Thaw the Biotinylated substrate on ice and dilute in kinase buffer (see Reaction Mixtures). Add 20 µL/well except to negative control wells. Instead, add 20 µL Kinase Buffer to these wells.
4) Dilute ATP (cold) and P33-ATP in kinase buffer (see Reaction Mixtures). Add 50 µL/well to start the reaction.
5) Allow the reaction to run for 2 hours at room temperature.
6) Stop reaction by adding 100 µL of the SPA beads/stop solution (see Reaction Mixtures) and leave to incubate for 15 minutes before harvest
7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 mL each wash; 1× with 2M NaCl; 1× with 2M NaCl/1% H3PO4
11) Allow filter plate to dry 15 minutes.
12) Put TopSeal-A adhesive on top of filter plate.
13) Run filter plate in Top Count
   Settings:
   Data mode: CPM
   Radio nuclide: Manual SPA:P33
   Scintillator: Liq/plast
   Energy Range Low
   IC$_{50}$ Determinations:
   Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate IC$_{50}$ values, the dose-response curves were then fitted to a standard sigmoidal curve and IC$_{50}$ values were derived by nonlinear regression analysis.

Selected Thiazole Derivatives of the present invention were tested using this assay and provided IC$_{50}$ values ranging from about 1 nM to about 5500 nM.

CDK2 Kinase Assay
Baculovirus Constructions:
Cyclin E was cloned into pVL1393 (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YDVPDYAS). The expressed protein was approximately 34 kDa in size.

Enzyme Production:
Recombinant baculoviruses expressing cyclin E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 mL of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed about 15 hours in 2 liters of kinase buffer containing 50 mM Tris pH 8.0, 1 mM DTT, 10 mM MgCl$_2$, 100 µM sodium orthovanadate and 20% glycerol. Enzyme was stored in aliquots at −70° C.

In Vitro Cyclin E/CDK2 Kinase Assays
Cyclin E/CDK2 kinase assays can be performed as described below in low protein binding 96-well plates (Corning Inc, Corning, N.Y.).

Enzyme is diluted to a final concentration of 50 µg/mL in kinase buffer containing 50 mM Tris pH 8.0, 10 mM MgCl$_2$, 1 mM DTT, and 0.1 mM sodium orthovanadate. The substrate used in these reactions is a biotinylated peptide derived from Histone H1 (from Amersham, UK). The substrate is thawed on ice and diluted to 2 µM in kinase buffer. Test compounds are diluted in 10% DMSO to desirable concentrations. For each kinase reaction, 20 µL of the 50 µg/mL enzyme solution (1 µg of enzyme) and 20 µl of the 2 µM substrate solution are mixed, then combined with 10 µL of diluted compound in each well for testing. The kinase reaction is initiated by addition of 50 µL of 2 µM ATP and 0.1 µCi of $^{33}$P-ATP (from Amersham, UK). The reaction is allowed to run for 1 hour at room temperature, then is stopped by adding 200 µL of stop buffer containing 0.1% Triton X-100, 1 mM ATP, 5 mM EDTA, and 5 mg/mL streptavidine coated SPA beads (from Amersham, UK) for 15 minutes. The SPA beads are then captured onto a 96-well GFIB filter plate (Packard/Perkin Elmer Life Sciences) using a Filtermate universal harvester (Packard/Perkin Elmer Life Sciences.). Non-specific signals are eliminated by washing the beads twice with 2M NaCl then twice with 2 M NaCl with 1% phosphoric acid. The radioactive signal can then be measured using, for example, a TopCount 96 well liquid scintillation counter (from Packard/Perkin Elmer Life Sciences).

IC$_{50}$ Determinations:
Dose-response curves are plotted from inhibition data generated, each in duplicate, from 8 point serial dilutions of inhibitory compounds. Concentration of compound is plotted against % kinase activity, calculated by CPM of treated samples divided by CPM of untreated samples. To generate IC$_{50}$ values, the dose-response curves are then fitted to a standard sigmoidal curve and IC$_{50}$ values can be derived using nonlinear regression analysis.

Compounds of the present invention exhibit mTOR IC$_{50}$ values of about 1 nM to about 5500 nM, CHK1 IC$_{50}$ values of about 100 nM to about 55000 nM, and CDK2 IC$_{50}$ values of about 800 nM to about 30000 nM. In all cases, the compounds are much more selective for mTOR over CHK1 and CDK2.

Table 15 shows the activity data for an illustrative list of compounds of the invention.

TABLE 15

| Compound ID | Structure | mTOR IC$_{50}$ (nM) | CHK1 IC$_{50}$ (nM) | CDK2 IC$_{50}$ (nM) |
|---|---|---|---|---|
| 1.2 | 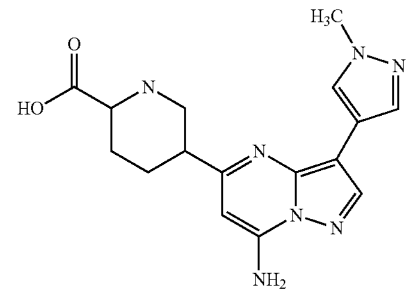 [SMILES: Cn1cc(-c2cnn3c(N)cc(C4CCC(C(=O)O)NC4)nc23)cn1] | 145.6 | 30000 | 30000 |
| 1.1 | 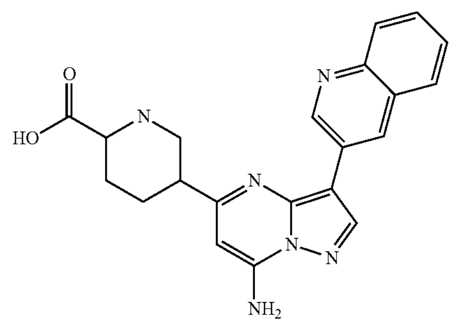 | 12.4 | 30000 | 30000 |
| 10.47 | 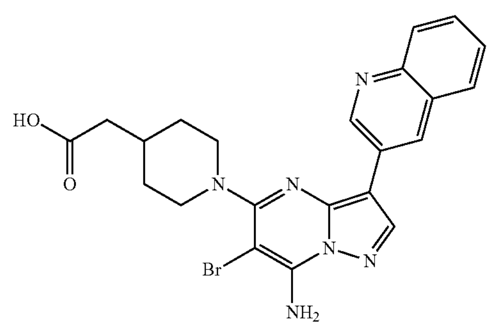 | 11.3 | 22000 | 10000 |
| 11.1 | 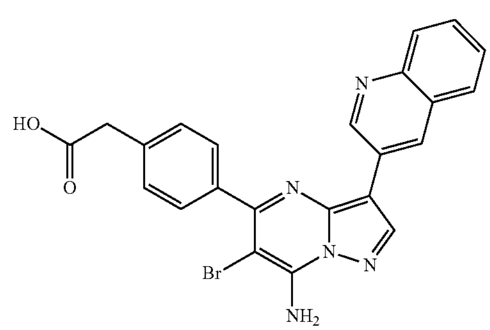 [SMILES: Nc1c(Br)c(-c2ccc(CC(=O)O)cc2)nc2c(-c3cnc4ccccc4c3)cnn12] | 14.8 | 30000 | 30000 |

TABLE 15-continued

| Compound ID | Structure | mTOR IC$_{50}$ (nM) | CHK1 IC$_{50}$ (nM) | CDK2 IC$_{50}$ (nM) |
|---|---|---|---|---|
| 6.6 | 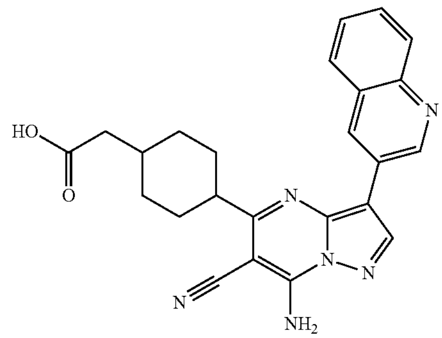 [SMILES: N#Cc1c(C2CCC(CC(=O)O)CC2)nc2c(-c3cnc4ccccc4c3)cnn2c1N] | 1.4 | 30000 | 30000 |

Table 16 also lists compounds of the invention with activity data whereby the IC$_{50}$ values are rated "A", "B," "C," "D," "E" or "F." The IC$_{50}$ values are rated "A" for IC$_{50}$ values less than 100 nM, "B" for IC$_{50}$ values in the range from 101 nM to 200 nM, "C" for IC$_{50}$ values in the range from 201 nM to 500 nM, "D" for IC$_{50}$ values in the range of about 501 nM to 1000 nM, "E" for IC$_{50}$ values in the range from 1001 nM to 5000 nM and "F" for IC$_{50}$ values greater than about 5000 nM.

TABLE 16

| Compound ID | Structure | mTOR IC$_{50}$ (nM) | CHK1 IC$_{50}$ (nM) | CDK2 IC$_{50}$ (nM) |
|---|---|---|---|---|
| 2.5 | 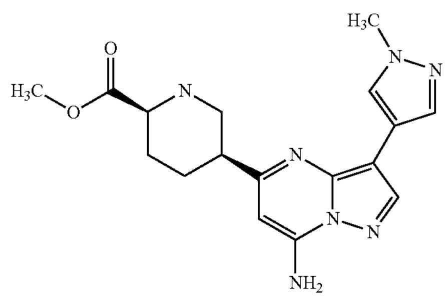 [SMILES: COC(=O)[C@@H]1CC[C@H](c2cc(N)n3ncc(-c4cnn(C)c4)c3n2)CN1] | B | D | F |
| 1.5 | 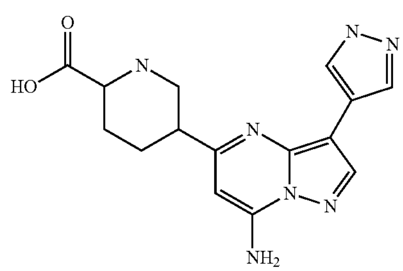 | A | F | F |
| 2.3 | 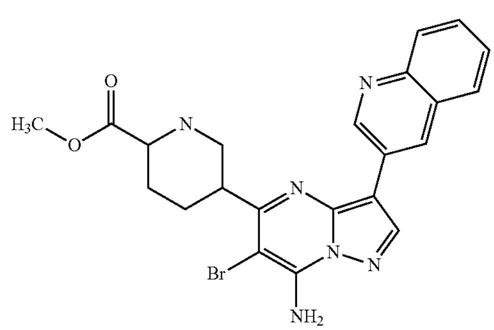 [SMILES: COC(=O)C1CCC(c2nc3c(-c4cnc5ccccc5c4)cnn3c(N)c2Br)CN1] | A | E | F |

TABLE 16-continued

| Compound ID | Structure | mTOR IC$_{50}$ (nM) | CHK1 IC$_{50}$ (nM) | CDK2 IC$_{50}$ (nM) |
| --- | --- | --- | --- | --- |
| 2.2 | 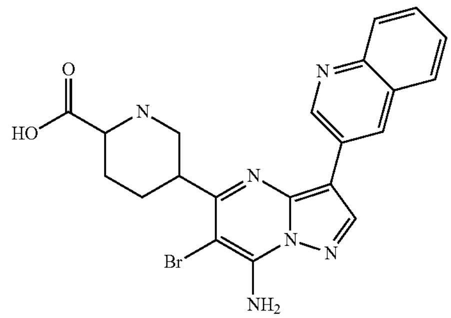 | A | F | F |
| 11.3 | 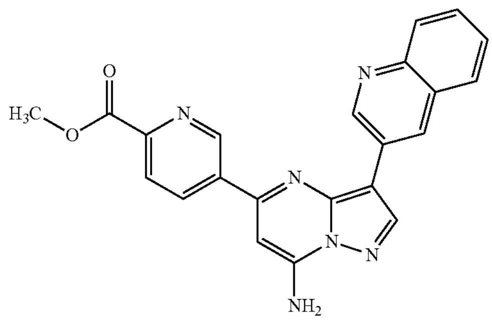 | E | F | F |
| 2.6 | 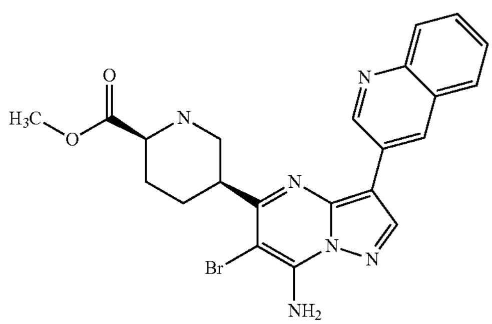 [SMILES: COC(=O)[C@@H]1CC[C@H](c2nc3c(-c4cnc5ccccc5c4)cnn3c(N)c2Br)CN1] | A | E | F |
| 2.7 | 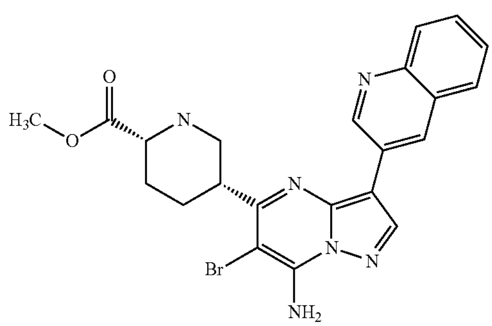 | B | F | F |
| 2.4 | 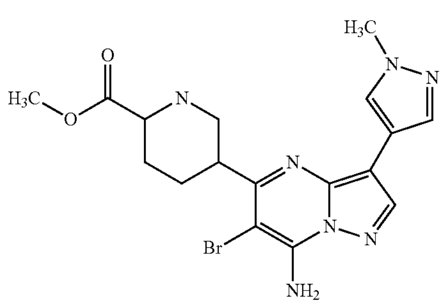 [SMILES: COC(=O)C1CCC(c2nc3c(-c4cnn(C)c4)cnn3c(N)c2Br)CN1] | A | B | F |

TABLE 16-continued
| Compound ID | Structure | mTOR IC$_{50}$ (nM) | CHK1 IC$_{50}$ (nM) | CDK2 IC$_{50}$ (nM) |
|---|---|---|---|---|
| 10.60 | 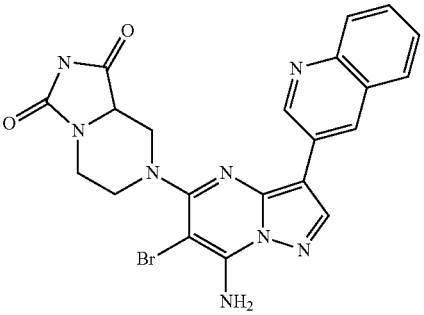 | A | F | F |
| 3.14 | 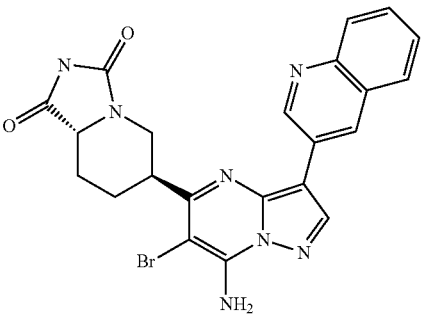 | A | F | F |
| 3.10 | 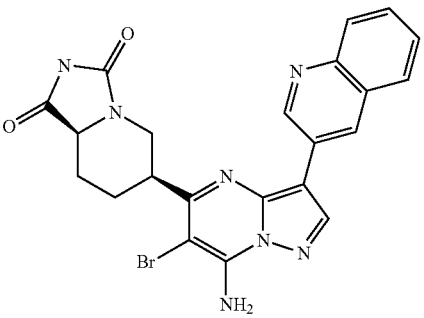 [SMILES: Nc1c(Br)c([C@H]2CC[C@H]3C(=O)NC(=O)N3C2)nc2c(-c3cnc4ccccc4c3)cnn12] | A | F | D |
| 4.5 | 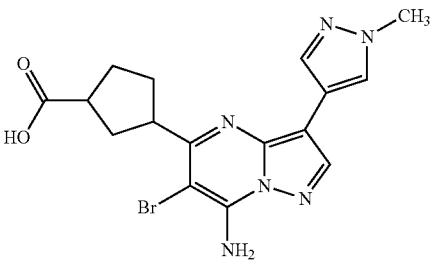 | B | F | F |
| 5.4 | 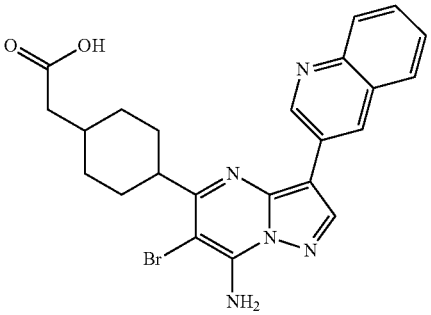 | A | F | F |

TABLE 16-continued

| Compound ID | Structure | mTOR IC$_{50}$ (nM) | CHK1 IC$_{50}$ (nM) | CDK2 IC$_{50}$ (nM) |
|---|---|---|---|---|
| 10.61 | 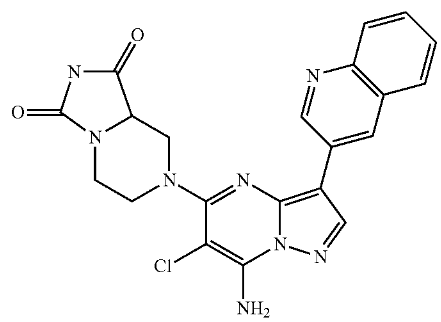 | A | F | F |
| 8.1 | 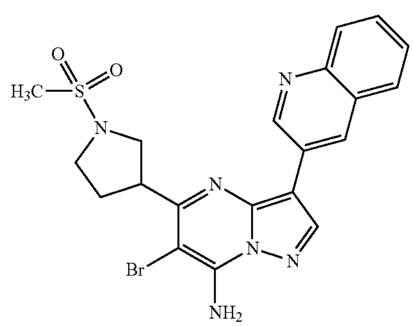 | A | F | F |
| 8.17 | 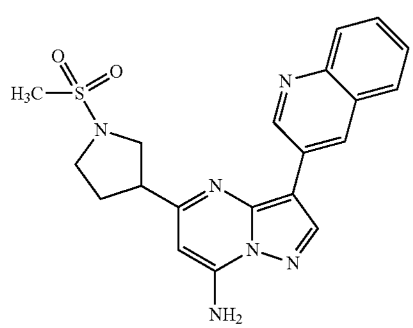 | A | F | F |
| 13.2 | 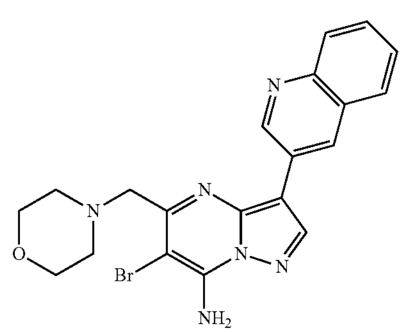 | A | F | F |

TABLE 16-continued

| Compound ID | Structure | mTOR IC$_{50}$ (nM) | CHK1 IC$_{50}$ (nM) | CDK2 IC$_{50}$ (nM) |
| --- | --- | --- | --- | --- |
| 5.2 | 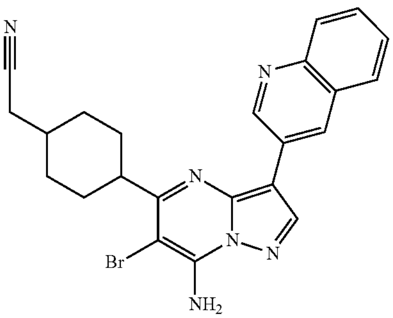 | A | F | F |
| 13.3 | 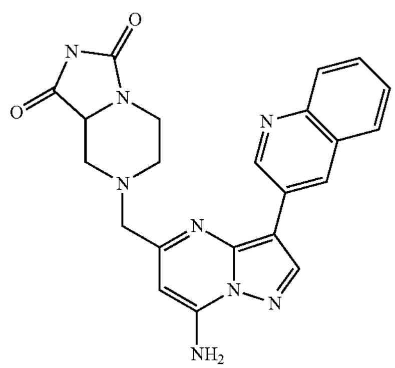 | C | F | F |
| 13.4 | 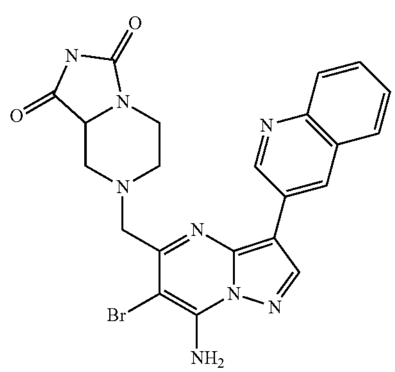 | A | F | F |
| 7.5 | 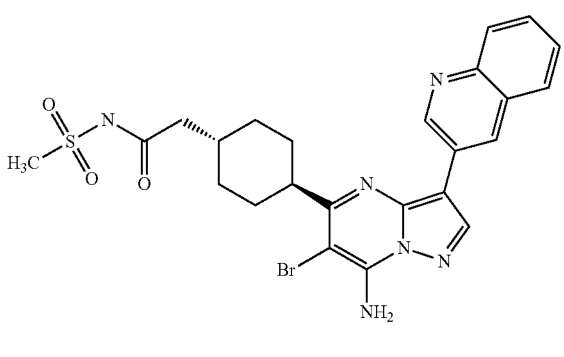 | A | F | F |

TABLE 16-continued

| Compound ID | Structure | mTOR IC$_{50}$ (nM) | CHK1 IC$_{50}$ (nM) | CDK2 IC$_{50}$ (nM) |
|---|---|---|---|---|
| 7.2 | 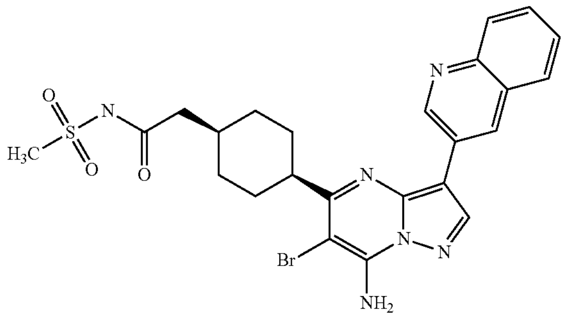 | A | F | F |
| 5.14 | 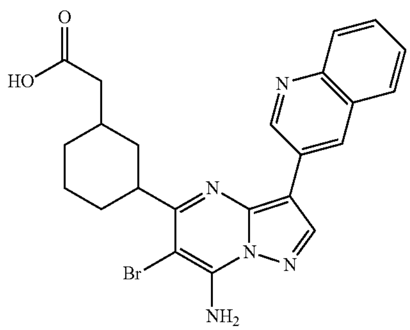 | A | F | F |
| 8.18 | 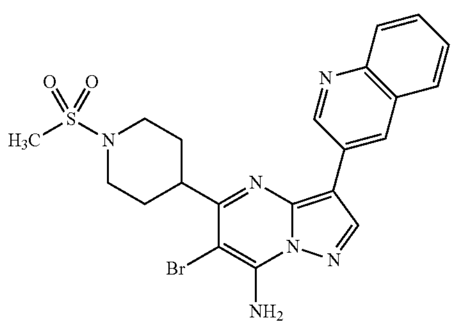 [SMILES: CS(=O)(=O)N1CCC(c2nc3c(-c4cnc5ccccc5c4)cnn3c(N)c2Br)CC1] | A | F | E |
| 10.5 | 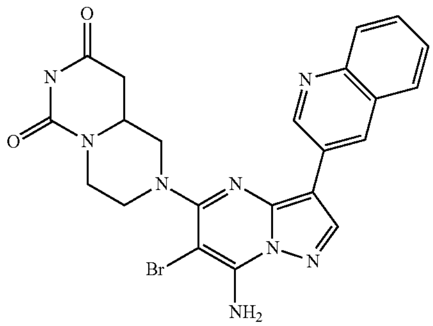 [SMILES: Nc1c(Br)c(N2CCN3C(=O)NC(=O)CC3C2)nc2c(-c3cnc4ccccc4c3)cnn12] | A | F | D |

TABLE 16-continued
| Compound ID | Structure | mTOR IC$_{50}$ (nM) | CHK1 IC$_{50}$ (nM) | CDK2 IC$_{50}$ (nM) |
|---|---|---|---|---|
| 10.19 | 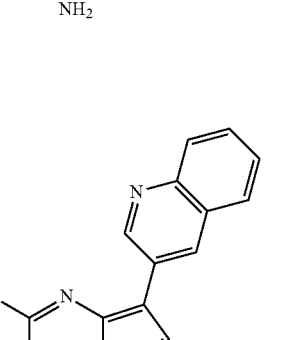 | A | F | F |
| 10.42 | 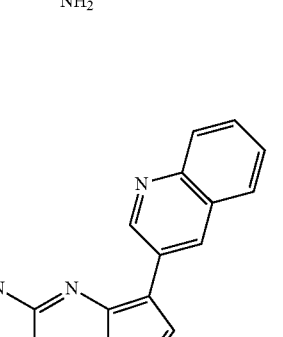 | A | F | F |
| 10.26 | 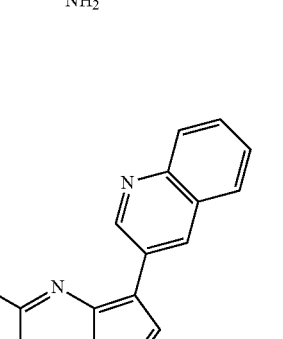 | A | F | F |
| 10.31 | 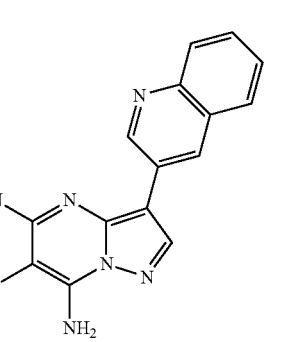 | A | F | F |

TABLE 16-continued

| Compound ID | Structure | mTOR IC$_{50}$ (nM) | CHK1 IC$_{50}$ (nM) | CDK2 IC$_{50}$ (nM) |
|---|---|---|---|---|
| 13.16 | 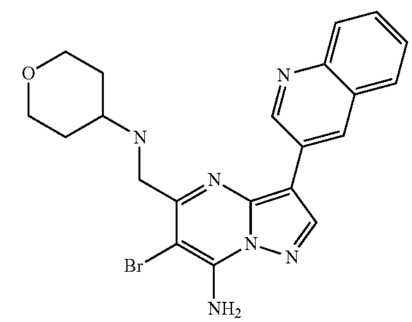 | A | F | F |
| 8.15 | 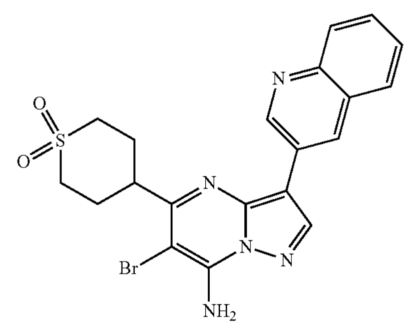 | A | F | F |
| 10.62 | 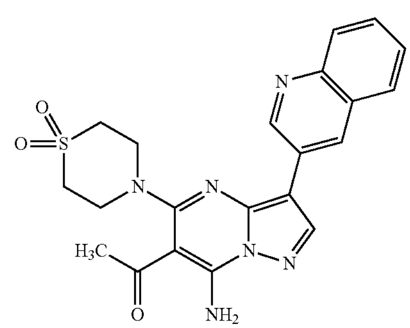 | A | F | F |
| 4.11 | 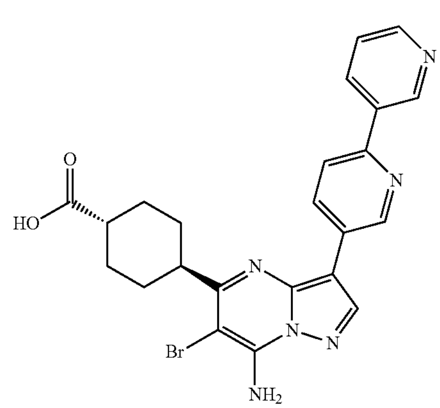 | A | F | F |

TABLE 16-continued

| Compound ID | Structure | mTOR IC$_{50}$ (nM) | CHK1 IC$_{50}$ (nM) | CDK2 IC$_{50}$ (nM) |
|---|---|---|---|---|
| 4.12 | 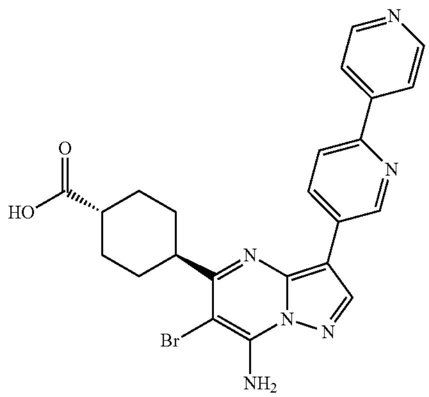 | A | F | F |
| 4.13 | 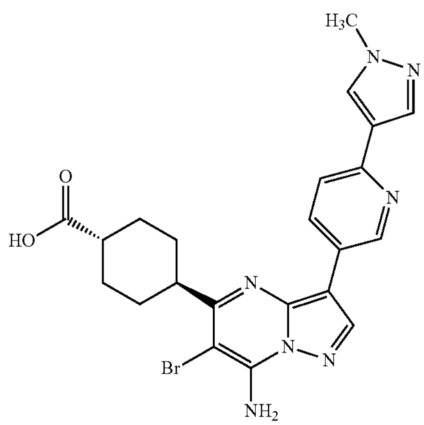 | A | F | F |
| 10.63 | 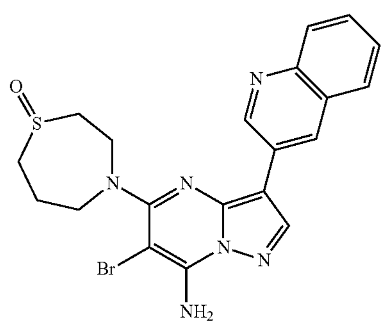 | A | F | F |
| 10.64 | 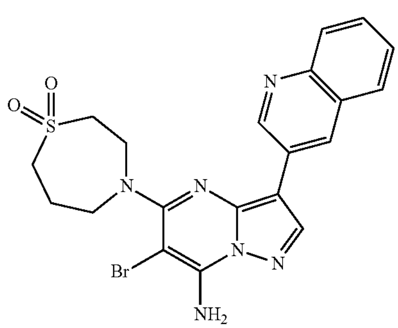 | A | F | F |

TABLE 16-continued

| Compound ID | Structure | mTOR IC$_{50}$ (nM) | CHK1 IC$_{50}$ (nM) | CDK2 IC$_{50}$ (nM) |
|---|---|---|---|---|
| 2.8 | 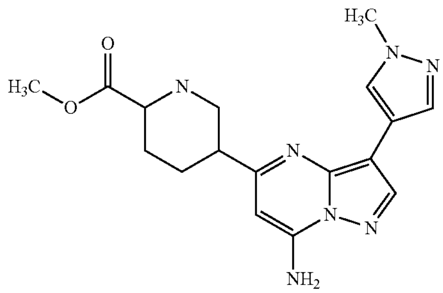 [SMILES: COC(=O)C1CCC(c2cc(N)n3ncc(-c4cnn(C)c4)c3n2)CN1] | D | E | F |
| 3.14 | 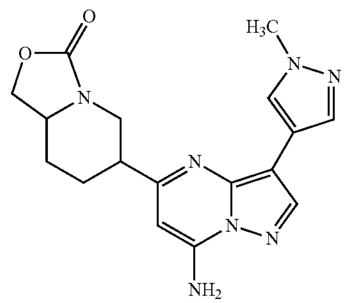 | F | F | |
| 2.9 | 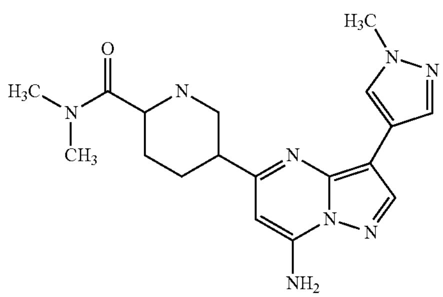 [SMILES: CN(C)C(=O)C1CCC(c2cc(N)n3ncc(-c4cnn(C)c4)c3n2)CN1] | E | F | |
| 8.7 | 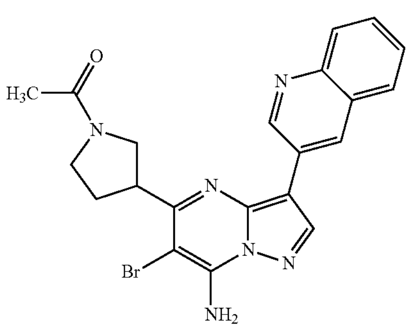 [SMILES: CC(=O)N1CCC(c2nc3c(-c4cnc5ccccc5c4)cnn3c(N)c2Br)C1] | A | F | |
| 6.7 | 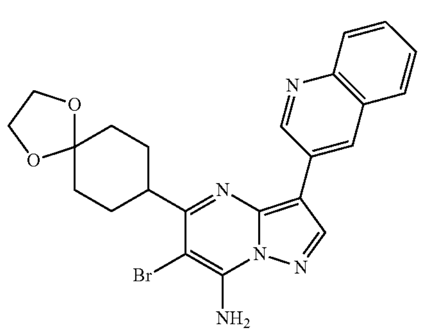 [SMILES: Nc1c(Br)c(C2CCC3(CC2)OCCO3)nc2c(-c3cnc4ccccc4c3)cnn12] | A | F | |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A method of treating a disease by inhibiting a mTOR, comprising administering to a patient in need of such treatment
an amount of a first compound represented by the structural Formula I:

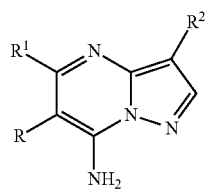

Formula I or a pharmaceutically acceptable salt, or ester thereof, wherein:
R is independently selected from the group consisting of halo, hydroxyl, amino, —CN, H, —($C_1$-$C_6$)alkyl, alkoxy, —C(=O)alkyl, heteroaryl and aryl, wherein each of said heteroaryl and aryl can be unsubstituted or substituted with one or more alkyl or halo;
$R^1$ is independently selected from the group consisting of heterocycloalkyl, spiroheterocycloalkyl, heterocyclenyl, —$NR^3R^4$, cycloalkyl, heteroaryl, aryl, alkynyl, heterocyclenylalkyl, cycloalkylalkyl, heteroarylalkyl, heteroarylalkynyl, —N-heteroaryl, and arylalkyl, wherein each of said heterocycloalkyl, spiroheterocycloalkyl, heterocyclenyl, cycloalkyl, heteroaryl, aryl, alkynyl, heterocyclenylalkyl, cycloalkylalkyl, heteroarylalkyl, heteroarylalkynyl, —N-heteroaryl and arylalkyl can be unsubstituted or substituted with one or moieties independently selected from the group X;
X is alkoxyl, alkyl, —C(O)alkyl, —C(O)-hydroxyalkyl, —C(O)$_2$alkyl, —C(O)$_2$H, hydroxyalkyl, —S(O)$_2$alkyl, hydroxyl, heterocycloalkyl, —NH-heterocycloalkyl, -trihaloalkyl, -dihaloalkyl, -monohaloalkyl, —N—S(O)$_2$-alkyl, —C(O)-heteroaryl, -alkyl-C(O)$_2$H, -alkyl(CO)N(CH$_3$)—O—CH$_3$, -alkyl(CO)-heteroaryl, —C(O)$_2$-alkyl, -alkyl-C(O)—NH$_2$, —NH$_2$, heteroaryl, -alkyl-CN, —C(O)$_2$-arylalkyl, halo, carboxyesteralkyl, —C(O)—NH$_2$, -alkyl-C(O)$_2$alkyl, heteroarylalkyl, —C(O)-heteroaryl, —C(O)-alkyl-O-alkyl, -alkyl(CO)NS(O)$_2$-cycloalkyl, -alkyl(CO)N—S(O)$_2$—CF$_3$, —N-alkyl, —SO$_2$-cycloalkyl, -alkyl(CO)NS(O)$_2$-alkyl, -alkyl-C(O)—N(alkyl)$_2$, -alkyl-NS(O)$_2$-alkyl, alkyl(CO)NS(O)$_2$-cycloalkyl, —CO—CO$_2$H, —C(O)$_2$-alkyl-aryl, —SO$_2$—CF$_3$ or —C(O)H, wherein each of said heterocycloalkyl, heteroaryl or —C(O)-heteroaryl can be unsubstituted or substituted with one or more alkyl;
$R^2$ is pyridyl optionally substituted with one or more moieties independently selected from the group consisting of alkyl, alkoxyl, —CN, aryloxyl, aryl, halo, hydroxyl, —C(CH$_3$)$_2$CN, trifluoromethyl, difluoromethyl, monofluoromethyl, heterocycloalkyl, and arylalkyl;
$R^3$ is cycloalkyl or heteroaryl, wherein each of said cycloalkyl or heteroaryl can be unsubstituted or substituted with one or more moieties independently selected from the group consisting of X; and
$R^4$ is H;
and optionally an amount of at least one second compound, said second compound being an anti-cancer agent;
wherein the amounts of the first compound and said second compound result in a therapeutic effect.

2. The method according to claim 1, wherein the one or more anti-cancer agents are selected from the group consisting of Adriamycin, Altretamine, Amidox, Aminoglutethimide, Amsacrine, Anastrazole, Antibodies to EGFR, 3-AP, Aphidicolon, Ara-C, Arsenic trioxide, L-Asparaginase, Bevacizumab, Bleomycin, BMS 214662, Bortezomib, Busulfan, Campath, Camptostar, Capecitabine, Carboplatin, Carmustine, Centrosome associated protein E ("CENP-E") inhibitors, Cetuximab, Cladribine, Chlorambucil, Chlormethine, Chlorotrianisene, Cisplatin, Clofarabine, cyclophosphamide, Cytarabine, a Cytostatic agent, Cytoxan, Dacarbazine, Dactinomycin, Daunorubicin, Dasatinib, Deforolimus, Deoxycoformycin, Didox, Diethylstilbestrol, Docetaxel, Doxorubicin, Dromostanolone, Droloxafine, Epirubicin, Epothilone, ERK inhibitors, Erlotinib, Etoposide, 17α-Ethinylestradiol, Estramustine, Exemestane, Floxuridine, Fludarabine, Fludarabine phosphate, 5-Fluorouracil, Fluoxymesterone, Flutamide, Fulvestrant, Gefitinib, Gemcitabine, Gemtuzumab ozogamcicin, Goserelin, GSK-923295, Hexamethylmelamine, Hydroxyprogesterone, Hydroxyurea, Ibritumomab Tiuxetan, Idarubicin, Ifosfamide, Imatinib mesylate, Intron, Irinotecan, ispinesib, KSP inhibitors, L778, 123, Lapatinib, Leucovirin, Leuprolide, Lerozole, Letrazole, Levamisole, Liposomal Doxorubicin, Liposomal, Lomustine, Lonafarnib, Medroxyprogesteroneacetate, Megestrolacetate, Melphalan, 6-Mercaptopurine, Methoxtrexate, Methylprednisolone, Methyltestosterone, Mithramycin, Mitomycin-C, Mitotane, Mitoxantrone, Navelbene, Nilotinib, Oxaliplatin, Paclitaxel, Panitubimab, Pentostatin, Pipobroman, Porfimer, Prednisolone, Prednisone propionate, Procarbazine, Reloxafine, Rituximab, Satriplatin, SB-743921, Sml1, Sorafinib, Streptozocin, Sunitinib, Tamoxifen, Taxotere, Taxol, Temozolomide, Teniposide, Testolactone, Testosterone, Tezacitabine, 6-Thioguanine, Thiotepa, Tipifarnib, Topotecan, Toremifene, Tositumomab, Trastuzumab, Triamcinolone, Triapine, Triethylenemelamine, Triethylenethiophosphoramine, Trimidox, Uracil mustard, Vinblastine, Vincristine, Vindesine, and Vinorelbine.

* * * * *

UNITED STATES PATENT AND TRADEMARK OFFICE
CERTIFICATE OF CORRECTION

PATENT NO. : 8,591,943 B2
APPLICATION NO. : 13/263193
DATED : November 26, 2013
INVENTOR(S) : Deng et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 17 days.

Signed and Sealed this
Twenty-second Day of September, 2015

Michelle K. Lee
*Director of the United States Patent and Trademark Office*